United States Patent
Lee et al.

(10) Patent No.: US 12,415,814 B2
(45) Date of Patent: Sep. 16, 2025

(54) HETEROCYCLIC COMPOUND AND ORGANIC LIGHT EMITTING DEVICE COMPRISING SAME

(71) Applicant: LT MATERIALS CO., LTD., Yongin-si (KR)

(72) Inventors: Yun-Ji Lee, Yongin-si (KR); Min-Ji Park, Yongin-si (KR); Won-Jang Jeong, Yongin-si (KR); Dong-Jun Kim, Yongin-si (KR)

(73) Assignee: LT MATERIALS CO., LTD., Yongin (KR)

( * ) Notice: Subject to any disclaimer, the term of this patent is extended or adjusted under 35 U.S.C. 154(b) by 905 days.

(21) Appl. No.: 17/615,643

(22) PCT Filed: Jul. 17, 2020

(86) PCT No.: PCT/KR2020/009424
§ 371 (c)(1),
(2) Date: Dec. 1, 2021

(87) PCT Pub. No.: WO2021/015497
PCT Pub. Date: Jan. 28, 2021

(65) Prior Publication Data
US 2022/0340585 A1    Oct. 27, 2022

(30) Foreign Application Priority Data

Jul. 22, 2019   (KR) .................. 10-2019-0088238

(51) Int. Cl.
| | | |
|---|---|---|
| *C07D 495/04* | (2006.01) | |
| *C07D 491/048* | (2006.01) | |
| *C07D 519/00* | (2006.01) | |
| *C07F 9/53* | (2006.01) | |
| *H10K 50/16* | (2023.01) | |

(Continued)

(52) U.S. Cl.
CPC ....... *C07D 495/04* (2013.01); *C07D 491/048* (2013.01); *C07D 519/00* (2013.01);
(Continued)

(58) Field of Classification Search
CPC .............. C07D 491/048; C07D 519/00; C07D 495/04; C07F 9/5325; H01L 51/0074;
(Continued)

(56) References Cited

U.S. PATENT DOCUMENTS

2016/0141515 A1    5/2016    Hayama et al.
2017/0133601 A1    5/2017    Sim et al.
(Continued)

FOREIGN PATENT DOCUMENTS

CN          112194670 A       1/2021
KR     10-2016-0002408 A      1/2016
(Continued)

OTHER PUBLICATIONS

International Search Report for PCT/KR2020/009424 mailed on Nov. 3, 2020.

*Primary Examiner* — Vu A Nguyen
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device including the same.

11 Claims, 2 Drawing Sheets

(51) Int. Cl.
*H10K 50/18* (2023.01)
*H10K 85/60* (2023.01)

(52) U.S. Cl.
CPC ......... *C07F 9/5325* (2013.01); *H10K 85/622* (2023.02); *H10K 85/624* (2023.02); *H10K 85/654* (2023.02); *H10K 85/656* (2023.02); *H10K 85/657* (2023.02); *H10K 85/6572* (2023.02); *H10K 85/6574* (2023.02); *H10K 85/6576* (2023.02); *H10K 50/16* (2023.02); *H10K 50/18* (2023.02)

(58) Field of Classification Search
CPC ............. H01L 51/0073; H01L 51/0072; H01L 51/0071; H01L 51/0067; H01L 51/0069; H01L 51/0054; H01L 51/0056; H01L 51/5072

See application file for complete search history.

(56) References Cited

U.S. PATENT DOCUMENTS

| | | |
|---|---|---|
| 2017/0133602 A1 | 5/2017 | Lee et al. |
| 2019/0103560 A1 | 4/2019 | Jung et al. |
| 2020/0066996 A1 | 2/2020 | La et al. |

FOREIGN PATENT DOCUMENTS

| | | | |
|---|---|---|---|
| KR | 10-2016-0018458 A | | 2/2016 |
| KR | 10-2016-0046703 A | | 4/2016 |
| KR | 10-2017-0053759 A | | 5/2017 |
| KR | 10-2017-0086277 A | | 7/2017 |
| KR | 10-2017-0090139 A | | 8/2017 |
| KR | 10-2018-0075398 A | | 7/2018 |
| KR | 10-2018-0076358 A | * | 7/2018 |

* cited by examiner

[FIG. 1]
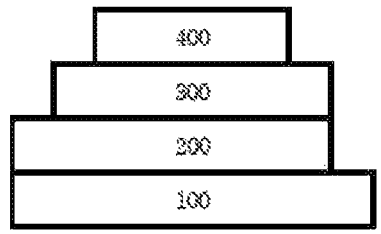
[FIG. 2]
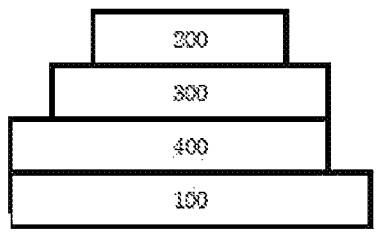
[FIG. 3]
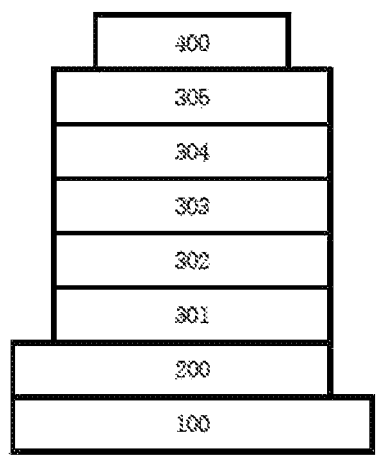

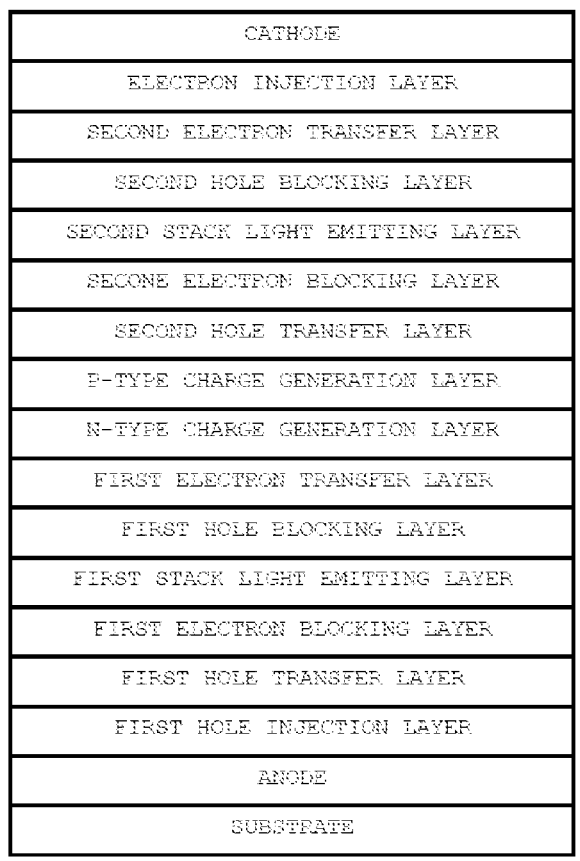
[FIG. 4]

HETEROCYCLIC COMPOUND AND ORGANIC LIGHT EMITTING DEVICE COMPRISING SAME

TECHNICAL FIELD

The present specification relates to a heterocyclic compound, and an organic light emitting device including the same.

The present specification claims priority to and the benefits of Korean Patent Application No. 10-2019-0088238, filed with the Korean Intellectual Property Office on Jul. 22, 2019, the entire contents of which are incorporated herein by reference.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

DISCLOSURE

Technical Problem

The present specification is directed to providing a heterocyclic compound, and an organic light emitting device including the same.

Technical Solution

One embodiment of the present specification provides a heterocyclic compound represented by the following Chemical Formula 1.

[Chemical Formula 1]

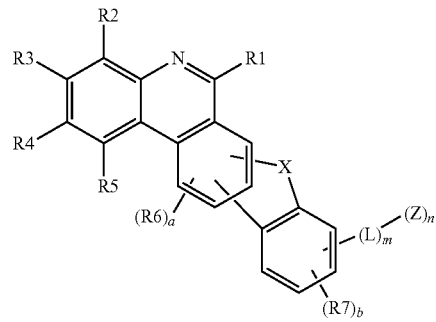

In Chemical Formula 1,

X is O or S,

L is a direct bond; a substituted or unsubstituted C6 to C60 arylene group; or a substituted or unsubstituted C2 to C60 heteroarylene group, Z and R1 are each independently a substituted or unsubstituted C1 to C60 alkyl group; a substituted or unsubstituted C2 to C60 alkenyl group; a substituted or unsubstituted C2 to C60 alkynyl group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; a substituted or unsubstituted C1 to C20 alkylamine group; a substituted or unsubstituted C6 to C60 arylamine group; a substituted or unsubstituted C2 to C60 heteroarylamine group; or a substituted or unsubstituted phosphine oxide group, R2 to R7 are each independently hydrogen; deuterium; a halogen group; a cyano group; a substituted or unsubstituted C1 to C60 alkyl group; a substituted or unsubstituted C3 to C60 cycloalkyl group; a substituted or unsubstituted C6 to C60 aryl group; or a substituted or unsubstituted C2 to C60 heteroaryl group, a is 1 or 2, b is an integer of 1 to 3, m and n are each an integer of 1 to 5, and when a, b, m and n are each 2 or greater, substituents in the parentheses are the same as or different from each other.

Another embodiment of the present application provides an organic light emitting device including a first electrode; a second electrode provided opposite to the first electrode; and an organic material layer provided between the first electrode and the second electrode, wherein the organic material layer includes the heterocyclic compound represented by Chemical Formula 1.

Another embodiment of the present application provides an organic light emitting device including a first electrode; a first stack provided on the first electrode and including a first light emitting layer; a charge generation layer provided on the first stack; a second stack provided on the charge generation layer and including a second light emitting layer; and a second electrode provided on the second stack, wherein the charge generation layer includes the heterocyclic compound represented by Chemical Formula 1.

Advantageous Effects

A compound described in the present specification can be used as a material of an organic material layer of an organic light emitting device. In the organic light emitting device, the compound is capable of performing a role of a hole injection material, a hole transfer material, a light emitting material, an electron transfer material, an electron injection material or the like. Particularly, the compound can be used as an electron transfer layer material or a charge generation layer material of an organic light emitting device.

Particularly, Chemical Formula 1 has a structure in which dibenzofuran or dibenzothiophene is fused to quinoline, and HOMO and LUMO levels can be adjusted by having various substituents in the benzene ring which is not fused to the quinoline in the dibenzofuran or dibenzothiophene. Accordingly, electrical properties of the structure can be enhanced by adjusting an energy band gap. In addition, electron transfer capability of a material can be enhanced through substituents having strong electron migration properties.

Specifically, when using the compound represented by Chemical Formula 1 in an organic material layer, a driving voltage of the device can be lowered, light efficiency can be enhanced, and lifetime properties of the device can be enhanced.

DESCRIPTION OF DRAWINGS

FIG. 1 to FIG. 4 each illustrate a lamination structure of an organic light emitting device according to one embodiment of the present specification.

100: Substrate
200: Anode
300: Organic Material Layer
301: Hole Injection Layer
302: Hole Transfer Layer
303: Light Emitting Layer
304: Electron Transfer Layer
305: Electron Injection Layer
400: Cathode

MODE FOR DISCLOSURE

Hereinafter, the present specification will be described in more detail.

In the present specification, a certain part "including" certain constituents means capable of further including other constituents, and does not exclude other constituents unless particularly stated on the contrary.

In the present specification, the term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, a "T1 value" means an energy level value in a triplet state.

In the present specification, "substituted or unsubstituted" means being substituted with one or more substituents selected from the group consisting of a halogen group; a cyano group; a C1 to C60 linear or branched alkyl group; a C2 to C60 linear or branched alkenyl group; a C2 to C60 linear or branched alkynyl group; a C3 to C60 monocyclic or polycyclic cycloalkyl group; a C2 to C60 monocyclic or polycyclic heterocycloalkyl group; a C6 to C60 monocyclic or polycyclic aryl group; a C2 to C60 monocyclic or polycyclic heteroaryl group; a silyl group; a phosphine oxide group; and an amine group, or being unsubstituted, or being substituted with a substituent linking two or more substituents selected from among the substituents illustrated above, or being unsubstituted.

In the present specification, the halogen may be fluorine, chlorine, bromine or iodine.

In the present specification, the alkyl group includes linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group includes linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group includes linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the cycloalkyl group includes monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group includes O, S, Se, N or Si as a heteroatom, includes monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group includes monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group includes a spiro group. The number of carbon atoms of the aryl group may be from 6 to 60, specifically from 6 to 40 and more specifically from 6 to 25. Specific examples of the aryl group may include a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the silyl group is a substituent including Si, having the Si atom directly linked as a radical, and is represented by —SiR$_{104}$R$_{105}$R$_{106}$. R$_{104}$ to R$_{106}$ are the same as or different from each other, and may be each independently a substituent formed with at least one of hydrogen; deuterium; a halogen group; an alkyl group; an alkenyl group; a cycloalkyl group; an aryl group; and a heterocyclic group. Specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted,

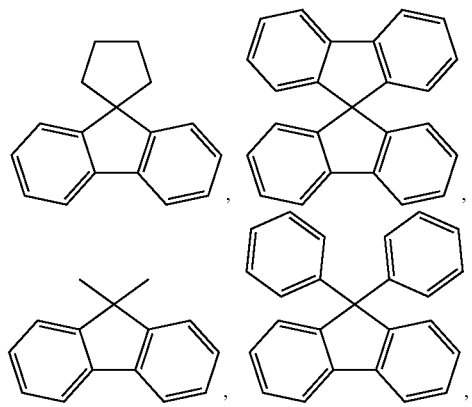

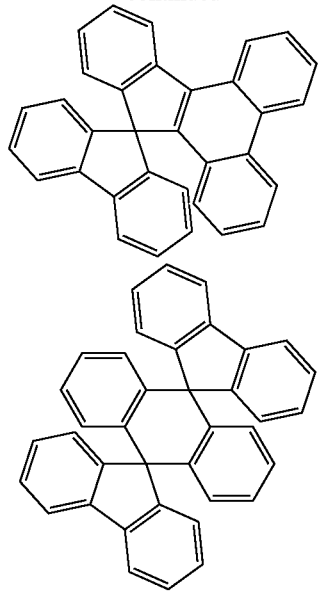

, and the like may be included, however, the structure is not limited thereto.

In the present specification, the heteroaryl group includes O, S, Se, N or Si as a heteroatom, includes monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may include a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydro-dibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl group, a pyrazolo[1,5-c]quinazolinyl group, a pyrido[1,2-b]indazolyl group, a pyrido[1,2-a]imidazo[1,2-e] indolinyl group, a 5,11-dihydroindeno[1,2-b]carbazolyl group and the like, but are not limited thereto.

In the present specification, the phosphine oxide group may be specifically substituted with an aryl group, and examples described above may be applied to the aryl group. Examples of the phosphine oxide group may include a diphenylphosphine oxide group, a dinaphthylphosphine oxide group and the like, but are not limited thereto.

In the present specification, the amine group may be selected from the group consisting of a monoalkylamine group; a monoarylamine group; a monoheteroarylamine group; —$NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the structures illustrated as the aryl group and the heteroaryl group described above may be used as the arylene group and the heteroarylene group except that they are not a monovalent group.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

As an aliphatic or aromatic hydrocarbon ring or heteroring that adjacent groups may form, the structures illustrated as the cycloalkyl group, the heterocycloalkyl group, the aryl group and the heteroaryl group described above may be applied except for those that are not a monovalent group.

One embodiment of the present specification provides a heterocyclic compound represented by Chemical Formula 1.

Particularly, Chemical Formula 1 has a structure in which dibenzofuran or dibenzothiophene is fused to quinoline, and HOMO and LUMO levels can be adjusted by having various substituents in the benzene ring which is not fused to the quinoline in the dibenzofuran or dibenzothiophene. Accordingly, electrical properties of the structure may be enhanced by adjusting an energy band gap. In addition, electron transfer capability of a material may be enhanced through substituents having strong electron migration properties.

In one embodiment of the present specification, X is O or S.

In one embodiment of the present specification, X is O.

In another embodiment, X is S.

In one embodiment of the present specification, L is a direct bond; a substituted or unsubstituted C6 to C60 arylene group; or a substituted or unsubstituted C2 to C60 heteroarylene group.

By the Z substituent and the core structure being separated by L in the compound, hole migration properties of the core structure and electron migration properties of the substituent are distinguished in the electron cloud distribution of the molecule. This is an excellent bipolar structure facilitating electron migration, and therefore, efficiency, lifetime and driving voltage may be significantly improved.

In one embodiment of the present specification, L is a direct bond; a substituted or unsubstituted C6 to C30 arylene group; or a substituted or unsubstituted C2 to C30 heteroarylene group.

In one embodiment of the present specification, L is a direct bond; a substituted or unsubstituted phenylene group; a substituted or unsubstituted biphenylene group; a substituted or unsubstituted terphenylene group; a substituted or unsubstituted naphthylene group; a substituted or unsubstituted anthracenylene group; a substituted or unsubstituted triphenylenylene group; a substituted or unsubstituted phenanthrenylene group; a substituted or unsubstituted divalent pyridine group; a substituted or unsubstituted divalent pyrimidine group; or a substituted or unsubstituted divalent triazine group.

In one embodiment of the present specification, L is a direct bond; a phenylene group unsubstituted or substituted with an aryl group or a heteroaryl group; a biphenylene group; a terphenylene group; a naphthylene group; an anthracenylene group; a triphenylenylene group; a phenanthrenylene group; a divalent pyridine group unsubstituted or substituted with an aryl group or a heteroaryl group; a divalent pyrimidine group unsubstituted or substituted with an aryl group; or a divalent triazine group unsubstituted or substituted with an aryl group or a heteroaryl group.

In one embodiment of the present specification, L is a direct bond; a phenylene group unsubstituted or substituted with a phenyl group or a carbazole group; a biphenylene group; a terphenylene group; a naphthylene group; an anthracenylene group; a triphenylenylene group; a phenanthrenylene group; a divalent pyridine group unsubstituted or substituted with a phenyl group or a pyridine group; a divalent pyrimidine group unsubstituted or substituted with a phenyl group or a biphenyl group; or a divalent triazine group unsubstituted or substituted with a phenyl group unsubstituted or substituted with a cyano group, a biphenyl group, a naphthyl group, or a carbazole group unsubstituted or substituted with a phenyl group.

In one embodiment of the present specification, Z is a substituted or unsubstituted C1 to C60 alkyl group; a substituted or unsubstituted C2 to C60 alkenyl group; a substituted or unsubstituted C2 to C60 alkynyl group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; a substituted or unsubstituted C1 to C20 alkylamine group; a substituted or unsubstituted C6 to C60 arylamine group; a substituted or unsubstituted C2 to C60 heteroarylamine group; or a substituted or unsubstituted phosphine oxide group.

In one embodiment of the present specification, Z is a substituted or unsubstituted C1 to C30 alkyl group; a substituted or unsubstituted C2 to C30 alkenyl group; a substituted or unsubstituted C2 to C30 alkynyl group; a substituted or unsubstituted C3 to C30 cycloalkyl group; a substituted or unsubstituted C2 to C30 heterocycloalkyl group; a substituted or unsubstituted C6 to C30 aryl group; a substituted or unsubstituted C2 to C30 heteroaryl group; a substituted or unsubstituted C1 to C10 alkylamine group; a substituted or unsubstituted C6 to C30 arylamine group; a substituted or unsubstituted C2 to C30 heteroarylamine group; or a substituted or unsubstituted phosphine oxide group.

In one embodiment of the present specification, Z is a substituted or unsubstituted C6 to C30 aryl group; a substituted or unsubstituted C2 to C30 heteroaryl group; or a substituted or unsubstituted phosphine oxide group.

In one embodiment of the present specification, Z is a substituted or unsubstituted phenyl group; a biphenyl group; a terphenyl group; a naphthyl group; a triphenylenyl group; a phenanthrenyl group; an anthracenyl group; a dimethylfluorenyl group; a diphenylfluorenyl group; a spirobifluorenyl group; an isoquinolinyl group; a quinazolinyl group; a phenoxazinyl group; a phenothiazinyl group; an indolocarbazole group; a substituted or unsubstituted pyridine group; a substituted or unsubstituted pyrimidine group; a substituted or unsubstituted triazine group; a substituted or unsubstituted carbazole group; a substituted or unsubstituted benzocarbazole group; a substituted or unsubstituted phenanthrolinyl group; a substituted or unsubstituted dibenzofuran group; a substituted or unsubstituted dibenzothiophene group; a substituted or unsubstituted dihydroacridine group; or a substituted or unsubstituted phosphine oxide group.

In one embodiment of the present specification, Z is a phenyl group unsubstituted or substituted with a cyano group, a phenyl group or a carbazole group; a biphenyl group; a terphenyl group; a naphthyl group; a triphenylenyl group; a phenanthrenyl group; an anthracenyl group; a dimethylfluorenyl group; a diphenylfluorenyl group; a spirobifluorenyl group; an isoquinolinyl group; a quinazolinyl group; a phenoxazinyl group; a phenothiazinyl group; an indolocarbazole group; a pyridine group unsubstituted or substituted with a phenyl group or a pyridine group; a pyrimidine group unsubstituted or substituted with a phenyl group or a biphenyl group; a triazine group unsubstituted or substituted with a phenyl group unsubstituted or substituted with a naphthyl group or a cyano group, a biphenyl group, a naphthyl group, a dimethylfluorenyl group, a dibenzofuran group, a dibenzothiophene group, or a carbazole group unsubstituted or substituted with a phenyl group; a carbazole group unsubstituted or substituted with a phenyl group; a benzocarbazole group; a phenanthrolinyl group unsubstituted or substituted with a phenyl group; a dibenzofuran group unsubstituted or substituted with a phenyl group; a dibenzothiophene group unsubstituted or substituted with a phenyl group; a dihydroacridine group unsubstituted or substituted with a methyl group or a phenyl group; or a phosphine oxide group unsubstituted or substituted with a phenyl group.

In one embodiment of the present specification, R1 is a substituted or unsubstituted C1 to C60 alkyl group; a substituted or unsubstituted C2 to C60 alkenyl group; a substituted or unsubstituted C2 to C60 alkynyl group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; a substituted or unsubstituted C1 to C20 alkylamine group; a substituted or unsubstituted C6 to C60 arylamine group; a substituted or unsubstituted C2 to C60 heteroarylamine group; or a substituted or unsubstituted phosphine oxide group.

In one embodiment of the present specification, R1 is a substituted or unsubstituted C1 to C60 alkyl group; a substituted or unsubstituted C3 to C60 cycloalkyl group; a substituted or unsubstituted C2 to C60 heterocycloalkyl group; a substituted or unsubstituted C6 to C60 aryl group; or a substituted or unsubstituted C2 to C60 heteroaryl group.

In one embodiment of the present specification, R1 is a substituted or unsubstituted C6 to C60 aryl group; or a substituted or unsubstituted C2 to C60 heteroaryl group.

In one embodiment of the present specification, R1 is a substituted or unsubstituted C6 to C30 aryl group; or a substituted or unsubstituted C2 to C30 heteroaryl group.

In one embodiment of the present specification, R1 is a substituted or unsubstituted C6 to C30 aryl group.

In one embodiment of the present specification, R1 is a substituted or unsubstituted phenyl group; a substituted or unsubstituted naphthyl group; a substituted or unsubstituted anthracenyl group; a substituted or unsubstituted phenanthrenyl group; a substituted or unsubstituted pyrenyl group; or a substituted or unsubstituted perylene group.

In one embodiment of the present specification, R1 is a phenyl group; a naphthyl group; an anthracenyl group; a phenanthrenyl group; a pyrenyl group; or a perylene group.

In one embodiment of the present specification, R2 to R7 are each independently hydrogen; deuterium; a halogen group; a cyano group; a substituted or unsubstituted C1 to C60 alkyl group; a substituted or unsubstituted C3 to C60 cycloalkyl group; a substituted or unsubstituted C6 to C60 aryl group; or a substituted or unsubstituted C2 to C60 heteroaryl group.

In one embodiment of the present specification, R2 to R7 are each independently hydrogen; deuterium; a substituted or unsubstituted C1 to C60 alkyl group; a substituted or unsubstituted C6 to C60 aryl group; or a substituted or unsubstituted C2 to C60 heteroaryl group.

In one embodiment of the present specification, R2 to R7 are each independently hydrogen; or deuterium.

In one embodiment of the present specification, R2 to R7 are hydrogen.

In one embodiment of the present specification, m may be 1 or 2.

In one embodiment of the present specification, n may be an integer of 1 to 5.

In one embodiment of the present specification, Chemical Formula 1 is represented by the following Chemical Formula 1-1.

[Chemical Formula 1-1]

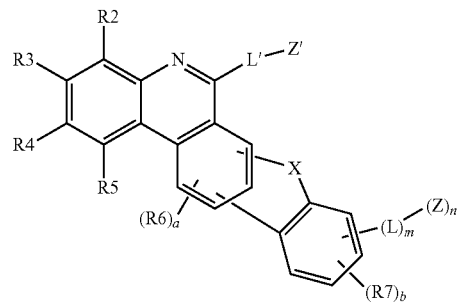

In Chemical Formula 1-1,
X, L, Z, R2 to R7, a, b, m and n have the same definitions as in Chemical Formula 1,
L' is a direct bond; a substituted or unsubstituted C6 to C60 arylene group; or a substituted or unsubstituted C2 to C60 heteroarylene group,
Z' is a substituted or unsubstituted C1 to C60 alkyl group; a substituted or unsubstituted C3 to C60 cycloalkyl group; a substituted or unsubstituted C2 to C60 heterocycloalkyl group; a substituted or unsubstituted C6 to C60 aryl group; or a substituted or unsubstituted C2 to C60 heteroaryl group.

In one embodiment of the present specification, L' is a direct bond.

In one embodiment of the present specification, Z' is a substituted or unsubstituted C6 to C60 aryl group; or a substituted or unsubstituted C2 to C60 heteroaryl group.

In one embodiment of the present specification, Z' is a substituted or unsubstituted C6 to C60 aryl group.

In one embodiment of the present specification, Z' is a substituted or unsubstituted C6 to C30 aryl group.

In one embodiment of the present specification, Z' is a phenyl group; a naphthyl group; an anthracenyl group; a phenanthrenyl group; a pyrenyl group; or a perylene group.

In the heterocyclic compound provided in one embodiment of the present specification, Chemical Formula 1 is represented by any one of the following Chemical Formulae 1-2 to 1-5.

[Chemical Formula 1-2]

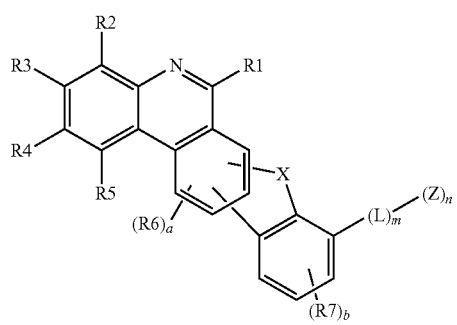

[Chemical Formula 1-3]

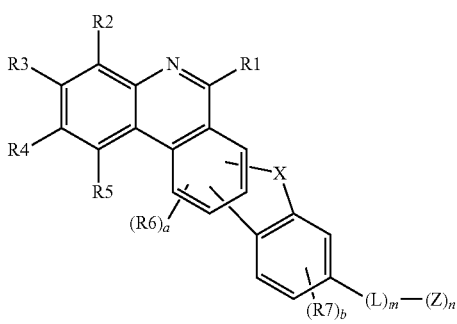

[Chemical Formula 1-4]

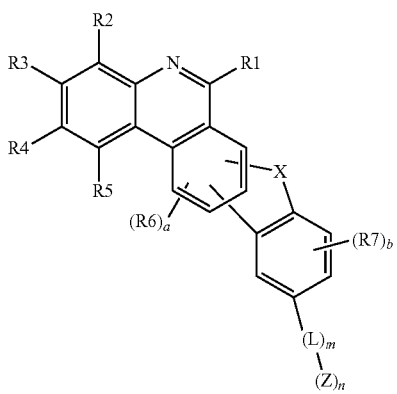

[Chemical Formula 1-5]

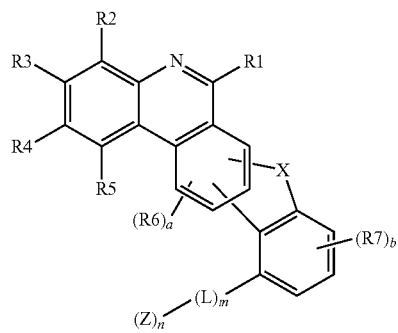

In Chemical Formulae 1-2 to 1-5,

X, L, Z, R1 to R7, a, b, m and n have the same definitions as in Chemical Formula 1.

In the heterocyclic compound provided in one embodiment of the present specification, Chemical Formula 1 is represented by any one of the following Chemical Formulae 2 to 4.

[Chemical Formula 2]

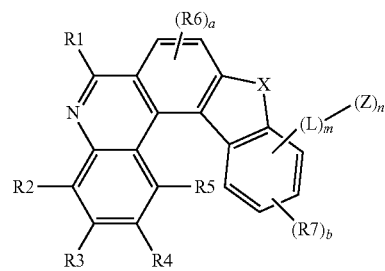

[Chemical Formula 3]

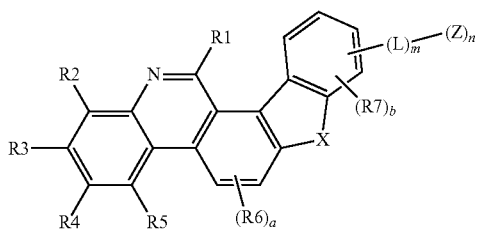

[Chemical Formula 4]

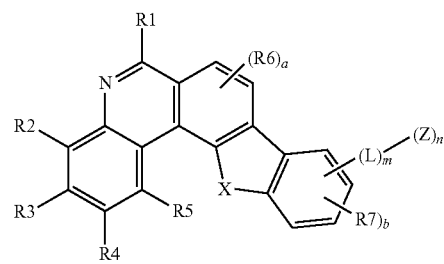

In Chemical Formulae 2 to 4,

X, L, Z, R1 to R7, a, b, m and n have the same definitions as in Chemical Formula 1.

In one embodiment of the present specification, Chemical Formula 1 may be represented by any one of the following compounds, but is not limited thereto.

1
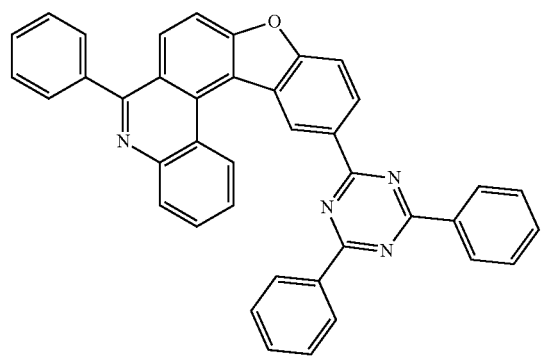
2
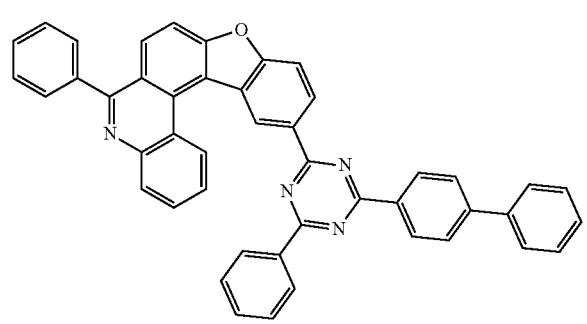
3
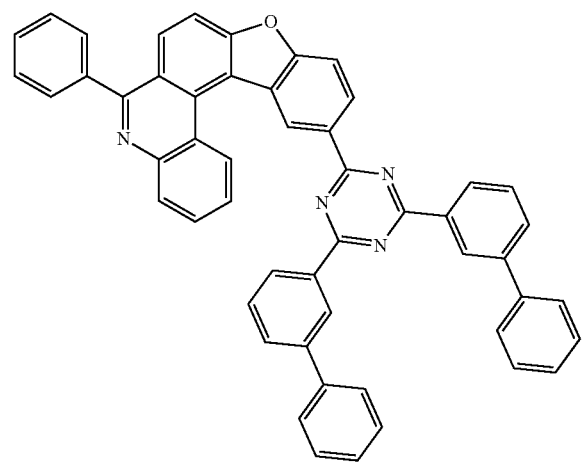
4
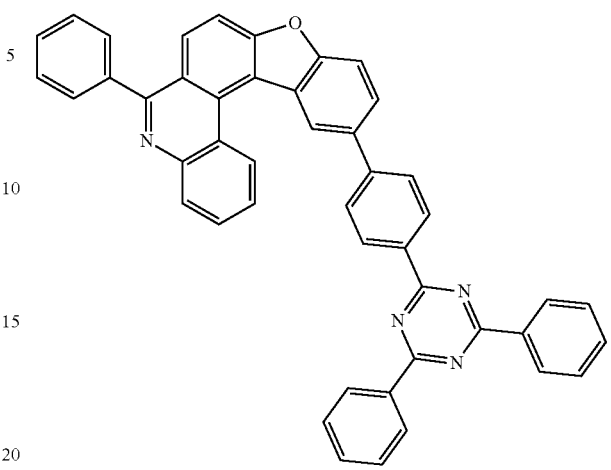
5
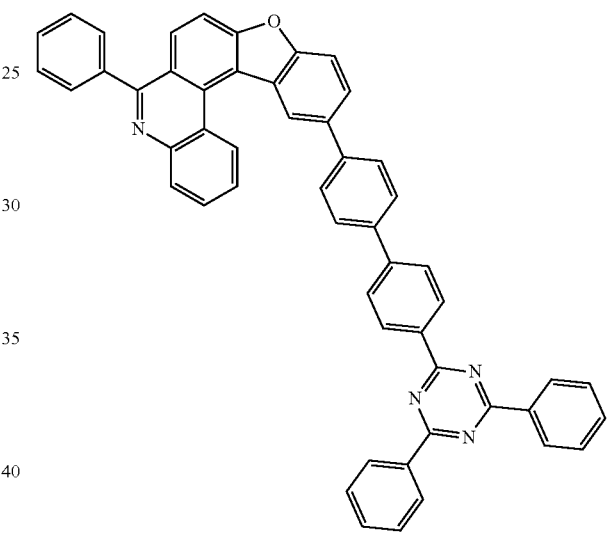
6
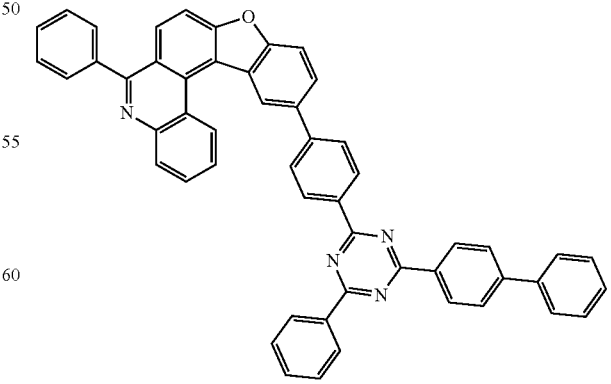

7
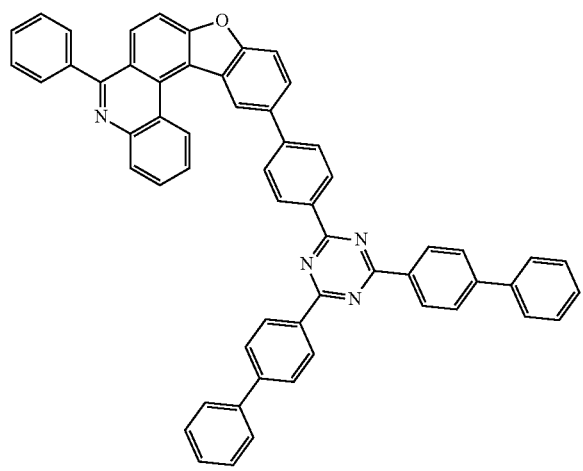
8
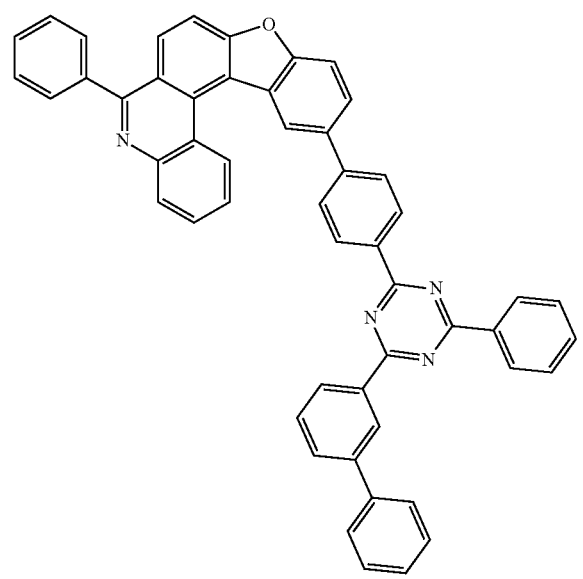
9
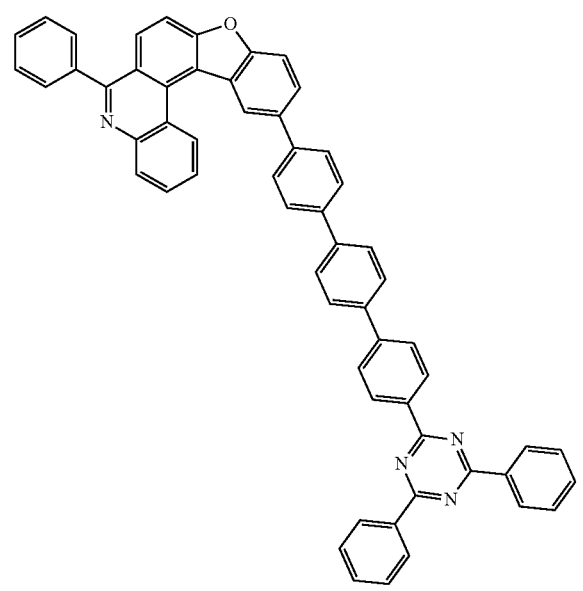
10
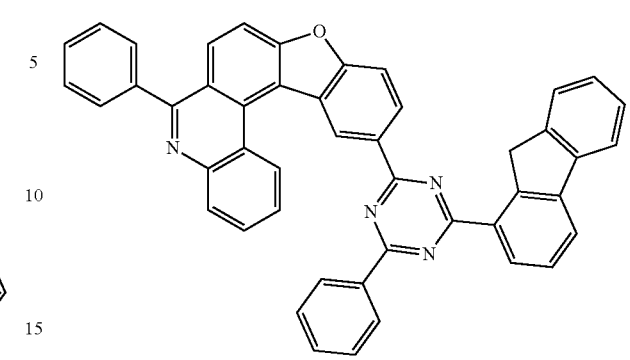
11
12
13

14
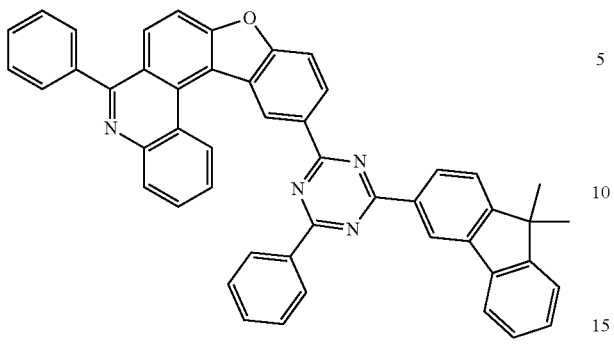
15
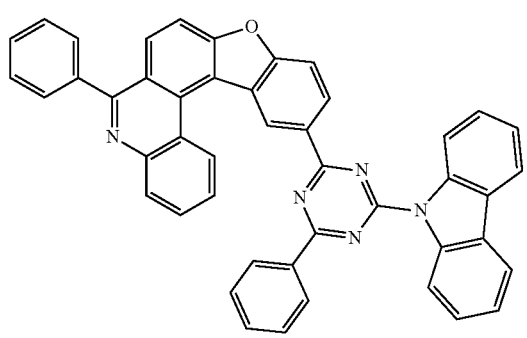
16
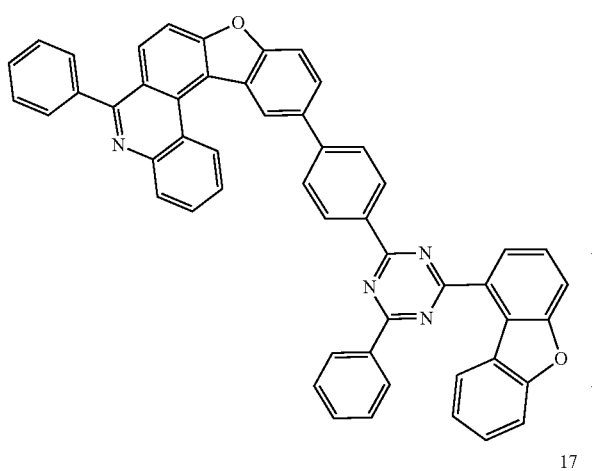
17
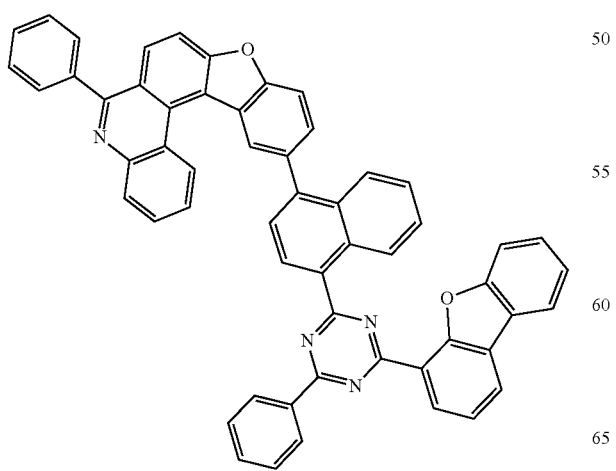
18
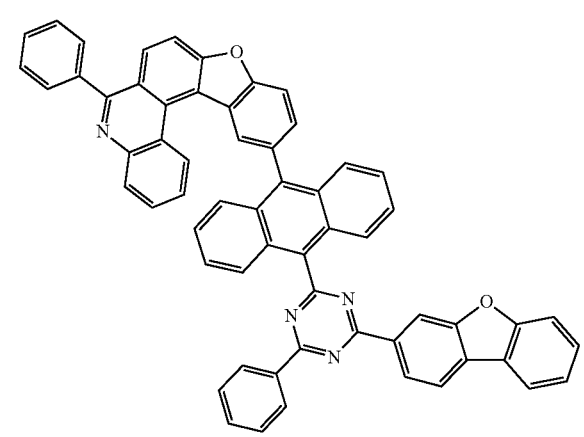
19
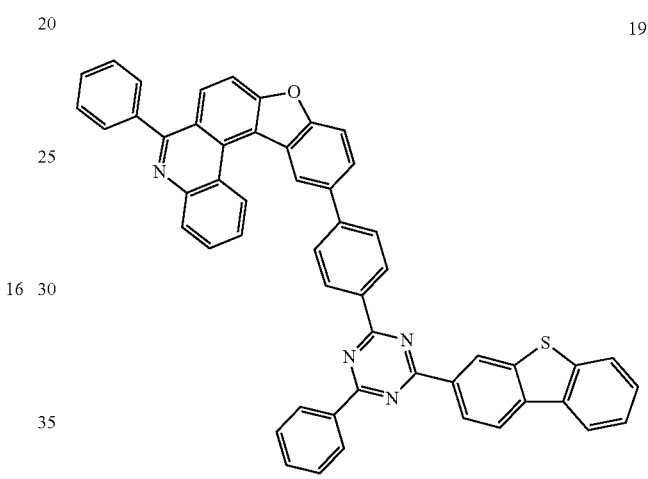
20
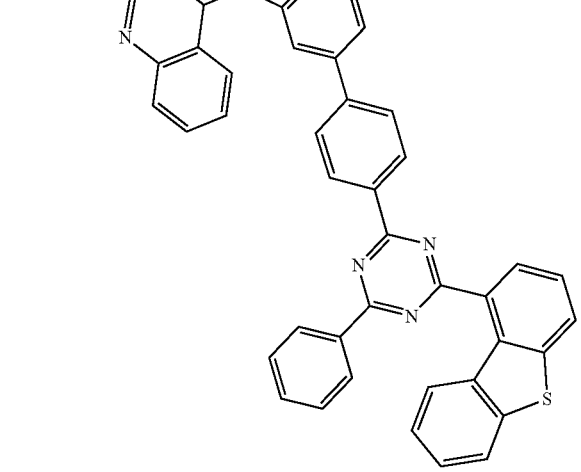

21
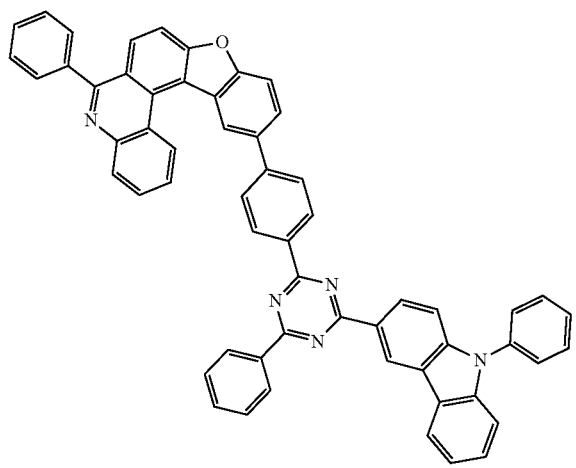
22
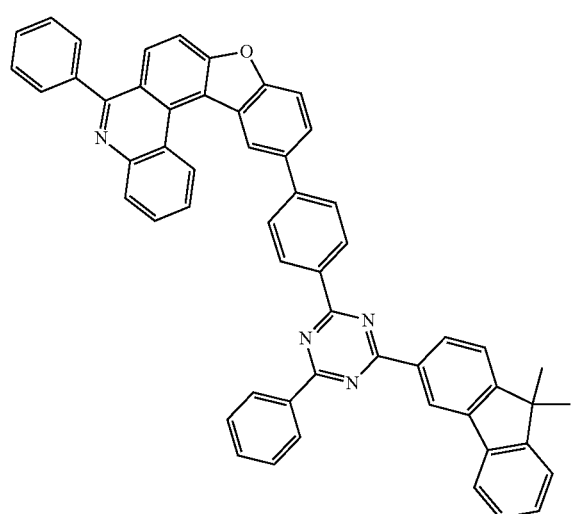
23
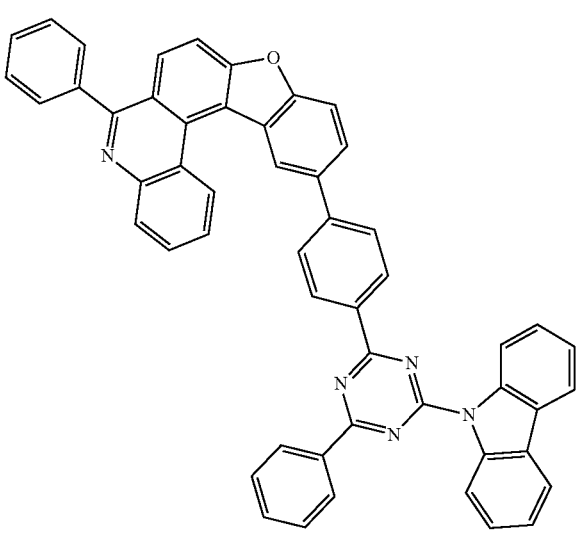
24
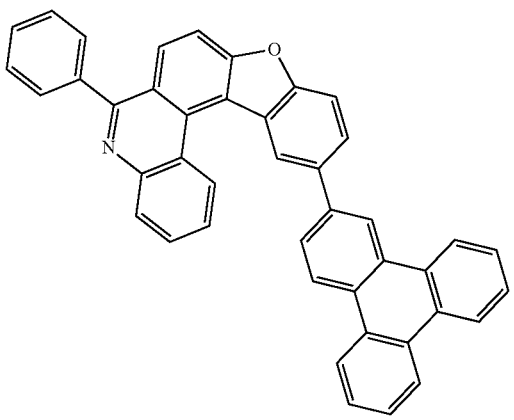
25
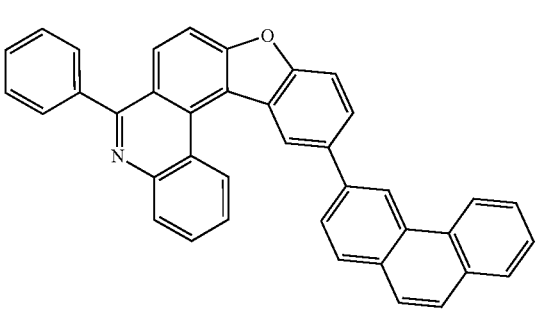
26
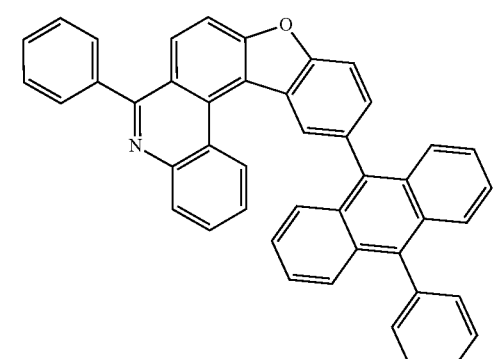
27
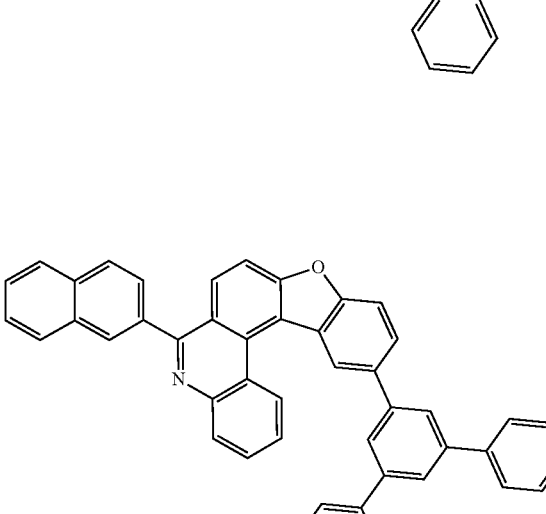

28
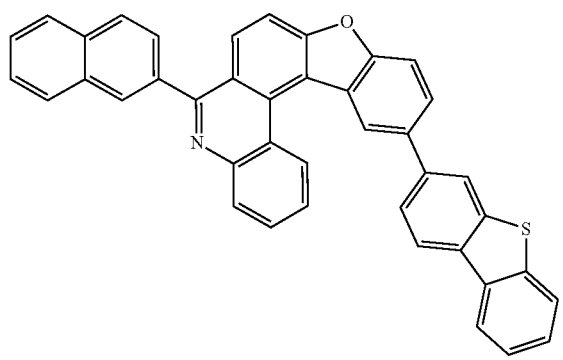
29
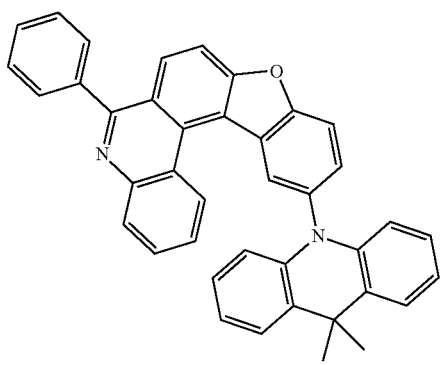
30
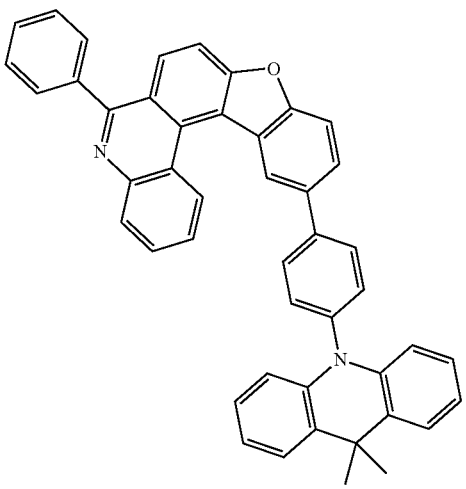
31
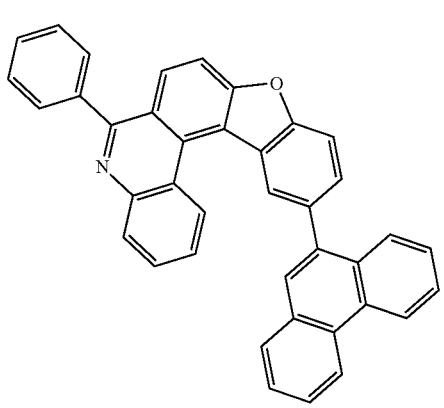
32
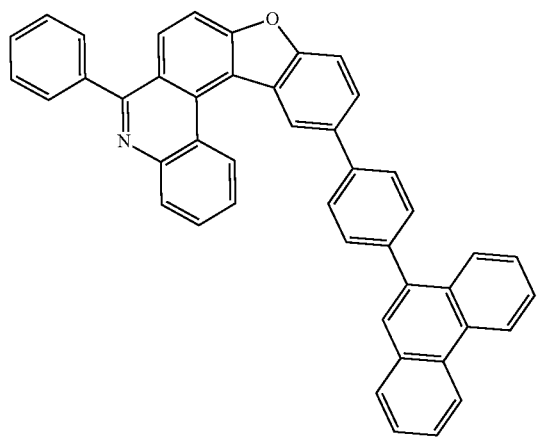
33
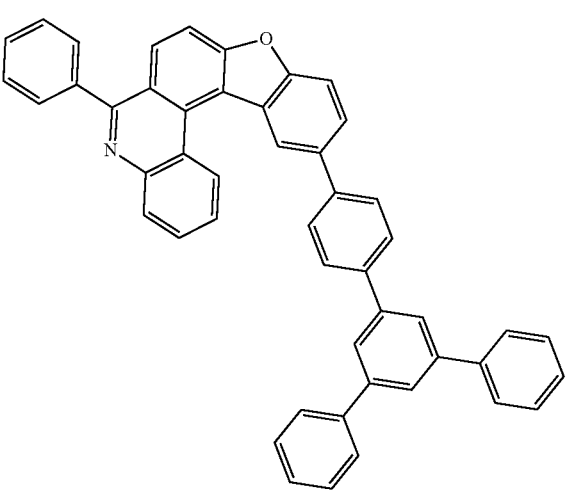
34
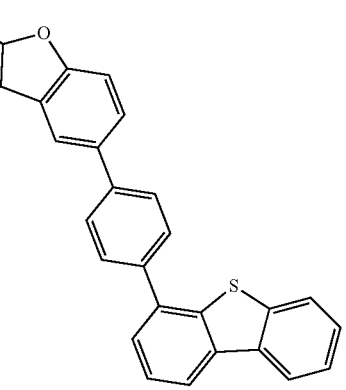

35
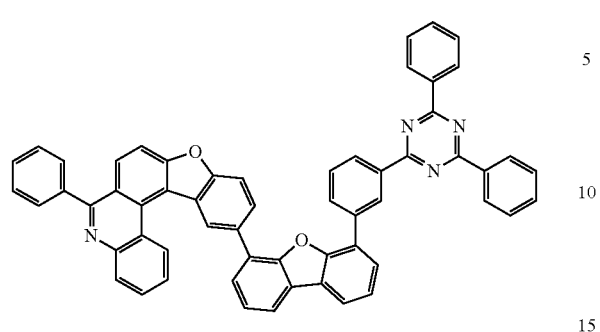
36
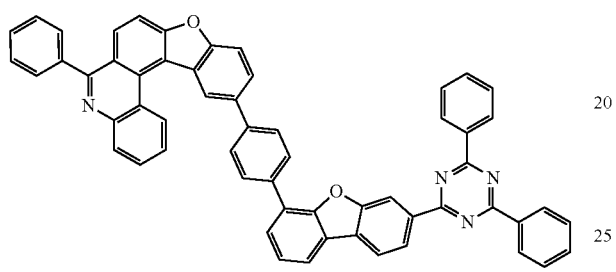
37
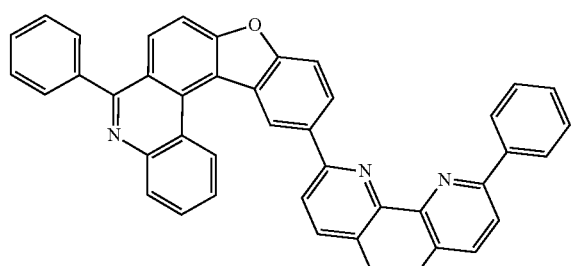
38
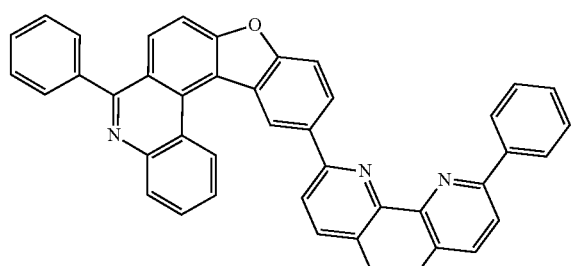
39
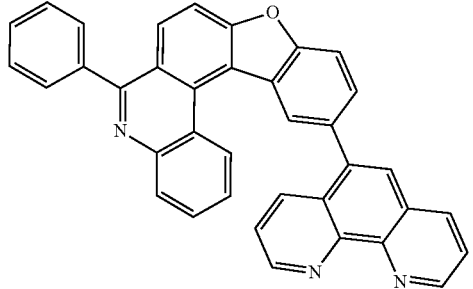
40
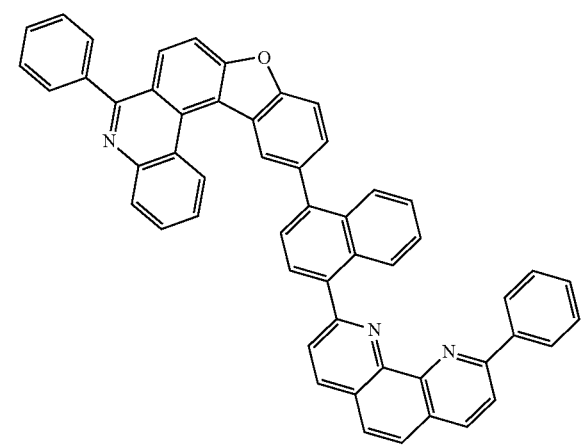
41
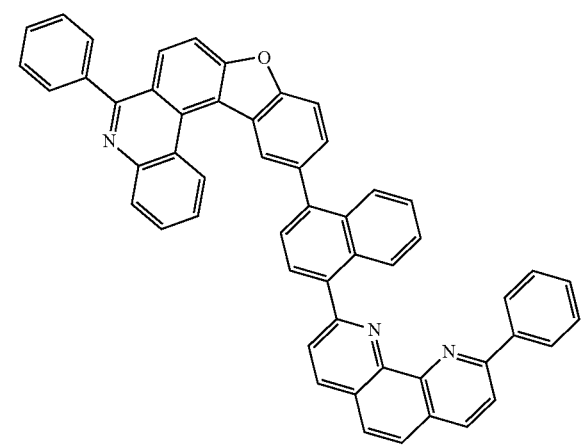

42
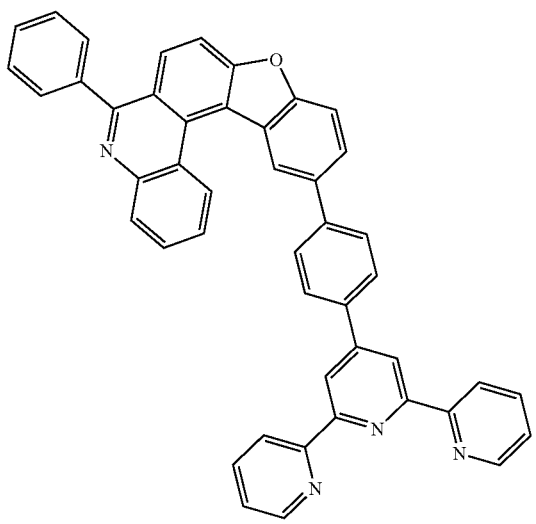
43
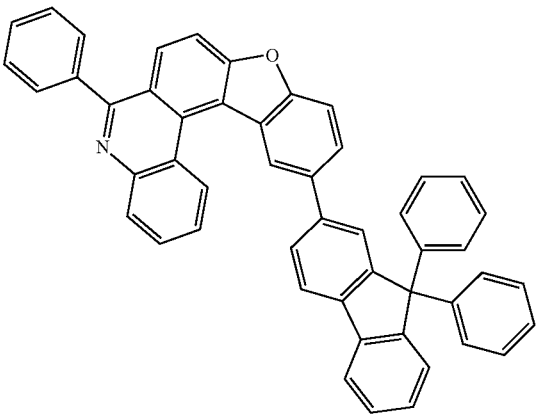
44
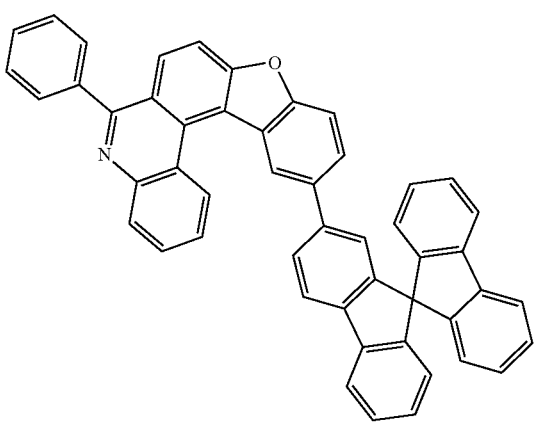
45
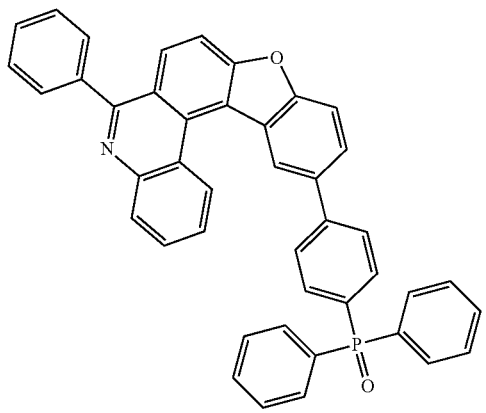
46
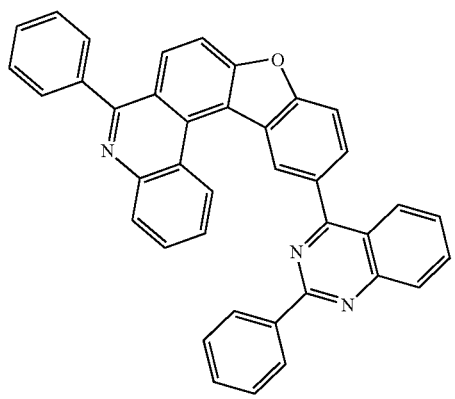
47
48
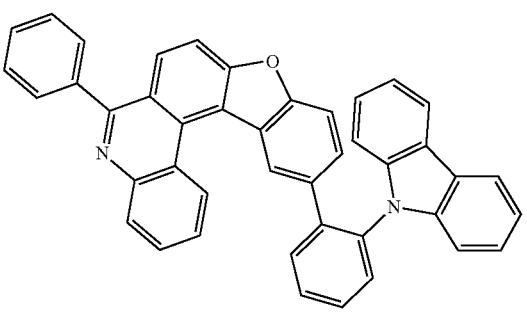

49
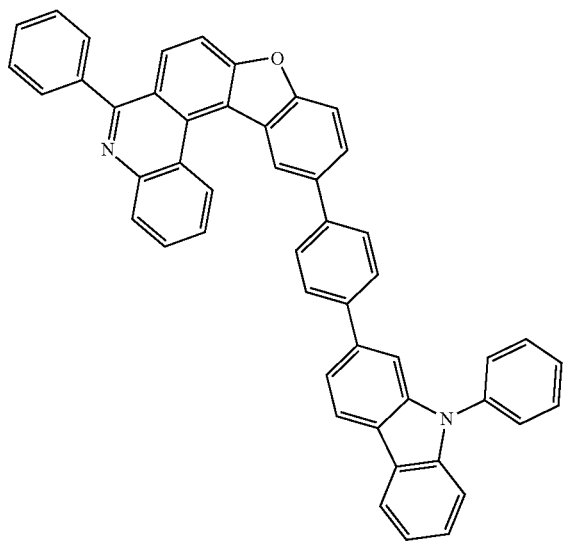
50
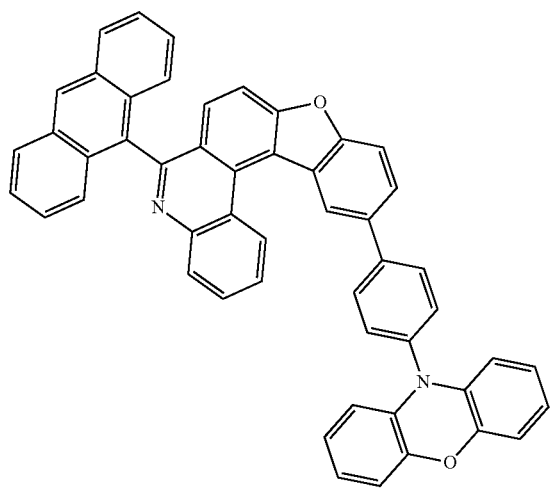
52
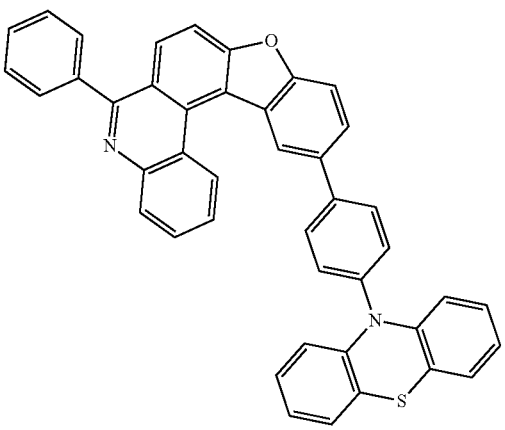
53
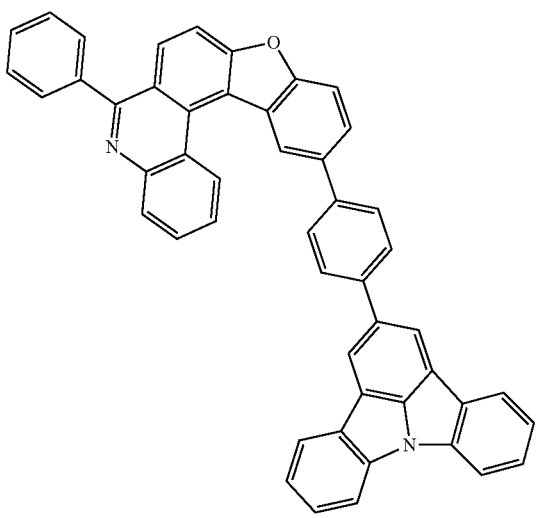
51
54
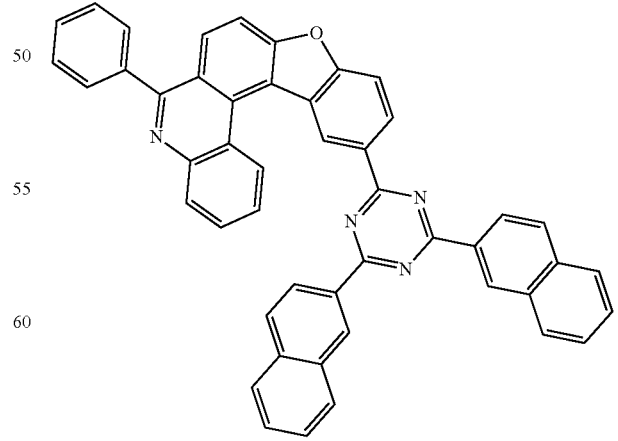

55
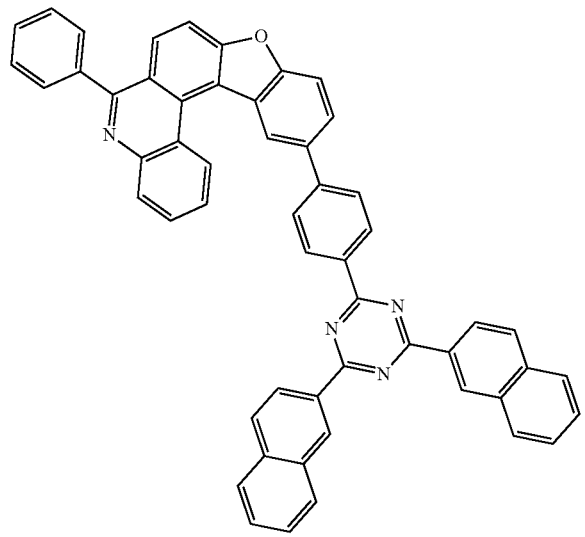
56
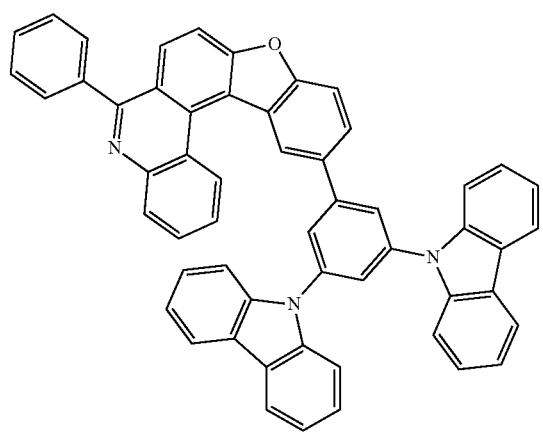
57
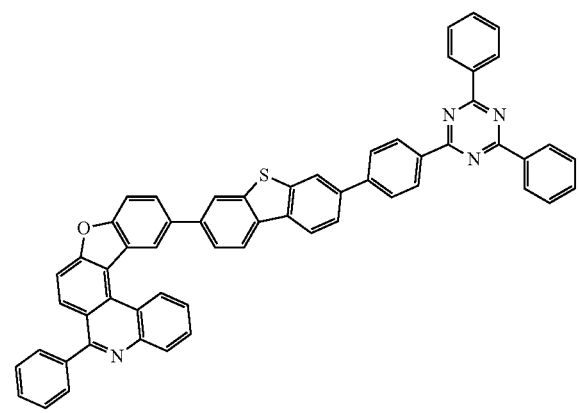
58
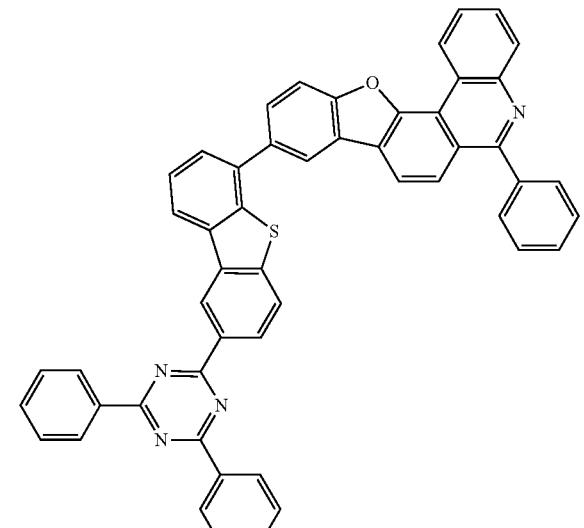
59
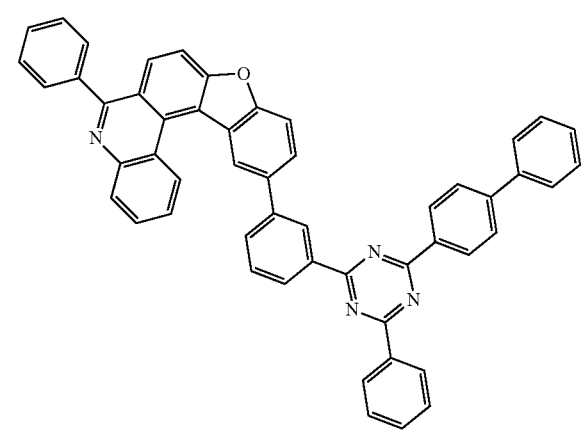
60

61
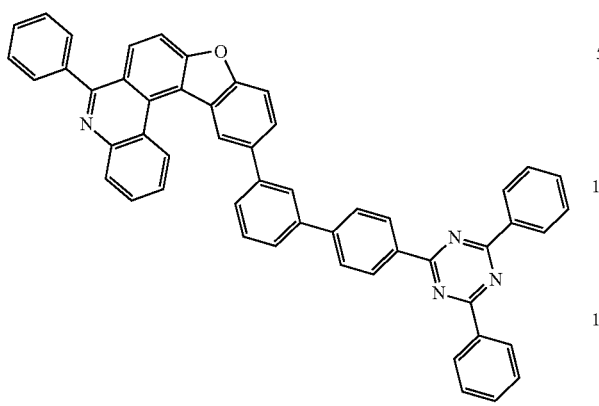
62
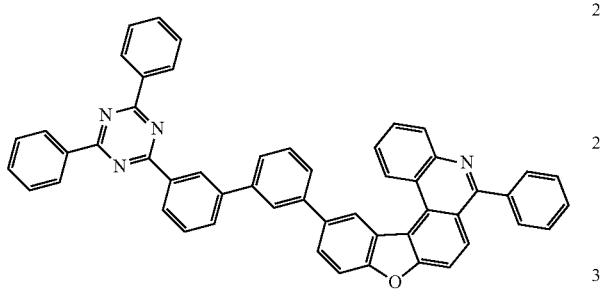
63
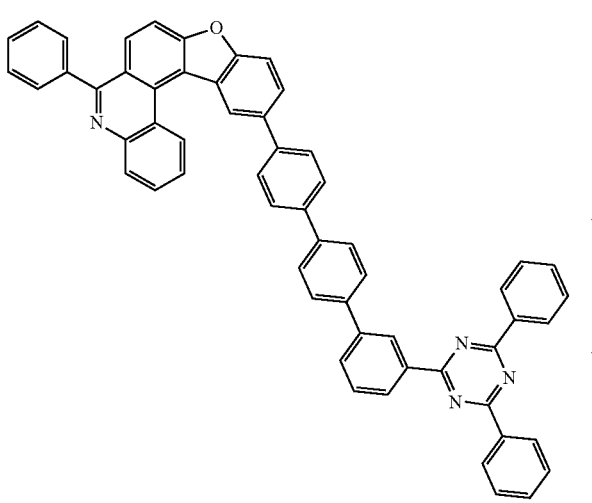
64
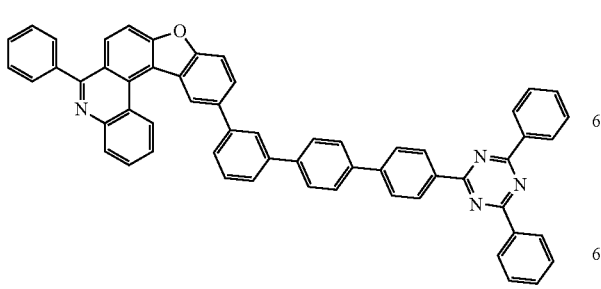
65
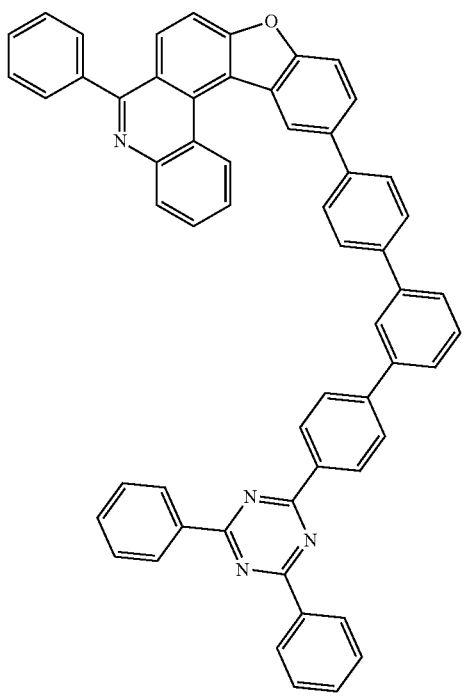
66
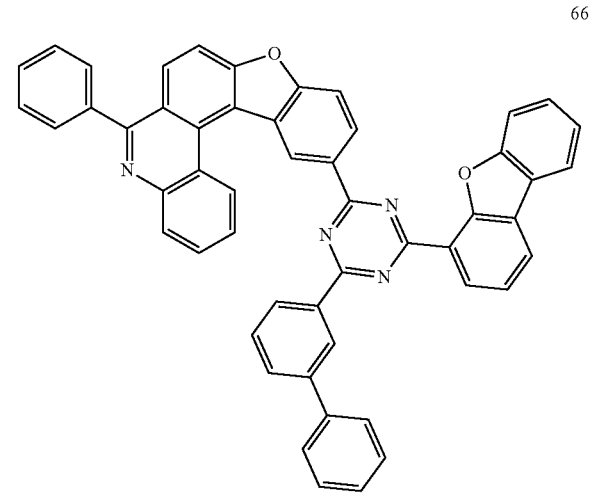
67
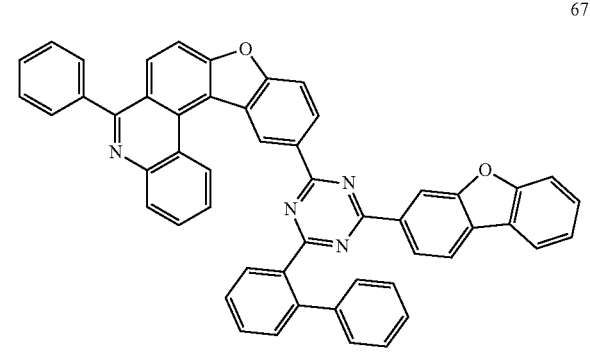

68
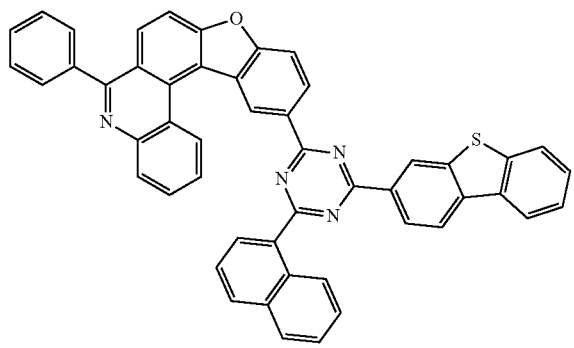
69
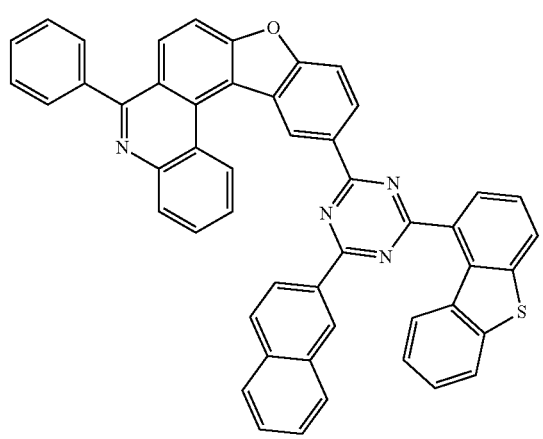
70
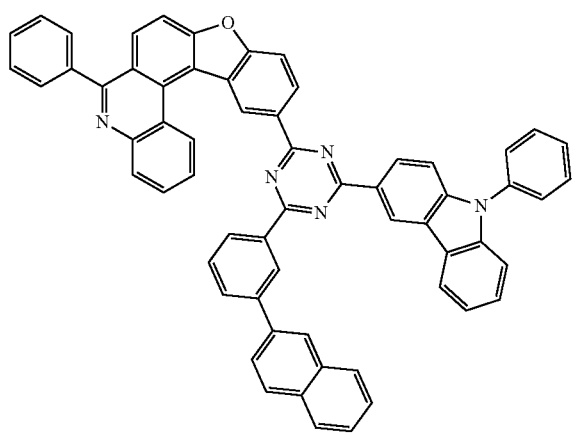
71
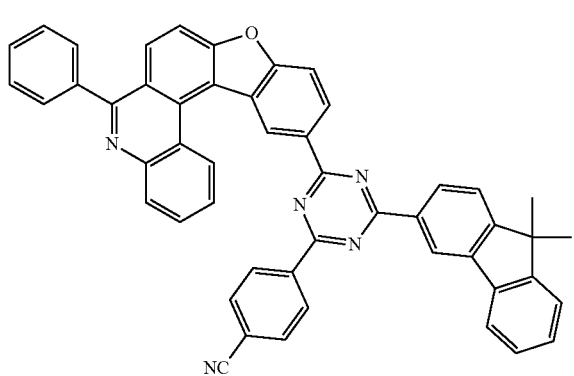
72
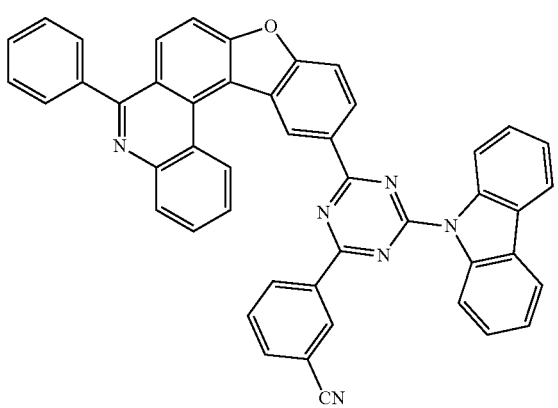
73
74
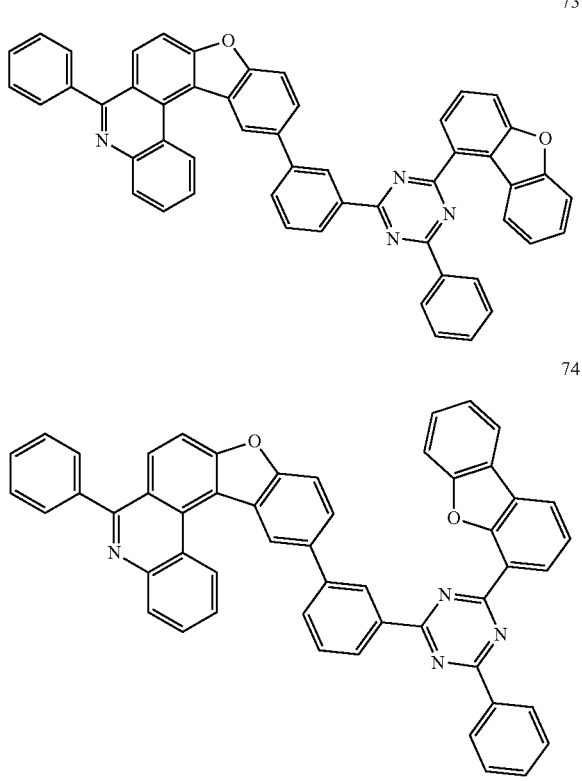
75
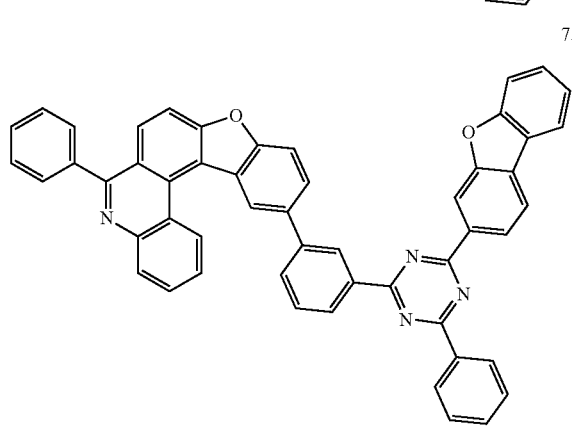

76
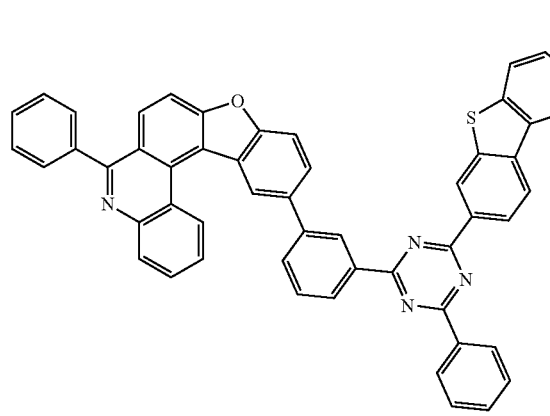
77
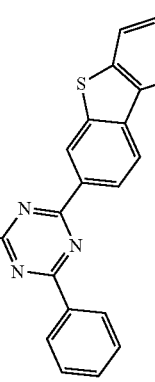
78
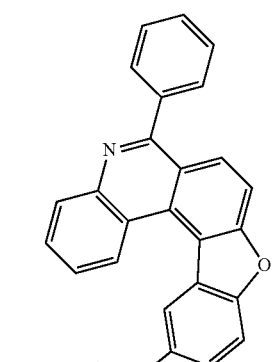
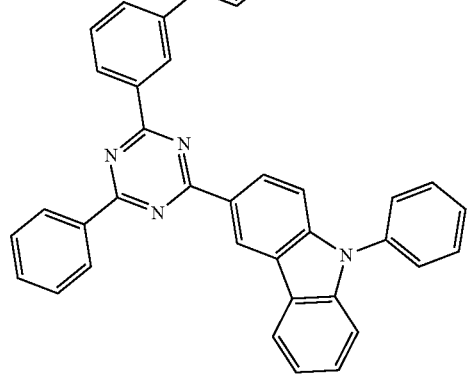
79
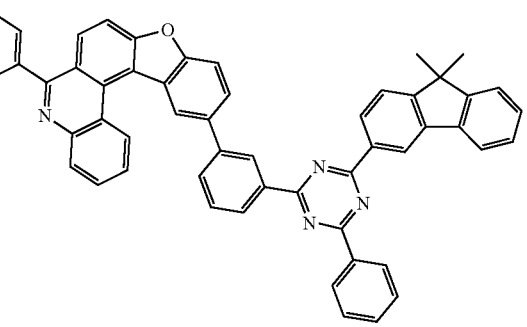
80
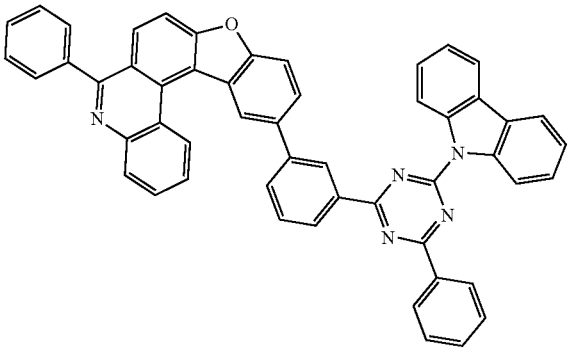
81
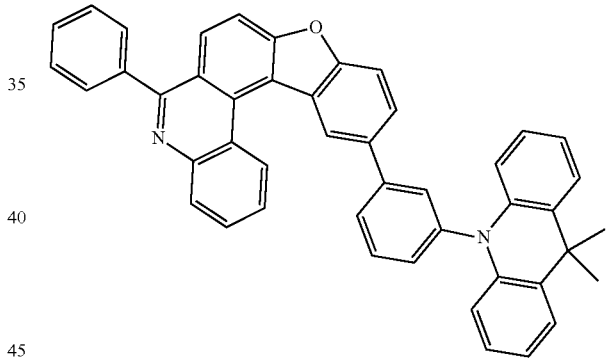
82
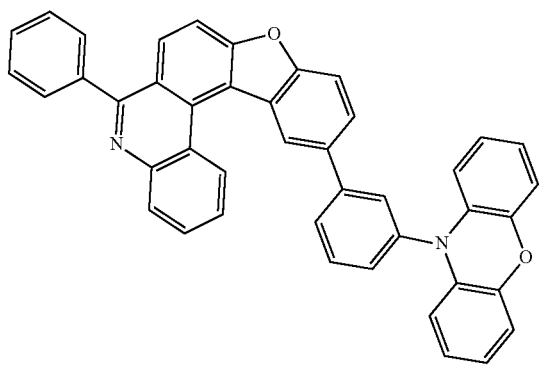

83
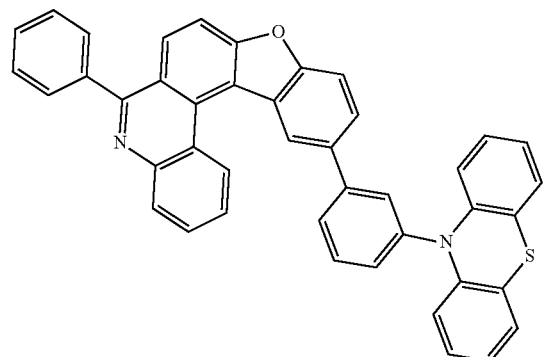
84
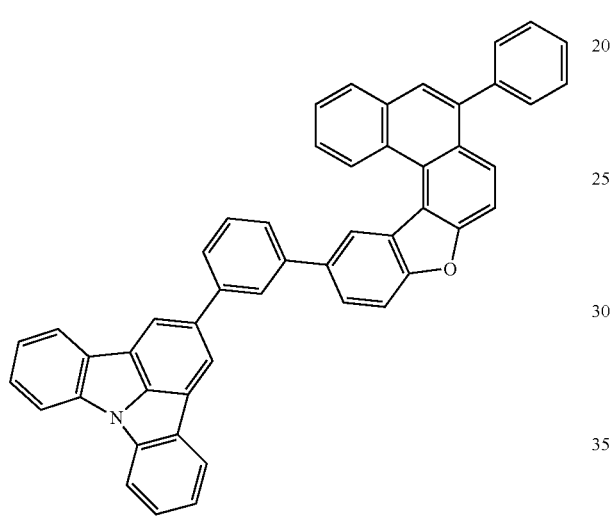
85
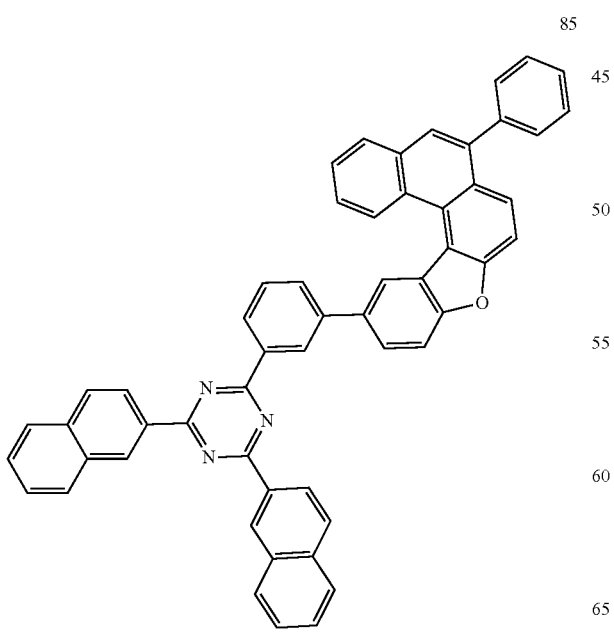
86
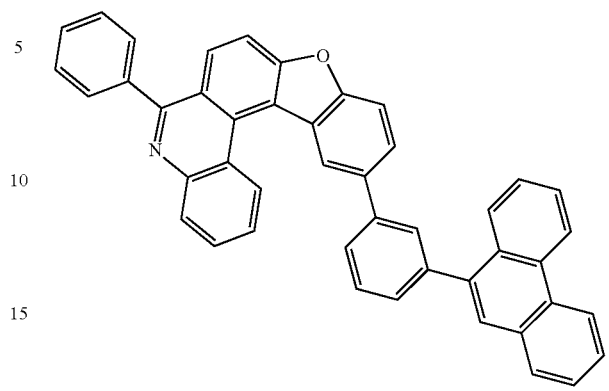
87
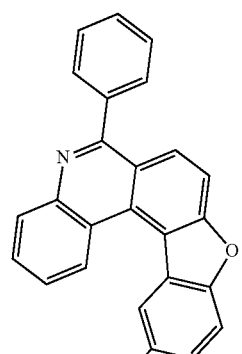
88
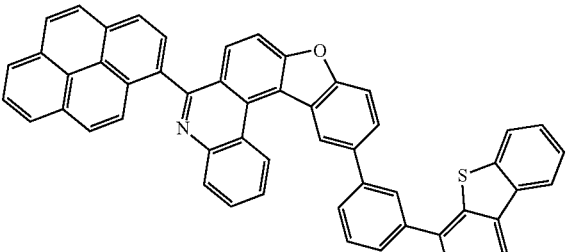

89
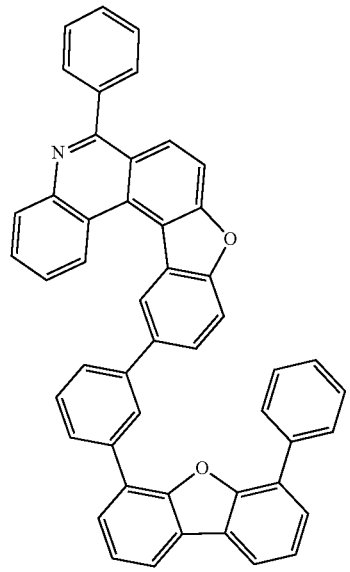
90
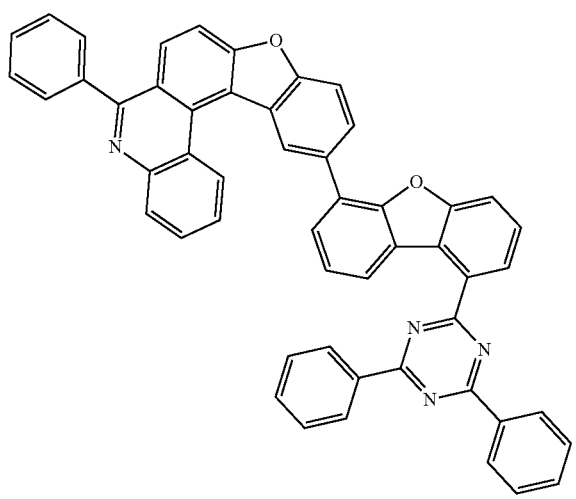
91
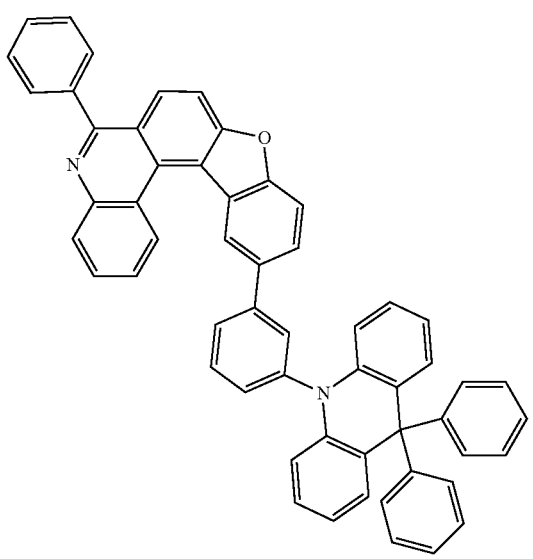
92
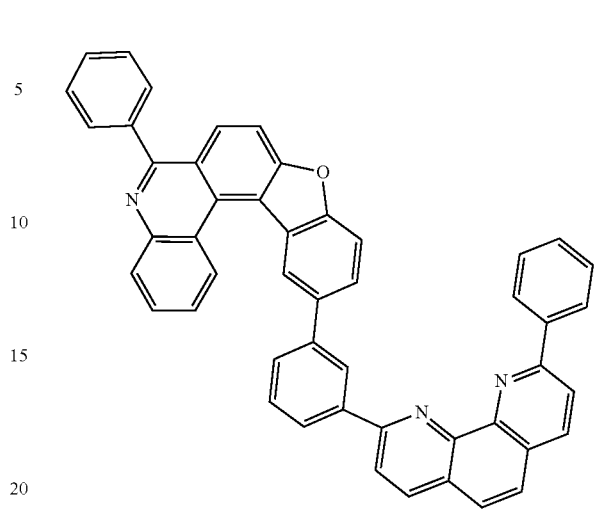
93
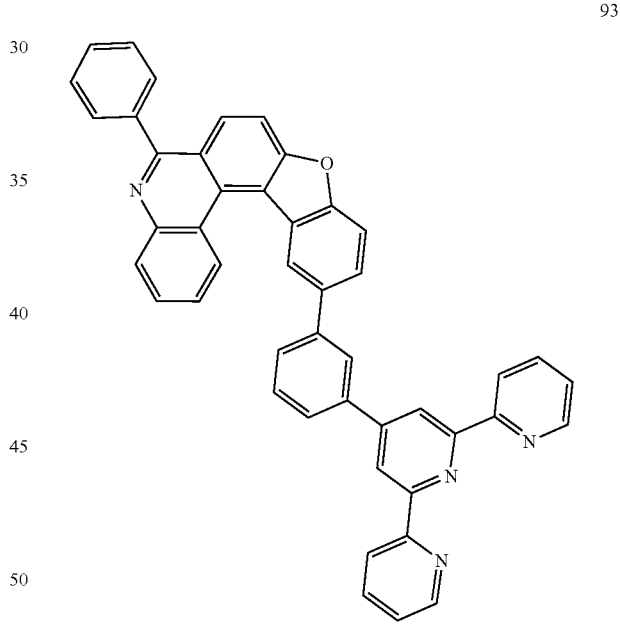
94
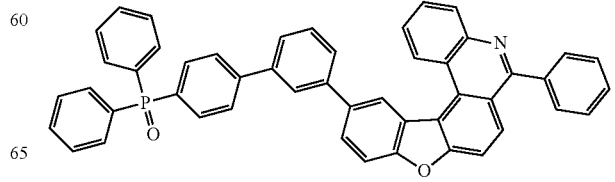

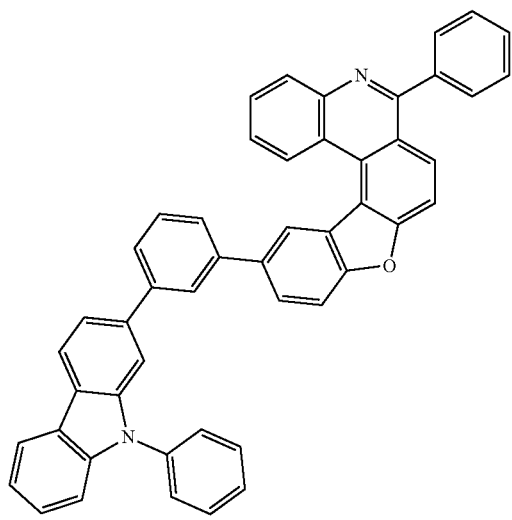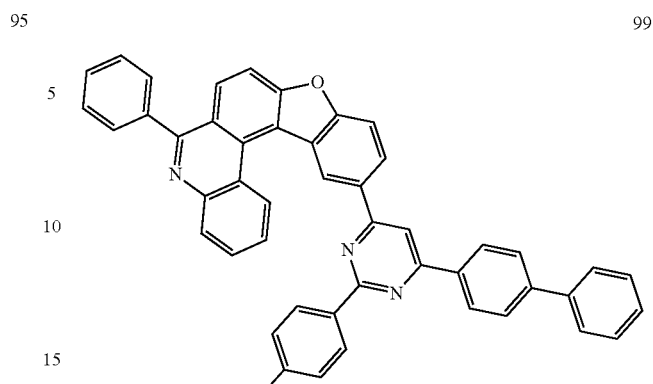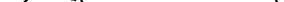

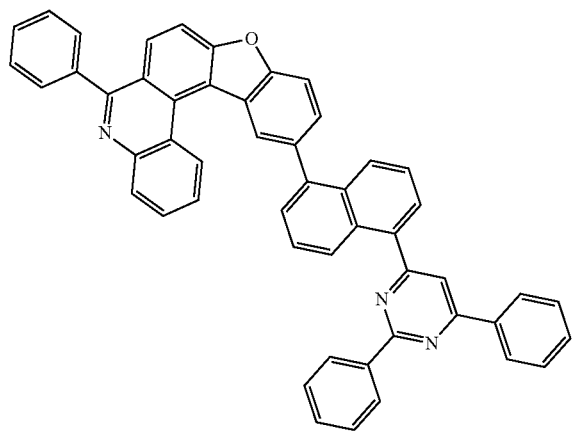
102
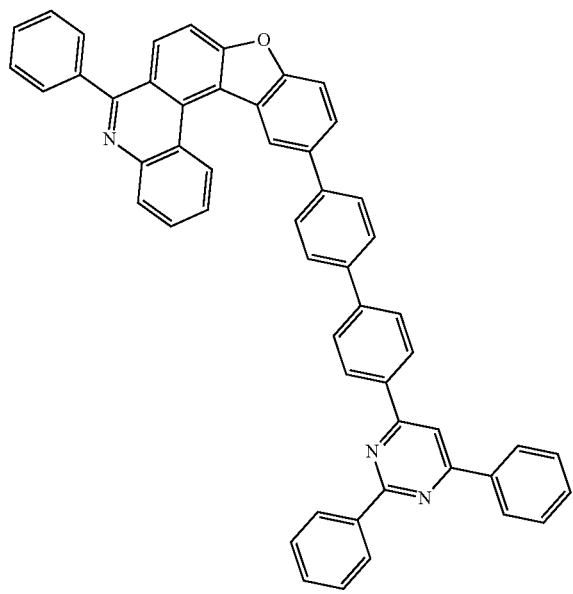
103
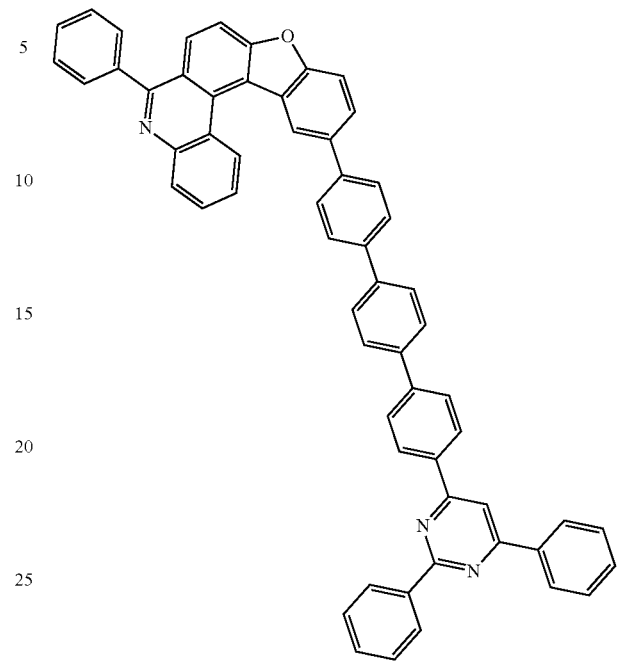
104
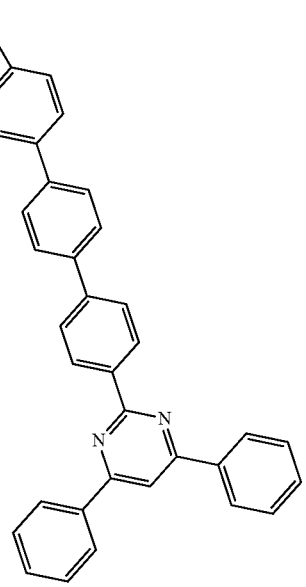
105

106
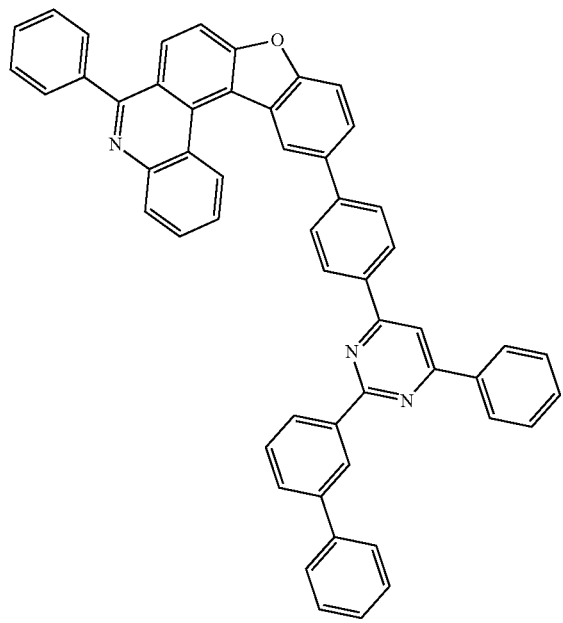
107
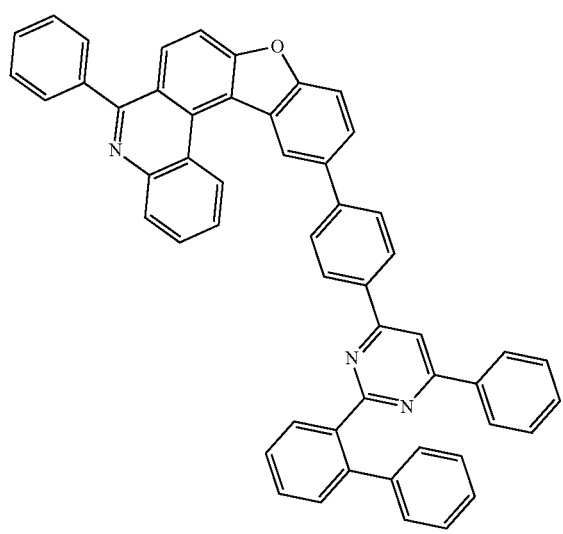
108
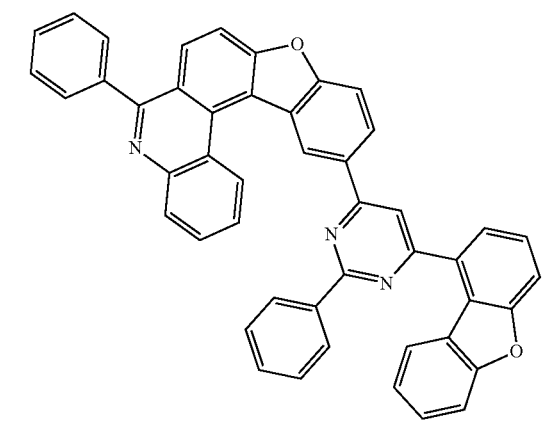
109
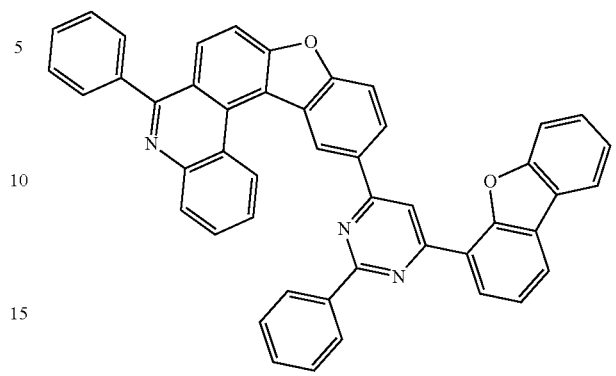
110
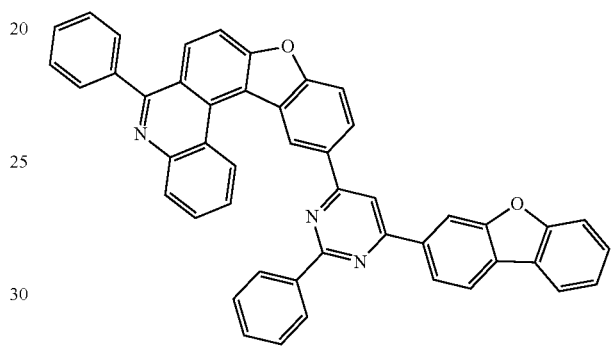
111
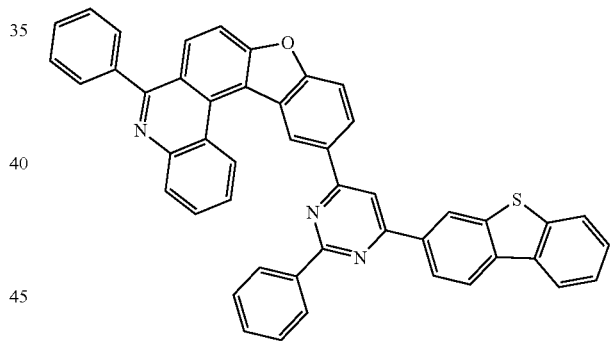
112
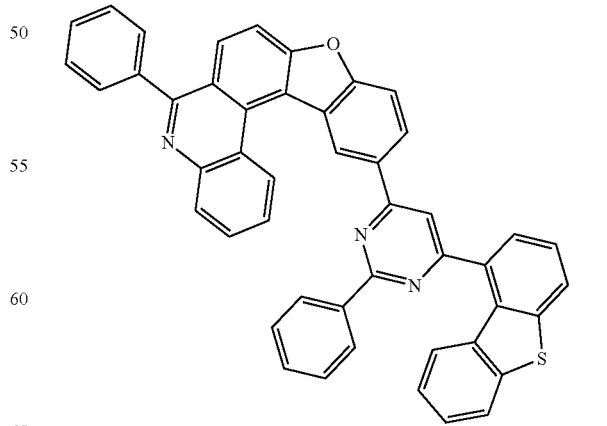

113
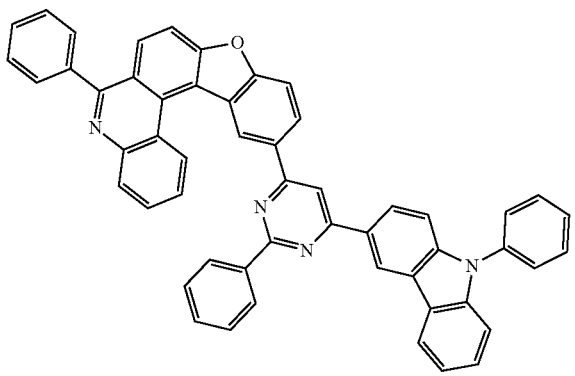
114
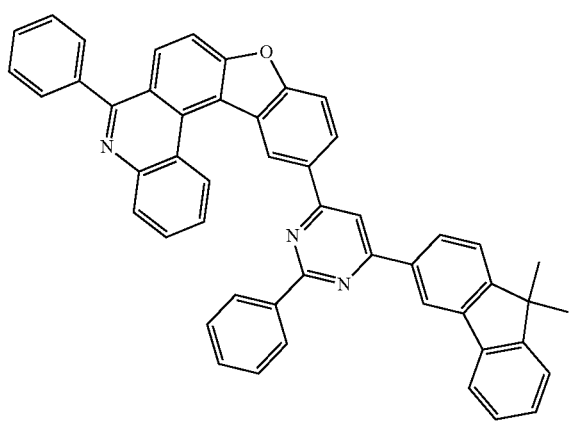
115
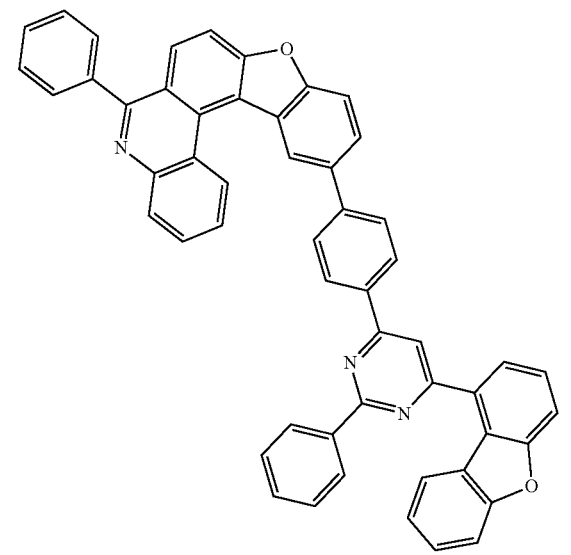
116
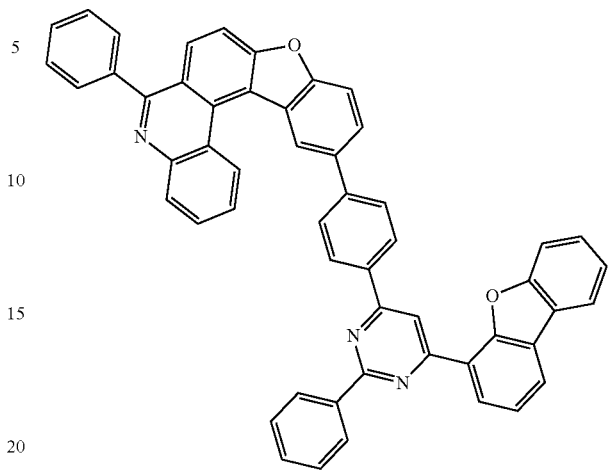
117
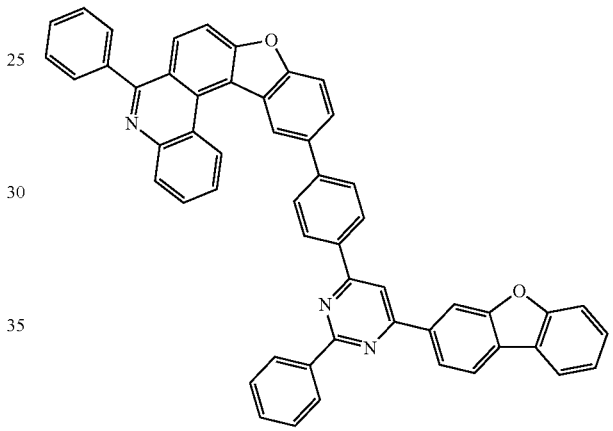
118
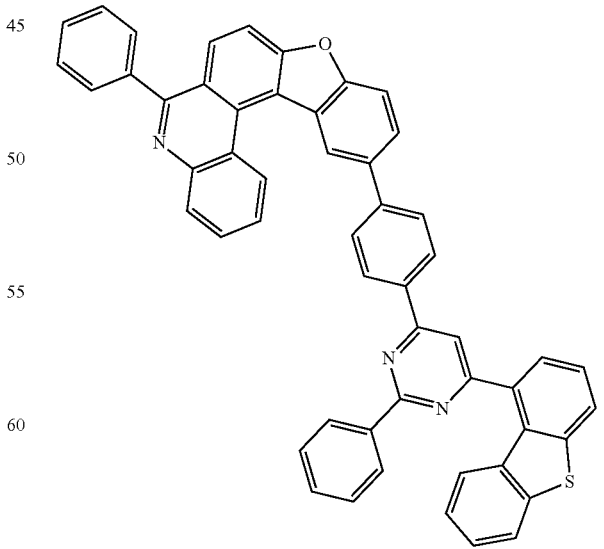

119
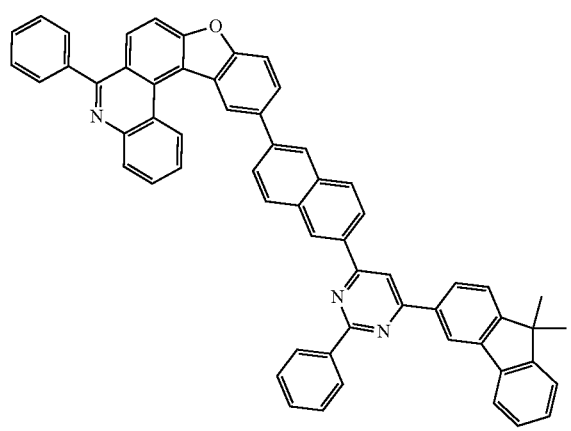
120
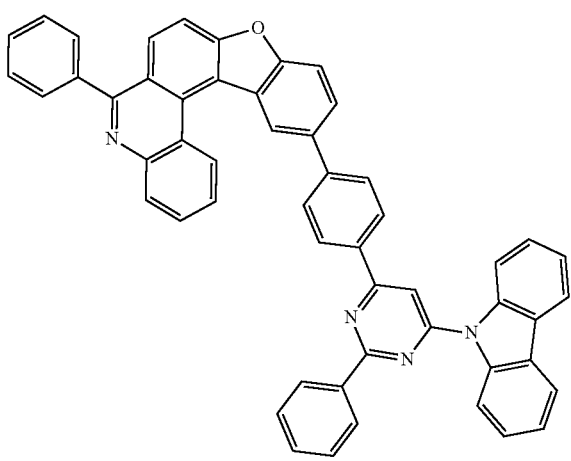
121
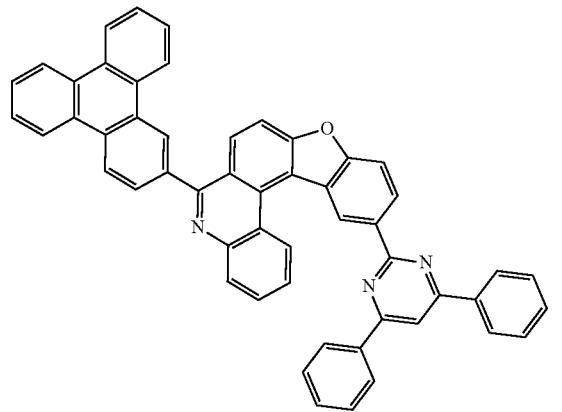
122
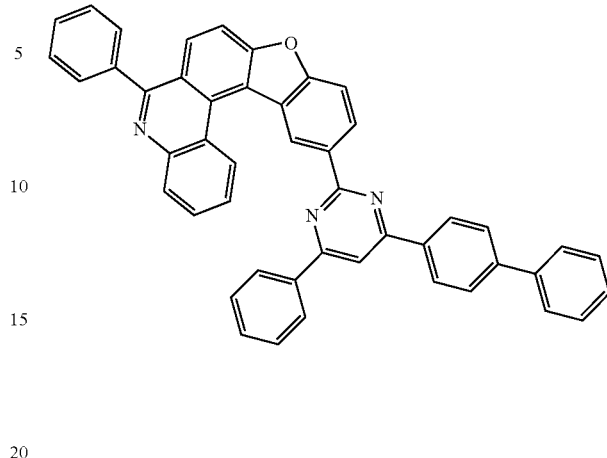
123
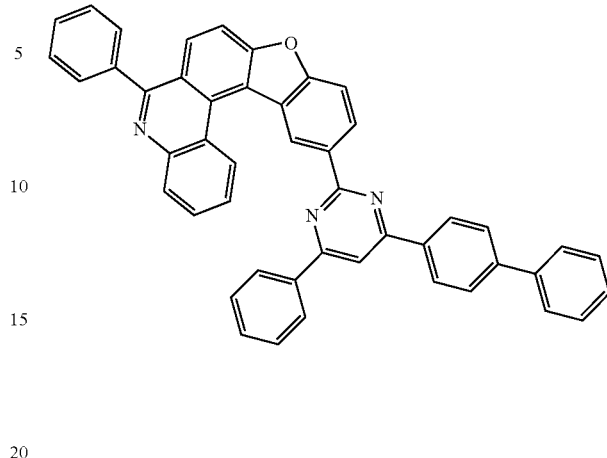
124
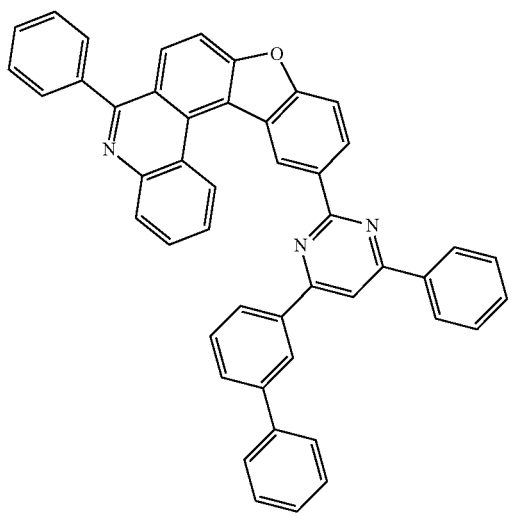

125

126

127

128

129

130

131
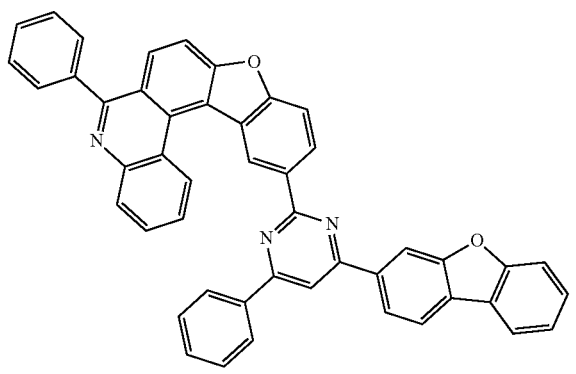
132
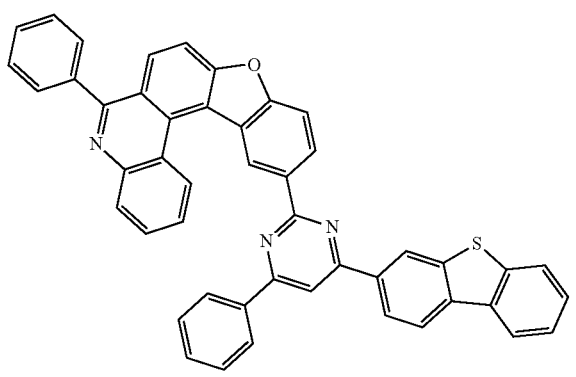
133
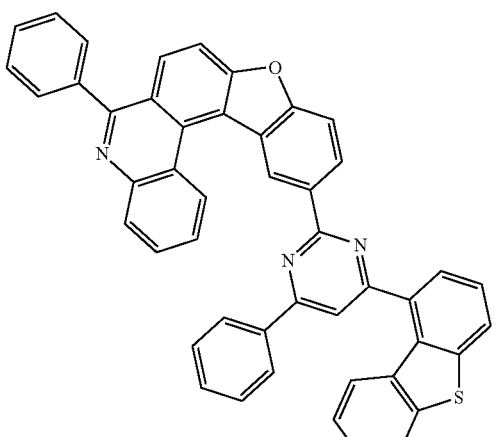
134
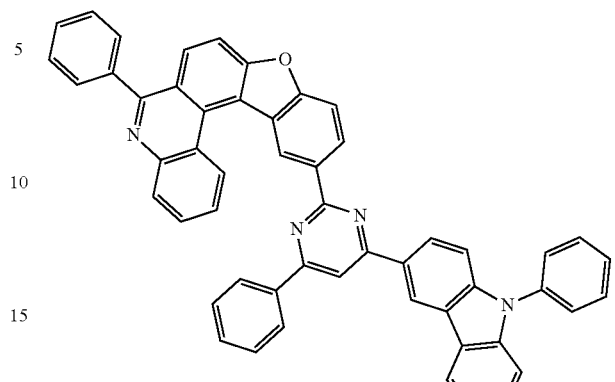
135
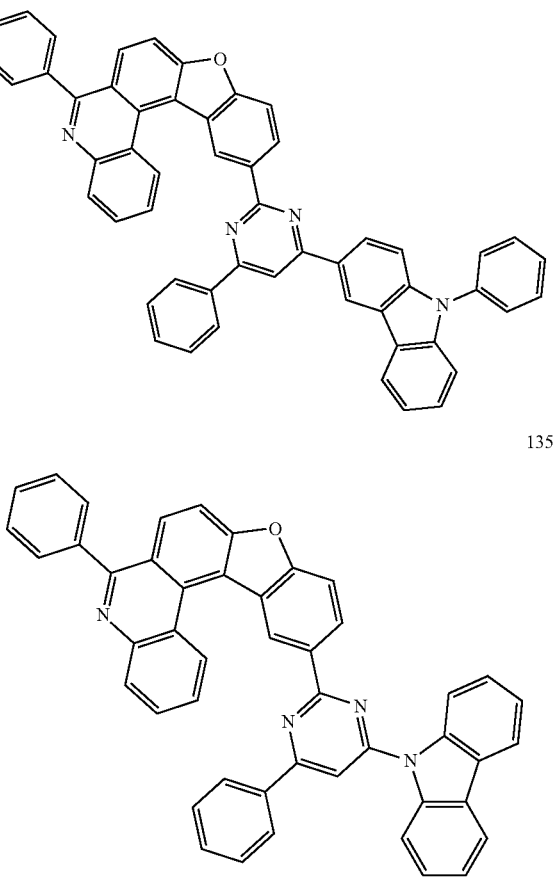
136
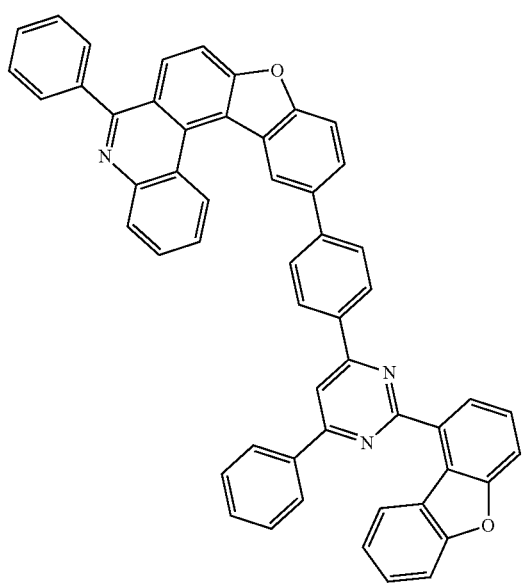

137
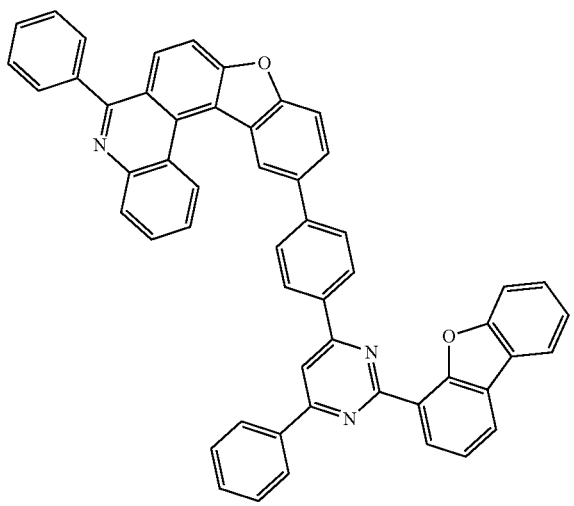
138
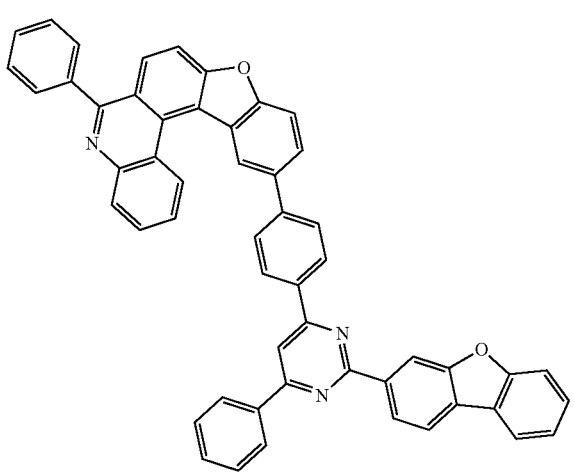
139
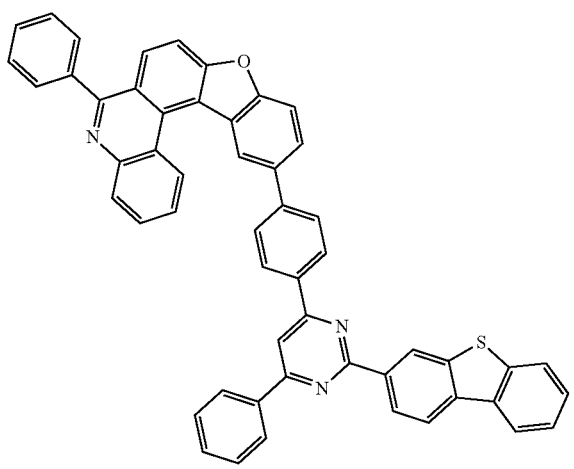
140
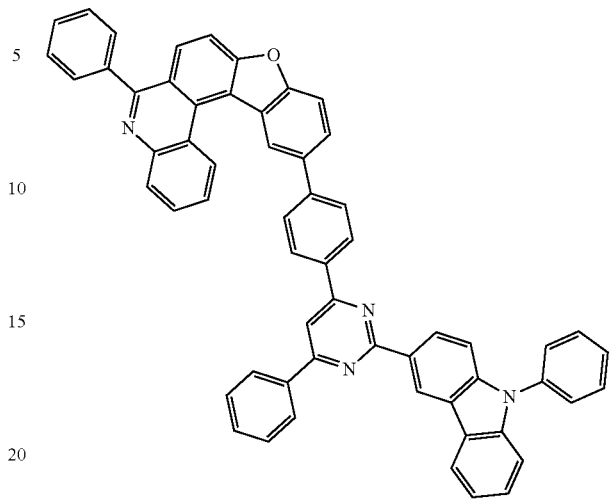
141
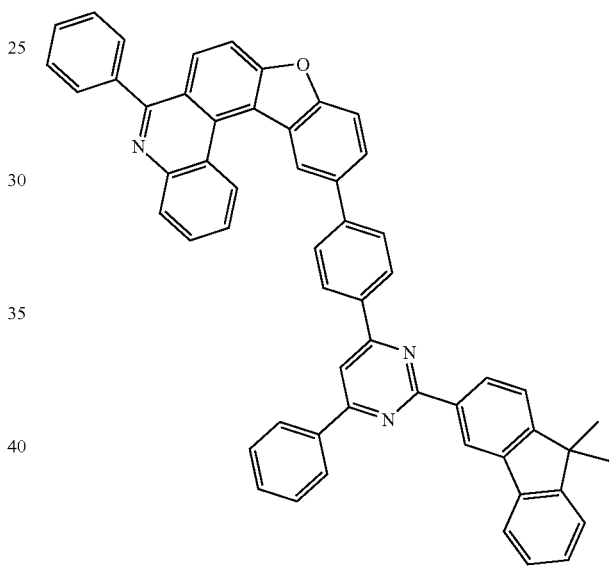
142
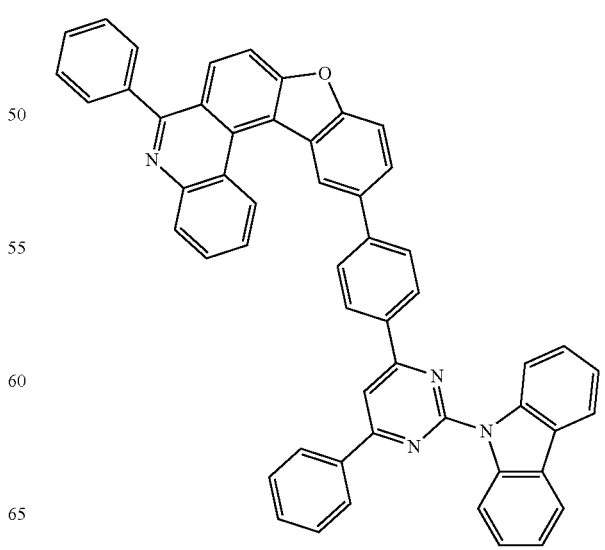

-continued
143
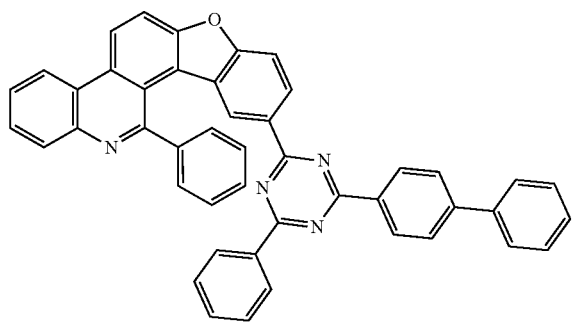
144
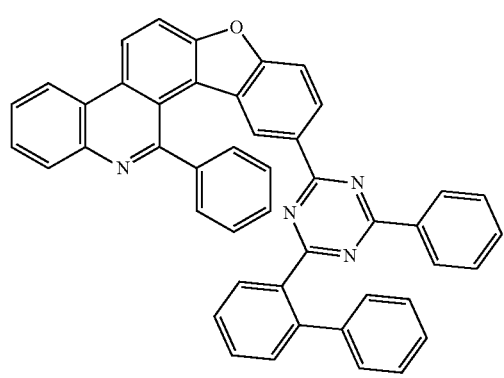
145
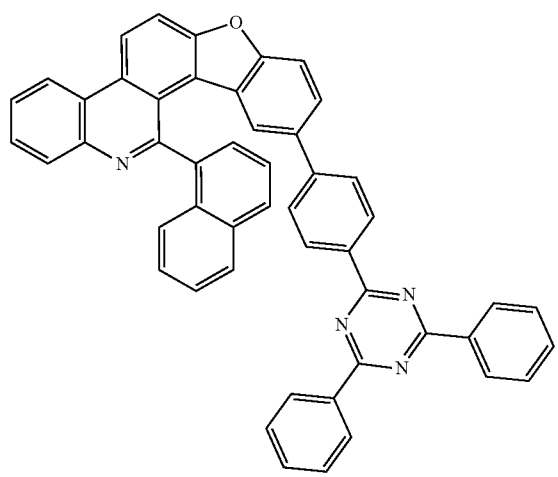
-continued
146
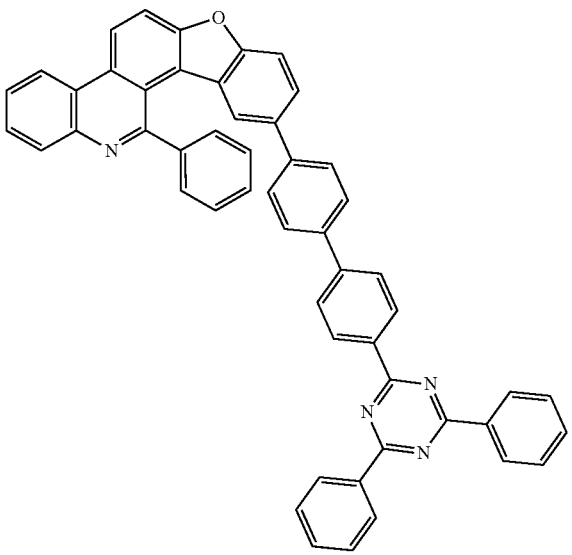
147
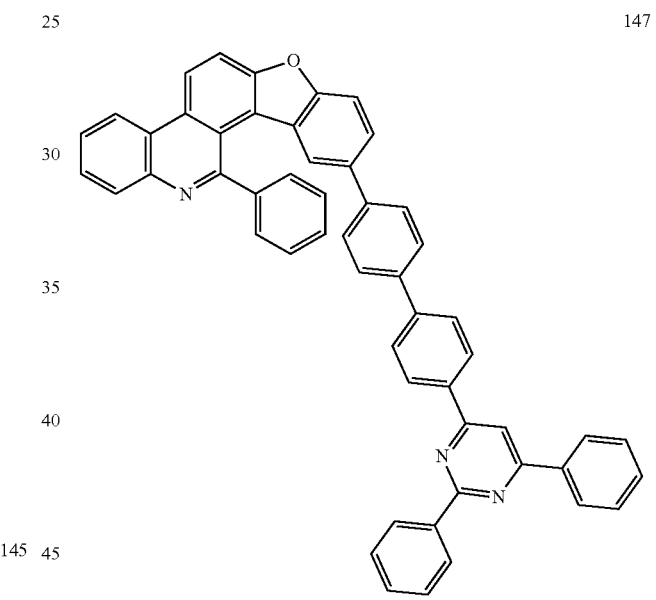
148
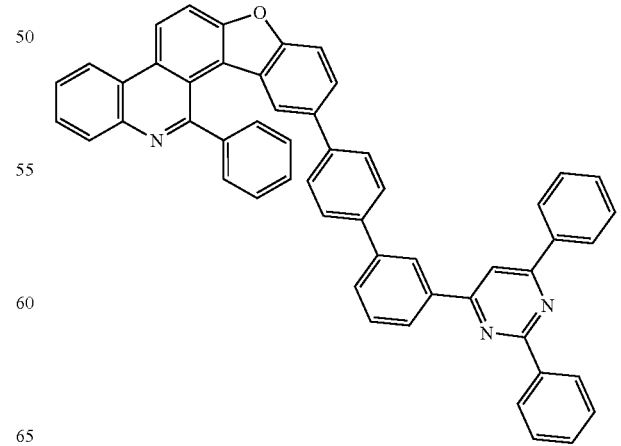

149
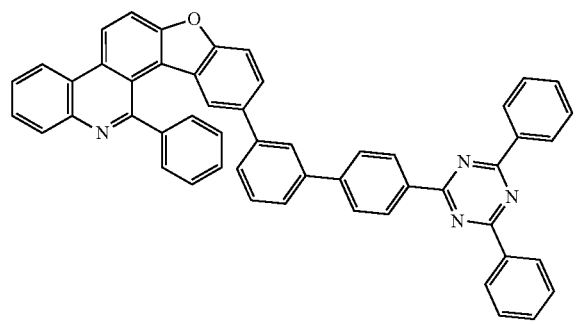
150
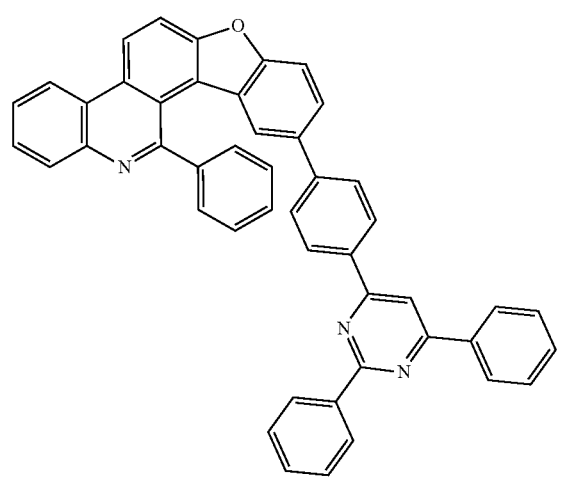
151
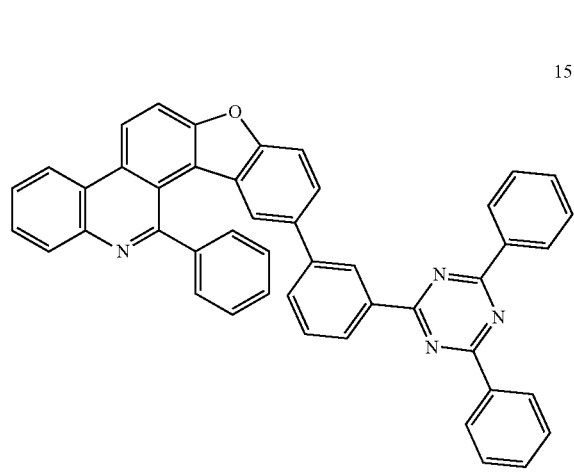
152
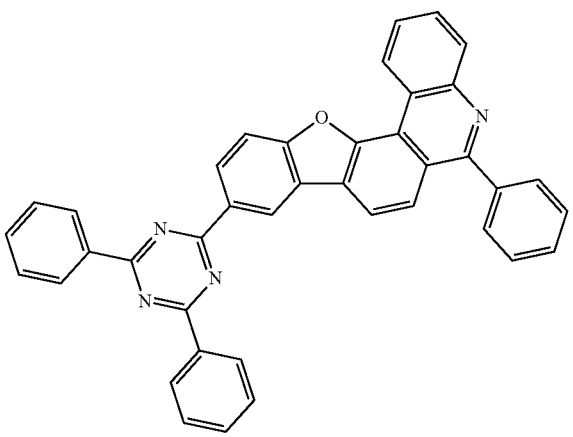
153
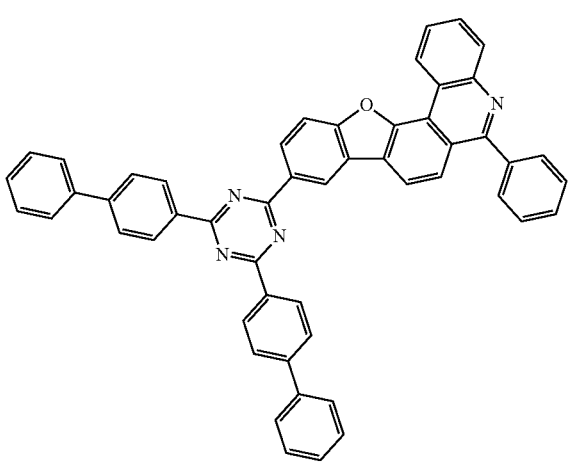
154

155
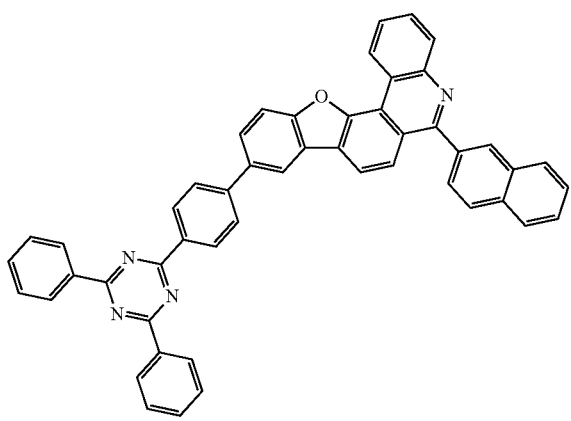
156
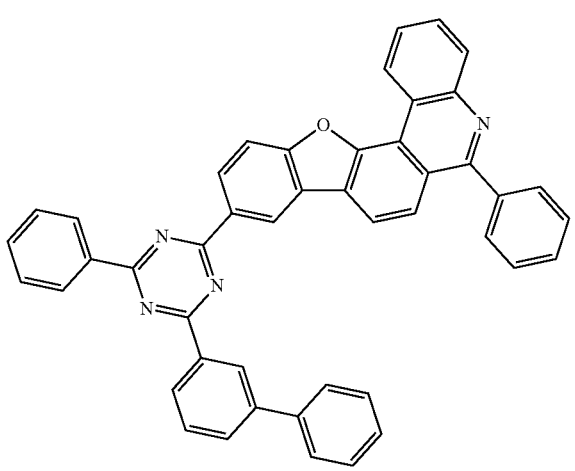
157
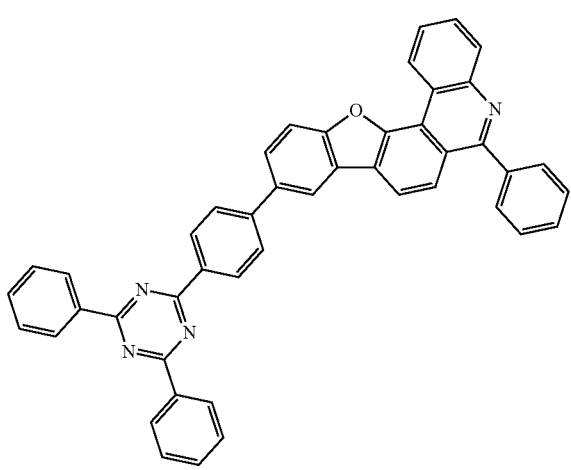
158
159
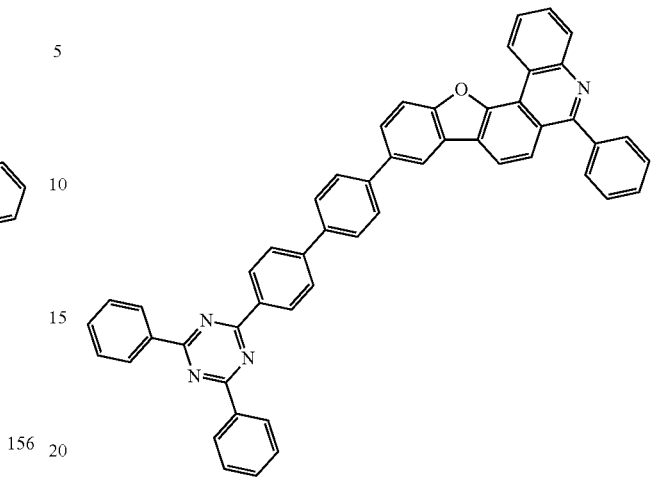
160

161
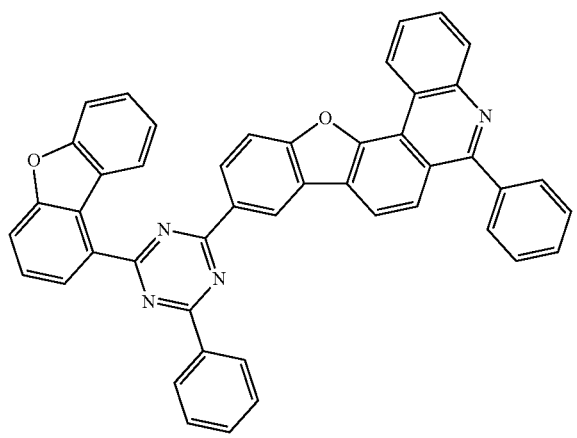
162
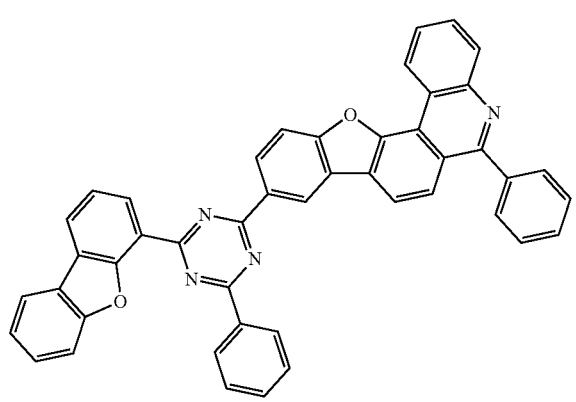
163
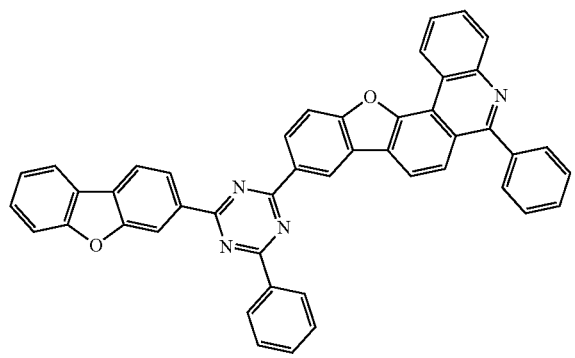
164
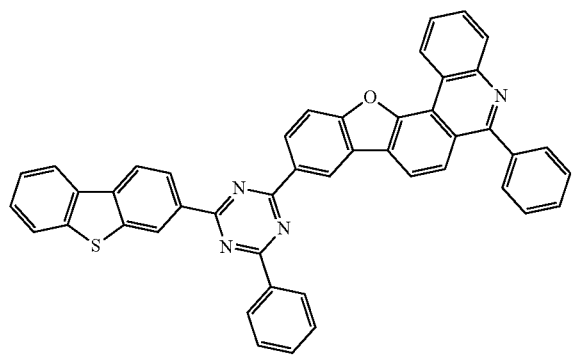
165
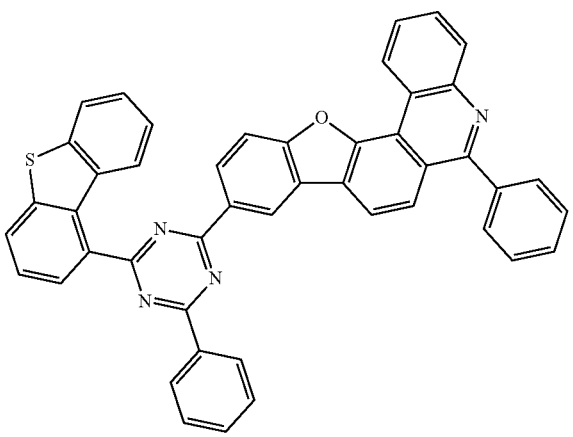
166
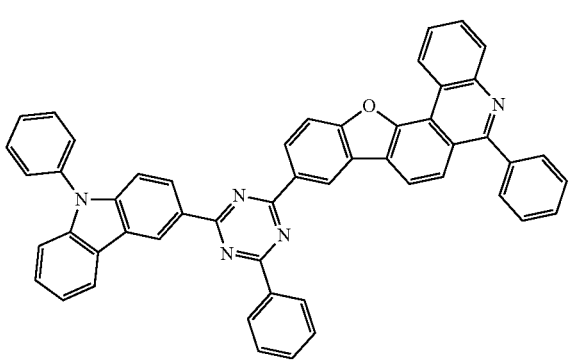
167
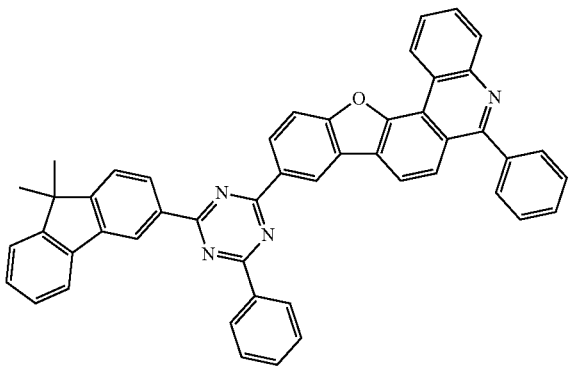
168
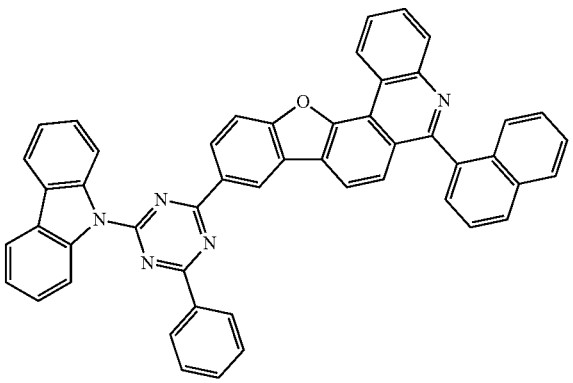

169
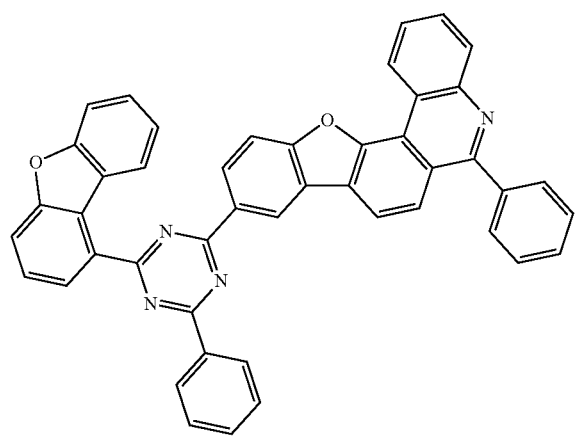
172
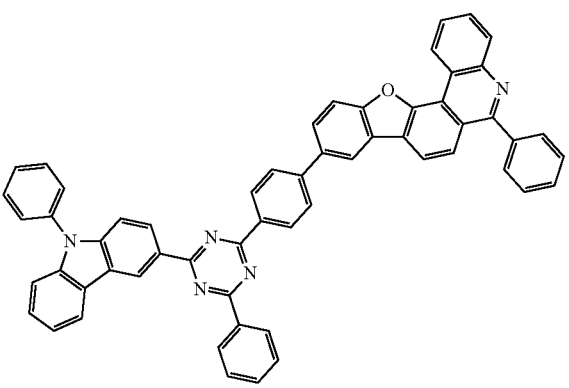
170
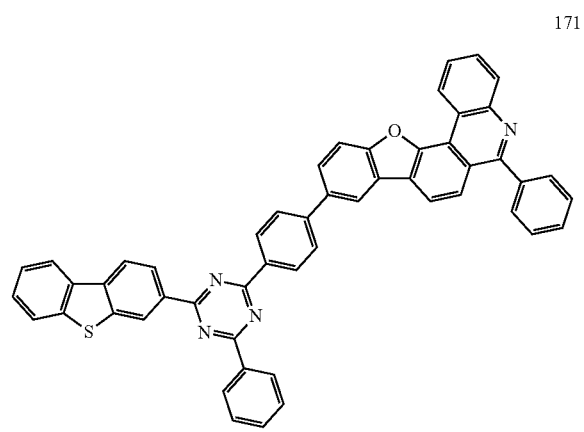
173
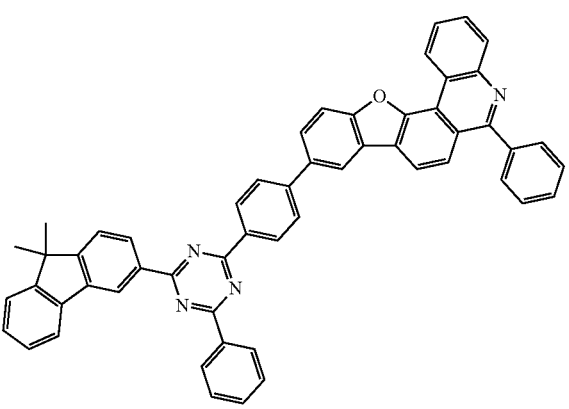
171
174
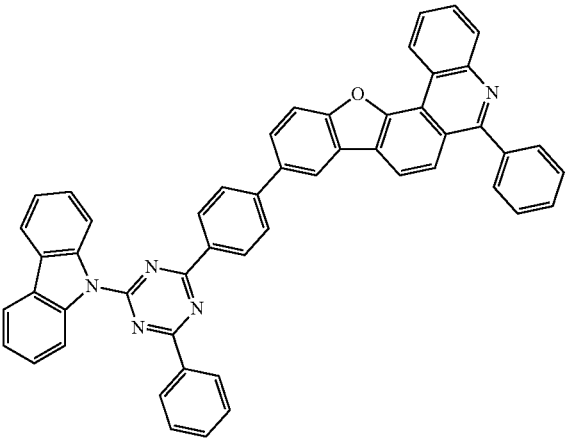

-continued
175
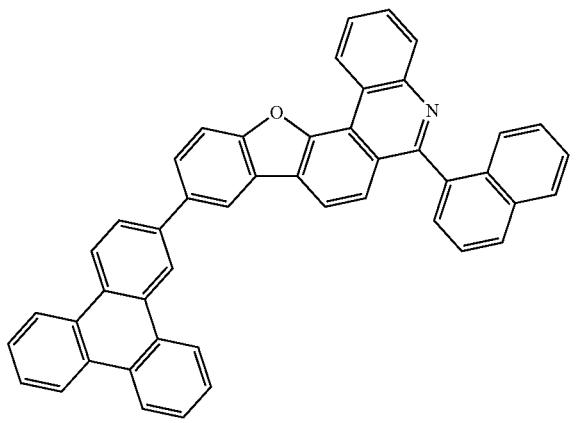
176
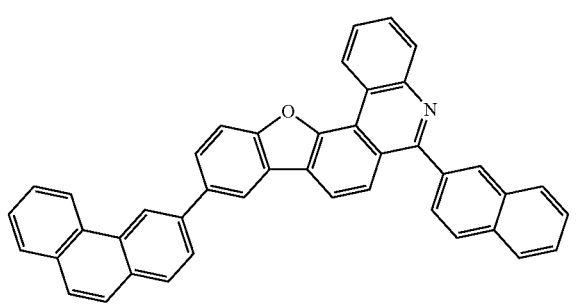
177
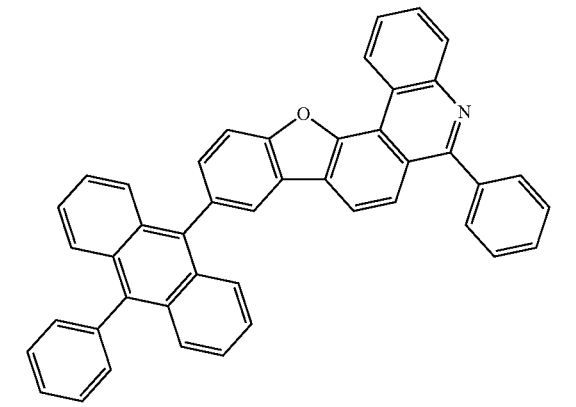
178
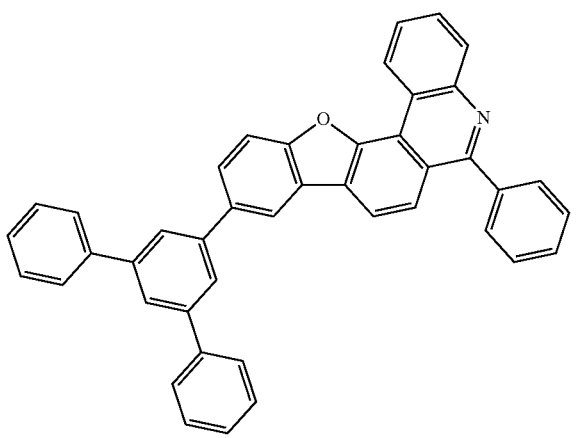
-continued
179
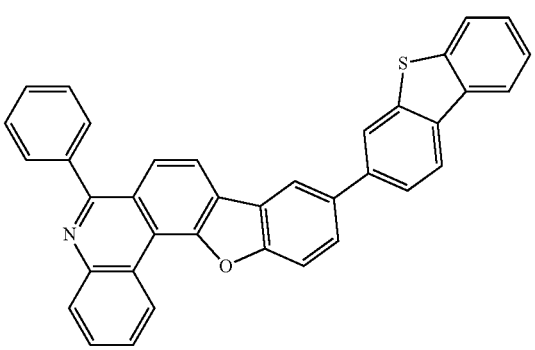
180
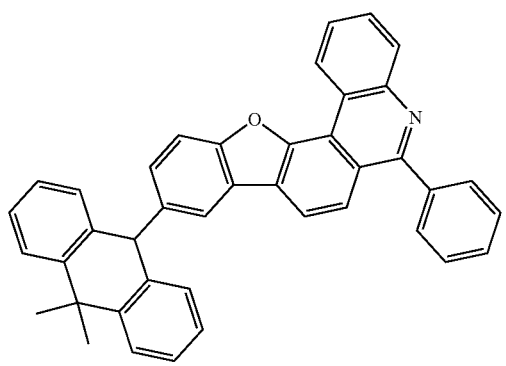
181
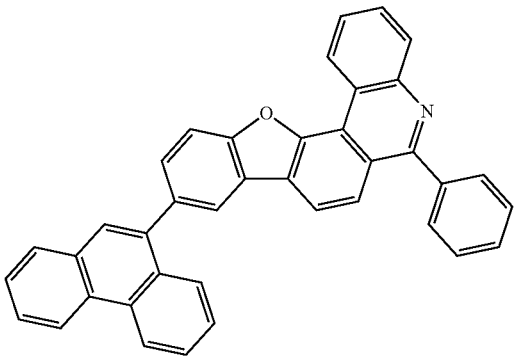
182
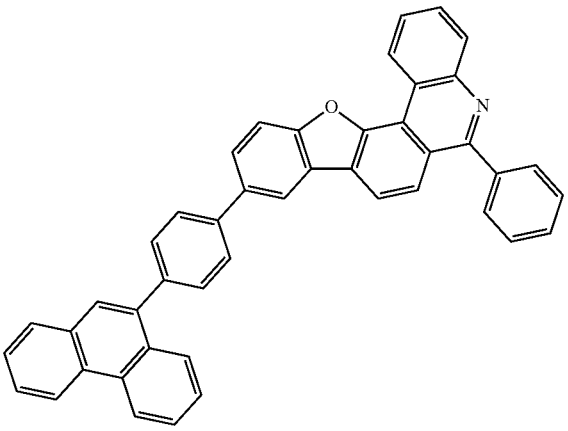

183
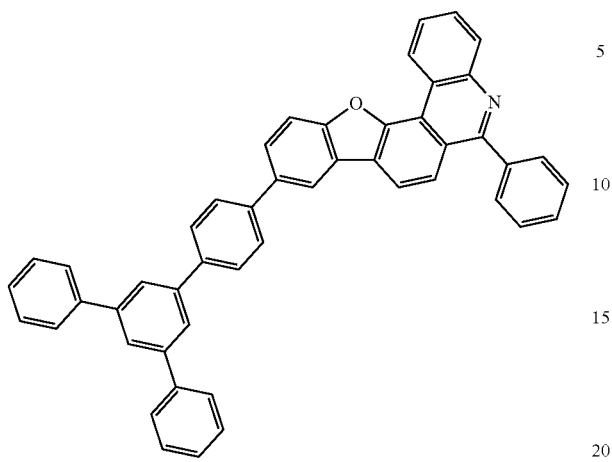
184
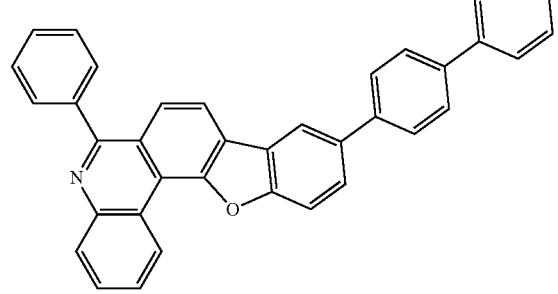
185
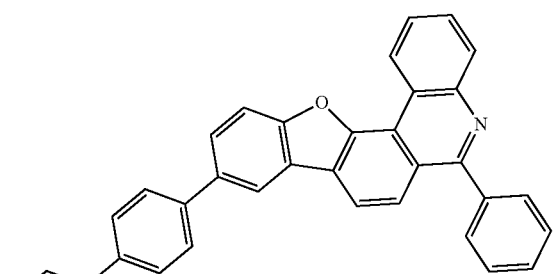
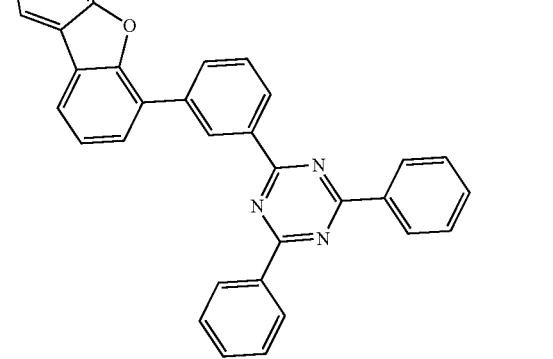
186
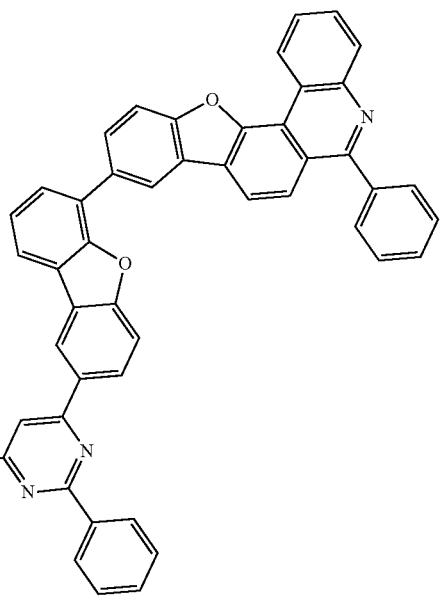
187
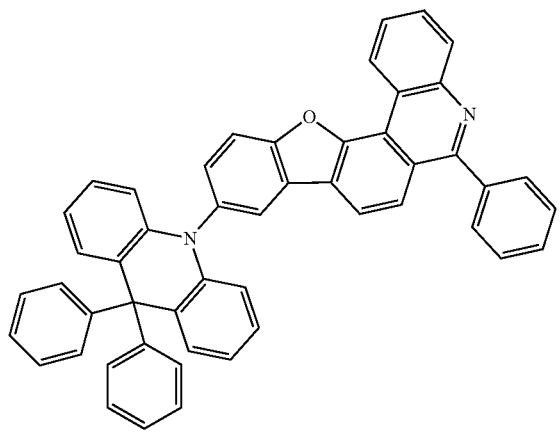
188
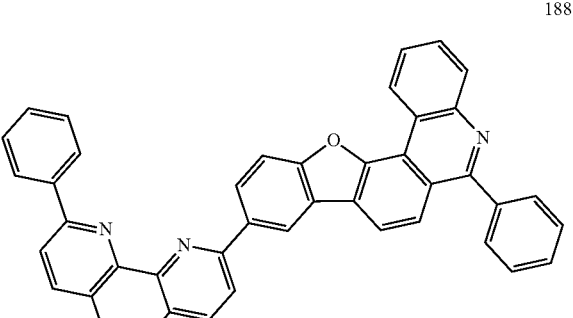

189
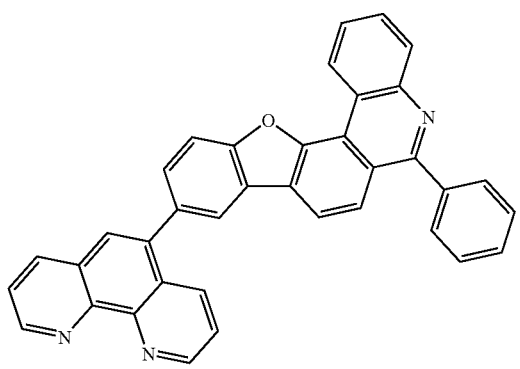
190
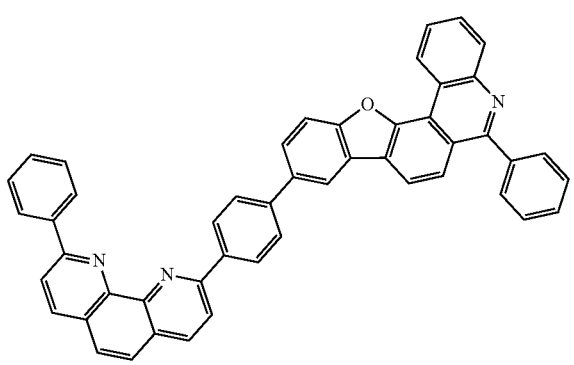
191
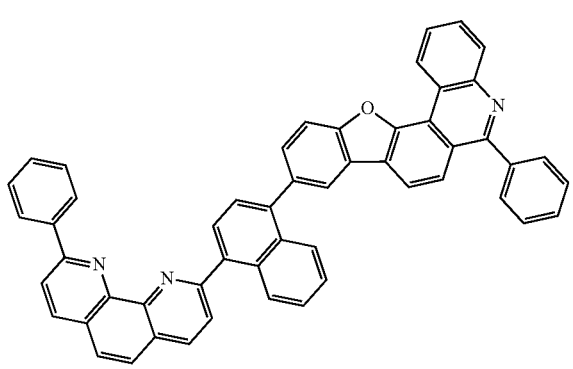
192
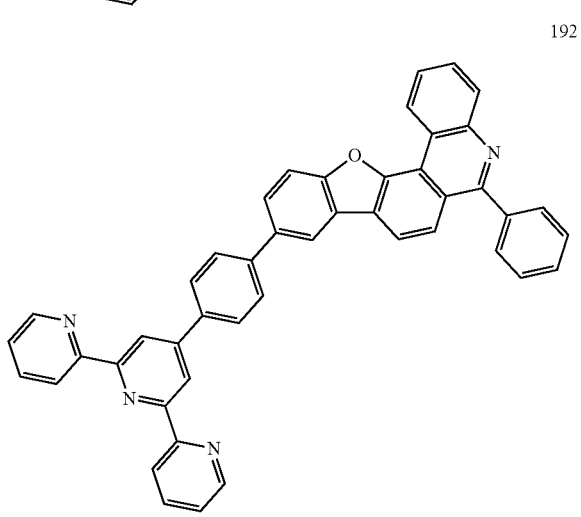
193
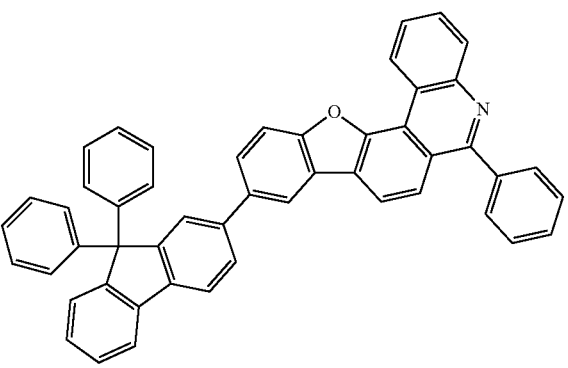
194
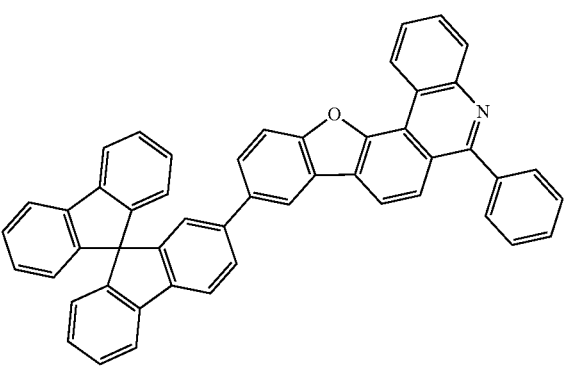
195
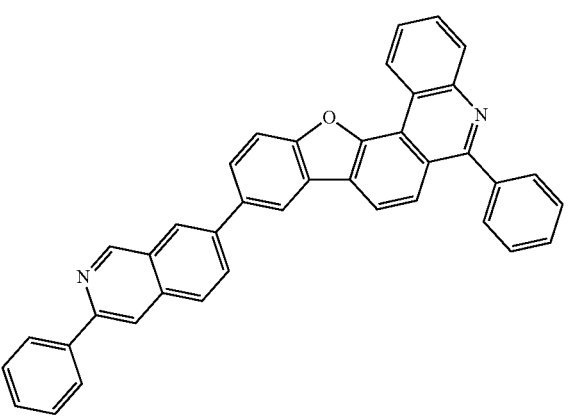

-continued
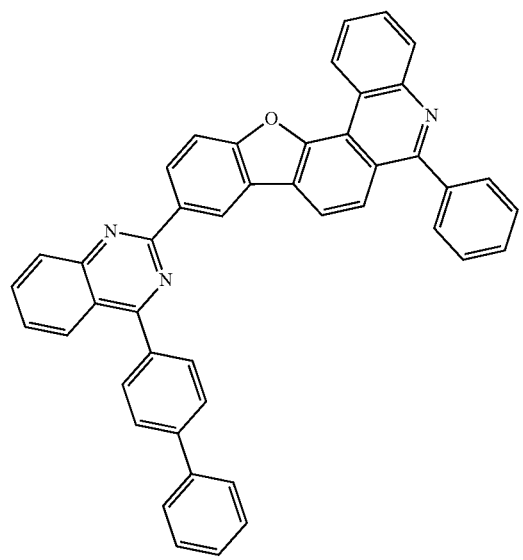
196
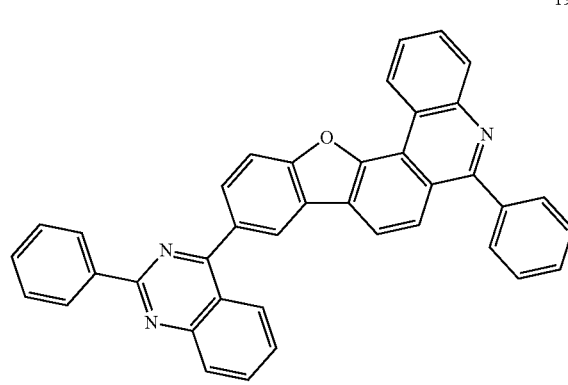
197
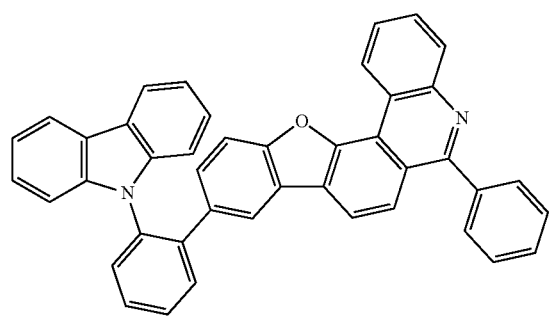
198
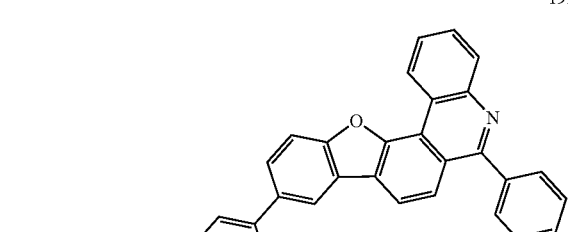
199
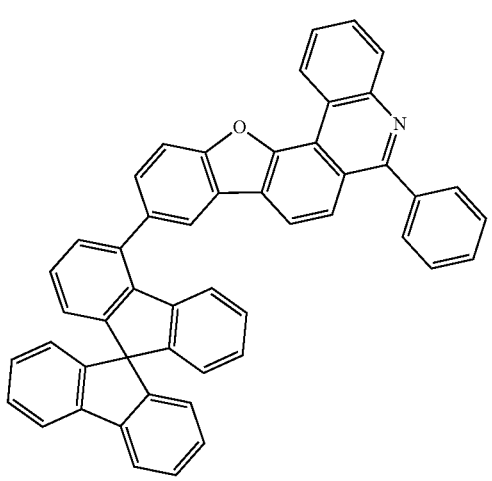
200
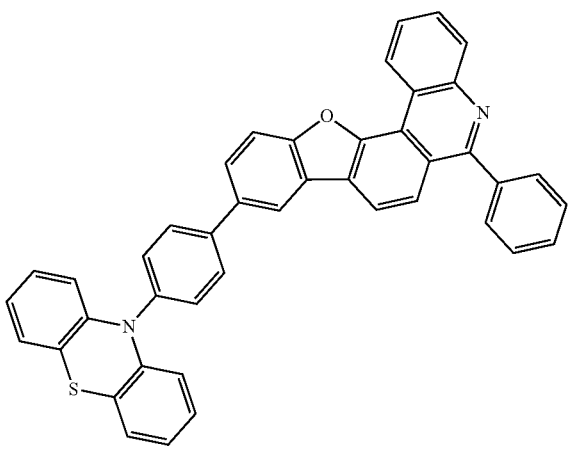
201

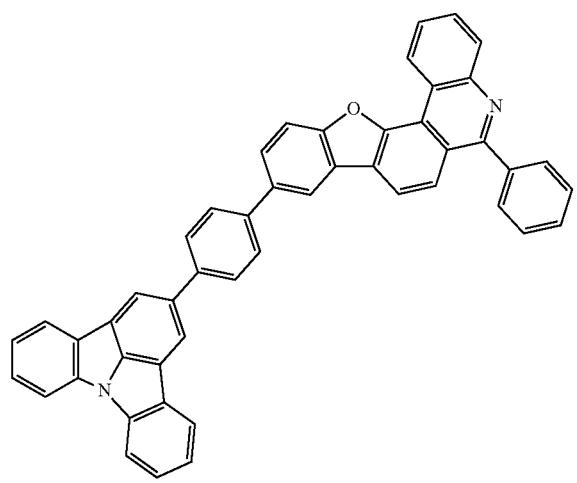
202
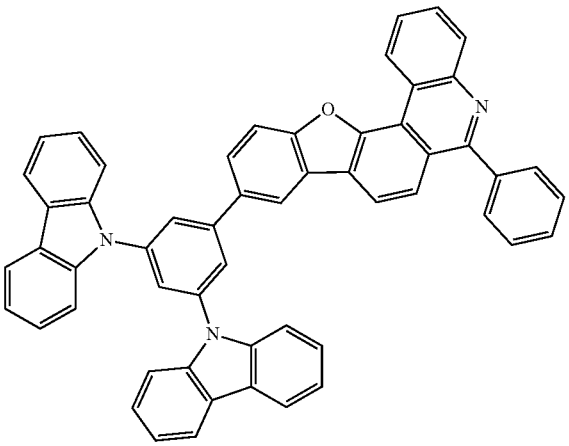
205
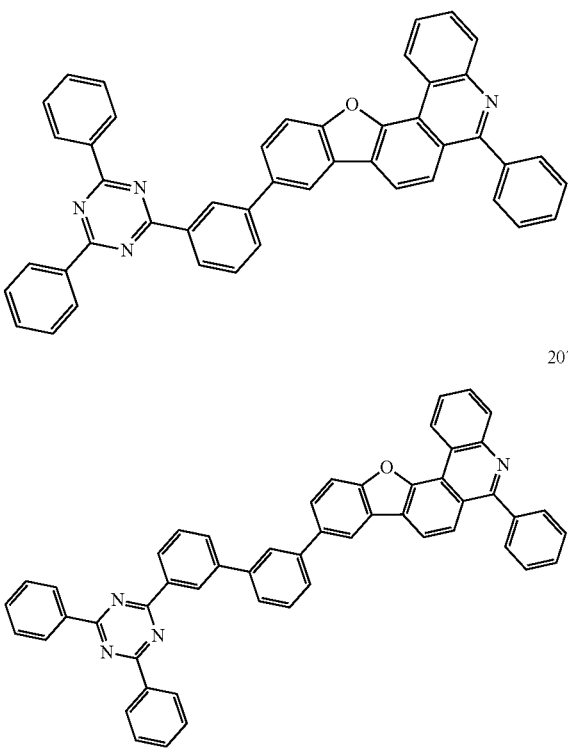
203
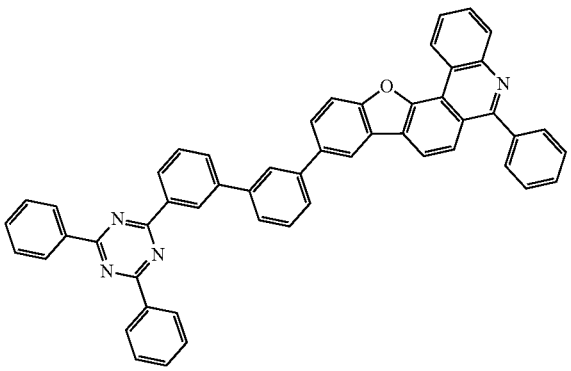
206
207
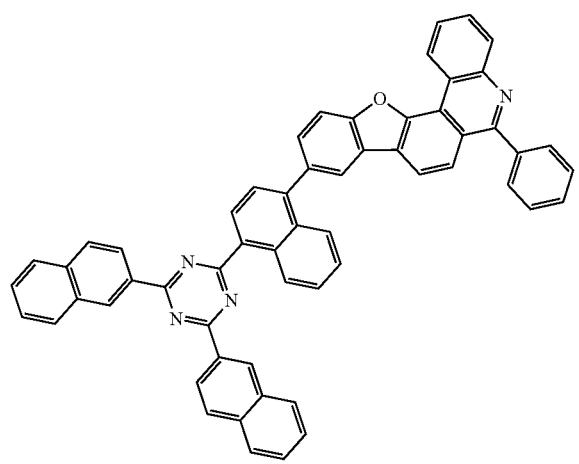
204
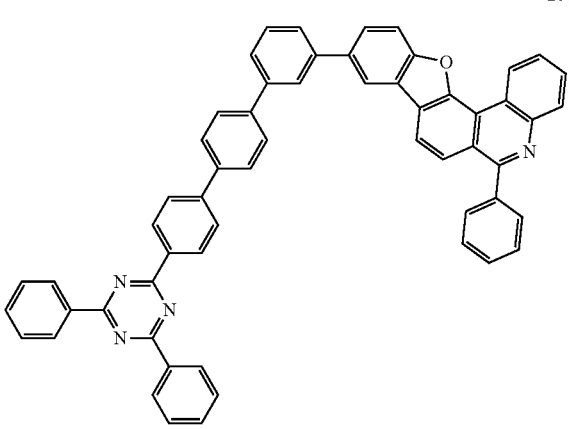
208

209
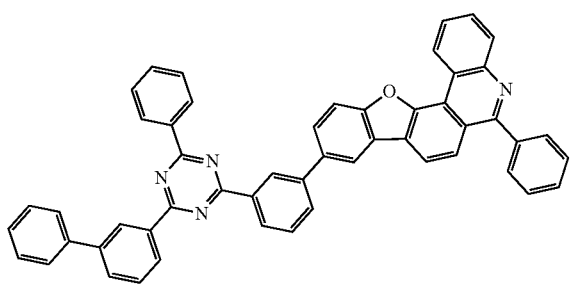
210
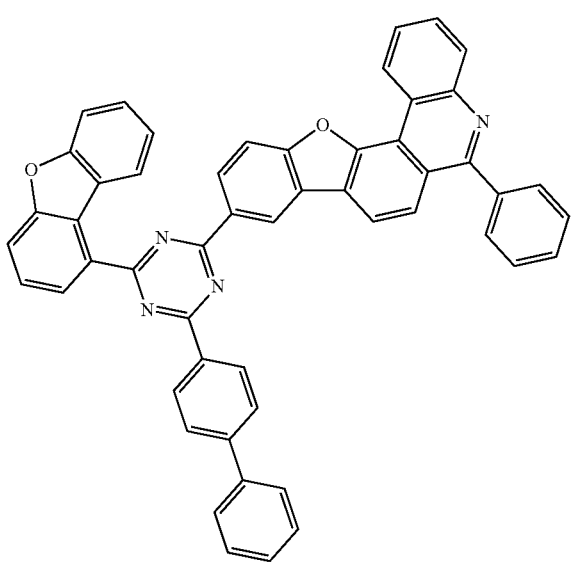
211
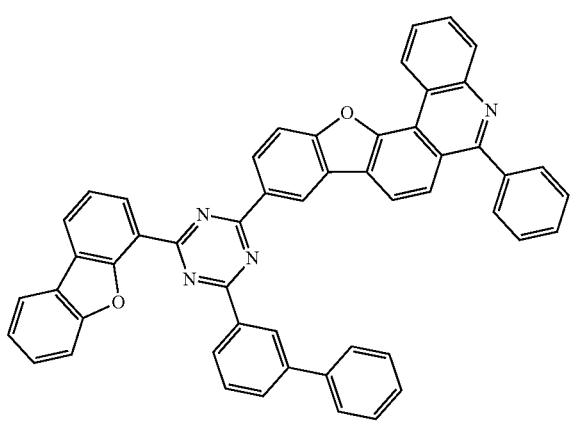
212
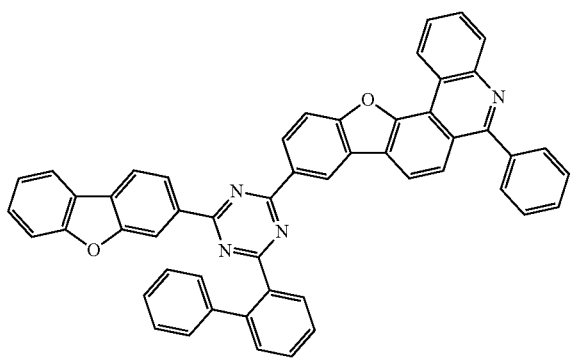
213
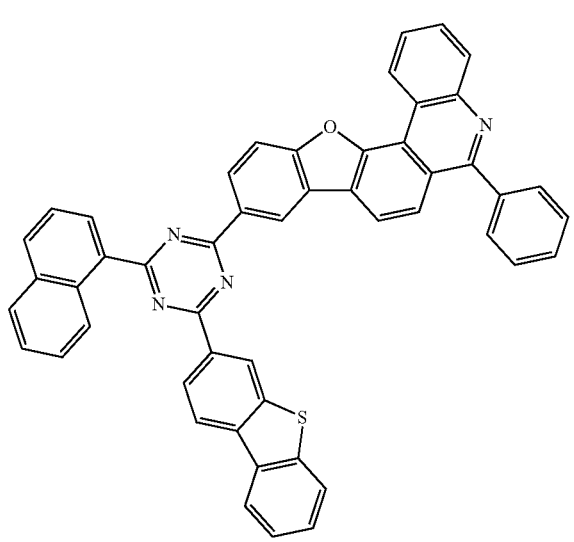
214
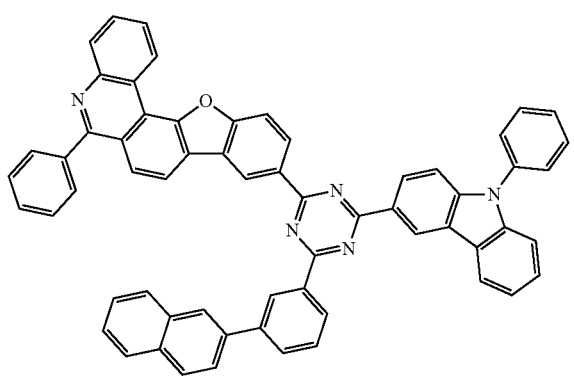

215
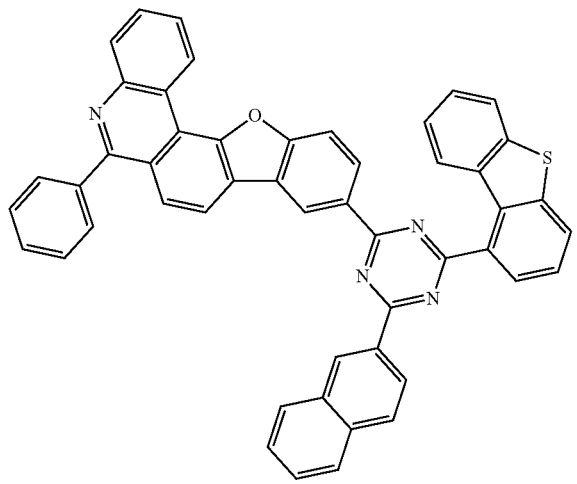
216
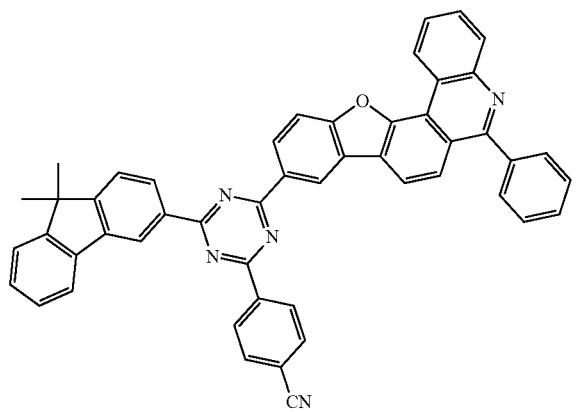
217
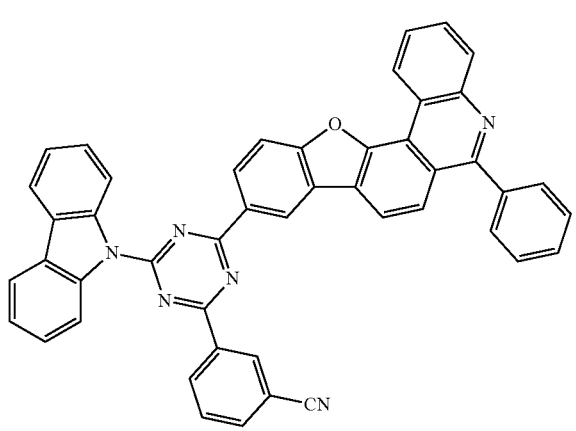
218
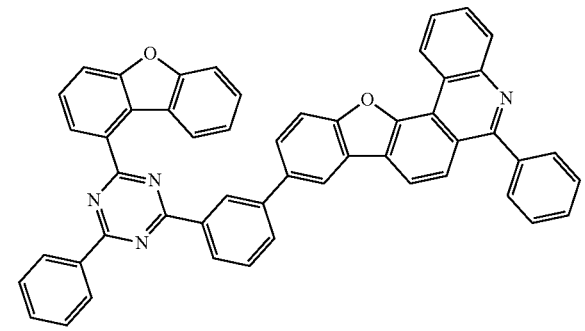
219
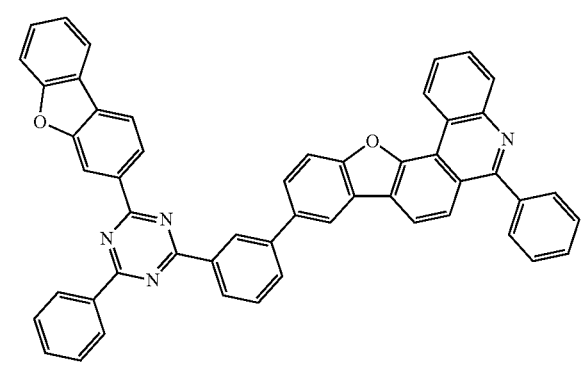
220
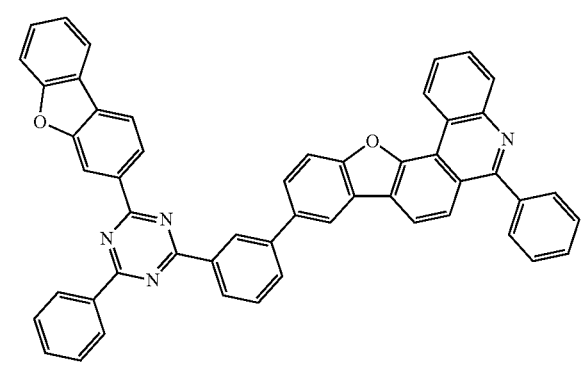
221
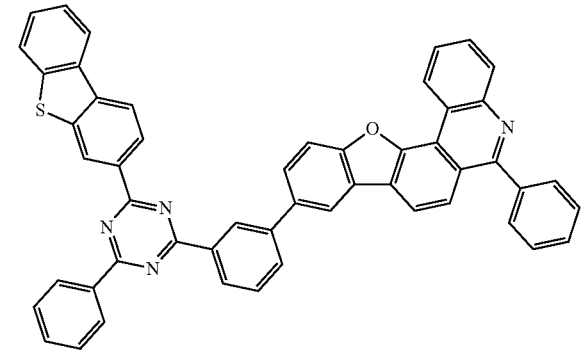

-continued
222
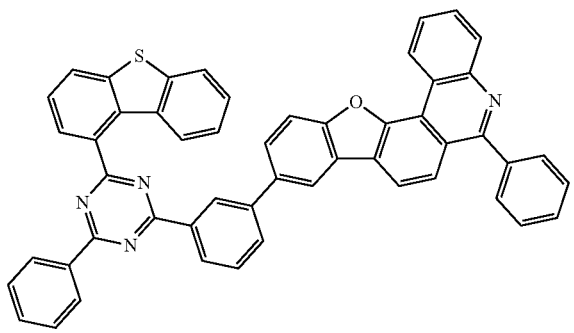
223
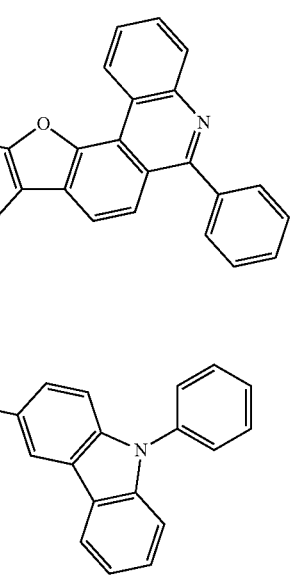
224
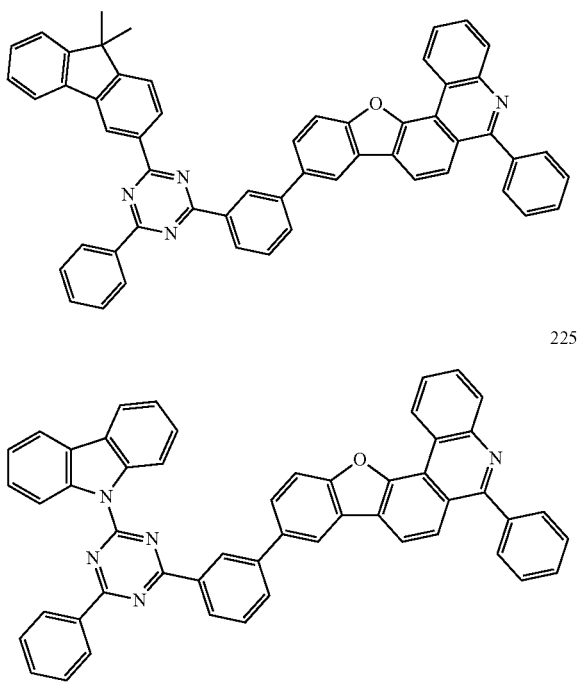
225
-continued
226
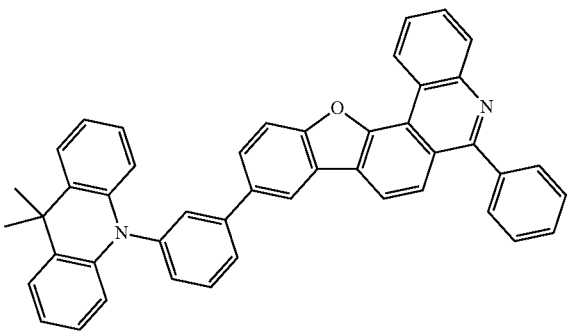
227
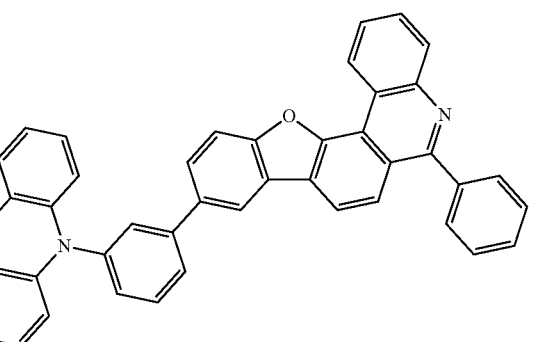
228
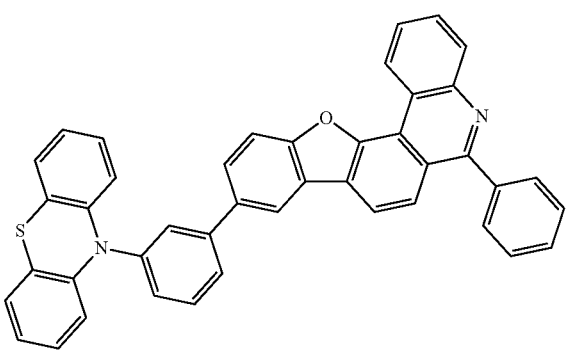
229
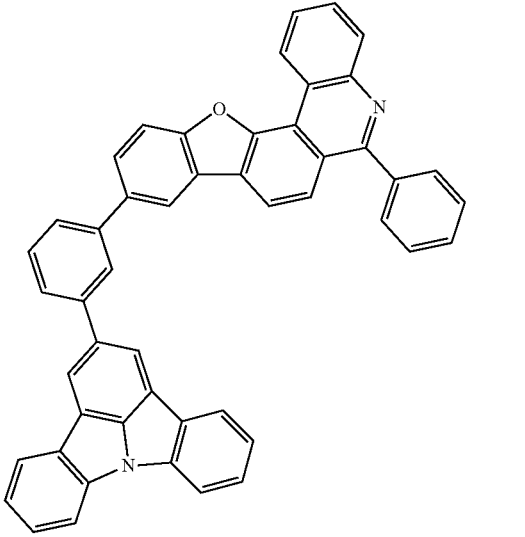

230
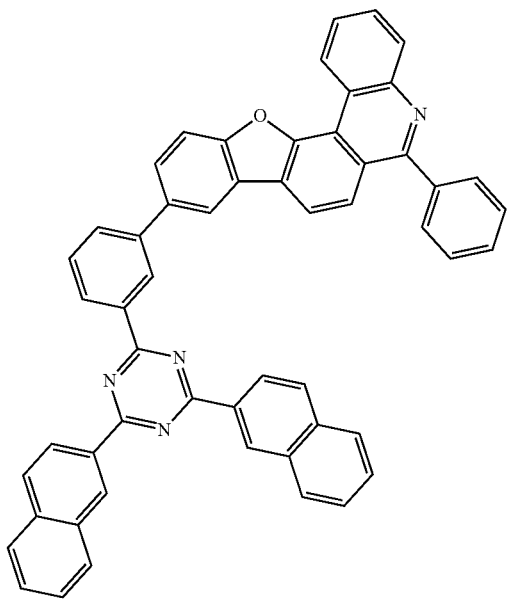
231
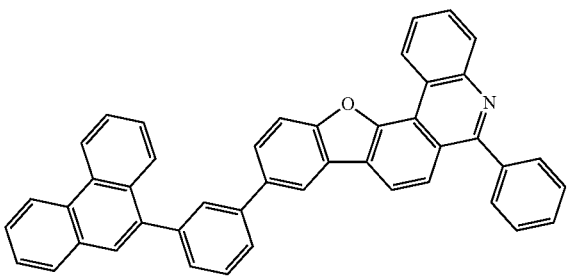
232
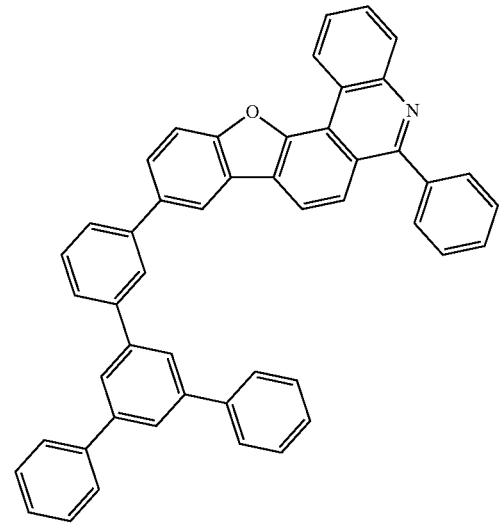
233
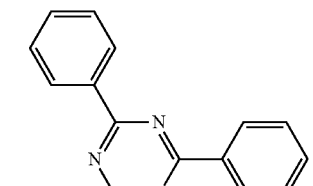
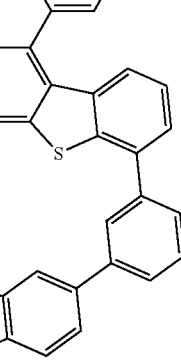
234
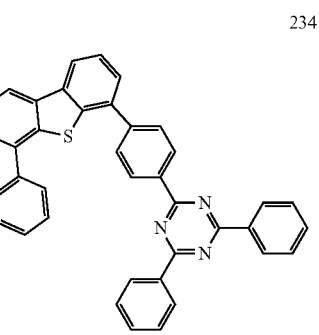
235
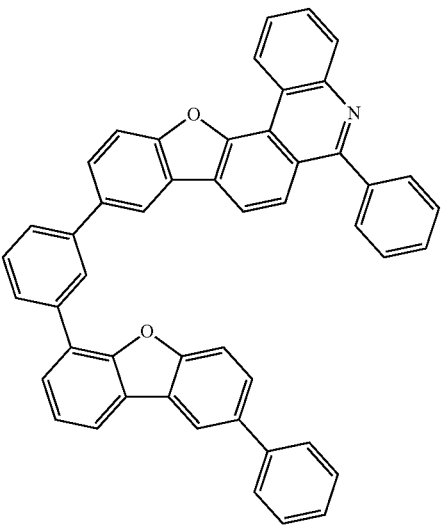

236
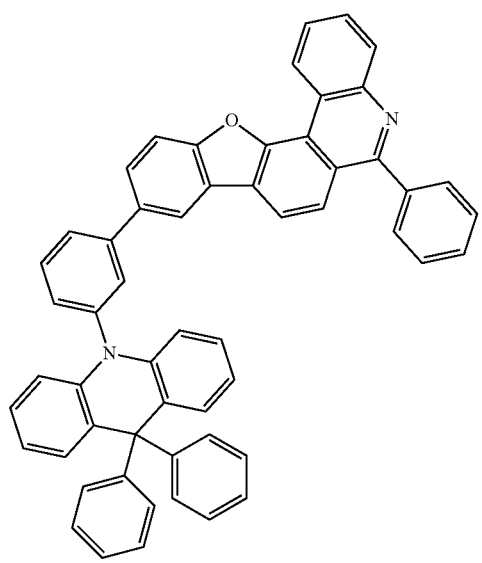
237
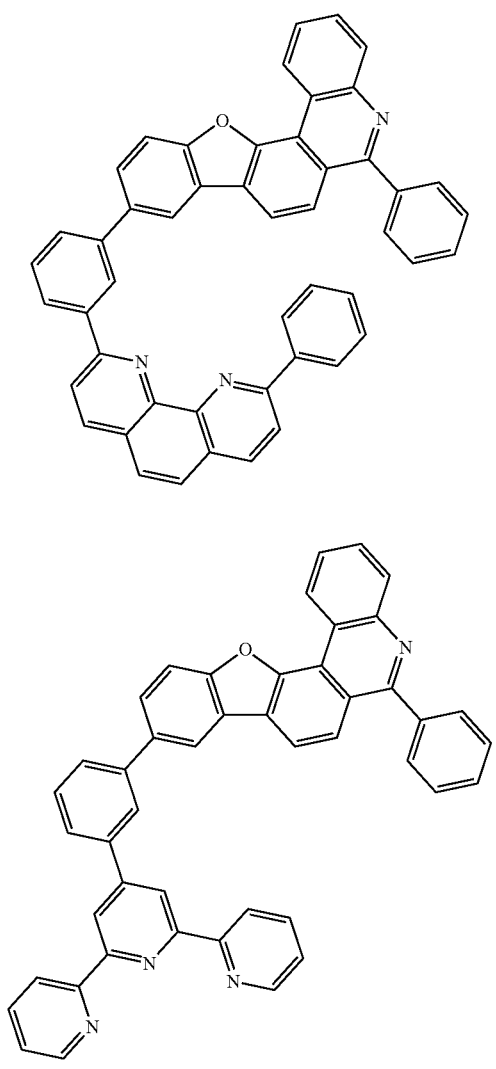
238
239
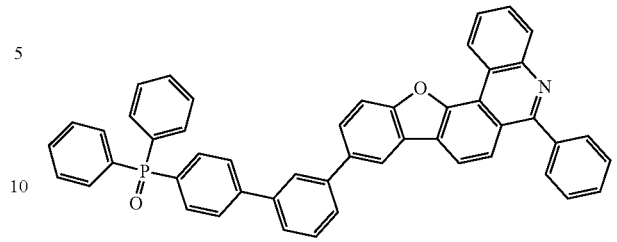
240
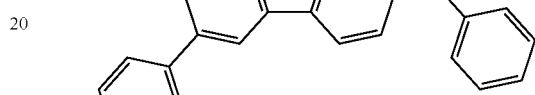
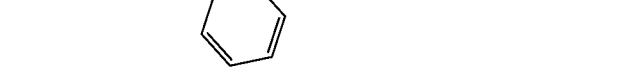
241
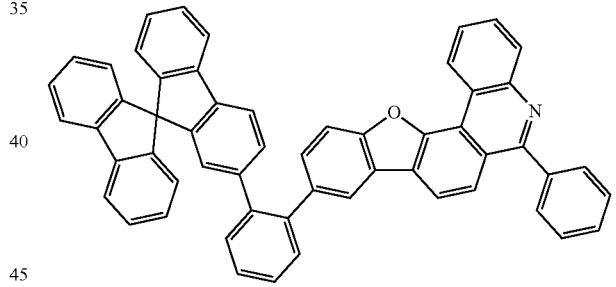
242
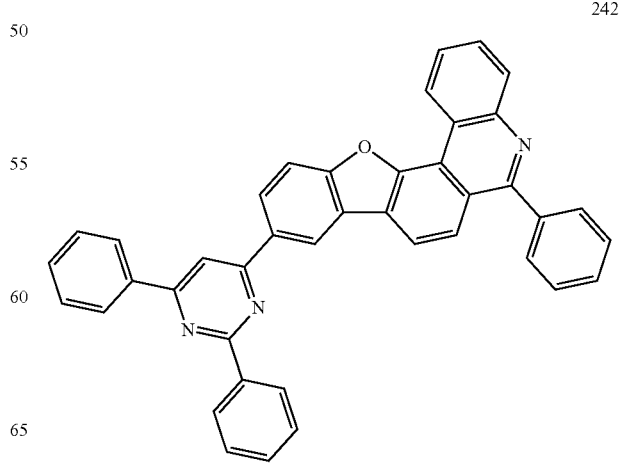

243
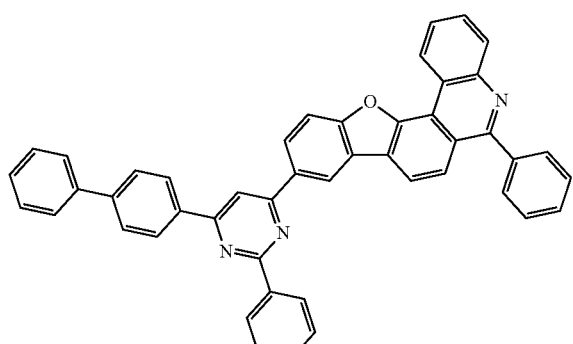
244
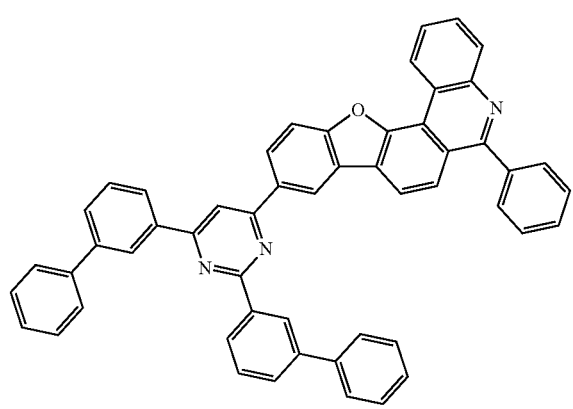
245
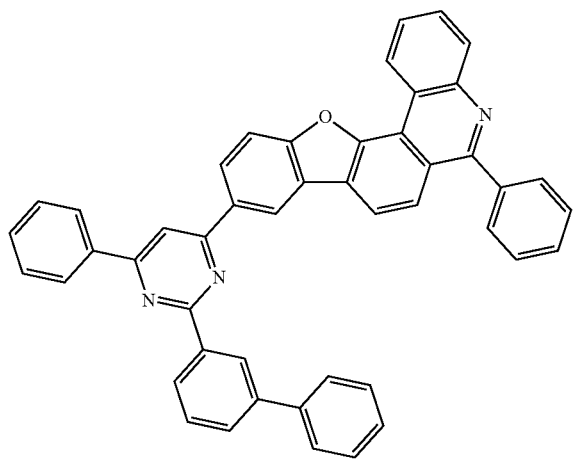
246
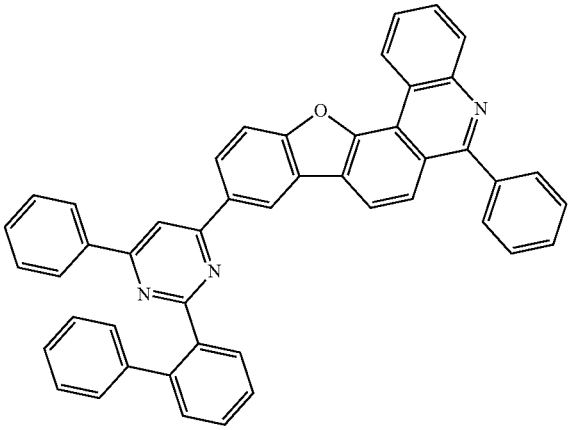
247
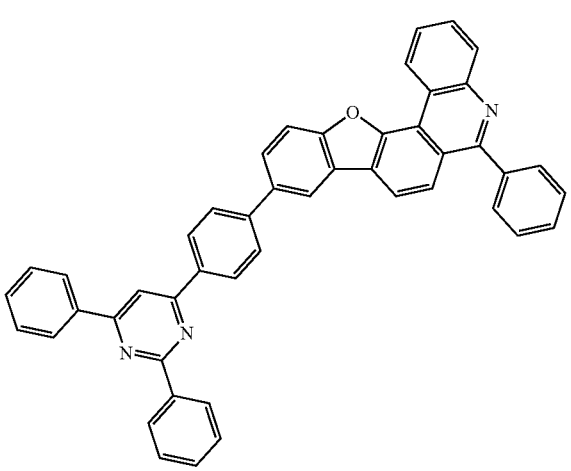
248
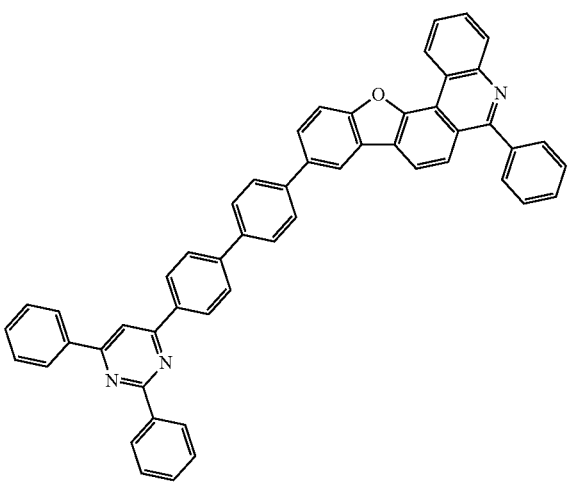

249
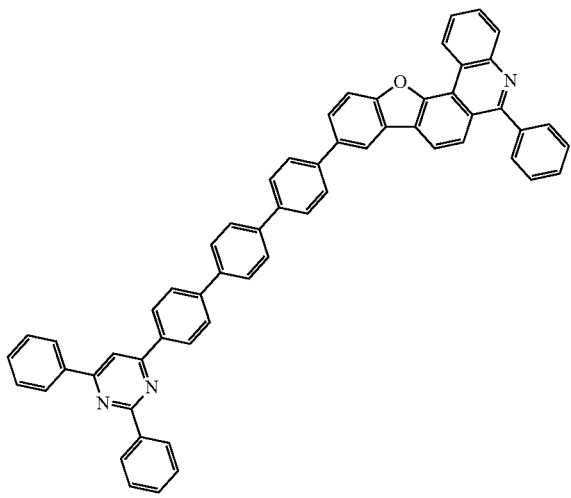
250
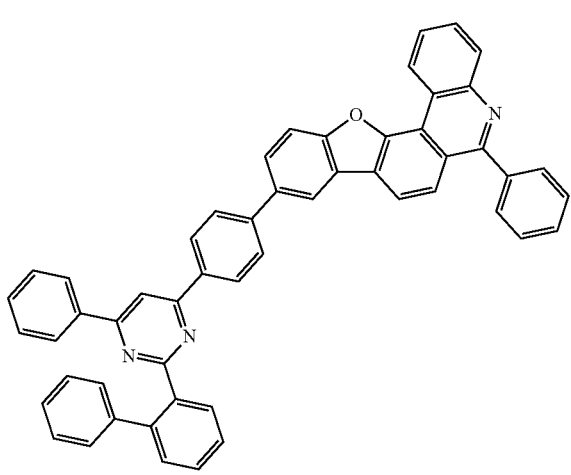
251
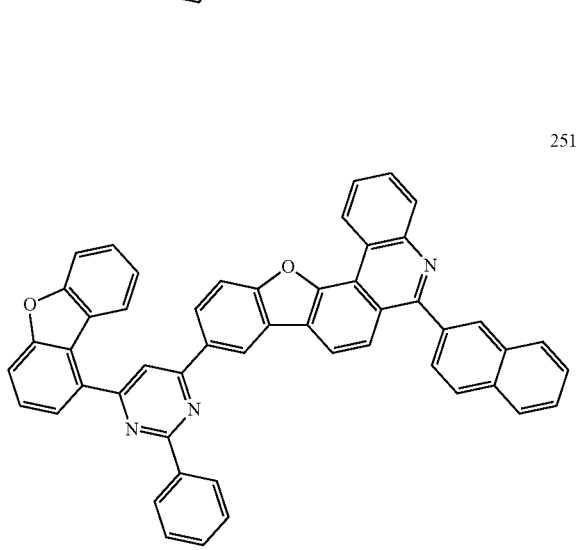
252
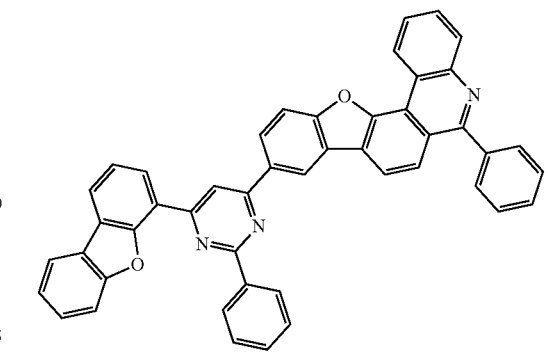
253
254
255
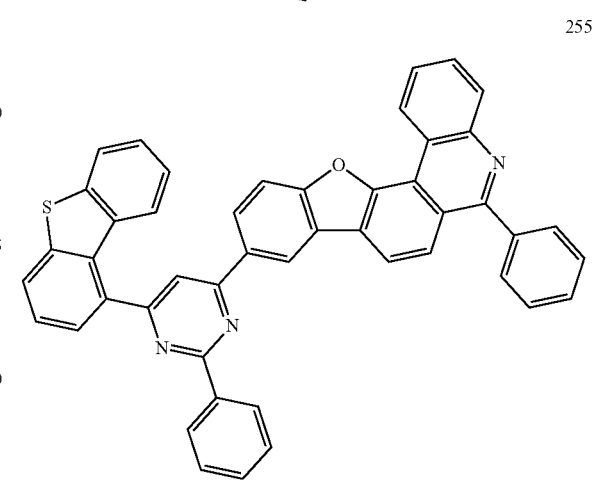

256
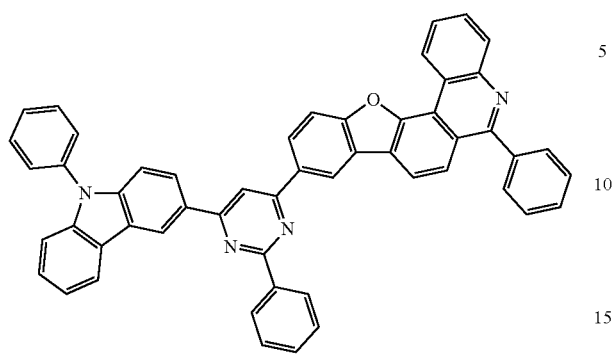
257
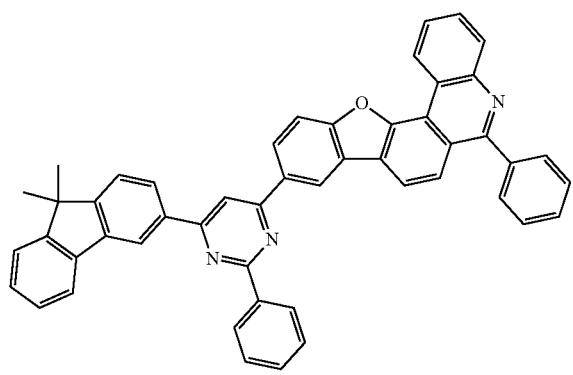
258
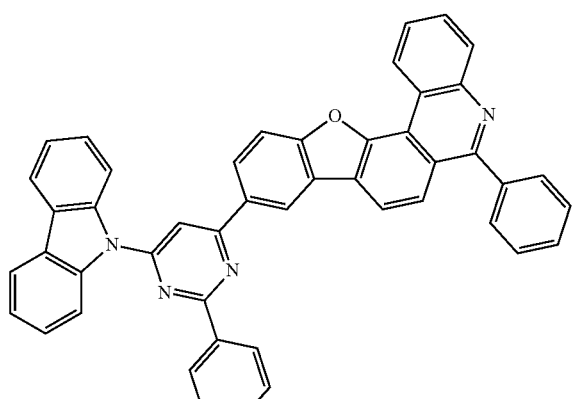
259
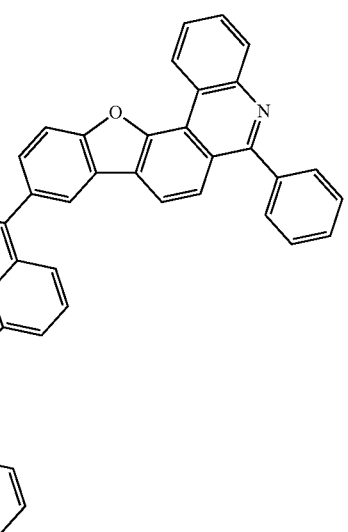
260
261
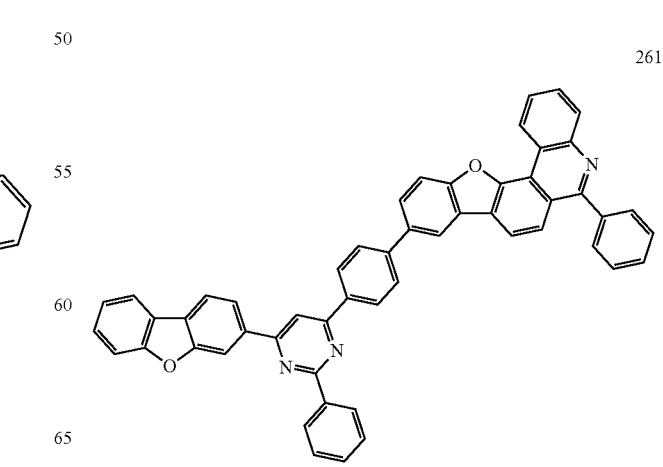

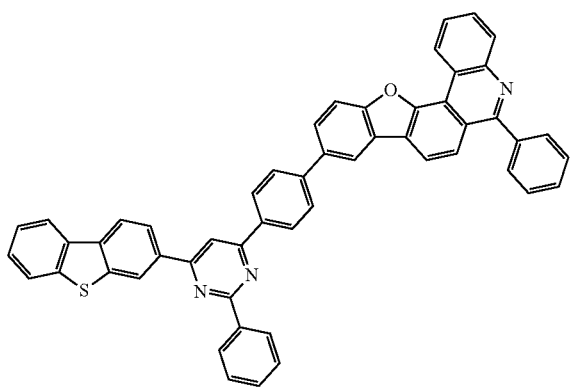
262
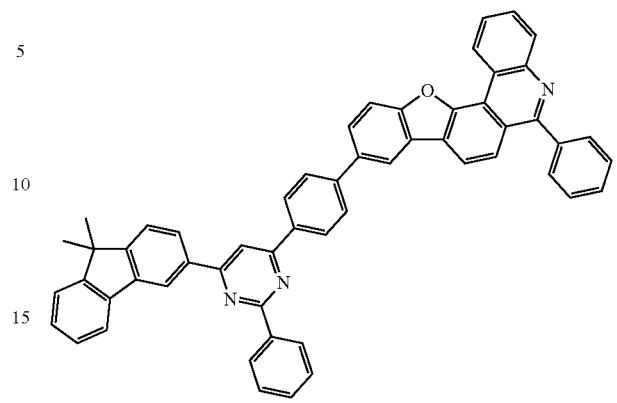
265
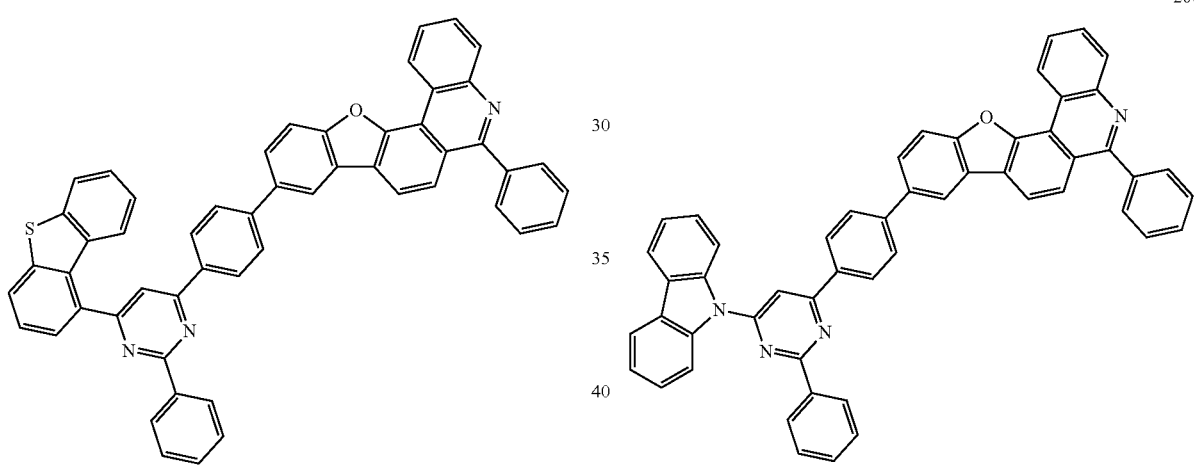
263
266
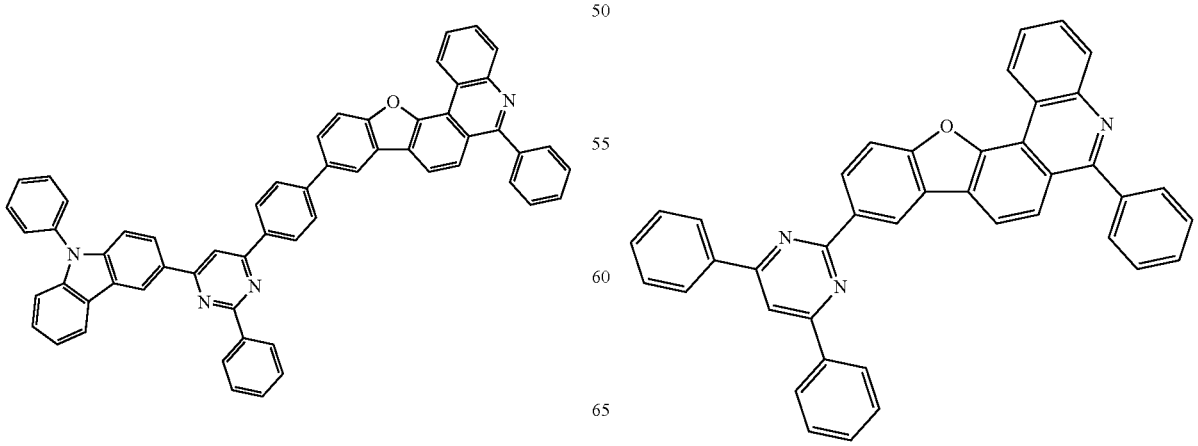
264
267

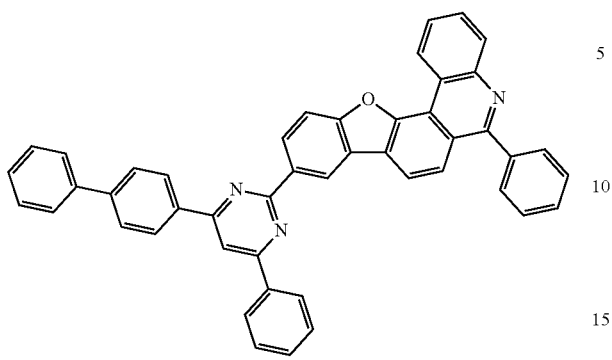
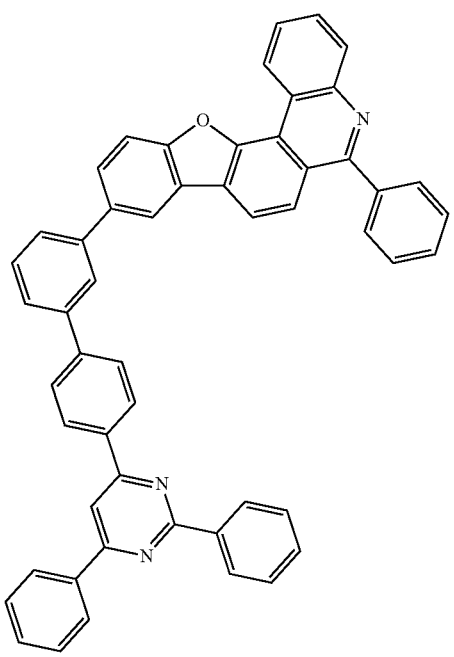
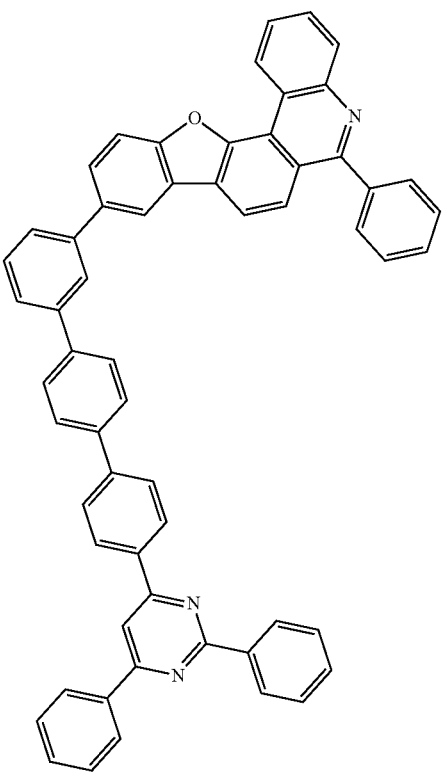

US 12,415,814 B2
97
-continued
273
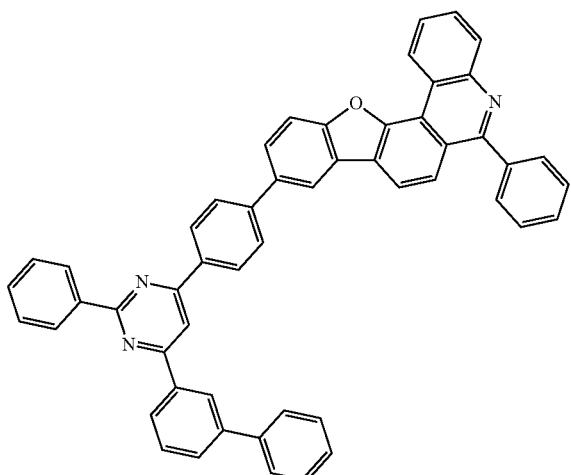
274
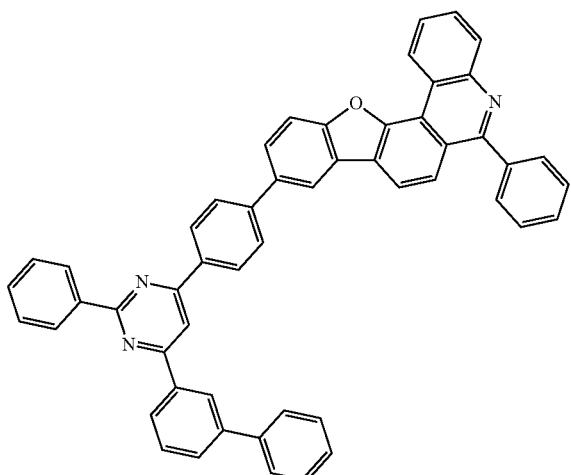
275
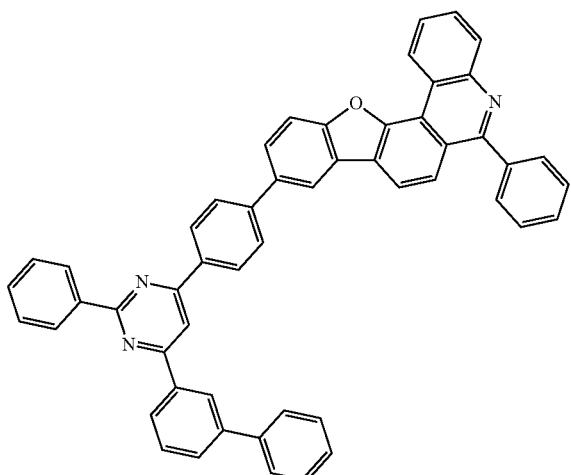
276
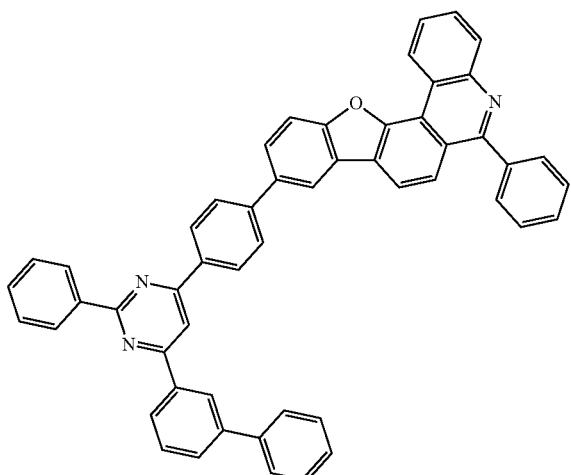
98
-continued
277
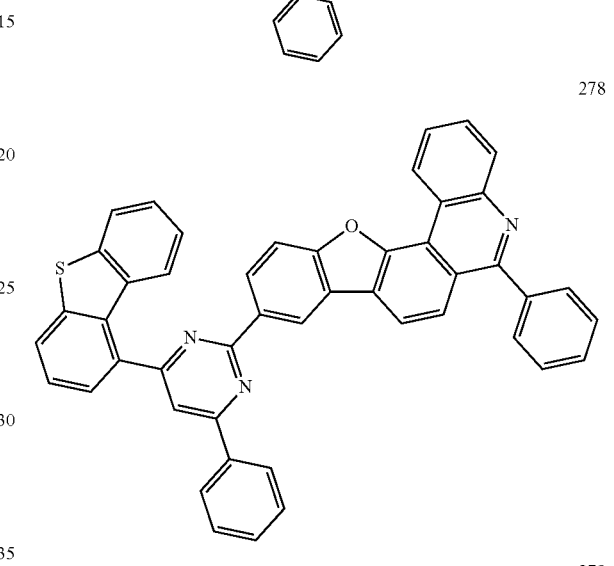
278
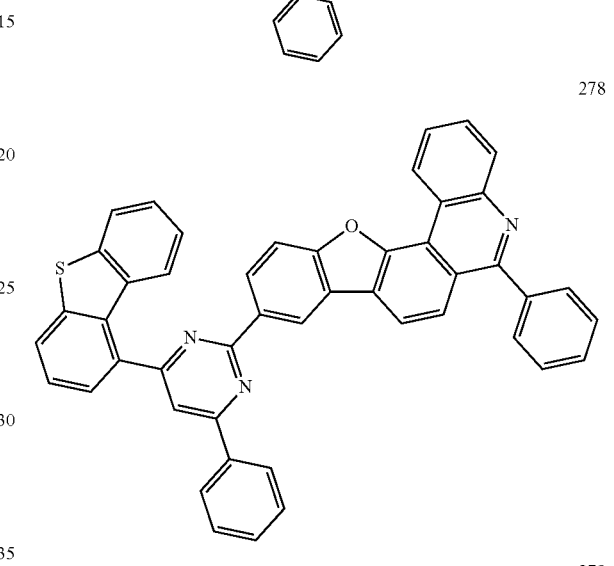
279
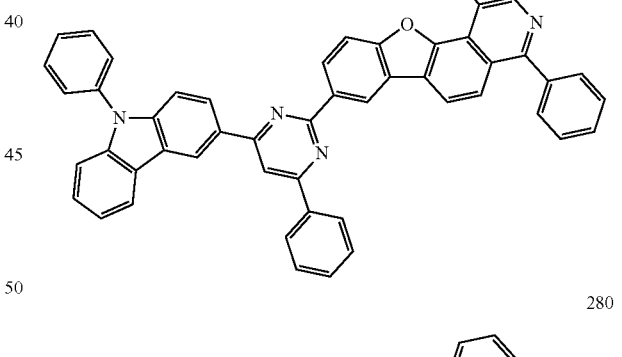
280
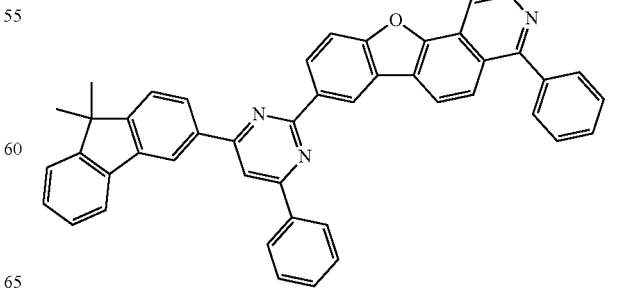

281
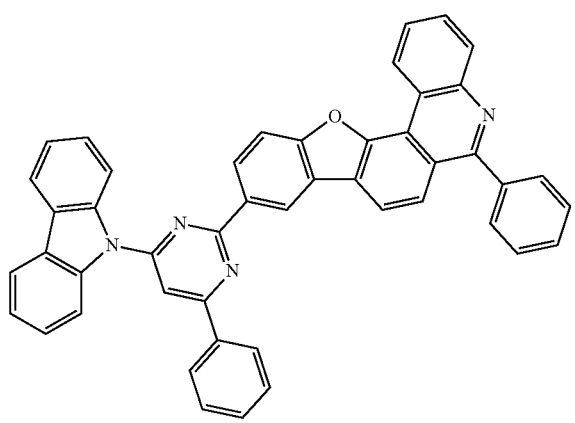
284
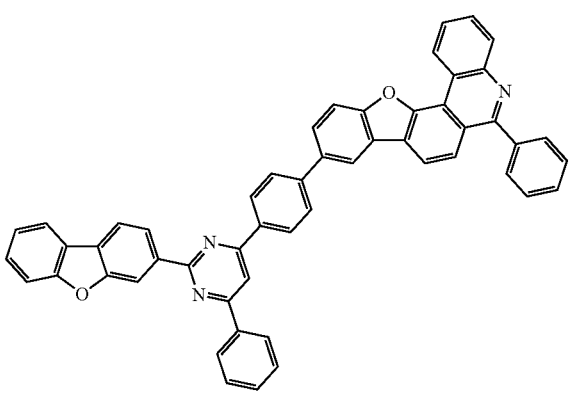
282
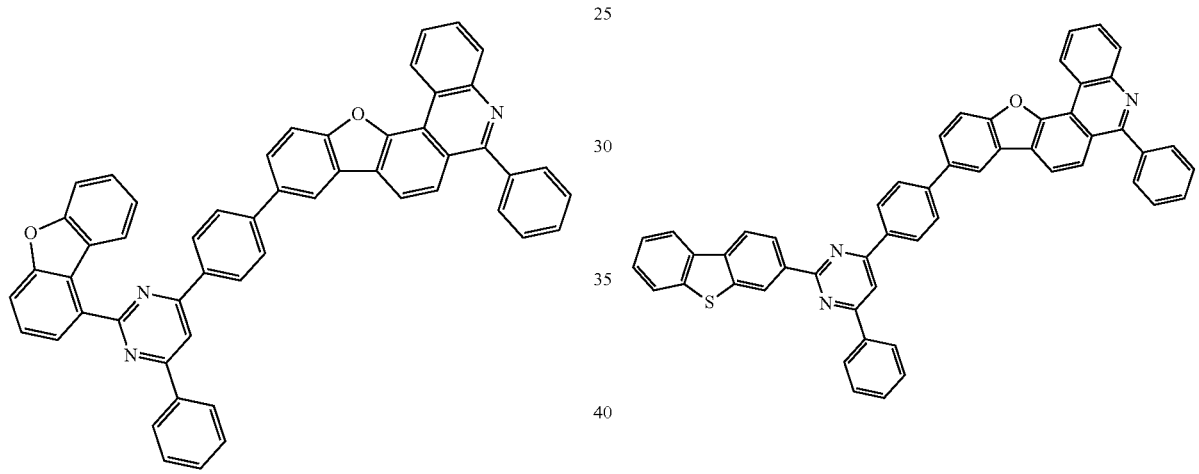
285
283
286
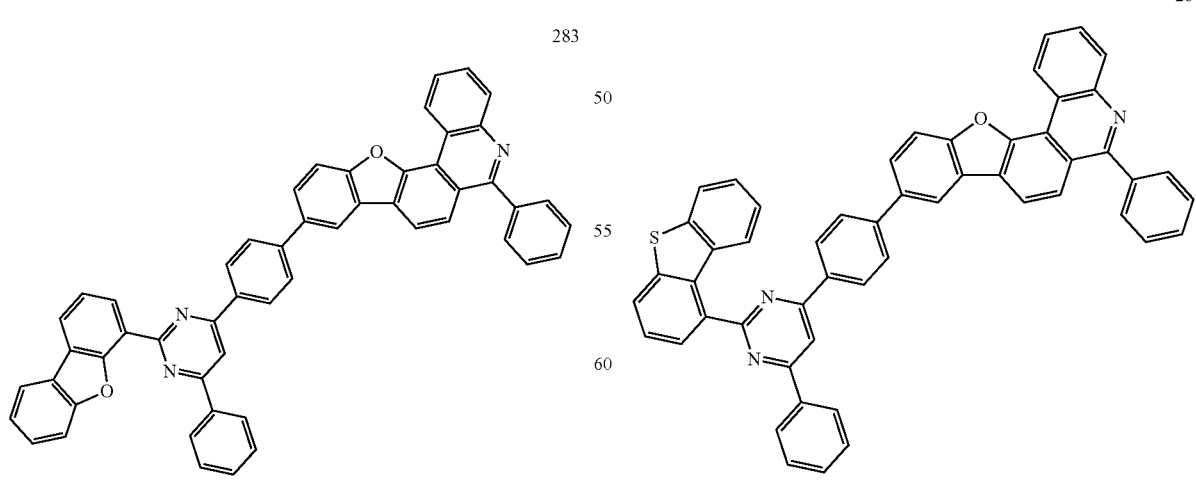

101
-continued
287
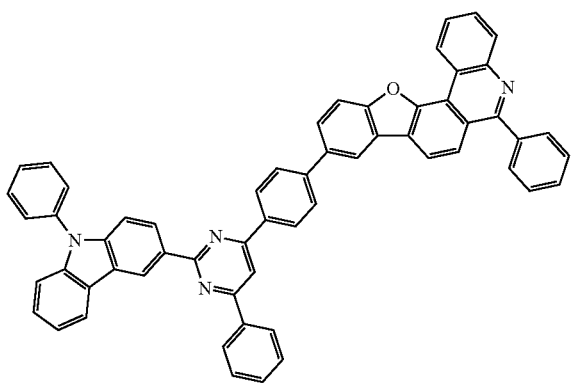
288
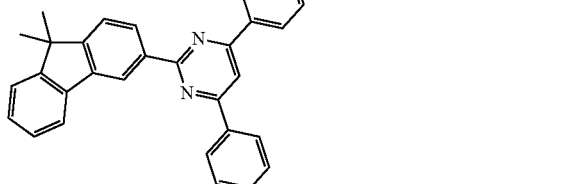
289
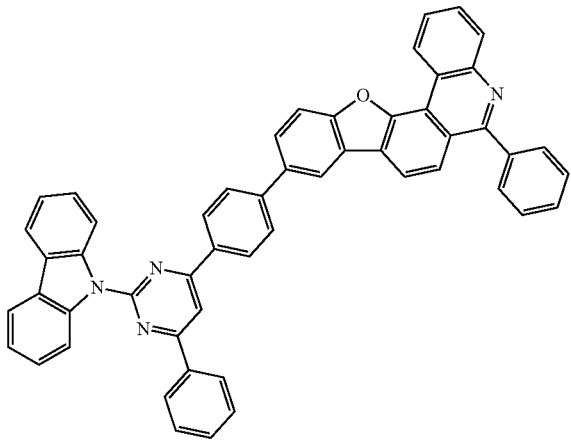
102
-continued
290
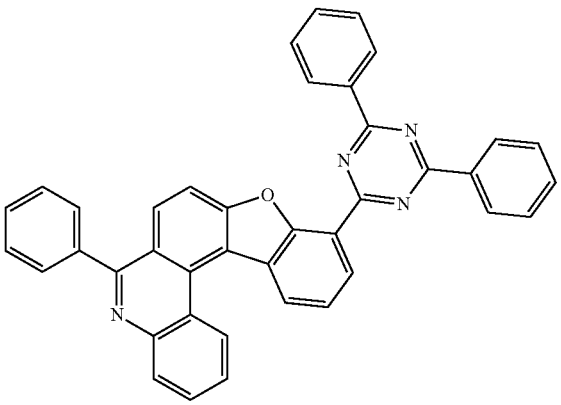
291
292
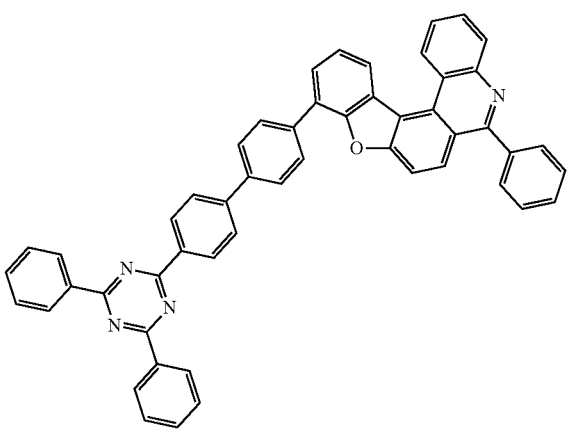

293
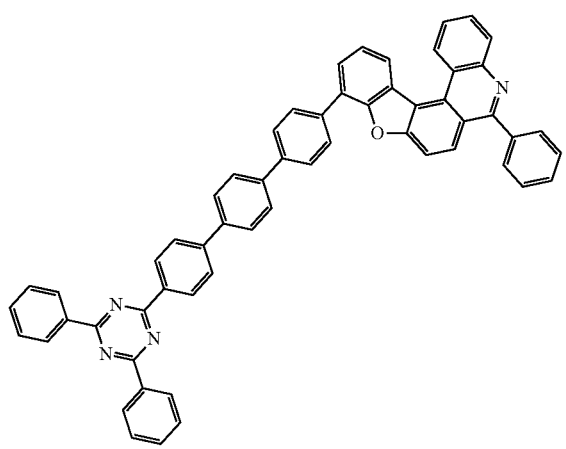
296
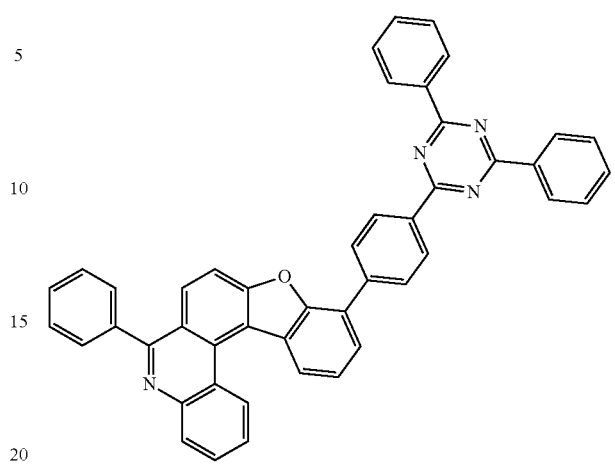
294
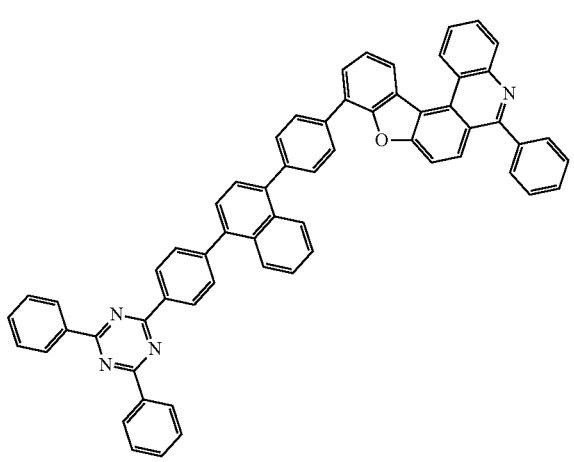
297
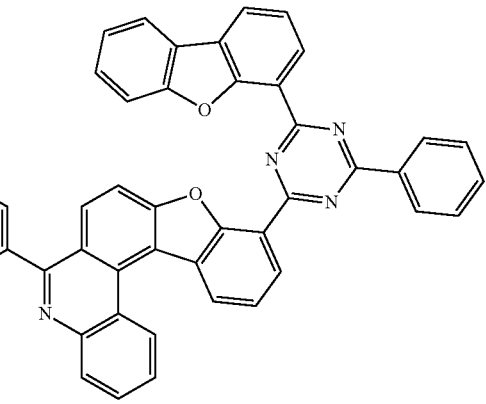
295
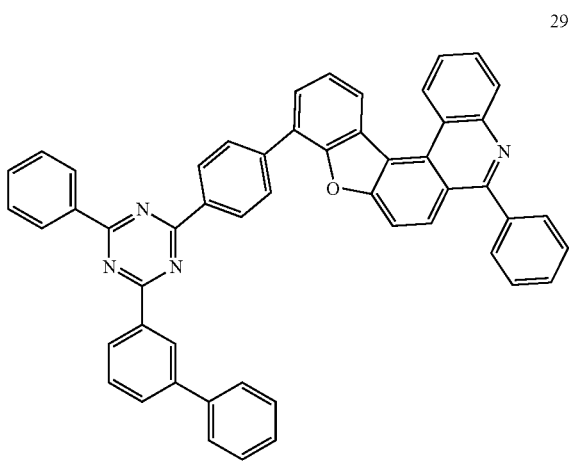
298
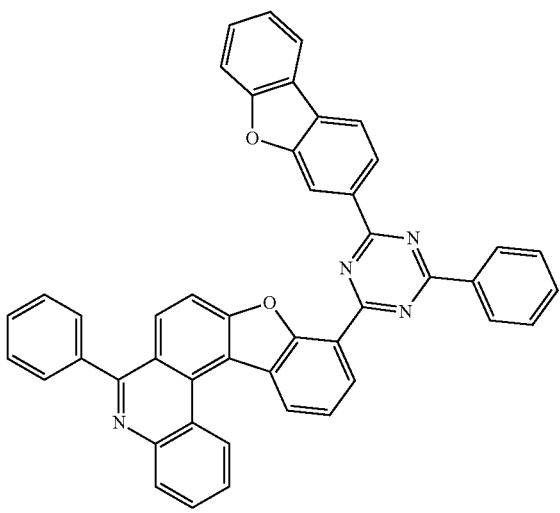

299
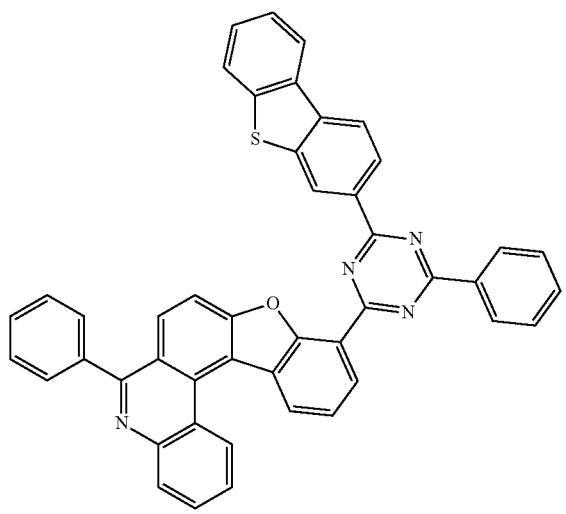
300
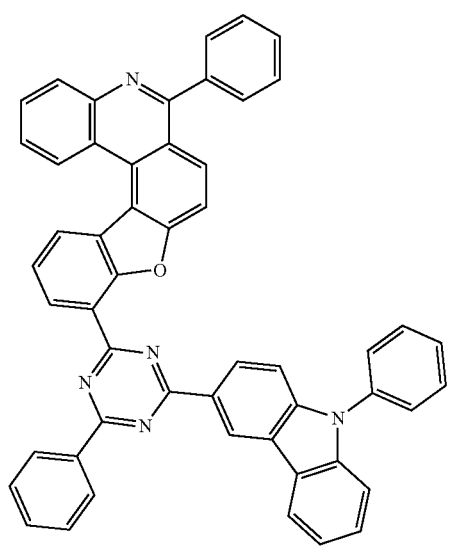
301
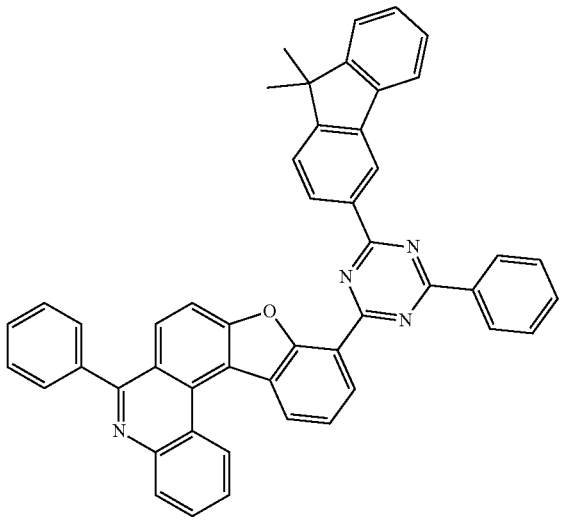
302
303
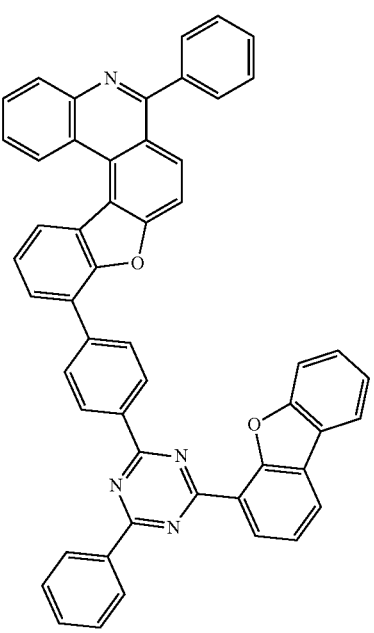

304
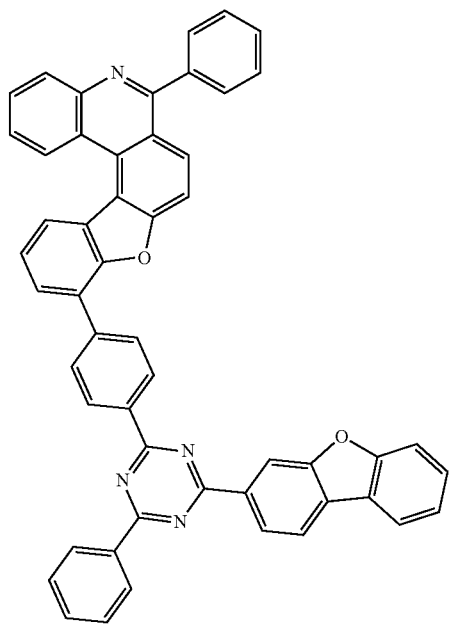
305
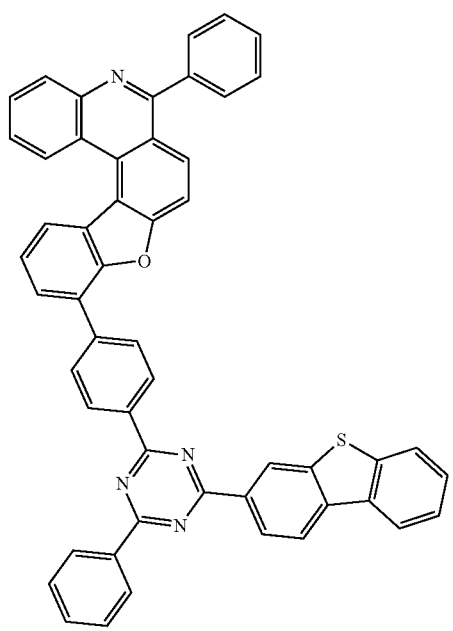
306
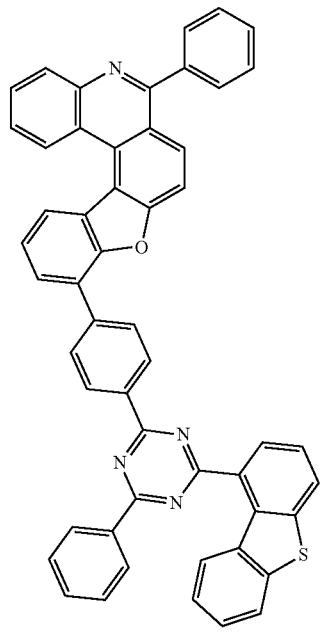
307
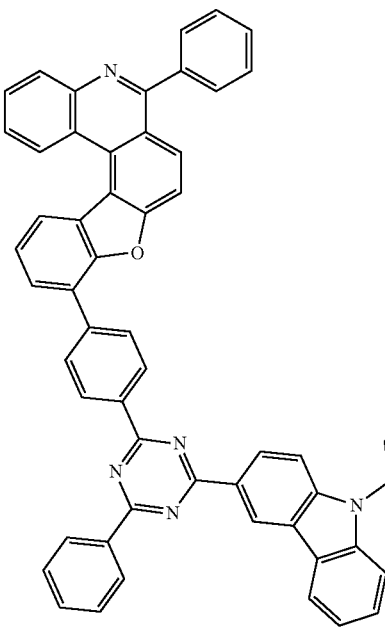

308
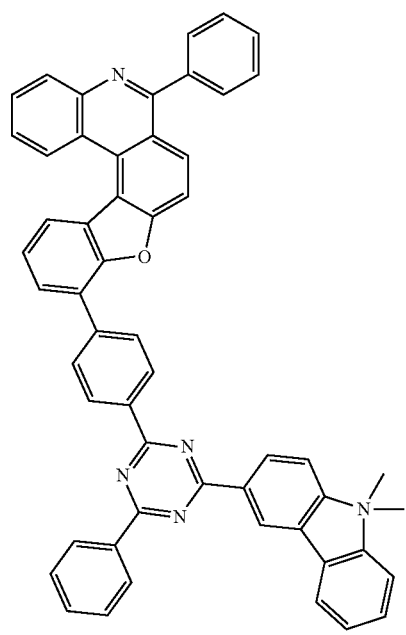
309
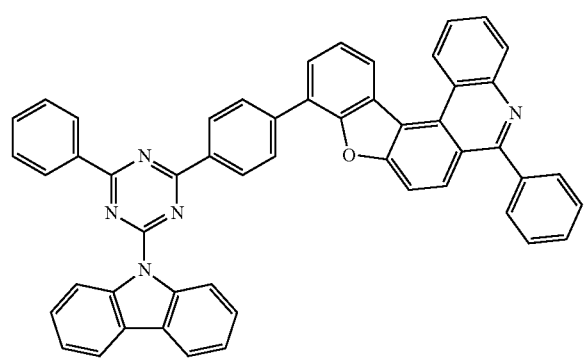
310
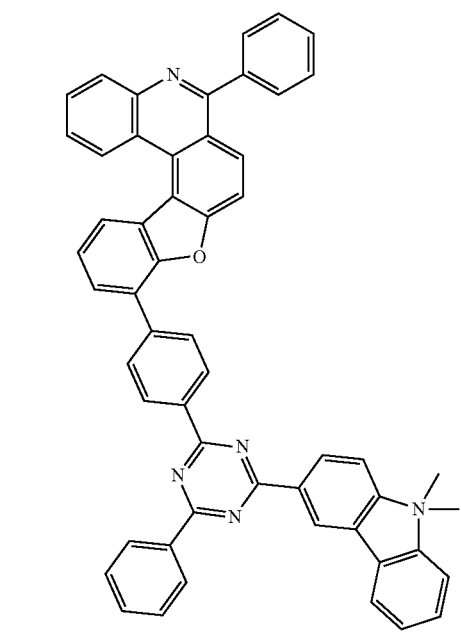
311
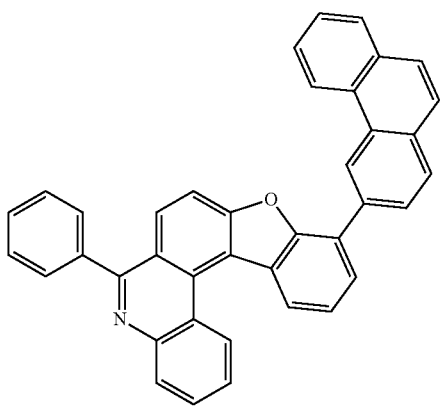
312
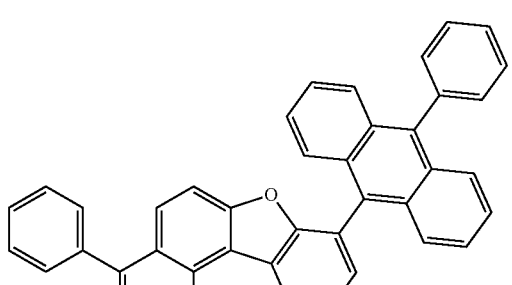
313
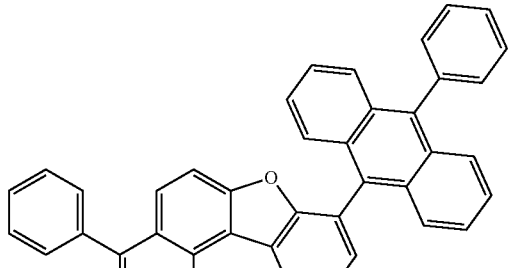
314
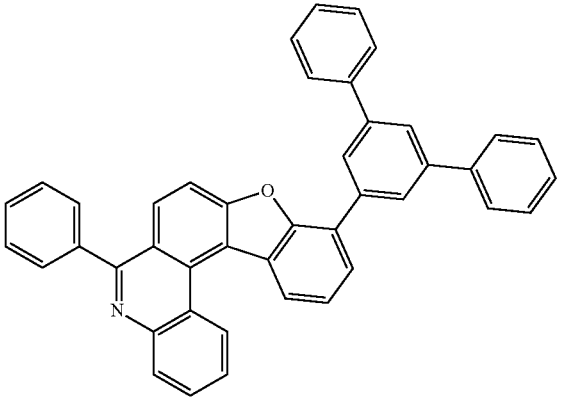

315
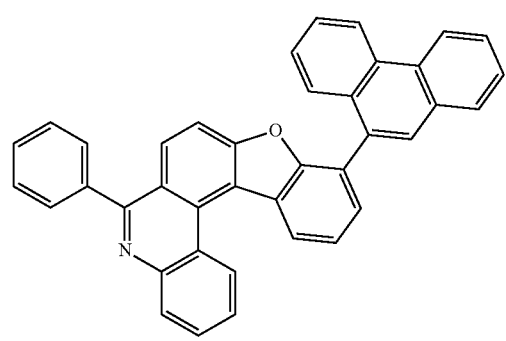
316
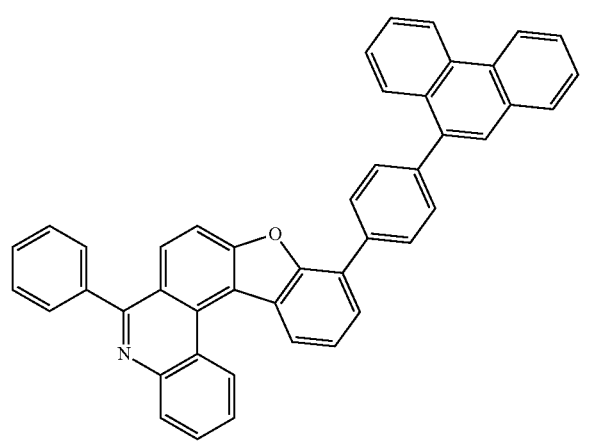
317
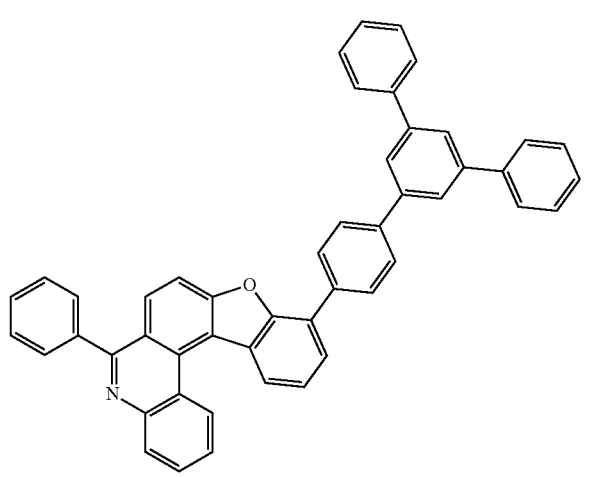
318
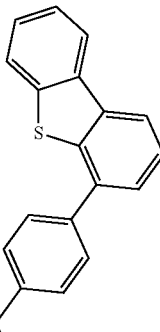
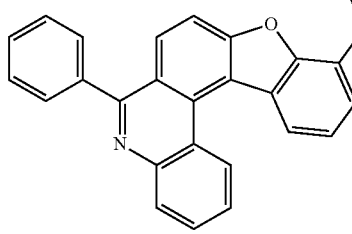
319
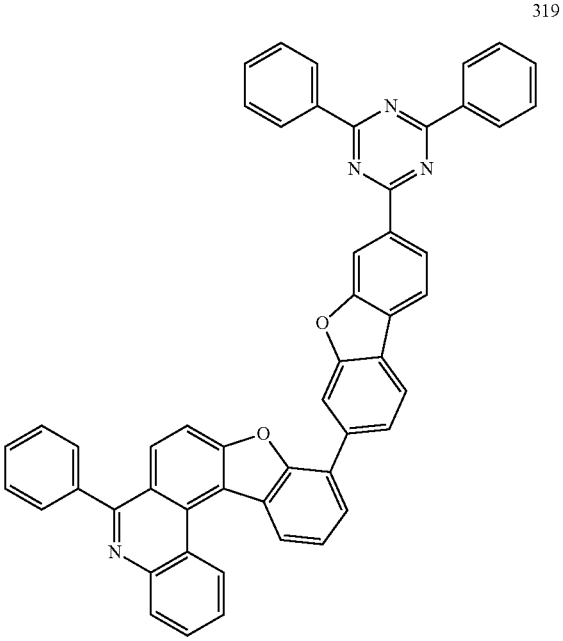

113
-continued
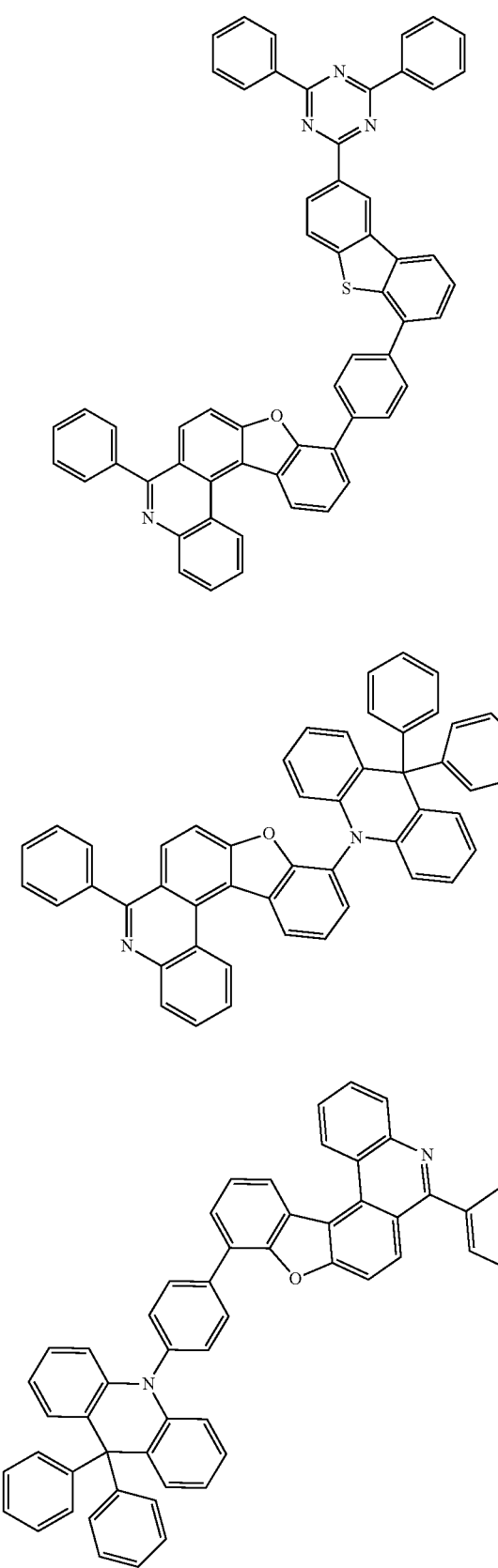
114
-continued
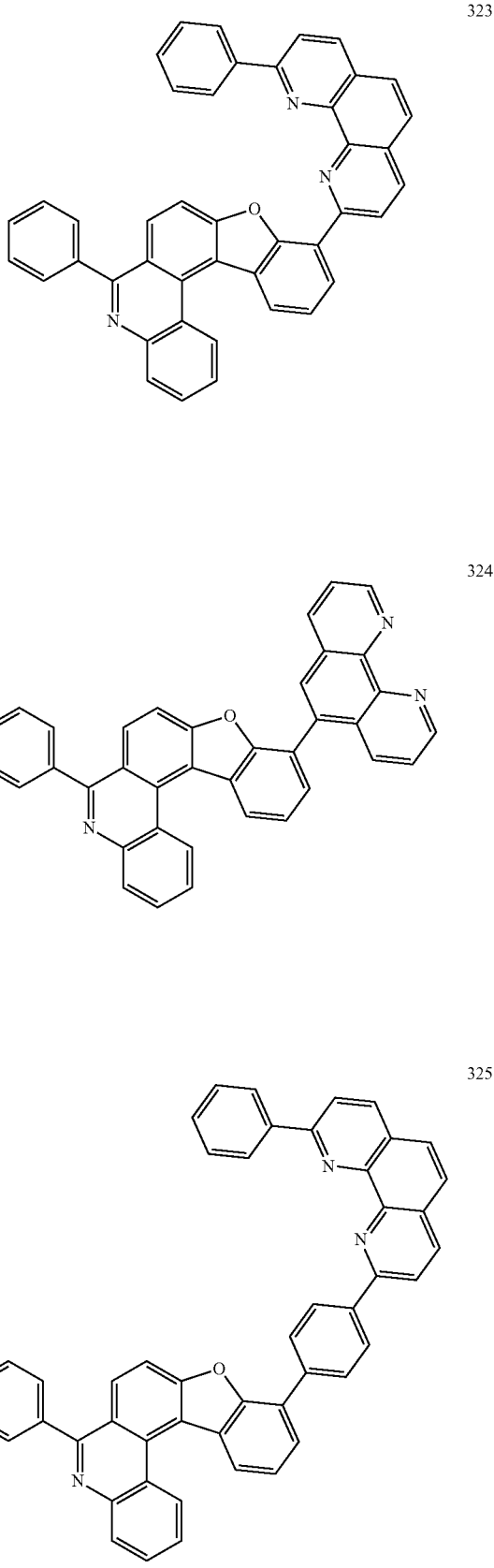

326
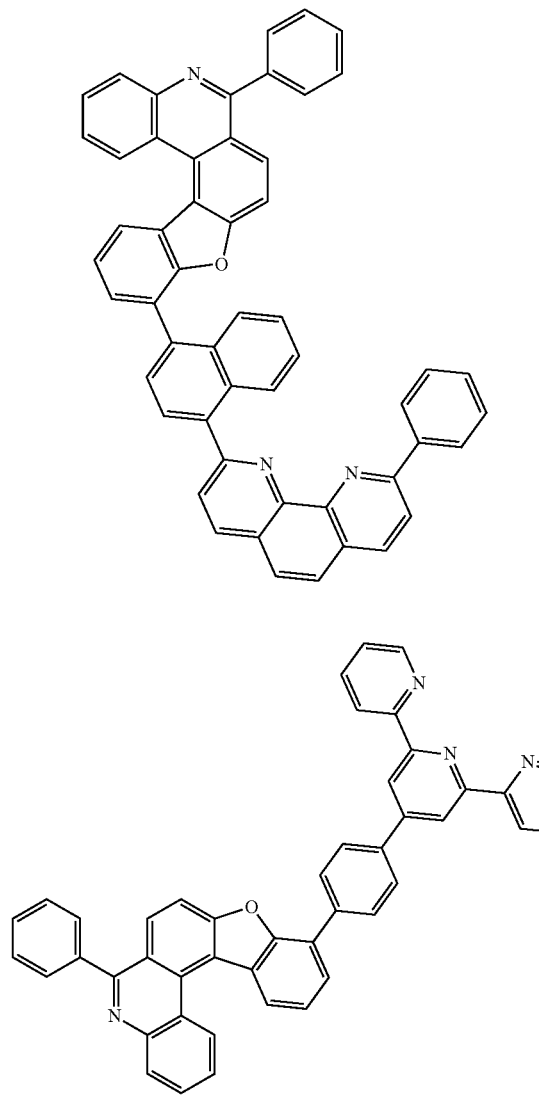
327
329
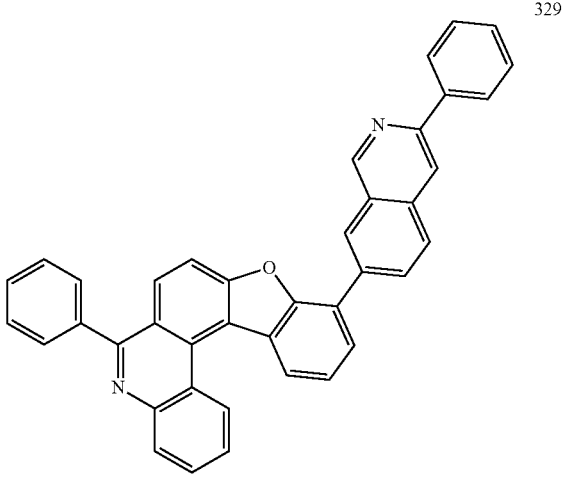
330
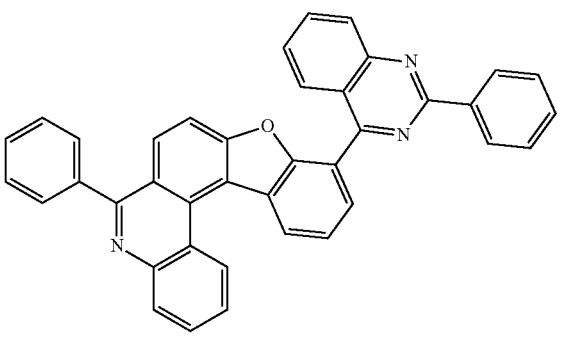
331
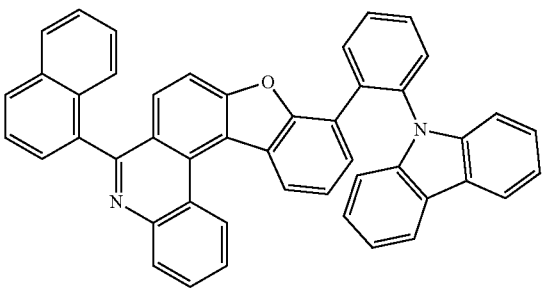
328
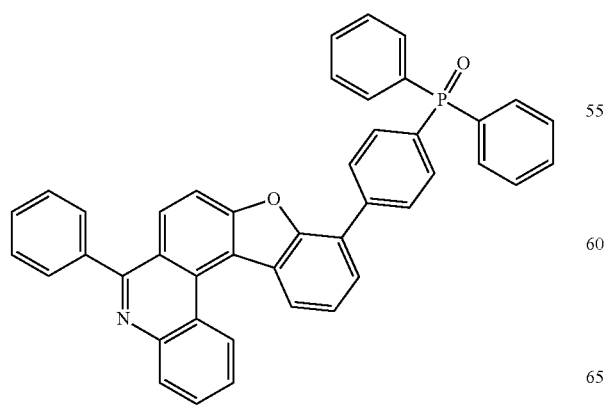
332
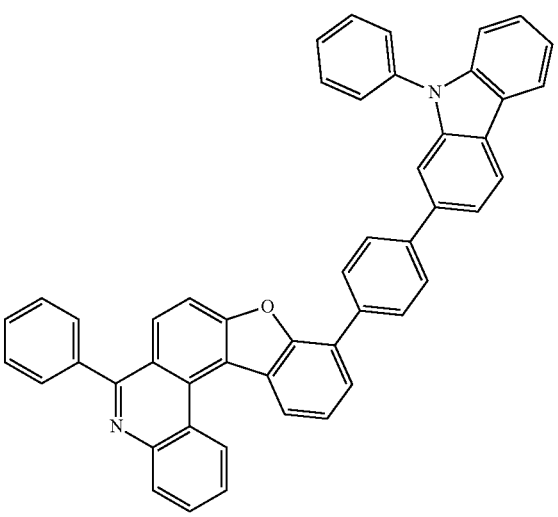

333
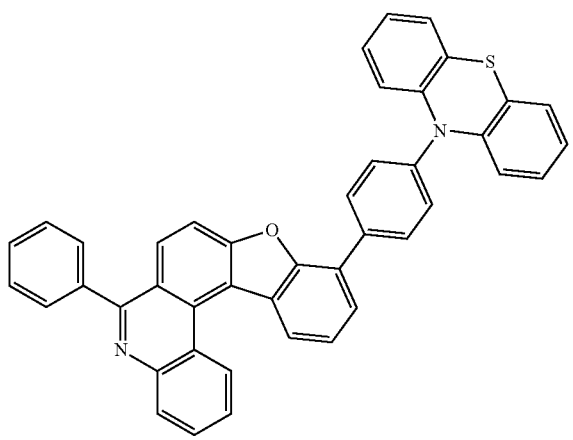
334
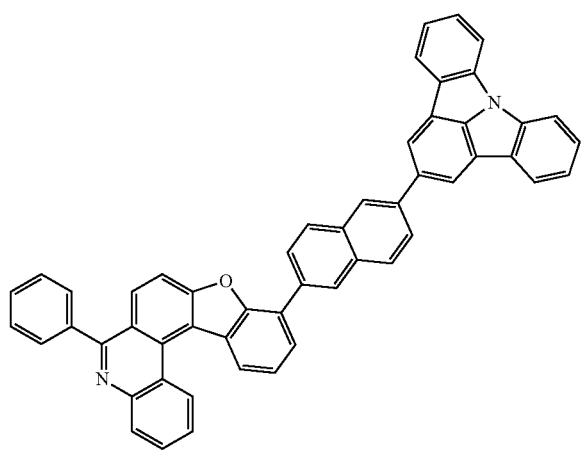
335
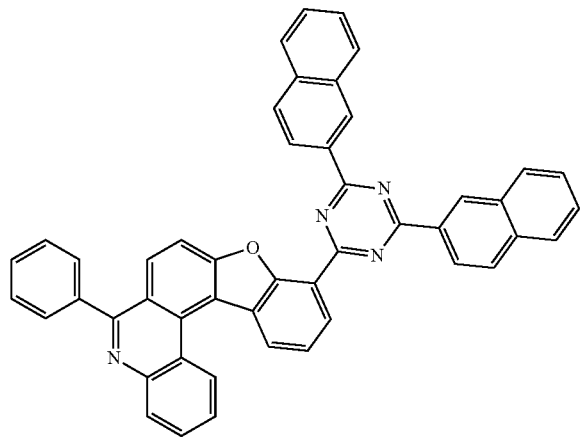
336
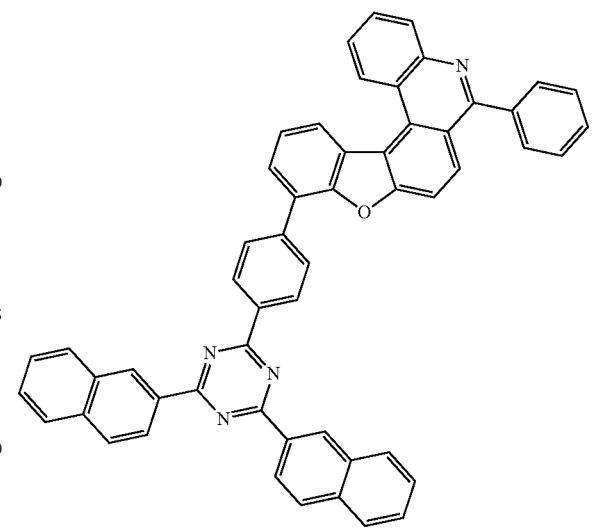
337
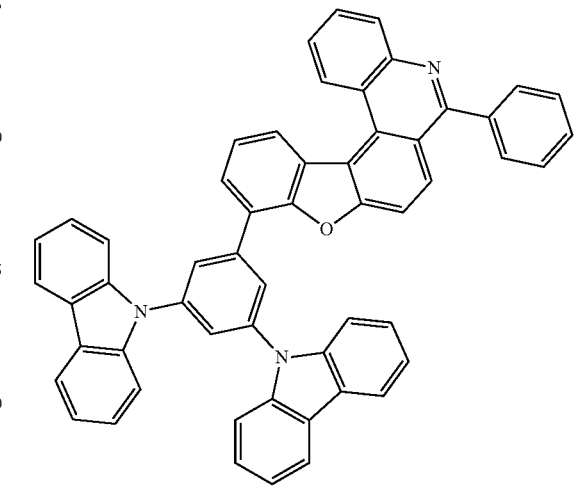
338
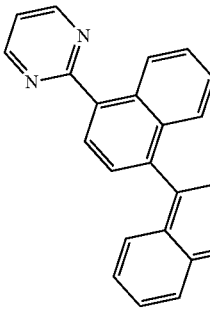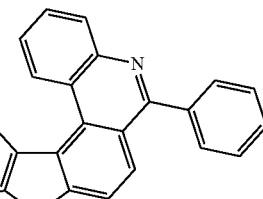

339
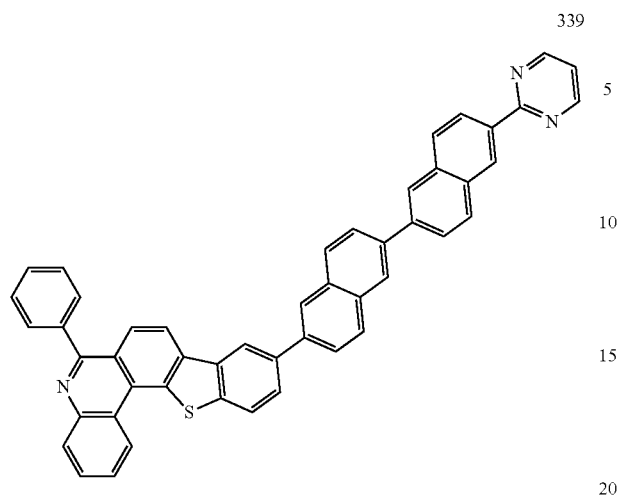
340
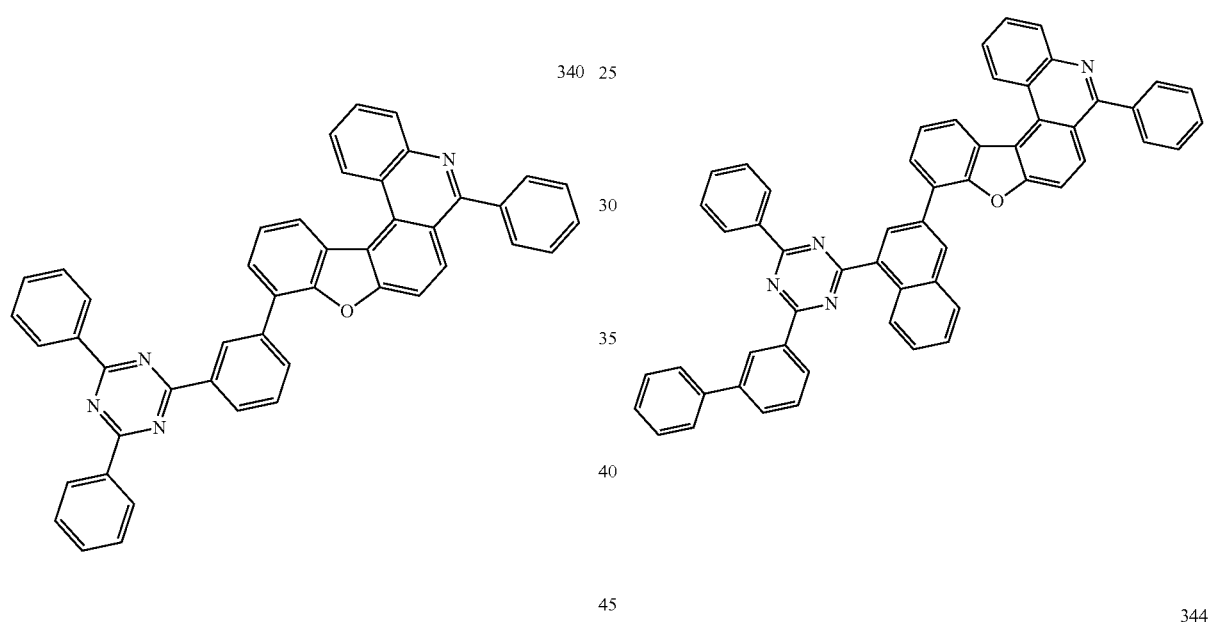
341
342
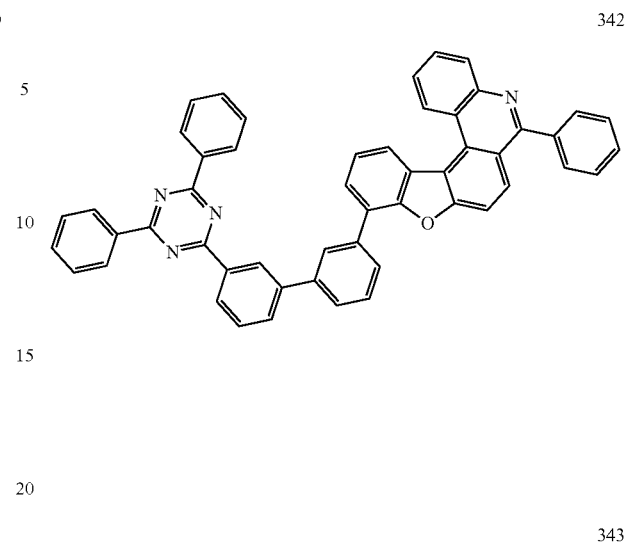
343
344
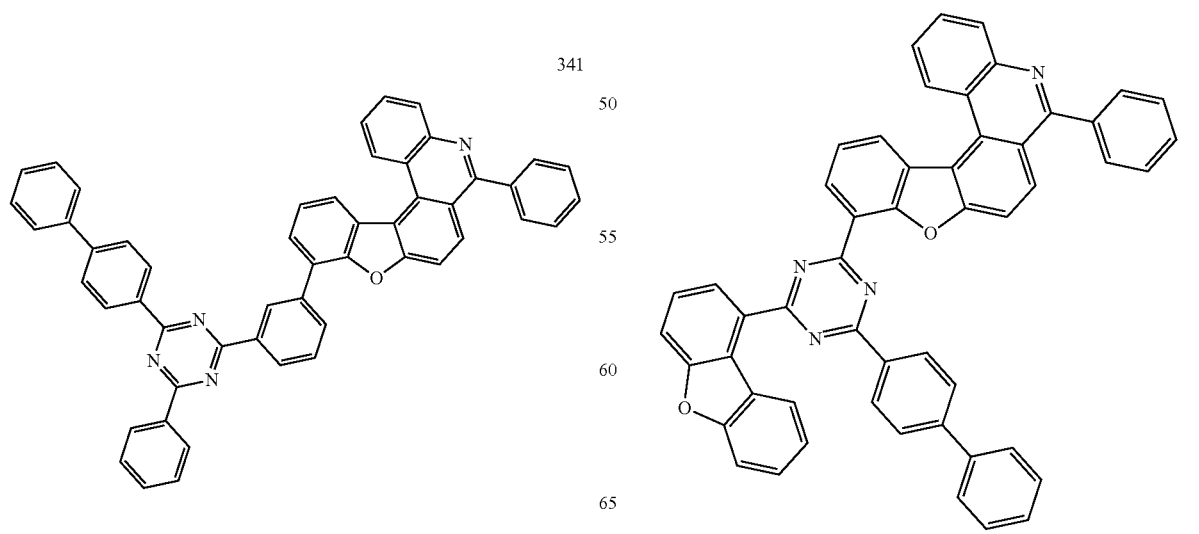

345
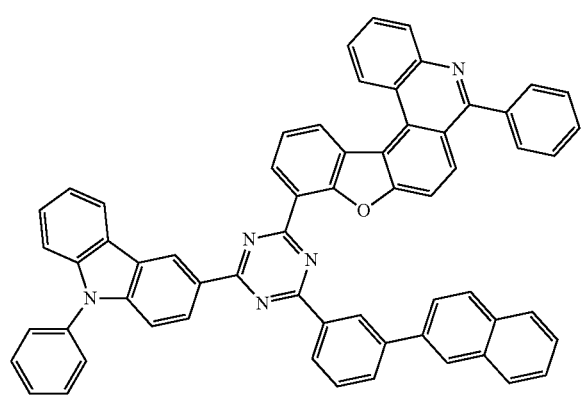
346
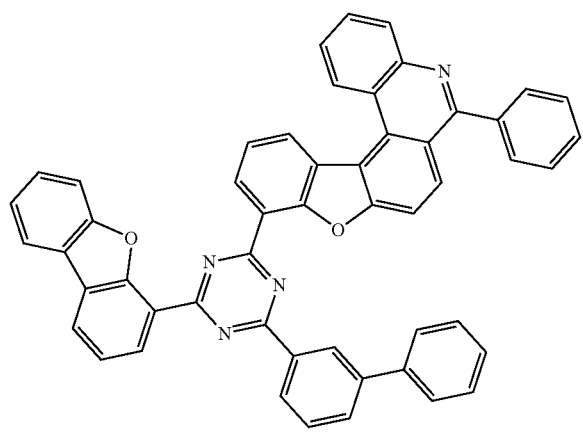
347
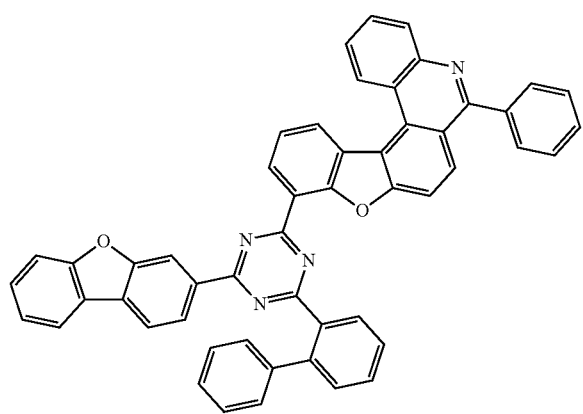
348
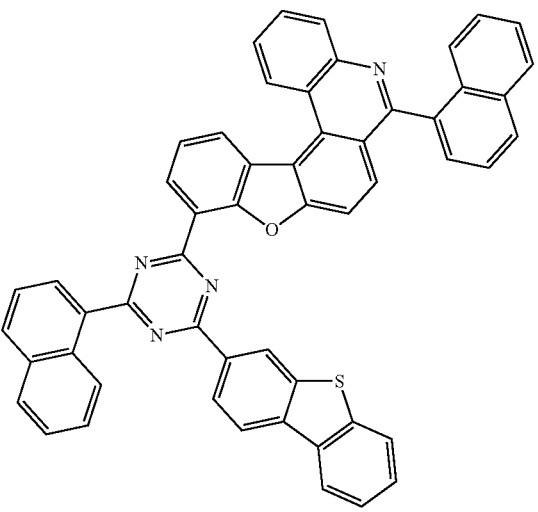
349
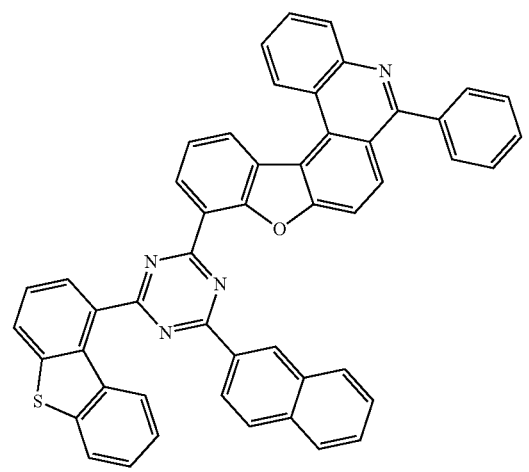
350
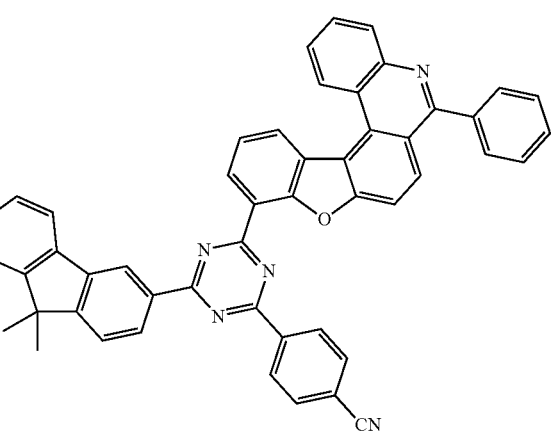

-continued
351
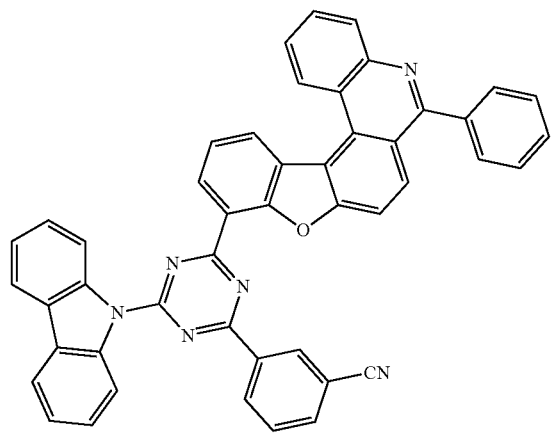
354
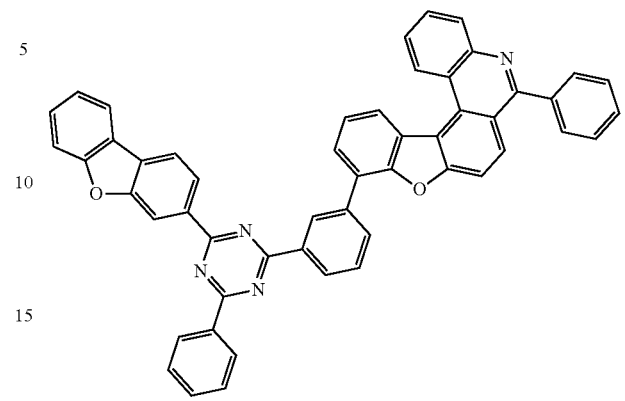
352
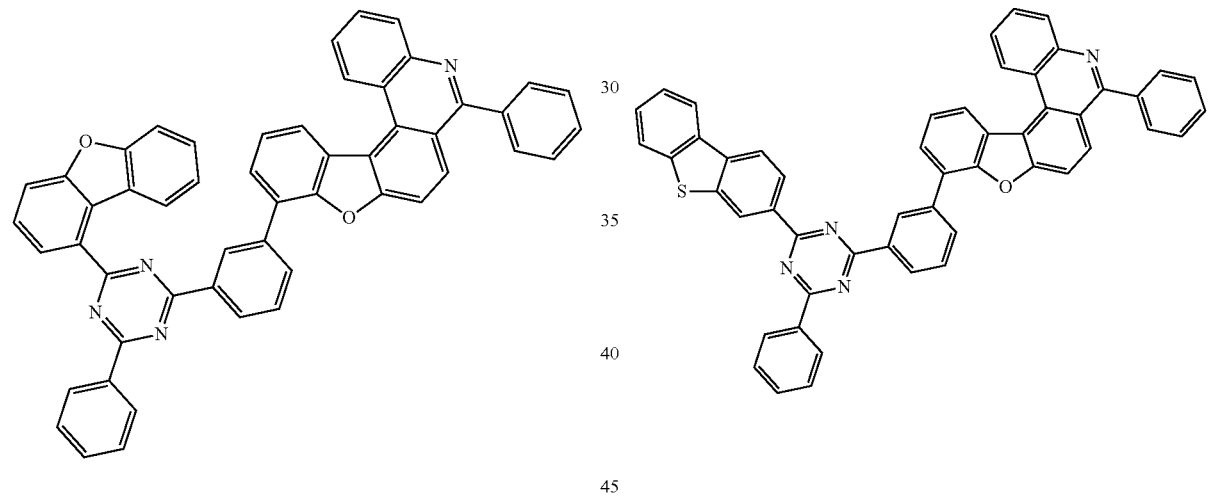
355
353
356
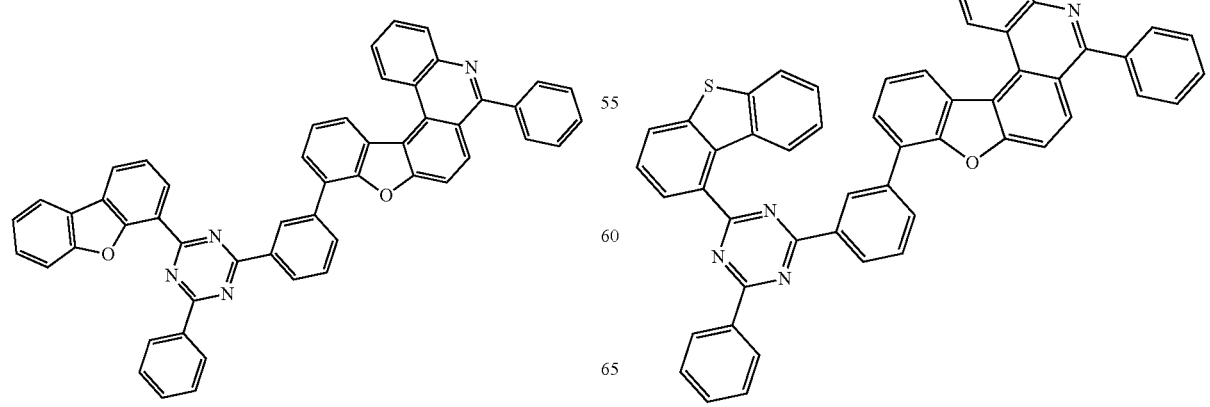

125
-continued
357
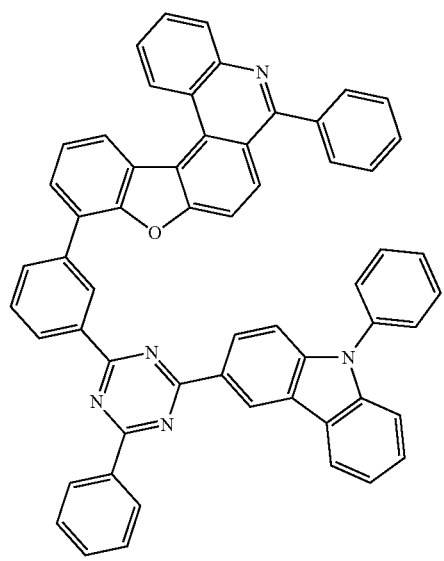
358
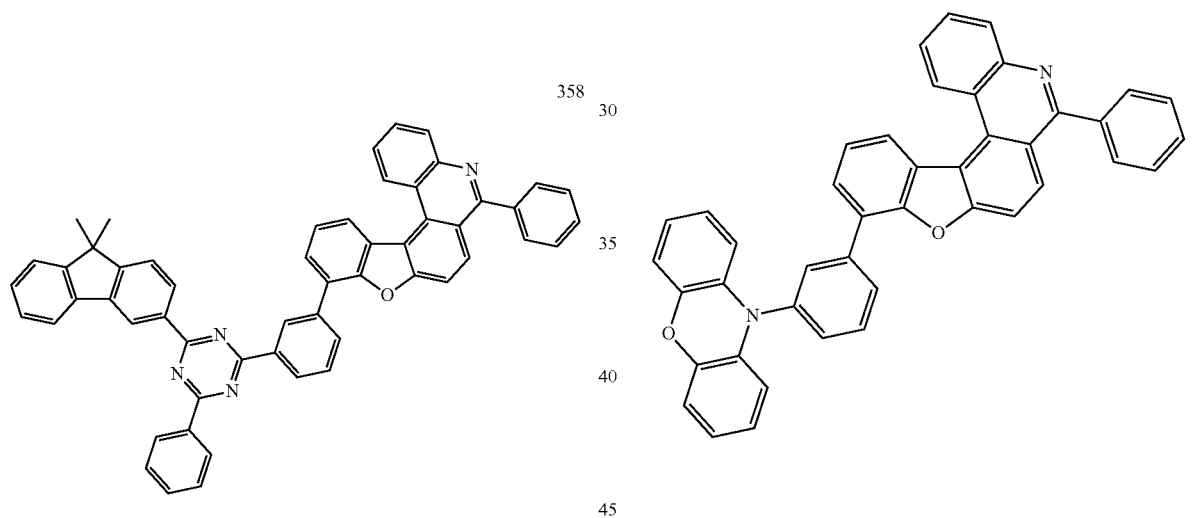
359
360
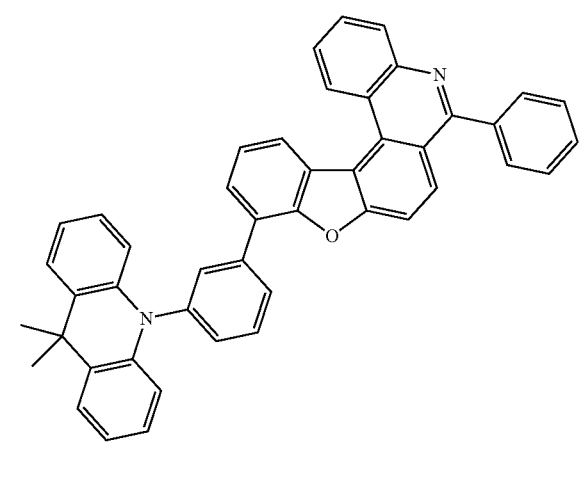
126
-continued
361
362
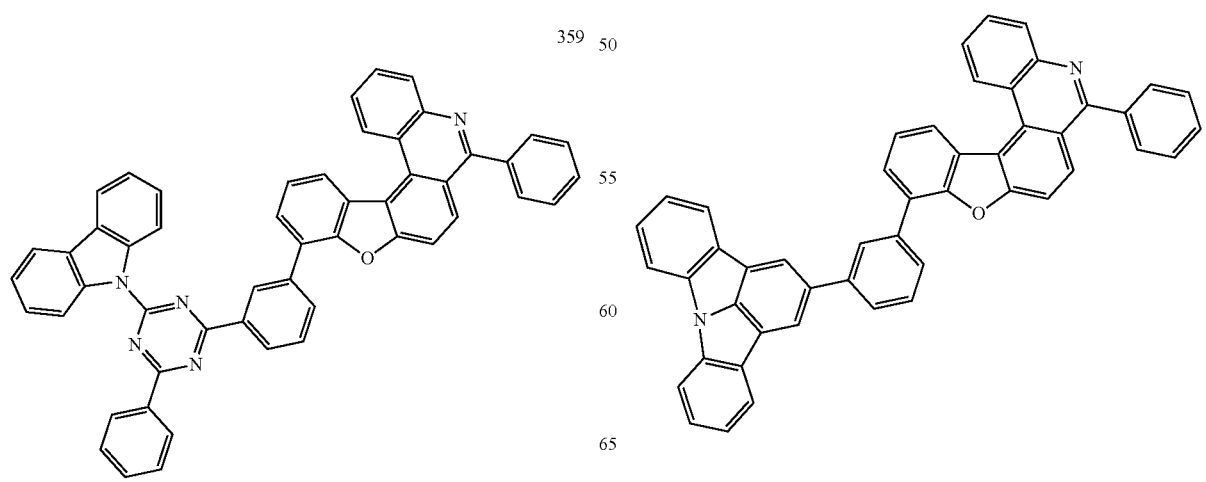

127
-continued
363
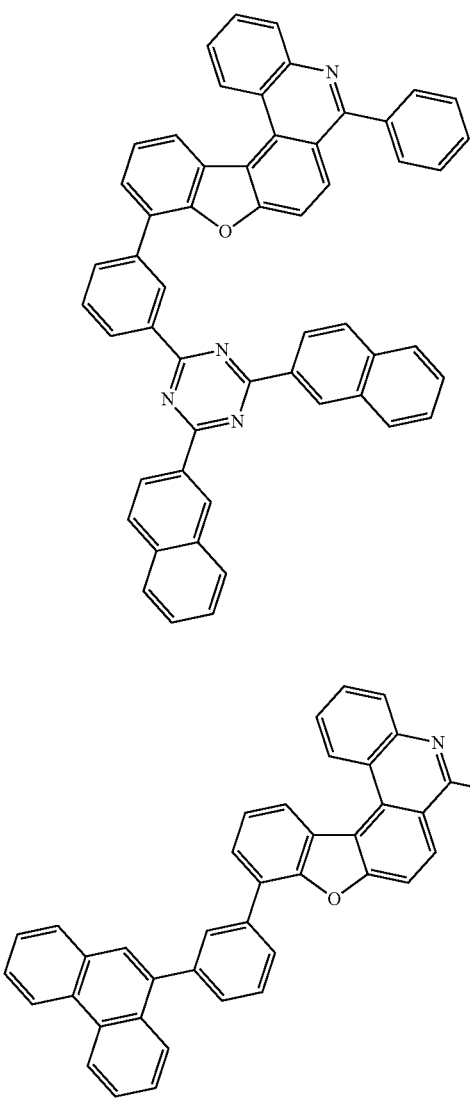
364
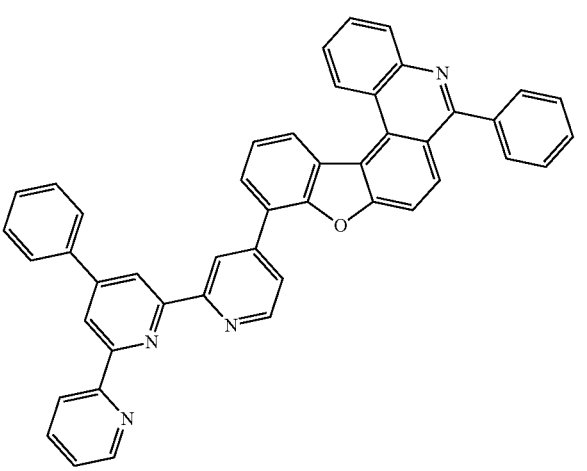
365
128
-continued
366
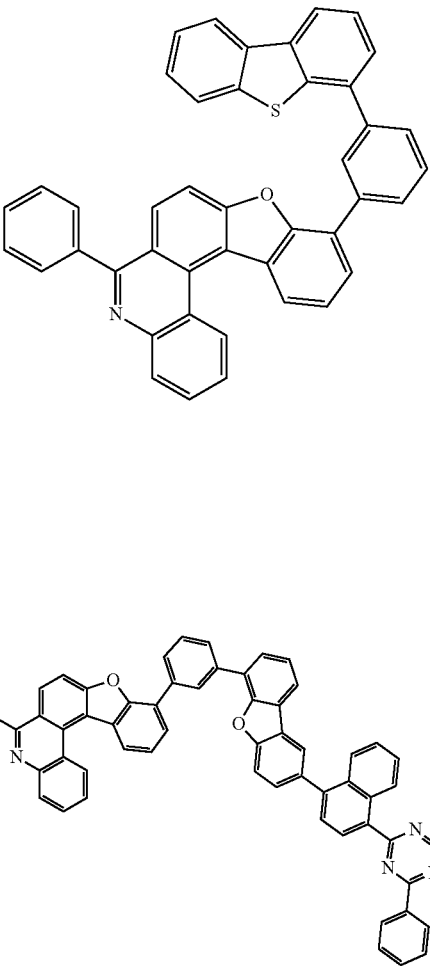
367
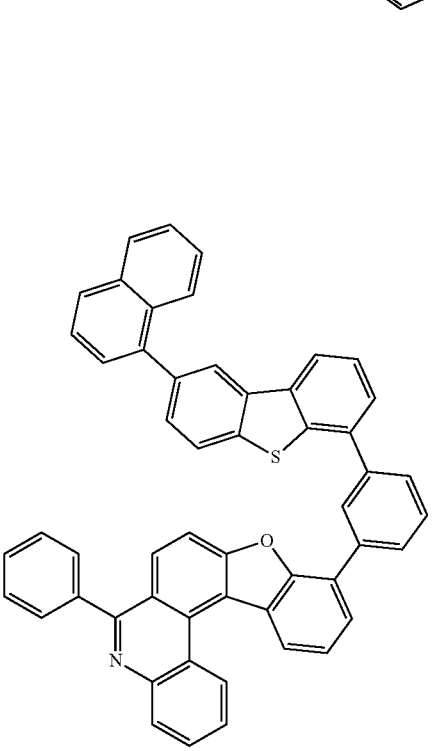
368

369
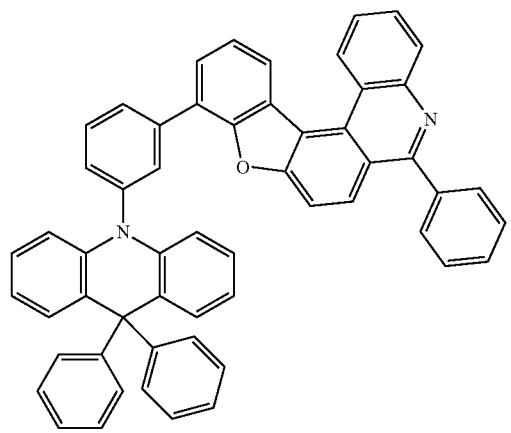
370
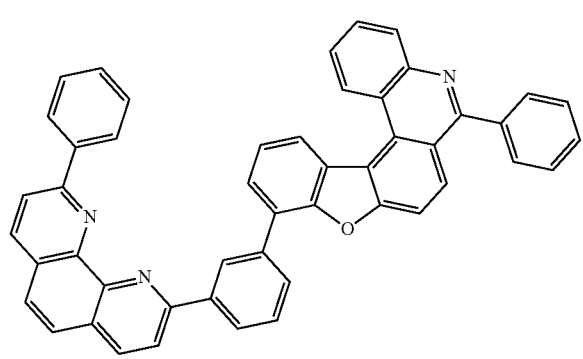
371
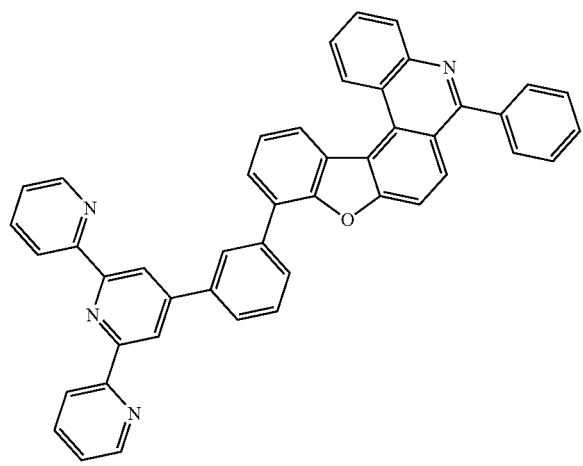
372
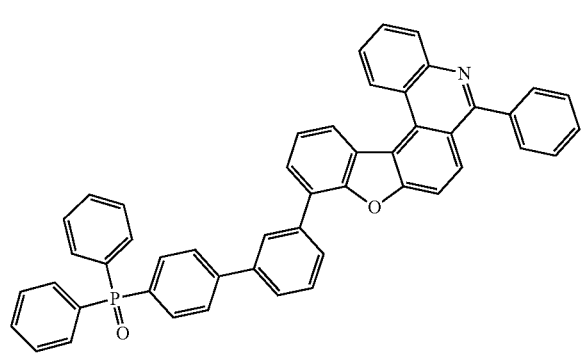
373
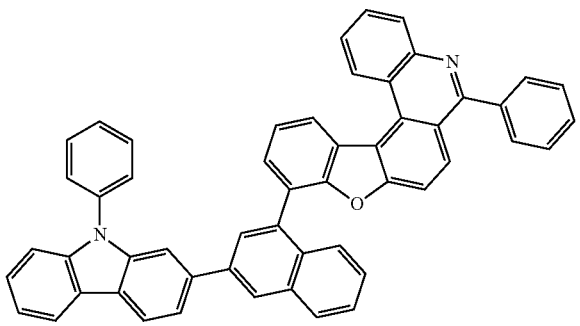
374
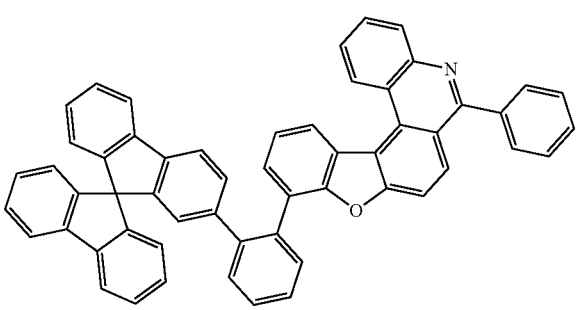
375
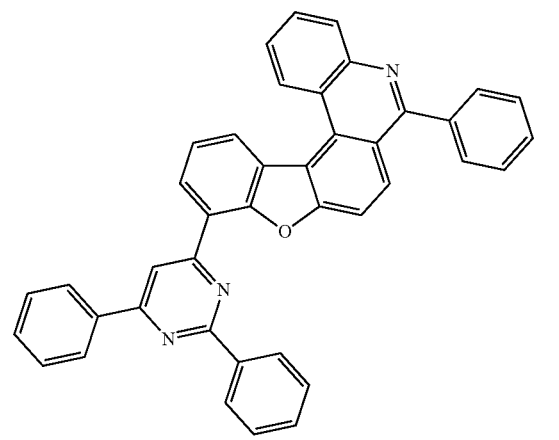
376
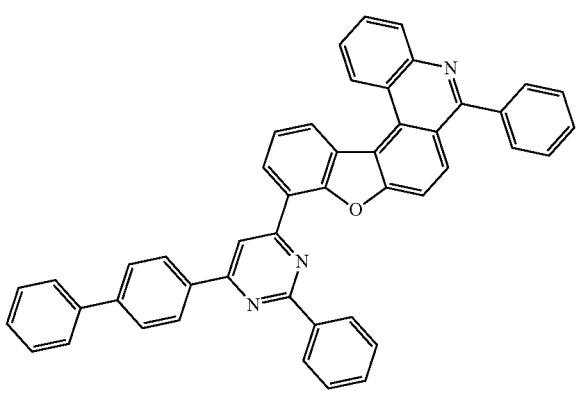

377
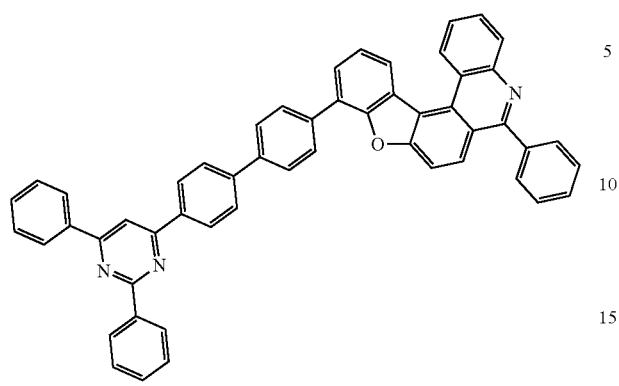
378
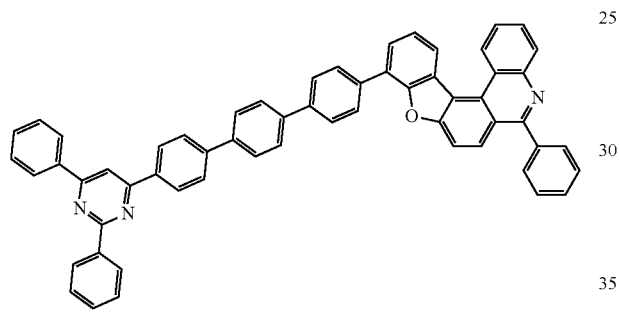
379
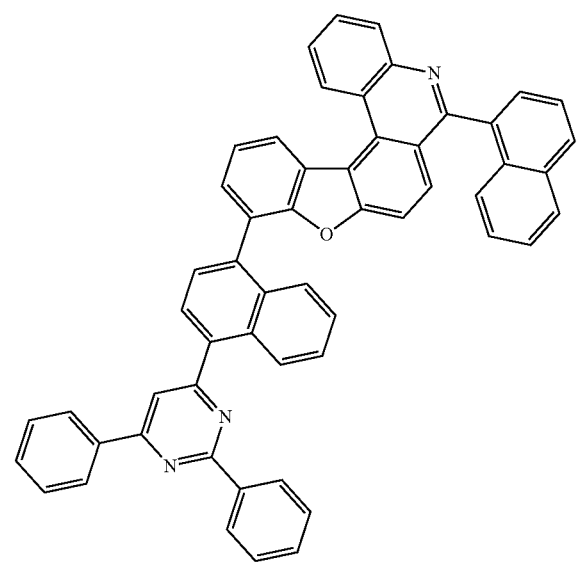
380
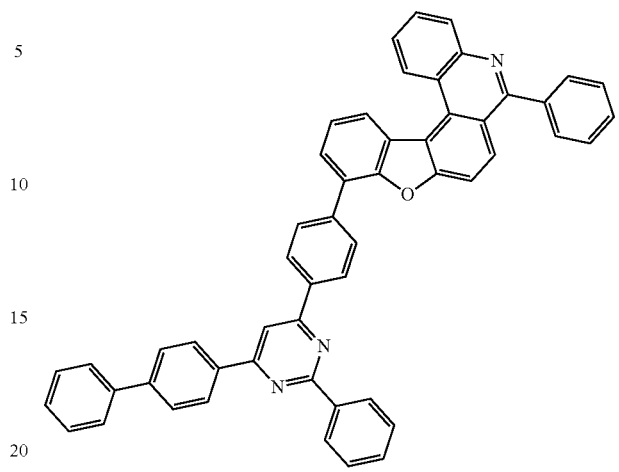
381
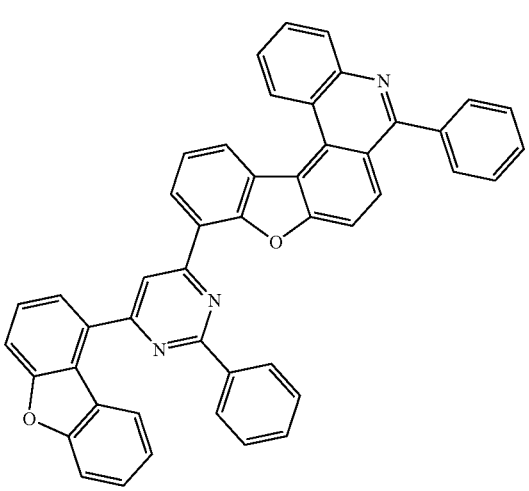
382

133
-continued
383
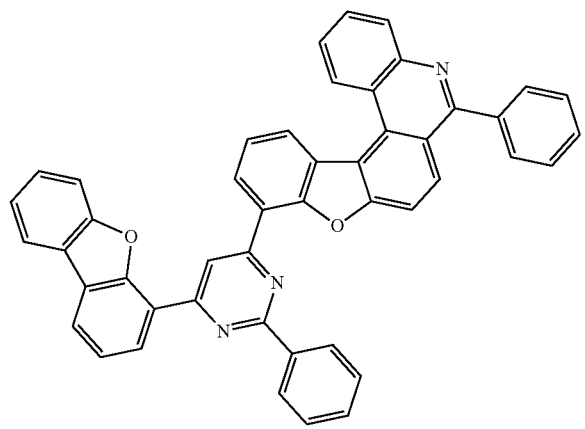
384
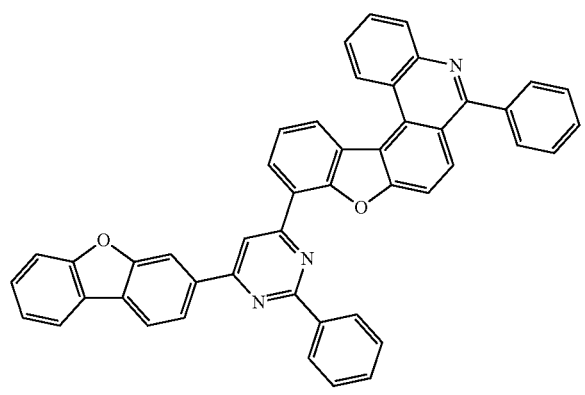
385
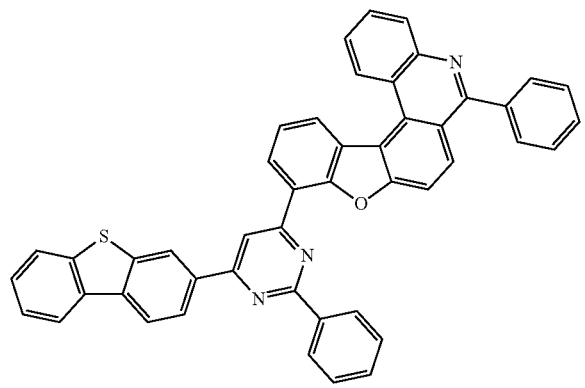
134
-continued
386
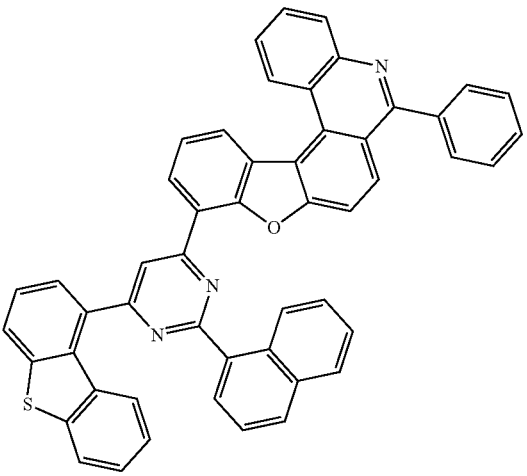
387
388
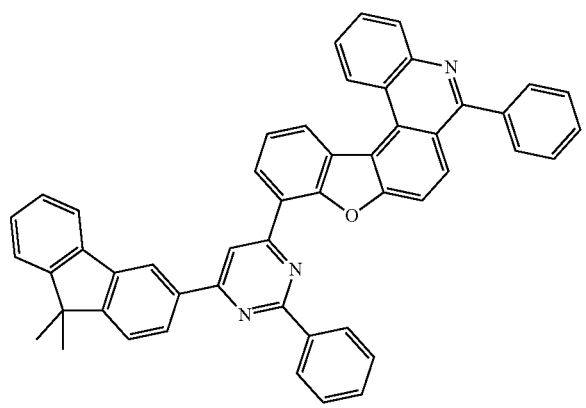

389
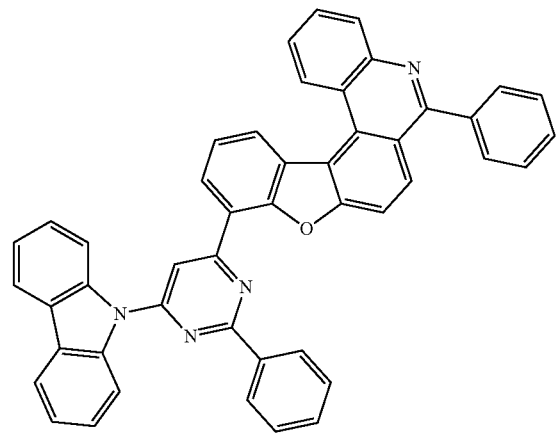
390
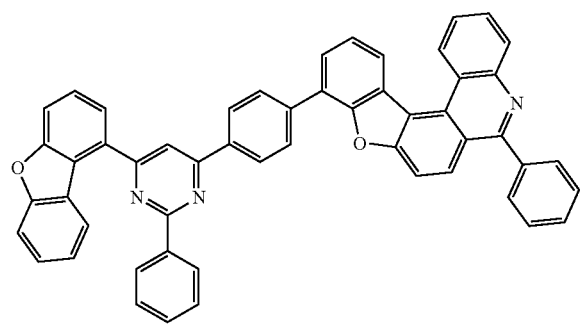
391
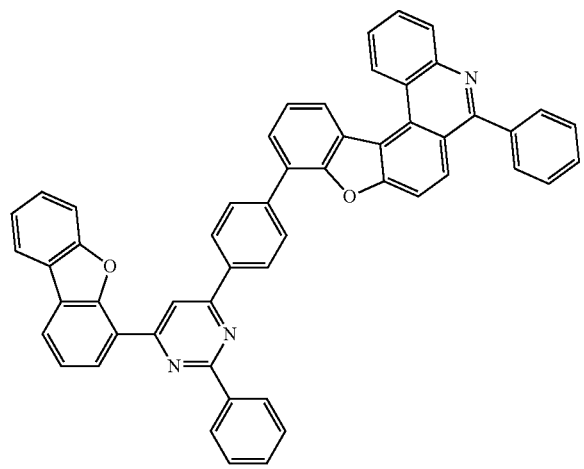
392
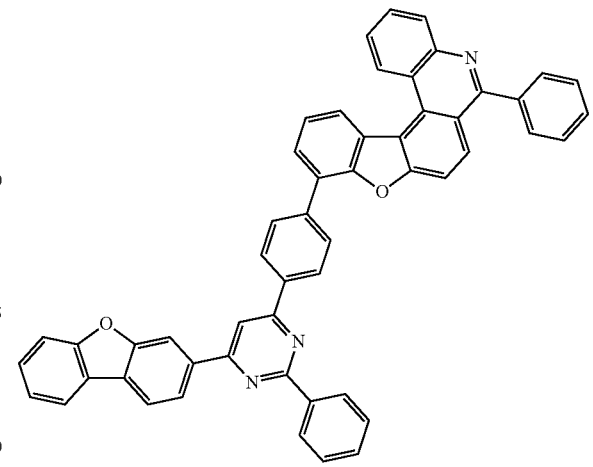
393
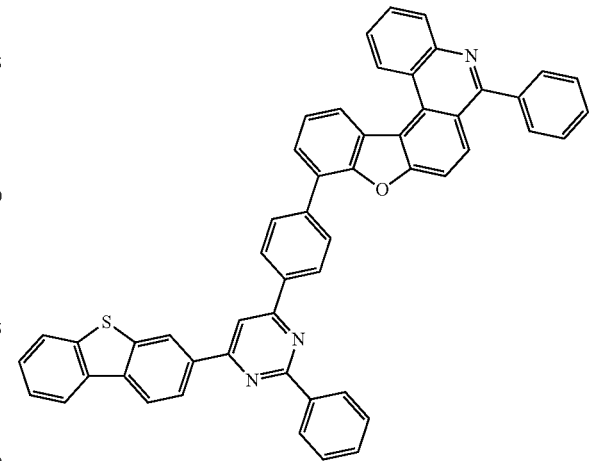
394
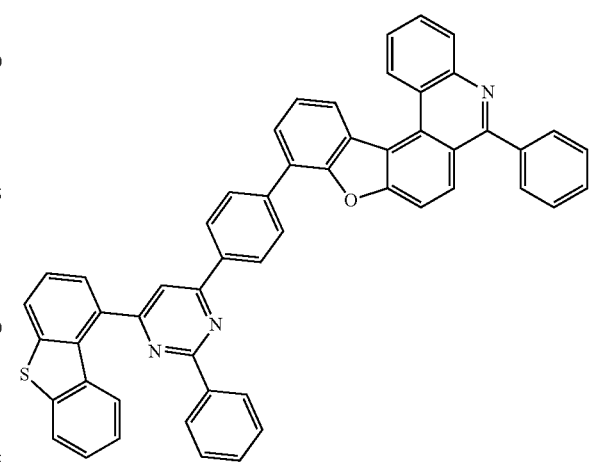

395
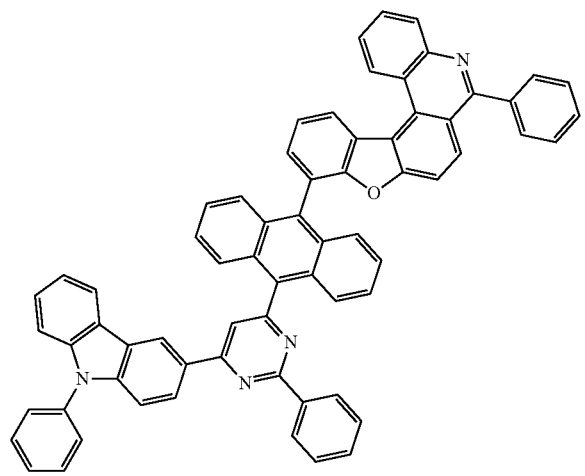
396
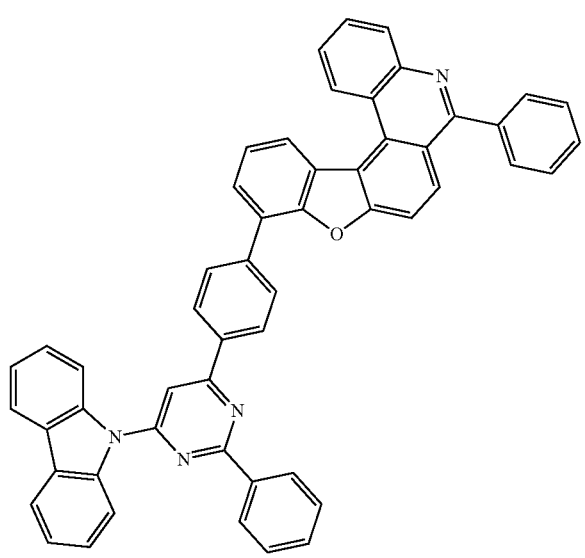
397
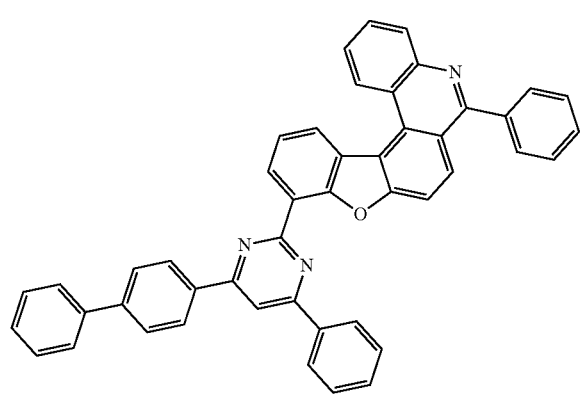
398
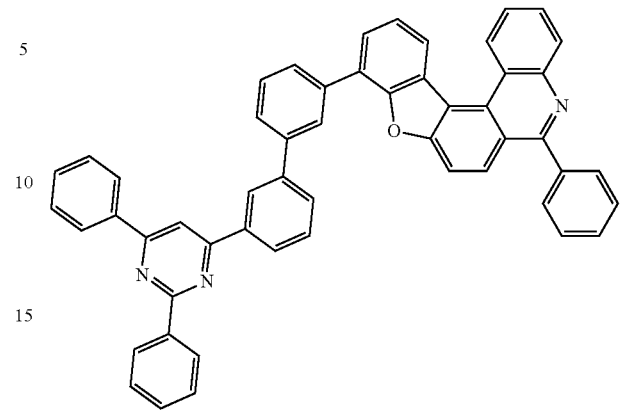
399
400
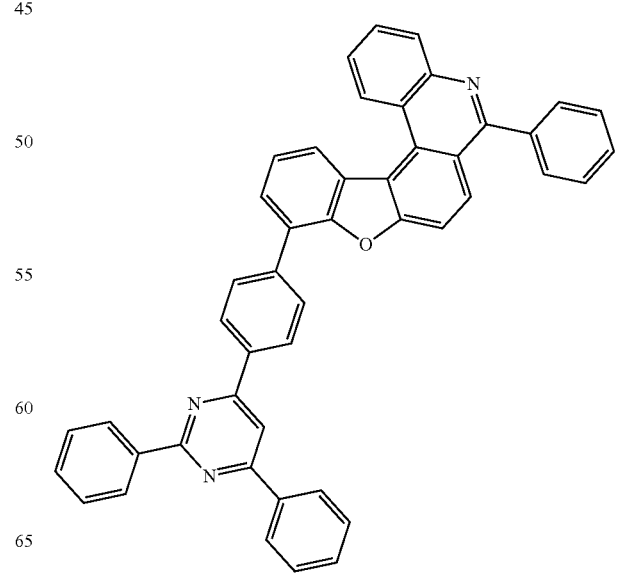

401
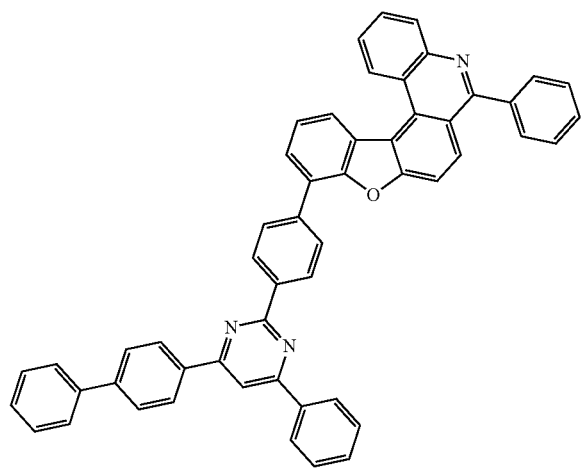
402
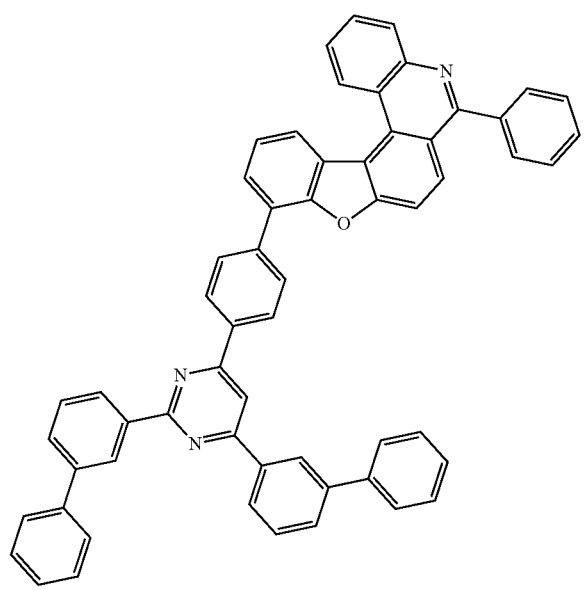
403
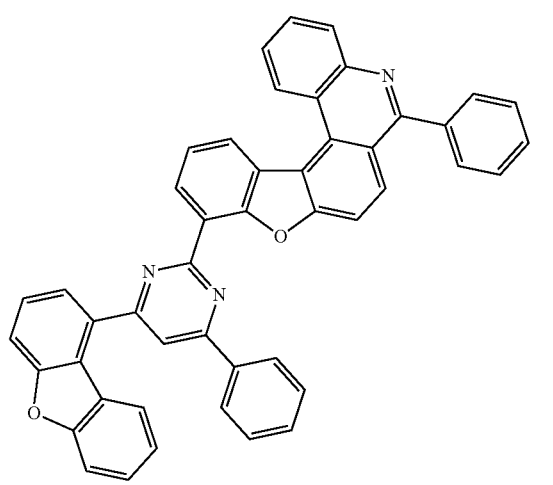
404
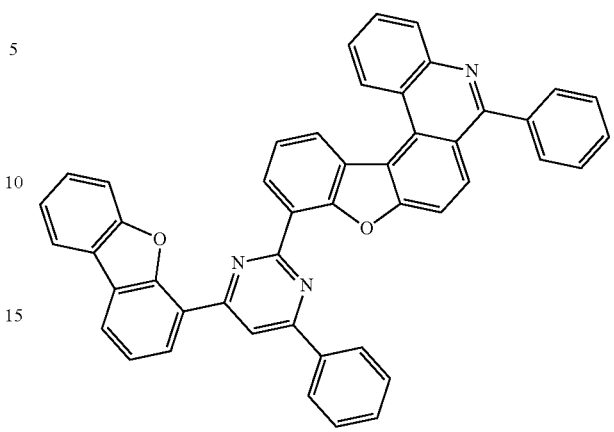
405
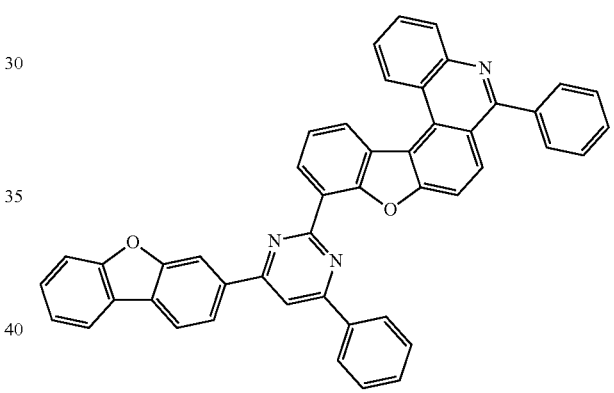
406
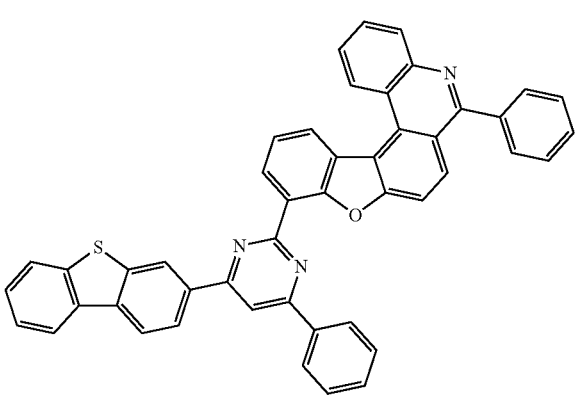

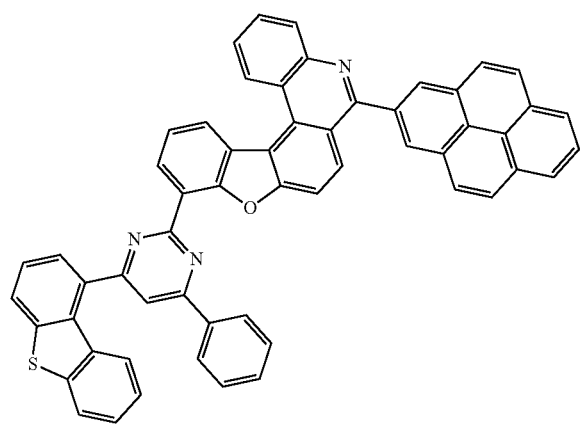
407
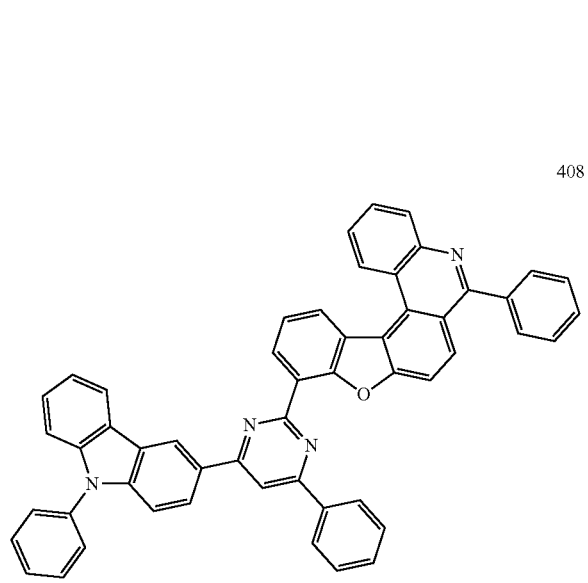
408
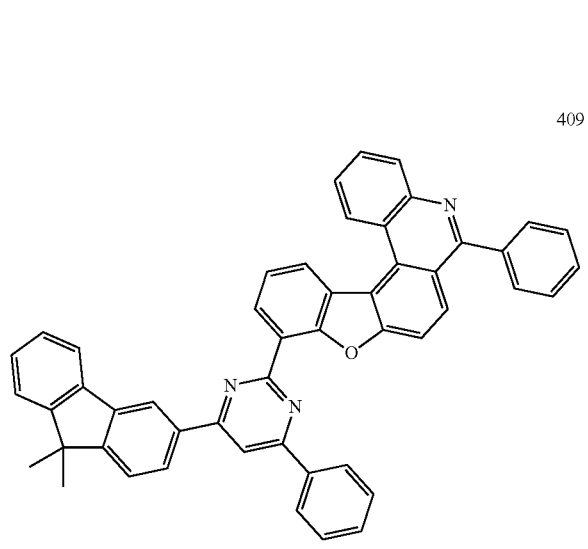
409
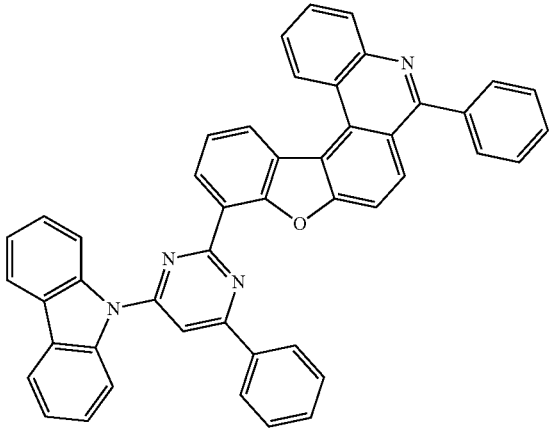
410
411
412

413
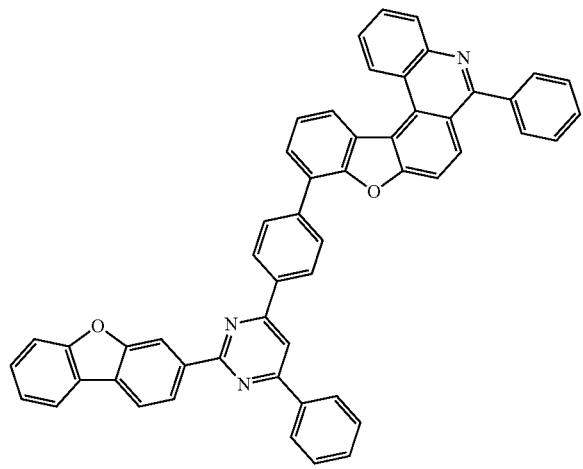
414
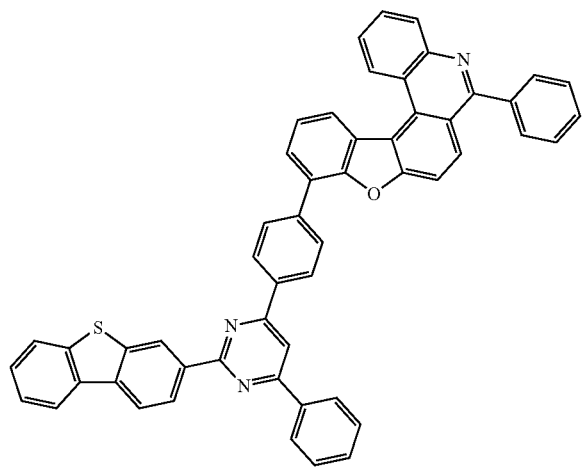
415
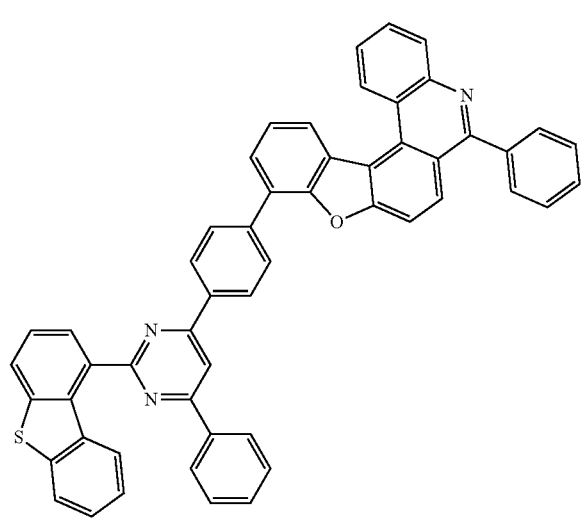
416
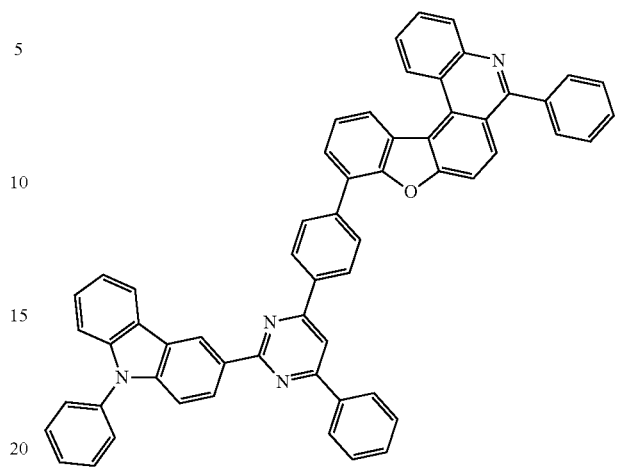
417
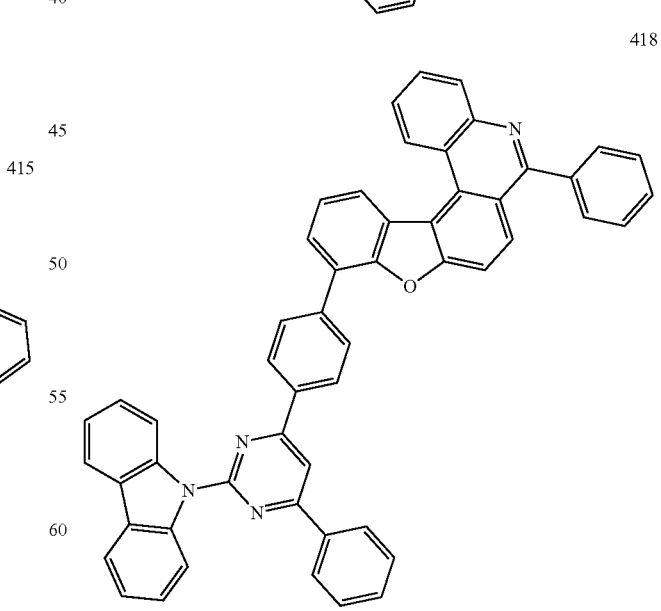
418

419
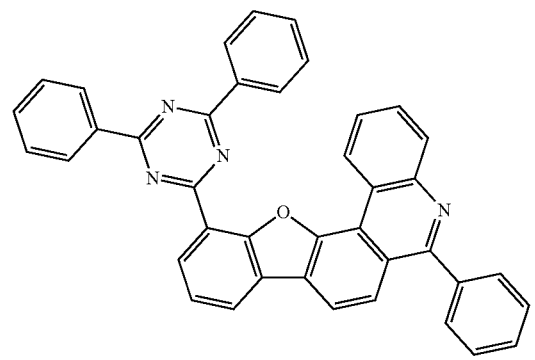
420
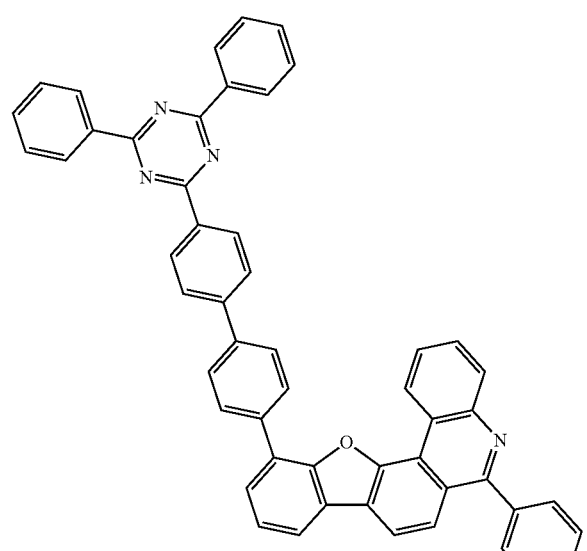
421
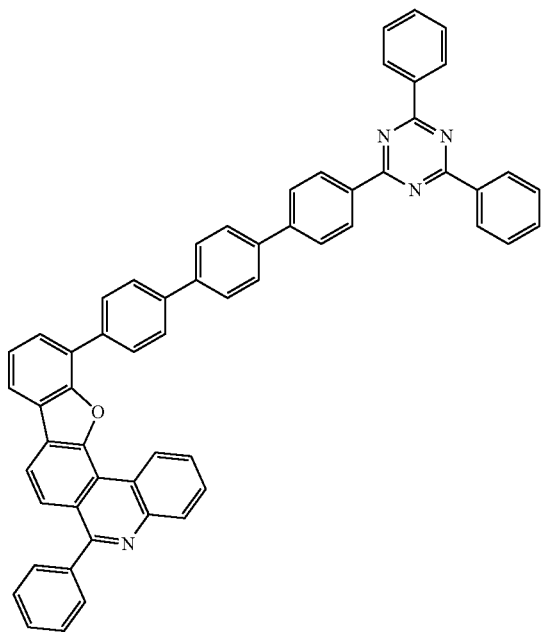
422
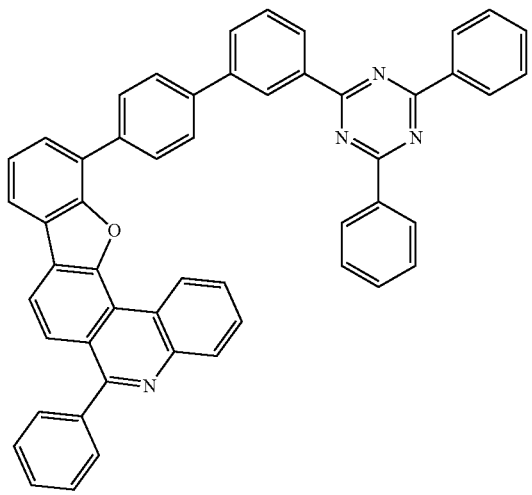
423
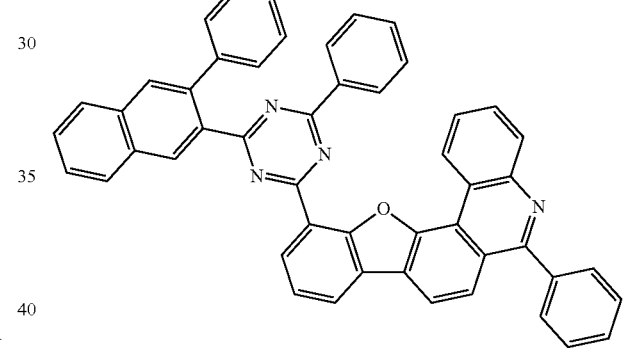
424
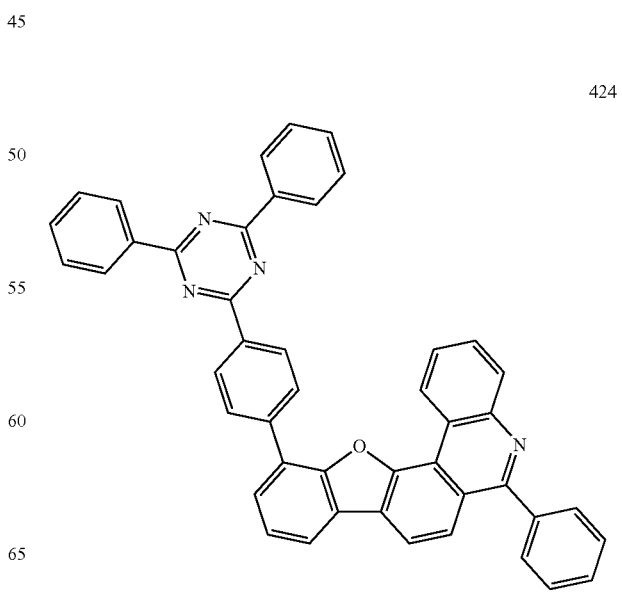

425
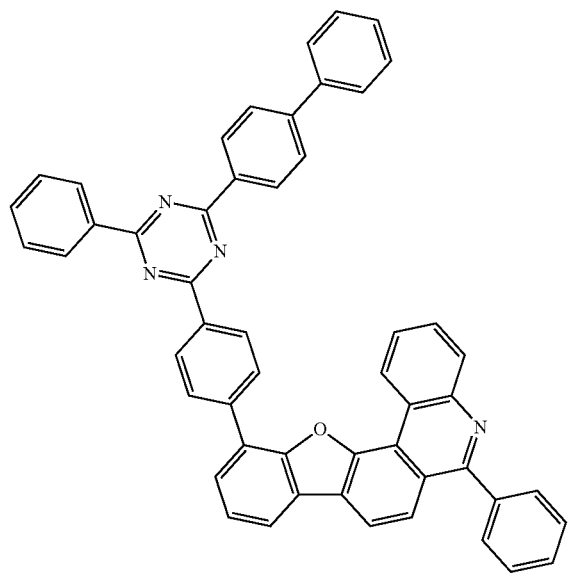
426
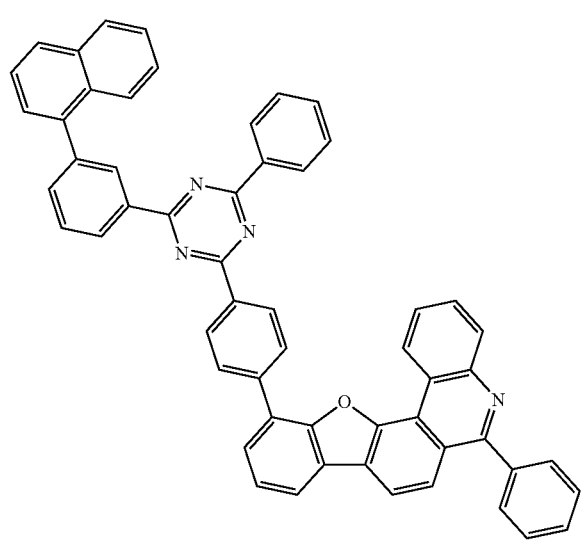
427
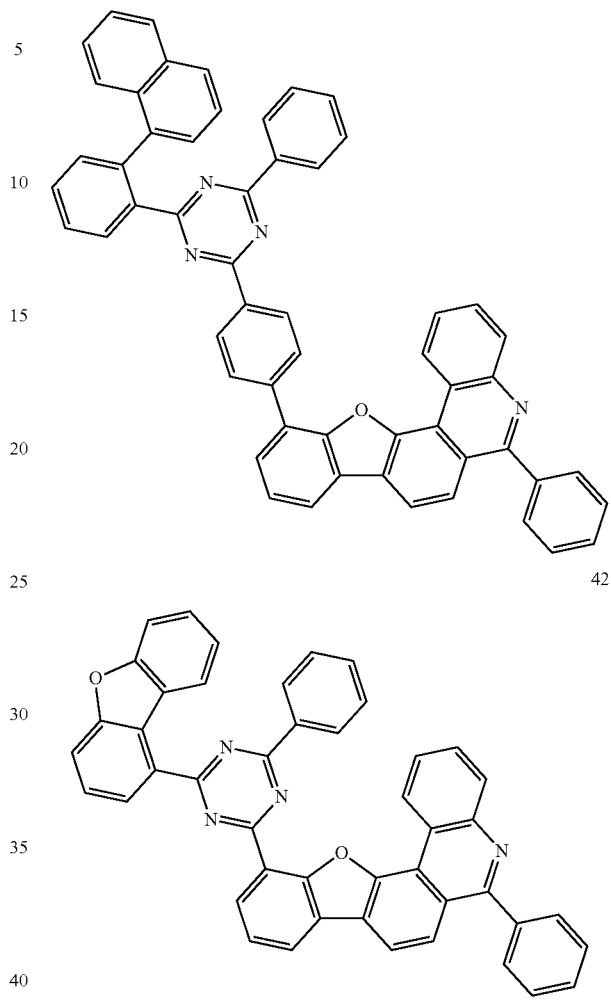
428
429
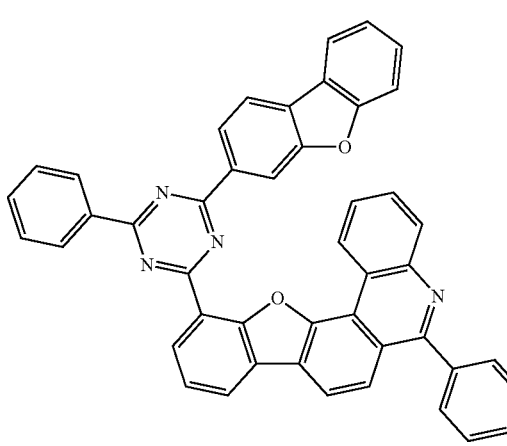

430
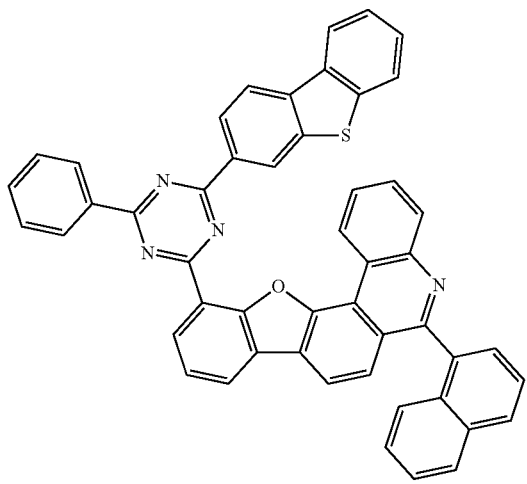
433
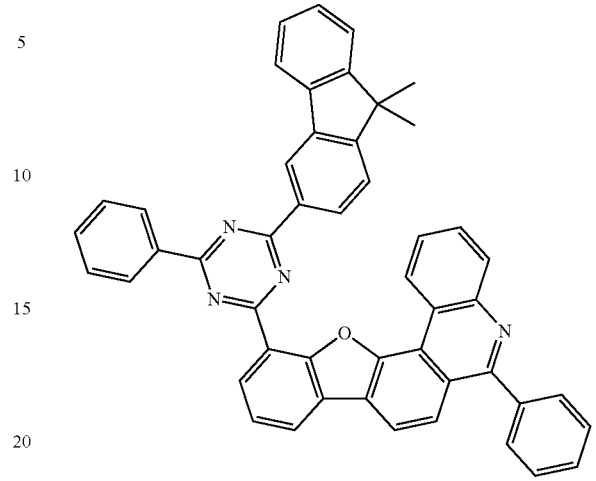
431
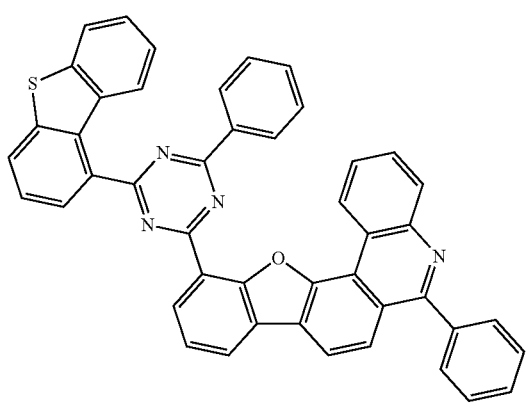
434
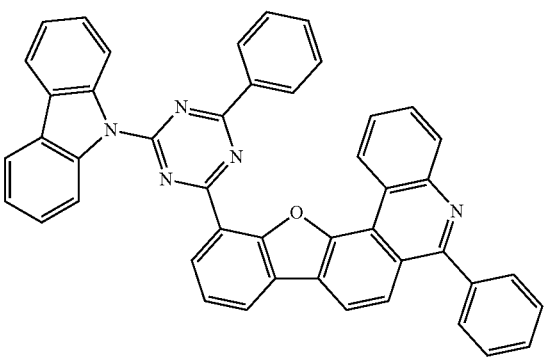
432
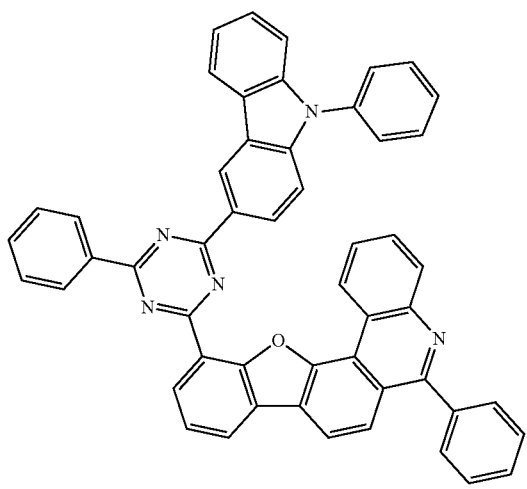
435
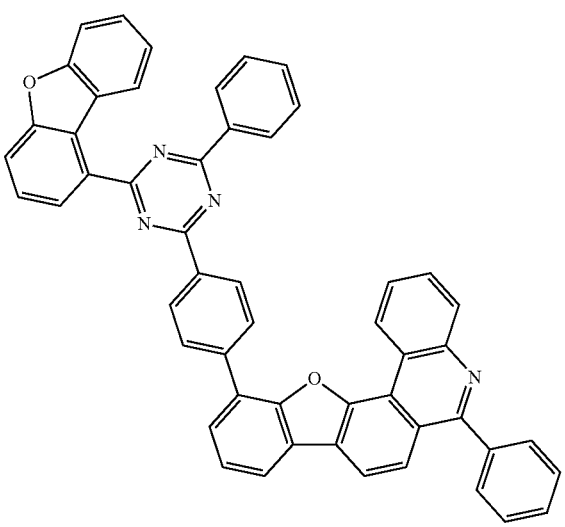

436
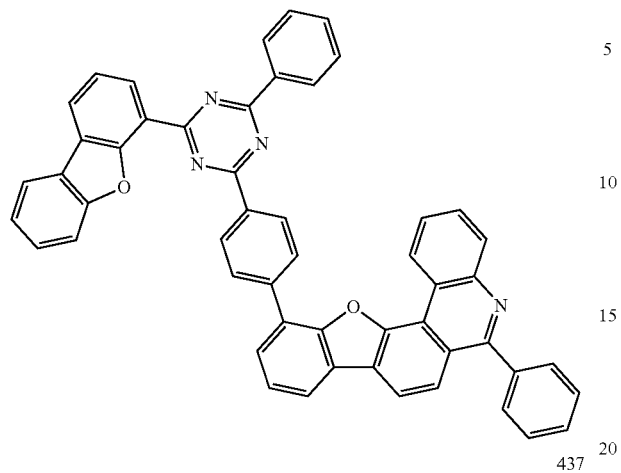
437
438
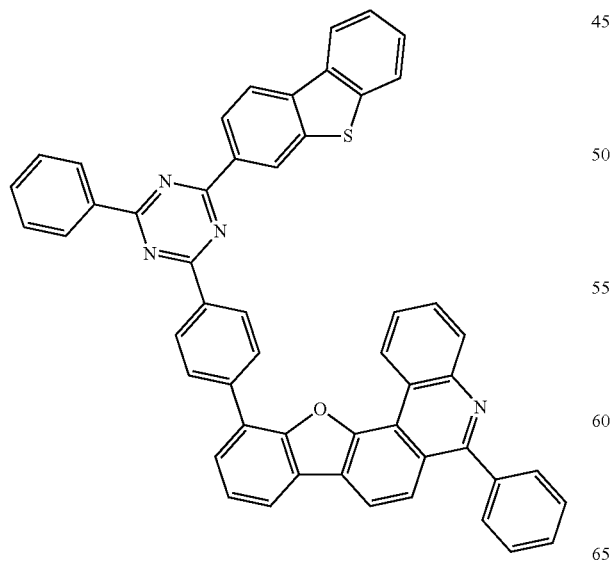
439
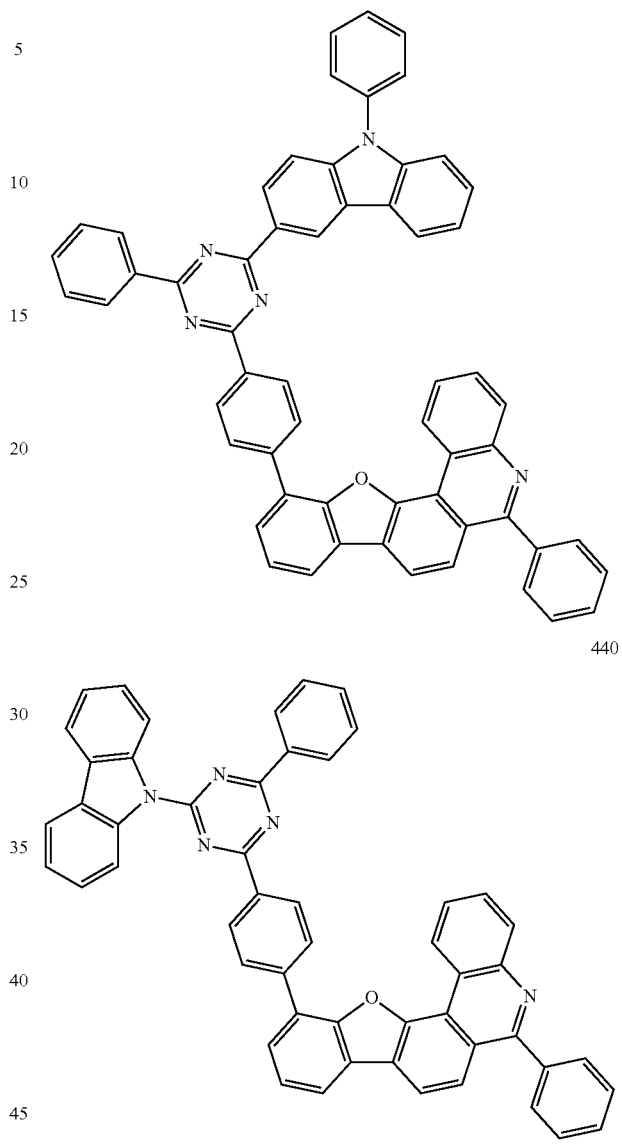
440
441
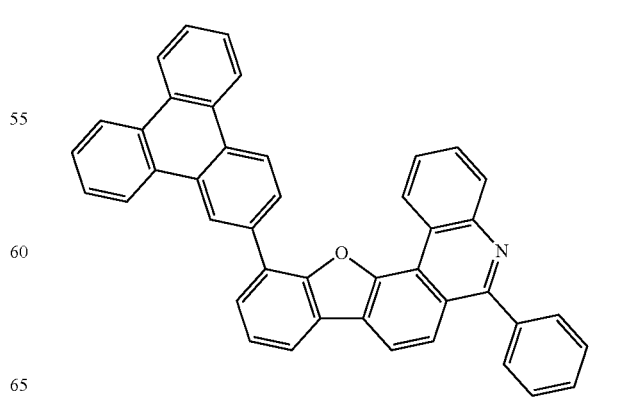

442
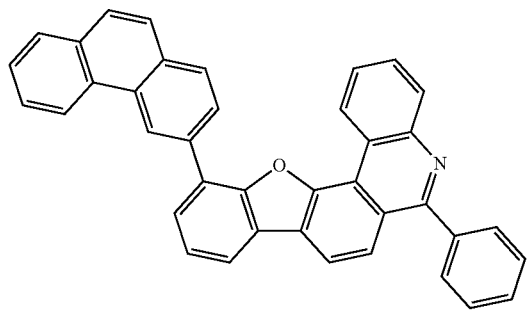
443
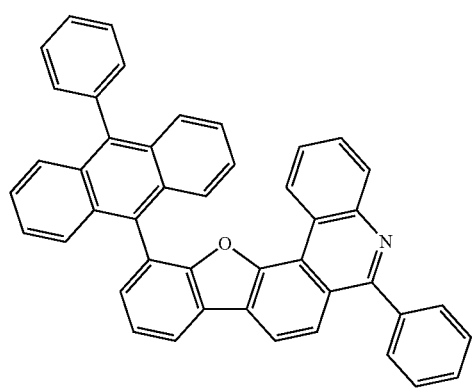
444
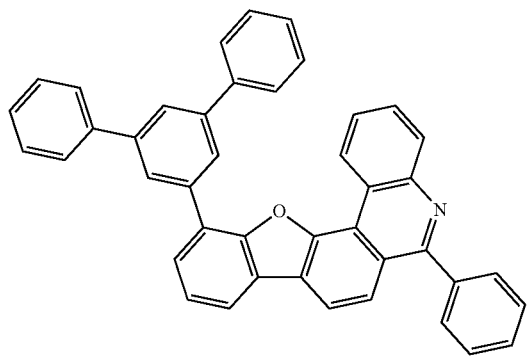
445
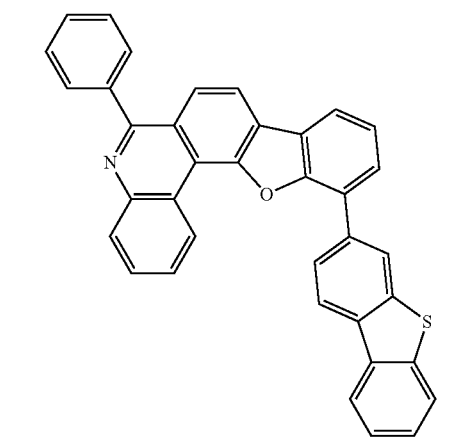
446
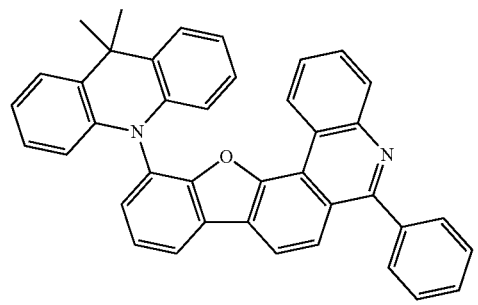
447
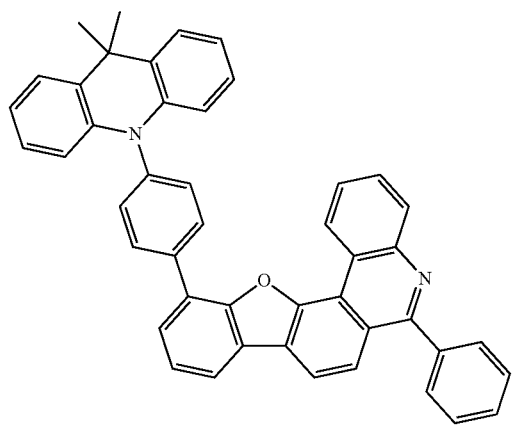
448
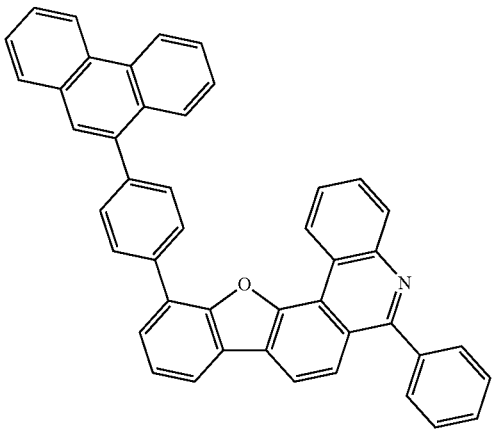
449
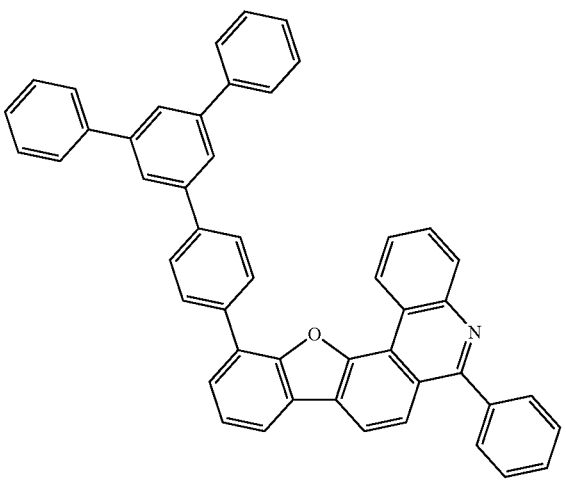

450
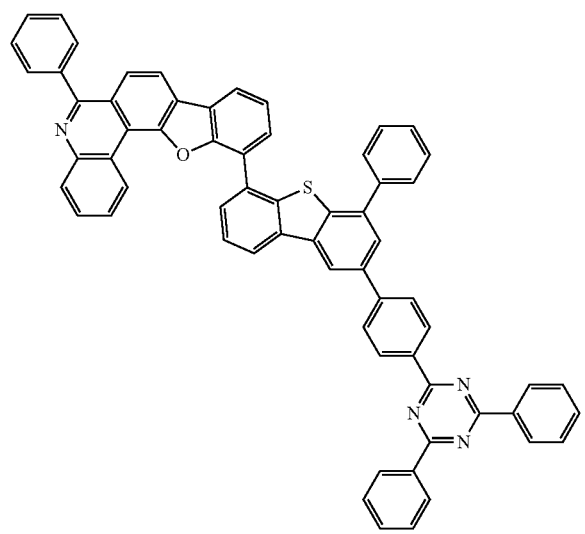
451
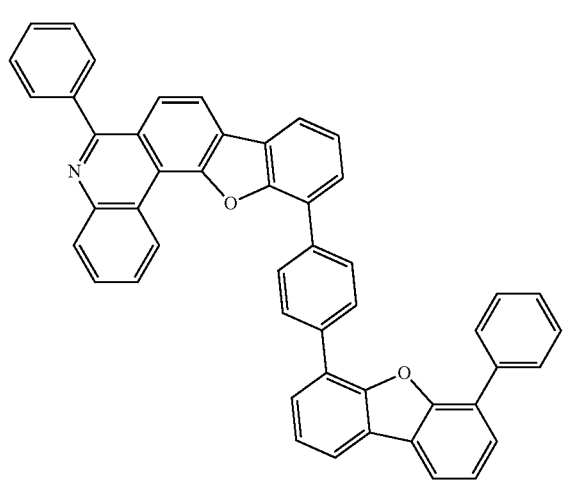
452
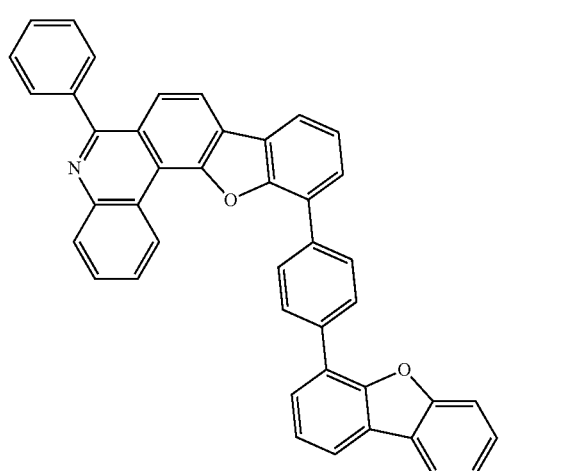
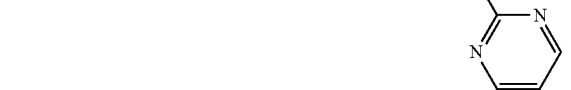
453
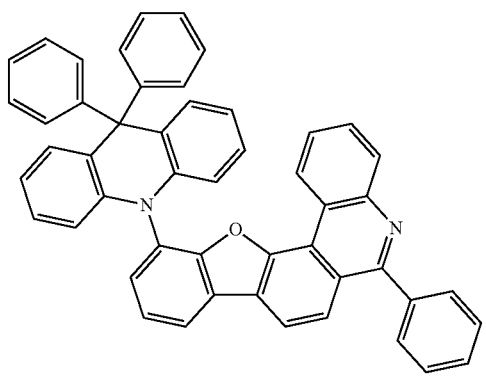
454
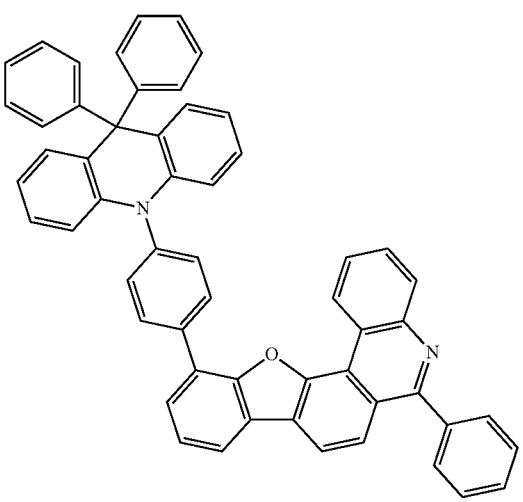
455
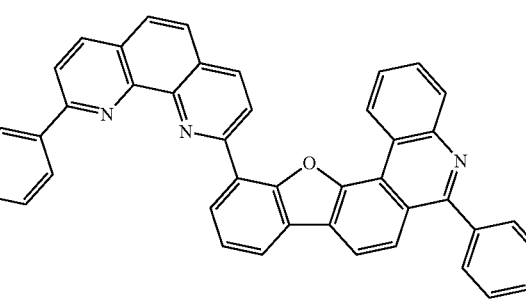
456
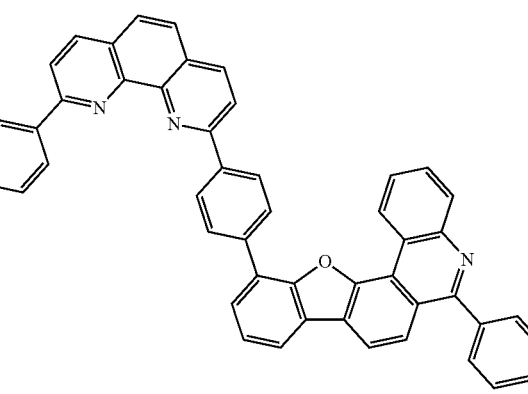

157
-continued
457
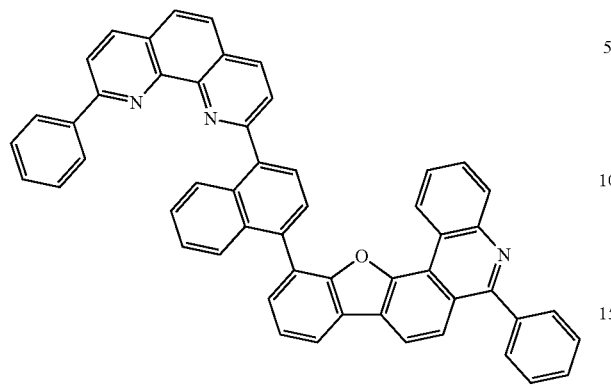
458
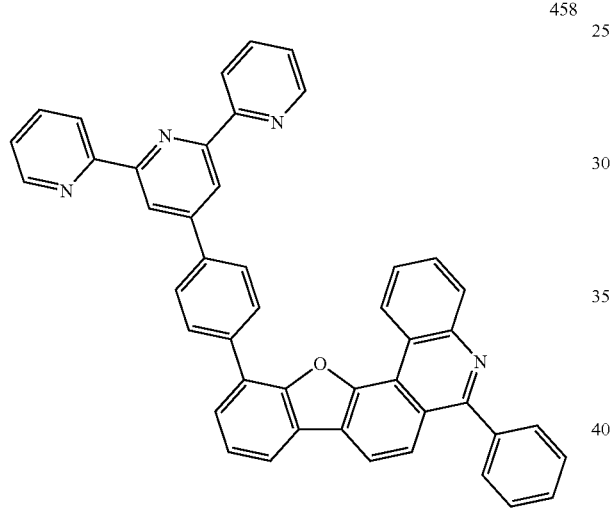
459
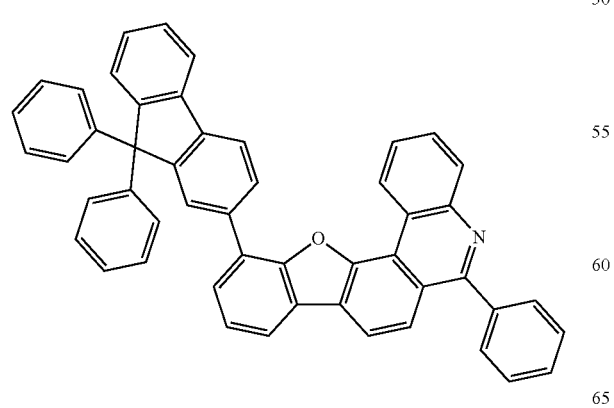
158
-continued
460
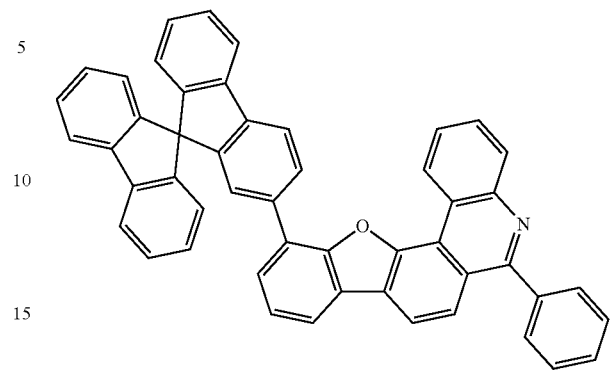
461
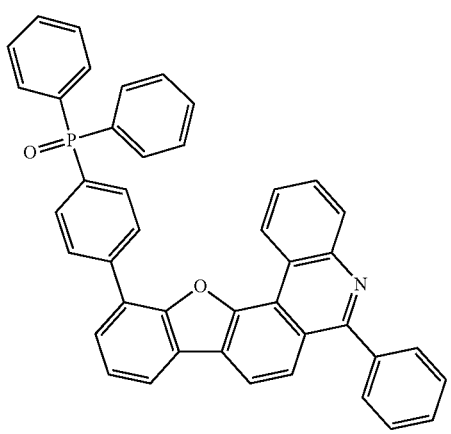
462

463
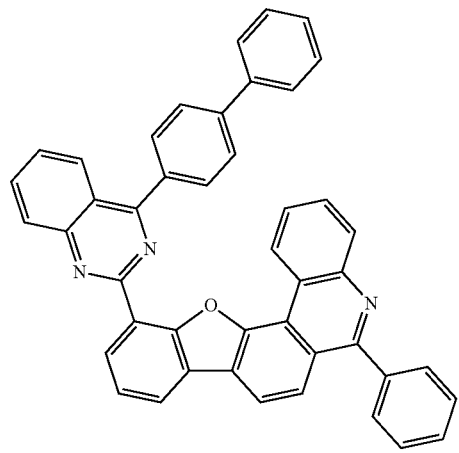
464
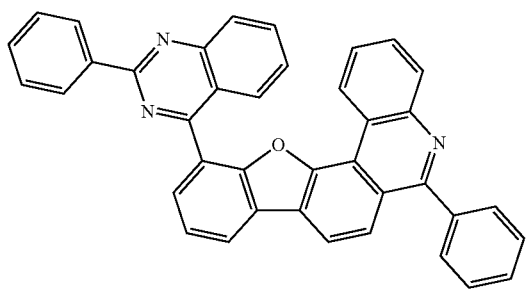
465
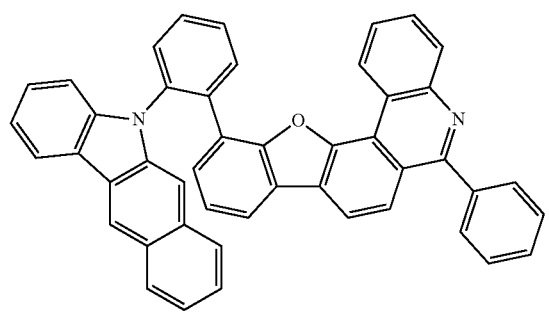
466
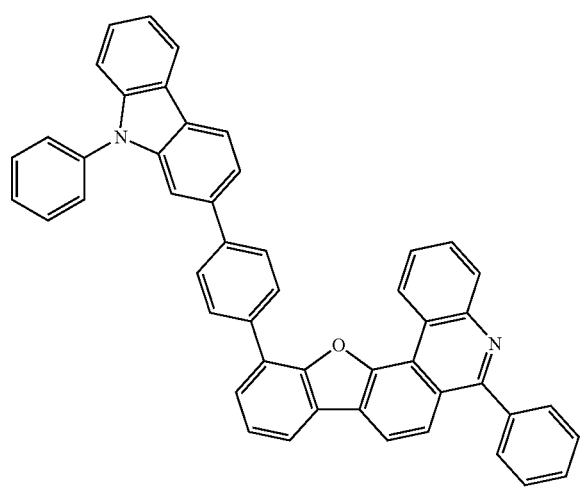
467
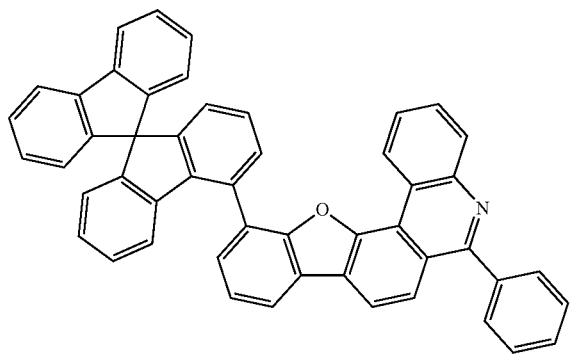
468
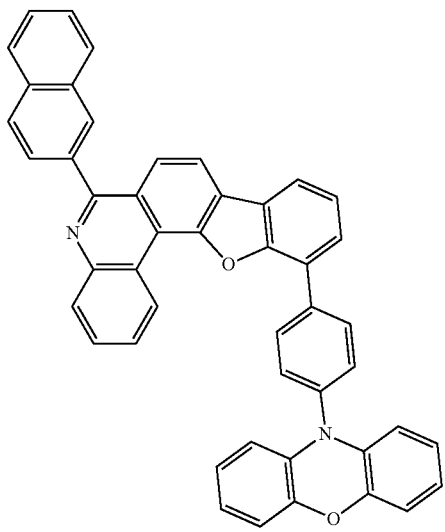
469
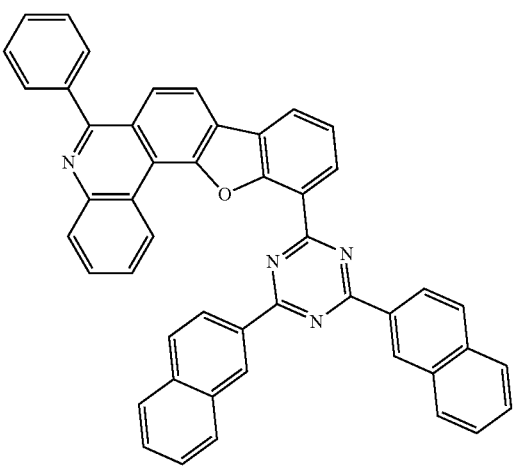

470
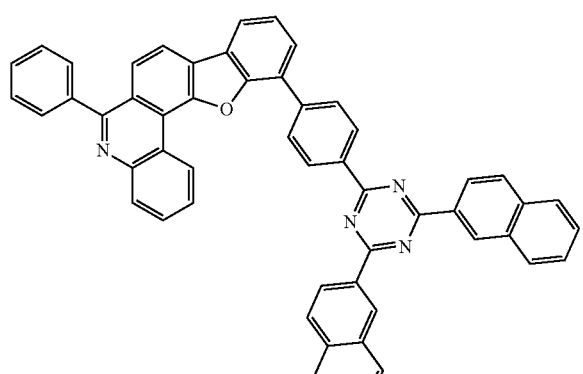
471
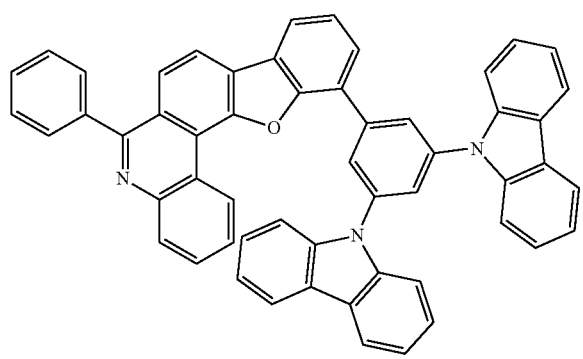
472
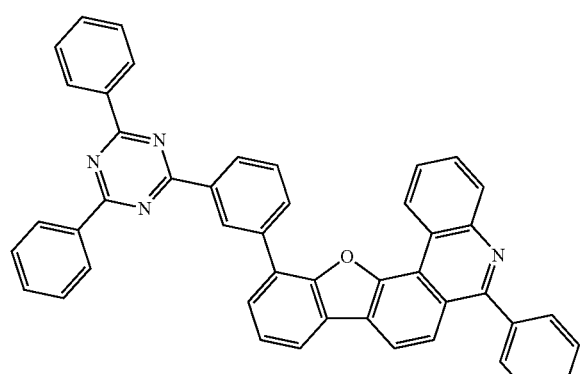
473
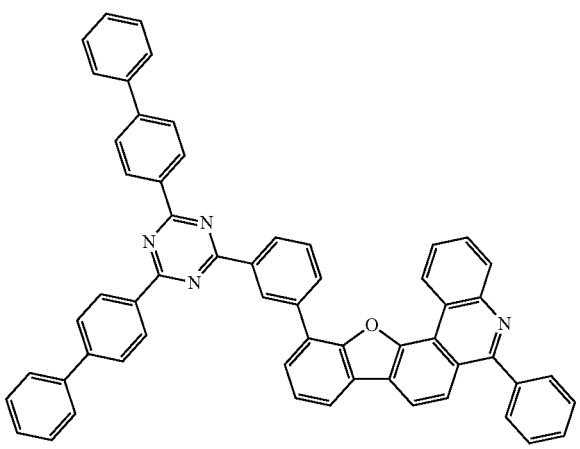
474
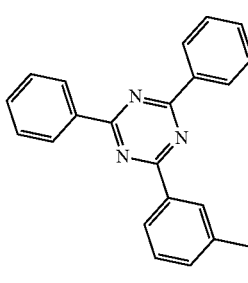
475
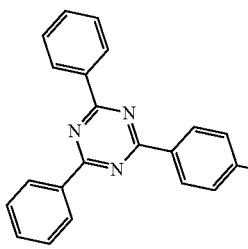

476
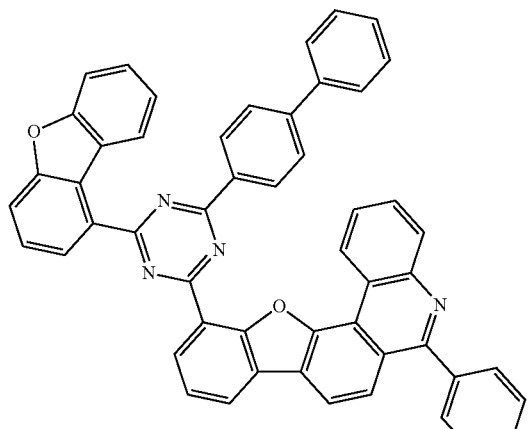
477
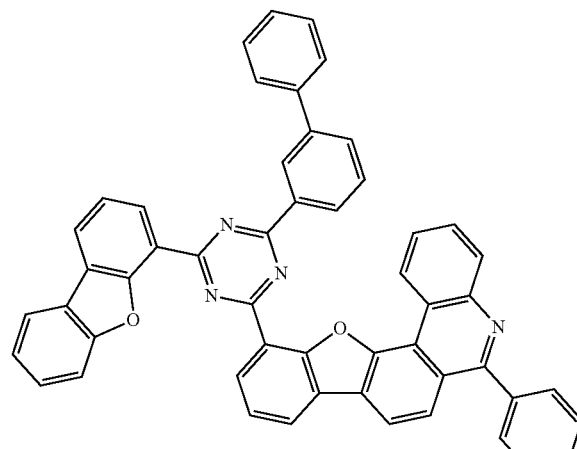
478
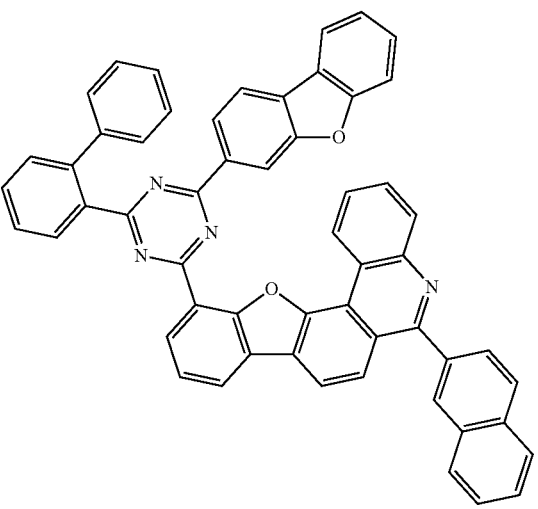
479
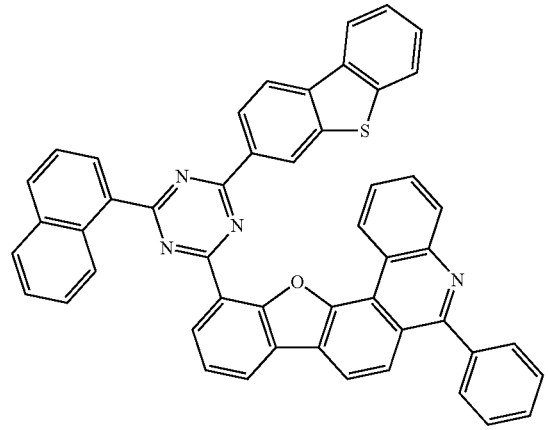
480
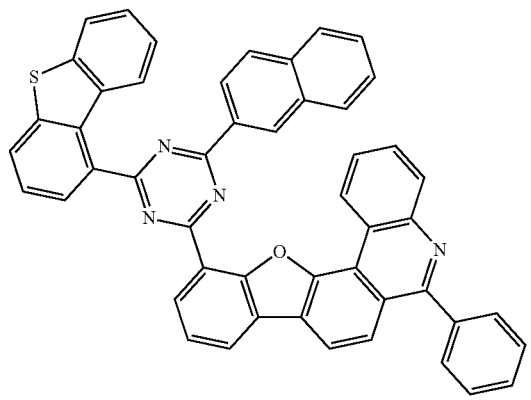
481
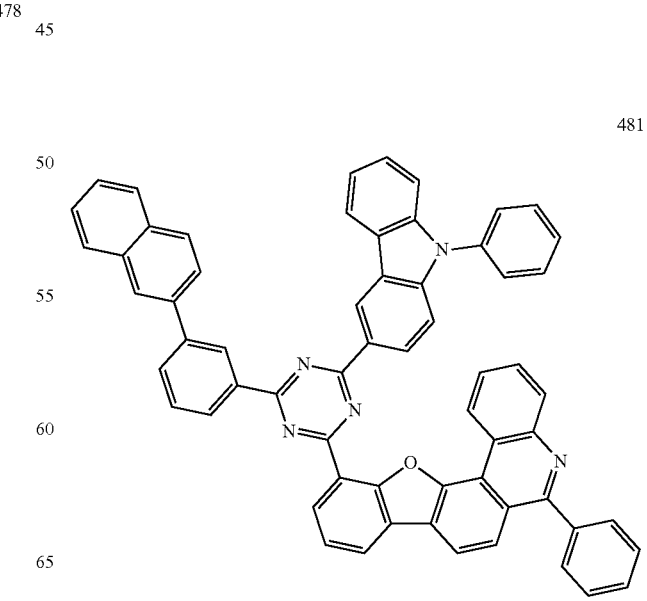

-continued
482
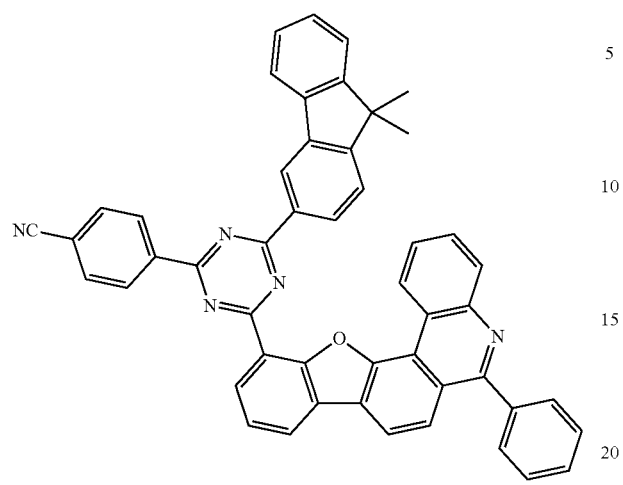
483
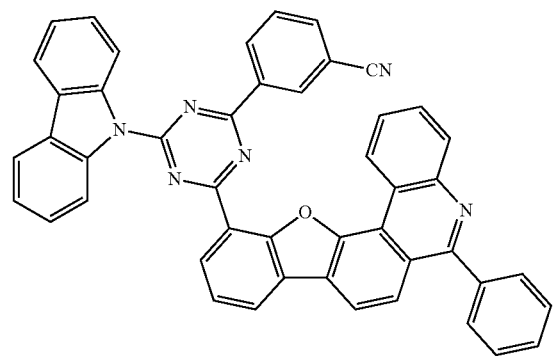
484
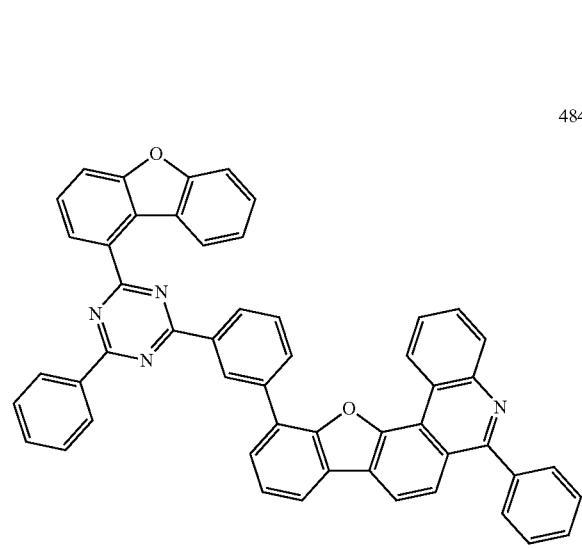
-continued
485
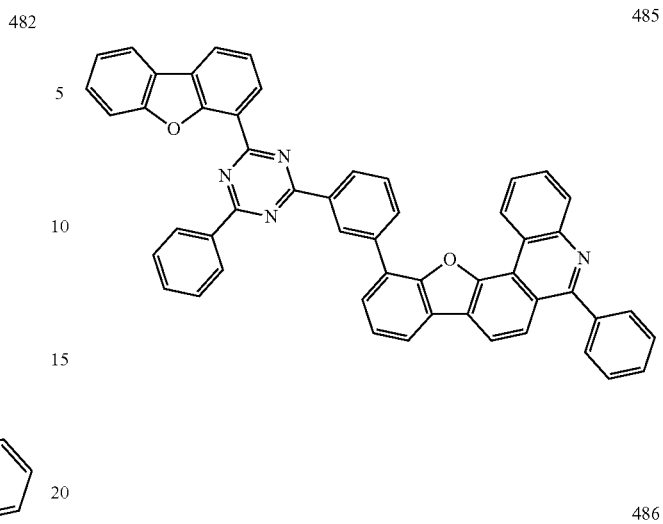
486
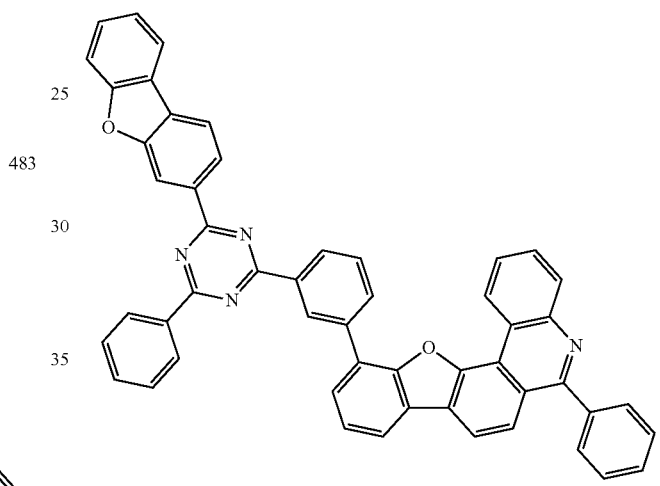
487
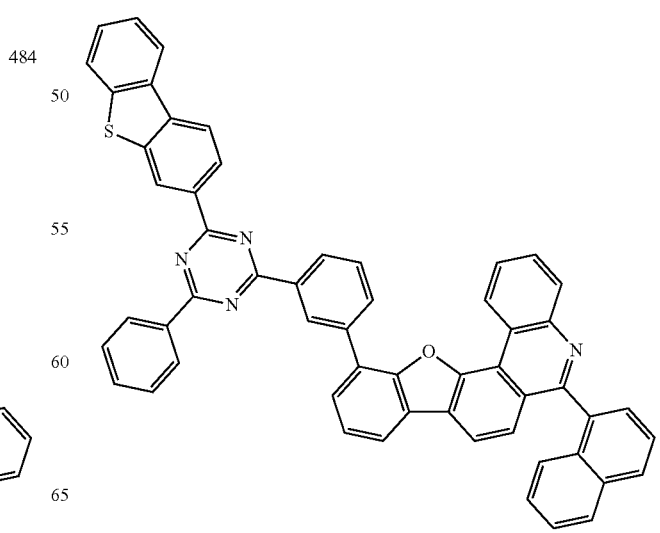

488
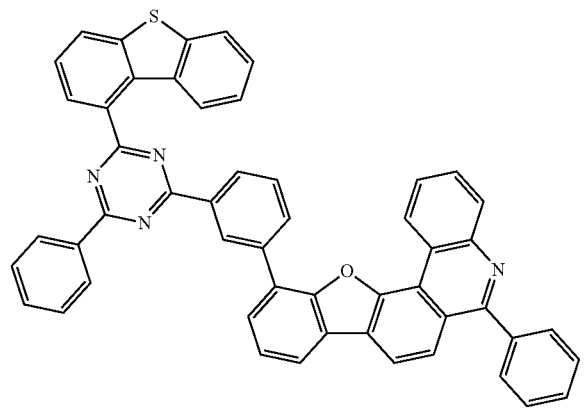
489
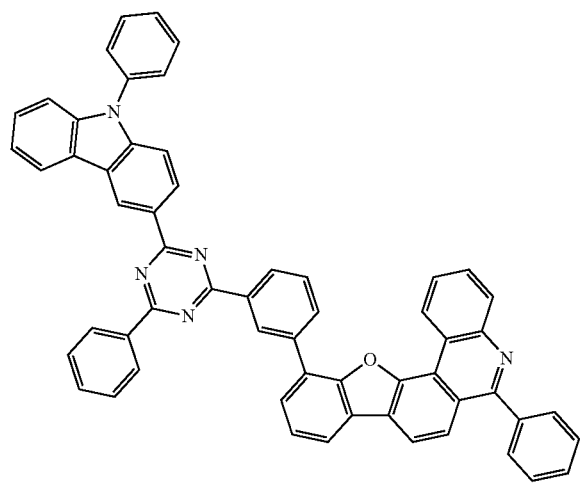
490
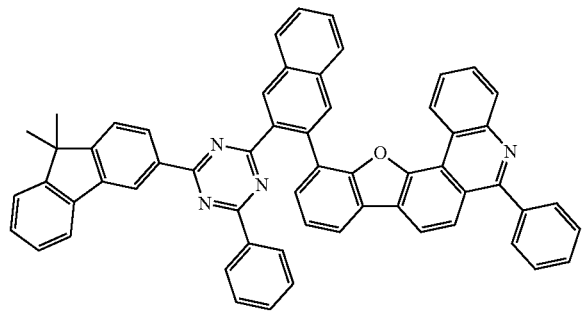
491
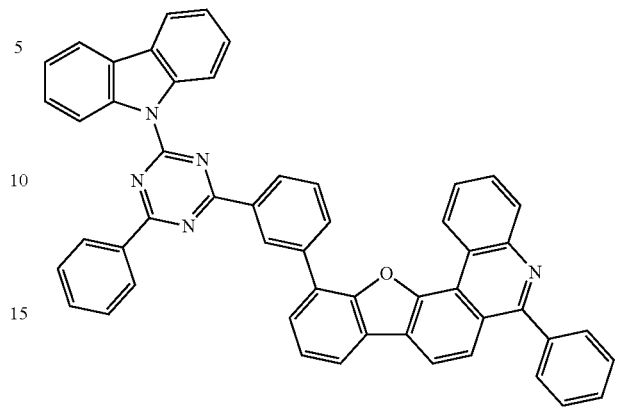
492
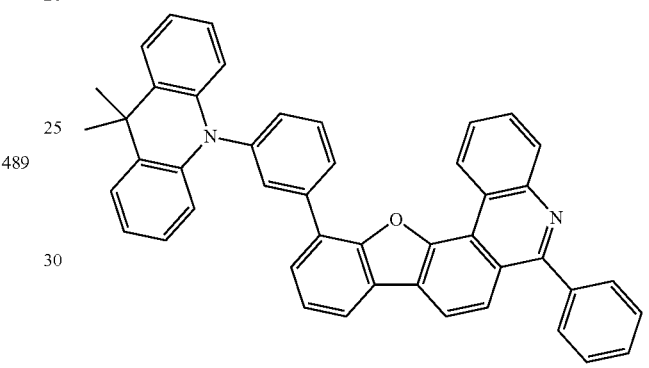
493
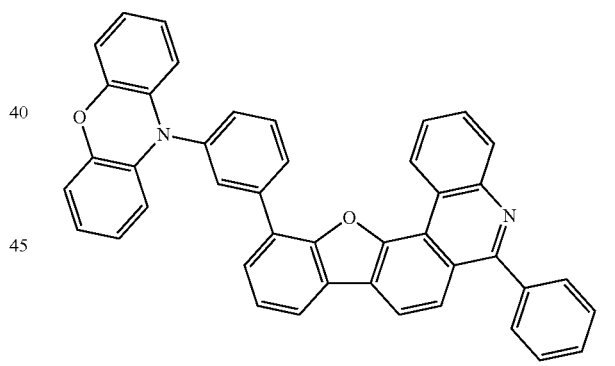
494
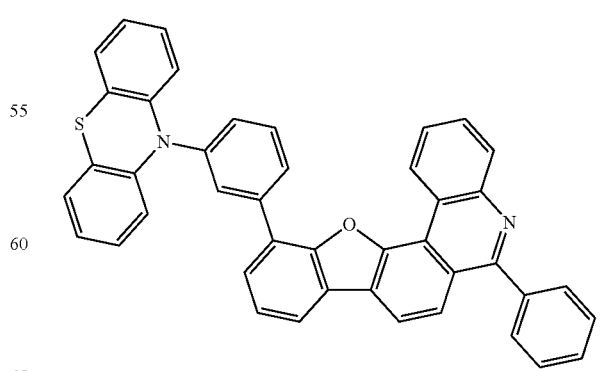

-continued
495
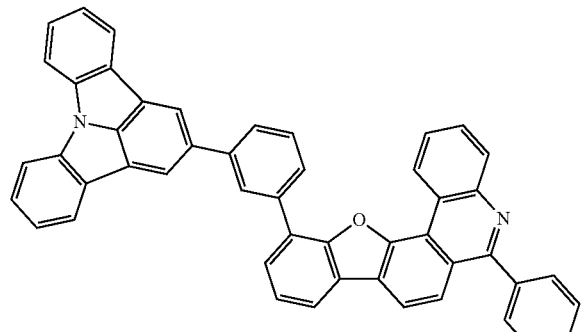
496
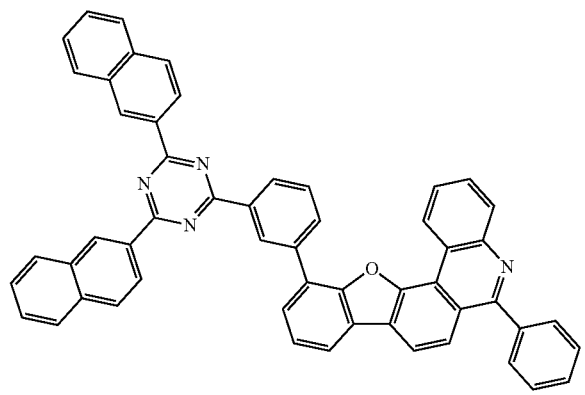
497
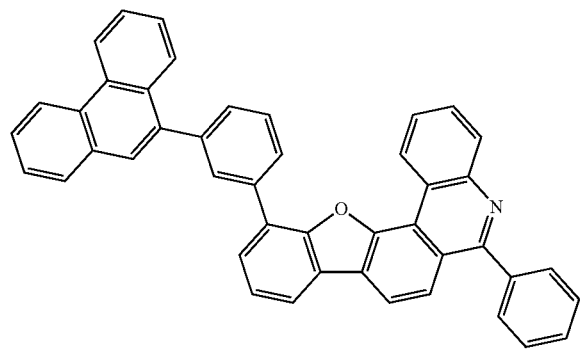
498
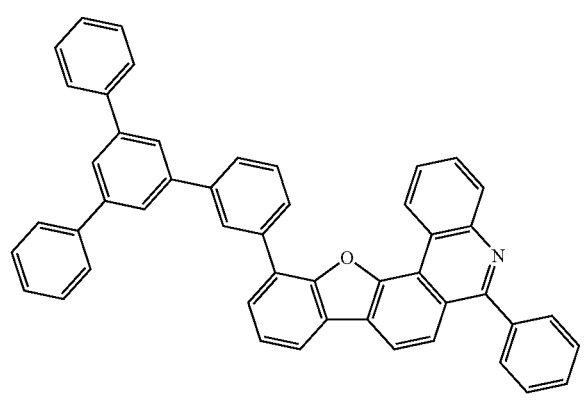
-continued
499
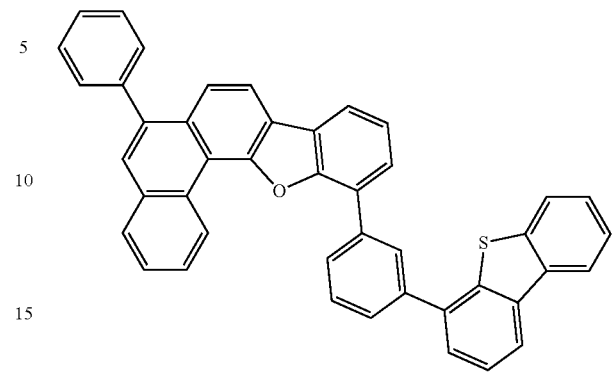
500
501
502

503
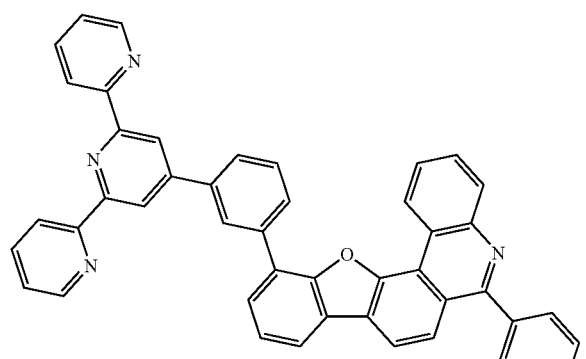
504
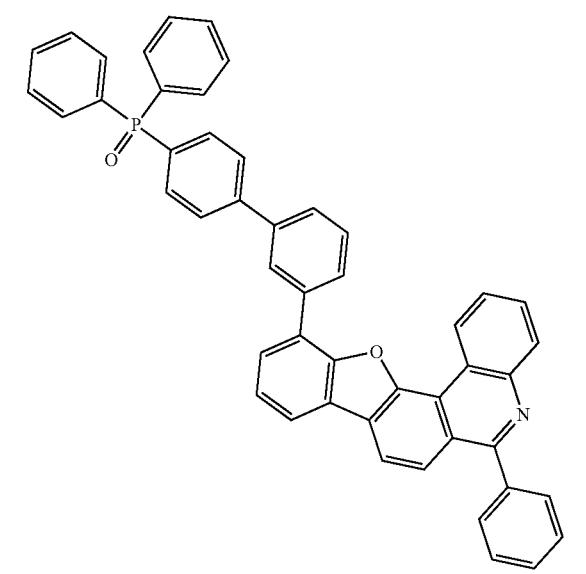
505
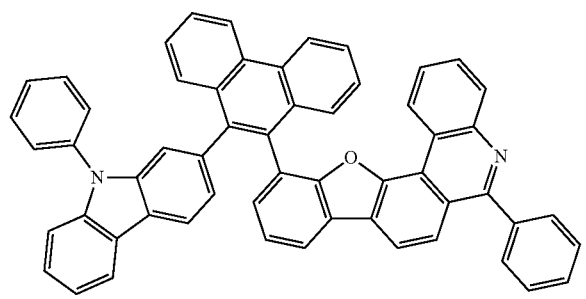
506
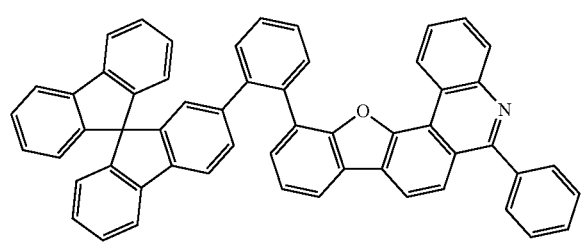
507

508
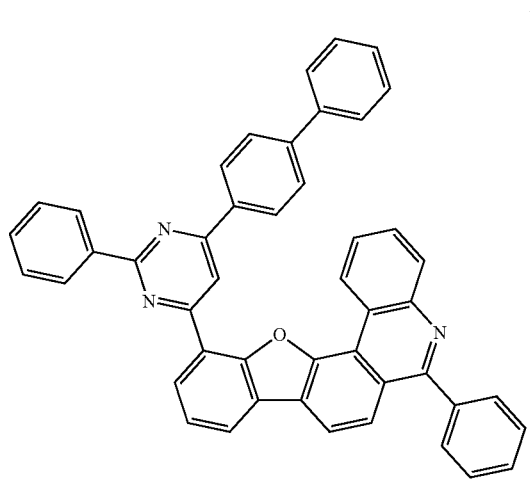
509
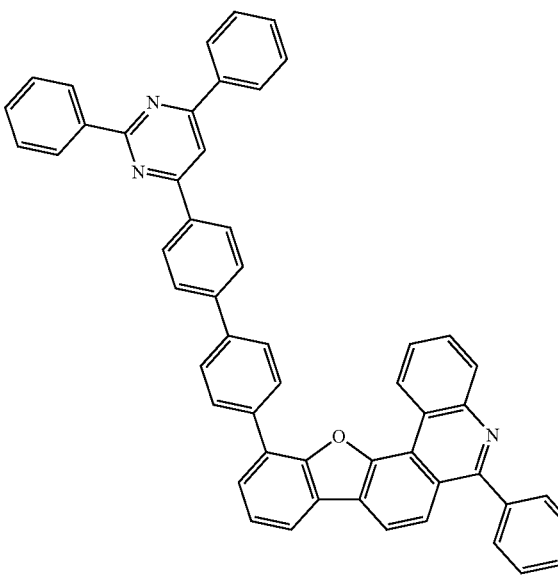

510
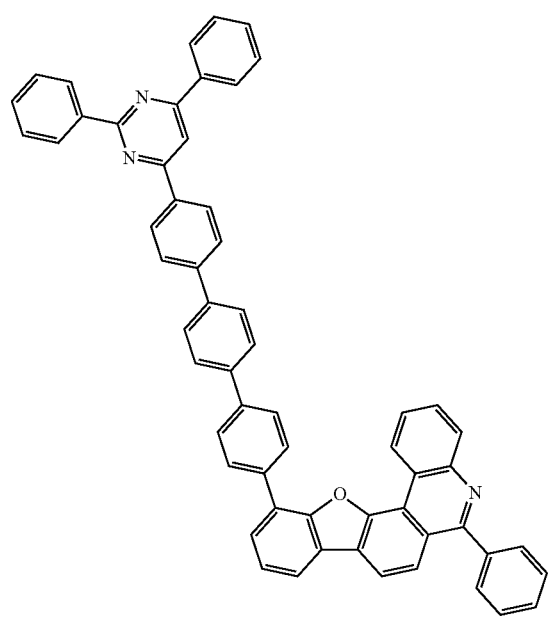
511
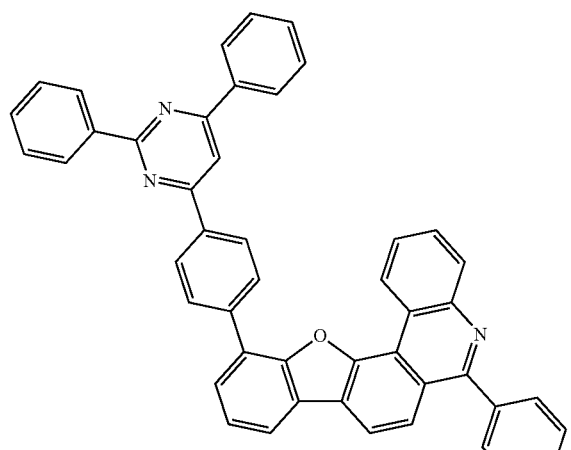
512
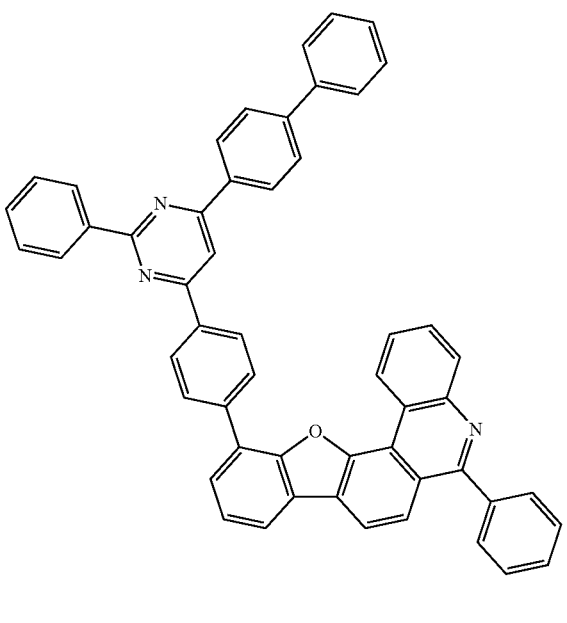
513
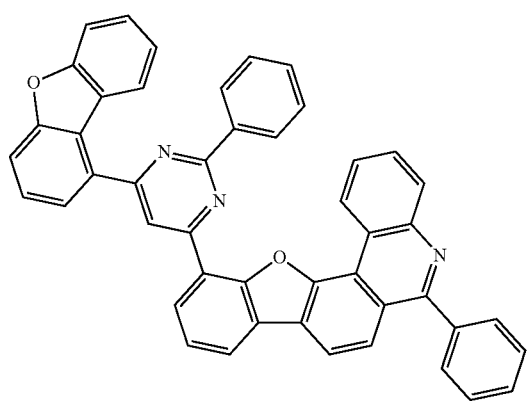
514
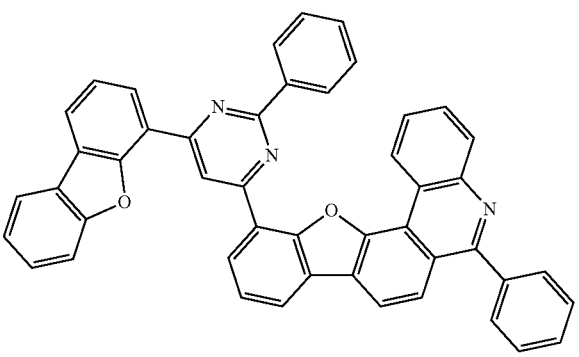

515
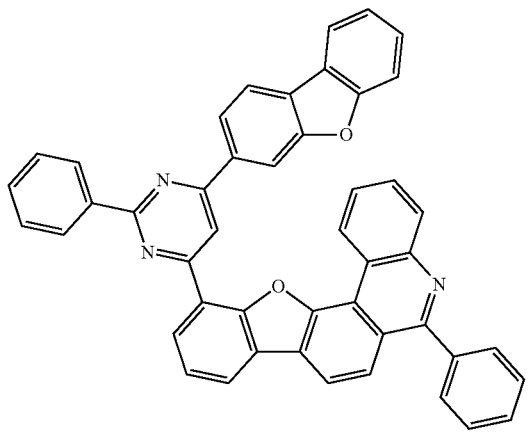
516
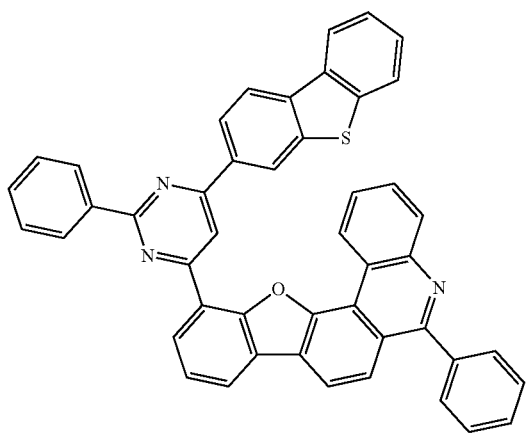
517
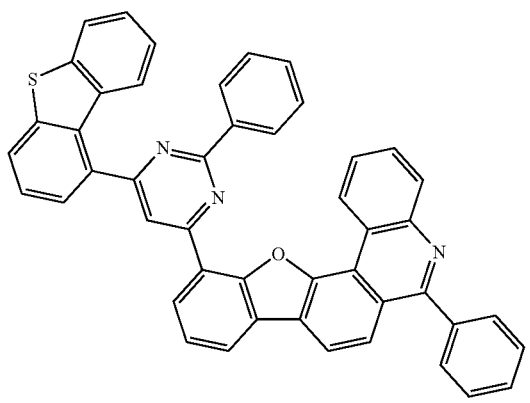
518
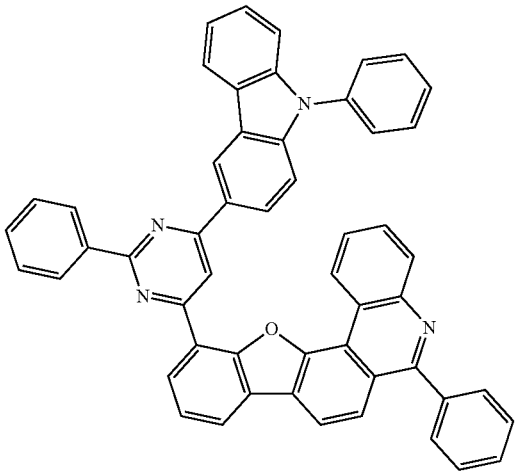
519
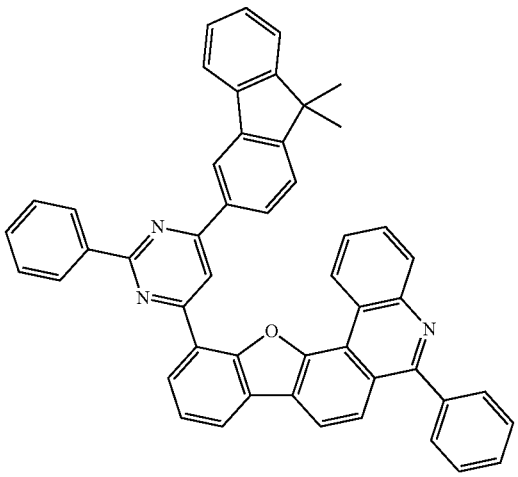
520
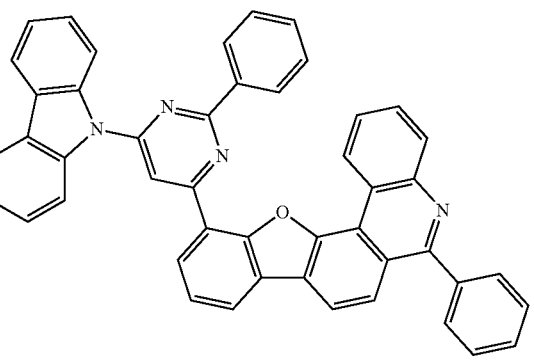

521
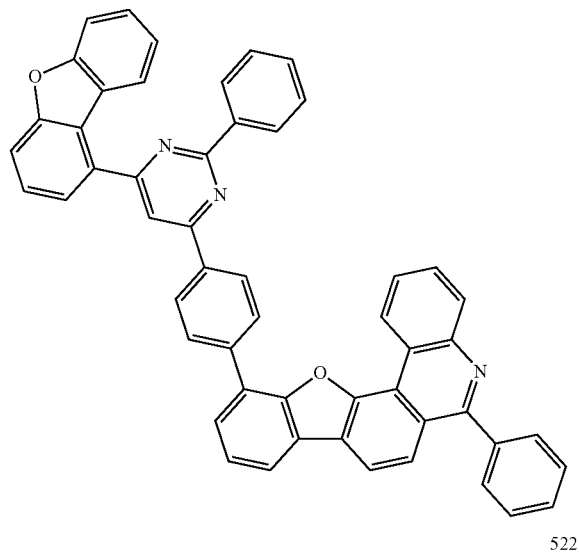
522
524
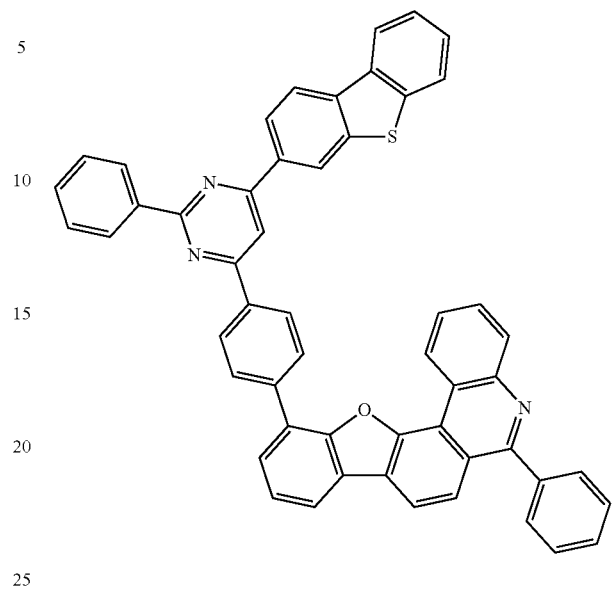
523
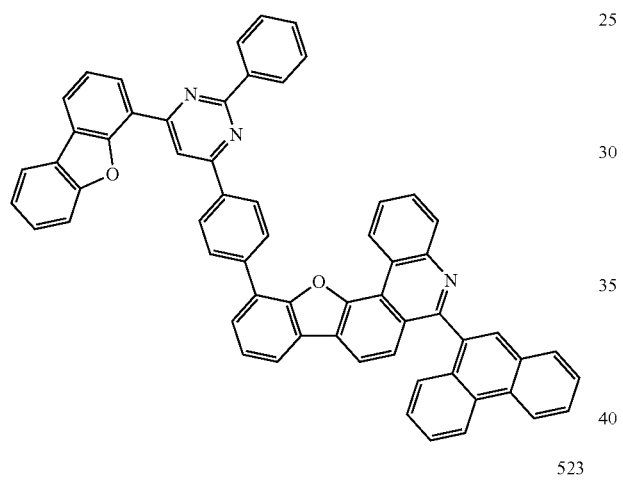
525
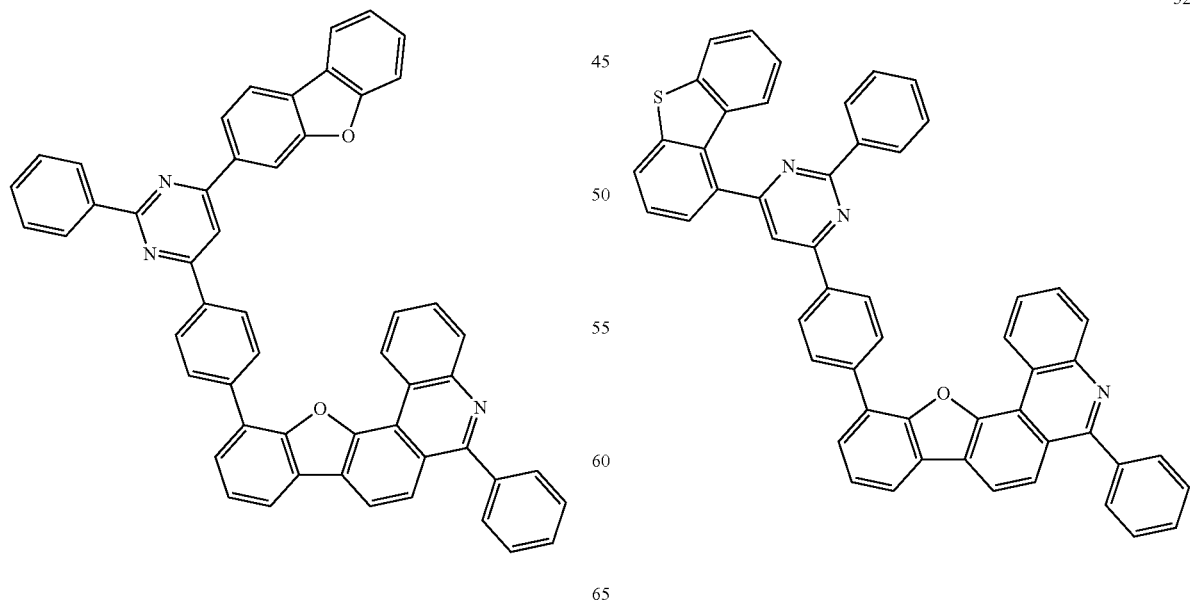

-continued
526
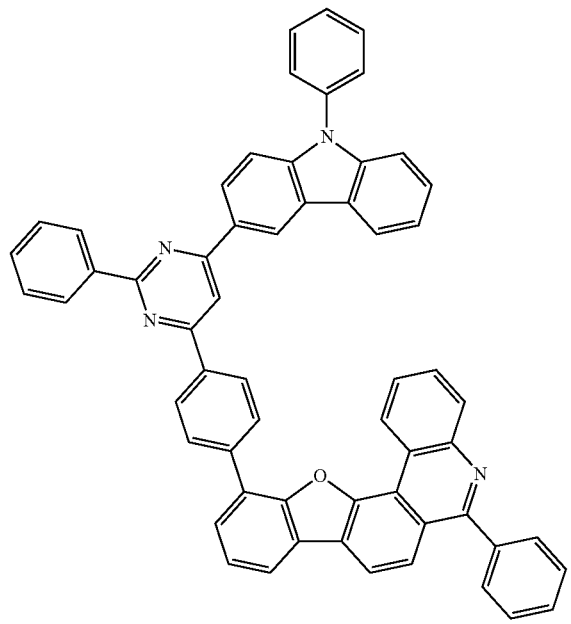
527
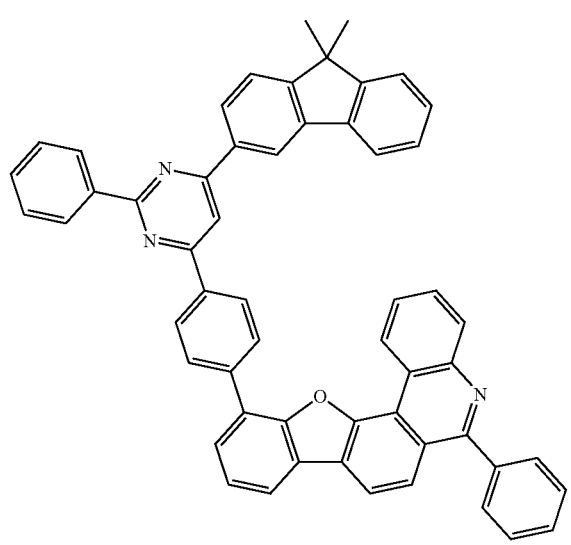
528
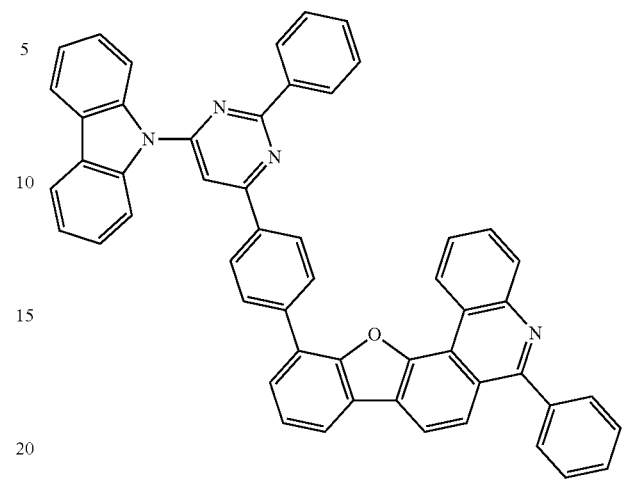
529
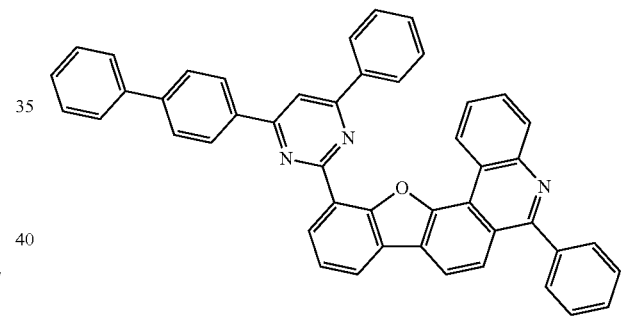
530
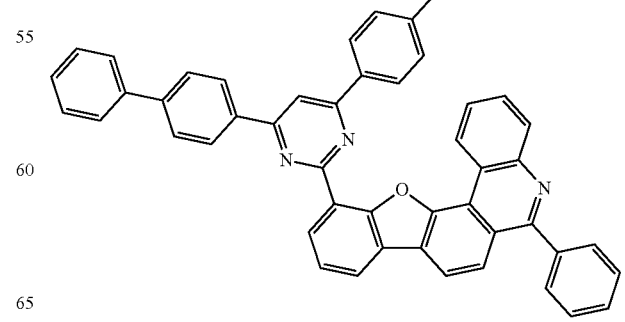

531
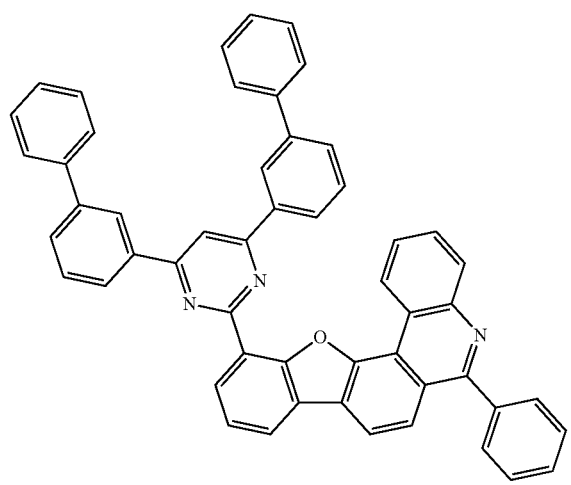
532
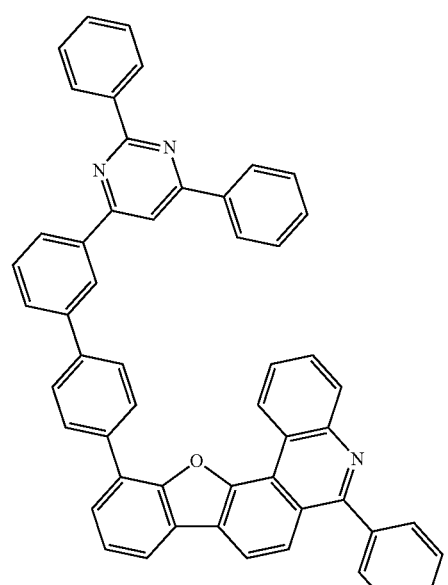
533
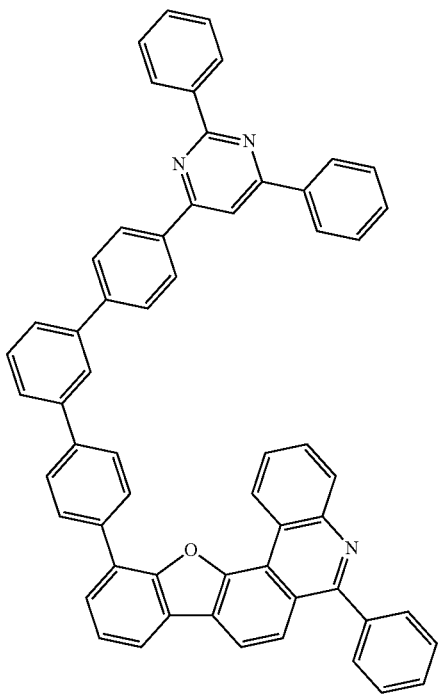
534
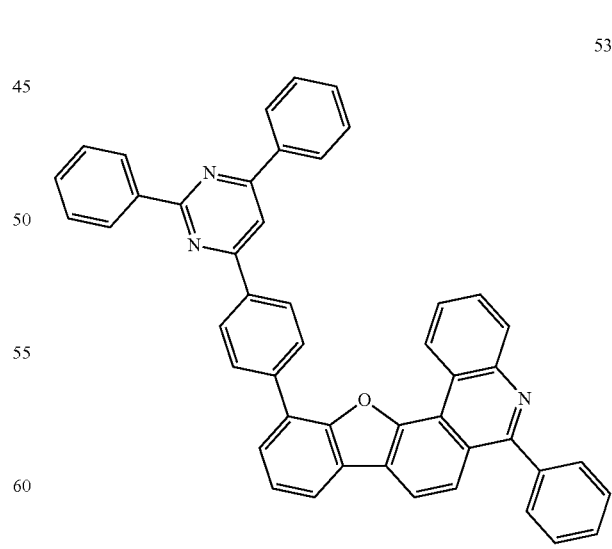

535
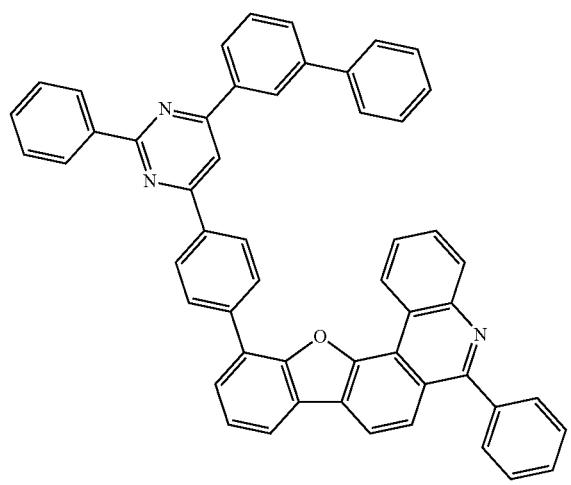
536
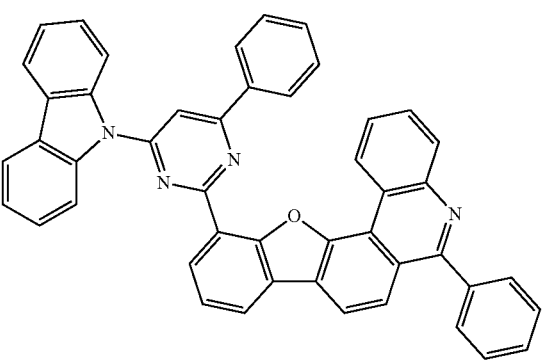
537
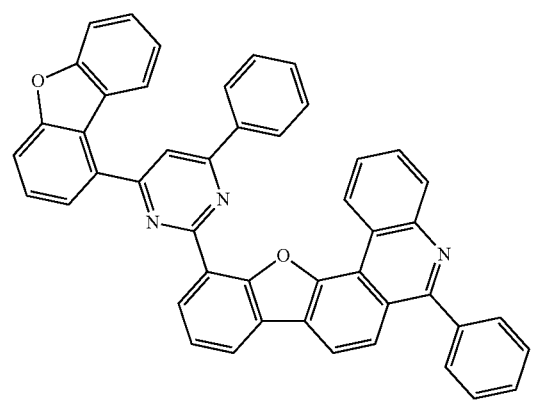
538
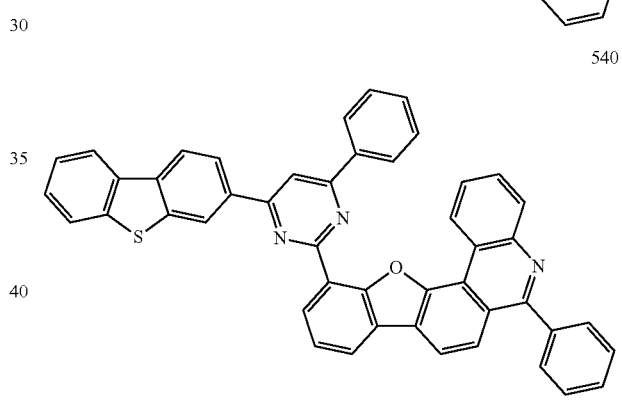
539
540
541
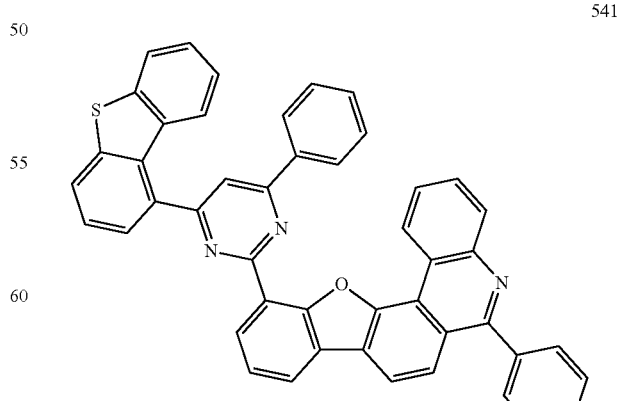

542
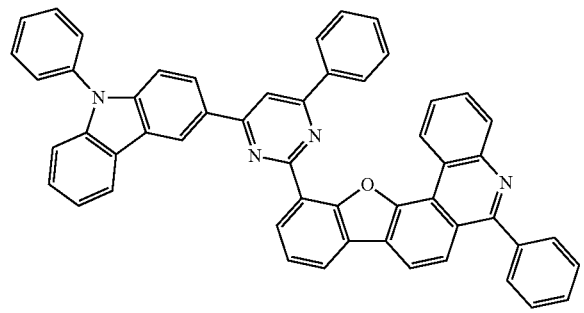
543
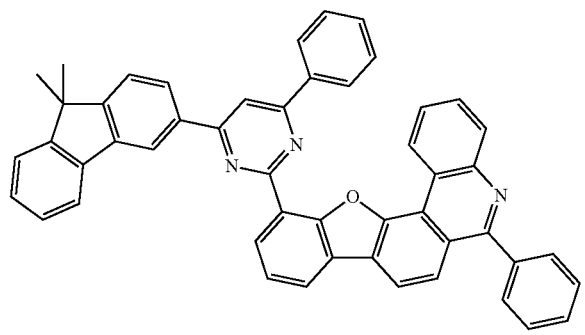
544
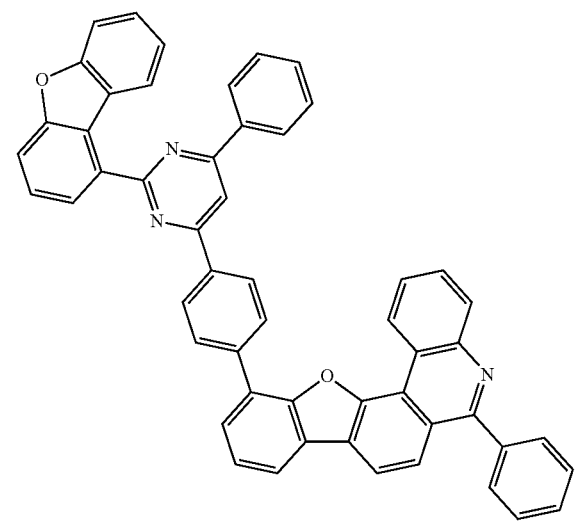
545
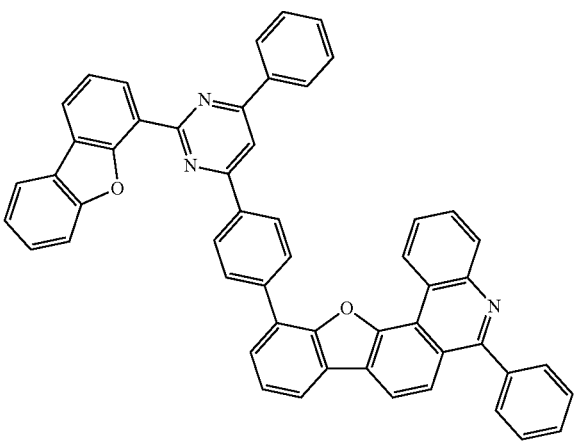
546
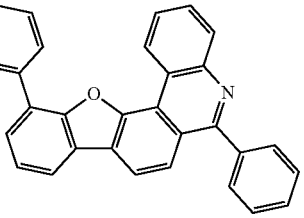
547
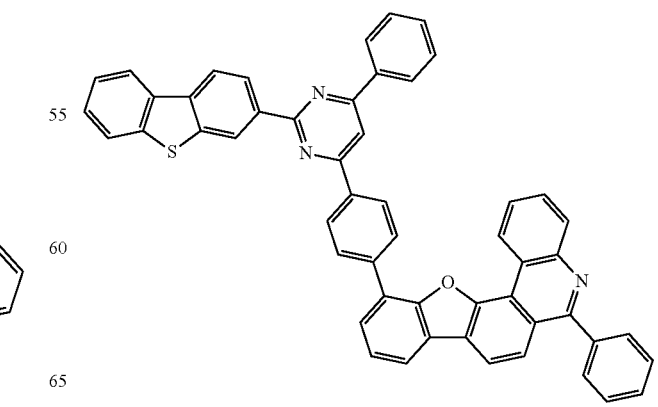

187
-continued
548
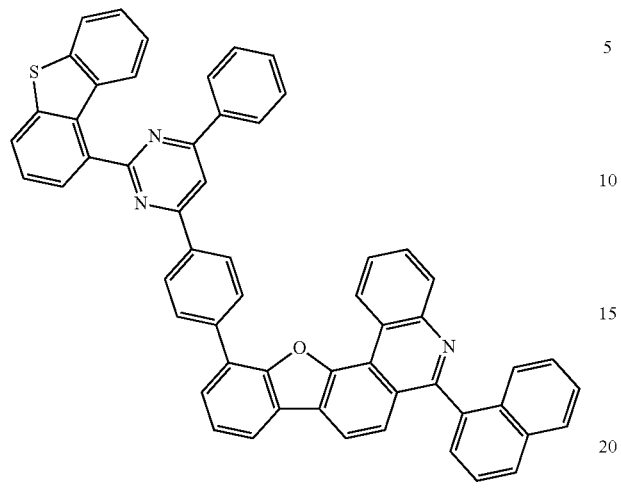
549
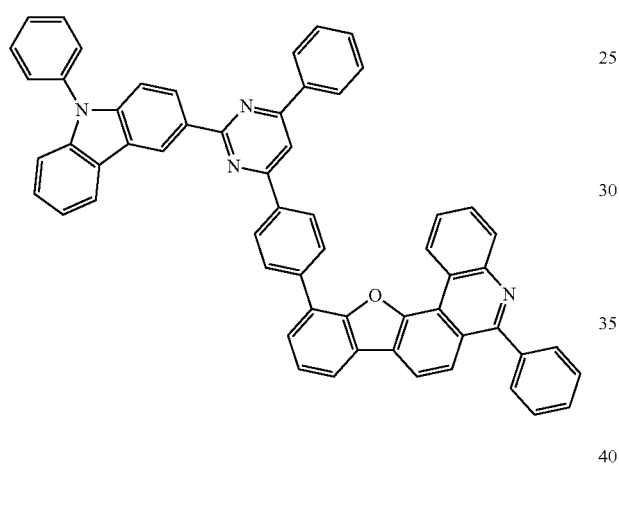
550
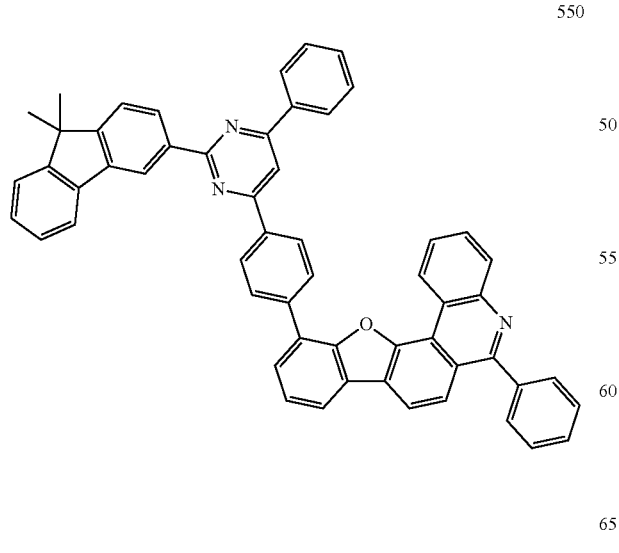
188
-continued
551
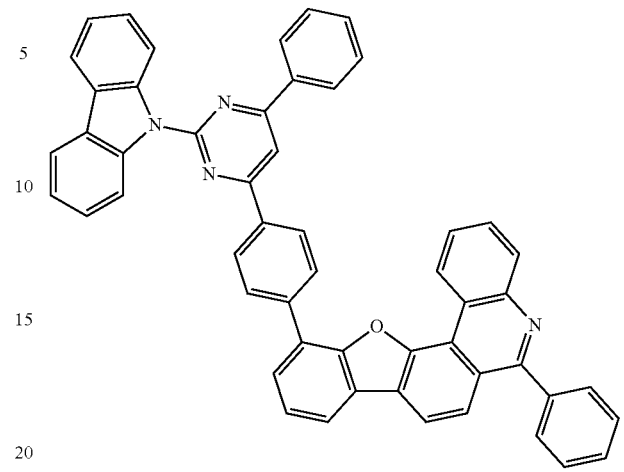
552
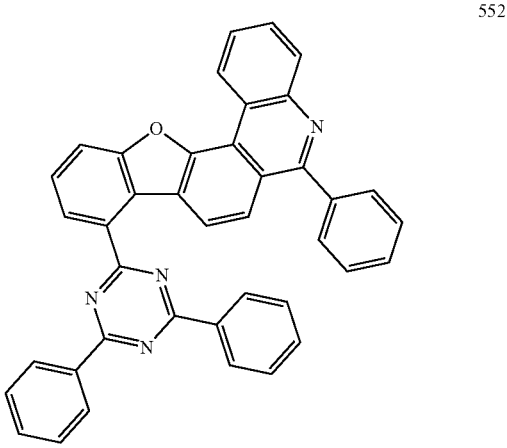
553
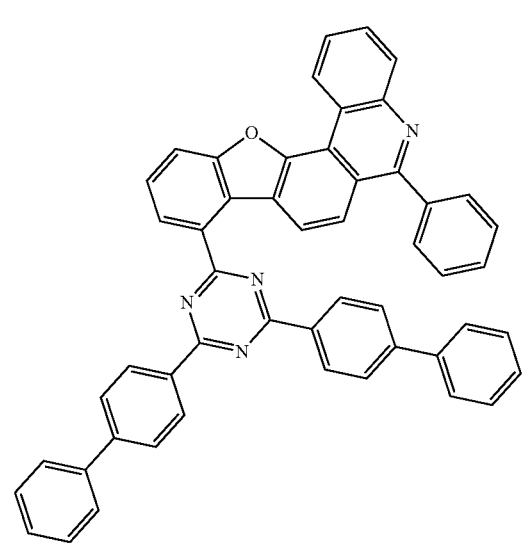

554
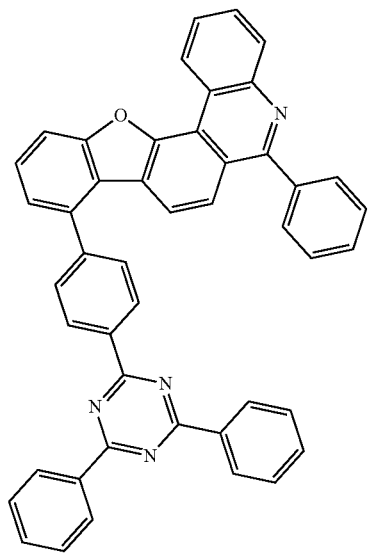
555
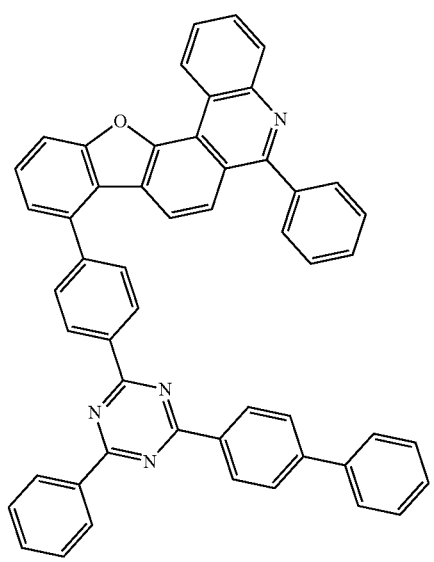
556
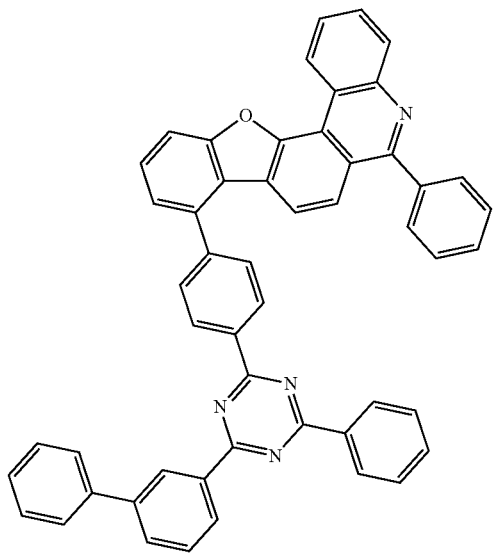
557
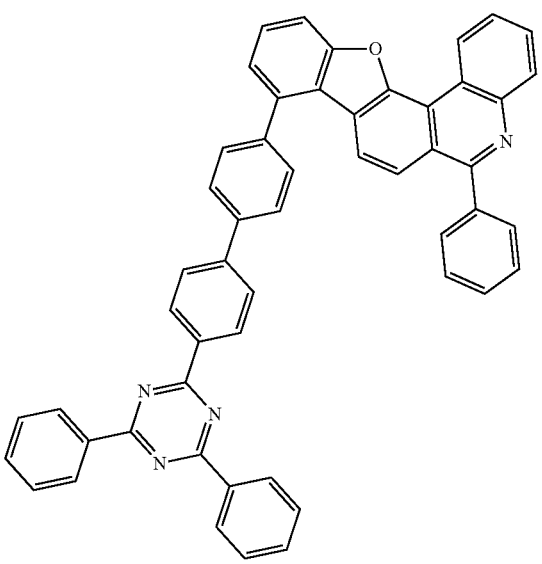

558
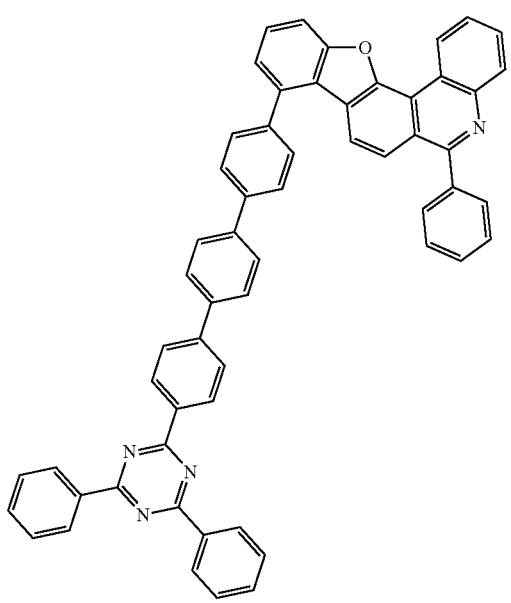
559
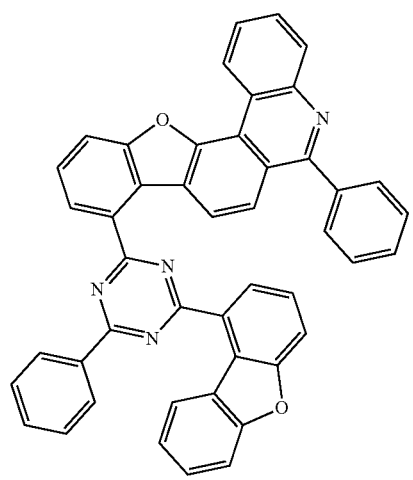
560
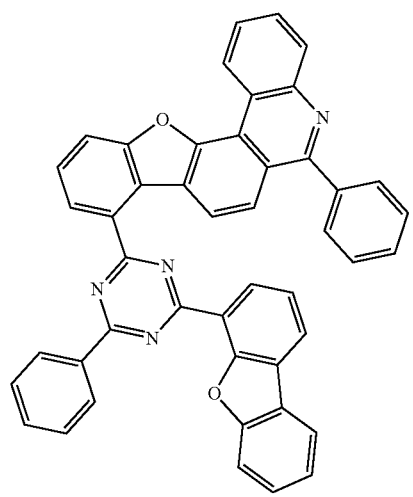
561
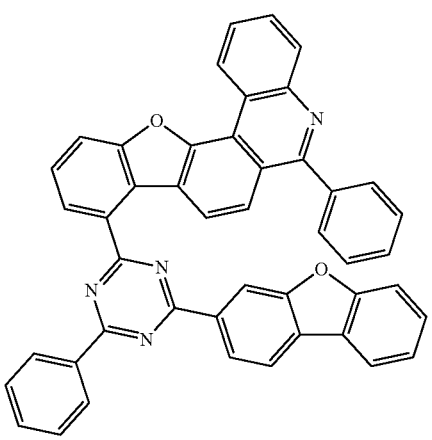
562
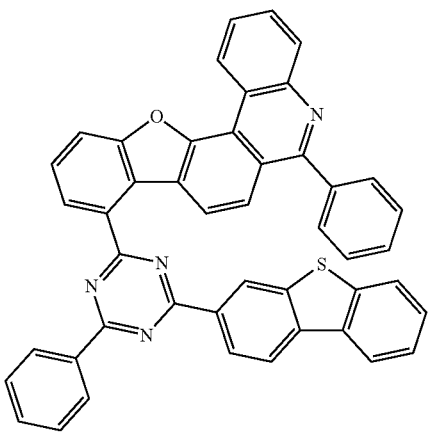
563
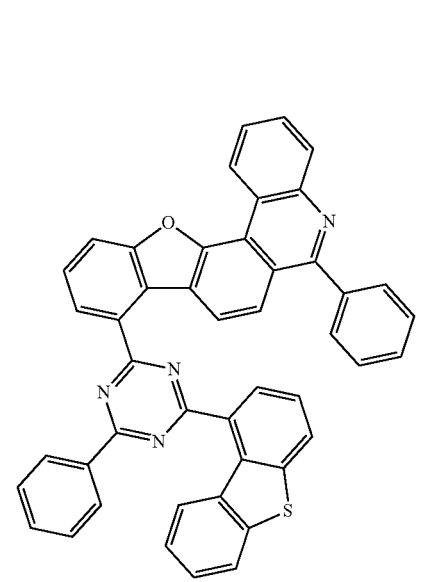

564
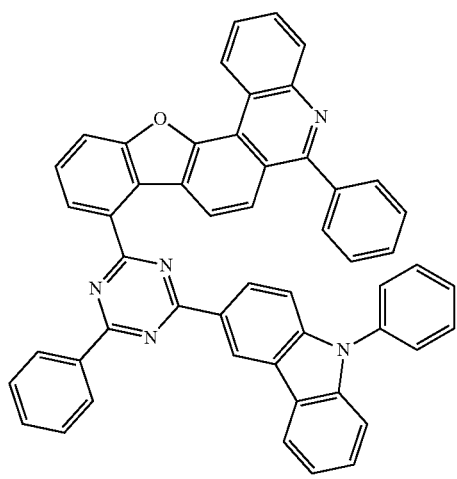
565
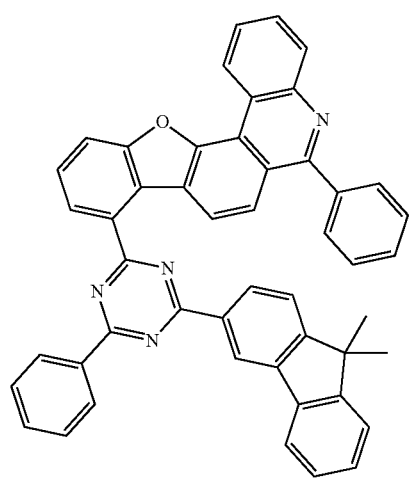
566
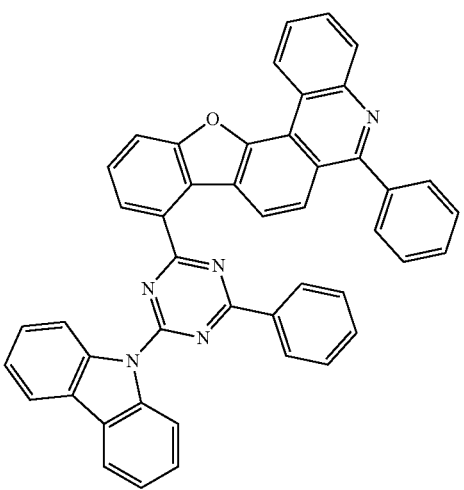
567
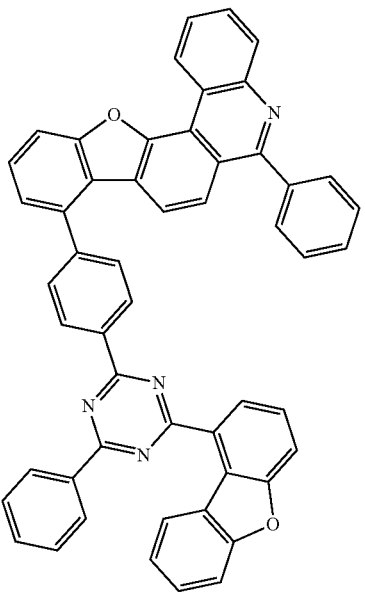
568
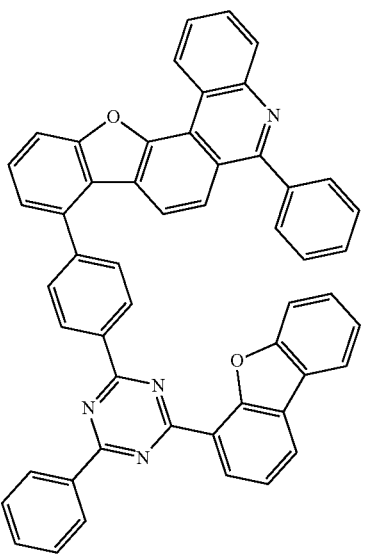

569
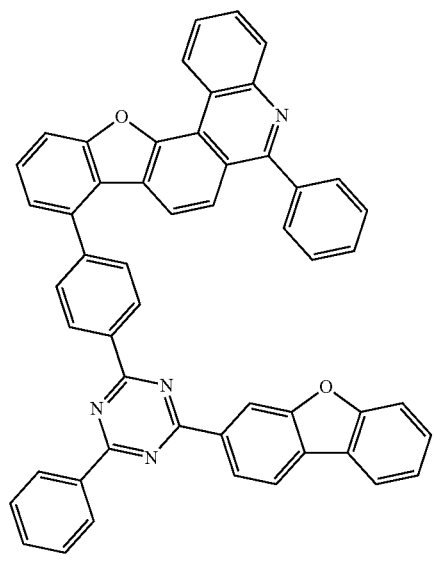
570
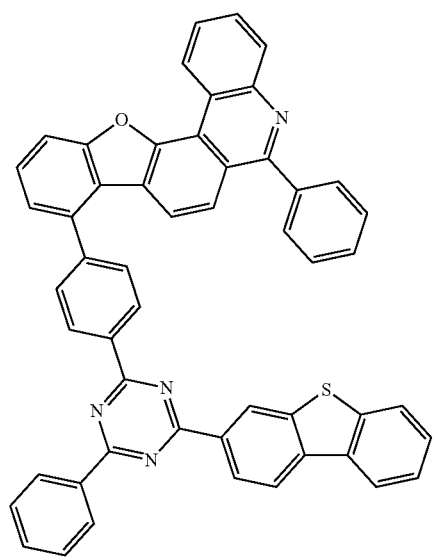
571
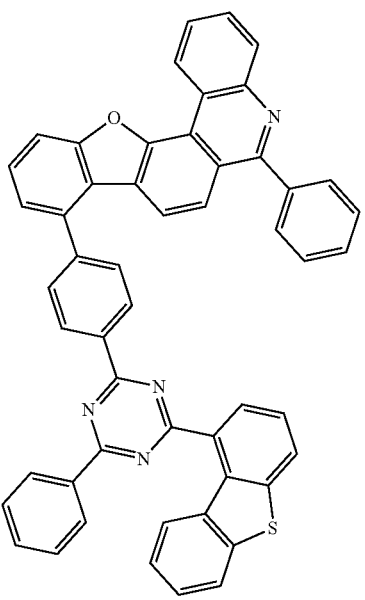
572
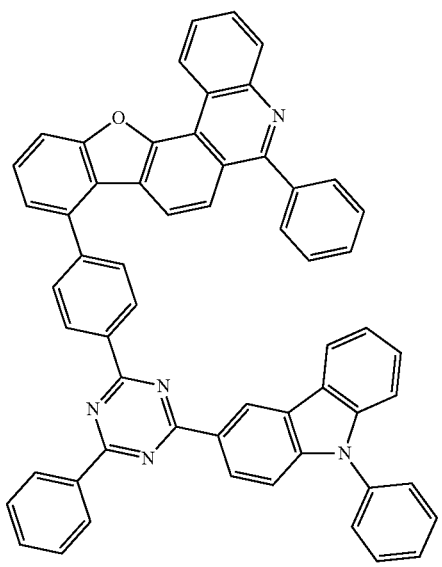

573
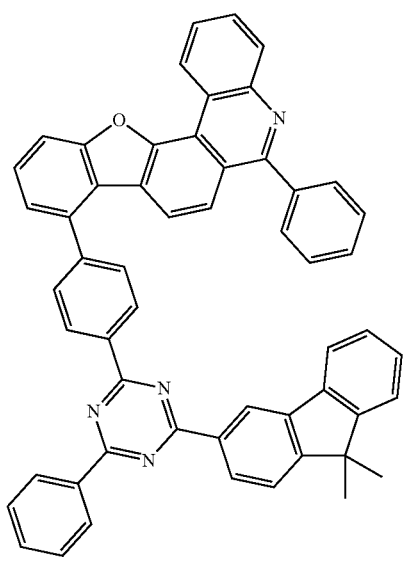
574
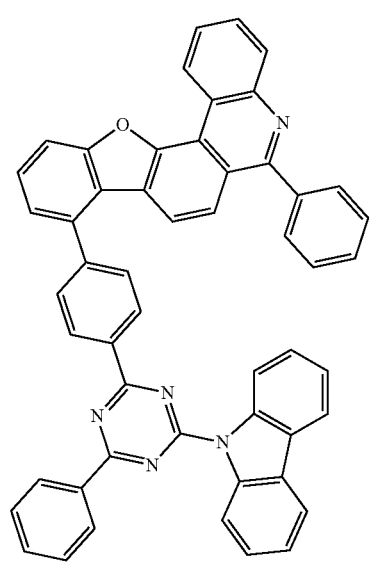
575
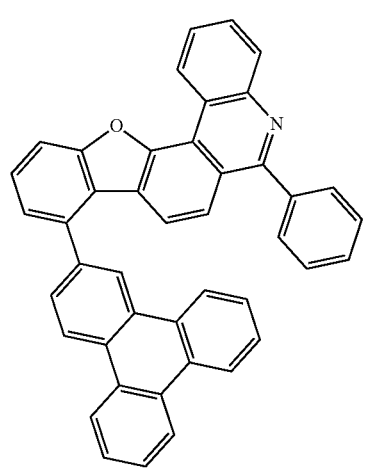
576
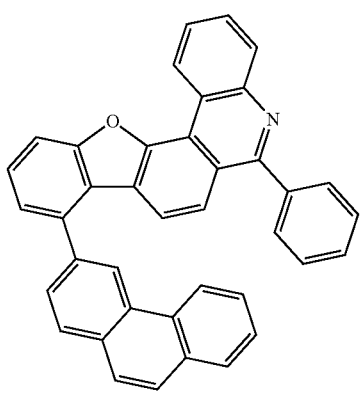
577
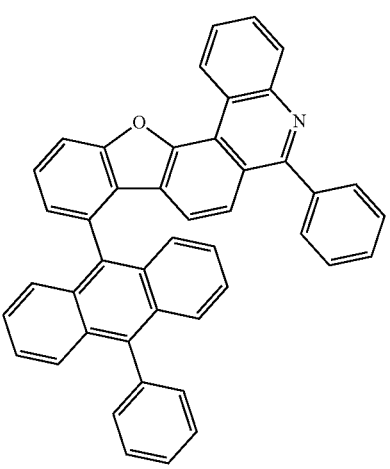
578
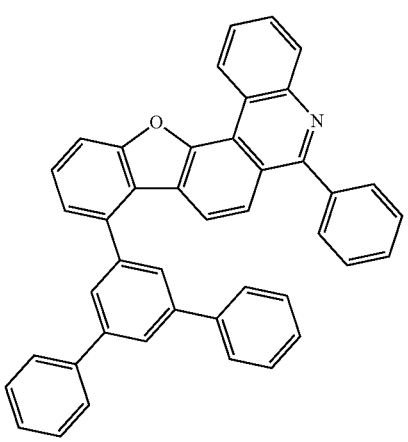

199
-continued
579
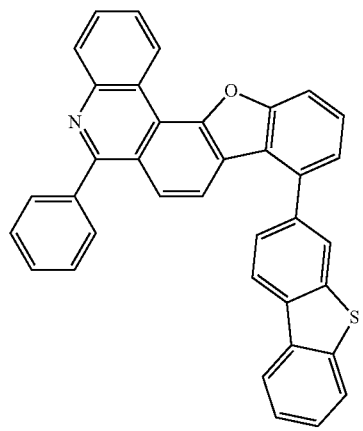
580
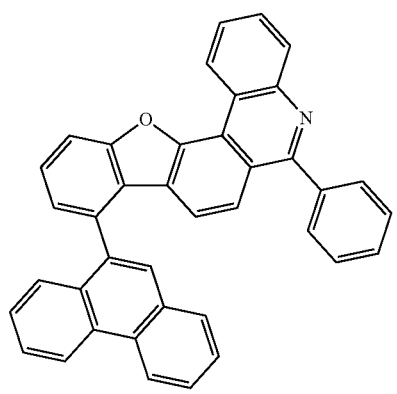
581
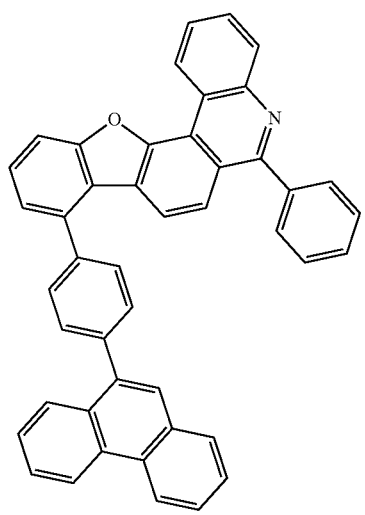
200
-continued
582
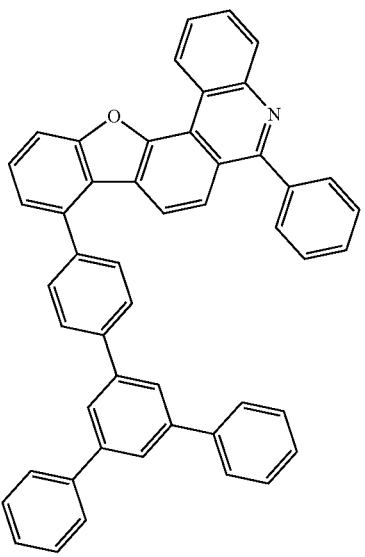
583
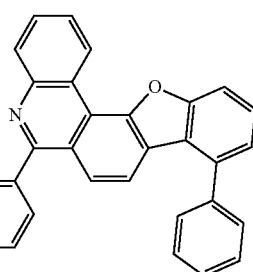
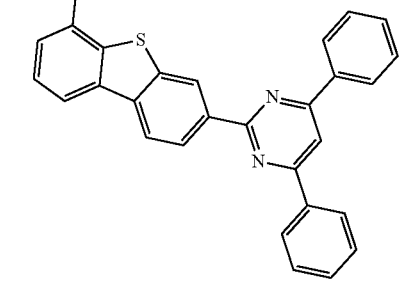
584
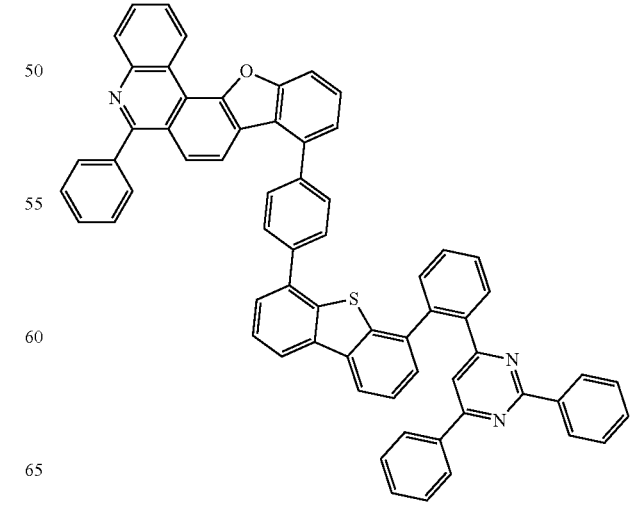

201
-continued
585
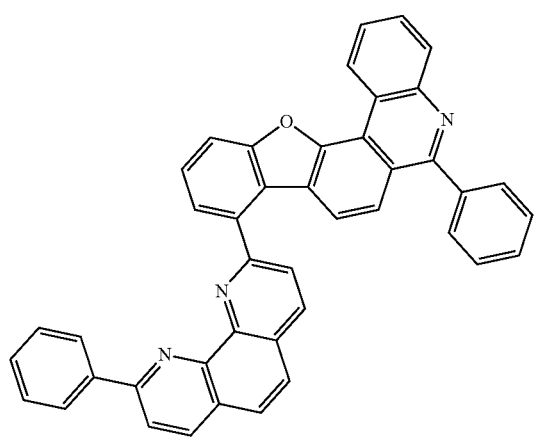
586
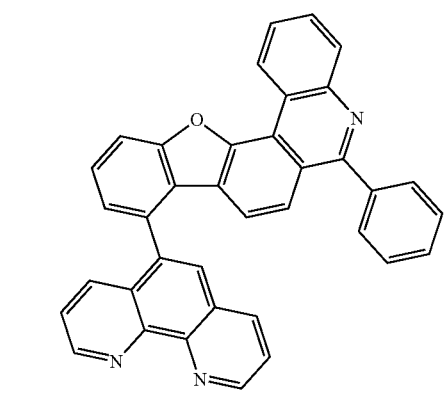
587
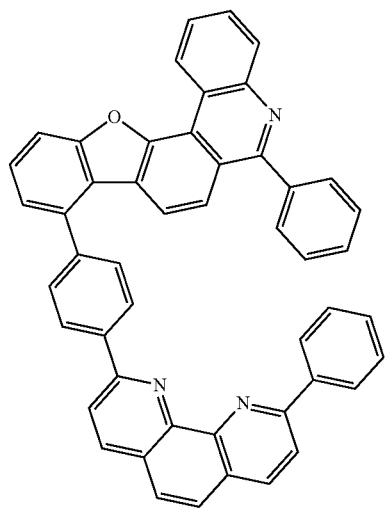
202
-continued
588
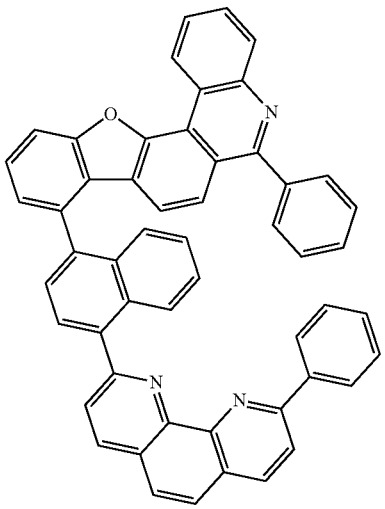
589
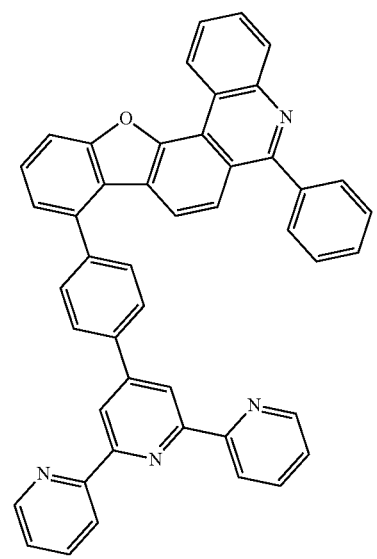
590
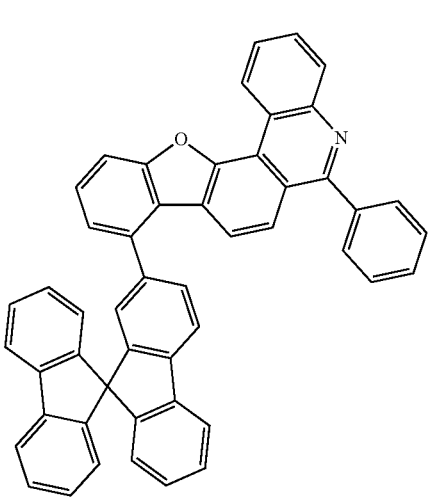

591
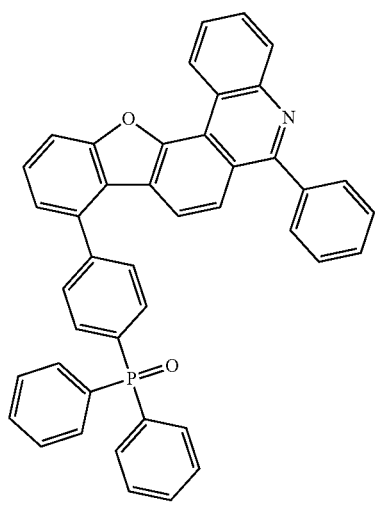
592
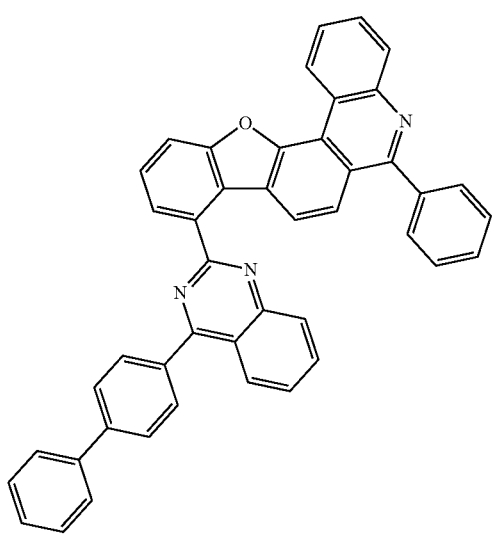
593
594
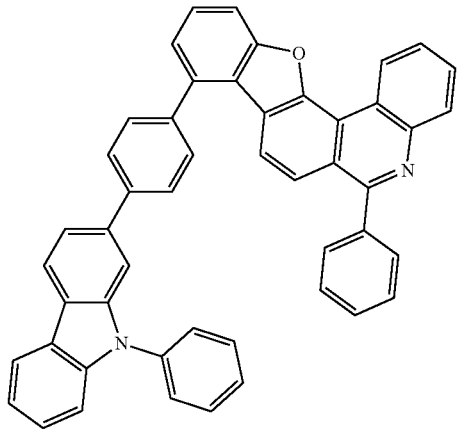
595
596
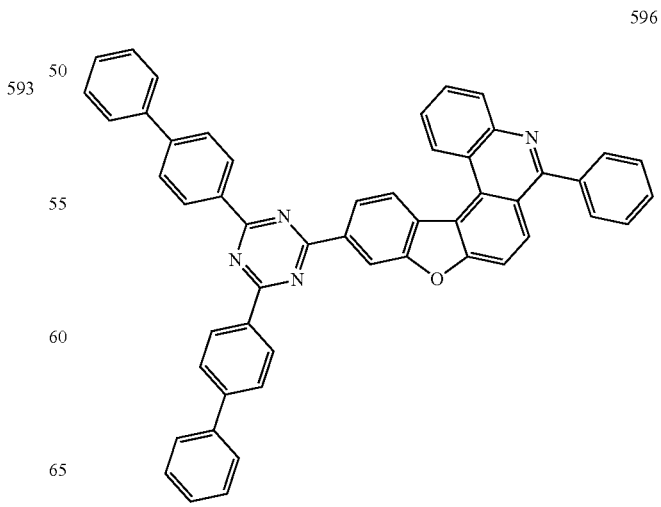

597
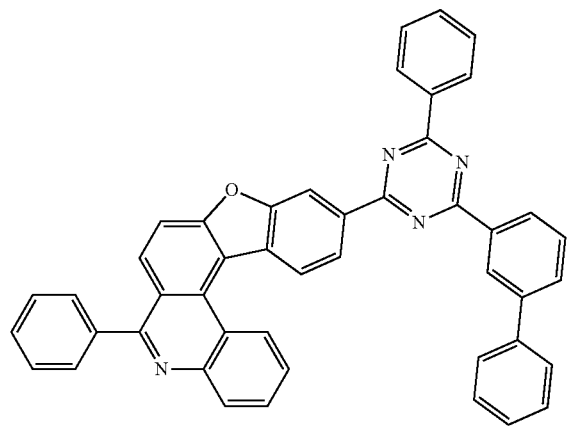
598
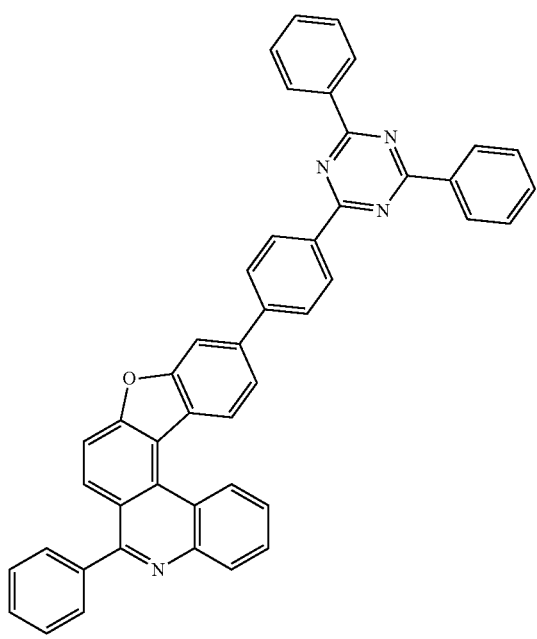
599
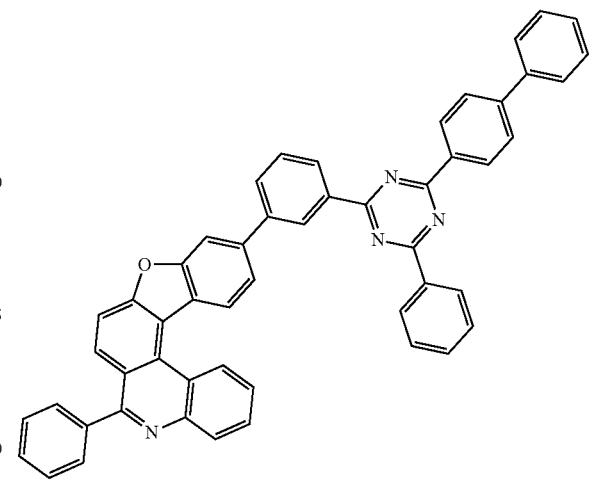
600
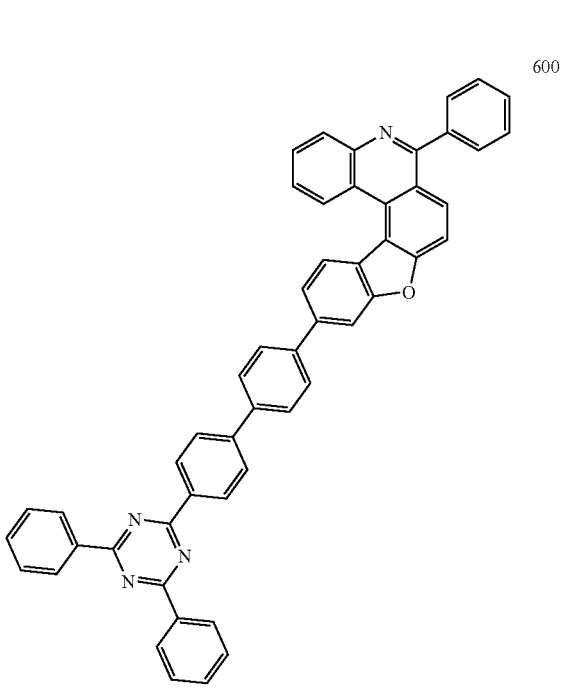 [SMILES: c1ccc(-c2nc(-c3ccccc3)nc(-c3ccc(-c4ccc(-c5ccc6c(c5)oc5ccc7c(-c8ccccc8)nc8ccccc8c7c56)cc4)cc3)n2)cc1]

207
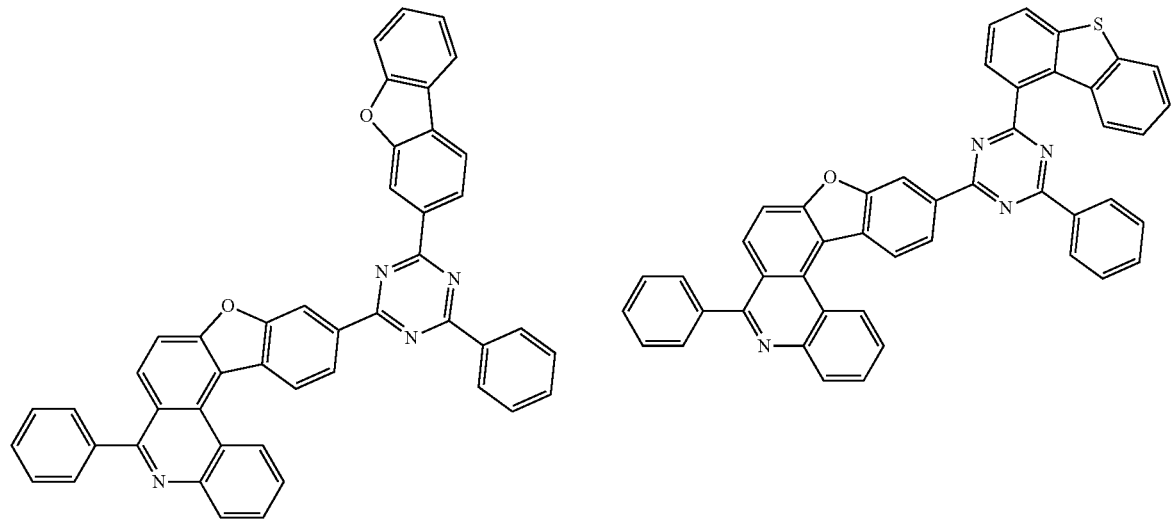
208
603
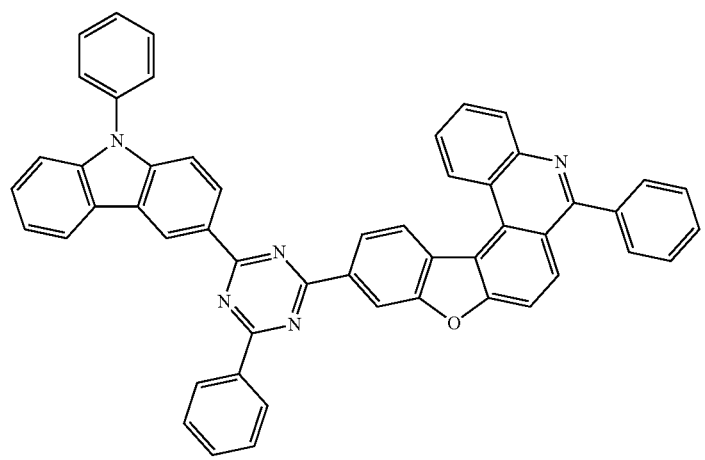
604
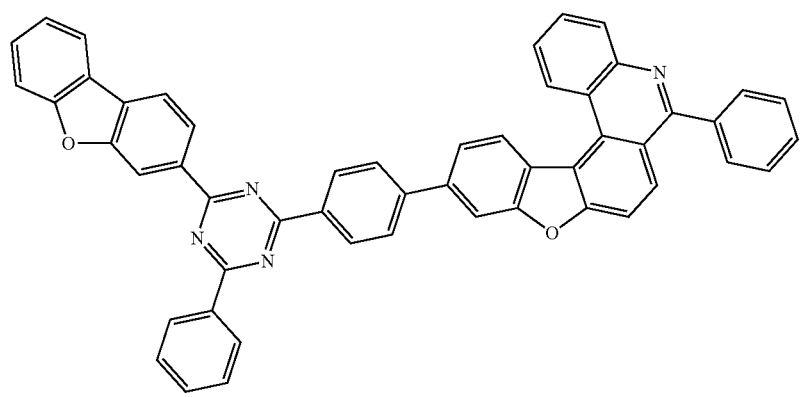

-continued
605
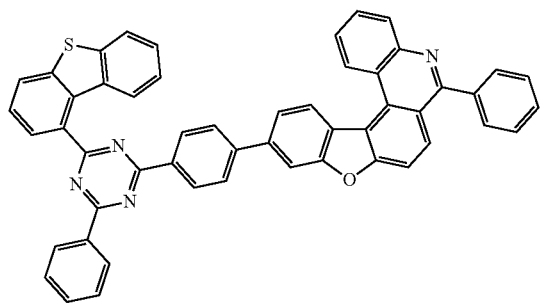
606
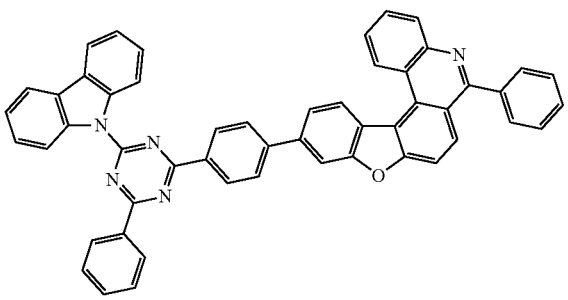
607
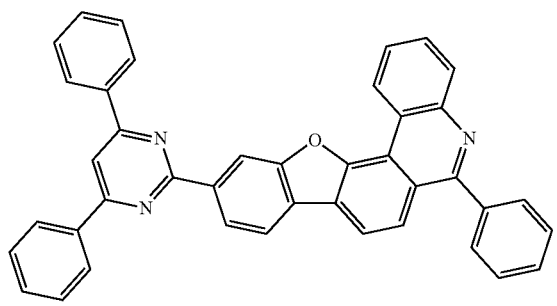
608
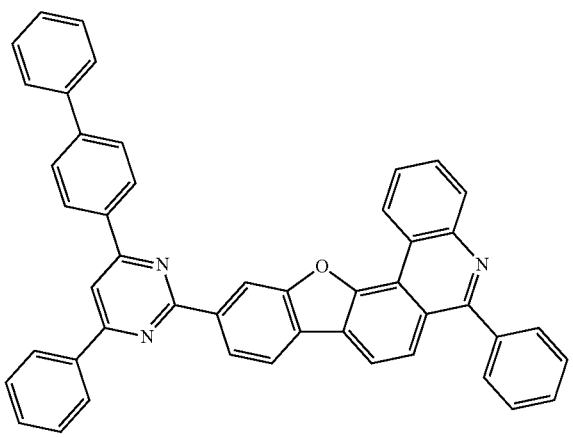
609
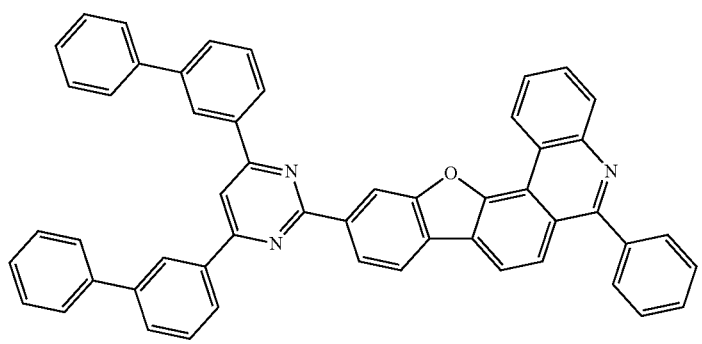
610
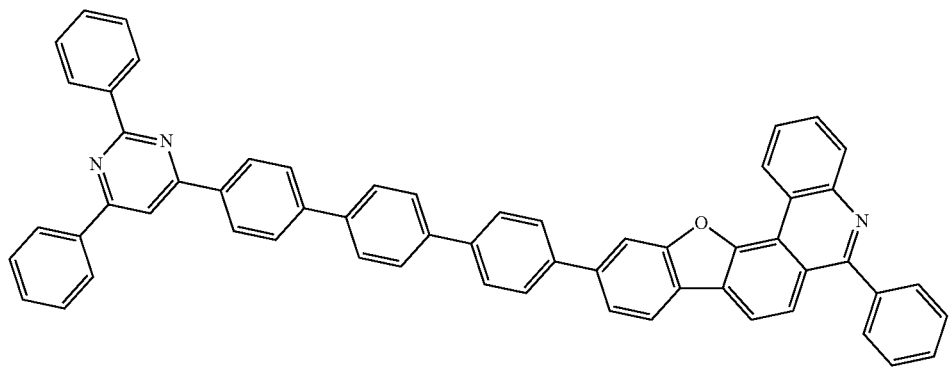

-continued
611
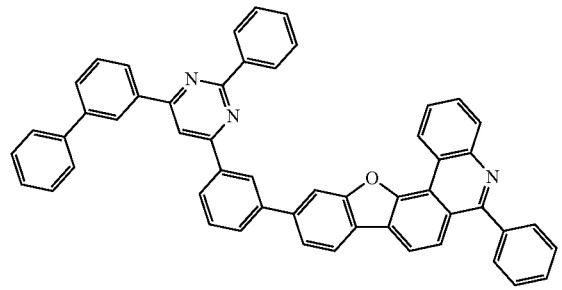
612
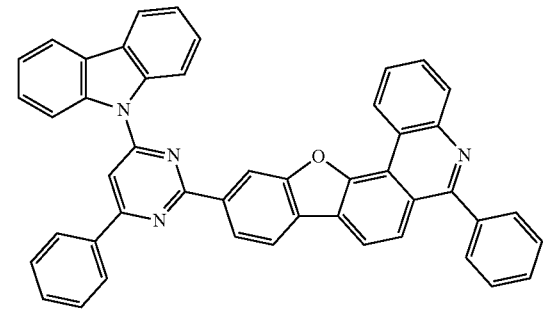
613
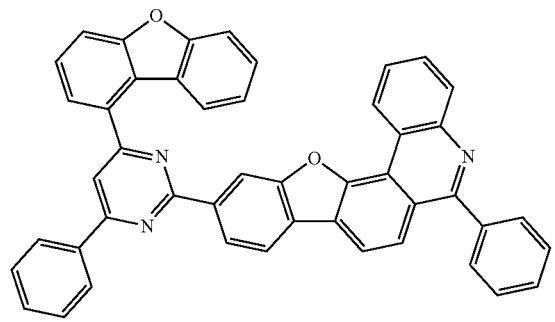
614
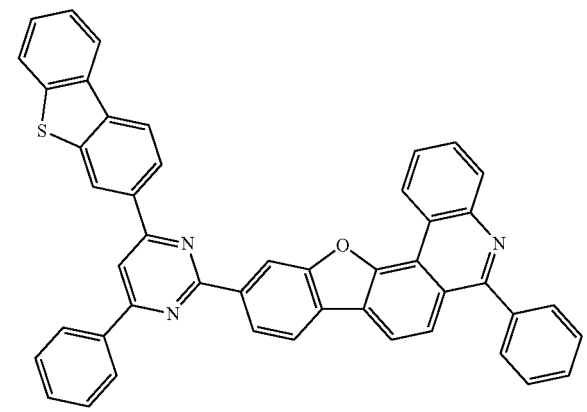
615
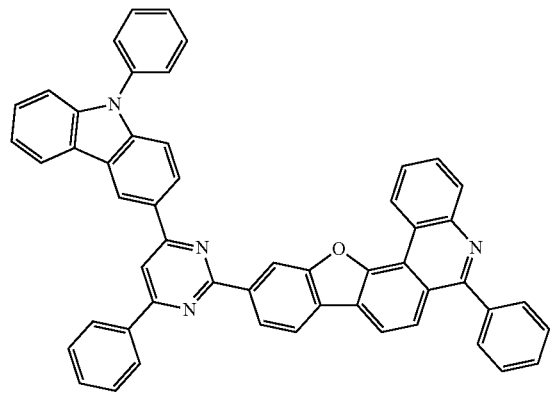
616
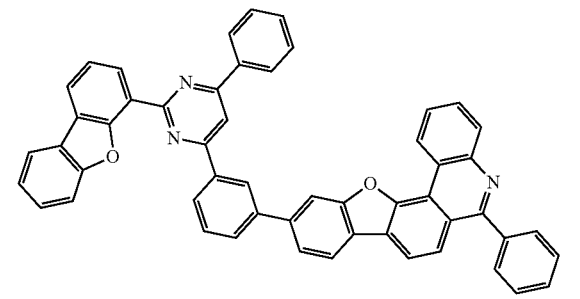
617
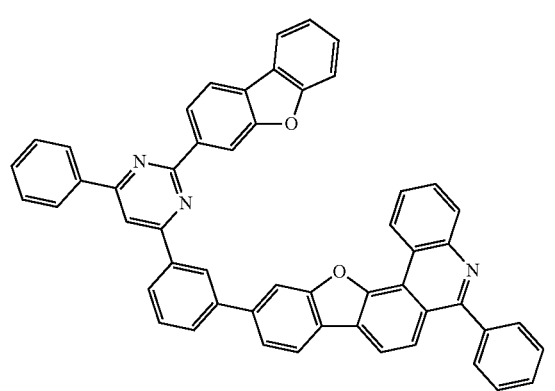
618
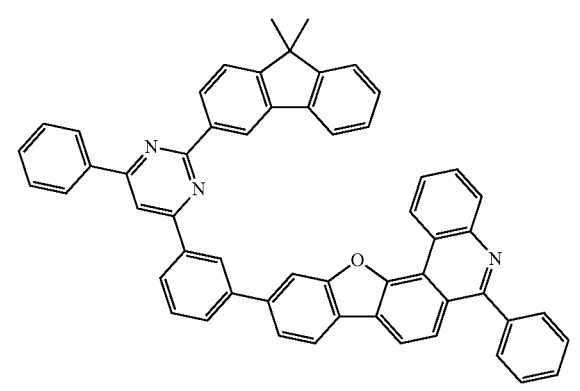

-continued
619
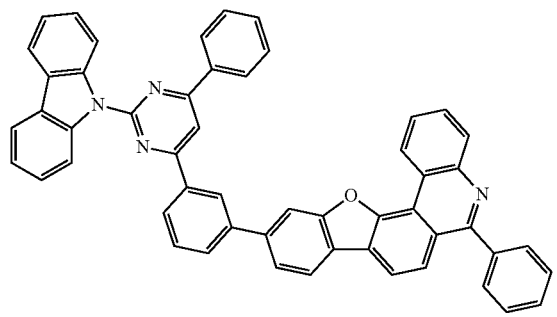
620
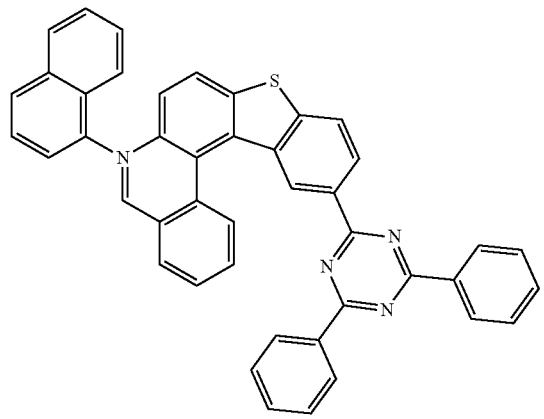
621
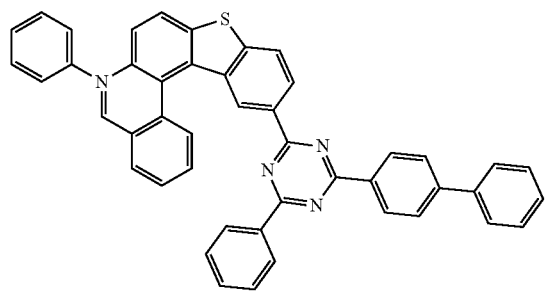
622
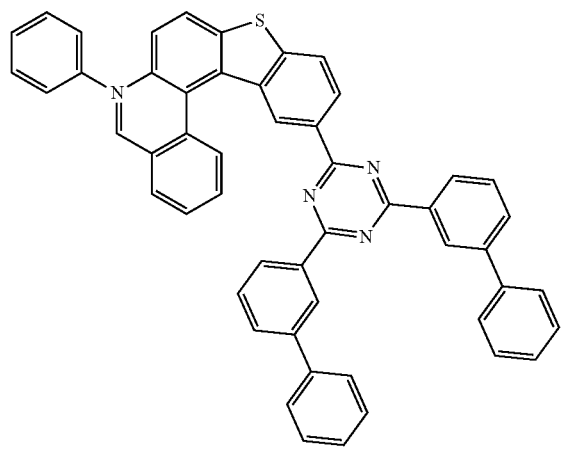
623
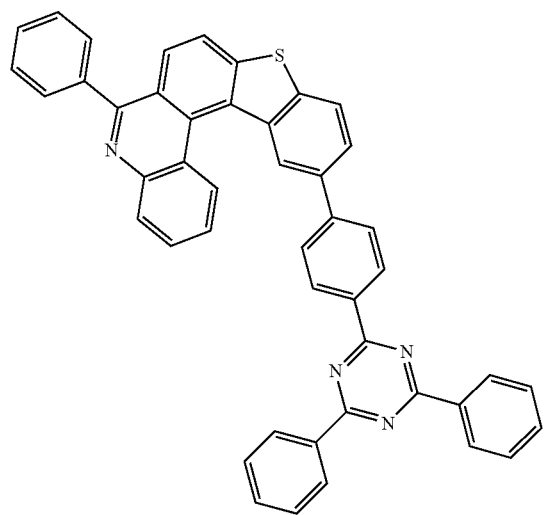
624
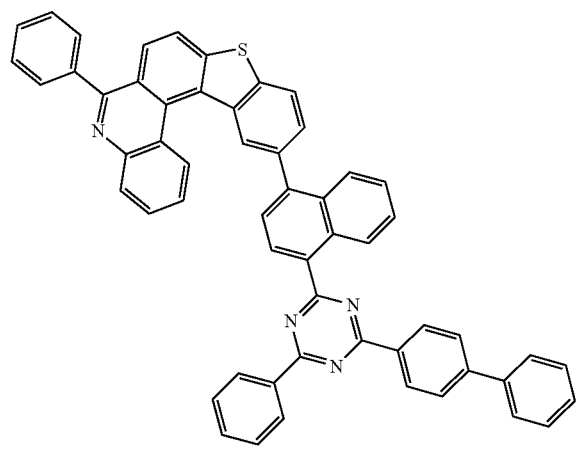

-continued
625
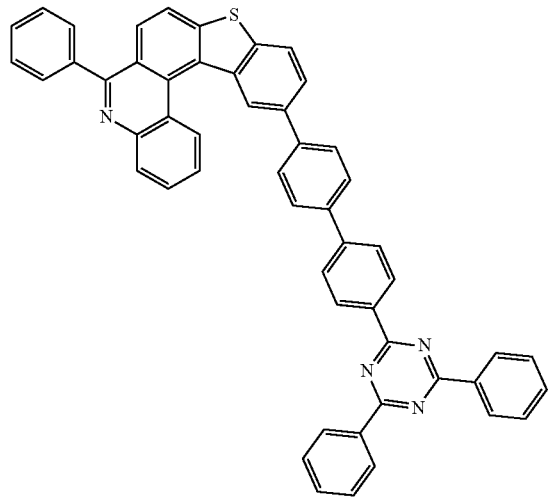
626
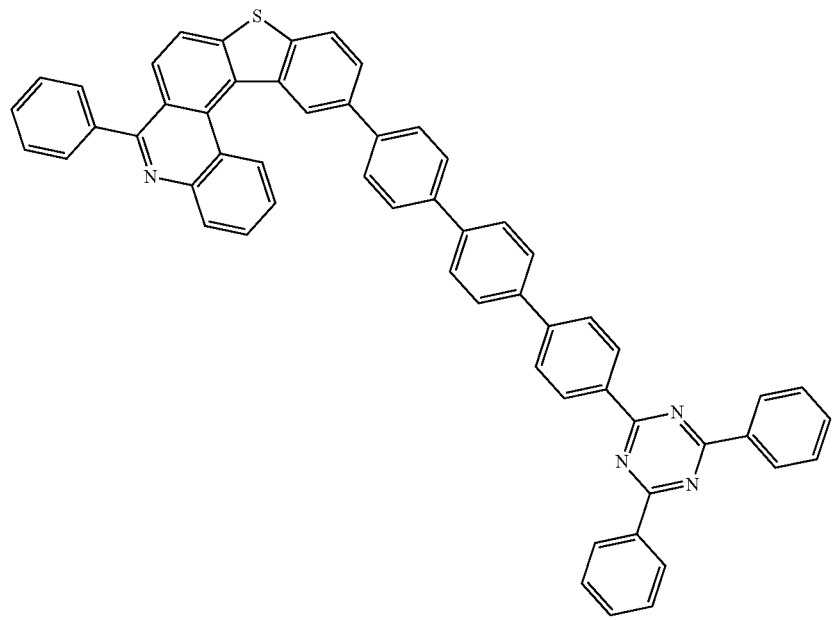
627
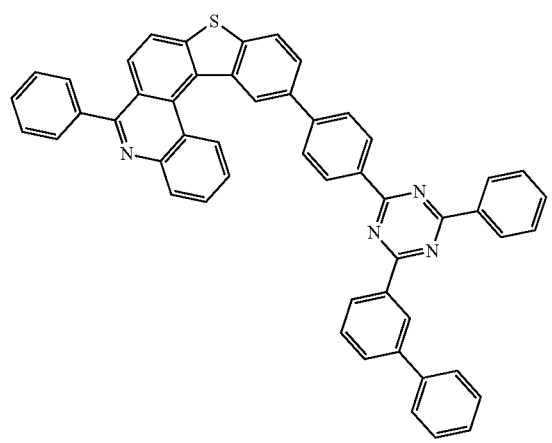
628
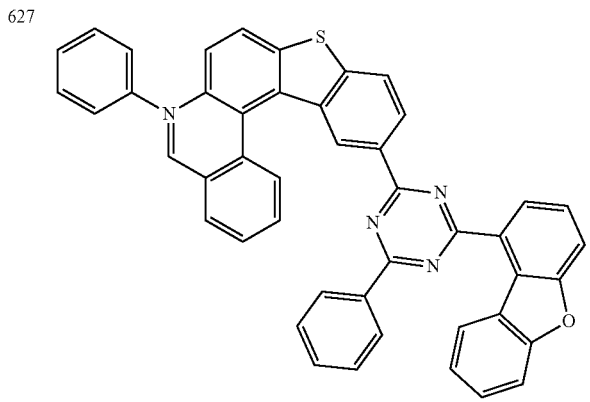

-continued
629
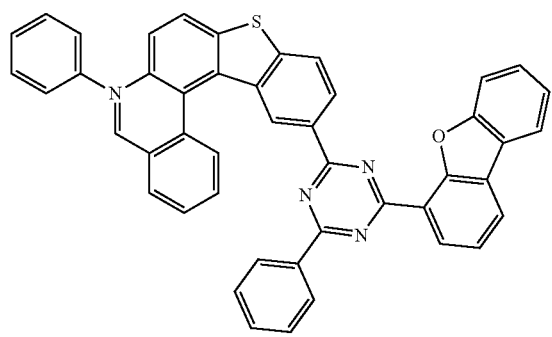
630
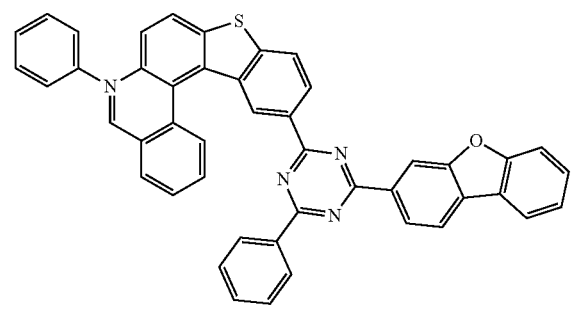
631
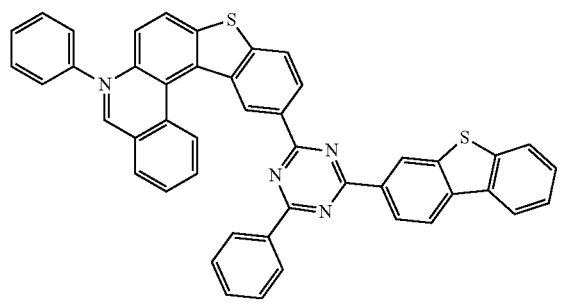
632
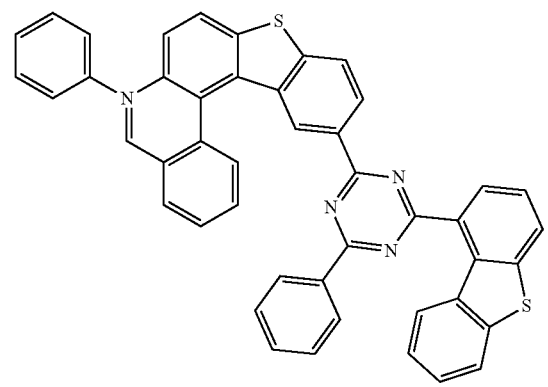 [SMILES: c1ccc(-c2nc(-c3ccc4oc5ccc6c(-c7ccccc7)nc7ccccc7c6c5c4c3)nc(-c3cccc4sc5ccccc5c34)n2)cc1]
633
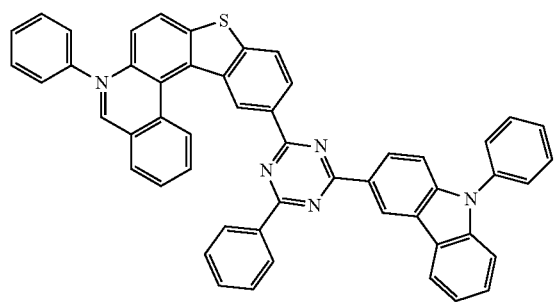
634
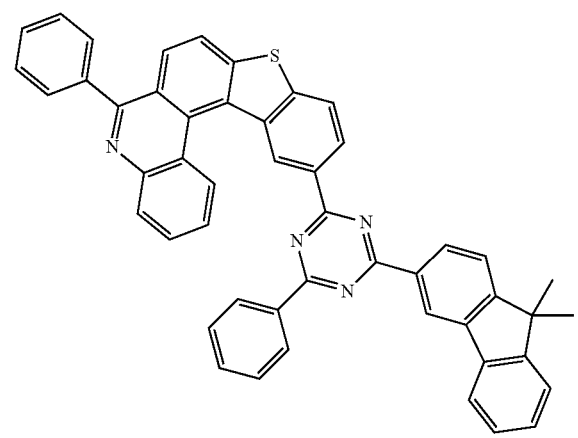

-continued
219
635
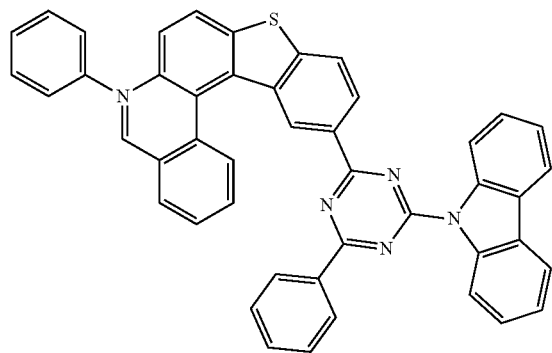
637
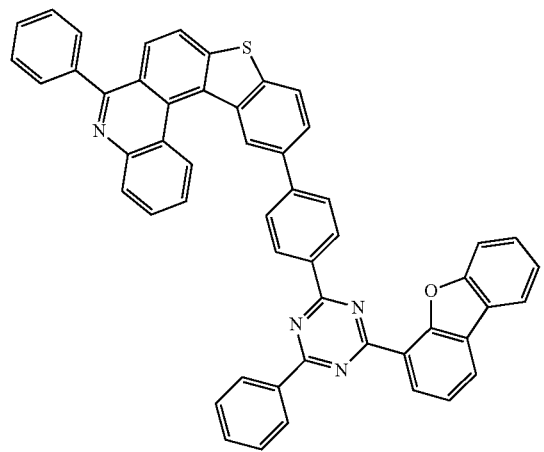
639
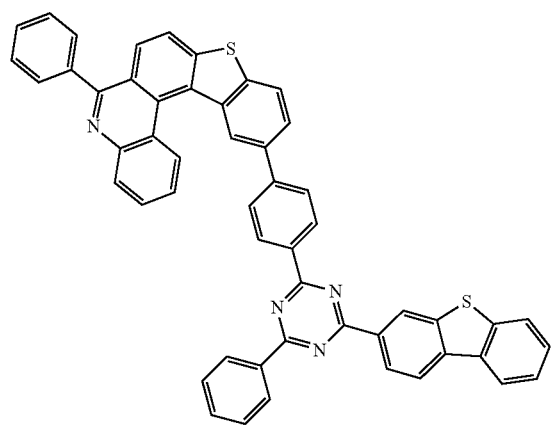
220
636
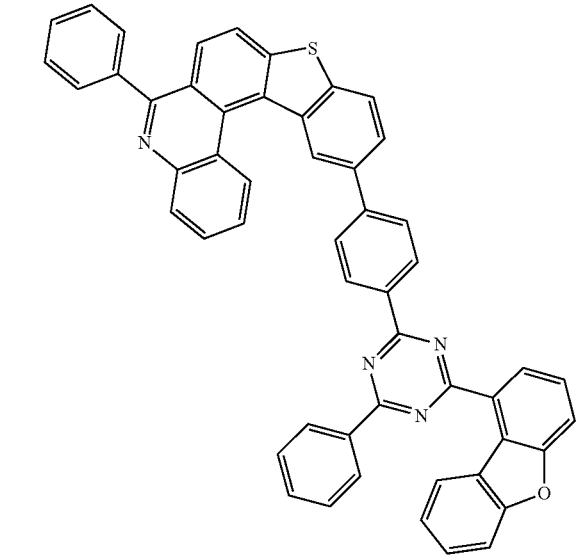
638
640
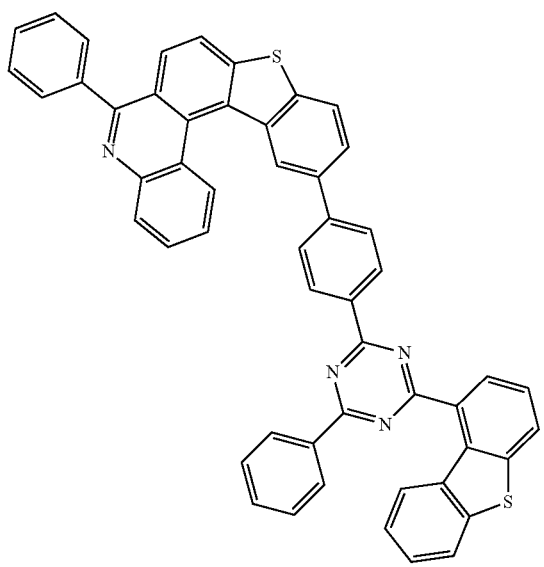

-continued
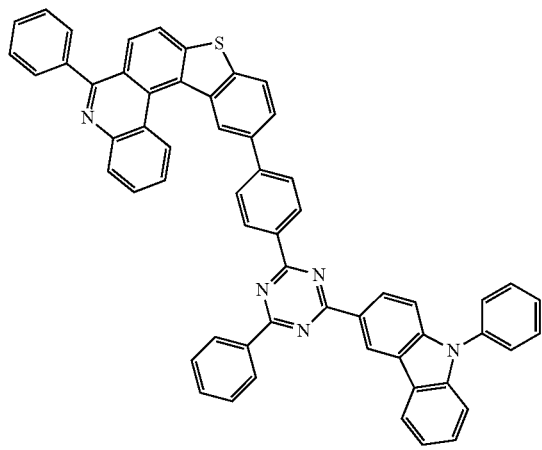
641
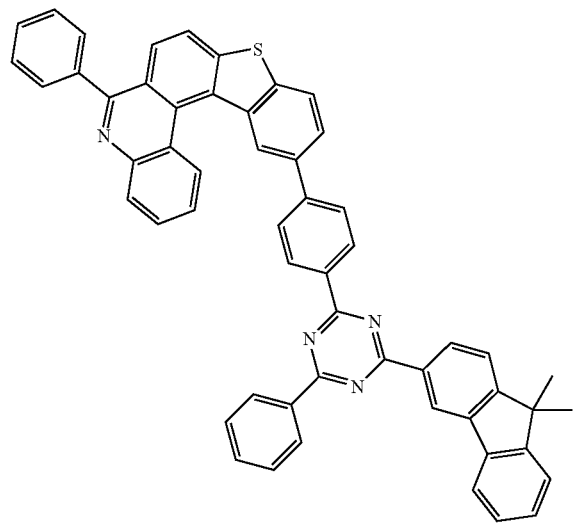
642
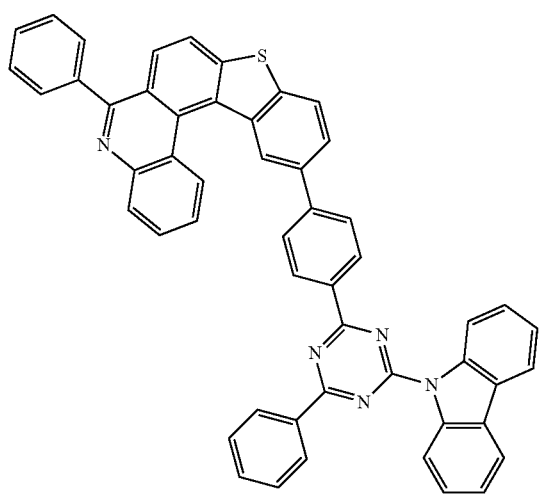
643
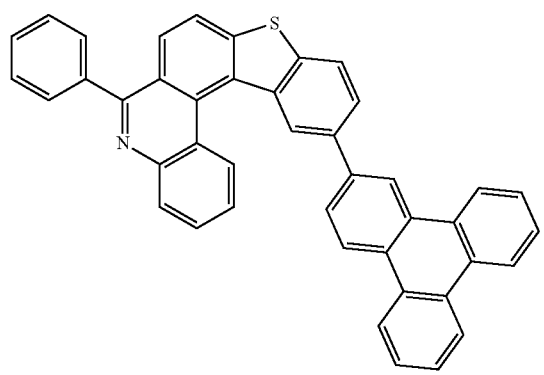 [SMILES: c1ccc(-c2nc3ccccc3c3c2ccc2oc4ccc(-c5ccc6c7ccccc7c7ccccc7c6c5)cc4c23)cc1]
644
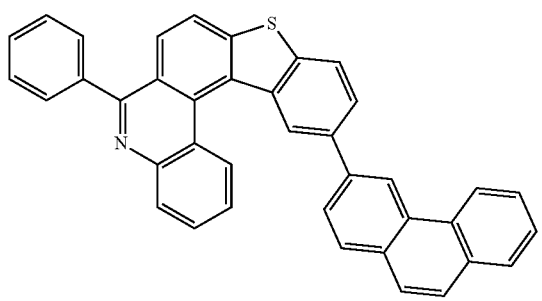 [SMILES: c1ccc(-c2nc3ccccc3c3c2ccc2oc4ccc(-c5ccc6ccc7ccccc7c6c5)cc4c23)cc1]
645
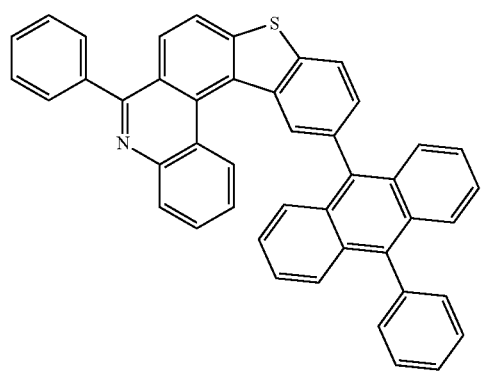
646

-continued
223
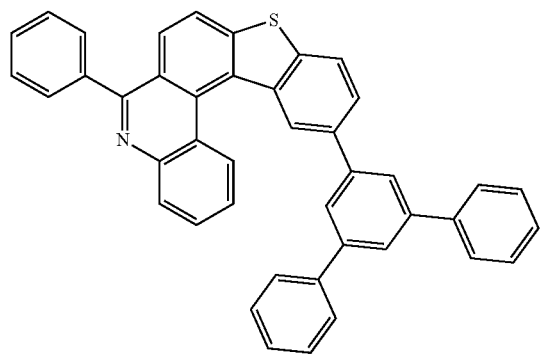
647
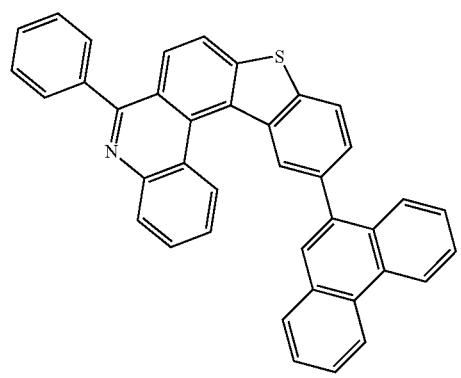
649
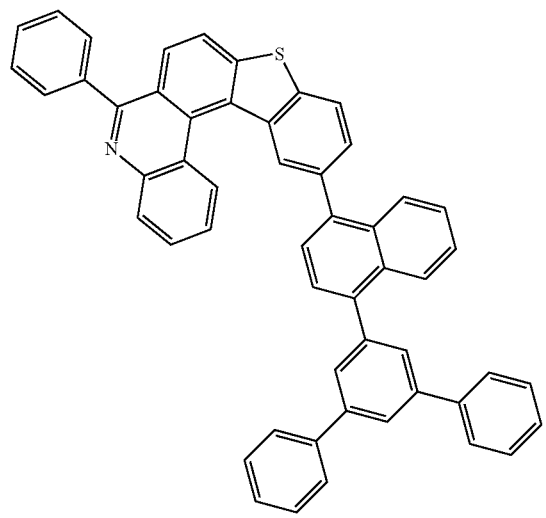
651
224
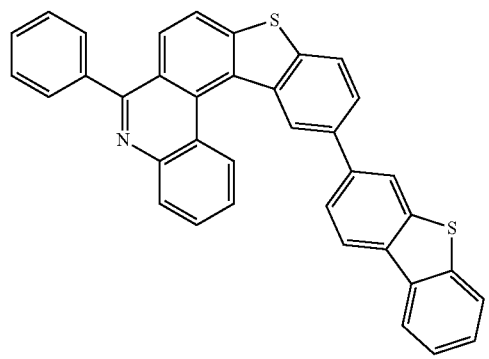
648
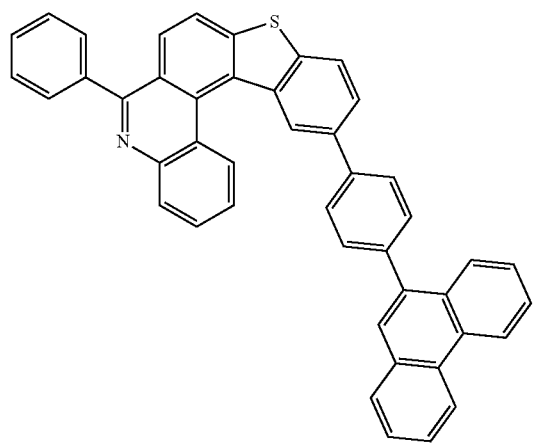
650
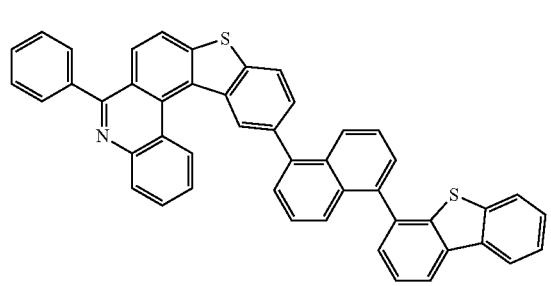
652

-continued
653
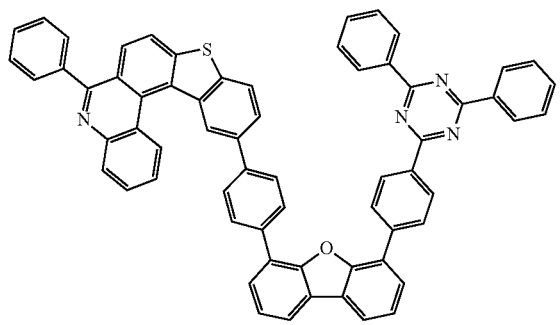
654
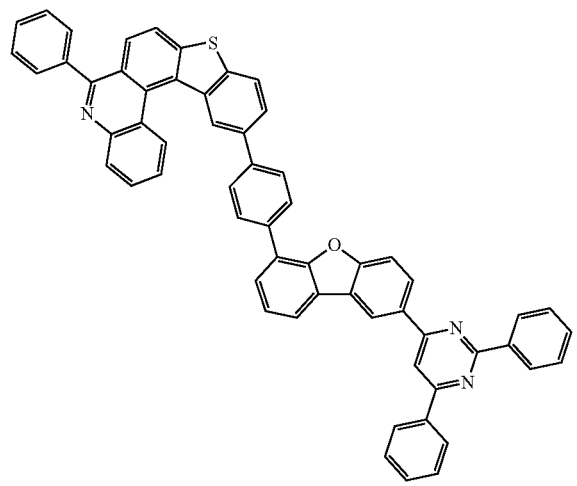
655
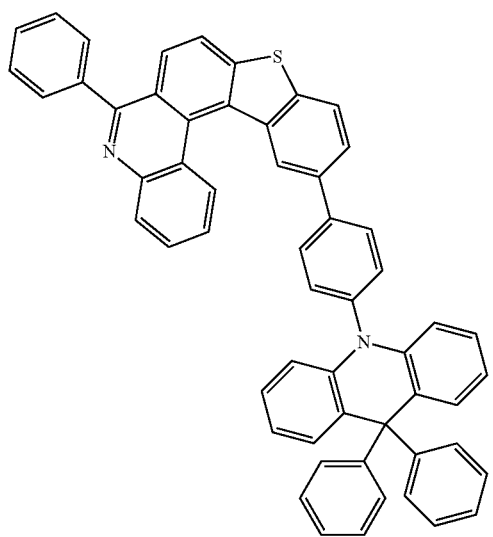
656
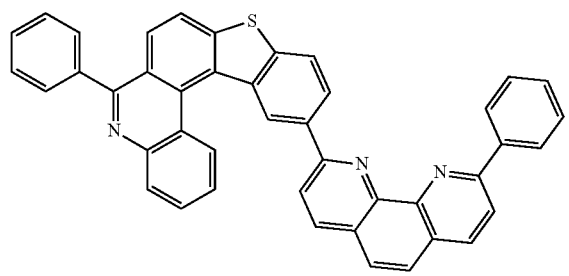
657
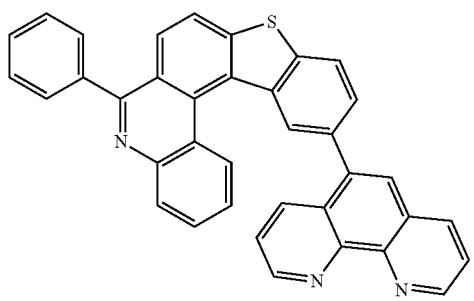
658
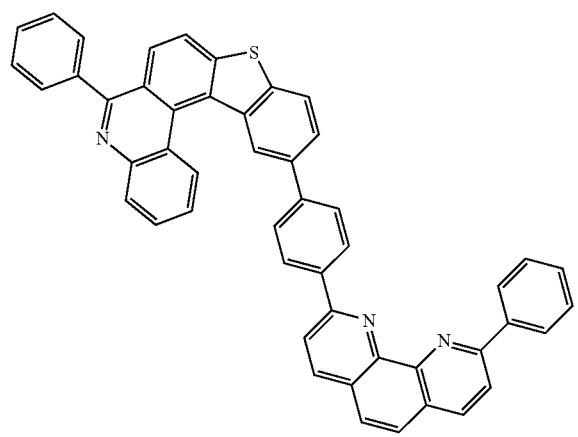

-continued
659
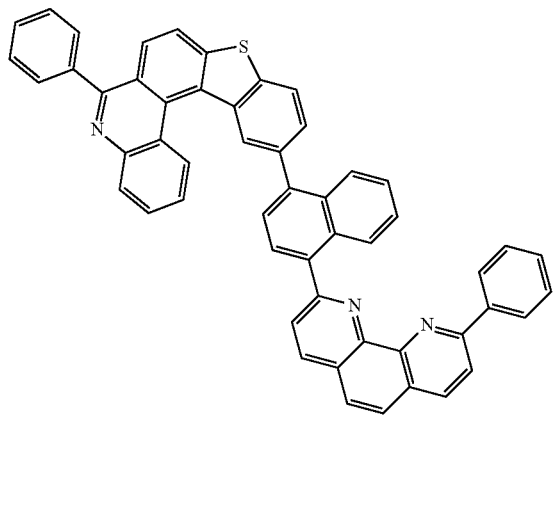
660
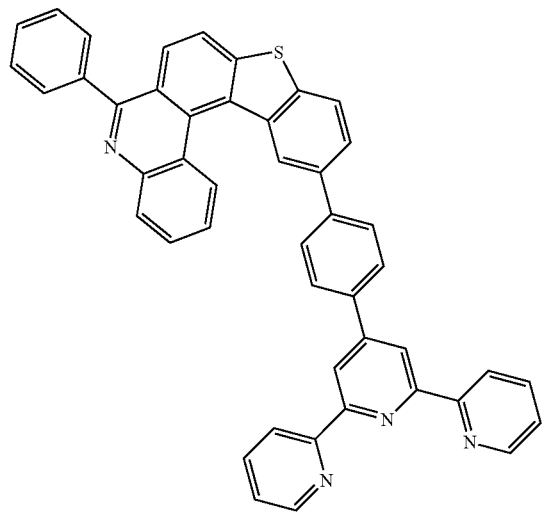
661
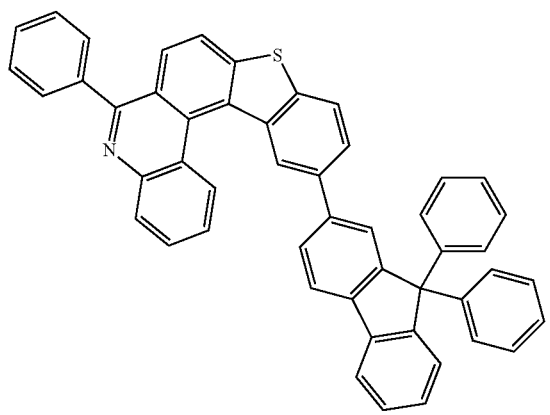
662
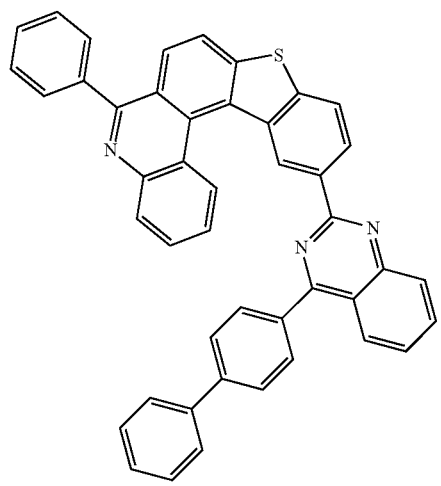
663
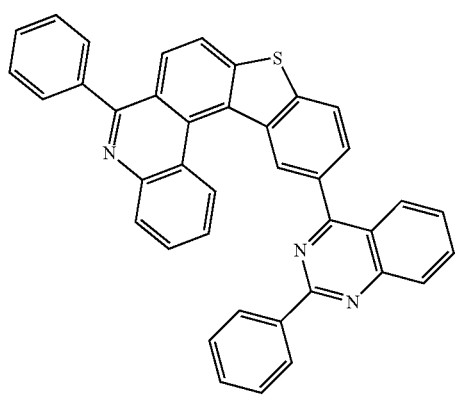
664
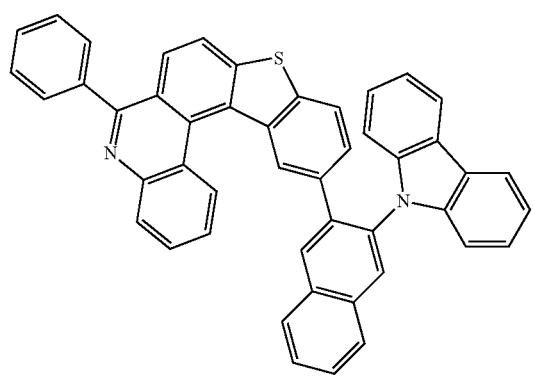

665
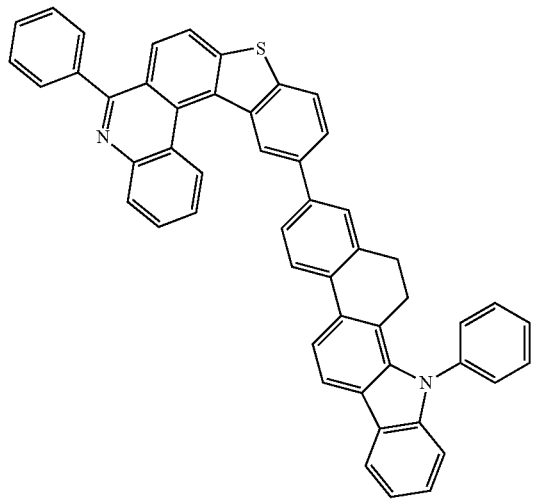
666
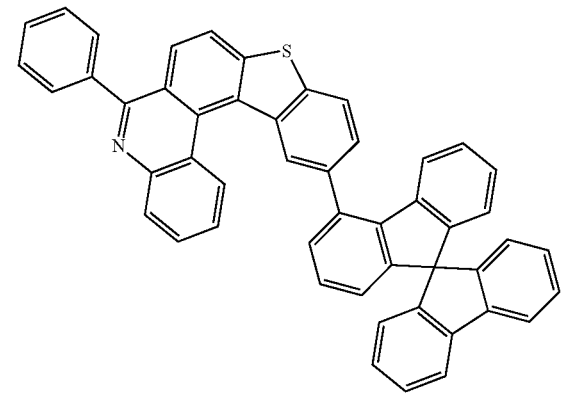
667
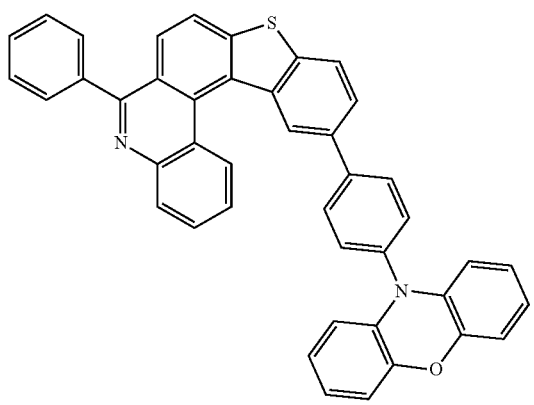
668
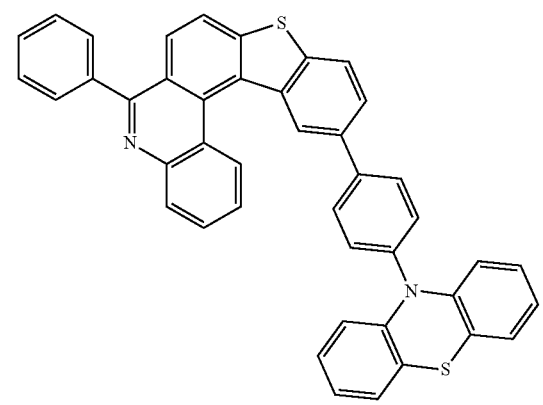
669
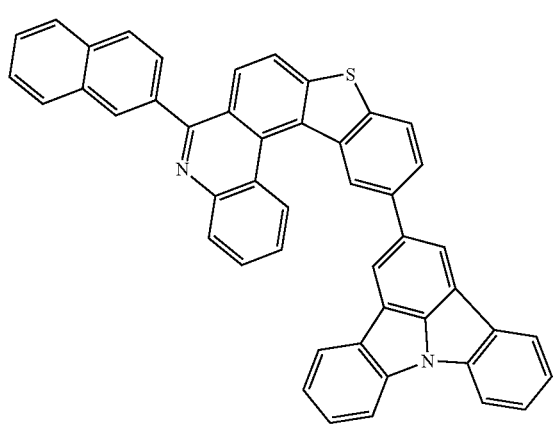
670
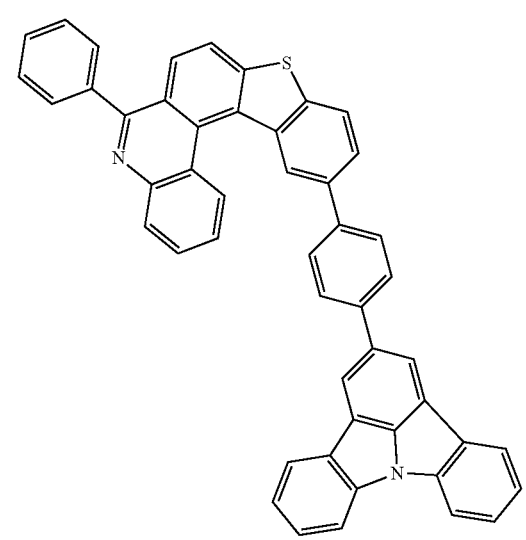

-continued
671
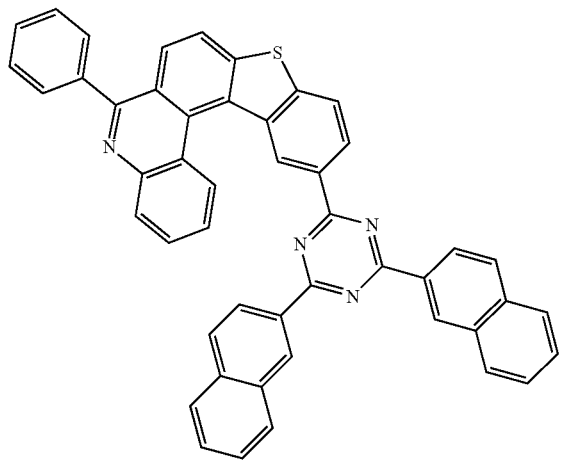
672
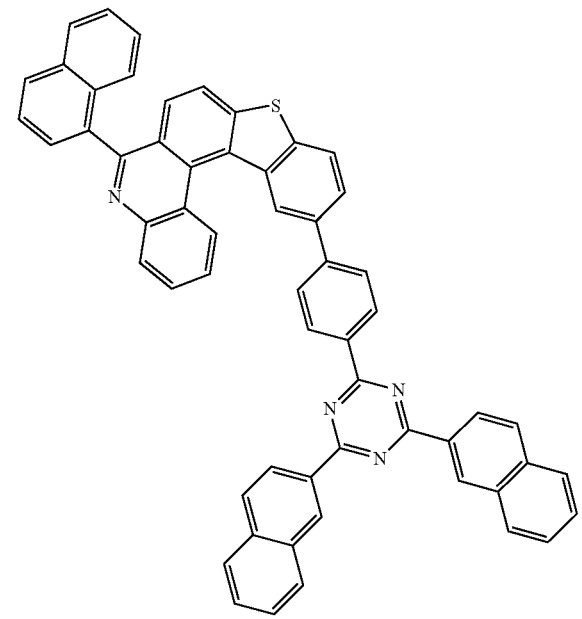
673
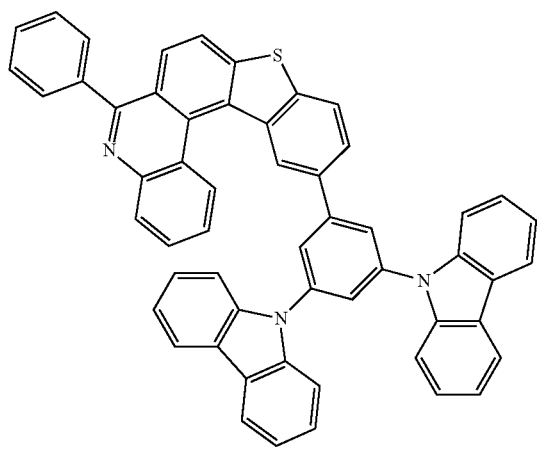
674
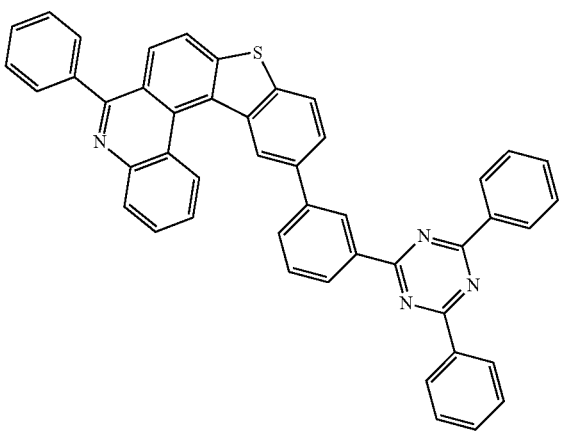
675
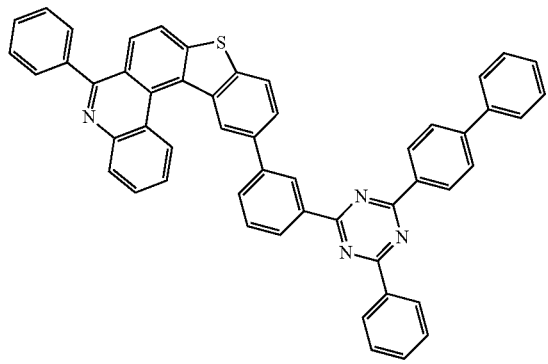
676
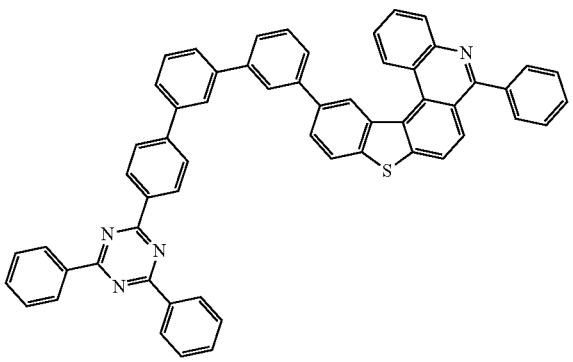

-continued
677 678
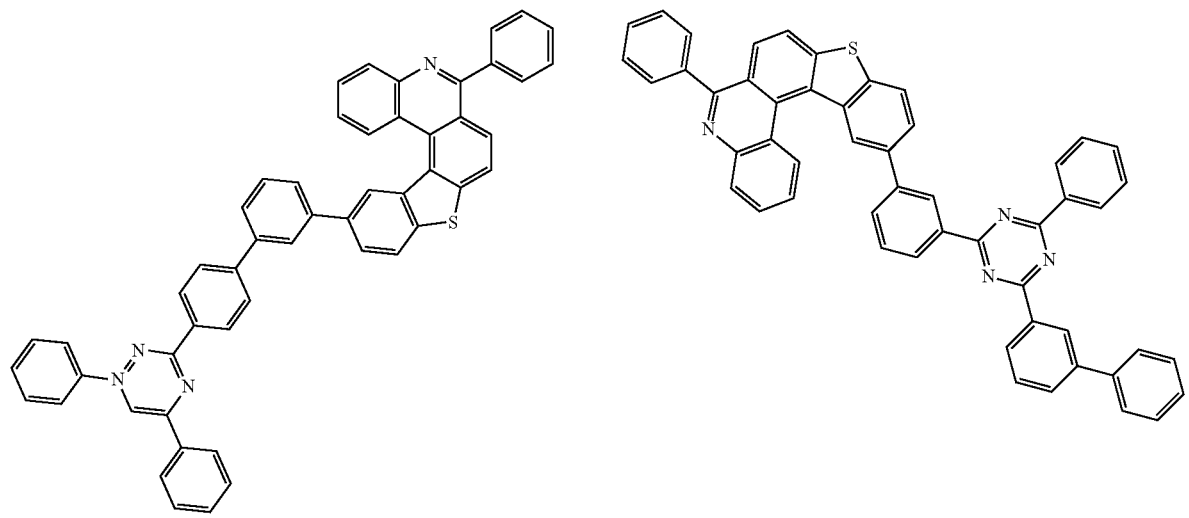
679 680
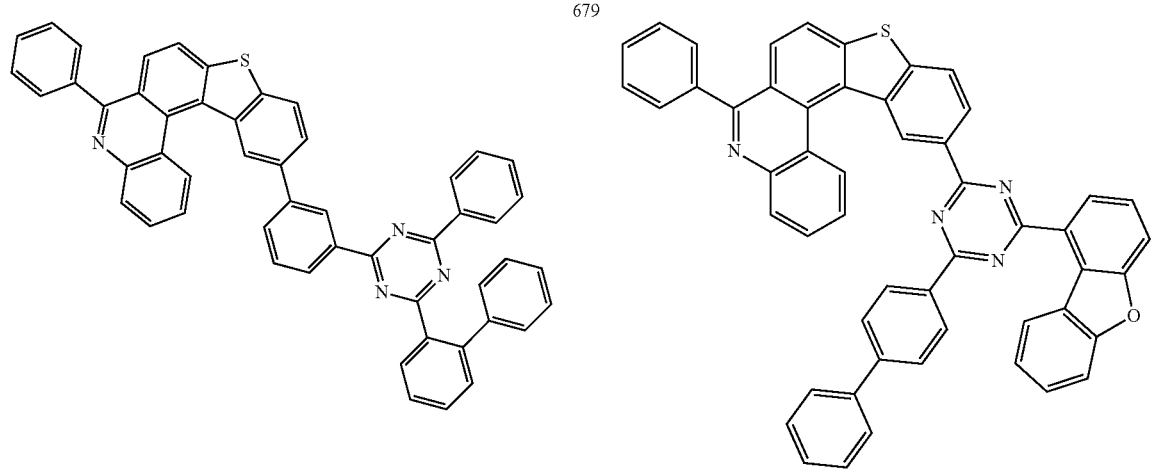
681 682
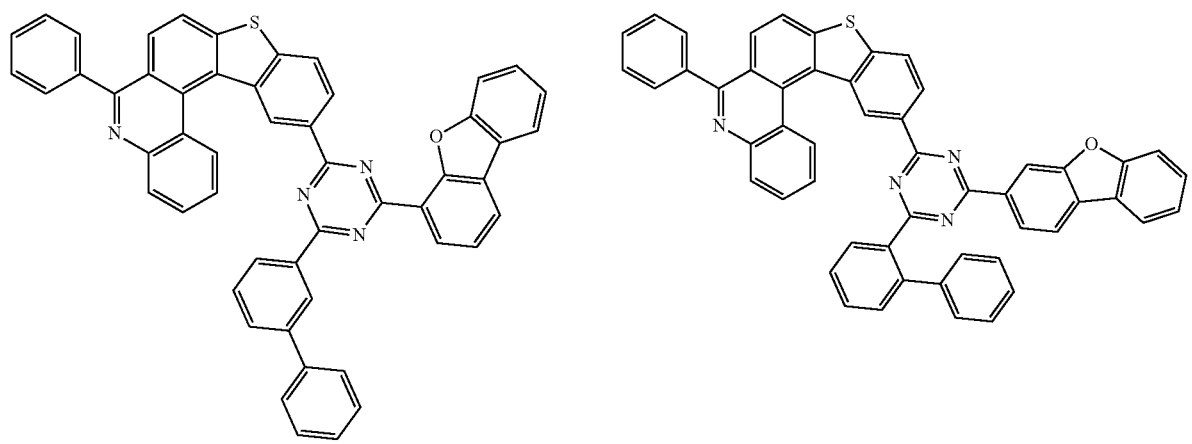

-continued
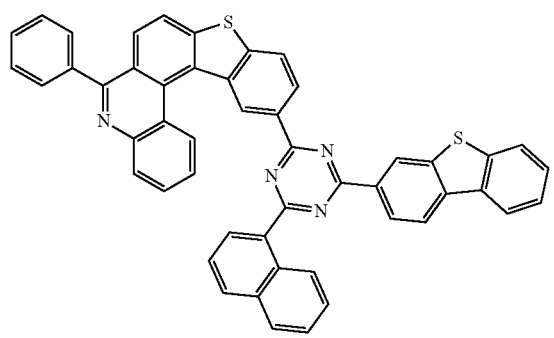
683
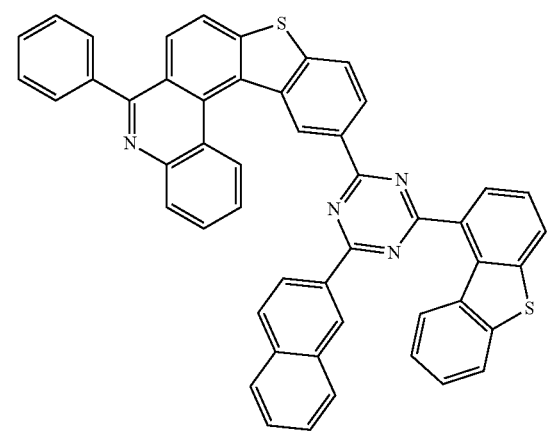
684
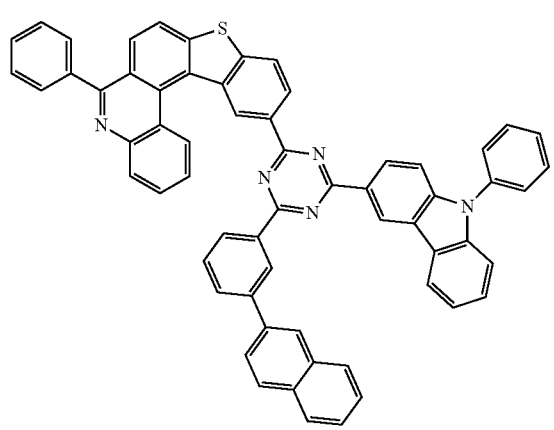
685
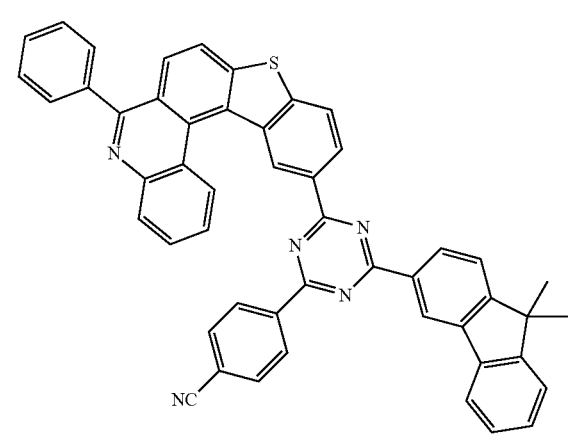
686
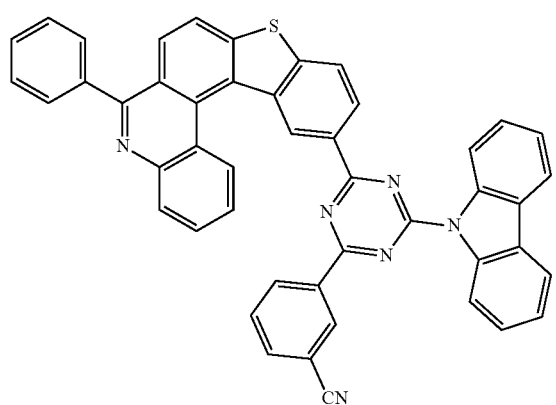
687
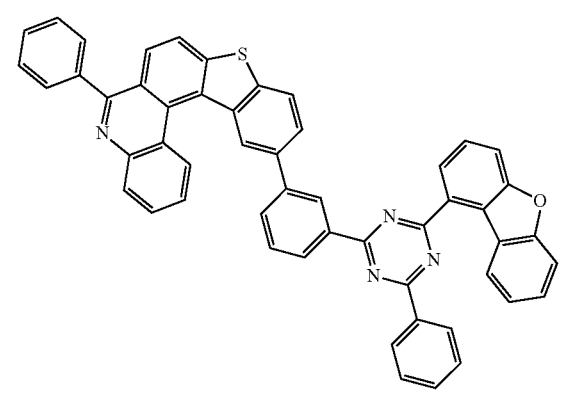
688

-continued
689
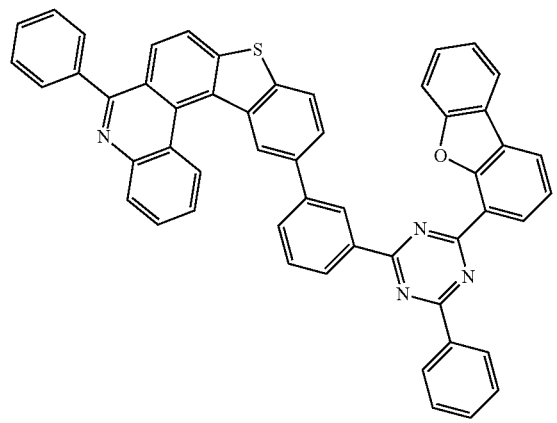
690
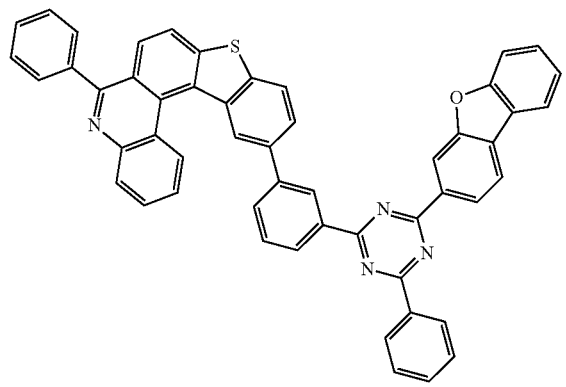
691
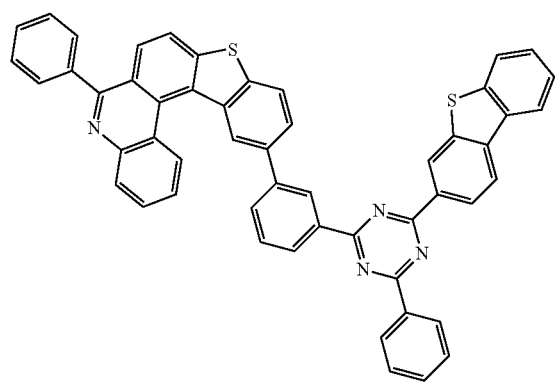
692
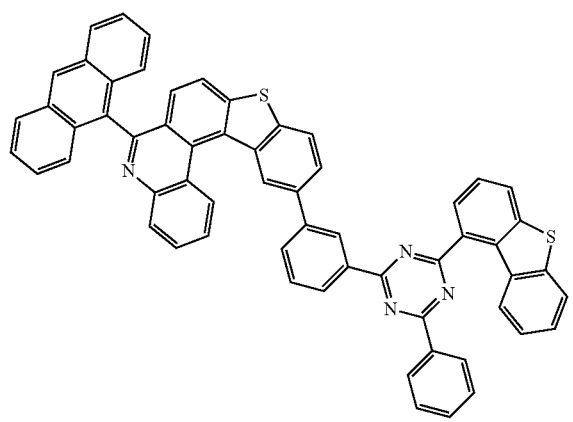
693
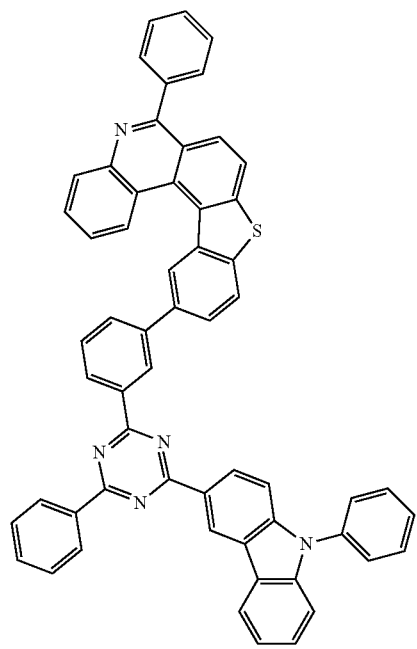
694
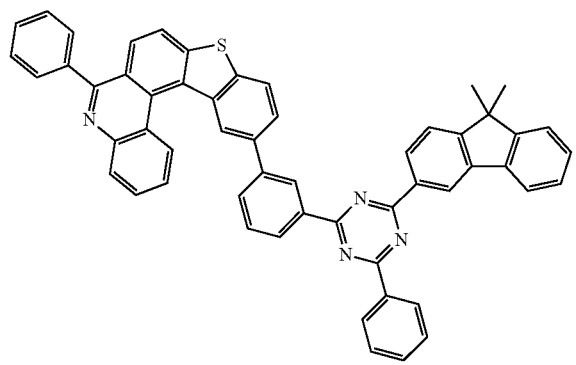

-continued
695
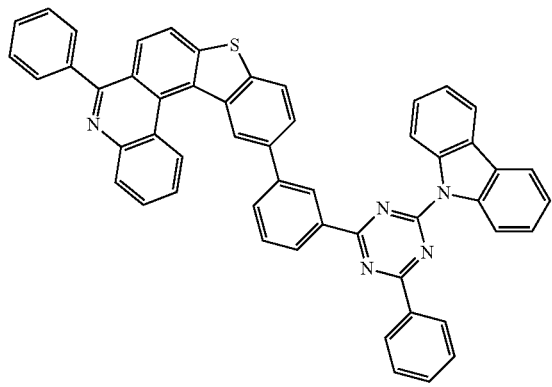
696
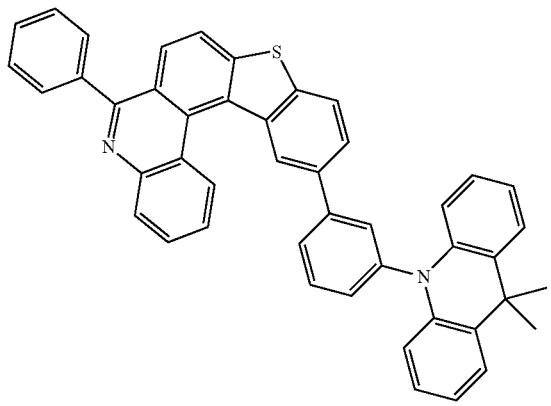
697
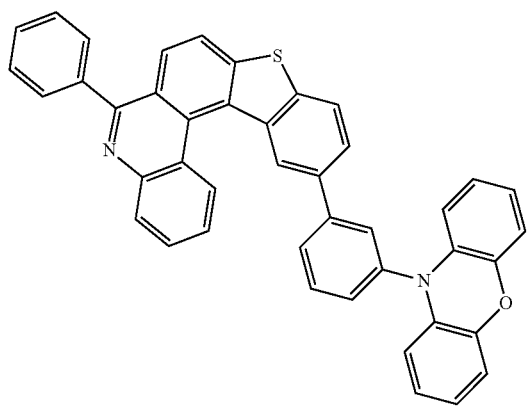
698
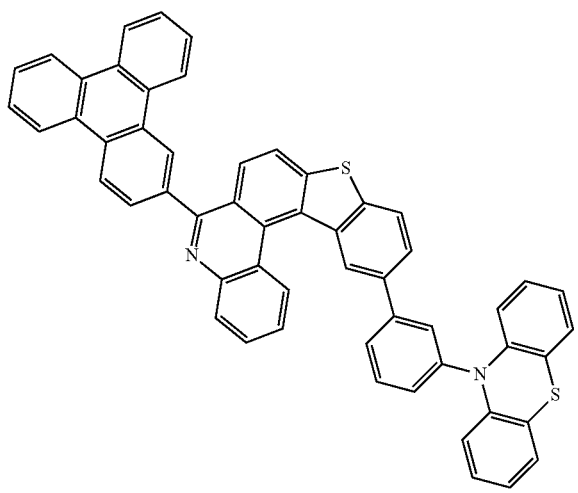
699
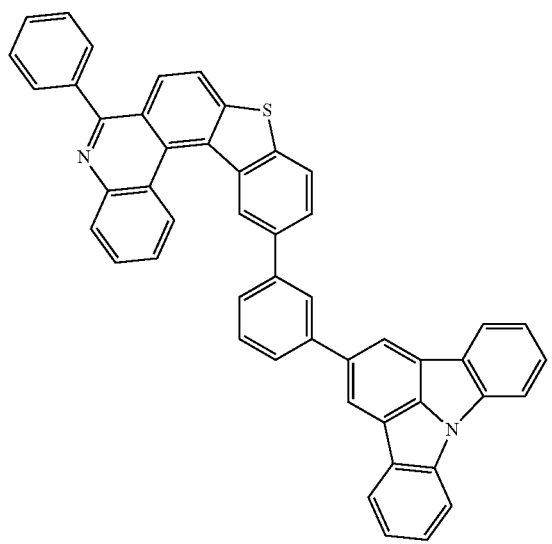
700
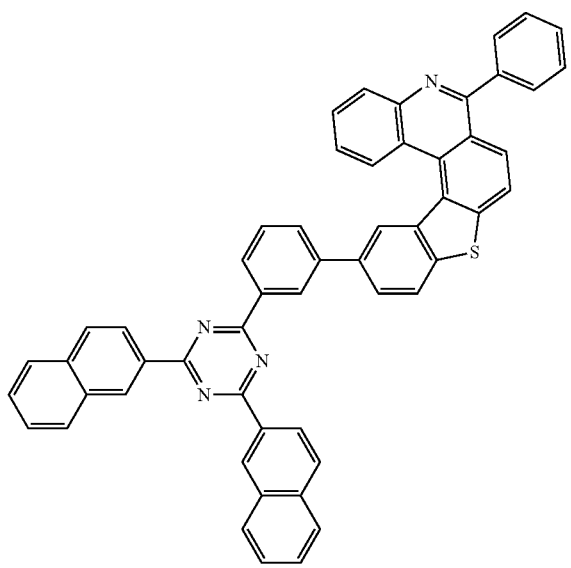

-continued
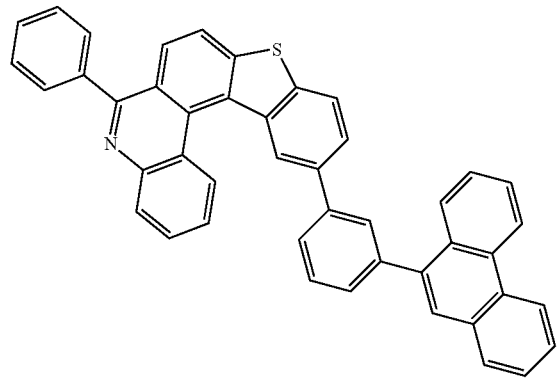
701
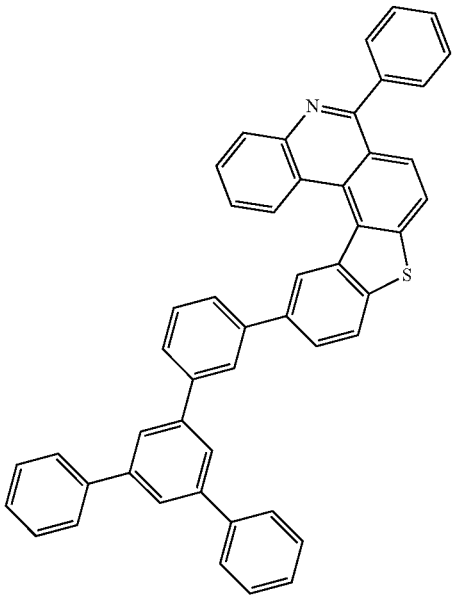
702
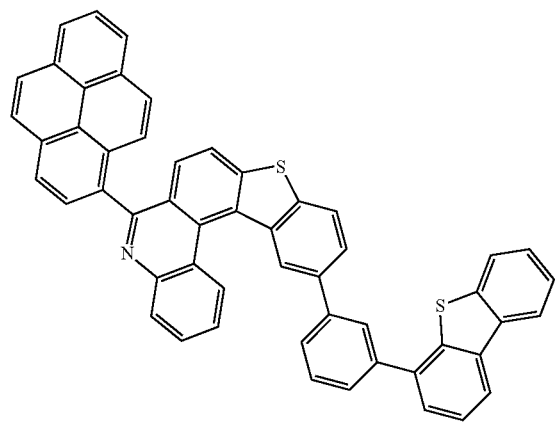
703
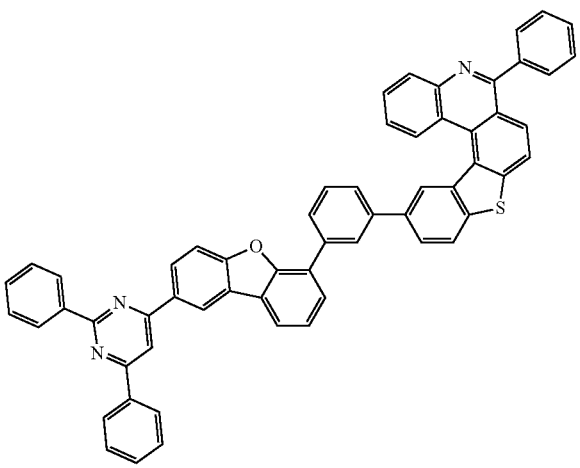
704
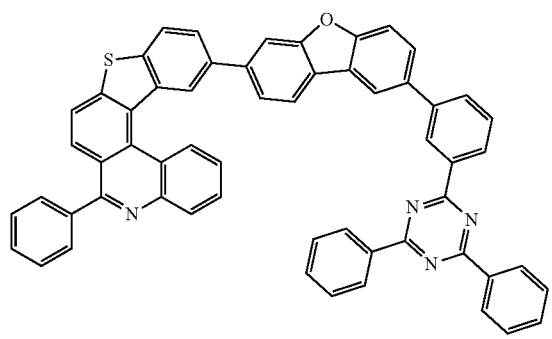
705
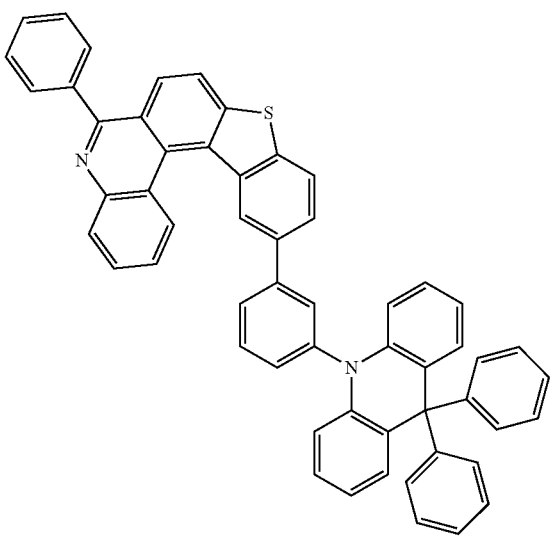
706

-continued
707
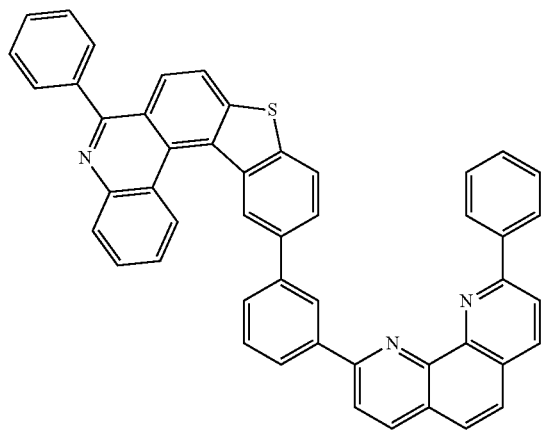
708
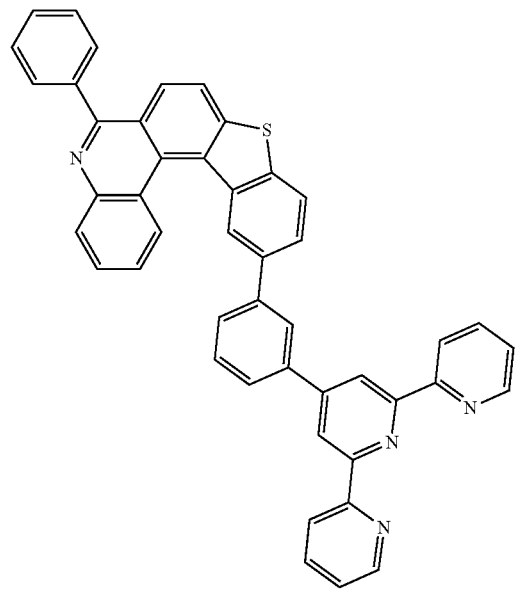
709
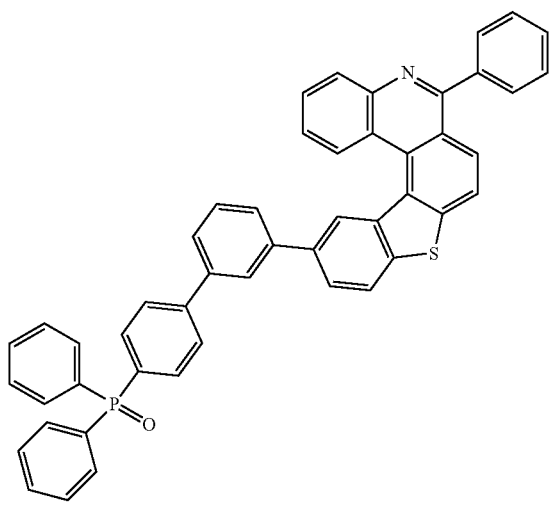
710
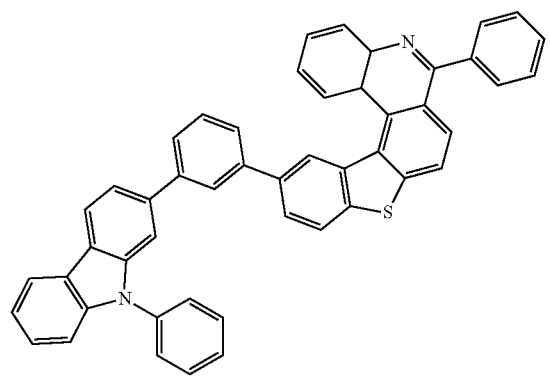
711
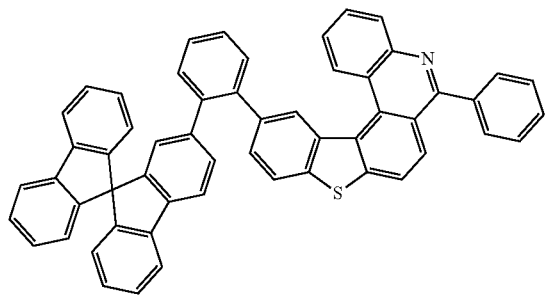
712
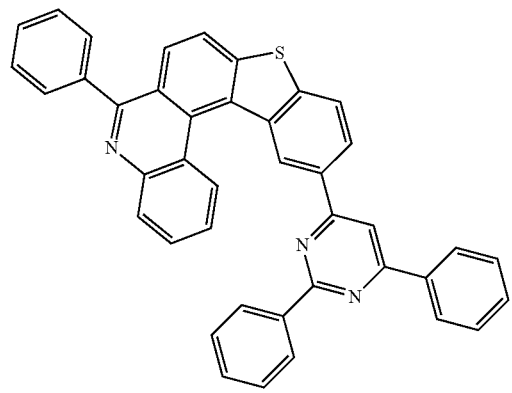

-continued
713
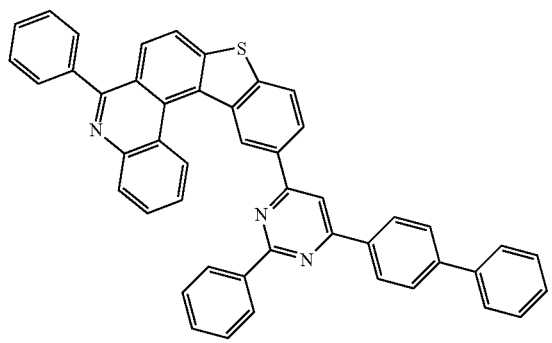
714
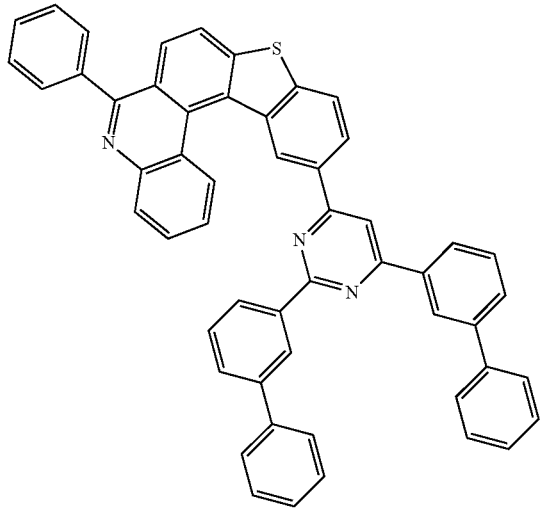
715
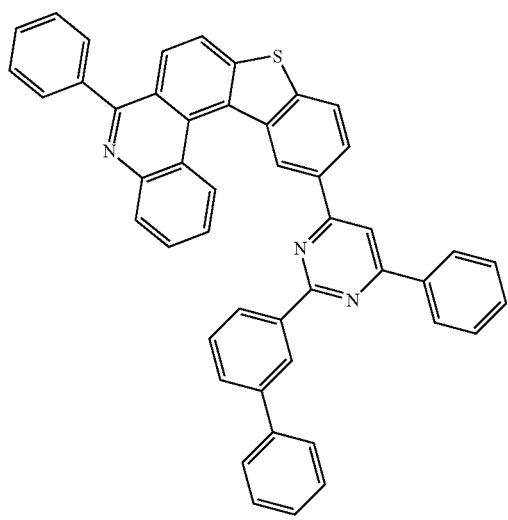
716
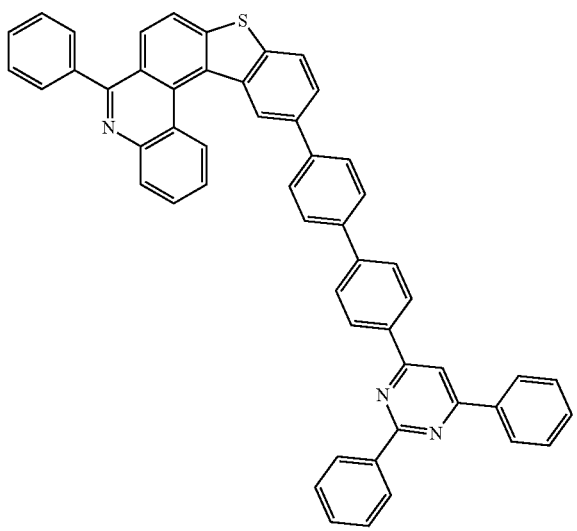
717
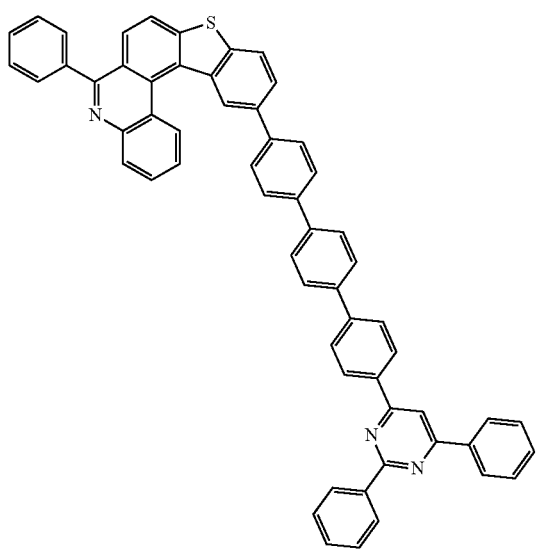
718
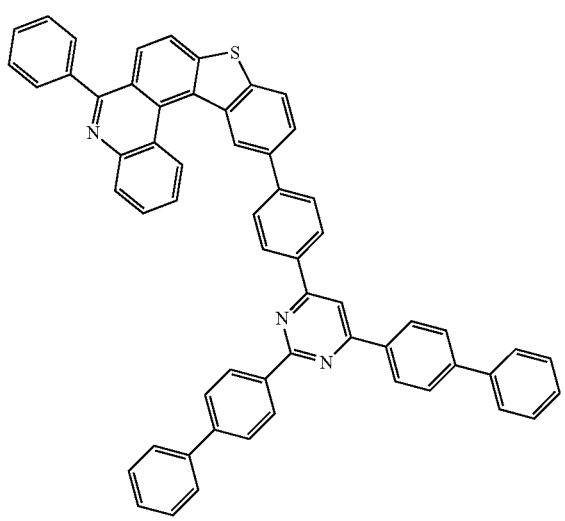

-continued
719
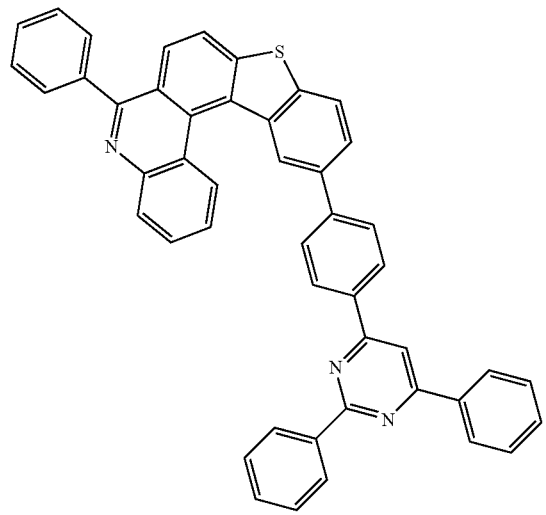
720
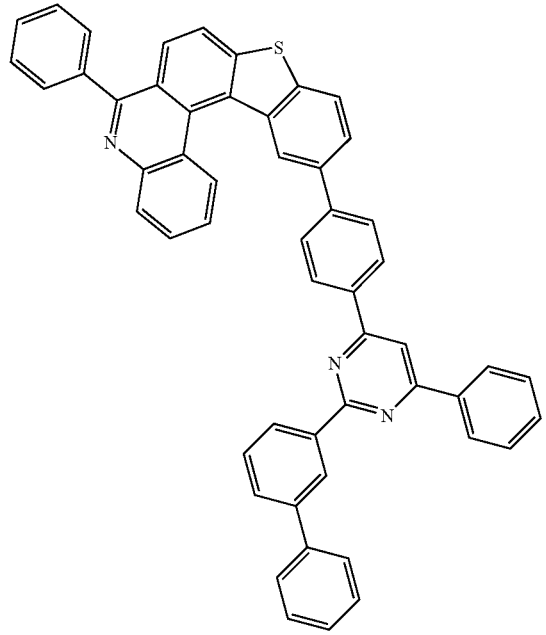
721
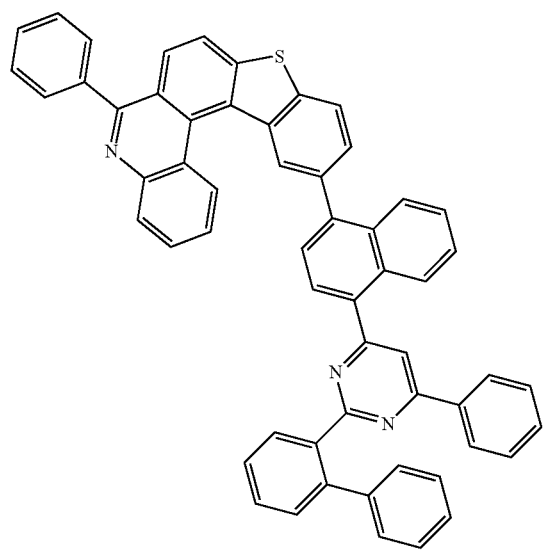
722
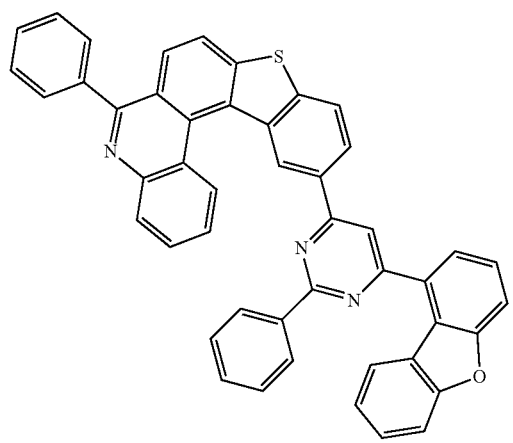
723
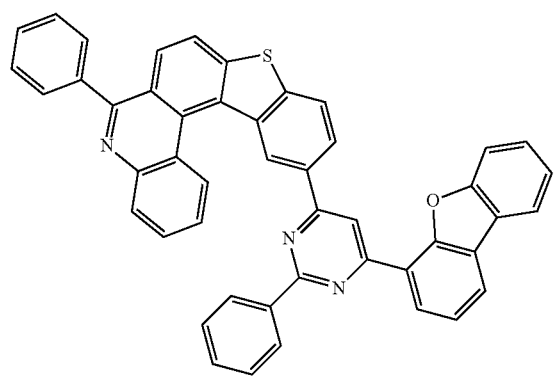
724
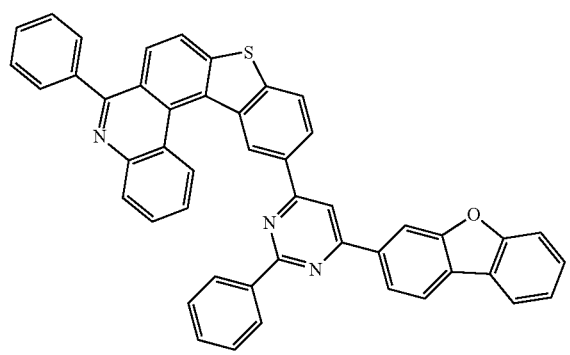

-continued
725
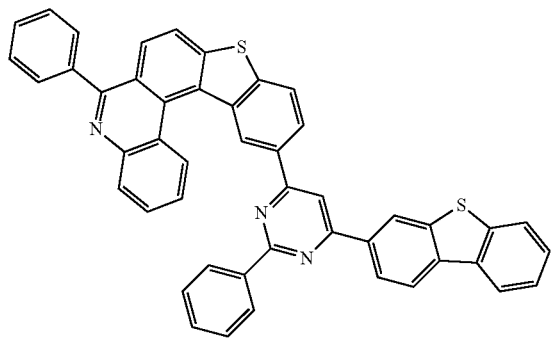
726
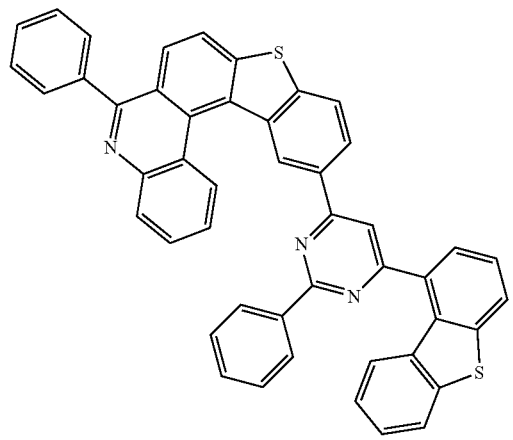
727
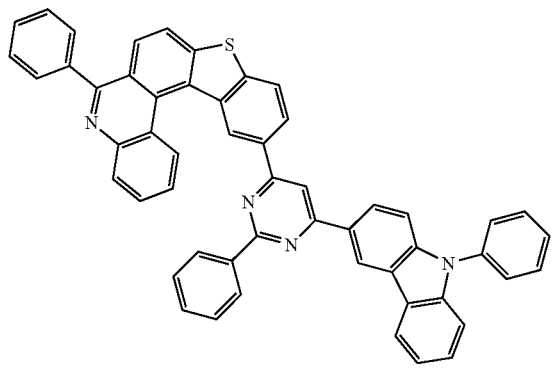
728
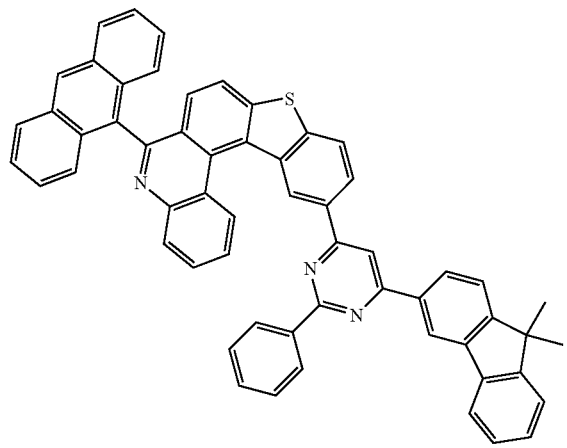
729
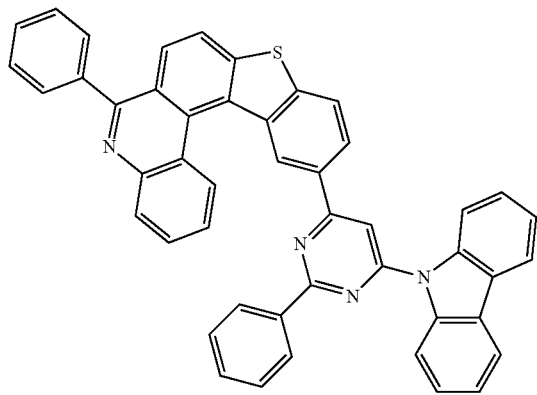
730
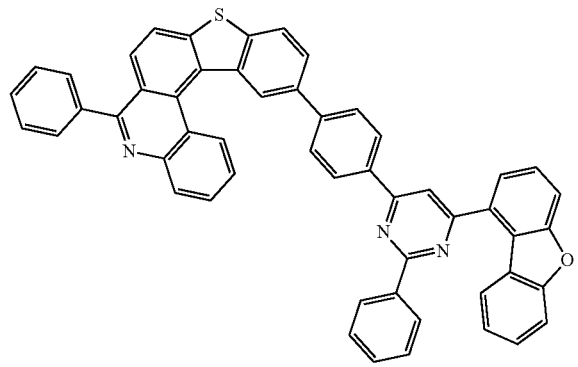

-continued
731
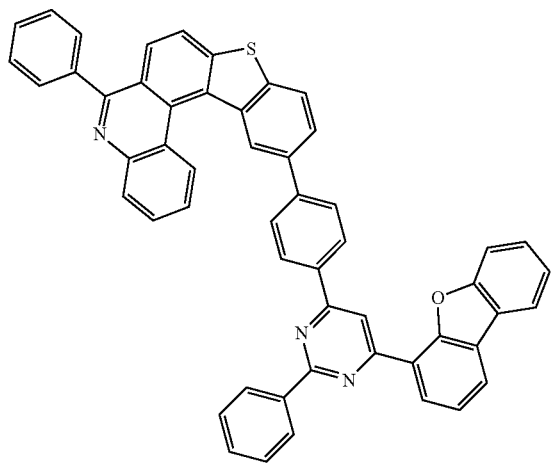
732
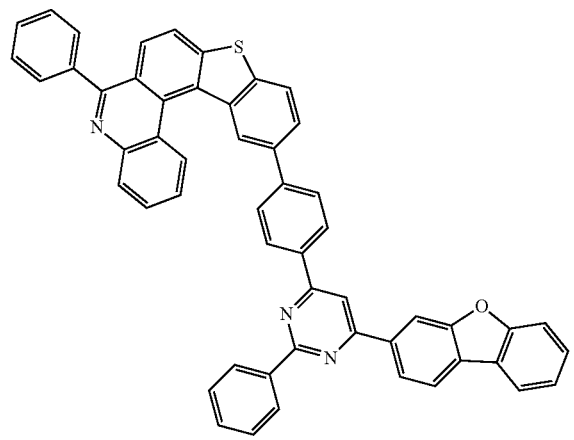
733
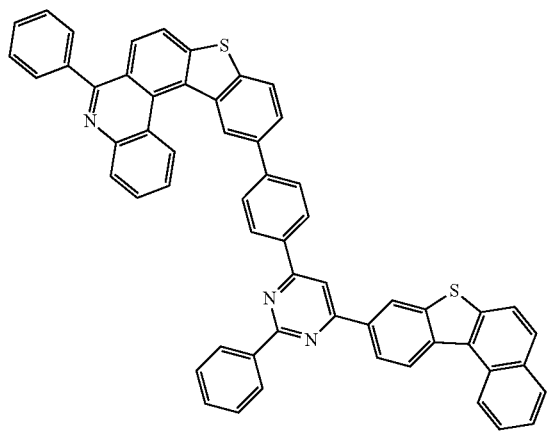
734
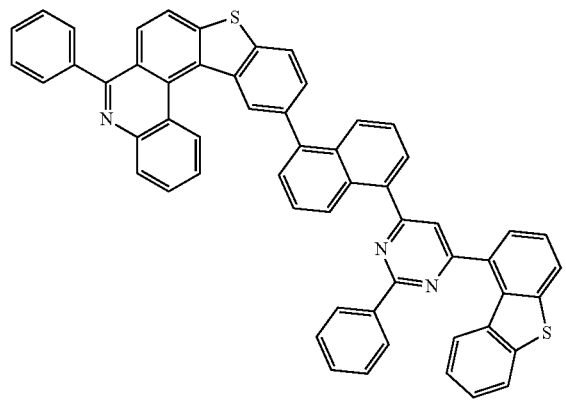
735
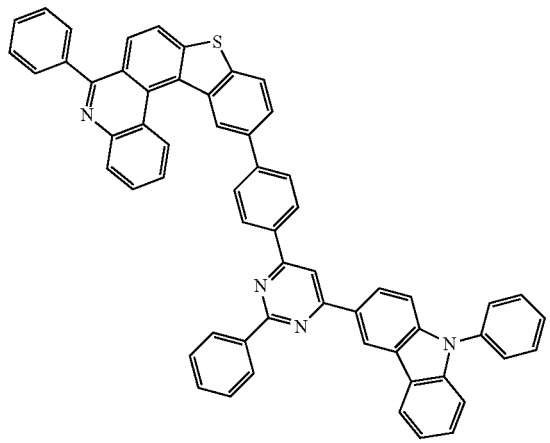
736
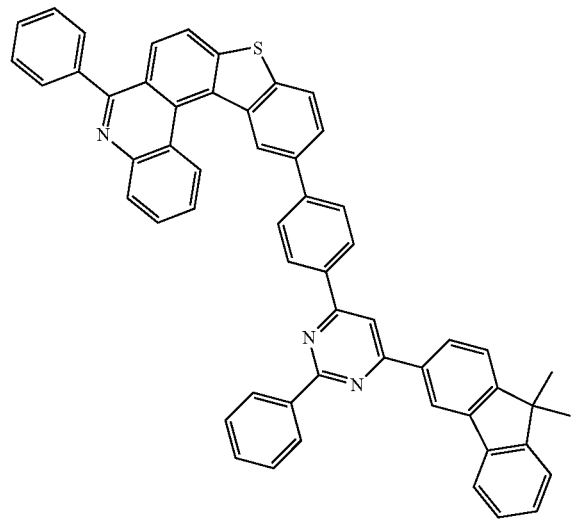

737
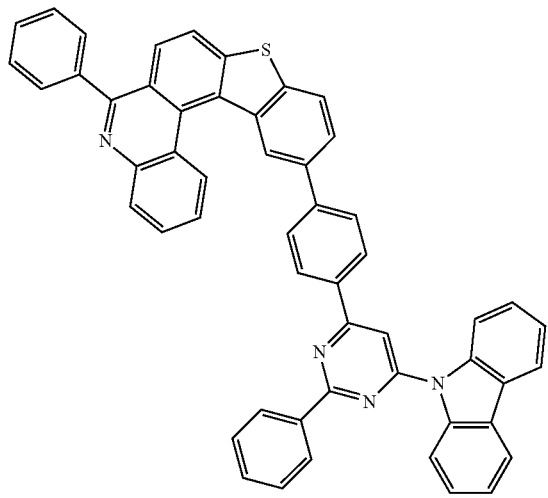
738
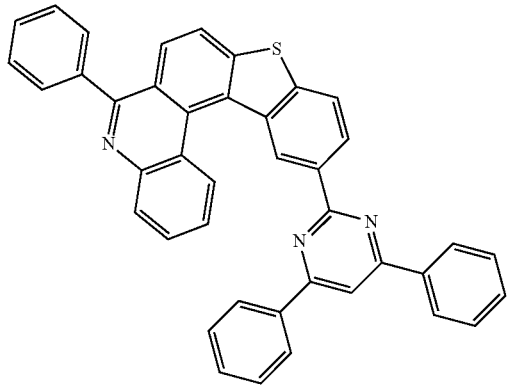
739
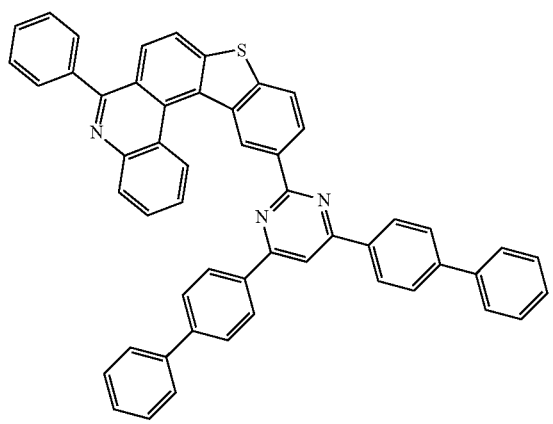
740
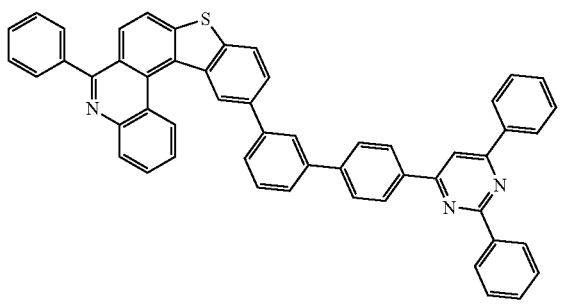
741
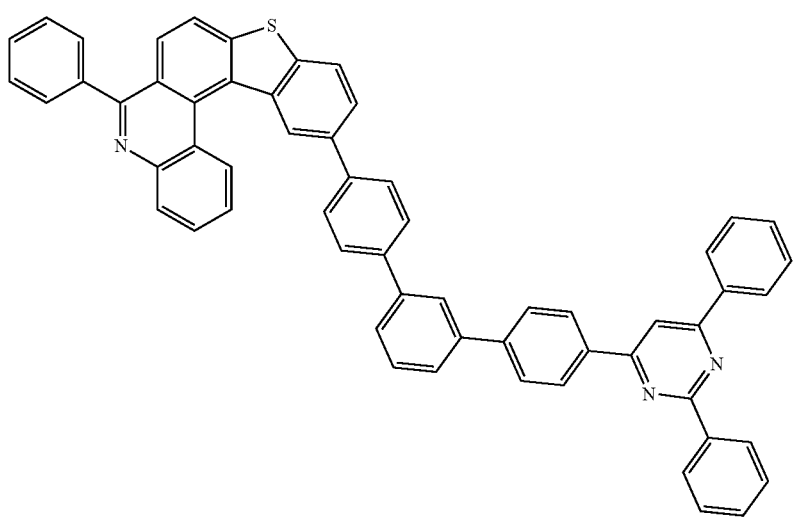

-continued
742
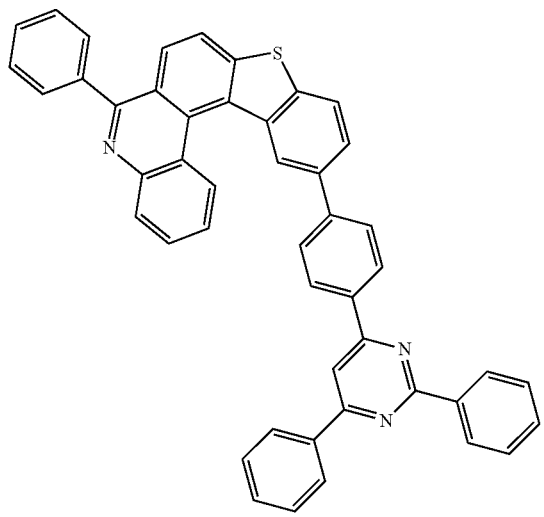
743
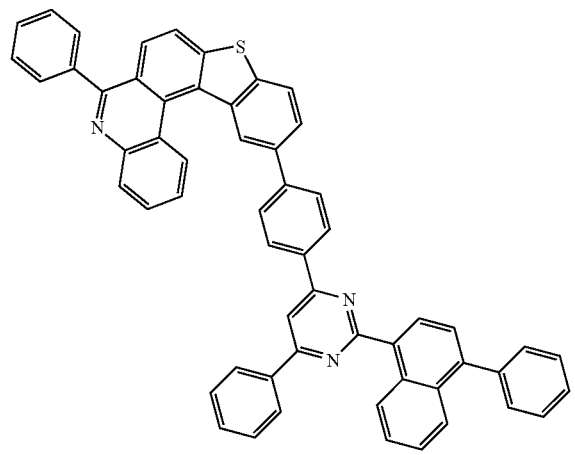
744
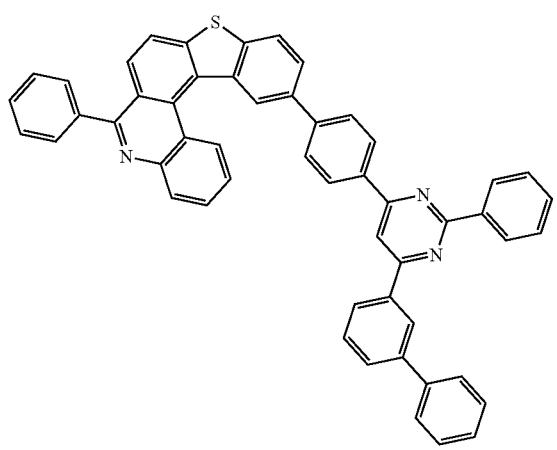
745
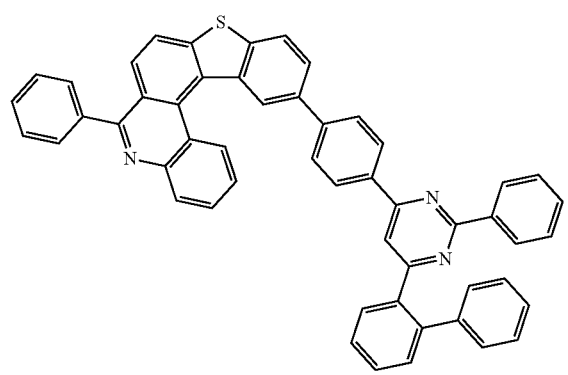
746
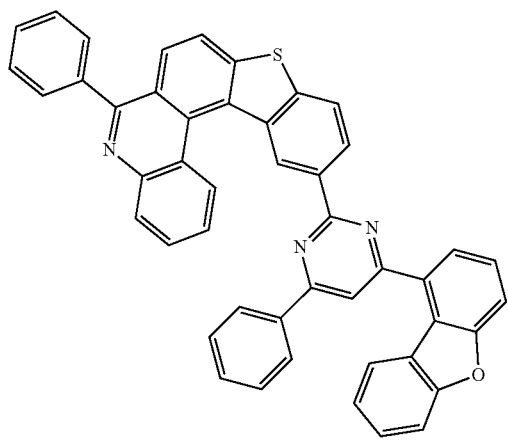
747
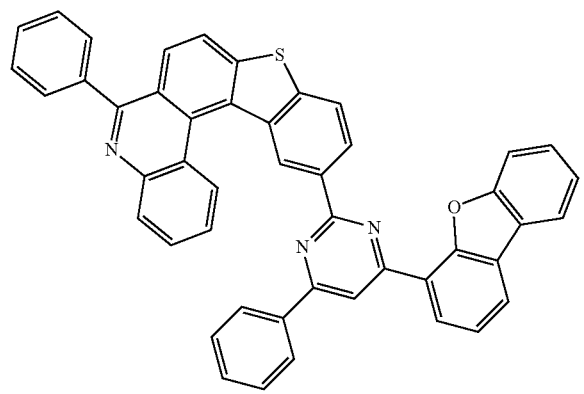

-continued
748
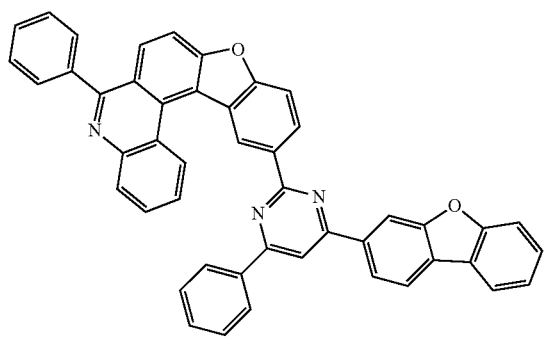
749
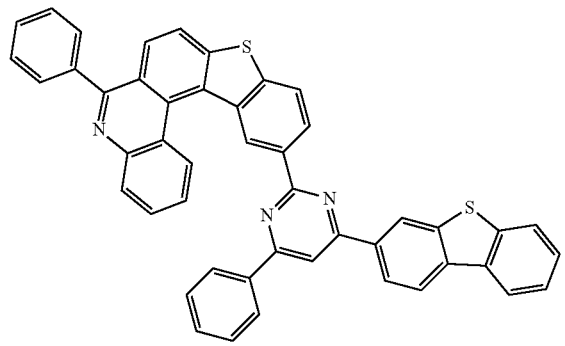
750
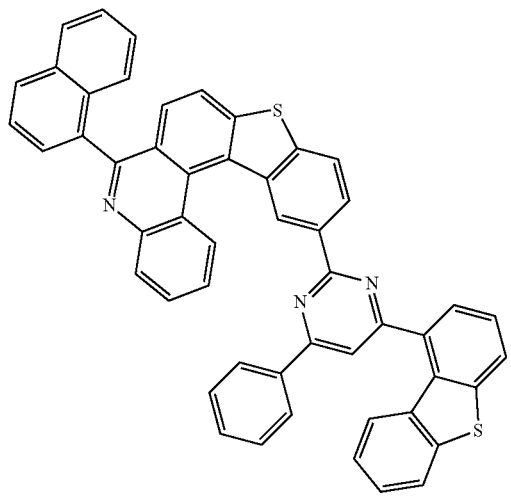
751
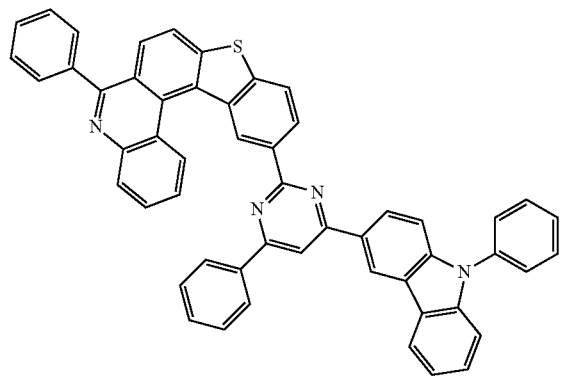
752
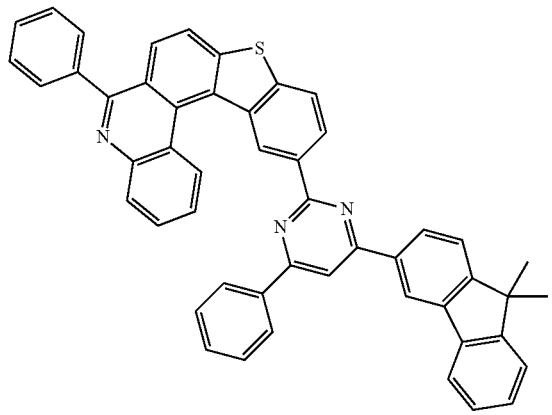
753
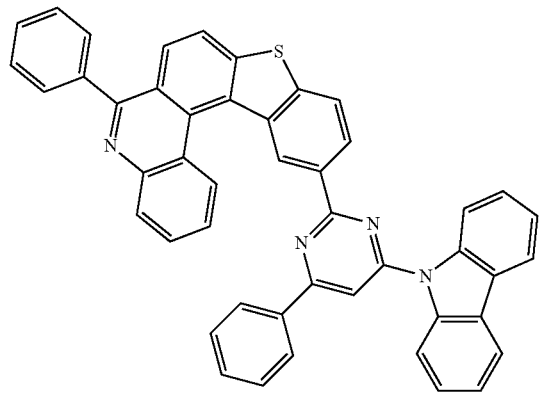

-continued
754
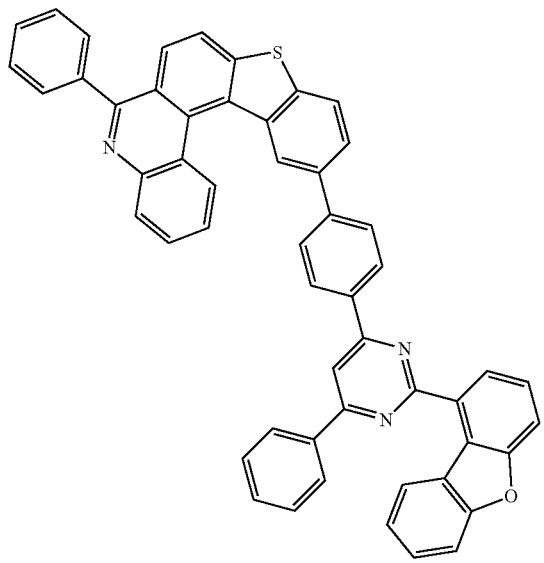
755
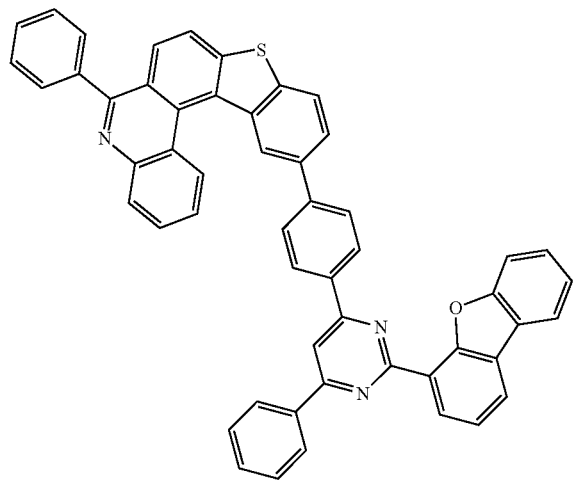
756
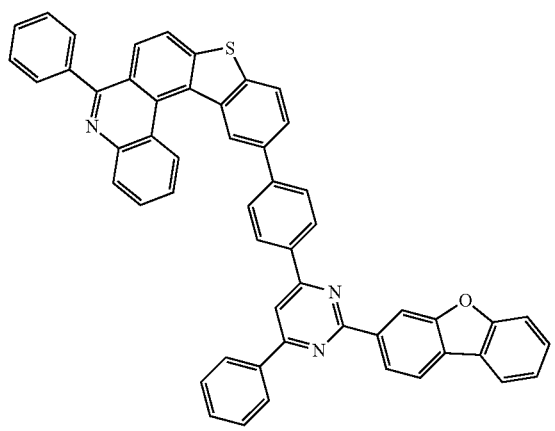
757
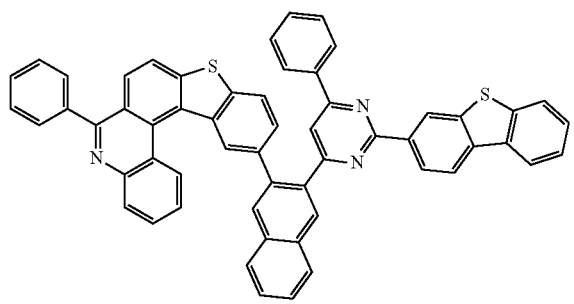
758
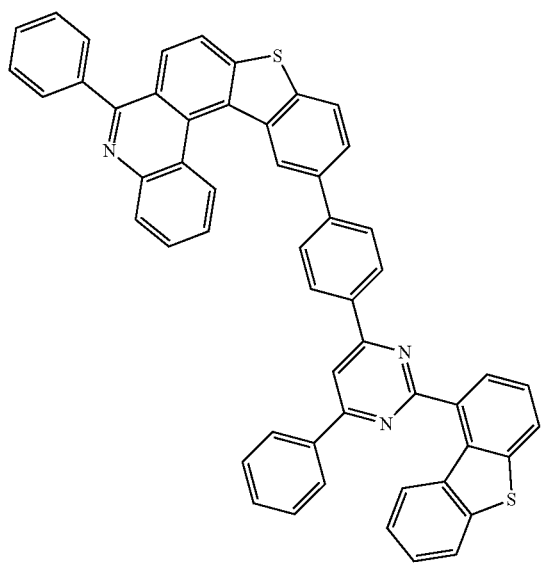
759
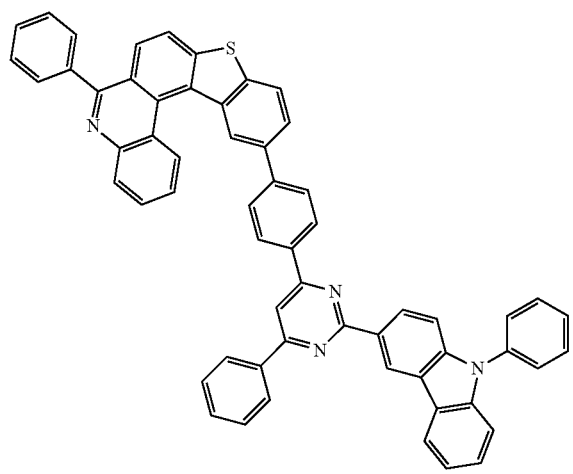

760
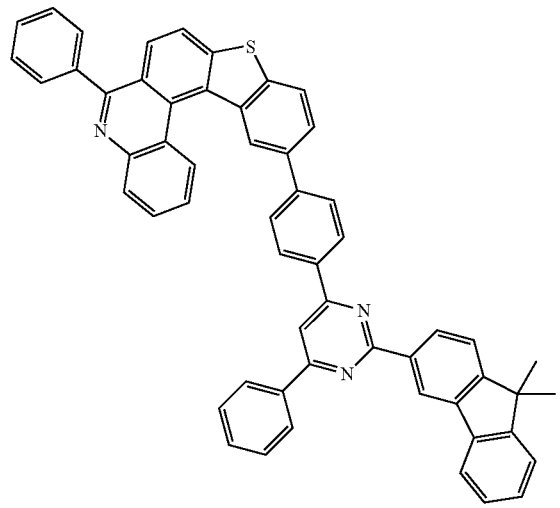
761
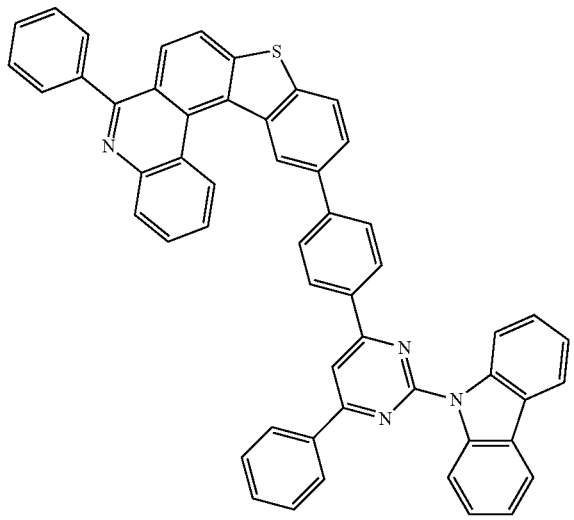
762
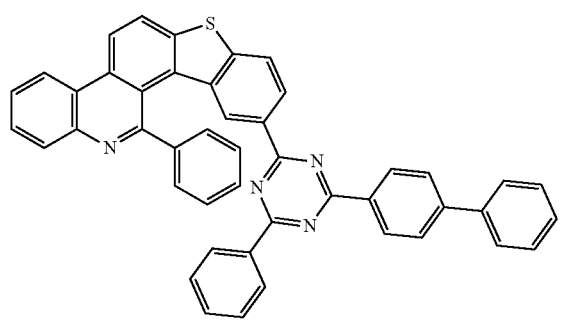
763
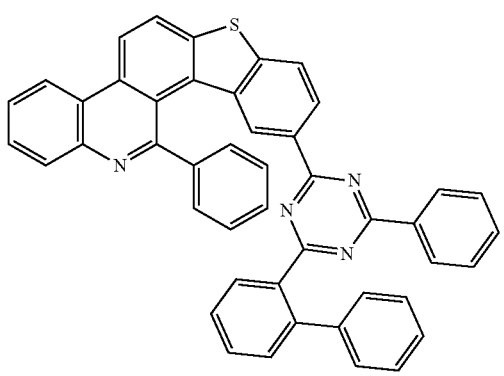
764
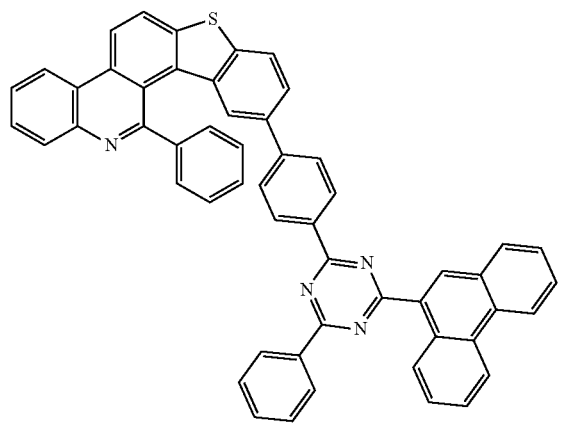
765
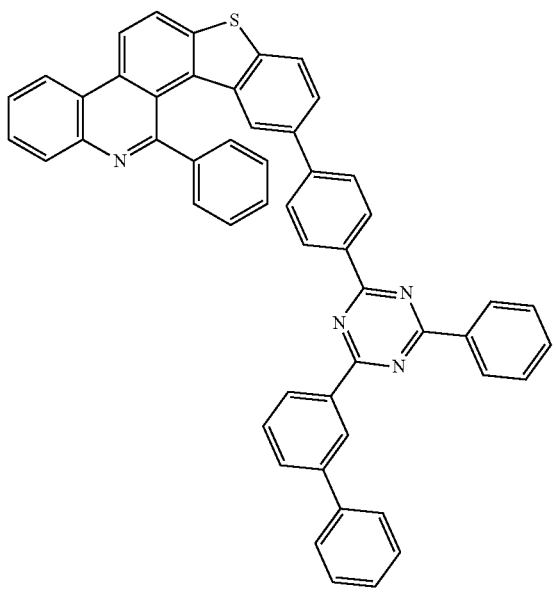

-continued
766
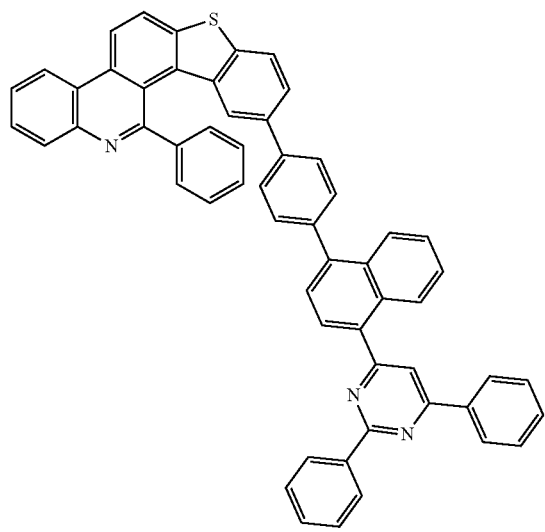
767
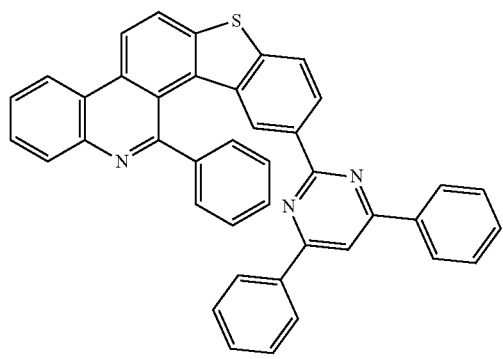
768
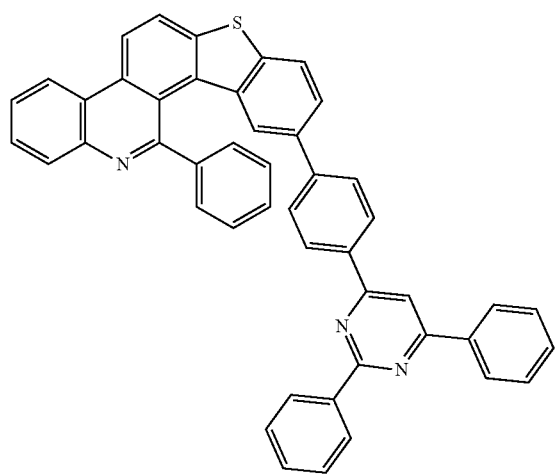
769
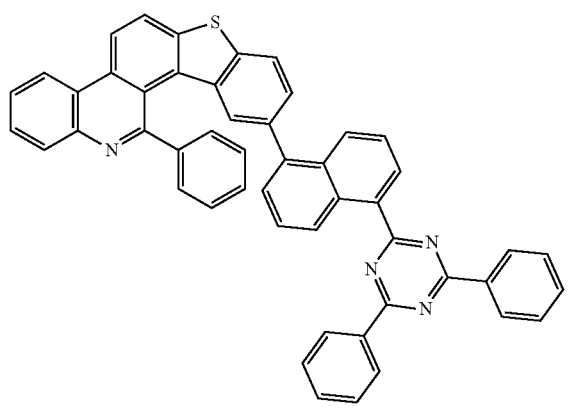
770
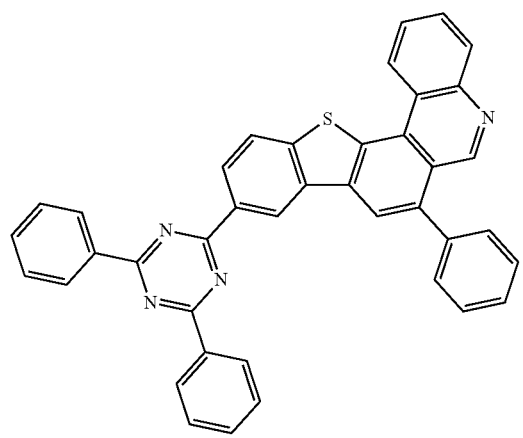
771
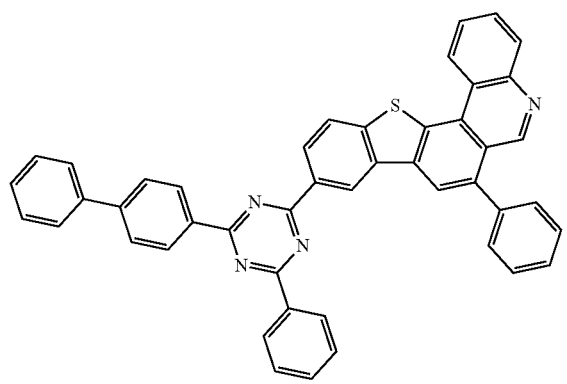

-continued
772
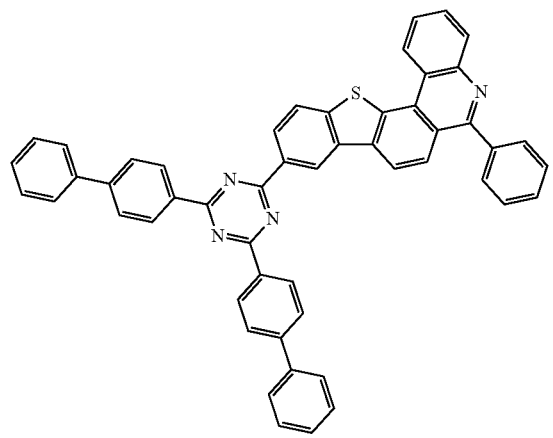
773
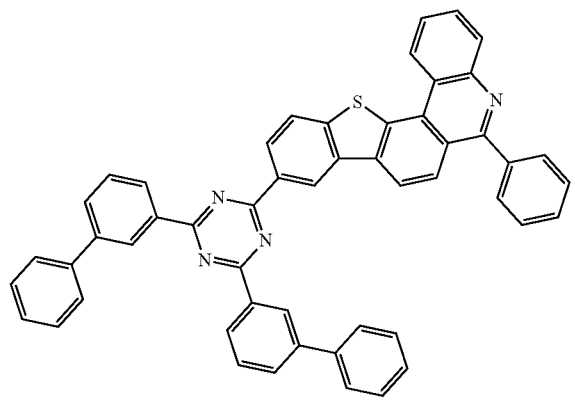
774
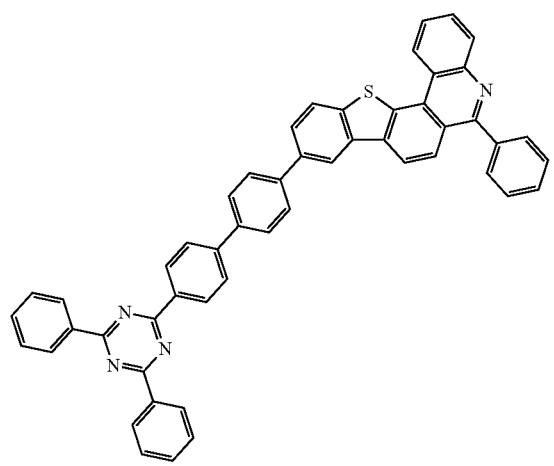
775
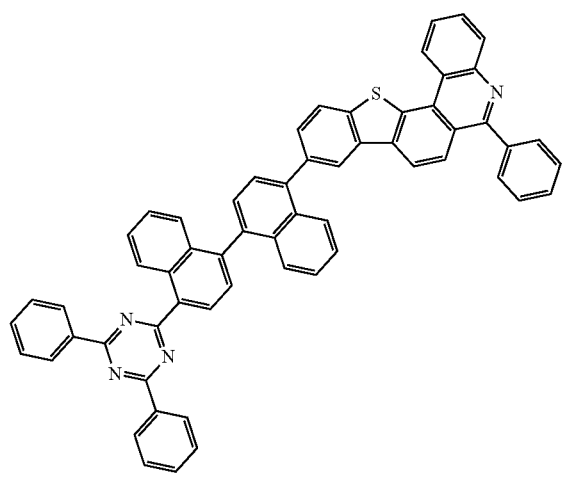
776
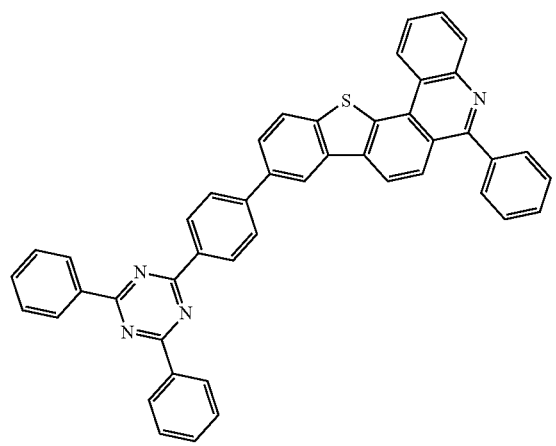
777
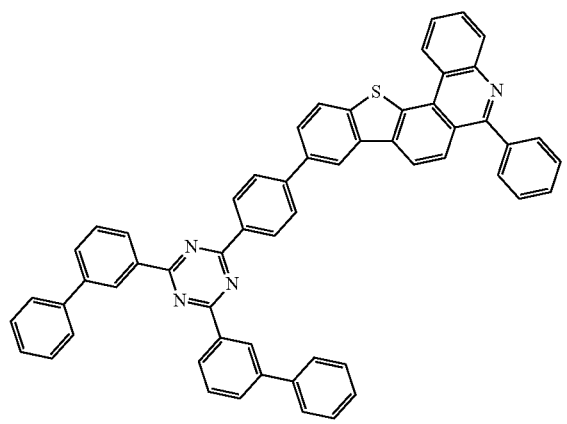

-continued
778
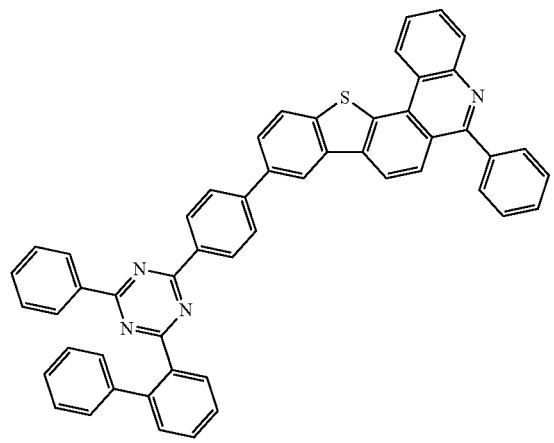
779
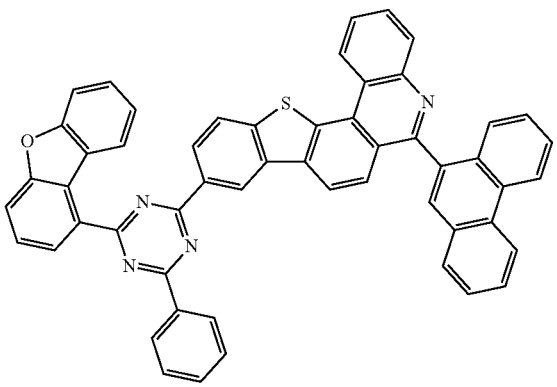
780
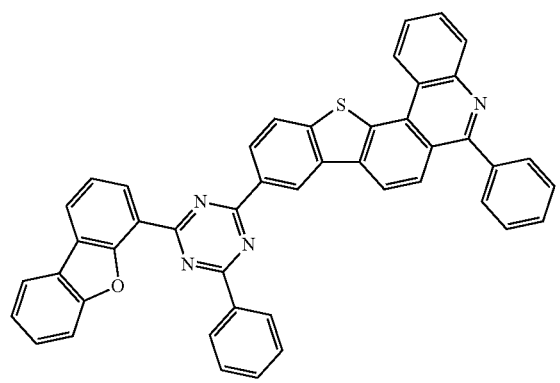
781
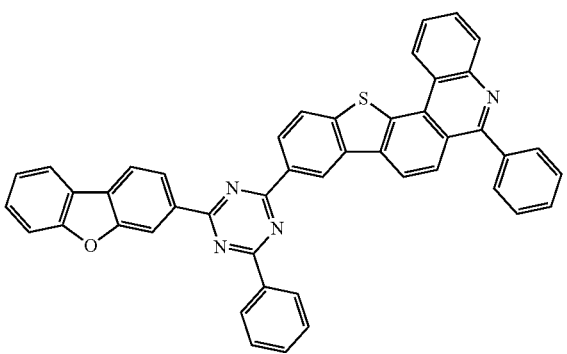
782
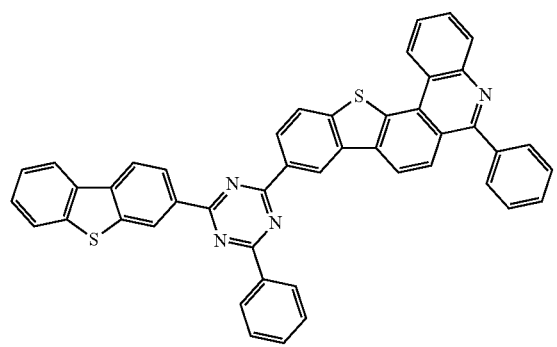
783
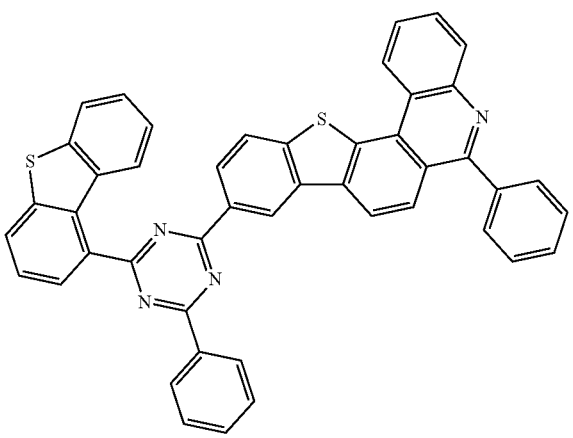

-continued
784
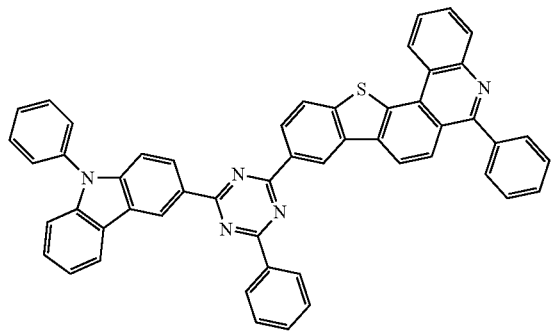
785
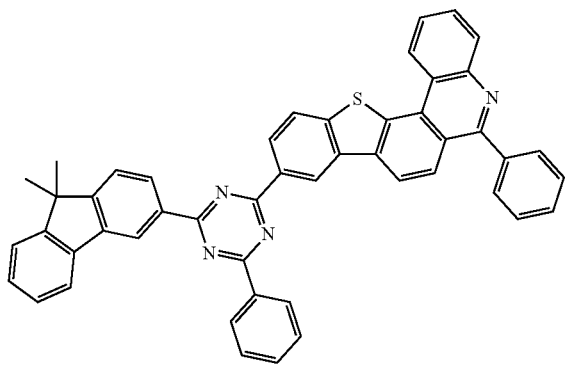
786
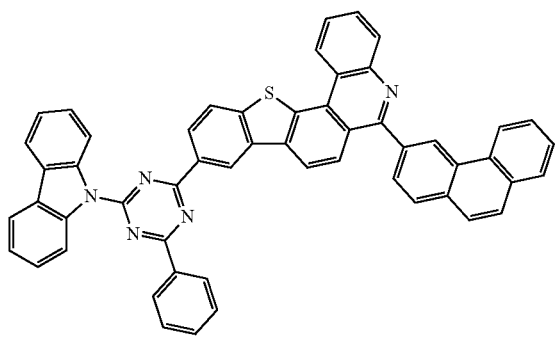
787
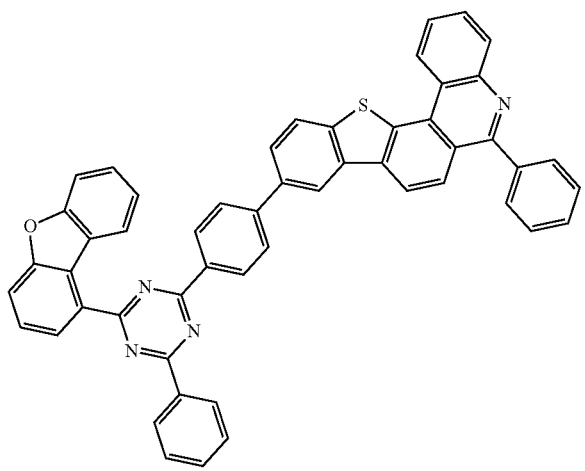
788
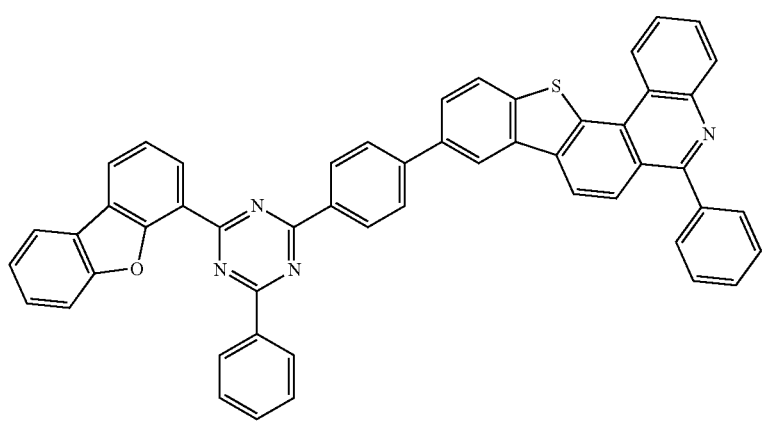

789
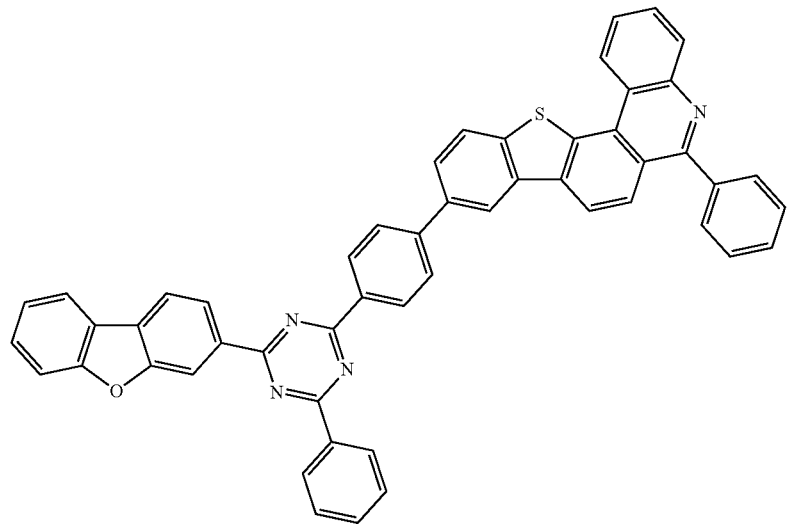
790
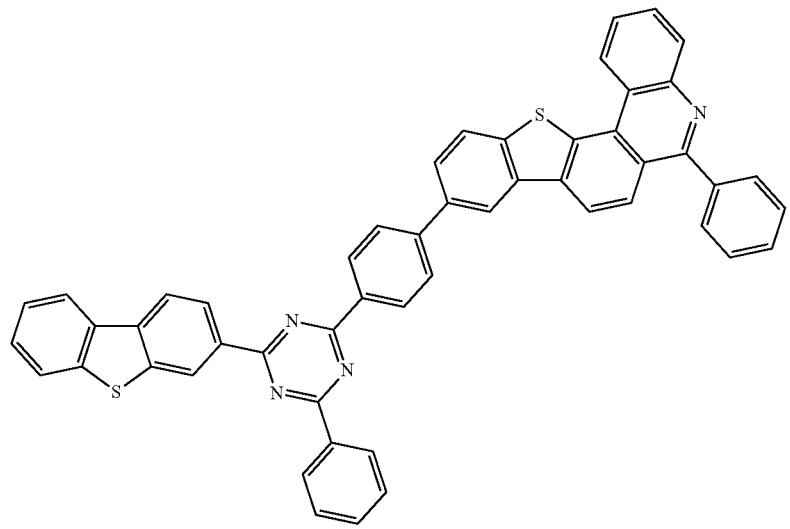
791
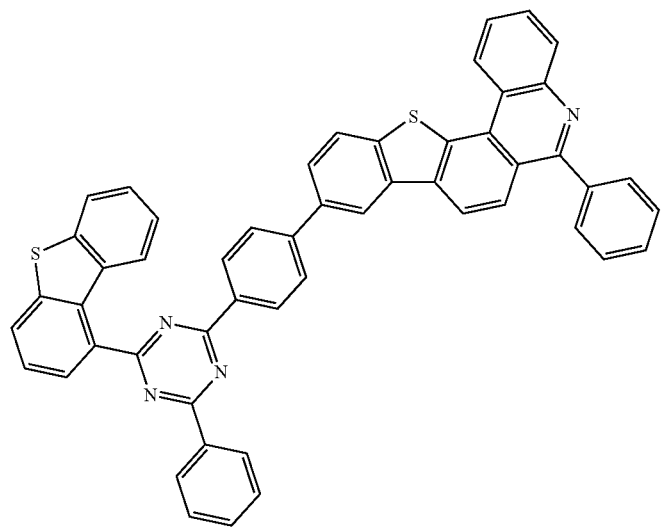

-continued
792
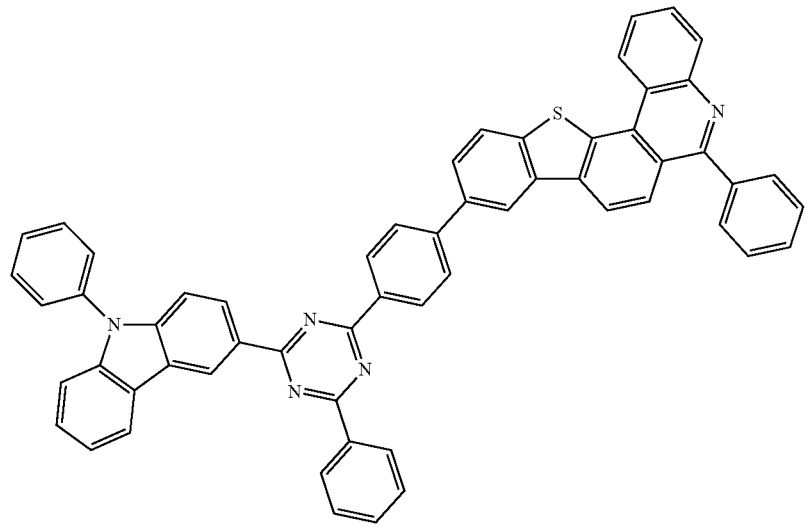
793 794
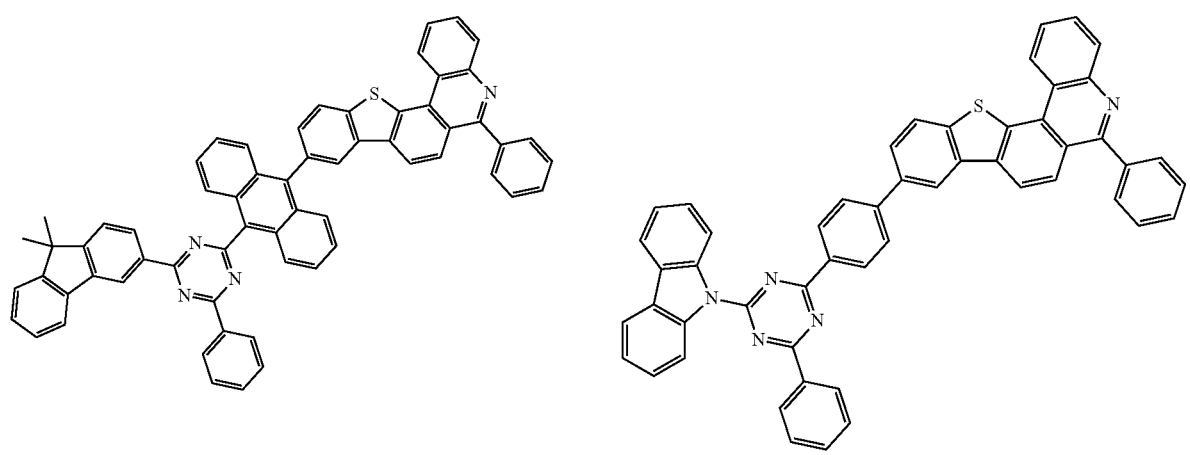
795 796
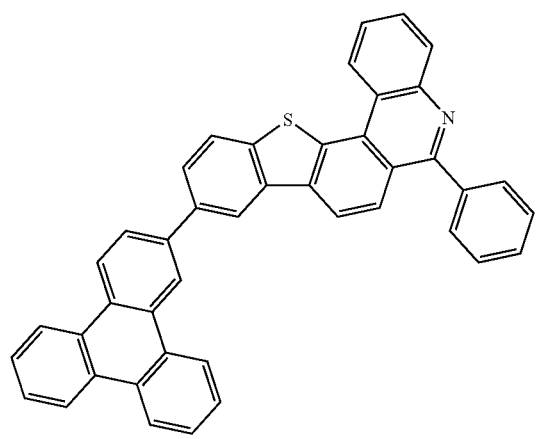 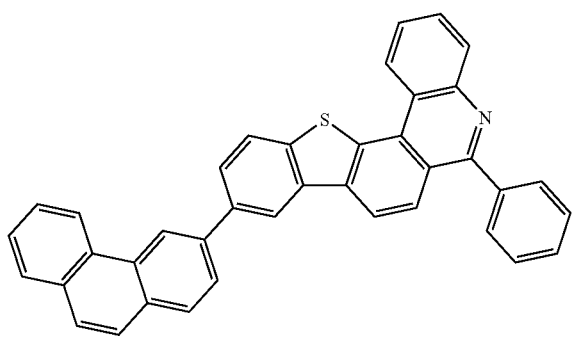

-continued
797
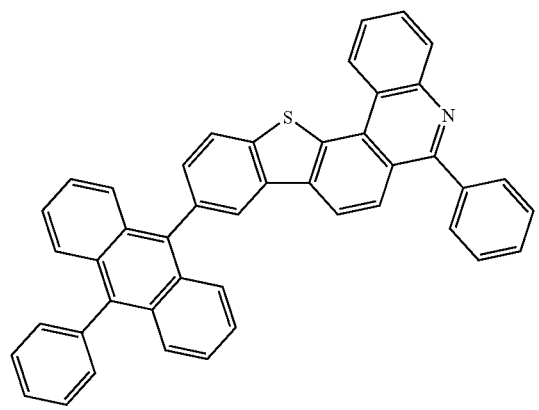
798
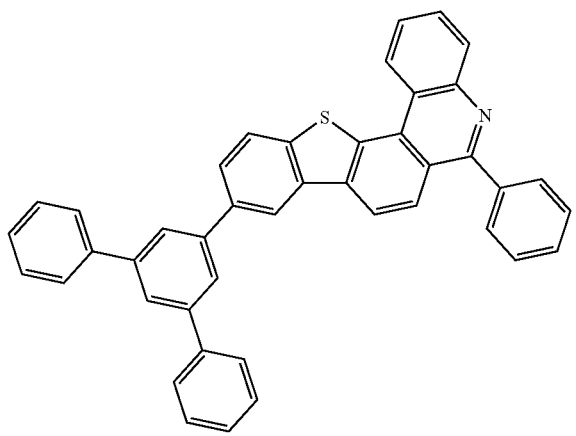
799
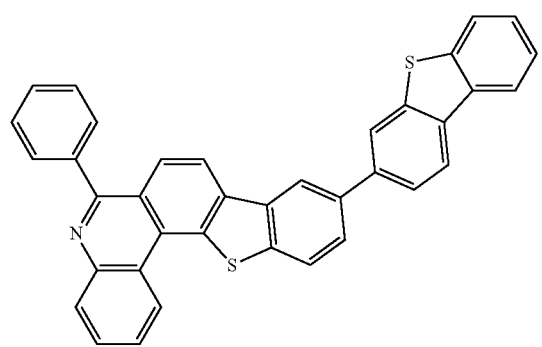
800
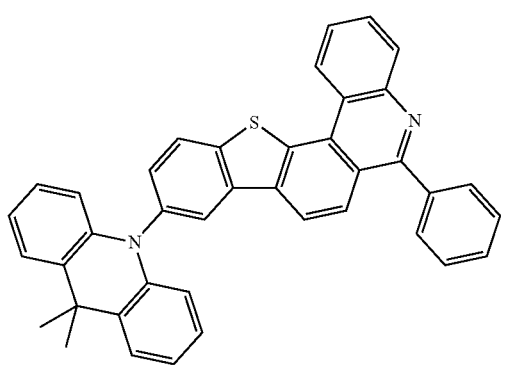
801
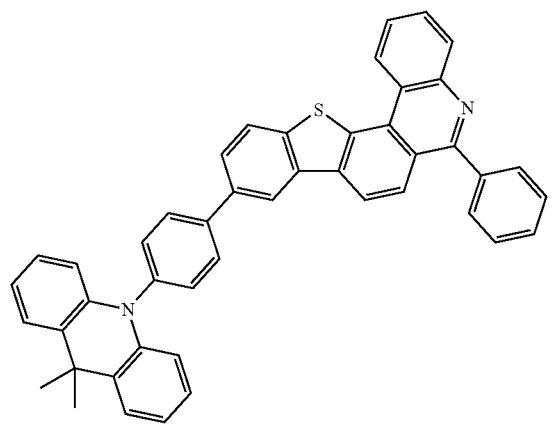
802
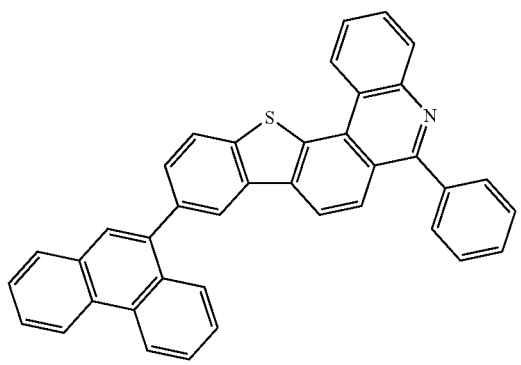

-continued
803
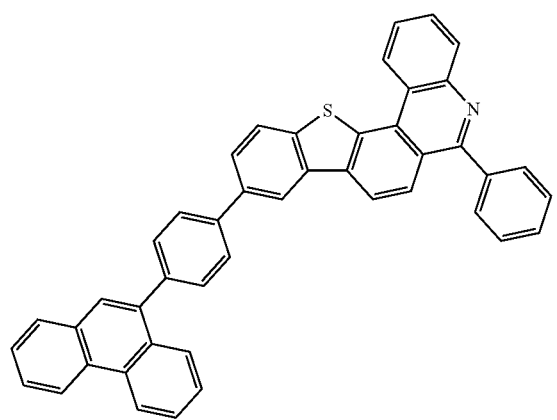
804
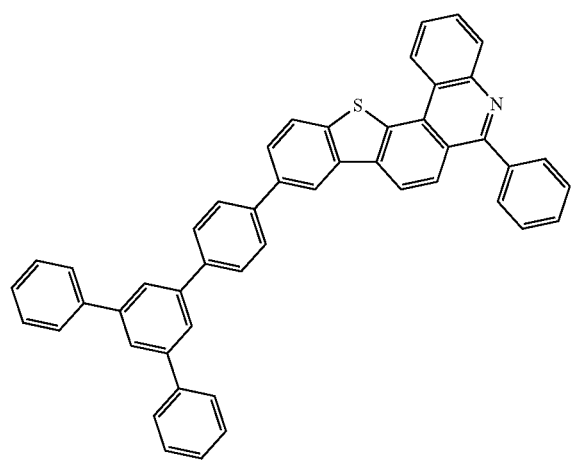
805
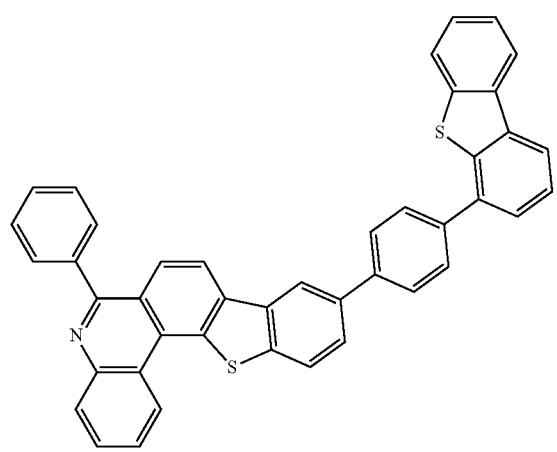
806
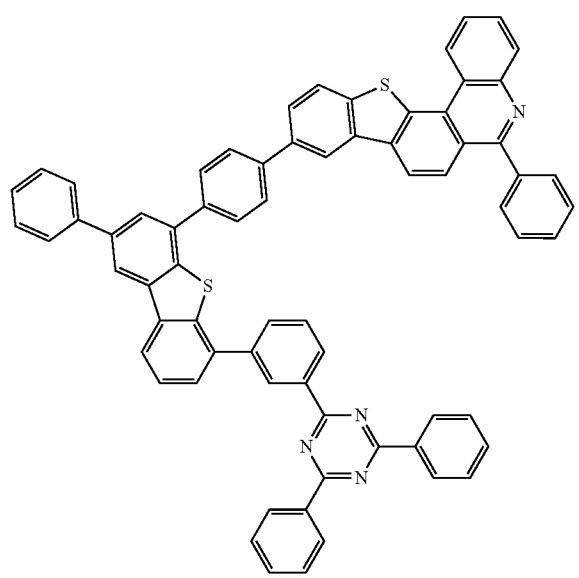

-continued
807
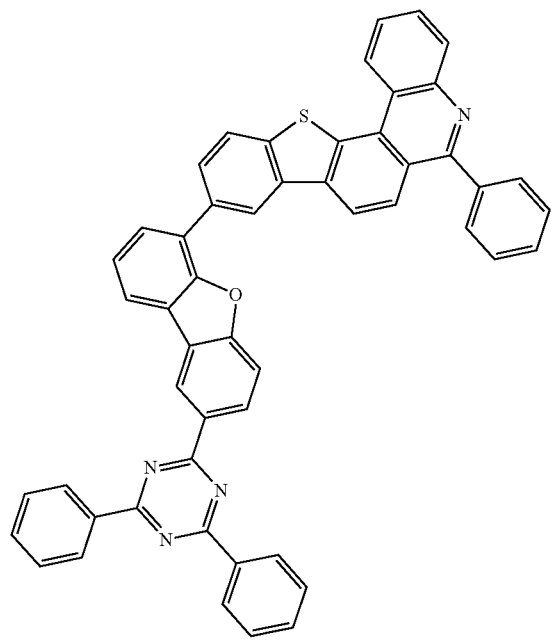
808
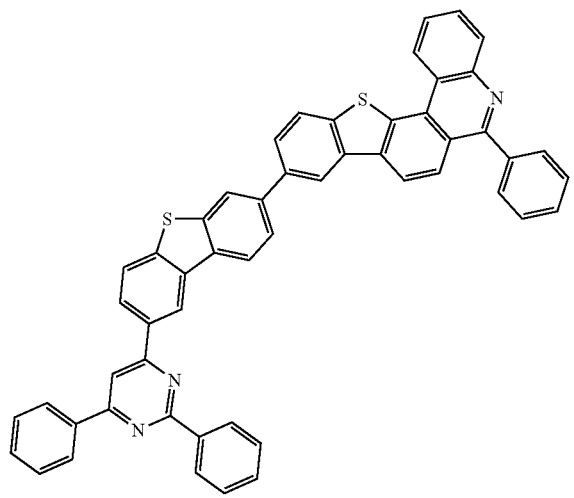
809
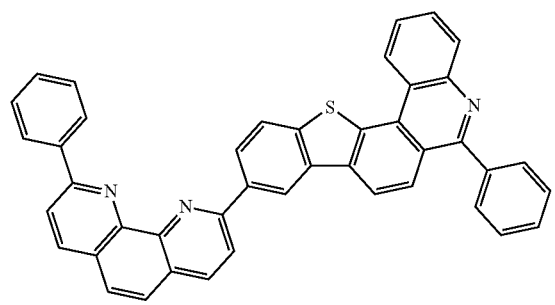
810
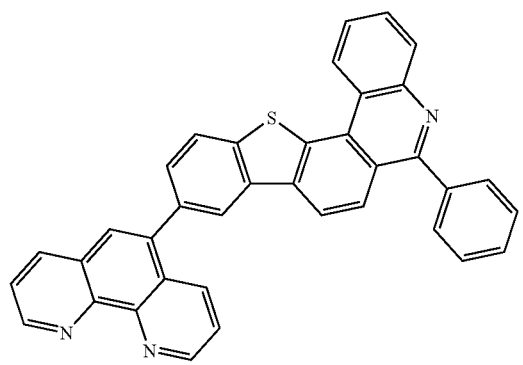
811
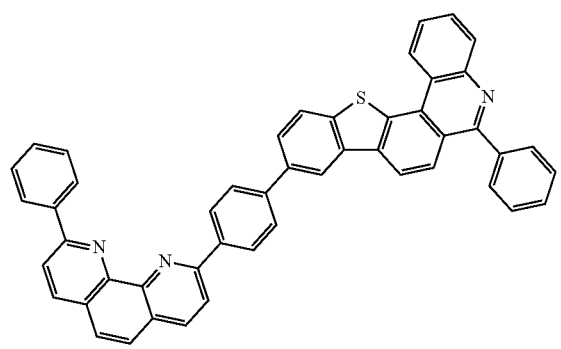
812
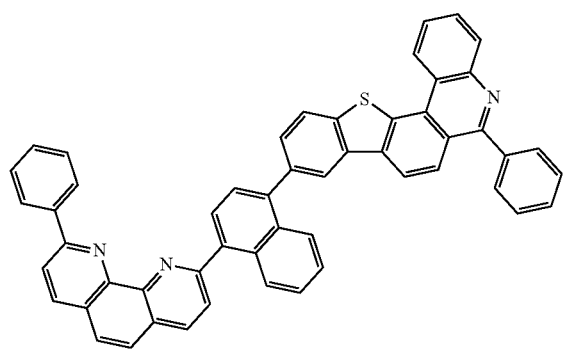

-continued
813
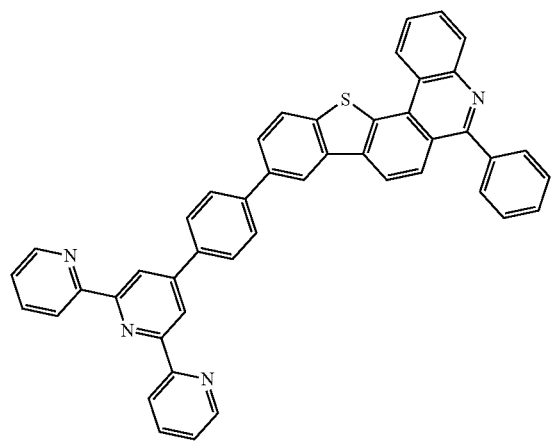
814
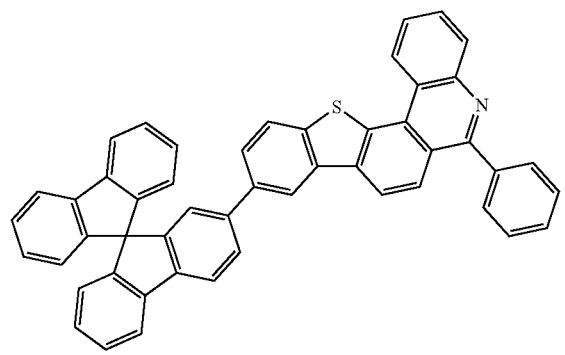
815
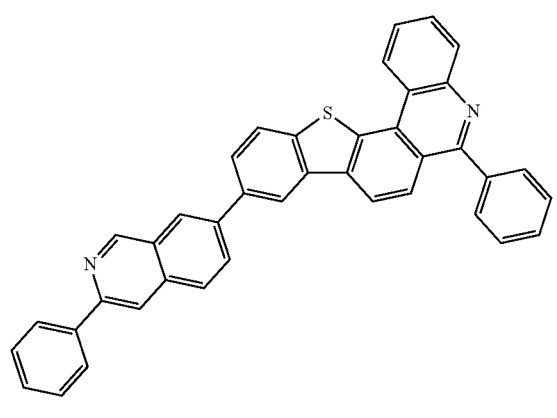
816
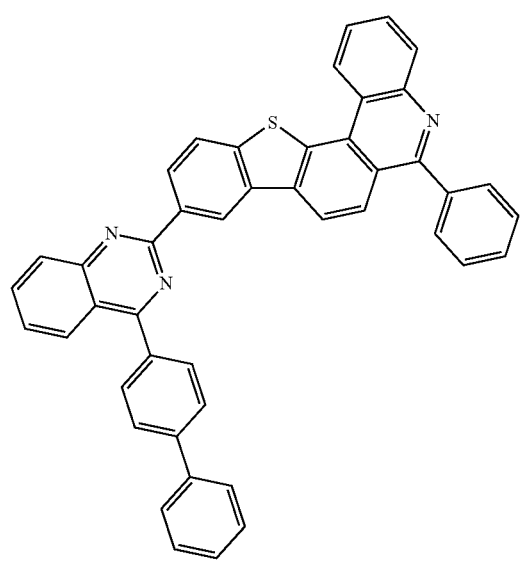
817
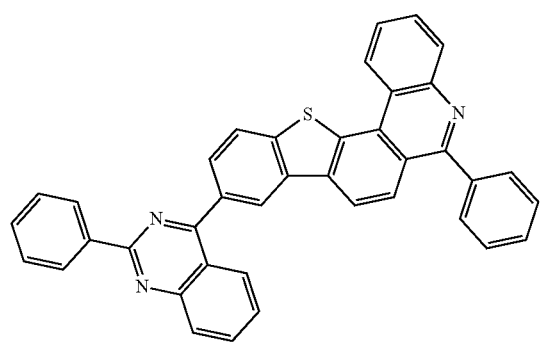
818
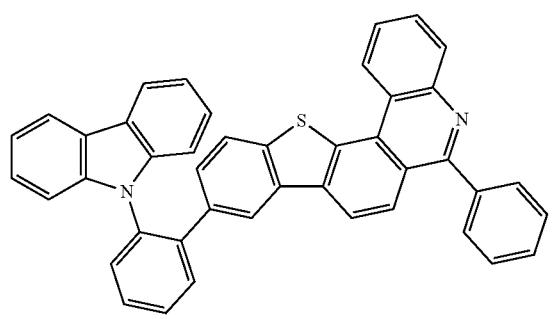

-continued
819
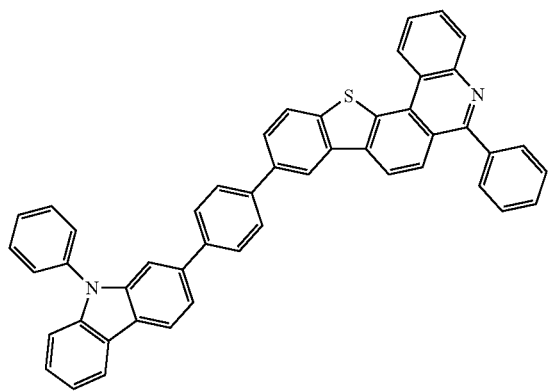
820
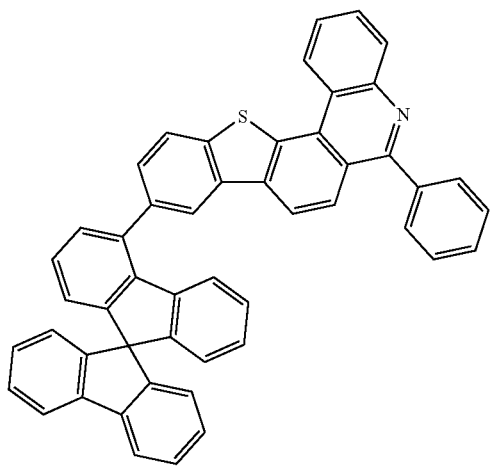
821
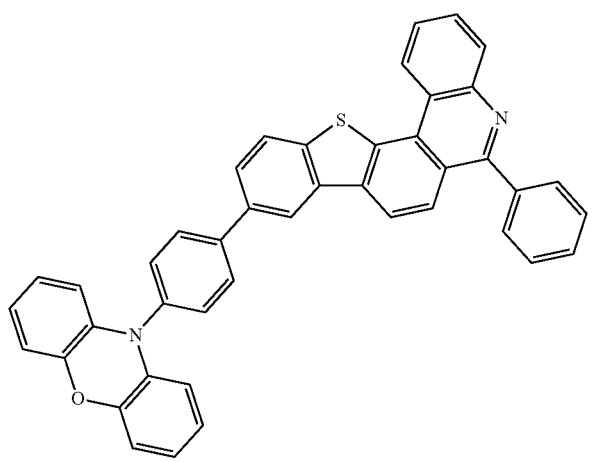
822
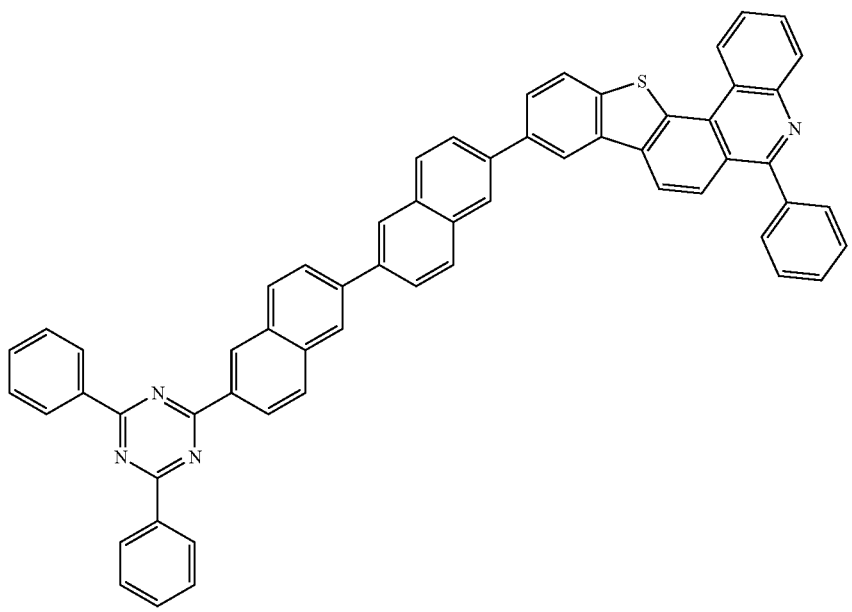

-continued
823
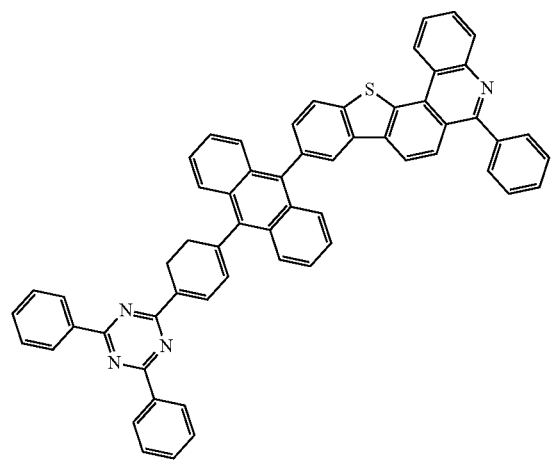
824
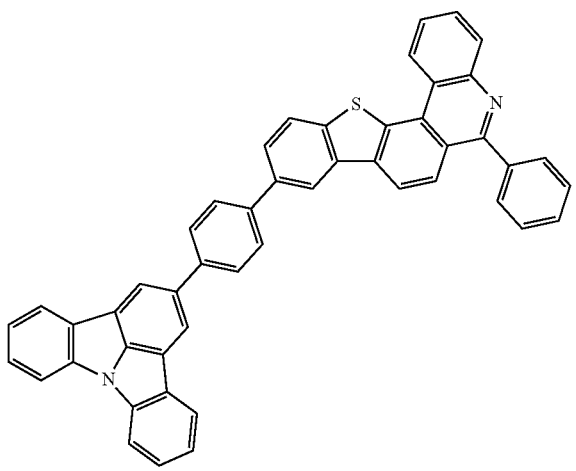
825
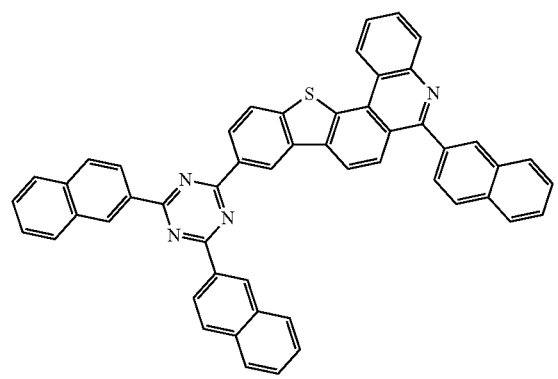
826
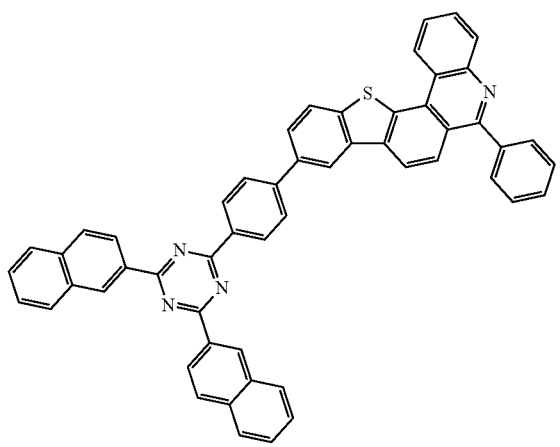
827
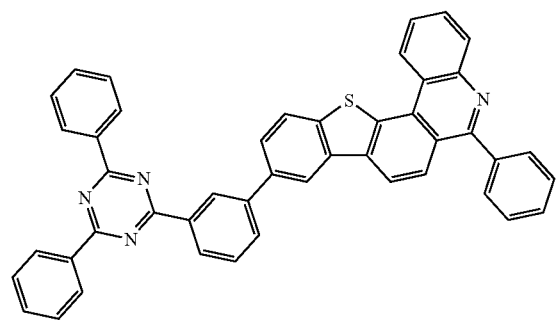
828
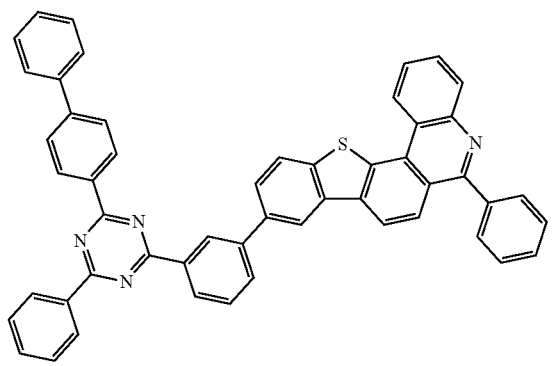

-continued
829
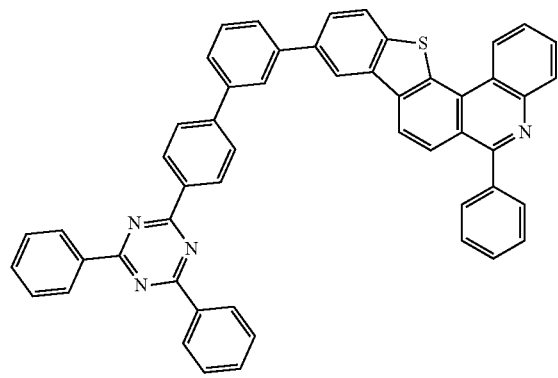
830
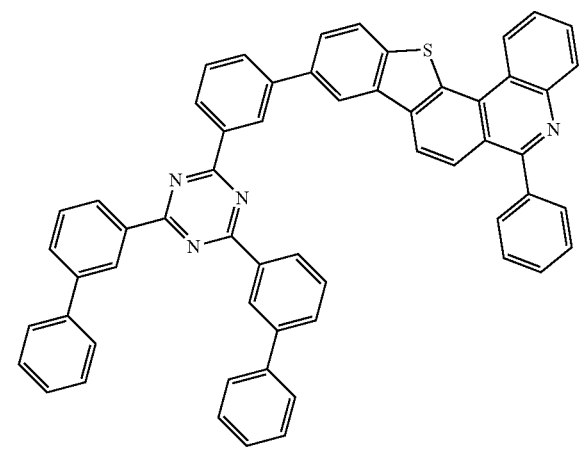
831
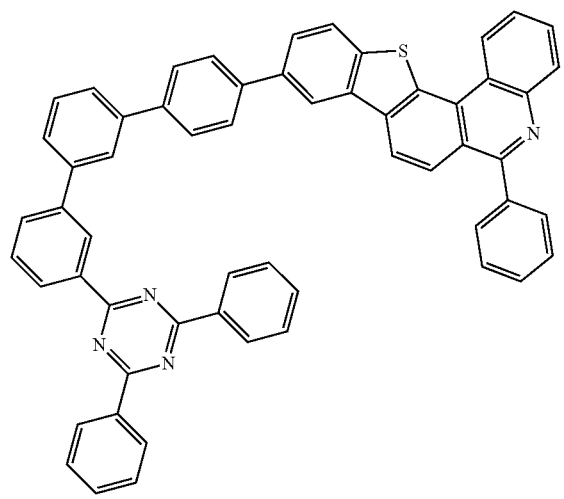
832
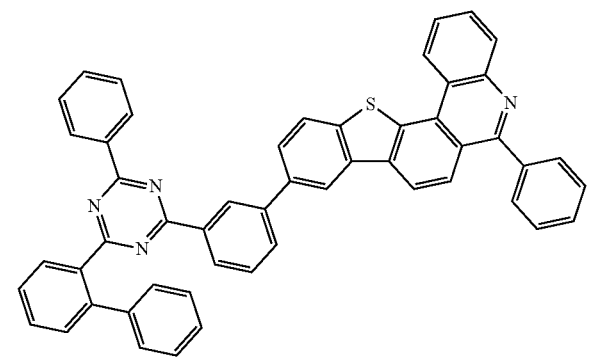
833
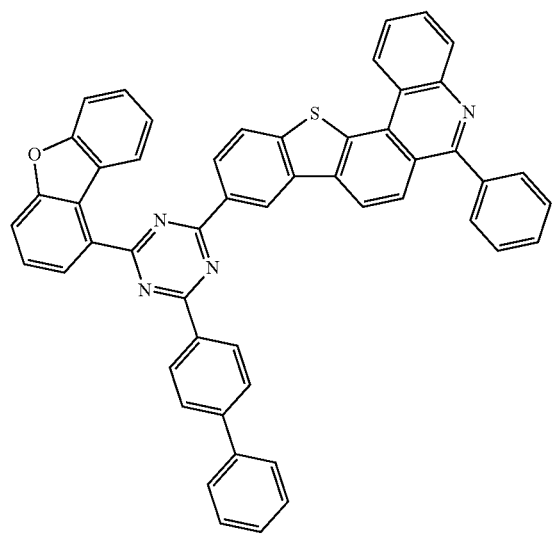
834
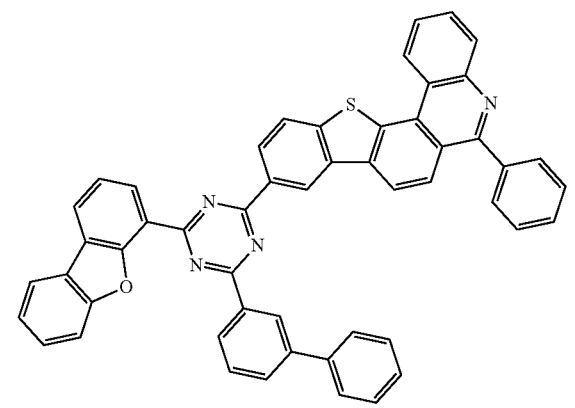

-continued
835
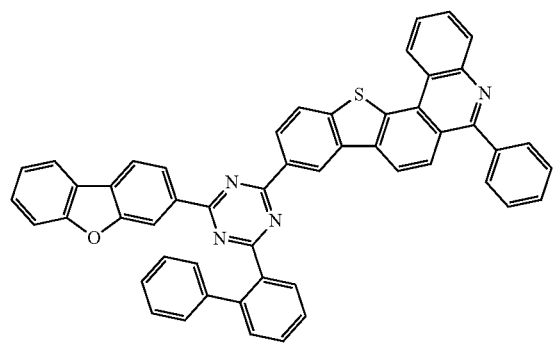
836
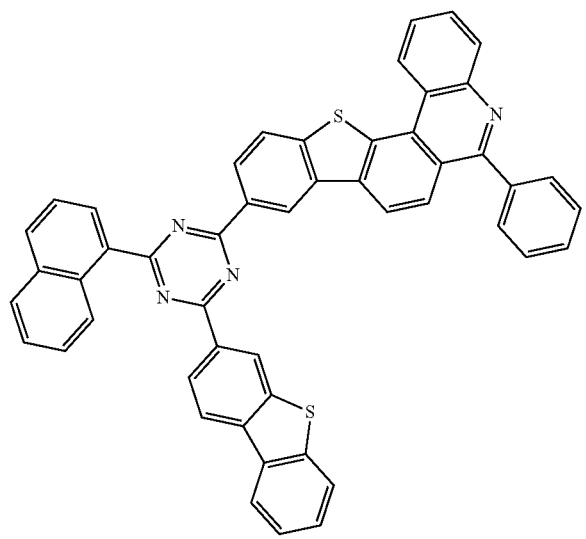
837
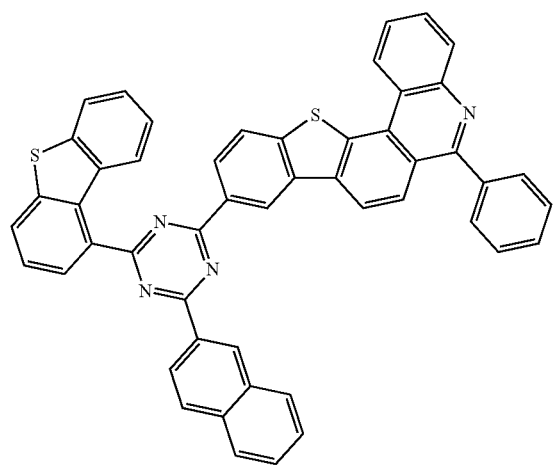
838
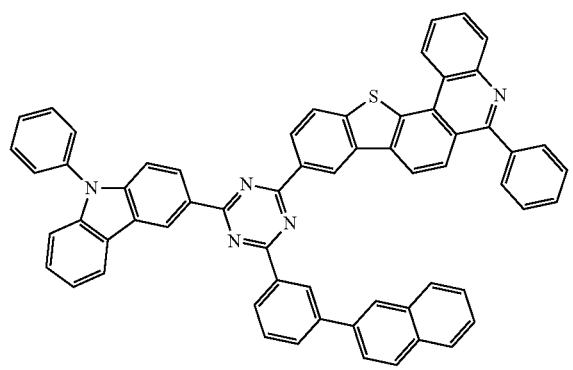
839
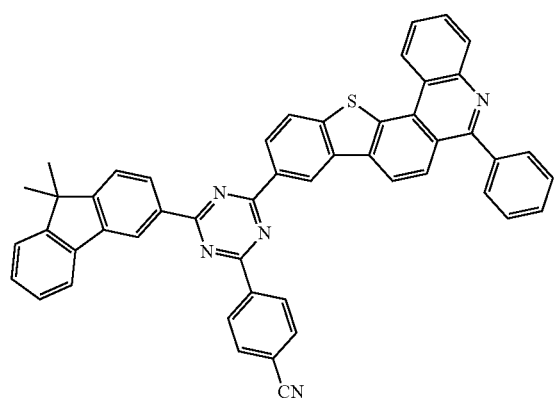
840
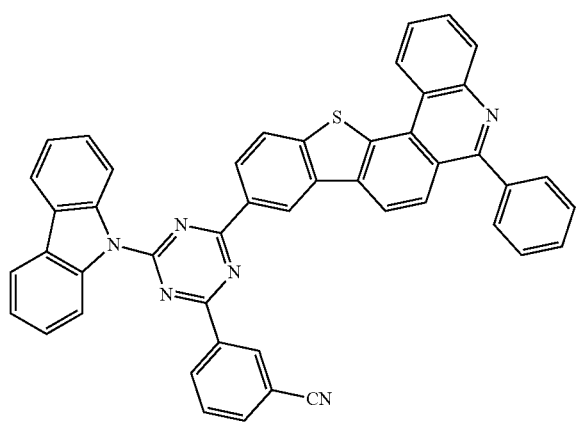

-continued
841
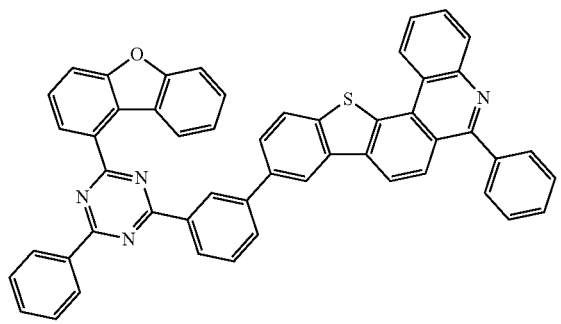
842
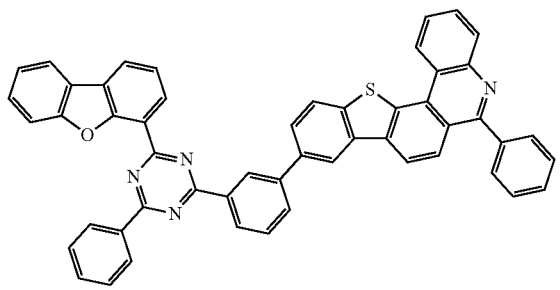
843
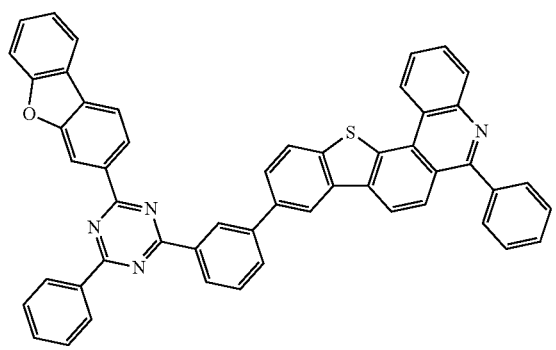
844
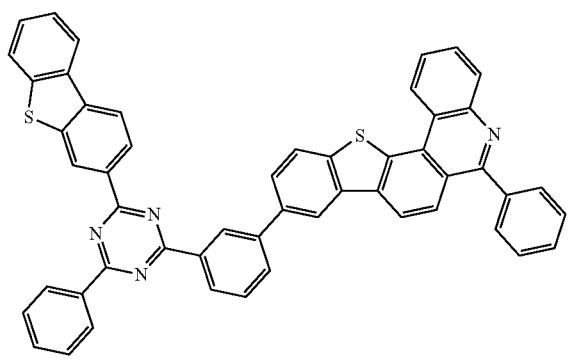
845
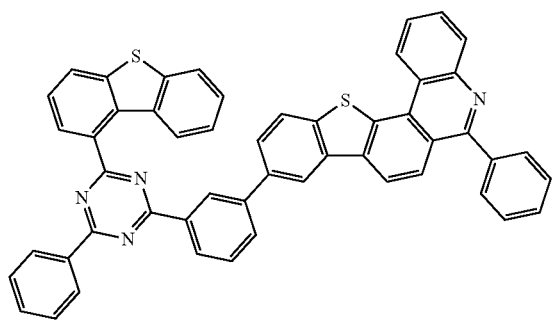
846
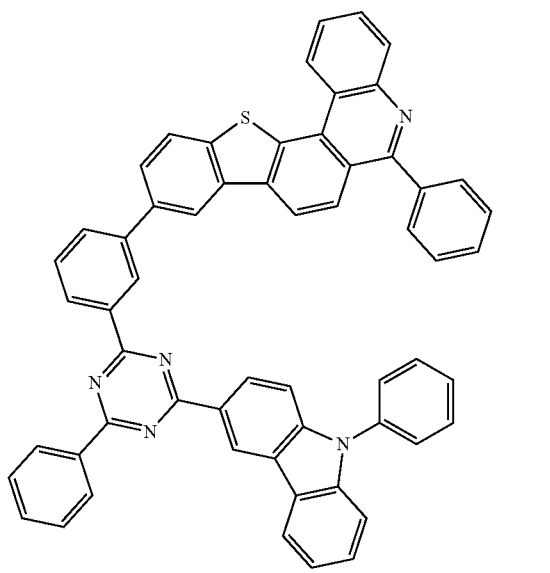
847
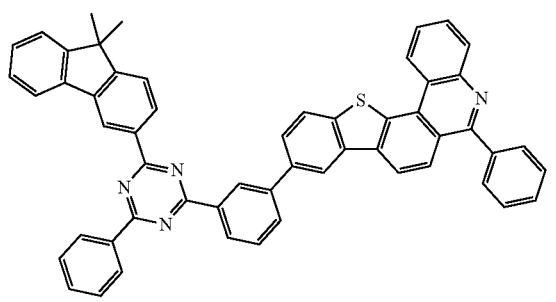
848
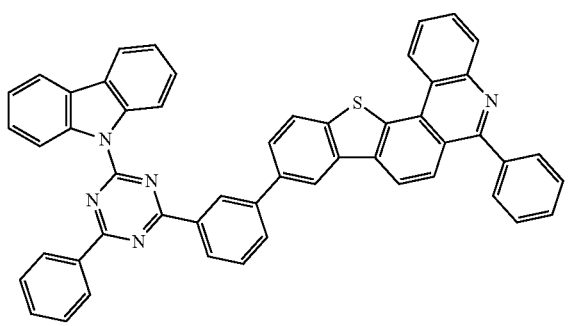

-continued
849
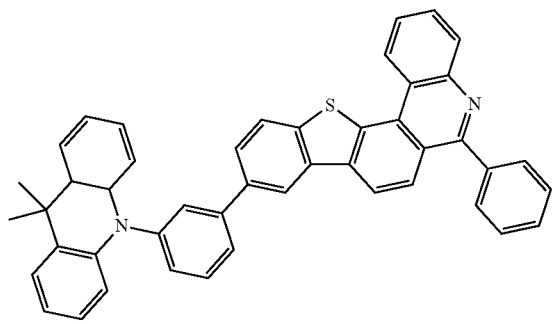
850
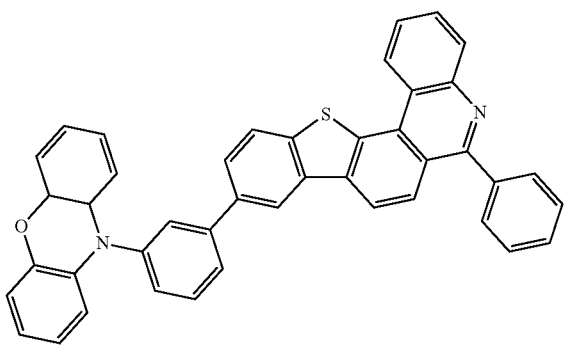
851
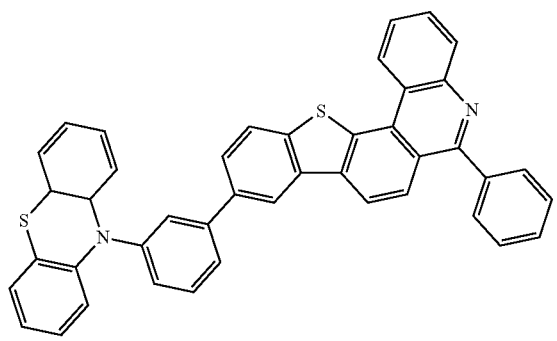
852
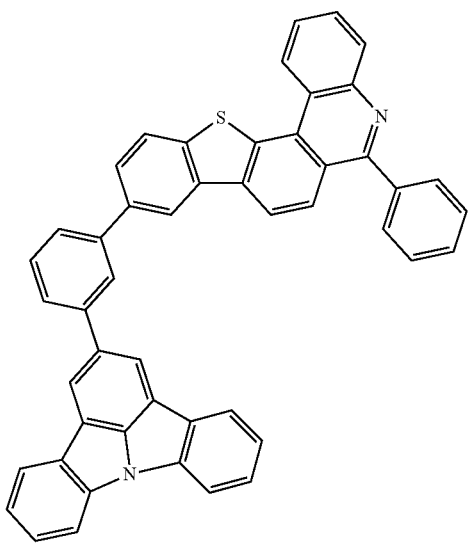
853
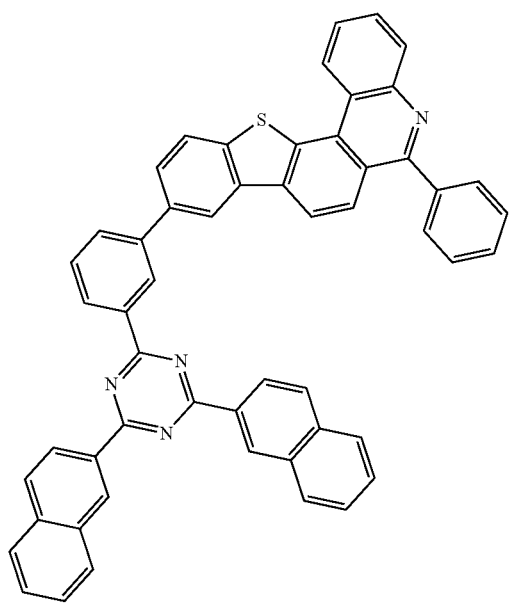
854
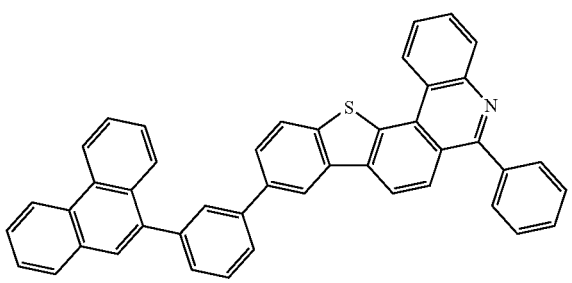

855
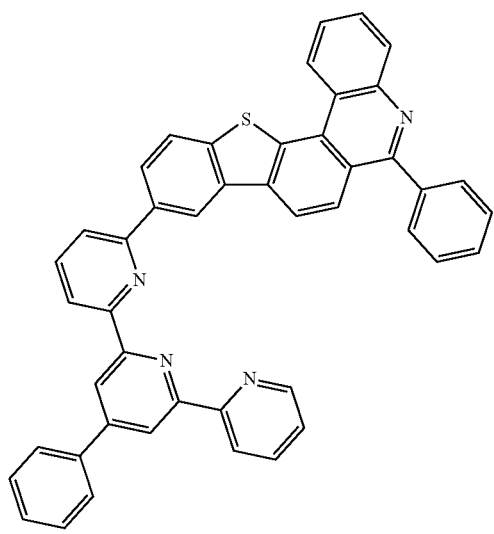
856
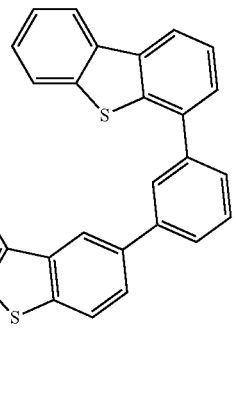
857
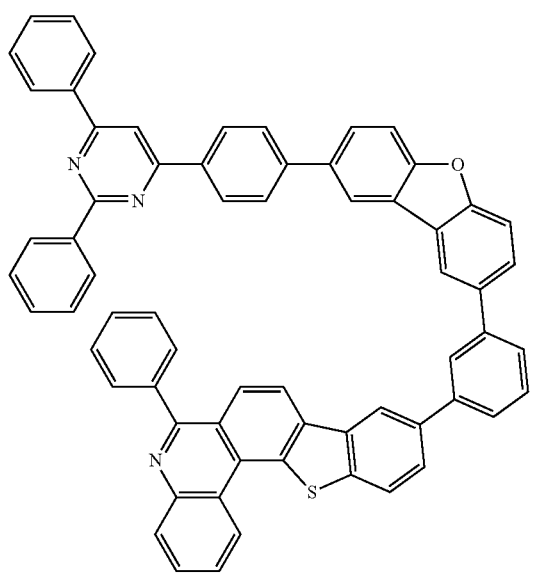
858
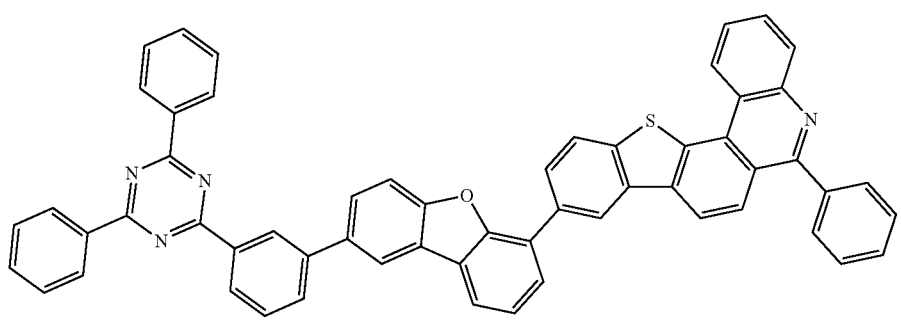

-continued
859
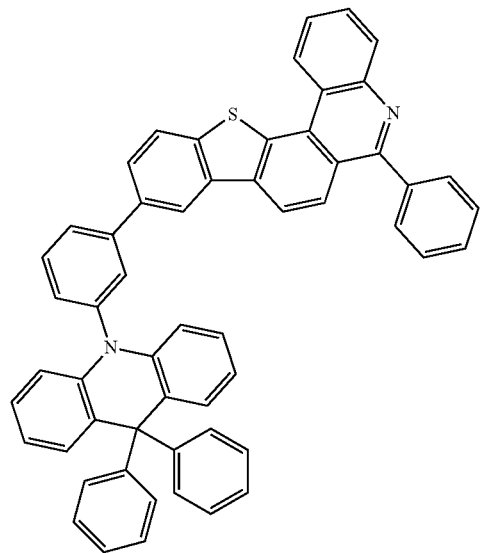
860
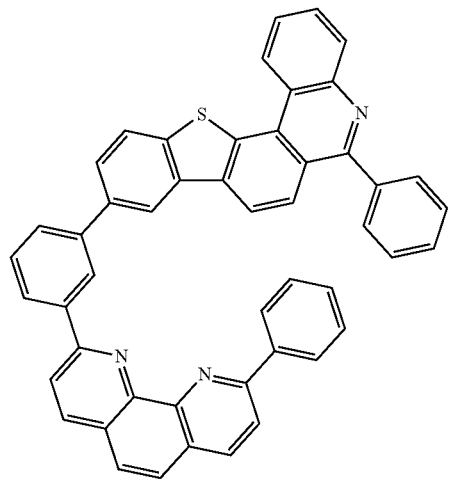
861
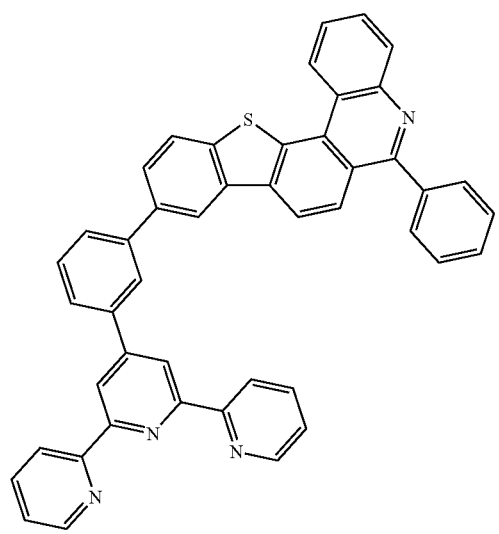
862
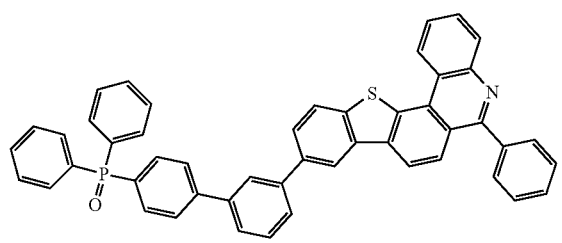
863
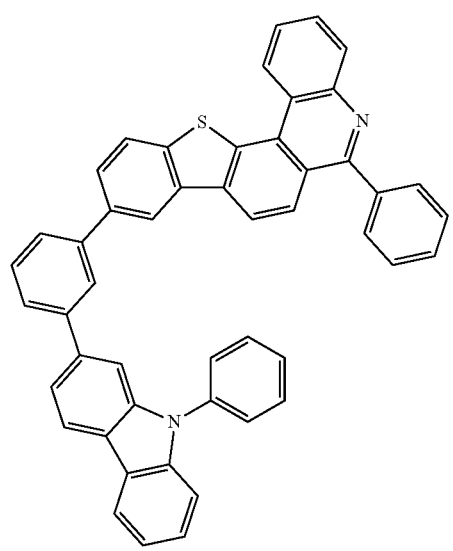
864
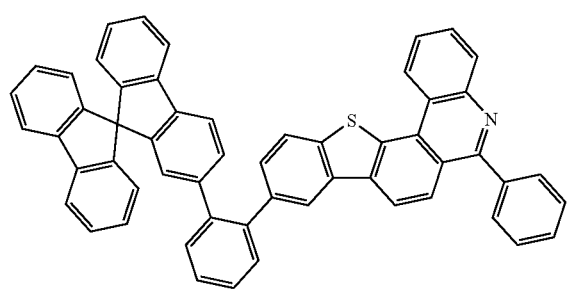

-continued
865
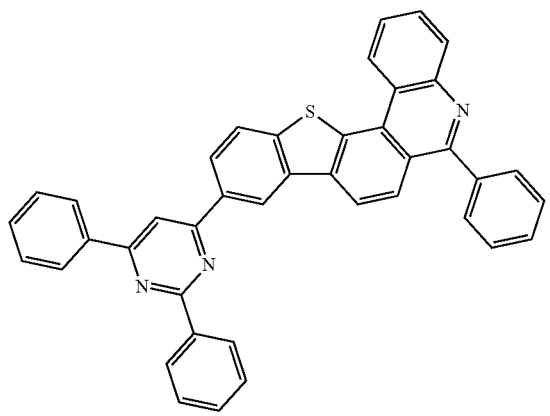
866
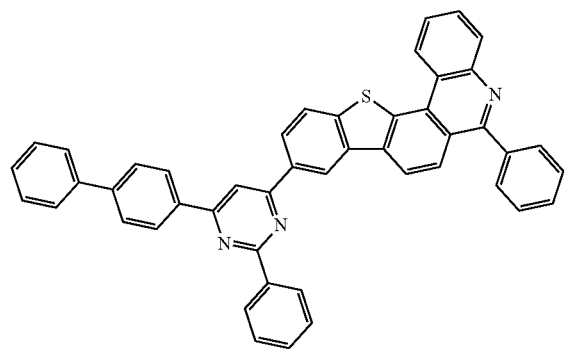
867
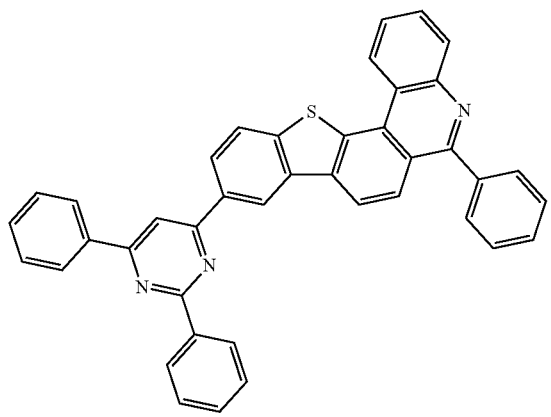
868
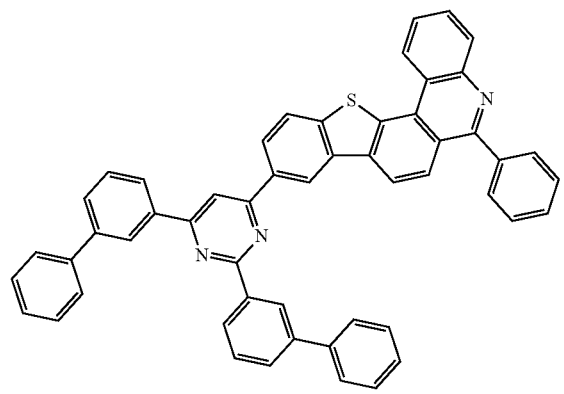
869
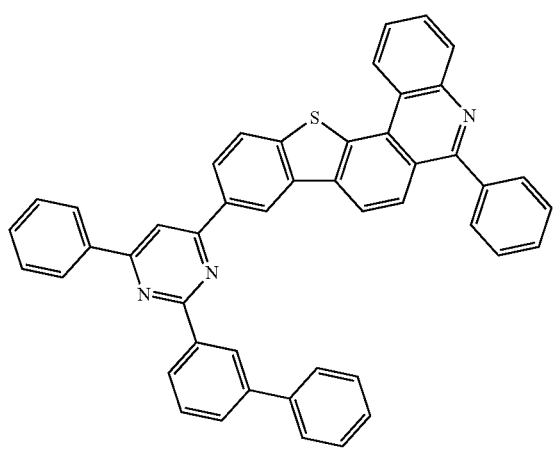
870
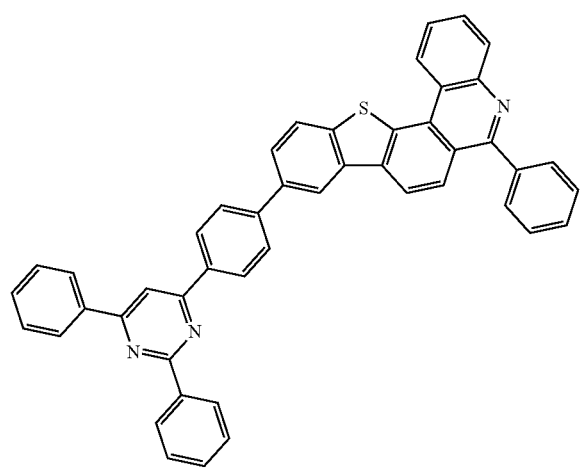

-continued
871
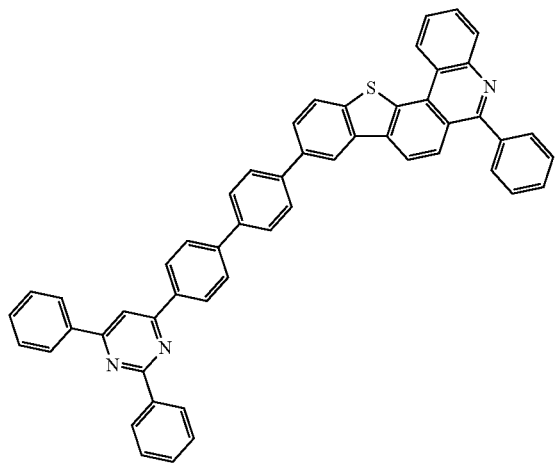
872
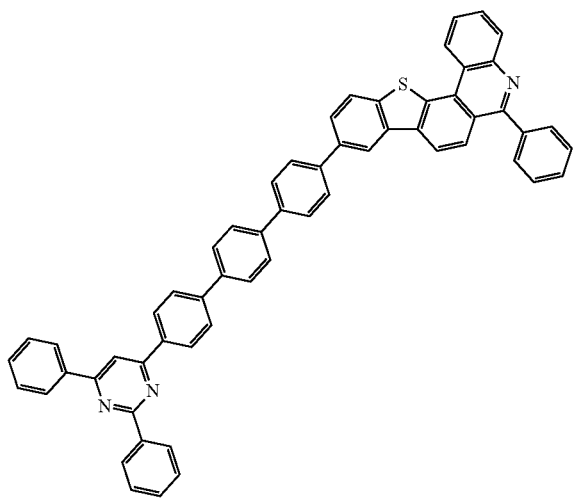
873
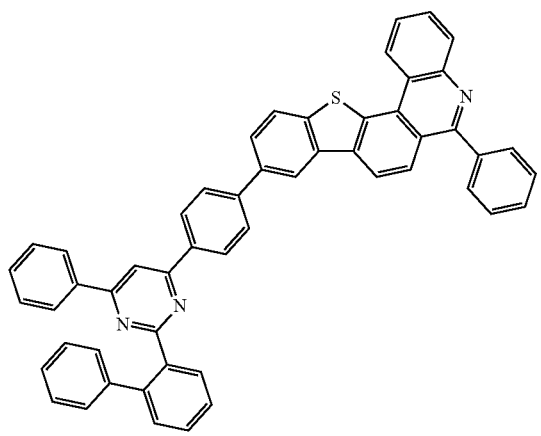
874
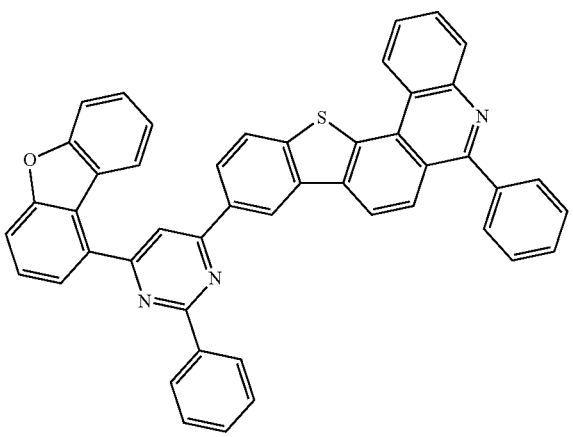
875
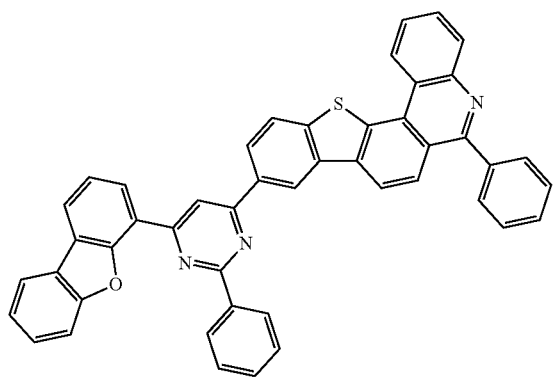
876
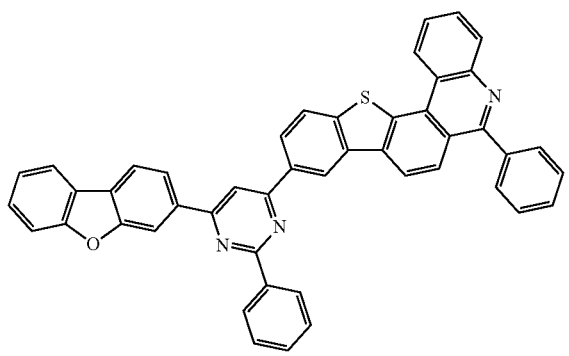

-continued
877
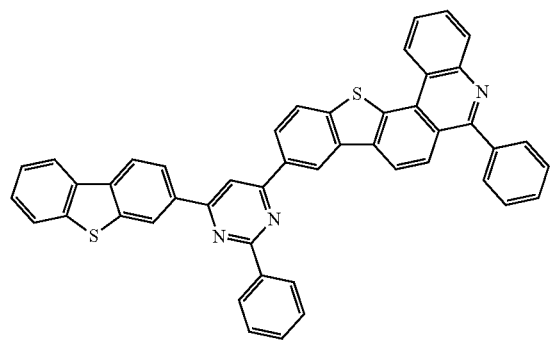
878
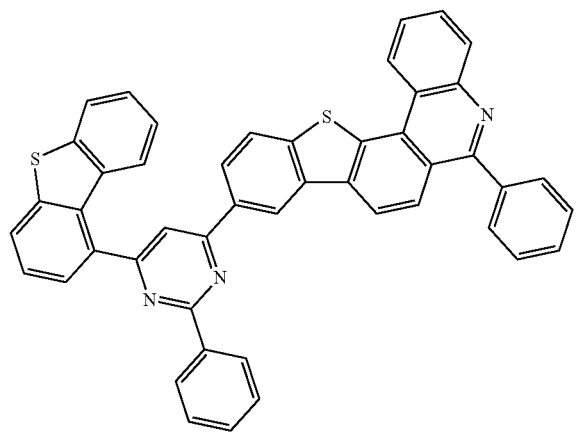
879
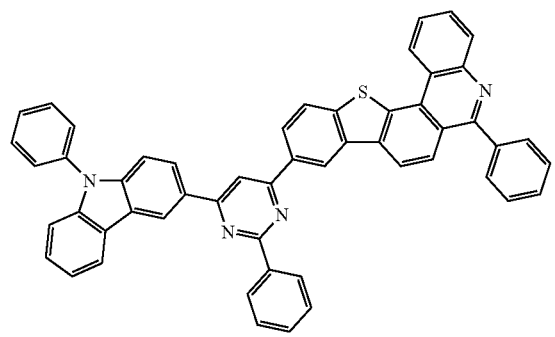
880
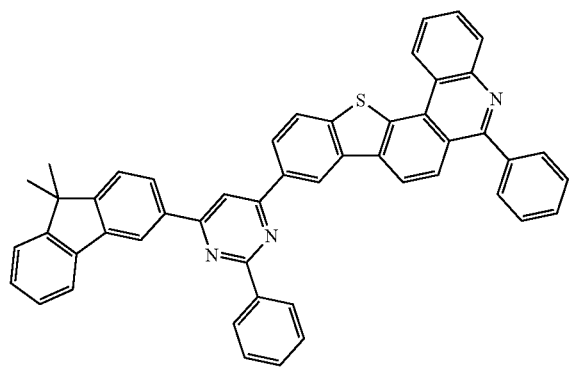
881
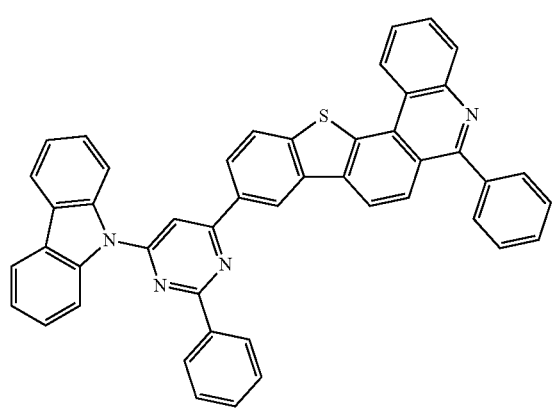
882
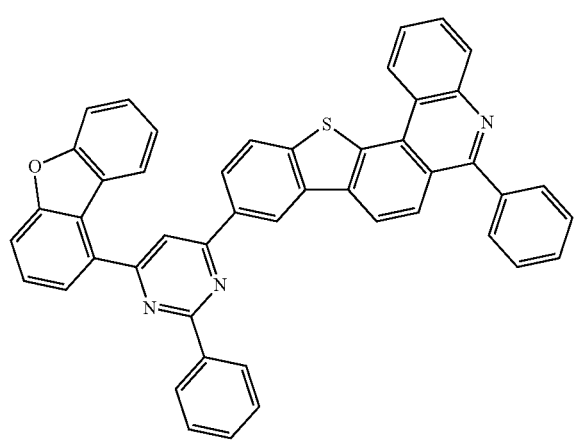

883
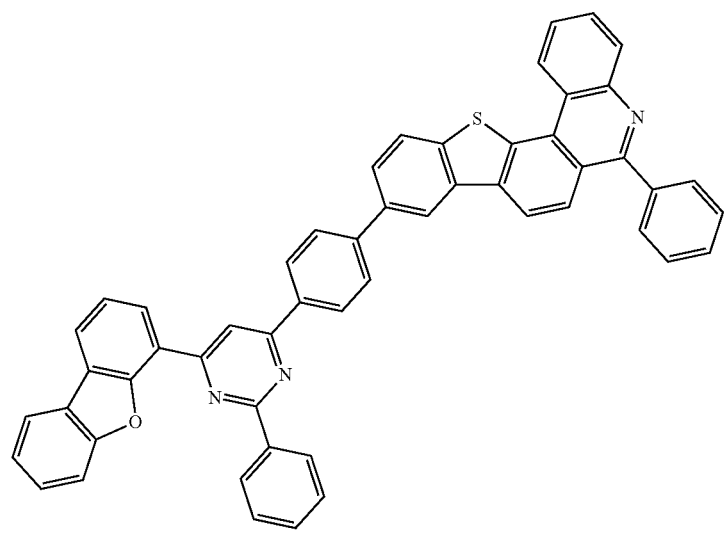
884
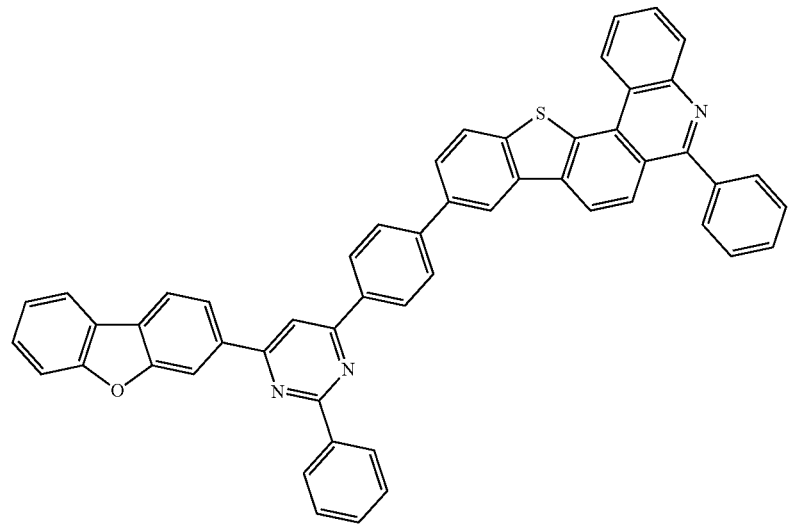
885
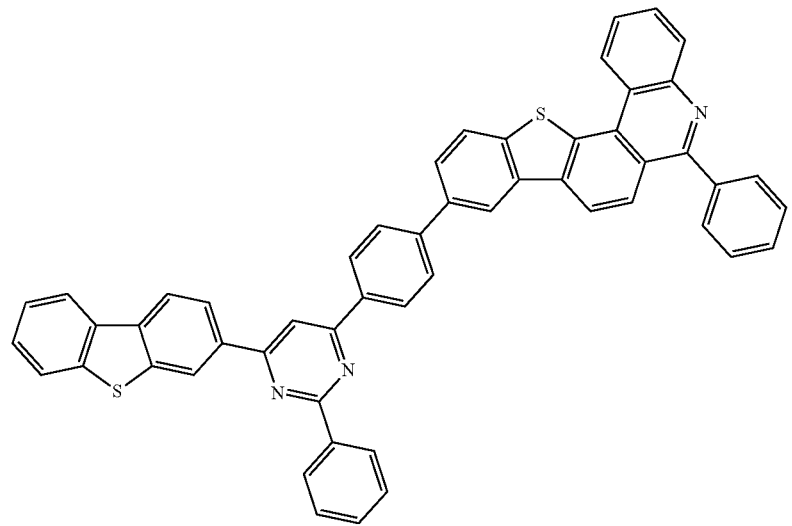

886
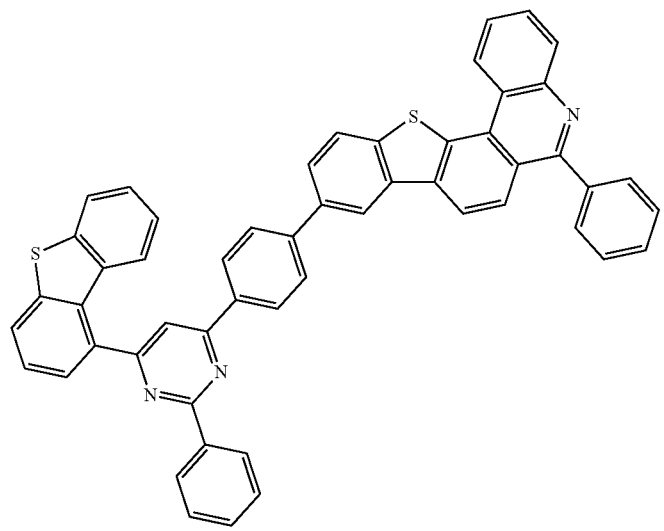
887
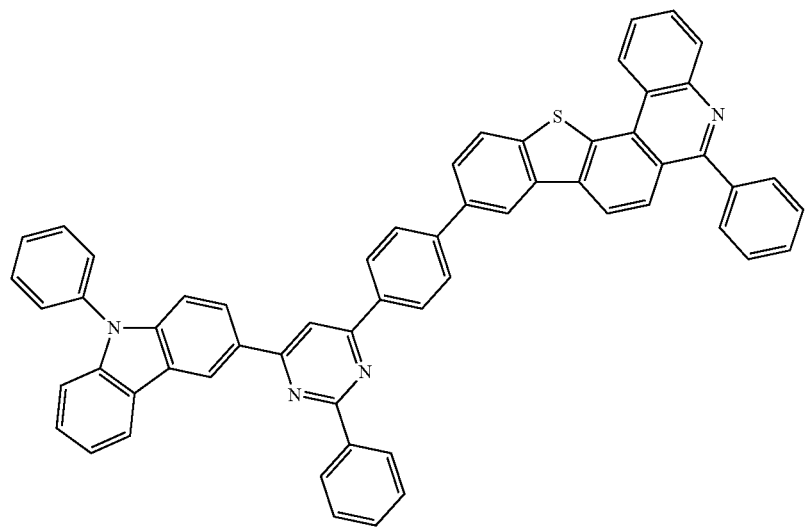
888
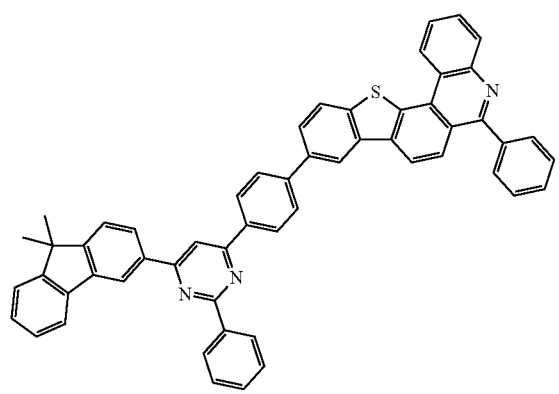
889
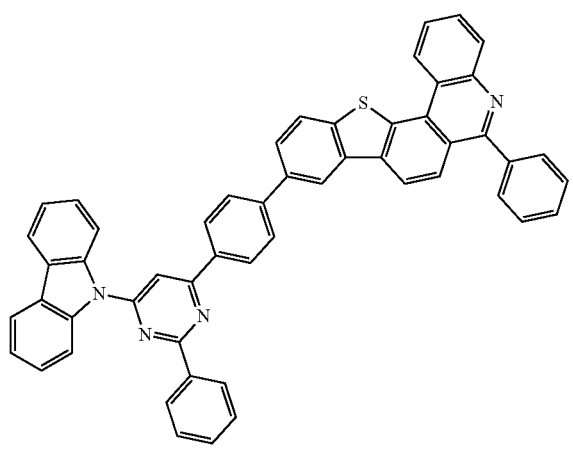

-continued
890
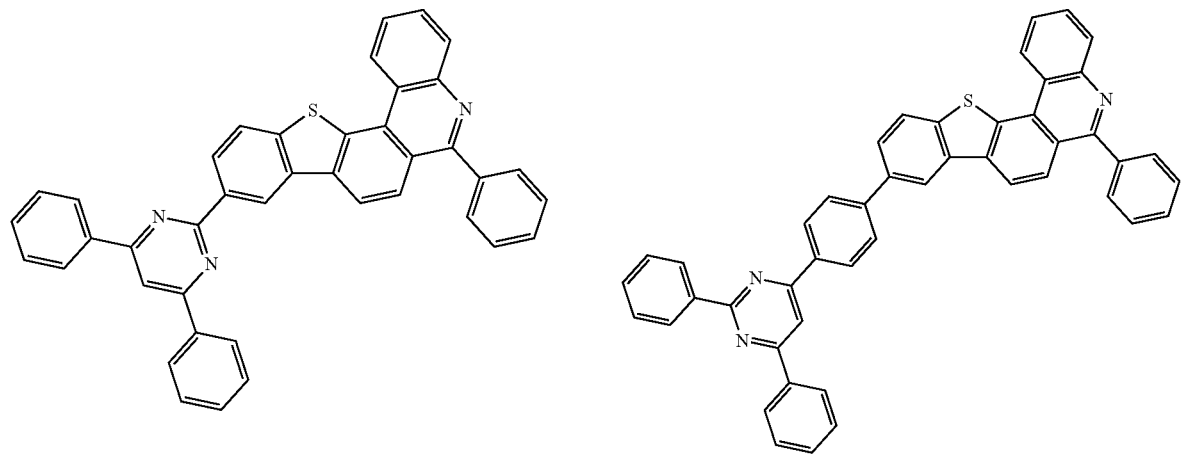
891
892
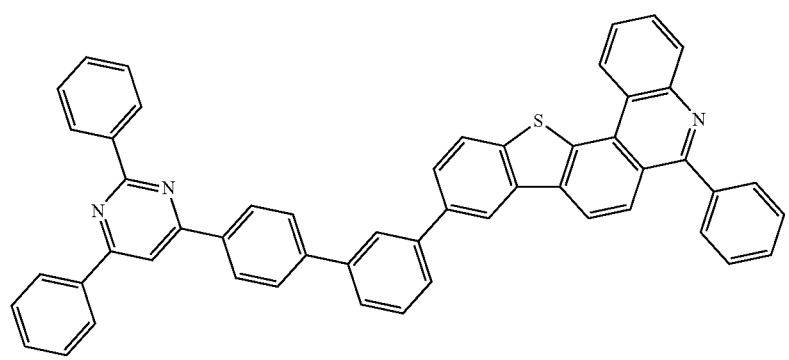
893
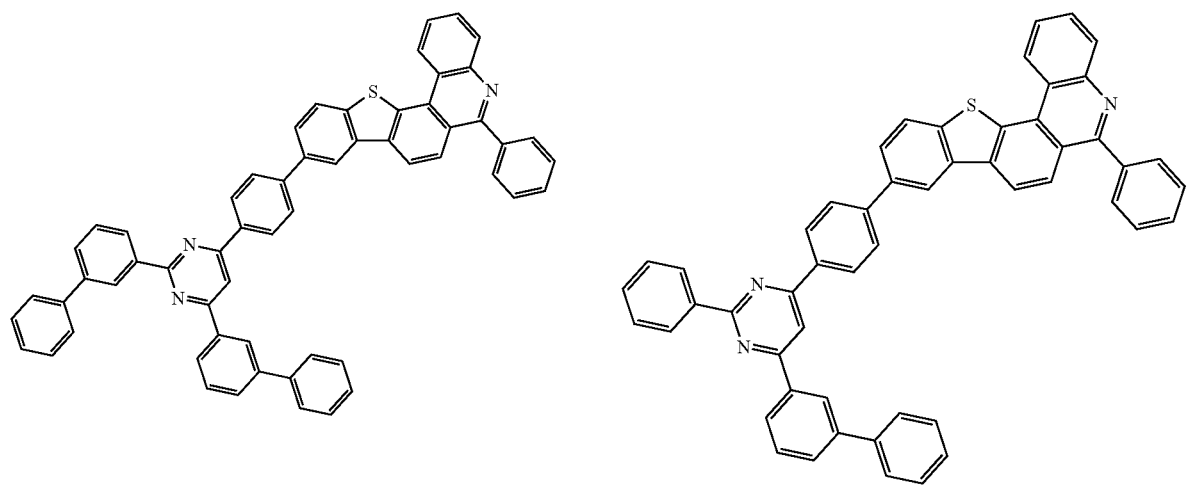
894

-continued
895
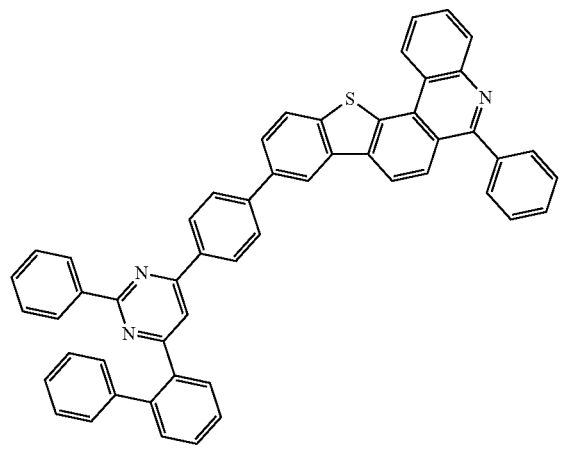
896
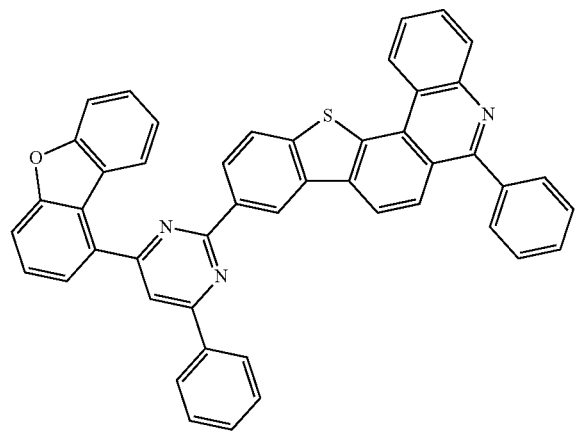
897
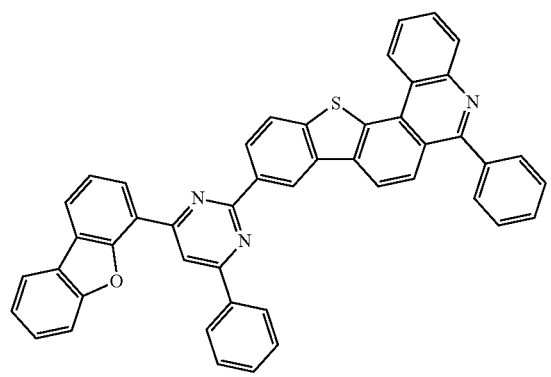
898
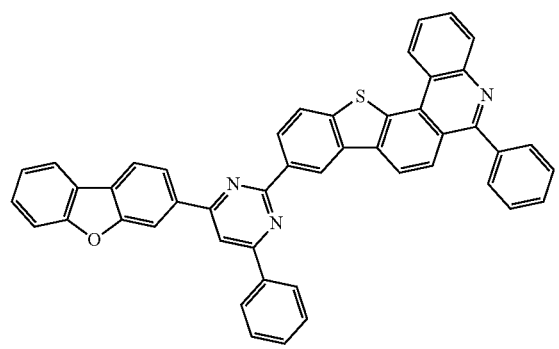
899
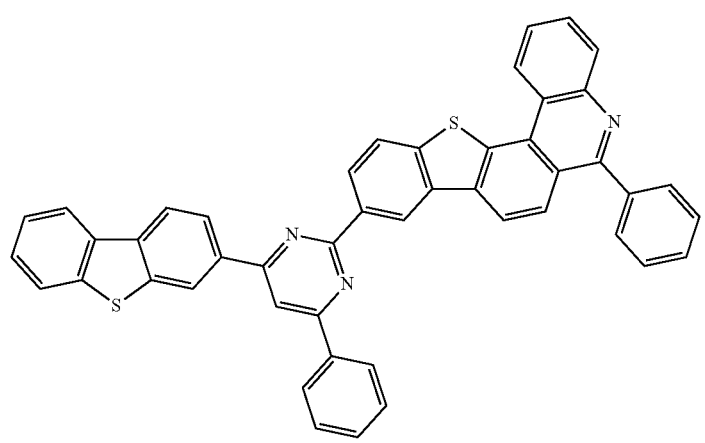

313 314
900
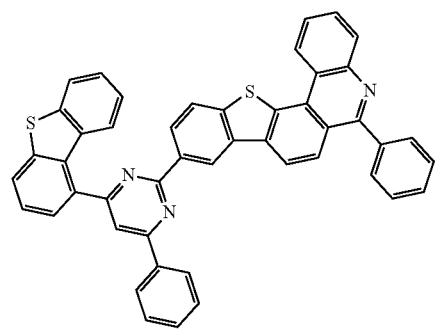
901
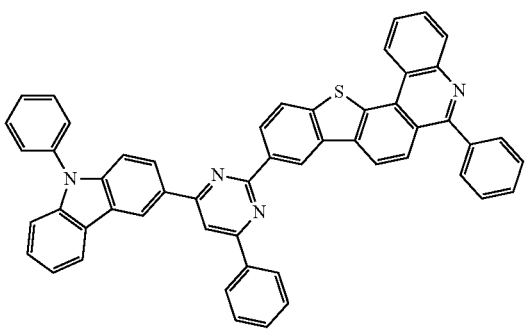
902
903
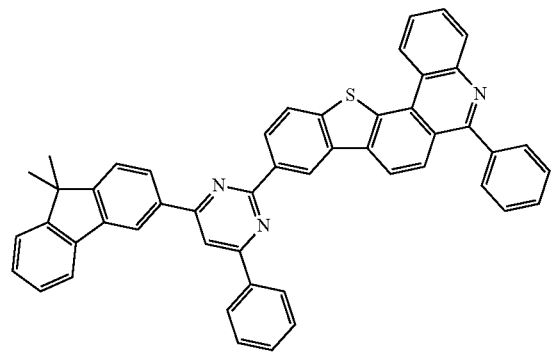
904
905
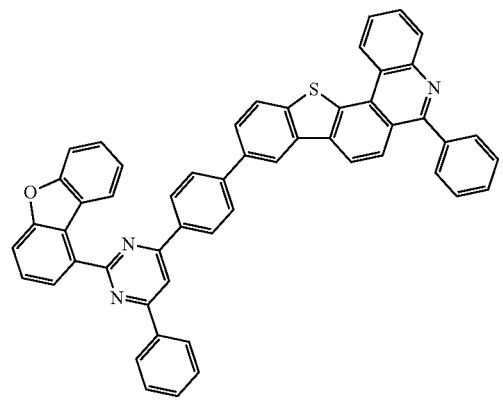
906
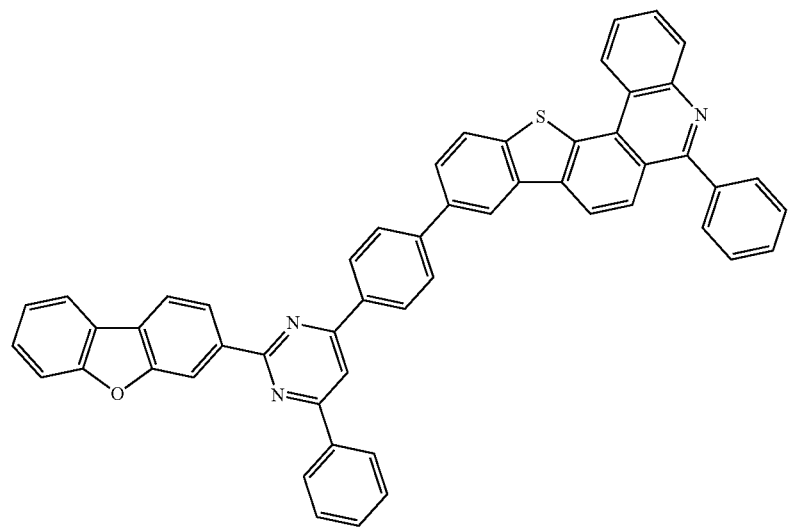

-continued
907
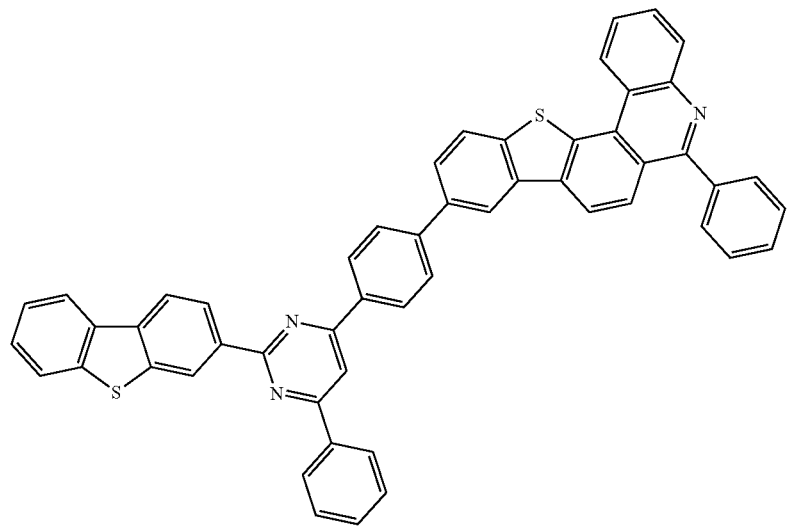
908
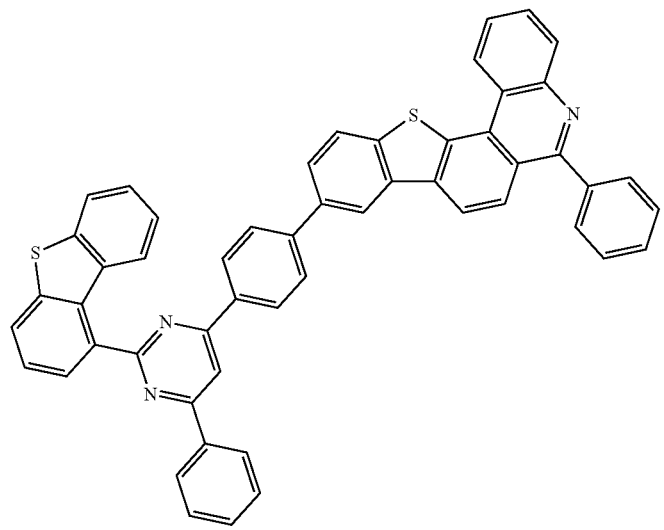
909
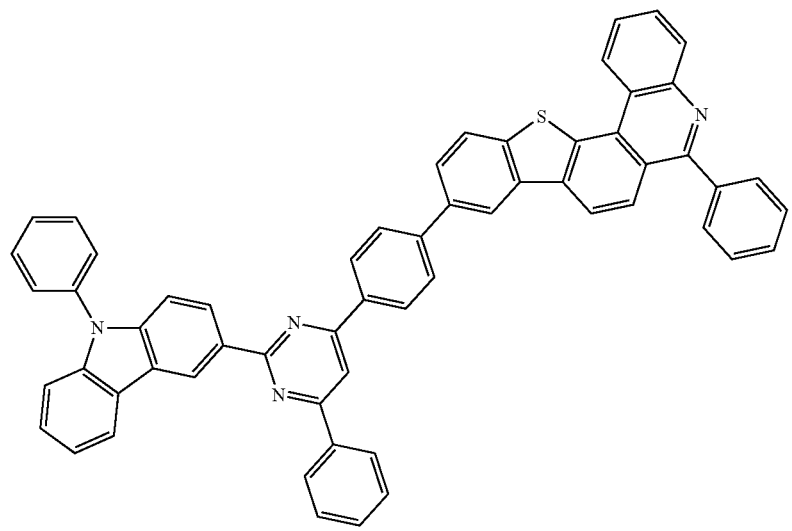

-continued
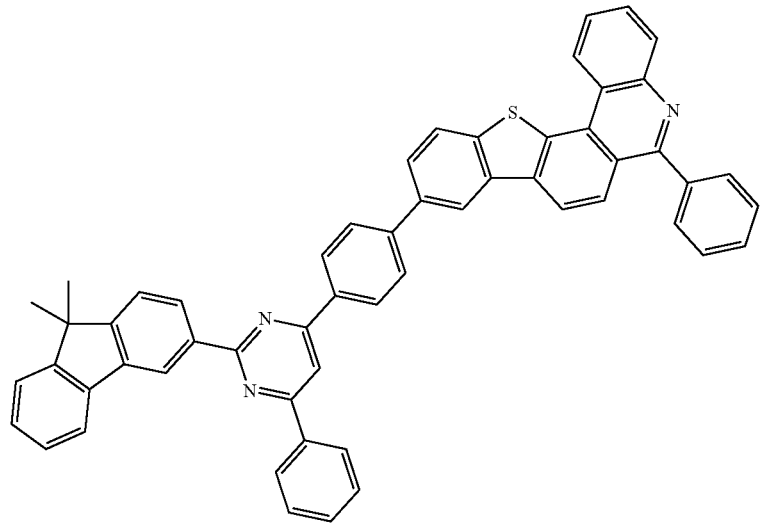
910
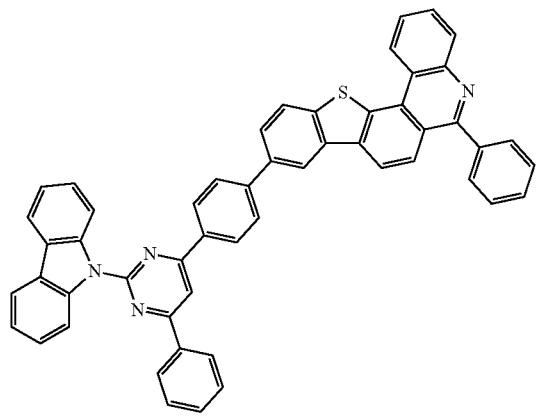
911
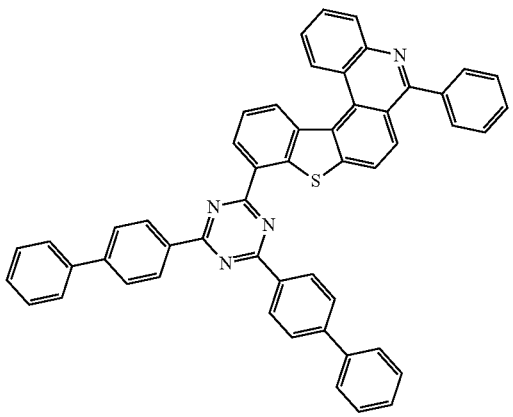
912
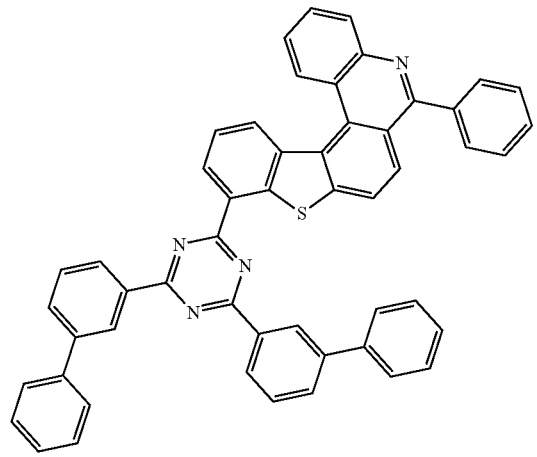
913
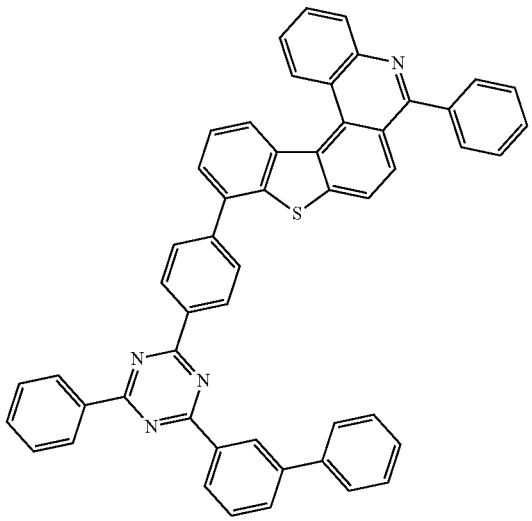
914

-continued
915
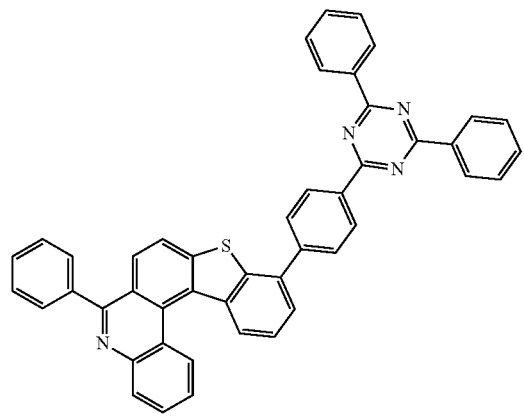
916
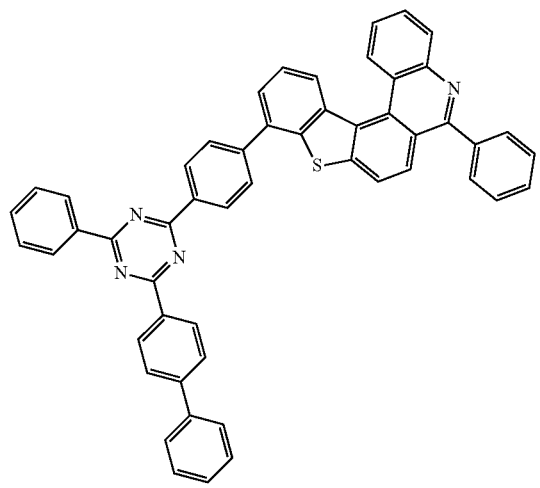
917
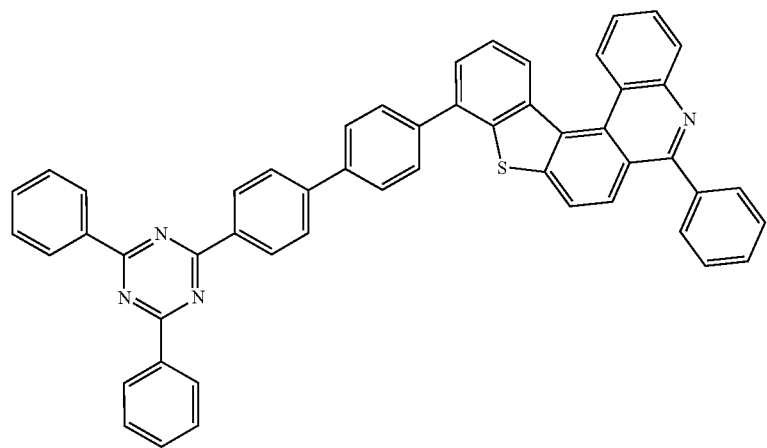
918
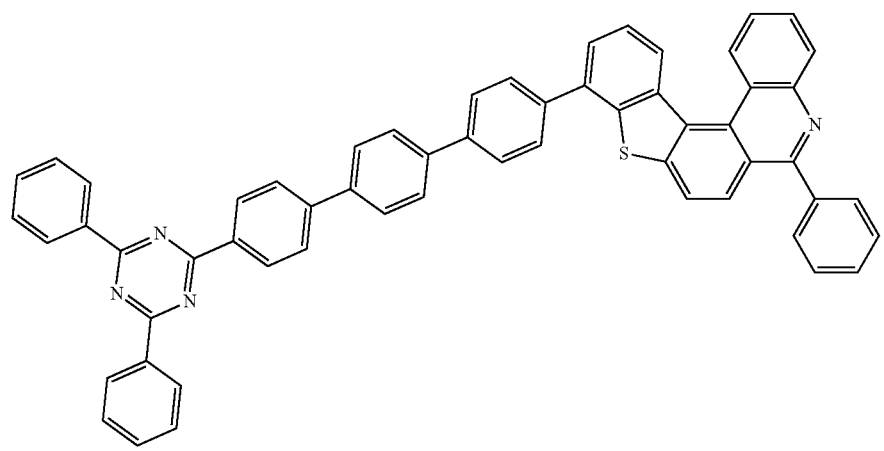

-continued
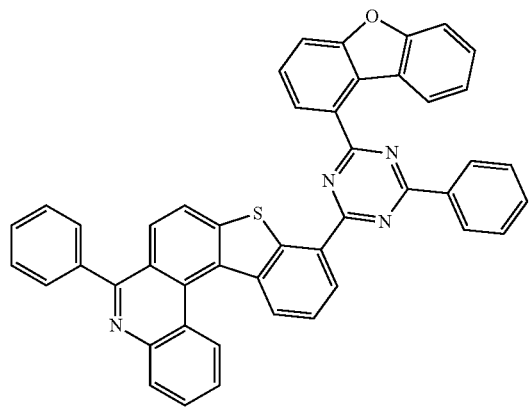
919
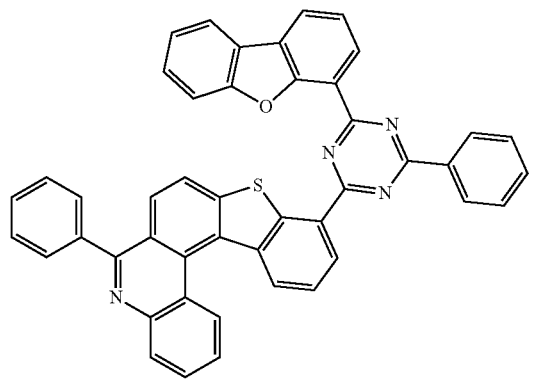
920
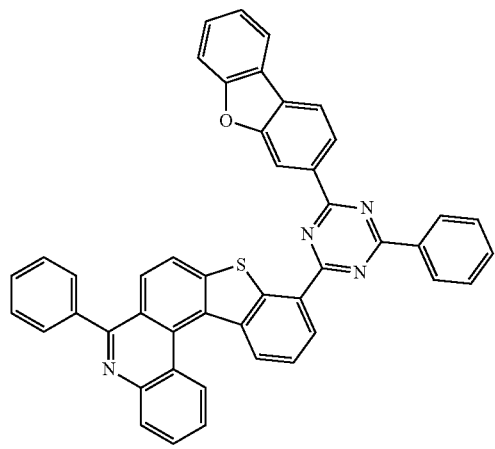
921
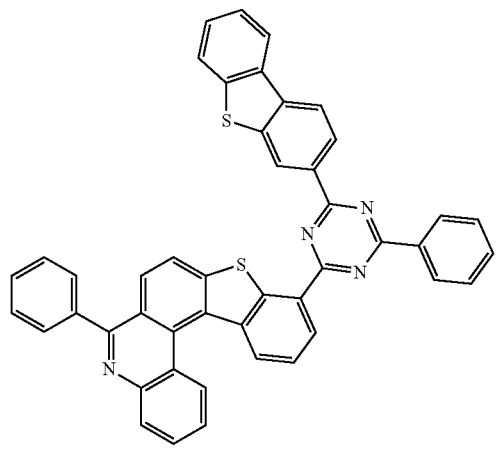
922
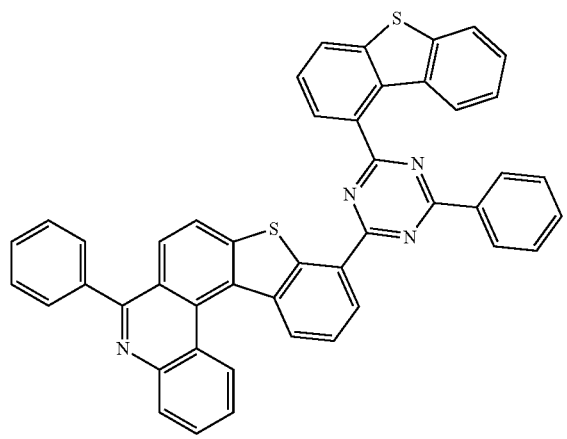
923
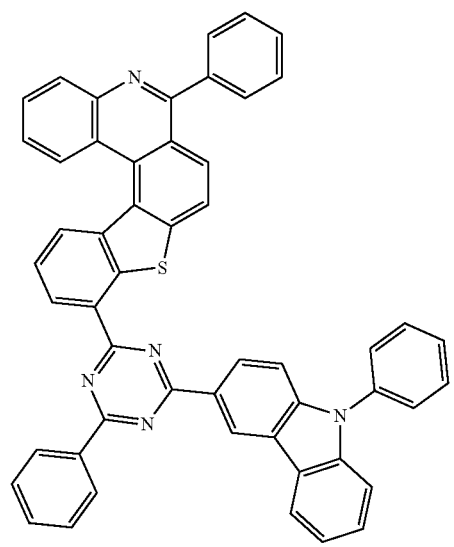
924

323
324
-continued
925
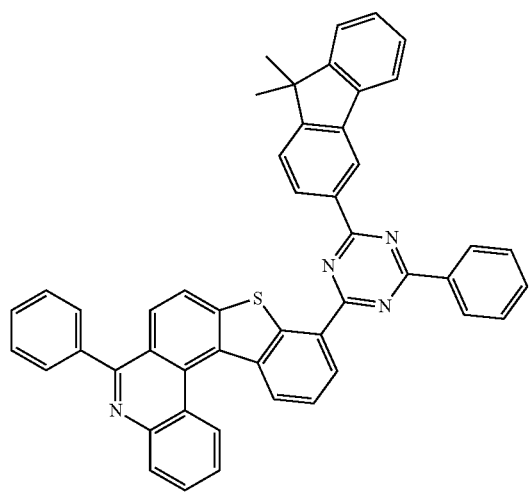
926
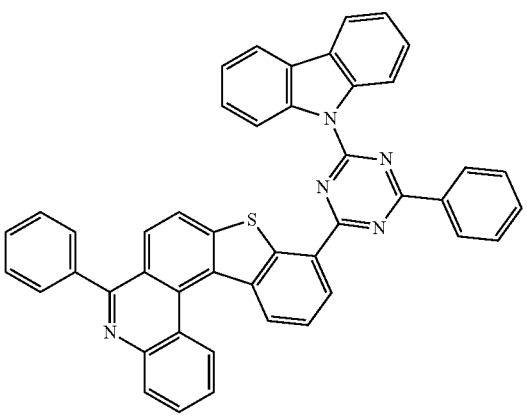
927
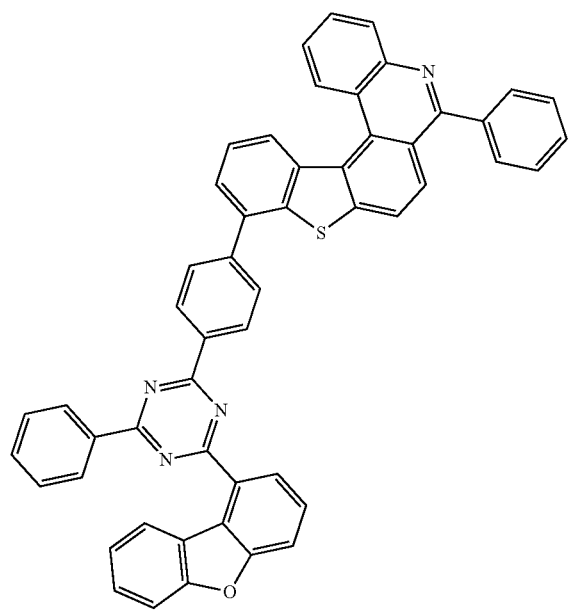
928
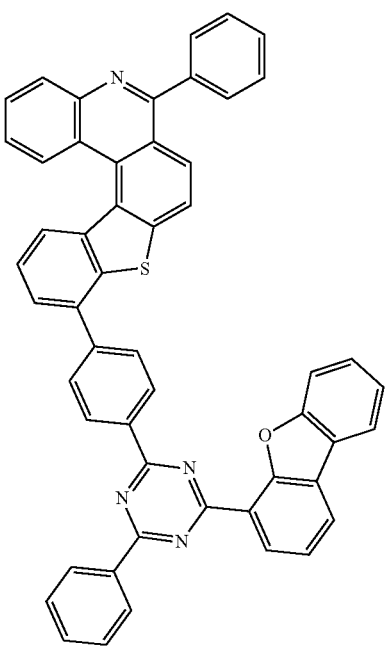

-continued
929 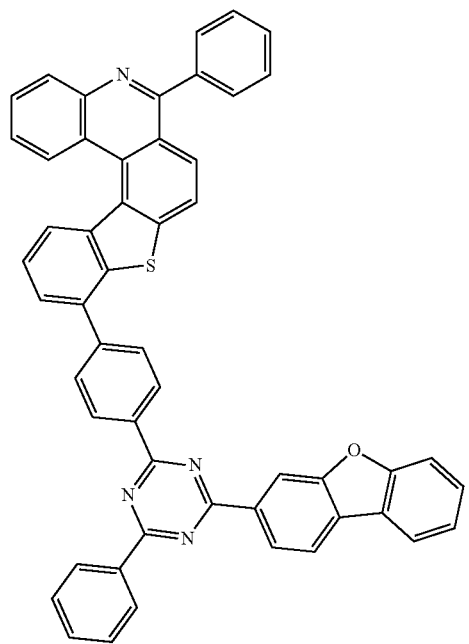
930 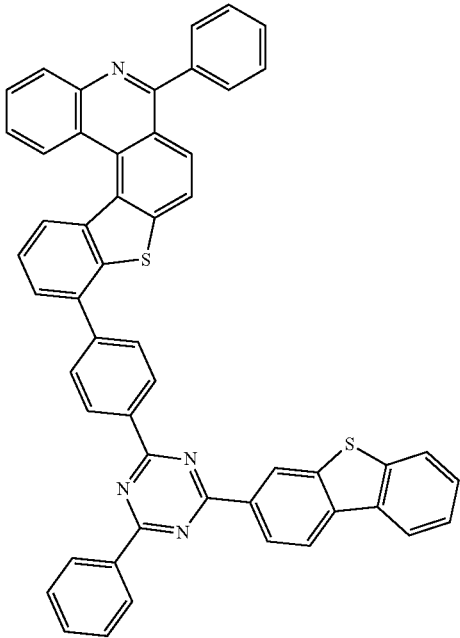
931 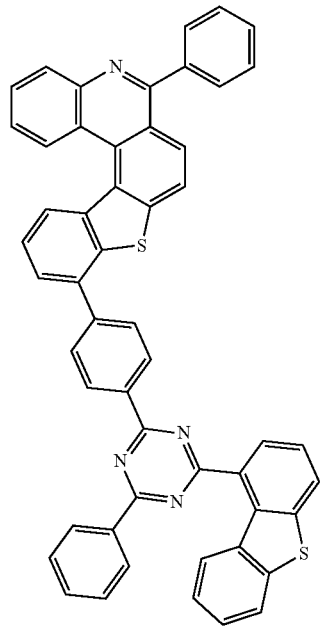
932 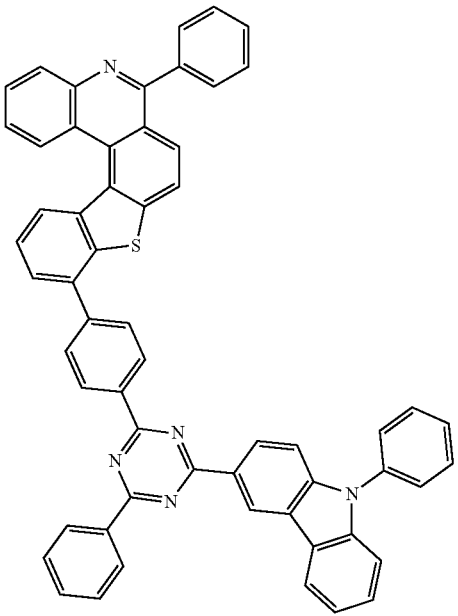

-continued
933
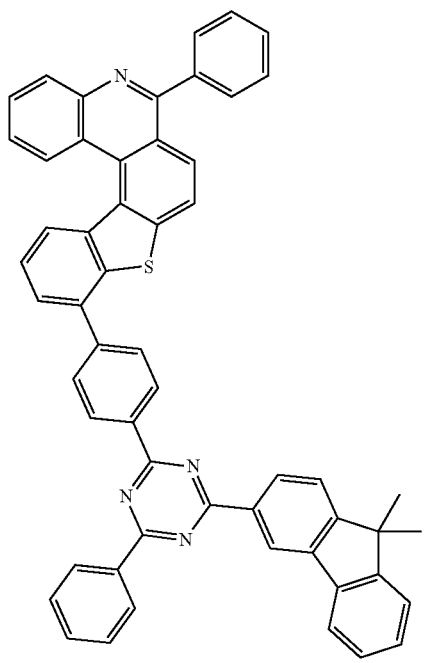
934
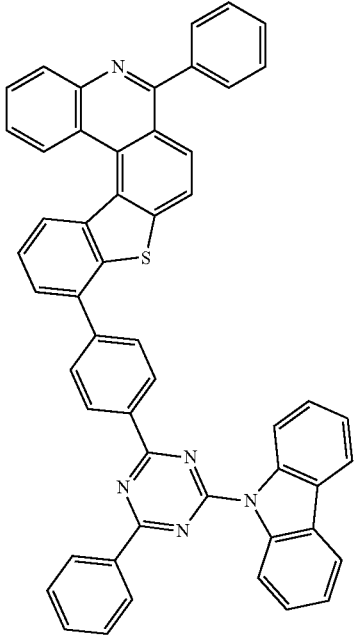
935
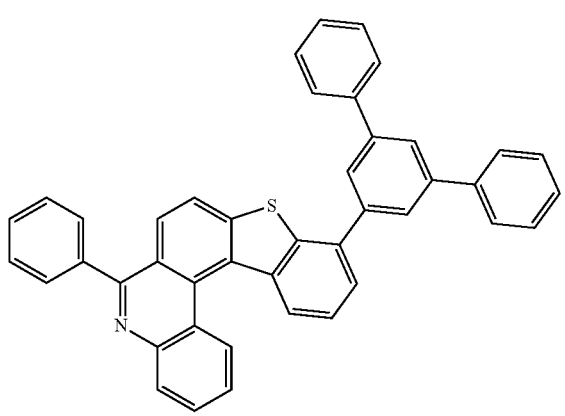
936
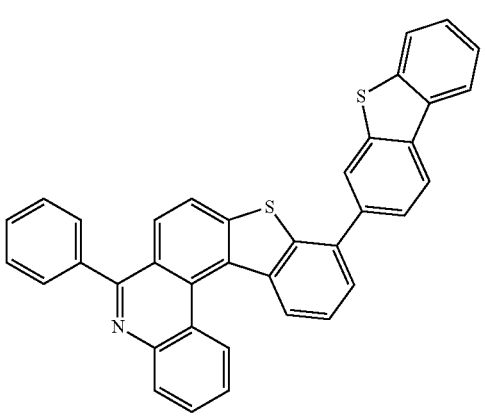
937
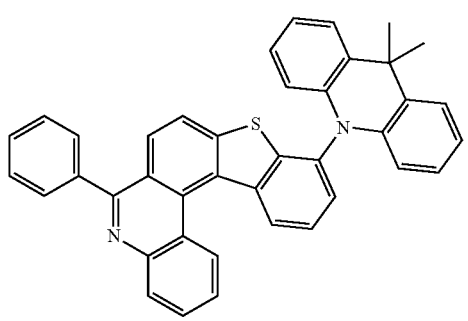
938
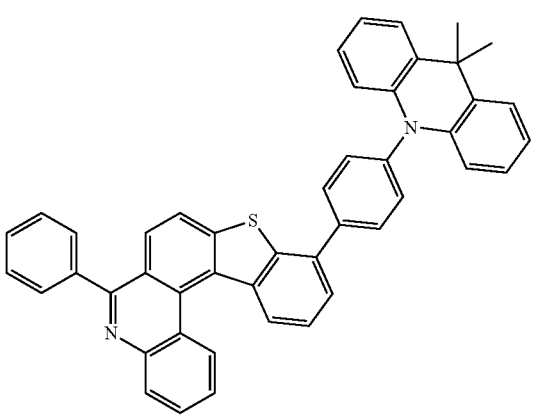

-continued
939
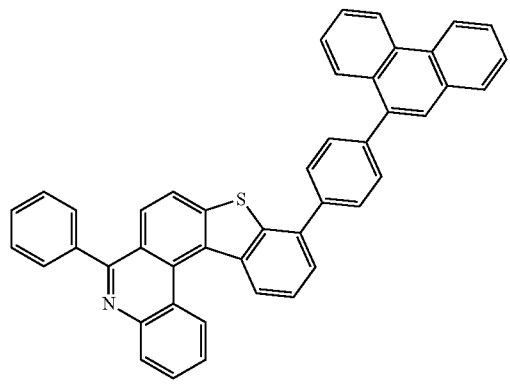
940
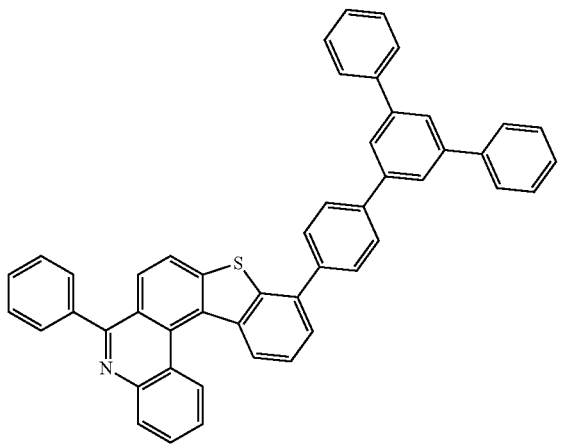
941
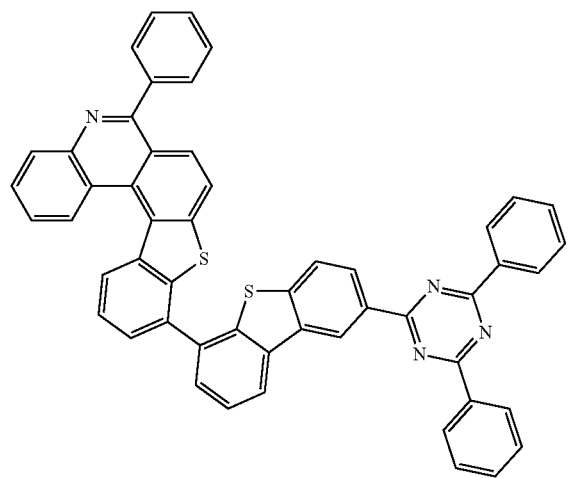
942
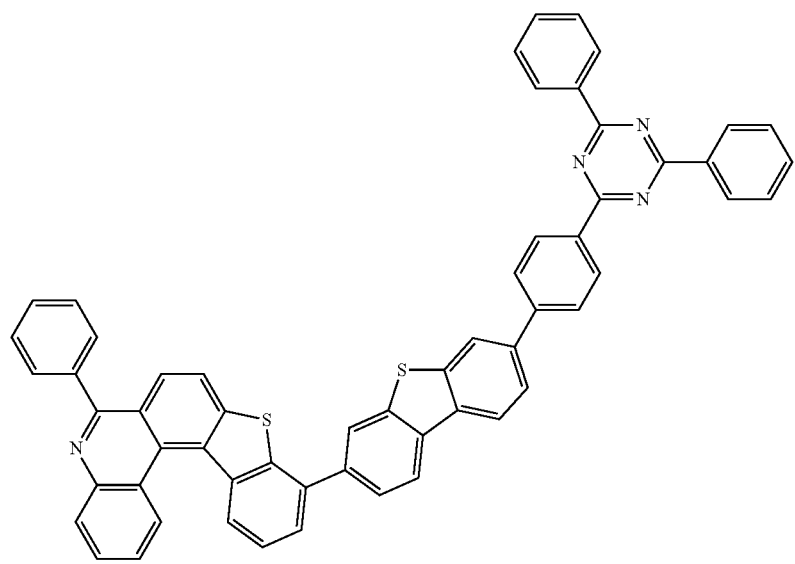

943
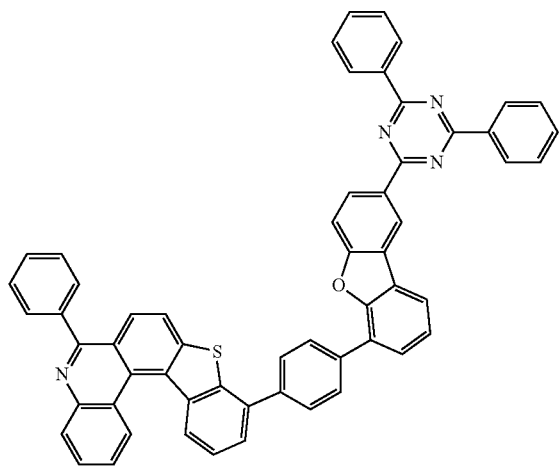
944
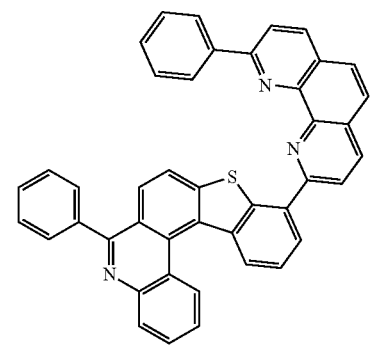
945
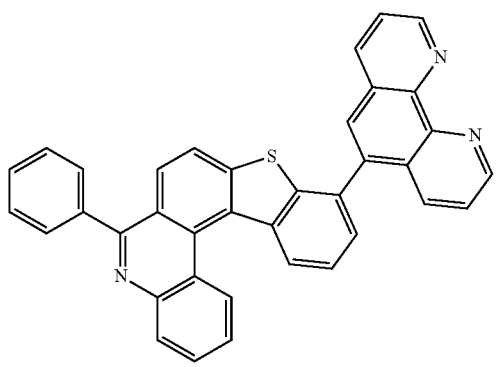
946
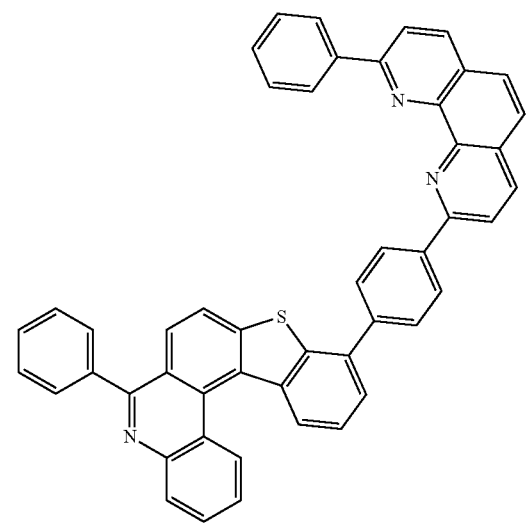
947
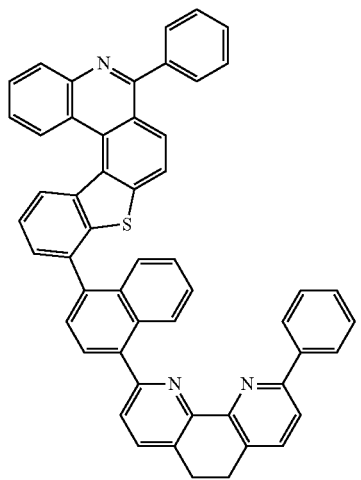
948
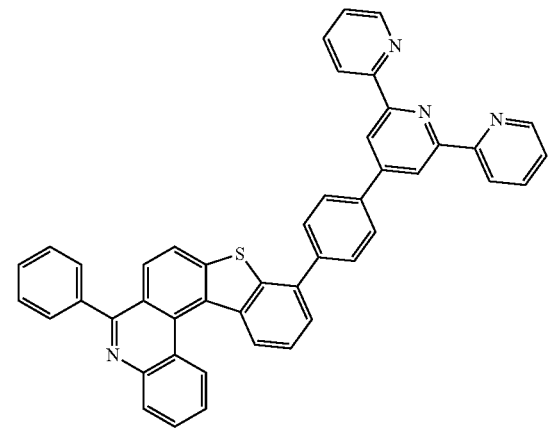

949
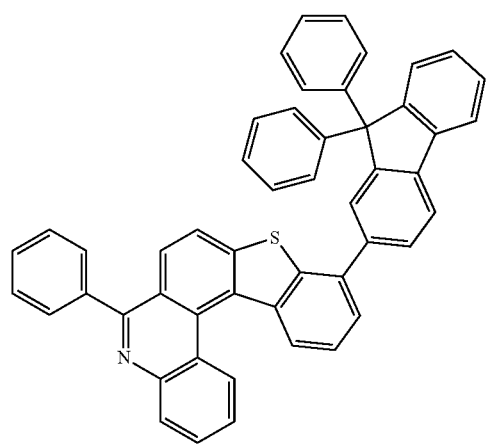
950
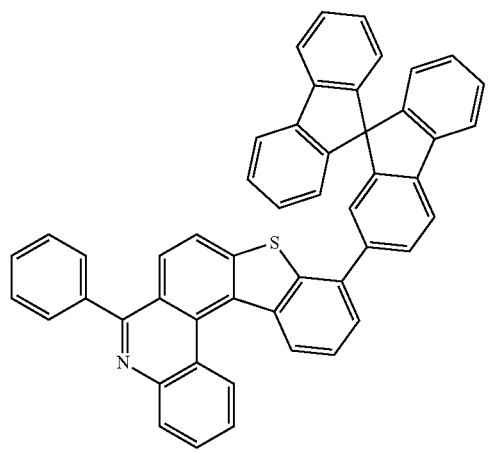
951
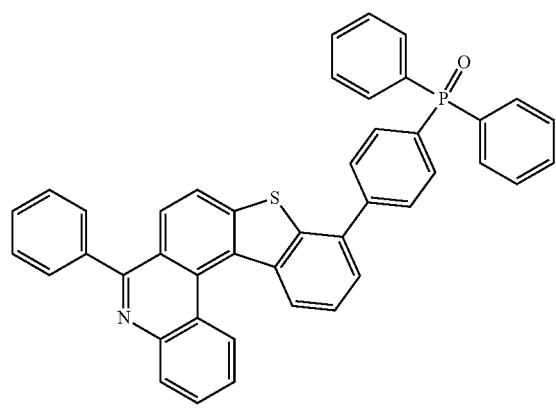
952
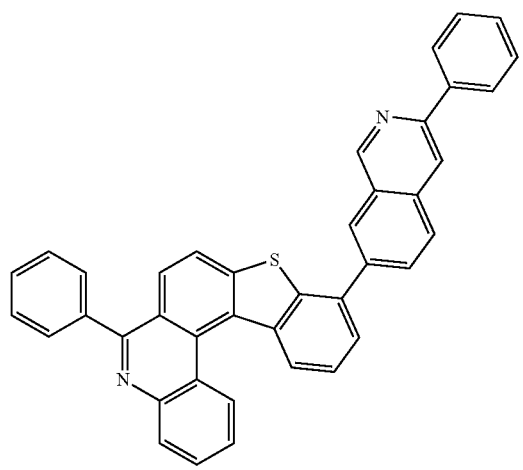
953
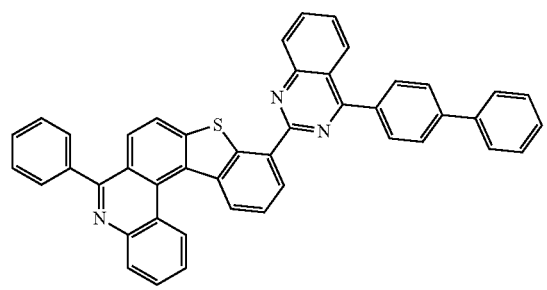
954
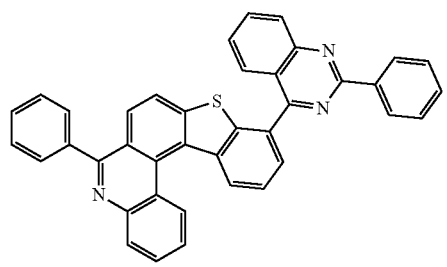

-continued
955 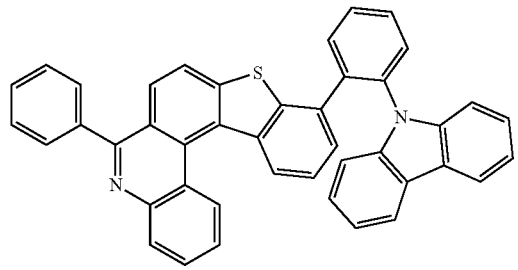
956 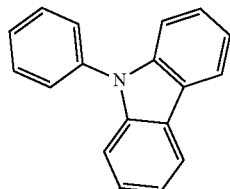
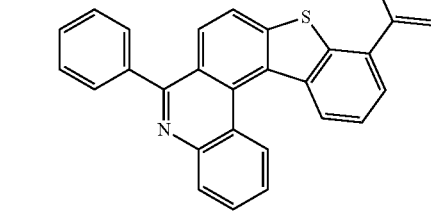
957 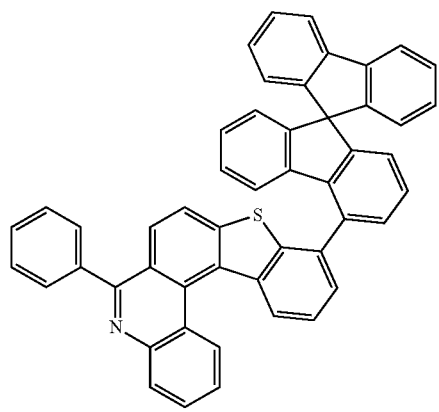
958 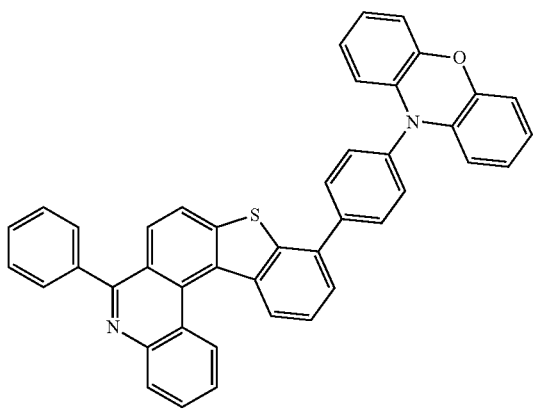
959 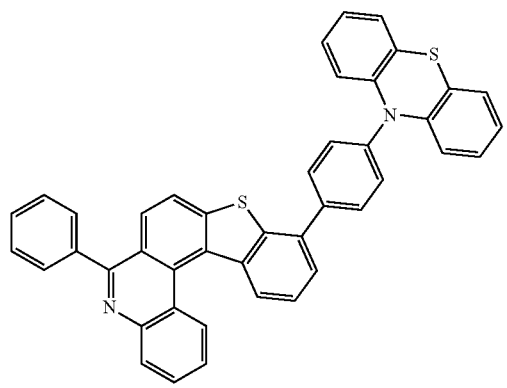
960 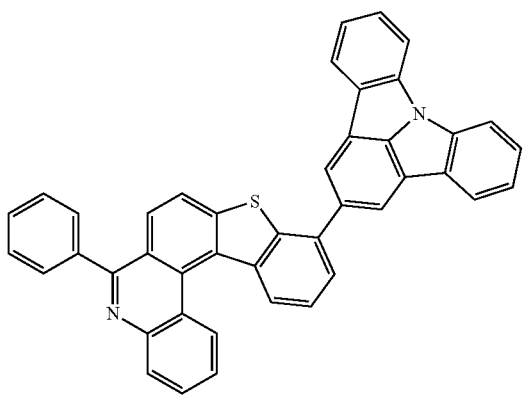

-continued
961
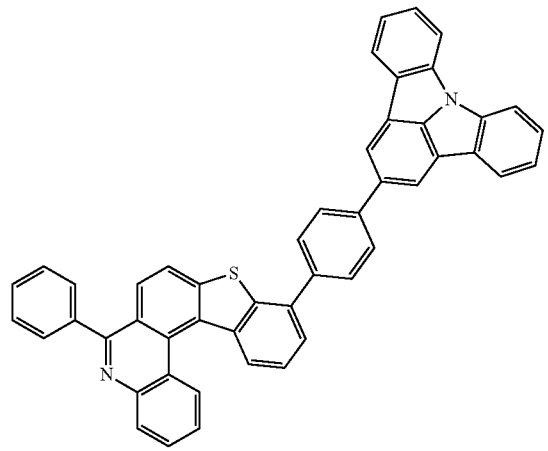
962
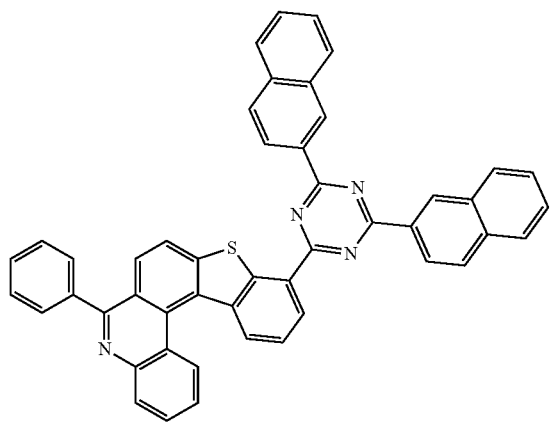
963
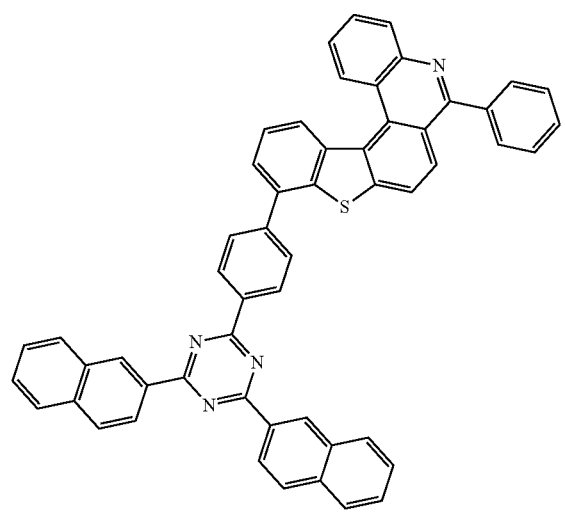
964
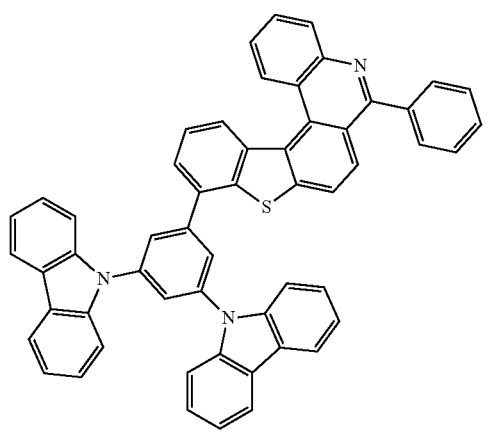
965
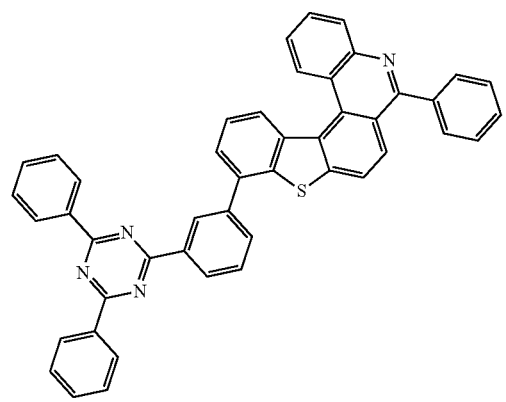
966
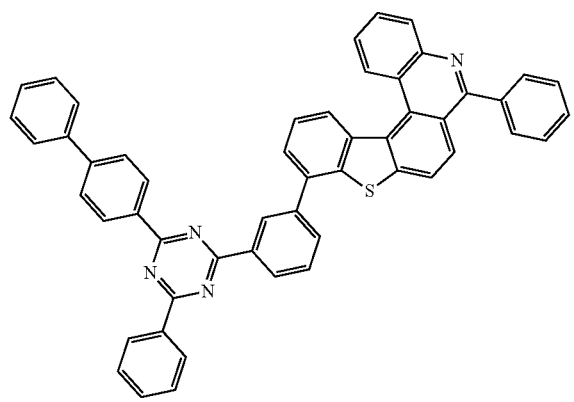

-continued
967
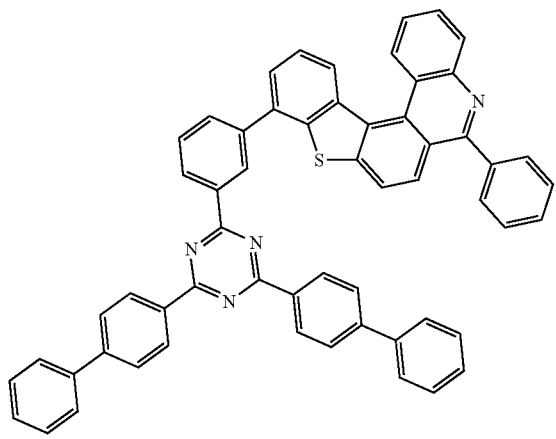
968
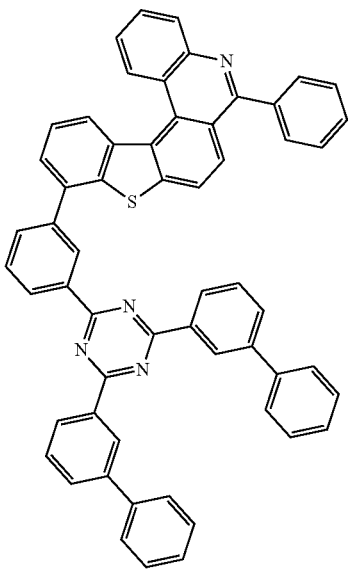
969
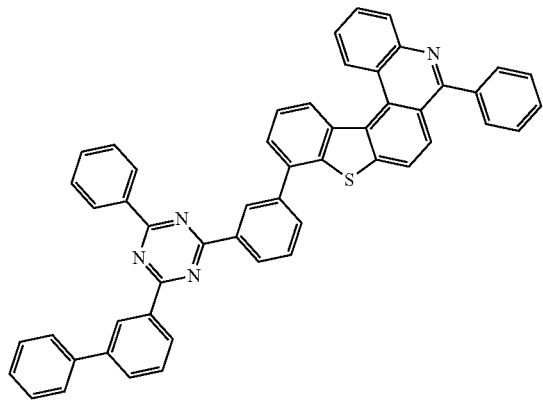
970
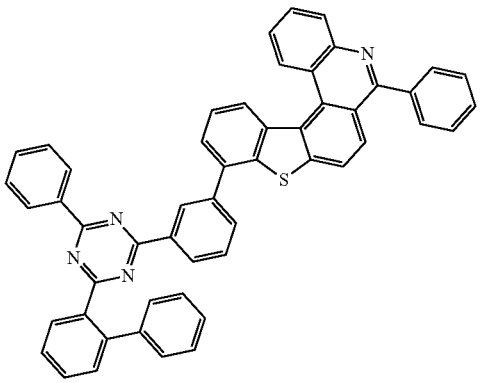
971
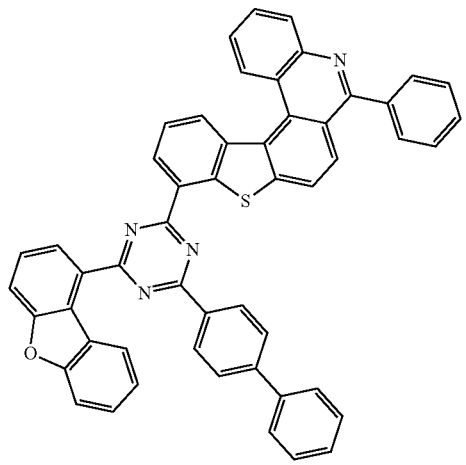
972
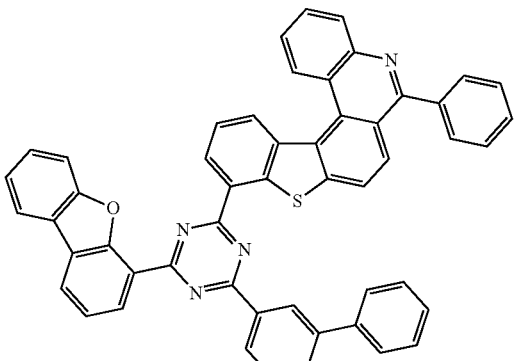

-continued
973
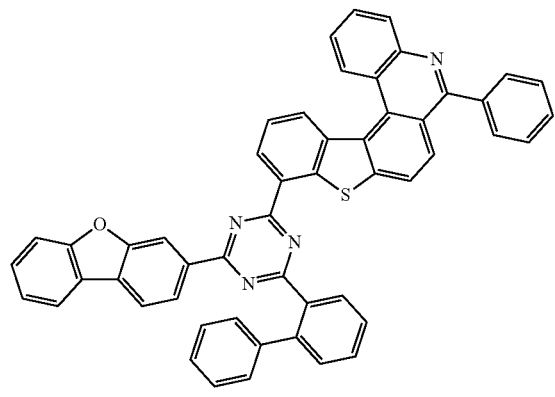
974
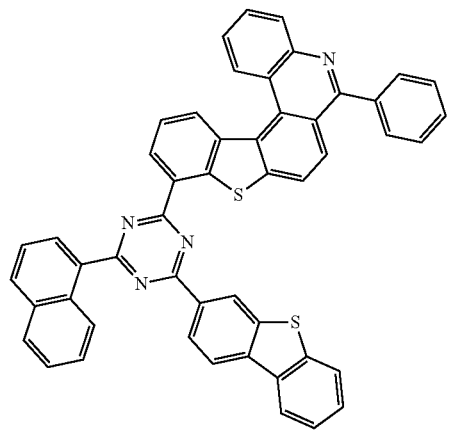
975
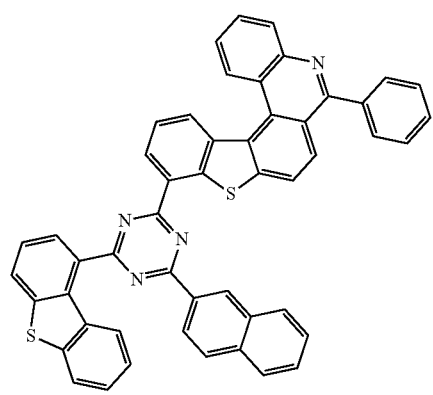
976
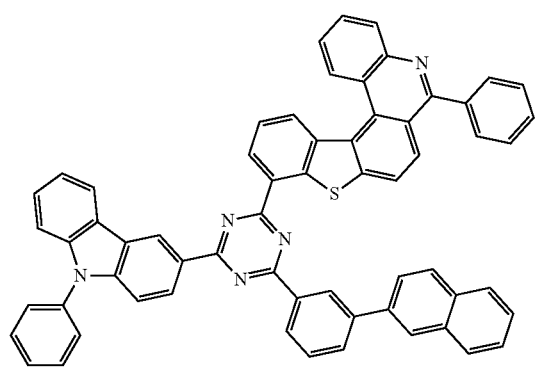
977
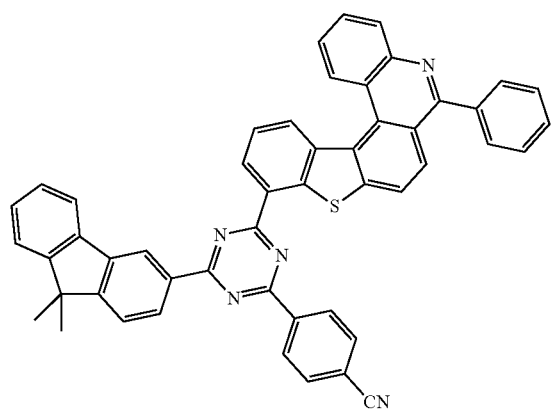
978
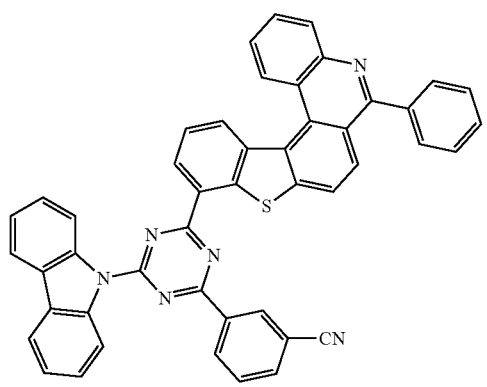

979
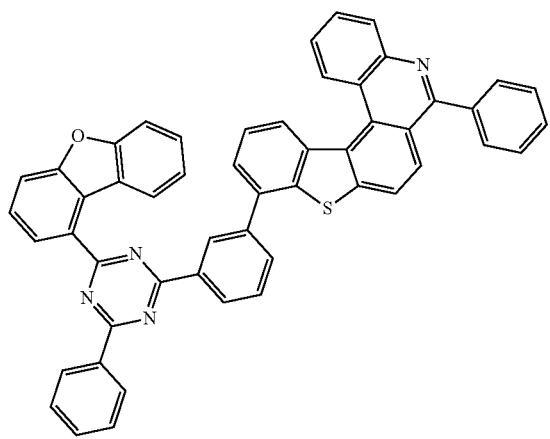
980
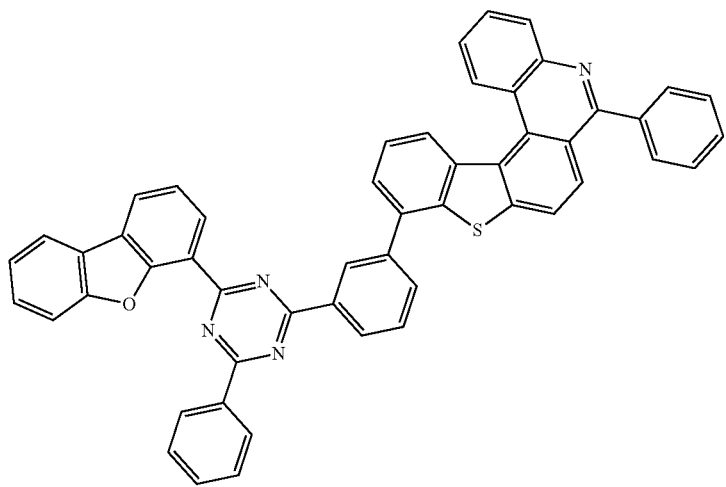
981 982
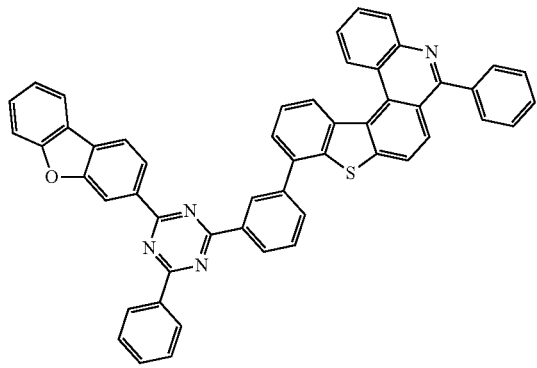

-continued
983
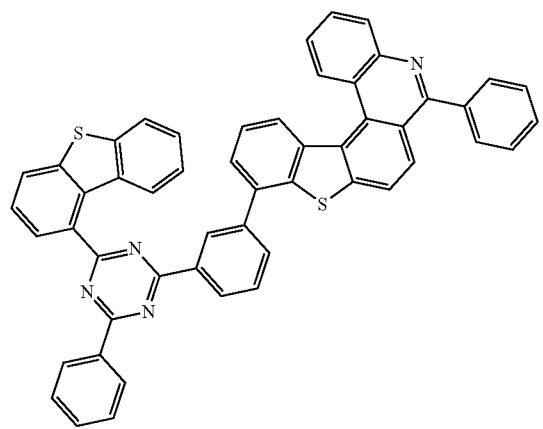
984
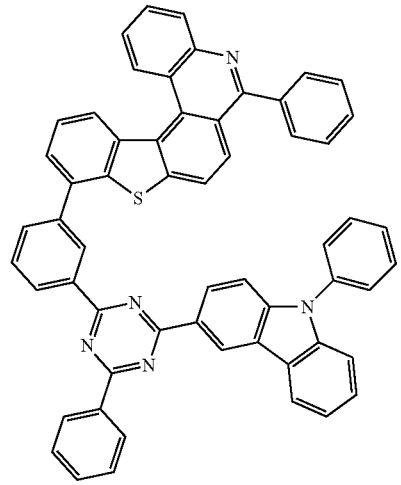
985
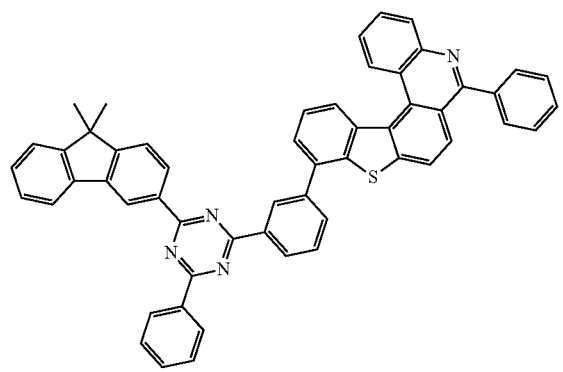
986
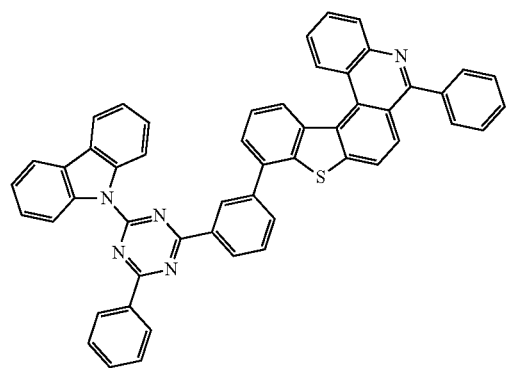
987
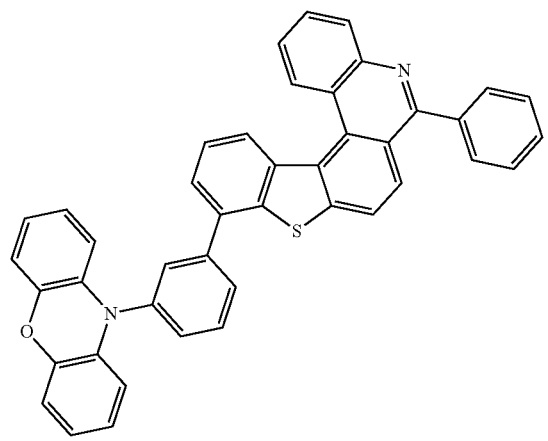
988
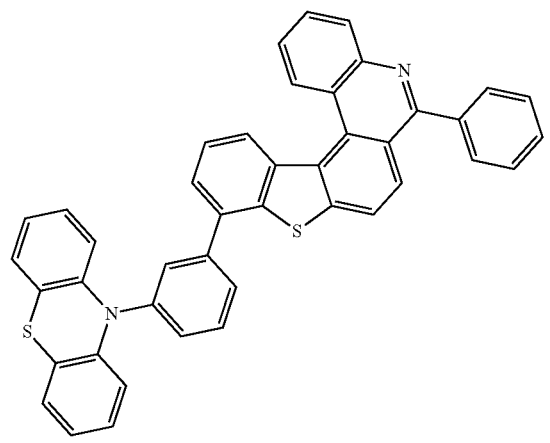

-continued
989
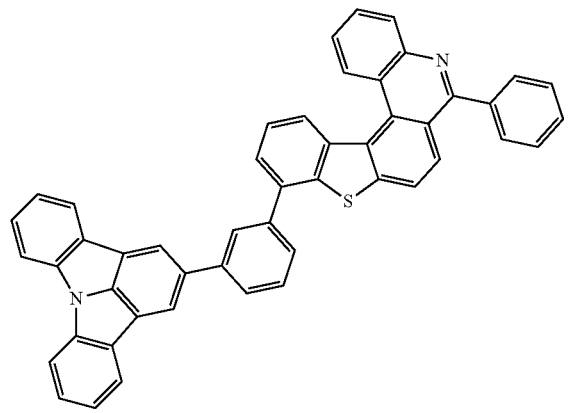
990
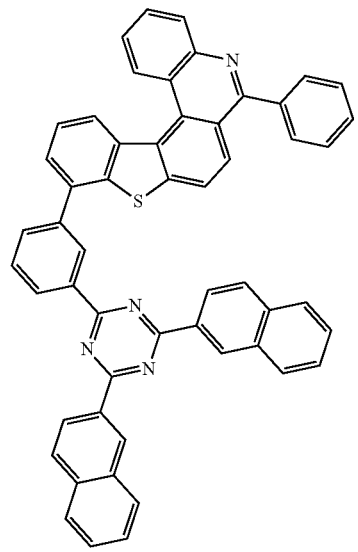
991
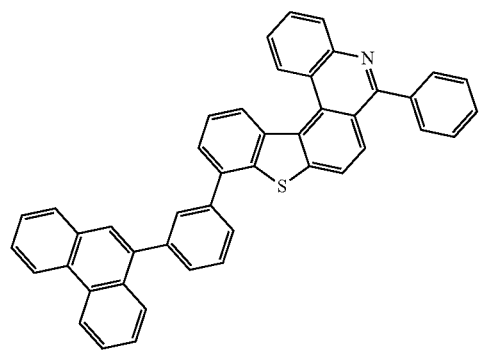
992
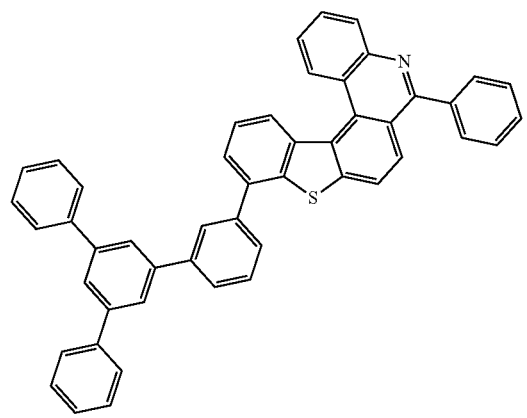
993
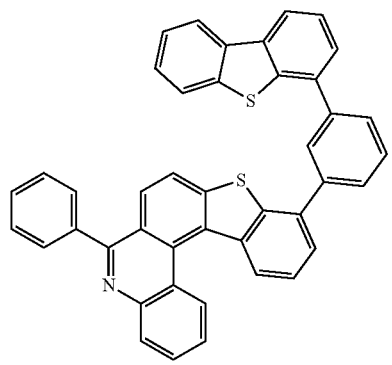
994
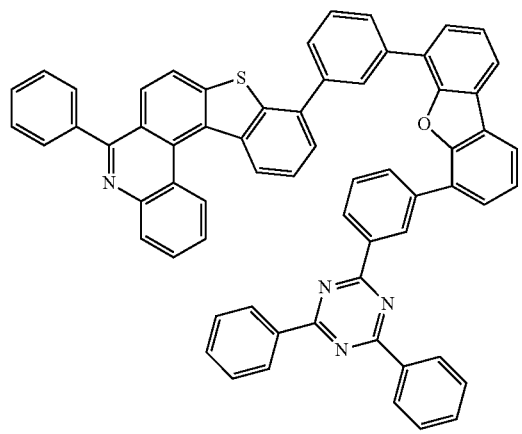

-continued
995 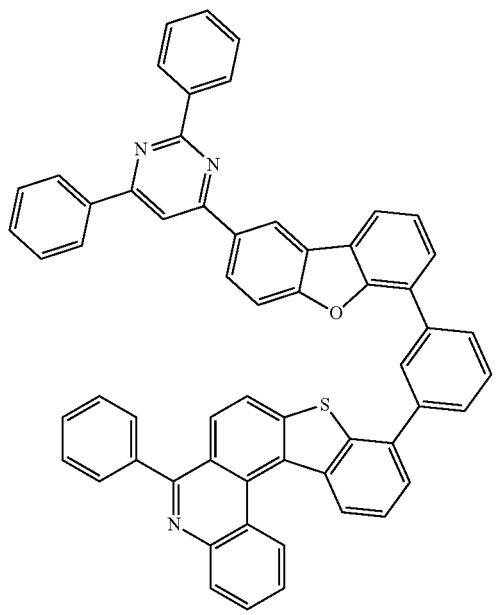
996 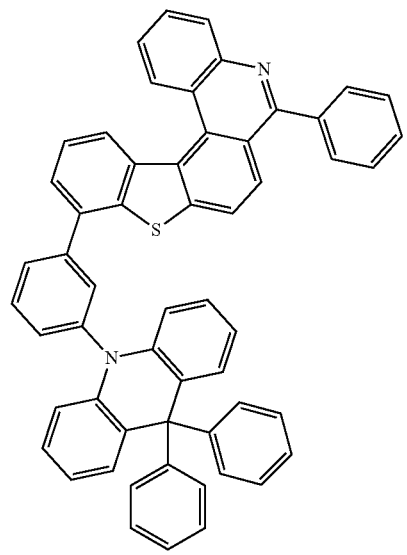
997 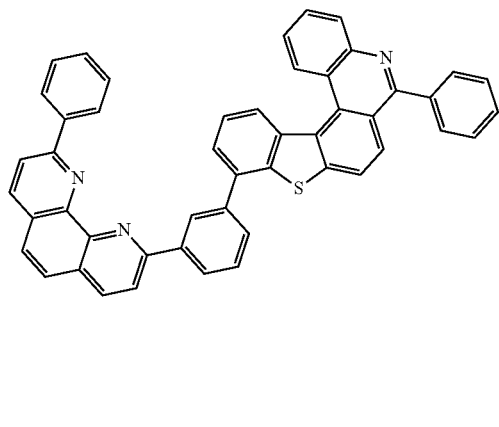
998 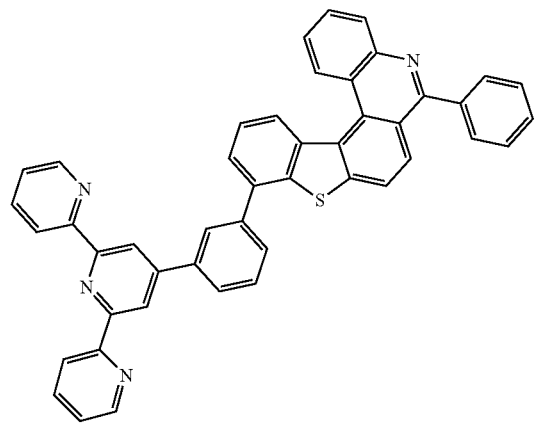
999 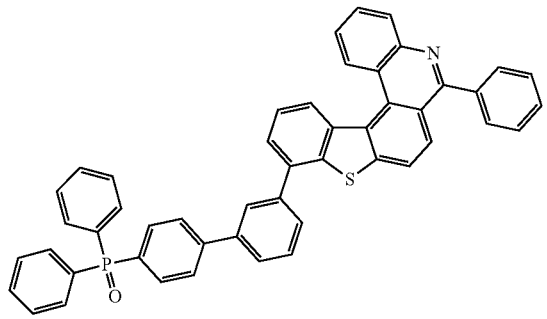
1000 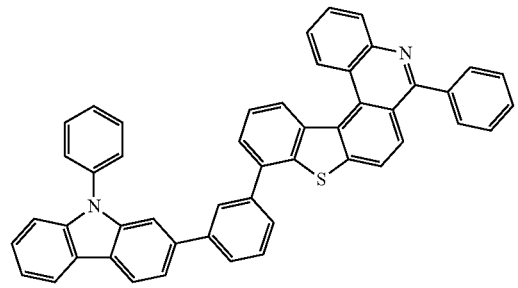

-continued
1001
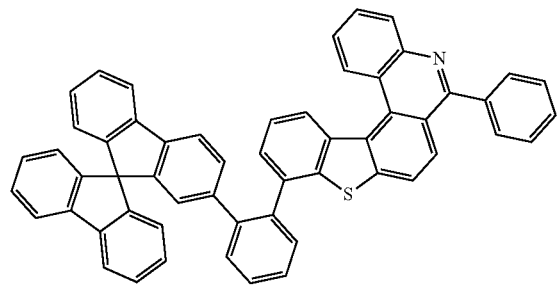
1002
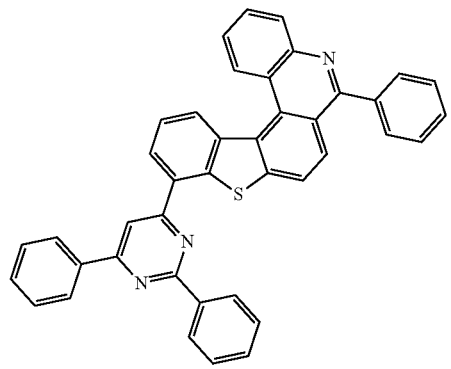
1003
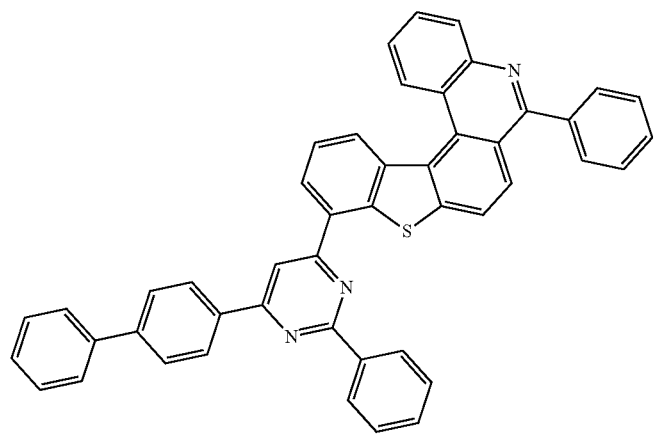
1004
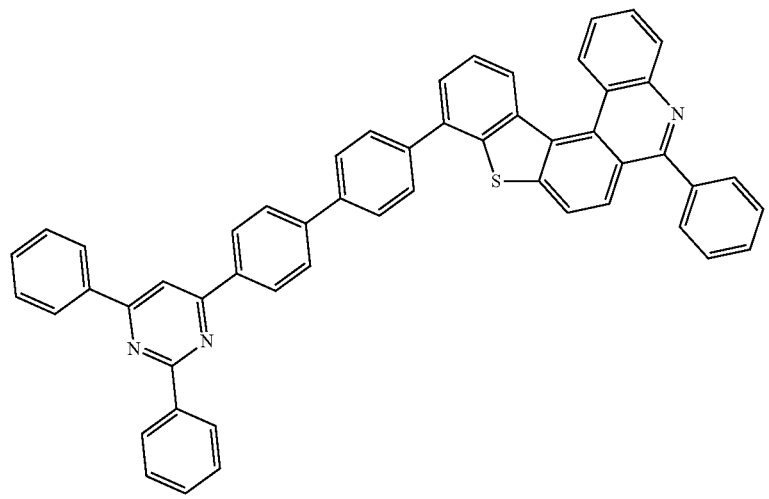

-continued
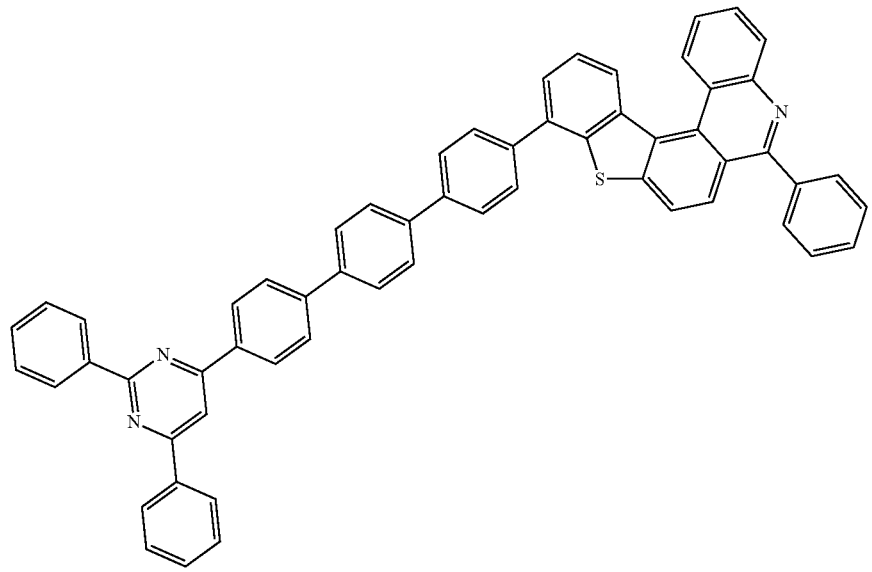
1005
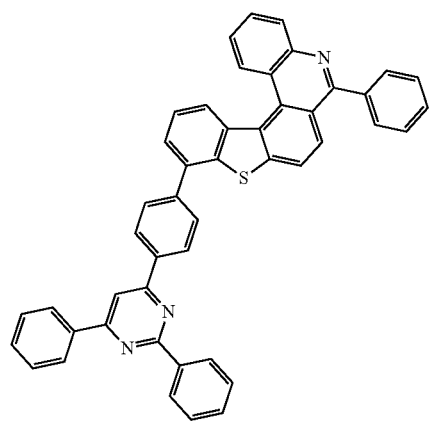
1006
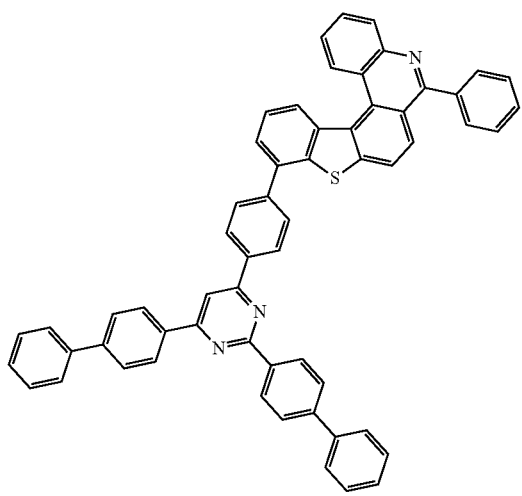
1007
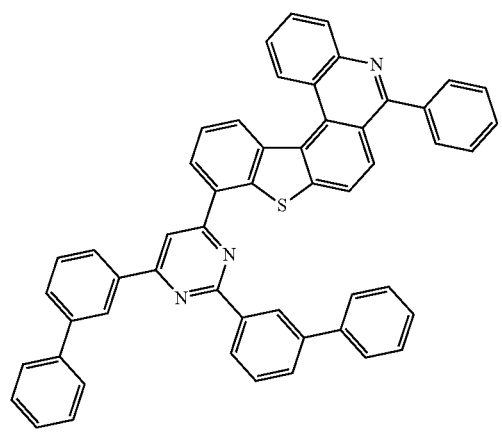
1008
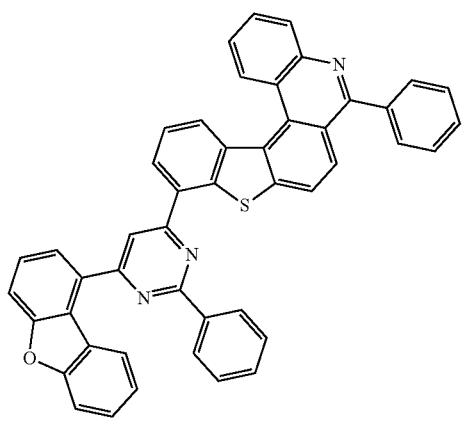
1009

-continued
1010
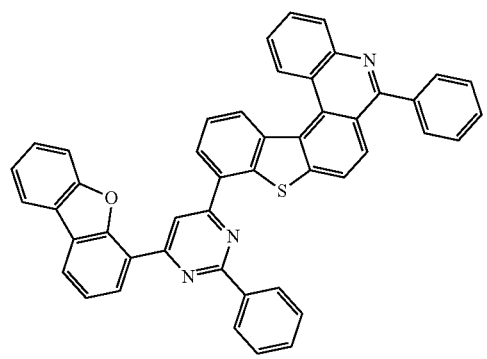
1011
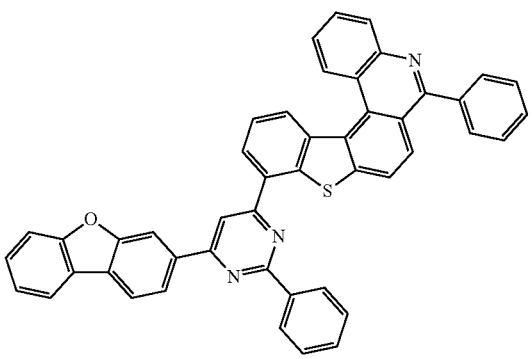
1012
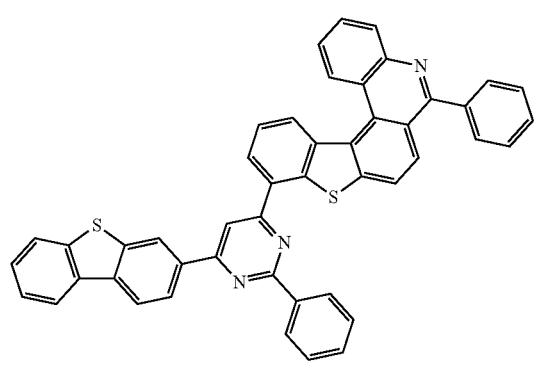
1013
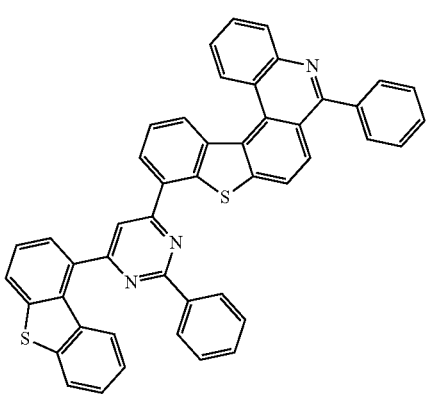
1014
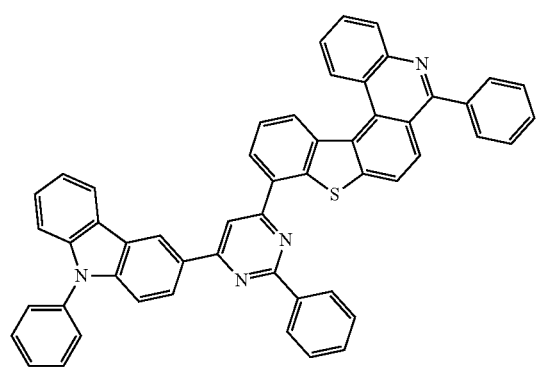
1015
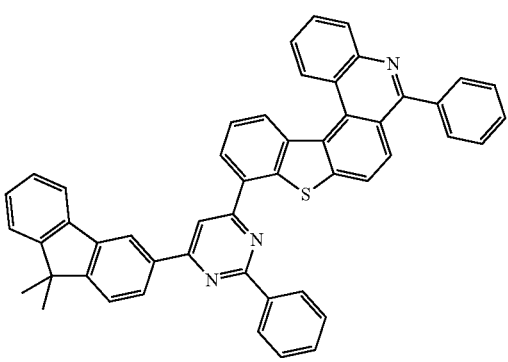

-continued
1016
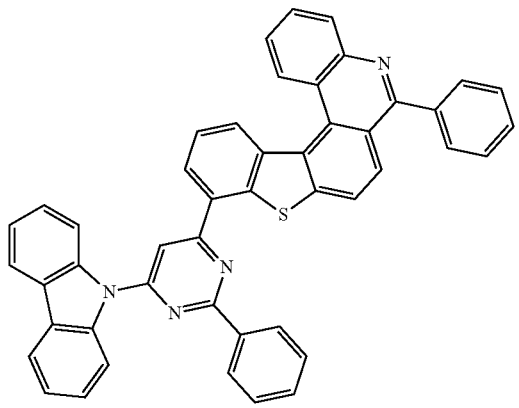
1017
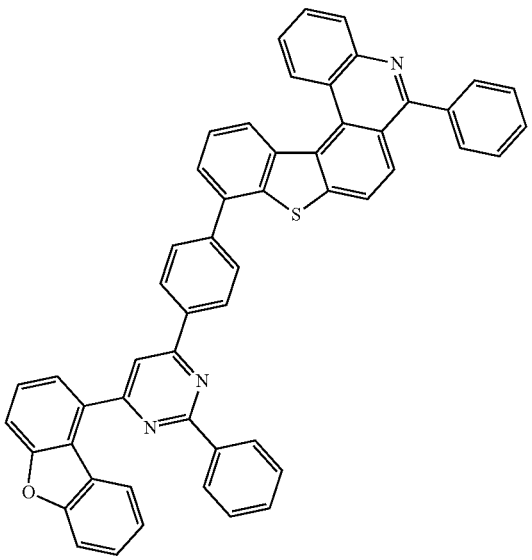
1018
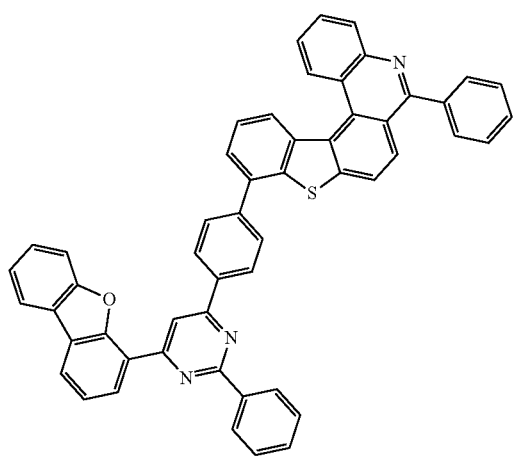
1019
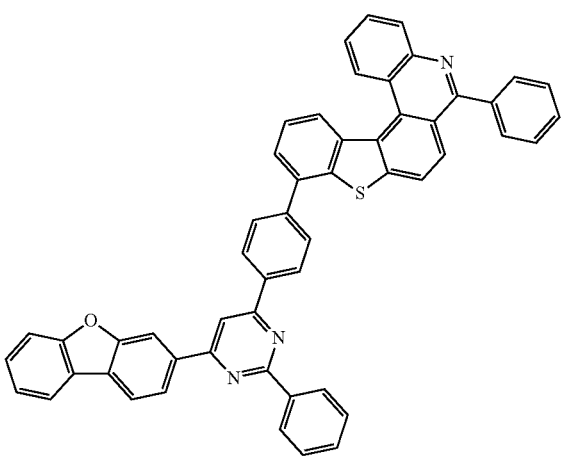
1020
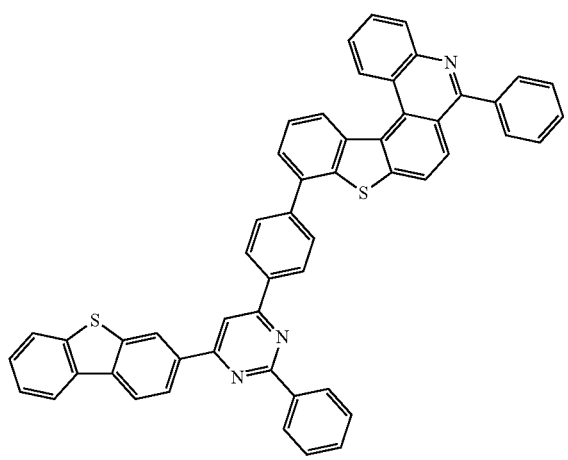
1021
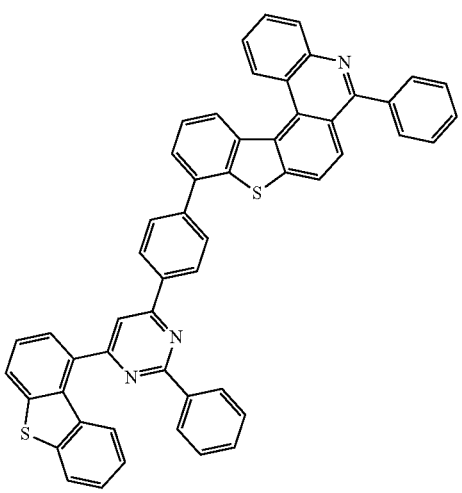

-continued
1022
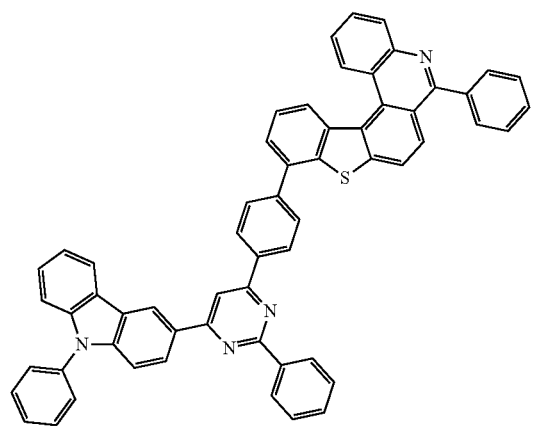
1023
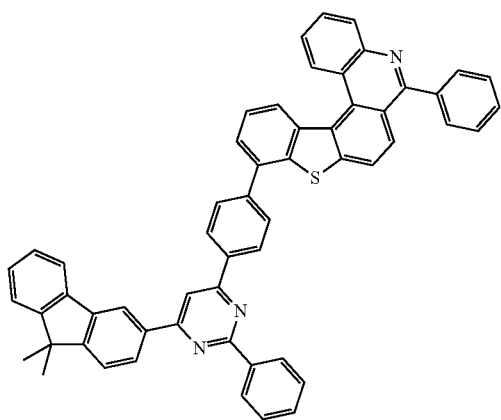
1024
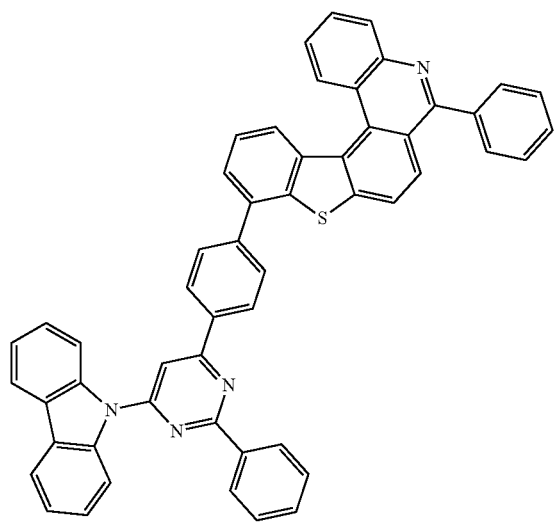
1025
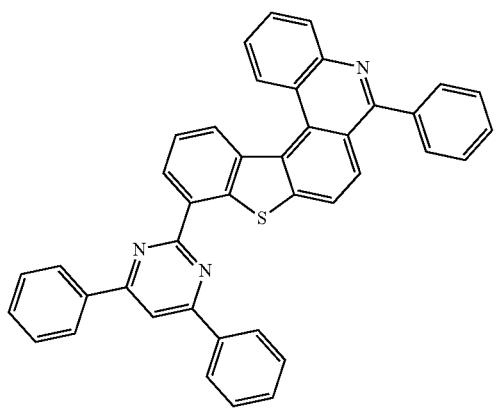
1026
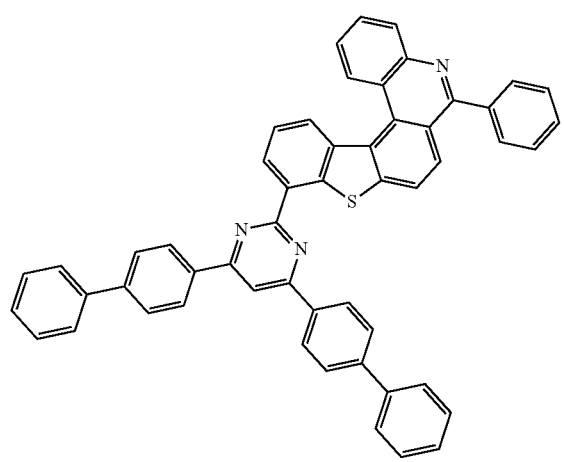
1027
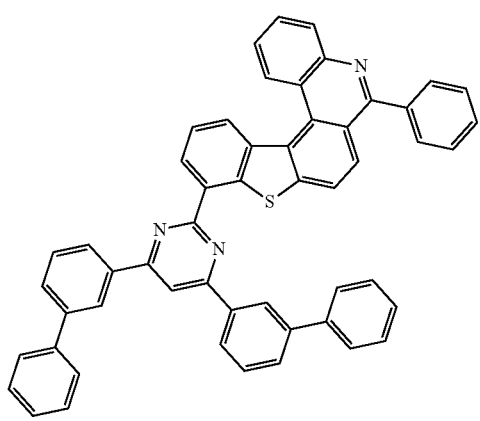

-continued
1028
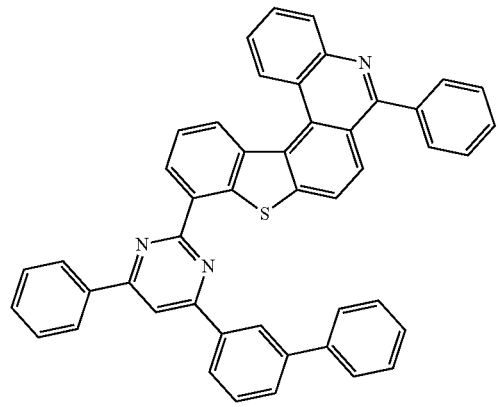
1029
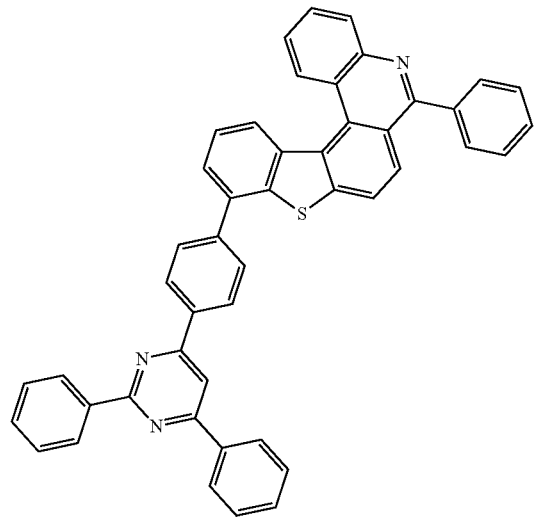
1030
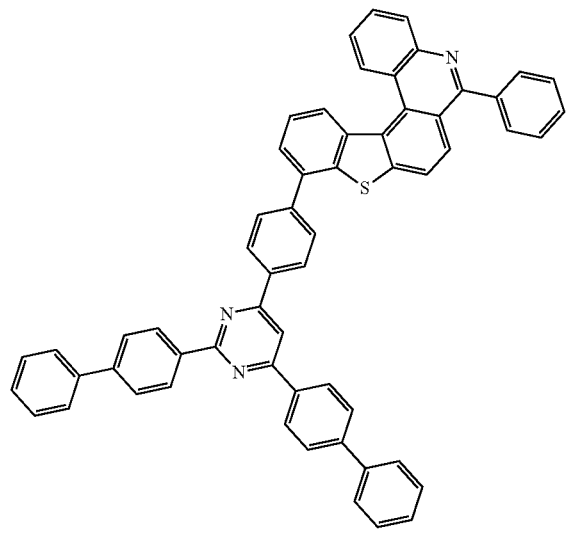
1031
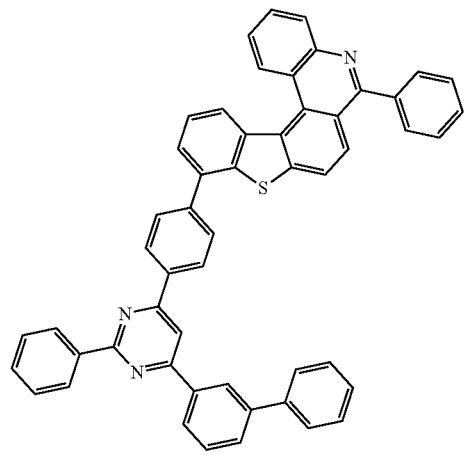
1032
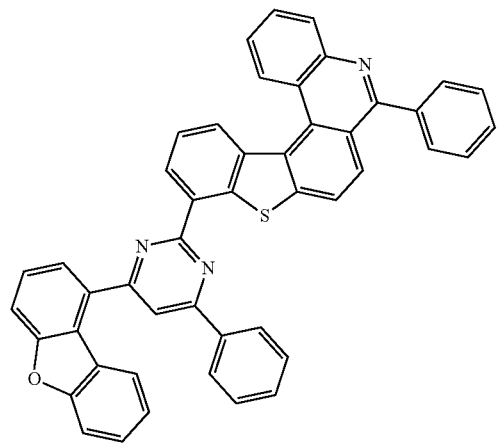
1033
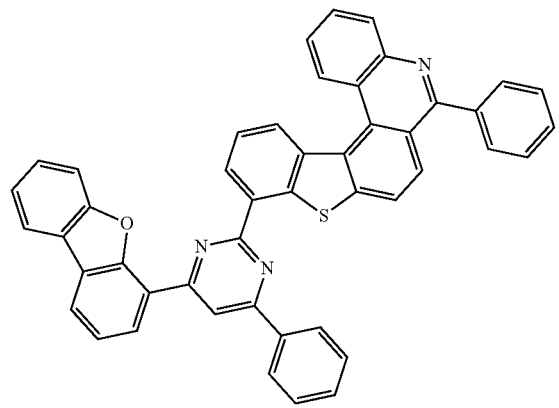

-continued
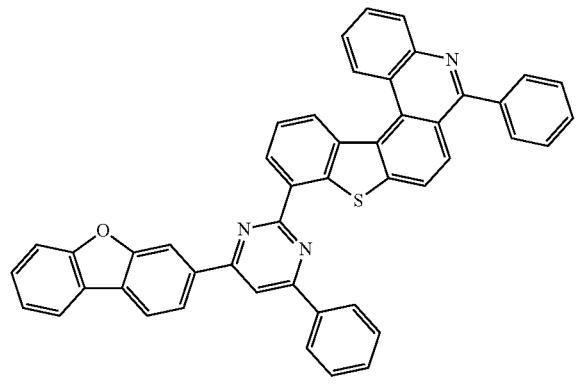
1034
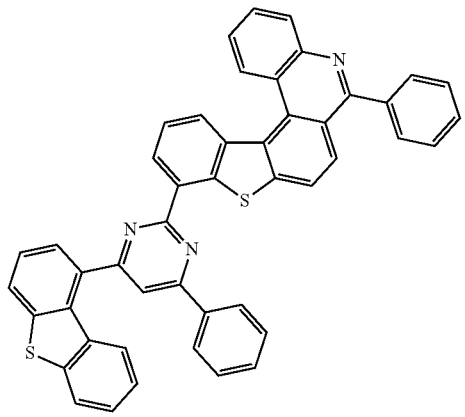
1035
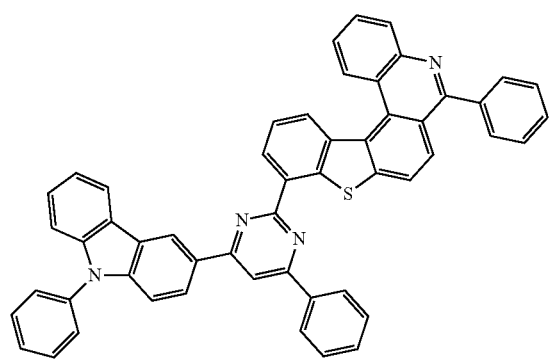
1036
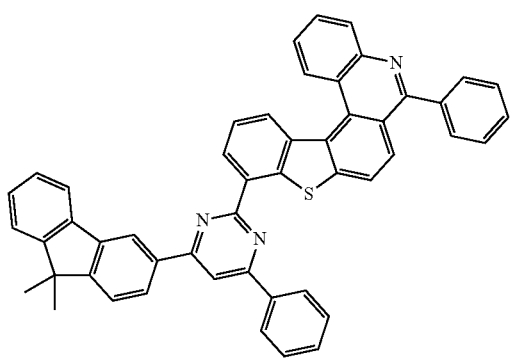
1037
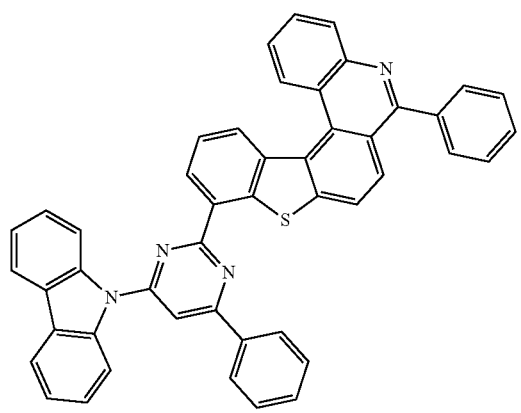
1038
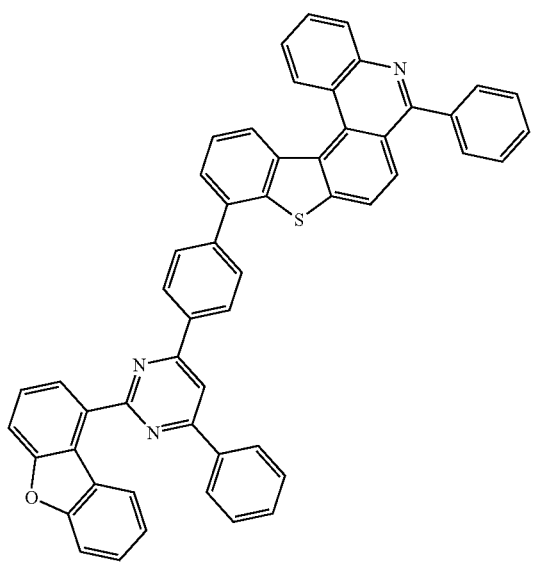
1039

-continued
1040
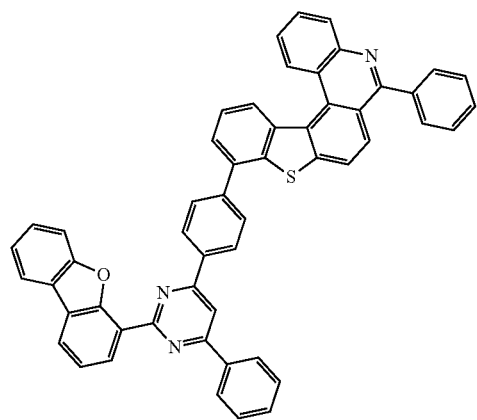
1041
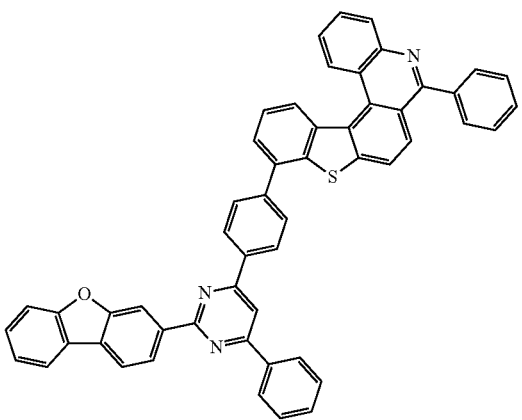
1042
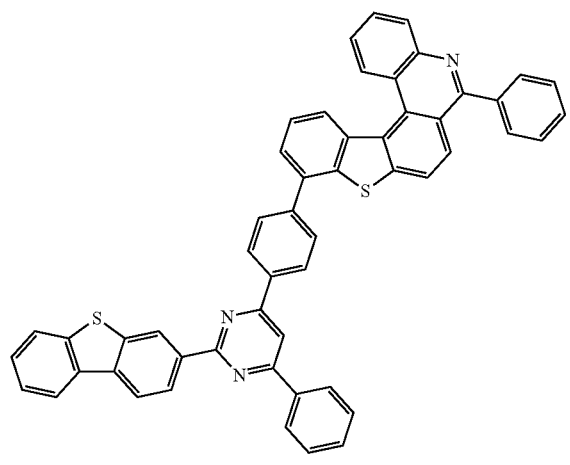
1043
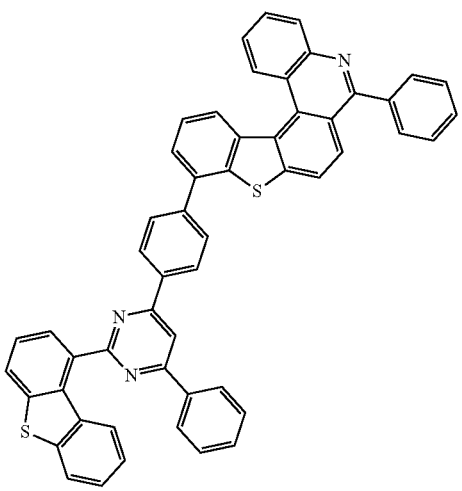
1044
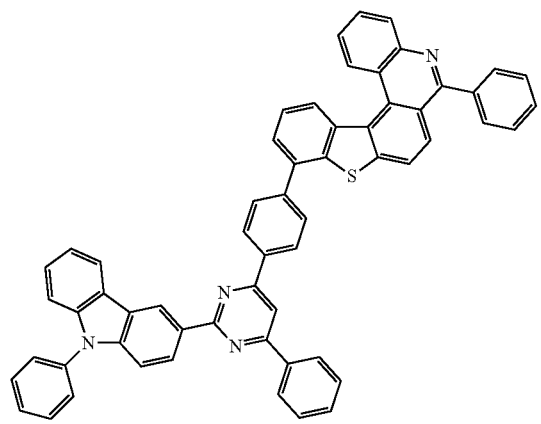
1045
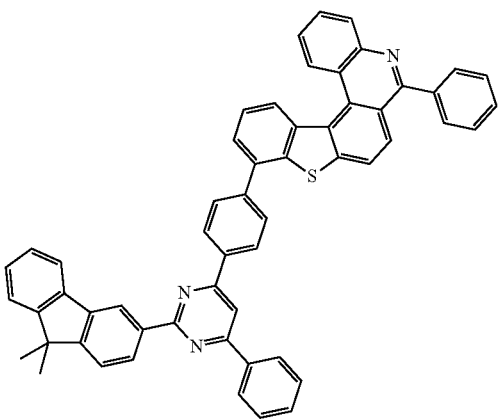

-continued
1046
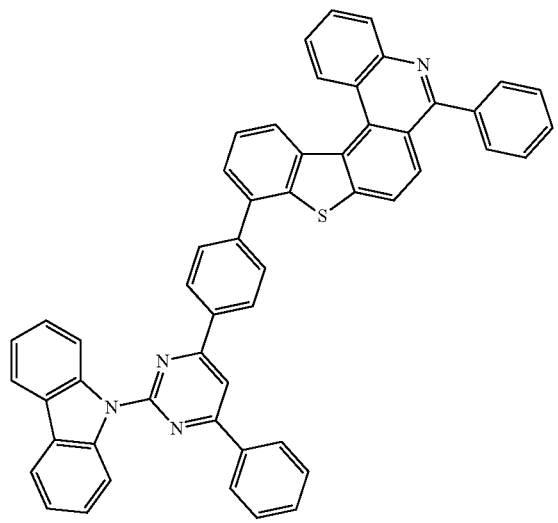
1047
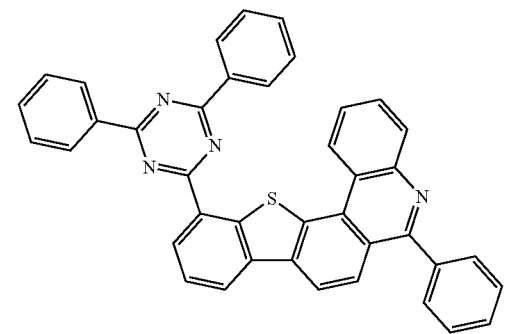
1048
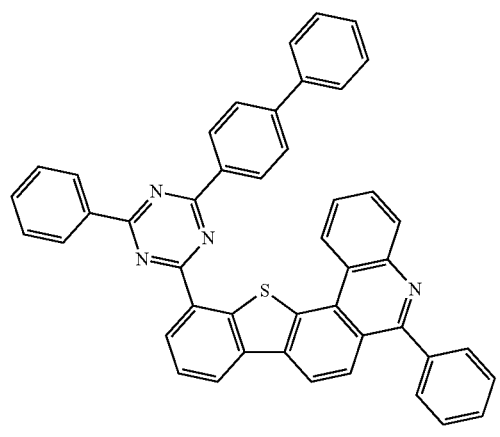
1049
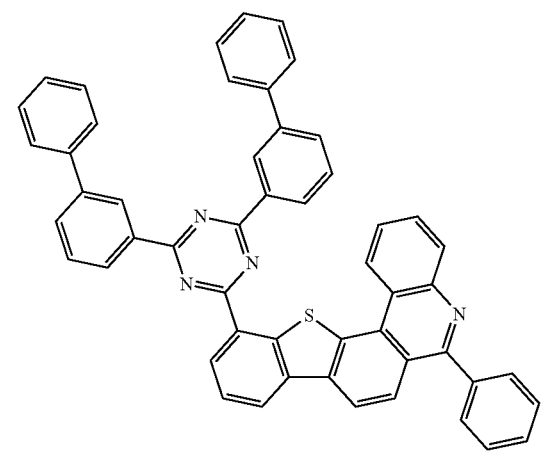
1050
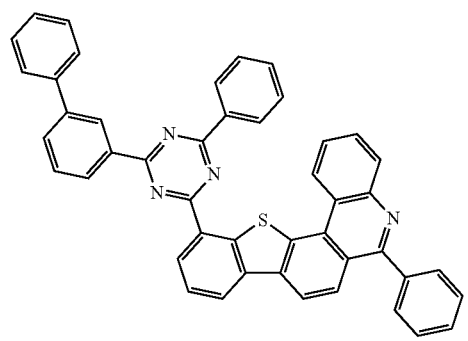
1051
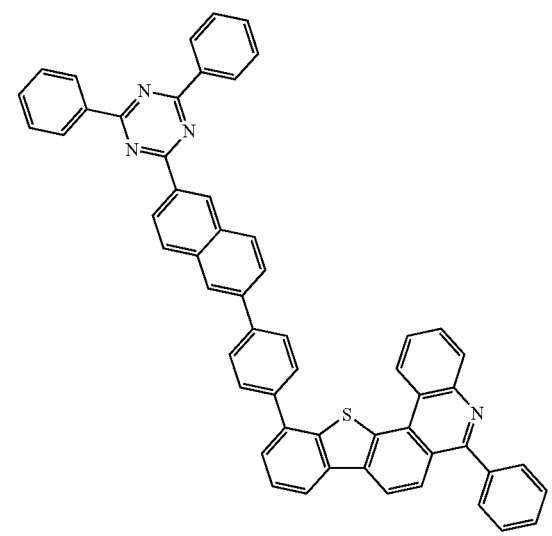

-continued
1052
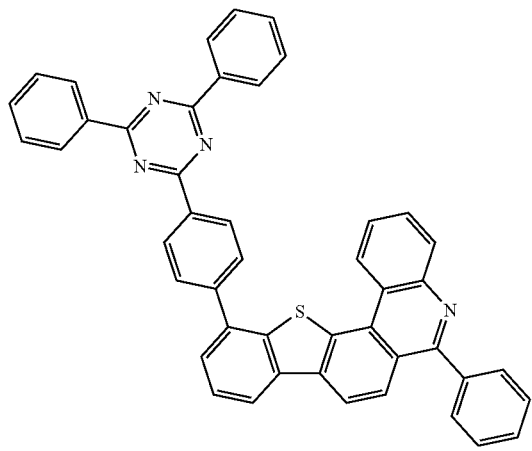
1053
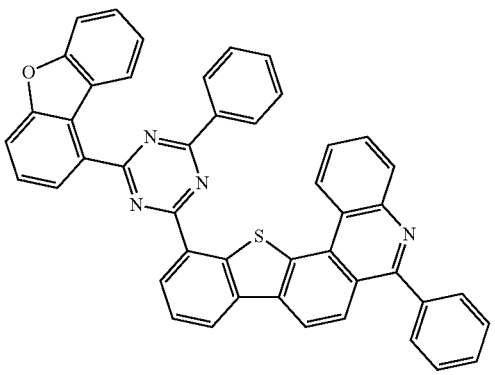
1054
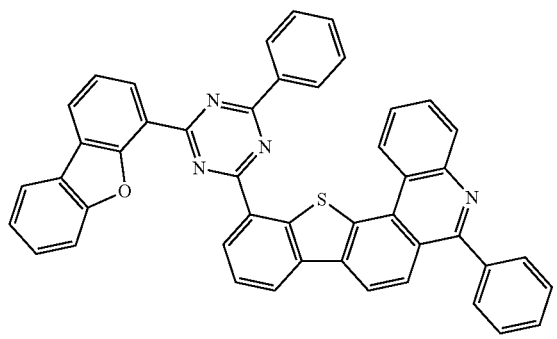
1055
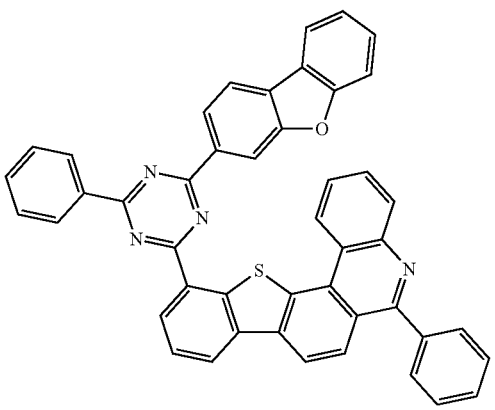
1056
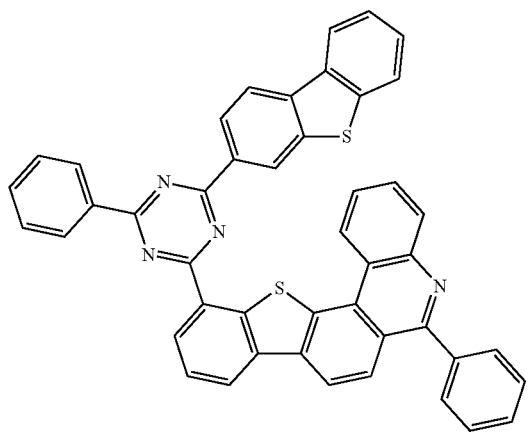
1057
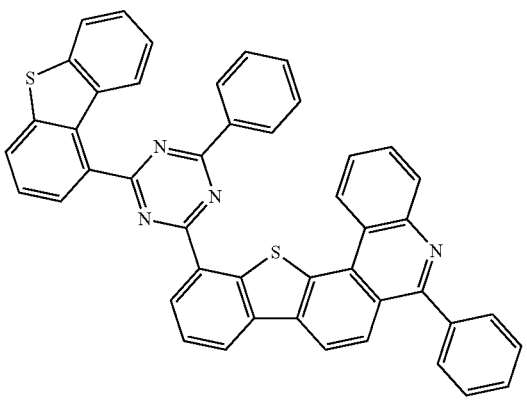

-continued
1058
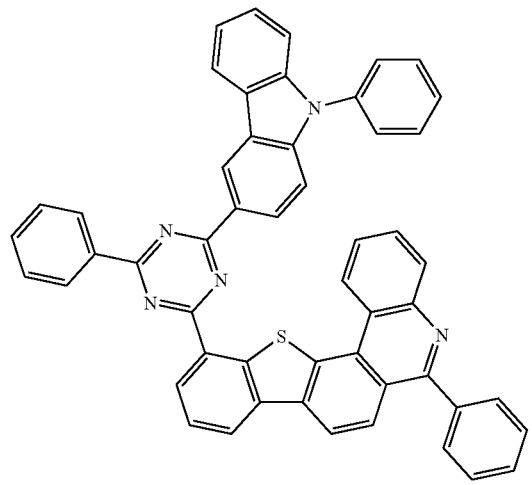
1059
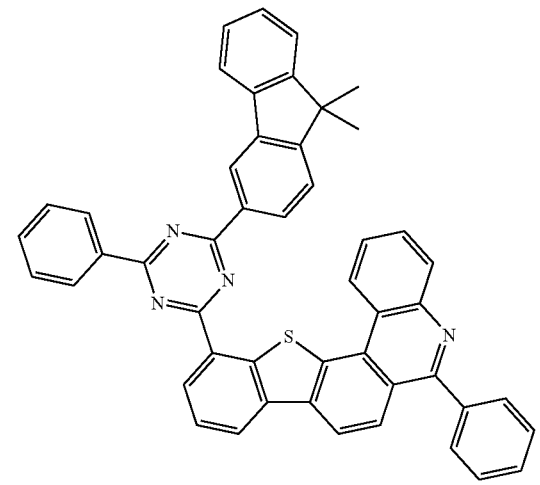
1060
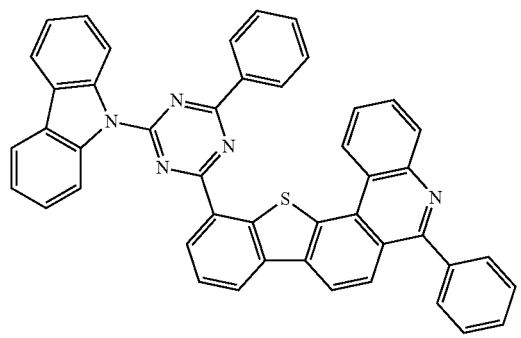
1061
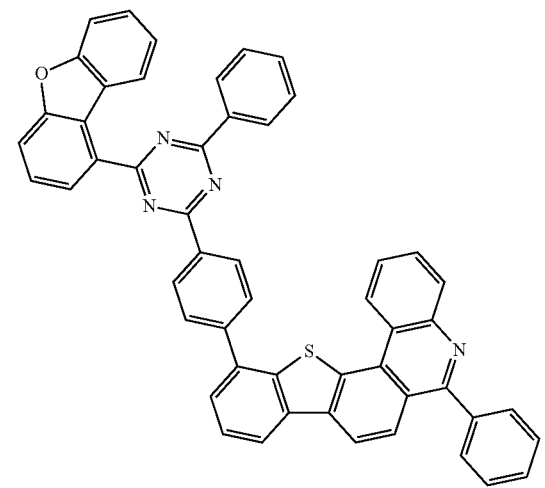
1062
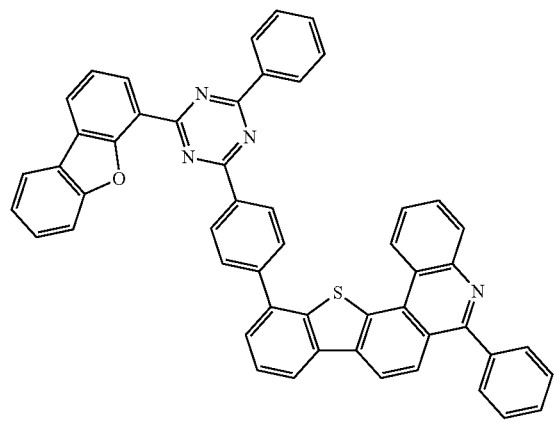
1063
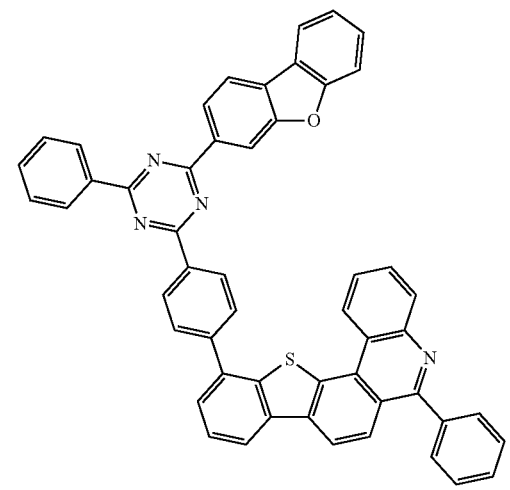

-continued
1064
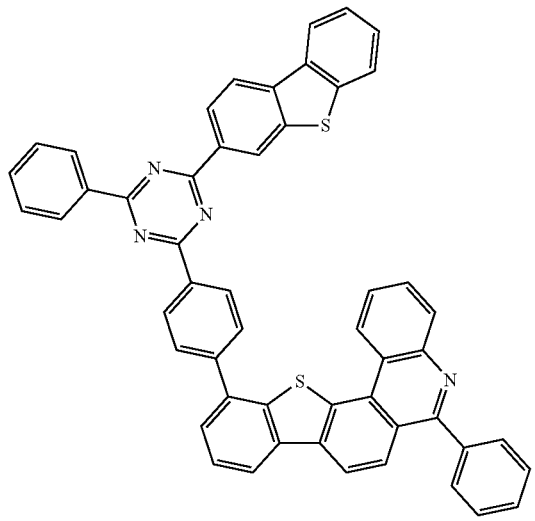
1065
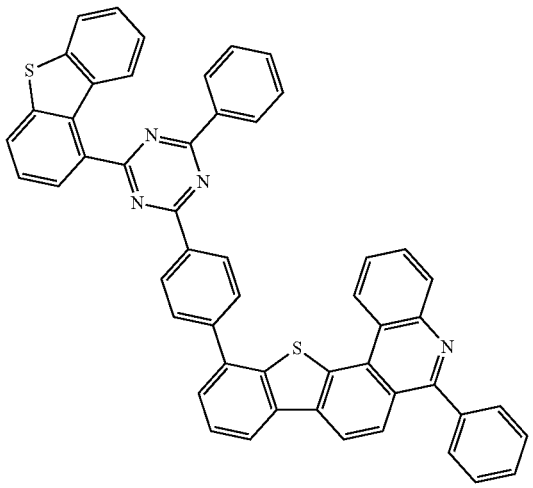
1066
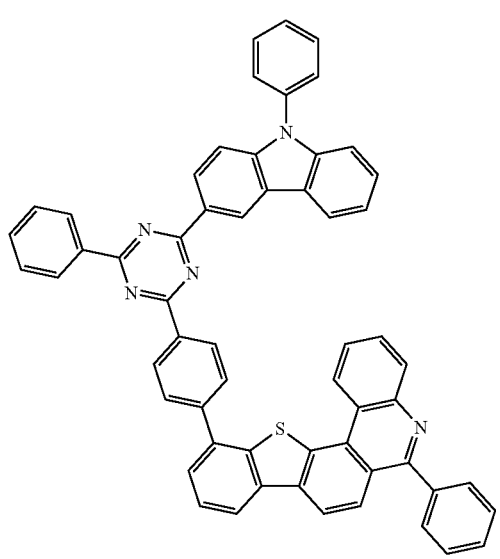
1067
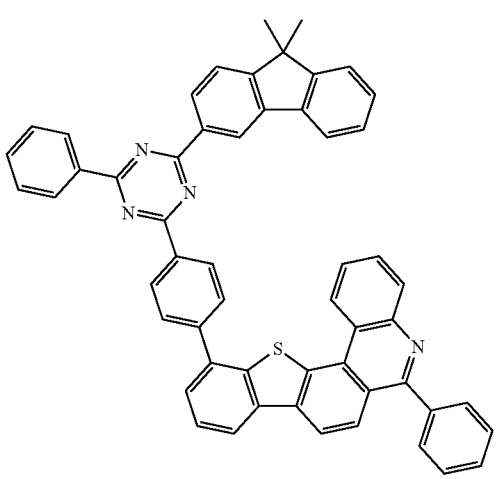
1068
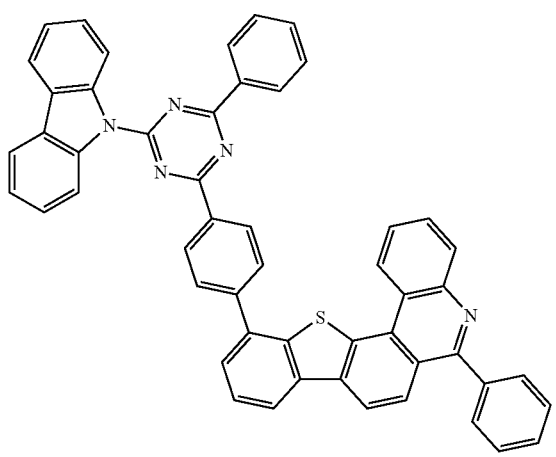
1069
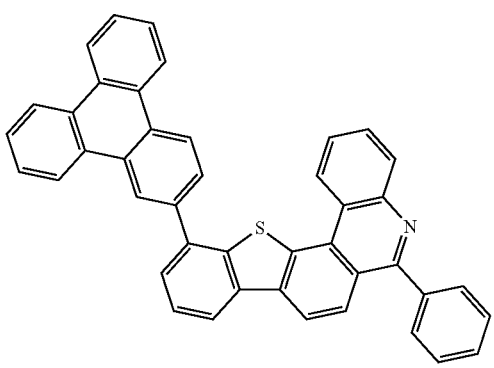

-continued
1070
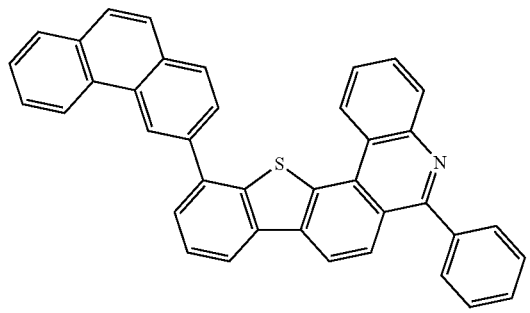
1071
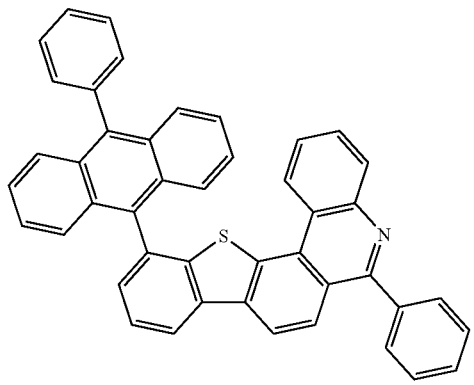
1072
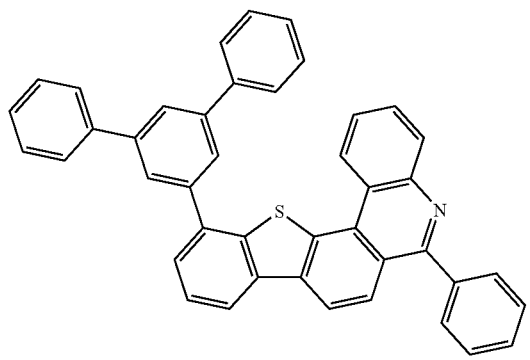
1073
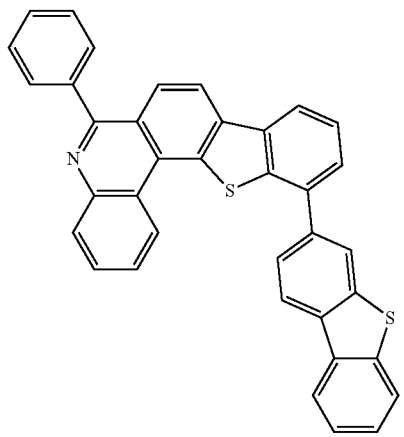
1074
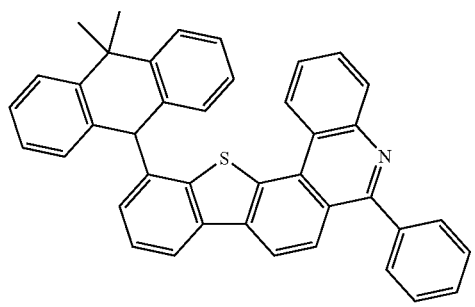
1075
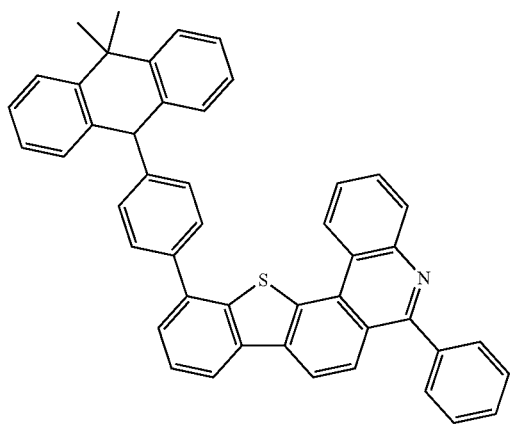

-continued
1076
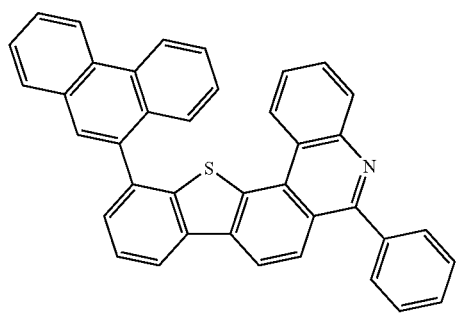
1077
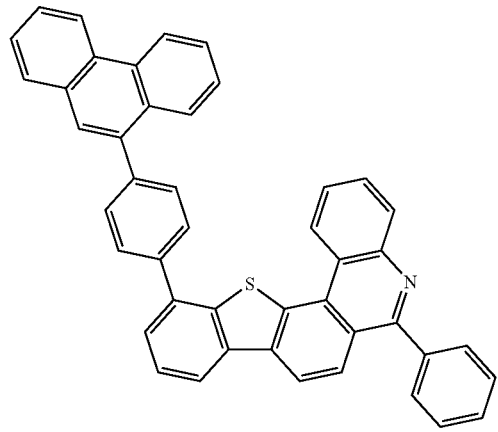
1078
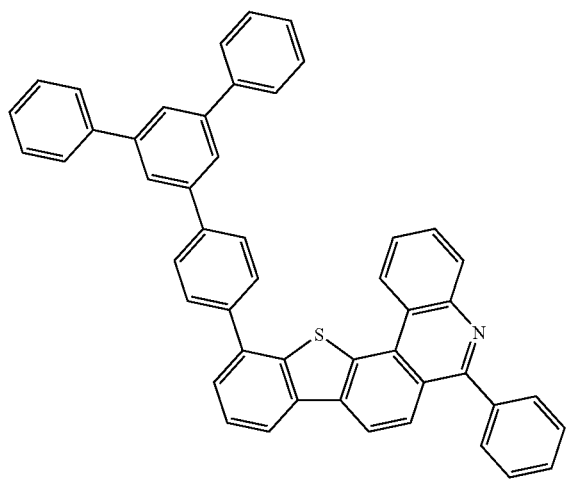
1079
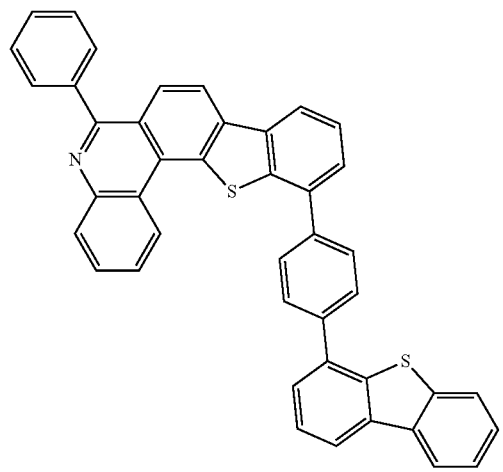
1080
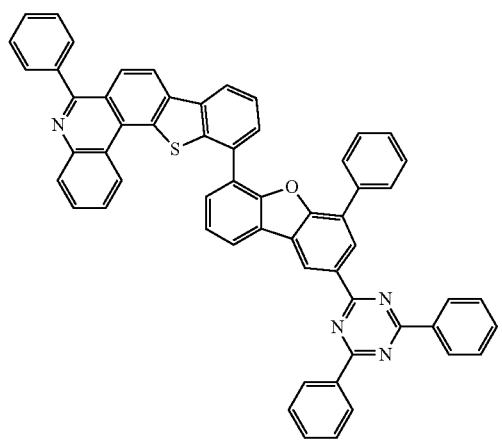
1081
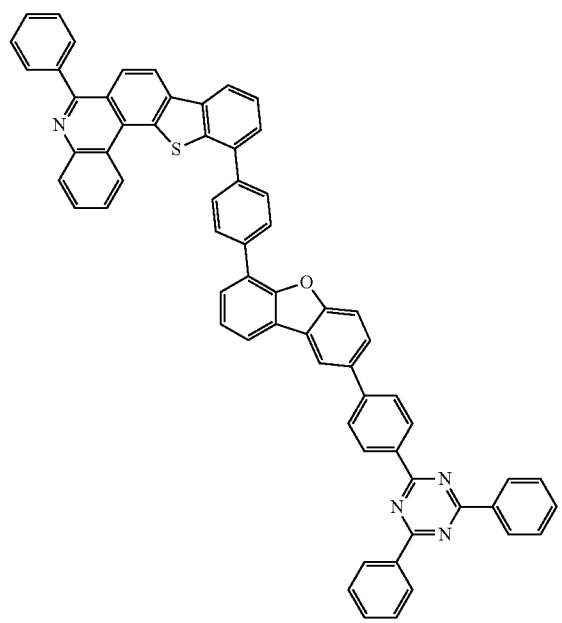

-continued
| 1082 | 1083 |
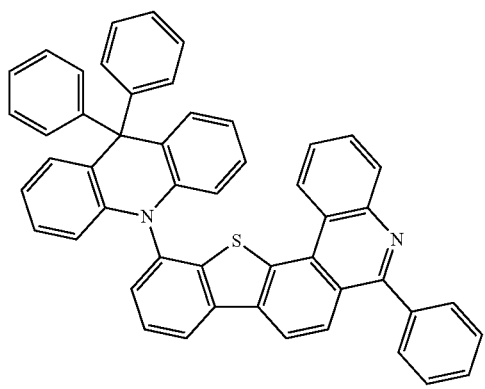
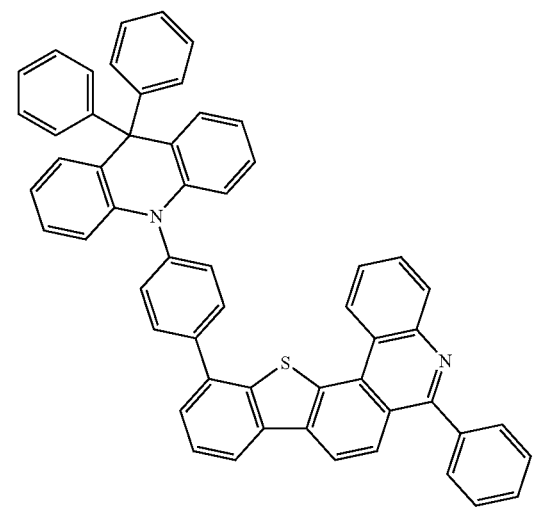
| 1084 | 1085 |
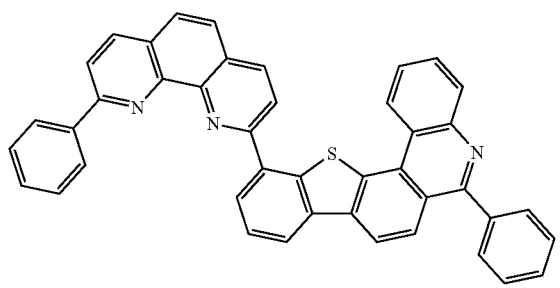
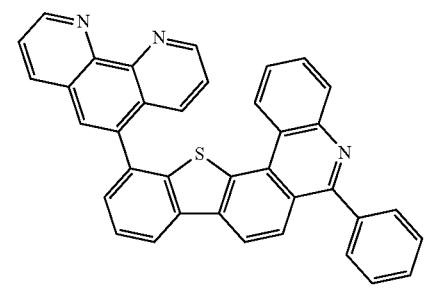
| 1086 | 1087 |
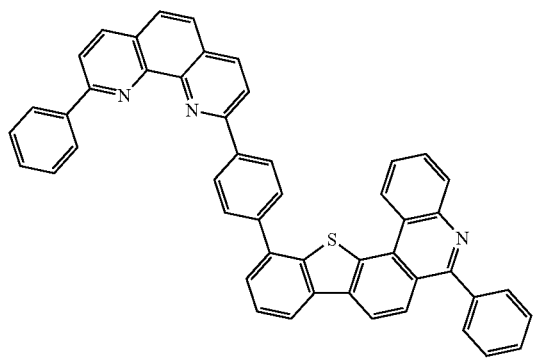
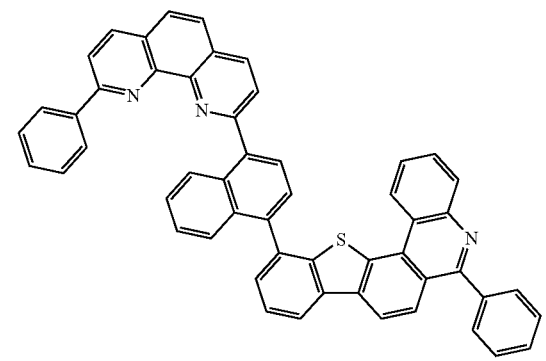
| 1088 | 1089 |
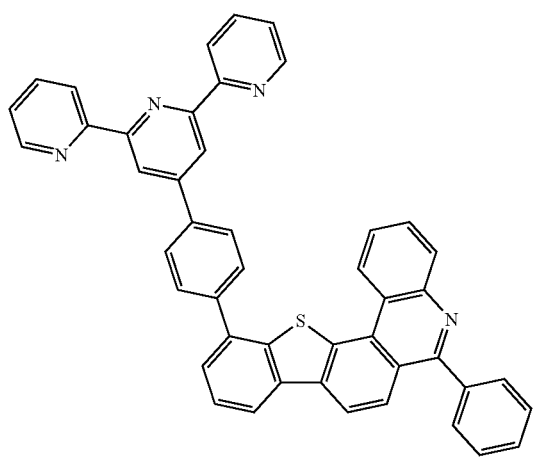
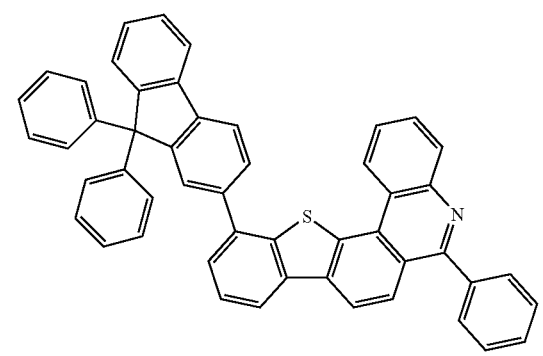

-continued
1090
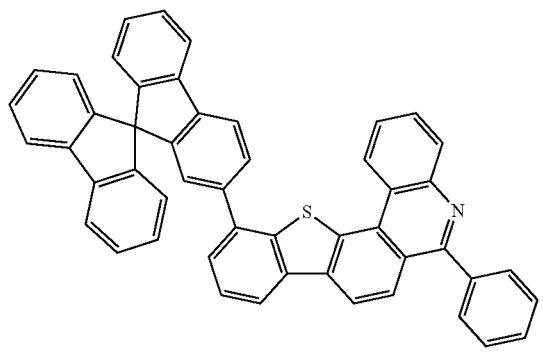
1091
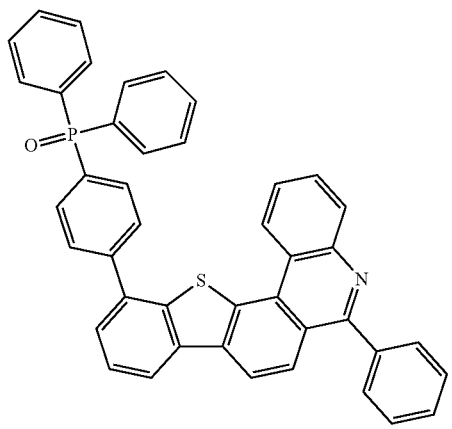
1092
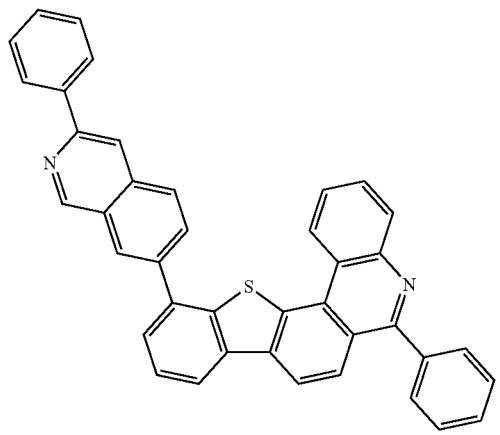
1093
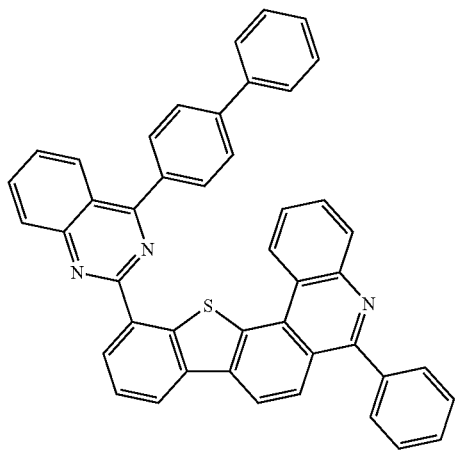
1094
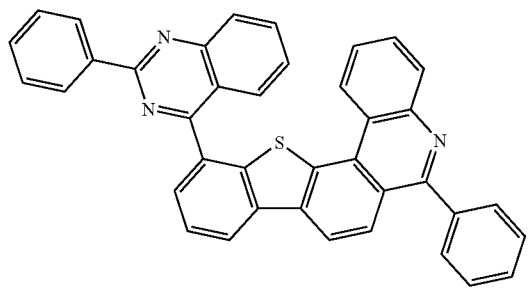
1095
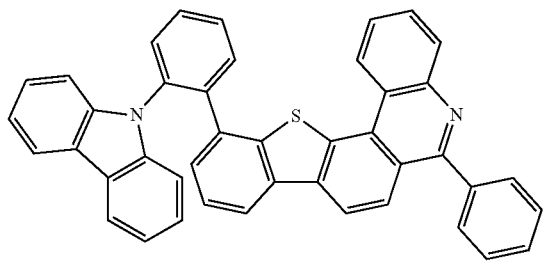
1096
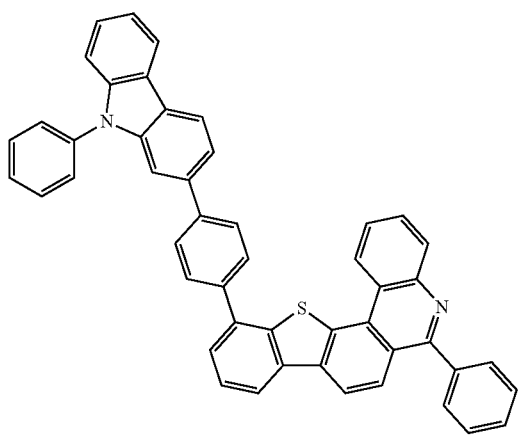
1907
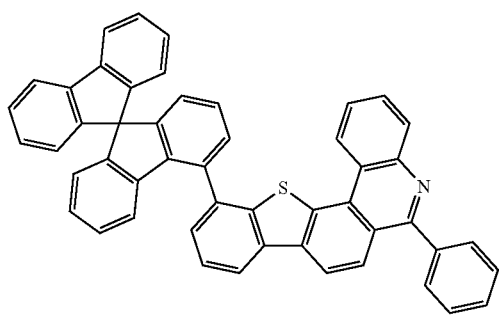

-continued
1098
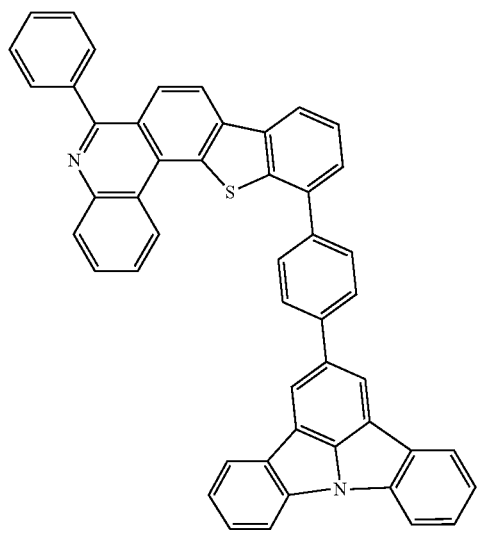
1099
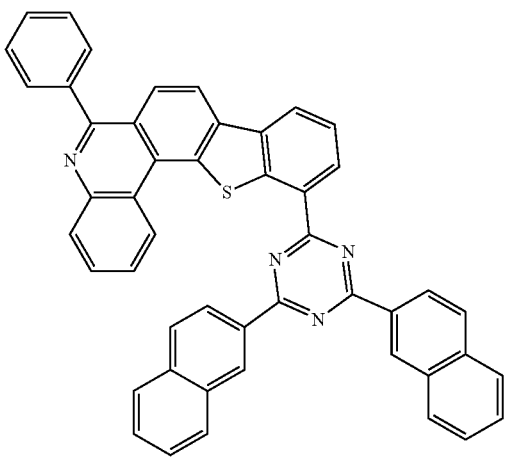
1100
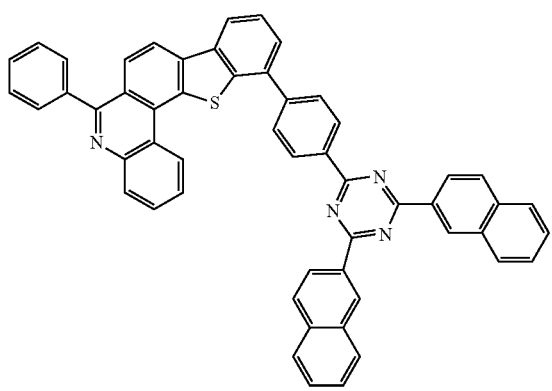
1101
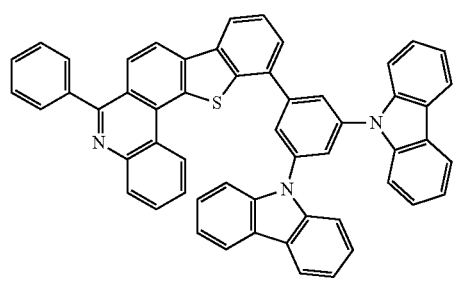
1102
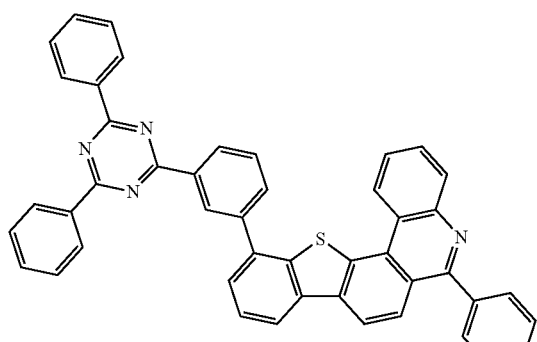
1103
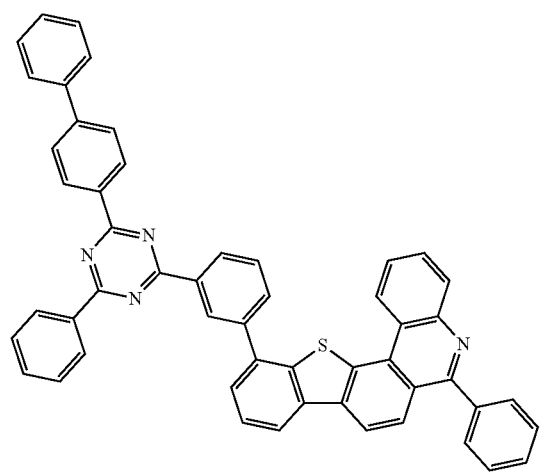

-continued
1104
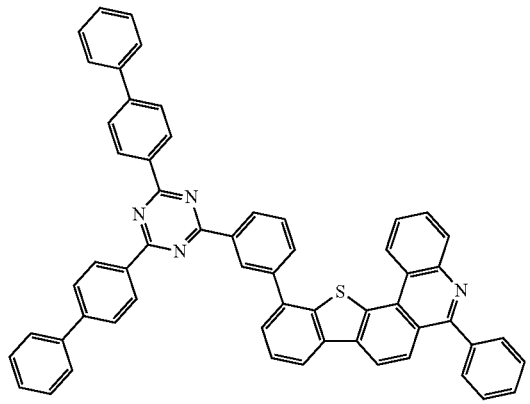
1105
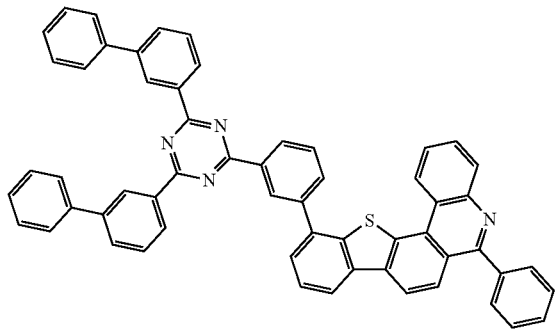
1106
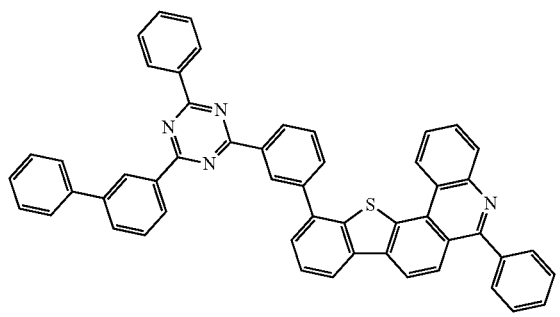
1107
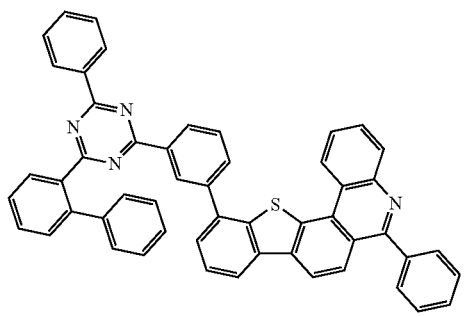
1108
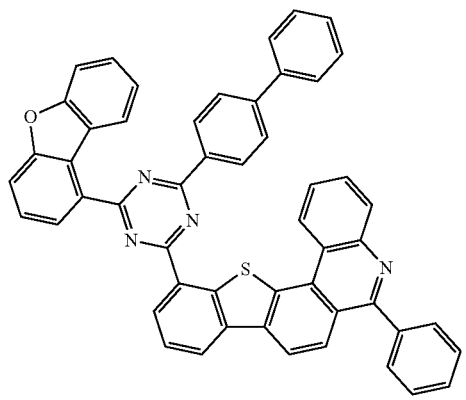
1109
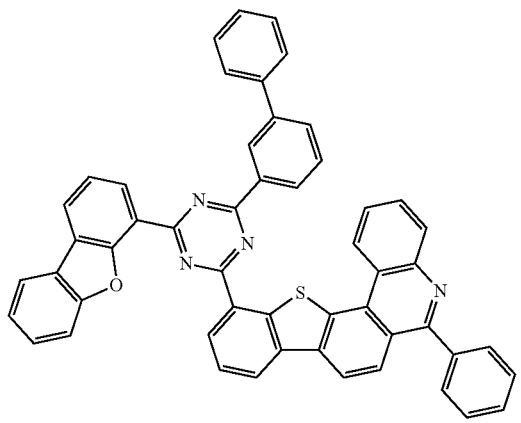
1110
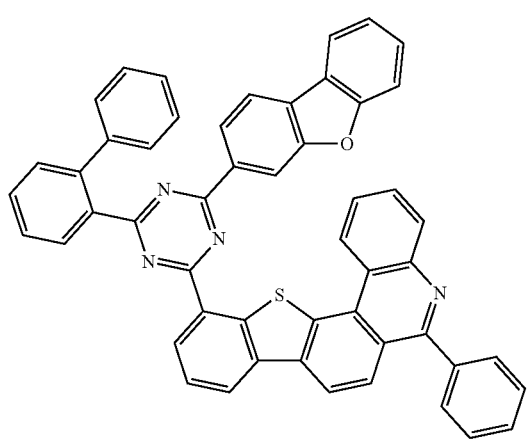
1111
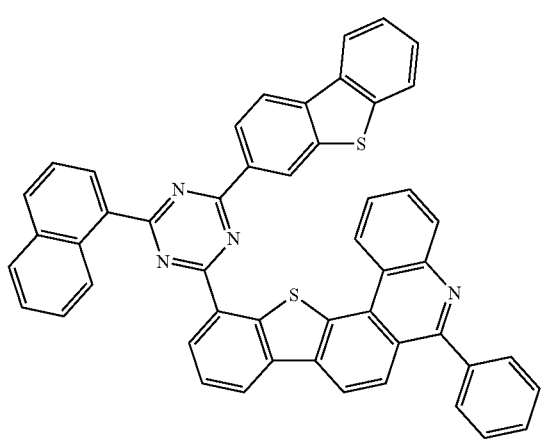

-continued
| 1112 | 1113 |
|---|---|
| 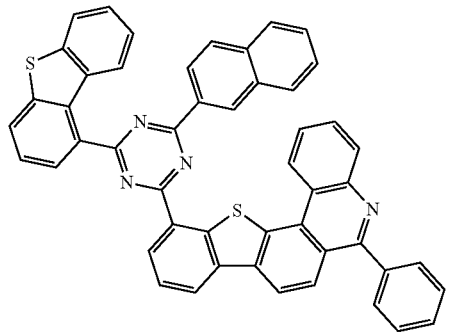 | 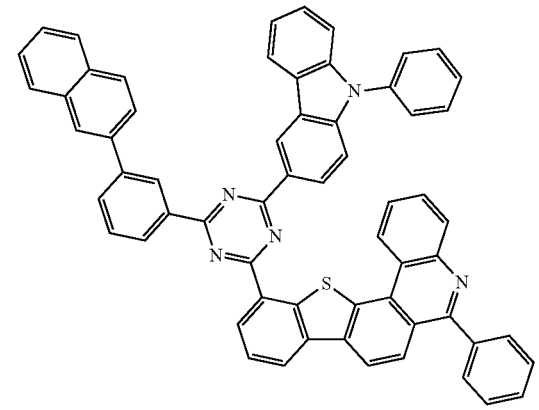 |
| 1114 | 1115 |
| 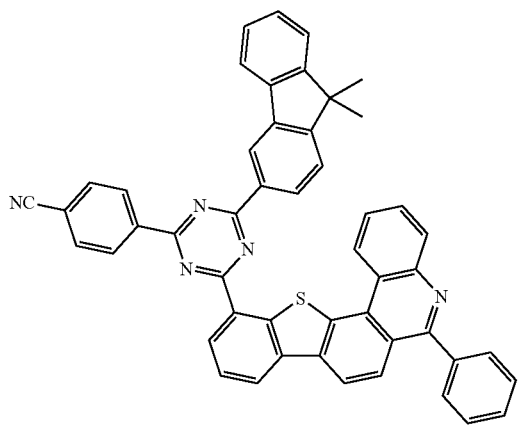 | 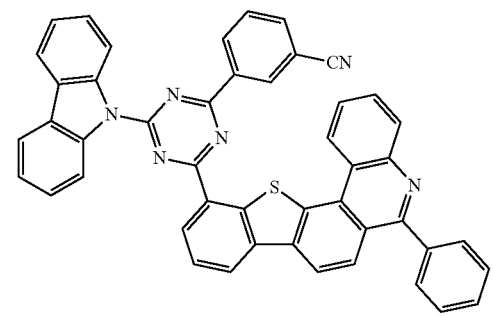 |
| 1116 | 1117 |
| 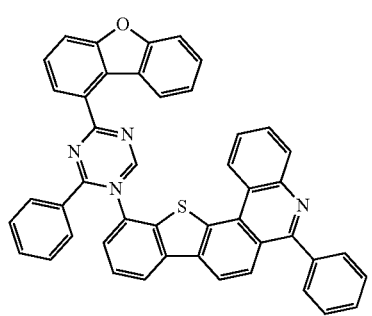 | 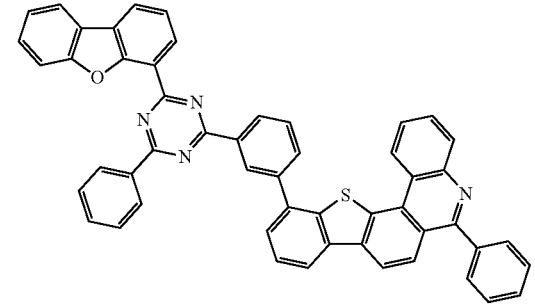 |
| 1118 | 1119 |
| 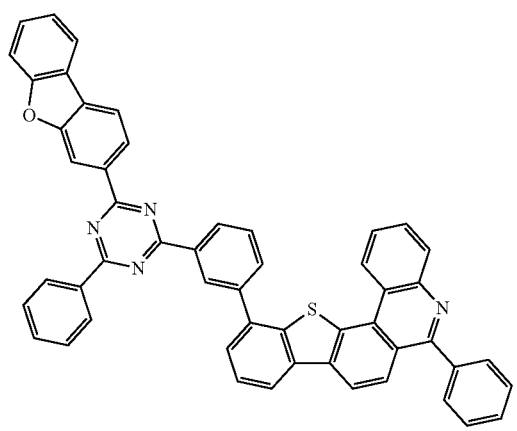 | 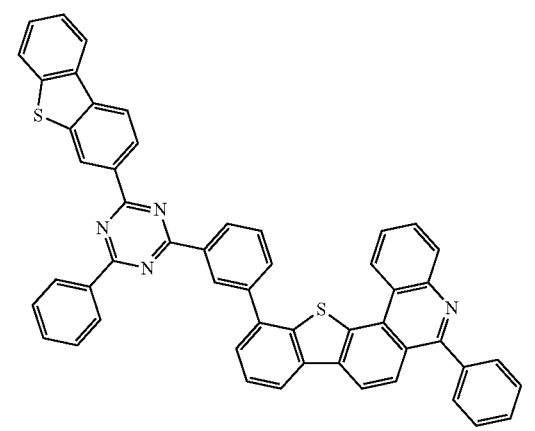 |

-continued
1120
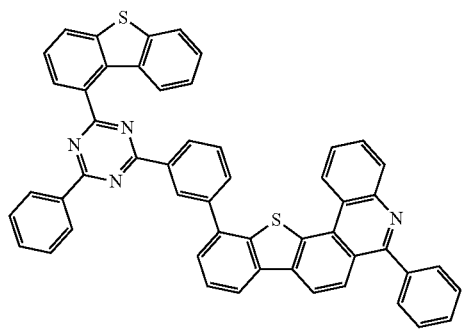
1121
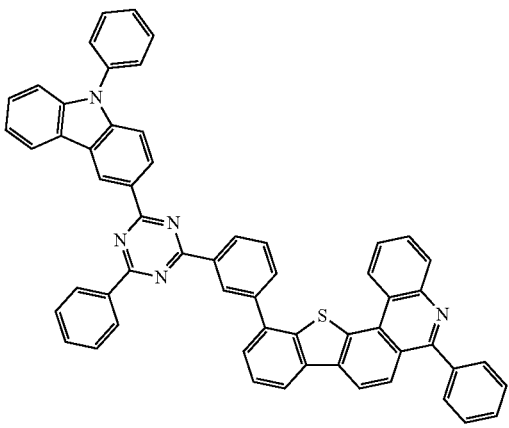
1122
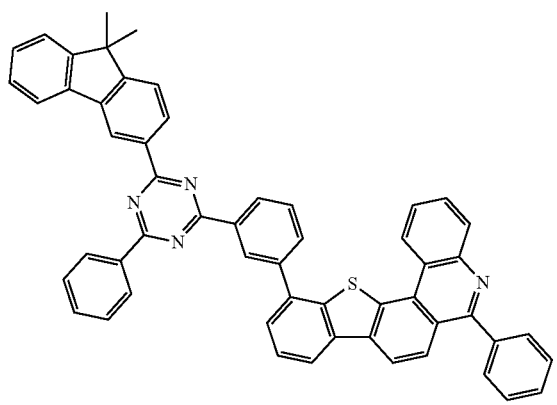
1123
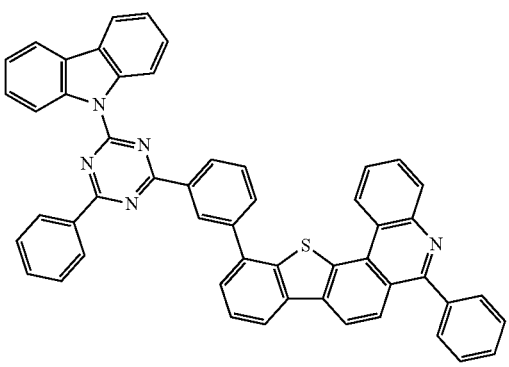
1124
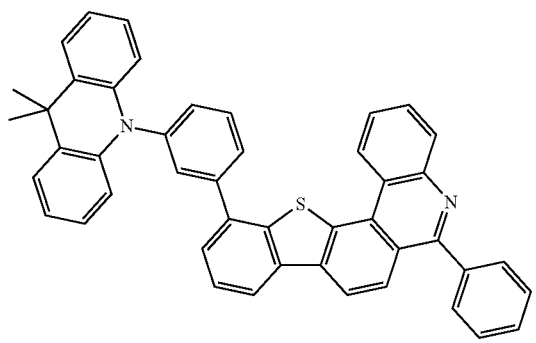
1125
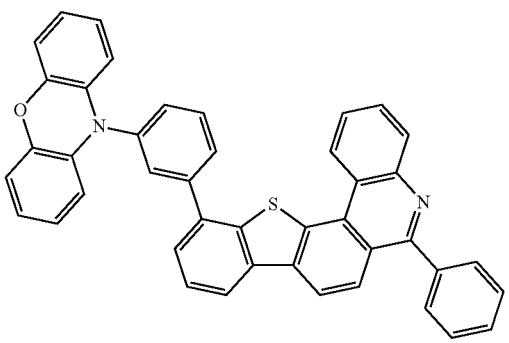
1126
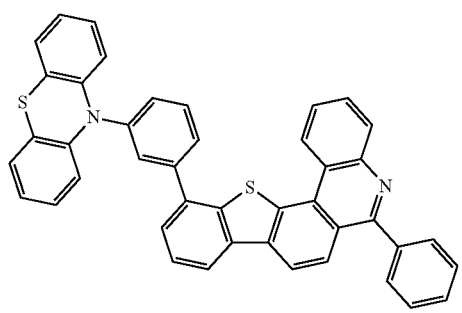
1127
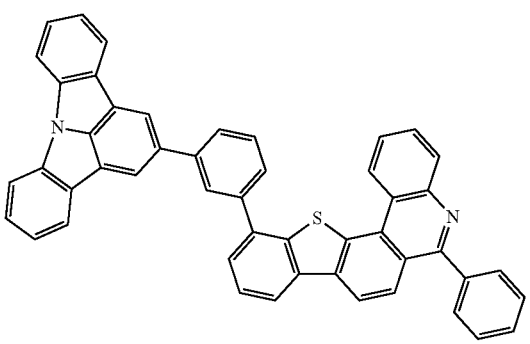

-continued
1128
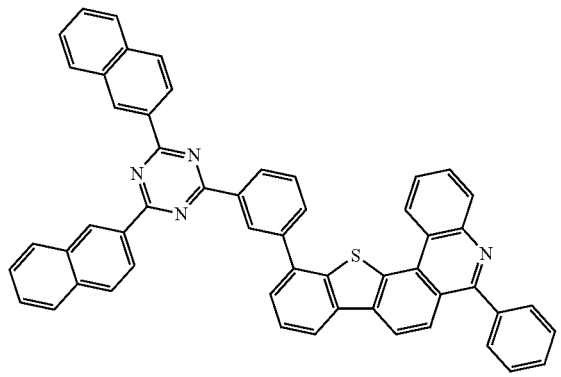
1129
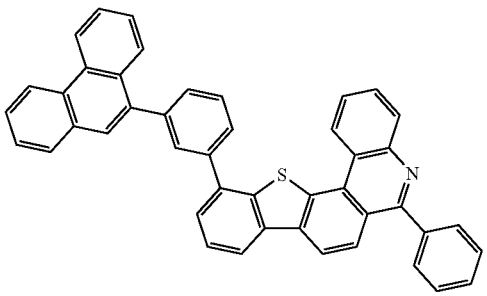
1130
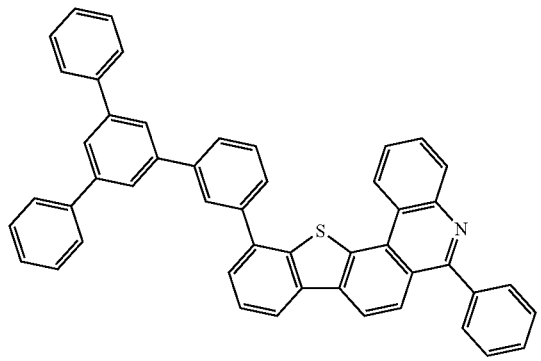
1131
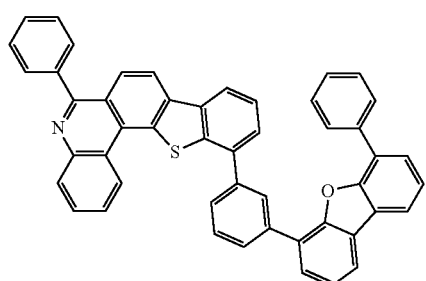
1132
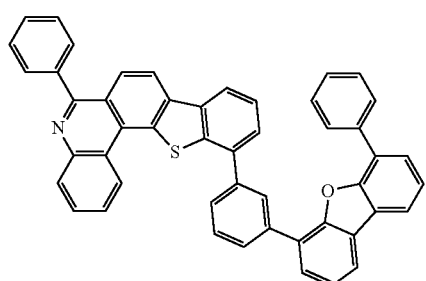
1133
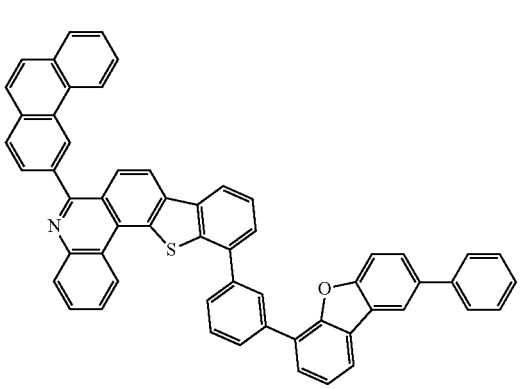
1134
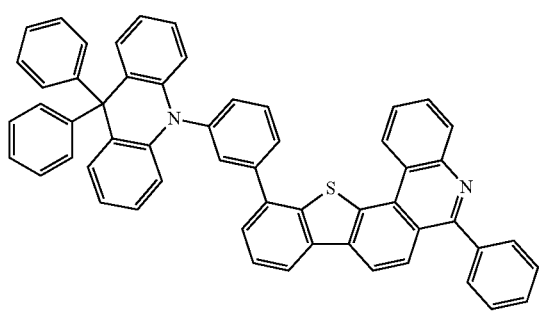
1135
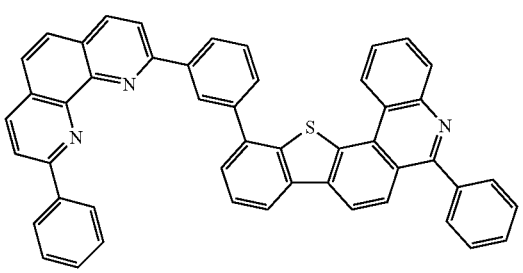

-continued
| | |
|---|---|
| 1136 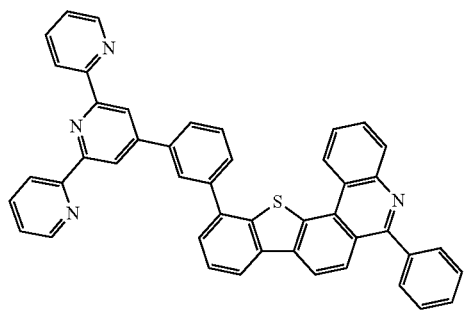 | 1137 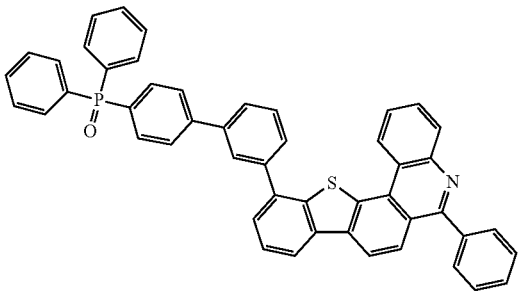 |
| 1138 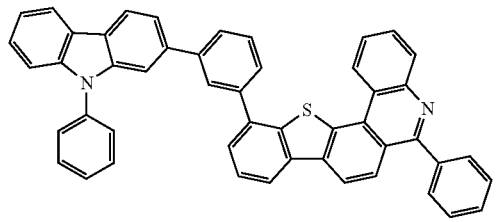 | 1139 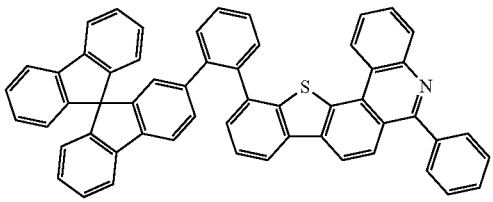 |
| 1140 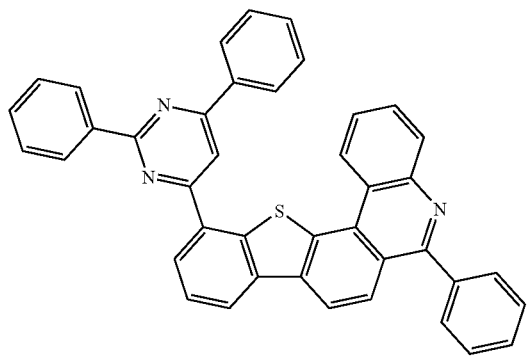 | 1141 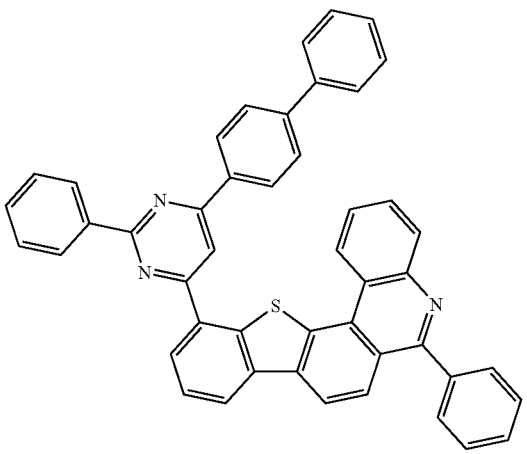 |
| 1142 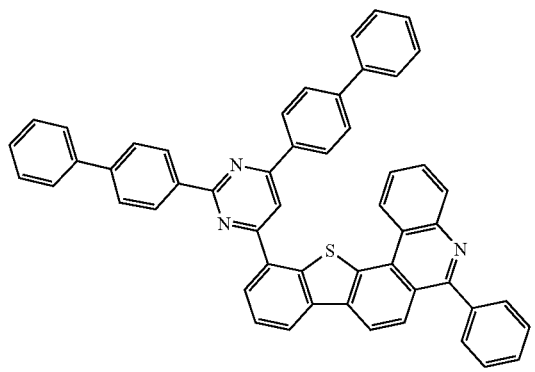 | 1143 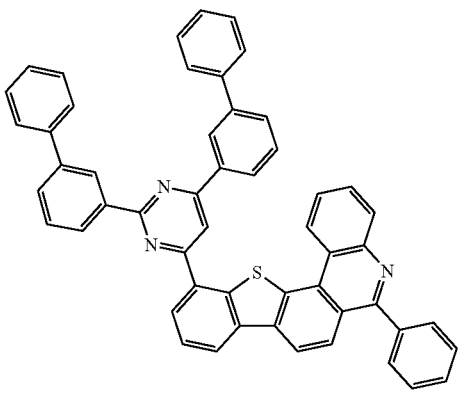 |

-continued
1144
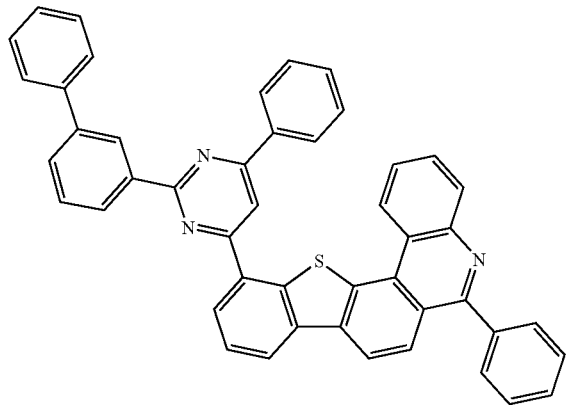
1145
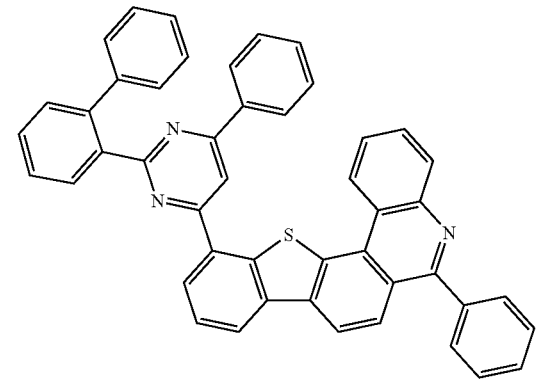
1146
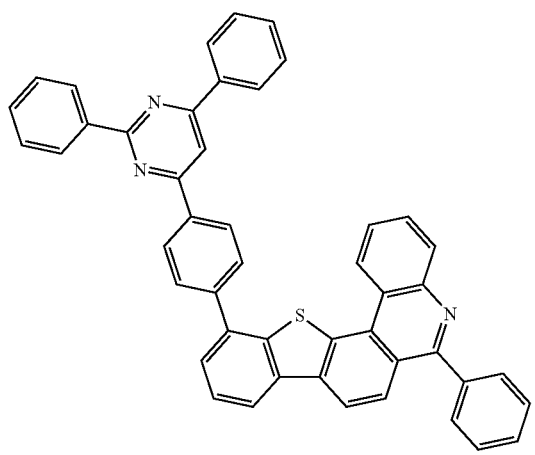
1147
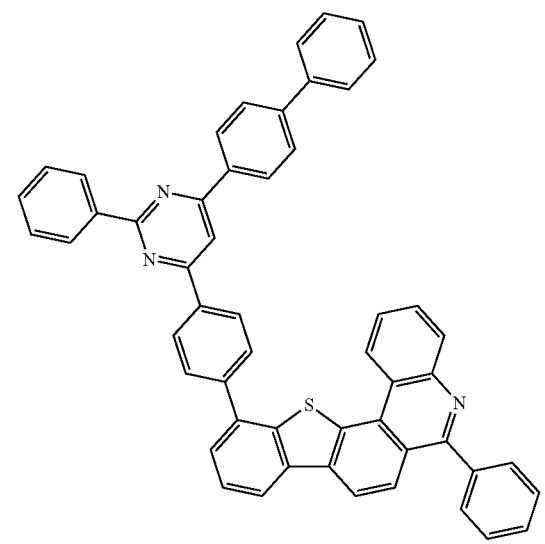
1148
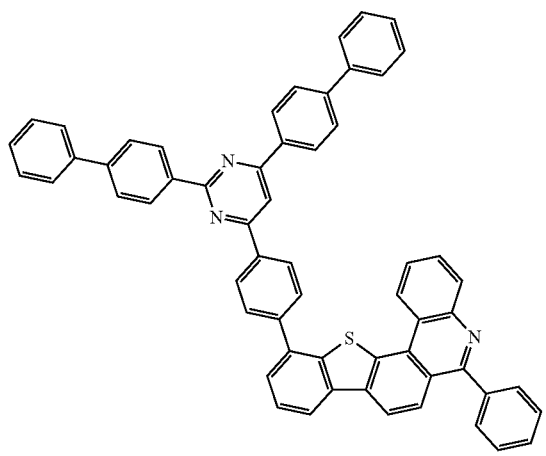
1149
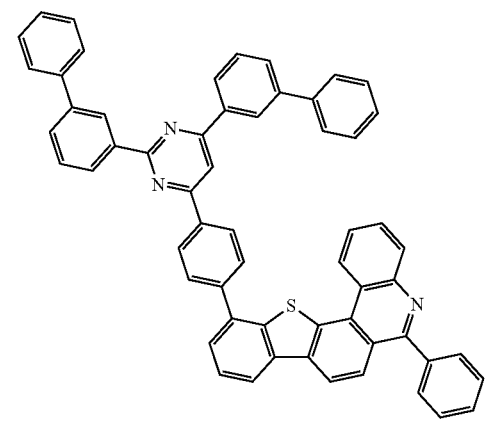

-continued
1150
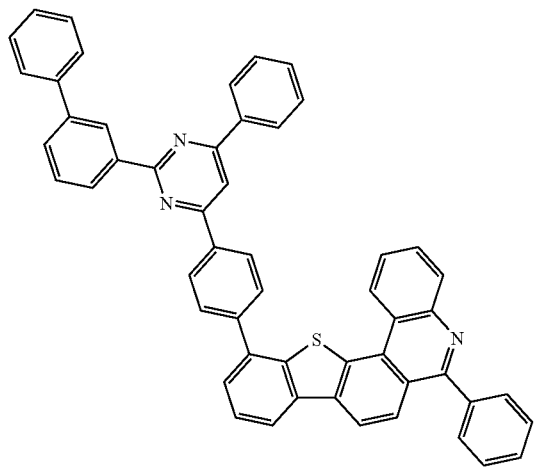
1151
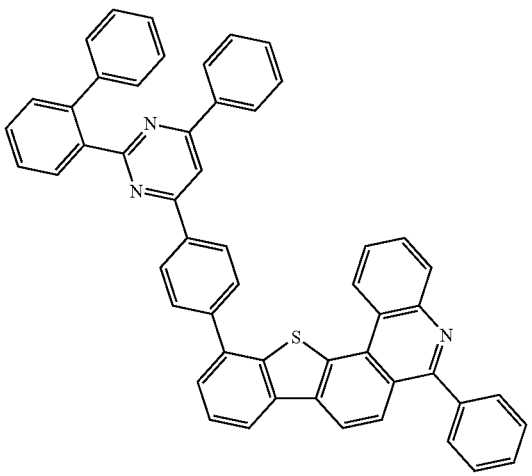
1152
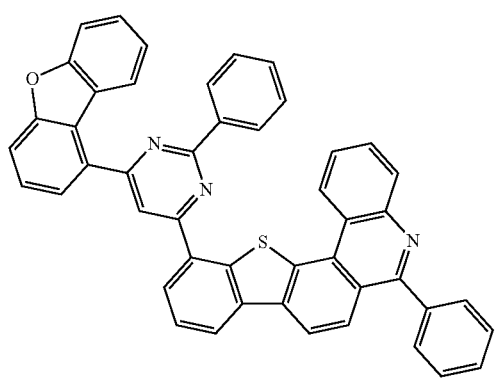
1153
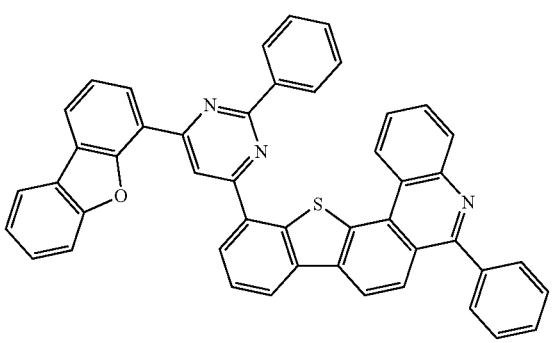
1154
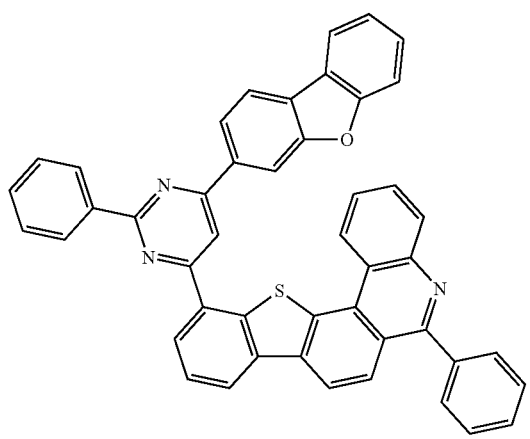
1155
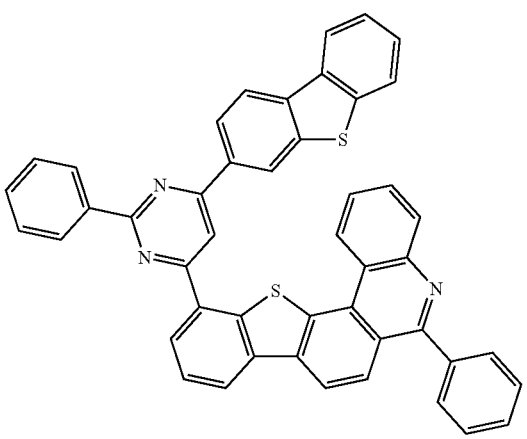

-continued
1156
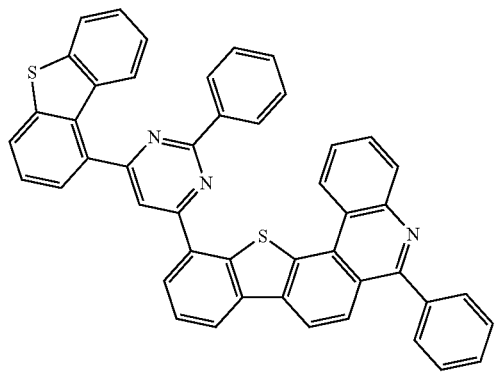
1157
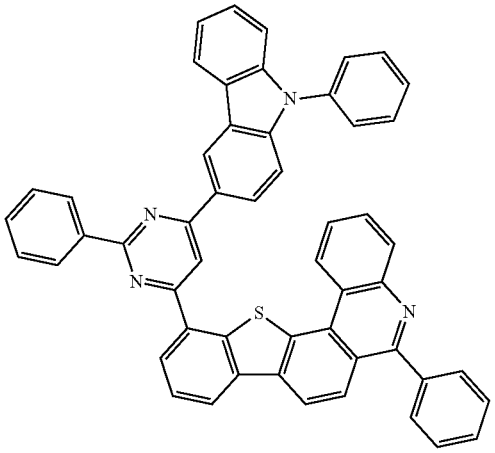
1158
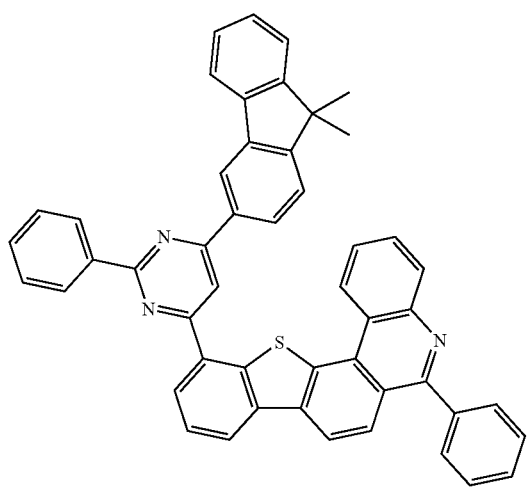
1159
1160
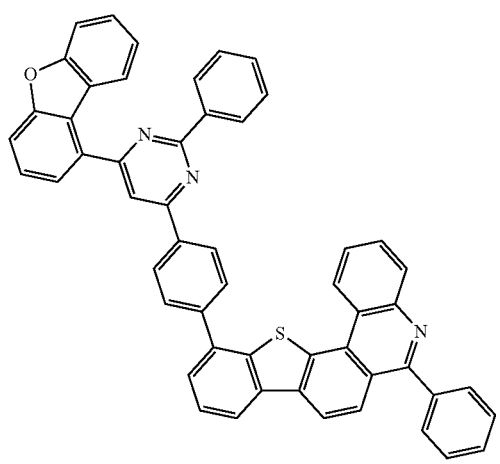
1161
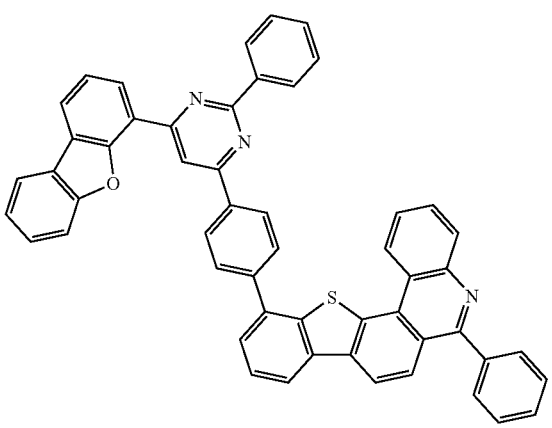

-continued
1162
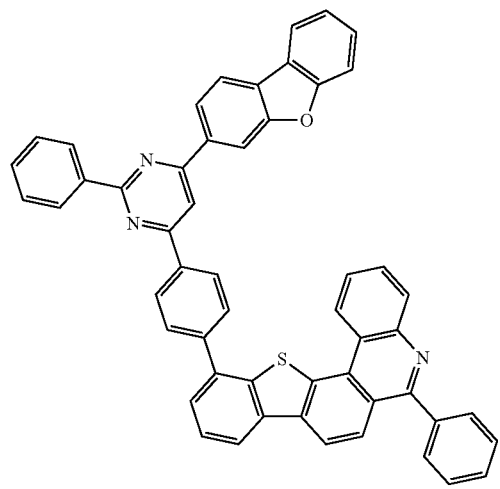
1163
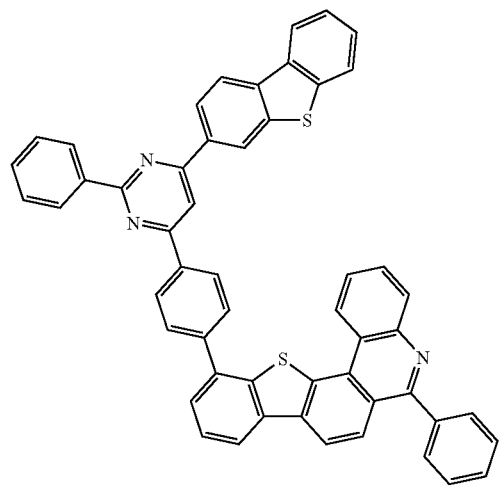
1164
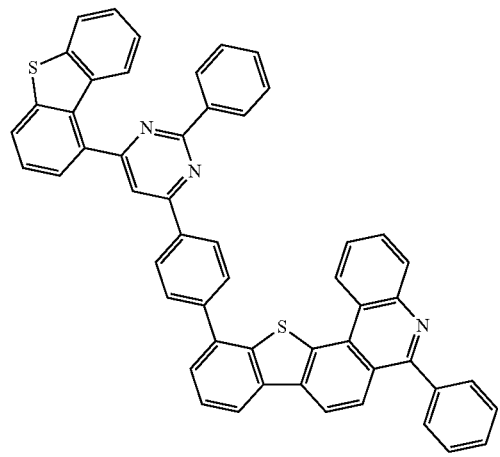
1165
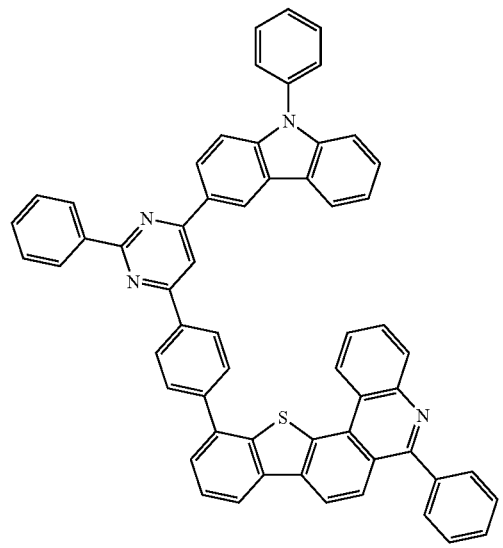
1166
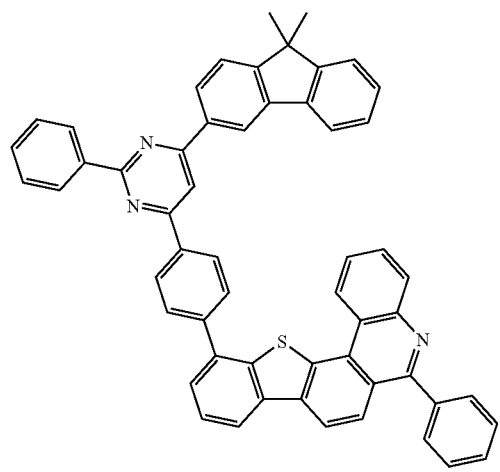
1167
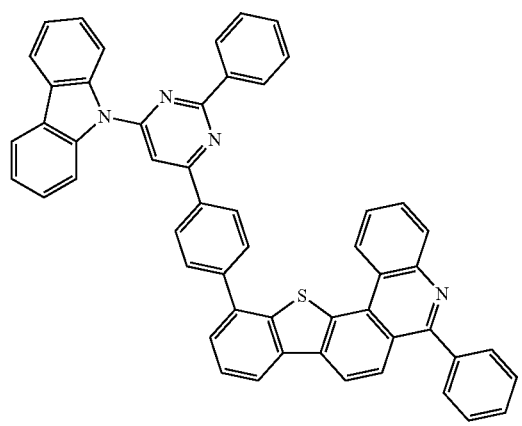

-continued
1168
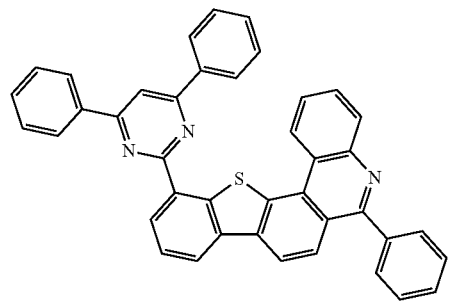
1169
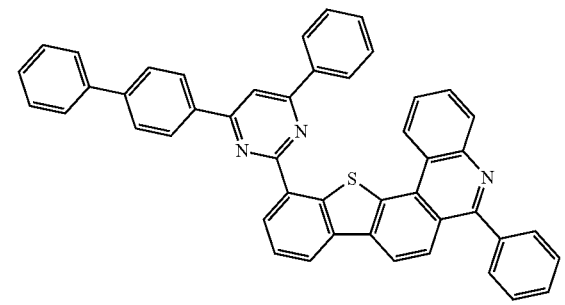
1170
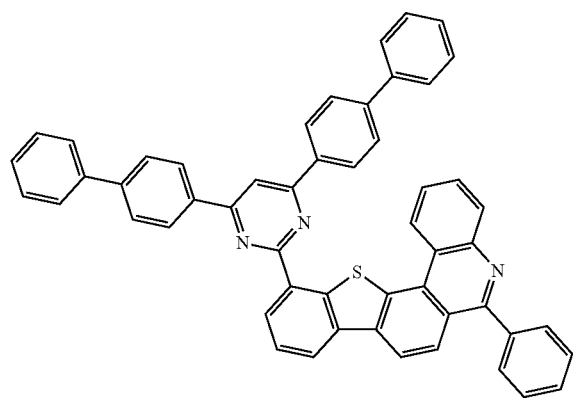
1171
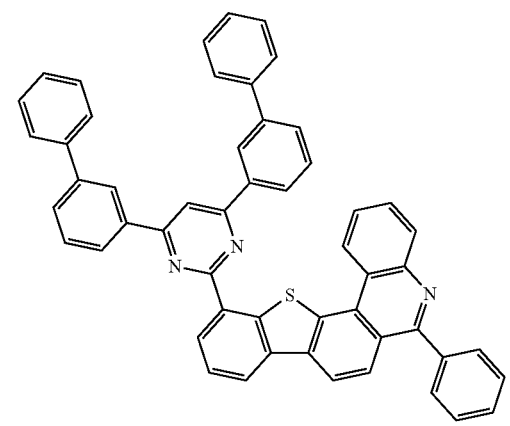
1172
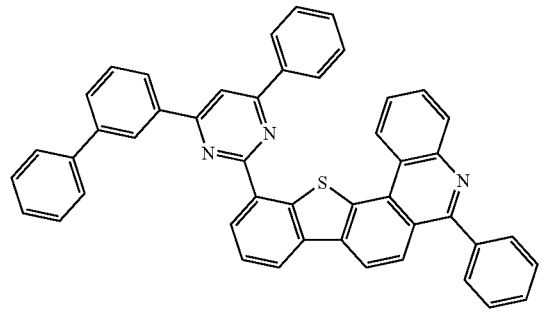
1173
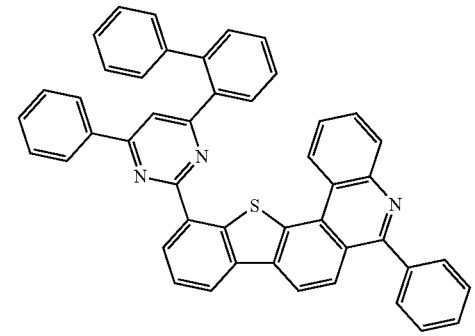
1174
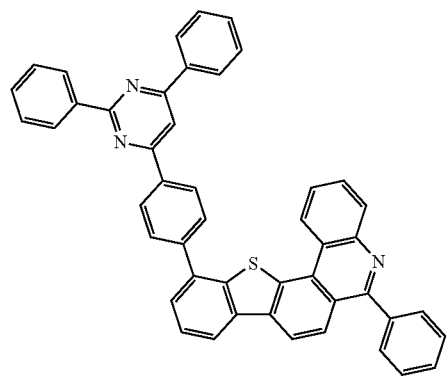
1175
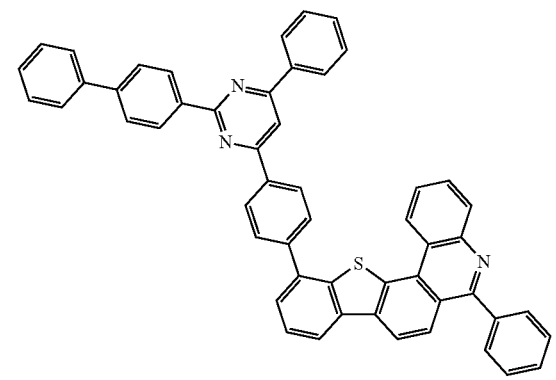

-continued
1176
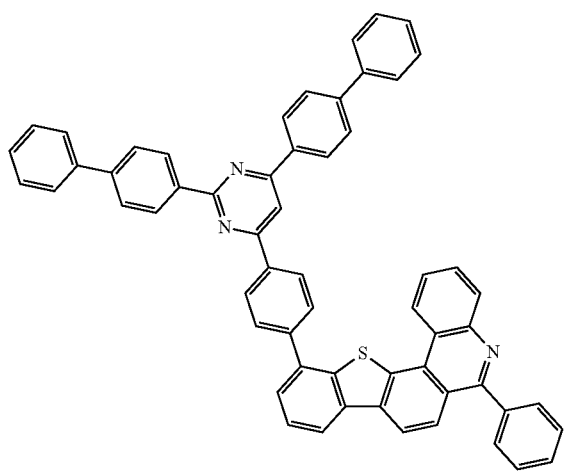
1177
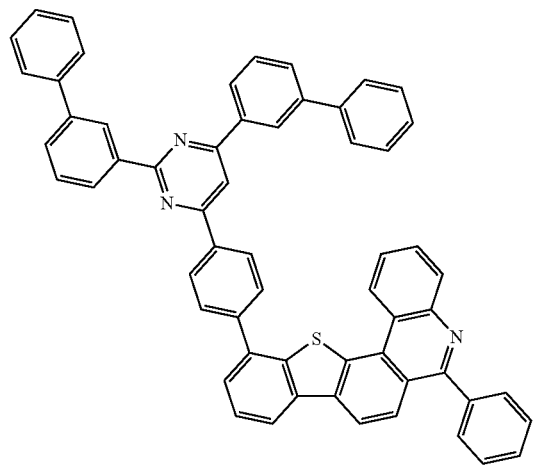
1178
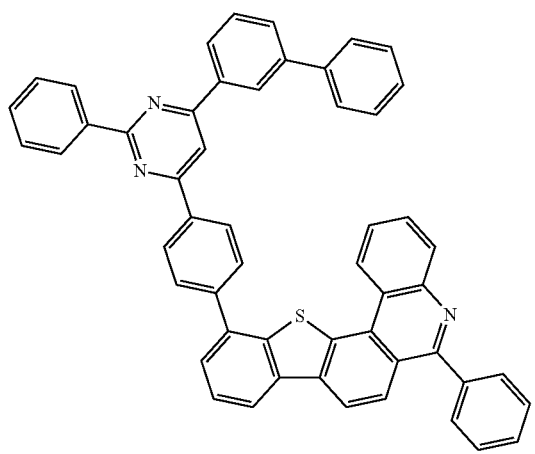
1179
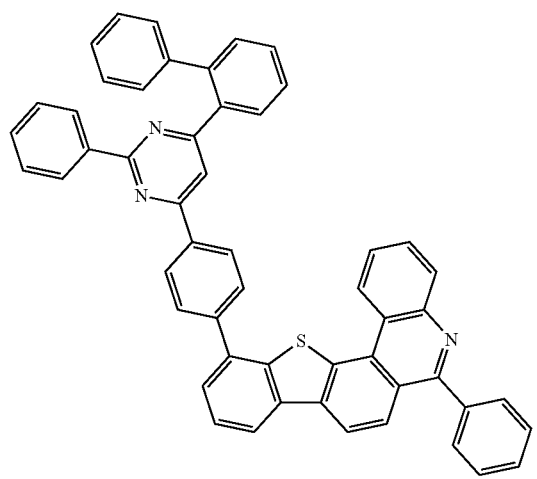
1180
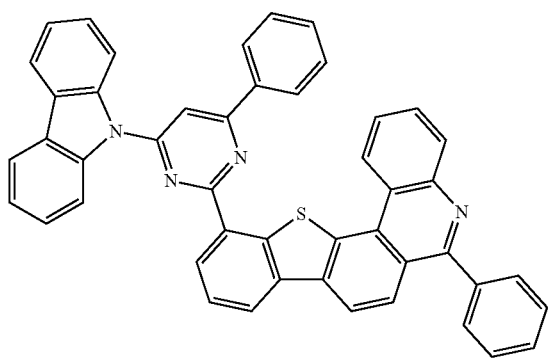
1181
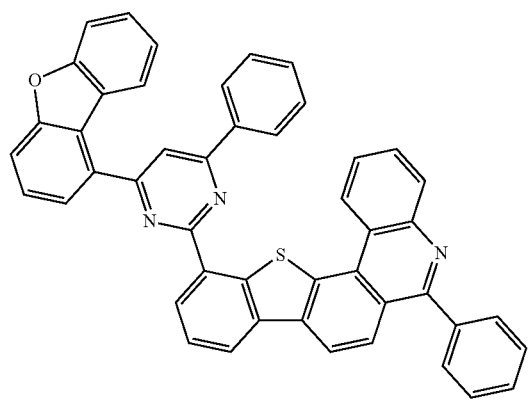

-continued
1182
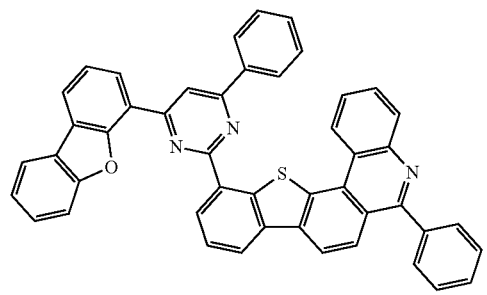
1183
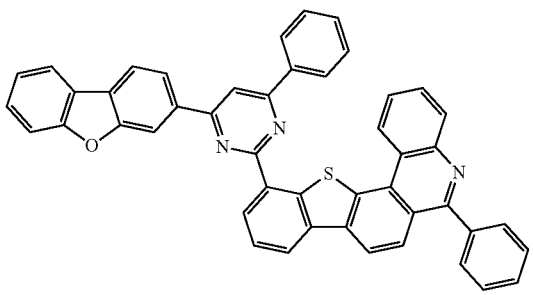
1184
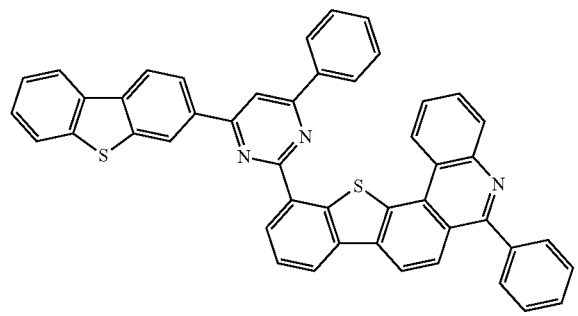
1185
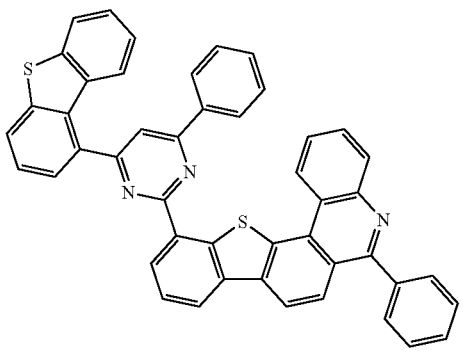
1186
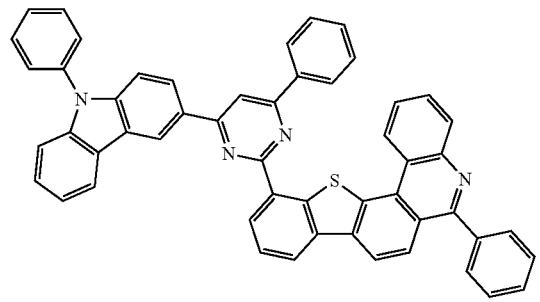
1187
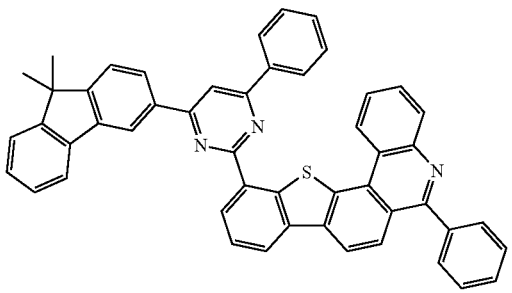
1188
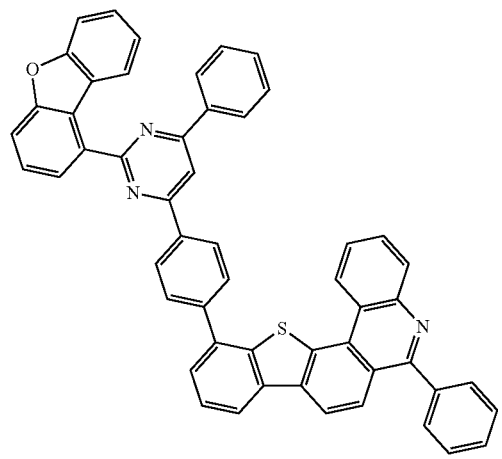
1189
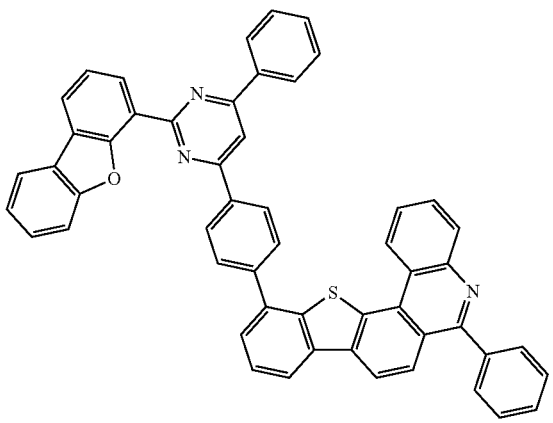

-continued
1190
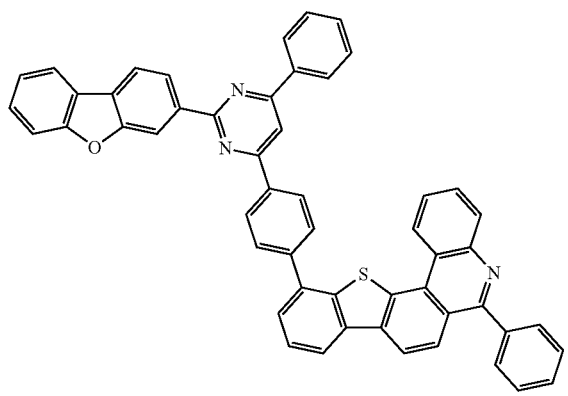
1191
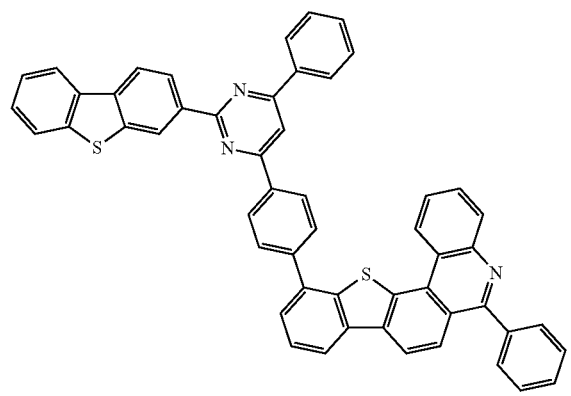
1192
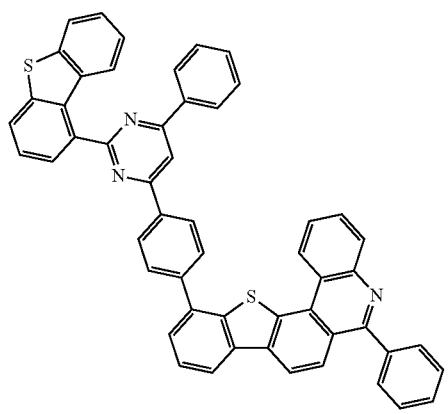
1193
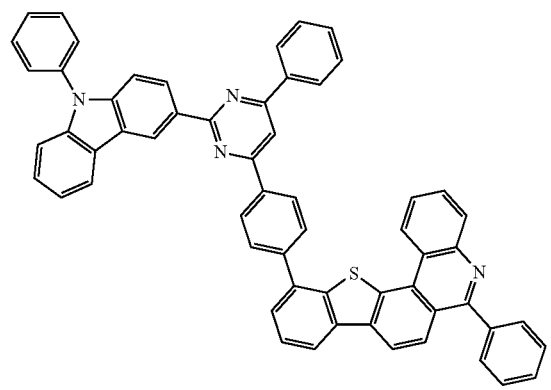
1194
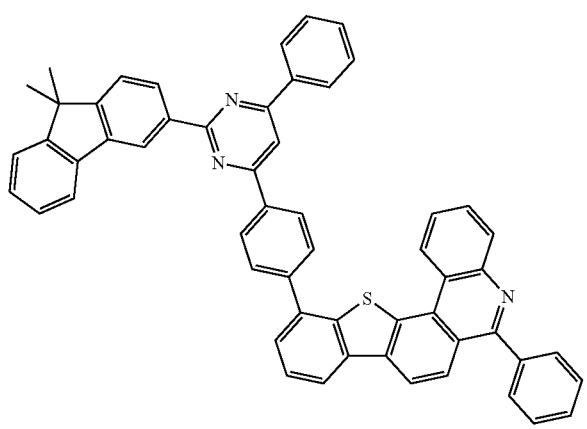
1196
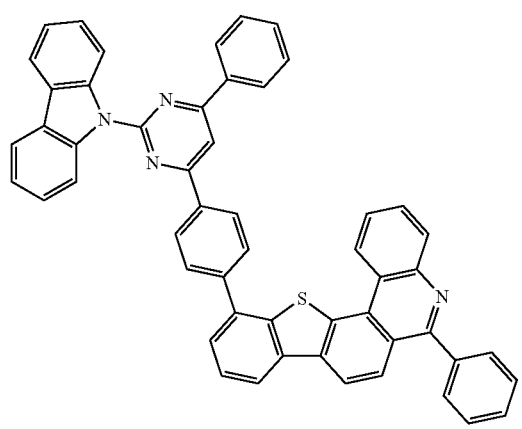

-continued
1196
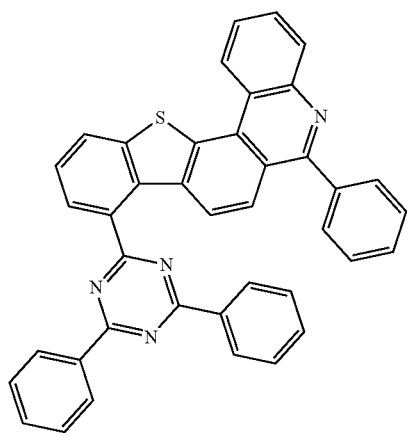
1197
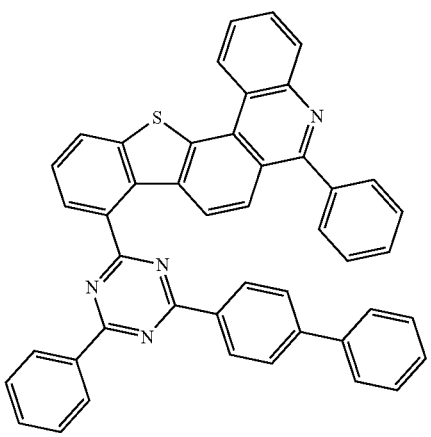
1198
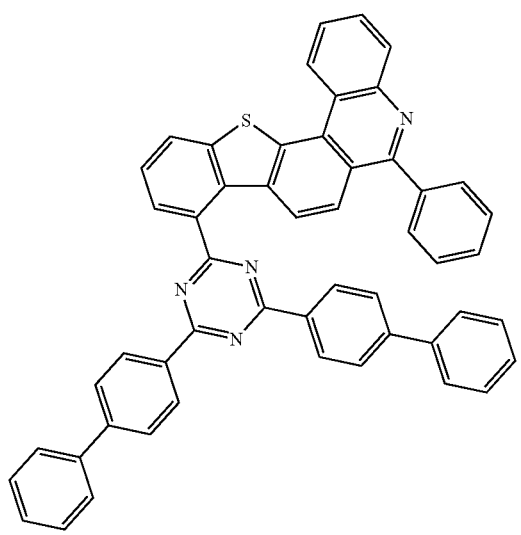
1199
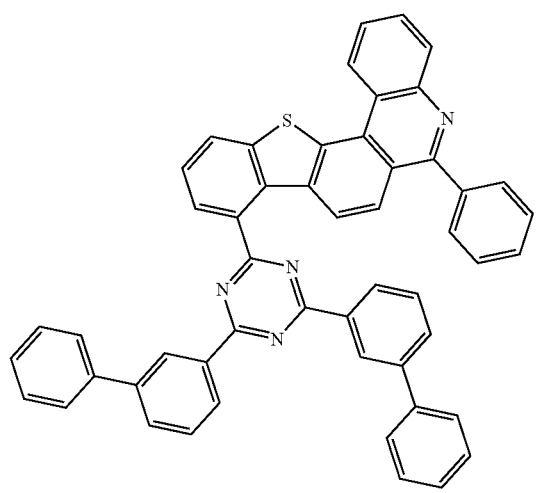
1200
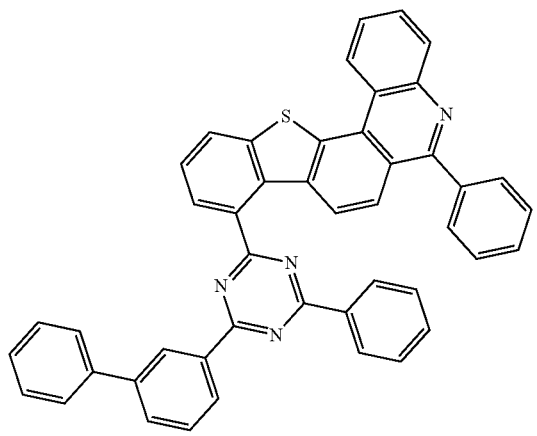
1201
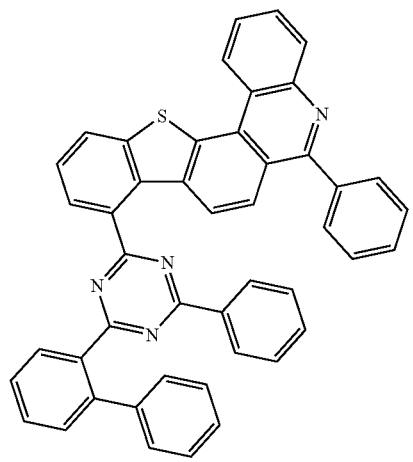

-continued
413
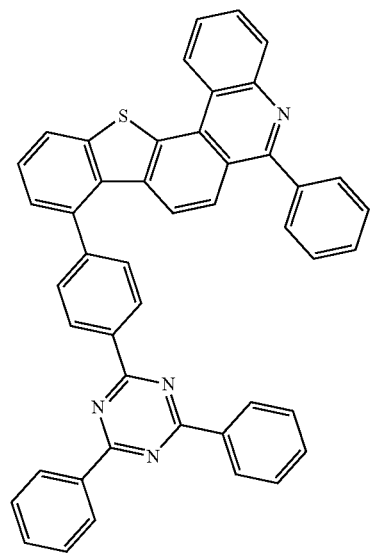
1202
414
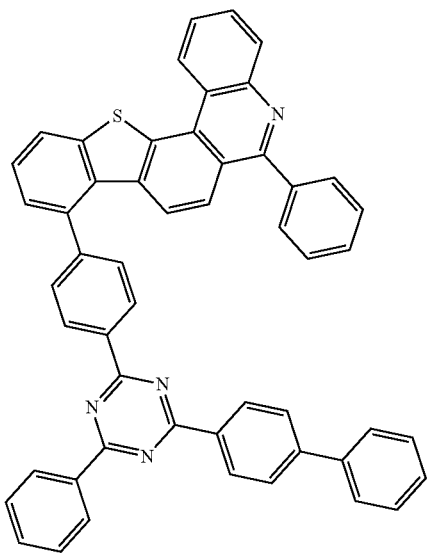
1203
1204
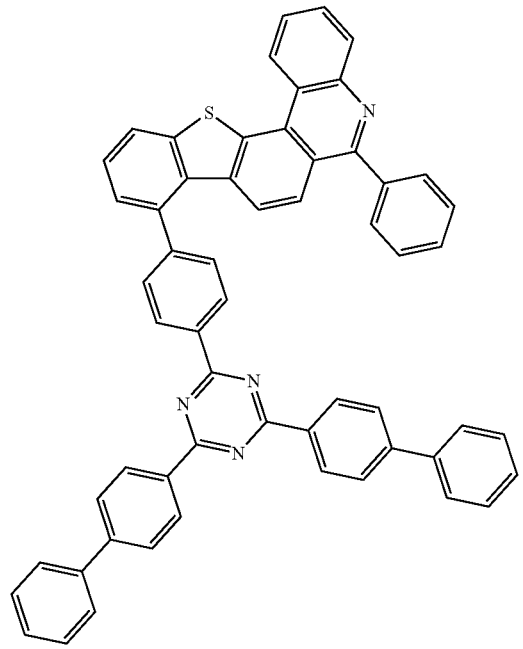
1205
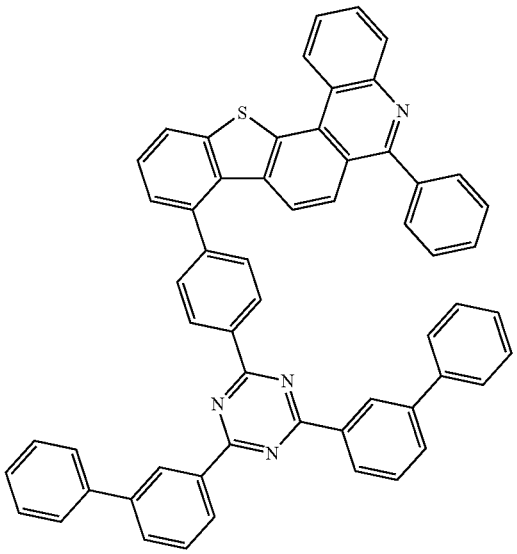

-continued
1206
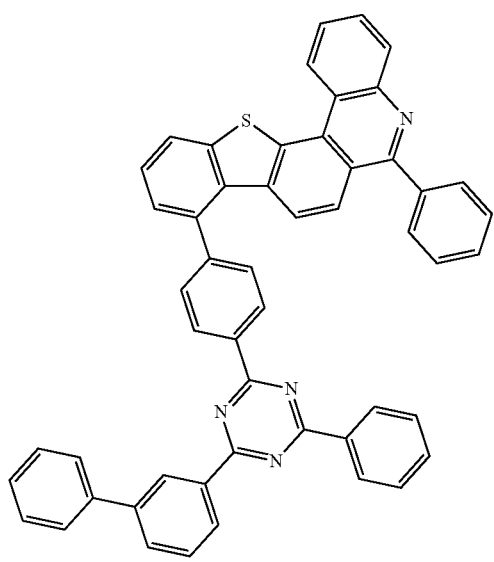
1207
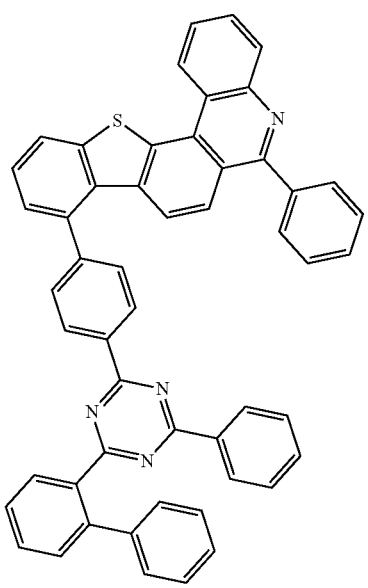
1208
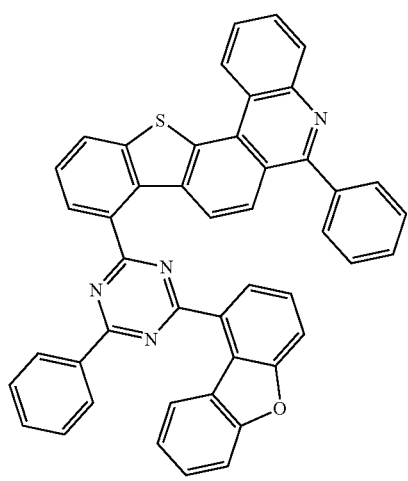
1209
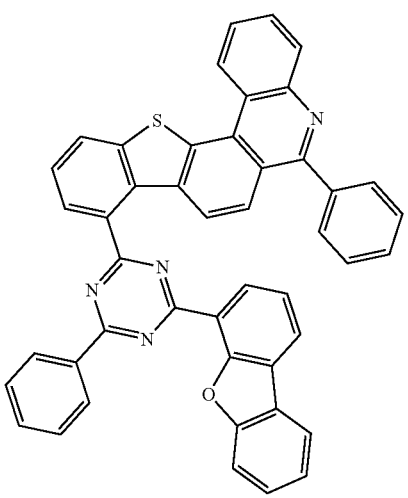
1210
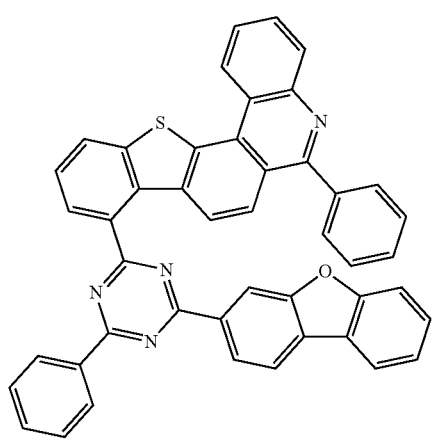
1211
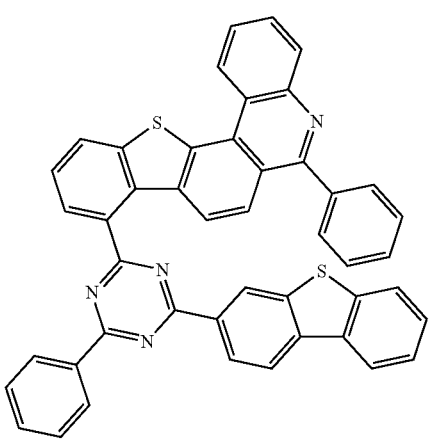

-continued
1212
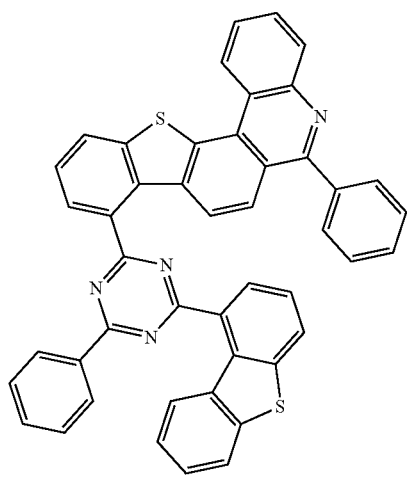
1213
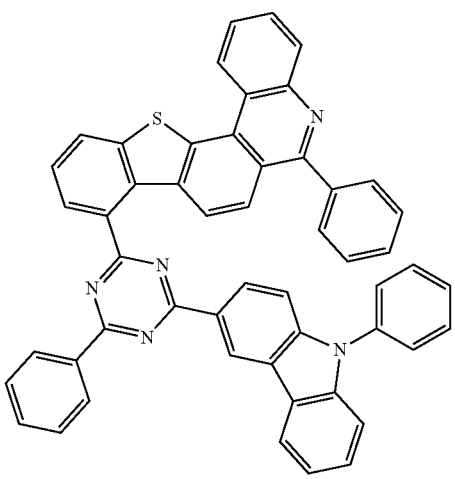
1214
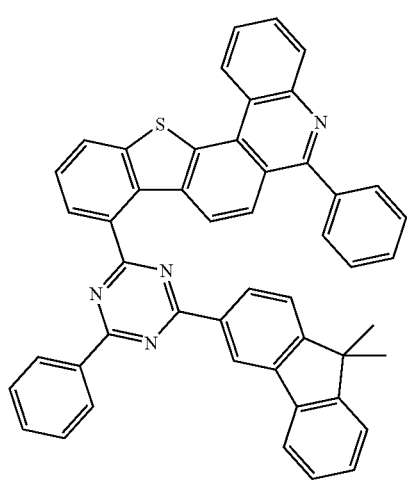
1215
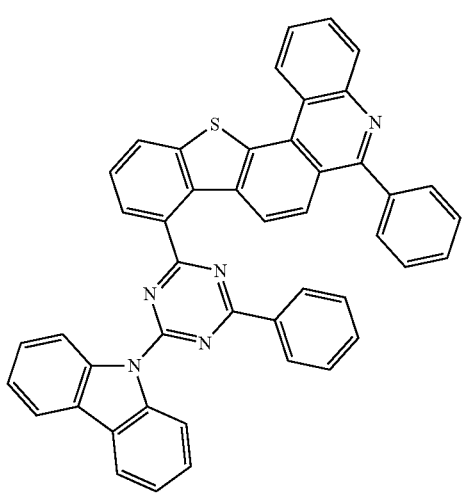
1216
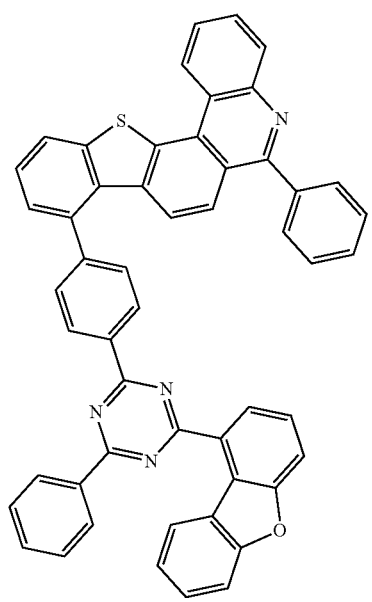
1217
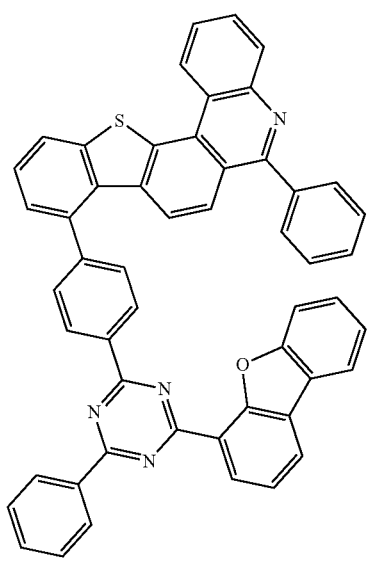

-continued
1218
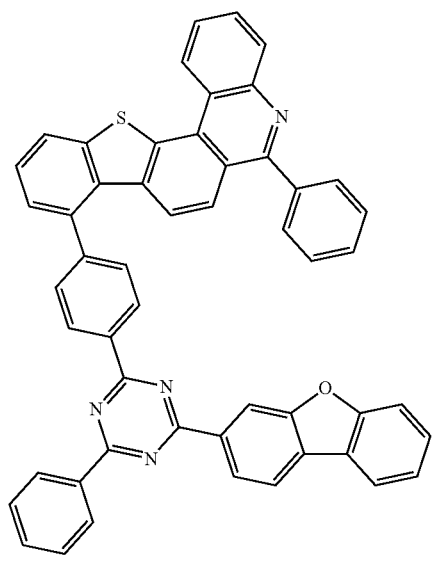
1219
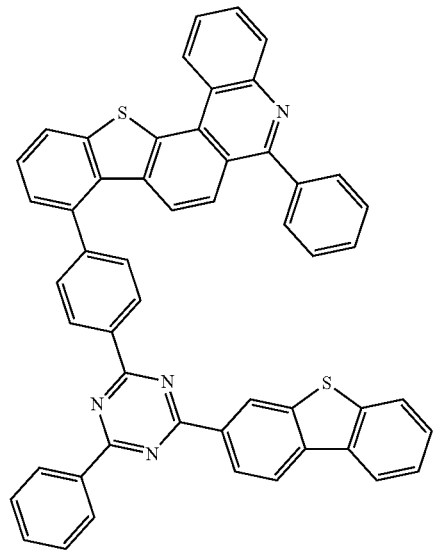
1220
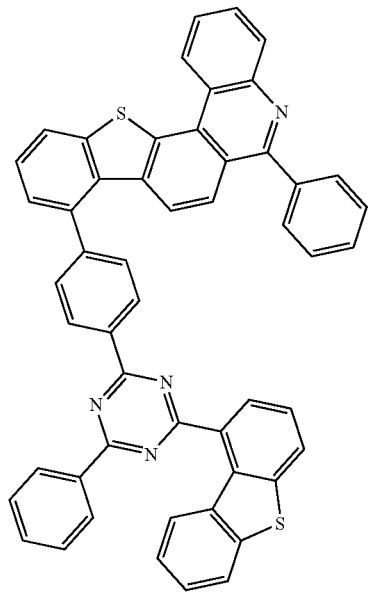
1221
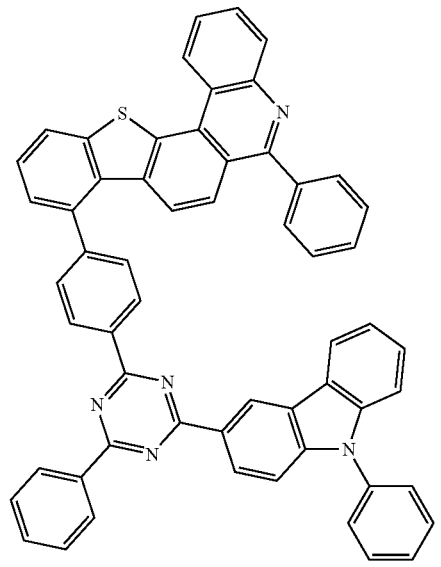

-continued
| 1222 | 1223 |
|---|---|
| 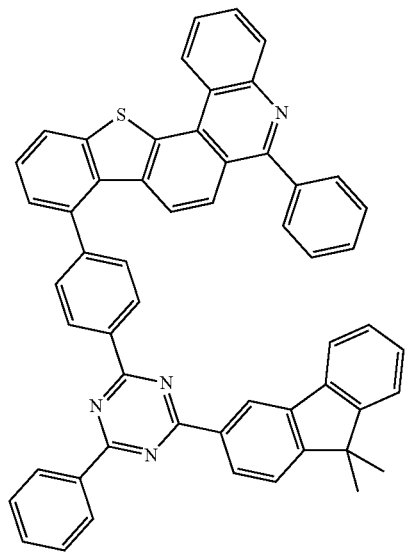 | 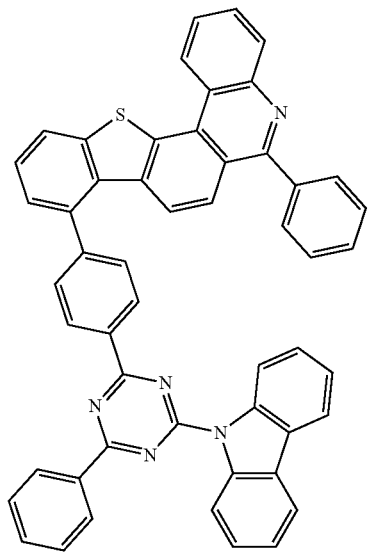 |
| 1224 | 1225 |
| 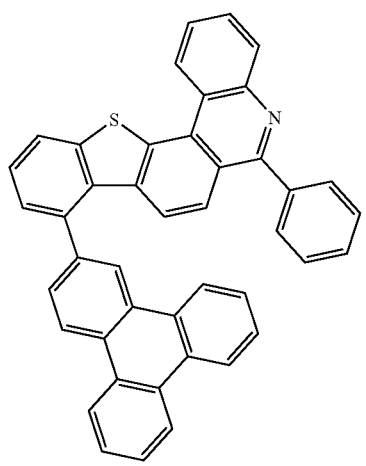 | 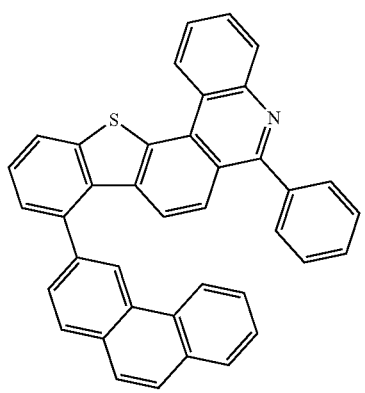 |
| 1226 | 1227 |
| 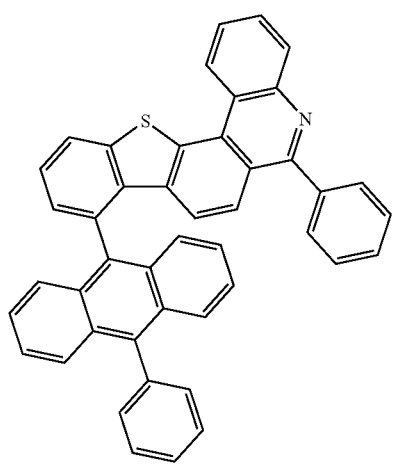 | 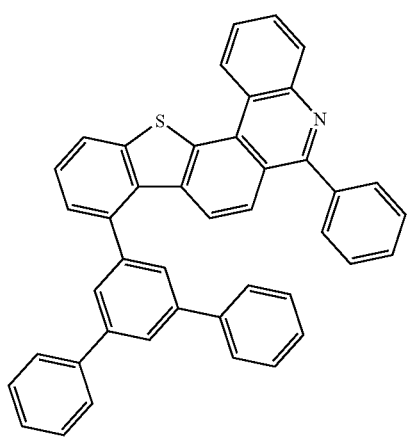 |

-continued
1228
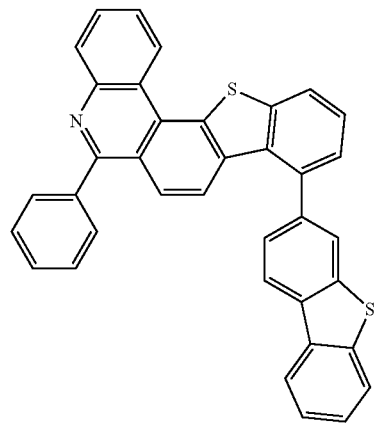
1229
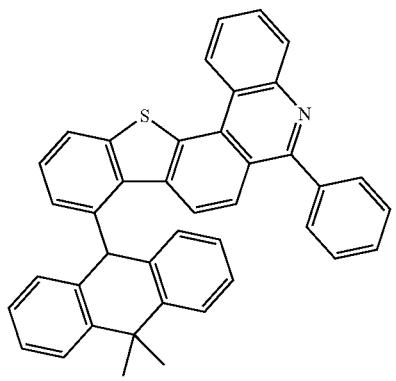
1230
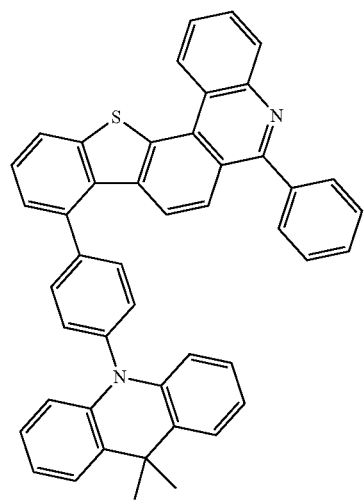
1231
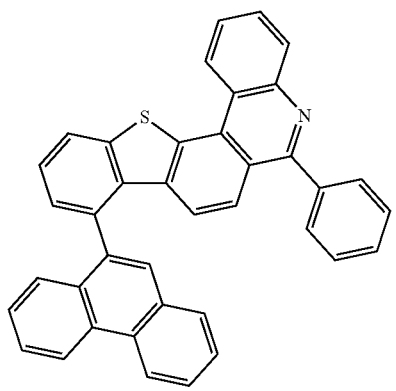
1232
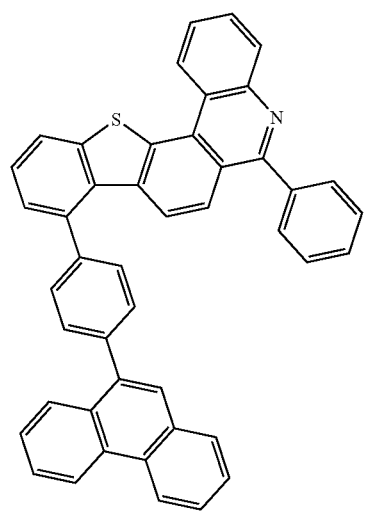
1233
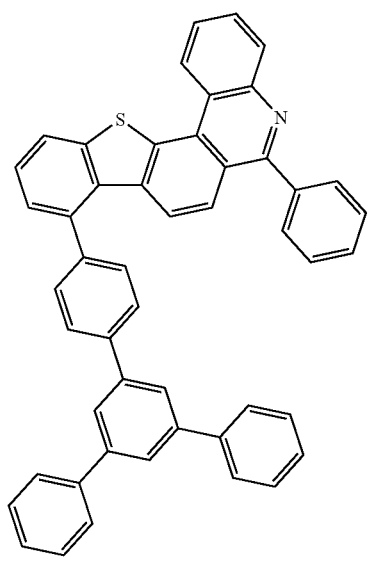

-continued
1234
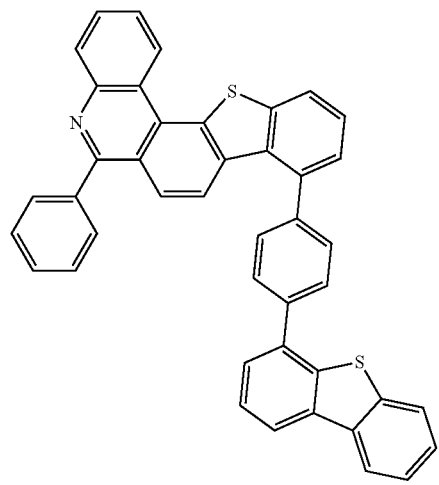
1235
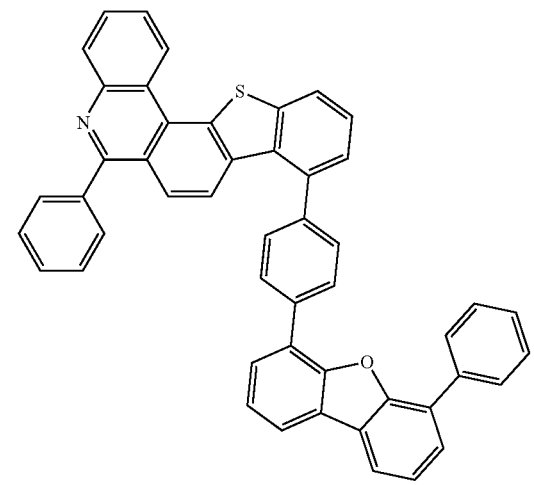
1236
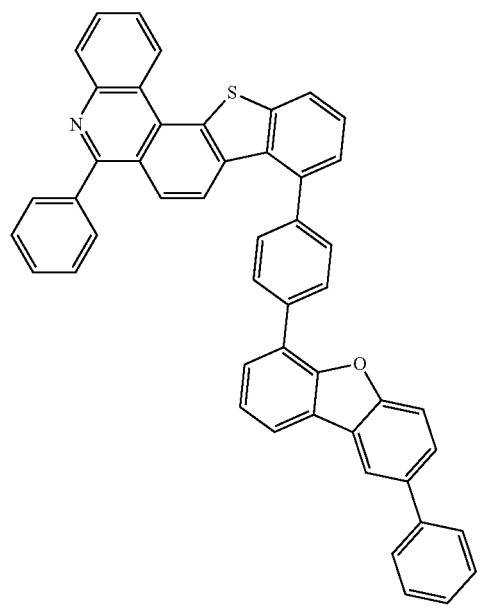
1237
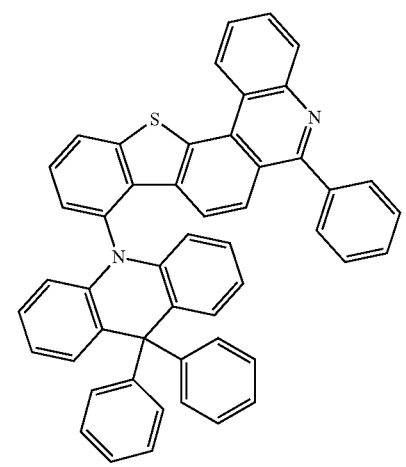
1238
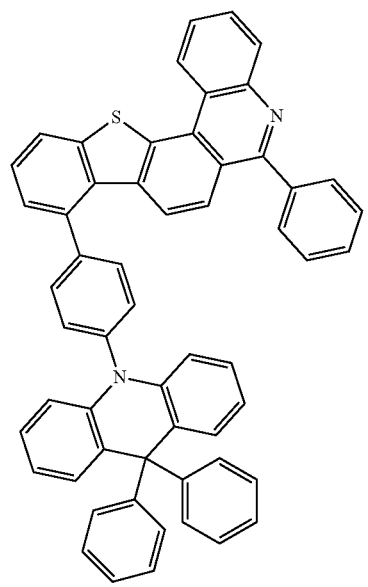
1239
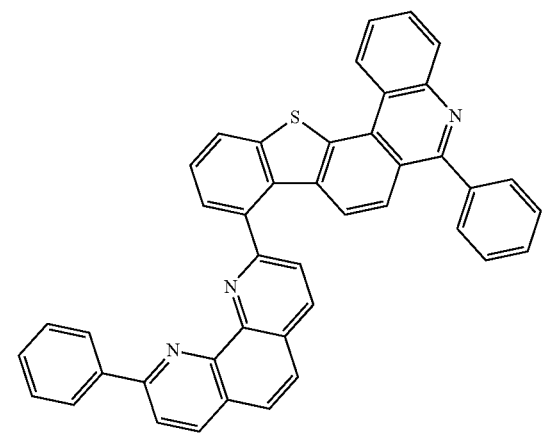

-continued
1240
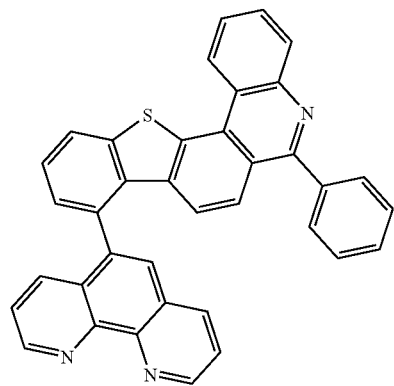
1241
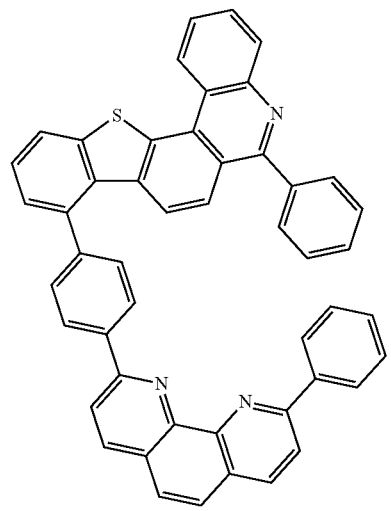
1242
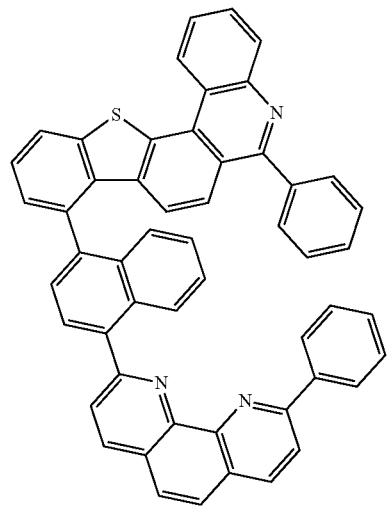
1243
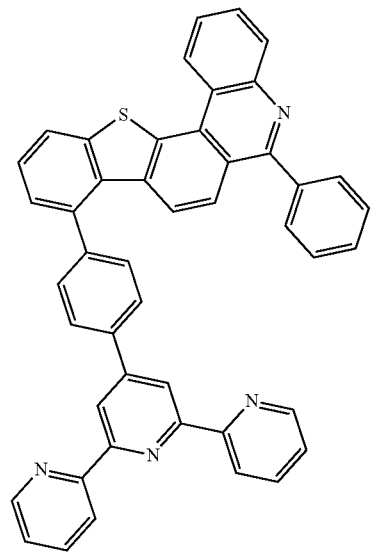
1244
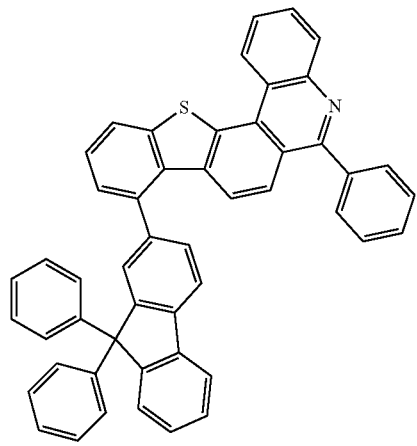
1245
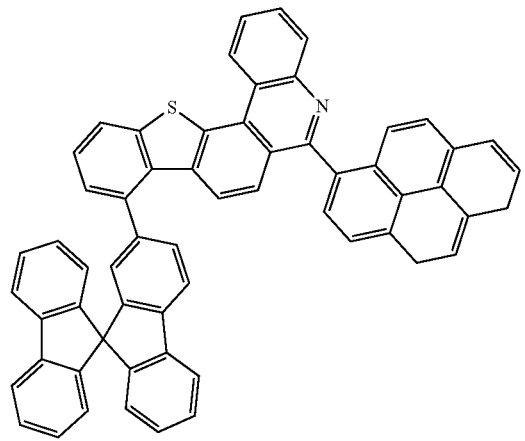

-continued
1246
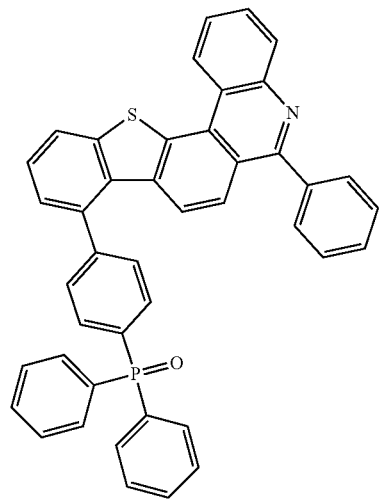
1247
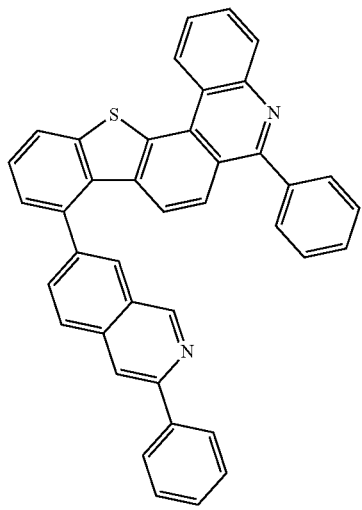
1248
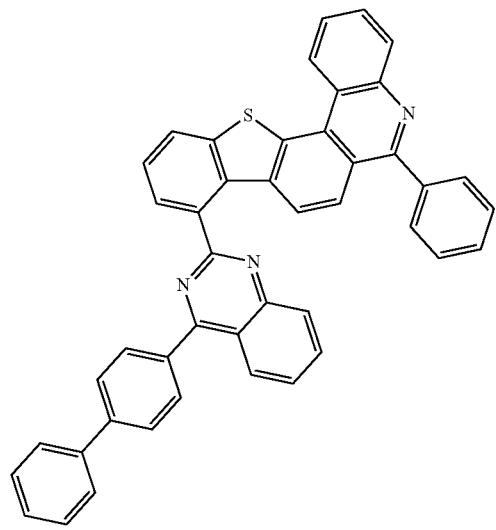
1249
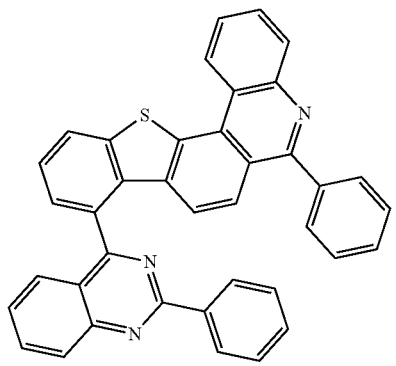
1250
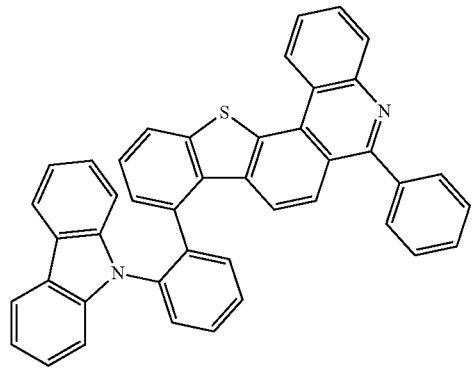
1251
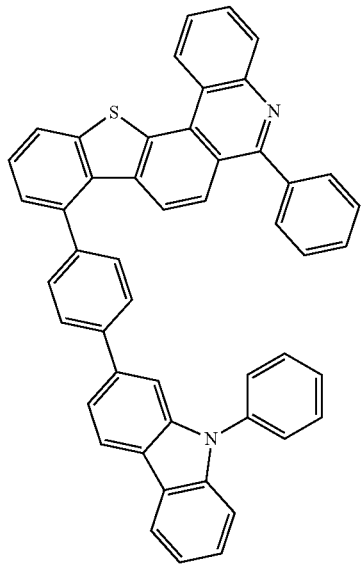

-continued
431
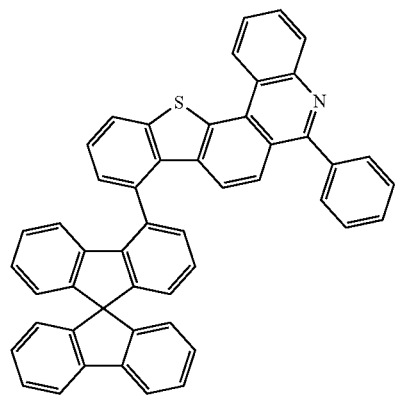
1252
432
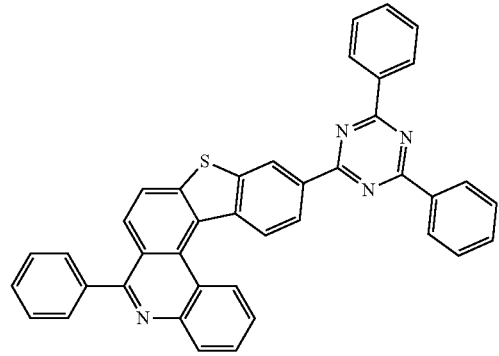
1253
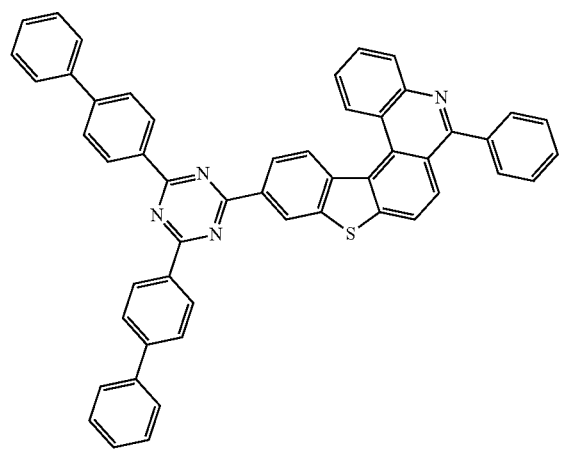
1254
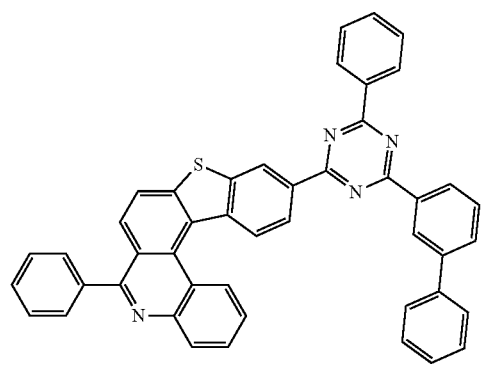
1255
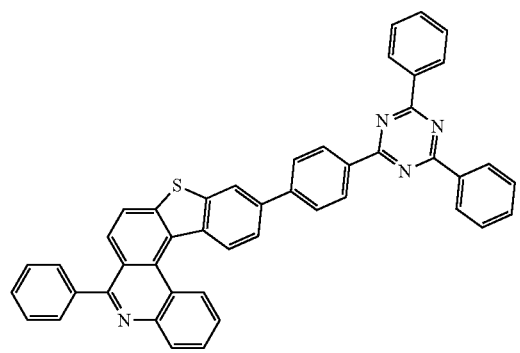
1256
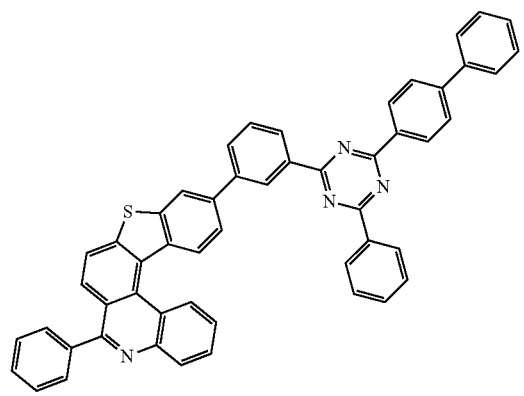
1257

-continued
| 1258 | 1259 |
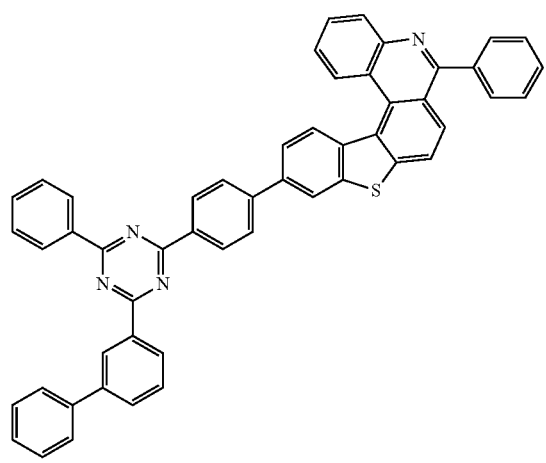
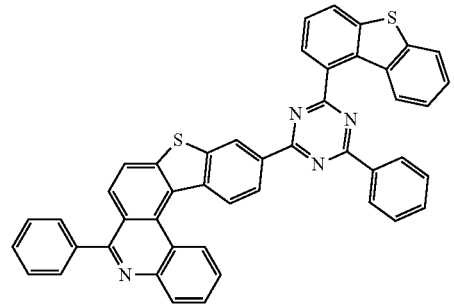
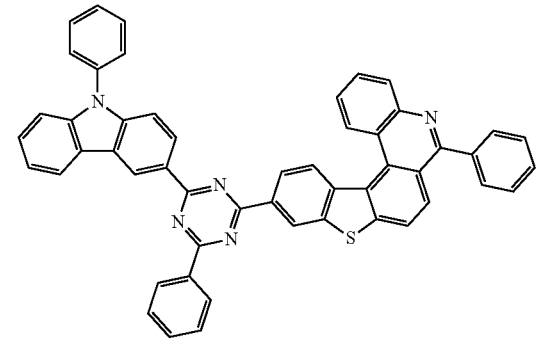
| 1260 | 1261 |
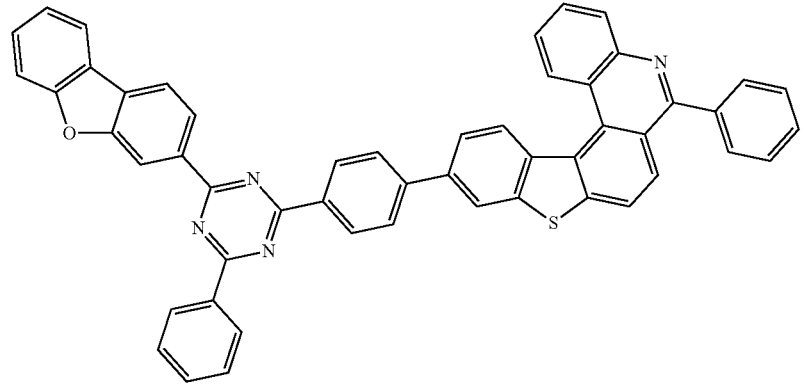
| 1262 |
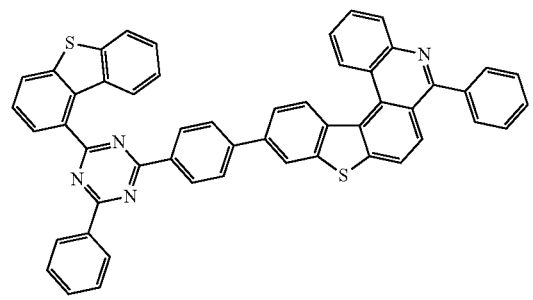
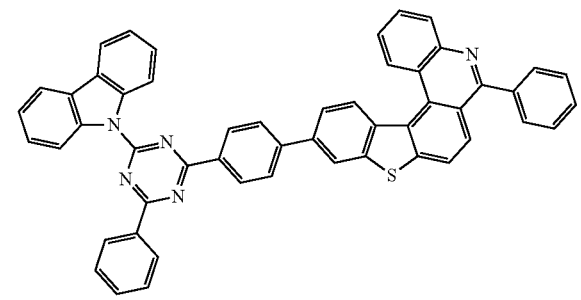
| 1263 | 1264 |

1265
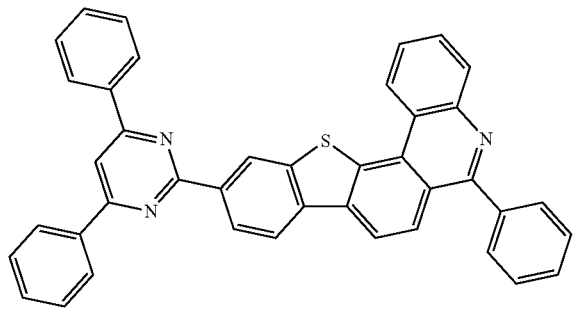
1266
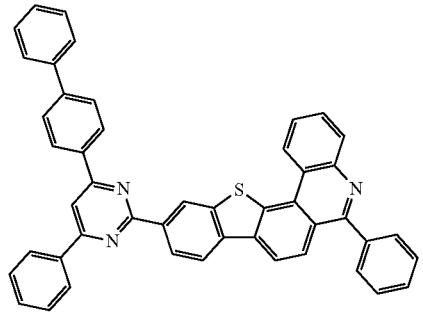
1267
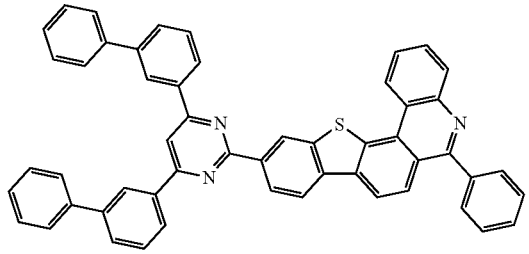
1268
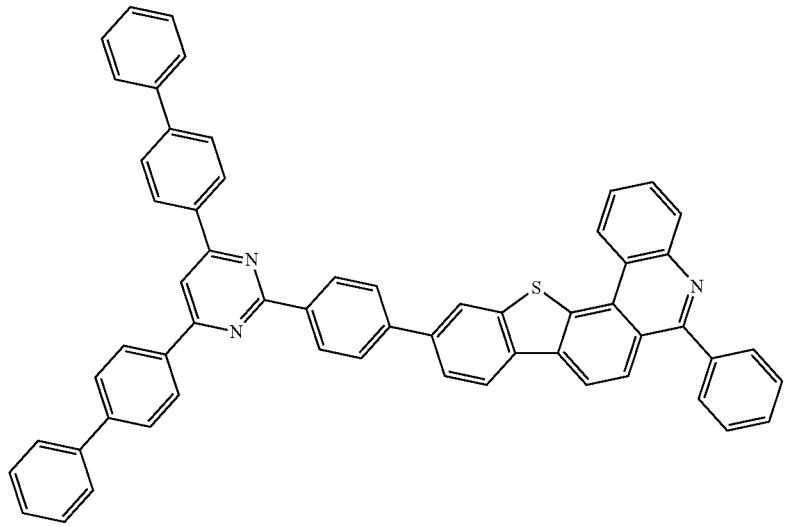
1269
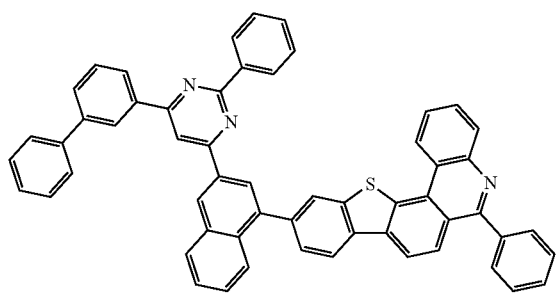
1270
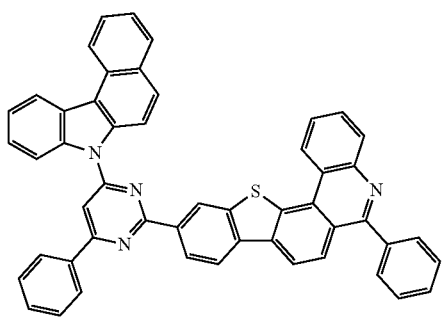

1271
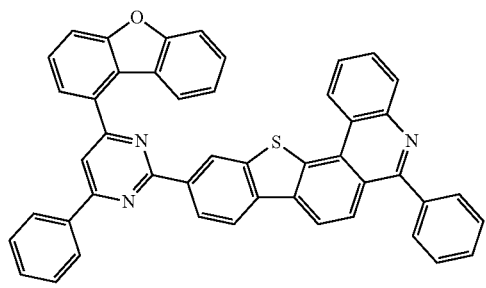
1272
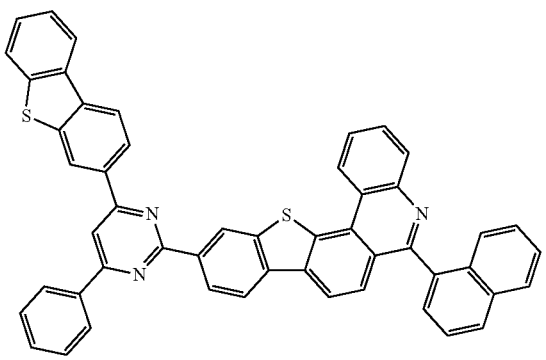
1273
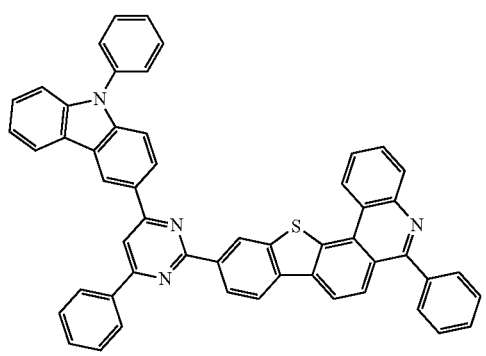
1274
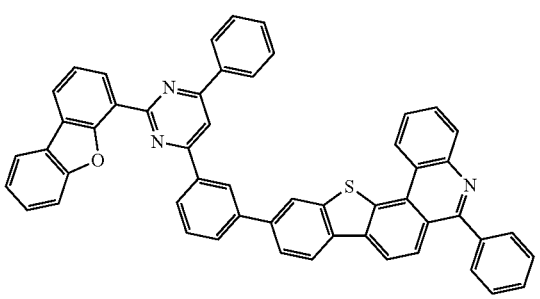
1275
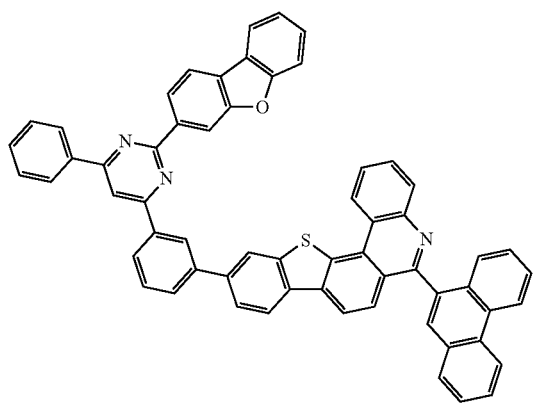
1276
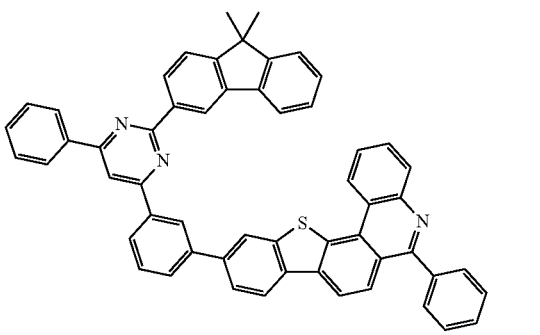
1277
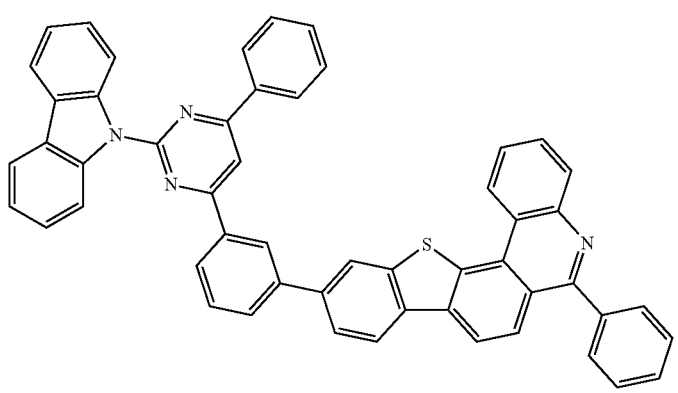
In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely adjusted, and by the high T1 value obtained therefrom, an organic light emitting device with superior efficiency may be provided.

One embodiment of the present specification provides an organic light emitting device including a first electrode; a second electrode; and an organic material layer provided between the first electrode and the second electrode, wherein the organic material layer includes the heterocyclic compound represented by Chemical Formula 1.

In one embodiment of the present specification, the first electrode may be an anode, and the second electrode may be a cathode.

In another embodiment of the present specification, the first electrode may be a cathode, and the second electrode may be an anode.

In one embodiment of the present specification, the organic light emitting device may be a blue organic light emitting device, and the heterocyclic compound according to Chemical Formula 1 may be used as a material of the blue organic light emitting device. For example, the heterocyclic compound according to Chemical Formula 1 may be included in a host material of a light emitting layer of the blue organic light emitting device.

In another embodiment of the present specification, the organic light emitting device may be a green organic light emitting device, and the heterocyclic compound according to Chemical Formula 1 may be used as a material of the green organic light emitting device. For example, the heterocyclic compound according to Chemical Formula 1 may be included in a host material of a light emitting layer of the green organic light emitting device.

In another embodiment of the present specification, the organic light emitting device may be a red organic light emitting device, and the heterocyclic compound according to Chemical Formula 1 may be used as a material of the red organic light emitting device. For example, the heterocyclic compound according to Chemical Formula 1 may be included in a host material of a light emitting layer of the red organic light emitting device.

Specific descriptions on the heterocyclic compound represented by Chemical Formula 1 are the same as the descriptions provided above.

The organic light emitting device of the present specification may be manufactured using common organic light emitting device manufacturing methods and materials except that one or more of the organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present specification may be formed in a single layer structure, but may be formed in a multilayer structure in which two or more organic material layers are laminated. For example, the organic light emitting device of the present disclosure may have a structure including a hole injection layer, a hole transfer layer, a light emitting layer, an electron transfer layer, an electron injection layer and the like as the organic material layer. However, the structure of the organic light emitting device is not limited thereto, and may include a smaller number of organic material layers.

In the organic light emitting device of the present specification, the organic material layer includes an electron transfer layer, and the electron transfer layer may include the heterocyclic compound of Chemical Formula 1. When using the heterocyclic compound as an electron transfer material, HOMO and LUMO may be adjusted depending on the substituent position, and excellent electron transfer efficiency is obtained. In addition, compared to existing electron transfer materials, migration of electrons in a reverse direction is prevented due to a difference in the T1 value, and as a result, superior device efficiency is obtained.

The organic light emitting device of the present disclosure may further include one, two or more layers selected from the group consisting of a light emitting layer, a hole injection layer, a hole transfer layer, an electron injection layer, an electron transfer layer, an electron blocking layer and a hole blocking layer.

FIG. 1 to FIG. 3 illustrate a lamination order of electrodes and organic material layers of an organic light emitting device according to one embodiment of the present specification. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 includes a hole injection layer (301), a hole transfer layer (302), a light emitting layer (303), an electron transfer layer (304) and an electron injection layer (305). However, the scope of the present application is not limited to such a lamination structure, and as necessary, layers other than the light emitting layer may not be included, and other necessary functional layers may be further included.

The organic material layer including the heterocyclic compound represented by Chemical Formula 1 may further include other materials as necessary.

The organic light emitting device according to one embodiment of the present specification includes a first electrode; a first stack provided on the first electrode and including a first light emitting layer; a charge generation layer provided on the first stack; a second stack provided on the charge generation layer and including a second light emitting layer; and a second electrode provided on the second stack, wherein the charge generation layer may include the heterocyclic compound represented by Chemical Formula 1.

The organic light emitting device according to one embodiment of the present specification includes a first electrode; a second electrode; and an organic material layer provided between the first electrode and the second electrode, wherein the organic material layer includes two or more stacks, and the two or more stacks each independently include a light emitting layer, a charge generation layer is included between the two or more stacks, and the charge generation layer may include the heterocyclic compound represented by Chemical Formula 1.

The organic light emitting device according to one embodiment of the present specification includes a first electrode; a second electrode; and an organic material layer provided between the first electrode and the second electrode, wherein the organic material layer includes a first stack including a first light emitting layer; a charge generation layer provided on the first stack; and a second stack including a second light emitting layer, and the charge generation layer may include the heterocyclic compound represented by Chemical Formula 1.

In addition, the organic light emitting device according to one embodiment of the present specification includes an anode, a cathode, and two or more stacks provided between the anode and the cathode, the two or more stacks each independently include a light emitting layer, a charge generation layer is included between the two or more stacks, and the charge generation layer includes the heterocyclic compound represented by Chemical Formula 1.

In addition, the organic light emitting device according to one embodiment of the present specification includes an anode, a first stack provided on the anode and including a first light emitting layer, a charge generation layer provided on the first stack, a second stack provided on the charge generation layer and including a second light emitting layer, and a cathode provided on the second stack. Herein, the charge generation layer may include the heterocyclic compound represented by Chemical Formula 1. When the heterocyclic compound is included in the charge generation layer, superior efficiency as a charge generation layer material is obtained by an electron-friendly substituent structure and a hole migration-friendly quinoline-dibenzofuran or quinoline-dibenzothiophene fused structure.

The organic light emitting device according to one embodiment of the present specification includes a first electrode; a first stack provided on the first electrode and including a first light emitting layer; a charge generation layer provided on the first stack; a second stack provided on the charge generation layer and including a second light emitting layer; and a second electrode provided on the second stack, wherein the charge generation layer is an N-type charge generation layer, and the charge generation layer may include the heterocyclic compound represented by Chemical Formula 1.

In addition, the first stack and the second stack may each independently further include one or more types of the hole injection layer, the hole transfer layer, the hole blocking layer, the electron transfer layer, the electron injection layer and the like described above.

The charge generation layer may be an N-type charge generation layer or a P-type charge generation layer, and the charge generation layer may further include a dopant known in the art in addition to the heterocyclic compound represented by Chemical Formula 1.

As the organic light emitting device according to one embodiment of the present specification, an organic light emitting device having a 2-stack tandem structure is illustrated in FIG. 4.

Herein, the first electron blocking layer, the first hole blocking layer, the second hole blocking layer and the like described in FIG. 4 may not be included in some cases.

In the organic light emitting device according to one embodiment of the present specification, materials other than the heterocyclic compound represented by Chemical Formula 1 are illustrated below, however, these are for illustrative purposes only and not for limiting the scope of the present application, and the materials may be replaced by materials known in the art.

As the anode material, materials having relatively large work function may be used, and transparent conductive oxides, metals, conductive polymers or the like may be used. Specific examples of the anode material include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene](PEDOT), polypyrrole and polyaniline, and the like, but are not limited thereto.

As the cathode material, materials having relatively small work function may be used, and metals, metal oxides, conductive polymers or the like may be used. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrenesulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used in addition to the heterocyclic compound, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected and used as a host material of a light emitting layer.

The organic light emitting device according to one embodiment of the present specification may be a top-emission type, a bottom-emission type or a dual-emission type depending on the materials used.

The heterocyclic compound according to one embodiment of the present specification may also be used in an organic electronic device including an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

[Preparation Example 1] Preparation of Compound 4

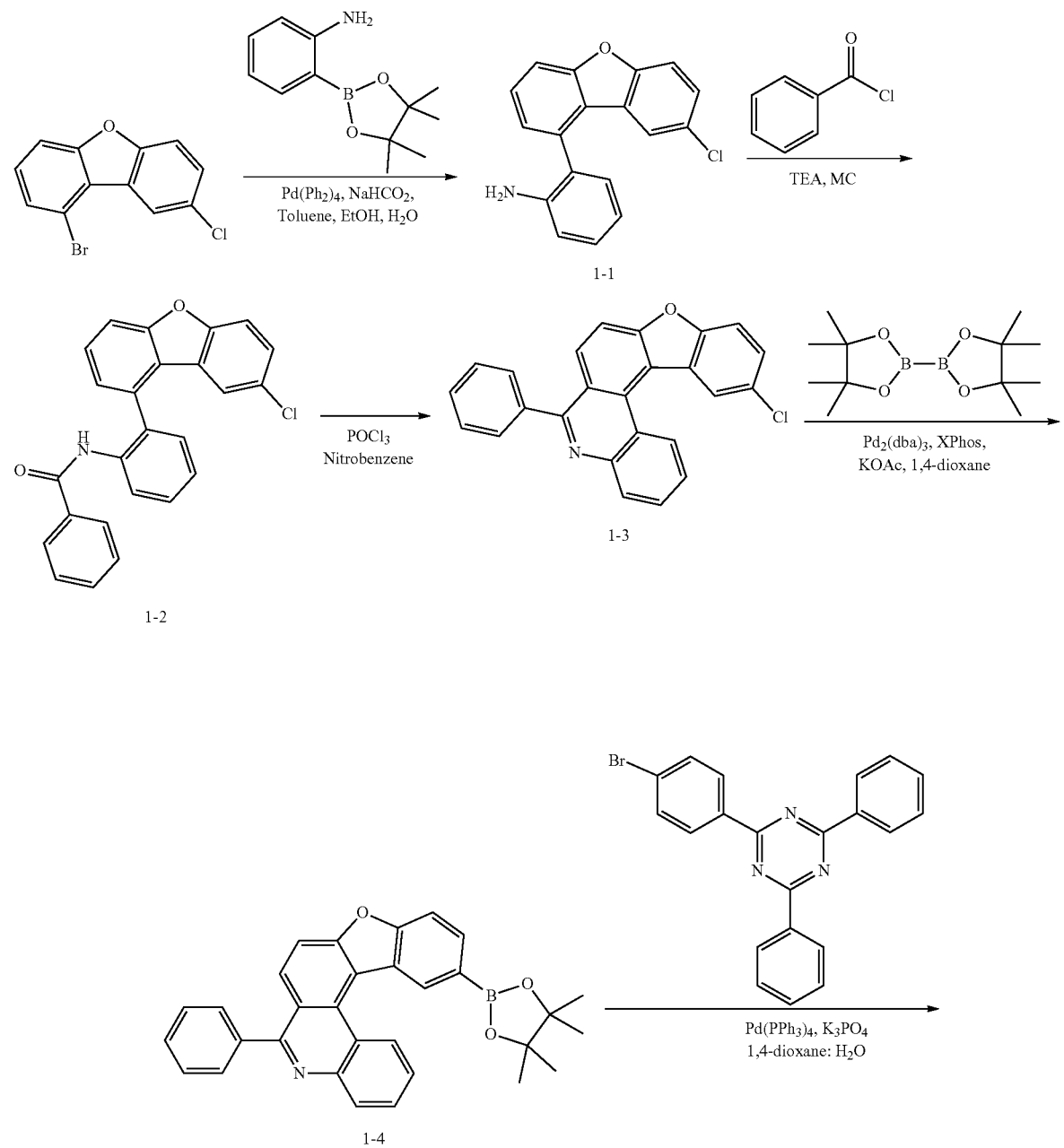

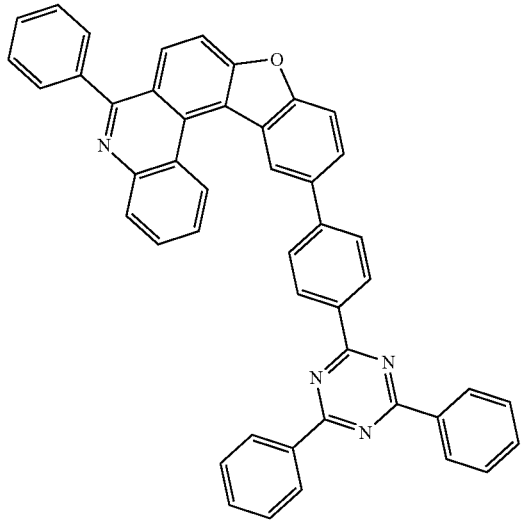

4

1) Preparation of Compound 1-1

After dissolving 1-bromo-8-chlorodibenzo[b,d]furan (100 g, 0.3552 mol) and 2-(4,4,5,5-tetramethyl-1,3,2-dioxaborolan-2-yl)aniline (77.8 g, 0.3552 mol) in toluene, ethanol and H$_2$O (2000 mL:200 mL:200 mL), Pd(PPh$_3$)$_4$ (tetrakis(triphenylphosphine)palladium(0)) (20.5 g, 0.017 mol) and NaHCO$_3$ (89 g, 1.06 mol) were introduced thereto, and the result was stirred for 3 hours at 100° C. After the reaction was completed, methylene chloride (MC) and distilled water were introduced to the reaction solution, and the result was extracted, then dried with anhydrous MgSO$_4$, and the solvent was removed using a rotary evaporator to obtain Compound 1-1 (77 g, 74%) in a liquid form.

2) Preparation of Compound 1-2

Compound 1-1 (77 g, 0.262 mol) and triethylamine (86 mL, 0.393 mol) were introduced to methylene chloride (1200 mL) and dissolved therein. To the mixture, benzoyl chloride (55 g, 0.393 mol) dissolved in methylene chloride (300 mL) was slowly added dropwise at 0° C. After the reaction was completed, white solids in the reaction solution were filtered and washed with hexane. These were dried to obtain Compound 1-2 (86 g, 83%) in a solid form.

3) Preparation of Compound 1-3

After dissolving Compound 1-2 (86 g, 0.216 mol) in nitrobenzene (1500 mL), POCl$_3$ (30 mL, 0.324 mol) was slowly added dropwise thereto, and the result was reacted for 15 hours at 140° C. After the reaction was completed, a solution obtained by dissolving NaHCO$_3$ in distilled water was slowly introduced to the reaction solution, and the result was stirred. Solids produced after that were filtered and collected, and the collected solids were recrystallized in MC and MeOH to obtain Compound 1-3 (41 g, 51%) in a solid form.

4) Preparation of Compound 1-4

After dissolving Compound 1-3 (41 g, 0.1079 mol) in 1,4-dioxane (800 mL), Pd$_2$(dba)$_3$ (tris(dibenzylideneacetone)dipalladium(0)) (9.8 g, 0.0107 mol), XPhos (2-dicyclohexylphosphino-2',4',6'-triisopropylbiphenyl) (5.1 g, 0.0107 mol) and KOAc (potassium acetate) (31 g, 0.3237 mol) were dissolved therein, and the result was reacted for 4 hours at 90° C. After the reaction was completed, water and methylene chloride were introduced to the reaction solution, and the result was extracted. Solids obtained after that were dried, and recrystallized with methylene chloride and methanol to obtain Compound 1-4 (30 g, 60%) in a solid form.

5) Preparation of Compound 4

After dissolving Compound 1-4 (6.4 g, 0.017 mol) and 2-(4-bromophenyl)-4,6-diphenyl-1,3,5-triazine (7.4 g, 0.017 mol) in 1,4-dioxane:H$_2$O=100 mL:20 mL, Pd(PPh$_3$)$_4$ (1.96 g, 0.0017 mol) and K$_3$PO$_4$ (20.8 g, 0.051 mol) were introduced thereto, and the result was stirred for 5 hours at 100° C. After the reaction was completed, solids produced in the reaction solution were washed with 1,4-dioxane and H$_2$O. After that, only the solids were purified using a recrystallization method in dichlorobenzene (DCB) to obtain Compound 4 (6.6 g, 60%).

447 448
[Preparation Example 2] Preparation of Compound 88
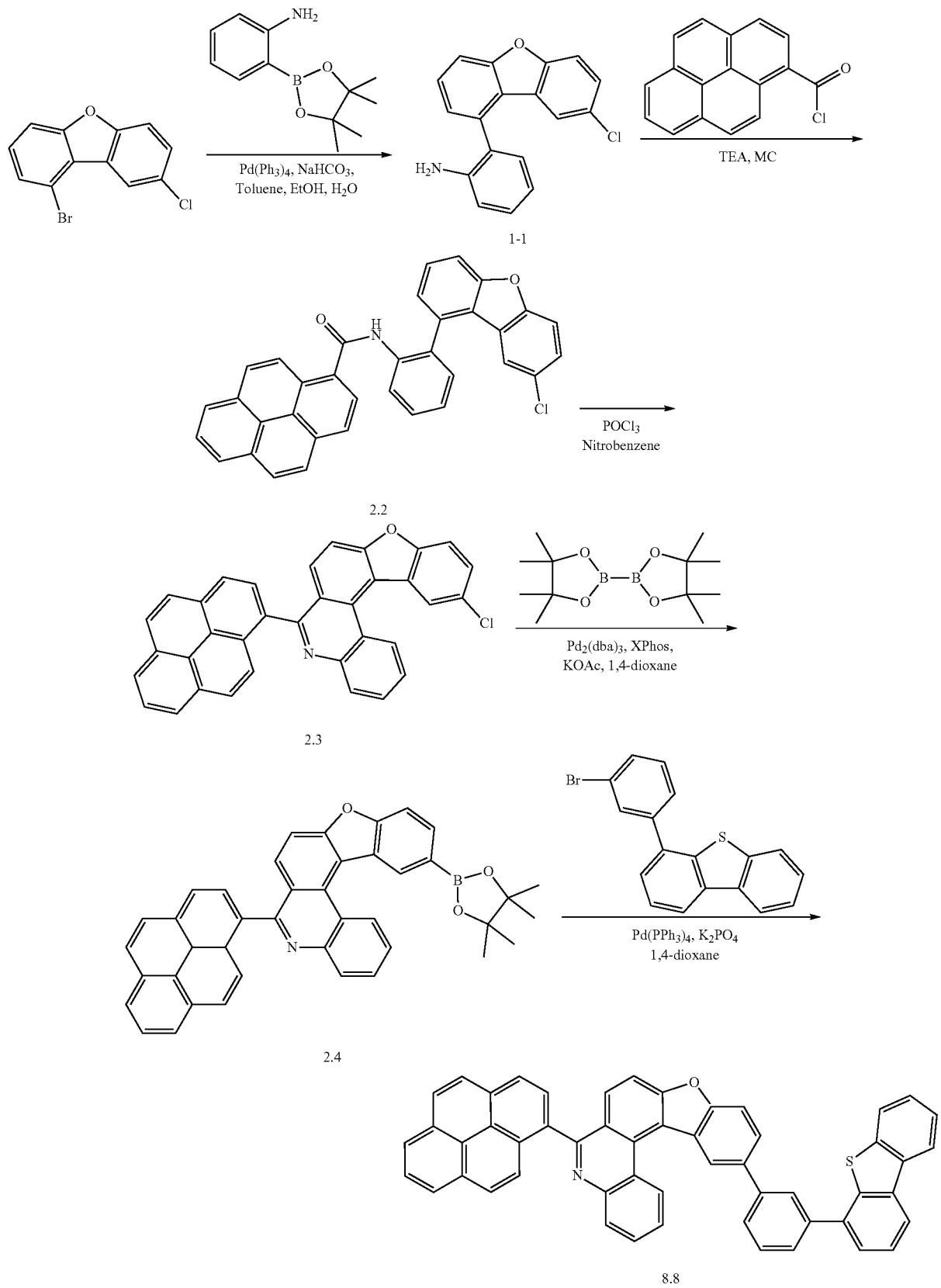

1) Preparation of Compound 1-1

Compound 1-1 was the same as Compound 1-1 of Preparation Example 1.

2) Preparation of Compound 2-2

Compound 1-1 (77 g, 0.262 mol) and triethylamine (86 mL, 0.393 mol) were introduced to MC (1200 mL) and dissolved therein. To the mixture, 1-pyrenecarbonyl chloride (104 g, 0.393 mol) dissolved in methylene chloride (300 mL) was slowly added dropwise at 0° C. After the reaction was completed, white solids in the reaction solution were filtered and washed with hexane. These were dried to obtain Compound 2-2 (75 g, 67%) in a solid form.

3) Preparation of Compound 2-3

After dissolving Compound 2-2 (86 g, 0.143 mol) in nitrobenzene (1500 mL), $POCl_3$ (20 mL, 0.215 mol) was slowly added dropwise thereto, and the result was reacted for 15 hours at 140° C. After the reaction was completed, a solution obtained by dissolving $NaHCO_3$ in distilled water was slowly introduced to the reaction solution, and the result was stirred. Solids produced after that were filtered and collected, and the collected solids were recrystallized in methylene chloride and methanol to obtain Compound 2-3 (29 g, 41%) in a solid form.

4) Preparation of Compound 2-4

After dissolving Compound 2-3 (29 g, 0.057 mol) in 1,4-dioxane (800 mL), $Pd_2(dba)_3$ (5.2 g, 0.0057 mol), XPhos (2.7 g, 0.0057 mol) and KOAc (16.7 g, 0.171 mol) were dissolved therein, and the result was reacted for 4 hours at 90° C. After the reaction was completed, water and MC were introduced to the reaction solution, and the result was extracted. After that, solids obtained by drying the result were recrystallized with methylene chloride and methanol to obtain Compound 2-4 (20 g, 60%) in a solid form.

5) Preparation of Compound 88

After dissolving Compound 2-4 (10 g, 0.017 mol) and 4-(3-bromophenyl)dibenzo[b,d]thiophene (5.7 g, 0.017 mol) in 1,4-dioxane:$H_2O$=100 mL:20 mL, $Pd(PPh_3)_4$ (1.96 g, 0.0017 mol) and $K_3PO_4$ (20.8 g, 0.051 mol) were introduced thereto, and the result was stirred for 5 hours at 100° C. After the reaction was completed, solids produced in the reaction solution were washed with 1,4-dioxane and $H_2O$. After that, only the solids were purified using a recrystallization method in dichlorobenzene (DCB) to obtain Compound 88 (4.9 g, 40%).

Target compounds were synthesized in the same manner as in Preparation Example 1 except that Intermediate A of the following Table 1 was used instead of 2-(4-bromophenyl)-4,6-diphenyl-1,3,5-triazine.

TABLE 1

| Compound | Intermediate A | Target Compound | Yield |
|---|---|---|---|
| 1 |  |  | 61% |
| 5 |  |  | 62% |

TABLE 1-continued

| Compound | Intermediate A | Target Compound | Yield |
|---|---|---|---|
| 7 | | | 51% |
| 8 | | | 60% |
| 9 | | | 61% |

TABLE 1-continued

| Compound | Intermediate A | Target Compound | Yield |
|---|---|---|---|
| 11 | | | 62% |
| 12 | | | 51% |
| 13 | | | 60% |
| 15 | | | 61% |

TABLE 1-continued

| Compound | Intermediate A | Target Compound | Yield |
|---|---|---|---|
| 16 | | | 62% |
| 17 | | | 51% |
| 18 | | | 60% |
| 24 | | | 61% |

TABLE 1-continued

| Compound | Intermediate A | Target Compound | Yield |
|---|---|---|---|
| 25 | | | 62% |
| 28 | | | 51% |
| 30 | | | 60% |
| 35 | | | 61% |

TABLE 1-continued
| Compound | Intermediate A | Target Compound | Yield |
|---|---|---|---|
| 36 | 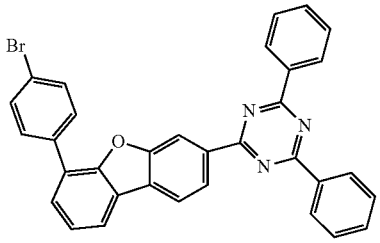 [SMILES: Brc1ccc(-c2cccc3c2oc2cc(-c4nc(-c5ccccc5)nc(-c5ccccc5)n4)ccc23)cc1] | 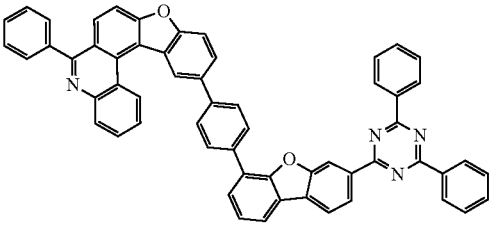 [SMILES: c1ccc(-c2nc(-c3ccccc3)nc(-c3ccc4c(c3)oc3c(-c5ccc(-c6ccc7oc8ccc9c(-c%10ccccc%10)nc%10ccccc%10c9c8c7c6)cc5)cccc34)n2)cc1] | 62% |
| 37 | 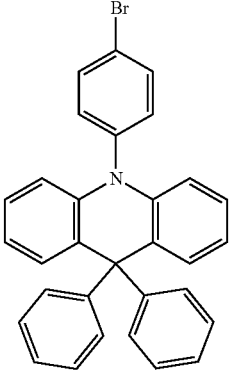 [SMILES: Brc1ccc(N2c3ccccc3C(c3ccccc3)(c3ccccc3)c3ccccc32)cc1] | 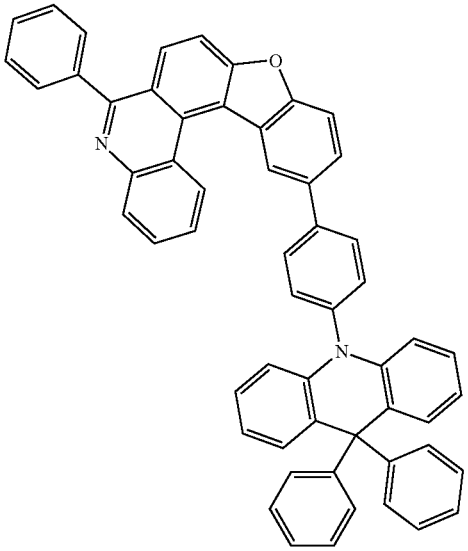 [SMILES: c1ccc(-c2nc3ccccc3c3c2ccc2oc4ccc(-c5ccc(N6c7ccccc7C(c7ccccc7)(c7ccccc7)c7ccccc76)cc5)cc4c23)cc1] | 51% |
| 38 | 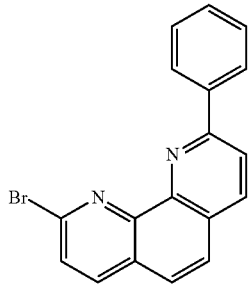 [SMILES: Brc1ccc2ccc3ccc(-c4ccccc4)nc3c2n1] | 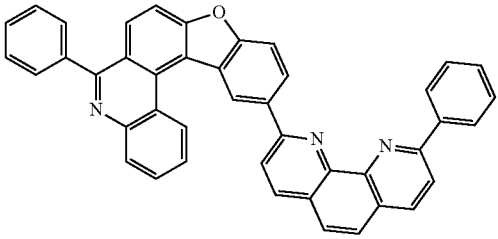 [SMILES: c1ccc(-c2ccc3ccc4ccc(-c5ccc6oc7ccc8c(-c9ccccc9)nc9ccccc9c8c7c6c5)nc4c3n2)cc1] | 60% |
| 41 | 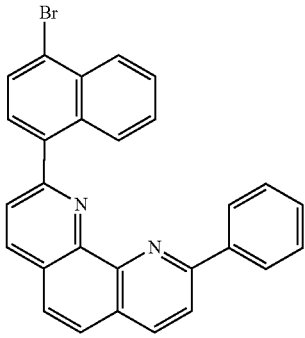 [SMILES: Brc1ccc(-c2ccc3ccc4ccc(-c5ccccc5)nc4c3n2)c2ccccc12] | 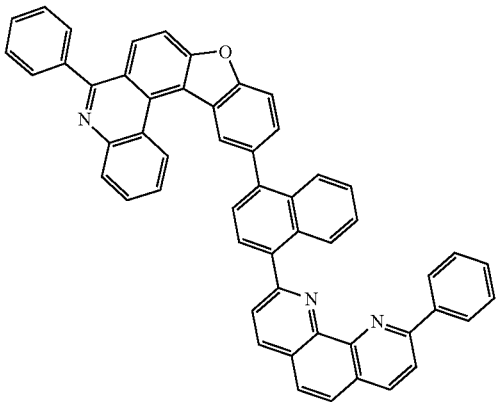 [SMILES: c1ccc(-c2ccc3ccc4ccc(-c5ccc(-c6ccc7oc8ccc9c(-c%10ccccc%10)nc%10ccccc%10c9c8c7c6)c6ccccc56)nc4c3n2)cc1] | 61% |

TABLE 1-continued

| Compound | Intermediate A | Target Compound | Yield |
|---|---|---|---|
| 42 | | | 62% |
| 44 | | | 51% |
| 45 | | | 60% |

TABLE 1-continued

| Compound | Intermediate A | Target Compound | Yield |
|---|---|---|---|
| 47 | | | 61% |
| 52 | | | 62% |
| 53 | | | 51% |

TABLE 1-continued
| Compound | Intermediate A | Target Compound | Yield |
|---|---|---|---|
| 56 | 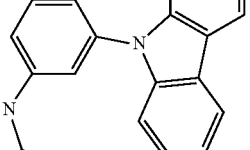 | 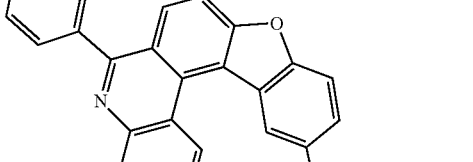 | 60% |
| 57 | 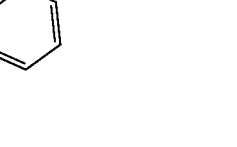 | 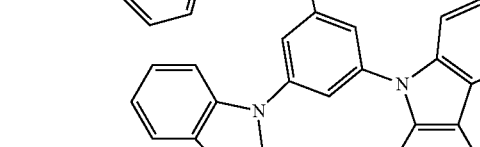 | 61% |
| 64 | 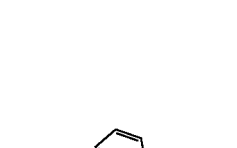 | 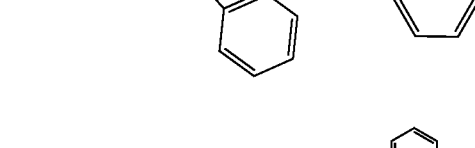 | 62% |
| 68 | 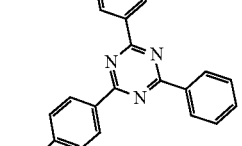 | 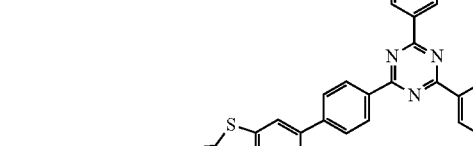 | 51% |

TABLE 1-continued

| Compound | Intermediate A | Target Compound | Yield |
|---|---|---|---|
| 69 | | | 60% |
| 70 | | | 61% |
| 72 | | | 62% |
| 75 | | | 51% |

TABLE 1-continued

| Compound | Intermediate A | Target Compound | Yield |
|---|---|---|---|
| 77 | | | 60% |
| 79 | | | 61% |
| 80 | | | 62% |
| 84 | | | 51% |

TABLE 1-continued

| Compound | Intermediate A | Target Compound | Yield |
|---|---|---|---|
| 86 | | | 60% |
| 89 | | | 62% |
| 91 | | | 51% |

TABLE 1-continued

| Compound | Intermediate A | Target Compound | Yield |
|---|---|---|---|
| 92 | | | 60% |
| 97 | | | 61% |
| 100 | | | 62% |

TABLE 1-continued

| Compound | Intermediate A | Target Compound | Yield |
|---|---|---|---|
| 102 | | | 51% |
| 103 | | | 60% |
| 107 | | | 61% |

TABLE 1-continued

| Compound | Intermediate A | Target Compound | Yield |
|---|---|---|---|
| 112 | | | 62% |
| 113 | | | 51% |
| 114 | | | 60% |

TABLE 1-continued

| Compound | Intermediate A | Target Compound | Yield |
|---|---|---|---|
| 116 | | | 61% |
| 119 | | | 62% |
| 120 | | | 51% |

TABLE 1-continued

| Compound | Intermediate A | Target Compound | Yield |
|---|---|---|---|
| 132 | | | 62% |
| 133 | | | 51% |
| 135 | | | 60% |
| 139 | | | 61% |

TABLE 1-continued

| Compound | Intermediate A | Target Compound | Yield |
|---|---|---|---|
| 140 | | | 62% |
| 141 | | | 51% |
| 142 | | | 60% |

Target compounds were synthesized in the same manner as in Preparation Example 2 except that Intermediate 1 of the following Table 2 was used instead of 1-pyrenecarbonyl chloride, and Intermediate B of the following Table 2 was used instead of 4-(3-bromophenyl)dibenzo[b,d]thiophene.

TABLE 2

| | Intermediate B | Intermediate 1 | Target Compound | |
|---|---|---|---|---|
| 121 | | | | 60% |
| 128 | | | | 61% |

Target compounds were synthesized in the same manner as in Preparation Example 1 except that 6-bromo-2-chlorodibenzo[b,d]furan was used instead of 1-bromo-8-chlorodibenzo[b,d]furan, and Intermediate C of the following Table 3 was used instead of 2-(4-bromophenyl)-4,6-diphenyl-1,3,5-triazine.

TABLE 3

| Compound | Intermediate C | Target Compound | Yield |
|---|---|---|---|
| 58 | | | 62% |
| 156 | | | 65% |
| 157 | | | 65% |
| 159 | | | 62% |

TABLE 3-continued

| Compound | Intermediate C | Target Compound | Yield |
|---|---|---|---|
| 161 | | | 51% |
| 165 | | | 60% |
| 166 | | | 61% |
| 170 | | | 62% |

TABLE 3-continued

| Compound | Intermediate C | Target Compound | Yield |
| --- | --- | --- | --- |
| 171 | | | 65% |
| 172 | | | 65% |
| 173 | | | 62% |
| 178 | | | 60% |

TABLE 3-continued
| Compound | Intermediate C | Target Compound | Yield |
|---|---|---|---|
| 179 | 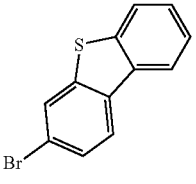 | 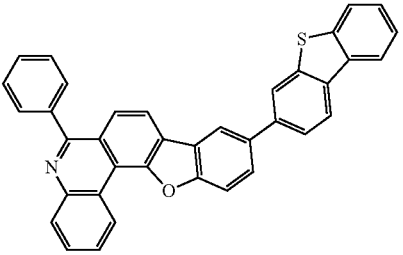 [SMILES: c1ccc(-c2nc3ccccc3c3c2ccc2c4cc(-c5ccc6c(c5)sc5ccccc56)ccc4oc23)cc1] | 61% |
| 180 | 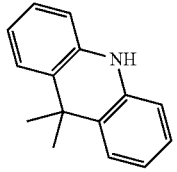 [SMILES: CC1(C)c2ccccc2Nc2ccccc21] | 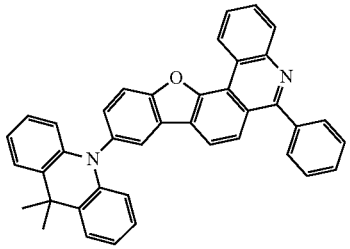 [SMILES: CC1(C)c2ccccc2N(c2ccc3oc4c(ccc5c(-c6ccccc6)nc6ccccc6c54)c3c2)c2ccccc21] | 60% |
| 185 | 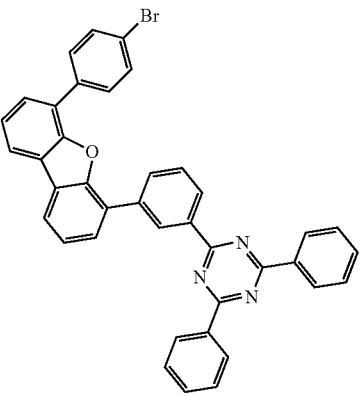 [SMILES: Brc1ccc(-c2cccc3c2oc2c(-c4cccc(-c5nc(-c6ccccc6)nc(-c6ccccc6)n5)c4)cccc23)cc1] | 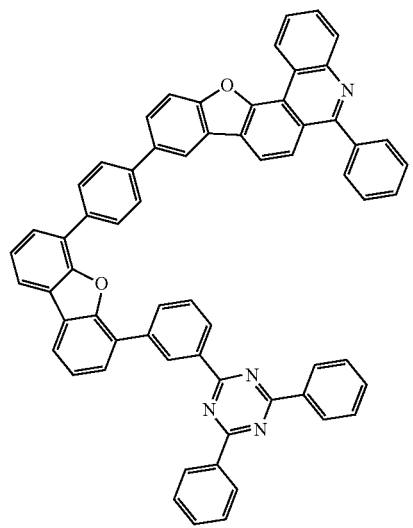 [SMILES: c1ccc(-c2nc(-c3ccccc3)nc(-c3cccc(-c4cccc5c4oc4c(-c6ccc(-c7ccc8oc9c(ccc%10c(-c%11ccccc%11)nc%11ccccc%11c%109)c8c7)cc6)cccc45)c3)n2)cc1] | 62% |
| 187 | 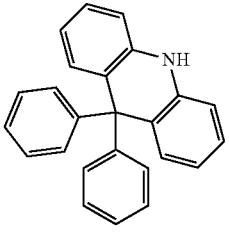 [SMILES: c1ccc(C2(c3ccccc3)c3ccccc3Nc3ccccc32)cc1] | 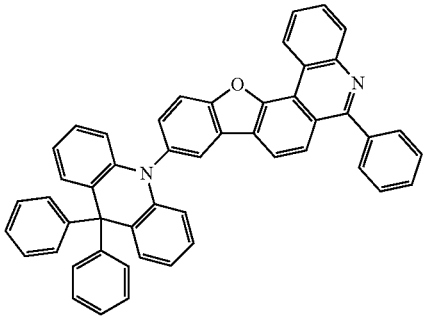 [SMILES: c1ccc(-c2nc3ccccc3c3c2ccc2c4cc(N5c6ccccc6C(c6ccccc6)(c6ccccc6)c6ccccc65)ccc4oc23)cc1] | 65% |

TABLE 3-continued
| Compound | Intermediate C | Target Compound | Yield |
|---|---|---|---|
| 190 | 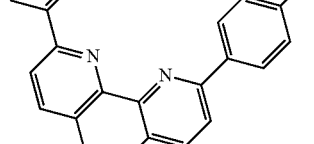 | 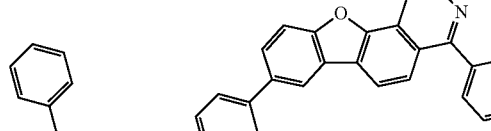 | 65% |
| 191 |  |  | 62% |
| 192 |  |  | 51% |
| 194 |  | 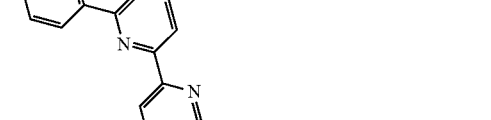 | 60% |

TABLE 3-continued

| Compound | Intermediate C | Target Compound | Yield |
|---|---|---|---|
| 195 | | | 61% |
| 196 | | | 60% |
| 200 | | | 55% |

Target compounds were synthesized in the same manner as in Preparation Example 2 except that Intermediate 2 of the following Table 4 was used instead of 1-pyrenecarbonyl chloride, 6-bromo-2-chlorodibenzo[b,d]furan was used instead of 1-bromo-8-chlorodibenzo[b,d]furan, and Intermediate D of the following Table 4 was used instead of 4-3 bromophenyl)dibenzo[b,d]thiophene.

TABLE 4

| | Intermediate D | Intermediate 2 | Target Compound | |
|---|---|---|---|---|
| 168 | 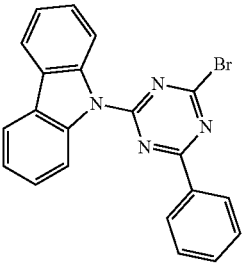 [SMILES: Brc1nc(-c2ccccc2)nc(-n2c3ccccc3c3ccccc32)n1] | 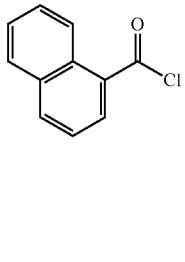 [SMILES: O=C(Cl)c1cccc2ccccc12] | 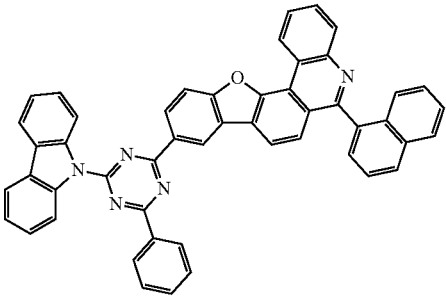 [SMILES: c1ccc(-c2nc(-c3ccc4oc5c(ccc6c(-c7cccc8ccccc78)nc7ccccc7c65)c4c3)nc(-n3c4ccccc4c4ccccc43)n2)cc1] | 60% |
| 176 | 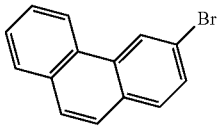 [SMILES: Brc1ccc2ccc3ccccc3c2c1] | 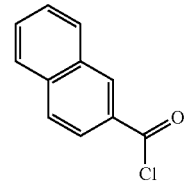 [SMILES: O=C(Cl)c1ccc2ccccc2c1] | 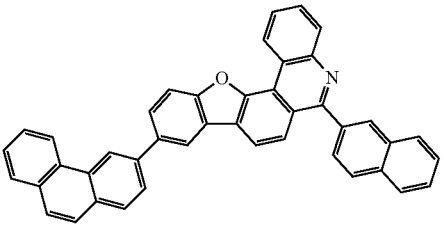 [SMILES: c1ccc2cc(-c3nc4ccccc4c4c3ccc3c5cc(-c6ccc7ccc8ccccc8c7c6)ccc5oc34)ccc2c1] | 61% |

A target compound was synthesized in the same manner as in Preparation Example 1 except that 2-bromo-8-chlorodibenzo[b,d]furan was used instead of 1-bromo-8-chlorodibenzo[b,d]furan, and Intermediate E of the following Table 5 was used instead of 2-(4-bromophenyl)-4,6-diphenyl-1,3,5-triazine.

TABLE 5

| Compound | Intermediate E | Target Compound | Yield |
|---|---|---|---|
| 149 | 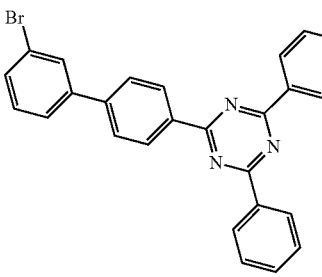 | 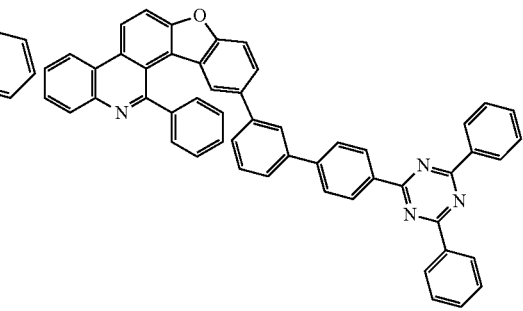 | 52% |

A target compound was synthesized in the same manner as in Preparation Example 2 except that Intermediate 3 of the following Table 6 was used instead of 1-pyrenecarbonyl chloride, 2-bromo-8-chlorodibenzo[b,d]furan was used instead of 1-bromo-8-chlorodibenzo[b,d]furan, and Intermediate F of the following Table 6 was used instead of 4-(3-bromophenyl)dibenzo[b,d]thiophene.

TABLE 6

| Compound | Intermediate F | Intermediate 3 | Target Compound | Yield |
|---|---|---|---|---|
| 145 | 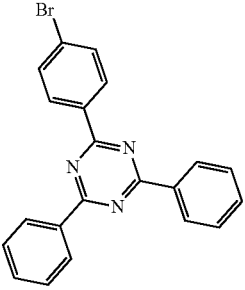 [SMILES: Brc1ccc(-c2nc(-c3ccccc3)nc(-c3ccccc3)n2)cc1] | 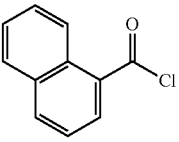 [SMILES: O=C(Cl)c1cccc2ccccc12] | 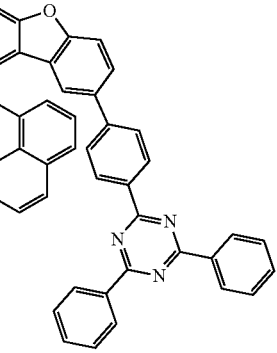 | 53% |

Target compounds were synthesized in the same manner as in Preparation Example 1 except that 1-bromo-6-chlorodibenzo[b,d]furan was used instead of 1-bromo-8-chlorodibenzo[b,d]furan, and Intermediate G of the following Table 7 was used instead of 2-(4-bromophenyl)-4,6-diphenyl-1,3,5-triazine.

TABLE 7

| Compound | Intermediate G | Target Compound | Yield |
|---|---|---|---|
| 384 | 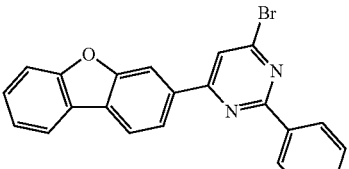 | 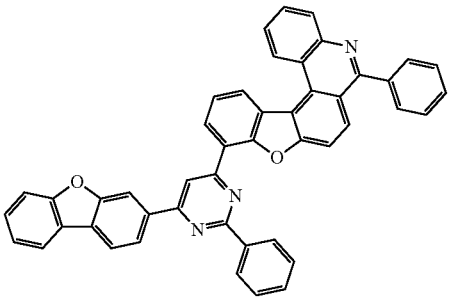 [SMILES: c1ccc(-c2nc(-c3ccc4c(c3)oc3ccccc34)cc(-c3cccc4c3oc3ccc5c(-c6ccccc6)nc6ccccc6c5c34)n2)cc1] | 53% |
| 386 | 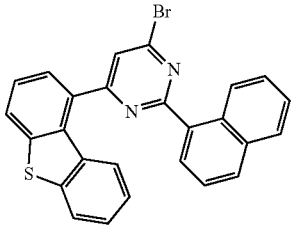 [SMILES: Brc1cc(-c2cccc3sc4ccccc4c23)nc(-c2cccc3ccccc23)n1] | 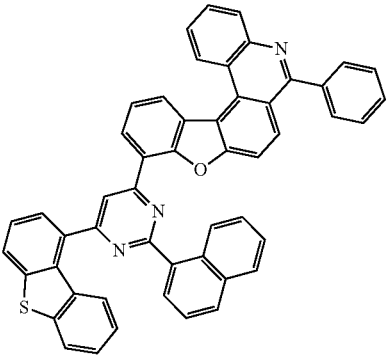 [SMILES: c1ccc(-c2nc3ccccc3c3c2ccc2oc4c(-c5cc(-c6cccc7sc8ccccc8c67)nc(-c6cccc7ccccc67)n5)cccc4c23)cc1] | 62% |
| 387 | 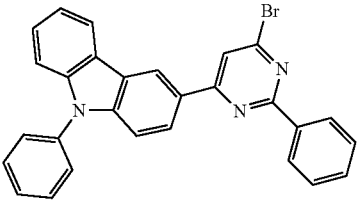 [SMILES: Brc1cc(-c2ccc3c(c2)c2ccccc2n3-c2ccccc2)nc(-c2ccccc2)n1] | 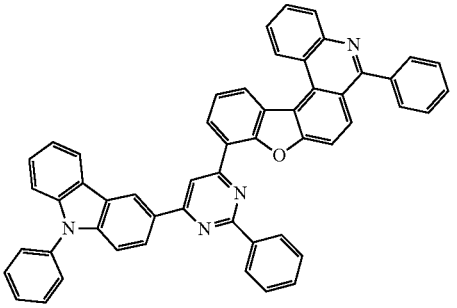 [SMILES: c1ccc(-c2nc(-c3ccc4c(c3)c3ccccc3n4-c3ccccc3)cc(-c3cccc4c3oc3ccc5c(-c6ccccc6)nc6ccccc6c5c34)n2)cc1] | 65% |

TABLE 7-continued

| Compound | Intermediate G | Target Compound | Yield |
|---|---|---|---|
| 388 | | | 65% |
| 392 | | | 62% |
| 395 | | | 51% |
| 396 | | | 60% |

TABLE 7-continued

| Compound | Intermediate G | Target Compound | Yield |
|---|---|---|---|
| 397 | | | 61% |
| 399 | | | 60% |
| 400 | | | 62% |
| 401 | | | 65% |

TABLE 7-continued

| Compound | Intermediate G | Target Compound | Yield |
|---|---|---|---|
| 404 | | | 65% |
| 408 | | | 51% |
| 409 | | | 60% |
| 411 | | | 61% |

TABLE 7-continued
| Compound | Intermediate G | Target Compound | Yield |
|---|---|---|---|
| 413 | 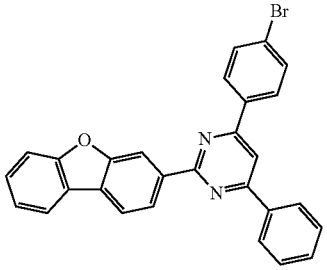 [SMILES: Brc1ccc(-c2cc(-c3ccccc3)nc(-c3ccc4c(c3)oc3ccccc34)n2)cc1] | 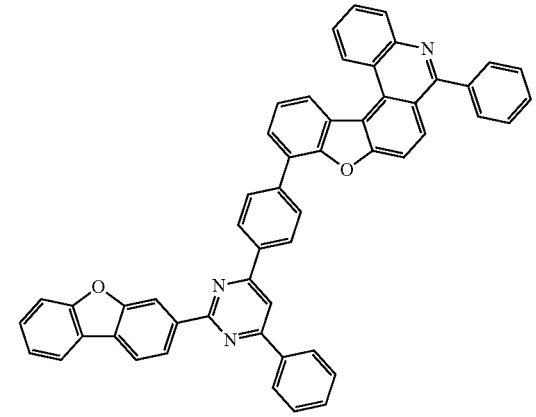 [SMILES: c1ccc(-c2cc(-c3ccc(-c4cccc5c4oc4ccc6c(-c7ccccc7)nc7ccccc7c6c45)cc3)nc(-c3ccc4c(c3)oc3ccccc34)n2)cc1] | 60% |
| 415 | 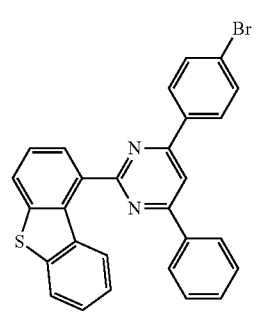 [SMILES: Brc1ccc(-c2cc(-c3ccccc3)nc(-c3cccc4sc5ccccc5c34)n2)cc1] | 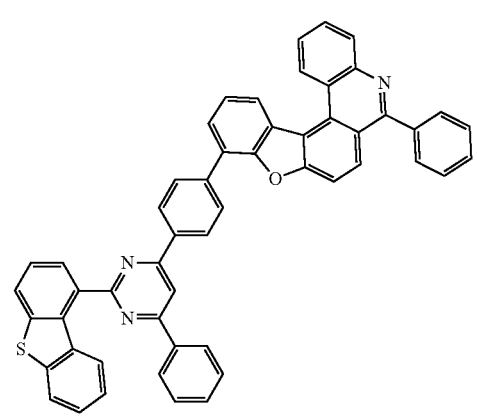 [SMILES: c1ccc(-c2cc(-c3ccc(-c4cccc5c4oc4ccc6c(-c7ccccc7)nc7ccccc7c6c45)cc3)nc(-c3cccc4sc5ccccc5c34)n2)cc1] | 62% |
| 416 | 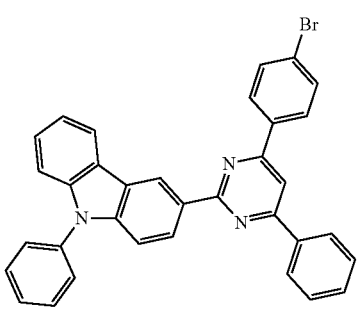 [SMILES: Brc1ccc(-c2cc(-c3ccccc3)nc(-c3ccc4c(c3)c3ccccc3n4-c3ccccc3)n2)cc1] | 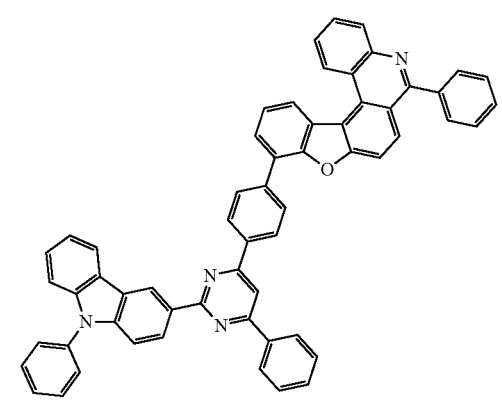 [SMILES: c1ccc(-c2cc(-c3ccc(-c4cccc5c4oc4ccc6c(-c7ccccc7)nc7ccccc7c6c45)cc3)nc(-c3ccc4c(c3)c3ccccc3n4-c3ccccc3)n2)cc1] | 65% |

TABLE 7-continued

| Compound | Intermediate G | Target Compound | Yield |
|---|---|---|---|
| 417 | 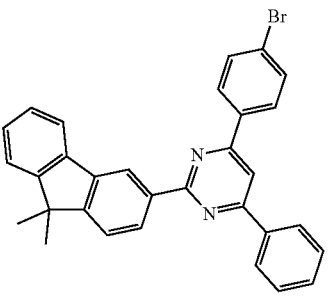 [SMILES: CC1(C)c2ccccc2-c2cc(-c3nc(-c4ccccc4)cc(-c4ccc(Br)cc4)n3)ccc21] | 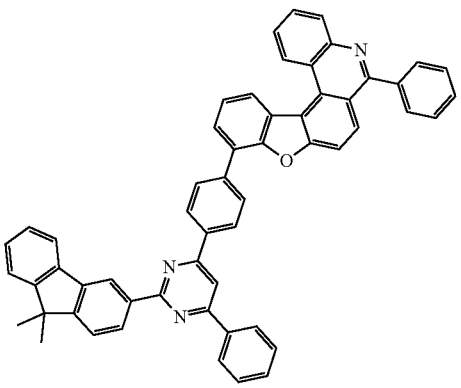 [SMILES: CC1(C)c2ccccc2-c2cc(-c3nc(-c4ccccc4)cc(-c4ccc(-c5cccc6c5oc5ccc7c(-c8ccccc8)nc8ccccc8c7c56)cc4)n3)ccc21] | 65% |

A target compound was synthesized in the same manner as in Preparation Example 2 except that Intermediate 4 of the following Table 8 was used instead of 1-pyrenecarbonyl chloride, 1-bromo-6-chlorodibenzo[b,d]furan was used instead of 1-bromo-8-chlorodibenzo[b,d]furan, and Intermediate H of the following Table 8 was used instead of 4-3 bromophenyl)dibenzo[b,d]thiophene.

TABLE 8

| Compound | Intermediate H | Intermediate 4 | Target Compound | Yield |
|---|---|---|---|---|
| 407 | 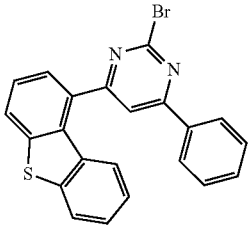 [SMILES: Brc1nc(-c2ccccc2)cc(-c2cccc3sc4ccccc4c23)n1] | 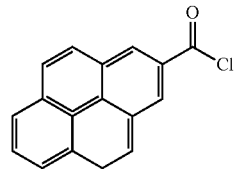 | 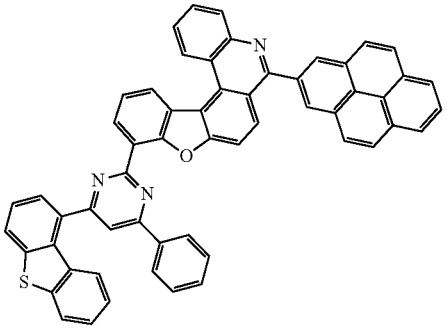 [SMILES: c1ccc(-c2cc(-c3cccc4sc5ccccc5c34)nc(-c3cccc4c3oc3ccc5c(-c6cc7ccc8cccc9ccc(c6)c7c89)nc6ccccc6c5c34)n2)cc1] | 53% |

Target compounds were synthesized in the same manner as in Preparation Example 1 except that 4,6-dibromodibenzo[b,d]furan was used instead of 1-bromo-8-chlorodibenzo[b,d]furan, and Intermediate I of the following Table 9 was used instead of 2-(4-bromophenyl)-4,6-diphenyl-1,3,5-triazine.

TABLE 9

| Compound | Intermediate I | Target Compound | Yield |
|---|---|---|---|
| 421 | | | 53% |
| 423 | | | 62% |
| 424 | | | 65% |

TABLE 9-continued

| Compound | Intermediate I | Target Compound | Yield |
|---|---|---|---|
| 426 | | | 65% |
| 431 | | | 62% |
| 432 | | | 51% |

TABLE 9-continued

| Compound | Intermediate I | Target Compound | Yield |
|---|---|---|---|
| 433 | | | 60% |
| 436 | | | 61% |
| 438 | | | 60% |

TABLE 9-continued

| Compound | Intermediate I | Target Compound | Yield |
|---|---|---|---|
| 440 | | | 62% |
| 441 | | | 65% |
| 443 | | | 65% |

TABLE 9-continued

| Compound | Intermediate I | Target Compound | Yield |
|---|---|---|---|
| 447 | | | 62% |
| 448 | | | 51% |
| 449 | | | 60% |

TABLE 9-continued

| Compound | Intermediate I | Target Compound | Yield |
|---|---|---|---|
| 450 | | | 61% |
| 452 | | | 60% |
| 456 | | | 62% |

TABLE 9-continued

| Compound | Intermediate I | Target Compound | Yield |
|---|---|---|---|
| 460 | | | 65% |
| 462 | | | 65% |
| 465 | | | 62% |
| 467 | | | 51% |

TABLE 9-continued

| Compound | Intermediate I | Target Compound | Yield |
|---|---|---|---|
| 470 | | | 61% |
| 475 | | | 60% |
| 476 | | | 62% |

TABLE 9-continued

| Compound | Intermediate I | Target Compound | Yield |
|---|---|---|---|
| 477 | | | 65% |
| 479 | | | 65% |
| 481 | | | 62% |

TABLE 9-continued

| Compound | Intermediate I | Target Compound | Yield |
| --- | --- | --- | --- |
| 482 | | | 51% |
| 485 | | | 60% |
| 488 | | | 61% |

TABLE 9-continued

| Compound | Intermediate I | Target Compound | Yield |
|---|---|---|---|
| 489 | | | 60% |
| 490 | | | 62% |
| 493 | | | 65% |
| 494 | | | 65% |

TABLE 9-continued

| Compound | Intermediate I | Target Compound | Yield |
|---|---|---|---|
| 495 | | | 62% |
| 500 | | | 51% |
| 504 | | | 60% |
| 505 | | | 61% |

TABLE 9-continued

| Compound | Intermediate I | Target Compound | Yield |
|---|---|---|---|
| 506 | | | 60% |
| 507 | | | 62% |
| 512 | | | 65% |

TABLE 9-continued

| Compound | Intermediate I | Target Compound | Yield |
|---|---|---|---|
| 513 | | | 65% |
| 516 | | | 62% |
| 517 | | | 51% |

TABLE 9-continued

| Compound | Intermediate I | Target Compound | Yield |
|---|---|---|---|
| 518 | | | 60% |
| 519 | | | 61% |
| 520 | | | 60% |

TABLE 9-continued
| Compound | Intermediate I | Target Compound | Yield |
| --- | --- | --- | --- |
| 524 | 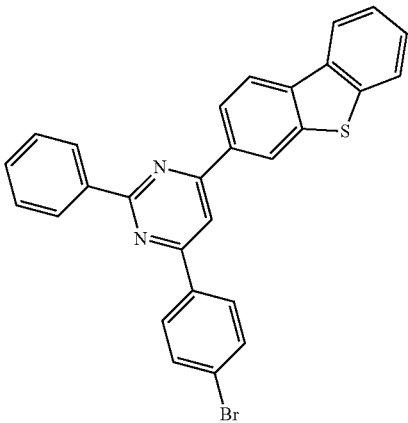 [SMILES: Brc1ccc(-c2cc(-c3ccc4c(c3)sc3ccccc34)nc(-c3ccccc3)n2)cc1] | 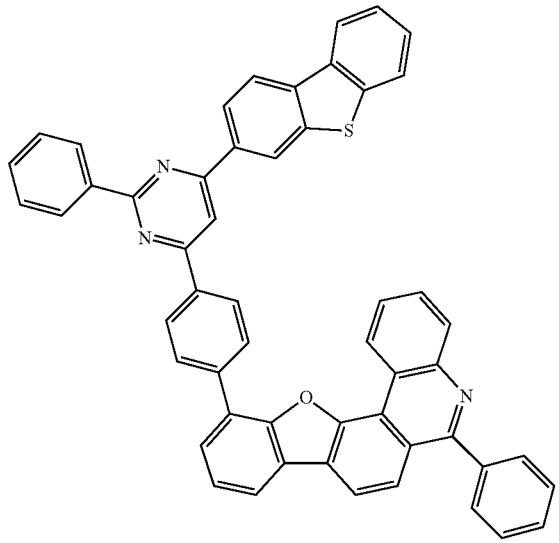 [SMILES: c1ccc(-c2nc(-c3ccc(-c4cccc5c4oc4c5ccc5c(-c6ccccc6)nc6ccccc6c54)cc3)cc(-c3ccc4c(c3)sc3ccccc34)n2)cc1] | 65% |
| 525 | 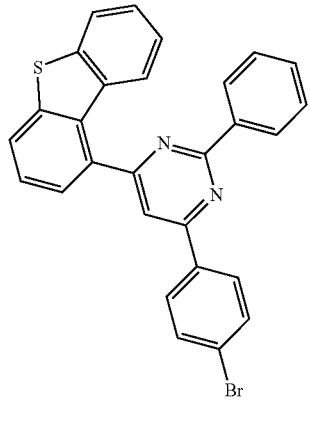 [SMILES: Brc1ccc(-c2cc(-c3cccc4sc5ccccc5c34)nc(-c3ccccc3)n2)cc1] | 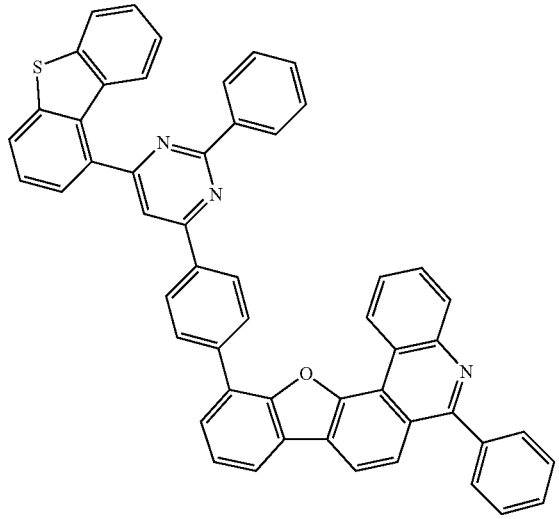 | 65% |

TABLE 9-continued

| Compound | Intermediate I | Target Compound | Yield |
|---|---|---|---|
| 527 | | | 62% |
| 528 | | | 51% |
| 531 | | | 60% |

TABLE 9-continued
| Compound | Intermediate I | Target Compound | Yield |
|---|---|---|---|
| 532 | 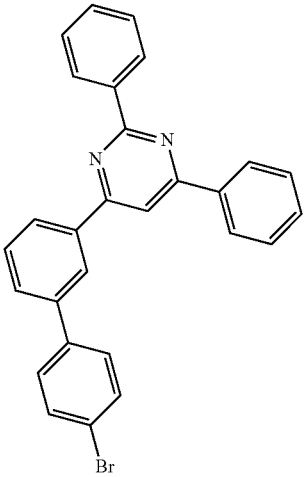 [SMILES: Brc1ccc(-c2cccc(-c3cc(-c4ccccc4)nc(-c4ccccc4)n3)c2)cc1] | 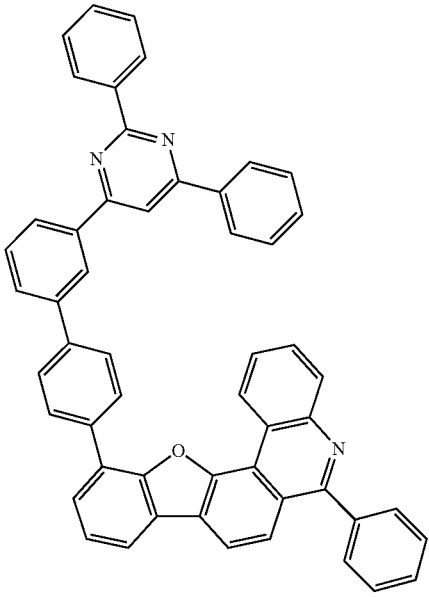 [SMILES: c1ccc(-c2cc(-c3cccc(-c4ccc(-c5cccc6c5oc5c6ccc6c(-c7ccccc7)nc7ccccc7c65)cc4)c3)nc(-c3ccccc3)n2)cc1] | 61% |
| 533 | 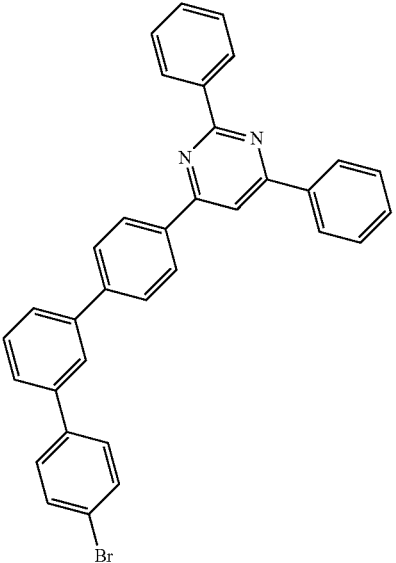 [SMILES: Brc1ccc(-c2cccc(-c3ccc(-c4cc(-c5ccccc5)nc(-c5ccccc5)n4)cc3)c2)cc1] | 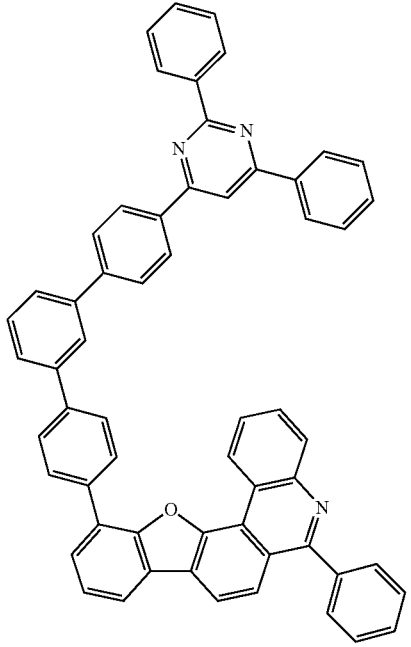 [SMILES: c1ccc(-c2cc(-c3ccc(-c4cccc(-c5ccc(-c6cccc7c6oc6c7ccc7c(-c8ccccc8)nc8ccccc8c76)cc5)c4)cc3)nc(-c3ccccc3)n2)cc1] | 60% |

TABLE 9-continued

| Compound | Intermediate I | Target Compound | Yield |
|---|---|---|---|
| 535 | | | 62% |
| 536 | | | 65% |
| 539 | | | 65% |
| 542 | | | 62% |

TABLE 9-continued

| Compound | Intermediate I | Target Compound | Yield |
|---|---|---|---|
| 543 | | | 51% |
| 544 | | | 60% |
| 547 | | | 61% |

TABLE 9-continued

| Compound | Intermediate I | Target Compound | Yield |
|---|---|---|---|
| 549 | | | 62% |
| 550 | | | 65% |

Target compounds were synthesized in the same manner as in Preparation Example 2 except that Intermediate 5 of the following Table 10 was used instead of 1-pyrenecarbonyl chloride, 4,6-dibromodibenzo[b,d]furan was used instead of 1-bromo-8-chlorodibenzo[b,d]furan, and Intermediate I of the following Table 10 was used instead of 4-(3-bromophenyl)dibenzo[b,d]thiophene.

TABLE 10
| Compound | Intermediate I | Intermediate 5 | Target Compound | Yield |
|---|---|---|---|---|
| 468 | 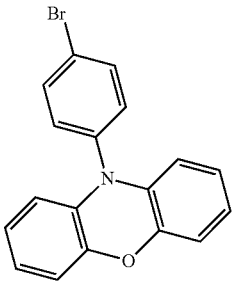 [SMILES: Brc1ccc(N2c3ccccc3Oc3ccccc32)cc1] | 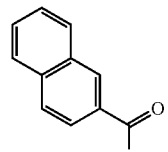 | 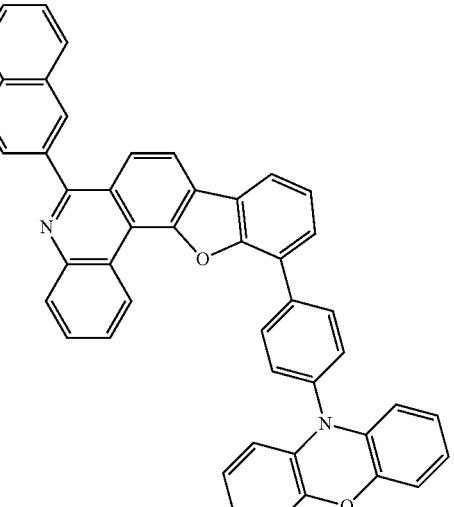 | 53% |
| 522 | 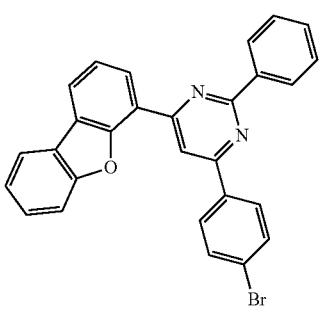 [SMILES: Brc1ccc(-c2cc(-c3cccc4c3oc3ccccc34)nc(-c3ccccc3)n2)cc1] | 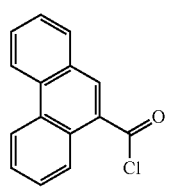 [SMILES: O=C(Cl)c1cc2ccccc2c2ccccc12] | 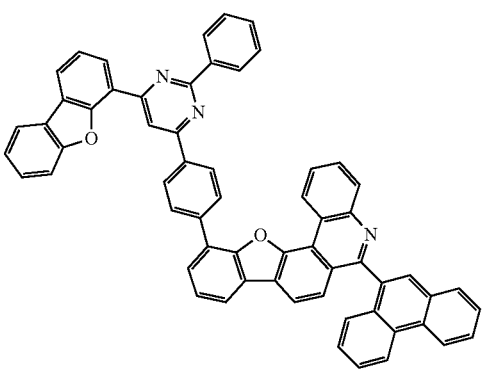 [SMILES: c1ccc(-c2nc(-c3ccc(-c4cccc5c4oc4c5ccc5c(-c6cc7ccccc7c7ccccc67)nc6ccccc6c54)cc3)cc(-c3cccc4c3oc3ccccc34)n2)cc1] | 52% |
| 548 | 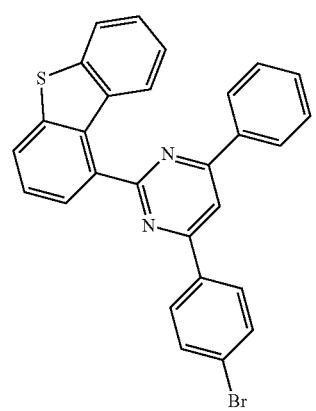 [SMILES: Brc1ccc(-c2cc(-c3ccccc3)nc(-c3cccc4sc5ccccc5c34)n2)cc1] | 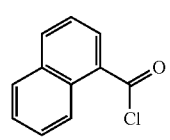 | 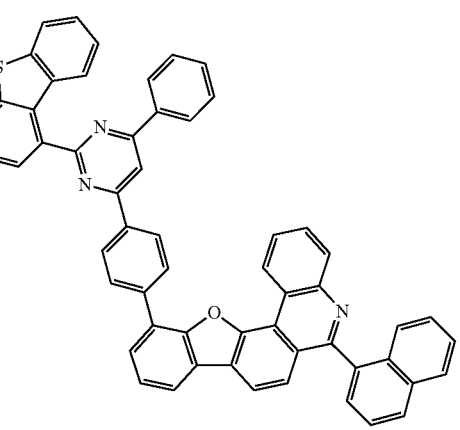 | 50% |
Target compounds were synthesized in the same manner as in Preparation Example 1 except that 1-chloro-6-fluorodibenzo[b,d]furan was used instead of 1-bromo-8-chlorodibenzo[b,d]furan, and Intermediate J of the following Table 11 was used instead of 2-(4-bromophenyl)-4,6-diphenyl-1,3,5-triazine.

TABLE 11

| Compound | Intermediate J | Target Compound | Yield |
|---|---|---|---|
| 554 | | | 53% |
| 555 | | | 62% |

TABLE 11-continued
| Compound | Intermediate J | Target Compound | Yield |
|---|---|---|---|
| 557 | 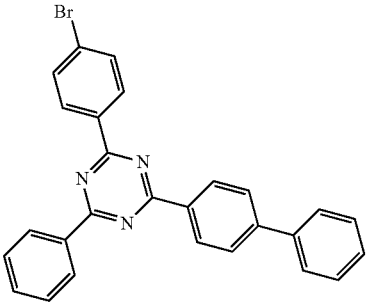 [SMILES: Brc1ccc(-c2nc(-c3ccccc3)nc(-c3ccc(-c4ccccc4)cc3)n2)cc1] | 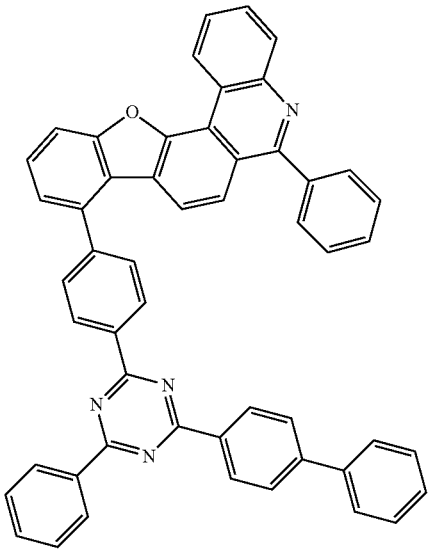 [SMILES: c1ccc(-c2ccc(-c3nc(-c4ccccc4)nc(-c4ccc(-c5cccc6oc7c(ccc8c(-c9ccccc9)nc9ccccc9c87)c56)cc4)n3)cc2)cc1] | 65% |
| 558 | 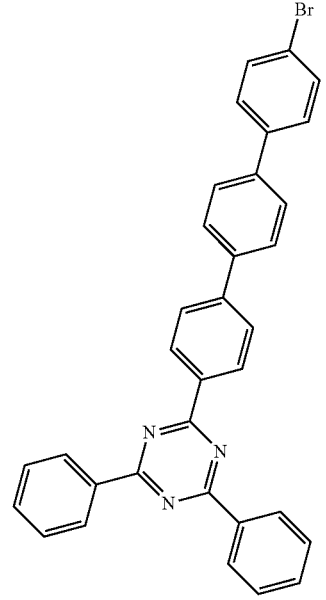 [SMILES: Brc1ccc(-c2ccc(-c3ccc(-c4nc(-c5ccccc5)nc(-c5ccccc5)n4)cc3)cc2)cc1] | 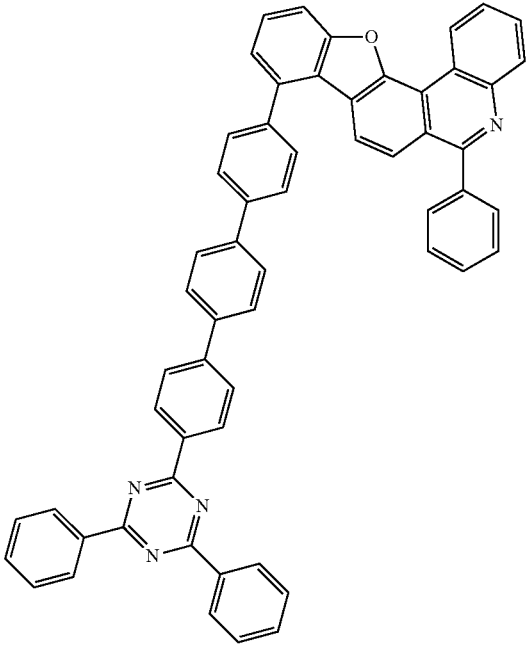 [SMILES: c1ccc(-c2nc(-c3ccccc3)nc(-c3ccc(-c4ccc(-c5ccc(-c6cccc7oc8c(ccc9c(-c%10ccccc%10)nc%10ccccc%10c98)c67)cc5)cc4)cc3)n2)cc1] | 65% |

TABLE 11-continued

| Compound | Intermediate J | Target Compound | Yield |
| --- | --- | --- | --- |
| 564 | | | 62% |
| 565 | | | 51% |
| 566 | | | 60% |

TABLE 11-continued
| Compound | Intermediate J | Target Compound | Yield |
|---|---|---|---|
| 569 | 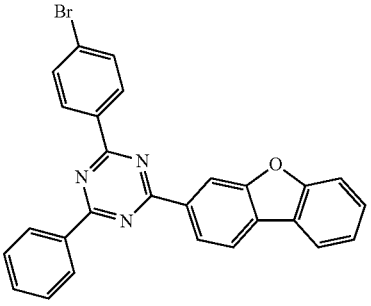 [SMILES: Brc1ccc(-c2nc(-c3ccccc3)nc(-c3ccc4c(c3)oc3ccccc34)n2)cc1] | 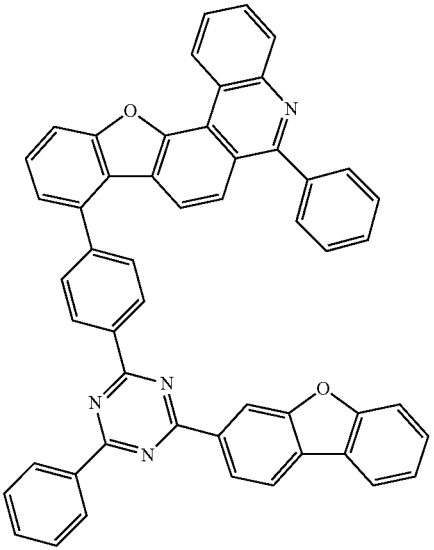 [SMILES: c1ccc(-c2nc(-c3ccc(-c4cccc5oc6c(ccc7c(-c8ccccc8)nc8ccccc8c76)c45)cc3)nc(-c3ccc4c(c3)oc3ccccc34)n2)cc1] | 61% |
| 573 | 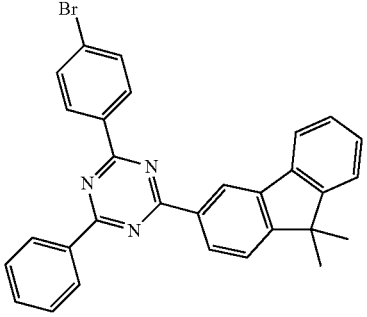 [SMILES: CC1(C)c2ccccc2-c2cc(-c3nc(-c4ccccc4)nc(-c4ccc(Br)cc4)n3)ccc21] | 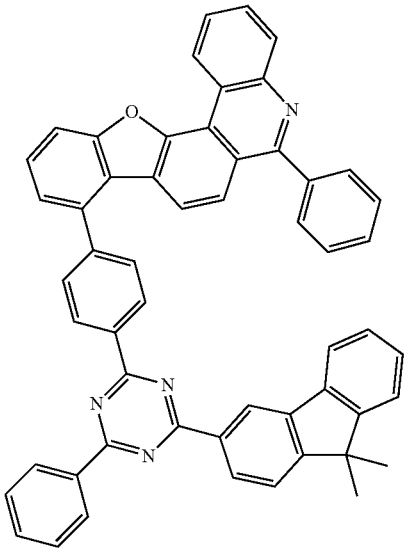 [SMILES: CC1(C)c2ccccc2-c2cc(-c3nc(-c4ccccc4)nc(-c4ccc(-c5cccc6oc7c(ccc8c(-c9ccccc9)nc9ccccc9c87)c56)cc4)n3)ccc21] | 60% |

TABLE 11-continued

| Compound | Intermediate J | Target Compound | Yield |
|---|---|---|---|
| 574 | | | 62% |
| 580 | | | 65% |
| 583 | | | 65% |

TABLE 11-continued

| Compound | Intermediate J | Target Compound | Yield |
|---|---|---|---|
| 584 | | | 62% |
| 585 | | | 51% |
| 587 | | | 60% |

TABLE 11-continued

| Compound | Intermediate J | Target Compound | Yield |
|---|---|---|---|
| 588 | | | 61% |
| 594 | | | 60% |

Target compounds were synthesized in the same manner as in Preparation Example 1 except that 7-chloro-1-fluorodibenzo[b,d]furan was used instead of 1-bromo-8-chlorodibenzo[b,d]furan, and Intermediate K of the following Table 12 was used instead of 2-(4-bromophenyl)-4,6-diphenyl-1,3,5-triazine.

TABLE 12

| Compound | Intermediate K | Target Compound | Yield |
| --- | --- | --- | --- |
| 597 | | | 53% |
| 598 | | | 62% |
| 599 | | | 65% |

TABLE 12-continued

| Compound | Intermediate K | Target Compound | Yield |
|---|---|---|---|
| 600 | | | 65% |
| 601 | | | 62% |
| 605 | | | 51% |

TABLE 12-continued

| Compound | Intermediate K | Target Compound | Yield |
|---|---|---|---|
| 606 | | | 60% |
| 611 | | | 61% |
| 612 | | | 60% |
| 615 | | | 51% |

TABLE 12-continued
| Compound | Intermediate K | Target Compound | Yield |
|---|---|---|---|
| 618 | 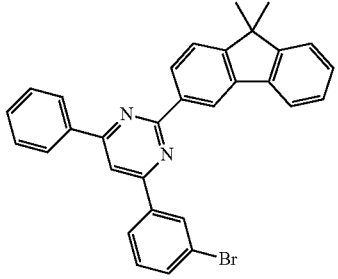 | 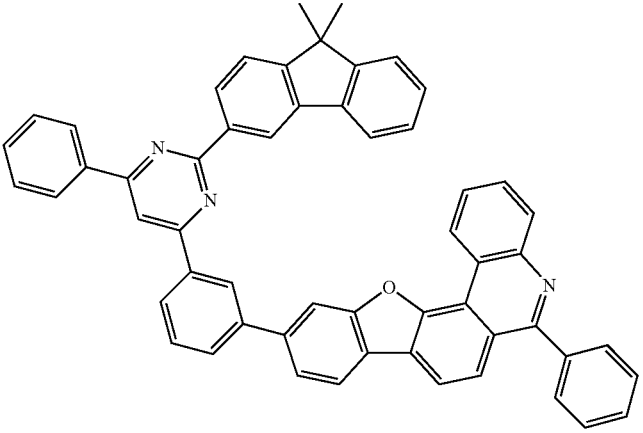 | 50% |
Target compounds were synthesized in the same manner as in Preparation Example 1 except that 1-bromo-8-chlorodibenzo[b,d]thiophene was used instead of 1-bromo-8-chlorodibenzo[b,d]furan, and Intermediate L of the following Table 13 was used instead of 2-(4-bromophenyl)-4,6-diphenyl-1,3,5-triazine.

TABLE 13

| Compound | Intermediate L | Target Compound | Yield |
|---|---|---|---|
| 623 | (structure) | (structure) | 62% |

TABLE 13-continued
| Compound | Intermediate L | Target Compound | Yield |
|---|---|---|---|
| 624 | 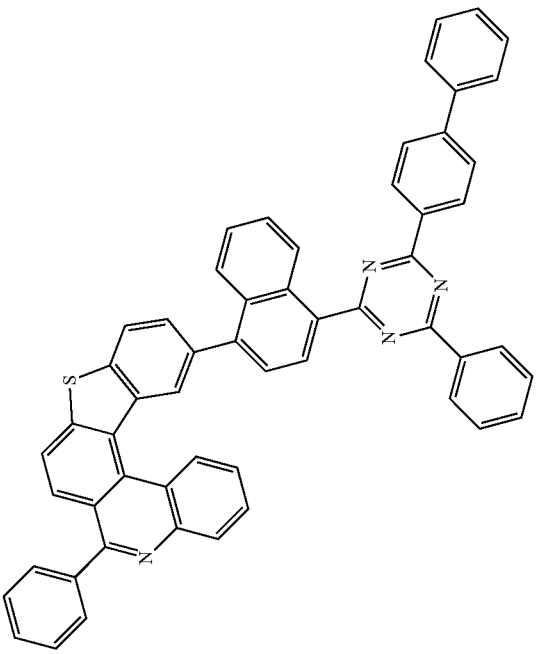 | 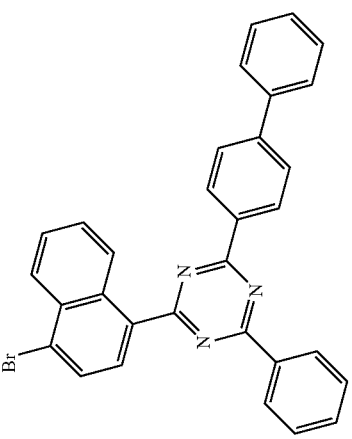 | 65% |

TABLE 13-continued

| Compound | Intermediate L | Target Compound | Yield |
|---|---|---|---|
| 626 | | | 65% |
| 629 | | | 62% |

TABLE 13-continued
| Compound | Intermediate L | Target Compound | Yield |
|---|---|---|---|
| 632 | 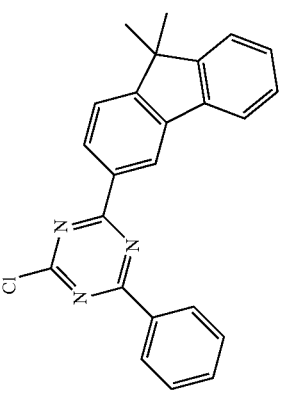 | 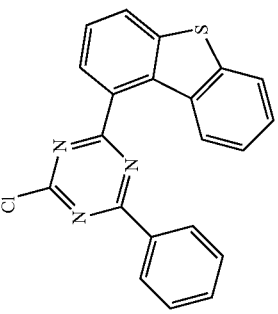 | 51% |
| 634 | 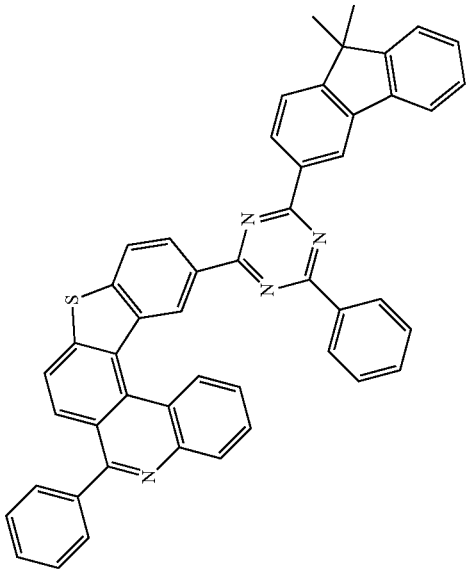 | 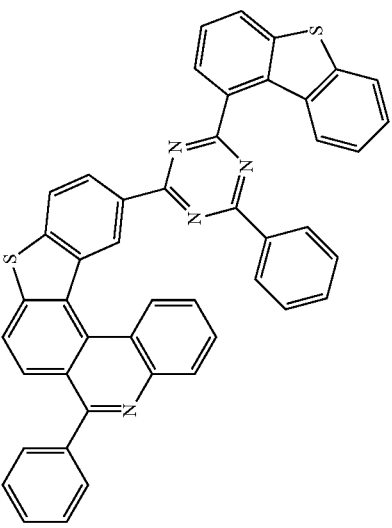 | 60% |

TABLE 13-continued

| Compound | Intermediate L | Target Compound | Yield |
|---|---|---|---|
| 635 | | | 61% |
| 636 | | | 60% |

TABLE 13-continued

| Compound | Intermediate L | Target Compound | Yield |
|---|---|---|---|
| 640 | | | 62% |

TABLE 13-continued

| Compound | Intermediate L | Target Compound | Yield |
|---|---|---|---|
| 641 | | | 65% |
| 644 | | | 65% |

TABLE 13-continued
| Compound | Intermediate L | Target Compound | Yield |
|---|---|---|---|
| 646 | 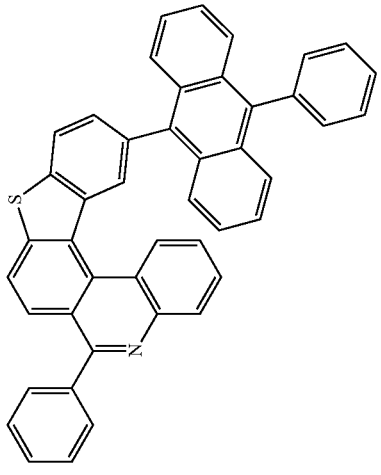 | 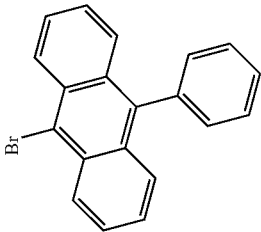 | 62% |
| 649 | 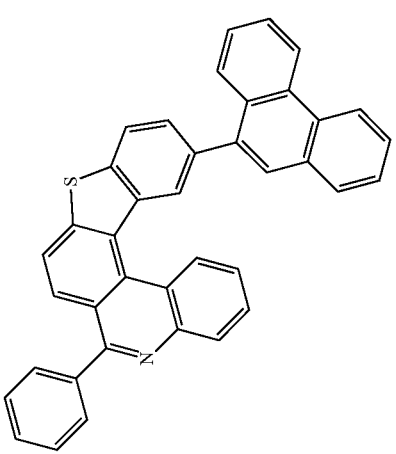 | 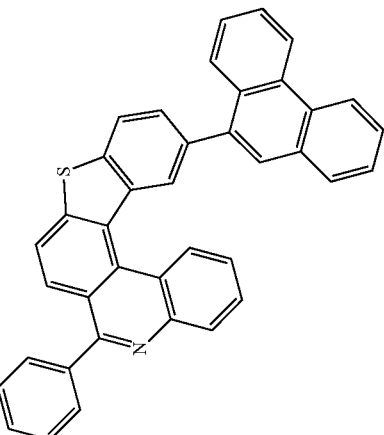 | 51% |

TABLE 13-continued
| Compound | Intermediate L | Target Compound | Yield |
|---|---|---|---|
| 651 | 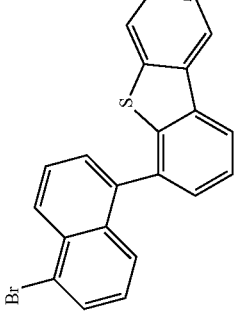 | 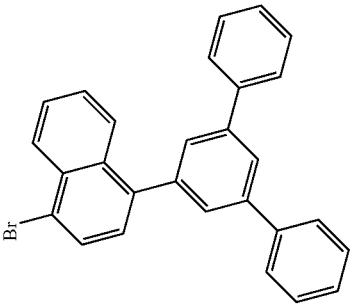 | 60% |
| 652 | 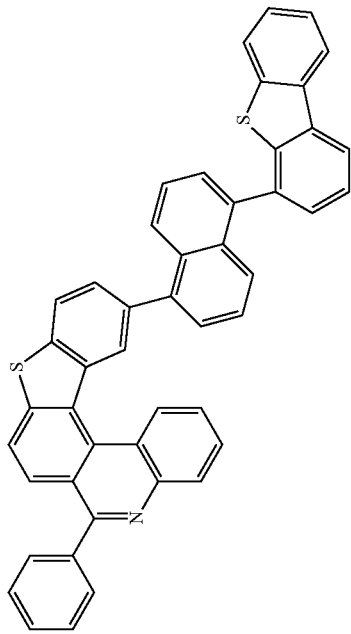 | 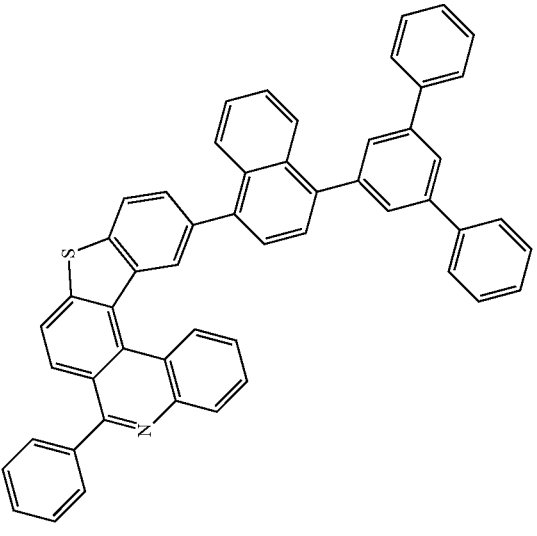 | 61% |

TABLE 13-continued
| Compound | Intermediate L | Target Compound | Yield |
|---|---|---|---|
| 653 | 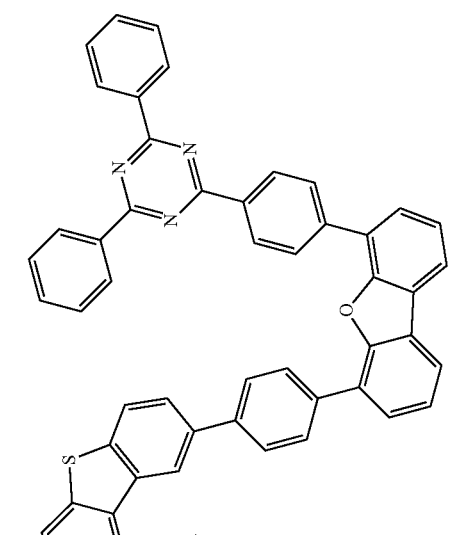 | 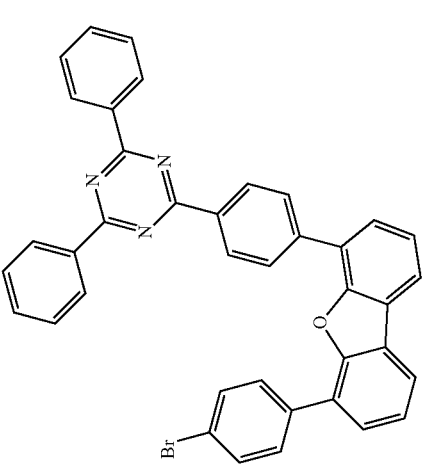 | 60% |

TABLE 13-continued
| Compound | Intermediate L | Target Compound | Yield |
|---|---|---|---|
| 654 | 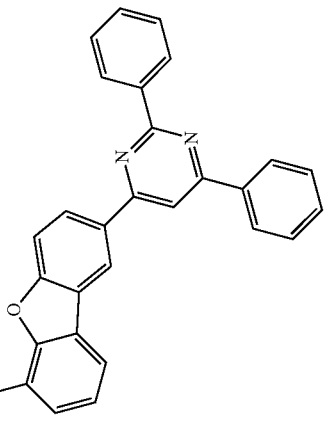 | 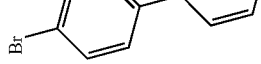 | 62% |

TABLE 13-continued
| Compound | Intermediate L | Target Compound | Yield |
|---|---|---|---|
| 655 | 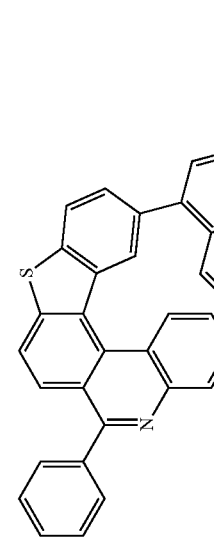 | 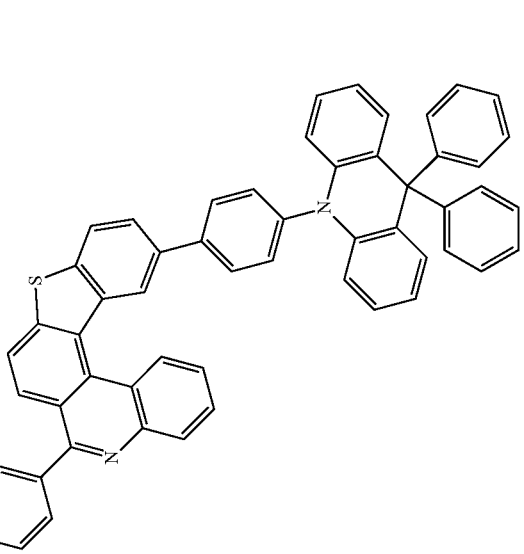 | 65% |
| 657 | 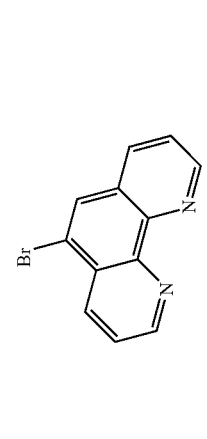 | 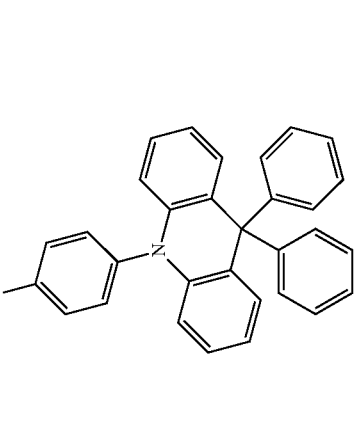 | 65% |

TABLE 13-continued

| Compound | Intermediate L | Target Compound | Yield |
|---|---|---|---|
| 659 | | | 62% |
| 660 | | | 51% |

TABLE 13-continued
| Compound | Intermediate L | Target Compound | Yield |
|---|---|---|---|
| 661 | 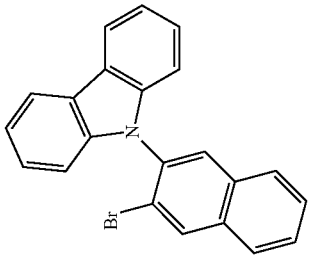 | 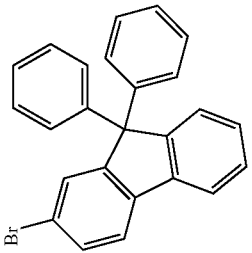 | 60% |
| 664 | 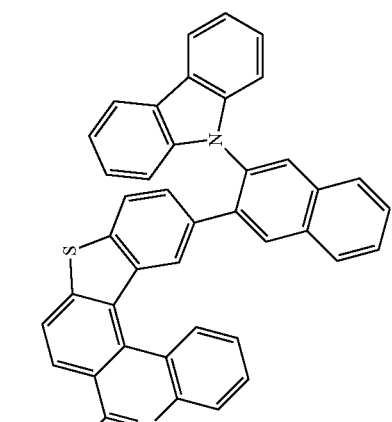 | 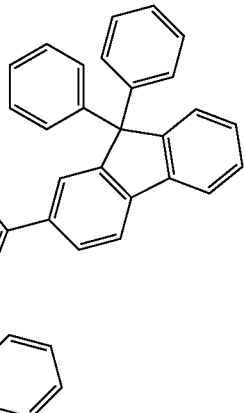 | 61% |

TABLE 13-continued

| Compound | Intermediate L | Target Compound | Yield |
|---|---|---|---|
| 665 | | | 60% |
| 666 | | | 62% |

TABLE 13-continued
| Compound | Intermediate L | Target Compound | Yield |
|---|---|---|---|
| 670 | 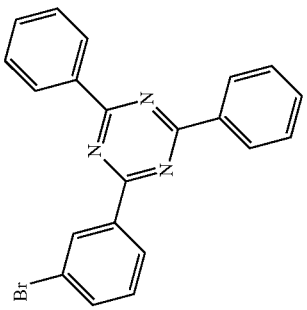 | 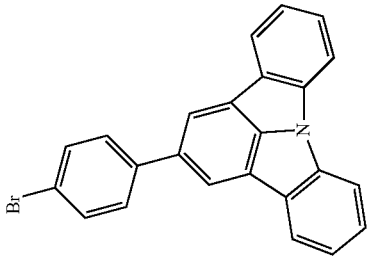 | 65% |
| 674 | 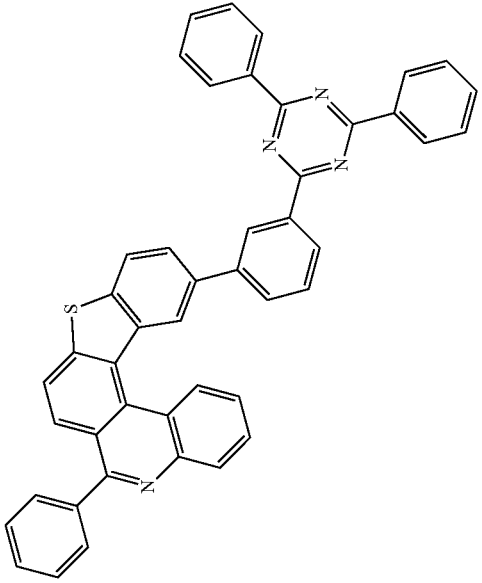 | 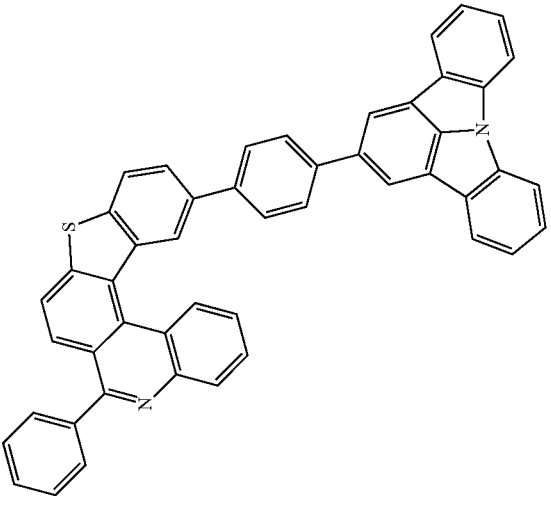 | 62% |

TABLE 13-continued

| Compound | Intermediate L | Target Compound | Yield |
|---|---|---|---|
| 675 | (structure) | (structure) | 51% |

TABLE 13-continued

| Compound | Intermediate L | Target Compound | Yield |
|---|---|---|---|
| 677 | | | 60% |
| 680 | | | 61% |

TABLE 13-continued
| Compound | Intermediate L | Target Compound | Yield |
|---|---|---|---|
| 682 | 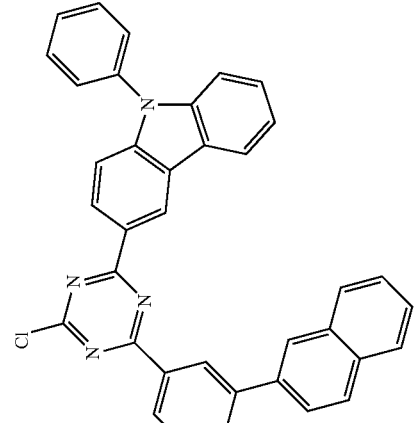 | 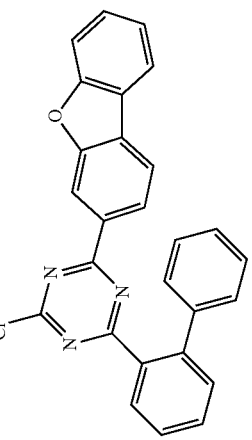 | 60% |
| 685 | 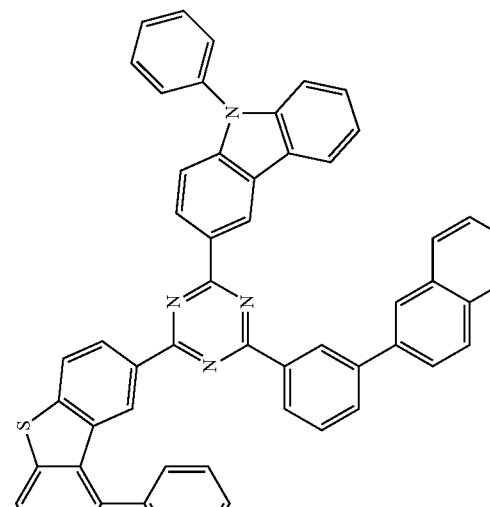 | 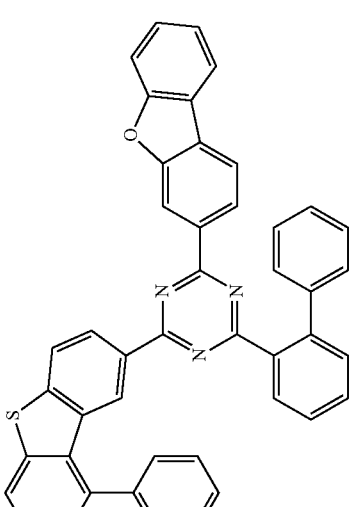 | 65% |

TABLE 13-continued

| Compound | Intermediate L | Target Compound | Yield |
|---|---|---|---|
| 687 | | | 65% |
| 688 | | | 62% |

TABLE 13-continued

| Compound | Intermediate L | Target Compound | Yield |
|---|---|---|---|
| 691 | | | 51% |
| 695 | | | 61% |

TABLE 13-continued
| Compound | Intermediate L | Target Compound | Yield |
|---|---|---|---|
| 696 | 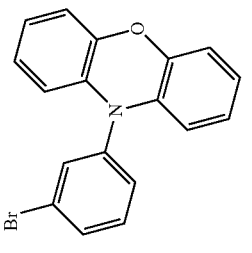 | 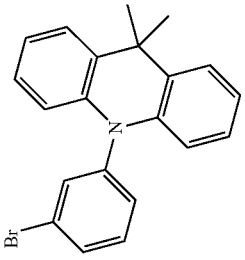 | 62% |
| 697 | 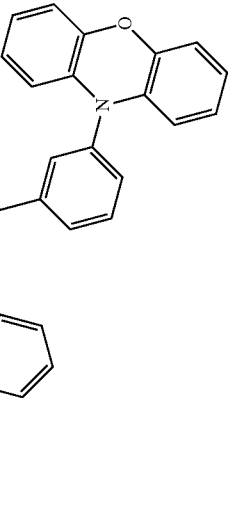 | 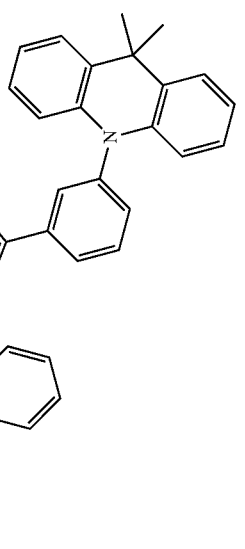 | 65% |

TABLE 13-continued

| Compound | Intermediate L | Target Compound | Yield |
|---|---|---|---|
| 700 | | | 65% |

TABLE 13-continued
| Compound | Intermediate L | Target Compound | Yield |
|---|---|---|---|
| 704 | 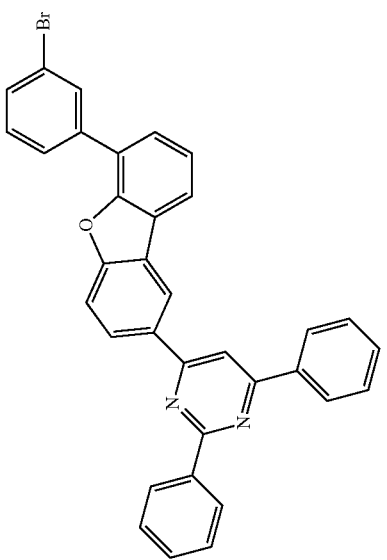 | 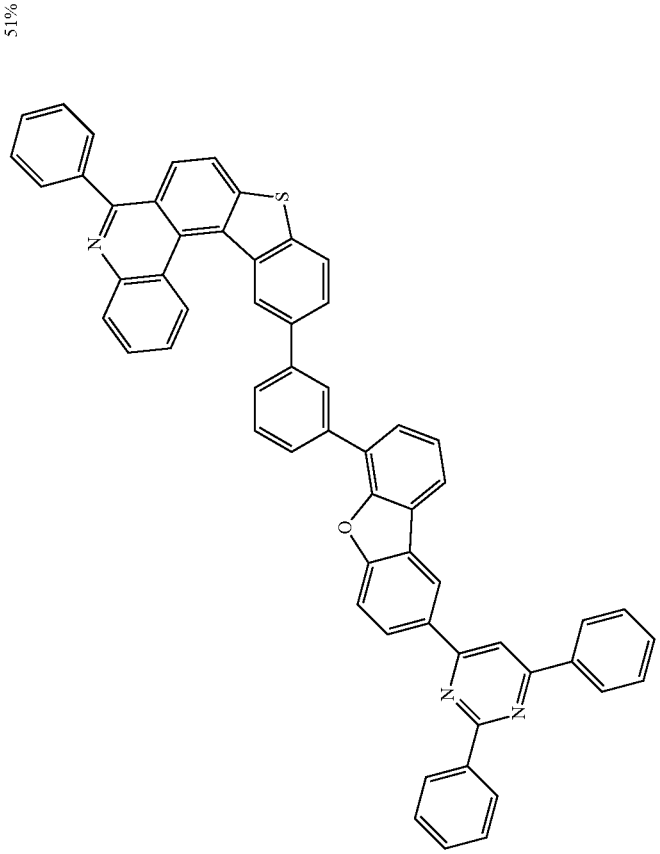 | 51% |

TABLE 13-continued

| Compound | Intermediate L | Target Compound | Yield |
|---|---|---|---|
| 707 | | | 60% |
| 708 | | | 62% |

TABLE 13-continued

| Compound | Intermediate L | Target Compound | Yield |
|---|---|---|---|
| 709 | (structure) | (structure) | 65% |
| 713 | (structure) | (structure) | 65% |

TABLE 13-continued
| Compound | Intermediate L | Target Compound | Yield |
|---|---|---|---|
| 714 | 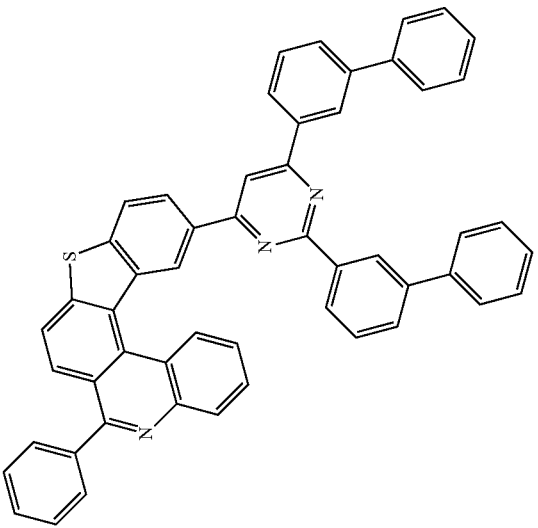 | 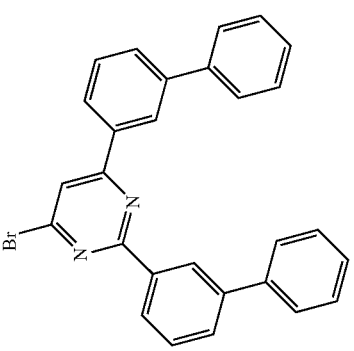 | 62% |

TABLE 13-continued

| Compound | Intermediate L | Target Compound | Yield |
|---|---|---|---|
| 716 | | | 51% |

TABLE 13-continued

| Compound | Intermediate L | Target Compound | Yield |
|---|---|---|---|
| 717 | | | 60% |

TABLE 13-continued
| Compound | Intermediate L | Target Compound | Yield |
|---|---|---|---|
| 721 | 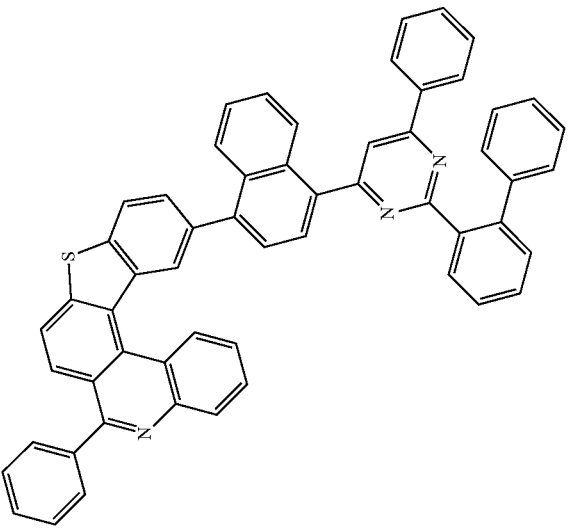 | 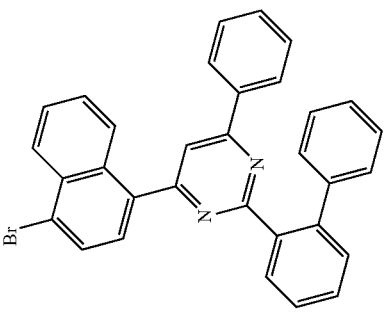 | 61% |

TABLE 13-continued

| Compound | Intermediate L | Target Compound | Yield |
|---|---|---|---|
| 728 | | | 60% |
| 729 | | | 62% |

TABLE 13-continued

| Compound | Intermediate L | Target Compound | Yield |
|---|---|---|---|
| 731 | | | 65% |
| 732 | | | 65% |

TABLE 13-continued

| Compound | Intermediate L | Target Compound | Yield |
|---|---|---|---|
| 733 | | | 62% |
| 734 | | | 51% |

TABLE 13-continued
| Compound | Intermediate L | Target Compound | Yield |
|---|---|---|---|
| 735 | 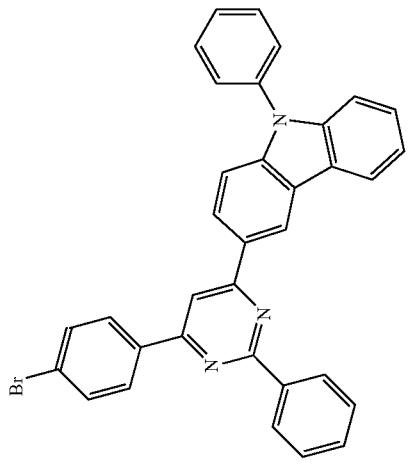 | 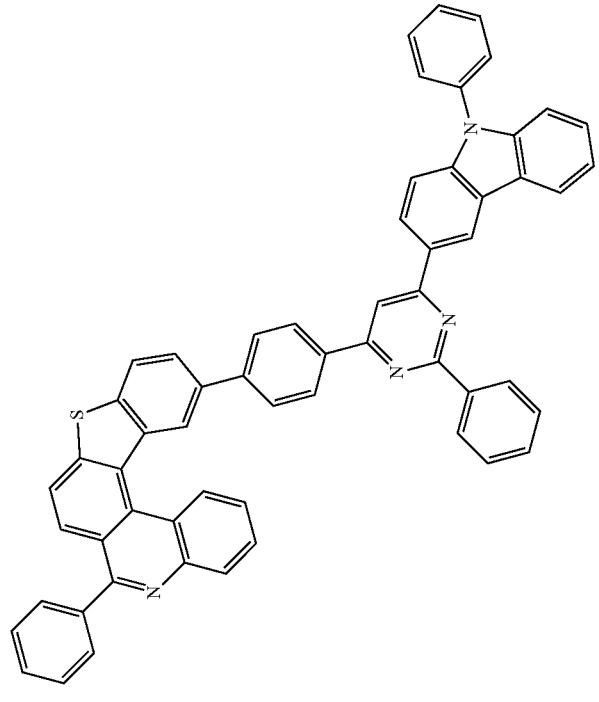 | 60% |

TABLE 13-continued

| Compound | Intermediate L | Target Compound | Yield |
|---|---|---|---|
| 736 | | | 61% |
| 741 | | | 60% |

TABLE 13-continued

| Compound | Intermediate L | Target Compound | Yield |
|---|---|---|---|
| 743 | | | 62% |
| 745 | | | 65% |

TABLE 13-continued

| Compound | Intermediate L | Target Compound | Yield |
|---|---|---|---|
| 748 | | | 65% |
| 752 | | | 51% |

TABLE 13-continued

| Compound | Intermediate L | Target Compound | Yield |
|---|---|---|---|
| 756 | | | 60% |
| 757 | | | 61% |

TABLE 13-continued

| Compound | Intermediate L | Target Compound | Yield |
|---|---|---|---|
| 761 | (structure) | (structure) | 60% |

Target compounds were synthesized in the same manner as in Preparation Example 2 except that Intermediate 6 of the following Table 14 was used instead of 1-pyrenecarbonyl chloride, 1-bromo-8-chlorodibenzo[b,d]thiophene was used instead of 1-bromo-8-chlorodibenzo[b,d]furan, and Intermediate M of the following Table 14 was used instead of 4-(3-bromophenyl)dibenzo[b,d]thiophene.

TABLE 14

| Compound | Intermediate M | Intermediate 6 | Target Compound | Yield |
|---|---|---|---|---|
| 620 | | | | 53% |
| 672 | | | | 62% |
| 683 | | | | 60% |

TABLE 14-continued
| Compound | Intermediate M | Intermediate 6 | Target Compound | Yield |
|---|---|---|---|---|
| 692 | 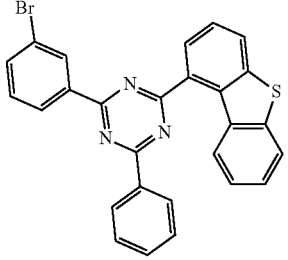 | 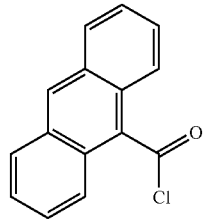 | 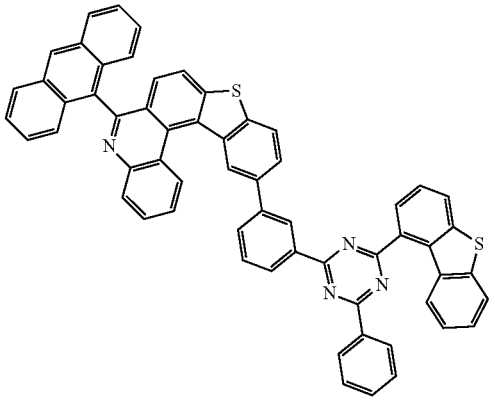 | 60% |
| 703 | 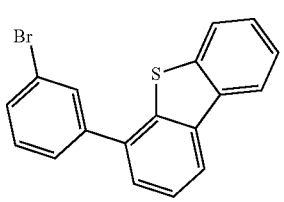 | 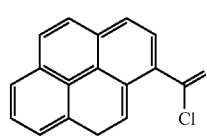 | 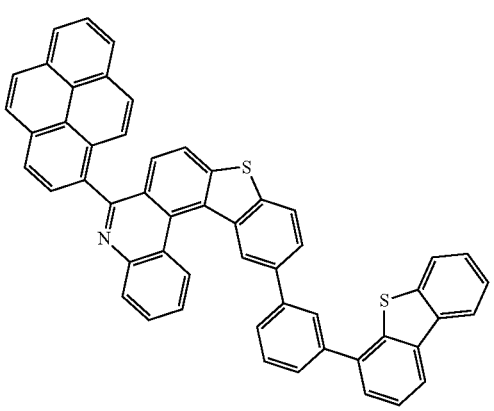 | 62% |
| 750 | 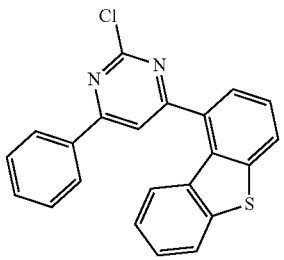 | 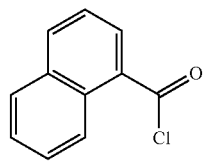 | 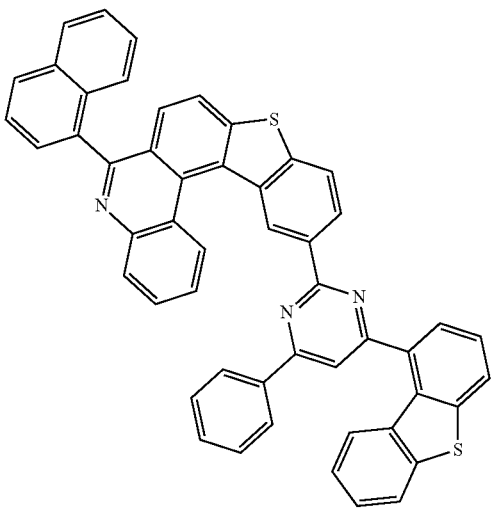 | 52% |
Target compounds were synthesized in the same manner as in Preparation Example 1 except that 2-bromo-8-chlorodibenzo[b,d]thiophene was used instead of 1-bromo-8-chlorodibenzo[b,d]furan, and Intermediate N of the following Table 15 was used instead of 2-(4-bromophenyl)-4,6-diphenyl-1,3,5-triazine.

TABLE 15

| Compound | Intermediate N | Target Compound | Yield |
|---|---|---|---|
| 764 | Br, 4-bromophenyl-substituted triazine bearing phenyl and phenanthrenyl groups | Thienyl-fused phenanthridine linked via phenylene to triazine with phenyl and phenanthrenyl substituents | 53% |
| 766 | Br, 4-bromo-1-(diphenylpyrimidinyl)naphthalene | Thienyl-fused phenanthridine linked via naphthalene to 2,6-diphenylpyrimidine | 62% |
| 767 | Cl, 2-chloro-4,6-diphenylpyrimidine | Thienyl-fused phenanthridine directly linked to 4,6-diphenylpyrimidine | 65% |

TABLE 15-continued

| Compound | Intermediate N | Target Compound | Yield |
|---|---|---|---|
| 769 | | | 65% |

Target compounds were synthesized in the same manner as in Preparation Example 1 except that 6-bromo-2-chlorodibenzo[b,d]thiophene was used instead of 1-bromo-8-chlorodibenzo[b,d]furan, and Intermediate O of the following Table 16 was used instead of 2-(4-bromophenyl)-4,6-diphenyl-1,3,5-triazine.

TABLE 16

| Compound | Intermediate O | Target Compound | Yield |
|---|---|---|---|
| 771 | | | 62% |
| 773 | | | 62% |

TABLE 16-continued
| Compound | Intermediate O | Target Compound | Yield |
|---|---|---|---|
| 775 | 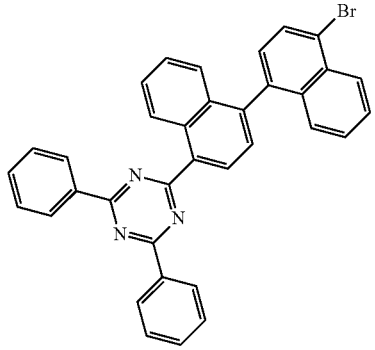 | 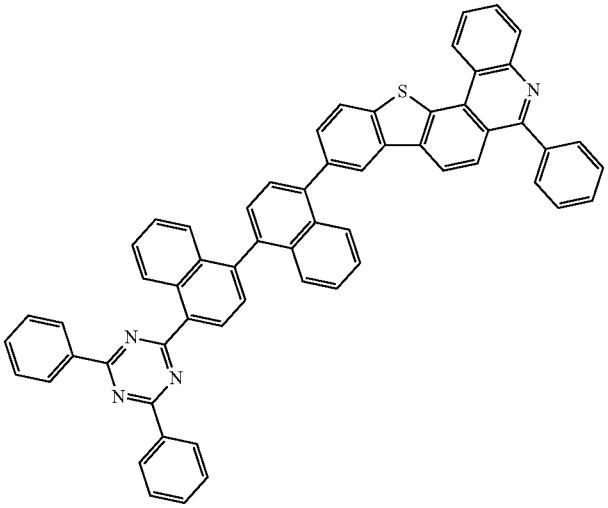 | 65% |
| 783 | 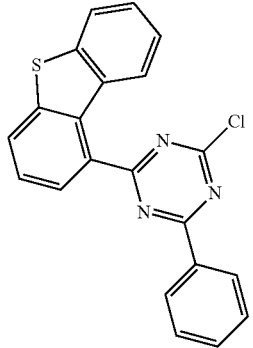 | 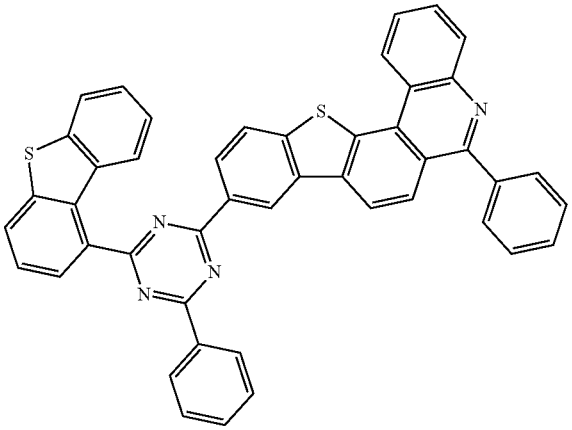 | 62% |
| 784 | 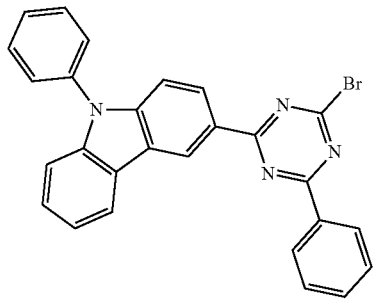 | 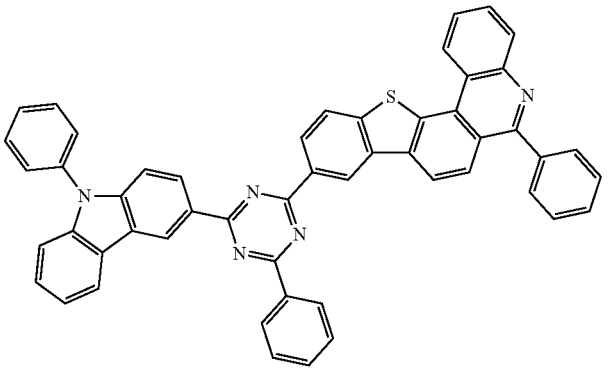 | 51% |

TABLE 16-continued

| Compound | Intermediate O | Target Compound | Yield |
|---|---|---|---|
| 787 | | | 61% |
| 789 | | | 60% |
| 791 | | | 62% |

TABLE 16-continued

| Compound | Intermediate O | Target Compound | Yield |
|---|---|---|---|
| 792 | | | 65% |
| 793 | | | 65% |
| 798 | | | 62% |

TABLE 16-continued
| Compound | Intermediate O | Target Compound | Yield |
|---|---|---|---|
| 801 | 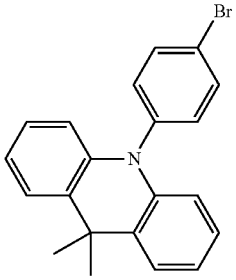 | 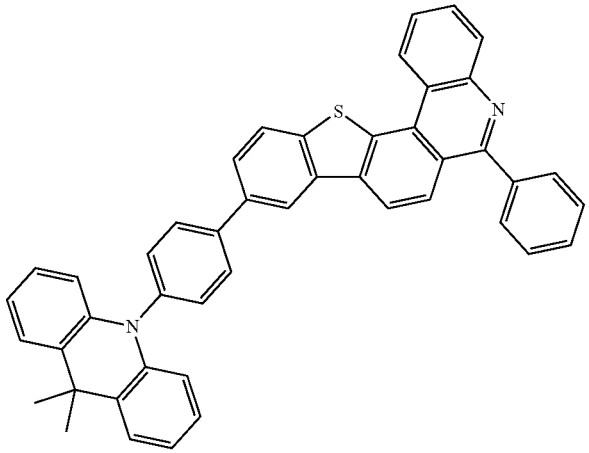 | 51% |
| 802 | 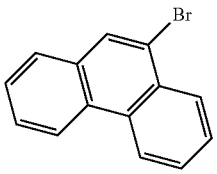 | 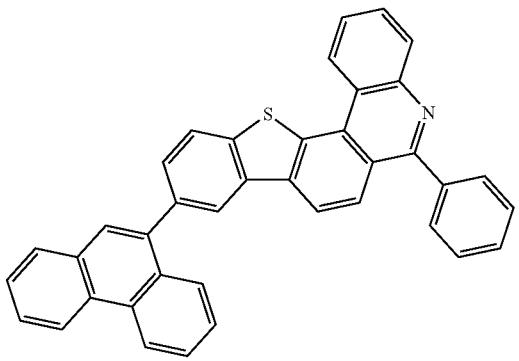 | 60% |
| 807 | 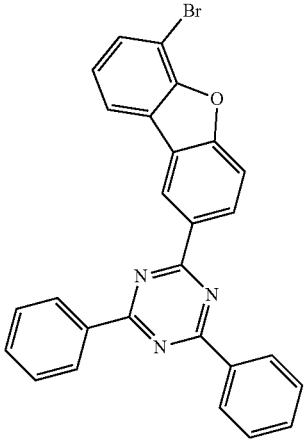 | 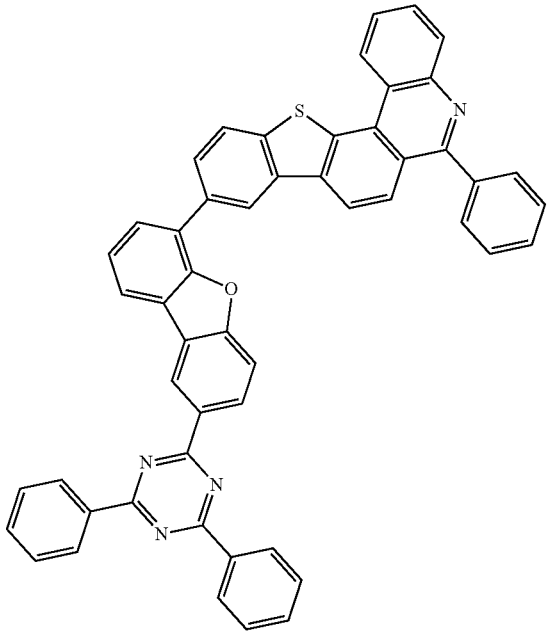 | 61% |

TABLE 16-continued
| Compound | Intermediate O | Target Compound | Yield |
|---|---|---|---|
| 809 | 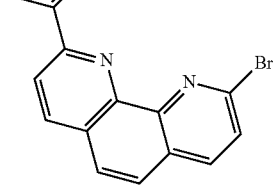 | 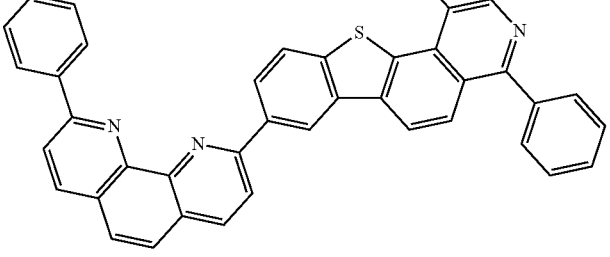 | 60% |
| 810 | 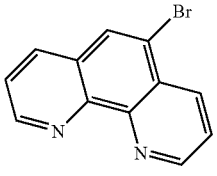 | 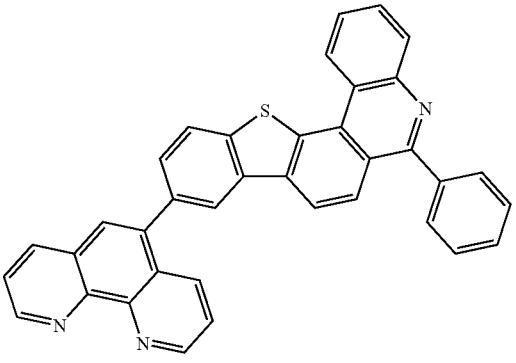 | 62% |
| 814 | 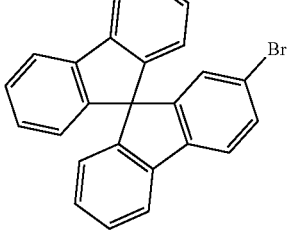 | 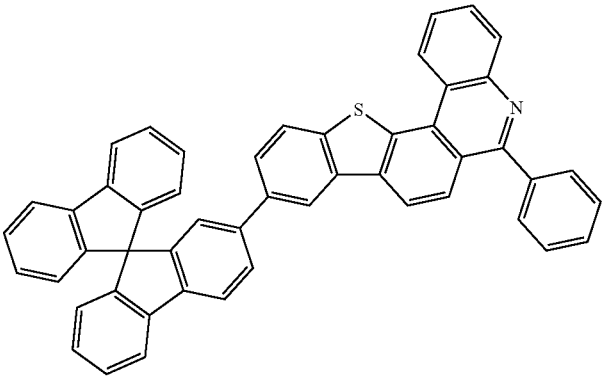 | 65% |

TABLE 16-continued

| Compound | Intermediate O | Target Compound | Yield |
|---|---|---|---|
| 816 | | | 65% |
| 817 | | | 62% |
| 818 | | | 51% |

TABLE 16-continued

| Compound | Intermediate O | Target Compound | Yield |
|---|---|---|---|
| 822 | | | 60% |
| 823 | | | 61% |
| 829 | | | 62% |

TABLE 16-continued

| Compound | Intermediate O | Target Compound | Yield |
|---|---|---|---|
| 830 | | | 65% |
| 831 | | | 65% |
| 833 | | | 62% |

TABLE 16-continued

| Compound | Intermediate O | Target Compound | Yield |
|---|---|---|---|
| 836 | | | 51% |
| 837 | | | 60% |
| 838 | | | 61% |

TABLE 16-continued

| Compound | Intermediate O | Target Compound | Yield |
|---|---|---|---|
| 842 | | | 60% |
| 844 | | | 62% |
| 847 | | | 65% |
| 848 | | | 65% |

TABLE 16-continued

| Compound | Intermediate O | Target Compound | Yield |
|---|---|---|---|
| 849 | | | 62% |
| 858 | | | 51% |
| 860 | | | 60% |

TABLE 16-continued

| Compound | Intermediate O | Target Compound | Yield |
|---|---|---|---|
| 861 | | | 61% |
| 862 | | | 60% |
| 863 | | | 62% |

TABLE 16-continued
| Compound | Intermediate O | Target Compound | Yield |
|---|---|---|---|
| 870 | 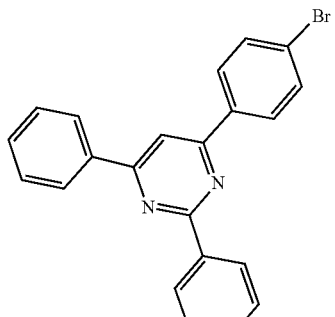 | 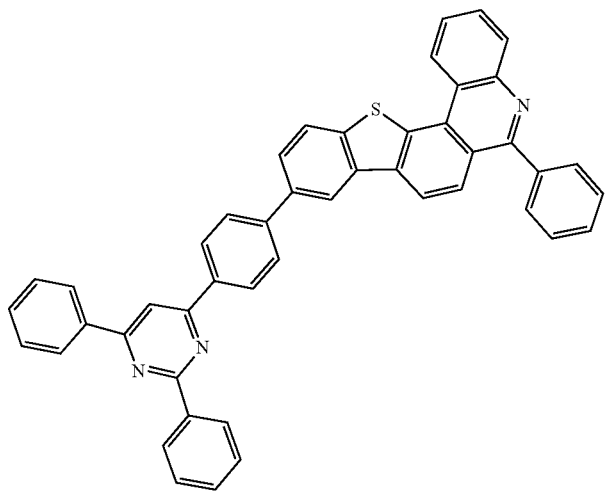 | 65% |
| 871 | 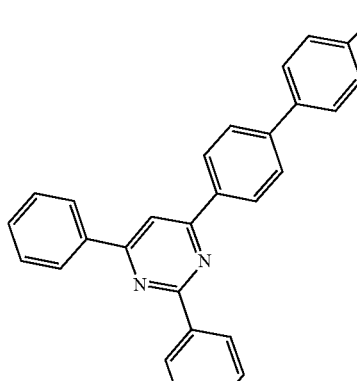 | 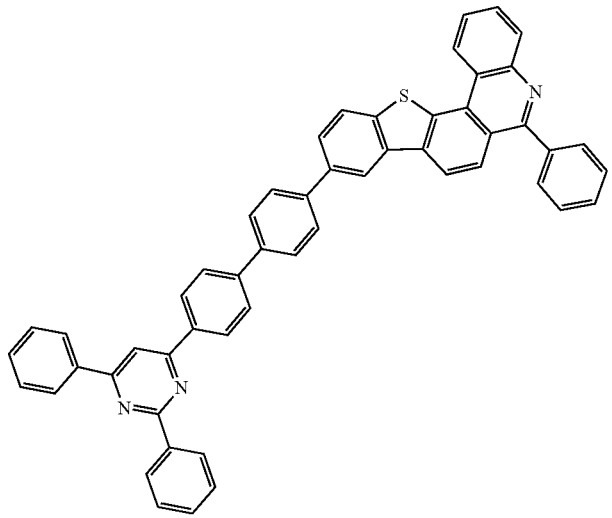 | 65% |
| 872 | 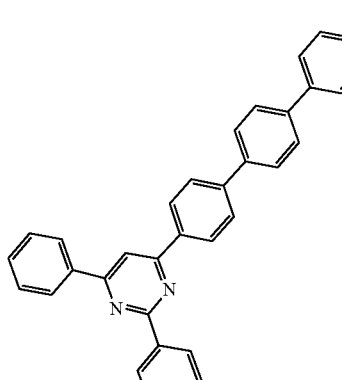 | 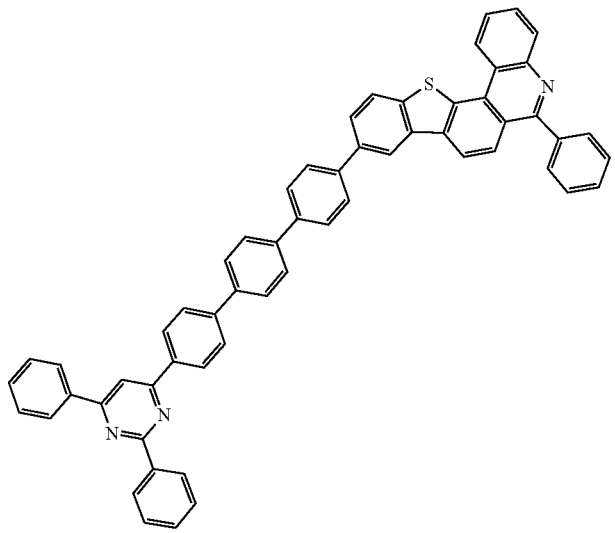 | 62% |

TABLE 16-continued

| Compound | Intermediate O | Target Compound | Yield |
|---|---|---|---|
| 883 | | | 51% |
| 884 | | | 60% |
| 887 | | | 61% |

TABLE 16-continued
| Compound | Intermediate O | Target Compound | Yield |
|---|---|---|---|
| 888 | 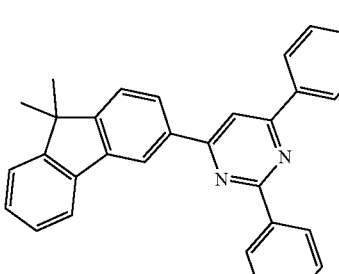 | 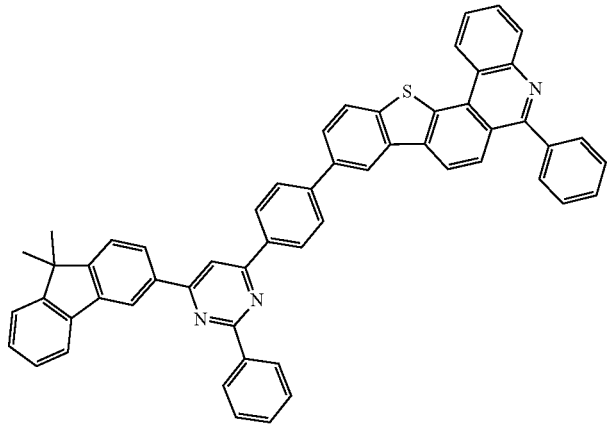 | 60% |
| 890 | 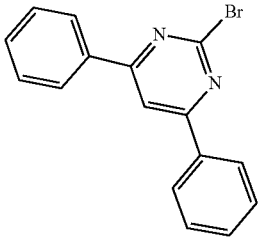 | 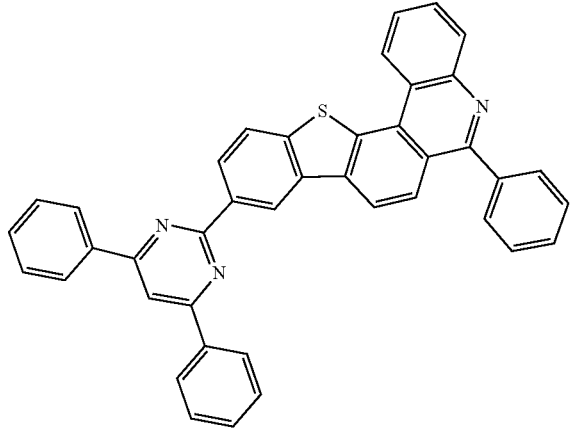 | 62% |
| 893 | 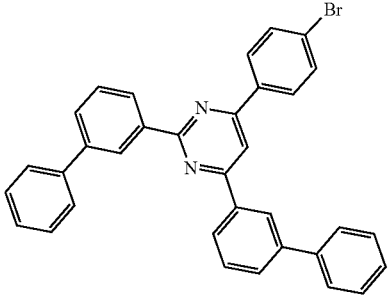 | 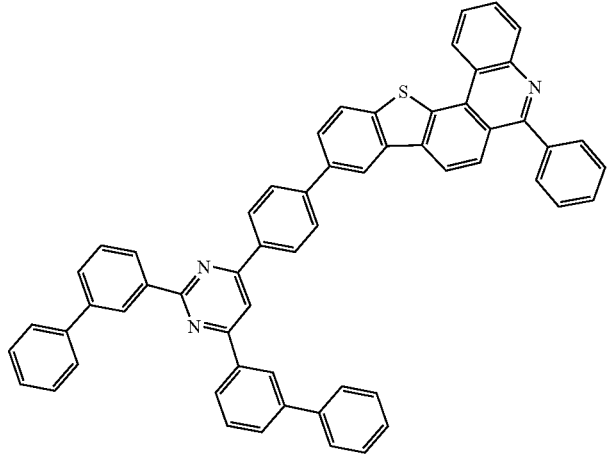 | 65% |

TABLE 16-continued

| Compound | Intermediate O | Target Compound | Yield |
|---|---|---|---|
| 905 | | | 65% |
| 908 | | | 62% |
| 910 | | | 51% |

TABLE 16-continued

| Compound | Intermediate O | Target Compound | Yield |
|---|---|---|---|
| 911 | | | 60% |

Target compounds were synthesized in the same manner as in Preparation Example 2 except that Intermediate 7 of the following Table 17 was used instead of 1-pyrenecarbonyl chloride, 6-bromo-2-chlorodibenzo[b,d]thiophene was used instead of 1-bromo-8-chlorodibenzo[b,d]furan, and Intermediate P of the following Table 17 was used instead of 4-(3-bromophenyl)dibenzo[b,d]thiophene.

TABLE 17

| Compound | Intermediate P | Intermediate 7 | Target Compound | Yield |
|---|---|---|---|---|
| 779 | | | | 56% |
| 786 | | | | 56% |

TABLE 17-continued

| Compound | Intermediate P | Intermediate 7 | Target Compound | Yield |
|---|---|---|---|---|
| 825 | 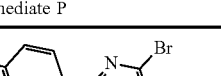 | | | 60% |

Target compounds were synthesized in the same manner as in Preparation Example 1 except that 1-bromo-6-chlorodibenzo[b,d]thiophene was used instead of 1-bromo-8-chlorodibenzo[b,d]furan, and Intermediate Q of the following Table 18 was used instead of 2-(4-bromophenyl)-4,6-diphenyl-1,3,5-triazine.

TABLE 18

| Compound | Intermediate Q | Target Compound | Yield |
|---|---|---|---|
| 916 | 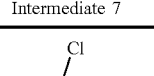 | | 53% |
| 918 | 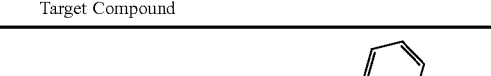 | | 62% |

TABLE 18-continued

| Compound | Intermediate Q | Target Compound | Yield |
|---|---|---|---|
| 919 | | | 65% |
| 920 | | | 65% |
| 923 | | | 62% |

TABLE 18-continued

| Compound | Intermediate Q | Target Compound | Yield |
|---|---|---|---|
| 924 | | | 51% |
| 930 | | | 60% |

TABLE 18-continued

| Compound | Intermediate Q | Target Compound | Yield |
|---|---|---|---|
| 931 | | | 61% |
| 932 | | | 62% |

TABLE 18-continued
| Compound | Intermediate Q | Target Compound | Yield |
|---|---|---|---|
| 943 | 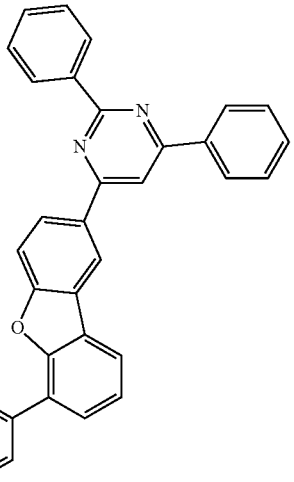 | 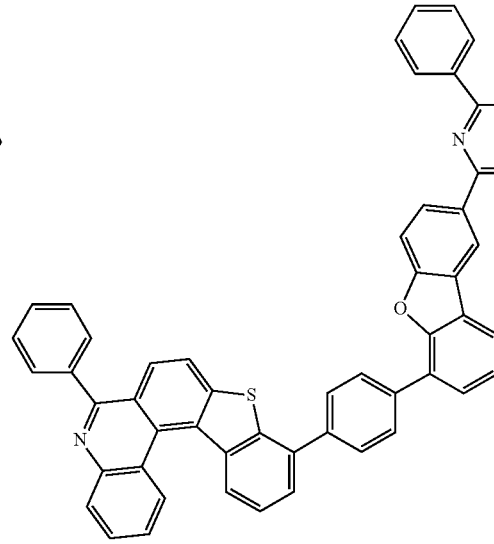 | 65% |
| 945 | 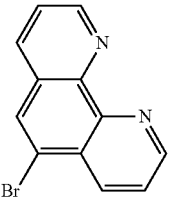 | 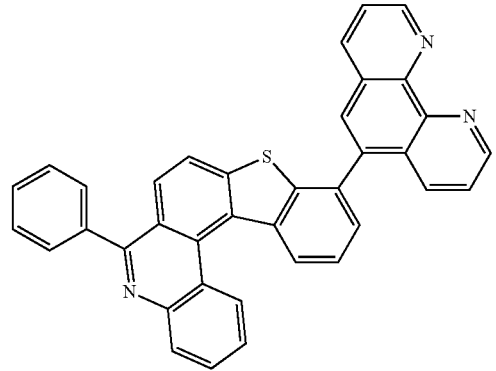 | 65% |
| 952 | 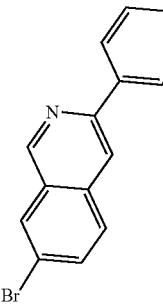 | 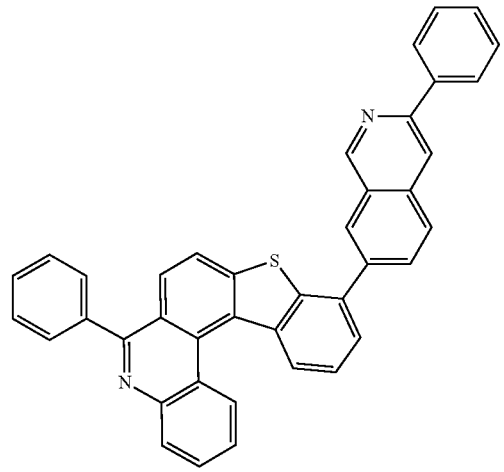 | 62% |

TABLE 18-continued

| Compound | Intermediate Q | Target Compound | Yield |
|---|---|---|---|
| 955 | | | 51% |
| 956 | | | 60% |
| 957 | | | 62% |

TABLE 18-continued
| Compound | Intermediate Q | Target Compound | Yield |
|---|---|---|---|
| 960 | 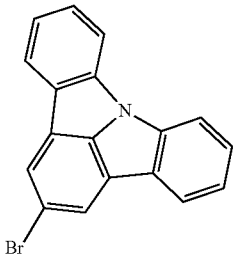 | 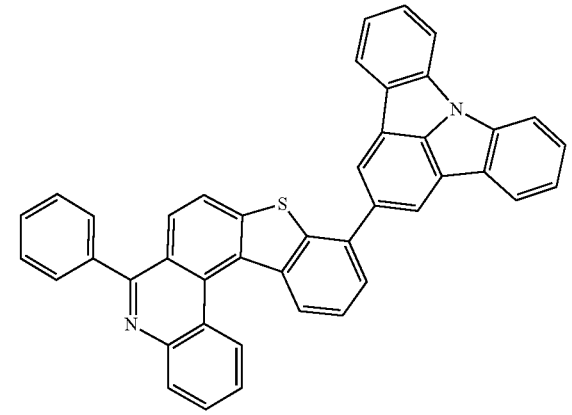 | 65% |
| 963 | 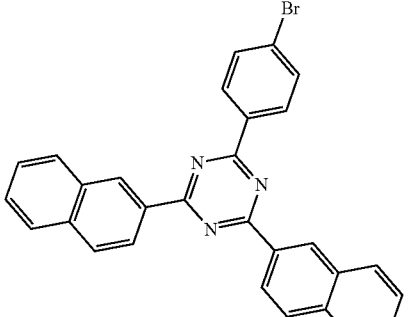 | 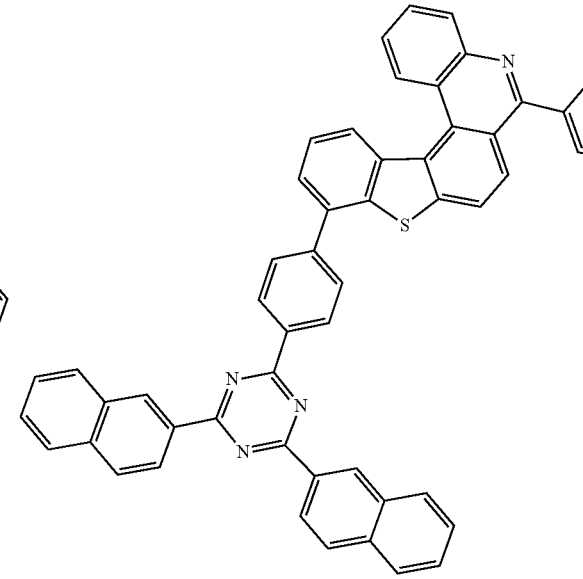 | 65% |
| 965 | 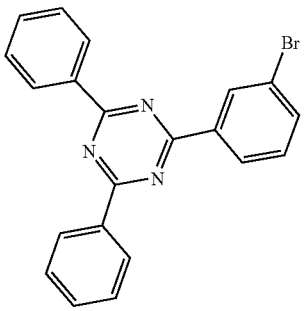 | 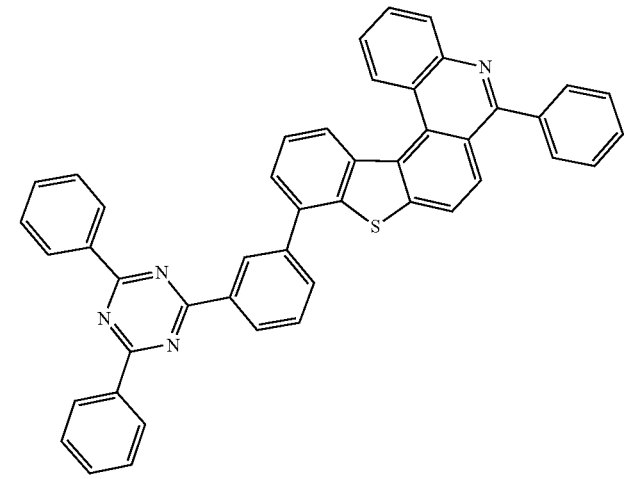 | 62% |

TABLE 18-continued

| Compound | Intermediate Q | Target Compound | Yield |
|---|---|---|---|
| 968 | | | 51% |
| 971 | | | 62% |

TABLE 18-continued

| Compound | Intermediate Q | Target Compound | Yield |
|---|---|---|---|
| 979 | | | 65% |
| 980 | | | 65% |
| 984 | | | 62% |

TABLE 18-continued
| Compound | Intermediate Q | Target Compound | Yield |
|---|---|---|---|
| 986 | 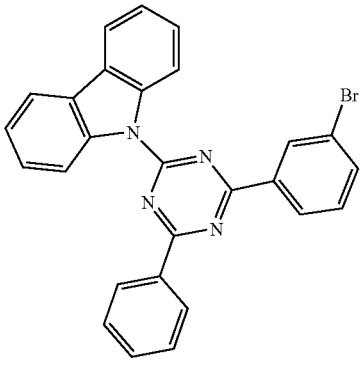 | 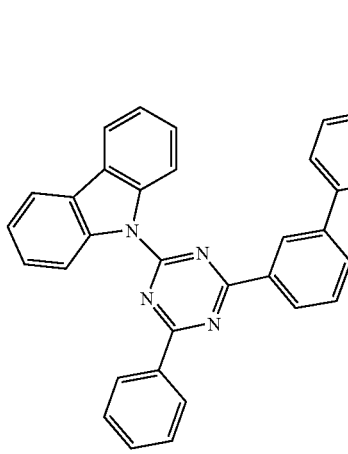 | 65% |
| 998 | 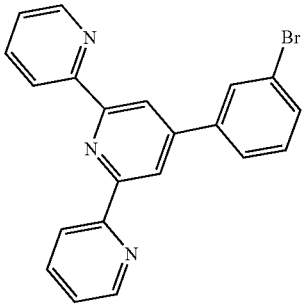 | 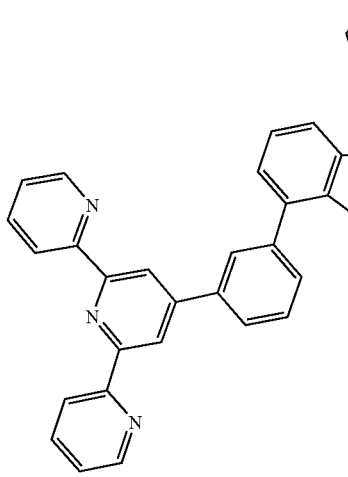 | 65% |
| 991 | 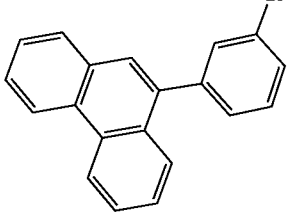 | 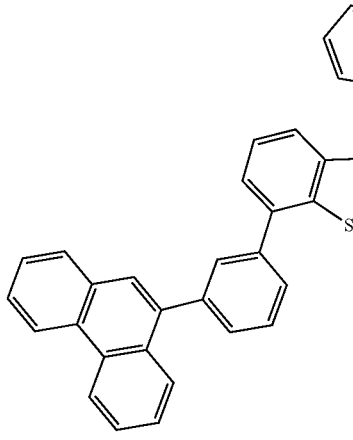 | 62% |

TABLE 18-continued

| Compound | Intermediate Q | Target Compound | Yield |
|---|---|---|---|
| 995 | | | 51% |
| 1000 | | | 60% |
| 1004 | | | 61% |

TABLE 18-continued
| Compound | Intermediate Q | Target Compound | Yield |
|---|---|---|---|
| 1006 | 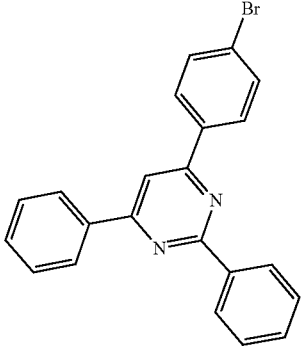 | 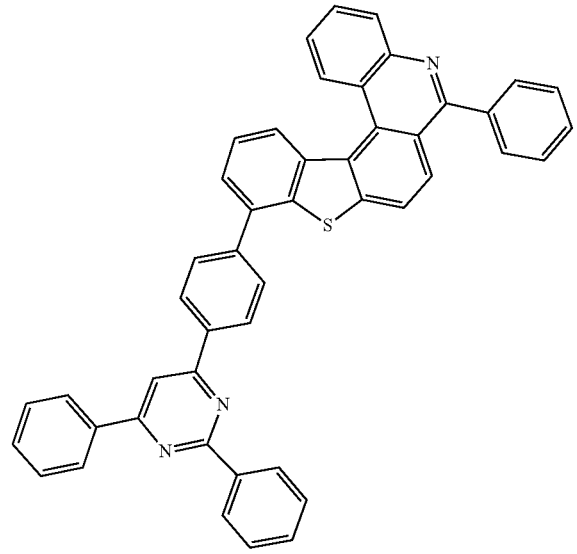 | 60% |
| 1011 | 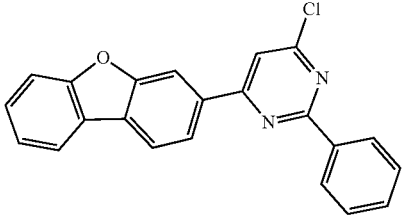 | 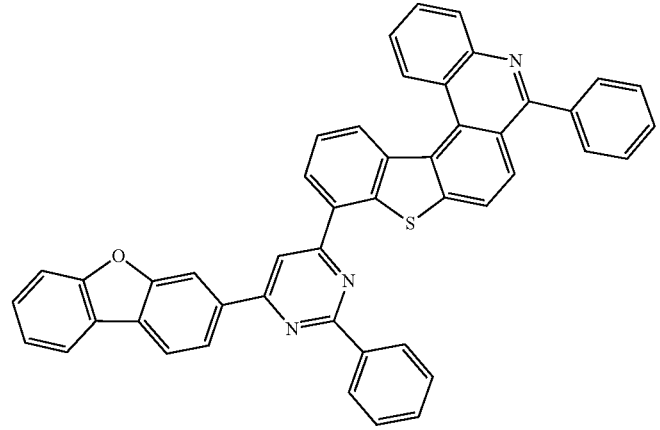 | 62% |
| 1015 | 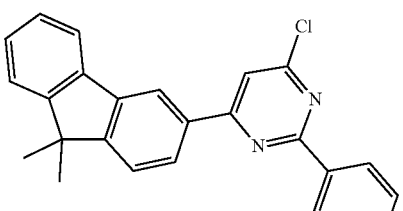 | 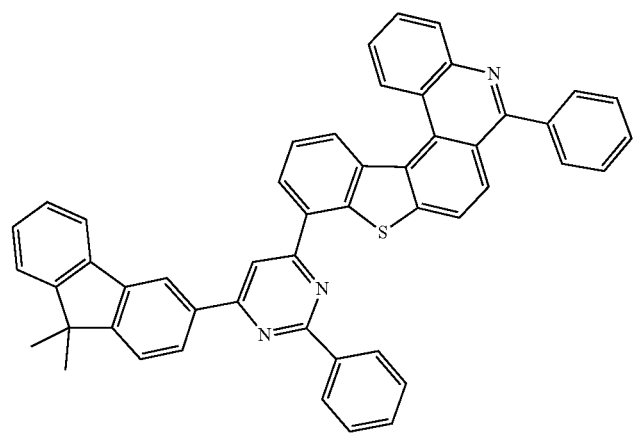 | 65% |

Synthesis identification results for the compounds prepared as above are shown in the following Table 19.

TABLE 19

| Compound | FD-MS | Compound | FD-MS |
|---|---|---|---|
| 1 | m/z = 576.65 (C40H24N4O = 576.195) | 4 | m/z = 652.75 (C46H28N4O = 652.226) |
| 5 | m/z = 728.85 (C52H32N4O = 728.25) | 7 | m/z = 804.95 (C58H36N4O = 804.28) |
| 8 | m/z = 728.85 (C52H32N4O = 728.25) | 9 | m/z = 804/95 (C58H36N4O = 804.28) |
| 11 | m/z = 666.74 (C46H26N4O2 = 666.20) | 12 | m/z = 682.80 (C46H26N4OS = 682.18) |
| 13 | m/z = 741.85 (C52H31N5O = 741.25) | 15 | m/z = 665.75 (C46H27N5O = 665.22) |
| 16 | m/z = 742.83 (C52H30N4O = 742.23) | 17 | m/z = 792.80 (C56H32N4O2 = 792.25) |
| 18 | m/z = 842.95 (C60H34N4O2 = 842.26) | 24 | m/z = 571.67 (C43H25NO = 571.19) |
| 25 | m/z = 521/61 (C39H23NO = 521.17) | 28 | m/z = 577.70 (C41H23NOS = 577.15) |
| 30 | m/z = 628.77 (C46H32N2O = 628.25) | 35 | m/z = 818.93 (C58H34N4O2 = 818.26) |
| 36 | m/z = 818.93 (C58H34N4O2 = 818.26) | 37 | m/z = 752.92 (C56H36N2O = 752.28) |
| 38 | m/z = 599/69 (C43H25N3O = 599.2) | 41 | m/z = 725.85 (C53H1N3O = 725.24) |
| 42 | m/z = 652.75 (C46H28N4O = 652.22) | 44 | m/z = 659.78 (C50H29NO = 659.22) |
| 45 | m/z = 621.67 (C43H28NO2P = 621.18) | 47 | m/z = 549.63 (C39H23N3O = 549.18) |
| 52 | m/z = 618.75 (C43H26N2OS = 618.17) | 53 | m/z = 660.77 (C49H28N2O = 660.22) |
| 56 | m/z = 751.88 (C55H33N3O = 751.26) | 57 | m/z = 834.99 (C58H34N4OS = 834.24) |
| 58 | m/z = 758.89 (C52H30N4OS = 758.21) | 64 | m/z = 804.95 (C58H36N4O = 804.28) |
| 68 | m/z = 732.86 (C50H28N4OS = 732.19) | 69 | m/z = 732.86 (C50H28N4OS = 732.19) |
| 70 | m/z = 868.01 (C62H37N5O = 867.30) | 72 | m/z = 690.76 (C47H26N6O = 690.21) |
| 75 | m/z = 742.83 (C52H30N4O2 = 742.23) | 77 | m/z = 758.89 (C52H30N4OS = 758.21) |
| 79 | m/z = 768.92 (C55H36N4O = 768.28) | 80 | m/z = 741.85 (C5231N5O = 741.25) |
| 84 | m/z = 660.77 (C49H28N2O = 660.22) | 86 | m/z = 597.71 (C45H27NO = 597.20) |
| 88 | m/z = 727.88 (C53H29NOS = 727.19) | 89 | m/z = 663.77 (C49H29NO2 = 663.22) |
| 91 | m/z = 752.91 (C56H36N2O = 752.28) | 92 | m/z = 675.79 (C49H29N3O = 675.23) |
| 97 | m/z = 575.67 (C41H25N3O = 575.20) | 100 | m/z = 727.86 (C53H33N3O = 727.26) |
| 102 | m/z = 701.82 (C51H31N3O = 701.24) | 103 | m/z = 727.86 (C53H33N3O = 727.26) |
| 107 | m/z = 727.86 (C53H33N3O = 727.26) | 112 | m/z = 681.81 (C47H27N3OS = 681.18) |
| 113 | m/z = 740.86 (C53H32N4O = 740.25) | 114 | m/z = 691.83 (C50H33N3O = 691.26) |
| 116 | m/z = 741.85 (C53H31N3O2 = 741.24) | 119 | m/z = 817.99 (C60H39N3O = 817.30) |
| 120 | m/z = 740.86 (C53H32N4O = 740/25) | 121 | m/z = 725.85 (C53H31N3O = 725.24) |
| 128 | m/z = 777.92 (C57H35N3O = 777.27) | 132 | m/z = 681.81 (C47H27N3OS = 681.18) |
| 133 | m/z = 681.81 (C47H27N3OS = 681.18) | 135 | m/z = 664.76 (C47H28N4O = 664.22) |
| 139 | m/z = 757.91 (C53H31N3OS = 757.21) | 140 | m/z = 816.96 (C59H36N4O = 816.28) |
| 141 | m/z = 767.93 (C56H37N3O = 767.29) | 142 | m/z = 740/86 (C53H32N4O = 740.25) |
| 145 | m/z = 702.81 (C50H30N4O = 702.24) | 149 | m/z = 728.85 (C52H32N4O = 728.25) |
| 156 | m/z = 652.75 (C46H26N4O = 652.22) | 157 | m/z = 652.75 (C46H28N4O = 652.22) |

TABLE 19-continued

| Compound | FD-MS | Compound | FD-MS |
|---|---|---|---|
| 159 | m/z = 804.95 (C58H36N4O = 804.28) | 161 | m/z = 666.74 (C46H26N4O2 = 666.20) |
| 165 | m/z = 682.80 (C46H26N4OS = 682.18) | 166 | m/z = 741.85 (C52H31N5O = 741.25) |
| 168 | m/z = 715.81 (C50H29N4O = 715.23) | 170 | m/z = 842.95 (C60H34N4O2 = 842.26) |
| 171 | m/z = 758.89 (C52H30N4OS = 758.21) | 172 | m/z = 817.95 (C58H35N5O = 817.28) |
| 173 | m/z = 768.92 (C55H36N4O = 768.28) | 176 | m/z = 571.67 (C43H25NO = 571.19) |
| 178 | m/z = 573.69 (C43H27NO = 573.20) | 179 | m/z = 527.64 (C37H21NOS = 527.13) |
| 180 | m/z = 552.67 (C40H28N2O = 552.22) | 185 | m/z = 895.03 (C64H38N4O2 = 894.29) |
| 187 | m/z = 676.81 (C50H32N2O = 676.25) | 190 | m/z = 675.79 (C49H29N3O = 675.23) |
| 191 | m/z = 725.85 (C53H31N3O = 725.24) | 192 | m/z = 652.75 (C46H28N4O = 652.22) |
| 194 | m/z = 659.78 (C50H29NO = 659.22) | 195 | m/z = 548.64 (C40H24N2O = 548.18) |
| 196 | m/z = 625.73 (C45H27N3O = 625.21) | 200 | m/z = 659.78 (C50H29NO = 659.22) |
| 202 | m/z = 660.77 (C49H28N2O = 660.22) | 204 | m/z = 802.93 (C58H34N4O = 802.27) |
| 207 | m/z = 728.85 (C52H32N4O = 728.25) | 210 | m/z = 742.83 (C52H30N4O2 = 742.23) |
| 213 | m/z = 732.86 (C50H28N4OS = 732.19) | 214 | m/z = 868.01 (C62H37N5O = 867.30) |
| 216 | m/z = 717.83 (C50H31N5O = 717.25) | 217 | m/z = 690.76 (C47H26N6O = 690.21) |
| 220 | m/z = 742.83 (C52H30N4O2 = 742.23) | 222 | m/z = 758.89 (C52H30N4OS = 758.21) |
| 223 | m/z = 817.95 (C58H35N5O = 817.28) | 224 | m/z = 768.92 (C55H36N4O = 768.28) |
| 225 | m/z = 741.85 (C52H31N5O = 741.25) | 227 | m/z = 602.69 (C43H26N2O2 = 602.19) |
| 228 | m/z = 618.75 (C43H26N2OS = 618.17) | 229 | m/z = 660.77 (C49H26N2O = 660.22) |
| 233 | m/z = 911.09 (C64H38N4OS = 910.27) | 237 | m/z = 675.79 (C49H29N3O = 675.23) |
| 240 | m/z = 662.79 (C49H30N2O = 662.23) | 243 | m/z = 651.76 (C47H29N3O = 651.23) |
| 245 | m/z = 651.76 (C47H29N3O = 651.23) | 247 | m/z = 651.76 (C47H29N3O = 651.23) |
| 249 | m/z = 803.96 (C59H37N3O = 803.29) | 251 | m/z = 715.81 (C51H29N3O2 = 715.22) |
| 256 | m/z = 740.86 (C53H32N4O = 740.25) | 257 | m/z = 691.83 (C50H33N3O = 691.26) |
| 259 | m/z = 791.91 (C57H33N3O2 = 791.25) | 260 | m/z = 741.85 (C53H31N3O2 = 741.24) |
| 262 | m/z = 757.91 (C53H31N3OS = 757.21) | 265 | m/z = 767.93 (C56H37N3O = 767.29) |
| 266 | m/z = 740.86 (C53H32N4O = 740.25) | 267 | m/z = 575.57 (C41H25N3O = 575.20) |
| 269 | m/z = 727.86 (C53H33N3O = 727.26) | 271 | m/z = 727.86 (C53H33N3O = 727.26) |
| 272 | m/z = 803.96 (C59H37N3O = 803.29) | 273 | m/z = 727.86 (C53H33N3O = 727.26) |
| 274 | m/z = 841.97 (C61H35N3O2 = 841.27) | 276 | m/z = 665.75 (C47H27N3O2 = 665.21) |
| 277 | m/z = 681.81 (C47H27N3OS = 681.18) | 279 | m/z = 740.86 (C53H32N4O = 740.25) |
| 281 | m/z = 664.76 (C47H28N4O = 662.22) | 284 | m/z = 741.85 (C53H31N3O2 = 741.24) |
| 285 | m/z = 757.91 (C53H31N3OS = 752.21) | 287 | m/z = 816.96 (C59H36N4O = 816.28) |
| 288 | m/z = 767.93 (C56H37N3O = 767.29) | 292 | m/z = 728.85 (C52H32N4O = 728.25) |
| 294 | m/z = 855.01 (C62H38N4O = 854.30) | 296 | m/z = 652.75 (C46H28N4O = 652.22) |
| 299 | m/z = 682.80 (C46H26N4OS = 682.18) | 302 | m/z = 665.75 (C46H27CN5O = 665.22) |
| 304 | m/z = 742.83 (C52H30N4O2 = 742.23) | 305 | m/z = 758/89 (C52H30N4OS = 758.21) |
| 307 | m/z = 817.95 (C58H35N4O = 817.28) | 308 | m/z = 768.92 (C55H36N4O = 768.28) |
| 309 | m/z = 741.85 (C52H31N5O = 741.25) | 310 | m/z = 571.67 (C43H25NO = 571.19) |

TABLE 19-continued

| Compound | FD-MS | Compound | FD-MS |
|---|---|---|---|
| 312 | m/z = 597.71 (C45H27NO = 597.20) | 313 | m/z = 753.69 (C43H27NO = 573.20) |
| 315 | m/z = 521.61 (C39H23NO = 521.17) | 316 | m/z = 597.71 (C45H27NO = 597.20) |
| 318 | m/z = 603.73 (C43H25NOS = 603.16) | 319 | m/z = 742.83 (C52H30N4O2 = 742.23) |
| 322 | m/z = 752.91 (C56H36N2O = 752.28) | 325 | m/z = 675.79 (C49H29N3O = 675.23) |
| 326 | m/z = 725.85 (C53H31N3O = 725.24) | 327 | m/z = 652.75 (C46H28N4O = 652.22) |
| 329 | m/z = 548.64 (C40H24N2O = 548.18) | 331 | m/z = 636.75 (C47H28N2O = 636.22) |
| 332 | m/z = 662.79 (C49H30N2O = 662.23) | 336 | m/z = 752.87 (C54H32N4O = 752.25) |
| 337 | m/z = 751.88 (C55H33N3O = 751.26) | 338 | m/z = 693.86 (C49H31N3S = 693.22) |
| 339 | m/z = 691.85 (C49H29N3S = 691.20) | 342 | m/z = 728.85 (C52H32N4O = 728.25) |
| 343 | m/z = 778.91 (C56H34N4O = 778.27) | 345 | m/z = 868.01 (C62H37N5O = 867.30) |
| 348 | m/z = 782.92 (C54H30N4OS = 782.21) | 350 | m/z = 717.83 (C50H31N5O = 717.25) |
| 353 | m/z = 742.83 (C52H30N4O2 = 742.23) | 355 | m/z = 758.89 (C52H30N4OS = 758.21) |
| 358 | m/z = 768.92 (C55H36N4O = 768.28) | 359 | m/z = 741.85 (C52H31N4O = 741.25) |
| 360 | m/z = 628.77 (C46H32N2O = 628.25) | 364 | m/z = 597.71 (C45H27NO = 597.20) |
| 365 | m/z = 652.75 (C46H28N4O = 652.22) | 367 | m/z = 945.09 (C68H40N4O2 = 944.31) |
| 368 | m/z = 713.83 (C53H31NO2 = 713.23) | 373 | m/z = 712.85 (C53H32N2O = 712.25) |
| 374 | m/z = 735.88 (C56H33NO = 735.25) | 377 | m/z = 727.86 (C53H33N3O = 727.26) |
| 378 | m/z = 803.95 (C59H27N3O = 803.29) | 379 | m/z = 751.88 (C55H33N3O = 751.26) |
| 380 | m/z = 727.86 (C53H33N3O = 727.26) | 384 | m/z = 665.75 (C47H27N3O2 = 665.21) |
| 386 | m/z = 731.87 (C51H29N3OS = 731.20) | 387 | m/z = 740.86 (C53H32N4O = 740/25) |
| 388 | m/z = 691.83 (C50H33N3O = 691.26) | 392 | m/z = 741.85 (C53H31N3O2 = 741.24) |
| 395 | m/z = 917.08 (C67H40N4O = 916.32) | 396 | m/z = 740.86 (C53H32N4O = 740.25) |
| 397 | m/z = 651.76 (C47H2N3O = 651.23) | 399 | m/z = 803.96 (C59H37N3O = 803.29) |
| 400 | m/z = 651.76 (C47H29N3O = 651.23) | 401 | m/z = 727.86 (C53H33N3O = 727.26) |
| 404 | m/z = 665.75 (C47H27N3O2 = 665.21) | 407 | m/z = 805.95 (C57H31N3OS = 805.21) |
| 408 | m/z = 740.86 (C53H32N4O = 740.25) | 409 | m/z = 691.83 (C50H33N3O = 691.25) |
| 411 | m/z = 741.85 (C53H31N3O2 = 741.24) | 413 | m/z = 741.85 (C53H31N3O2 = 741.24) |
| 415 | m/z = 757.91 (C53H31N3OS = 757.21) | 416 | m/z = 816.96 (C59H36N4O = 816.28) |
| 417 | m/z = 767.93 (C56H37N3O = 767.29) | 421 | m/z = 804.95 (C58H36N4O = 804.28) |
| 423 | m/z = 702.81 (C50H30N4O = 702.24) | 424 | m/z = 652.75 (C46H26N4O = 652.22) |
| 426 | m/z = 778.91 (C56H34N4O = 778.27) | 431 | m/z = 682.80 (C46H26N4OS = 682.18) |
| 432 | m/z = 741.85 (C52H31N5O = 741.25) | 433 | m/z = 692.82 (C49H32N4O = 692.25) |
| 436 | m/z = 742.83 (C52H30N4O2 = 742.23) | 438 | m/z = 758.89 (C52H30N4OS = 758.21) |
| 440 | m/z = 741.85 (C52H31N5O = 741.25) | 441 | m/z = 571.67 (C43H25NO = 571.19) |
| 443 | m/z = 597.71 (C54H27NO = 597.20) | 447 | m/z = 628.77 (C46H32N2O = 628.25) |
| 448 | m/z = 597.71 (C45H27NO = 597.20) | 449 | m/z = 649.79 (C49H31NO = 649.24) |
| 450 | m/z = 911.09 (C64H38N4OS = 910.27) | 452 | m/z = 665.75 (C47H27N3O2 = 665.21) |
| 456 | m/z = 675.79 (C49H29N3O = 675.23) | 460 | m/z = 659.78 (C50H29NO = 659.22) |
| 462 | m/z = 548.64 (C40H24N2O = 548.18) | 465 | m/z = 636.75 (C47H28N2O = 636.22) |

TABLE 19-continued

| Compound | FD-MS | Compound | FD-MS |
| --- | --- | --- | --- |
| 467 | m/z = 659.78 (C50H29NO = 659.22) | 468 | m/z = 652.75 (C47H28N2O = 652.21) |
| 470 | m/z = 752.87 (C54H32N4O = 752.25) | 475 | m/z = 728.85 (C52H32N4O = 728.25) |
| 476 | m/z = 742.83 (C52H30N4O2 = 742.23) | 477 | m/z = 742.83 (C52H30N4O2 = 742.23) |
| 479 | m/z = 732.86 (C50H28N4OS = 732.19) | 481 | m/z = 868.01 (C62H37N5O = 867.30) |
| 482 | m/z = 717.83 (C50H31N5O = 717.25) | 485 | m/z = 742.83 (C52H30N4O2 = 742.23) |
| 488 | m/z = 758.89 (C52H30N4OS = 758.21) | 489 | m/z = 817.95 (C58H35N5O = 817.28) |
| 490 | m/z = 818.98 (C59H38N4O = 818.30) | 493 | m/z = 602.69 (C43H26N2O2 = 602.19) |
| 494 | m/z = 618.75 (C43H26N2OS = 618.17) | 495 | m/z = 660.77 (C49H28N2O = 660.22) |
| 500 | m/z = 663.77 (C49H29NO2 = 663.22) | 504 | m/z = 697.77 (C49H32NO2P = 697.21) |
| 505 | m/z = 762.91 (C57H34N2O = 762.26) | 506 | m/z = 735.88 (C56H33NO = 735.25) |
| 509 | m/z = 727.86 (C53H33N3O = 727.26) | 512 | m/z = 727.86 (C53H33N3O = 727.26) |
| 513 | m/z = 665.75 (C47H27N3O2 = 556.21) | 516 | m/z = 681.81 (C47H27N3OS = 681.18) |
| 517 | m/z = 681.81 (C47H27N3OS = 681.18) | 518 | m/z = 740.86 (C53H32N4O = 740.25) |
| 519 | m/z = 691.83 (C50H33N3O = 691.26) | 520 | m/z = 664.76 (C47H26N4O = 664.22) |
| 522 | m/z = 841.97 (C61H35N3O2 = 841.27) | 524 | m/z = 757.91 (C53H31N3OS = 757.21) |
| 525 | m/z = 757.91 (C53H31N3OS = 757.21) | 527 | m/z = 767.93 (C56H37N3O = 767.29) |
| 528 | m/z = 740.86 (C53H32N4O = 740.25) | 531 | m/z = 727.86 (C53H33N3O = 727.26) |
| 532 | m/z = 727.86 (C53H33N3O = 727.26) | 533 | m/z = 803.96 (C59H37N3O = 803.29) |
| 535 | m/z = 727.86 (C53H33N3O = 727.26) | 536 | m/z = 664.76 (C47H28N4O = 664.22) |
| 539 | m/z = 665.75 (C47H27N3O2 = 665.21) | 542 | m/z = 640.86 (C53H32N4O = 740.25) |
| 543 | m/z = 691.83 (C50H33N3O = 691.26) | 544 | m/z = 741.85 (C53H31N3O2 = 741.24) |
| 547 | m/z = 757.91 (C53H31N3OS = 757.21) | 548 | m/z = 807.97 (C57H33N3OS = 807.23) |
| 549 | m/z = 816.96 (C59H36N4O = 816.28) | 550 | m/z = 767.93 (C56H37N3O = 767.29) |
| 554 | m/z = 665.75 (C46H26N4O = 652.22) | 555 | m/z = 728.85 (C52H32N4O = 728.25) |
| 557 | m/z = 728.85 (C52H32N4O = 728.25) | 558 | m/z = 804.95 (C58H36N4O = 804.28) |
| 564 | m/z = 741.85 (C52H31N5O = 741.25) | 565 | m/z = 692.82 (C49H32N4O = 692.26) |
| 566 | m/z = 665.75 (C46H27N5O = 665.22) | 569 | m/z = 742.84 (C52H30N4O2 = 742.24) |
| 573 | m/z = 768.92 (C55H36N4O = 768.29) | 574 | m/z = 741.85 (C52H31N5O = 741.25) |
| 580 | m/z = 521.62 (C39H23NO = 521.18) | 564 | m/z = 741.85 (C52H31N5O = 741.25) |
| 565 | m/z = 692.82 (C49H32N4O=692.26) | 566 | m/z = 665.76 (C46H27N5O=665.22) |
| 569 | m/z = 742.84 (C52H30N4O2 = 742.24) | 573 | m/z = 768.92 (C55H36N4O = 768.29) |
| 574 | m/z = 741.85 (C52H31N5O = 741.25) | 580 | m/z = 521.62 (C39H23NO = 521.18) |
| 583 | m/z = 834.01 (C59H35N3OS = 833.25) | 584 | m/z = 894.05 (C65H39N3O2 = 893.30) |
| 585 | m/z = 599.69 (C43H25N3O = 599.20) | 587 | m/z = 675.79 (C49H29N3O = 675.23) |
| 588 | m/z = 725.85 (C53H31N3O = 725.25) | 594 | m/z = 662.79 (C49H30N2O = 662.24) |
| 597 | m/z = 652.76 (C46H28N4O = 652.23) | 598 | m/z = 652.76 (C46H28N4O = 652.23) |
| 599 | m/z = 728.86 (C52H32N4O = 728.26) | 600 | m/z = 728.86 (C52H32N4O = 728.26) |
| 601 | m/z = 666.74 (C46H26H4O2 = 666.21) | 605 | m/z = 758.90 (C52H30N4OS = 758.21) |
| 606 | m/z = 741.85 (C52H31N5O = 741.25) | 611 | m/z = 727.87 (C53H33N3O = 727.26) |

TABLE 19-continued

| Compound | FD-MS | Compound | FD-MS |
| --- | --- | --- | --- |
| 612 | m/z = 664.77 (C47H28N4O = 664.23) | 615 | m/z = 740.87 (C53H32N4O = 740.26) |
| 618 | m/z = 767.93 (C56H37N3O = 767.29) | 620 | m/z = 642.78 (C44H26N4S = 642.19) |
| 623 | m/z = 668.82 (C46H28N4S = 668.20) | 624 | m/z = 794.98 (C56H34N4S = 794.25) |
| 626 | m/z = 821.01 (C56H36N4S = 820.27) | 629 | m/z = 682.80 (C46H26N4OS = 682.18) |
| 632 | m/z = 698.86 (C46H26N4S2 = 698.16) | 634 | m/z = 708.88 (C49H32N4S = 708.23) |
| 635 | m/z = 681.82 (C46H27N5S = 681.20) | 636 | m/z = 758.90 (C52H30N4OS = 758.21) |
| 640 | m/z = 774.96 (C52H30N4S2 = 774.19) | 641 | m/z = 834.01 (C58H35N5S = 833.26) |
| 644 | m/z = 587.74 (C43H25NS = 587.17) | 646 | m/z = 613.78 (C45H27NS = 613.19) |
| 649 | m/z = 537.68 (C39H23NS = 537.16) | 651 | m/z = 715.91 (C53H33NS = 715.23) |
| 652 | m/z = 669.86 (C47H27NS2 = 669.16) | 653 | m/z = 911.10 (C64H38N4OS = 910.28) |
| 654 | m/z = 834.01 (C59H35N3OS = 833.25) | 655 | m/z = 768.98 (C56H36N2S = 768.26) |
| 657 | m/z = 539.66 (C37H21N3S = 539.15) | 659 | m/z = 741.91 (C53H31N3S = 741.22) |
| 660 | m/z = 668.82 (C46H28N4S = 668.20) | 661 | m/z = 677.87 (C50H31NS = 677.22) |
| 664 | m/z = 652.82 (C47H28N2S = 652.20) | 665 | m/z = 678.85 (C49H30N2S = 678.21) |
| 666 | m/z = 675.85 (C50H29NS = 675.2) | 670 | m/z = 676.84 (C49H28N2S = 676.20) |
| 672 | m/z = 891.00 (C58H34N4S = 818.25) | 674 | m/z = 668.82 (C46H28N4S = 668.2) |
| 675 | m/z = 744.92 (C52H32N4S = 744.23) | 677 | m/z = 744.92 (C52H32N4S = 744.23) |
| 680 | m/z = 758.90 (C52H30N4OS = 758.21) | 682 | m/z = 758.90 (C52H30N4OS = 758.21) |
| 683 | m/z = 849.04 (C58H32N4S2 = 848.21) | 685 | m/z = 884.07 (C62H37N5S = 883.28) |
| 687 | m/z = 706.83 (C47H26N6S = 706.19) | 688 | m/z = 758.90 (C52H30N4OS = 758.21) |
| 691 | m/z = 774.96 (C52H30N4S2 = 774.19) | 692 | m/z = 875.08 (C60H34N4S2 = 874.22) |
| 695 | m/z = 757.91 (C52H31N5S = 757.23) | 696 | m/z = 644.84 (C46H32N2S = 644.23) |
| 697 | m/z = 618.75 (C43H26N2OS = 618.18) | 700 | m/z = 768.94 (C54H32N4S = 768.23) |
| 703 | m/z = 743.94 (C53H29NS2 = 743.17) | 704 | m/z = 834.01 (C59H35N3OS = 833.25) |
| 707 | m/z = 691.85 (C49H29N3S = 691.21) | 708 | m/z = 668.82 (C46H28N4S = 668.20) |
| 709 | m/z = 713.83 (C49H32NOPS = 713.19) | 713 | m/z = 667.83 (C47H29N3S = 667.21) |
| 714 | m/z = 743.93 (C53H33N3S = 743.24) | 716 | m/z = 743.93 (C53H33N3S = 743.24) |
| 717 | m/z = 820.03 (C59H37N3S = 819.27) | 721 | m/z = 793.99 (C57H35N3S = 793.26) |
| 728 | m/z = 808.01 (C58H37N3S = 807.27) | 729 | m/z = 680.83 (C47H28N4S = 680.20) |
| 731 | m/z = 757.91 (C53H31N3OS = 757.22) | 732 | m/z = 757.91 (C53H31N3OS = 757.22) |
| 733 | m/z = 824.03 (C57H33N3S2 = 823.21) | 734 | m/z = 824.03 (C57H33N3S2 = 823.21) |
| 735 | m/z = 833.03 (C59H36N4S = 832.27) | 736 | m/z = 783.99 (C56H37N3S = 783.27) |
| 741 | m/z = 820.03 (C59H37N3S = 819.27) | 743 | m/z = 793.99 (C57H35N3S = 793.26) |
| 745 | m/z = 743.93 (C53H33N3S = 743.24) | 748 | m/z = 665.75 (C47H27N3O2 = 664.21) |
| 750 | m/z = 747.93 (C51H29N3S2 = 747.18) | 752 | m/z = 707.89 (C50H33N3S = 707.24) |
| 756 | m/z = 757.91 (C53H31N3OS = 757.22) | 757 | m/z = 824.03 (C57H33N3S2 = 823.21) |
| 761 | m/z = 756.93 (C53H32N4S = 756.23) | 764 | m/z = 768.94 (C54H32N4S = 768.23) |
| 766 | m/z = 793.99 (C57H35N3S = 793.26) | 767 | m/z = 591.73 (C41H25N3S = 591.18) |
| 769 | m/z = 718.88 (C50H30N4S = 718.22) | 771 | m/z = 668.82 (C46H28N4S = 668.20) |

TABLE 19-continued

| Compound | FD-MS | Compound | FD-MS |
|---|---|---|---|
| 773 | m/z = 744.92 (C52H32N4S = 744.23) | 775 | m/z = 845.04 (C60H36N4S = 844.27) |
| 779 | m/z = 782.92 (C54H30N4OS = 782.21) | 783 | m/z = 698.86 (C46H26N4S2 = 698.16) |
| 784 | m/z = 757.91 (C52H31N5S = 757.23) | 786 | m/z = 781.94 (C54H31N5S = 781.23) |
| 787 | m/z = 758.90 (C52H30N4OS = 758.21) | 789 | m/z = 758.90 (C52H30N4OS = 758.21) |
| 791 | m/z = 774.96 (C52H30N4S2 = 774.19) | 792 | m/z = 834.01 (C58H35N5S = 833.26) |
| 793 | m/z = 885.10 (C63H40N4S = 884.30) | 798 | m/z = 589.76 (C43H27NS = 589.19) |
| 801 | m/z = 644.84 (C46H32N2S = 644.23) | 802 | m/z = 537.68 (C39H23NS = 537.16) |
| 807 | m/z = 758.90 (C52H30N4OS = 758.21) | 809 | m/z = 615.75 (C43H25N3S = 615.18) |
| 810 | m/z = 539.66 (C37H21N3S = 539.15) | 814 | m/z = 675.85 (C50H29NS = 675.20) |
| 816 | m/z = 641.79 (C4527N3S = 641.19) | 817 | m/z = 565.69 (C39H23N3S = 565.16) |
| 818 | m/z = 602.75 (C43H26N2S = 602.18) | 822 | m/z = 845.04 (C60H36N4S = 844.27) |
| 823 | m/z = 847.05 (C60H38N4S = 846.28) | 825 | m/z = 742.90 (C52H30N4S = 742.22) |
| 829 | m/z = 744.92 (C52H32N4S = 744.23) | 831 | m/z = 821.01 (C58H36N4S = 820.27) |
| 833 | m/z = 758.90 (C52H30N4OS = 758.21) | 836 | m/z = 748.92 (C50H28N4S2 = 748.18) |
| 838 | m/z = 884.07 (C62H37N5S = 883.28) | 842 | m/z = 758.90 (C52H30N4OS = 758.21) |
| 844 | m/z = 774.96 (C52H304S2 = 774.19) | 847 | m/z = 784.98 (C55H36N4S = 784.27) |
| 848 | m/z = 757.91 (C52H31N5S = 757.23) | 849 | m/z = 644.84 (C46H32N2S = 644.23) |
| 858 | m/z = 835.00 (C58H34N4OS = 834.25) | 860 | m/z = 691.85 (C49H29N3S = 691.21) |
| 861 | m/z = 668.82 (C46H28N4S = 668.20) | 862 | m/z = 713.83 (C49H32OPS = 713.19) |
| 863 | m/z = 678.85 (C49H30N2S = 679.21) | 870 | m/z = 667.83 (C47H29N3S = 667.21) |
| 871 | m/z = 743.93 (C53H33N3S = 743.24) | 872 | m/z = 820.03 (C59H37N3S = 819.27) |
| 883 | m/z = 757.91 (C53H31N3OS = 757.22) | 884 | m/z = 757.91 (C53H31N3OS = 757.22) |
| 887 | m/z = 833.03 (C59H36N4S = 832.27) | 888 | m/z = 783.99 (C56H37N3S = 783.27) |
| 890 | m/z = 591.73 (C41H25N3S = 591.18) | 893 | m/z = 820.03 (C59H37N3S = 819.27) |
| 905 | m/z = 757.91 (C53H31N3OS = 757.22) | 908 | m/z = 773.97 (C53H31N3S2 = 773.20) |
| 910 | m/z = 783.99 (C56H37N3S = 783.27) | 911 | m/z = 756.93 (C53H32N4S = 756.23) |
| 916 | m/z = 744.92 (C52H32N4S = 744.23) | 918 | m/z = 821.01 (C58H36N4S = 820.27) |
| 919 | m/z = 682.80 (C46H26N4OS = 682.18) | 920 | m/z = 682.80 (C46H26N4OS = 682.18) |
| 923 | m/z = 698.86 (C46H26N4S2 = 698.16) | 924 | m/z = 757.91 (C52H31N5S = 757.23) |
| 930 | m/z = 774.96 (C52H30N4S2 = 774.19) | 931 | m/z = 774.96 (C52H30N4S2 = 774.19) |
| 932 | m/z = 834.01 (C58H35N5S = 833.26) | 943 | m/z = 834.01 (C59H35N3OS = 833.25) |
| 945 | m/z = 539.66 (C37H21N3S = 539.15) | 952 | m/z = 564.71 (C40H24N2S = 563.17) |
| 956 | m/z = 678.85 (C49H30N2S = 678.21) | 957 | m/z = 675.85 (C50H29NS = 675.20) |
| 960 | m/z = 600.74 (C43H24N2S = 600.17) | 963 | m/z = 768.94 (C54H32N4S = 768.23) |
| 965 | m/z = 668.82 (C46H28N4S = 668.20) | 968 | m/z = 821.01 (C58H36N4S = 820.27) |
| 971 | m/z = 758.90 (C52H30N4OS = 758.21) | 979 | m/z = 758.90 (C52H30N4OS = 758.21) |
| 980 | m/z = 758.90 (C52H30N4OS = 758.21) | 984 | m/z = 834.01 (C58H35H5S = 833.26) |
| 986 | m/z = 757.91 (C52H31N5S = 757.23) | 991 | m/z = 613.78 (C45H27NS = 613.19) |
| 998 | m/z = 668.82 (C46H28N4S = 668.20) | 995 | m/z = 834.01 (C59H35N3OS = 833.25) |

TABLE 19-continued

| Compound | FD-MS | Compound | FD-MS |
|---|---|---|---|
| 1000 | m/z = 678.85 (C49H30N2S = 678.21) | 1004 | m/z = 743.93 (C53H33N3S = 743.24) |
| 1006 | m/z = 667.83 (C47H29N3S = 667.21) | 1011 | m/z = 681.81 (C47H27N3SO = 681.19) |
| 1015 | m/z = 707.89 (C50H33N3S = 707.24) | 1080 | m/z = 835.00 (C58H34N4OS = 834.25) |
| 1086 | m/z = 691.85 (C49H29N3S = 691.21) | 1098 | m/z = 676.64 (C49H28N2S = 676.20) |
| 1099 | m/z = 692.84 (C48H26N4S = 692.20) | | |

<Experimental Example 1> Manufacture of Organic Light Emitting Device

Comparative Example 1

1) Manufacture of Organic Light Emitting Device

A transparent indium tin oxide (ITO) electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4',4"-tris(N,N-(2-naphthyl)-phenylamino)triphenylamine (2-TNATA) was introduced to a cell in the vacuum deposition apparatus.

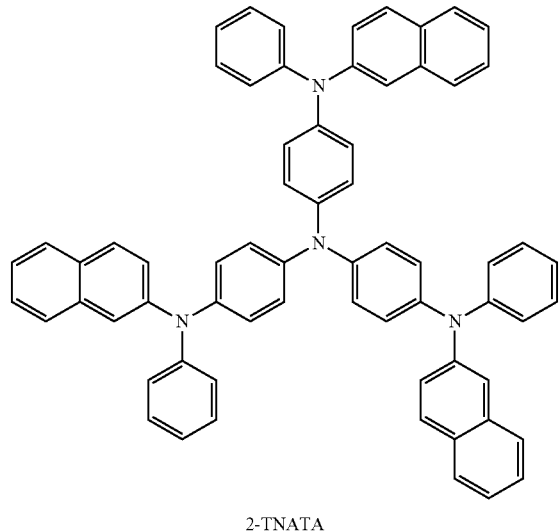

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

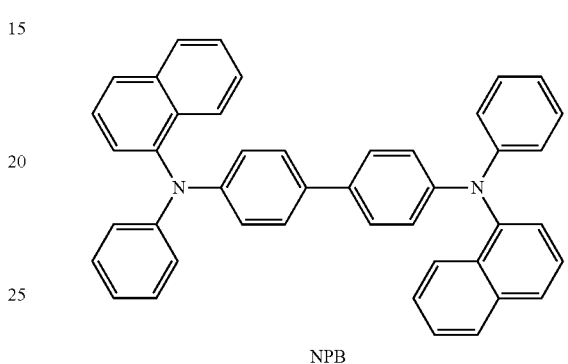

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

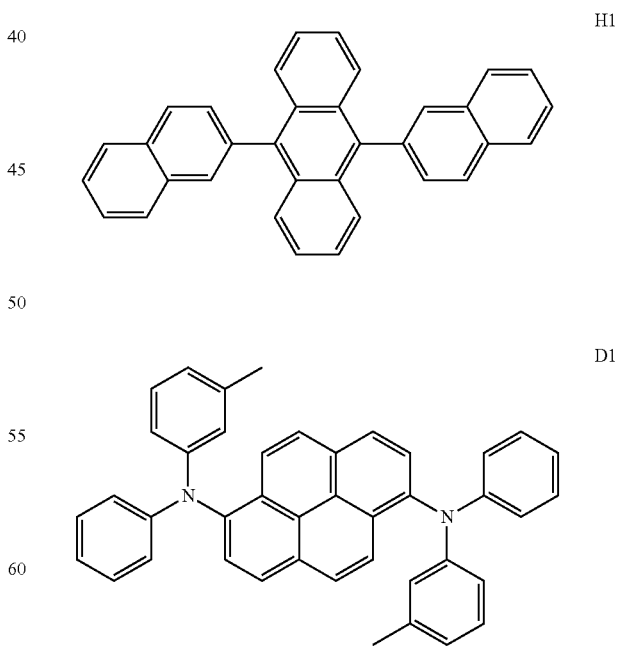

Subsequently, a compound of the following Structural Formula E1 was deposited to a thickness of 300 Å as an electron transfer layer.

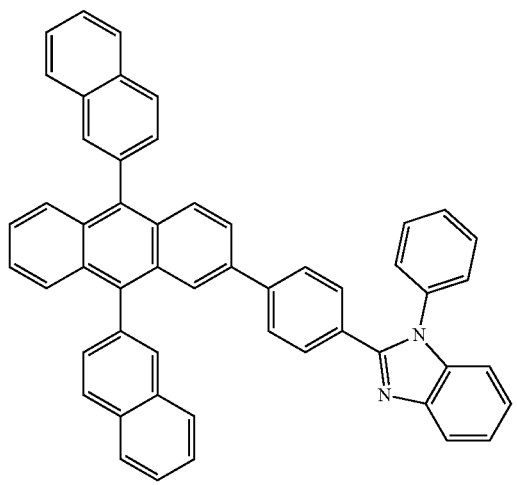

E1

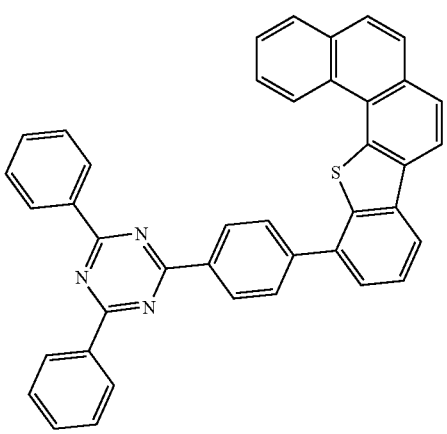

C

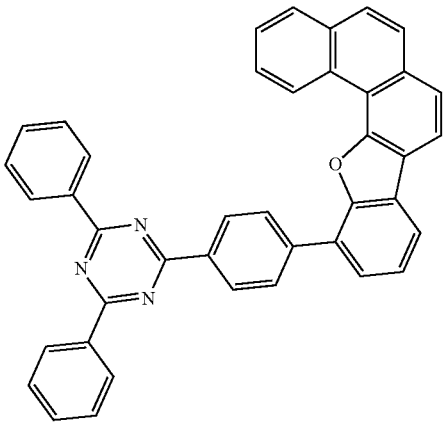

D

As an electron injection layer, lithium fluoride (LiF) was deposited to a thickness of 10 Å, and an Al cathode was employed to a thickness of 1,000 Å, and as a result, an OLED was manufactured.

Meanwhile, all the organic compounds required to manufacture the OLED were vacuum sublimation purified under $10^{-8}$ torr to $10^{-6}$ torr by each material to be used in the OLED manufacture.

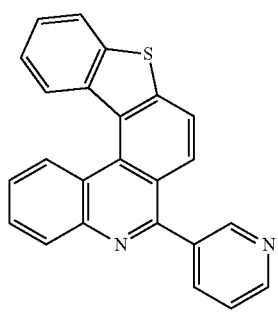

A

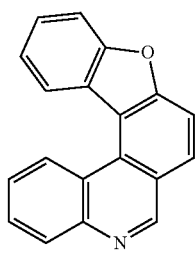

B

Comparative Example 2 to Comparative Example 5

Organic electroluminescent devices were manufactured in the same manner as in Comparative Example 1 except that Compound A, Compound B, Compound C and Compound D were used instead of E1 used when forming the electron transfer layer.

Example 1 to Example 469

Organic electroluminescent devices were manufactured in the same manner as in Comparative Example 1 except that compounds listed in the following Table 20 were used instead of E1 used when forming the electron transfer layer.

Results of measuring driving voltage, light emission efficiency, color coordinate (CIE) and lifetime of each of the blue organic light emitting devices manufactured according to the present disclosure are as shown in the following Table 20.

TABLE 20

| | Compound | Driving Voltage (V) | Light Emission Efficiency (cd/A) | CIE (x, y) | Lifetime (T95) |
|---|---|---|---|---|---|
| Comparative Example 1 | E1 | 5.21 | 4.11 | (0.134, 0.100) | 24 |
| Comparative Example 2 | A | 4.13 | 3.20 | (0.134, 0.104) | 13 |

TABLE 20-continued

| Compound | | Driving Voltage (V) | Light Emission Efficiency (cd/A) | CIE (x, y) | Lifetime (T95) |
|---|---|---|---|---|---|
| Comparative Example 3 | B | 4.11 | 3.12 | (0.134, 0.104) | 10 |
| Comparative Example 4 | C | 5.67 | 5.11 | (0.134, 0.104) | 21 |
| Comparative Example 5 | D | 5.67 | 5.12 | (0.134, 0.104) | 20 |
| Example 1 | 1 | 5.44 | 6.47 | (0.134, 0.102) | 36 |
| Example 2 | 4 | 4.47 | 6.87 | (0.134, 0.100) | 40 |
| Example 3 | 5 | 4.67 | 6.64 | (0.129, 0.100) | 38 |
| Example 4 | 7 | 4.82 | 6.55 | (0.130, 0.099) | 36 |
| Example 5 | 8 | 4.44 | 6.97 | (0.134, 0.101) | 40 |
| Example 6 | 9 | 4.61 | 6.89 | (0.134, 0.103) | 40 |
| Example 7 | 11 | 5.35 | 6.30 | (0.134, 0.102) | 33 |
| Example 8 | 12 | 5.62 | 5.95 | (0.134, 0.103) | 42 |
| Example 9 | 13 | 5.40 | 6.12 | (0.134, 0.101) | 39 |
| Example 10 | 15 | 5.50 | 5.89 | (0.134, 0.100) | 41 |
| Example 11 | 16 | 5.44 | 6.01 | (0.134, 0.101) | 36 |
| Example 12 | 17 | 5.34 | 6.58 | (0.134, 0.100) | 45 |
| Example 13 | 18 | 5.38 | 6.93 | (0.134, 0.100) | 43 |
| Example 14 | 24 | 4.91 | 6.32 | (0.134, 0.100) | 41 |
| Example 15 | 25 | 4.98 | 6.44 | (0.134, 0.100) | 40 |
| Example 16 | 28 | 5.62 | 6.38 | (0.134, 0.100) | 35 |
| Example 17 | 30 | 5.66 | 6.04 | (0.131, 0.102) | 30 |
| Example 18 | 35 | 5.40 | 6.49 | (0.134, 0.101) | 31 |
| Example 19 | 36 | 5.60 | 6.22 | (0.129, 0.100) | 29 |
| Example 20 | 37 | 4.70 | 6.01 | (0.134, 0.101) | 36 |
| Example 21 | 38 | 5.40 | 6.12 | (0.134, 0.103) | 44 |
| Example 22 | 41 | 5.60 | 6.21 | (0.134, 0.102) | 43 |
| Example 23 | 42 | 5.45 | 6.22 | (0.134, 0.101) | 37 |
| Example 24 | 44 | 5.39 | 5.95 | (0.134, 0.102) | 33 |
| Example 25 | 45 | 4.96 | 5.95 | (0.134, 0.101) | 42 |
| Example 26 | 47 | 4.91 | 6.13 | (0.134, 0.101) | 39 |
| Example 27 | 52 | 4.91 | 5.85 | (0.134, 0.100) | 41 |
| Example 28 | 53 | 4.98 | 6.38 | (0.134, 0.101) | 42 |
| Example 29 | 56 | 4.91 | 5.85 | (0.134, 0.100) | 41 |
| Example 30 | 57 | 4.98 | 6.38 | (0.134, 0.101) | 42 |
| Example 31 | 58 | 5.44 | 6.47 | (0.134, 0.102) | 36 |
| Example 32 | 64 | 4.47 | 6.87 | (0.134, 0.100) | 40 |
| Example 33 | 68 | 4.67 | 6.64 | (0.129, 0.100) | 38 |
| Example 34 | 69 | 4.82 | 6.55 | (0.130, 0.099) | 36 |
| Example 35 | 70 | 4.44 | 6.97 | (0.134, 0.101) | 40 |
| Example 36 | 72 | 4.61 | 6.89 | (0.134, 0.103) | 40 |
| Example 37 | 75 | 5.35 | 6.30 | (0.134, 0.102) | 33 |
| Example 38 | 77 | 5.62 | 5.95 | (0.134, 0.103) | 42 |
| Example 39 | 79 | 5.40 | 6.12 | (0.134, 0.101) | 39 |
| Example 40 | 80 | 5.50 | 5.89 | (0.134, 0.100) | 41 |
| Example 41 | 84 | 5.44 | 6.01 | (0.134, 0.101) | 36 |
| Example 42 | 86 | 5.34 | 6.58 | (0.134, 0.100) | 45 |
| Example 43 | 88 | 5.38 | 6.93 | (0.134, 0.100) | 43 |
| Example 44 | 89 | 4.91 | 6.32 | (0.134, 0.100) | 41 |
| Example 45 | 91 | 4.98 | 6.44 | (0.134, 0.100) | 40 |
| Example 46 | 92 | 5.62 | 6.38 | (0.134, 0.100) | 35 |
| Example 47 | 97 | 5.66 | 6.04 | (0.131, 0.102) | 30 |
| Example 48 | 100 | 5.40 | 6.49 | (0.134, 0.101) | 31 |
| Example 49 | 102 | 5.60 | 6.22 | (0.129, 0.100) | 29 |
| Example 50 | 103 | 4.70 | 6.01 | (0.134, 0.101) | 36 |
| Example 51 | 107 | 5.40 | 6.12 | (0.134, 0.103) | 44 |
| Example 52 | 112 | 5.60 | 6.21 | (0.134, 0.102) | 43 |
| Example 53 | 113 | 5.45 | 6.22 | (0.134, 0.101) | 37 |
| Example 54 | 114 | 5.39 | 5.95 | (0.134, 0.102) | 33 |
| Example 55 | 116 | 4.96 | 5.95 | (0.134, 0.101) | 42 |
| Example 56 | 119 | 5.44 | 6.47 | (0.134, 0.102) | 36 |
| Example 57 | 120 | 4.47 | 6.87 | (0.134, 0.100) | 40 |
| Example 58 | 121 | 4.67 | 6.64 | (0.129, 0.100) | 38 |
| Example 59 | 128 | 4.82 | 6.55 | (0.130, 0.099) | 36 |
| Example 60 | 132 | 4.44 | 6.97 | (0.134, 0.101) | 40 |
| Example 61 | 133 | 4.61 | 6.89 | (0.134, 0.103) | 40 |
| Example 62 | 135 | 5.35 | 6.30 | (0.134, 0.102) | 33 |
| Example 63 | 139 | 5.62 | 5.95 | (0.134, 0.103) | 42 |
| Example 64 | 140 | 5.40 | 6.12 | (0.134, 0.101) | 39 |
| Example 65 | 141 | 5.50 | 5.89 | (0.134, 0.100) | 41 |
| Example 66 | 142 | 5.44 | 6.01 | (0.134, 0.101) | 36 |
| Example 67 | 145 | 5.34 | 6.58 | (0.134, 0.100) | 45 |
| Example 68 | 149 | 5.44 | 6.47 | (0.134, 0.102) | 36 |
| Example 69 | 156 | 4.47 | 6.87 | (0.134, 0.100) | 40 |
| Example 70 | 157 | 4.67 | 6.64 | (0.129, 0.100) | 38 |

TABLE 20-continued

| | Compound | Driving Voltage (V) | Light Emission Efficiency (cd/A) | CIE (x, y) | Lifetime (T95) |
|---|---|---|---|---|---|
| Example 71 | 159 | 4.82 | 6.55 | (0.130, 0.099) | 36 |
| Example 72 | 161 | 4.44 | 6.97 | (0.134, 0.101) | 40 |
| Example 73 | 165 | 4.61 | 6.89 | (0.134, 0.103) | 40 |
| Example 74 | 166 | 5.35 | 6.30 | (0.134, 0.102) | 33 |
| Example 75 | 168 | 5.62 | 5.95 | (0.134, 0.103) | 42 |
| Example 76 | 170 | 5.40 | 6.12 | (0.134, 0.101) | 39 |
| Example 77 | 171 | 5.50 | 5.89 | (0.134, 0.100) | 41 |
| Example 78 | 172 | 5.44 | 6.01 | (0.134, 0.101) | 36 |
| Example 79 | 173 | 5.34 | 6.58 | (0.134, 0.100) | 45 |
| Example 80 | 176 | 5.38 | 6.93 | (0.134, 0.100) | 43 |
| Example 81 | 178 | 4.91 | 6.32 | (0.134, 0.100) | 41 |
| Example 82 | 179 | 4.98 | 6.44 | (0.134, 0.100) | 40 |
| Example 83 | 180 | 5.62 | 6.38 | (0.134, 0.100) | 35 |
| Example 84 | 185 | 5.66 | 6.04 | (0.131, 0.102) | 30 |
| Example 85 | 187 | 5.40 | 6.49 | (0.134, 0.101) | 31 |
| Example 86 | 190 | 5.60 | 6.22 | (0.129, 0.100) | 29 |
| Example 87 | 191 | 4.70 | 6.01 | (0.134, 0.101) | 36 |
| Example 88 | 192 | 5.40 | 6.12 | (0.134, 0.103) | 44 |
| Example 89 | 194 | 5.60 | 6.21 | (0.134, 0.102) | 43 |
| Example 90 | 195 | 5.45 | 6.22 | (0.134, 0.101) | 37 |
| Example 91 | 196 | 5.39 | 5.95 | (0.134, 0.102) | 33 |
| Example 92 | 200 | 4.96 | 5.95 | (0.134, 0.101) | 42 |
| Example 93 | 202 | 4.91 | 6.13 | (0.134, 0.101) | 39 |
| Example 94 | 204 | 4.91 | 5.85 | (0.134, 0.100) | 41 |
| Example 95 | 207 | 4.98 | 6.38 | (0.134, 0.101) | 42 |
| Example 96 | 210 | 4.74 | 6.75 | (0.134, 0.101) | 51 |
| Example 97 | 213 | 4.81 | 6.82 | (0.134, 0.102) | 53 |
| Example 98 | 214 | 5.16 | 6.20 | (0.134, 0.101) | 38 |
| Example 99 | 216 | 5.15 | 6.42 | (0.134, 0.102) | 39 |
| Example 100 | 217 | 5.31 | 6.30 | (0.134, 0.103) | 37 |
| Example 101 | 220 | 4.82 | 6.35 | (0.134, 0.100) | 50 |
| Example 102 | 222 | 4.91 | 6.12 | (0.134, 0.101) | 42 |
| Example 103 | 223 | 4.98 | 6.51 | (0.134, 0.101) | 39 |
| Example 104 | 224 | 5.62 | 6.21 | (0.134, 0.100) | 41 |
| Example 105 | 225 | 5.39 | 5.95 | (0.134, 0.101) | 34 |
| Example 106 | 227 | 4.96 | 6.88 | (0.134, 0.100) | 45 |
| Example 107 | 228 | 4.91 | 6.93 | (0.134, 0.102) | 43 |
| Example 108 | 229 | 4.76 | 6.95 | (0.134, 0.102) | 50 |
| Example 109 | 233 | 4.77 | 6.90 | (0.134, 0.102) | 51 |
| Example 110 | 237 | 4.98 | 6.05 | (0.134, 0.101) | 34 |
| Example 111 | 240 | 5.22 | 6.03 | (0.134, 0.101) | 43 |
| Example 112 | 243 | 4.82 | 6.84 | (0.134, 0.101) | 52 |
| Example 113 | 245 | 4.84 | 6.97 | (0.134, 0.102) | 51 |
| Example 114 | 247 | 5.38 | 6.88 | (0.134, 0.100) | 41 |
| Example 115 | 249 | 5.60 | 6.93 | (0.134, 0.101) | 32 |
| Example 116 | 251 | 5.45 | 6.95 | (0.134, 0.100) | 45 |
| Example 117 | 256 | 4.91 | 6.93 | (0.134, 0.100) | 43 |
| Example 118 | 257 | 4.91 | 6.95 | (0.134, 0.100) | 41 |
| Example 119 | 259 | 4.98 | 6.23 | (0.134, 0.100) | 40 |
| Example 120 | 260 | 5.62 | 5.98 | (0.134, 0.100) | 36 |
| Example 121 | 262 | 4.72 | 6.51 | (0.134, 0.102) | 48 |
| Example 122 | 265 | 4.91 | 6.93 | (0.134, 0.100) | 43 |
| Example 123 | 266 | 4.91 | 6.95 | (0.134, 0.100) | 41 |
| Example 124 | 267 | 4.98 | 6.26 | (0.134, 0.100) | 40 |
| Example 125 | 269 | 5.62 | 5.98 | (0.134, 0.100) | 33 |
| Example 126 | 271 | 4.91 | 6.32 | (0.134, 0.100) | 41 |
| Example 127 | 272 | 4.98 | 6.44 | (0.134, 0.100) | 40 |
| Example 128 | 273 | 5.62 | 6.38 | (0.134, 0.100) | 35 |
| Example 129 | 274 | 5.44 | 6.34 | (0.134, 0.102) | 36 |
| Example 130 | 276 | 5.62 | 6.20 | (0.134, 0.101) | 39 |
| Example 131 | 277 | 5.62 | 6.22 | (0.134, 0.100) | 47 |
| Example 132 | 279 | 5.62 | 5.98 | (0.134, 0.100) | 33 |
| Example 133 | 281 | 4.72 | 6.55 | (0.134, 0.102) | 48 |
| Example 134 | 284 | 4.72 | 6.20 | (0.134, 0.102) | 43 |
| Example 135 | 285 | 5.40 | 6.12 | (0.134, 0.101) | 39 |
| Example 136 | 287 | 5.44 | 6.21 | (0.134, 0.100) | 41 |
| Example 137 | 288 | 5.39 | 6.20 | (0.134, 0.101) | 36 |
| Example 138 | 292 | 4.96 | 6.88 | (0.134, 0.100) | 45 |
| Example 139 | 294 | 4.91 | 6.93 | (0.134, 0.100) | 43 |
| Example 140 | 296 | 4.96 | 6.88 | (0.134, 0.100) | 45 |
| Example 141 | 299 | 4.91 | 6.93 | (0.134, 0.102) | 43 |
| Example 142 | 302 | 4.98 | 6.22 | (0.134, 0.100) | 40 |
| Example 143 | 304 | 4.72 | 6.53 | (0.134, 0.102) | 48 |

TABLE 20-continued

| Compound | Driving Voltage (V) | Light Emission Efficiency (cd/A) | CIE (x, y) | Lifetime (T95) |
|---|---|---|---|---|
| Example 144 | 305 | 4.74 | 6.75 | (0.134, 0.101) | 51 |
| Example 145 | 307 | 4.81 | 6.82 | (0.134, 0.102) | 53 |
| Example 146 | 308 | 5.16 | 6.20 | (0.134, 0.101) | 38 |
| Example 147 | 309 | 5.15 | 6.42 | (0.134, 0.102) | 39 |
| Example 148 | 310 | 4.74 | 6.75 | (0.134, 0.101) | 51 |
| Example 149 | 312 | 4.81 | 6.82 | (0.134, 0.102) | 53 |
| Example 150 | 313 | 5.16 | 6.20 | (0.134, 0.101) | 38 |
| Example 151 | 315 | 5.15 | 6.42 | (0.134, 0.102) | 39 |
| Example 152 | 316 | 5.31 | 6.30 | (0.134, 0.103) | 37 |
| Example 153 | 318 | 4.82 | 6.35 | (0.134, 0.100) | 50 |
| Example 154 | 319 | 4.91 | 6.12 | (0.134, 0.101) | 42 |
| Example 155 | 322 | 4.98 | 6.51 | (0.134, 0.101) | 39 |
| Example 156 | 325 | 5.62 | 6.21 | (0.134, 0.100) | 41 |
| Example 157 | 326 | 5.39 | 5.95 | (0.134, 0.101) | 34 |
| Example 158 | 327 | 4.96 | 6.88 | (0.134, 0.100) | 45 |
| Example 159 | 329 | 4.91 | 6.93 | (0.134, 0.102) | 43 |
| Example 160 | 331 | 4.76 | 6.95 | (0.134, 0.102) | 50 |
| Example 161 | 332 | 4.77 | 6.90 | (0.134, 0.102) | 51 |
| Example 162 | 336 | 4.98 | 6.05 | (0.134, 0.101) | 34 |
| Example 163 | 337 | 5.22 | 6.03 | (0.134, 0.101) | 43 |
| Example 164 | 338 | 4.82 | 6.84 | (0.134, 0.101) | 52 |
| Example 165 | 339 | 4.84 | 6.97 | (0.134, 0.102) | 51 |
| Example 166 | 342 | 5.38 | 6.88 | (0.134, 0.100) | 41 |
| Example 167 | 343 | 5.60 | 6.93 | (0.134, 0.101) | 32 |
| Example 168 | 345 | 5.45 | 6.95 | (0.134, 0.100) | 45 |
| Example 169 | 348 | 4.91 | 6.93 | (0.134, 0.100) | 43 |
| Example 170 | 350 | 4.91 | 6.95 | (0.134, 0.100) | 41 |
| Example 171 | 353 | 4.98 | 6.23 | (0.134, 0.100) | 40 |
| Example 172 | 355 | 5.62 | 5.98 | (0.134, 0.100) | 36 |
| Example 173 | 358 | 4.72 | 6.51 | (0.134, 0.102) | 48 |
| Example 174 | 359 | 4.91 | 6.93 | (0.134, 0.100) | 43 |
| Example 175 | 360 | 4.91 | 6.95 | (0.134, 0.100) | 41 |
| Example 176 | 364 | 4.98 | 6.26 | (0.134, 0.100) | 40 |
| Example 177 | 365 | 5.62 | 5.98 | (0.134, 0.100) | 33 |
| Example 178 | 367 | 4.91 | 6.32 | (0.134, 0.100) | 41 |
| Example 179 | 368 | 4.98 | 6.44 | (0.134, 0.100) | 40 |
| Example 180 | 373 | 5.62 | 6.38 | (0.134, 0.100) | 35 |
| Example 181 | 374 | 5.44 | 6.34 | (0.134, 0.102) | 36 |
| Example 182 | 377 | 5.62 | 6.20 | (0.134, 0.101) | 39 |
| Example 183 | 378 | 5.62 | 6.22 | (0.134, 0.100) | 47 |
| Example 184 | 379 | 5.62 | 5.98 | (0.134, 0.100) | 33 |
| Example 185 | 380 | 4.72 | 6.55 | (0.134, 0.102) | 48 |
| Example 186 | 384 | 4.72 | 6.20 | (0.134, 0.102) | 43 |
| Example 187 | 386 | 5.40 | 6.12 | (0.134, 0.101) | 39 |
| Example 188 | 387 | 5.44 | 6.21 | (0.134, 0.100) | 41 |
| Example 189 | 388 | 5.39 | 6.20 | (0.134, 0.101) | 36 |
| Example 190 | 392 | 4.96 | 6.88 | (0.134, 0.100) | 45 |
| Example 191 | 395 | 4.91 | 6.93 | (0.134, 0.100) | 43 |
| Example 192 | 396 | 4.96 | 6.88 | (0.134, 0.100) | 45 |
| Example 193 | 397 | 4.91 | 6.93 | (0.134, 0.102) | 43 |
| Example 194 | 399 | 4.98 | 6.22 | (0.134, 0.100) | 40 |
| Example 195 | 400 | 4.72 | 6.53 | (0.134, 0.102) | 48 |
| Example 196 | 401 | 4.72 | 6.53 | (0.134, 0.102) | 48 |
| Example 197 | 404 | 5.45 | 6.95 | (0.134, 0.100) | 45 |
| Example 198 | 407 | 4.91 | 6.93 | (0.134, 0.100) | 43 |
| Example 199 | 408 | 4.91 | 6.95 | (0.134, 0.100) | 41 |
| Example 200 | 409 | 4.98 | 6.23 | (0.134, 0.100) | 40 |
| Example 201 | 411 | 5.62 | 5.98 | (0.134, 0.100) | 36 |
| Example 202 | 413 | 4.72 | 6.51 | (0.134, 0.102) | 48 |
| Example 203 | 415 | 4.91 | 6.93 | (0.134, 0.100) | 43 |
| Example 204 | 416 | 4.91 | 6.95 | (0.134, 0.100) | 41 |
| Example 205 | 417 | 4.98 | 6.26 | (0.134, 0.100) | 40 |
| Example 206 | 421 | 5.62 | 5.98 | (0.134, 0.100) | 33 |
| Example 207 | 423 | 4.91 | 6.32 | (0.134, 0.100) | 41 |
| Example 208 | 424 | 4.98 | 6.44 | (0.134, 0.100) | 40 |
| Example 209 | 426 | 4.91 | 6.95 | (0.134, 0.100) | 41 |
| Example 210 | 431 | 4.98 | 6.23 | (0.134, 0.100) | 40 |
| Example 211 | 432 | 5.62 | 5.98 | (0.134, 0.100) | 36 |
| Example 212 | 433 | 4.72 | 6.51 | (0.134, 0.102) | 48 |
| Example 213 | 436 | 4.91 | 6.93 | (0.134, 0.100) | 43 |
| Example 214 | 438 | 4.91 | 6.95 | (0.134, 0.100) | 41 |
| Example 215 | 440 | 4.98 | 6.26 | (0.134, 0.100) | 40 |
| Example 216 | 441 | 5.62 | 5.98 | (0.134, 0.100) | 33 |

TABLE 20-continued

| Compound | Driving Voltage (V) | Light Emission Efficiency (cd/A) | CIE (x, y) | Lifetime (T95) |
|---|---|---|---|---|
| Example 217 | 443 | 4.91 | 6.32 | (0.134, 0.100) | 41 |
| Example 218 | 447 | 4.98 | 6.44 | (0.134, 0.100) | 40 |
| Example 219 | 448 | 5.62 | 6.38 | (0.134, 0.100) | 35 |
| Example 220 | 449 | 5.44 | 6.34 | (0.134, 0.102) | 36 |
| Example 221 | 450 | 5.62 | 6.20 | (0.134, 0.101) | 39 |
| Example 222 | 452 | 5.62 | 6.22 | (0.134, 0.100) | 47 |
| Example 223 | 456 | 5.62 | 5.98 | (0.134, 0.100) | 33 |
| Example 224 | 460 | 4.72 | 6.55 | (0.134, 0.102) | 48 |
| Example 225 | 462 | 4.72 | 6.20 | (0.134, 0.102) | 43 |
| Example 226 | 465 | 5.40 | 6.12 | (0.134, 0.101) | 39 |
| Example 227 | 467 | 5.44 | 6.21 | (0.134, 0.100) | 41 |
| Example 228 | 468 | 5.39 | 6.20 | (0.134, 0.101) | 36 |
| Example 229 | 470 | 4.96 | 6.88 | (0.134, 0.100) | 45 |
| Example 230 | 475 | 4.91 | 6.93 | (0.134, 0.100) | 43 |
| Example 231 | 476 | 4.96 | 6.88 | (0.134, 0.100) | 45 |
| Example 232 | 477 | 4.91 | 6.93 | (0.134, 0.102) | 43 |
| Example 233 | 479 | 4.98 | 6.22 | (0.134, 0.100) | 40 |
| Example 234 | 481 | 4.72 | 6.53 | (0.134, 0.102) | 48 |
| Example 235 | 482 | 4.72 | 6.53 | (0.134, 0.102) | 48 |
| Example 236 | 485 | 5.45 | 6.95 | (0.134, 0.100) | 45 |
| Example 237 | 488 | 4.91 | 6.93 | (0.134, 0.100) | 43 |
| Example 238 | 489 | 4.91 | 6.95 | (0.134, 0.100) | 41 |
| Example 239 | 490 | 4.98 | 6.23 | (0.134, 0.100) | 40 |
| Example 240 | 493 | 4.74 | 6.75 | (0.134, 0.101) | 51 |
| Example 241 | 494 | 4.81 | 6.82 | (0.134, 0.102) | 53 |
| Example 242 | 495 | 5.16 | 6.20 | (0.134, 0.101) | 38 |
| Example 243 | 500 | 5.15 | 6.42 | (0.134, 0.102) | 39 |
| Example 244 | 504 | 5.31 | 6.30 | (0.134, 0.103) | 37 |
| Example 245 | 505 | 4.82 | 6.35 | (0.134, 0.100) | 50 |
| Example 246 | 506 | 4.91 | 6.12 | (0.134, 0.101) | 42 |
| Example 247 | 509 | 4.98 | 6.51 | (0.134, 0.101) | 39 |
| Example 248 | 512 | 5.62 | 6.21 | (0.134, 0.100) | 41 |
| Example 249 | 513 | 5.39 | 5.95 | (0.134, 0.101) | 34 |
| Example 250 | 516 | 4.96 | 6.88 | (0.134, 0.100) | 45 |
| Example 251 | 517 | 4.91 | 6.93 | (0.134, 0.102) | 43 |
| Example 252 | 518 | 4.76 | 6.95 | (0.134, 0.102) | 50 |
| Example 253 | 519 | 4.77 | 6.90 | (0.134, 0.102) | 51 |
| Example 254 | 520 | 4.98 | 6.05 | (0.134, 0.101) | 34 |
| Example 255 | 522 | 5.22 | 6.03 | (0.134, 0.101) | 43 |
| Example 256 | 524 | 4.82 | 6.84 | (0.134, 0.101) | 52 |
| Example 257 | 525 | 4.84 | 6.97 | (0.134, 0.102) | 51 |
| Example 258 | 527 | 5.38 | 6.88 | (0.134, 0.100) | 41 |
| Example 259 | 528 | 5.60 | 6.93 | (0.134, 0.101) | 32 |
| Example 260 | 531 | 5.45 | 6.95 | (0.134, 0.100) | 45 |
| Example 261 | 532 | 4.91 | 6.93 | (0.134, 0.100) | 43 |
| Example 262 | 533 | 4.91 | 6.95 | (0.134, 0.100) | 41 |
| Example 263 | 535 | 4.98 | 6.23 | (0.134, 0.100) | 40 |
| Example 264 | 536 | 5.62 | 5.98 | (0.134, 0.100) | 36 |
| Example 265 | 539 | 4.72 | 6.51 | (0.134, 0.102) | 48 |
| Example 266 | 542 | 4.91 | 6.93 | (0.134, 0.100) | 43 |
| Example 267 | 543 | 4.91 | 6.95 | (0.134, 0.100) | 41 |
| Example 268 | 544 | 4.98 | 6.26 | (0.134, 0.100) | 40 |
| Example 269 | 547 | 5.62 | 5.98 | (0.134, 0.100) | 33 |
| Example 270 | 548 | 4.91 | 6.32 | (0.134, 0.100) | 41 |
| Example 271 | 549 | 4.98 | 6.44 | (0.134, 0.100) | 40 |
| Example 272 | 550 | 5.62 | 6.38 | (0.134, 0.100) | 35 |
| Example 273 | 554 | 5.44 | 6.34 | (0.134, 0.102) | 36 |
| Example 274 | 555 | 5.62 | 6.20 | (0.134, 0.101) | 39 |
| Example 275 | 557 | 5.62 | 6.22 | (0.134, 0.100) | 47 |
| Example 276 | 558 | 5.62 | 5.98 | (0.134, 0.100) | 33 |
| Example 277 | 564 | 4.72 | 6.55 | (0.134, 0.102) | 48 |
| Example 278 | 564 | 4.72 | 6.20 | (0.134, 0.102) | 43 |
| Example 279 | 565 | 5.40 | 6.12 | (0.134, 0.101) | 39 |
| Example 280 | 565 | 5.44 | 6.21 | (0.134, 0.100) | 41 |
| Example 281 | 566 | 5.39 | 6.20 | (0.134, 0.101) | 36 |
| Example 282 | 566 | 4.96 | 6.88 | (0.134, 0.100) | 45 |
| Example 283 | 569 | 4.91 | 6.93 | (0.134, 0.100) | 43 |
| Example 284 | 569 | 4.96 | 6.88 | (0.134, 0.100) | 45 |
| Example 285 | 573 | 4.91 | 6.93 | (0.134, 0.102) | 43 |
| Example 286 | 573 | 4.98 | 6.22 | (0.134, 0.100) | 40 |
| Example 287 | 574 | 4.72 | 6.53 | (0.134, 0.102) | 48 |
| Example 288 | 574 | 4.74 | 6.75 | (0.134, 0.101) | 51 |
| Example 289 | 580 | 4.81 | 6.82 | (0.134, 0.102) | 53 |

TABLE 20-continued

| Compound | Driving Voltage (V) | Light Emission Efficiency (cd/A) | CIE (x, y) | Lifetime (T95) |
|---|---|---|---|---|
| Example 290 | 580 | 5.16 | 6.20 | (0.134, 0.101) | 38 |
| Example 291 | 583 | 5.15 | 6.42 | (0.134, 0.102) | 39 |
| Example 292 | 584 | 4.74 | 6.75 | (0.134, 0.101) | 51 |
| Example 293 | 585 | 4.81 | 6.82 | (0.134, 0.102) | 53 |
| Example 294 | 587 | 5.16 | 6.20 | (0.134, 0.101) | 38 |
| Example 295 | 588 | 5.15 | 6.42 | (0.134, 0.102) | 39 |
| Example 296 | 594 | 5.31 | 6.30 | (0.134, 0.103) | 37 |
| Example 297 | 597 | 4.82 | 6.35 | (0.134, 0.100) | 50 |
| Example 298 | 598 | 4.91 | 6.12 | (0.134, 0.101) | 42 |
| Example 299 | 599 | 4.98 | 6.51 | (0.134, 0.101) | 39 |
| Example 300 | 600 | 5.62 | 6.21 | (0.134, 0.100) | 41 |
| Example 301 | 601 | 5.39 | 5.95 | (0.134, 0.101) | 34 |
| Example 302 | 605 | 4.96 | 6.88 | (0.134, 0.100) | 45 |
| Example 303 | 606 | 4.91 | 6.93 | (0.134, 0.102) | 43 |
| Example 304 | 611 | 4.76 | 6.95 | (0.134, 0.102) | 50 |
| Example 305 | 612 | 4.77 | 6.90 | (0.134, 0.102) | 51 |
| Example 306 | 615 | 4.98 | 6.05 | (0.134, 0.101) | 34 |
| Example 307 | 618 | 5.22 | 6.03 | (0.134, 0.101) | 43 |
| Example 308 | 620 | 4.82 | 6.84 | (0.134, 0.101) | 52 |
| Example 309 | 623 | 4.84 | 6.97 | (0.134, 0.102) | 51 |
| Example 310 | 624 | 5.38 | 6.88 | (0.134, 0.100) | 41 |
| Example 311 | 626 | 5.60 | 6.93 | (0.134, 0.101) | 32 |
| Example 312 | 629 | 5.45 | 6.95 | (0.134, 0.100) | 45 |
| Example 313 | 632 | 4.91 | 6.93 | (0.134, 0.100) | 43 |
| Example 314 | 634 | 4.91 | 6.95 | (0.134, 0.100) | 41 |
| Example 315 | 635 | 4.98 | 6.23 | (0.134, 0.100) | 40 |
| Example 316 | 636 | 5.62 | 5.98 | (0.134, 0.100) | 36 |
| Example 317 | 640 | 4.72 | 6.51 | (0.134, 0.102) | 48 |
| Example 318 | 641 | 4.91 | 6.93 | (0.134, 0.100) | 43 |
| Example 319 | 644 | 4.91 | 6.95 | (0.134, 0.100) | 41 |
| Example 320 | 646 | 4.98 | 6.26 | (0.134, 0.100) | 40 |
| Example 321 | 649 | 5.62 | 5.98 | (0.134, 0.100) | 33 |
| Example 322 | 651 | 4.91 | 6.32 | (0.134, 0.100) | 41 |
| Example 323 | 652 | 4.98 | 6.44 | (0.134, 0.100) | 40 |
| Example 324 | 653 | 5.62 | 6.38 | (0.134, 0.100) | 35 |
| Example 325 | 654 | 5.44 | 6.34 | (0.134, 0.102) | 36 |
| Example 326 | 655 | 5.62 | 6.20 | (0.134, 0.101) | 39 |
| Example 327 | 657 | 5.62 | 6.22 | (0.134, 0.100) | 47 |
| Example 328 | 659 | 5.62 | 5.98 | (0.134, 0.100) | 33 |
| Example 329 | 660 | 4.72 | 6.55 | (0.134, 0.102) | 48 |
| Example 330 | 661 | 4.72 | 6.20 | (0.134, 0.102) | 43 |
| Example 331 | 664 | 5.40 | 6.12 | (0.134, 0.101) | 39 |
| Example 332 | 665 | 5.44 | 6.21 | (0.134, 0.100) | 41 |
| Example 333 | 666 | 5.39 | 6.20 | (0.134, 0.101) | 36 |
| Example 334 | 670 | 4.96 | 6.88 | (0.134, 0.100) | 45 |
| Example 335 | 672 | 4.91 | 6.93 | (0.134, 0.100) | 43 |
| Example 336 | 674 | 4.96 | 6.88 | (0.134, 0.100) | 45 |
| Example 337 | 675 | 4.91 | 6.93 | (0.134, 0.102) | 43 |
| Example 338 | 677 | 4.98 | 6.22 | (0.134, 0.100) | 40 |
| Example 339 | 680 | 4.72 | 6.53 | (0.134, 0.102) | 48 |
| Example 340 | 682 | 4.72 | 6.53 | (0.134, 0.102) | 48 |
| Example 341 | 683 | 5.45 | 6.95 | (0.134, 0.100) | 45 |
| Example 342 | 685 | 4.91 | 6.93 | (0.134, 0.100) | 43 |
| Example 343 | 687 | 4.91 | 6.95 | (0.134, 0.100) | 41 |
| Example 344 | 688 | 4.98 | 6.23 | (0.134, 0.100) | 40 |
| Example 345 | 691 | 5.62 | 5.98 | (0.134, 0.100) | 36 |
| Example 346 | 692 | 4.72 | 6.51 | (0.134, 0.102) | 48 |
| Example 347 | 695 | 4.91 | 6.93 | (0.134, 0.100) | 43 |
| Example 348 | 696 | 4.91 | 6.95 | (0.134, 0.100) | 41 |
| Example 349 | 697 | 4.98 | 6.26 | (0.134, 0.100) | 40 |
| Example 350 | 700 | 5.62 | 5.98 | (0.134, 0.100) | 33 |
| Example 351 | 703 | 4.91 | 6.32 | (0.134, 0.100) | 41 |
| Example 352 | 704 | 4.98 | 6.44 | (0.134, 0.100) | 40 |
| Example 353 | 707 | 4.91 | 6.95 | (0.134, 0.100) | 41 |
| Example 354 | 708 | 4.98 | 6.23 | (0.134, 0.100) | 40 |
| Example 355 | 709 | 5.62 | 5.98 | (0.134, 0.100) | 36 |
| Example 356 | 713 | 4.72 | 6.51 | (0.134, 0.102) | 48 |
| Example 357 | 714 | 4.91 | 6.93 | (0.134, 0.100) | 43 |
| Example 358 | 716 | 4.91 | 6.95 | (0.134, 0.100) | 41 |
| Example 359 | 717 | 4.98 | 6.26 | (0.134, 0.100) | 40 |
| Example 360 | 721 | 5.62 | 5.98 | (0.134, 0.100) | 33 |
| Example 361 | 728 | 4.91 | 6.32 | (0.134, 0.100) | 41 |
| Example 362 | 729 | 4.98 | 6.44 | (0.134, 0.100) | 40 |

TABLE 20-continued

| | Compound | Driving Voltage (V) | Light Emission Efficiency (cd/A) | CIE (x, y) | Lifetime (T95) |
|---|---|---|---|---|---|
| Example 363 | 731 | 5.62 | 6.38 | (0.134, 0.100) | 35 |
| Example 364 | 732 | 5.44 | 6.34 | (0.134, 0.102) | 36 |
| Example 365 | 733 | 5.62 | 6.20 | (0.134, 0.101) | 39 |
| Example 366 | 734 | 5.62 | 6.22 | (0.134, 0.100) | 47 |
| Example 367 | 735 | 5.62 | 5.98 | (0.134, 0.100) | 33 |
| Example 368 | 736 | 4.72 | 6.55 | (0.134, 0.102) | 48 |
| Example 369 | 741 | 4.72 | 6.20 | (0.134, 0.102) | 43 |
| Example 370 | 743 | 4.74 | 6.75 | (0.134, 0.101) | 51 |
| Example 371 | 745 | 4.81 | 6.82 | (0.134, 0.102) | 53 |
| Example 372 | 748 | 5.16 | 6.20 | (0.134, 0.101) | 38 |
| Example 373 | 750 | 5.15 | 6.42 | (0.134, 0.102) | 39 |
| Example 374 | 752 | 5.31 | 6.30 | (0.134, 0.103) | 37 |
| Example 375 | 756 | 4.82 | 6.35 | (0.134, 0.100) | 50 |
| Example 376 | 757 | 4.91 | 6.12 | (0.134, 0.101) | 42 |
| Example 377 | 761 | 4.98 | 6.51 | (0.134, 0.101) | 39 |
| Example 378 | 764 | 5.62 | 6.21 | (0.134, 0.100) | 41 |
| Example 379 | 766 | 5.39 | 5.95 | (0.134, 0.101) | 34 |
| Example 380 | 767 | 4.96 | 6.88 | (0.134, 0.100) | 45 |
| Example 381 | 769 | 4.91 | 6.93 | (0.134, 0.102) | 43 |
| Example 382 | 771 | 4.76 | 6.95 | (0.134, 0.102) | 50 |
| Example 383 | 773 | 4.77 | 6.90 | (0.134, 0.102) | 51 |
| Example 384 | 775 | 4.98 | 6.05 | (0.134, 0.101) | 34 |
| Example 385 | 779 | 5.22 | 6.03 | (0.134, 0.101) | 43 |
| Example 386 | 783 | 4.82 | 6.84 | (0.134, 0.101) | 52 |
| Example 387 | 784 | 4.84 | 6.97 | (0.134, 0.102) | 51 |
| Example 388 | 786 | 5.38 | 6.88 | (0.134, 0.100) | 41 |
| Example 389 | 787 | 5.60 | 6.93 | (0.134, 0.101) | 32 |
| Example 390 | 789 | 5.45 | 6.95 | (0.134, 0.100) | 45 |
| Example 391 | 791 | 4.91 | 6.93 | (0.134, 0.100) | 43 |
| Example 392 | 792 | 4.91 | 6.95 | (0.134, 0.100) | 41 |
| Example 393 | 793 | 4.98 | 6.23 | (0.134, 0.100) | 40 |
| Example 394 | 798 | 5.62 | 5.98 | (0.134, 0.100) | 36 |
| Example 395 | 801 | 4.72 | 6.51 | (0.134, 0.102) | 48 |
| Example 396 | 802 | 4.91 | 6.93 | (0.134, 0.100) | 43 |
| Example 397 | 807 | 4.91 | 6.95 | (0.134, 0.100) | 41 |
| Example 398 | 809 | 4.98 | 6.26 | (0.134, 0.100) | 40 |
| Example 399 | 810 | 5.62 | 5.98 | (0.134, 0.100) | 33 |
| Example 400 | 814 | 4.91 | 6.32 | (0.134, 0.100) | 41 |
| Example 401 | 816 | 4.98 | 6.44 | (0.134, 0.100) | 40 |
| Example 402 | 817 | 5.62 | 6.38 | (0.134, 0.100) | 35 |
| Example 403 | 818 | 5.44 | 6.34 | (0.134, 0.102) | 36 |
| Example 404 | 822 | 5.62 | 6.20 | (0.134, 0.101) | 39 |
| Example 405 | 823 | 5.62 | 6.22 | (0.134, 0.100) | 47 |
| Example 406 | 825 | 5.62 | 5.98 | (0.134, 0.100) | 33 |
| Example 407 | 829 | 4.72 | 6.55 | (0.134, 0.102) | 48 |
| Example 408 | 831 | 4.72 | 6.20 | (0.134, 0.102) | 43 |
| Example 409 | 833 | 5.40 | 6.12 | (0.134, 0.101) | 39 |
| Example 410 | 836 | 5.44 | 6.21 | (0.134, 0.100) | 41 |
| Example 411 | 838 | 5.39 | 6.20 | (0.134, 0.101) | 36 |
| Example 412 | 842 | 4.96 | 6.88 | (0.134, 0.100) | 45 |
| Example 413 | 844 | 4.91 | 6.93 | (0.134, 0.100) | 43 |
| Example 414 | 847 | 4.96 | 6.88 | (0.134, 0.100) | 45 |
| Example 415 | 848 | 4.91 | 6.93 | (0.134, 0.102) | 43 |
| Example 416 | 849 | 4.98 | 6.22 | (0.134, 0.100) | 40 |
| Example 417 | 858 | 4.72 | 6.53 | (0.134, 0.102) | 48 |
| Example 418 | 860 | 4.74 | 6.75 | (0.134, 0.101) | 51 |
| Example 419 | 861 | 4.81 | 6.82 | (0.134, 0.102) | 53 |
| Example 420 | 862 | 5.16 | 6.20 | (0.134, 0.101) | 38 |
| Example 421 | 863 | 5.15 | 6.42 | (0.134, 0.102) | 39 |
| Example 422 | 870 | 4.74 | 6.75 | (0.134, 0.101) | 51 |
| Example 423 | 871 | 4.81 | 6.82 | (0.134, 0.102) | 53 |
| Example 424 | 872 | 5.16 | 6.20 | (0.134, 0.101) | 38 |
| Example 425 | 883 | 5.15 | 6.42 | (0.134, 0.102) | 39 |
| Example 426 | 884 | 5.31 | 6.30 | (0.134, 0.103) | 37 |
| Example 427 | 887 | 4.82 | 6.35 | (0.134, 0.100) | 50 |
| Example 428 | 888 | 4.91 | 6.12 | (0.134, 0.101) | 42 |
| Example 429 | 890 | 4.98 | 6.51 | (0.134, 0.101) | 39 |
| Example 430 | 893 | 5.62 | 6.21 | (0.134, 0.100) | 41 |
| Example 431 | 905 | 5.39 | 5.95 | (0.134, 0.101) | 34 |
| Example 432 | 908 | 4.96 | 6.88 | (0.134, 0.100) | 45 |
| Example 433 | 910 | 4.91 | 6.93 | (0.134, 0.102) | 43 |
| Example 434 | 911 | 4.76 | 6.95 | (0.134, 0.102) | 50 |
| Example 435 | 916 | 4.77 | 6.90 | (0.134, 0.102) | 51 |

TABLE 20-continued

| Compound | Driving Voltage (V) | Light Emission Efficiency (cd/A) | CIE (x, y) | Lifetime (T95) |
|---|---|---|---|---|
| Example 436 | 918 | 4.98 | 6.05 | (0.134, 0.101) | 34 |
| Example 437 | 919 | 5.22 | 6.03 | (0.134, 0.101) | 43 |
| Example 438 | 920 | 4.82 | 6.84 | (0.134, 0.101) | 52 |
| Example 439 | 923 | 4.84 | 6.97 | (0.134, 0.102) | 51 |
| Example 440 | 924 | 5.38 | 6.88 | (0.134, 0.100) | 41 |
| Example 441 | 930 | 5.60 | 6.93 | (0.134, 0.101) | 32 |
| Example 442 | 931 | 5.45 | 6.95 | (0.134, 0.100) | 45 |
| Example 443 | 932 | 4.91 | 6.93 | (0.134, 0.100) | 43 |
| Example 444 | 943 | 4.91 | 6.95 | (0.134, 0.100) | 41 |
| Example 445 | 945 | 4.98 | 6.23 | (0.134, 0.100) | 40 |
| Example 446 | 952 | 5.62 | 5.98 | (0.134, 0.100) | 36 |
| Example 447 | 956 | 4.72 | 6.51 | (0.134, 0.102) | 48 |
| Example 448 | 957 | 4.91 | 6.93 | (0.134, 0.100) | 43 |
| Example 449 | 960 | 4.91 | 6.95 | (0.134, 0.100) | 41 |
| Example 450 | 963 | 4.98 | 6.26 | (0.134, 0.100) | 40 |
| Example 451 | 965 | 5.62 | 5.98 | (0.134, 0.100) | 33 |
| Example 452 | 968 | 4.91 | 6.32 | (0.134, 0.100) | 41 |
| Example 453 | 971 | 4.98 | 6.44 | (0.134, 0.100) | 40 |
| Example 454 | 979 | 5.62 | 6.38 | (0.134, 0.100) | 35 |
| Example 455 | 980 | 5.44 | 6.34 | (0.134, 0.102) | 36 |
| Example 456 | 984 | 5.62 | 6.20 | (0.134, 0.101) | 39 |
| Example 457 | 986 | 5.62 | 6.22 | (0.134, 0.100) | 47 |
| Example 458 | 991 | 5.62 | 5.98 | (0.134, 0.100) | 33 |
| Example 459 | 995 | 4.72 | 6.55 | (0.134, 0.102) | 48 |
| Example 460 | 998 | 4.72 | 6.20 | (0.134, 0.102) | 43 |
| Example 461 | 1000 | 5.40 | 6.12 | (0.134, 0.101) | 39 |
| Example 462 | 1004 | 5.44 | 6.21 | (0.134, 0.100) | 41 |
| Example 463 | 1006 | 5.39 | 6.20 | (0.134, 0.101) | 36 |
| Example 464 | 1011 | 4.96 | 6.88 | (0.134, 0.100) | 45 |
| Example 465 | 1015 | 4.91 | 6.93 | (0.134, 0.100) | 43 |
| Example 466 | 1080 | 4.96 | 6.88 | (0.134, 0.100) | 45 |
| Example 467 | 1086 | 4.91 | 6.93 | (0.134, 0.102) | 43 |
| Example 468 | 1098 | 4.98 | 6.22 | (0.134, 0.100) | 40 |
| Example 469 | 1099 | 4.72 | 6.53 | (0.134, 0.102) | 48 |

As seen from Table 20, the organic light emitting device using the compound of the present disclosure as an electron transfer layer material of a blue organic light emitting device had lower driving voltage and improved light emission efficiency and lifetime compared to Comparative Example 1, Comparative Example 2, Comparative Example 3 and Comparative Example 4. Such results are due to the fact that the compound is a bipolar type having both a p-type and an n-type, and therefore, hole leakage is prevented and electrons are effectively injected to a light emitting layer.

The invention claimed is:

1. A heterocyclic compound represented by the following Chemical Formula 1:

[Chemical Formula 1-1]

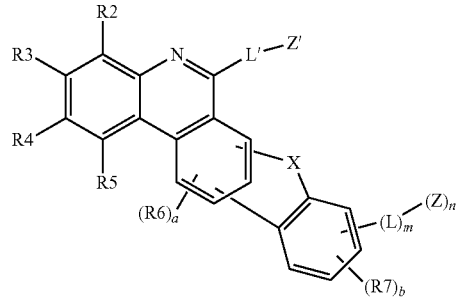

wherein, in Chemical Formula 1,

X is O or S,

L is a direct bond; a substituted or unsubstituted C6 to C60 arylene group; or a substituted or unsubstituted C2 to C60 heteroarylene group, Z is a substituted or unsubstituted C6 to C30 aryl group; a substituted or unsubstituted C2 to C30 heteroaryl group; or a substituted or unsubstituted phosphine oxide group, R1 is a substituted or unsubstituted C6 to C30 aryl group, R2 to R7 are each independently hydrogen; or deuterium, a is 1 or 2, b is an integer of 1 to 3, m and n are each an integer of 1 to 5, and when a, b, m and n are each 2 or greater, substituents in the parentheses are the same as or different from each other.

2. The heterocyclic compound of claim 1, wherein Chemical Formula 1 is represented by any one of the following Chemical Formula 2 to Chemical Formula 4:

[Chemical Formula 2]

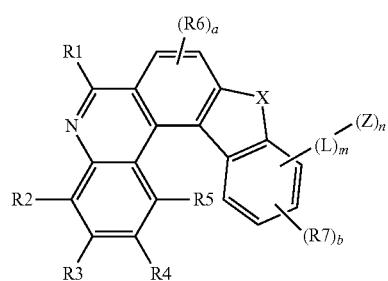

[Chemical Formula 3]

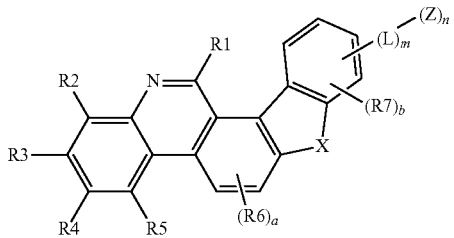

[Chemical Formula 4]

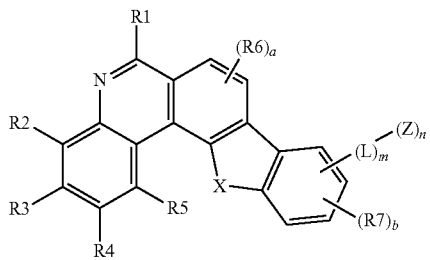

in Chemical Formulae 2 to 4,

X, L, Z, R1 to R7, a, b, m and n have the same definitions as in Chemical Formula 1.

3. The heterocyclic compound of claim 1, wherein L is a direct bond; a substituted or unsubstituted phenylene group; a substituted or unsubstituted biphenylene group; a substituted or unsubstituted terphenylene group; a substituted or unsubstituted naphthylene group; a substituted or unsubstituted anthracenylene group; a substituted or unsubstituted triphenylenylene group; a substituted or unsubstituted phenanthrenylene group; a substituted or unsubstituted divalent pyridine group; a substituted or unsubstituted divalent pyrimidine group; or a substituted or unsubstituted divalent triazine group.

4. The heterocyclic compound of claim 1, wherein Z is a substituted or unsubstituted phenyl group; a biphenyl group; a terphenyl group; a naphthyl group; a triphenylenyl group; a phenanthrenyl group; an anthracenyl group; a dimethylfluorenyl group; a diphenylfluorenyl group; a spirobifluorenyl group; an isoquinolinyl group; a quinazolinyl group; a phenoxazinyl group; a phenothiazinyl group; an indolocarbazole group; a substituted or unsubstituted pyridine group; a substituted or unsubstituted pyrimidine group; a substituted or unsubstituted triazine group; a substituted or unsubstituted carbazole group; a substituted or unsubstituted benzocarbazole group; a substituted or unsubstituted phenanthrolinyl group; a substituted or unsubstituted dibenzofuran group; a substituted or unsubstituted dibenzothiophene group; a substituted or unsubstituted dihydroacridine group; or a substituted or unsubstituted phosphine oxide group.

5. The heterocyclic compound of claim 1, wherein Chemical Formula 1 is represented by any one of the following compounds:

1

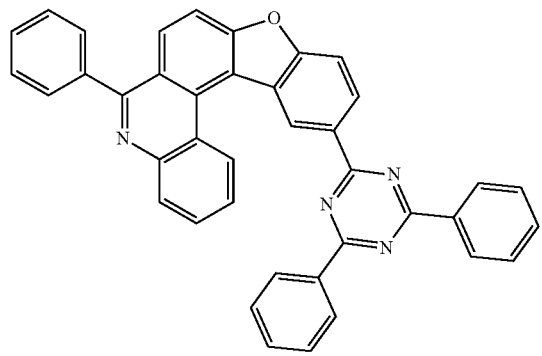

2

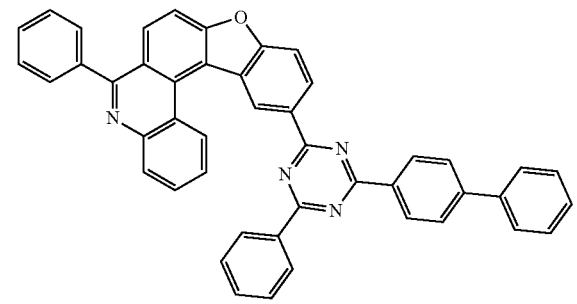

3

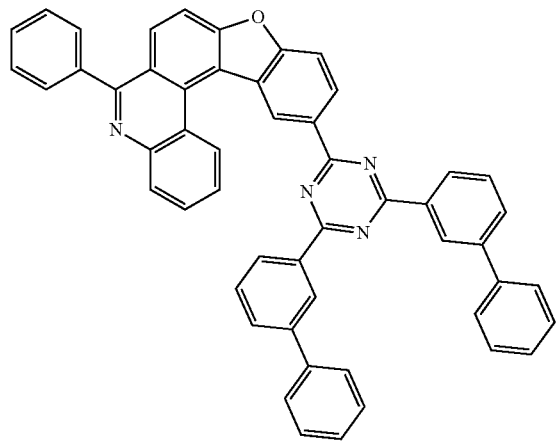

4

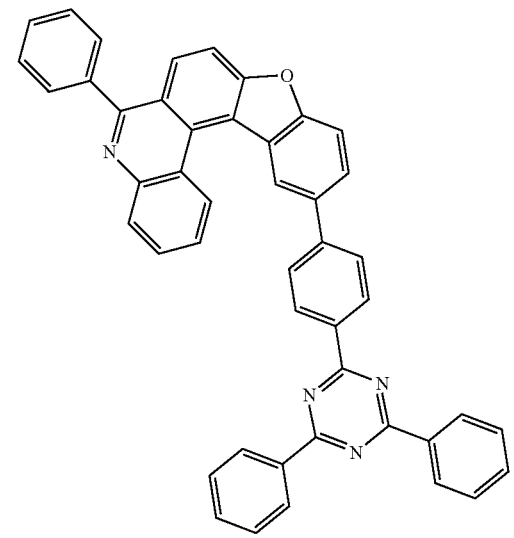

-continued
755
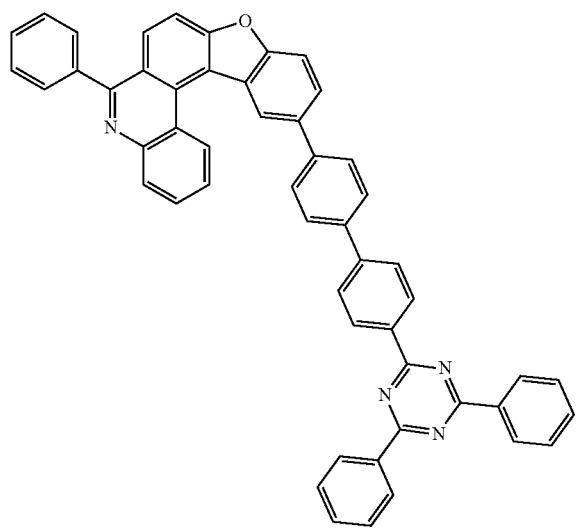
756
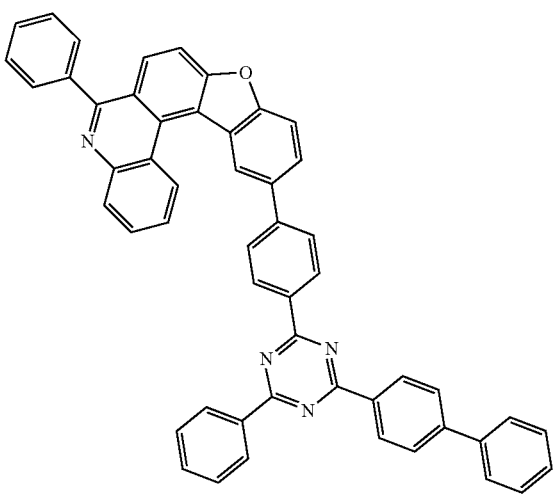
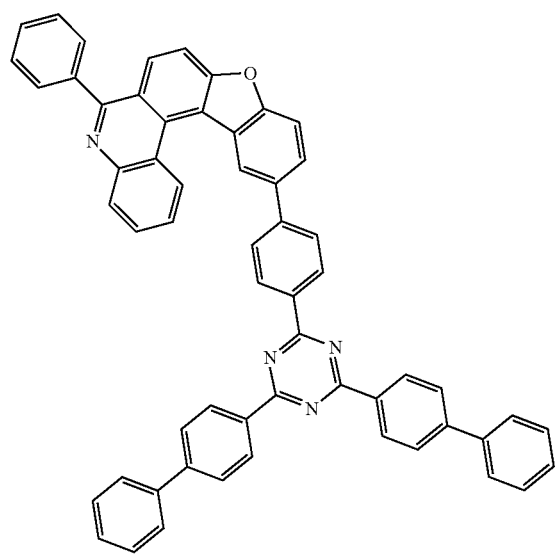
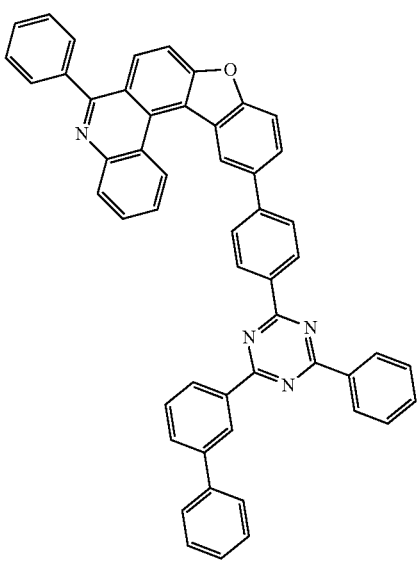

-continued
9
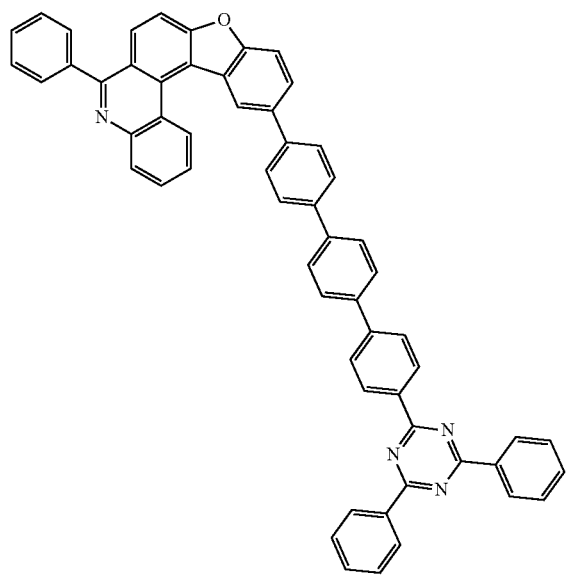
10
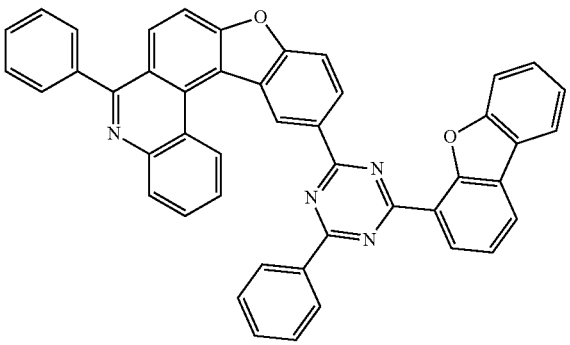
11
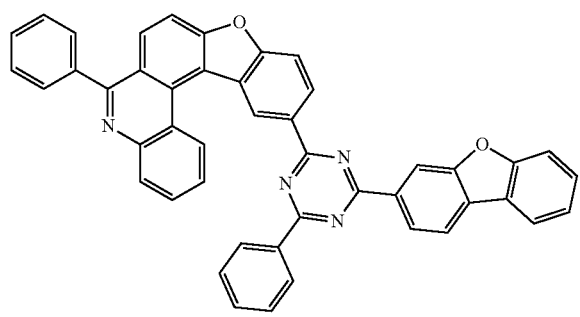
12
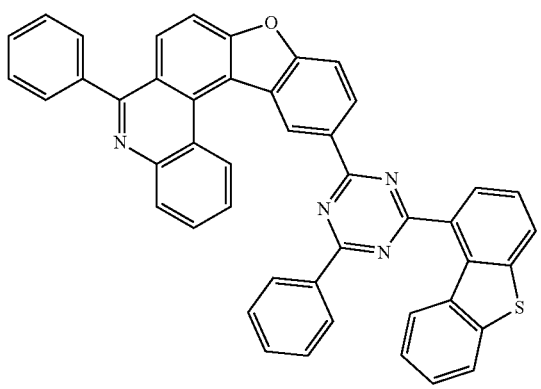
13
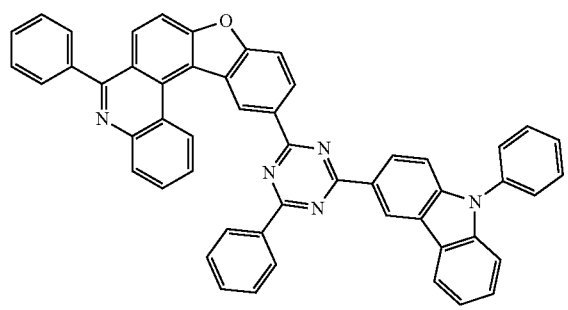
14
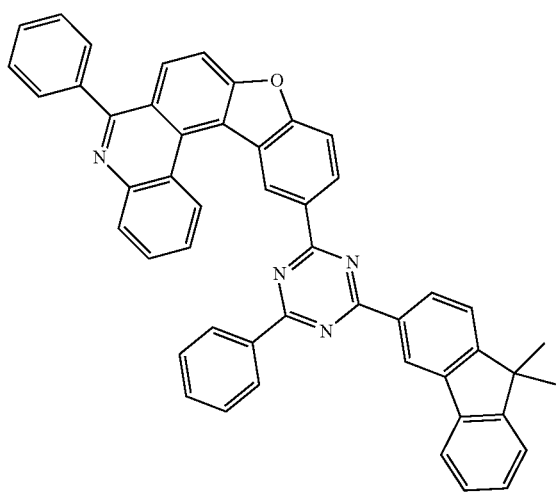

-continued
15
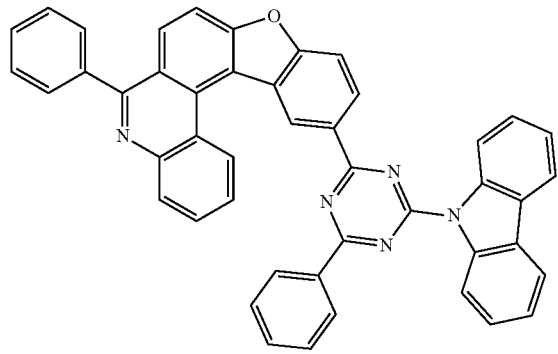
16
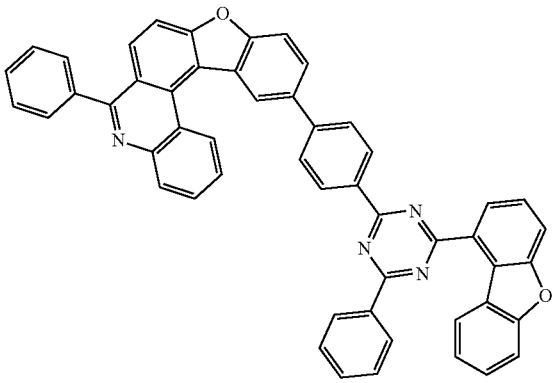
17
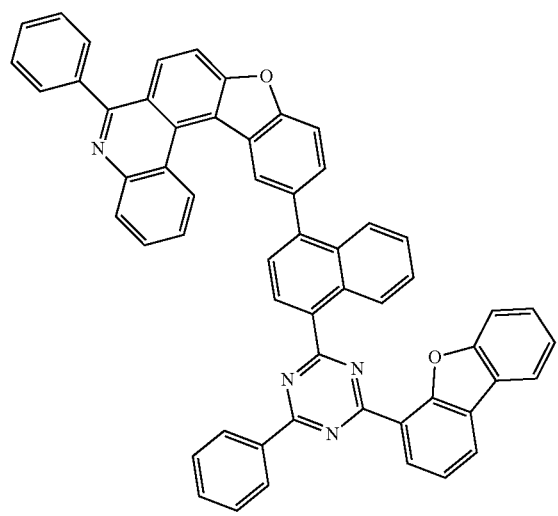
18
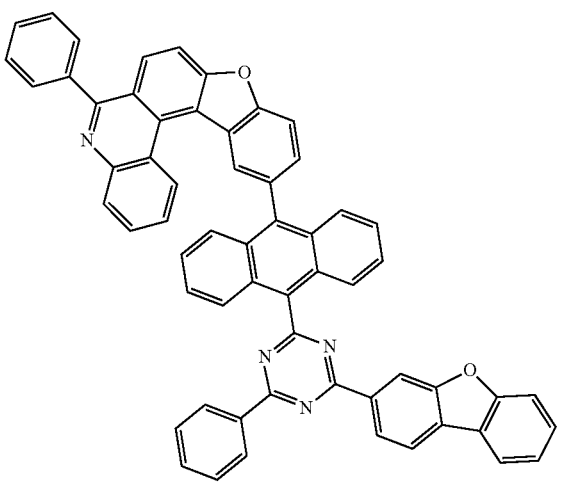
19
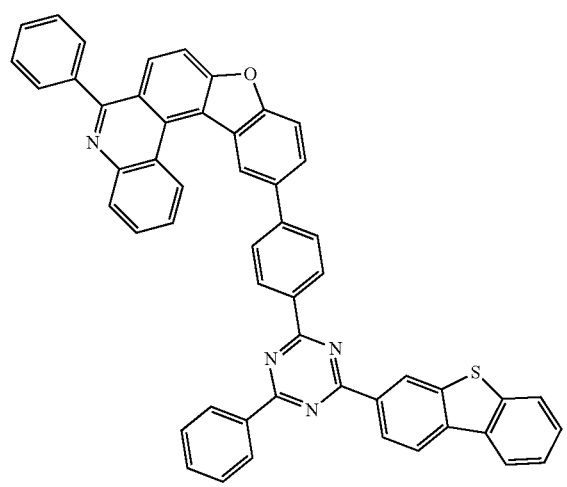
20
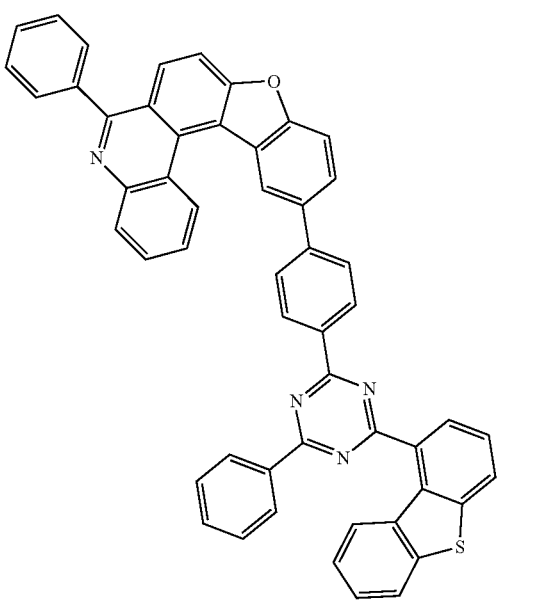

-continued
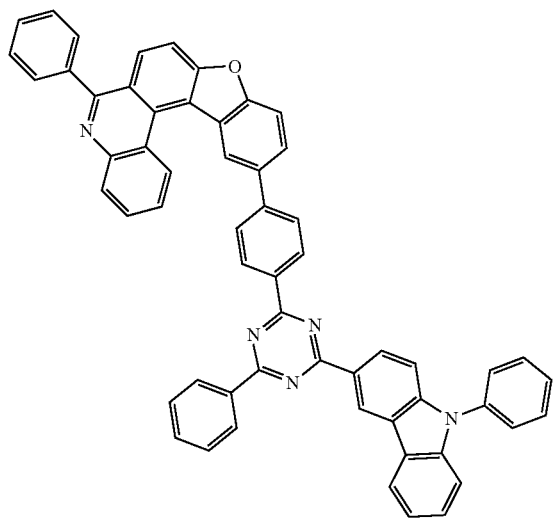
21
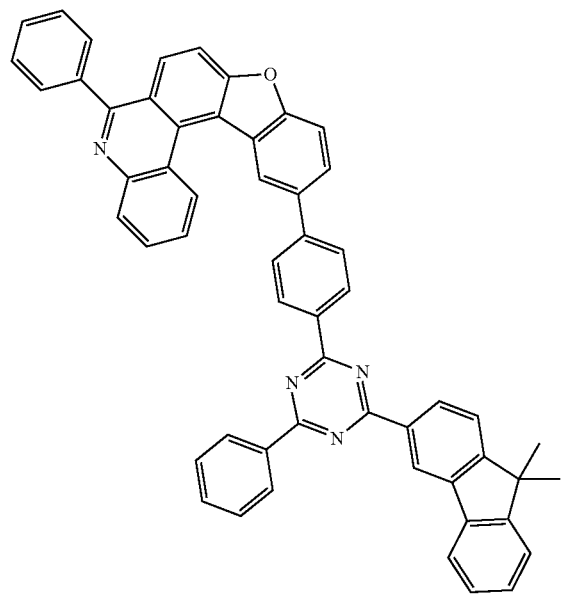
22
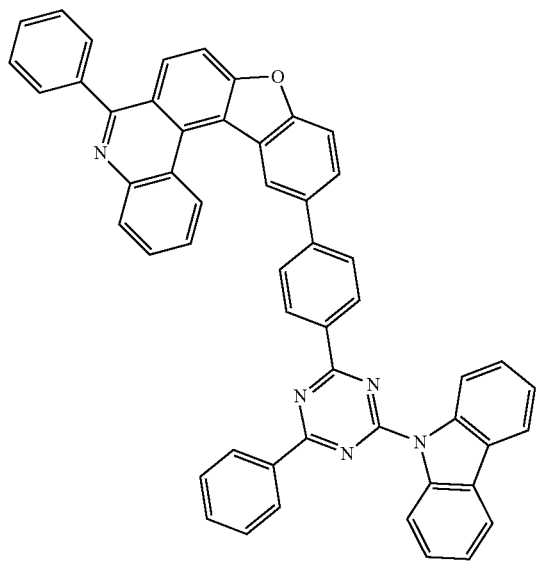
23
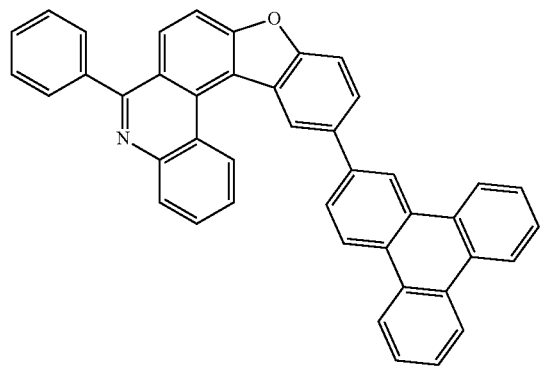
24
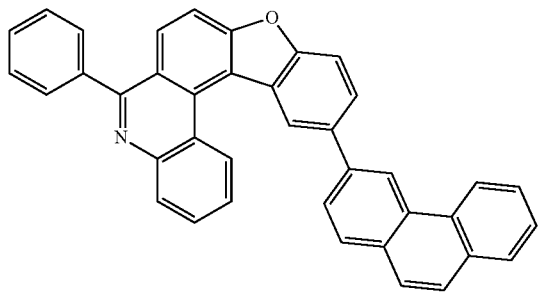
25
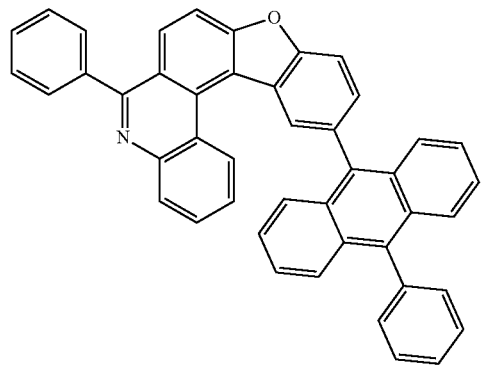
26

-continued
| 27 | 28 |
|---|---|
| 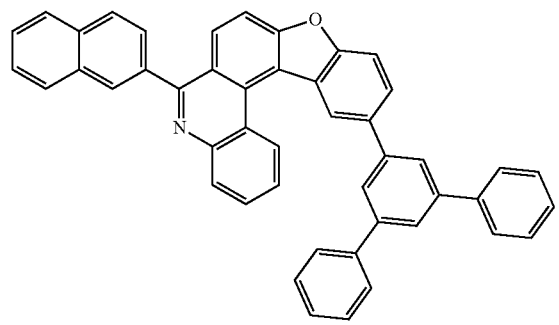 | 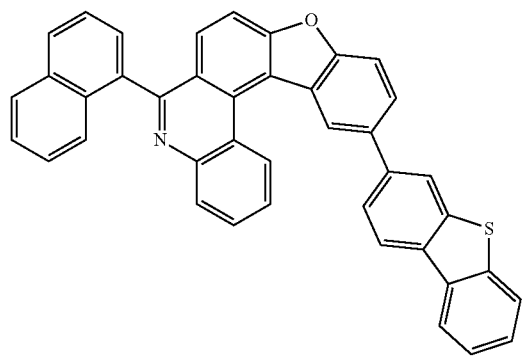 |
| 29 | 30 |
|---|---|
| 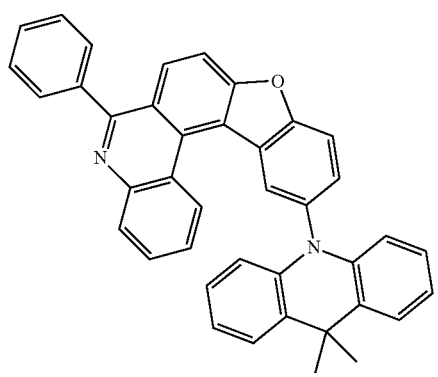 | 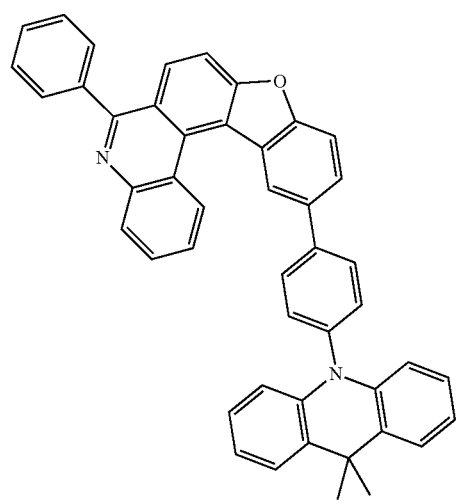 |
| 31 | 32 |
|---|---|
| 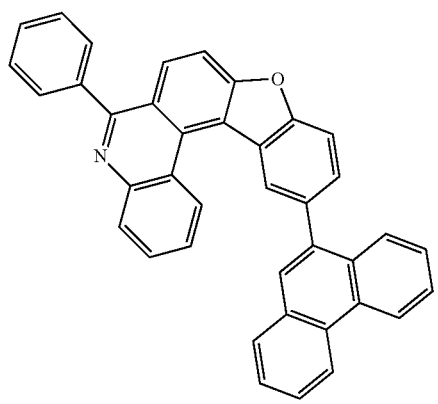 | 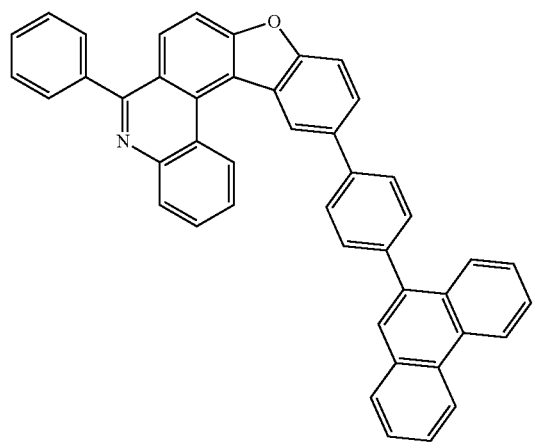 |

-continued
765
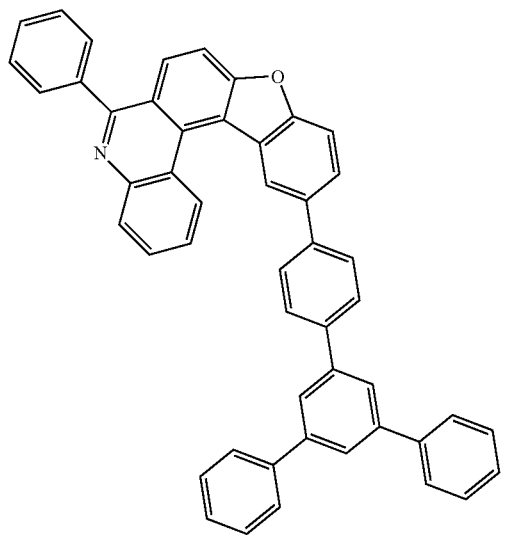
33
766
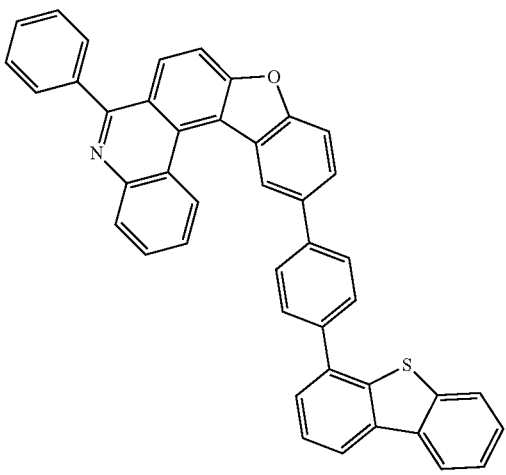
34
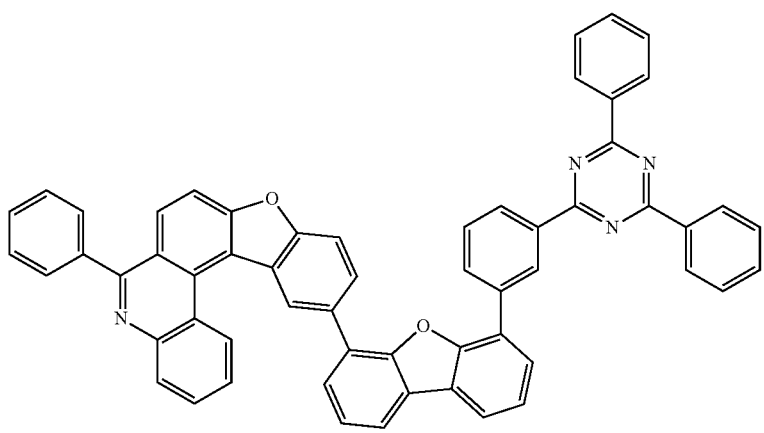
35
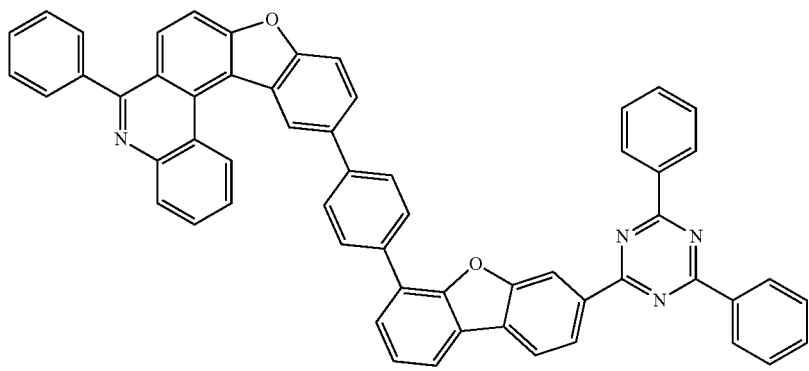
36

-continued
37
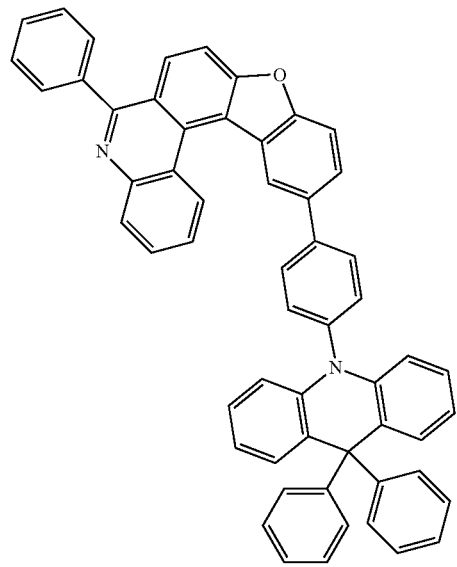
38
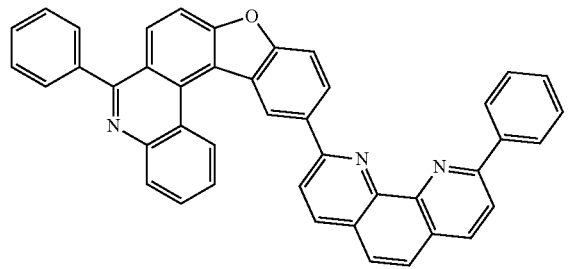
39
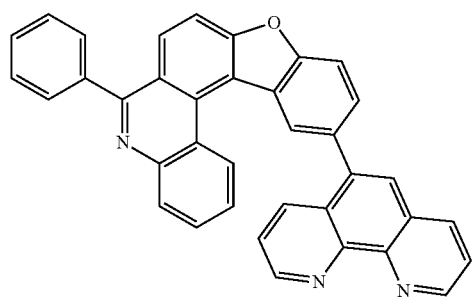
40
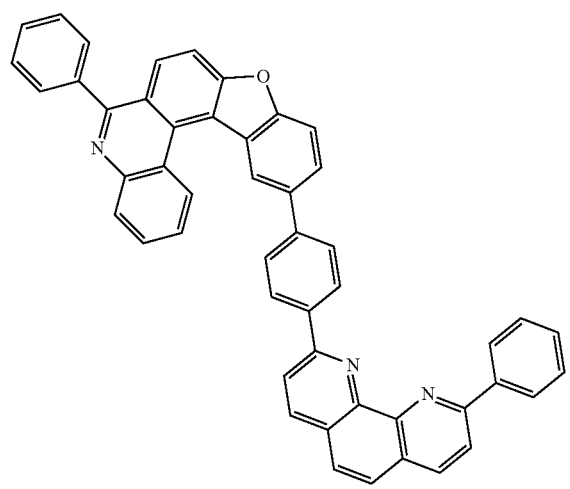
41
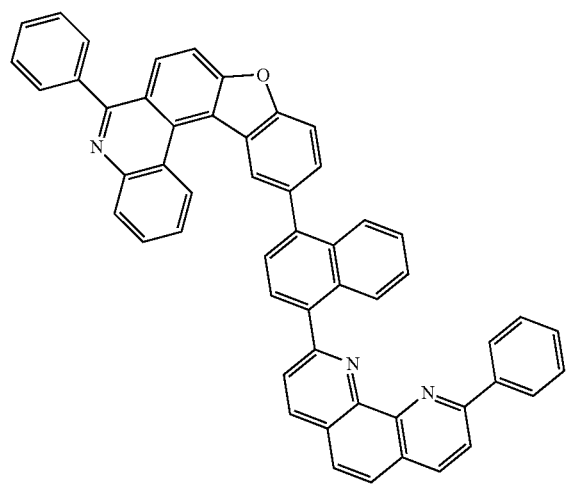
42
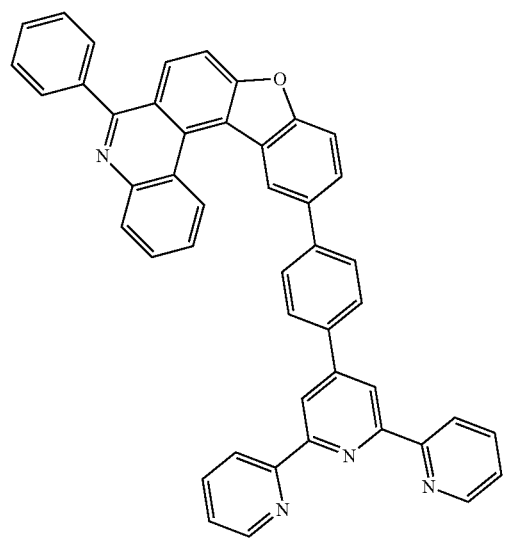

43
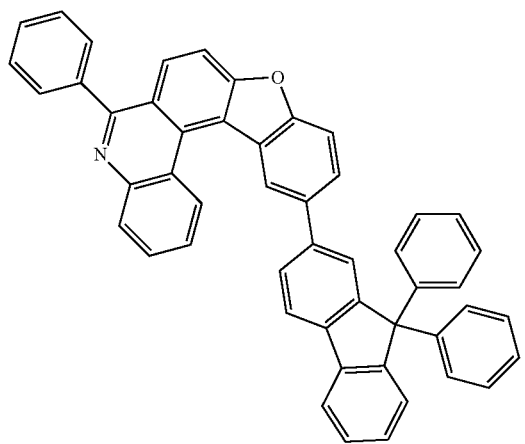
44
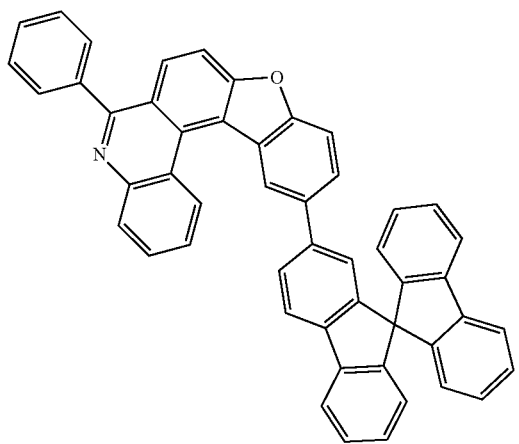
45
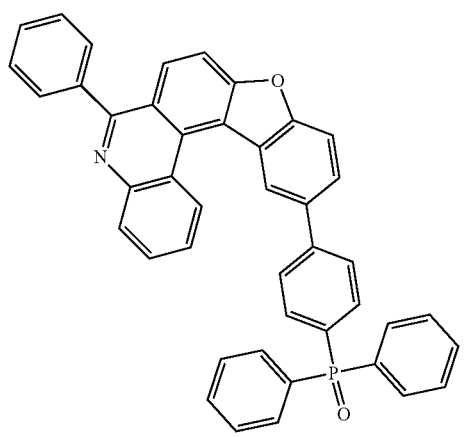
46
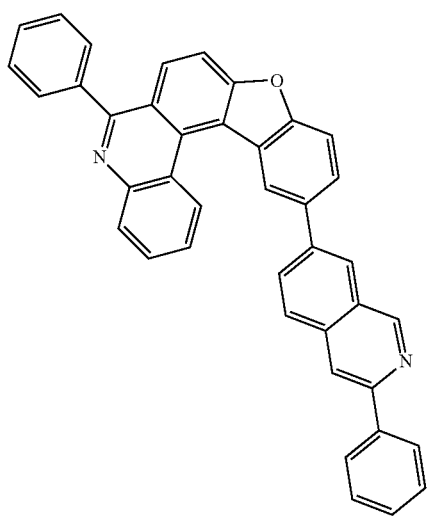
47
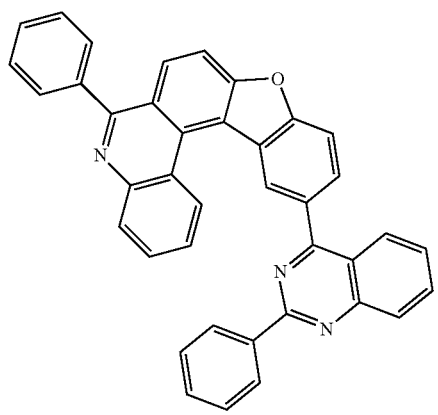
48
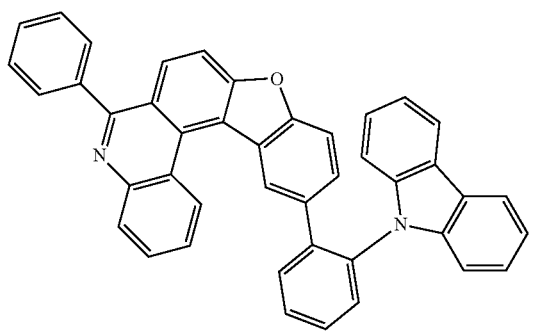

-continued
49
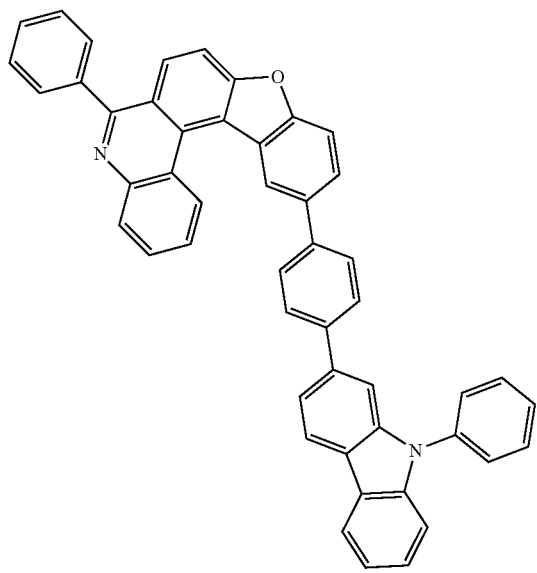
50
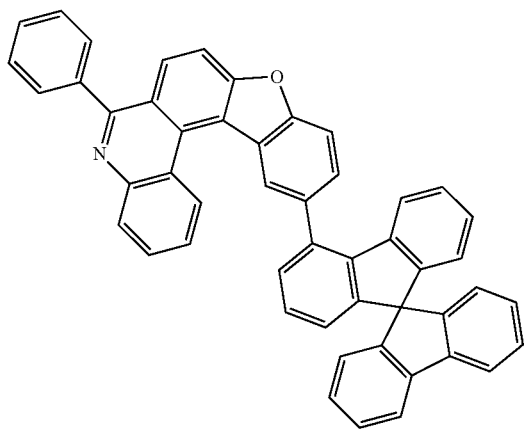
51
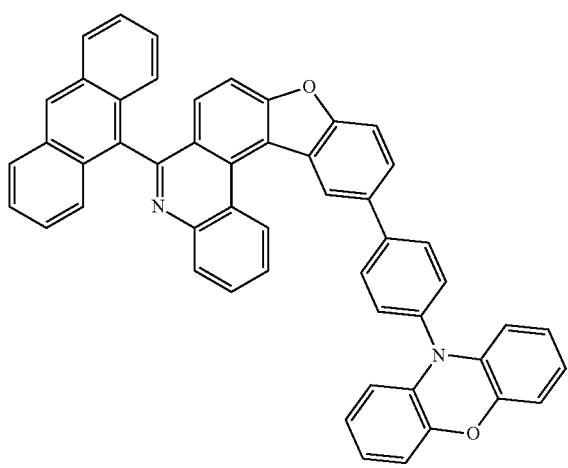
52
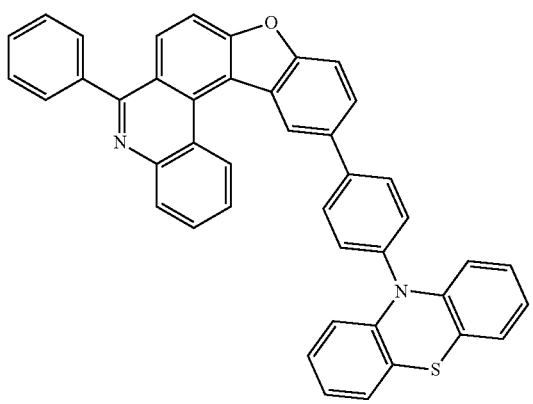
53
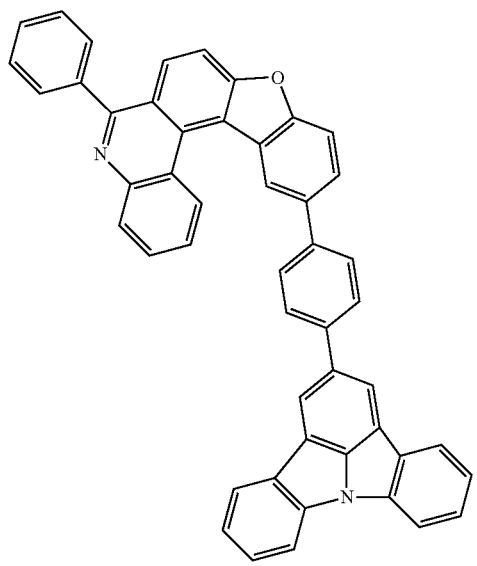
54
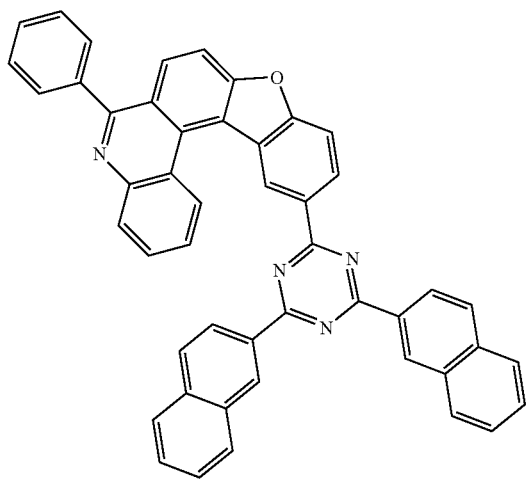

773
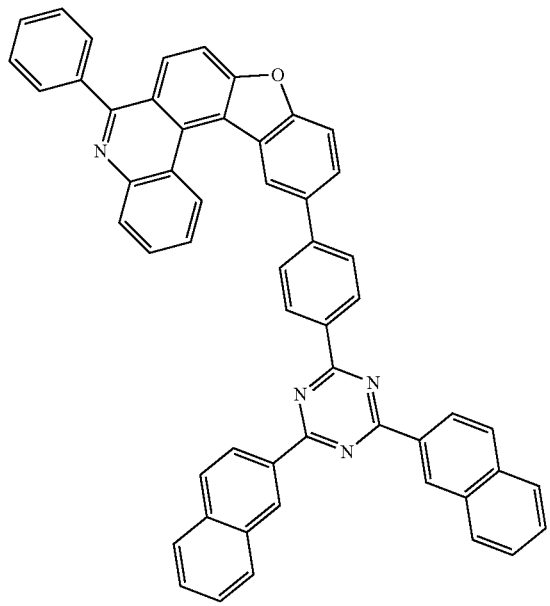
55
774
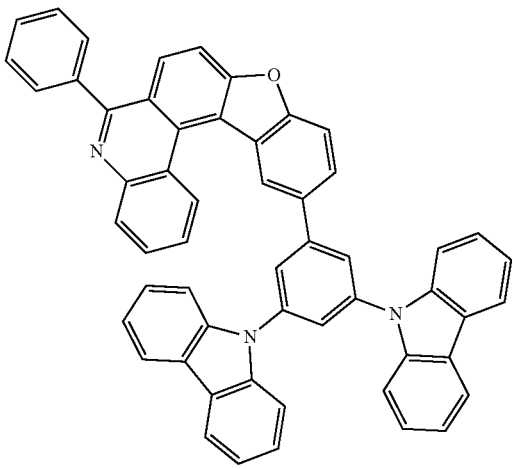
56
57
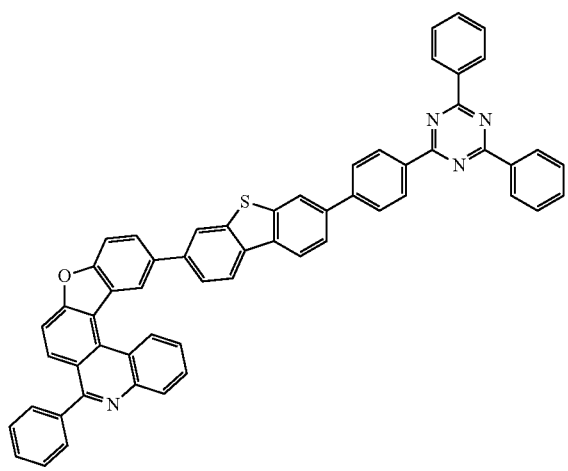
58
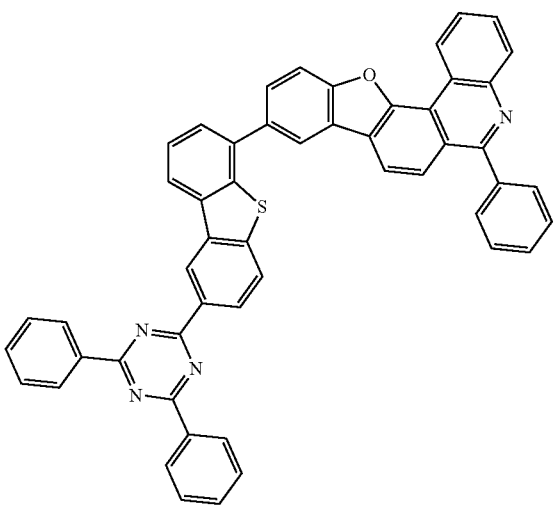
59
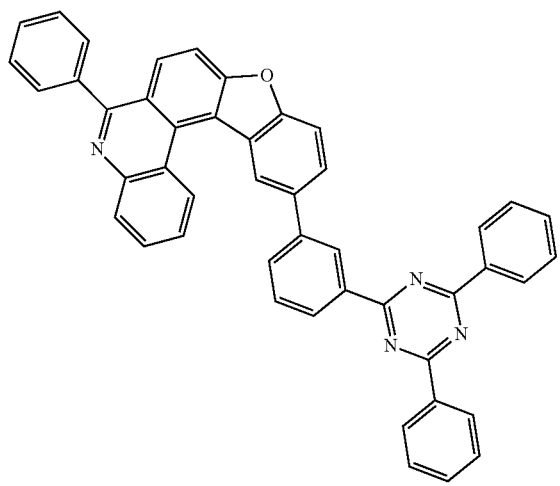
60
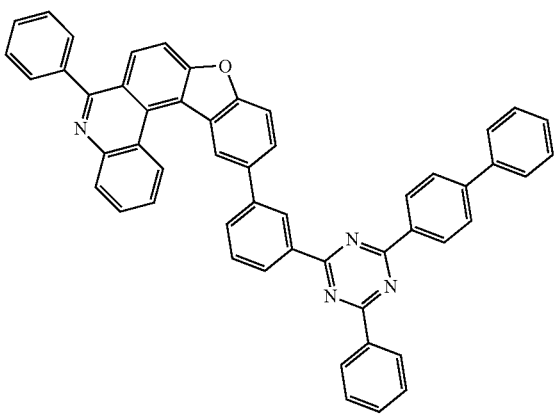

61
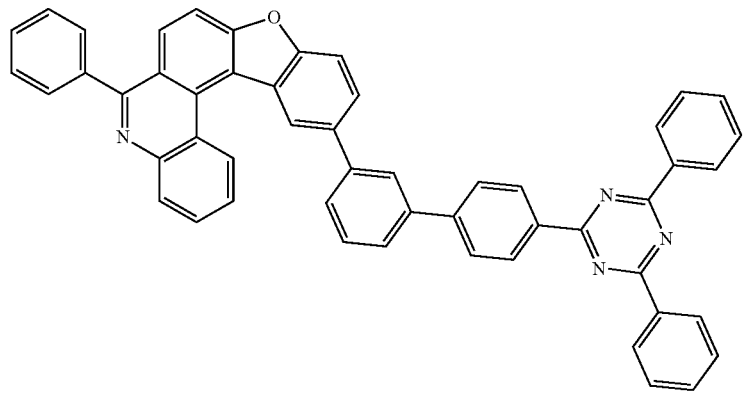
62
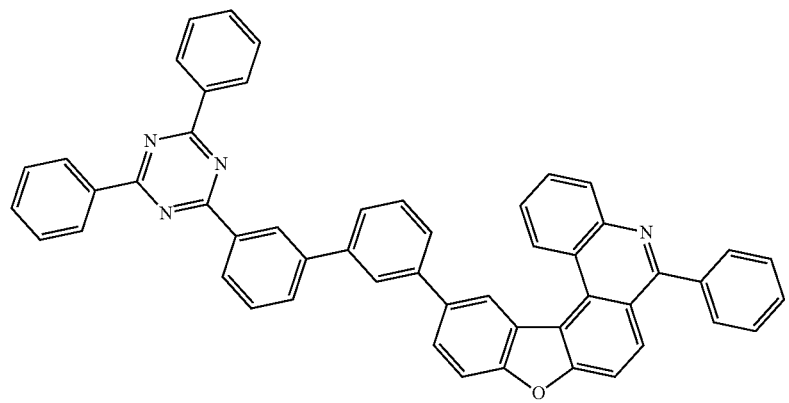
63
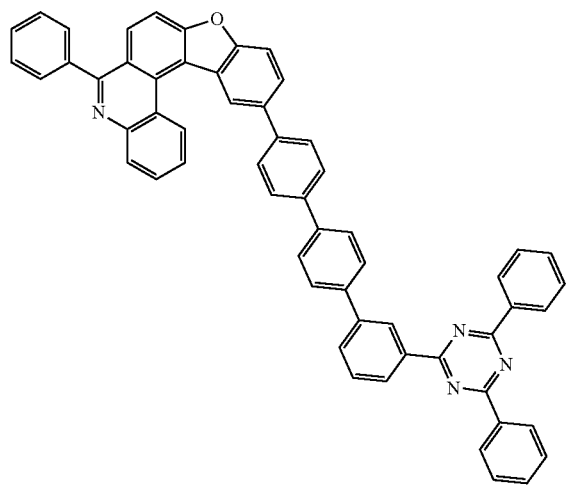

777 778
-continued
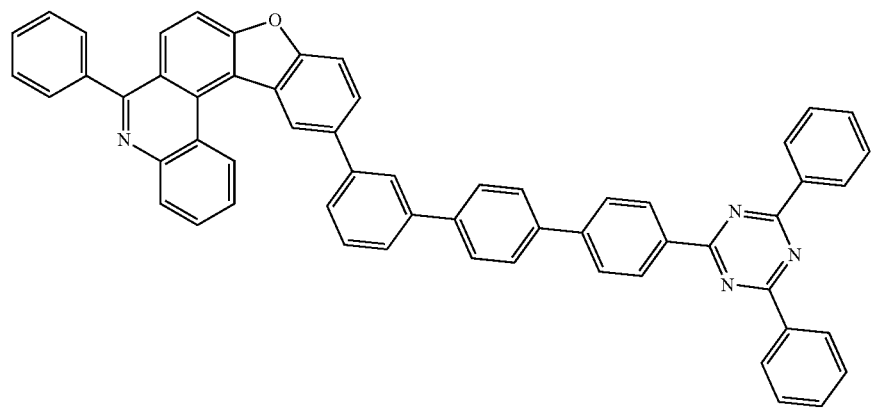
64
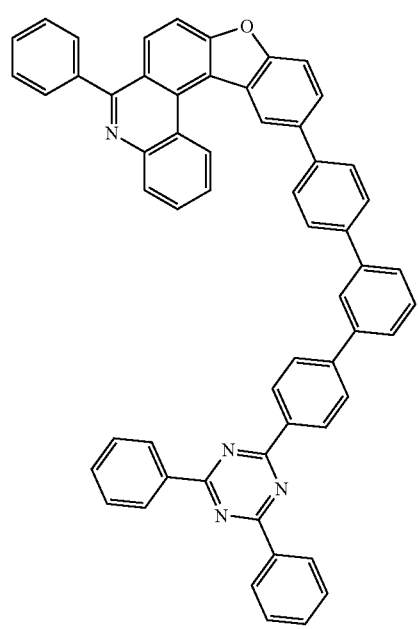
65
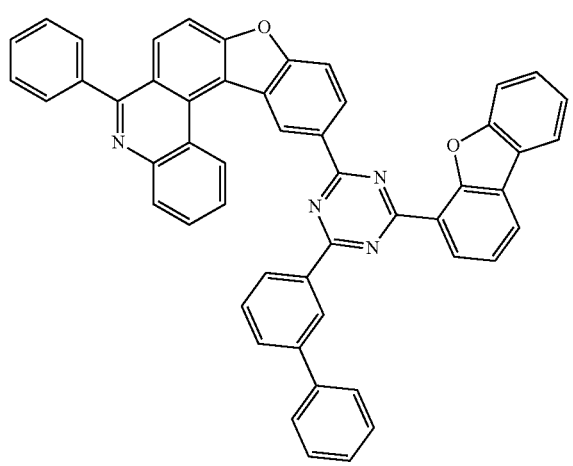
66
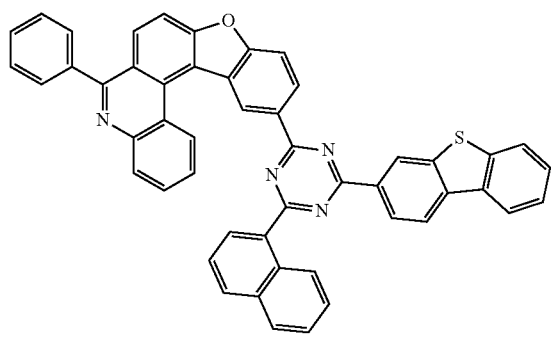
67 68

-continued
69
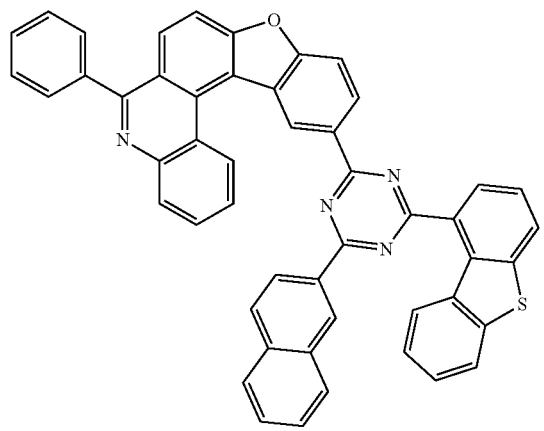
70
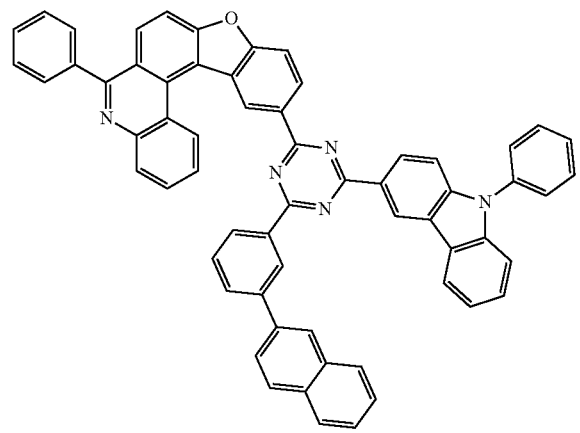
71
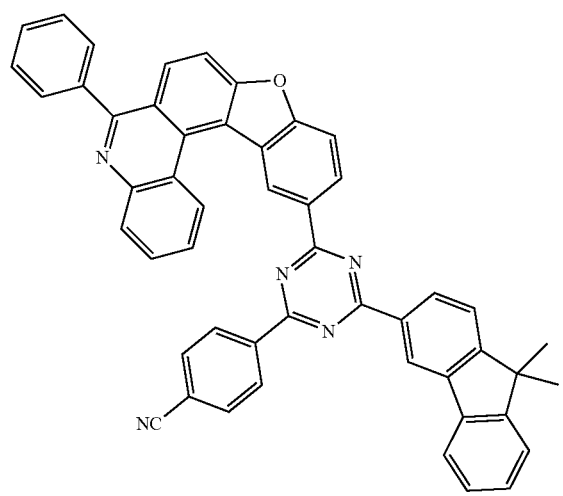
72
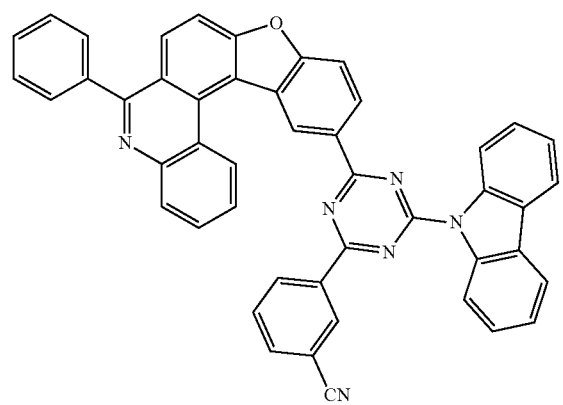
73
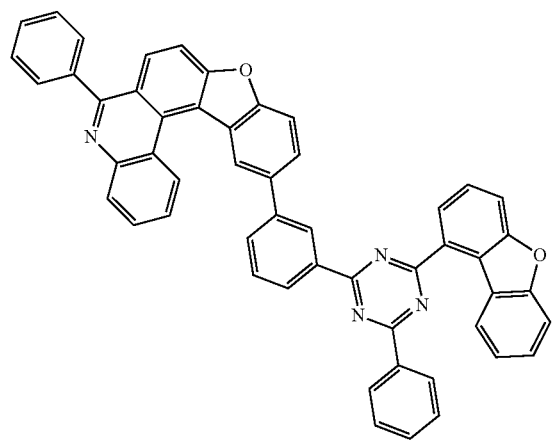
74
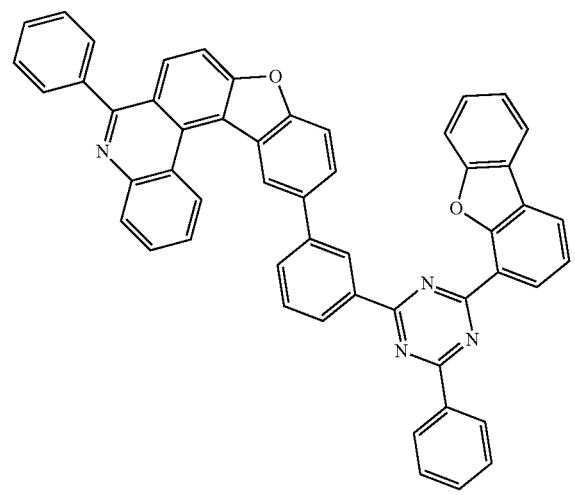

75
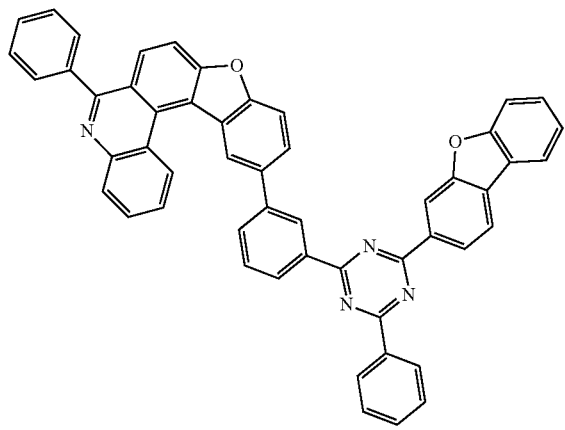
76
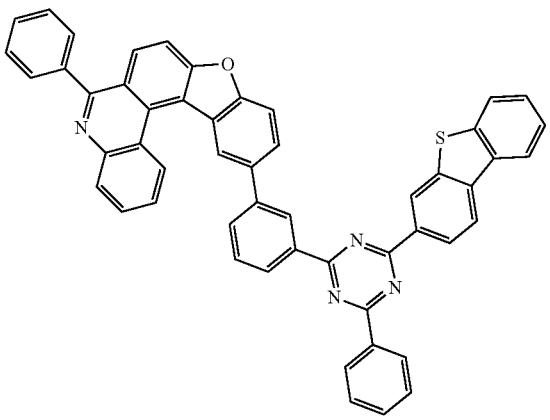
77
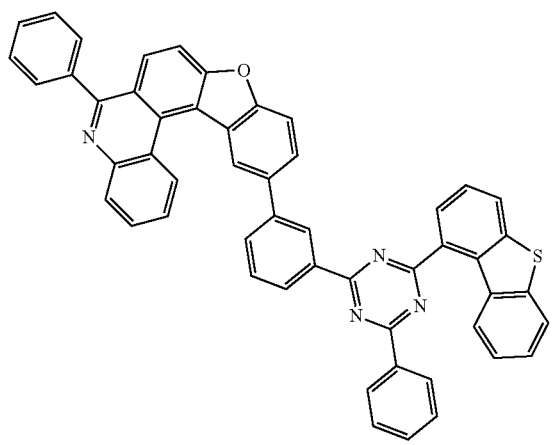
78
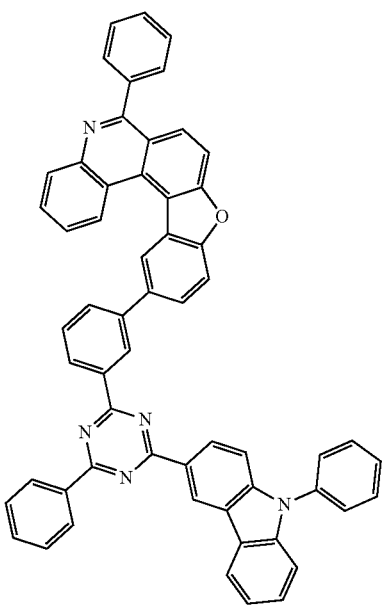
79
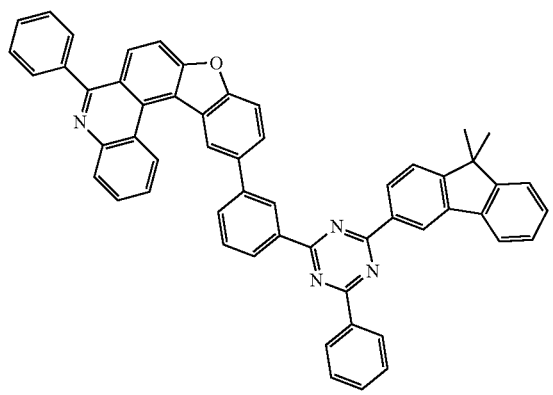
80
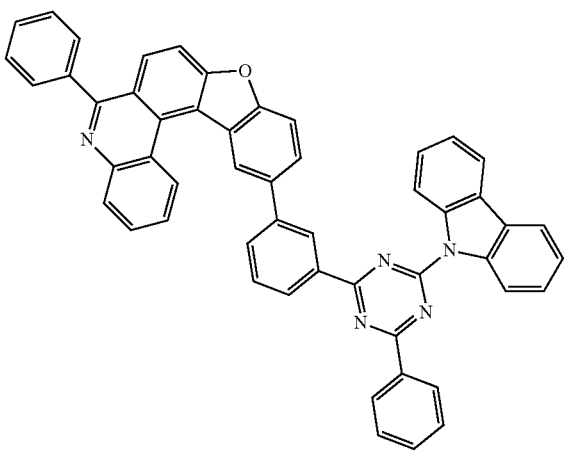

-continued
81
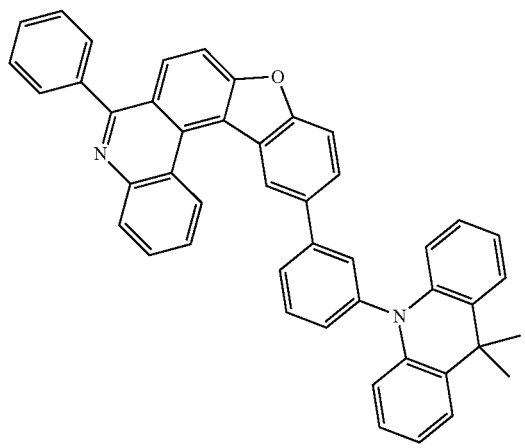
82
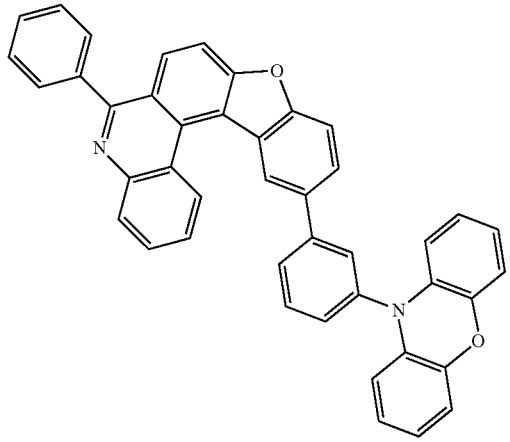
83
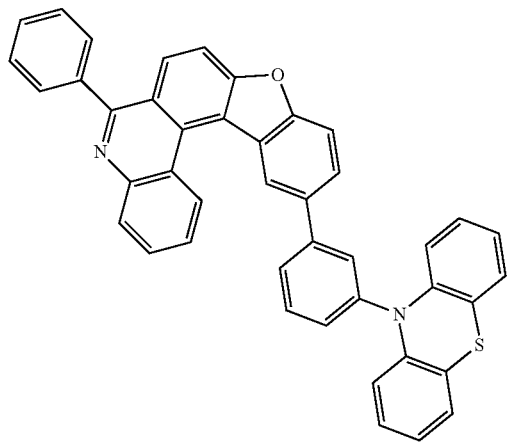
84
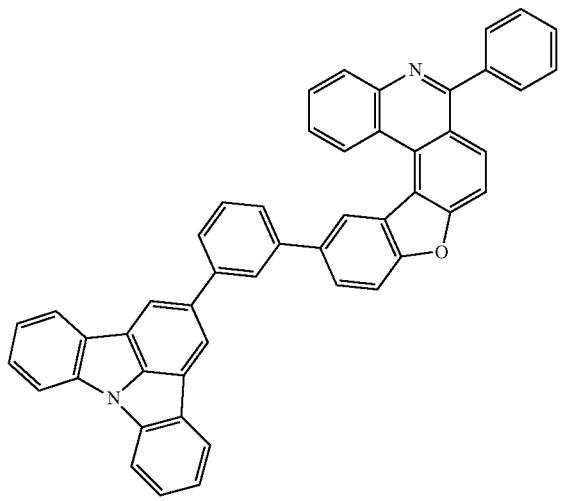
85
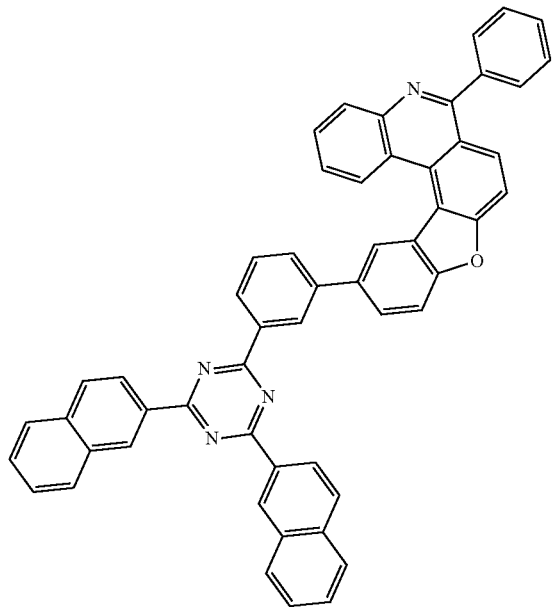
86
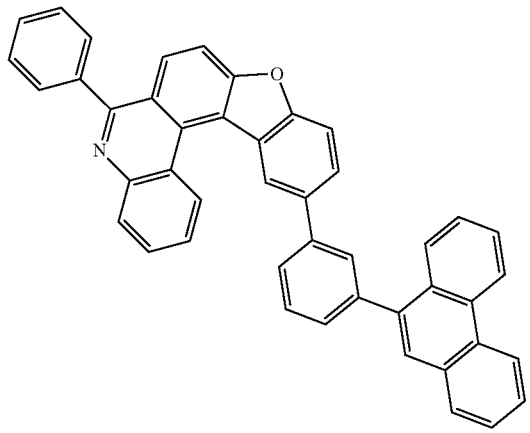

87
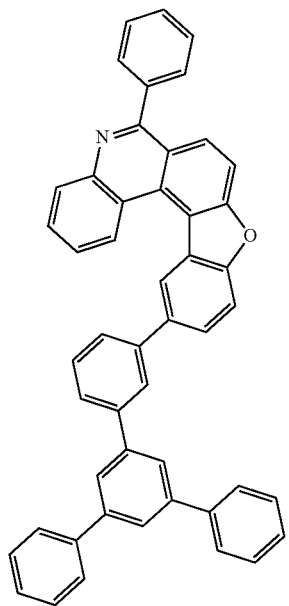
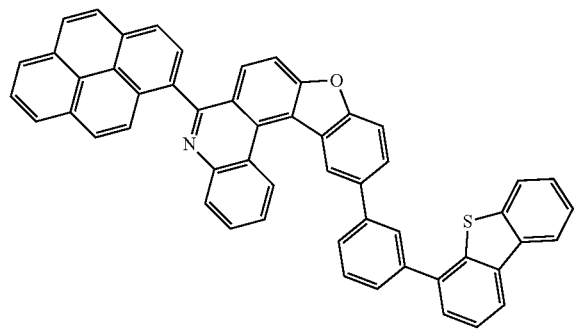
88
89
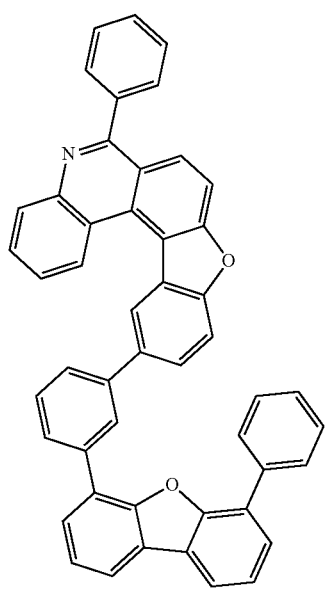
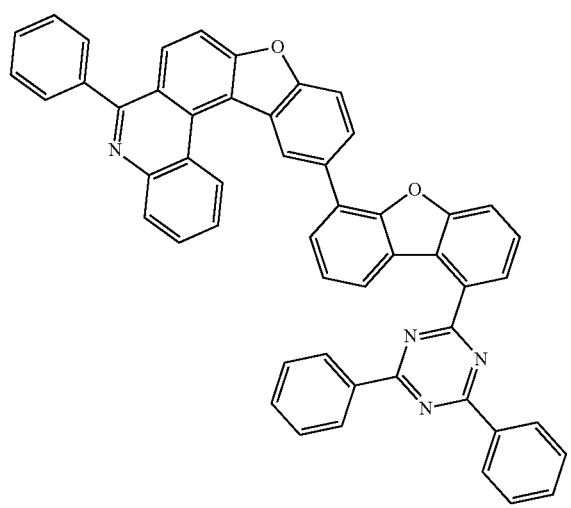
90

-continued
91
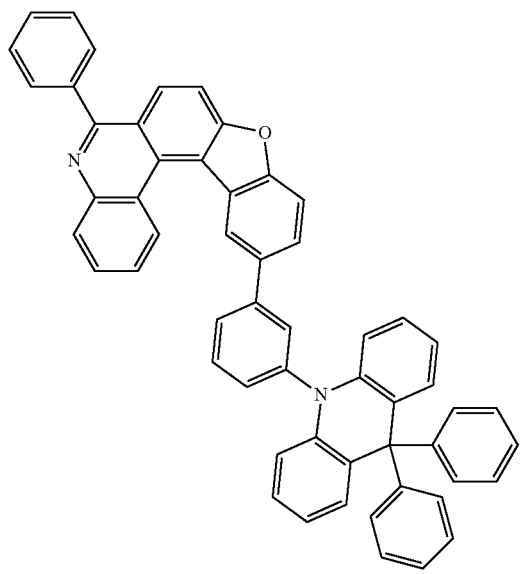
92
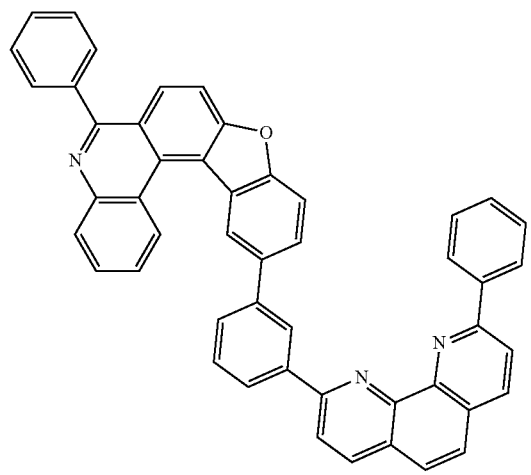
93
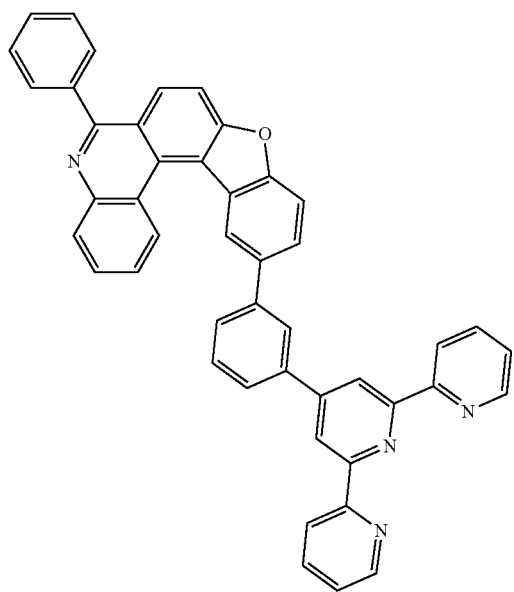
94
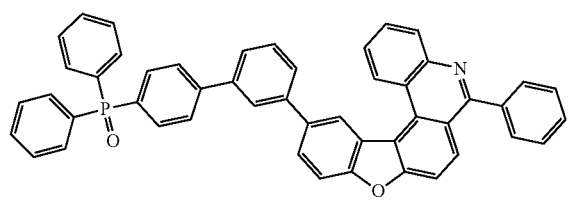

-continued
95
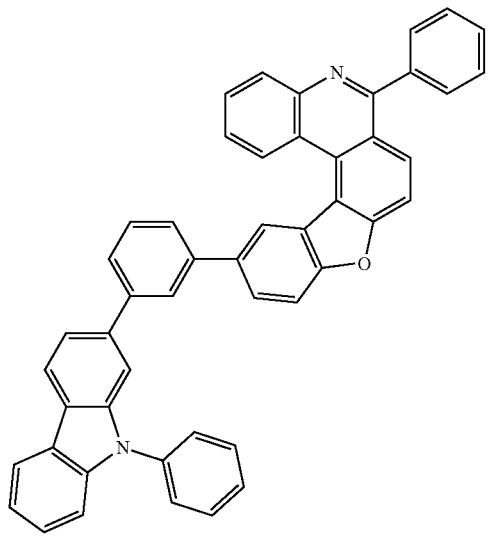
96
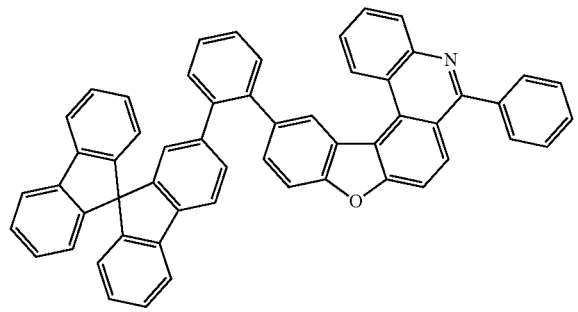
97
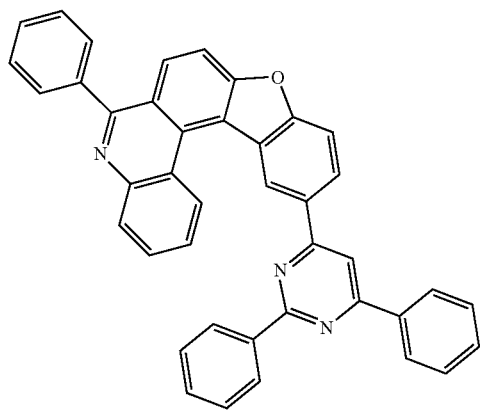
98
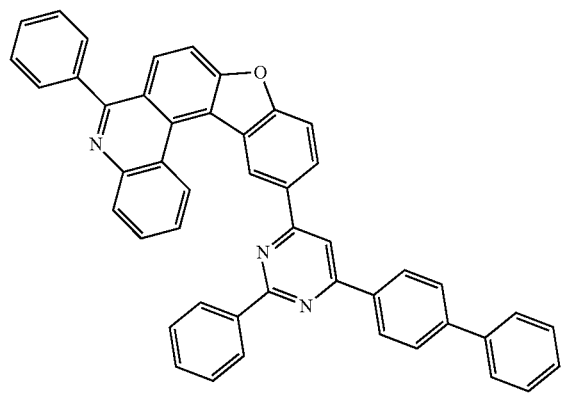
99
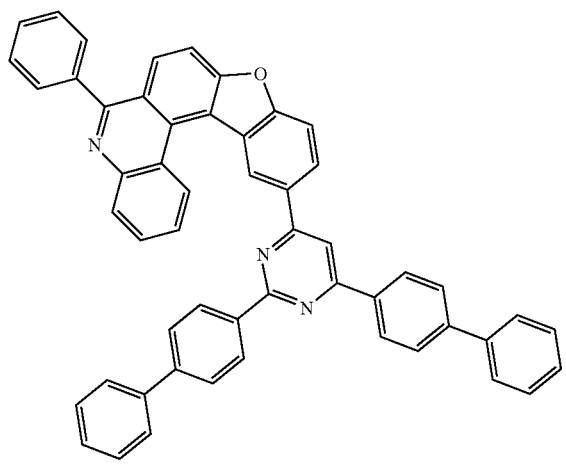
100
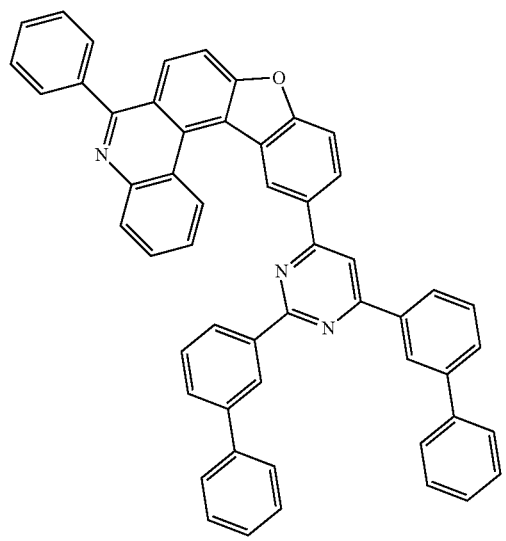

101
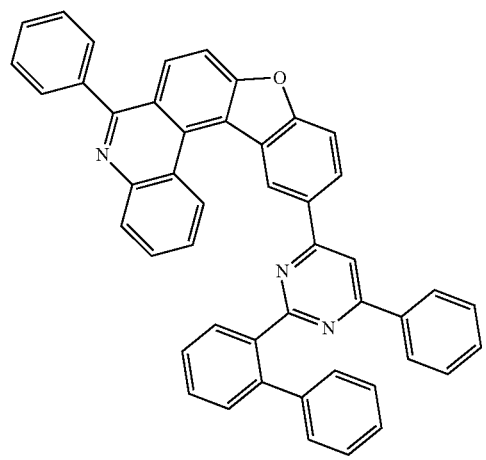
102
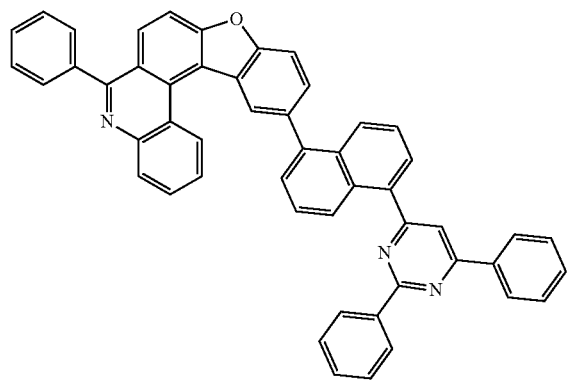
103
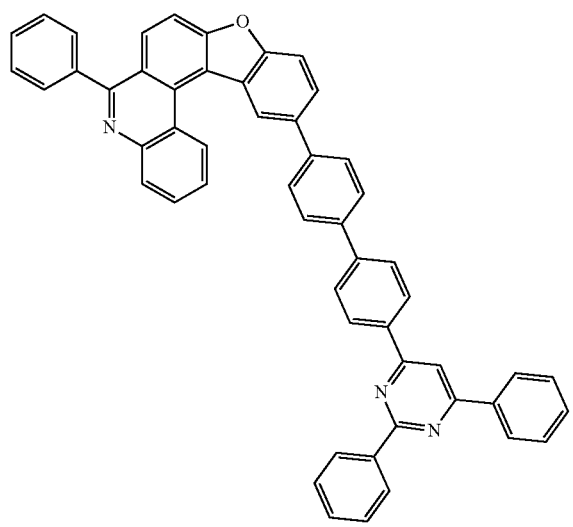
104
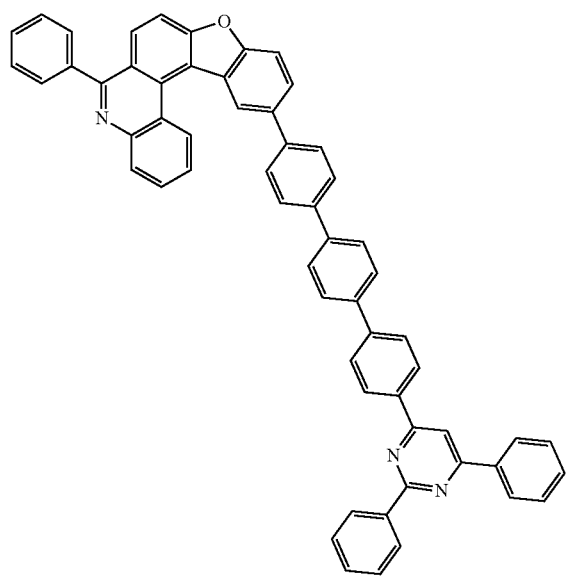

-continued
105
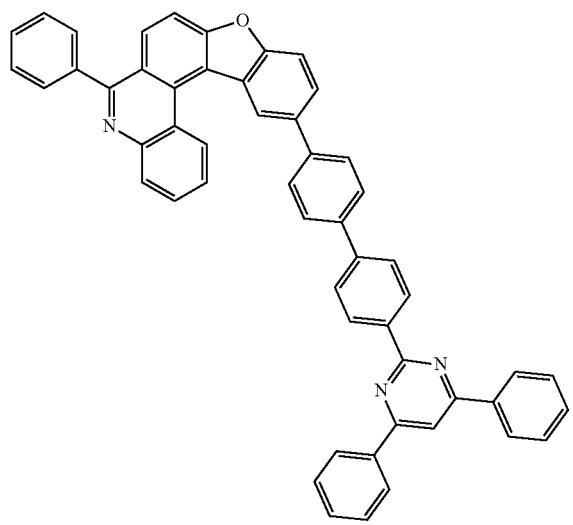
106
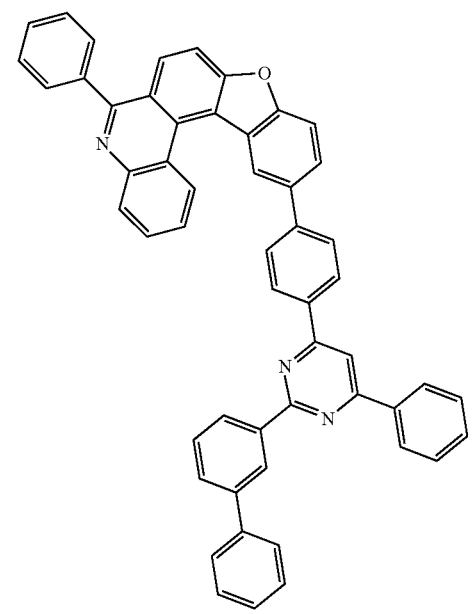
107
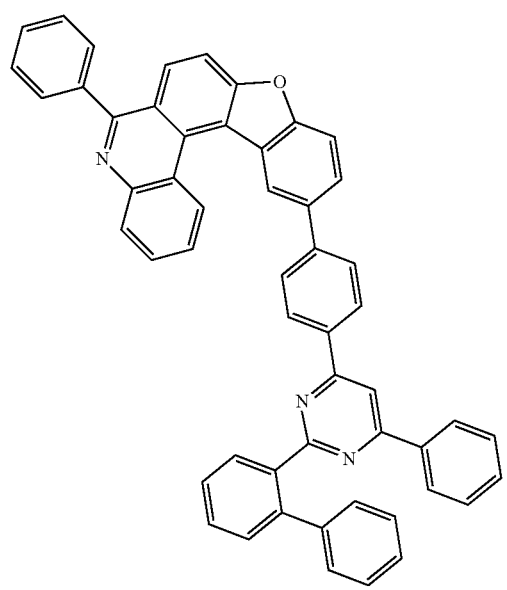
108
109
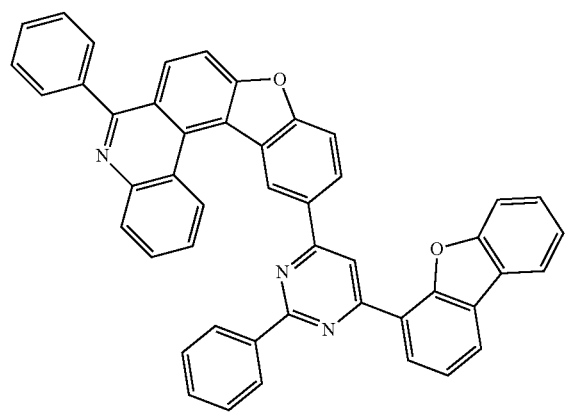
110
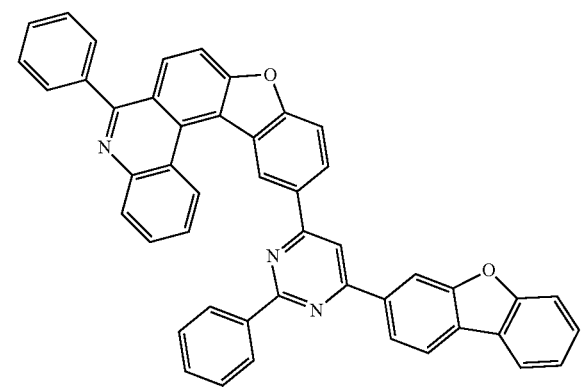

111
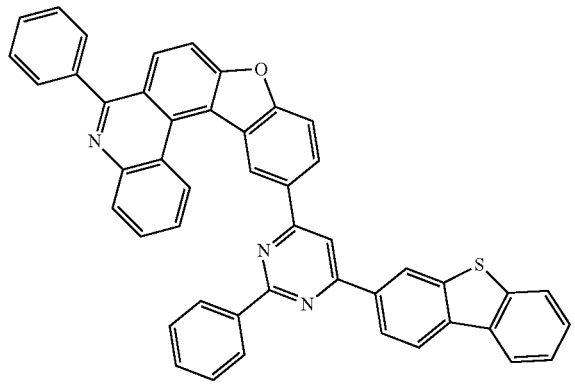
112
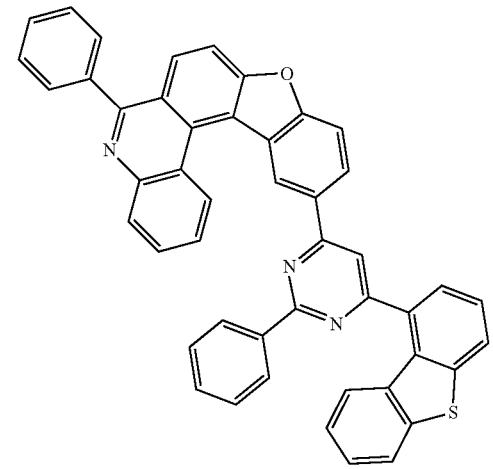
113
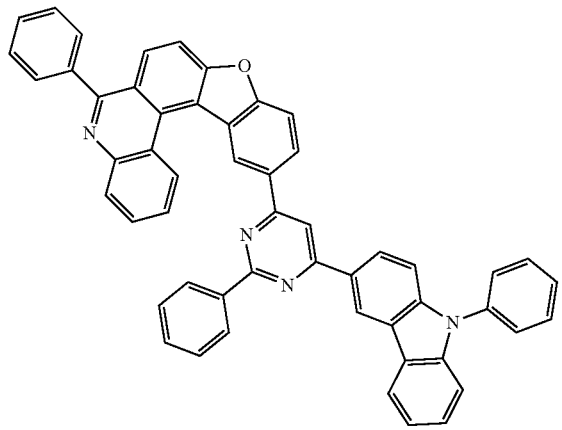
114
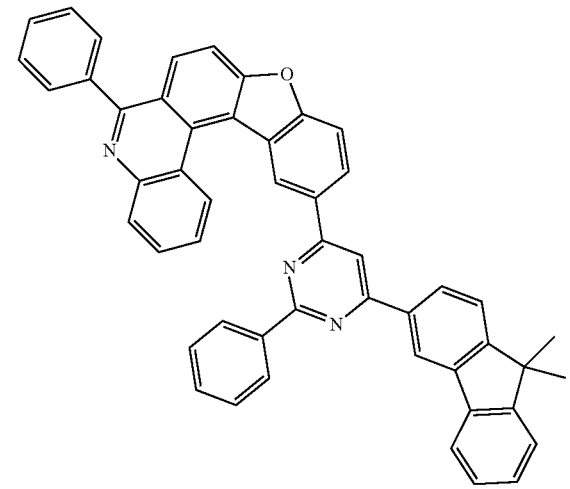
115
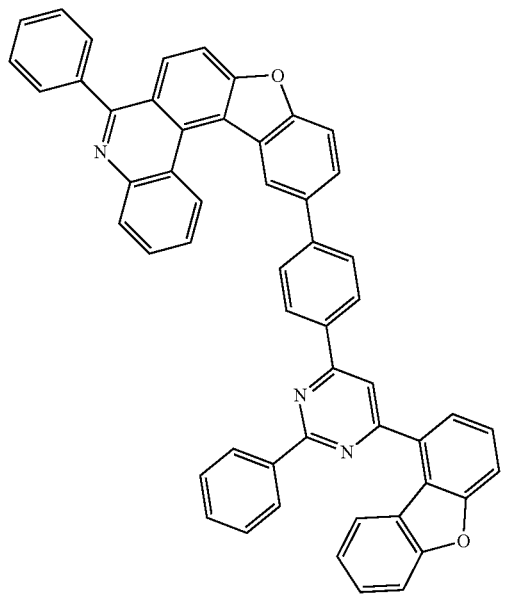
116
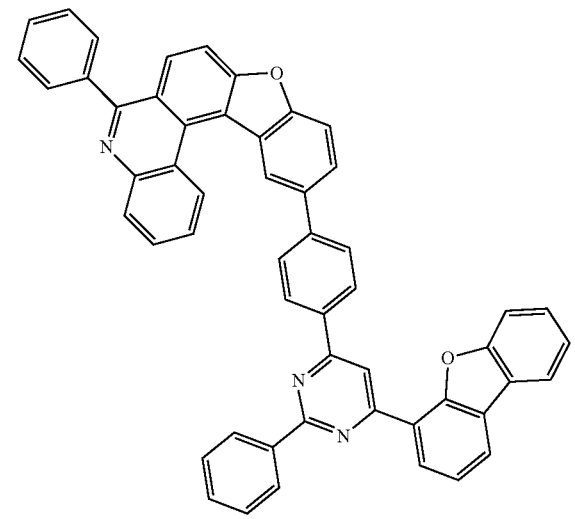

797
798
-continued
117
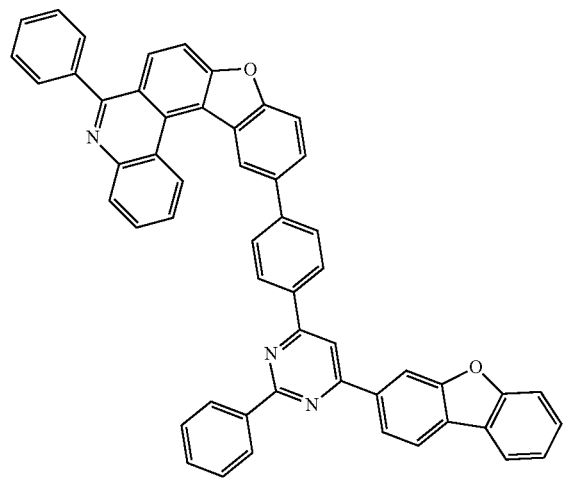
118
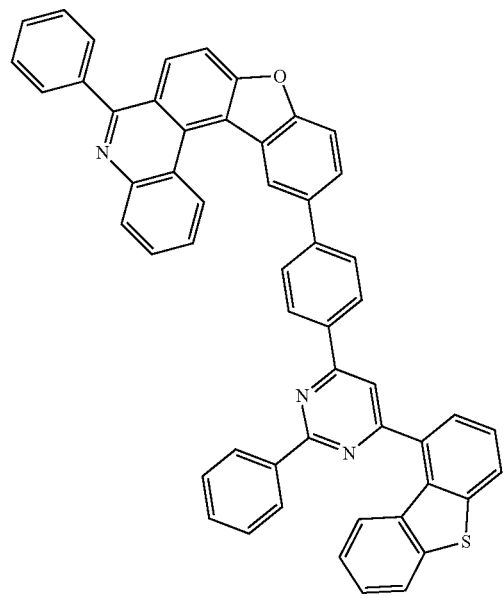
119
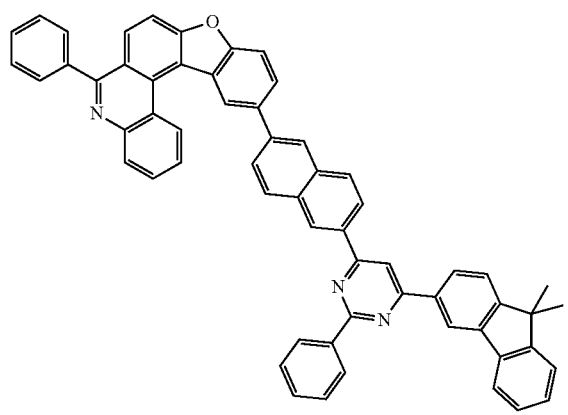
120
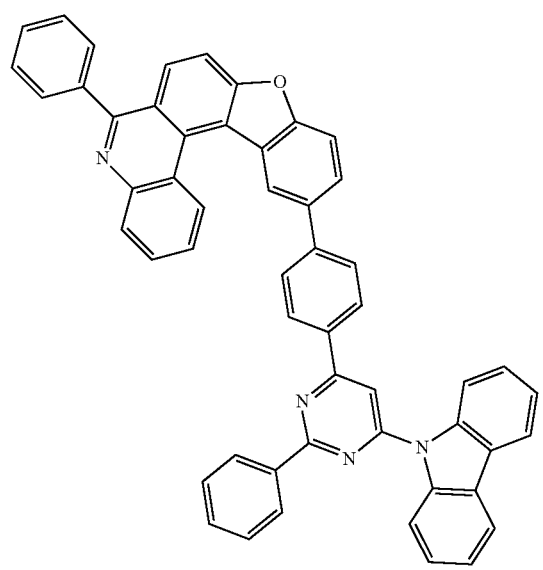

121
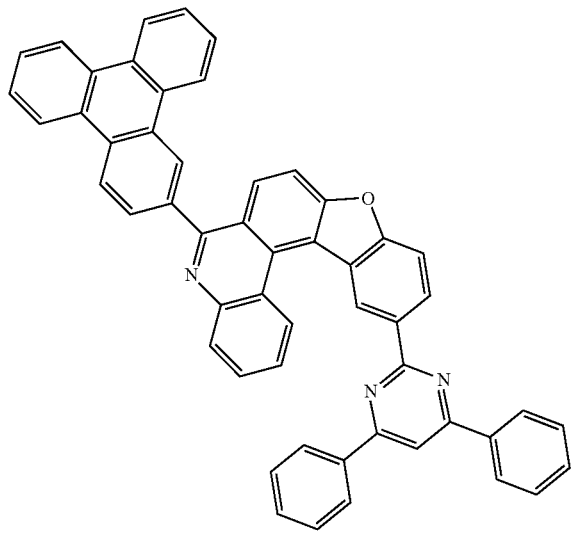
122
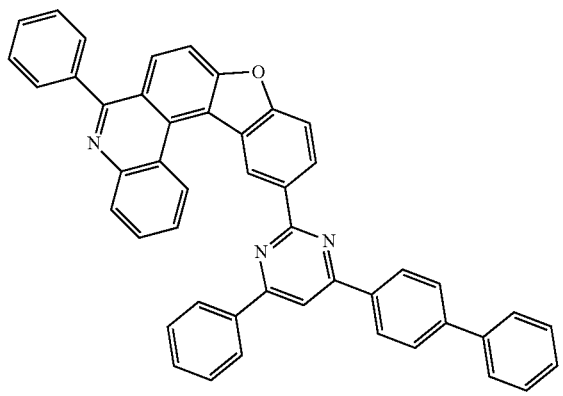
123
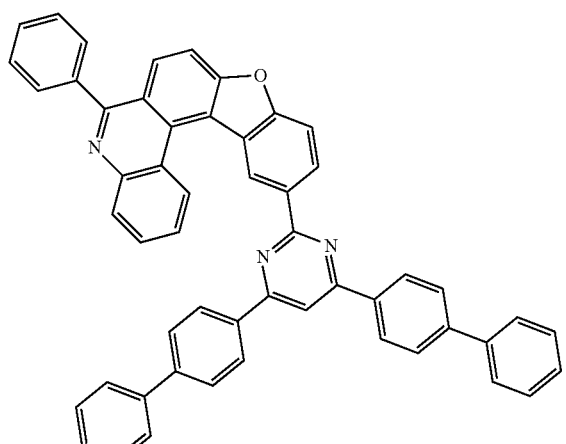
124
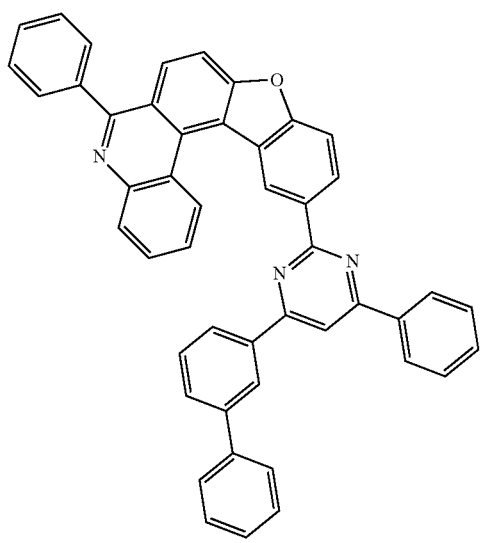
125
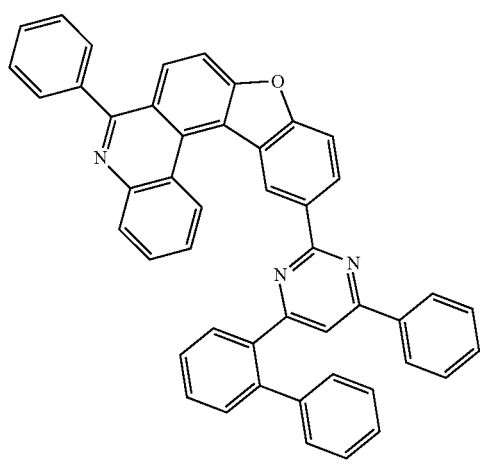
126
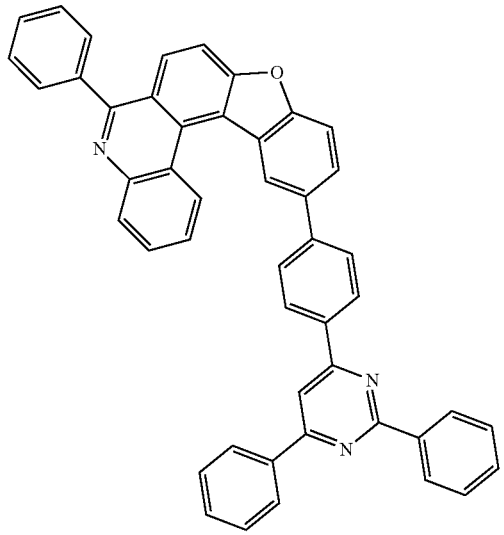

127
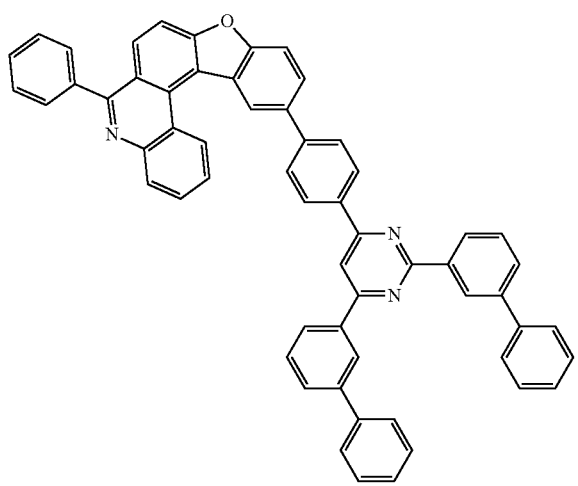
128
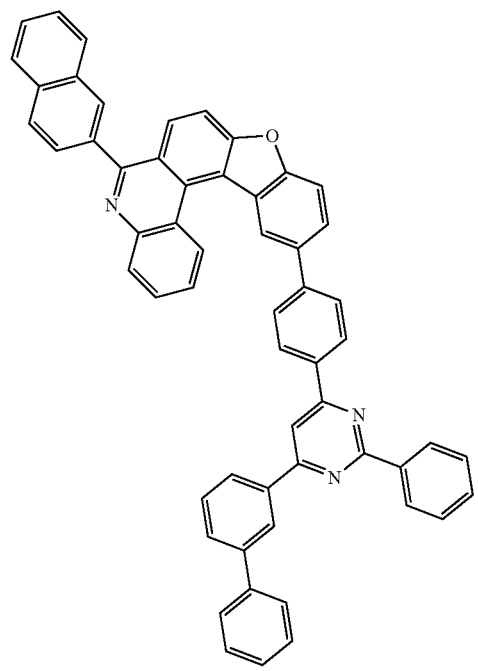
129
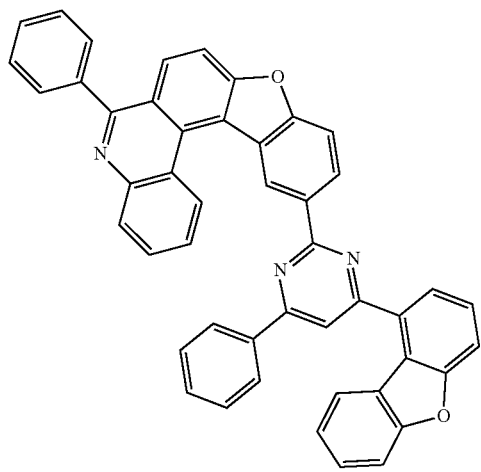
130
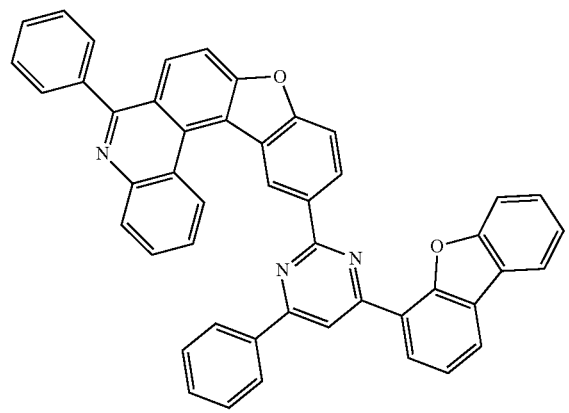
131
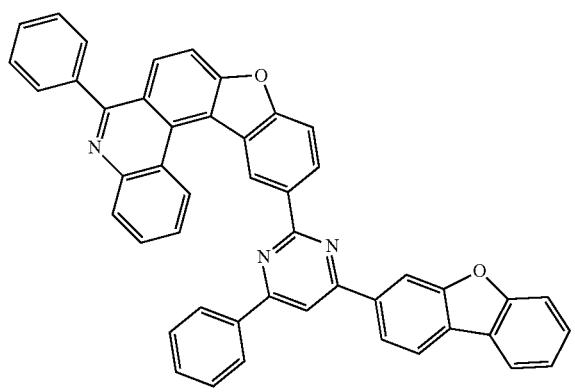
132
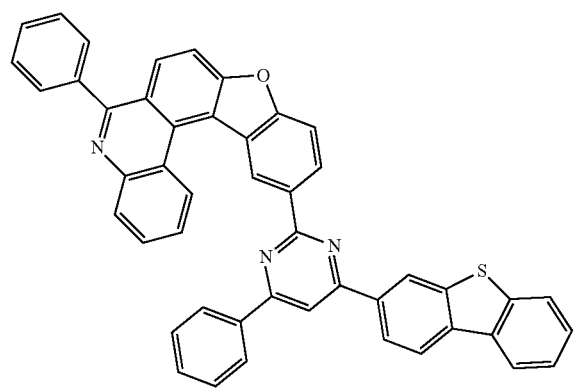

-continued
133
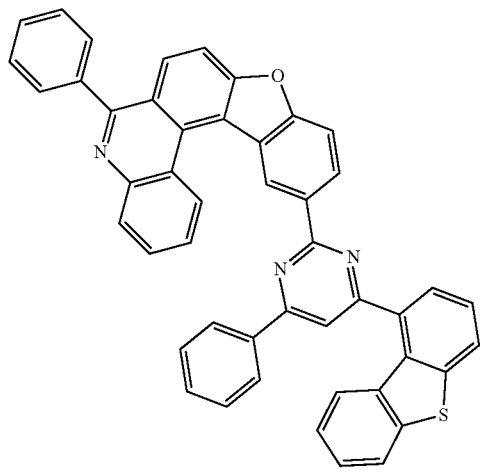
134
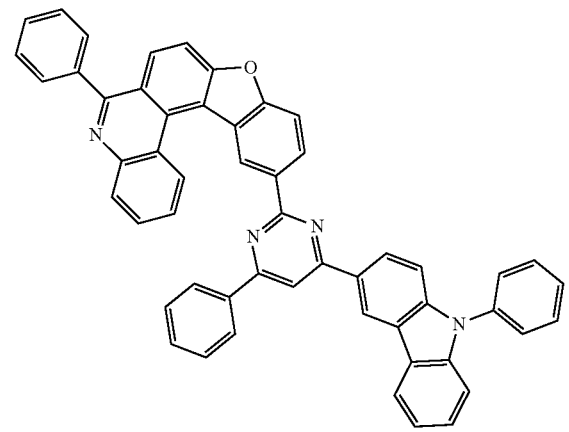
135
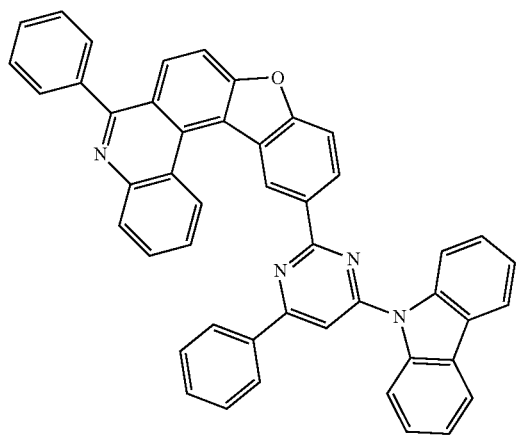
136
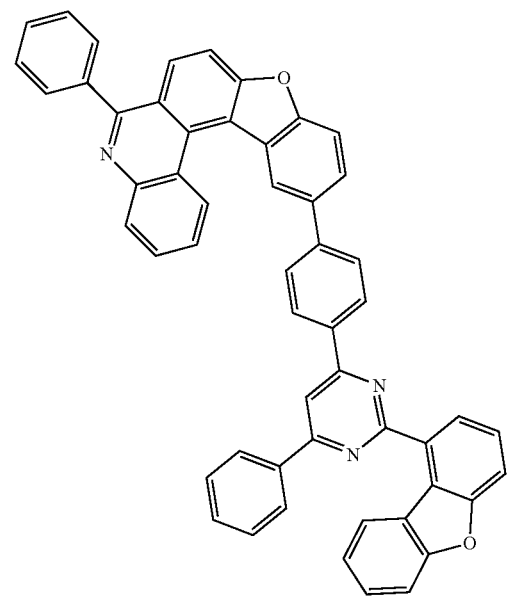
137
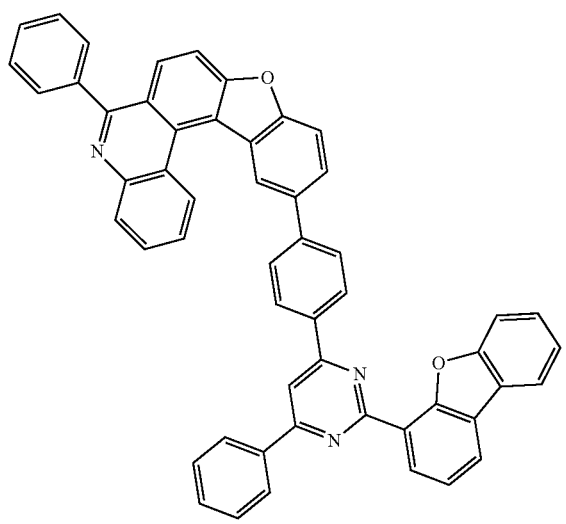
138
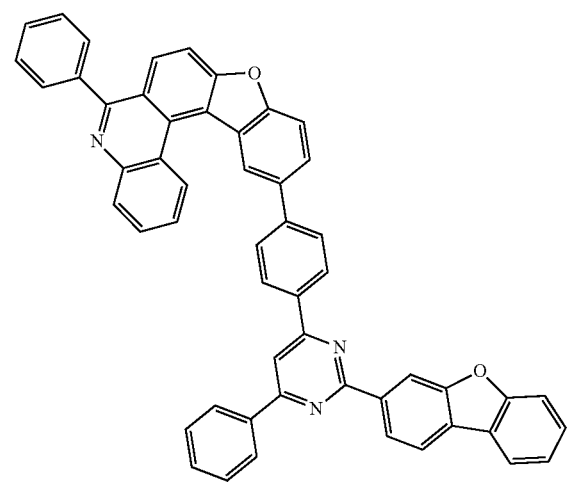

-continued
139
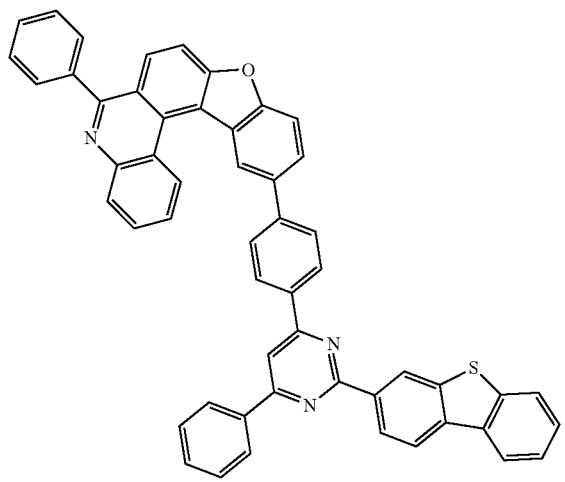
140
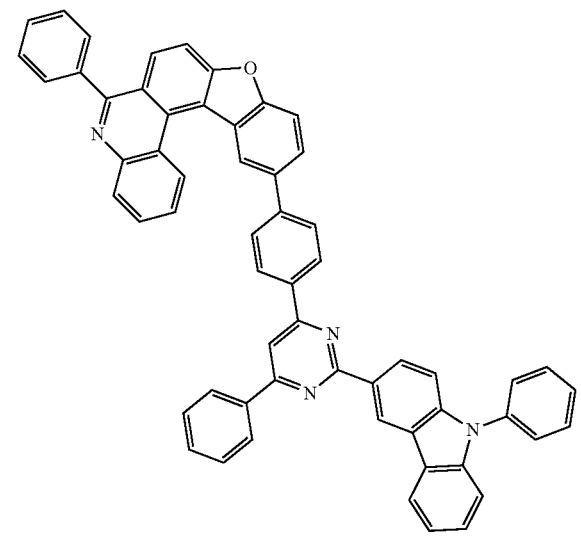
141
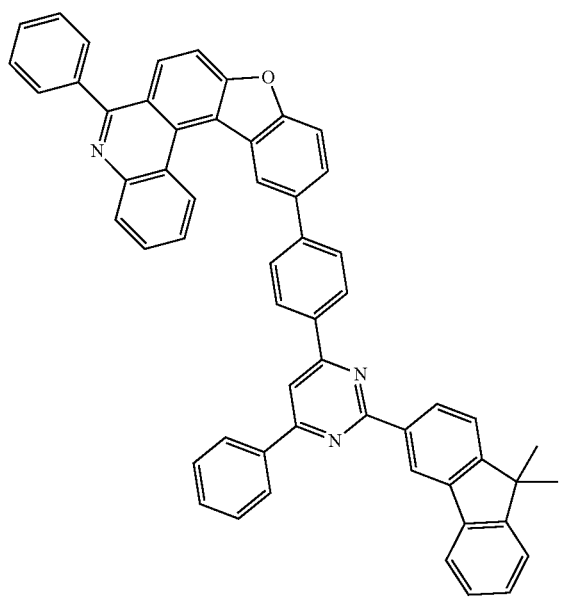
142
143
144
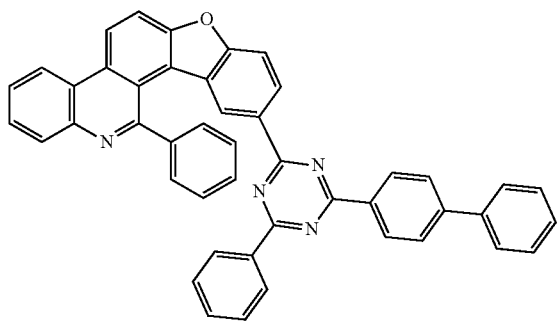
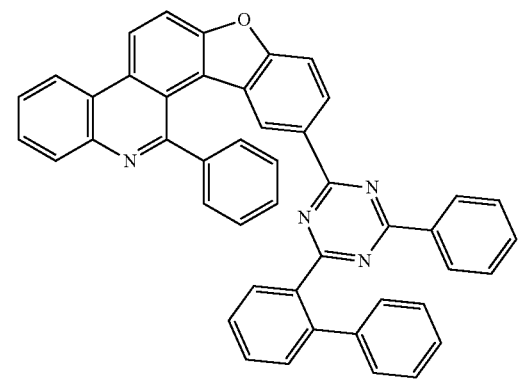

-continued
145
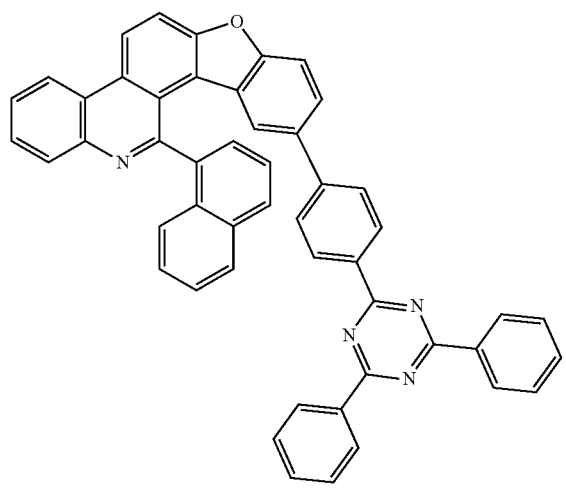
146
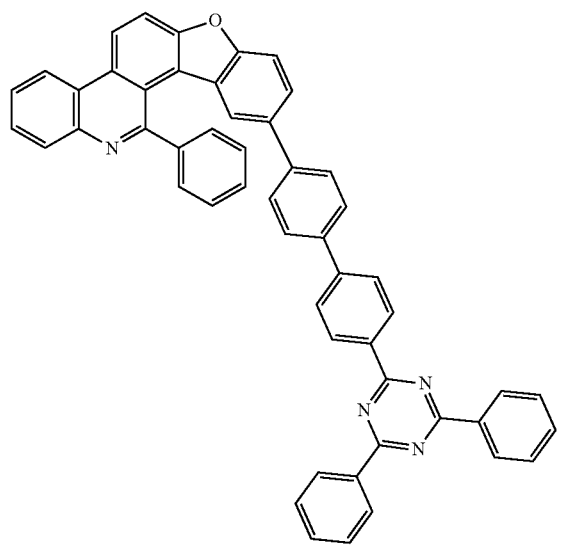
147
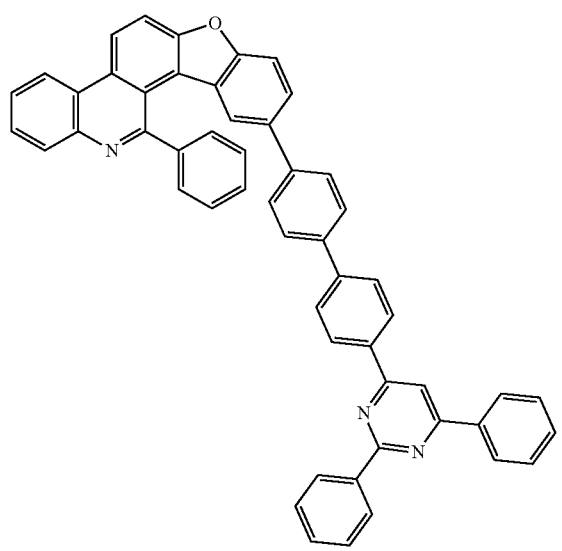
148
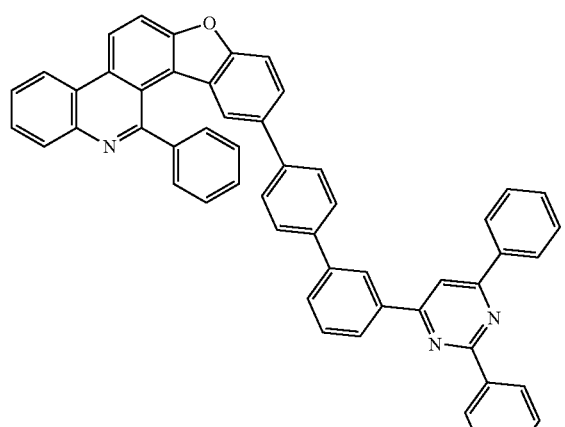
149
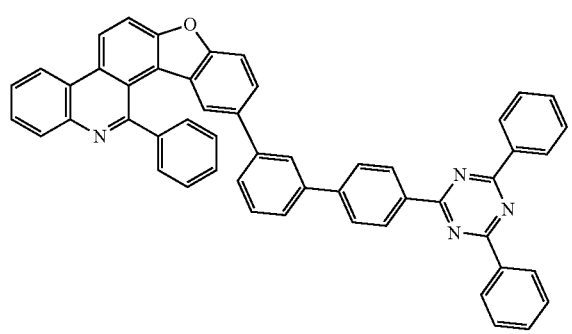
150
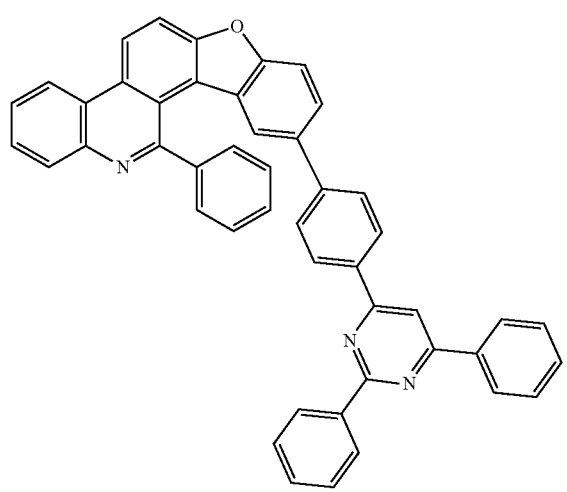

-continued
151
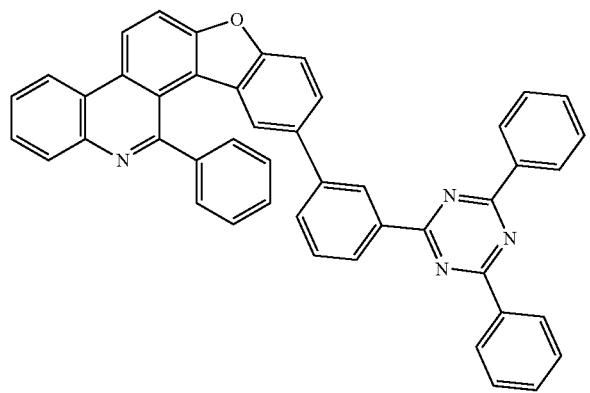
152
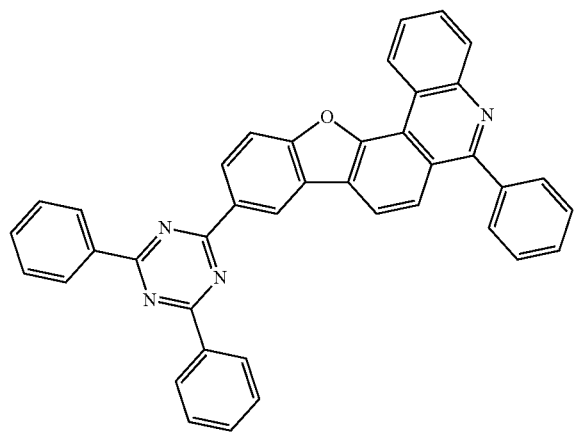
153
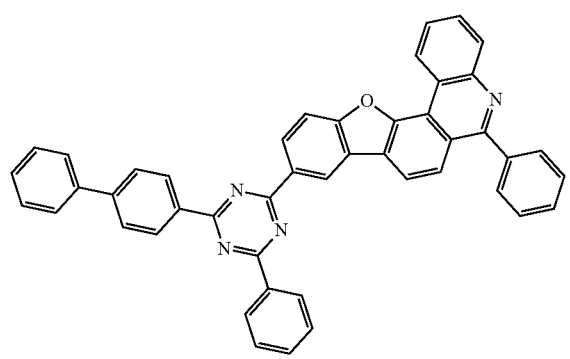
154
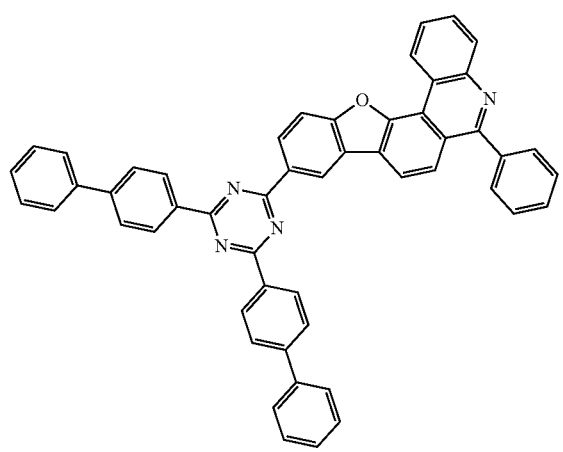
155
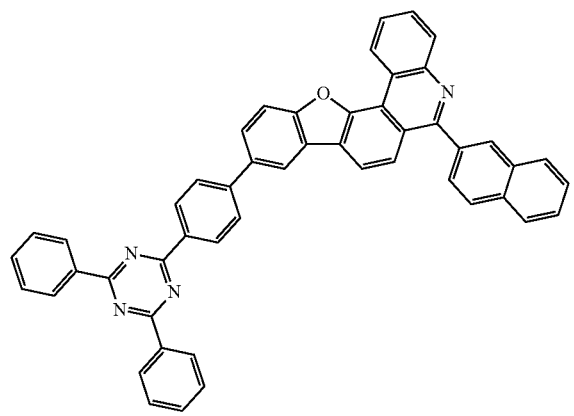
156
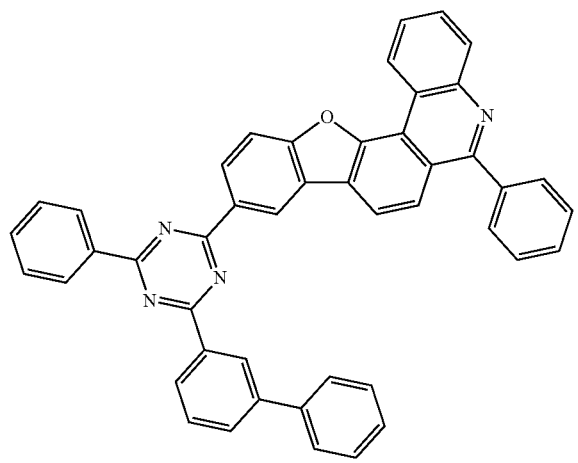

-continued
157
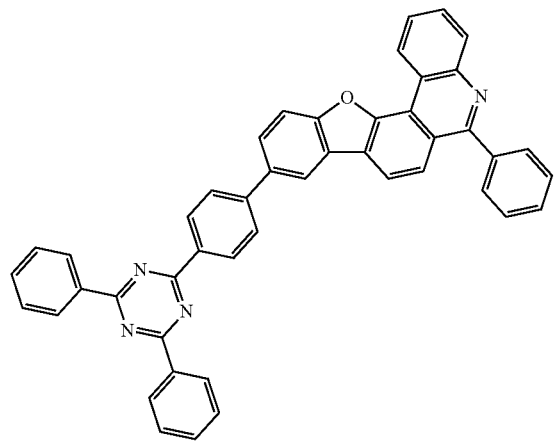
158
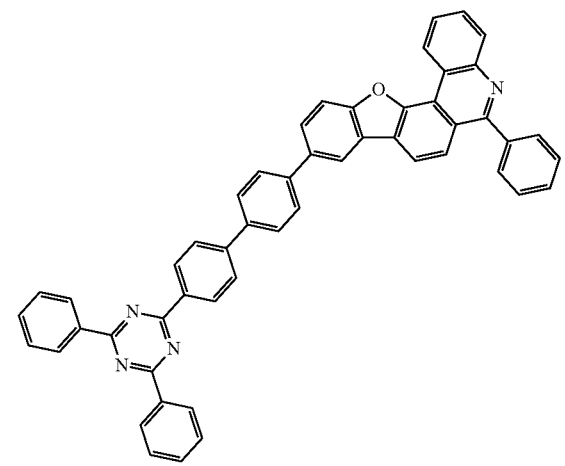
159
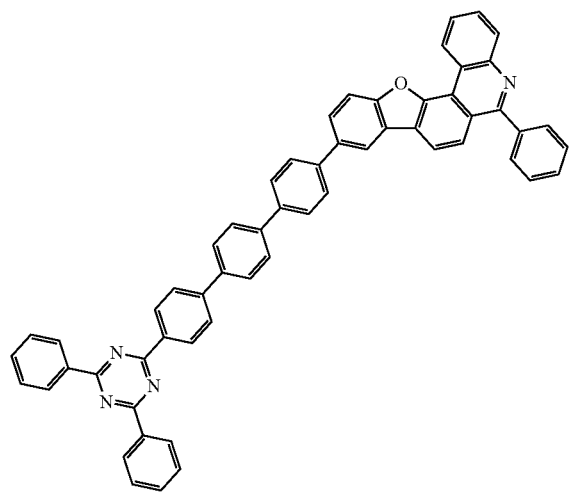
160
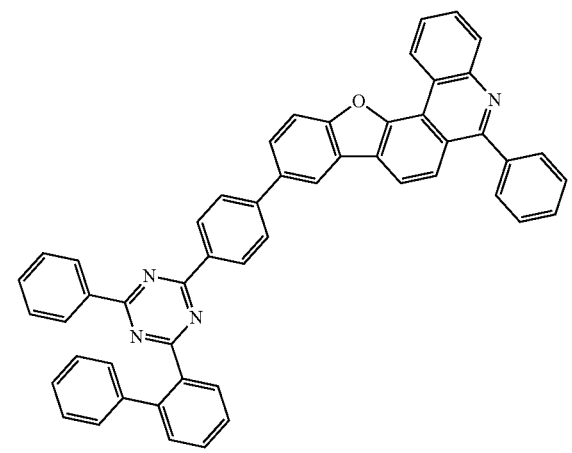
161
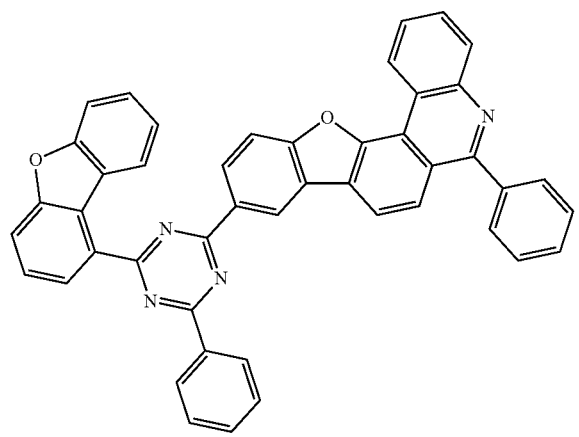
162
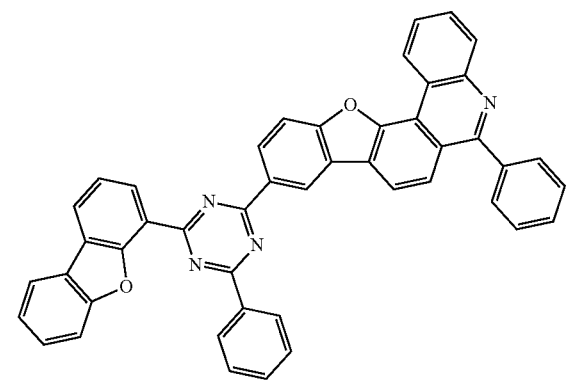

-continued
163
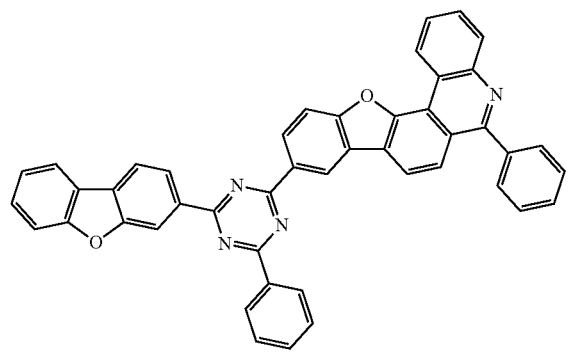
164
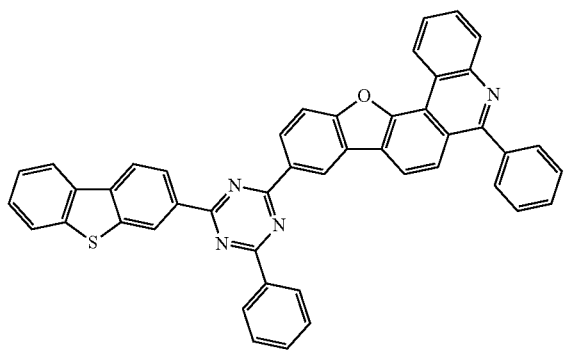
165
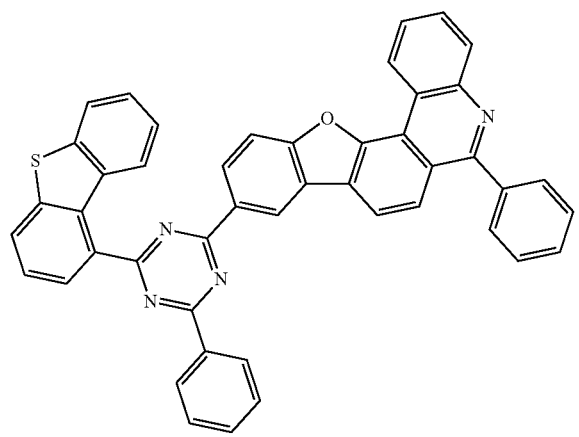
166
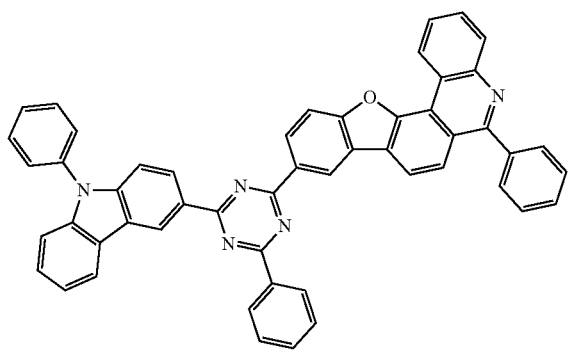
167
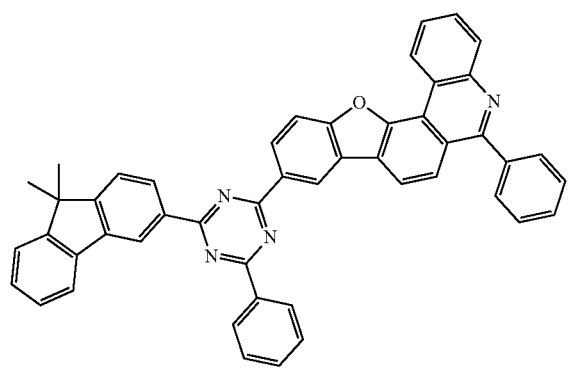
168
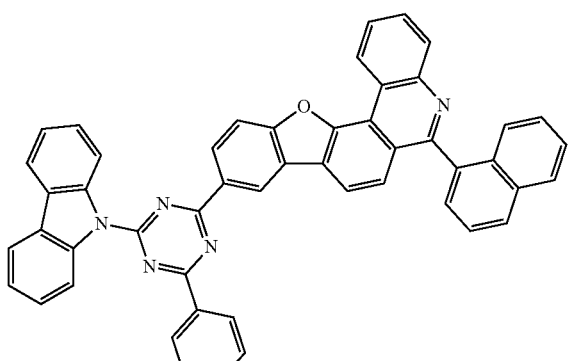

169
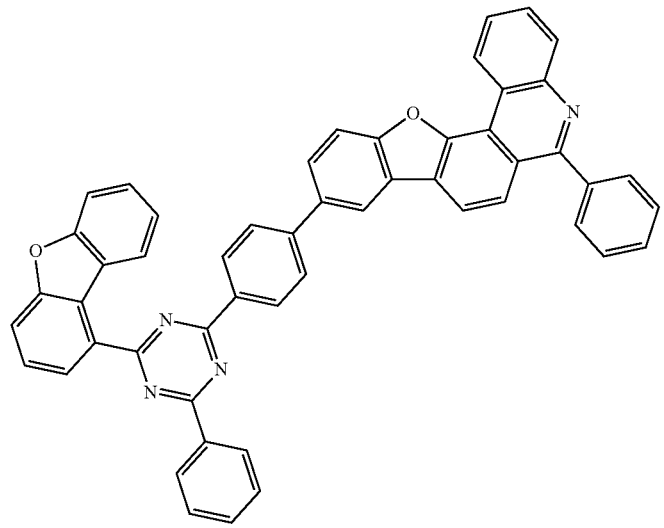
170
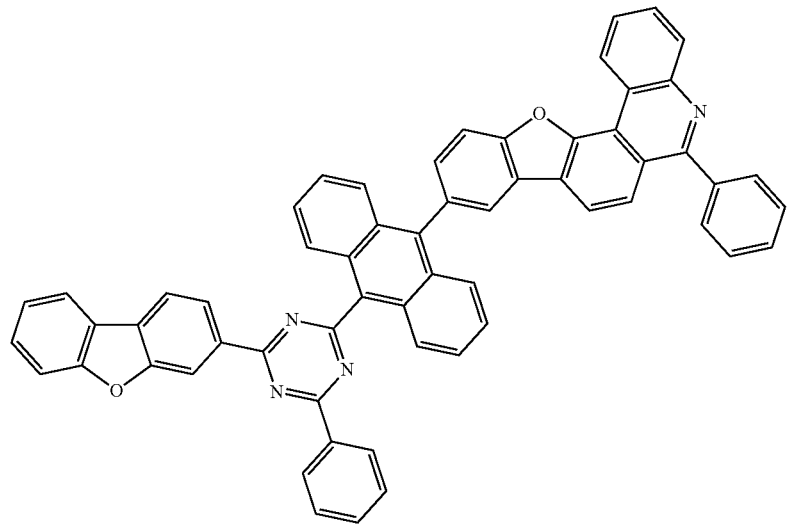
171
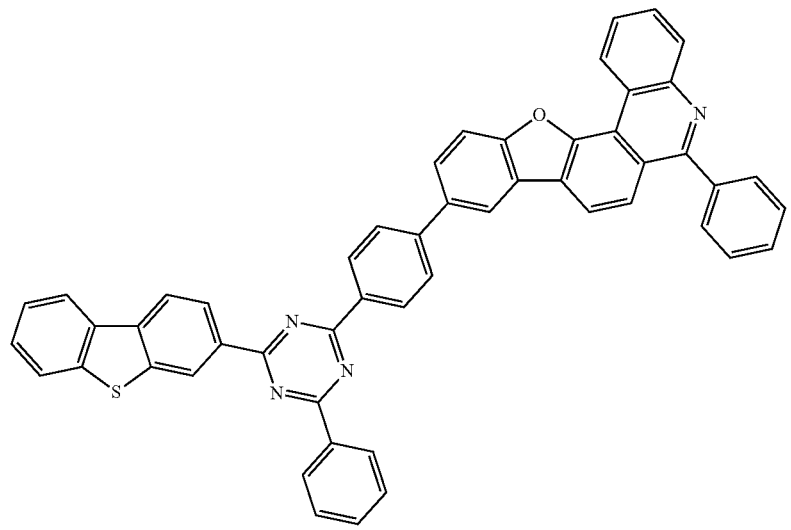

-continued
172
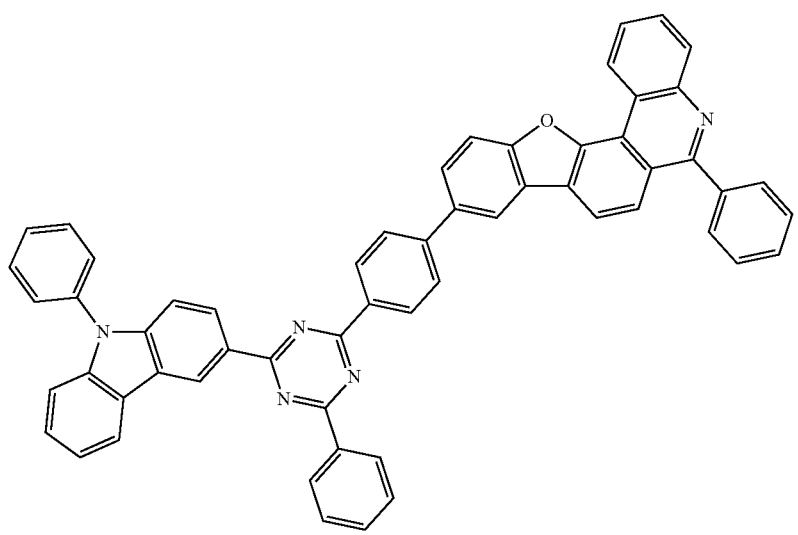
173
174
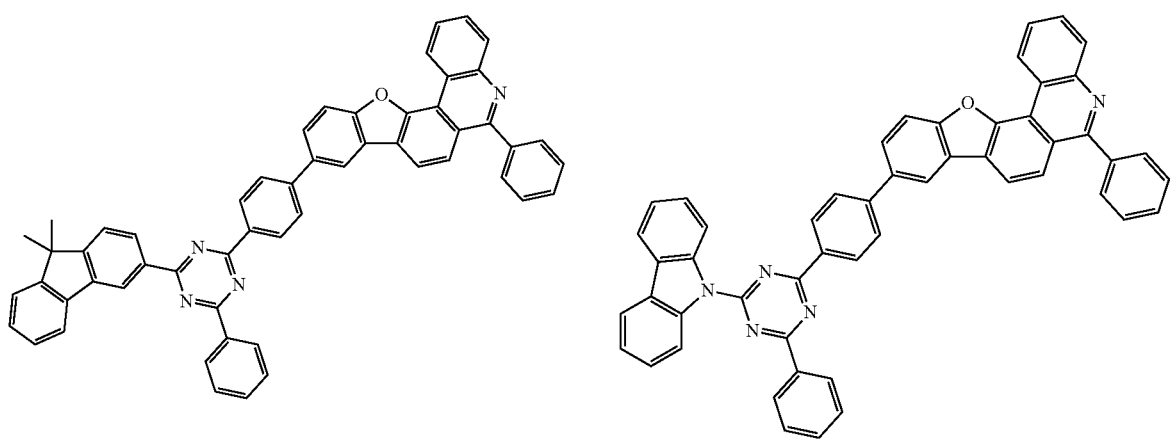
175
176
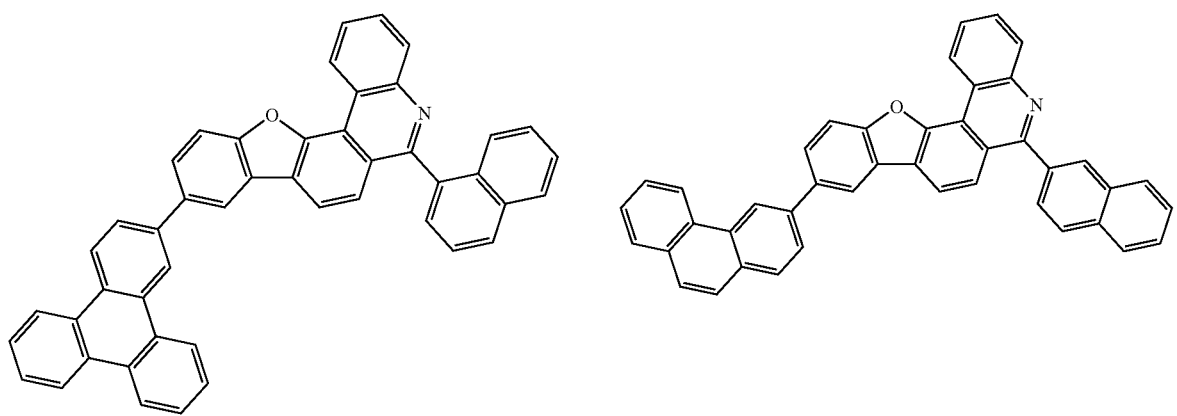

-continued
177
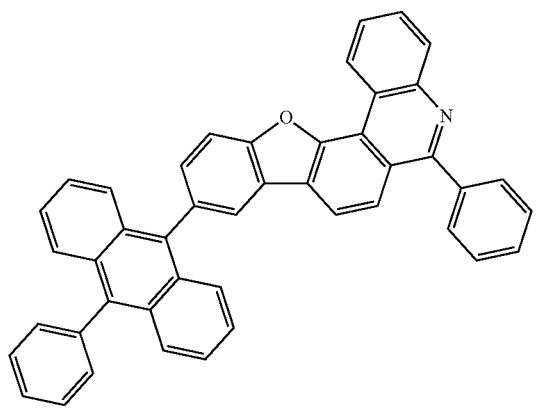
178
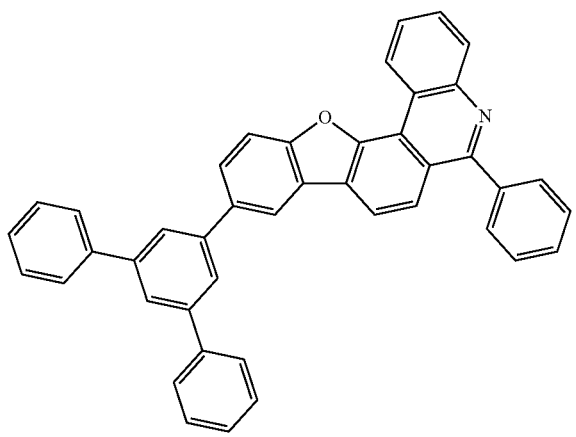
179
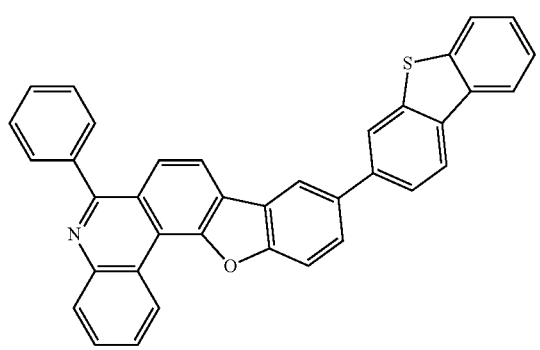
180
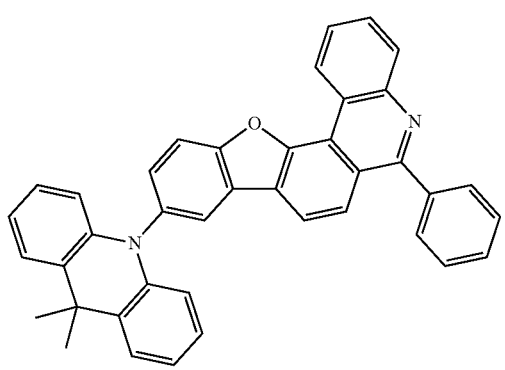
181
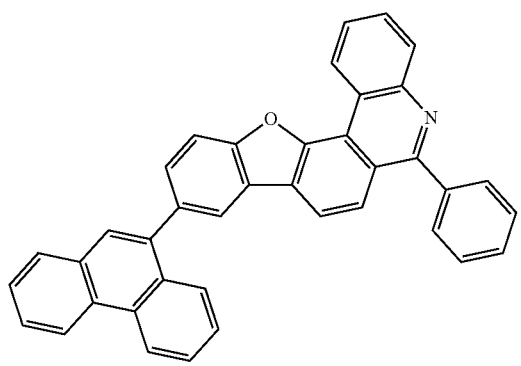
182
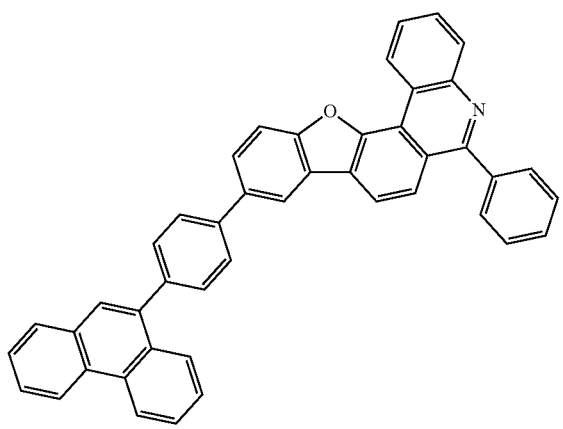

183
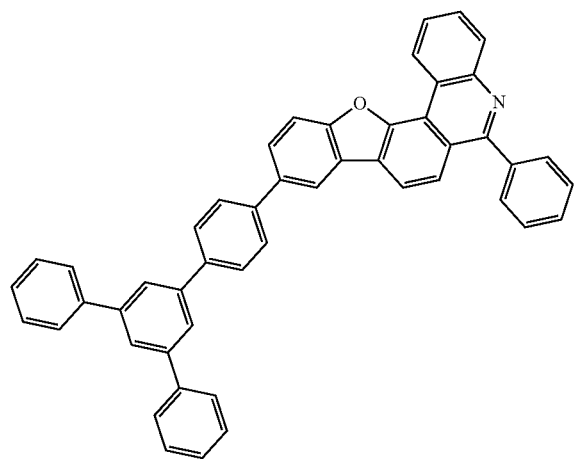
184
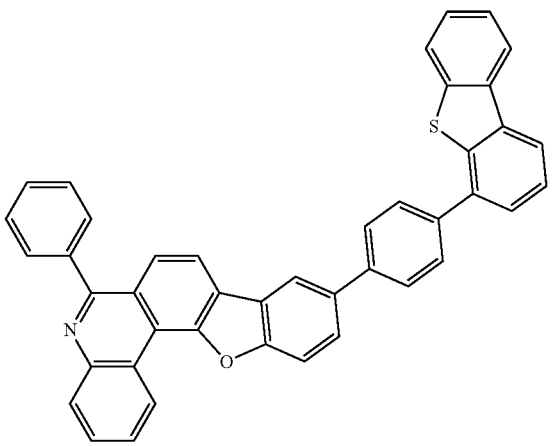
185
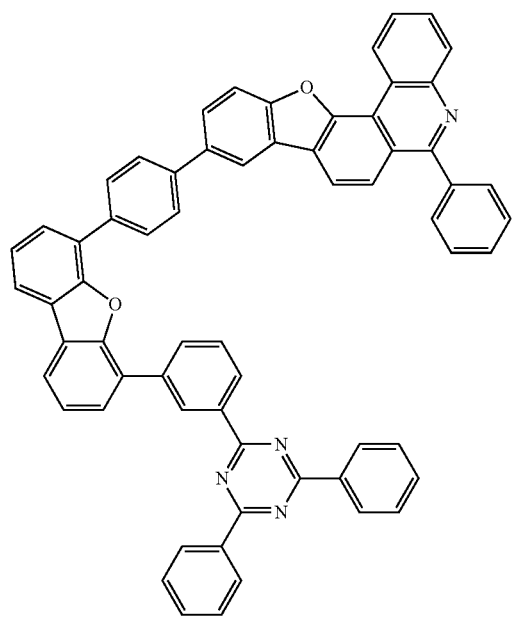
186
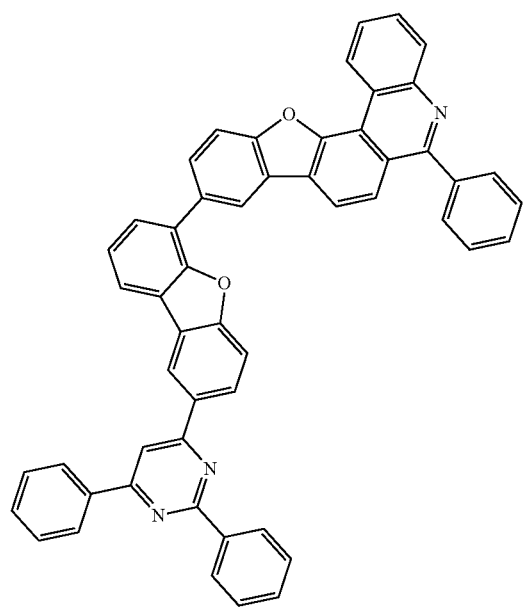
187
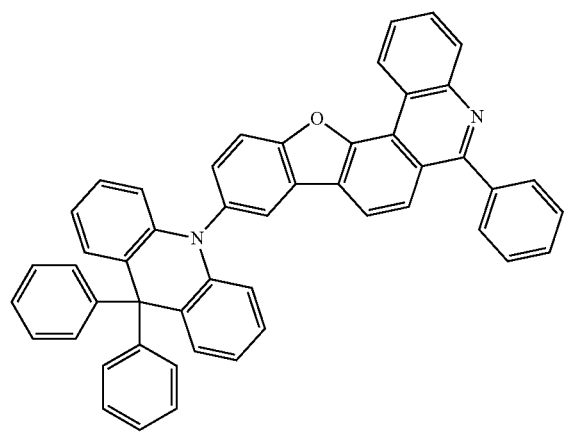
188
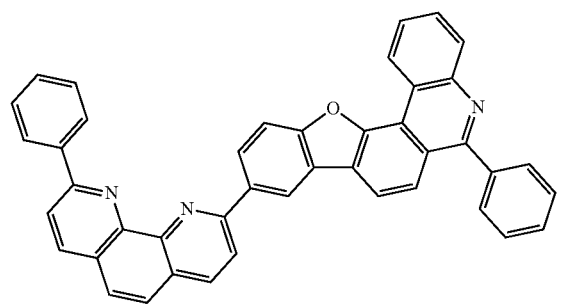

-continued
189
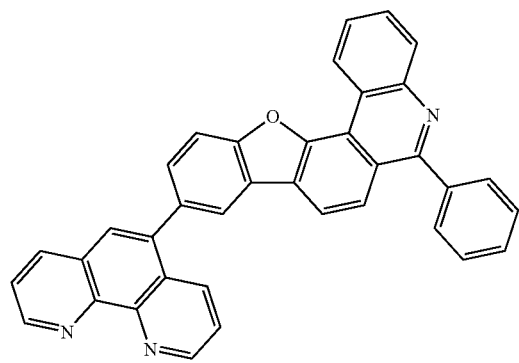
190
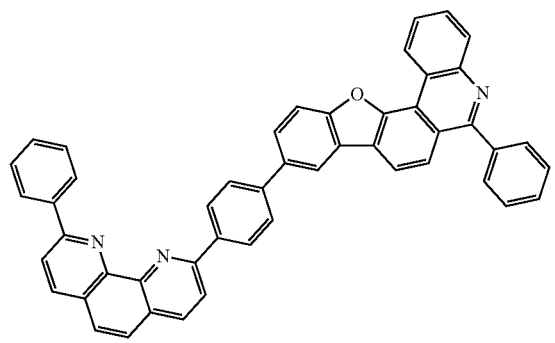
191
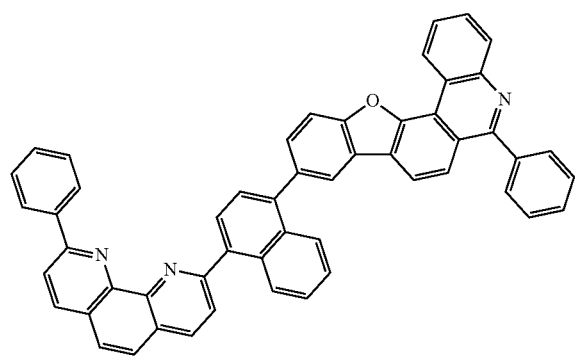
192
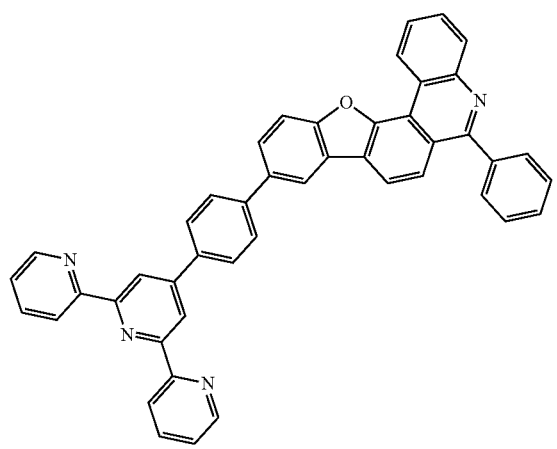
193
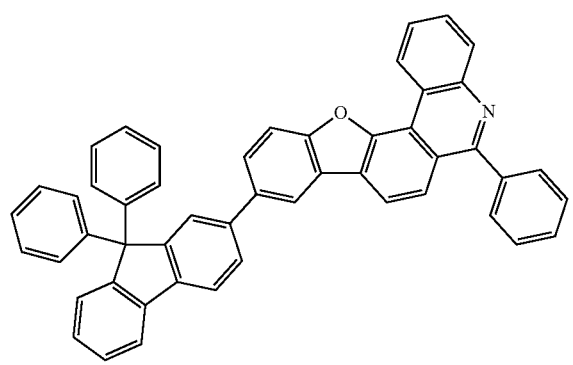
194
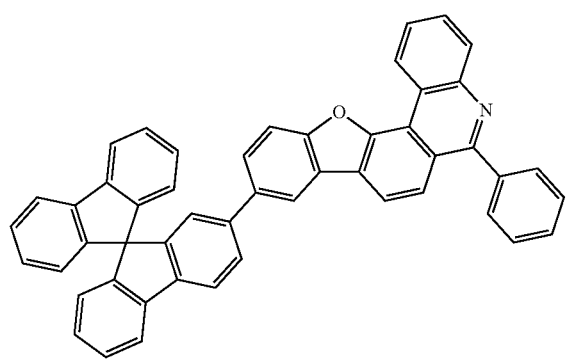

-continued
195
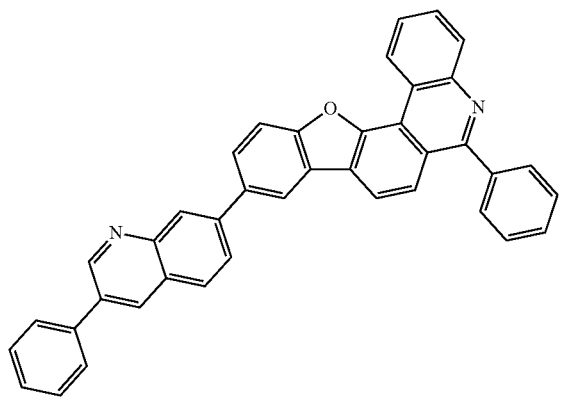
196
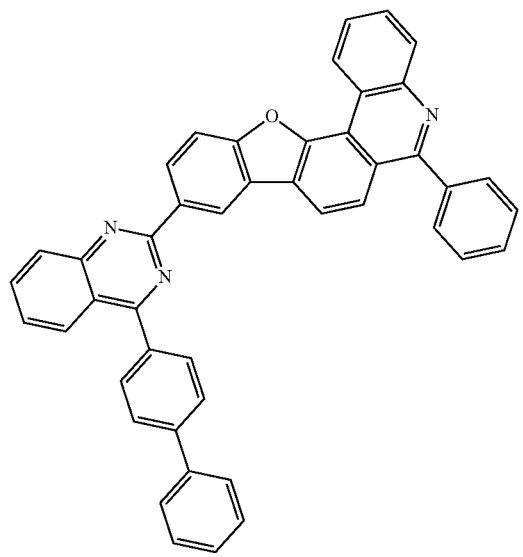
197
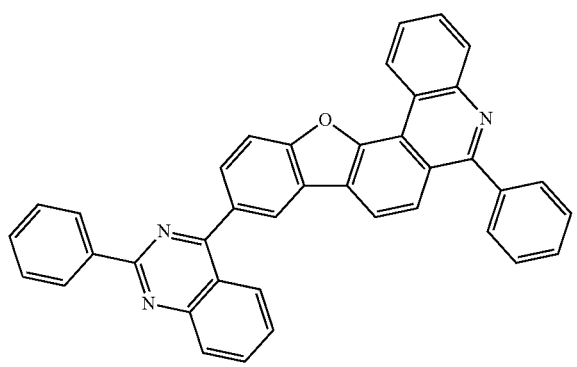
198
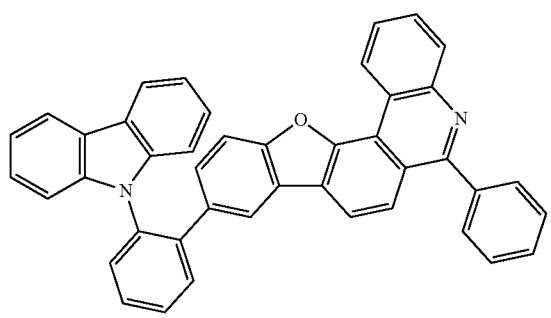
199
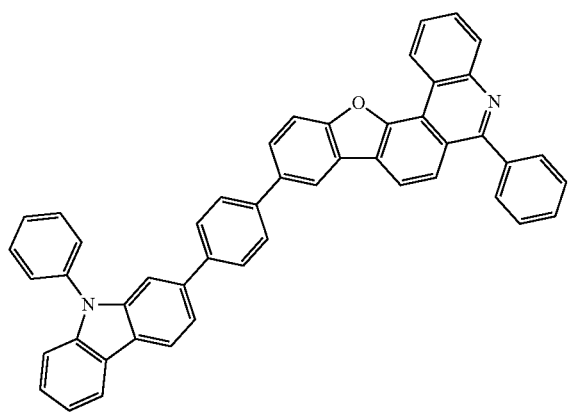
200
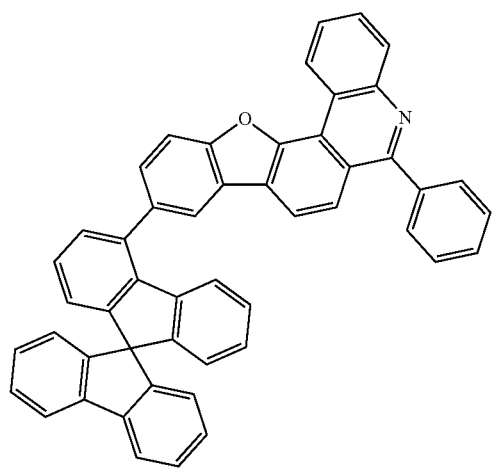

-continued
201
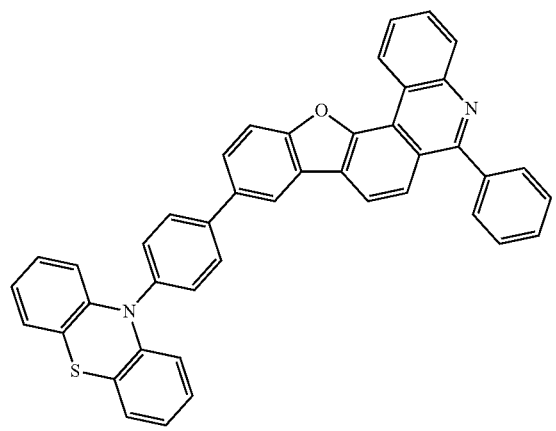
202
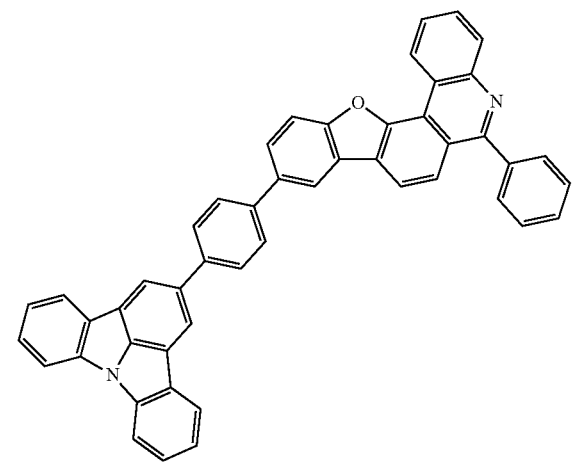
203
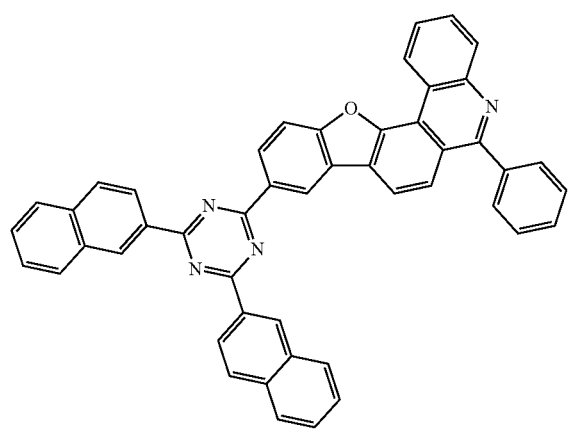
204
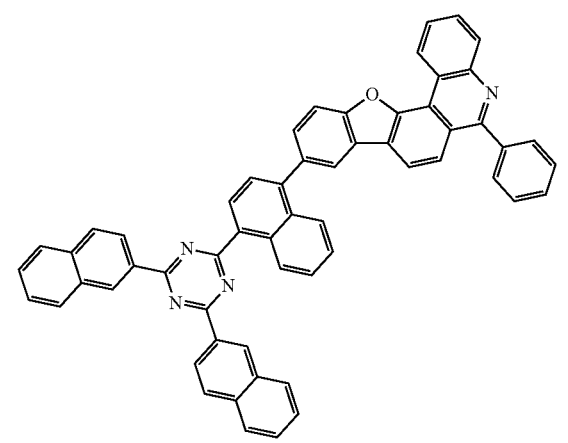
205
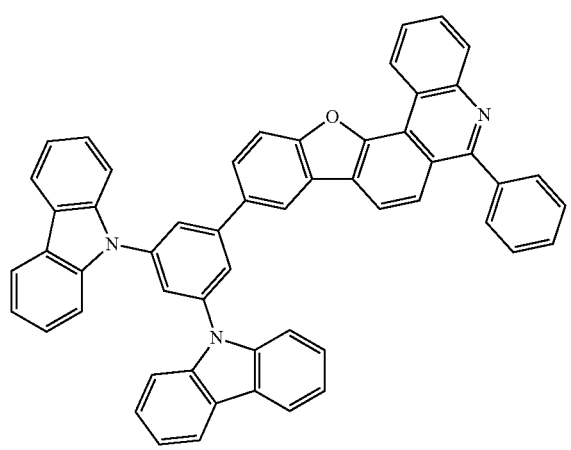
206
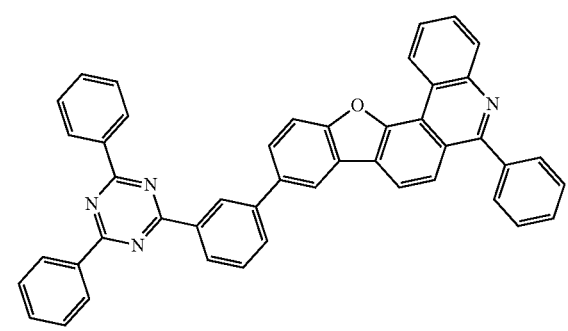

207
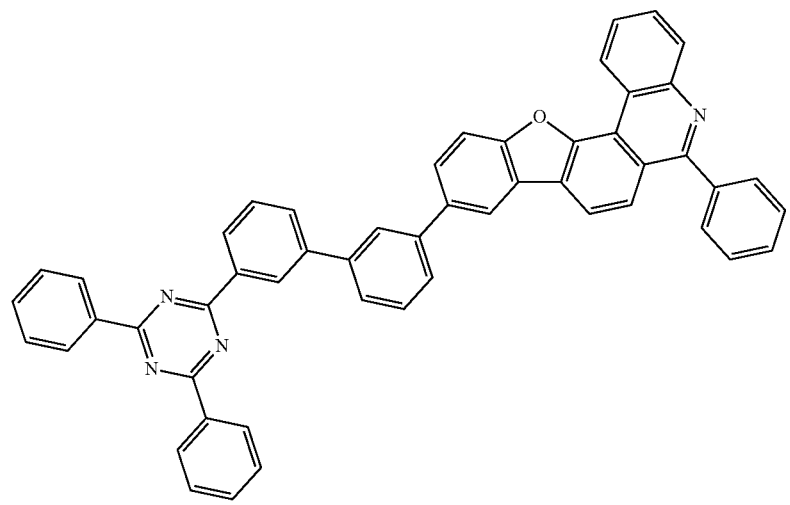
208
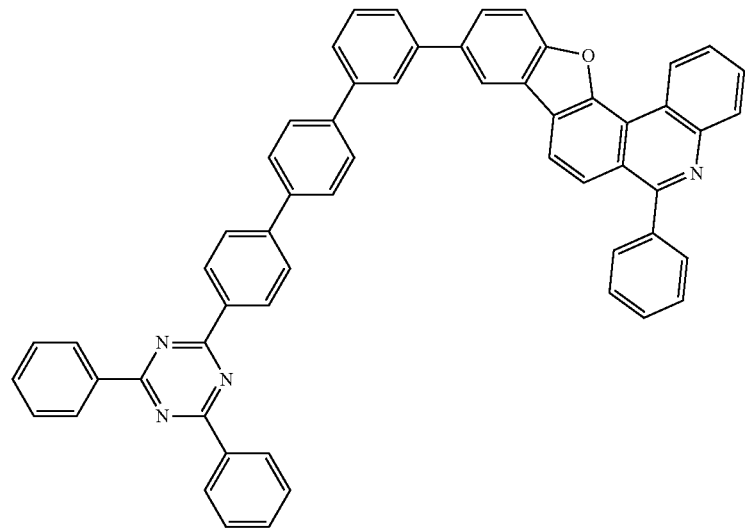
209
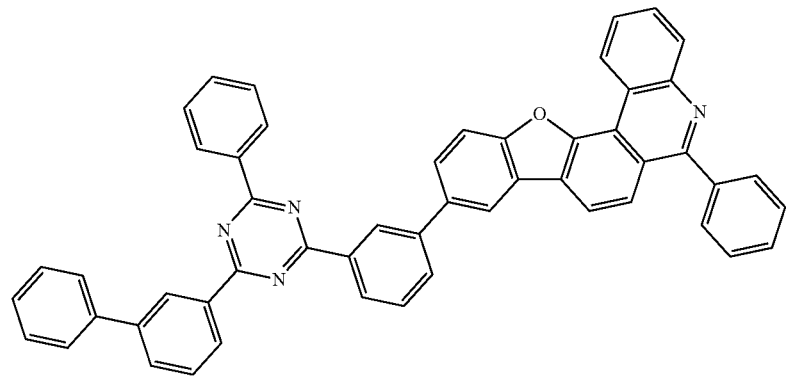

-continued
210
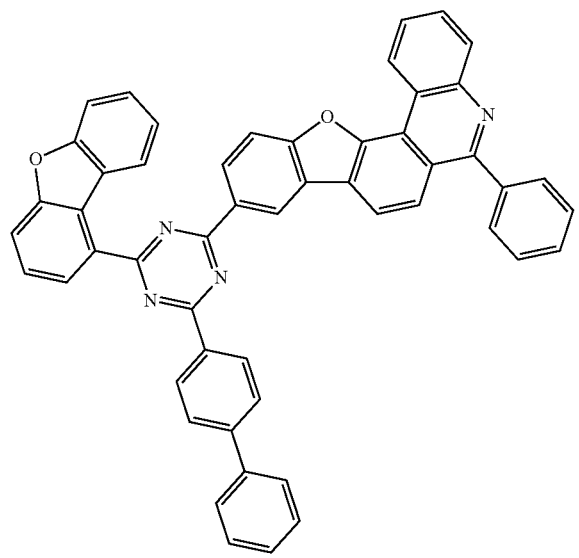
211
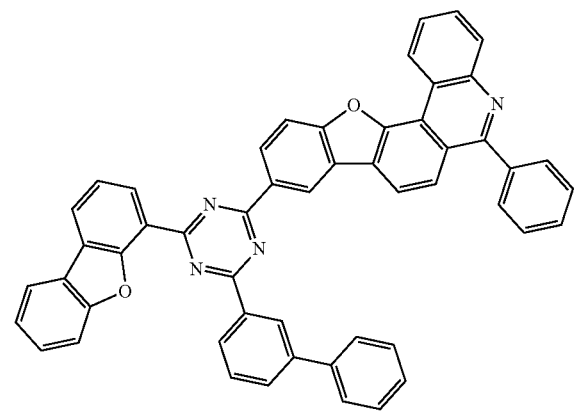
212
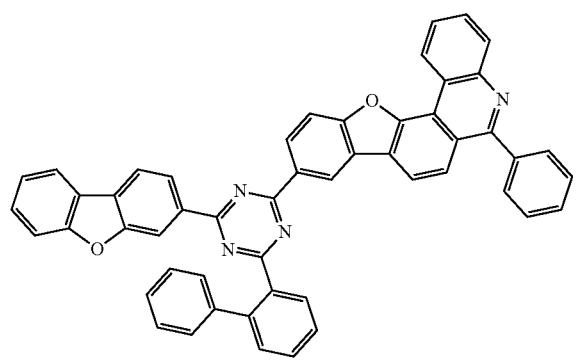
213
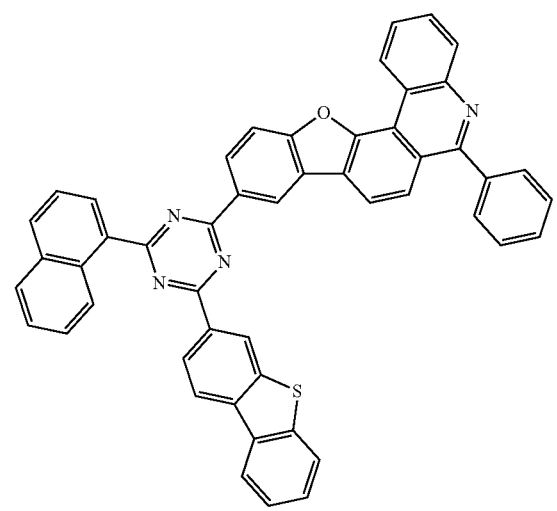
214
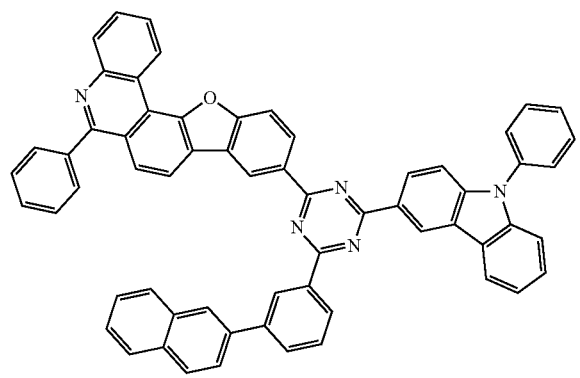
215
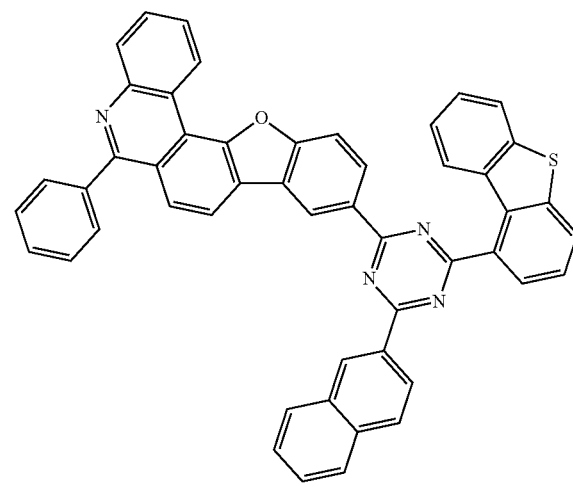

216 217
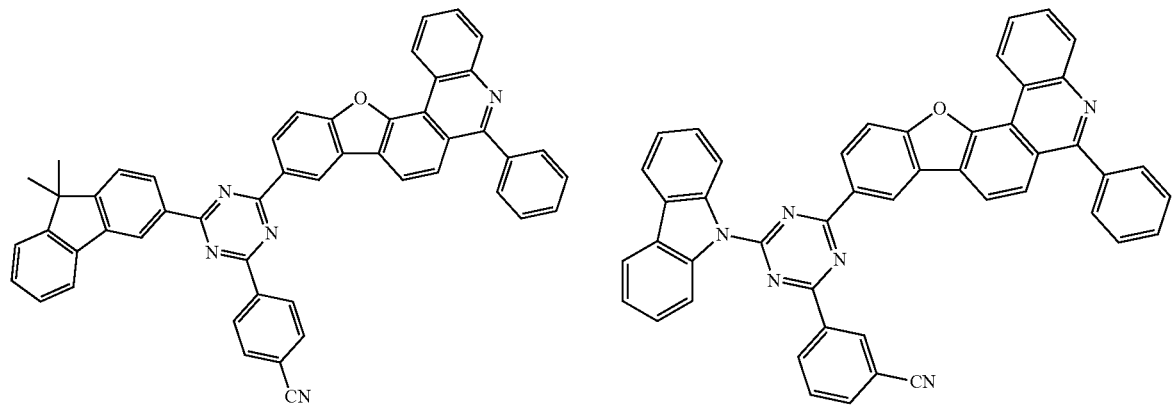
218 219
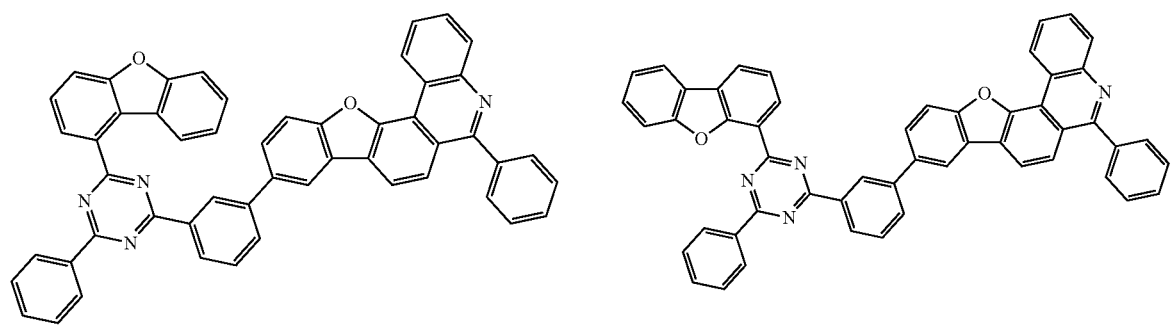
220 221
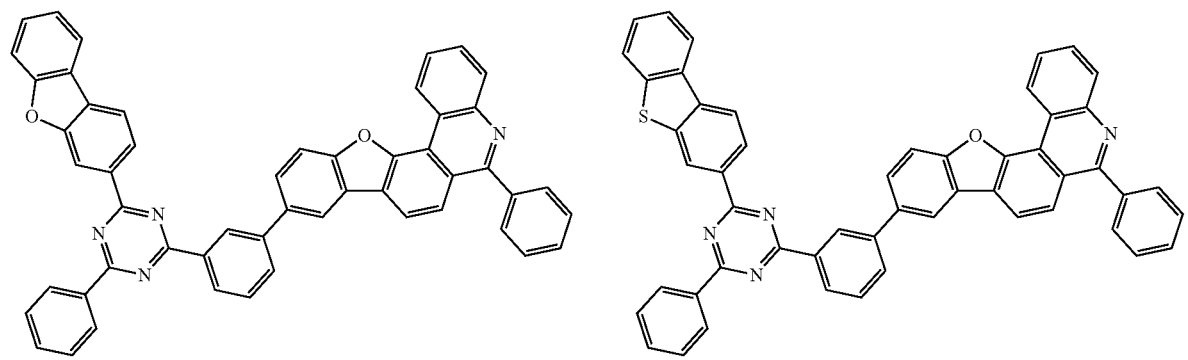

-continued
222
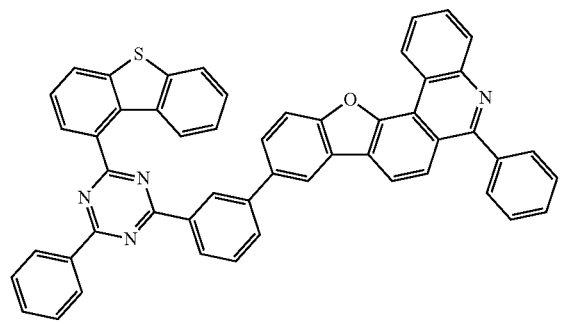
223
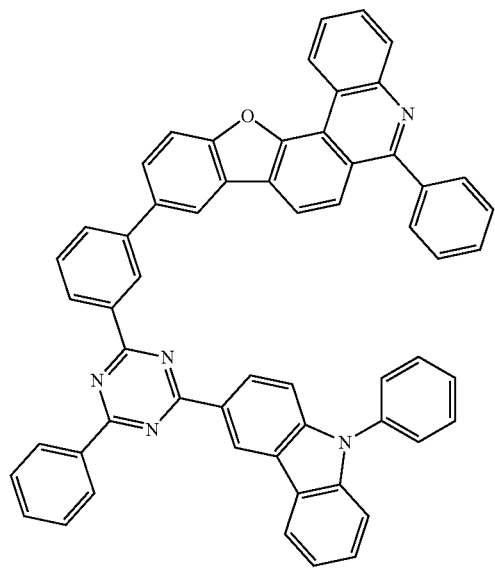
224
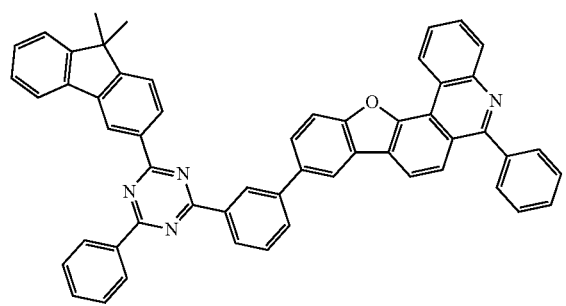
225
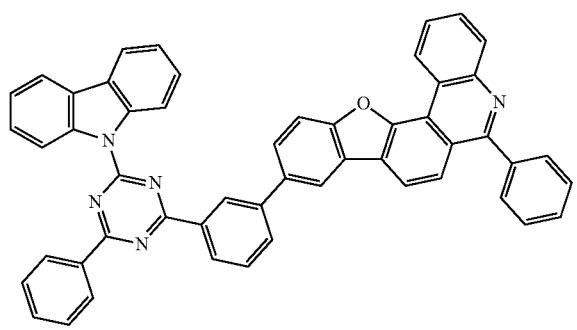
226
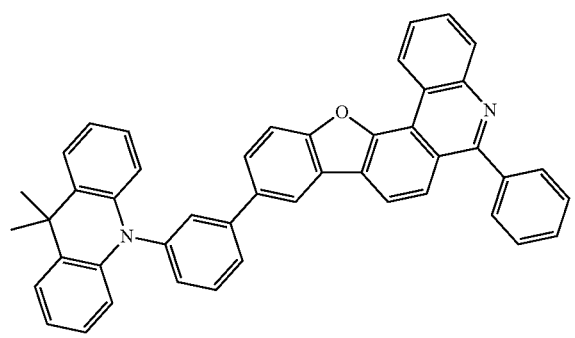
227
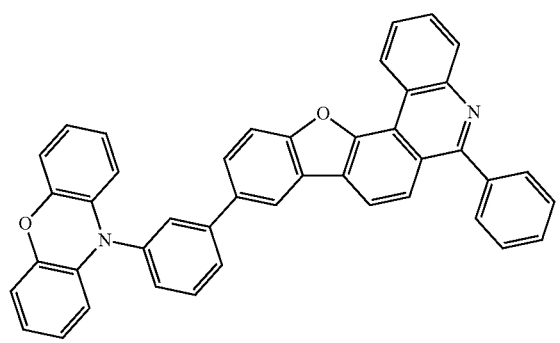

228
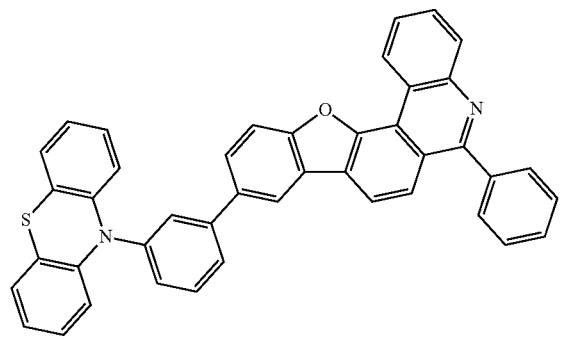
229
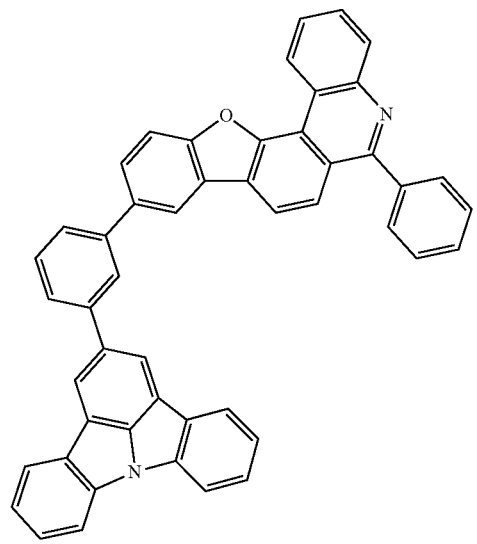
230
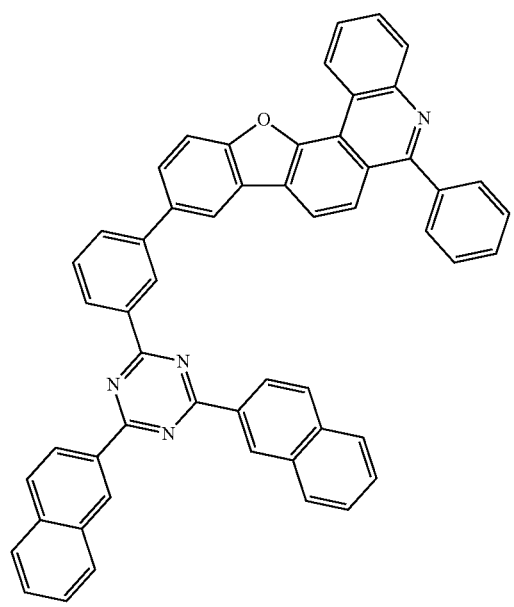
231
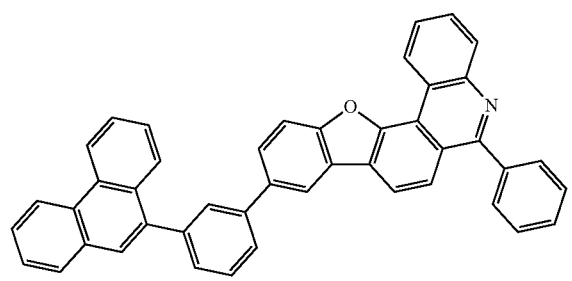

232
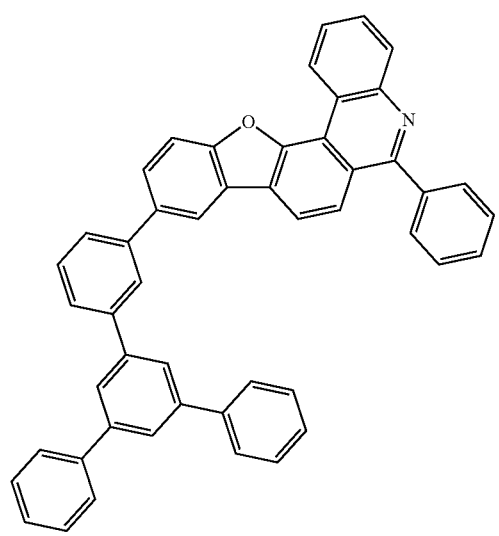
233
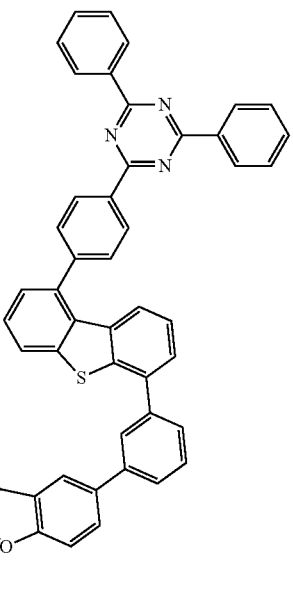
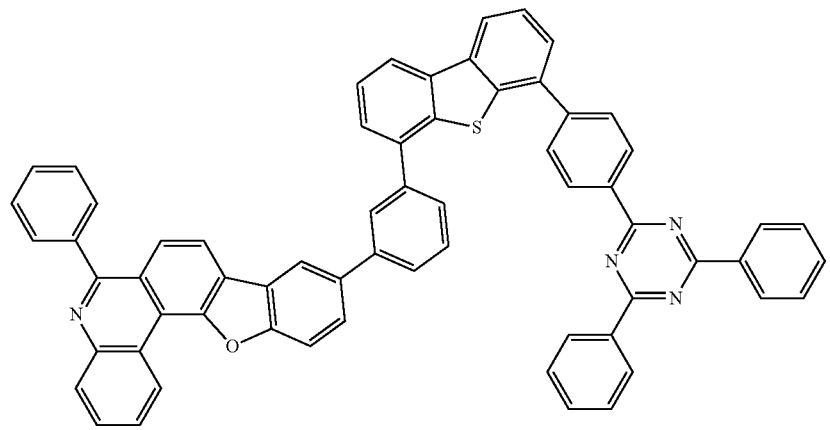
235
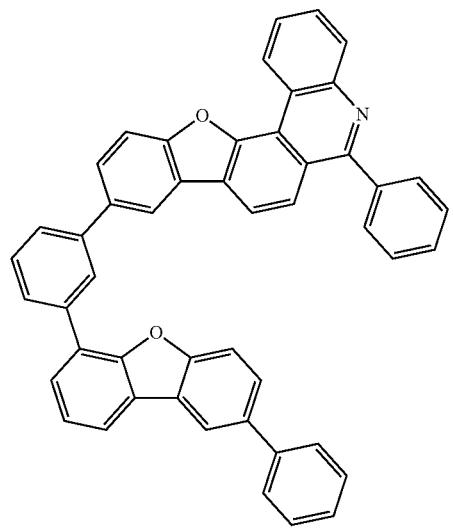
236
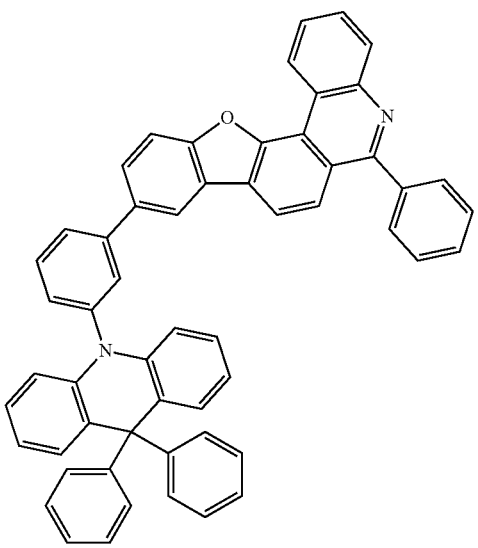

-continued
237
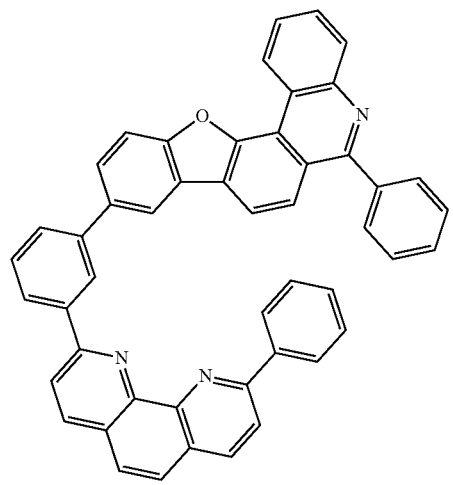
238
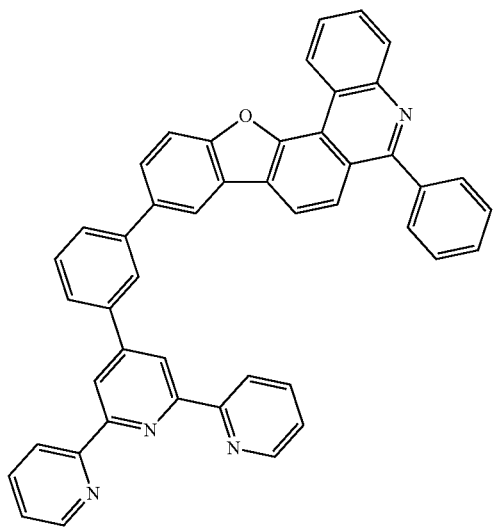
239
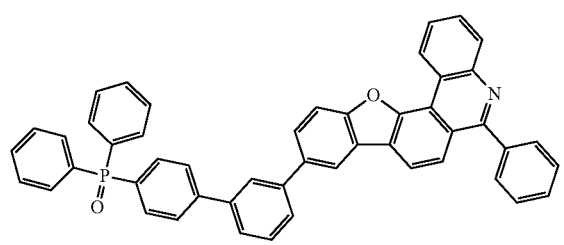
240
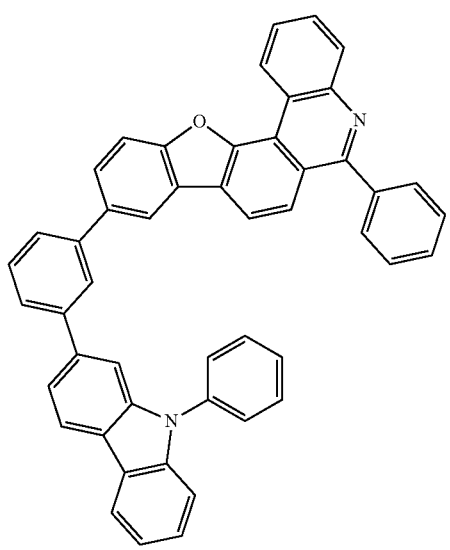
241
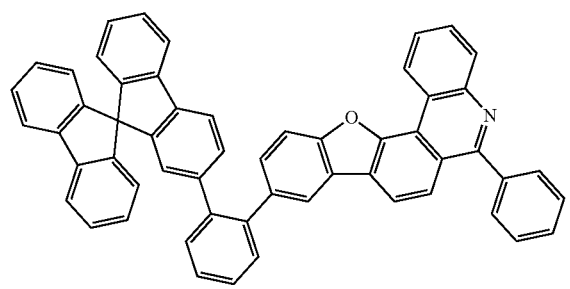
242
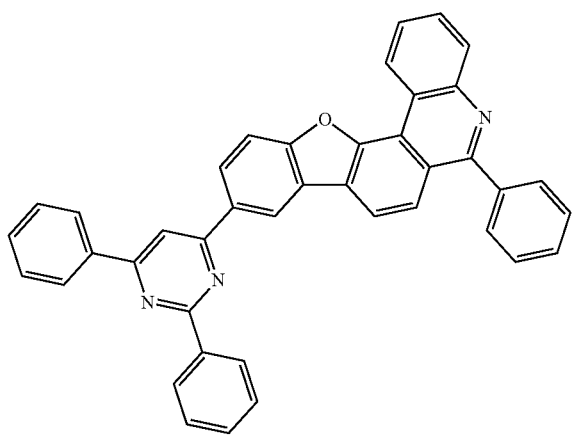

243
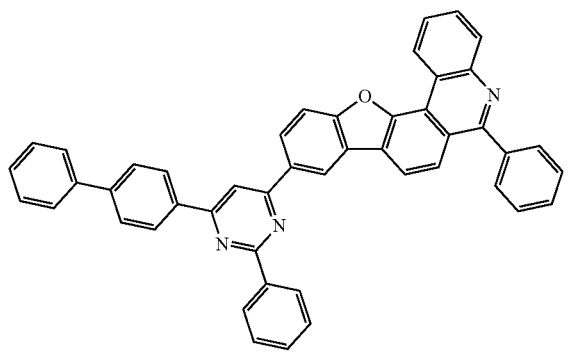
244
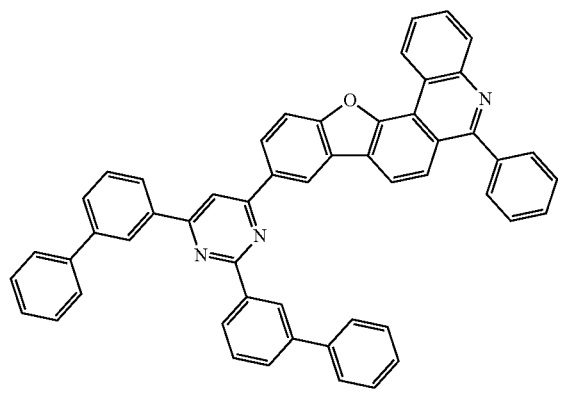
245
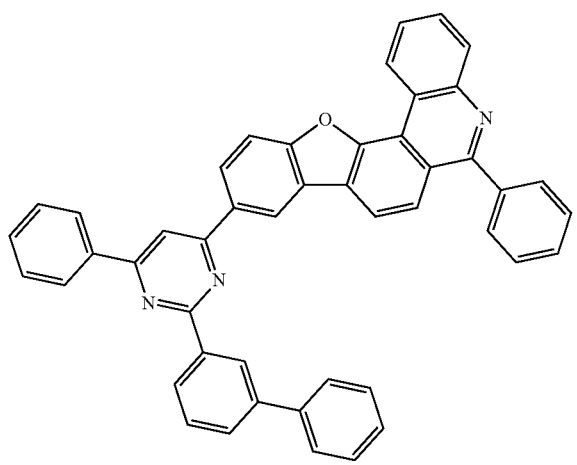
246
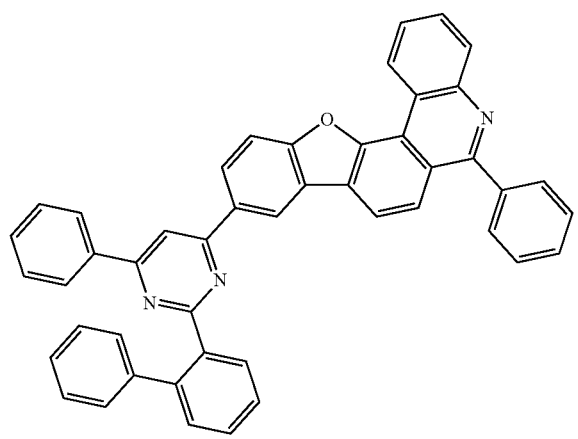
247
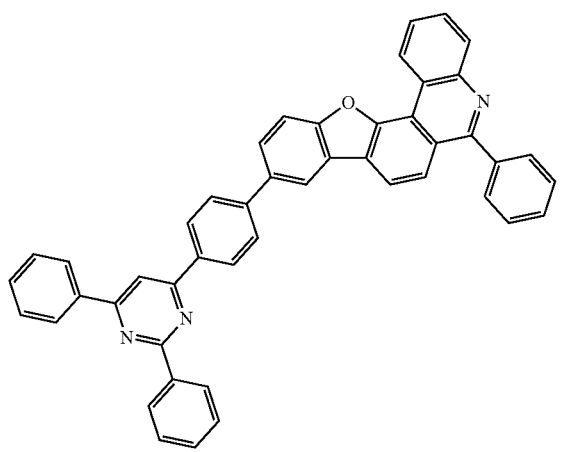
248
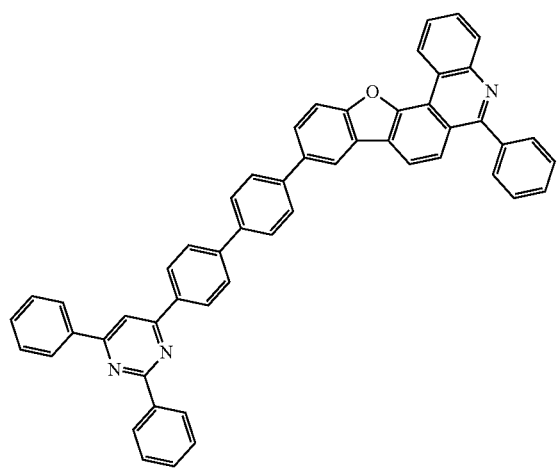

-continued
249
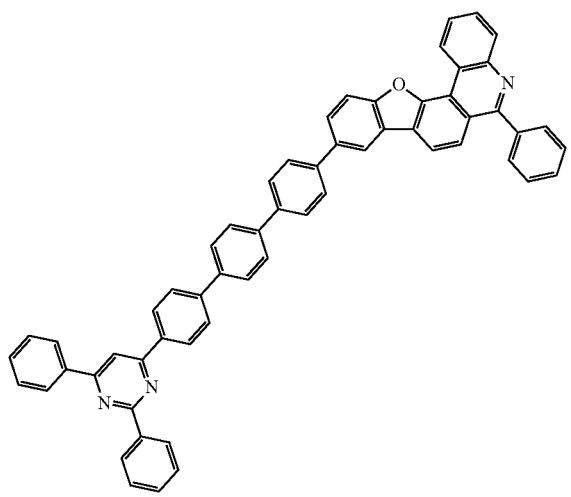
250
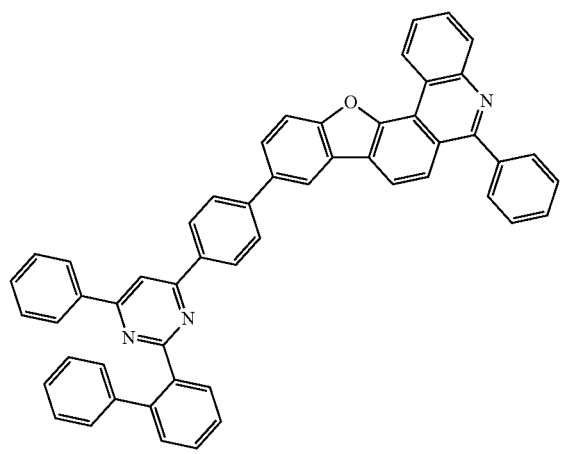
251
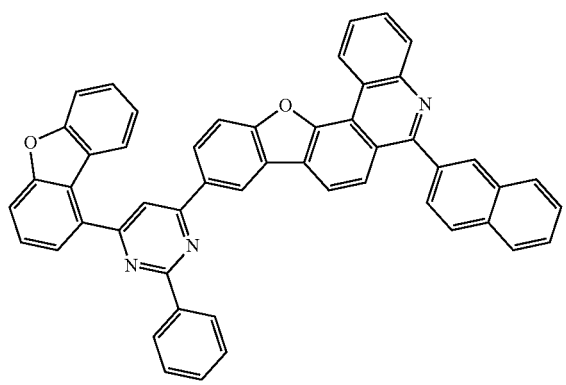
252
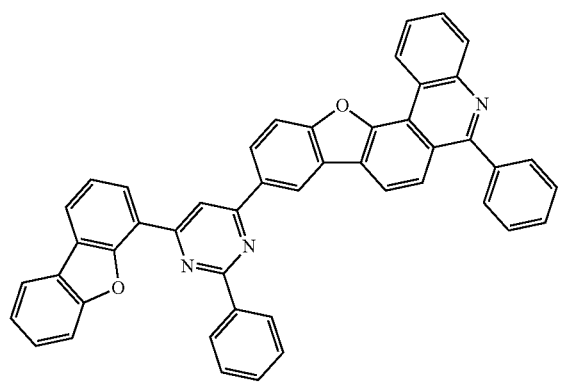
253
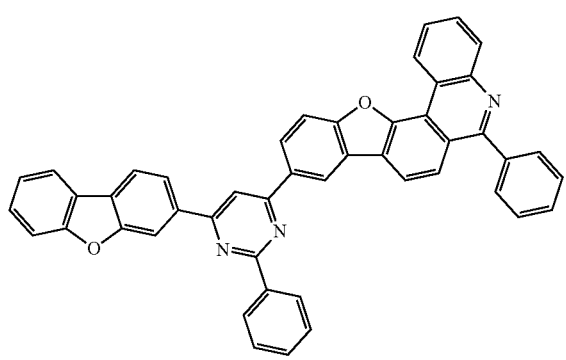
254
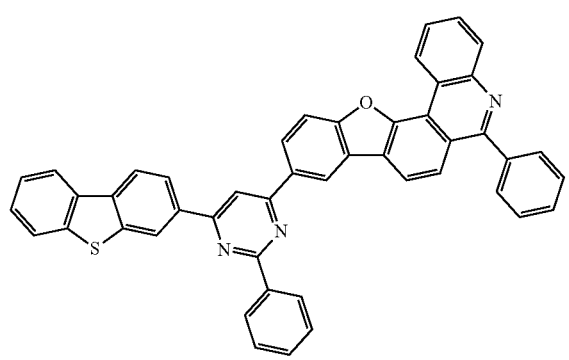

255
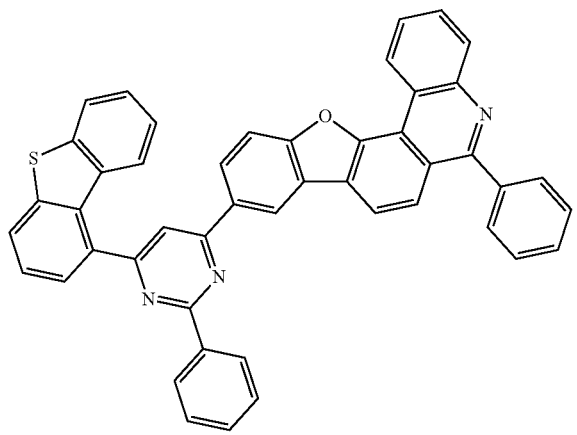
256
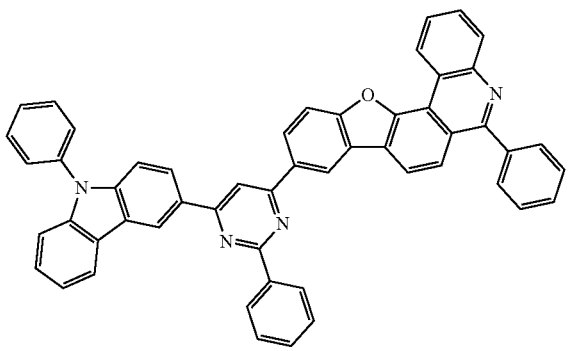
257
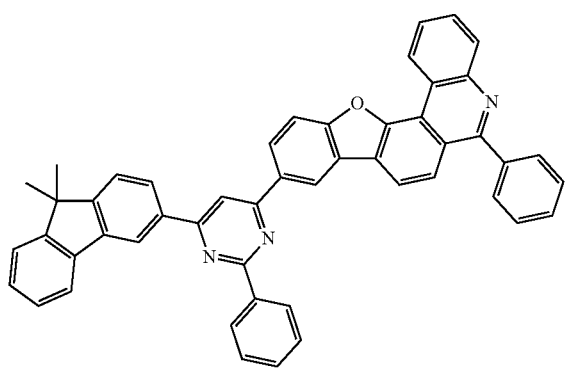
258
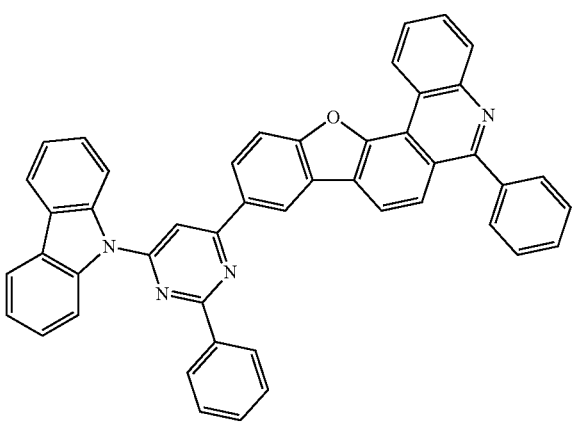
259
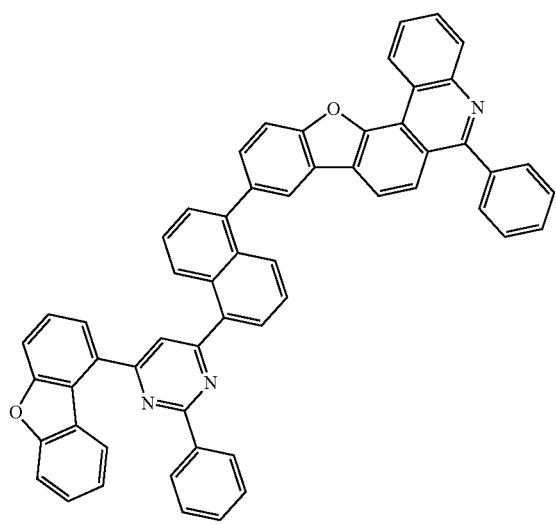
260
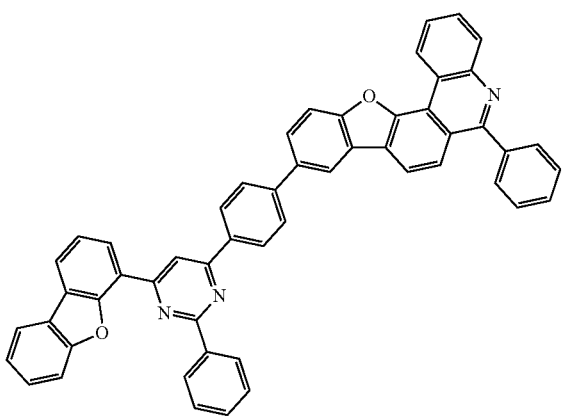

-continued
261
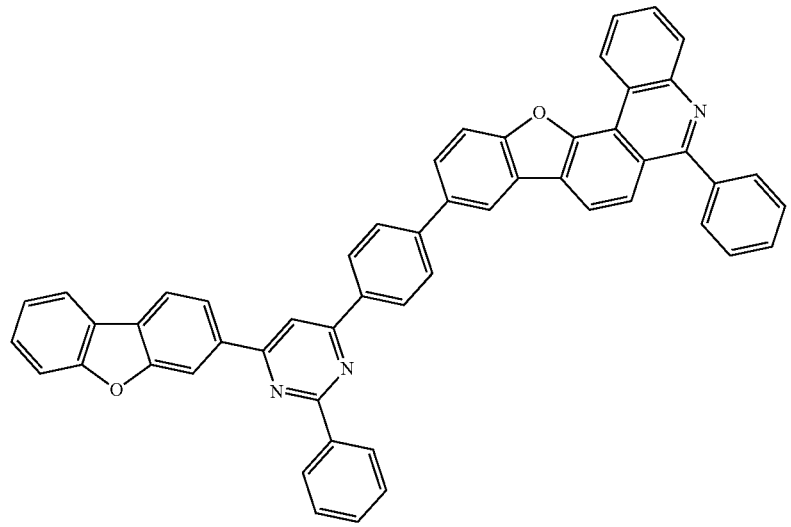
262
263

-continued
264
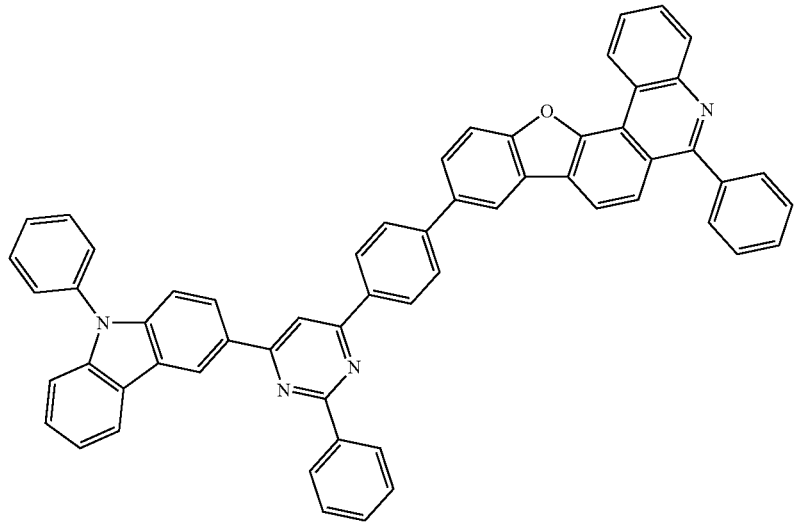
265
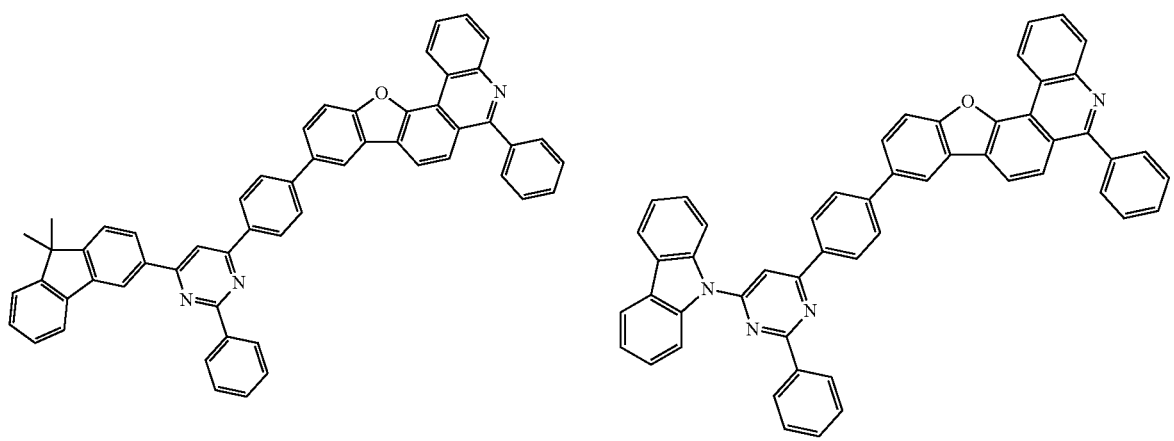
266
267
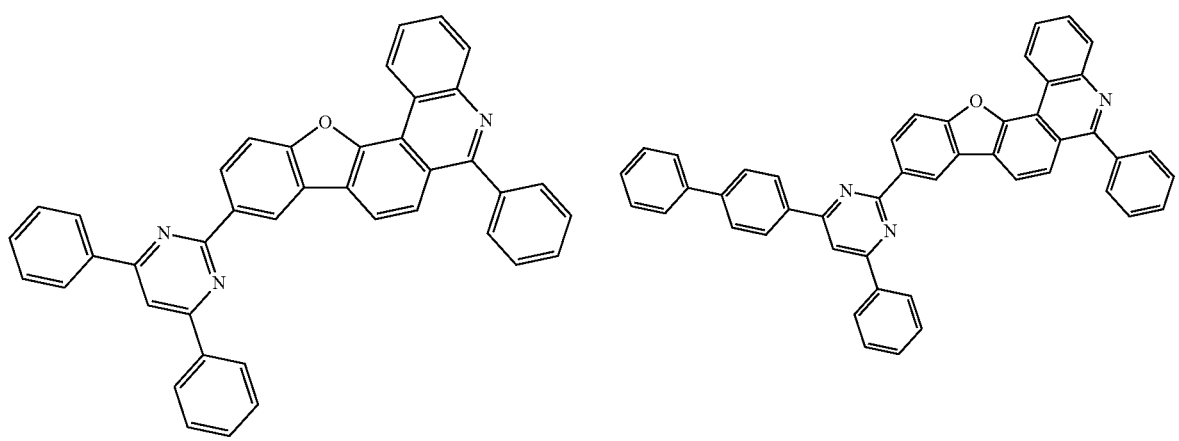
268

-continued
269
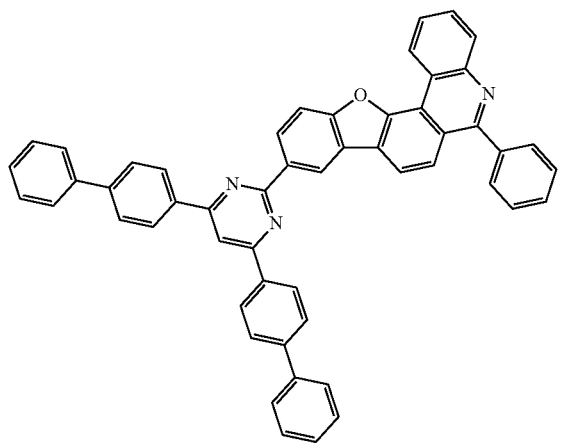
270
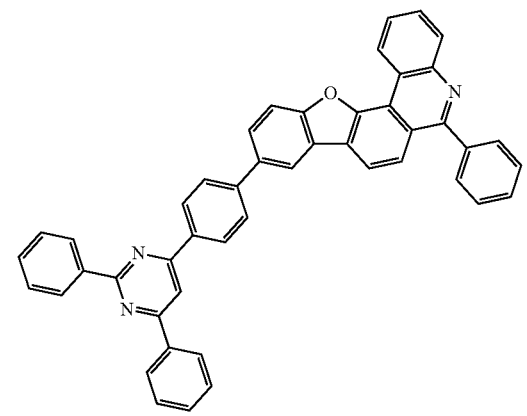
271
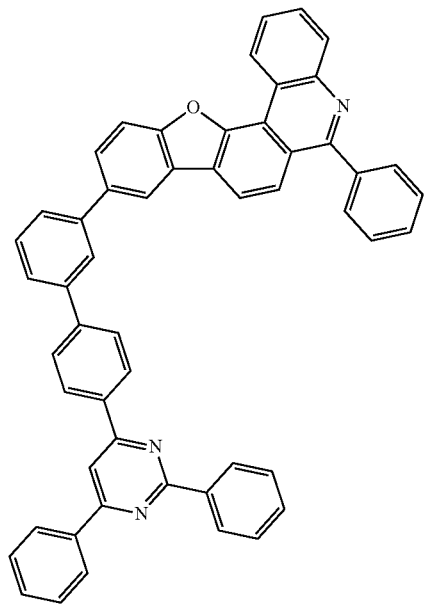
272
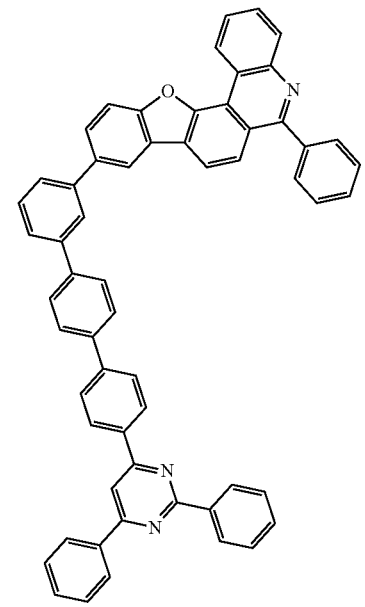
273
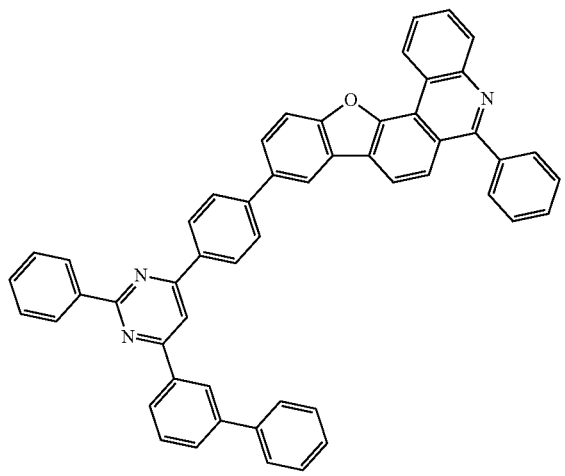
274
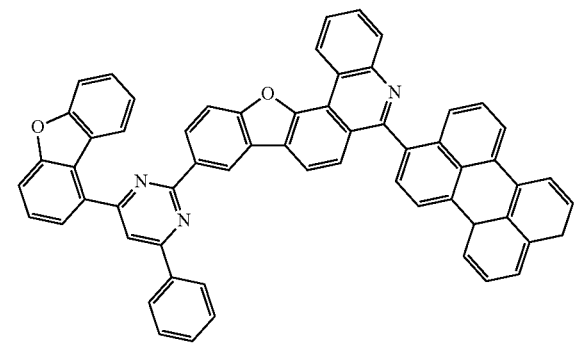

275
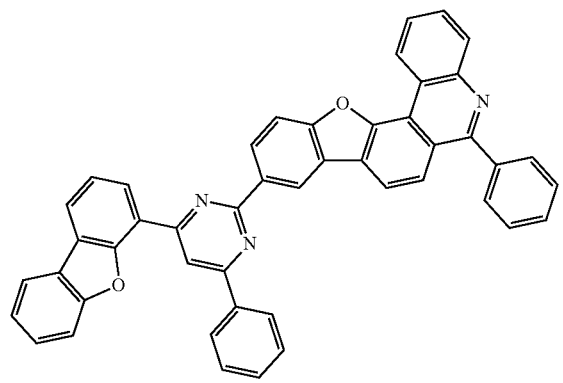
276
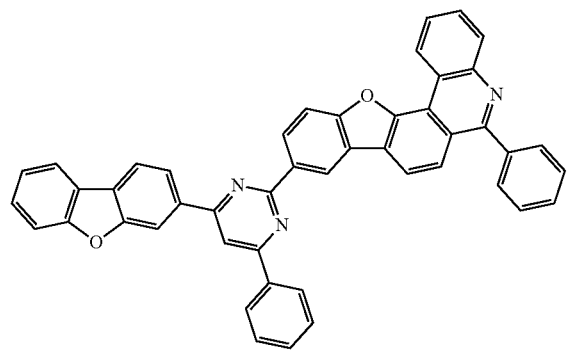
277
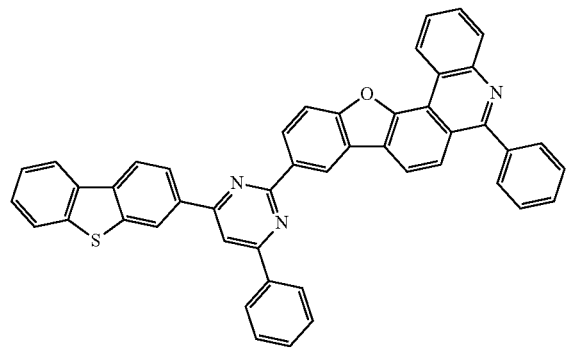
278
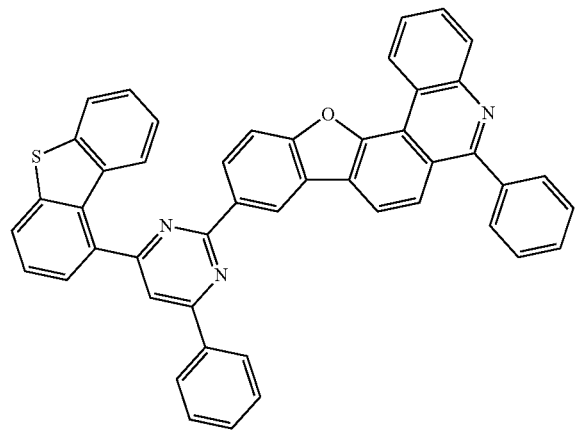
279
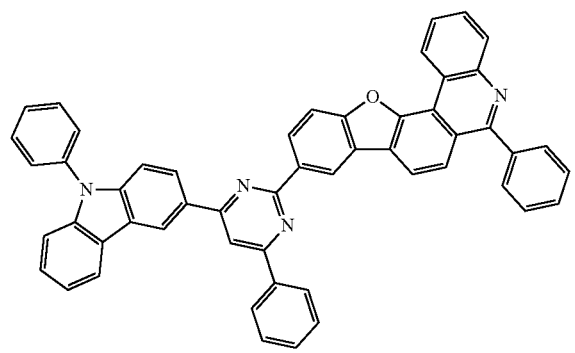
280
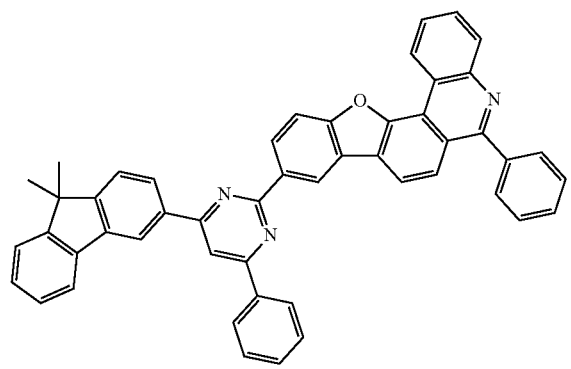

281
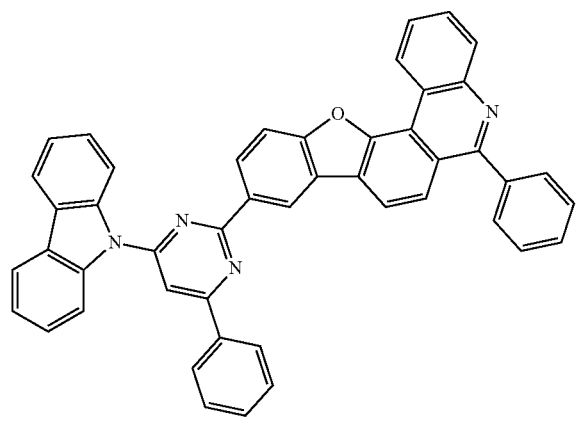
282
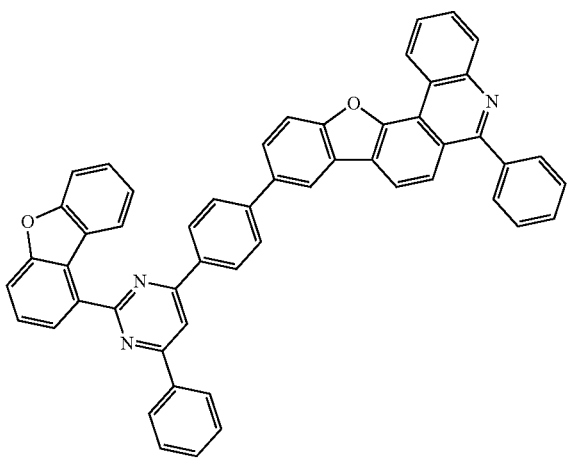
283
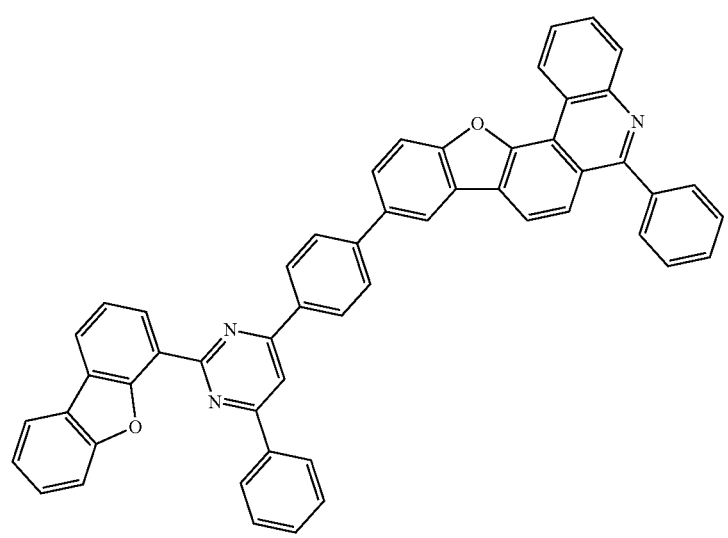
284
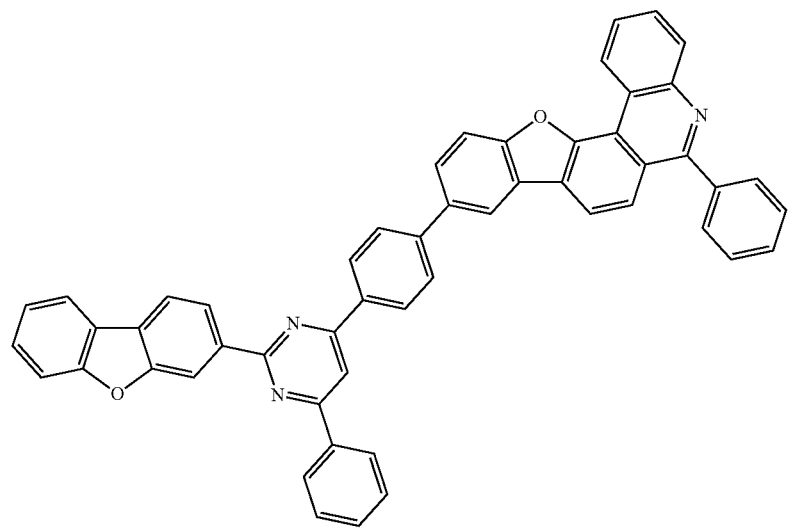

285
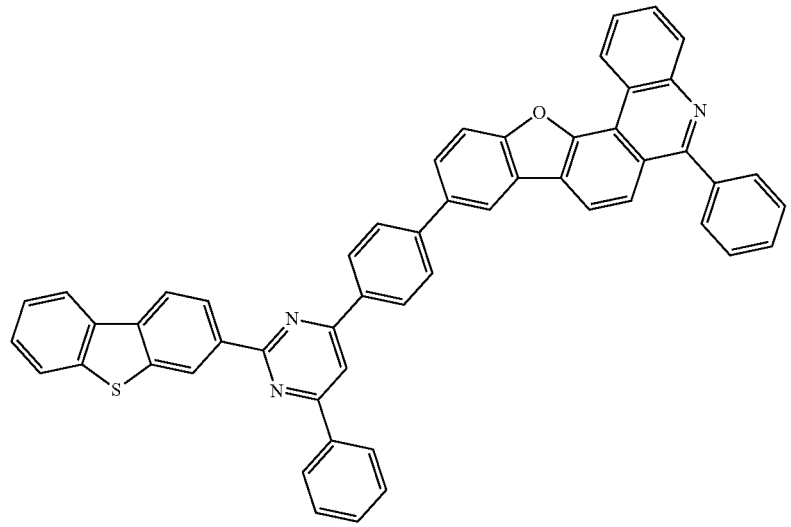
286
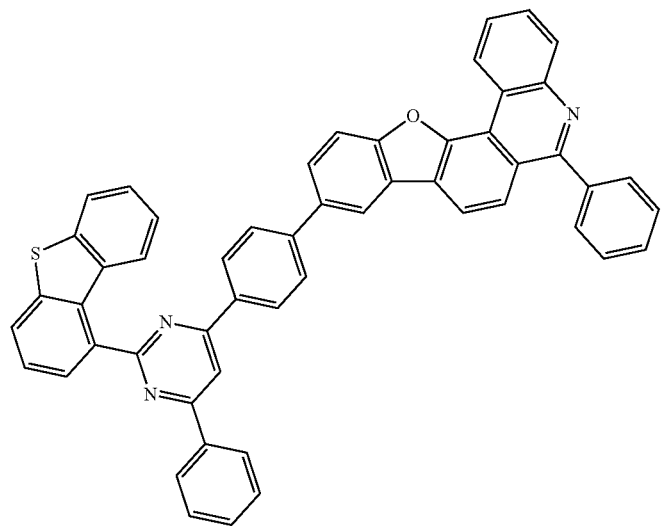
287
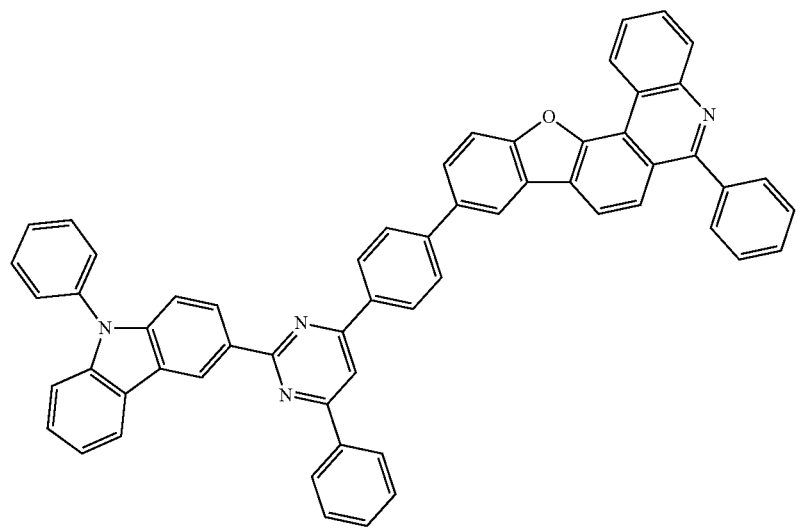

-continued
288
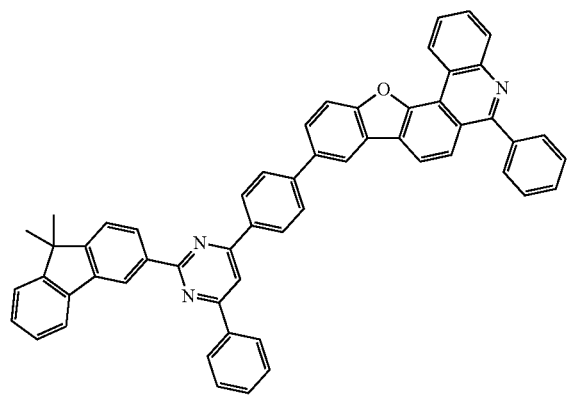
289
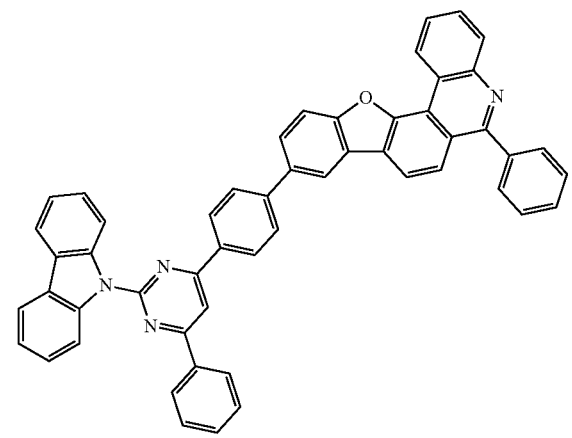
290
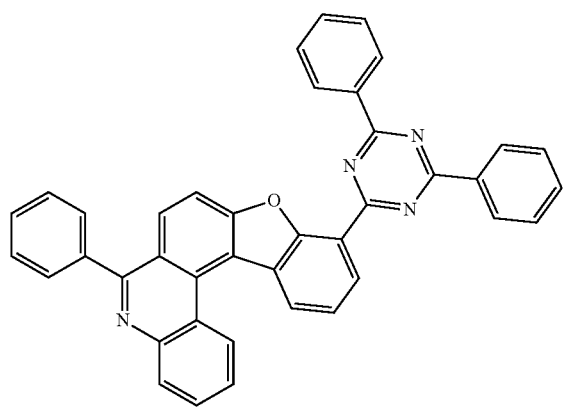
291
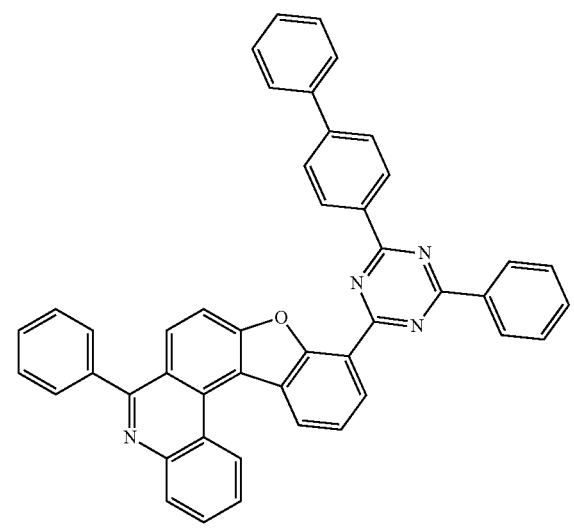
292
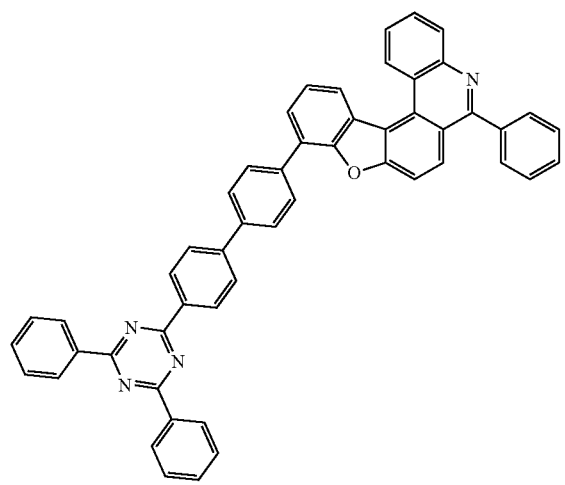
293
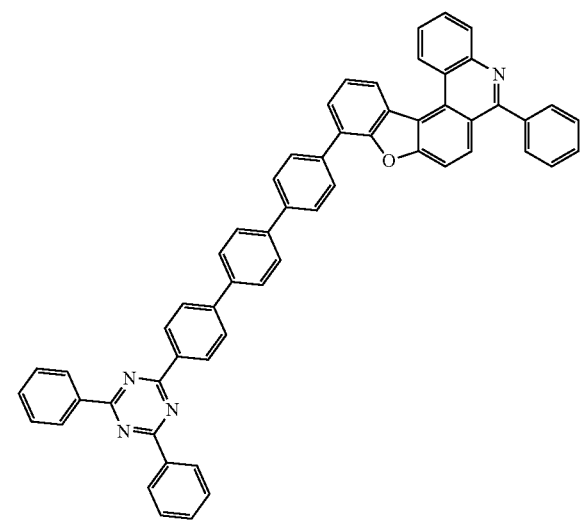

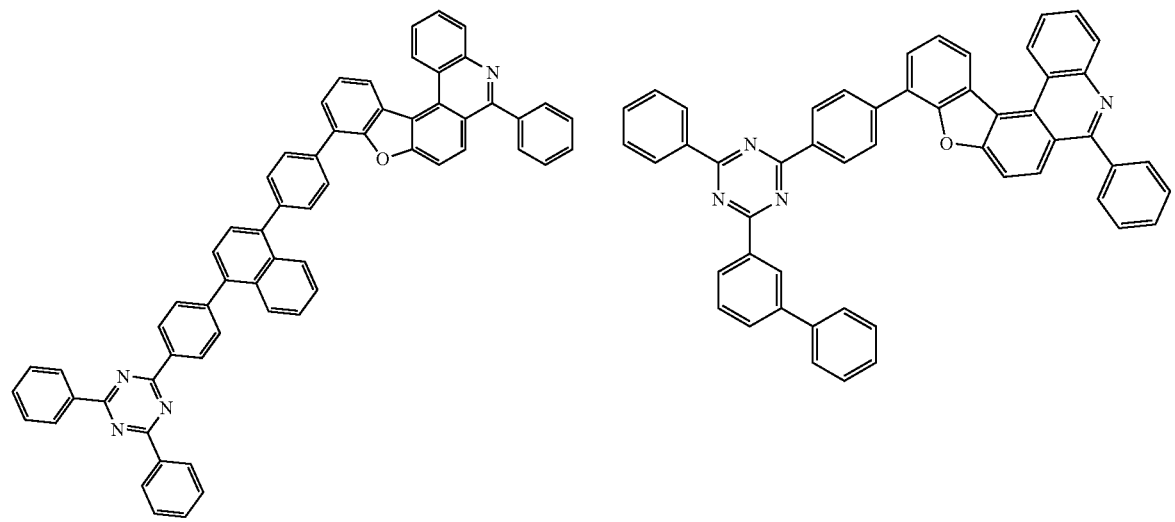
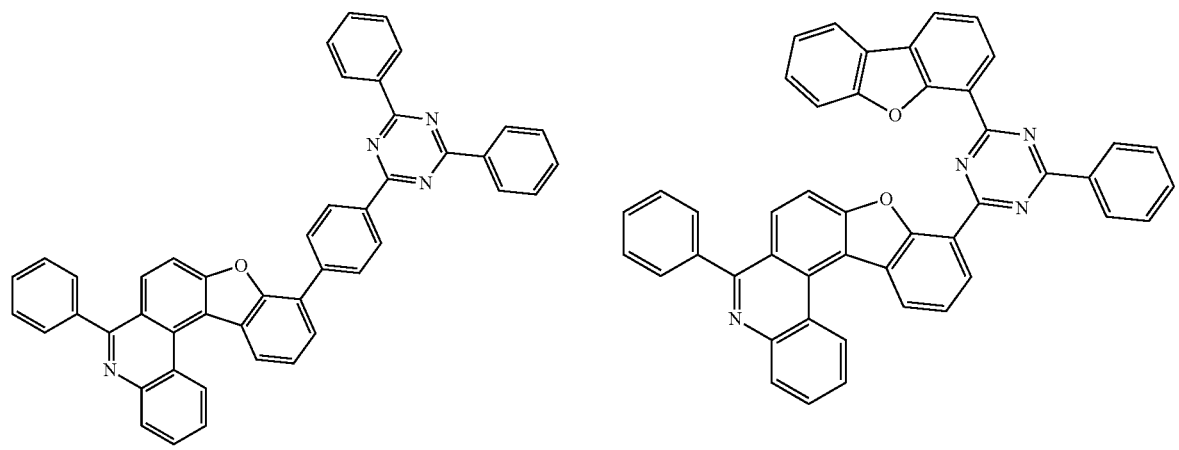
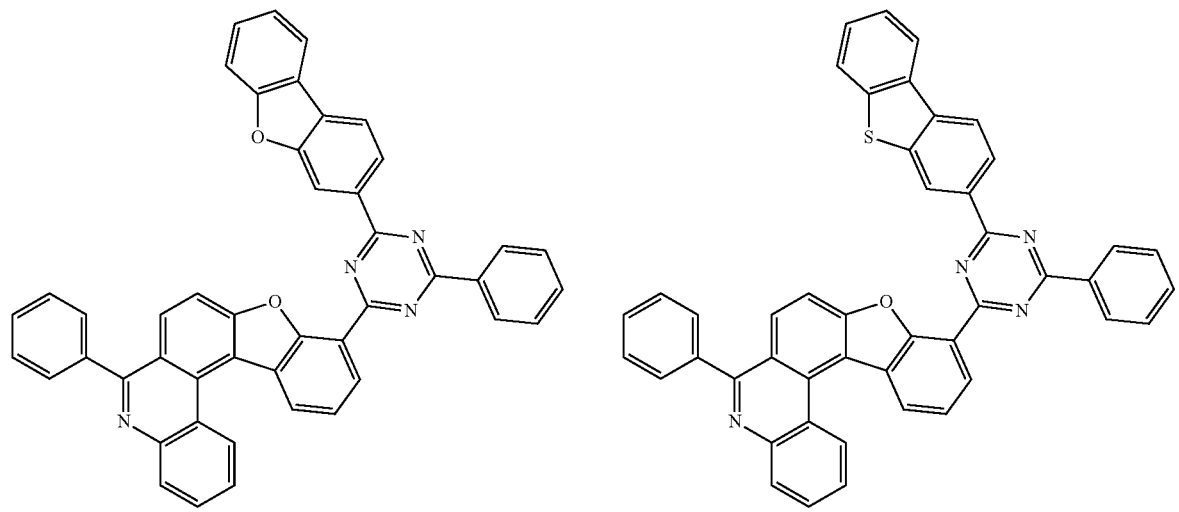

-continued
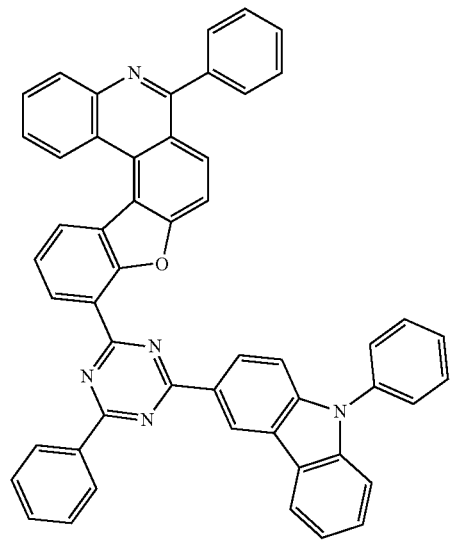
300
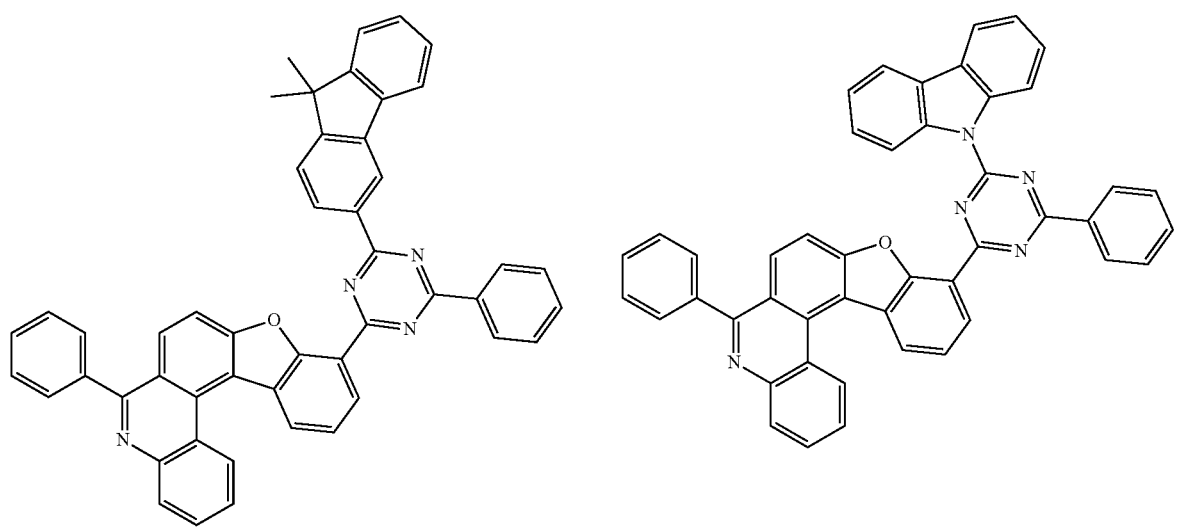

-continued
303
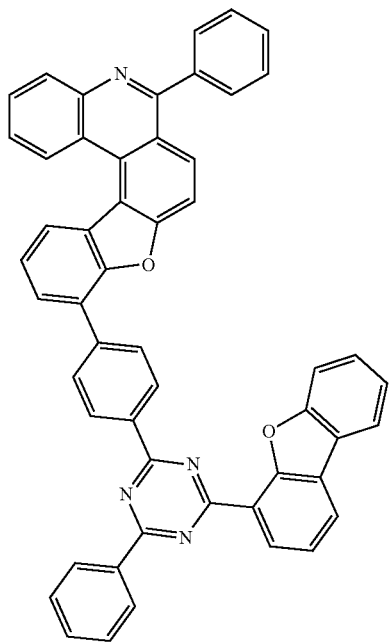
304
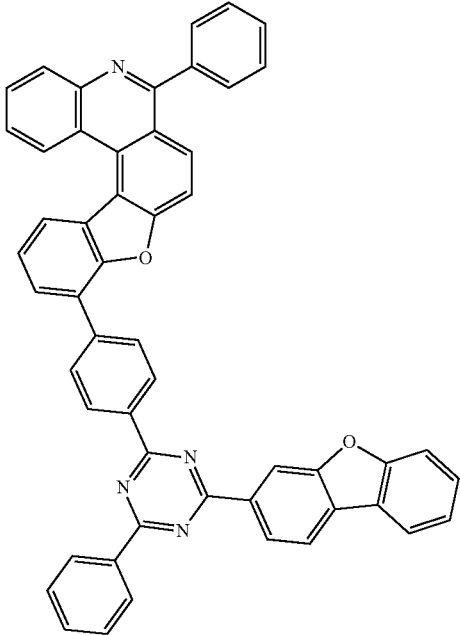
305
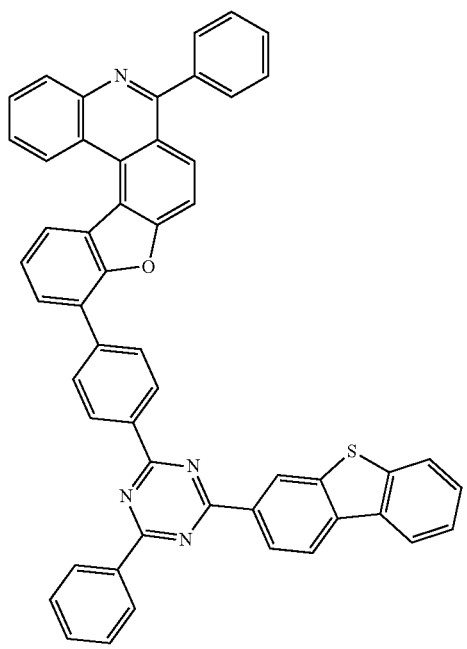
306
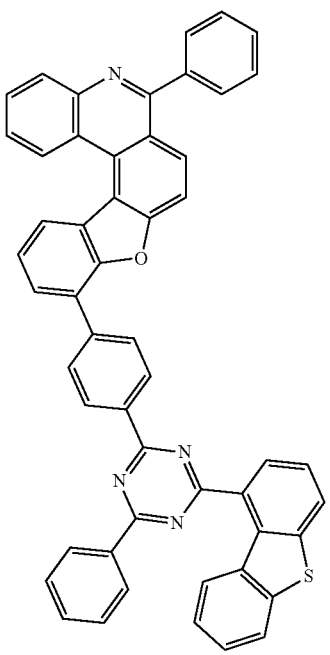

-continued
307
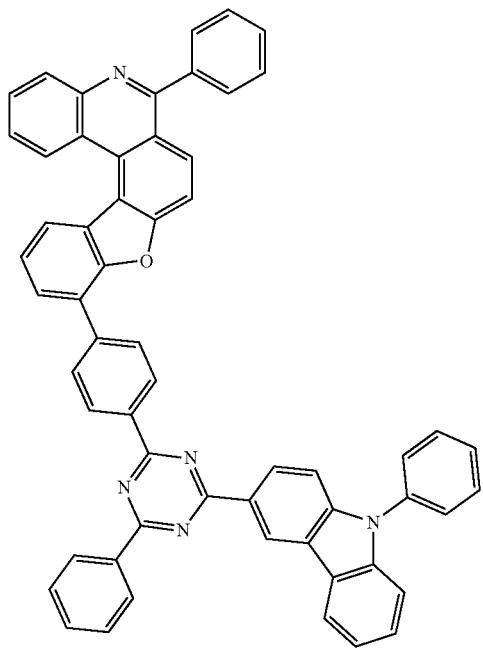
308
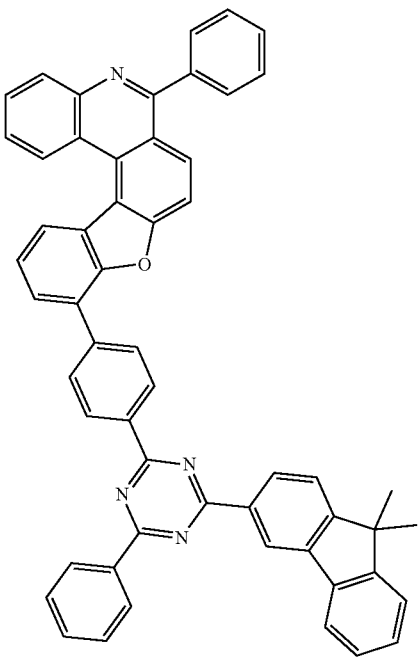
309
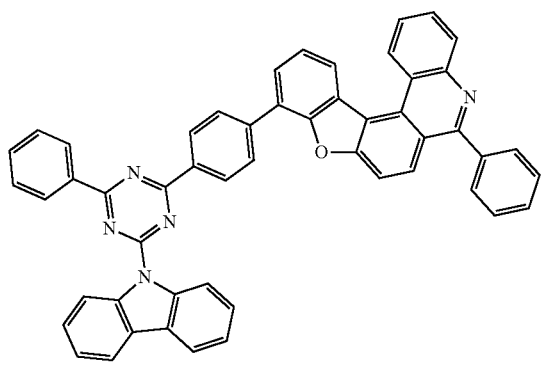
310
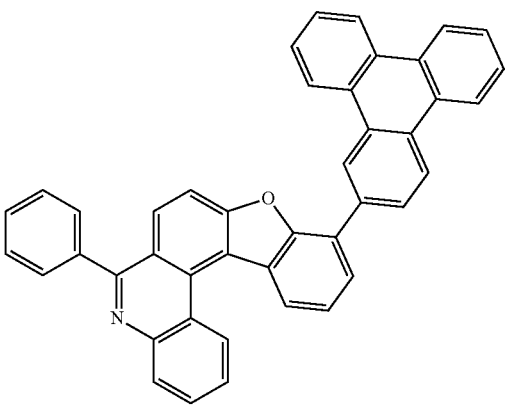
311
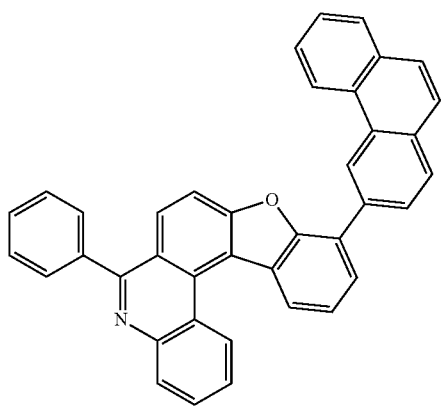
312
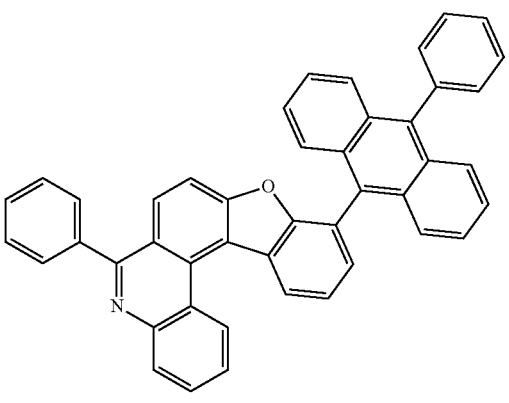

-continued
313
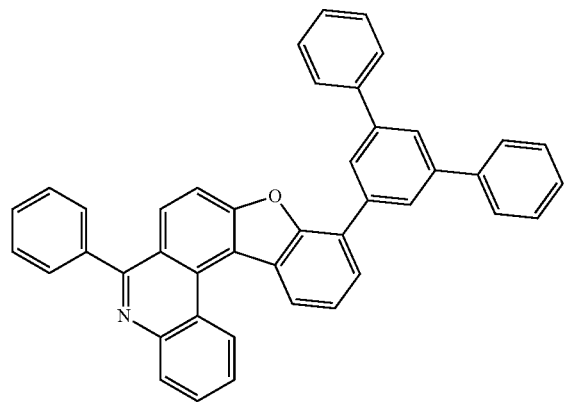
314
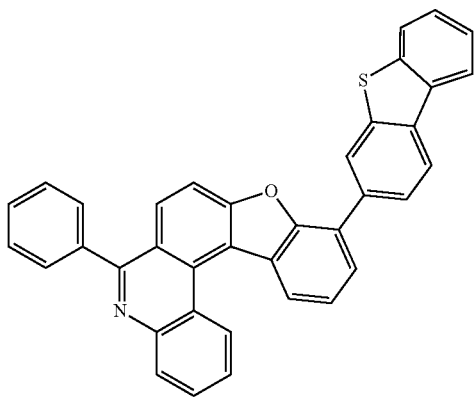
315
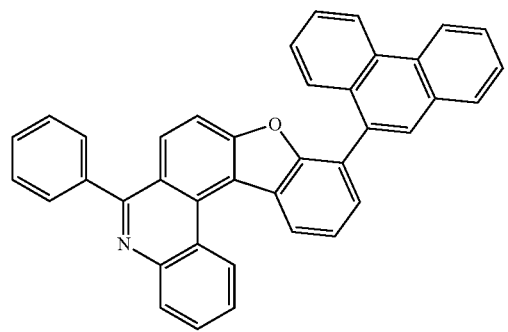
316
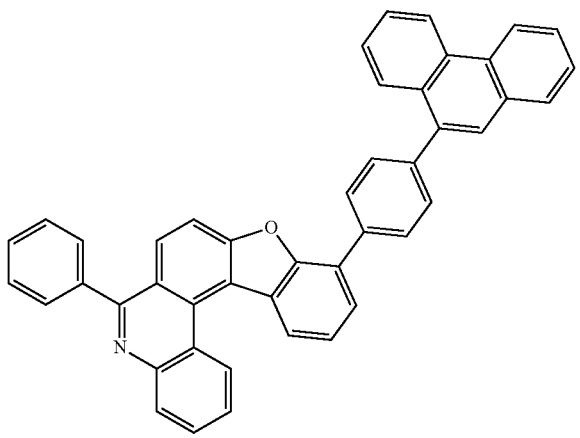
317
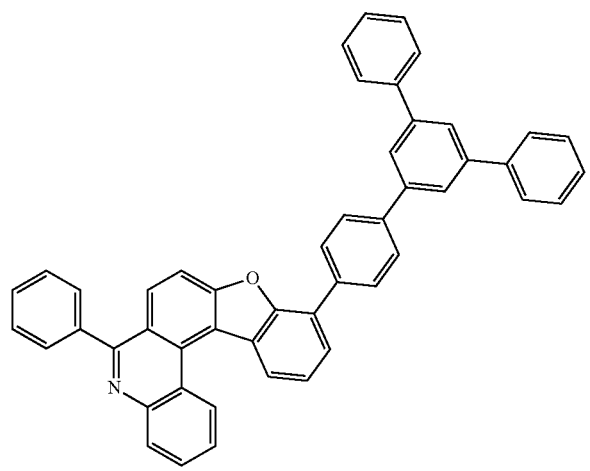
318
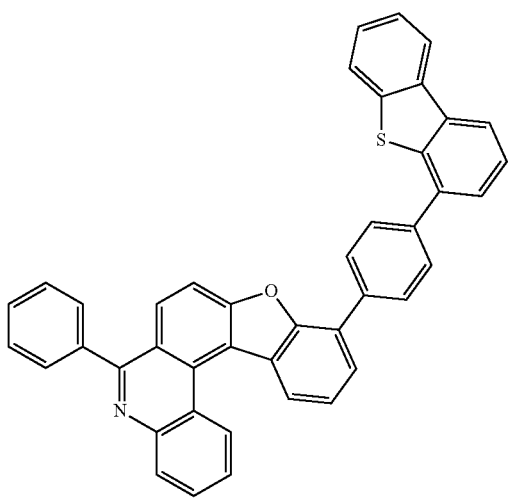

319
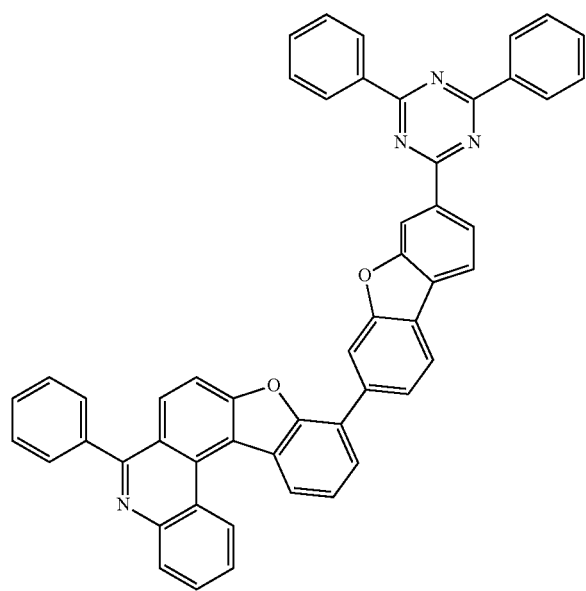
873
320
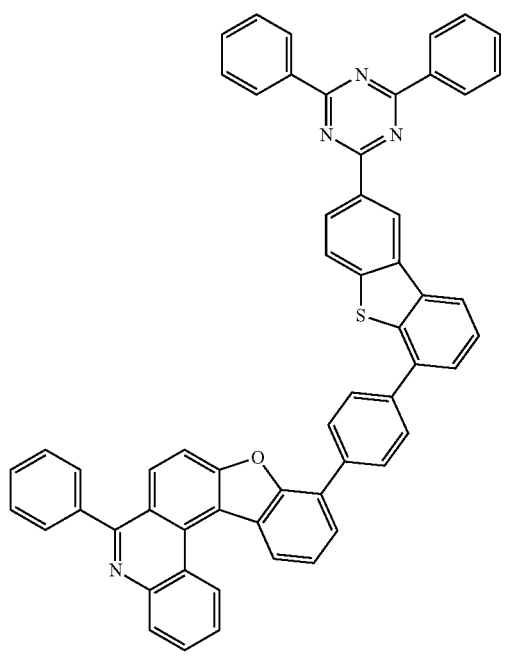
874
321
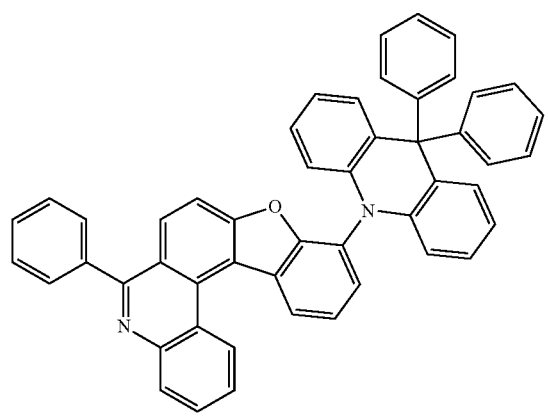
322
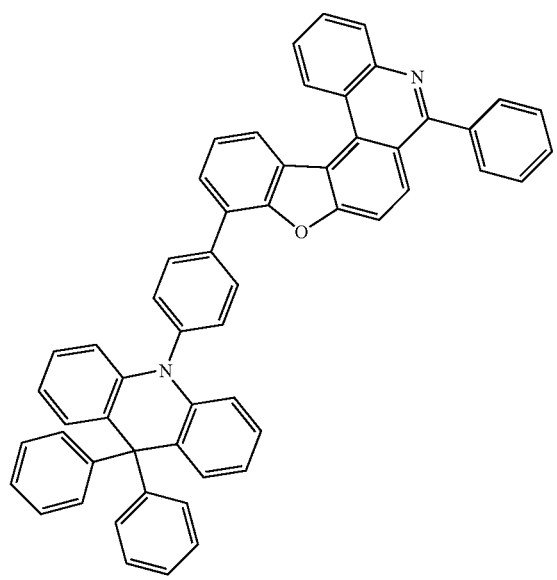

-continued
323
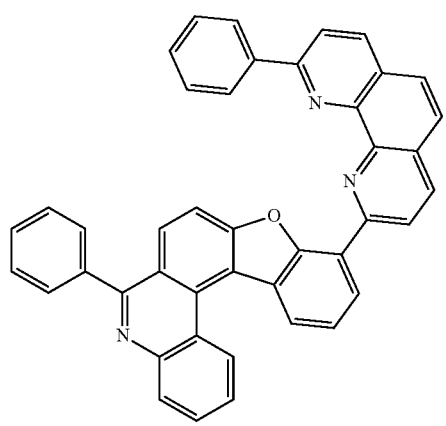
324
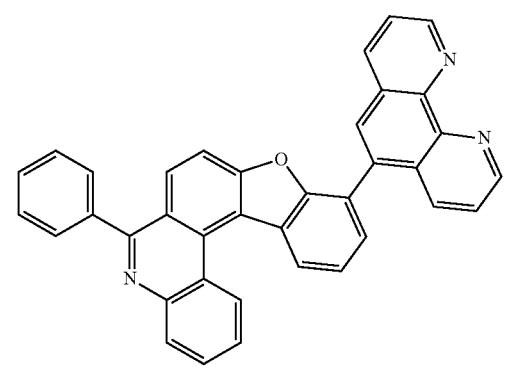
325
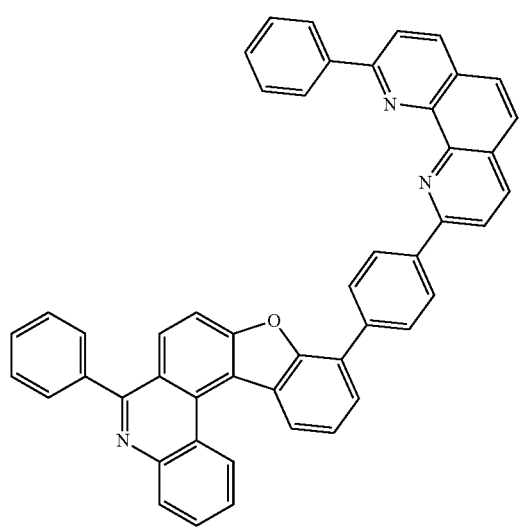
326
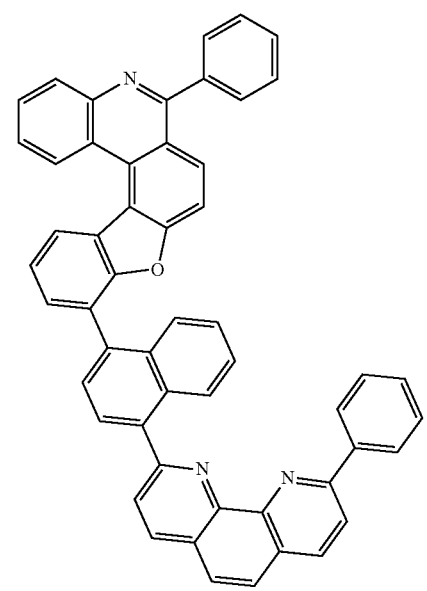
327
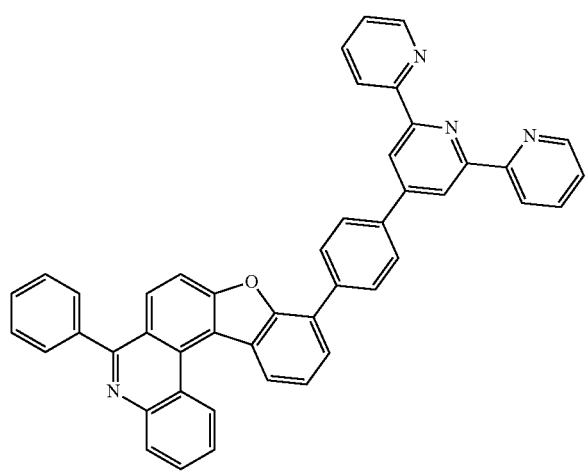
328
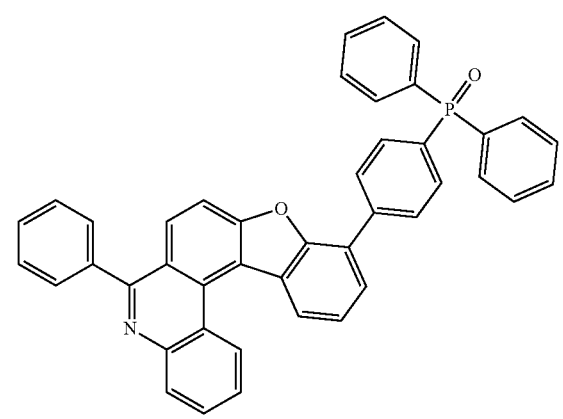

-continued
329
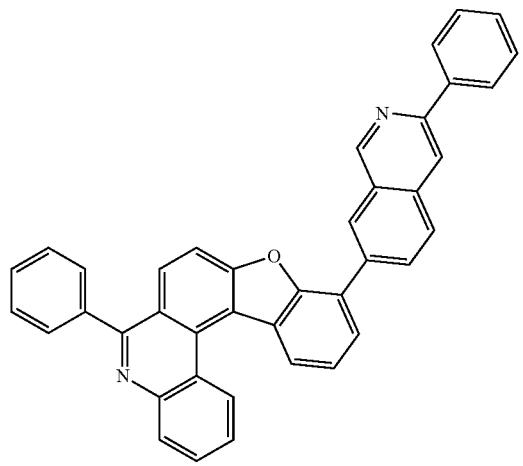
330
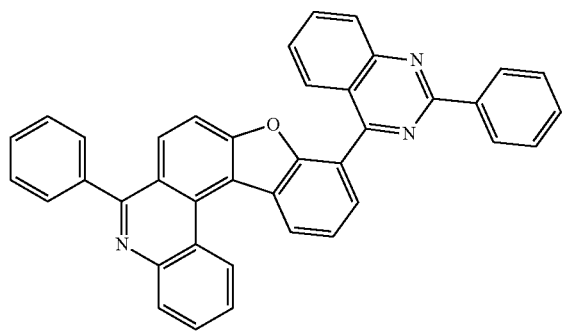
331
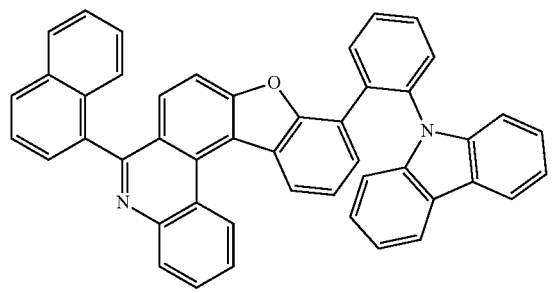
332
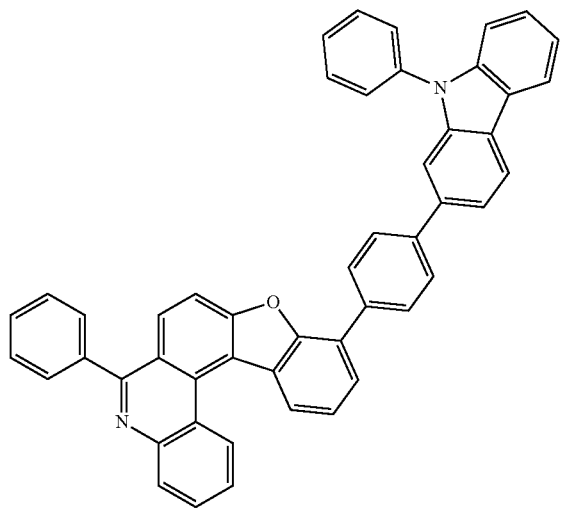
333
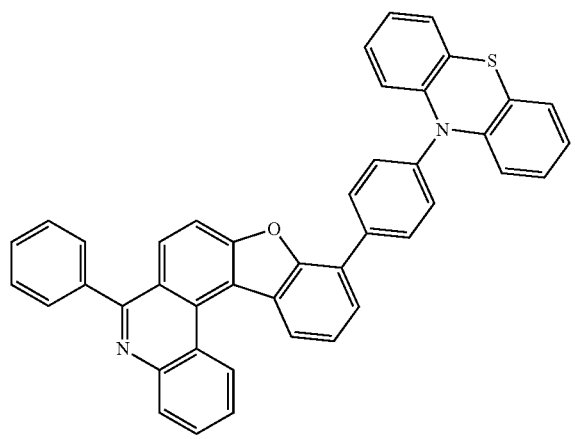
334
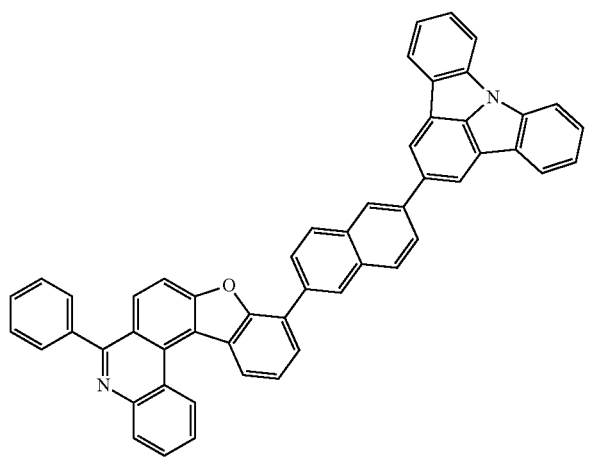

-continued
335
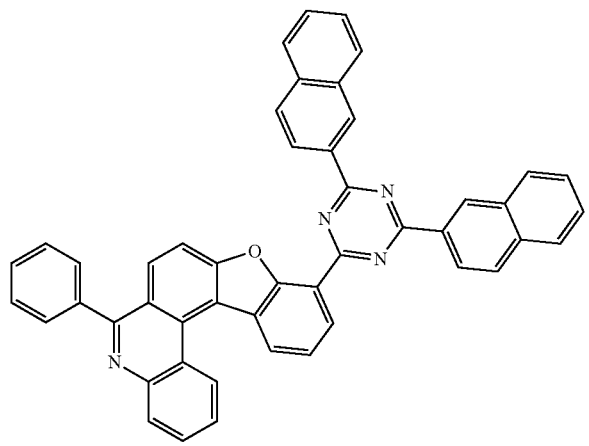
336
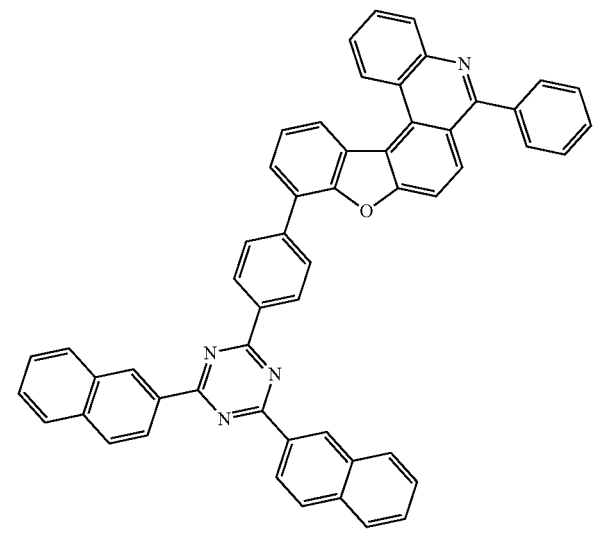
337
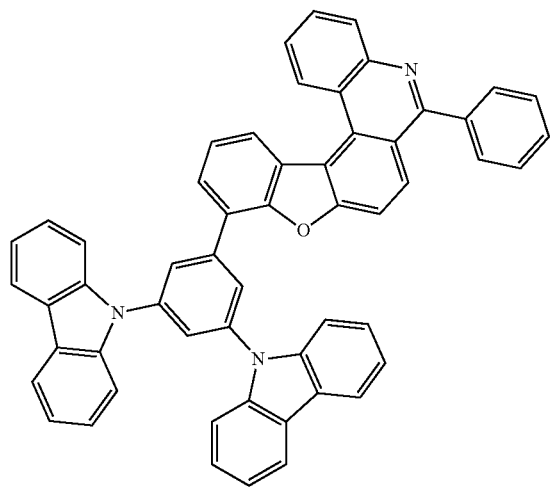
338
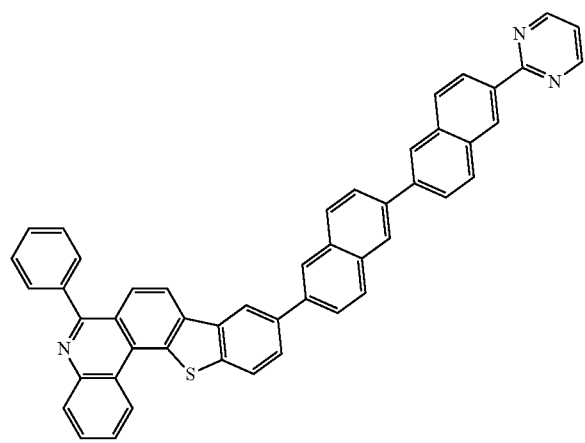
339
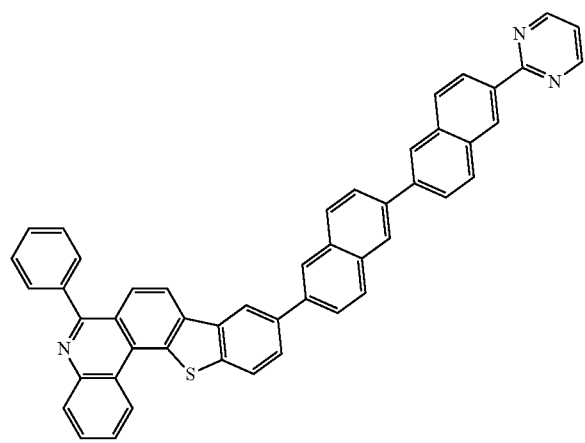
340
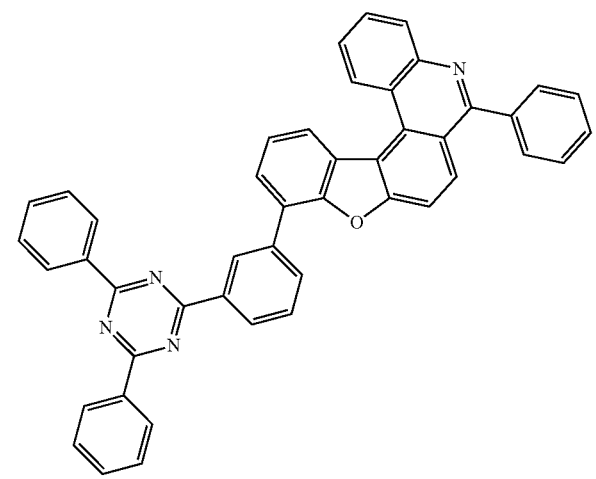

-continued
341
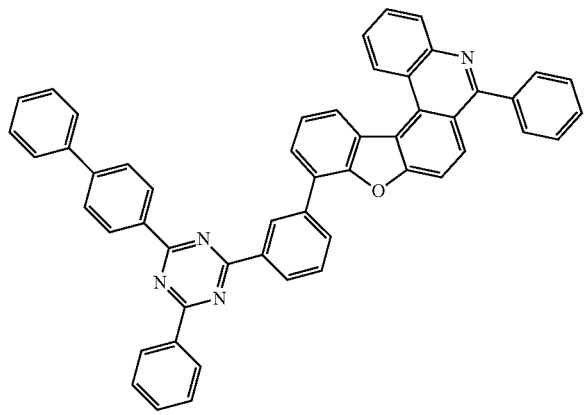
342
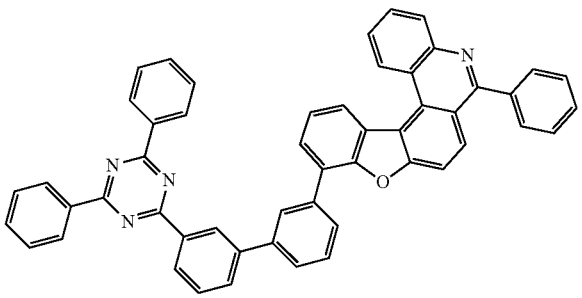
343
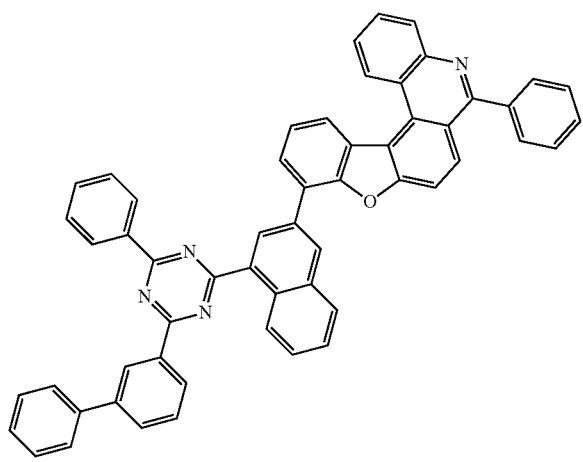
344
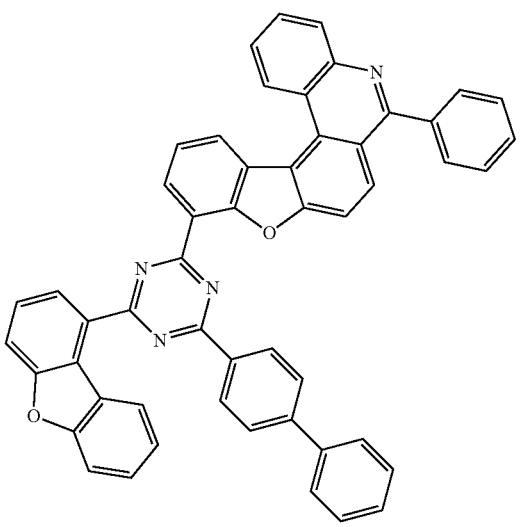
345
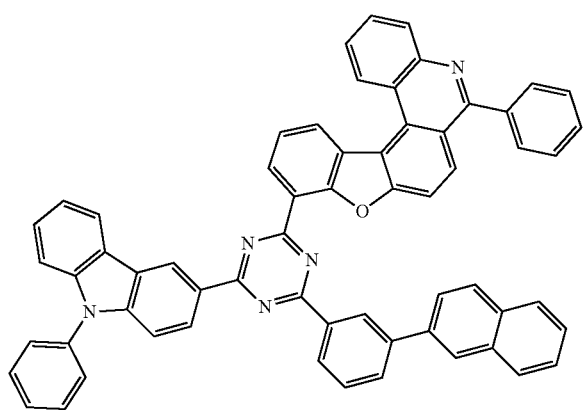
346
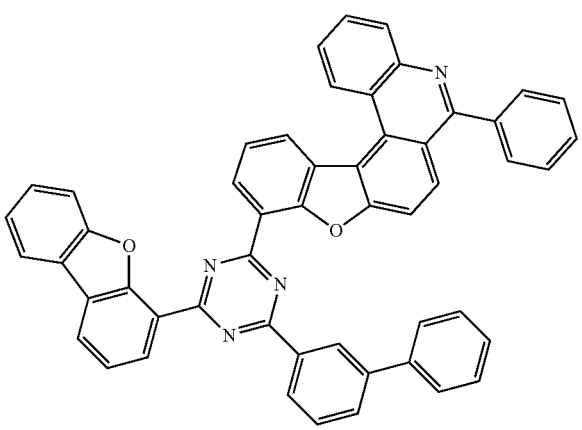

-continued
347
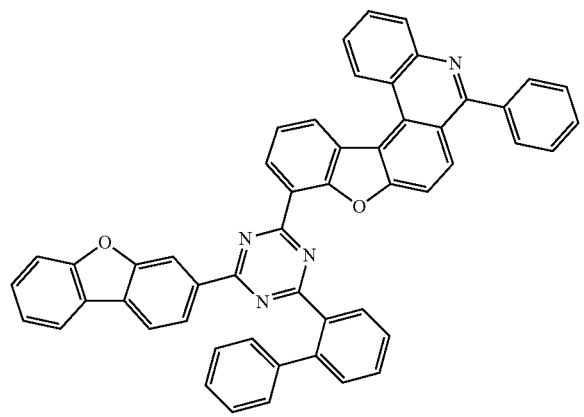
348
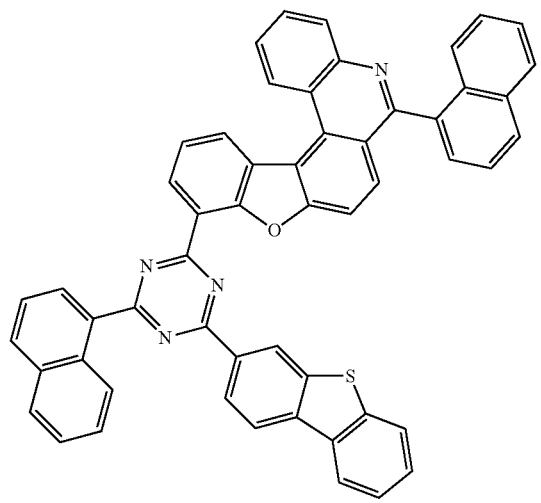
349
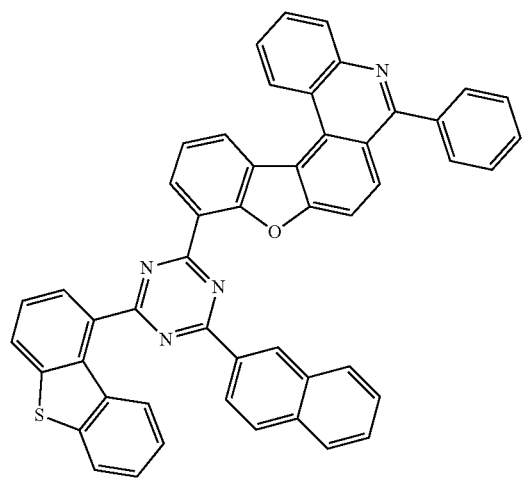
350
351
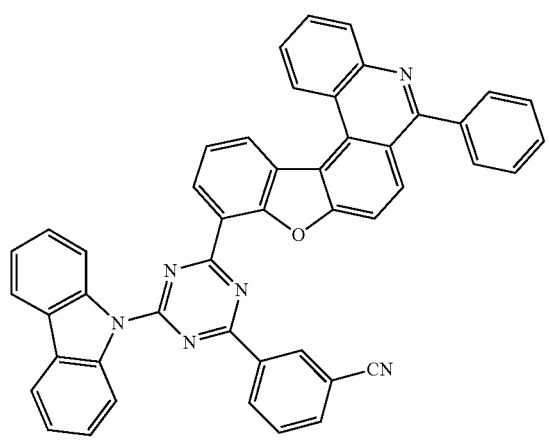
352
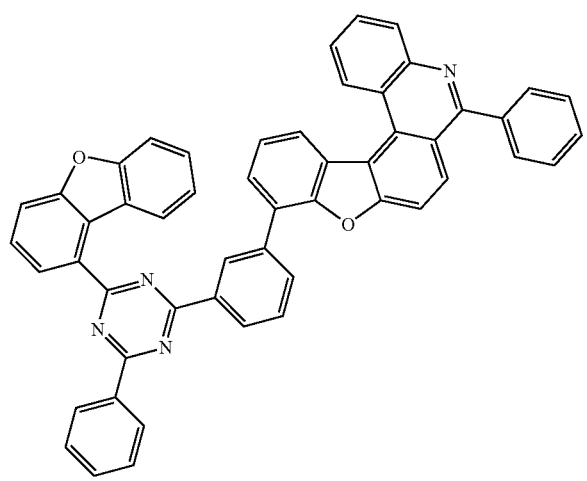

-continued
353
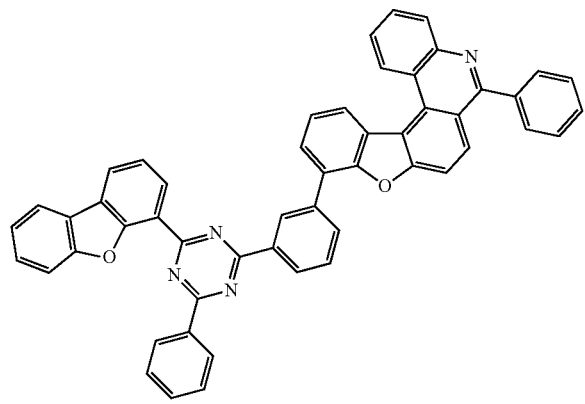
354
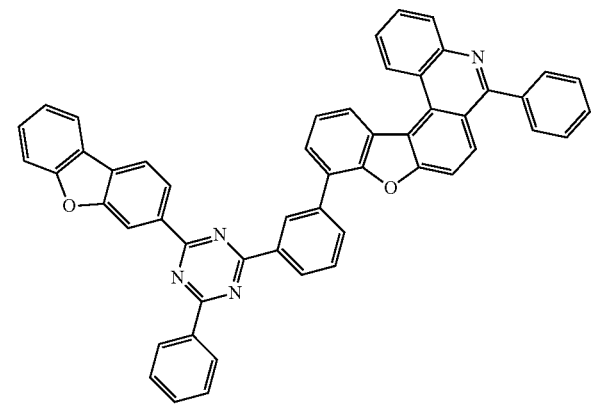
355
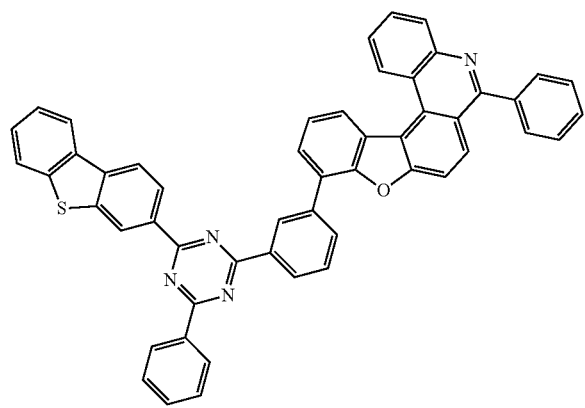
356
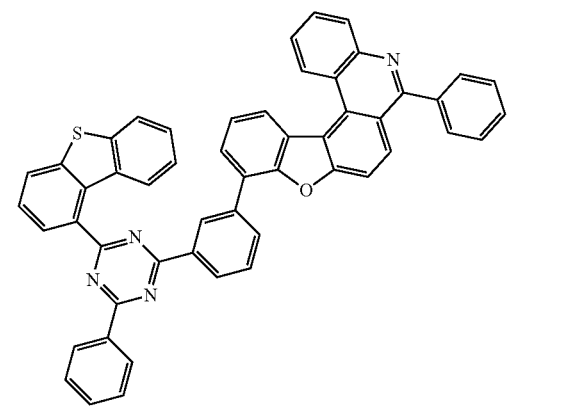
357
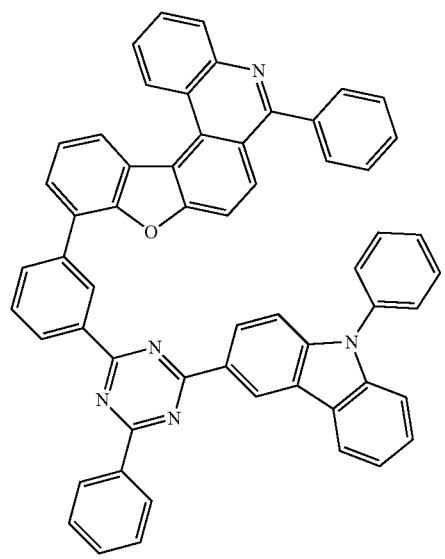
358
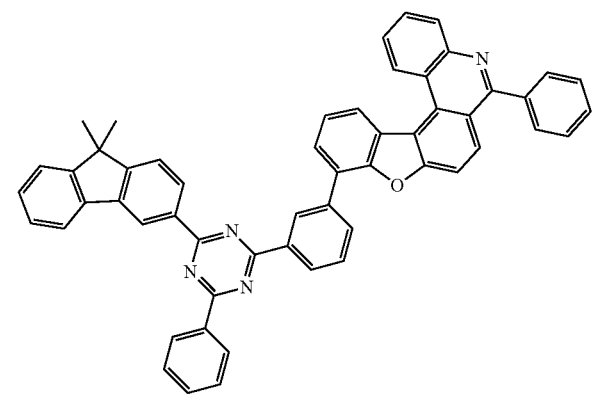

-continued
359
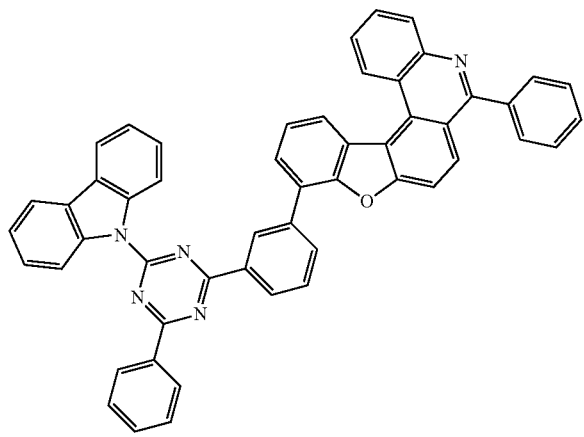
360
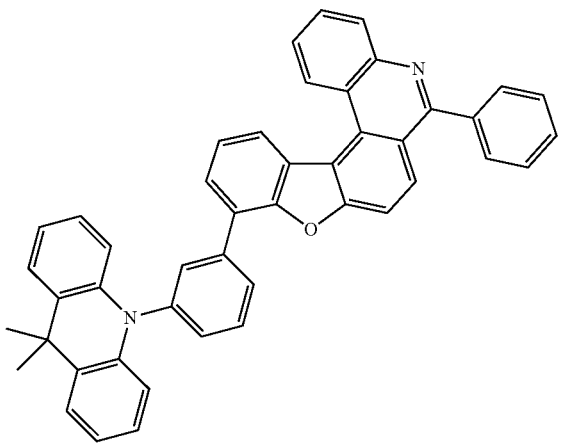
361
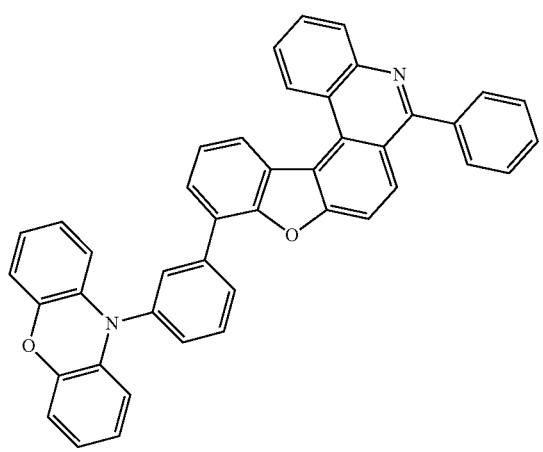
362
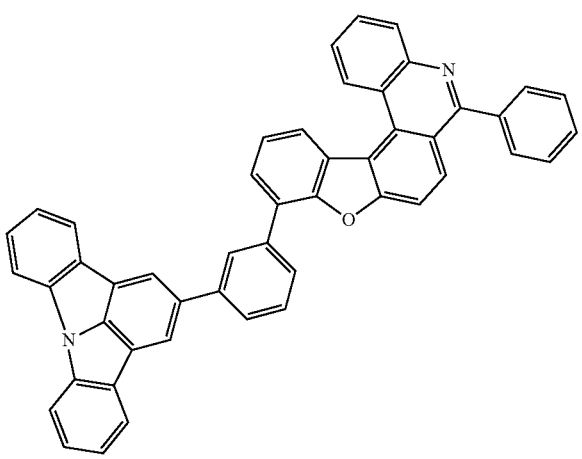
363
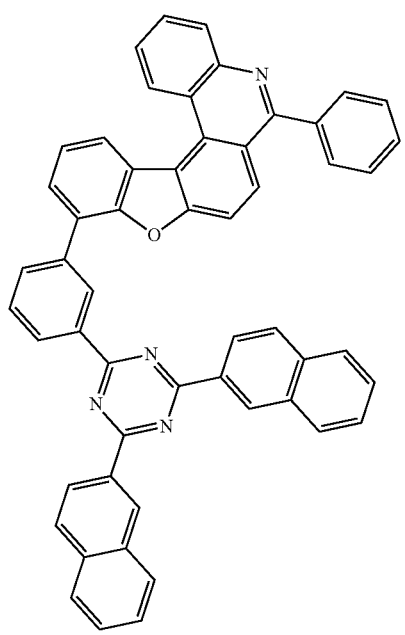
364
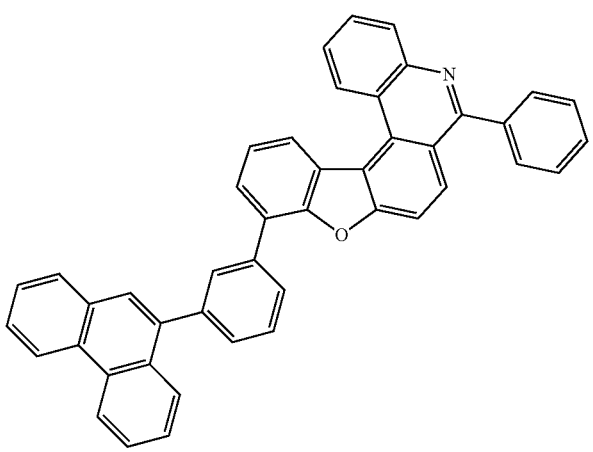

365
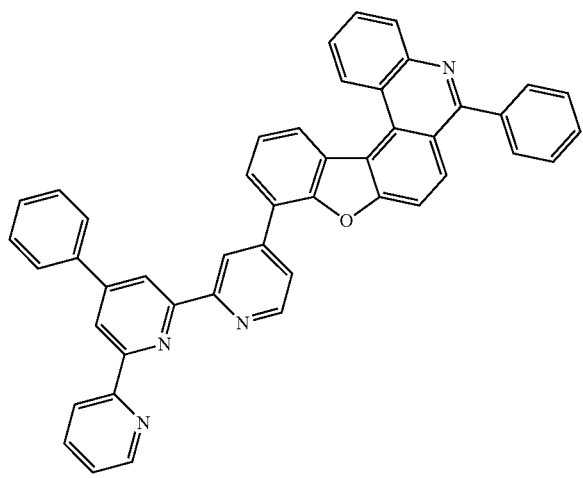
366
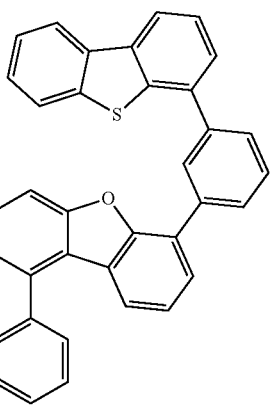
367
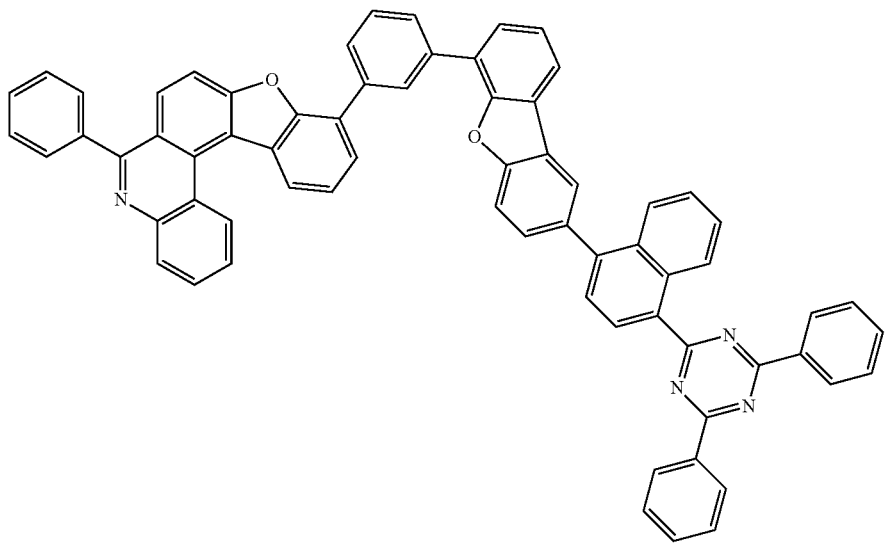
368
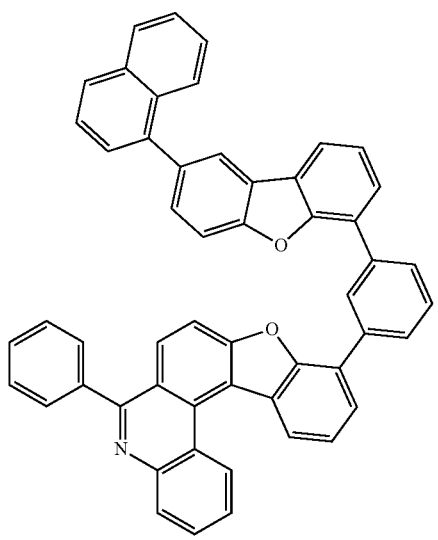
369
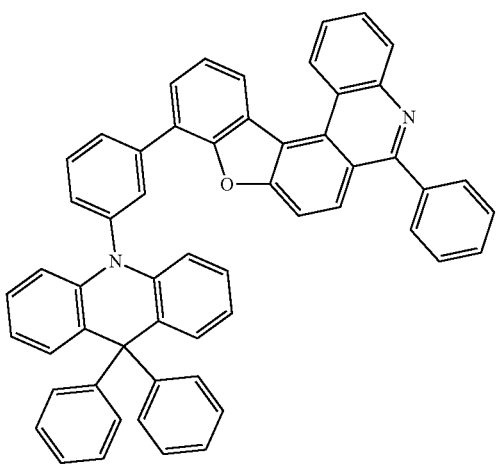

-continued
370
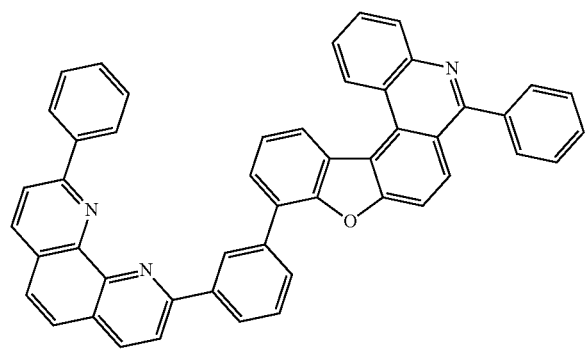
371
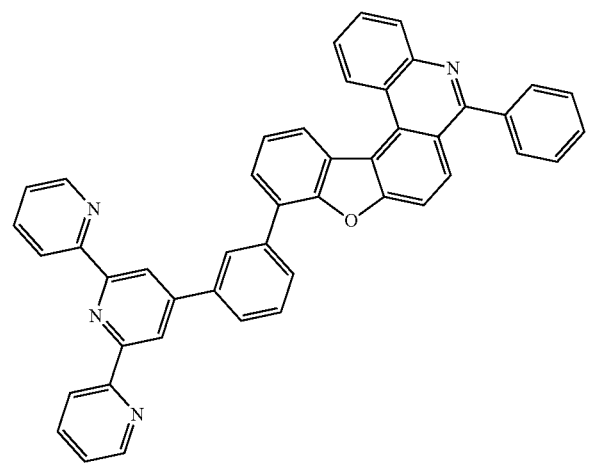
372
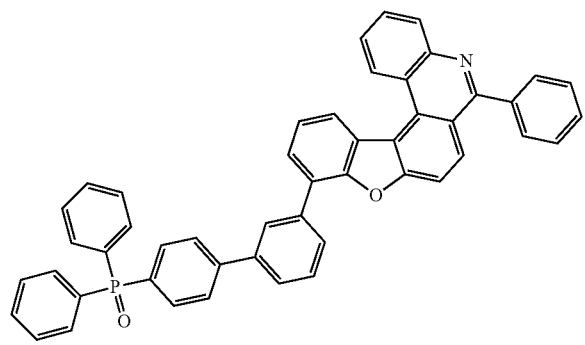
373
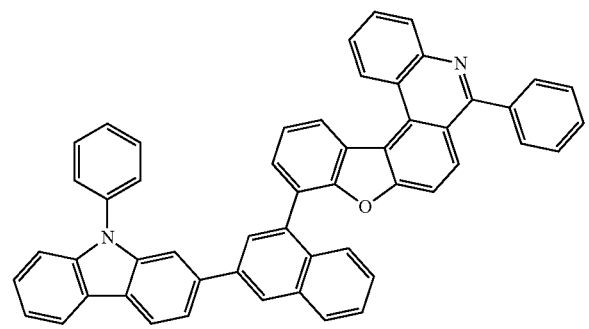
374
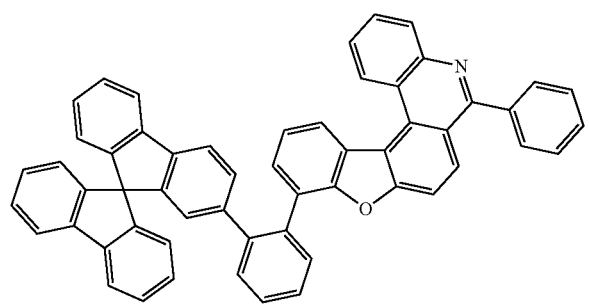
375
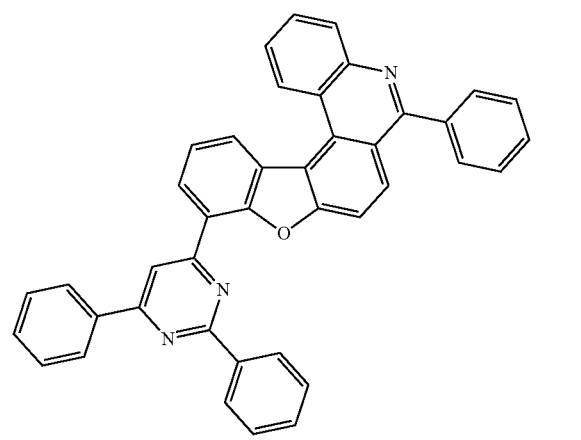

376
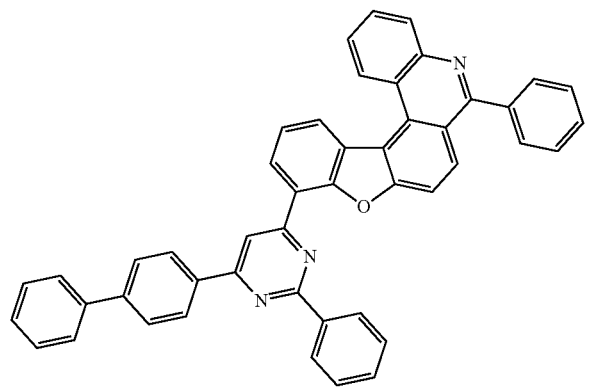
377
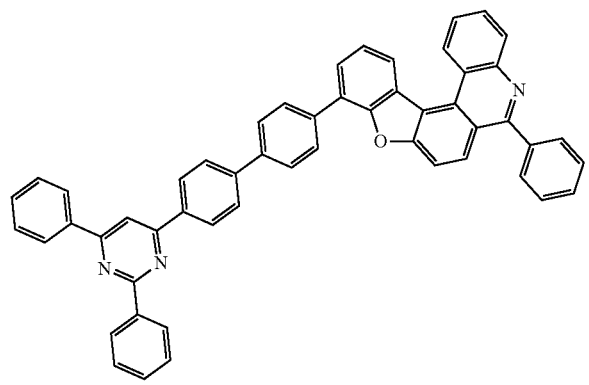
378
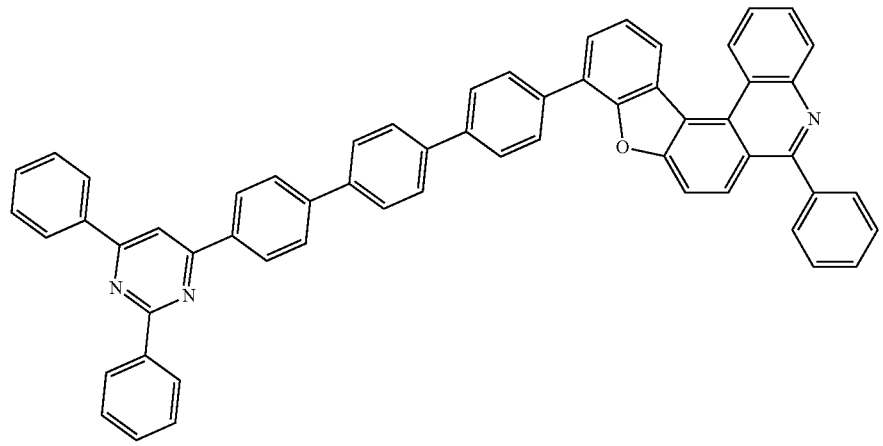
379
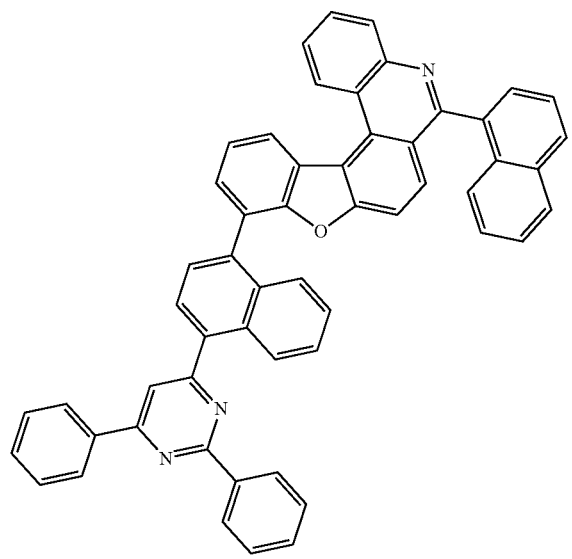
380
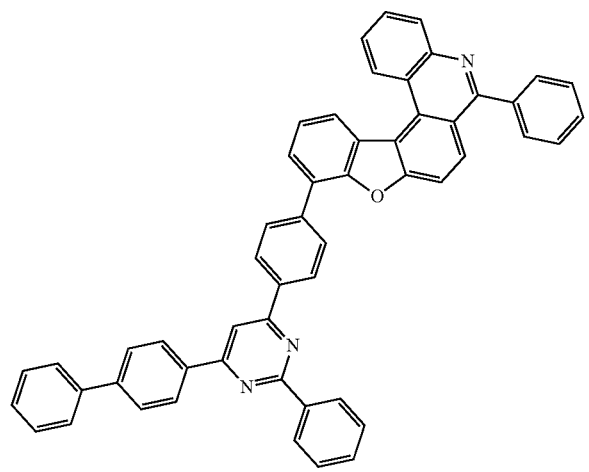

-continued
381
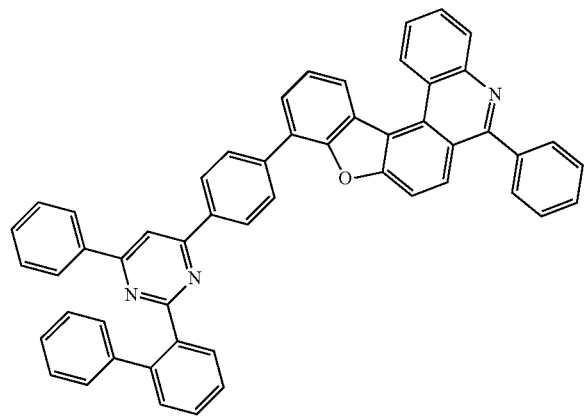
382
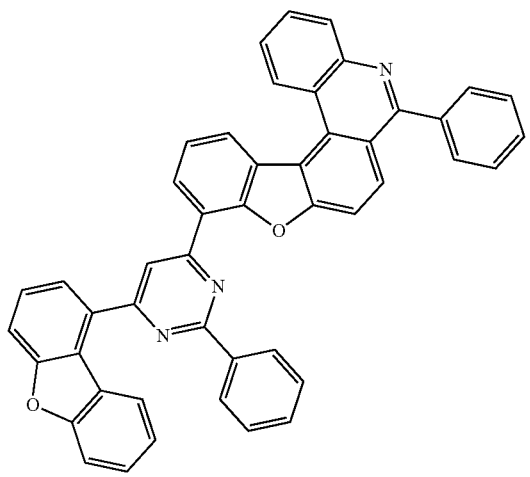
383
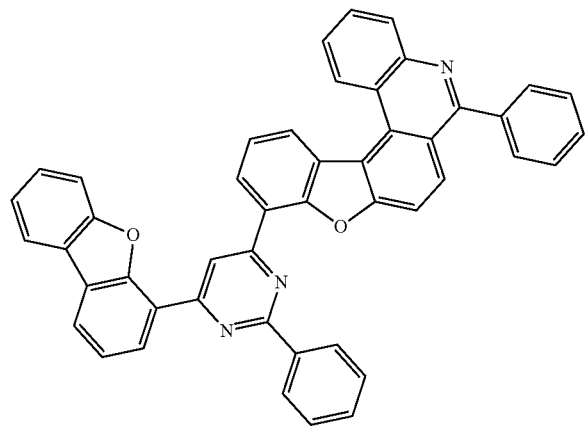
384
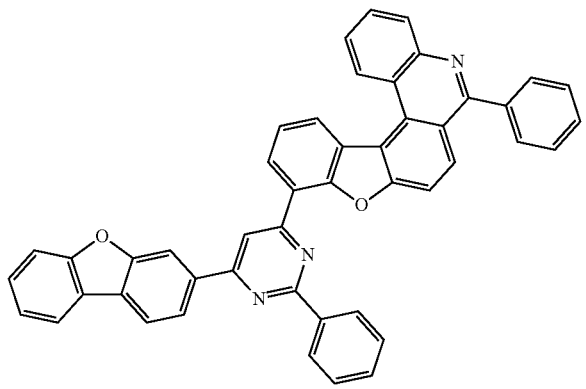
385
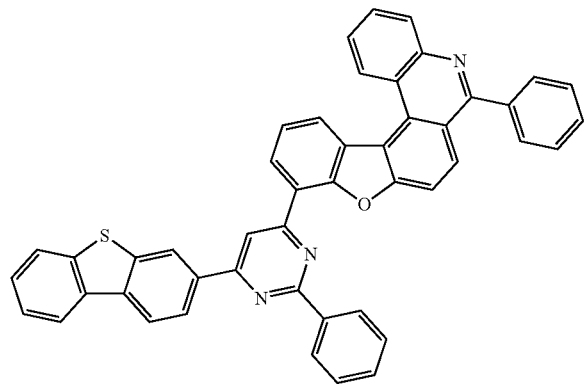
386
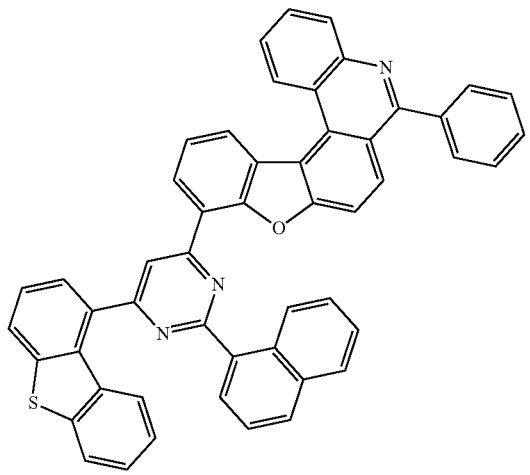

-continued
387
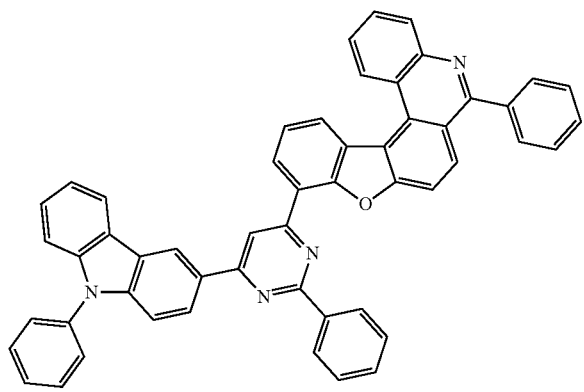
388
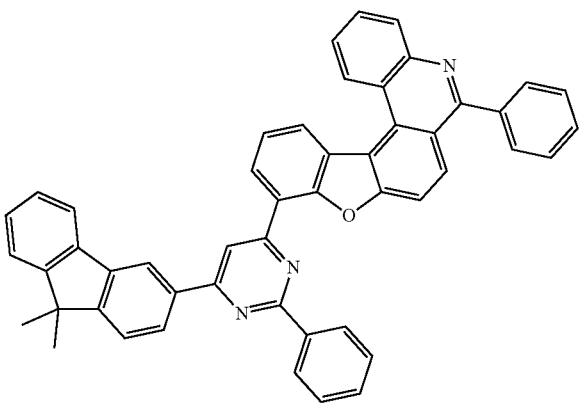
389
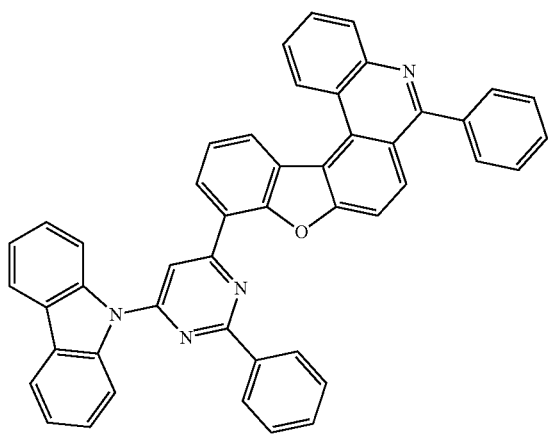
390
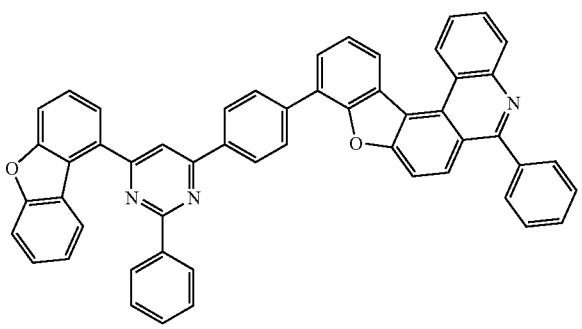
391
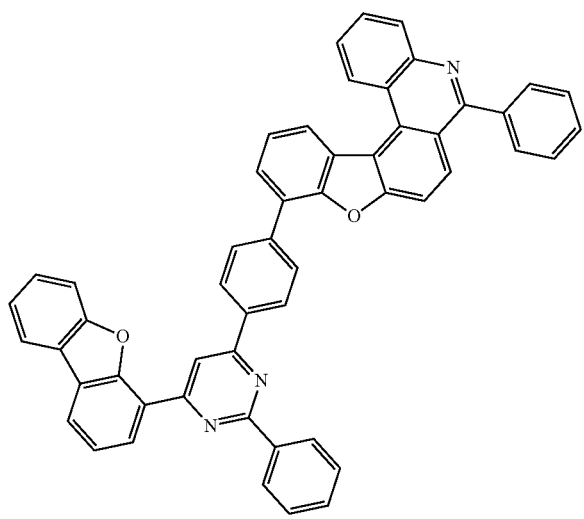
392
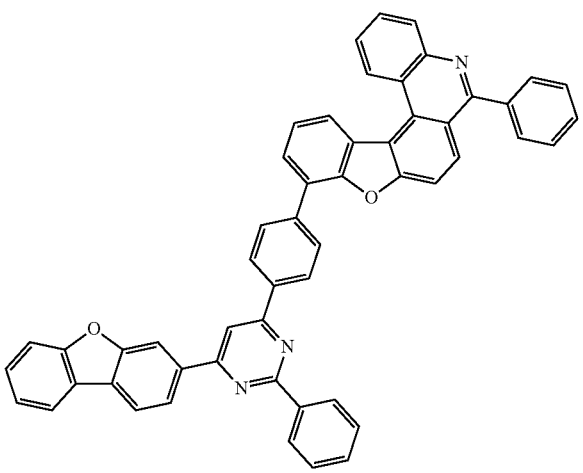

393
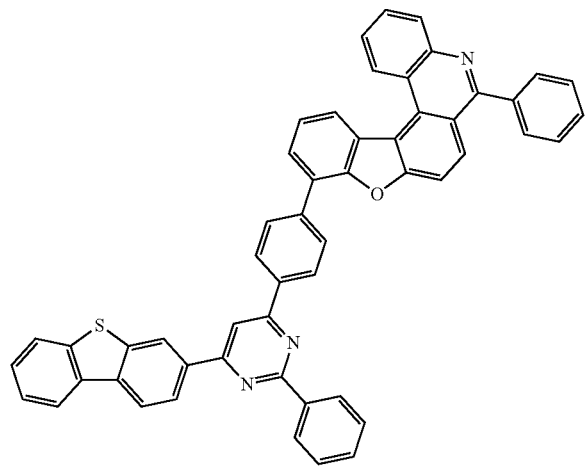
394
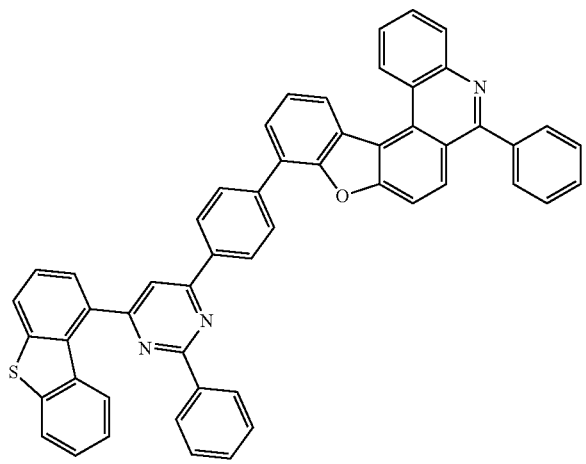
395
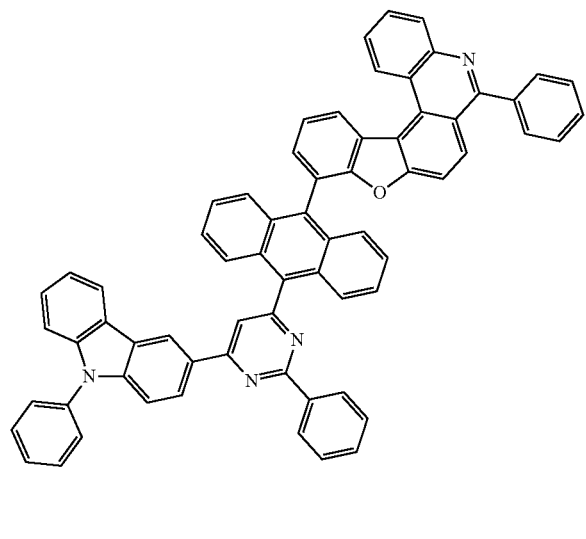
396
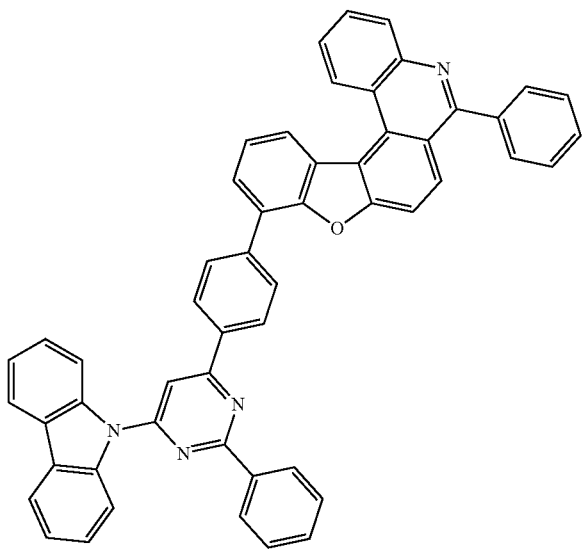
397
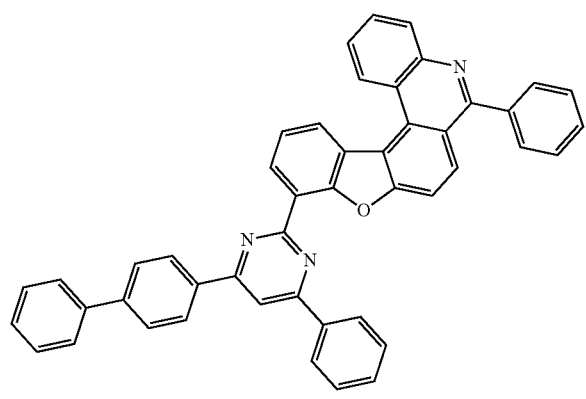
398
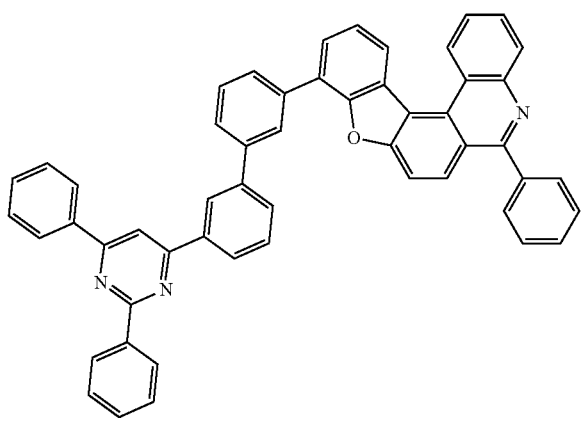

-continued
399
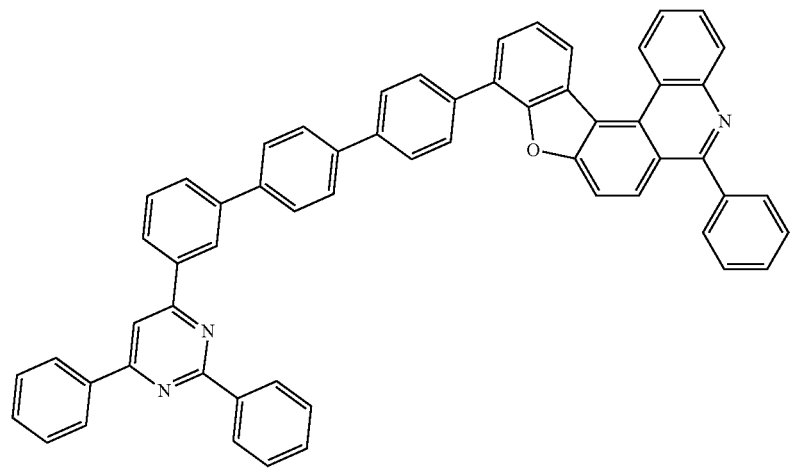
400
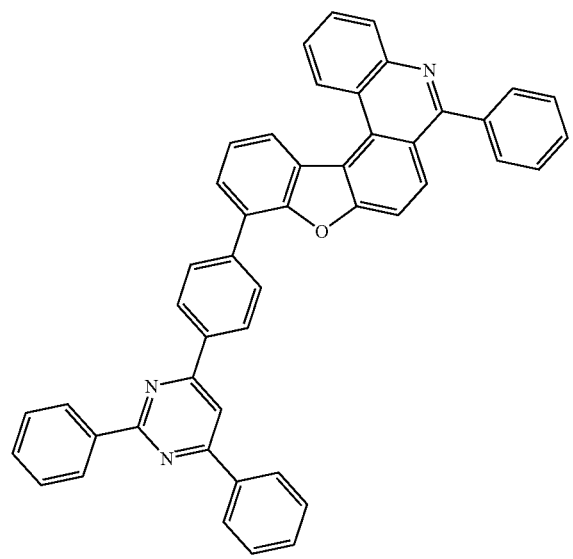
401
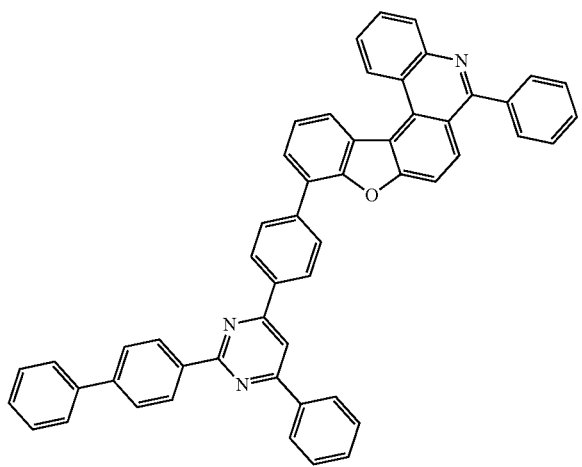
402
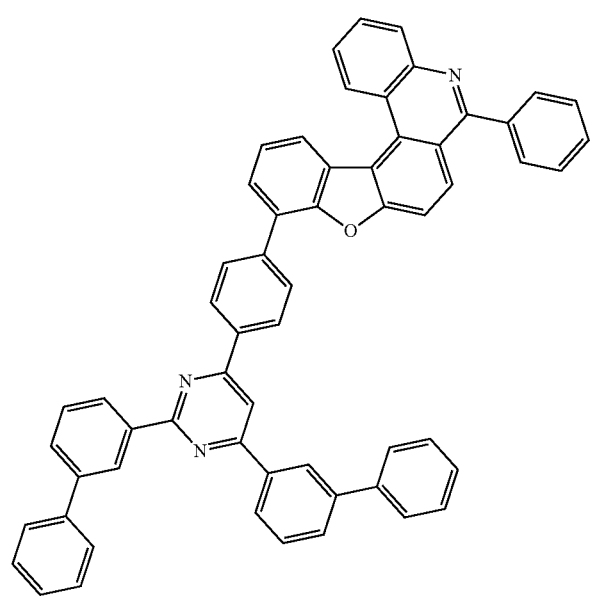
403
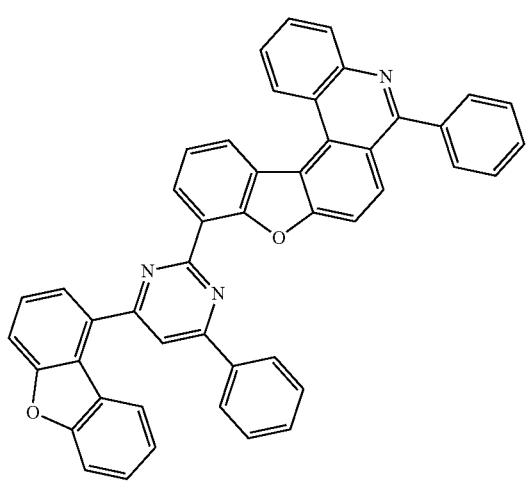

-continued
903
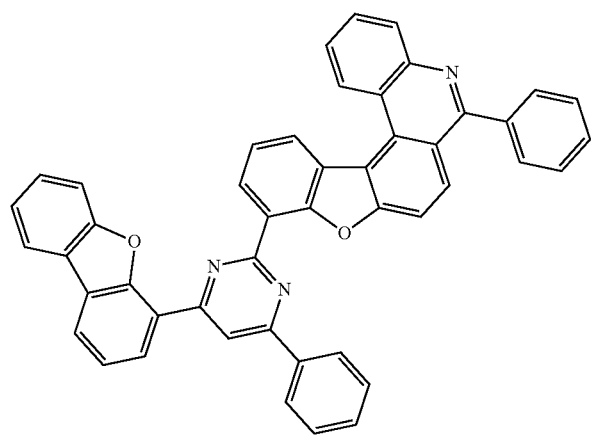
904
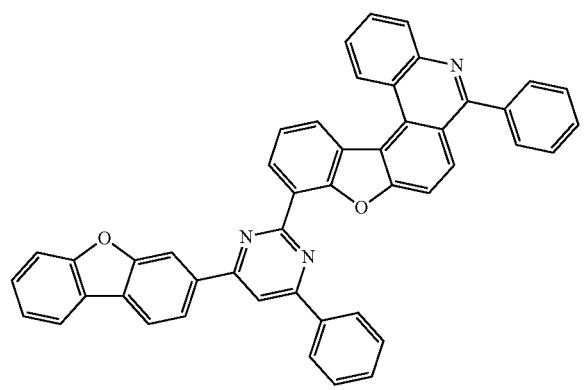
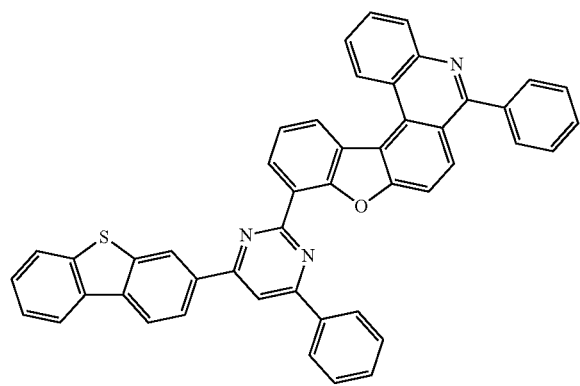
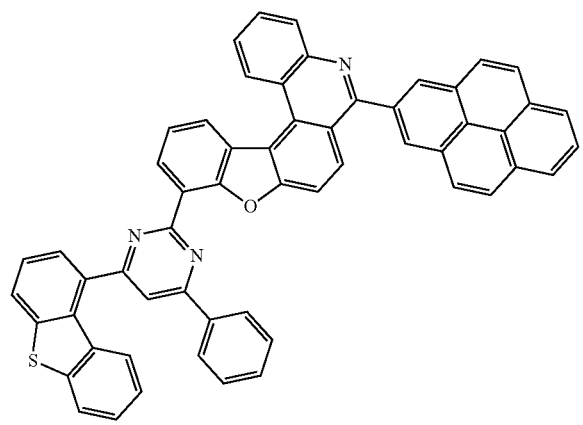
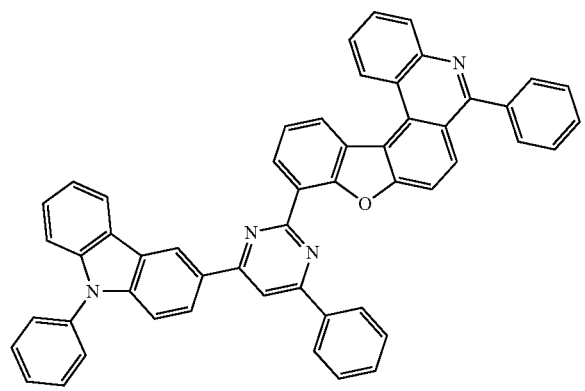
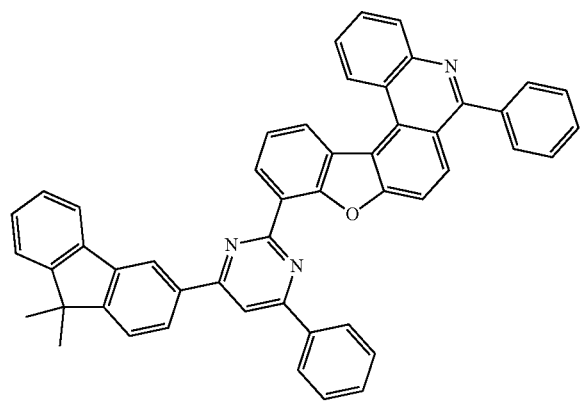

-continued
410
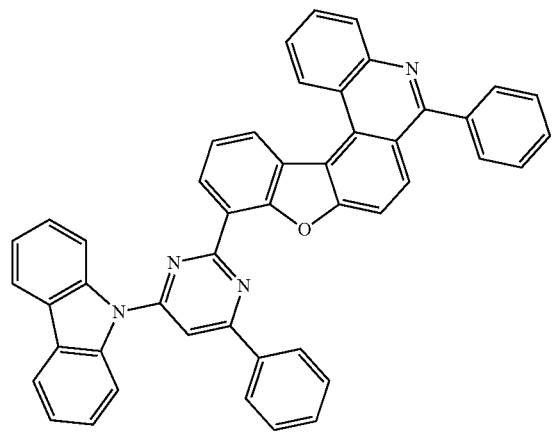
411
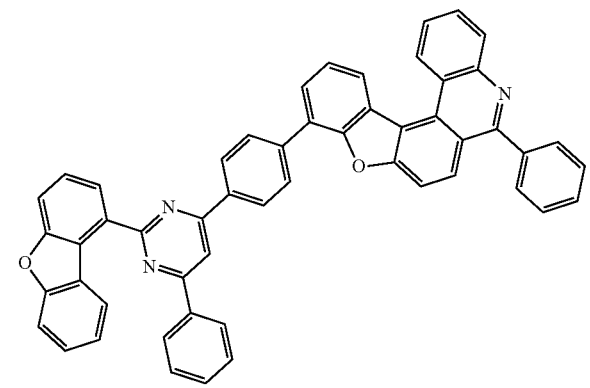
412
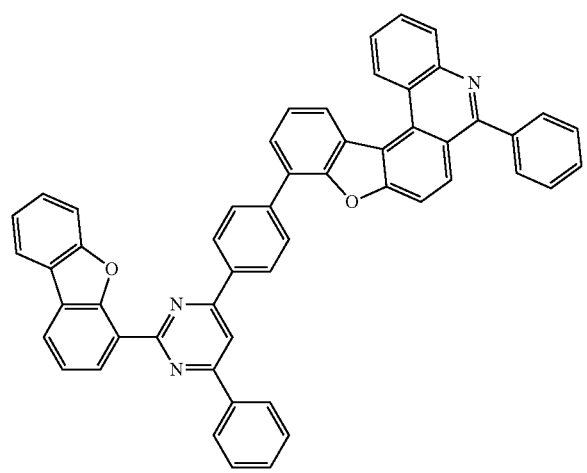
413
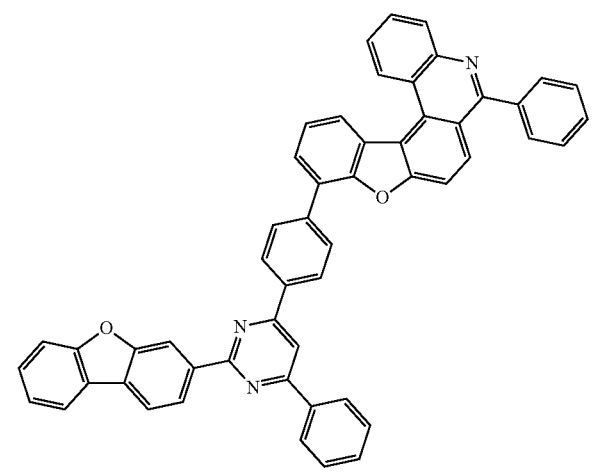
414
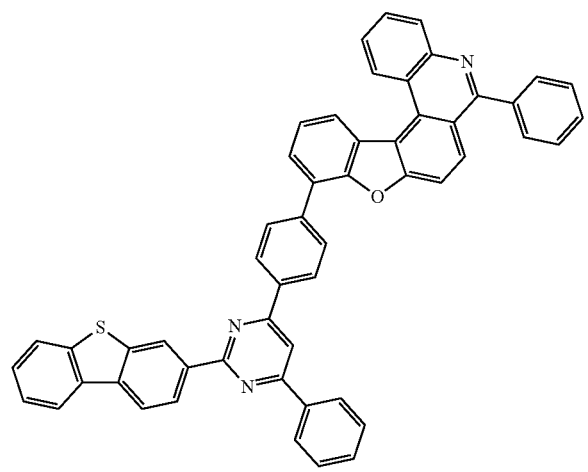
415
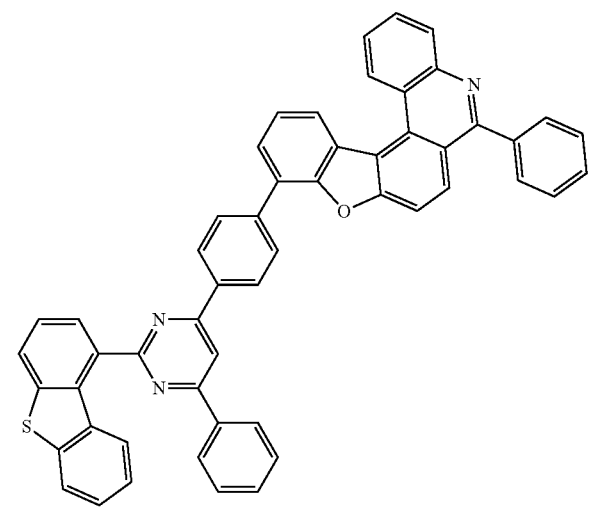

-continued
907
416
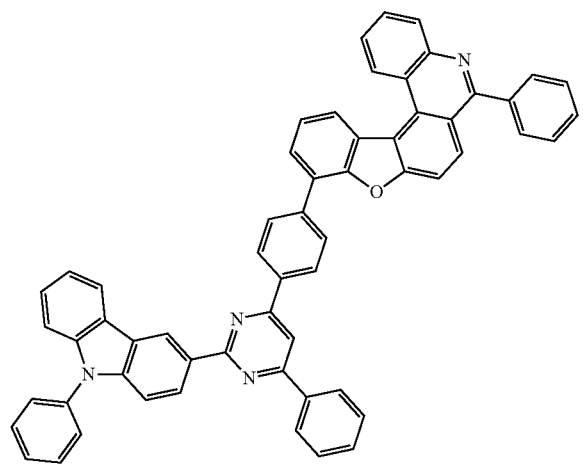
908
417
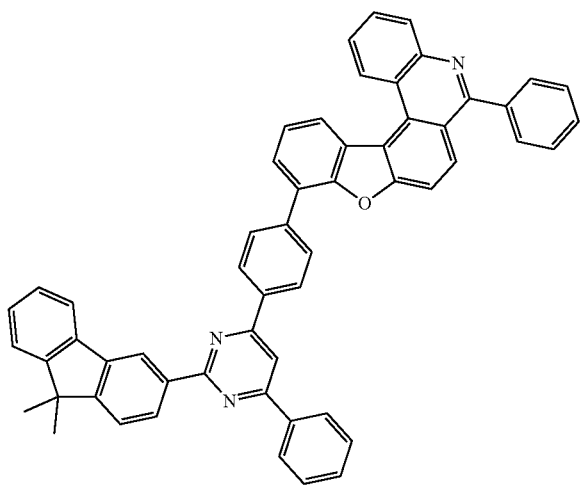
418
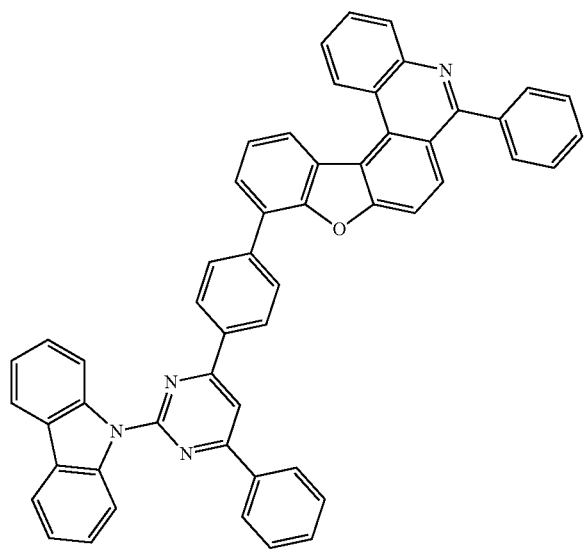
419
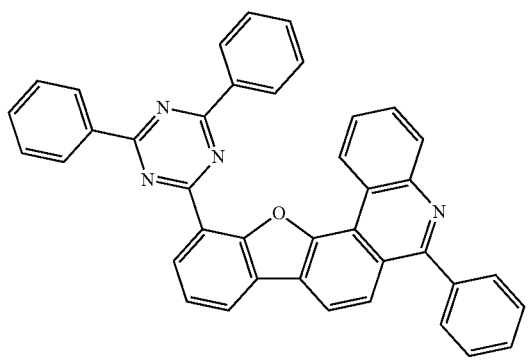

909 910
-continued
420
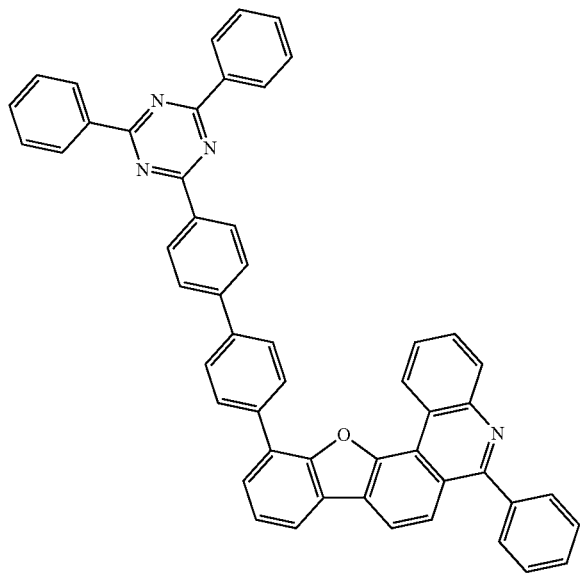
421
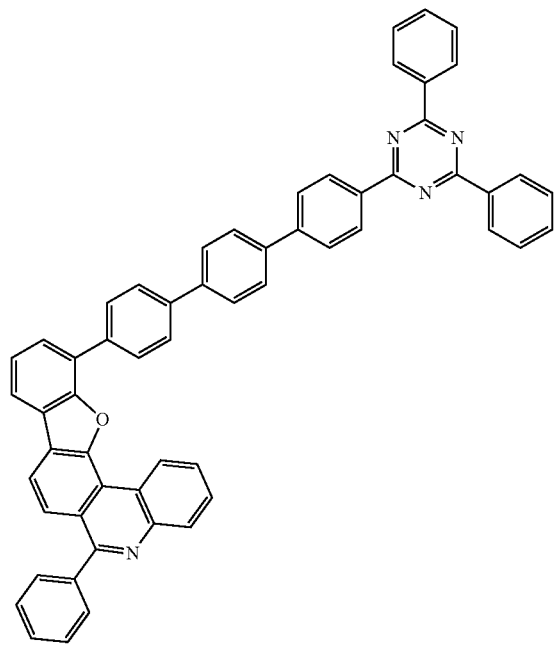
422
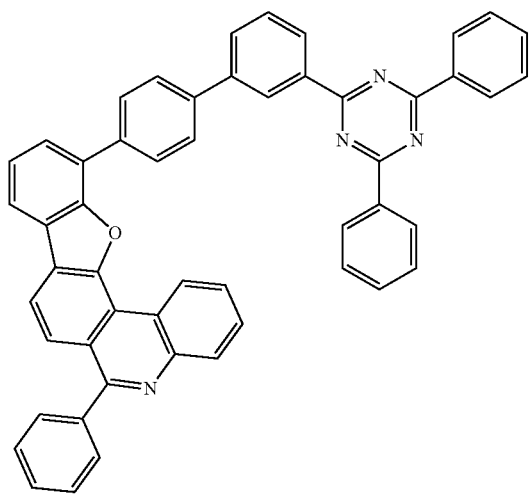
423
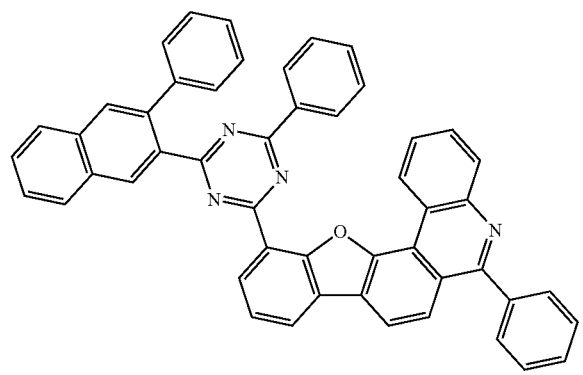

| 911 | 912 |
|---|---|
| 424 | 425 |
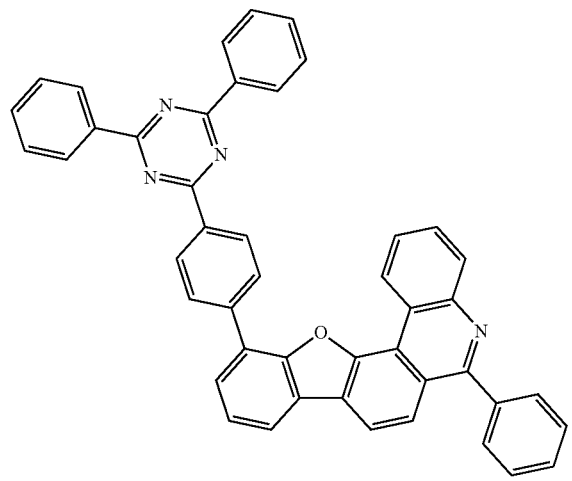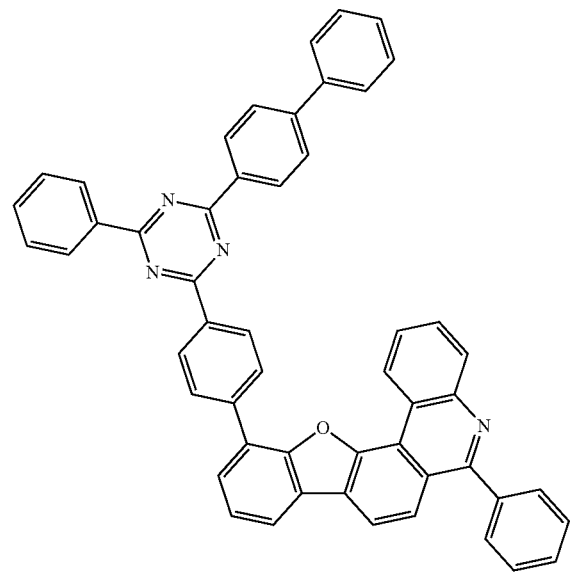
| 426 | 427 |
|---|---|
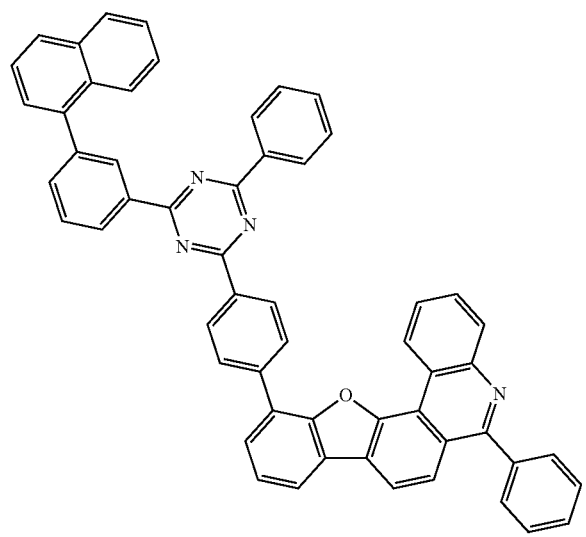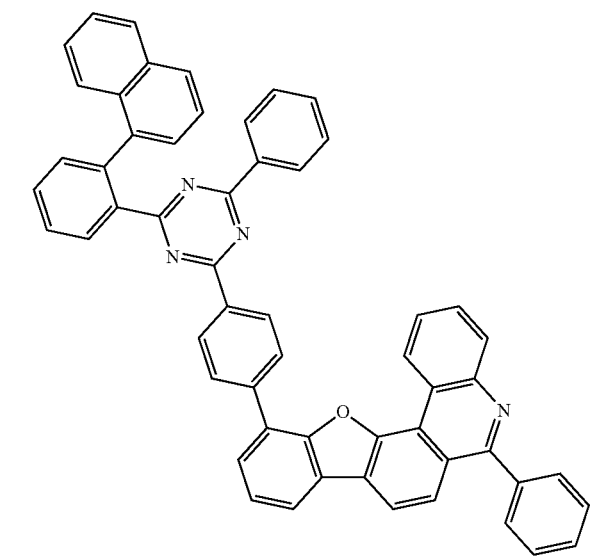
| 428 | 429 |
|---|---|
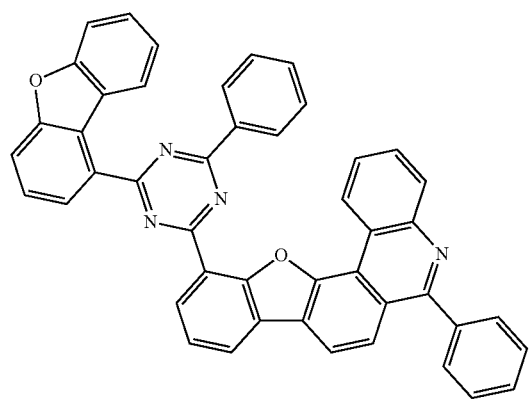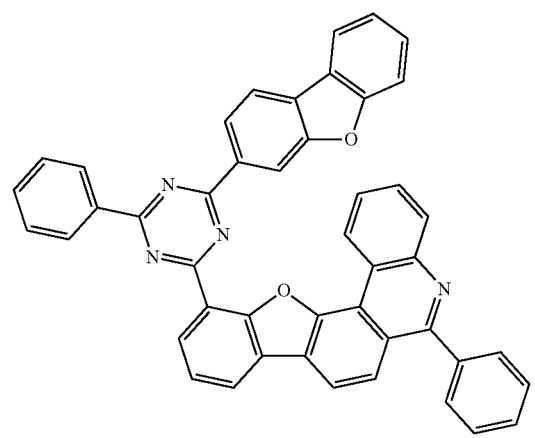

913 914
-continued
430
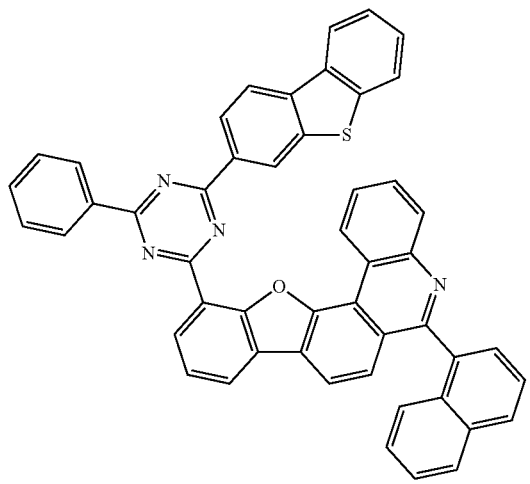
431
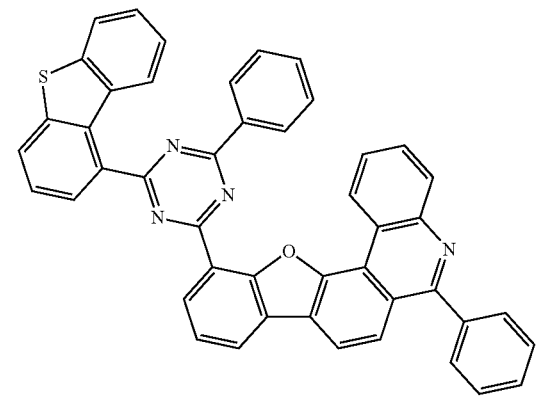
432
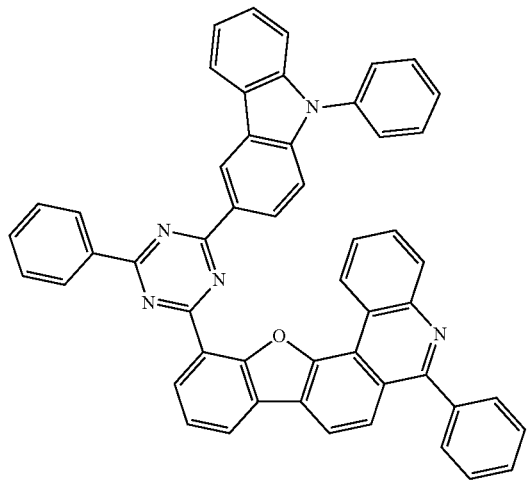
433
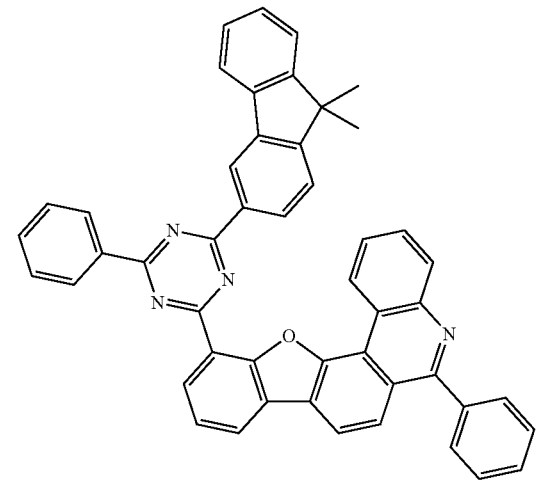
434
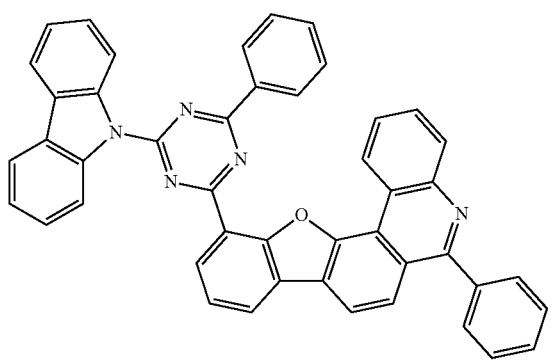
435
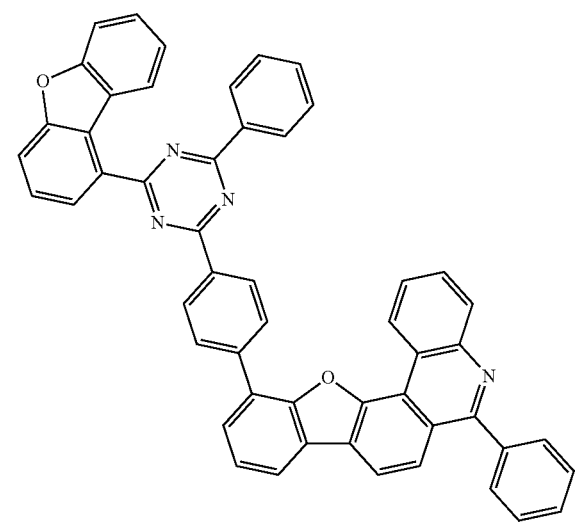

915 916
-continued
436 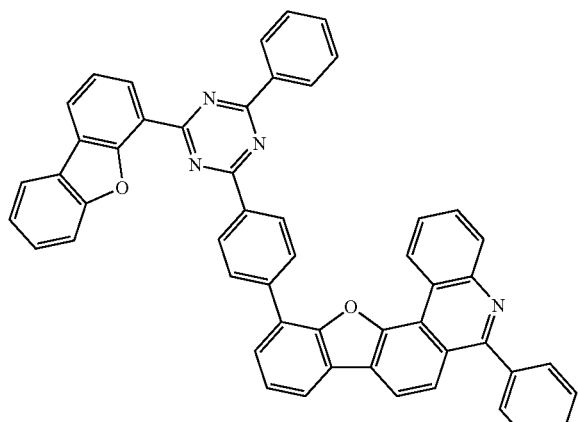 437 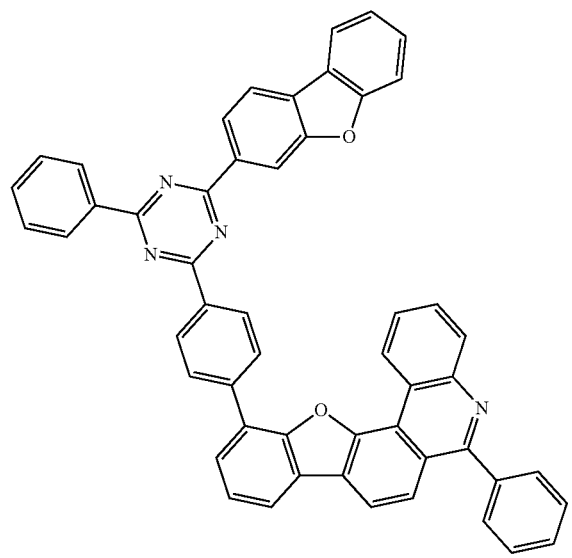
438 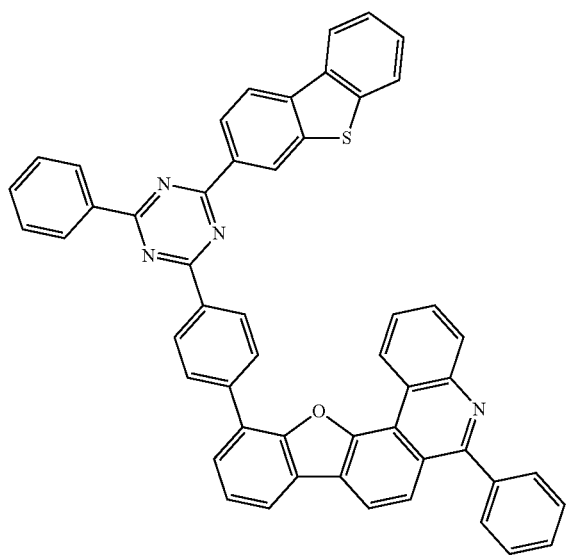 439 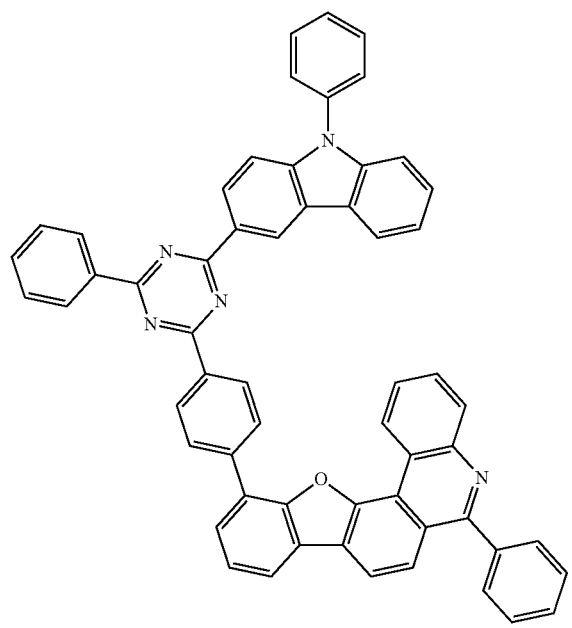

-continued
440
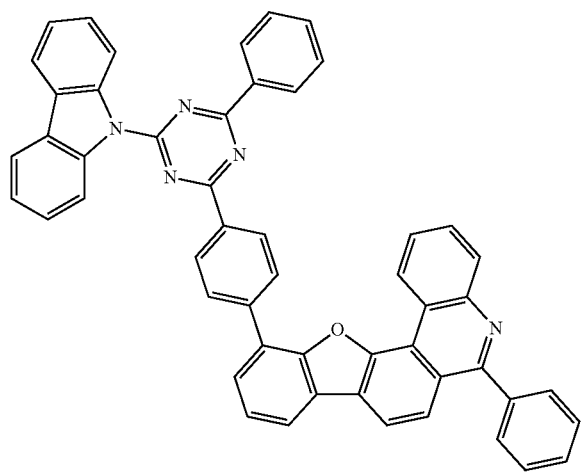
441
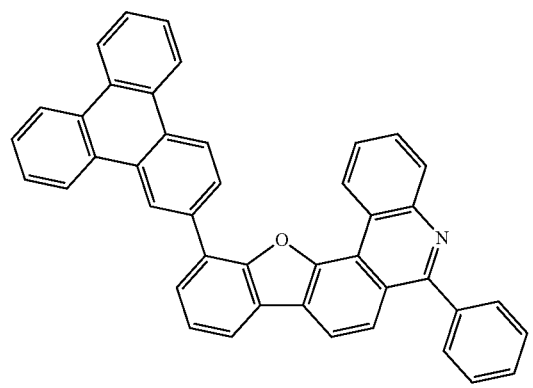
442
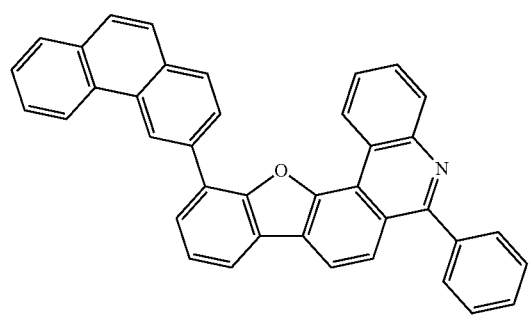
443
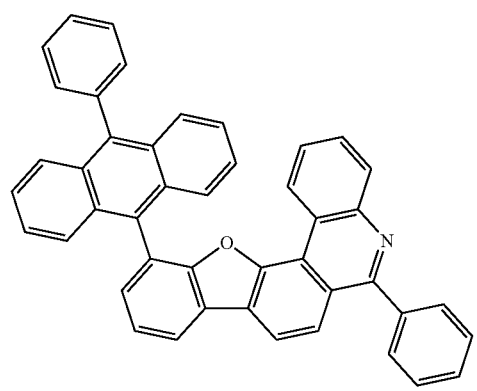
444
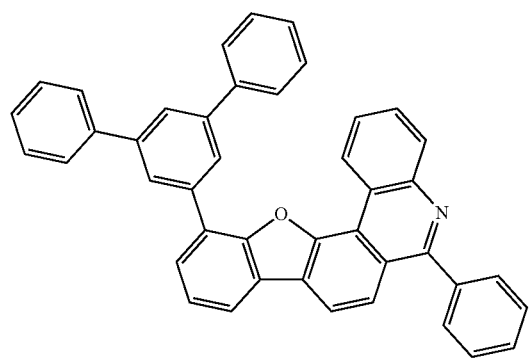
445
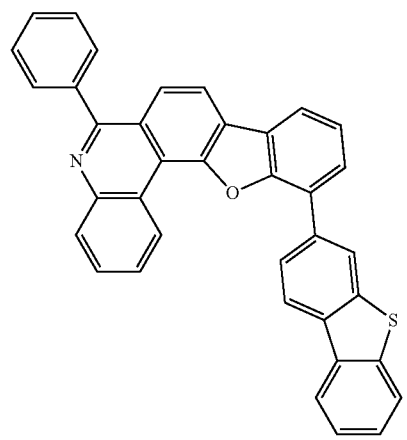

-continued
446
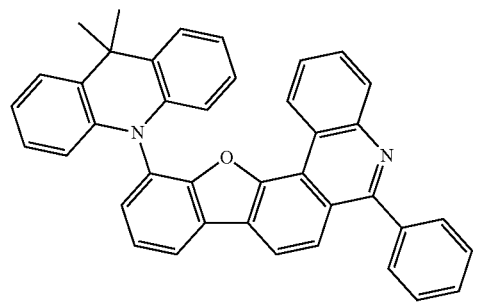
447
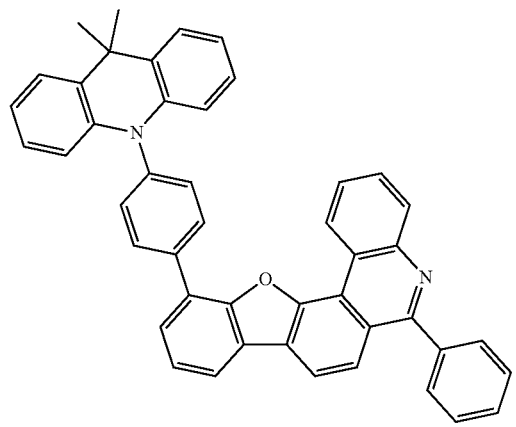
448
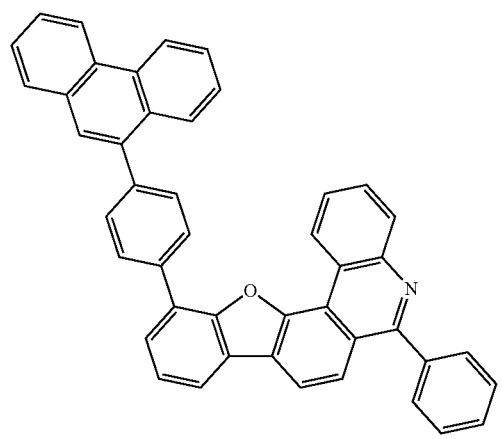
449
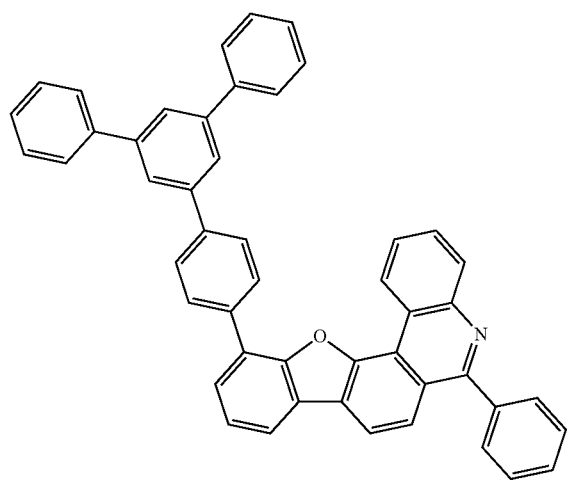
450
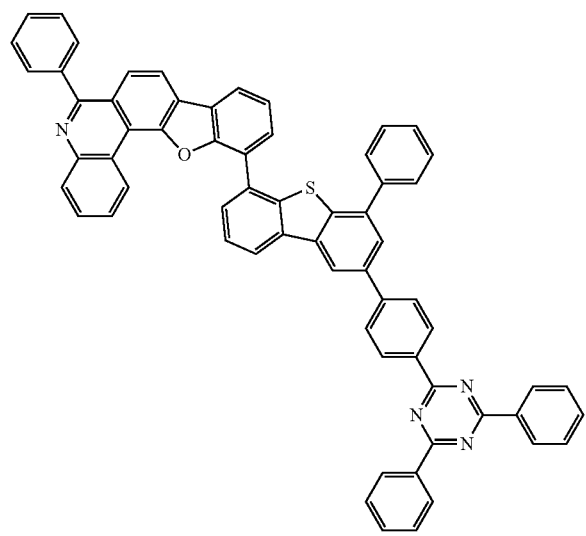
451
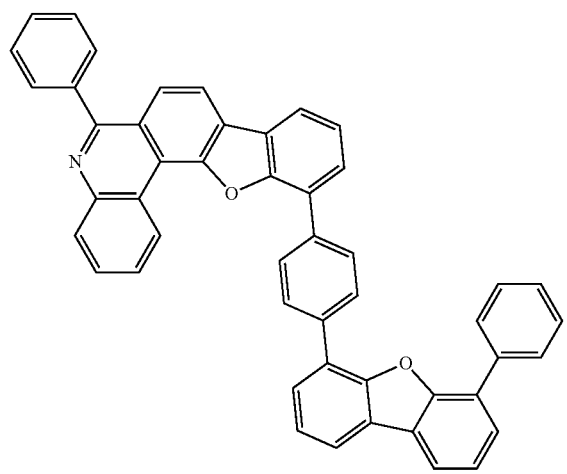

-continued
452
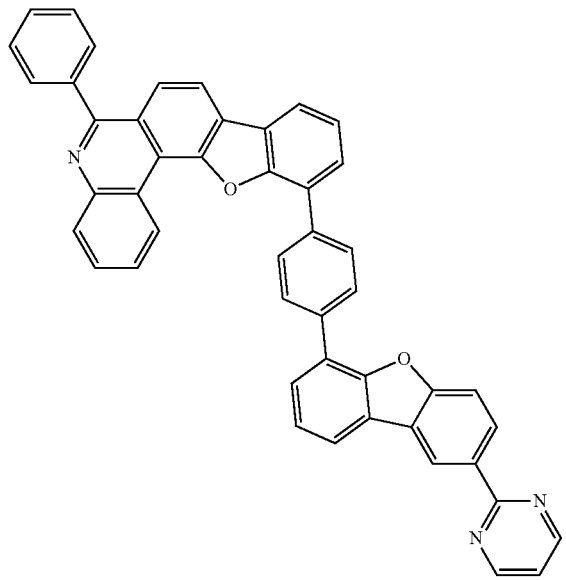
453
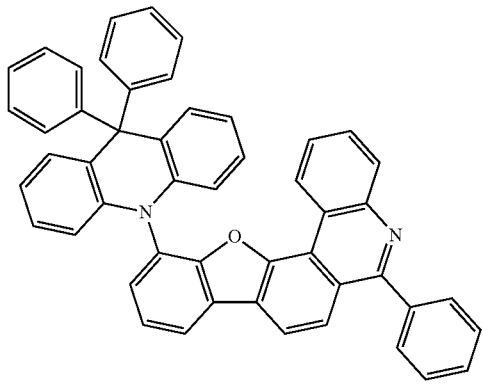
454
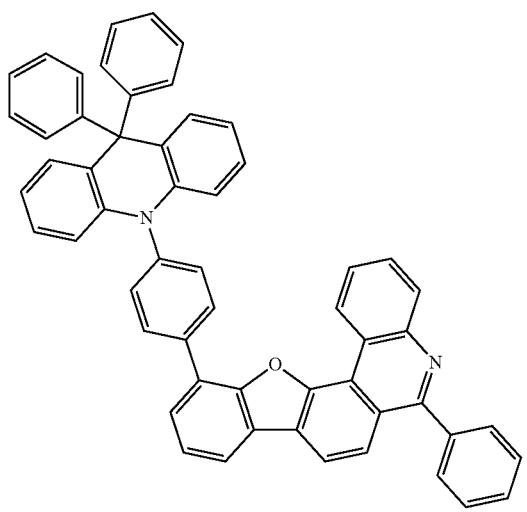
455
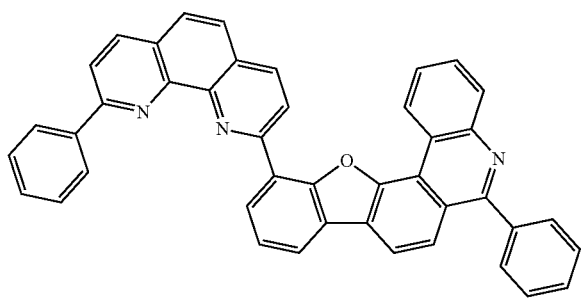
456
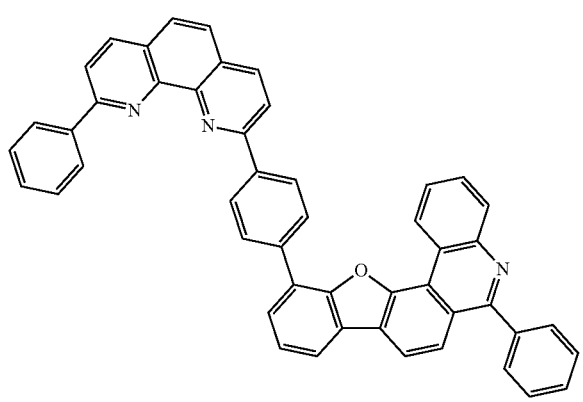
457
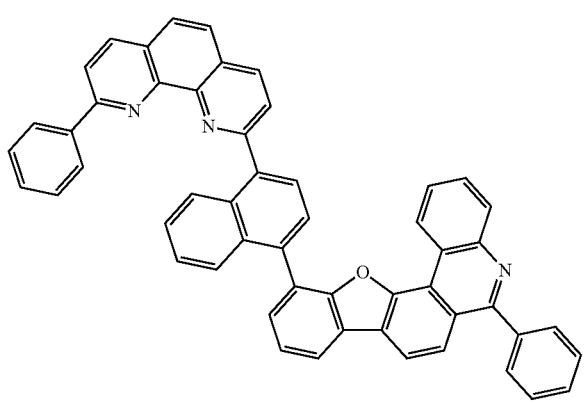

-continued
458
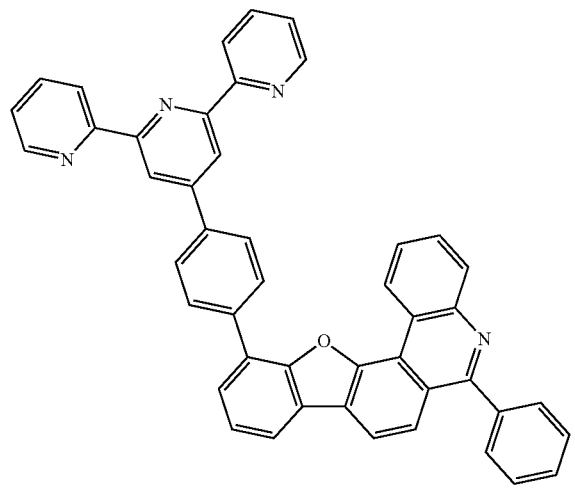
459
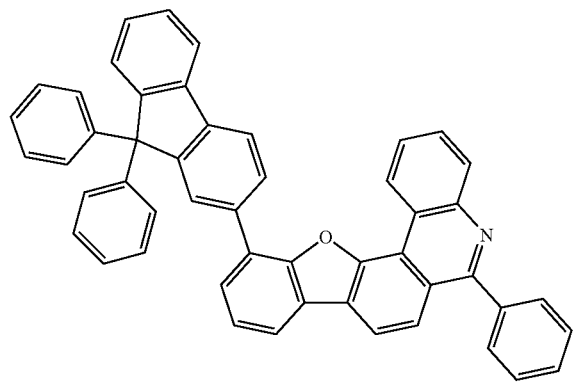
460
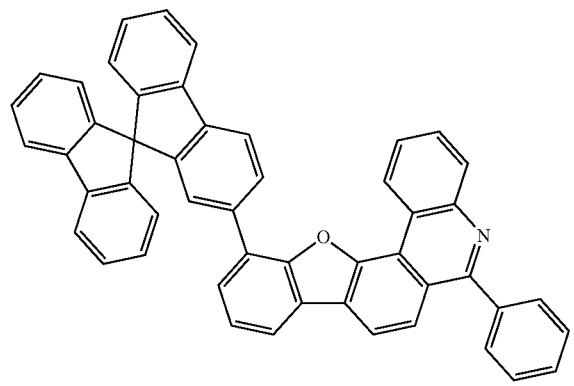
461
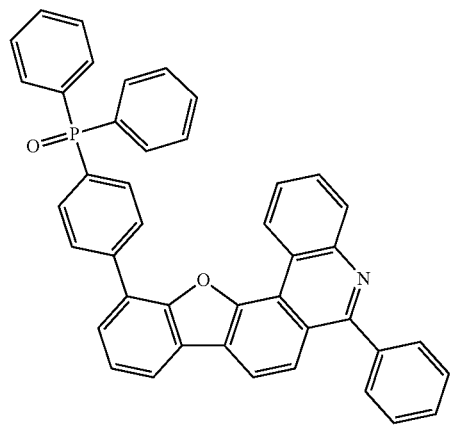
462
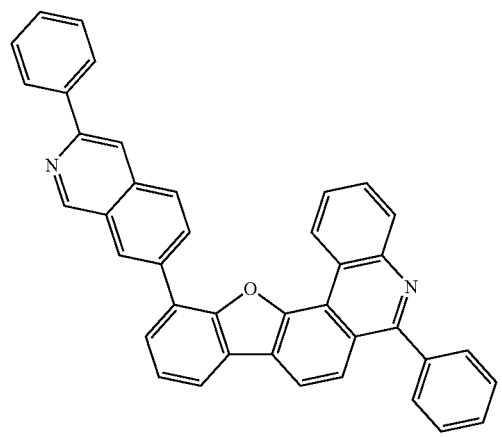
463
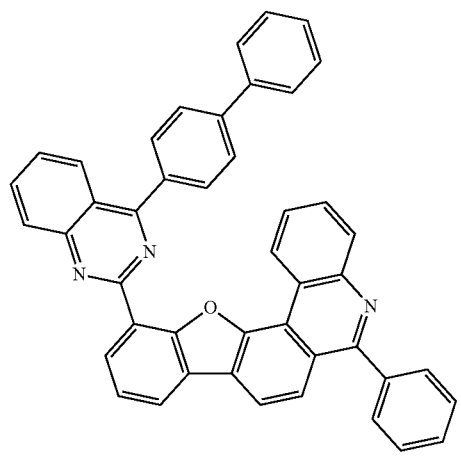

-continued
925
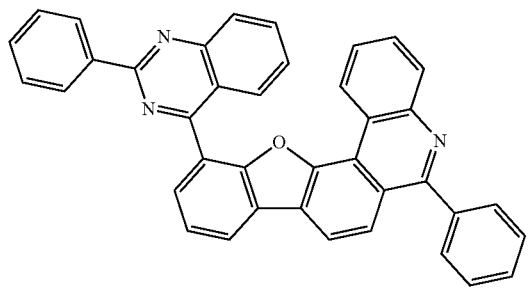
464
926
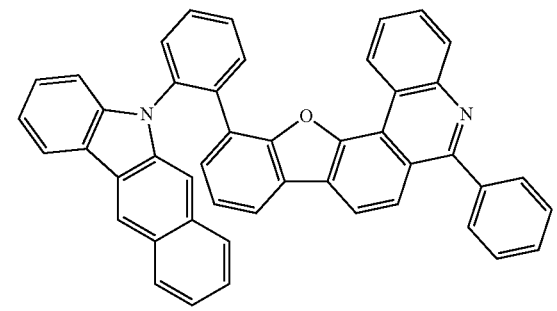
465
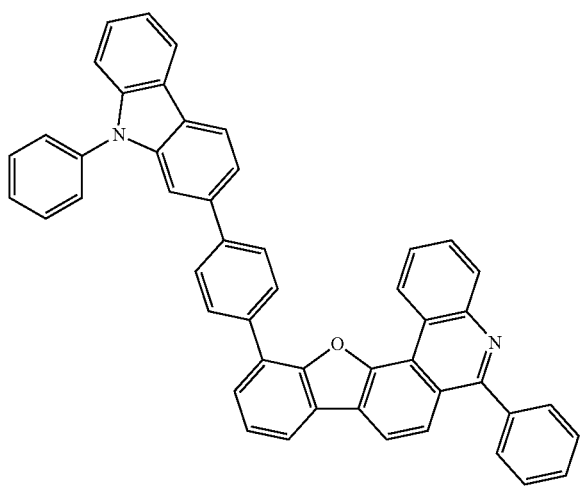
466
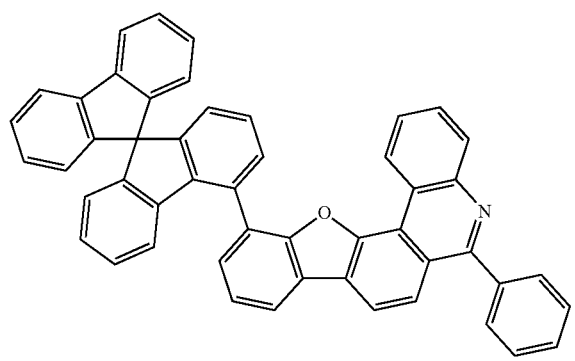
467
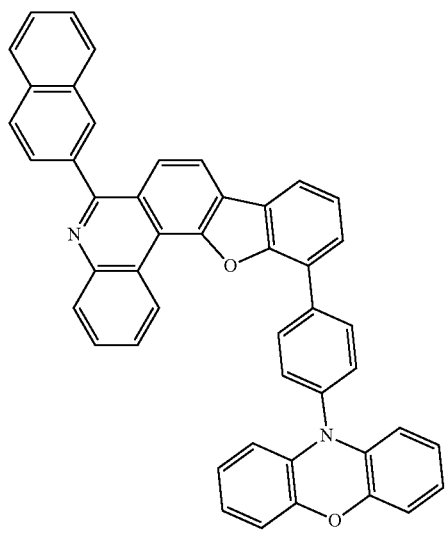
468
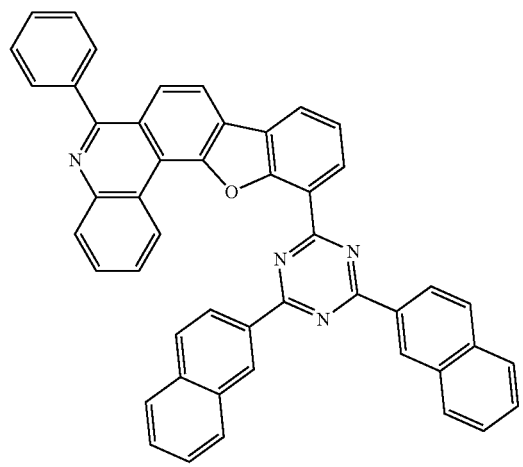
469

-continued
927
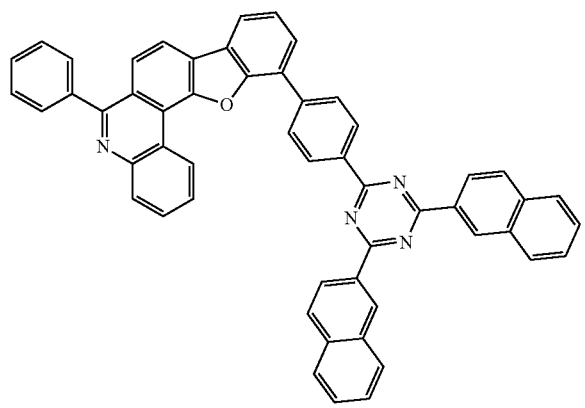
470
928
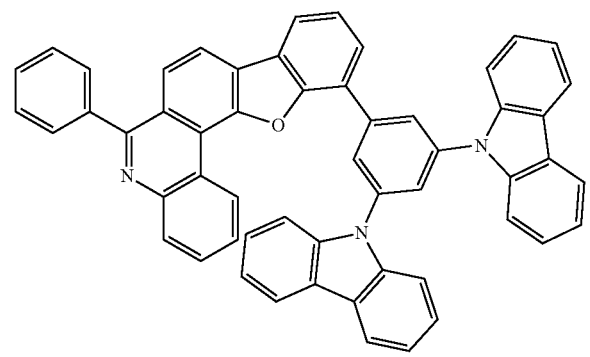
471
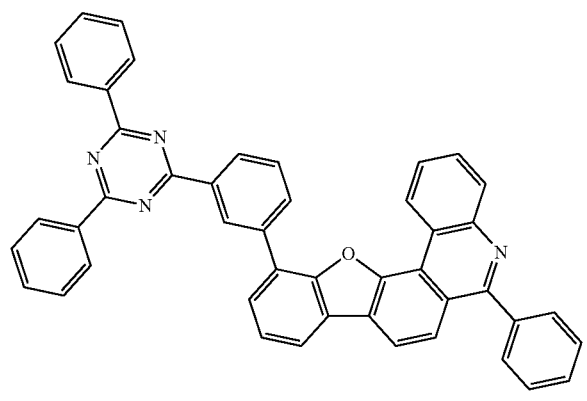
472
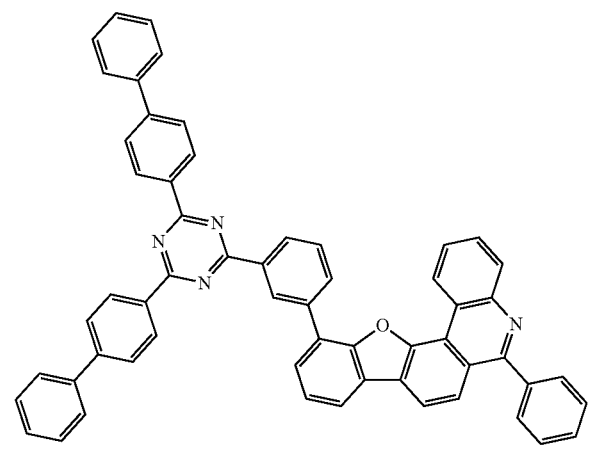
473
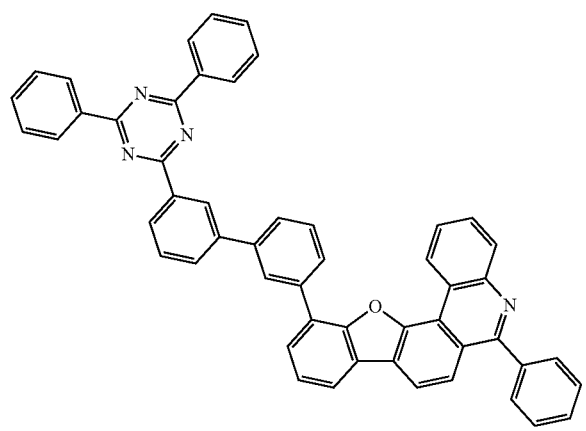
474
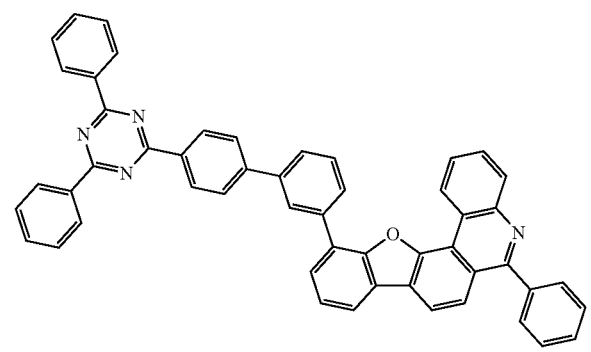
475

-continued
476
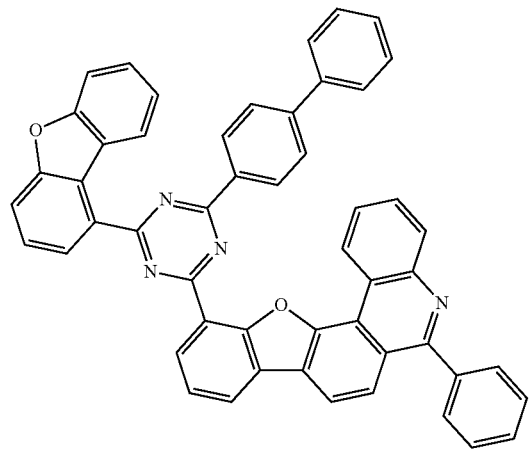
477
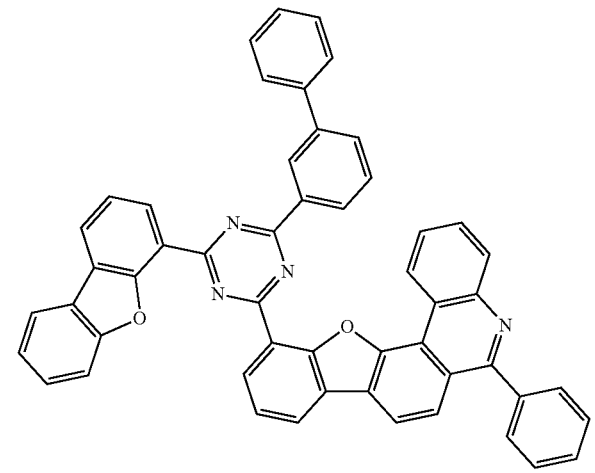
478
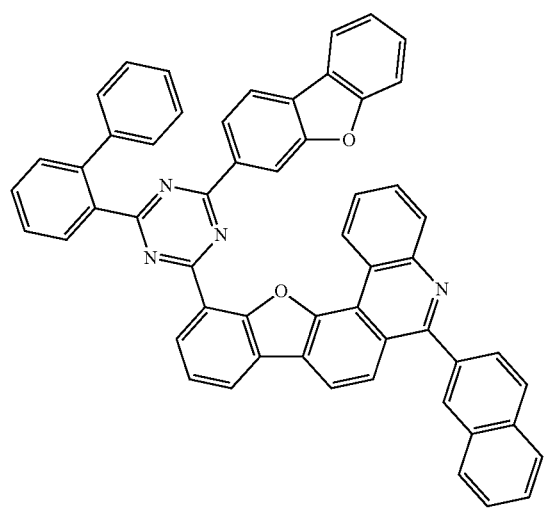
479
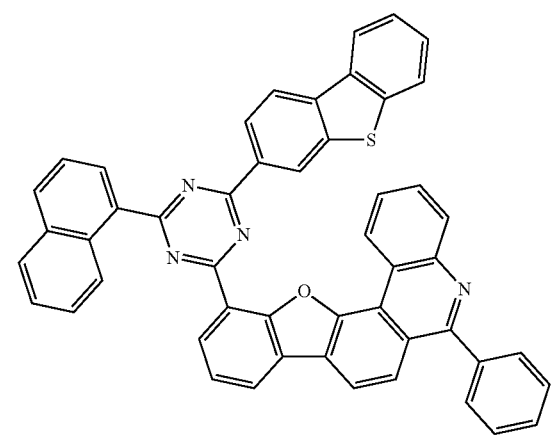
480
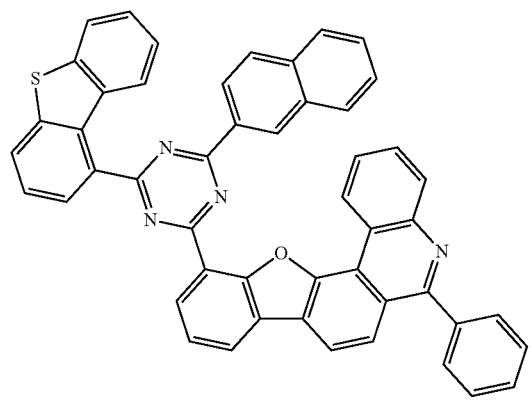
481
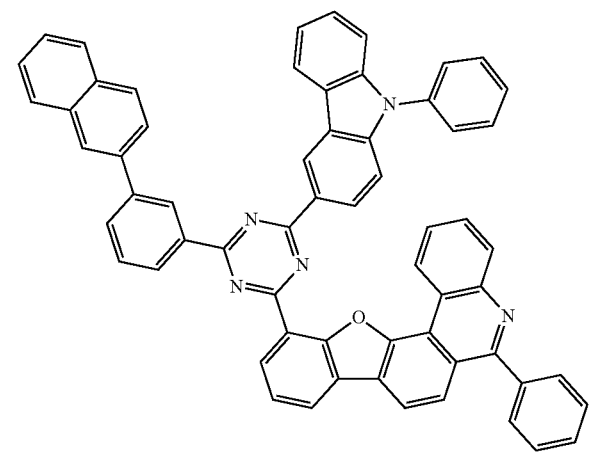

482
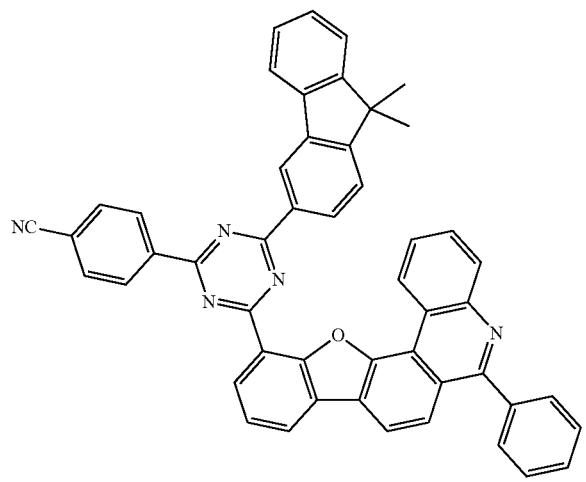
483
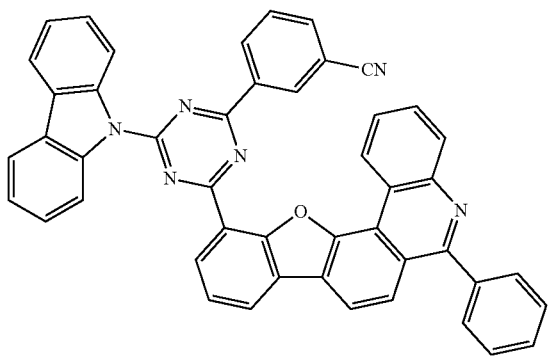
484
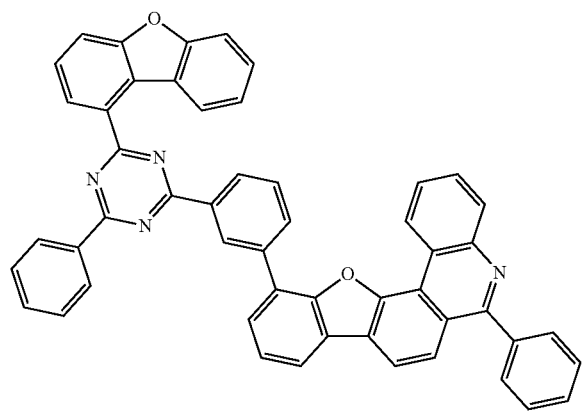
485
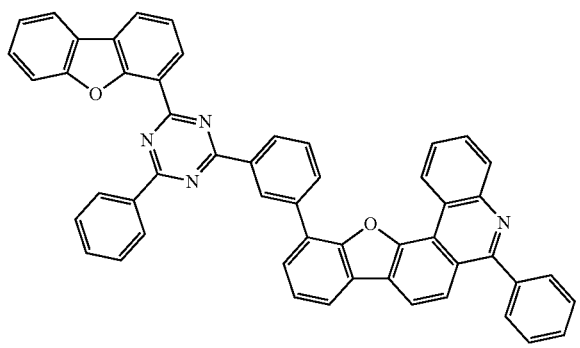
486
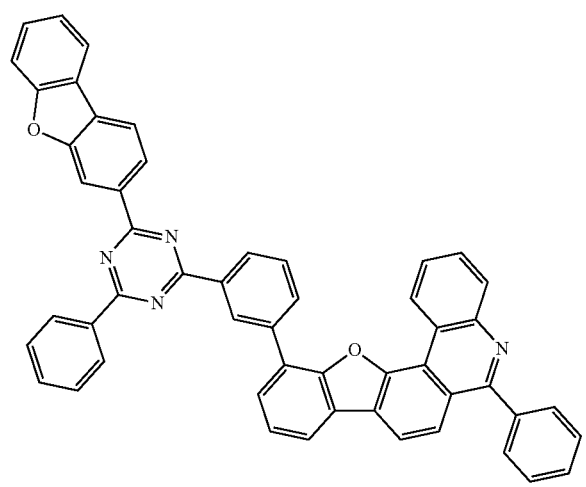
487
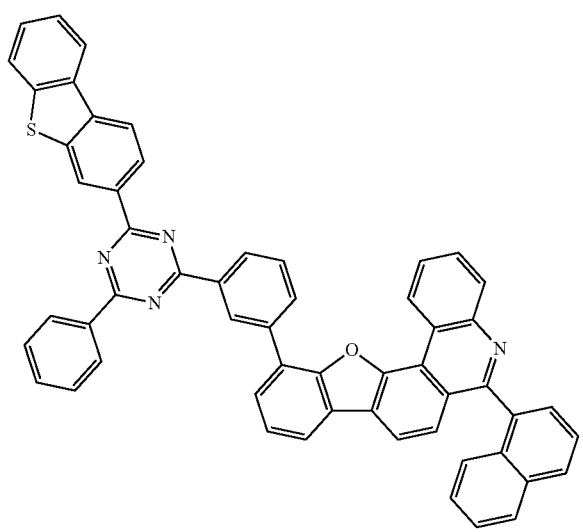

-continued
488
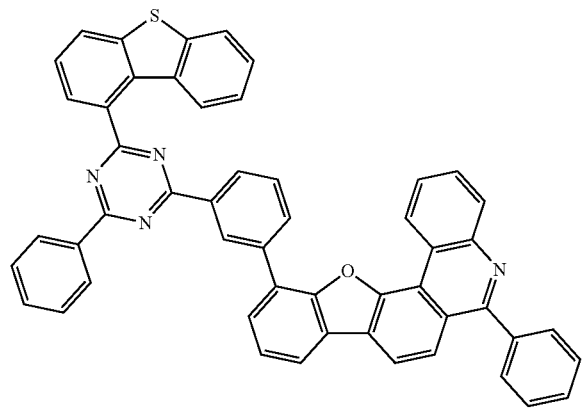
489
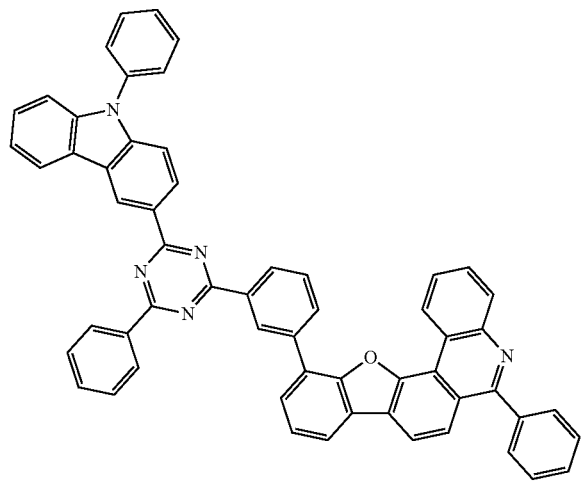
490
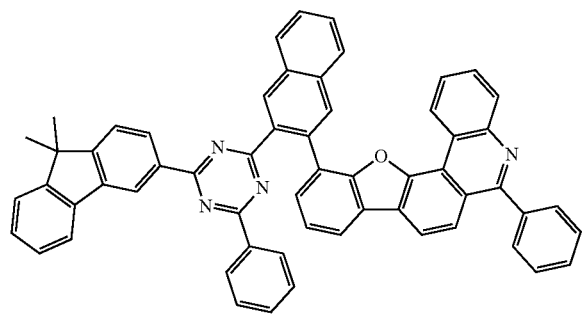
491
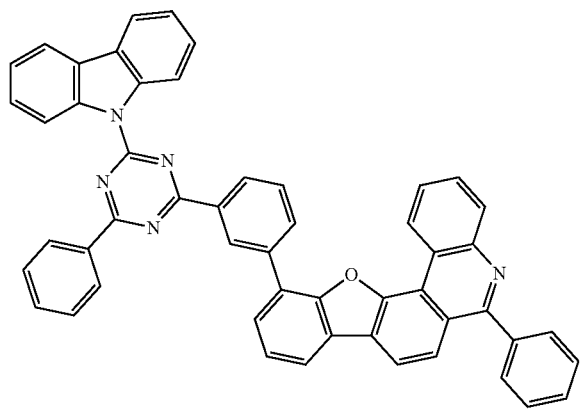
492
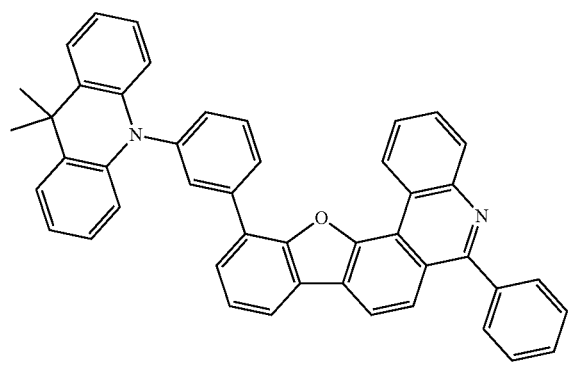
493
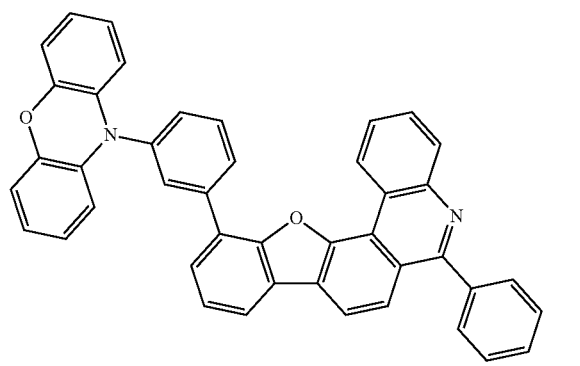

-continued
| 494 | 495 |
|---|---|
| 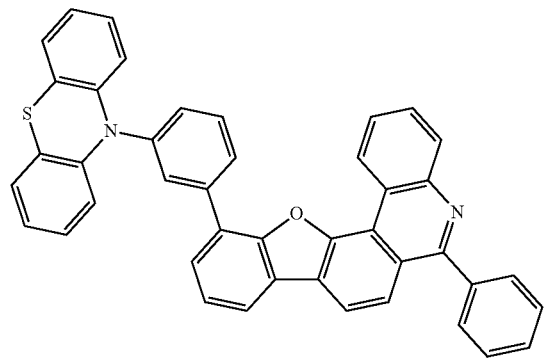 | 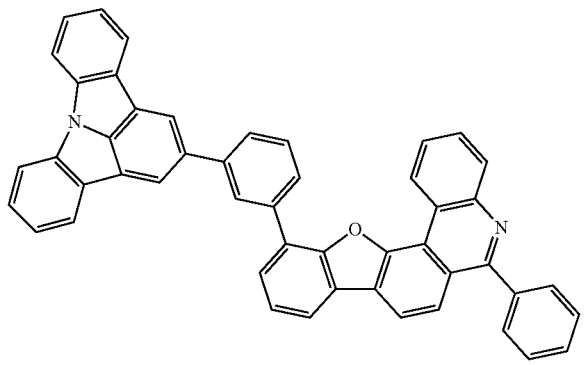 |
| 496 | 497 |
| 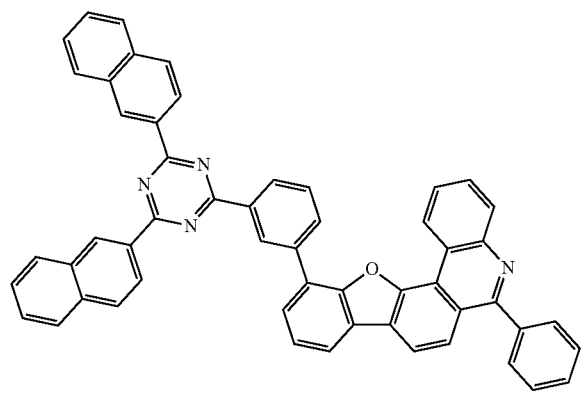 | 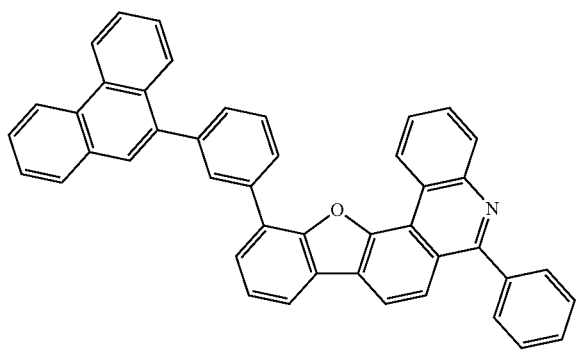 |
| 498 | 499 |
| 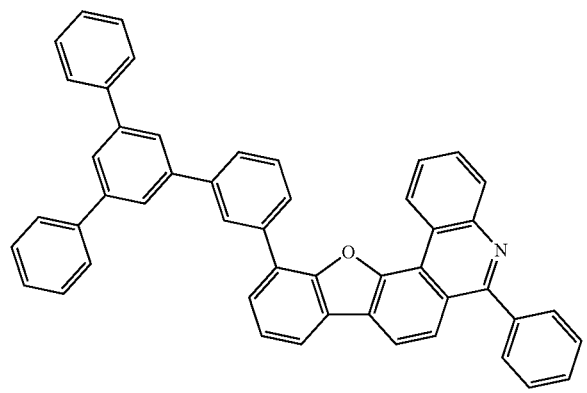 | 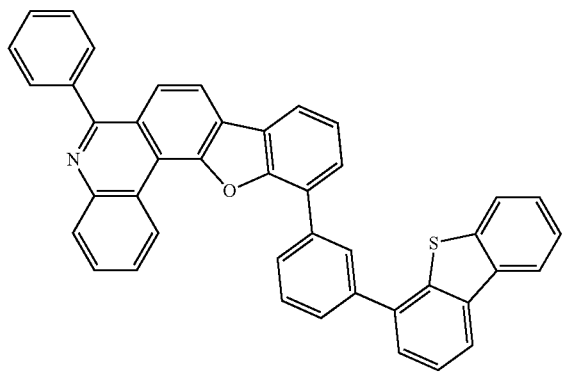 |
| 500 | 501 |
| 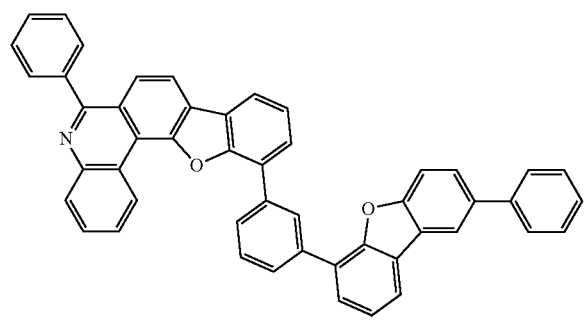 | 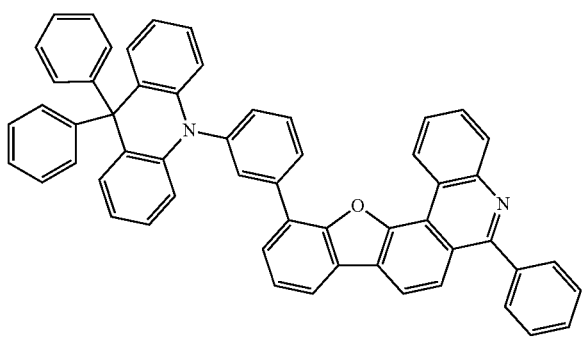 |

-continued
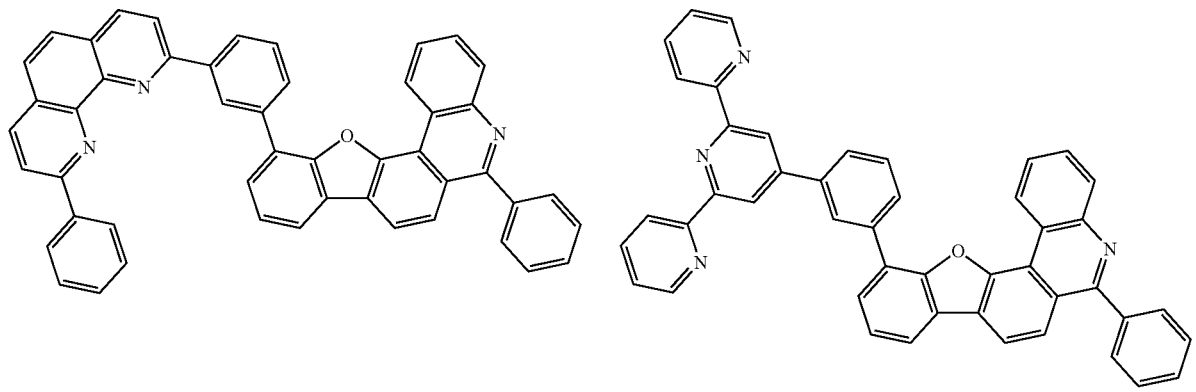
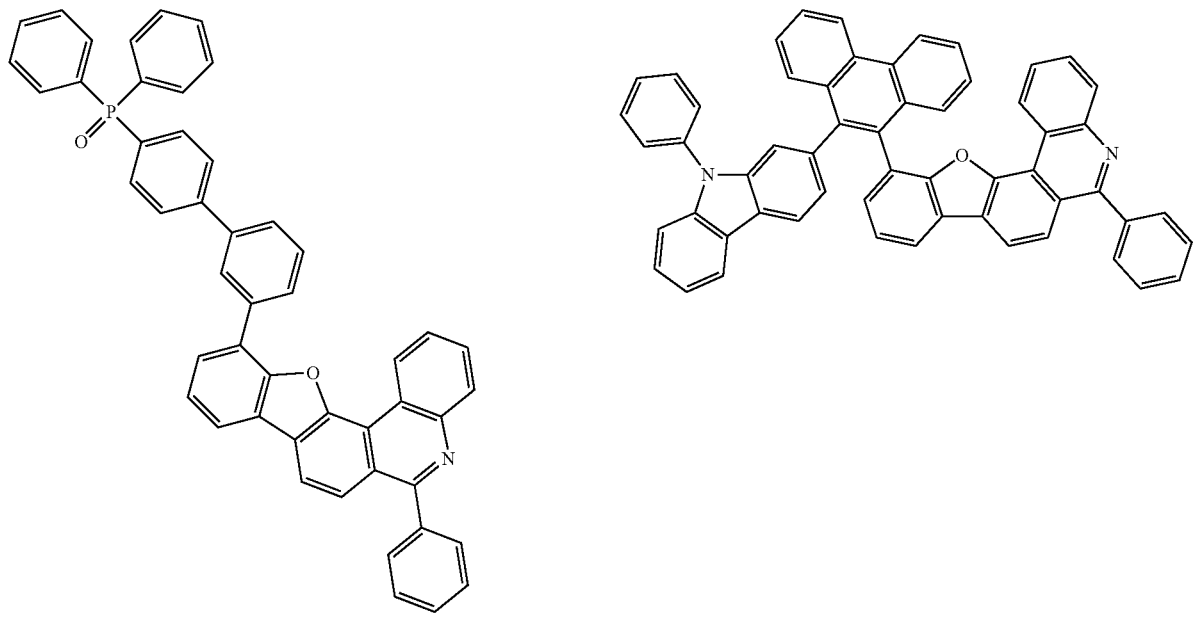
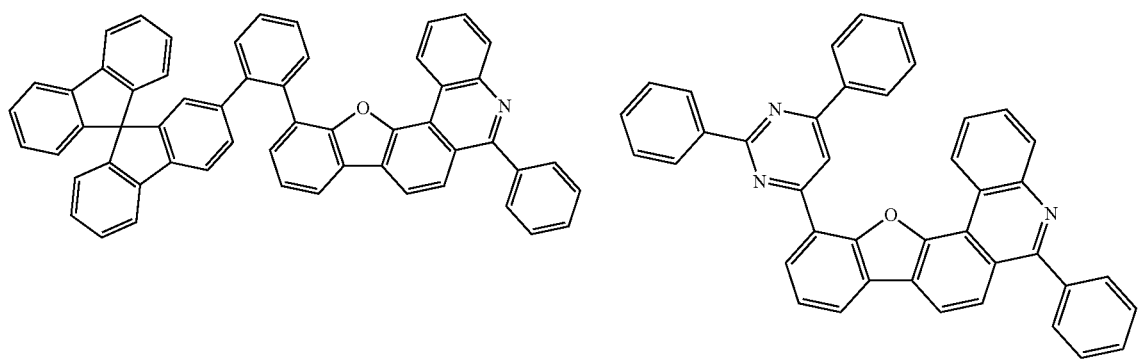

-continued
508
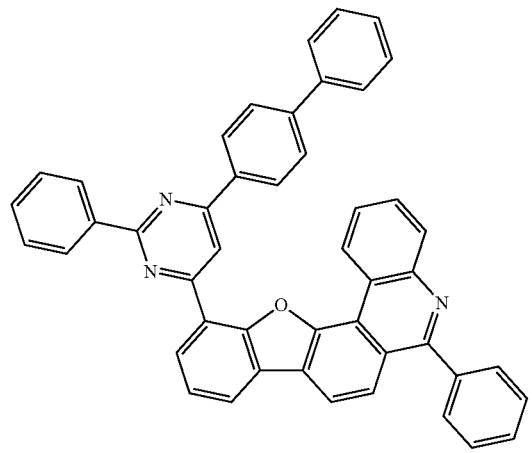
509
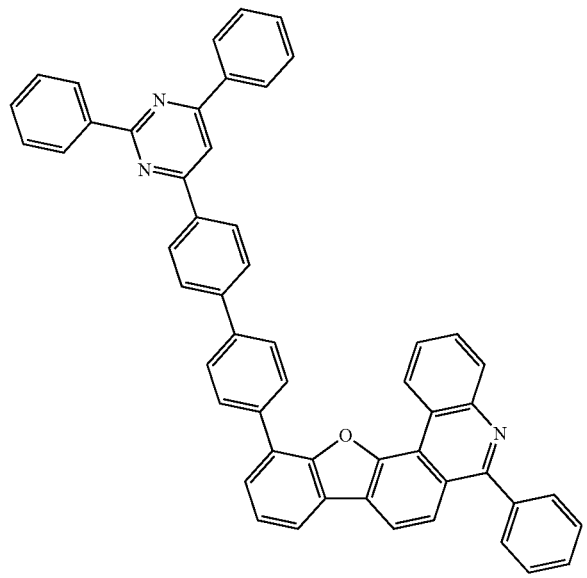
510
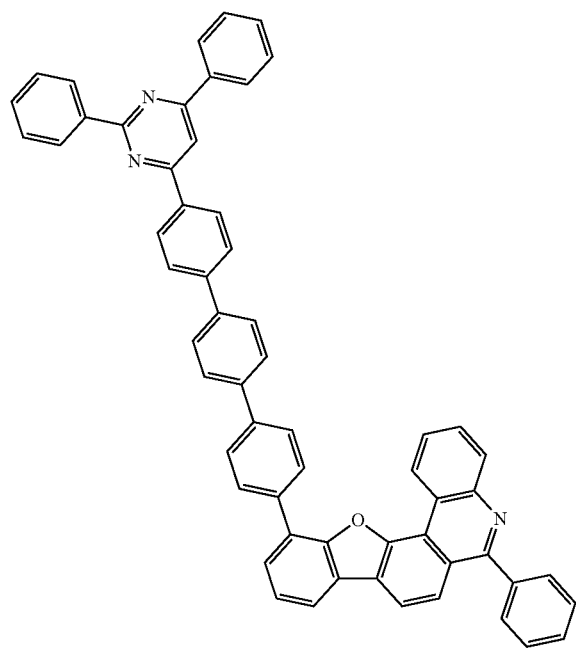
511
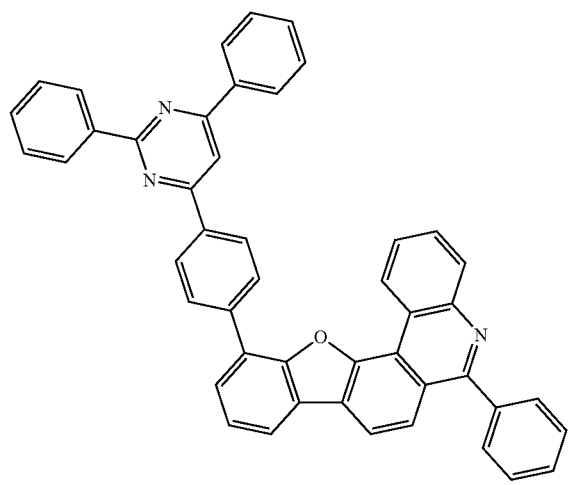

-continued
| 941 | 942 |
|---|---|
| 512 | 513 |
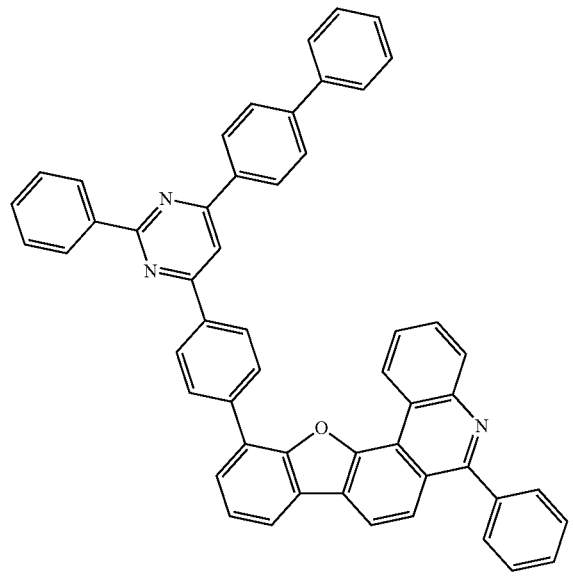
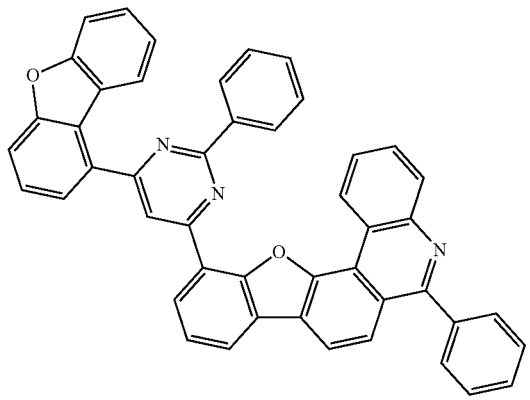
514  515
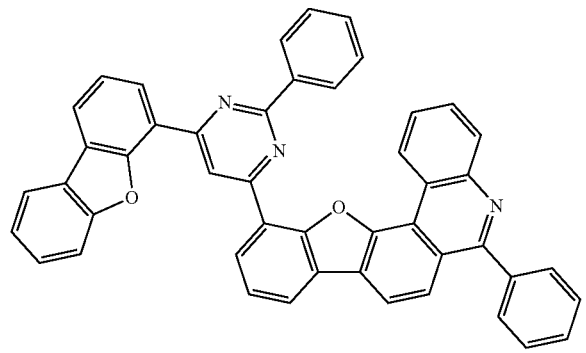
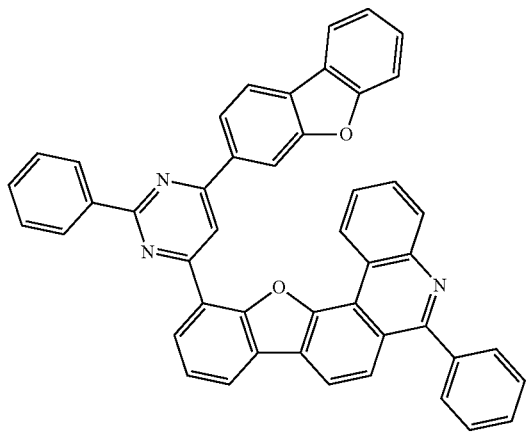
516  517
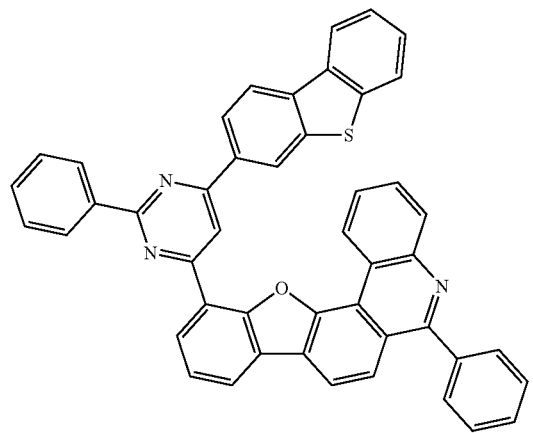
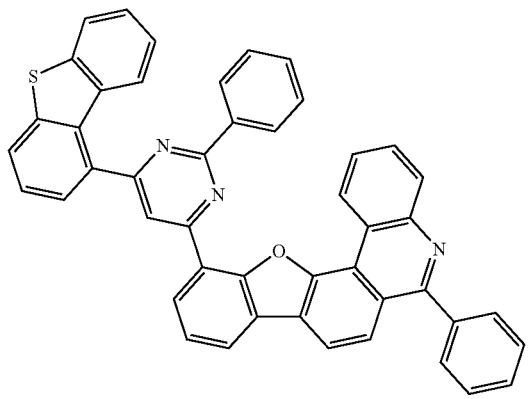

-continued
518
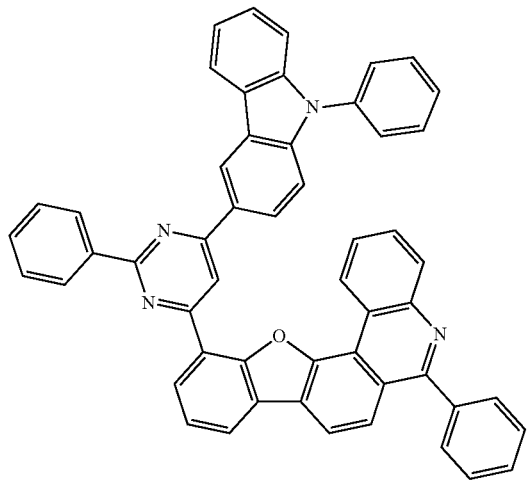
519
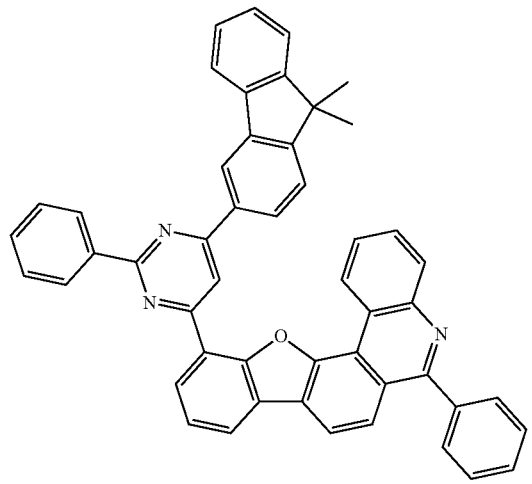
520
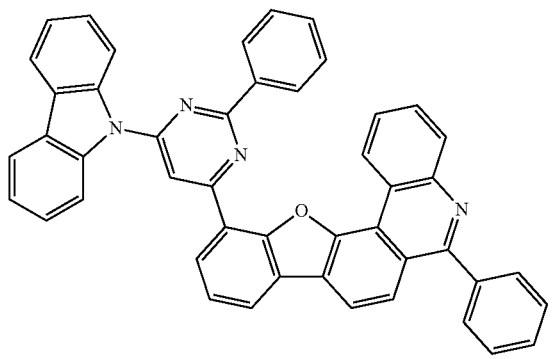
521
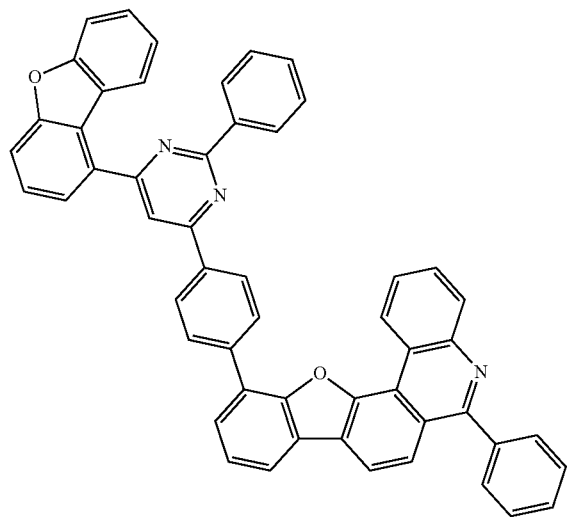
522
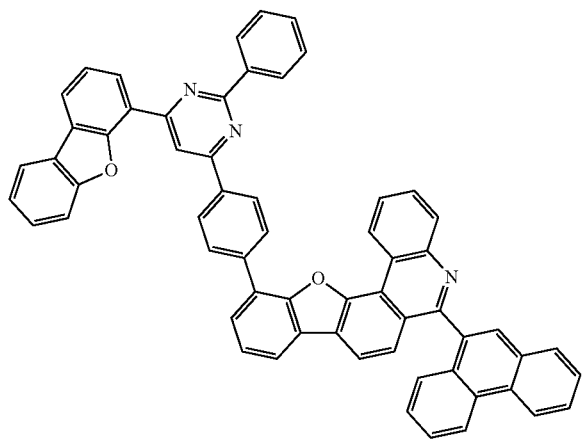
523
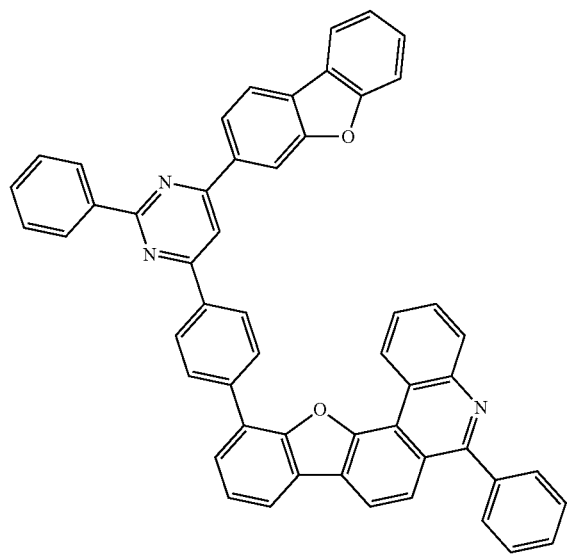

-continued
524
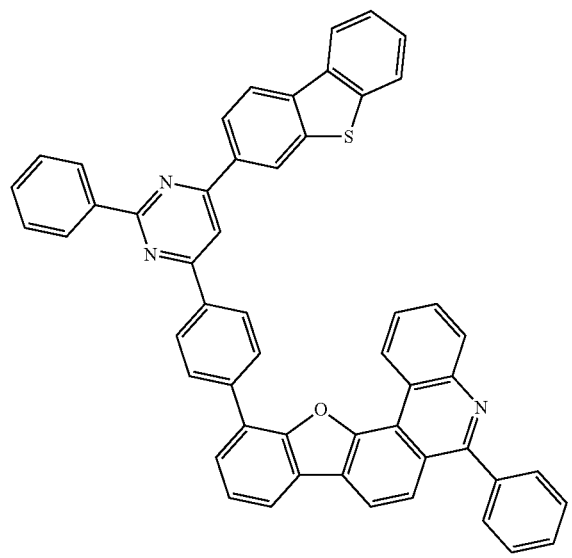
525
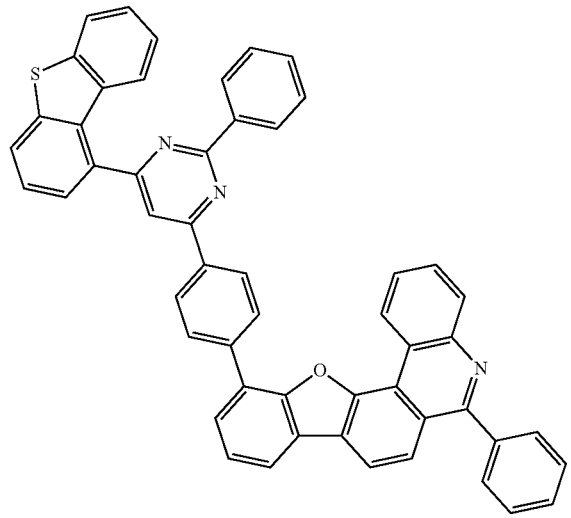
526
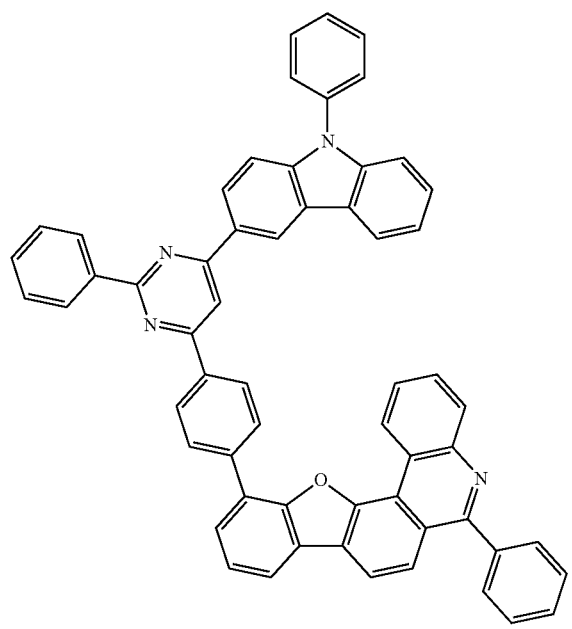
527
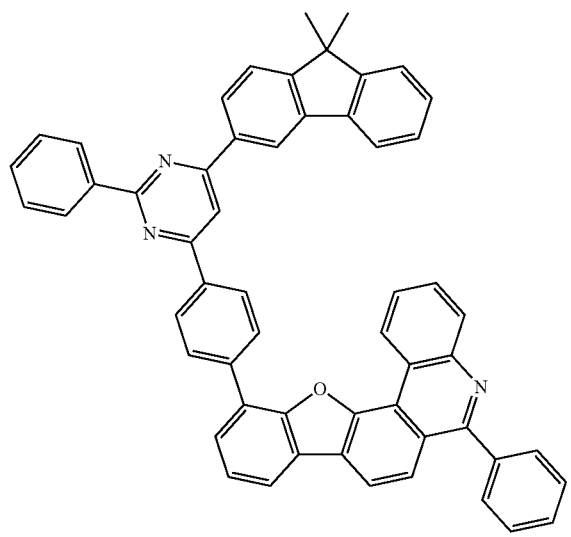

-continued
| 528 | 529 |
|---|---|
| 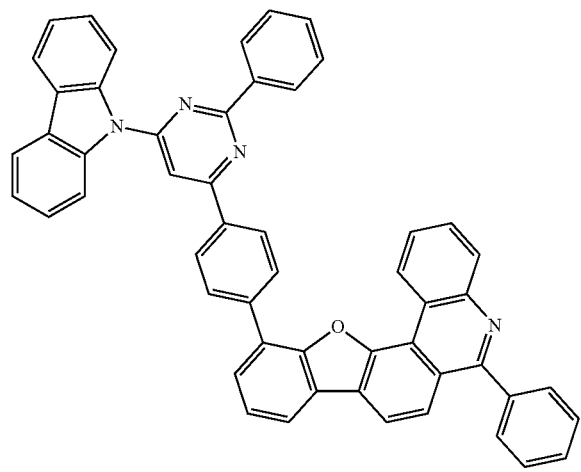 | 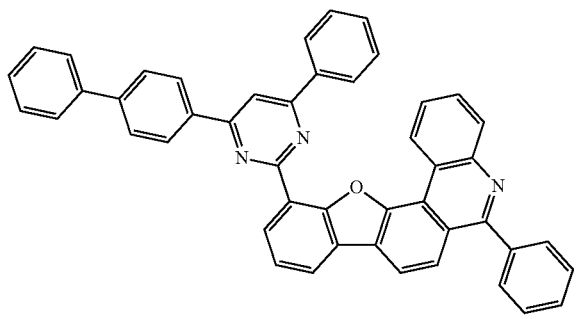 |
| 530 | 531 |
| 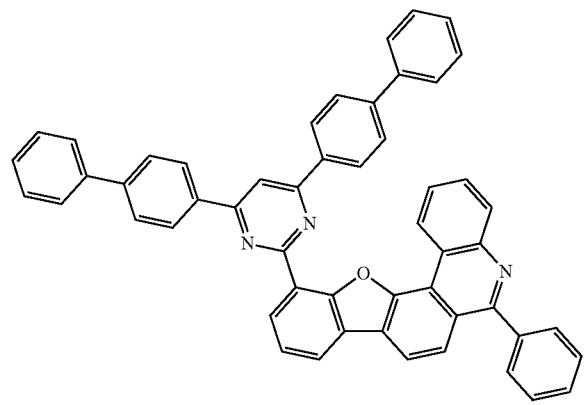 | 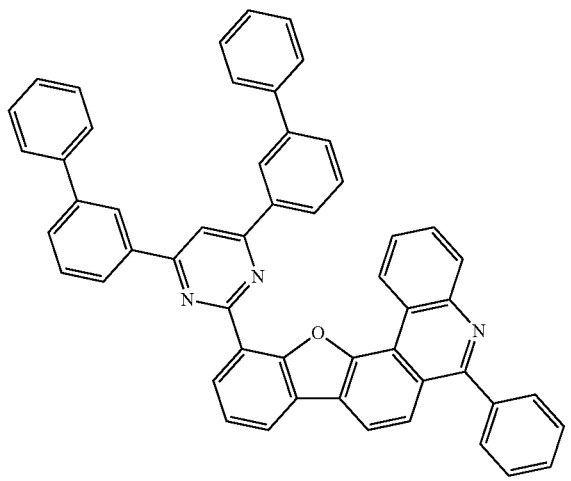 |
| 532 | 533 |
| 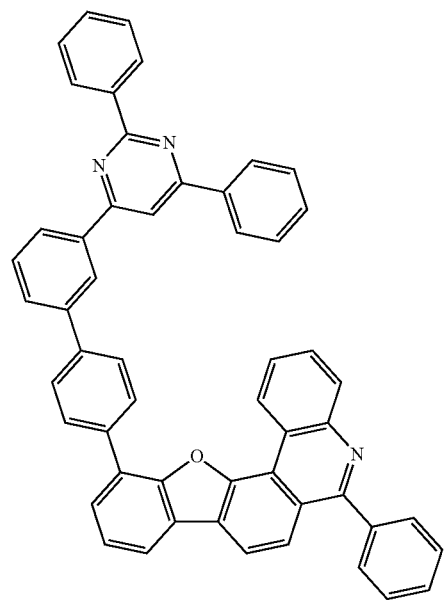 | 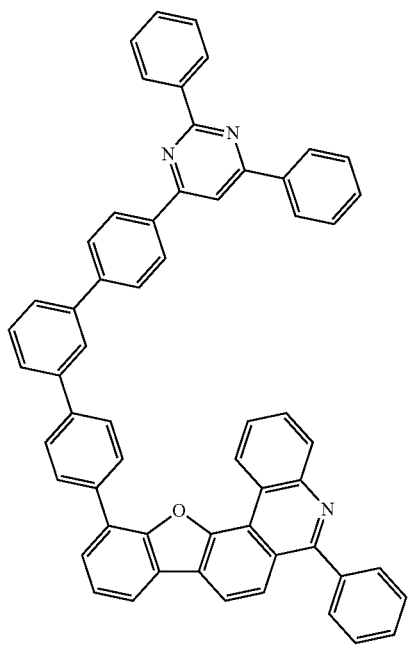 |

-continued
534
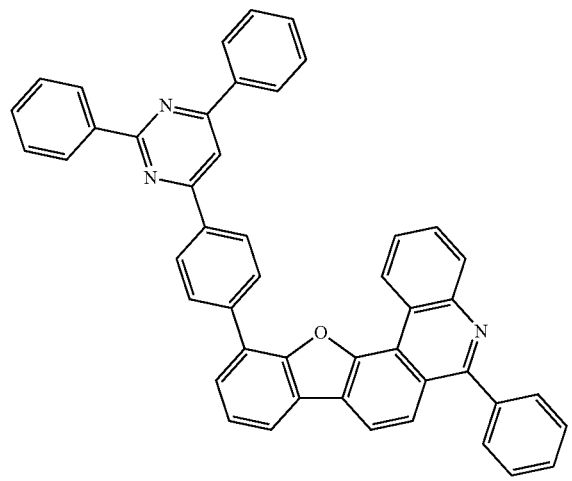
535
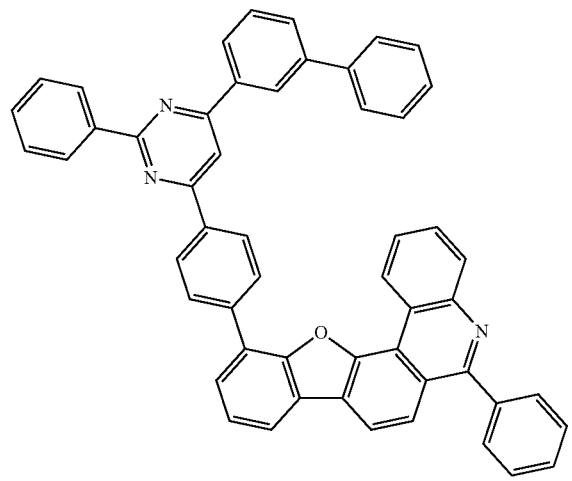
536
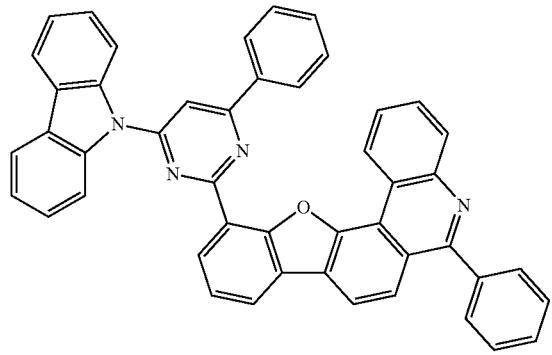
537
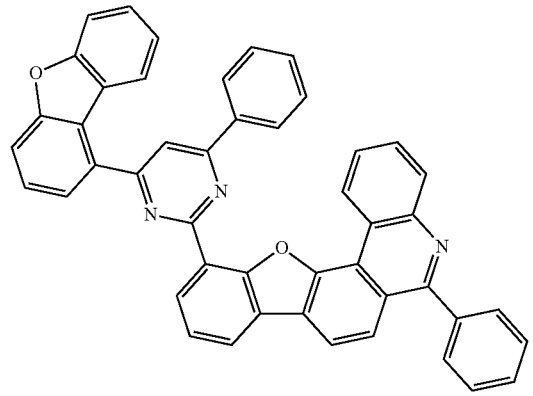
538
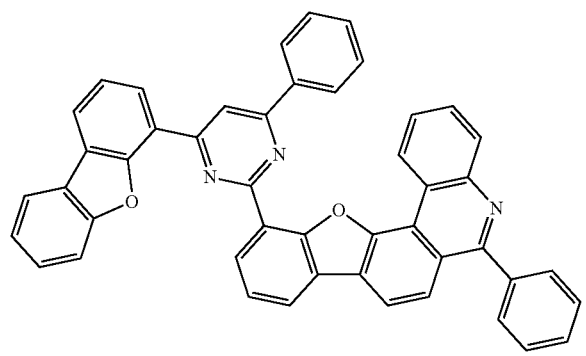
539
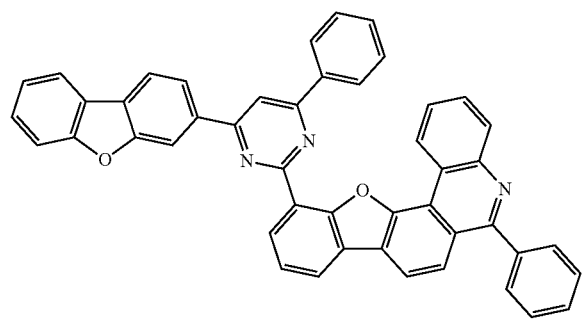

-continued
540
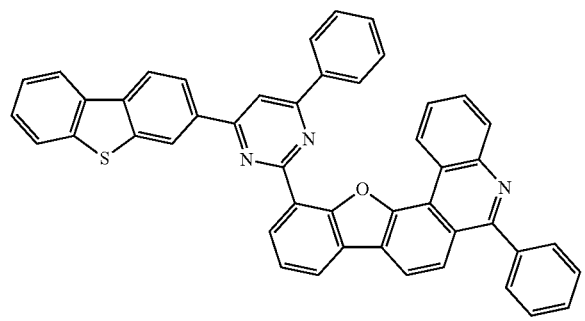
541
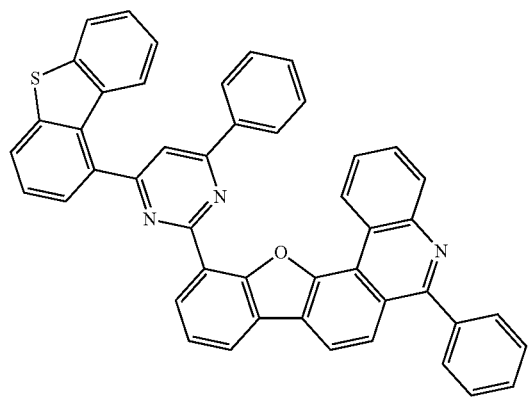
542
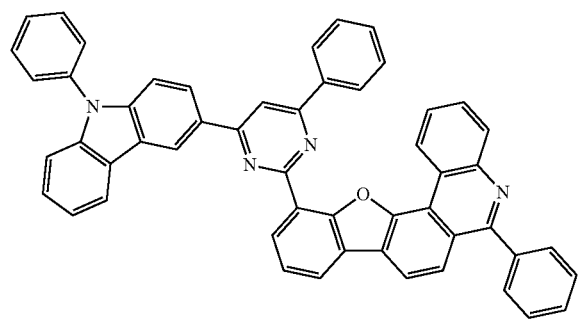
543
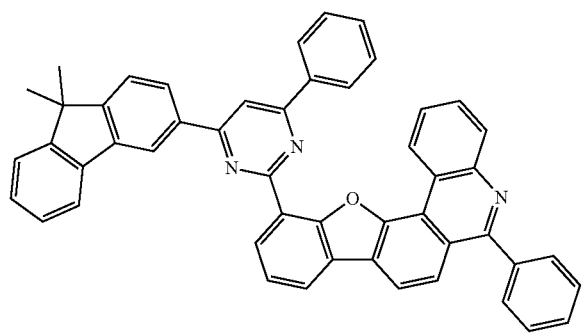
544
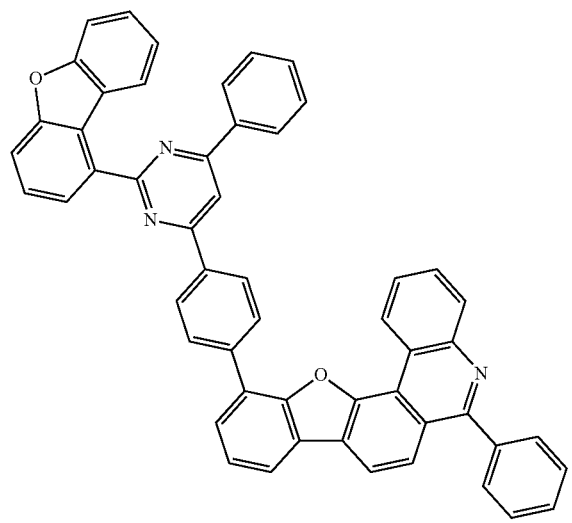
545
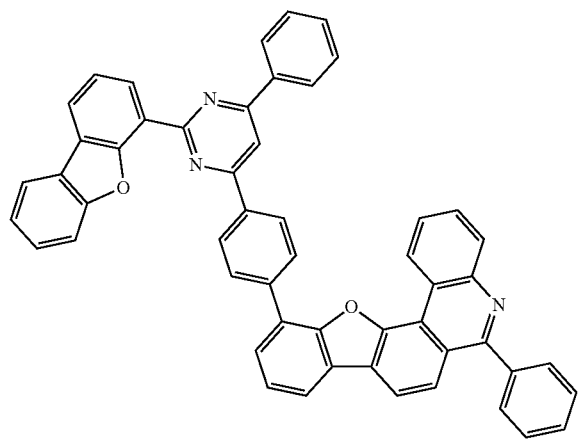

-continued
| 546 | 547 |
|---|---|
| 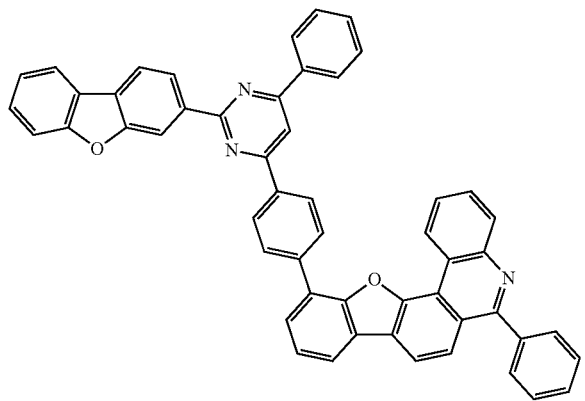 | 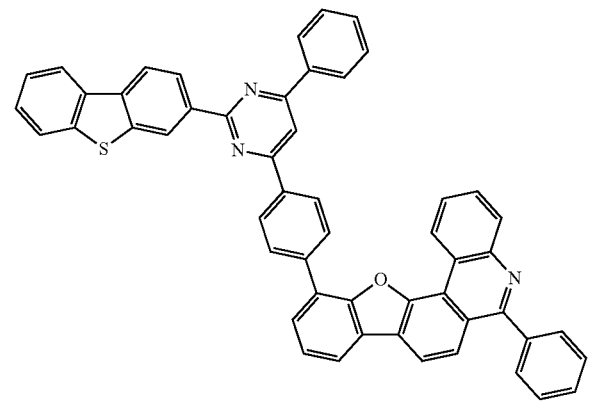 |
| 548 | 549 |
| 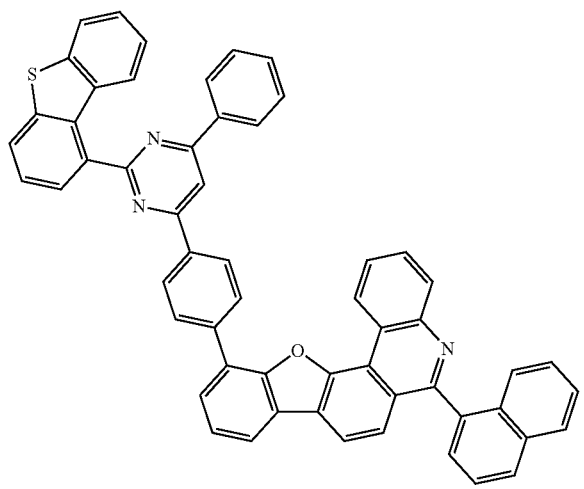 | 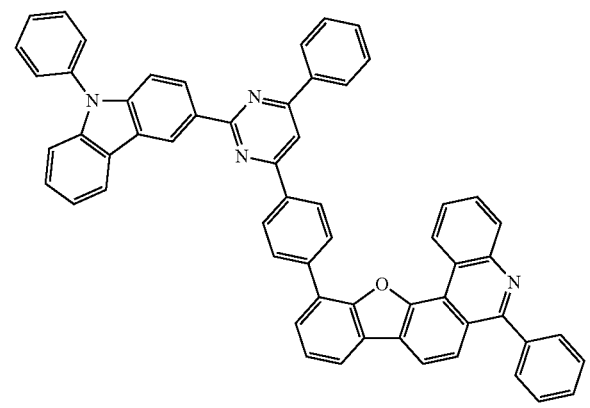 |
| 550 | 551 |
| 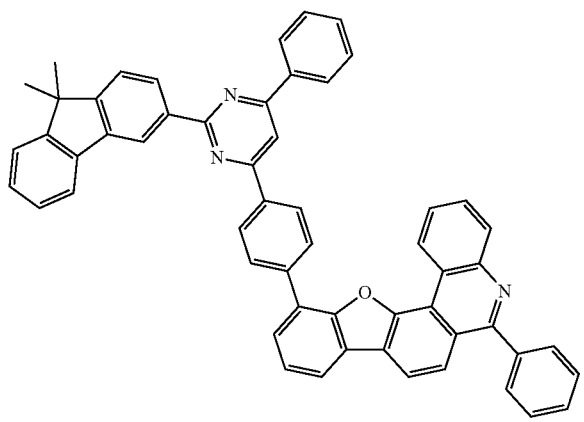 | 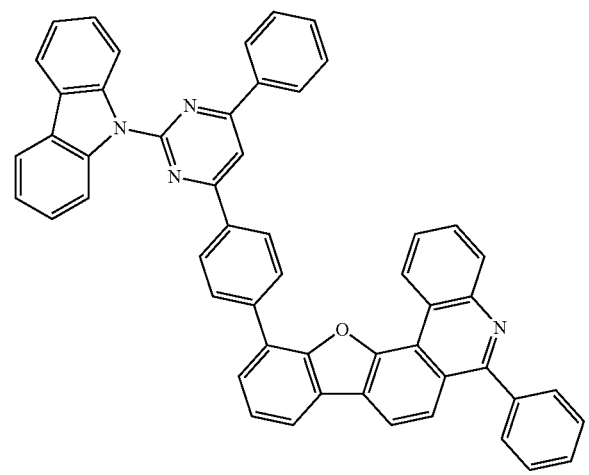 |

-continued
552
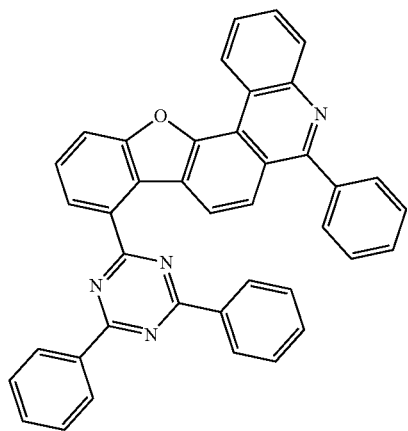
553
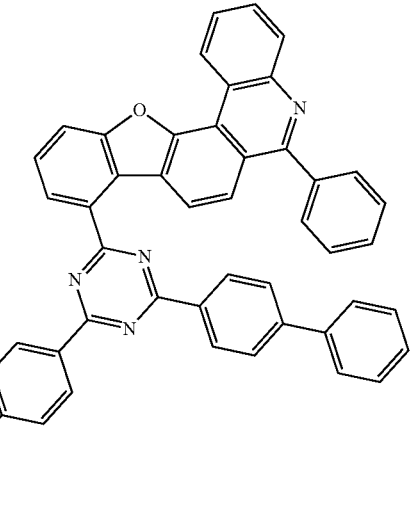
554
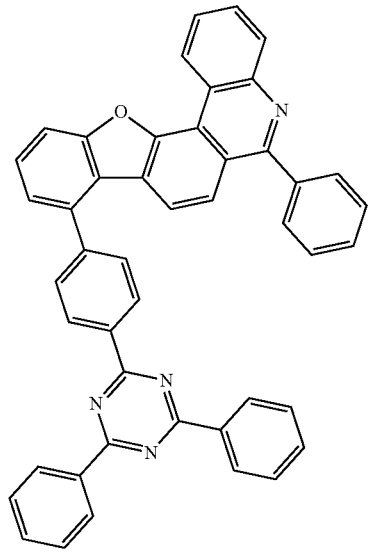
555
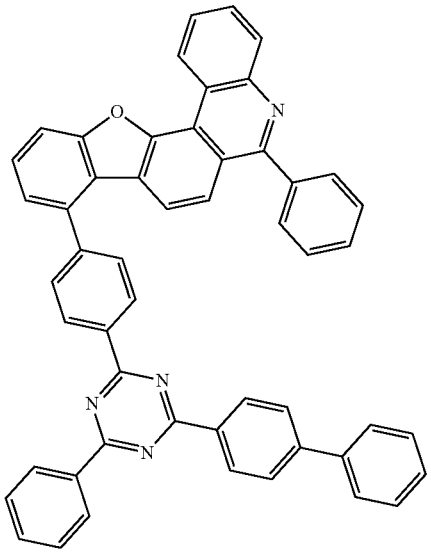
556
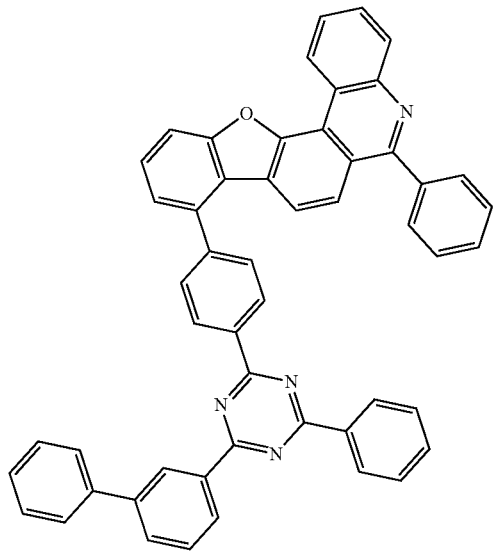
557
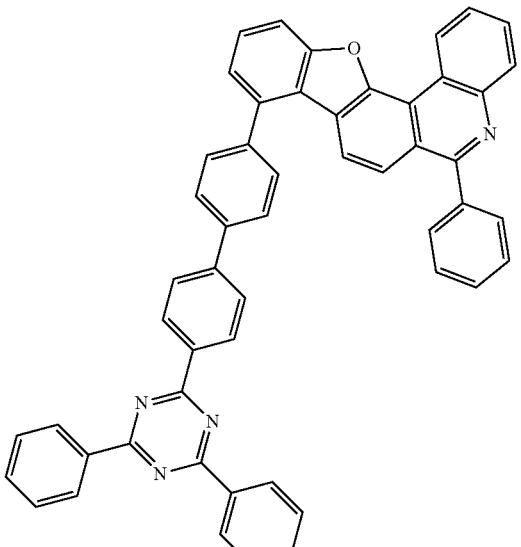

558
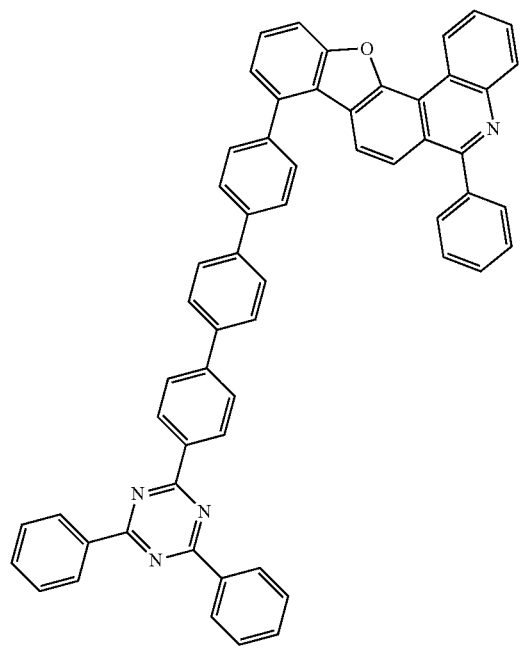
559
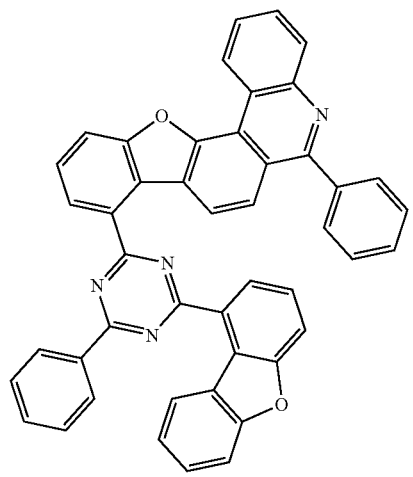
560
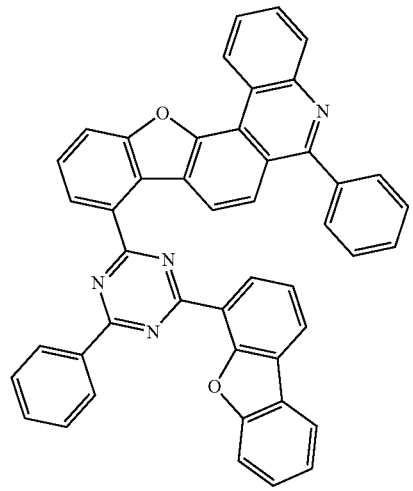
561
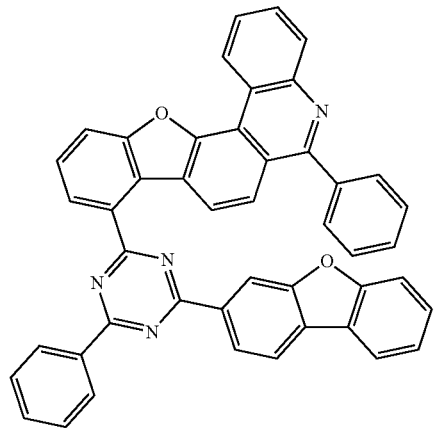
562
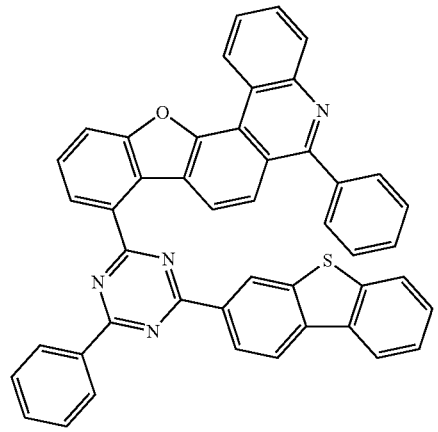
563
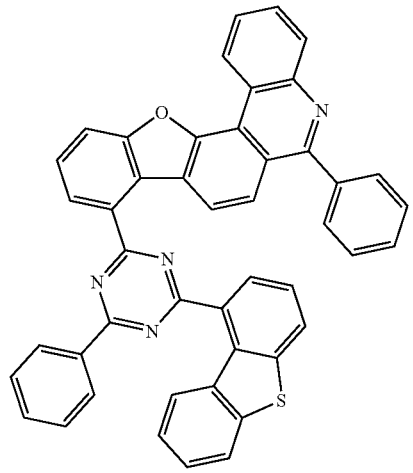

-continued
564
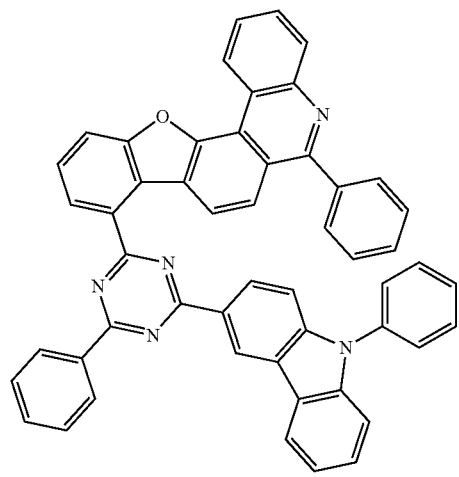
565
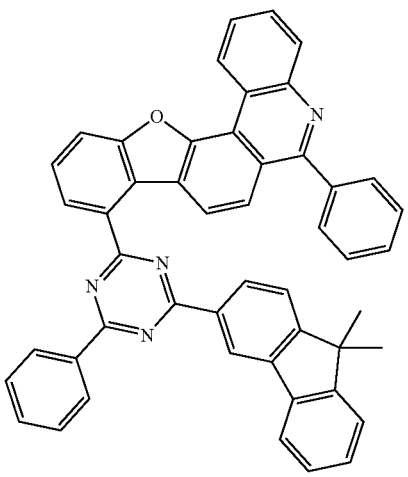
566
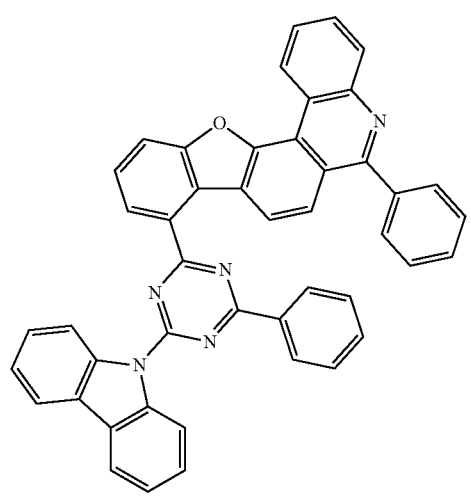
567
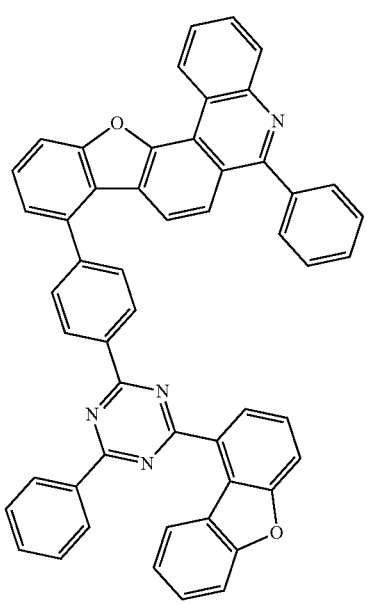
568
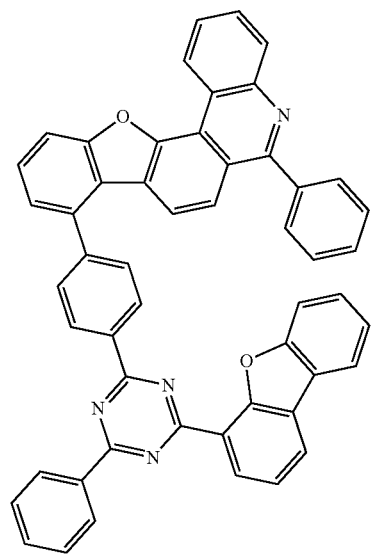
569
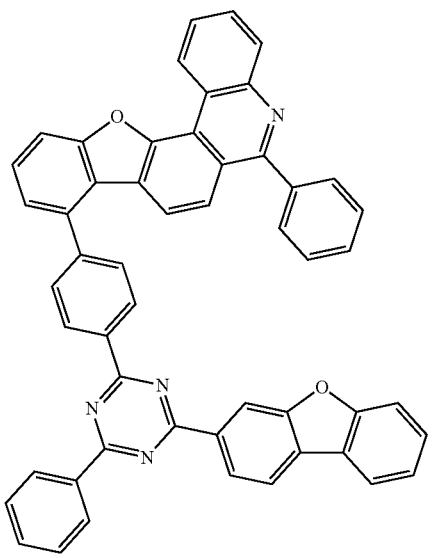

-continued
961
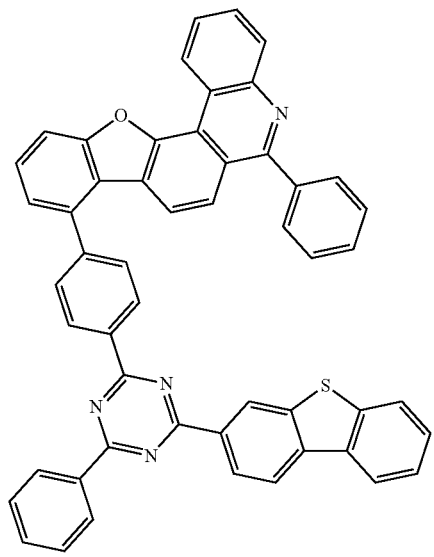
570
962
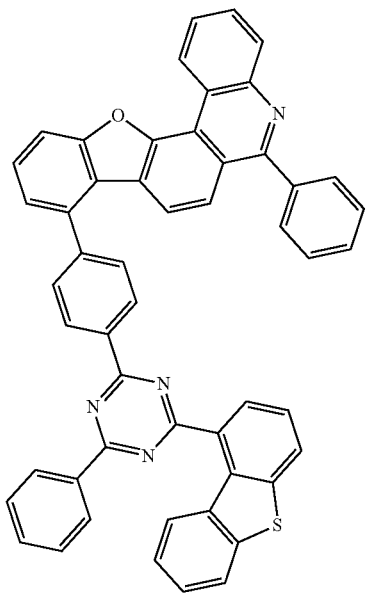
571
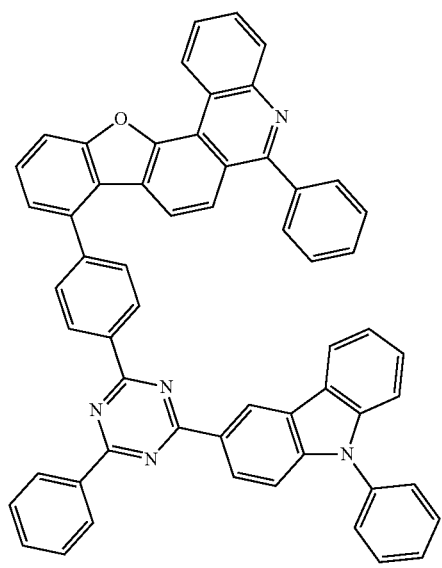
572
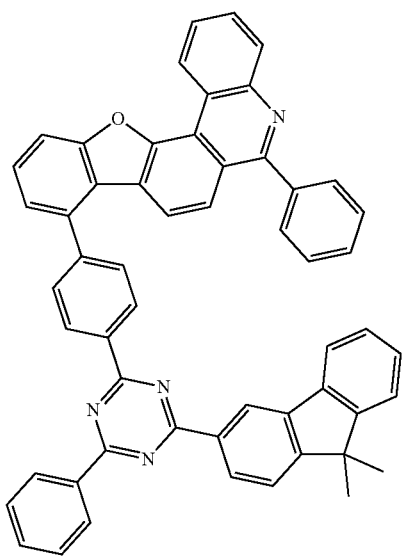
573

-continued
| 574 | 575 |
|---|---|
| 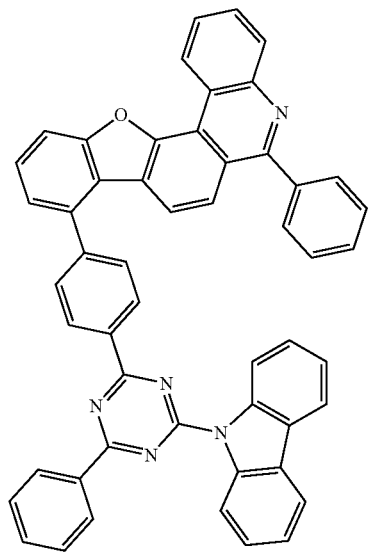 | 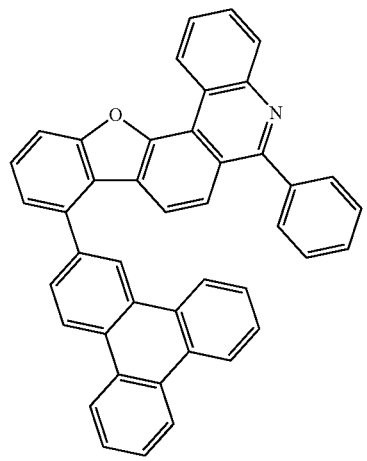 |
| 576 | 577 |
| 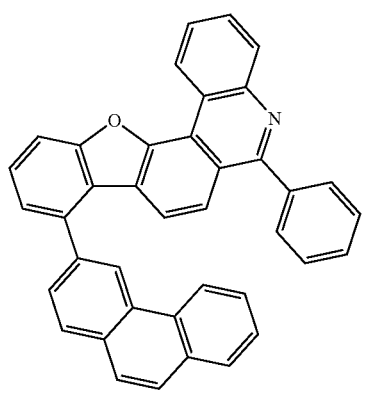 | 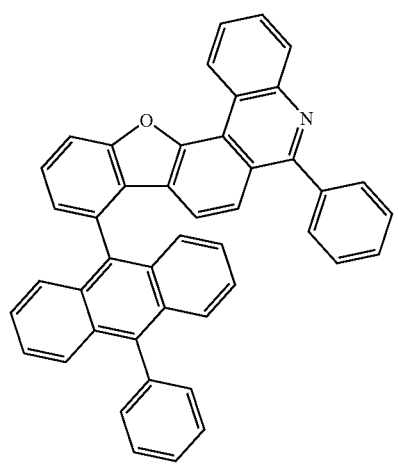 |
| 578 | 579 |
| 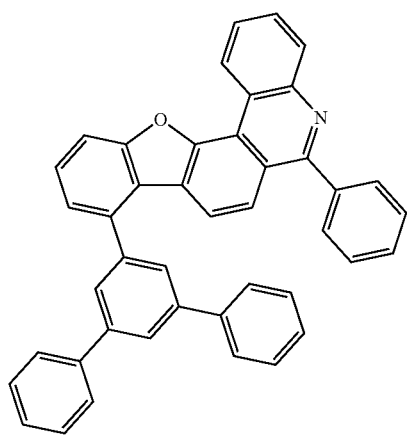 | 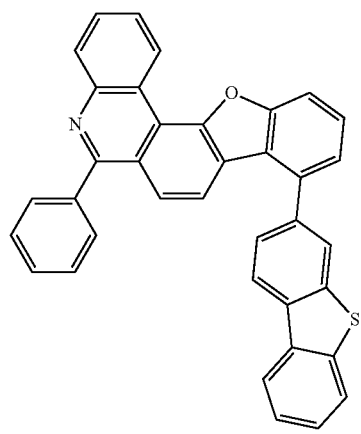 |

580
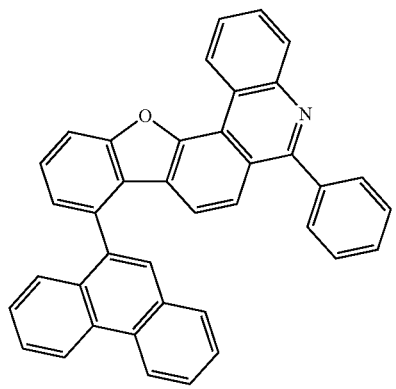
581
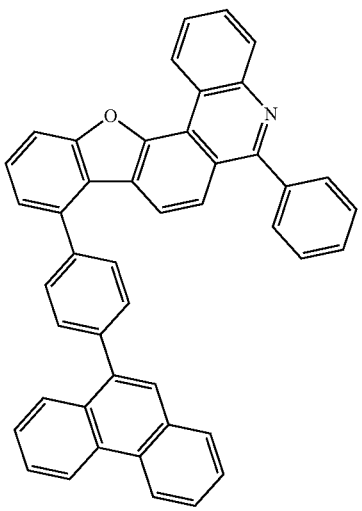
582
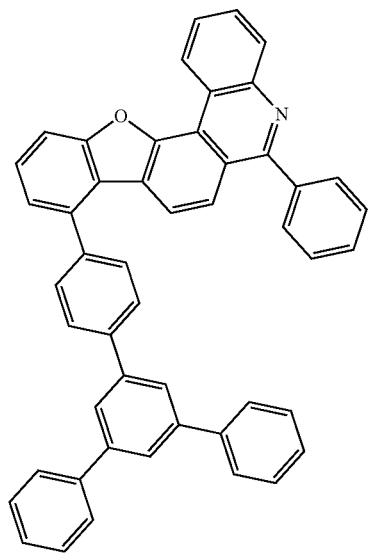
583
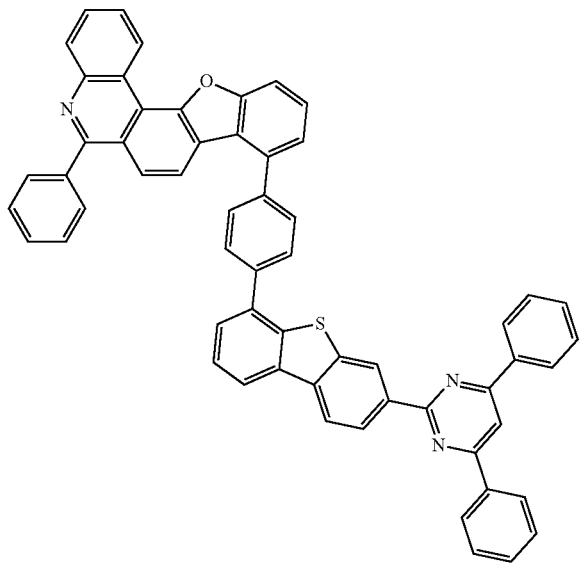
584
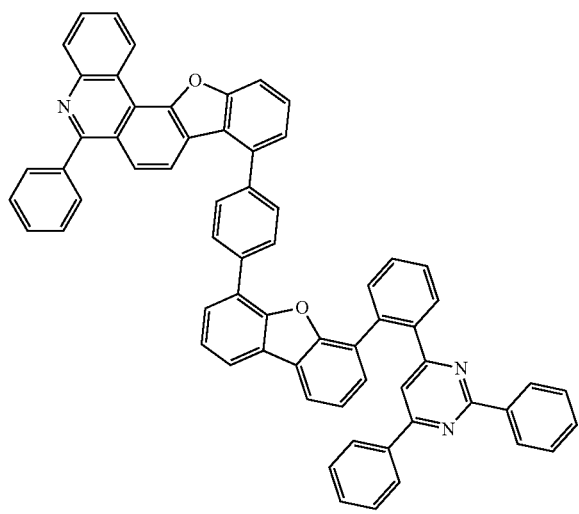
585
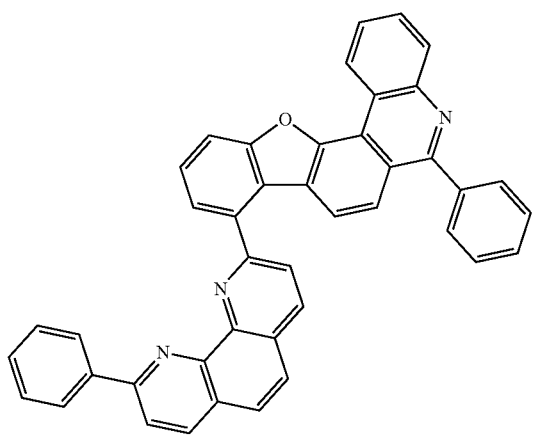

-continued
586
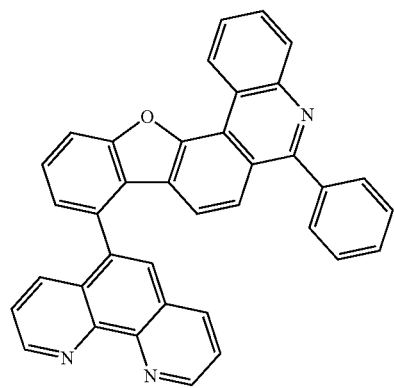
587
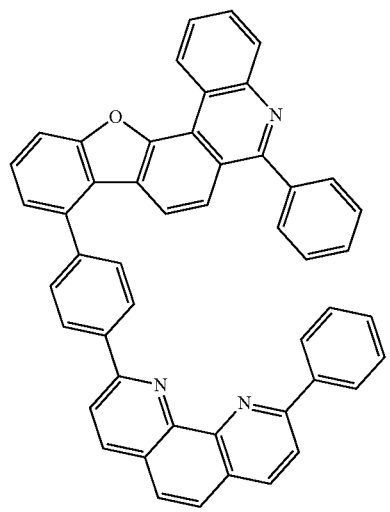
588
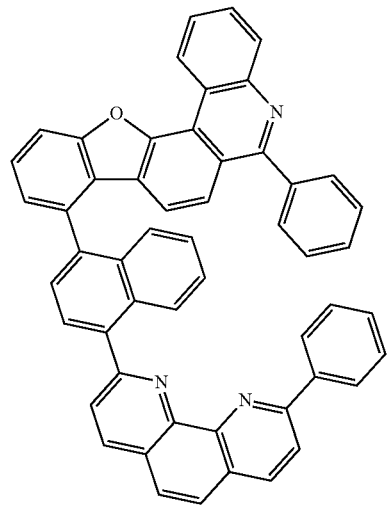
589
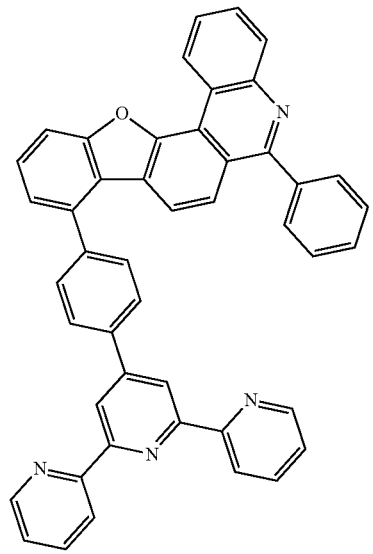
590
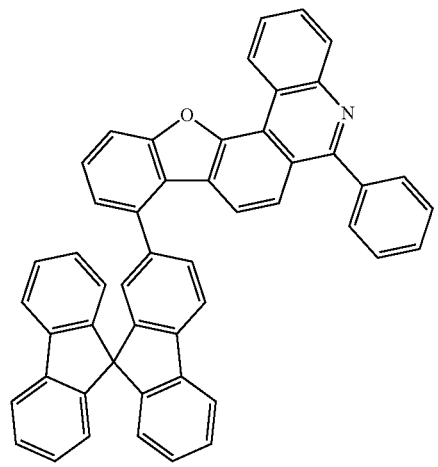
591
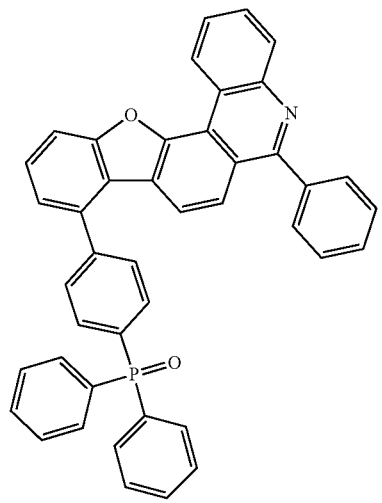

592
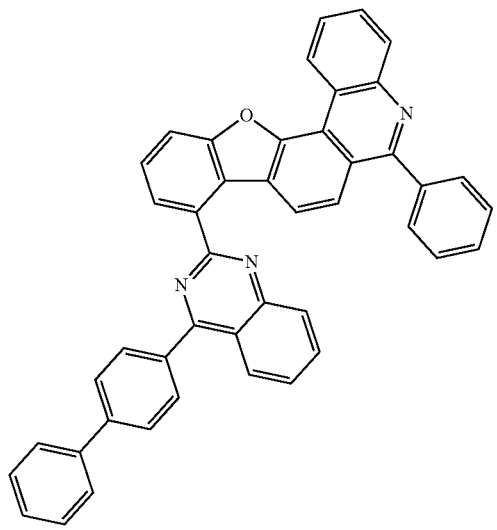
593
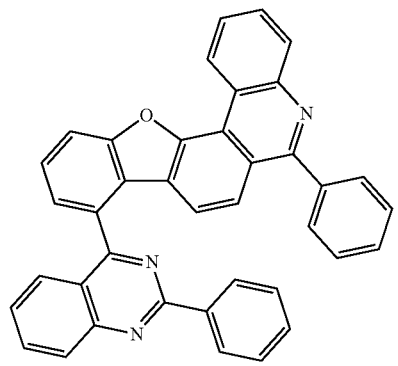
594
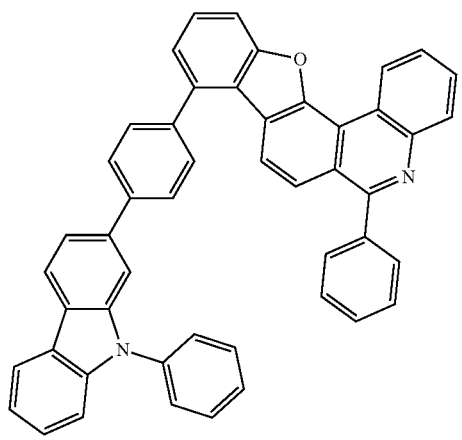
595
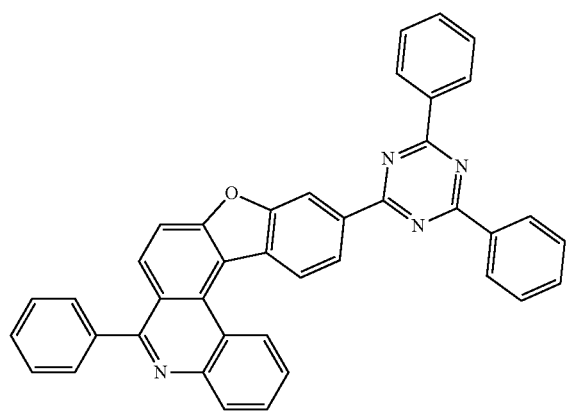
596
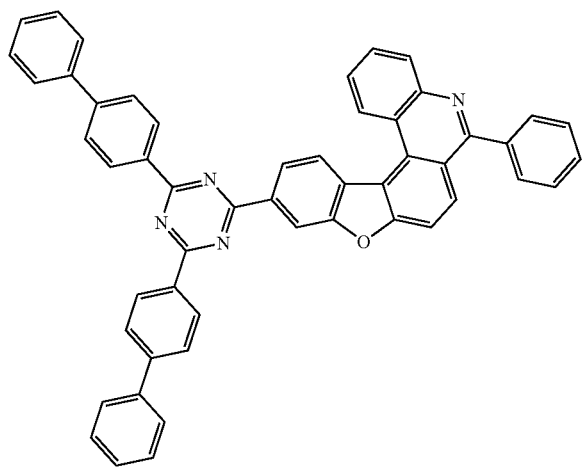
597
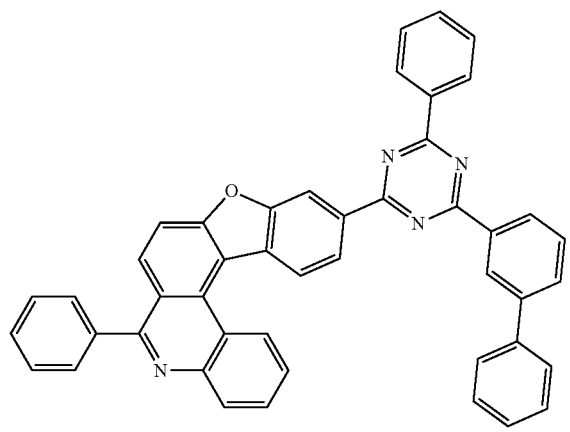

971 972
598 599
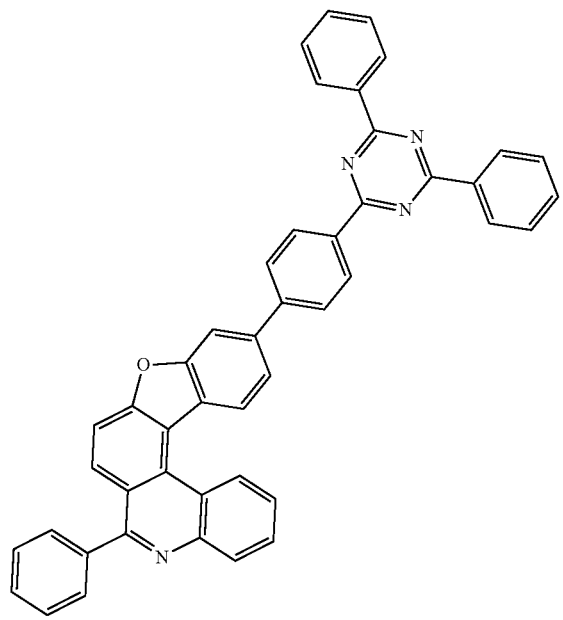
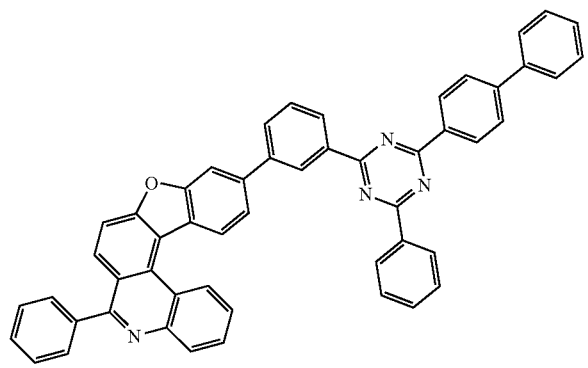
600
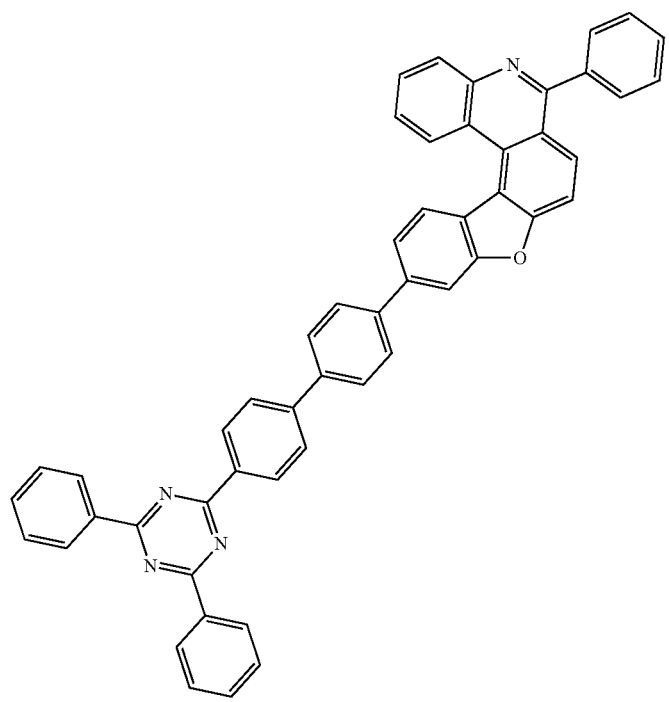

973 974
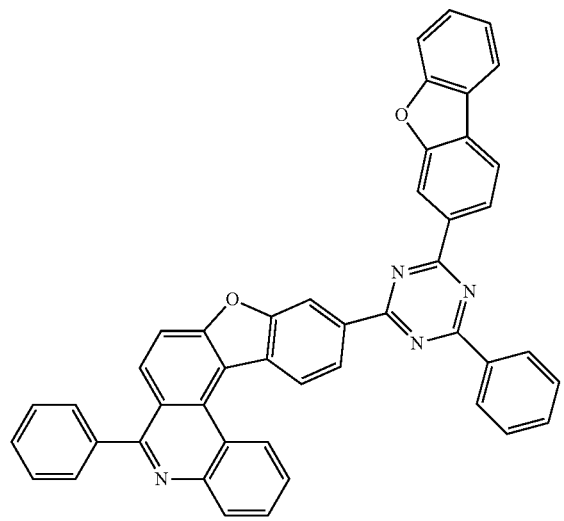 [SMILES: c1ccc(-c2nc(-c3ccc4c(c3)oc3ccccc34)nc(-c3ccc4c(c3)oc3ccc5c(-c6ccccc6)nc6ccccc6c5c34)n2)cc1]
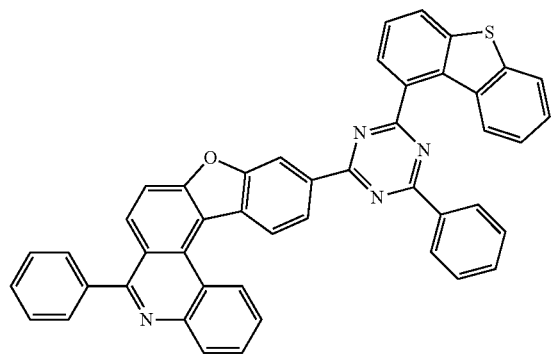
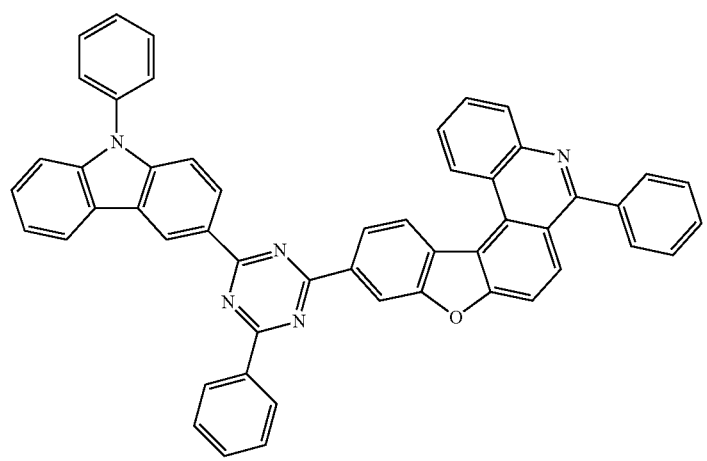
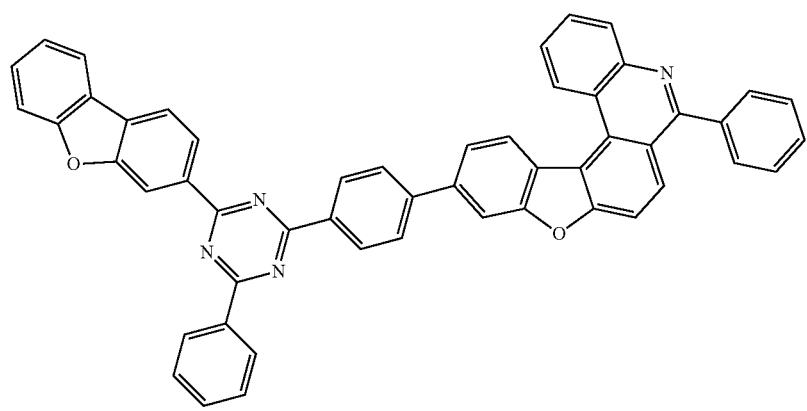

-continued
605
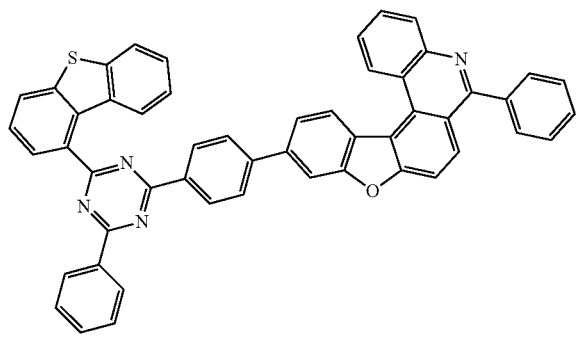
606
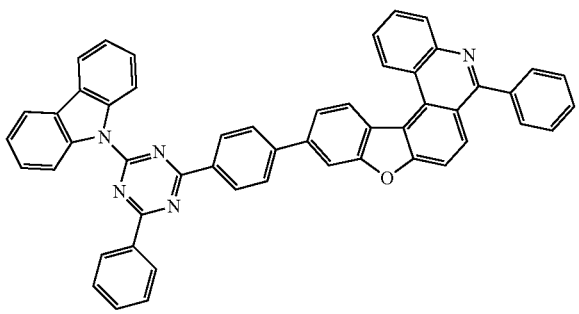 [SMILES: c1ccc(-c2nc(-c3ccc(-c4ccc5c(c4)oc4ccc6c(-c7ccccc7)nc7ccccc7c6c45)cc3)nc(-n3c4ccccc4c4ccccc43)n2)cc1]
607
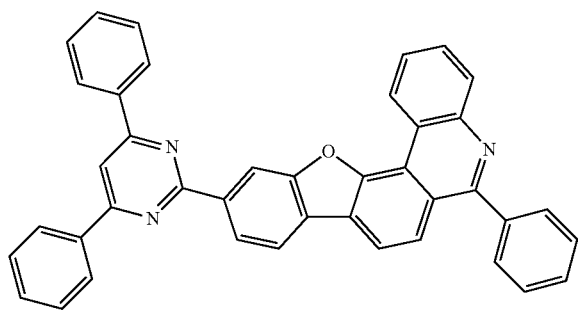
608
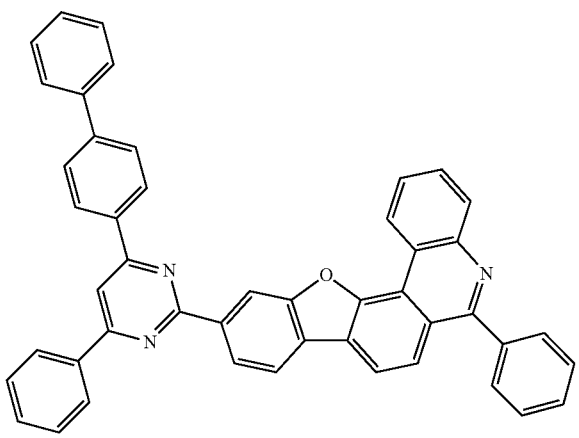
609
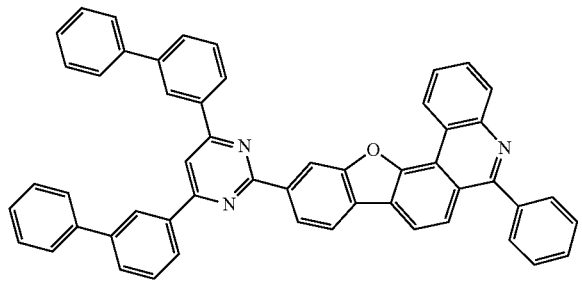
610
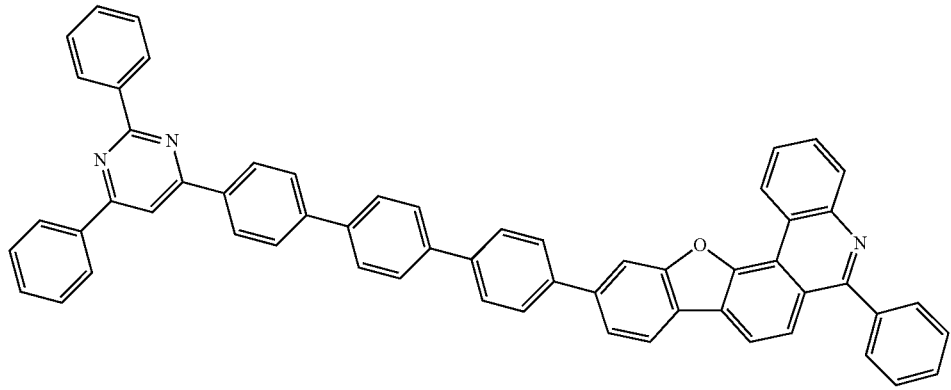

-continued
611
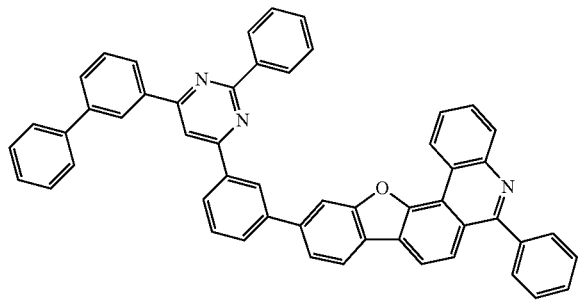 [SMILES: c1ccc(-c2cccc(-c3cc(-c4cccc(-c5ccc6c(c5)oc5c6ccc6c(-c7ccccc7)nc7ccccc7c65)c4)nc(-c4ccccc4)n3)c2)cc1]
612
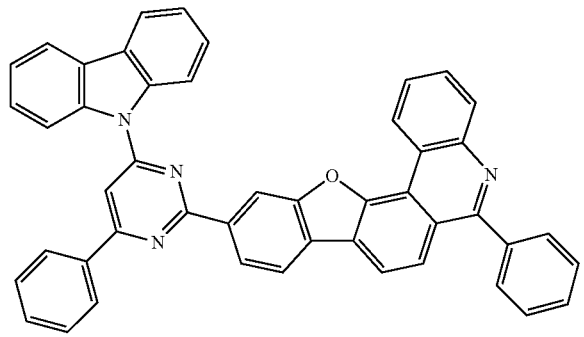 [SMILES: c1ccc(-c2cc(-n3c4ccccc4c4ccccc43)nc(-c3ccc4c(c3)oc3c4ccc4c(-c5ccccc5)nc5ccccc5c43)n2)cc1]
613
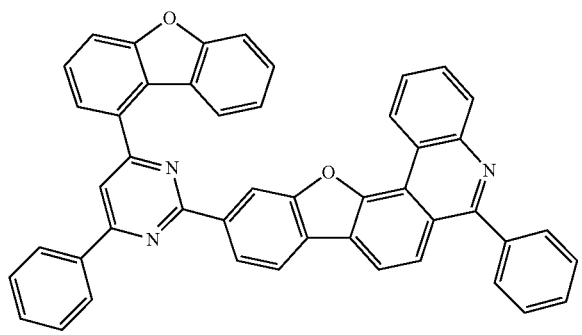
614
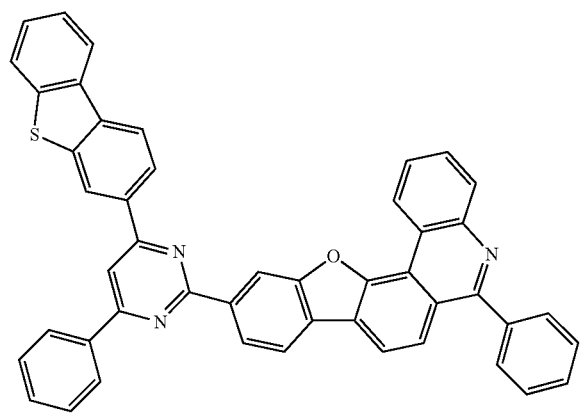
615
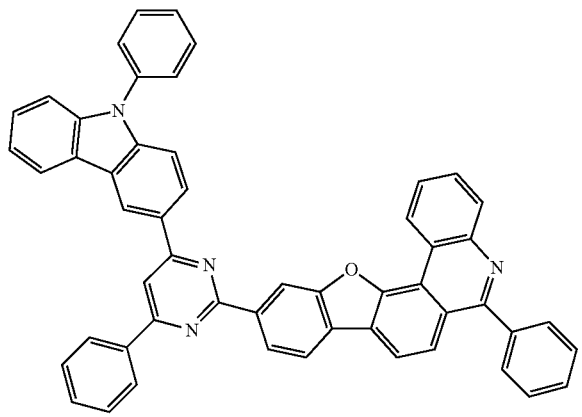
616
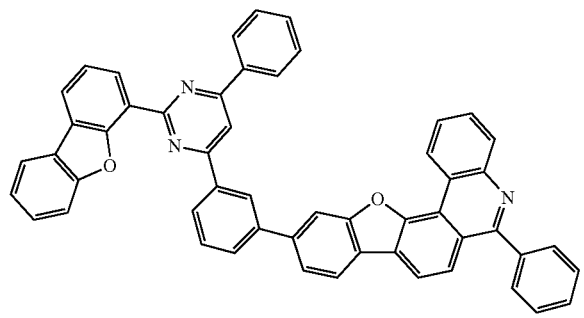
617
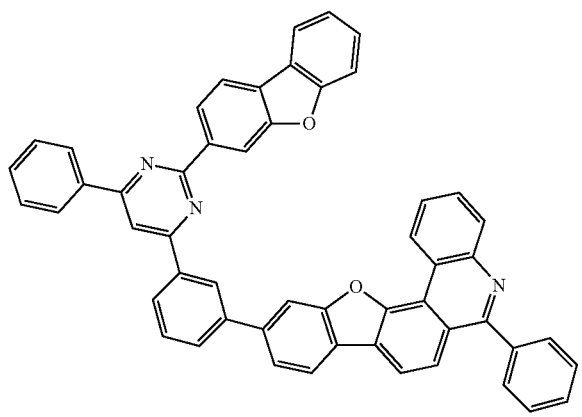
618
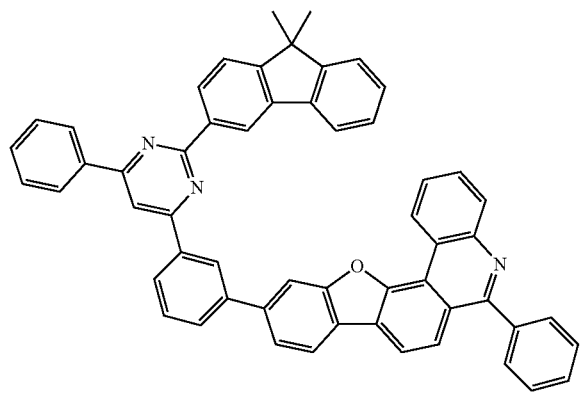

-continued
619
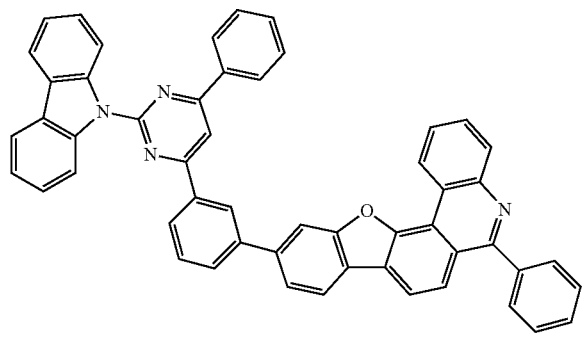
620
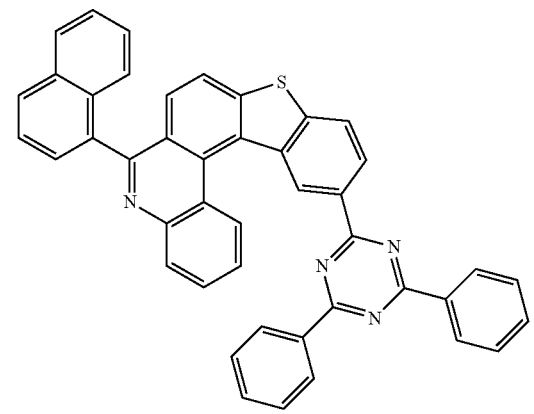
621
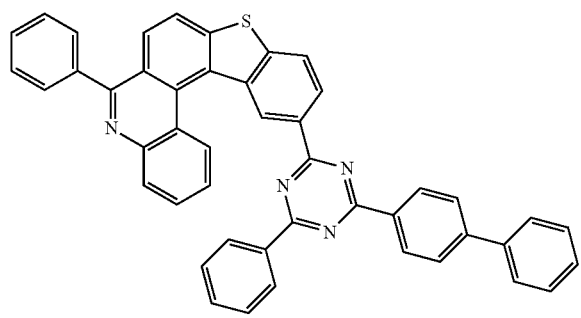
622
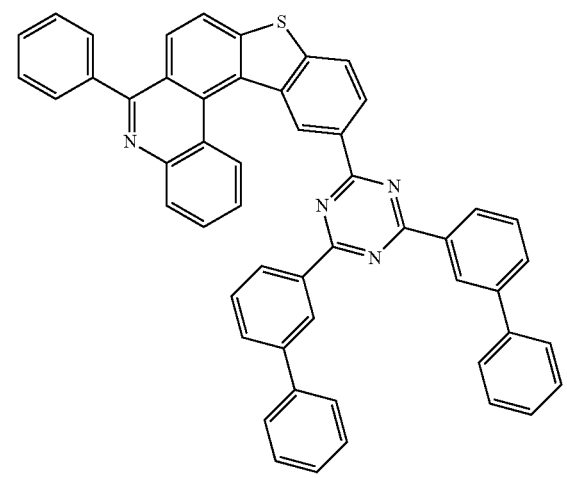
623
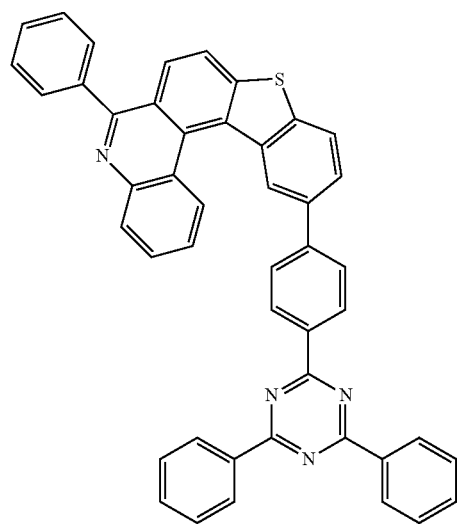
624
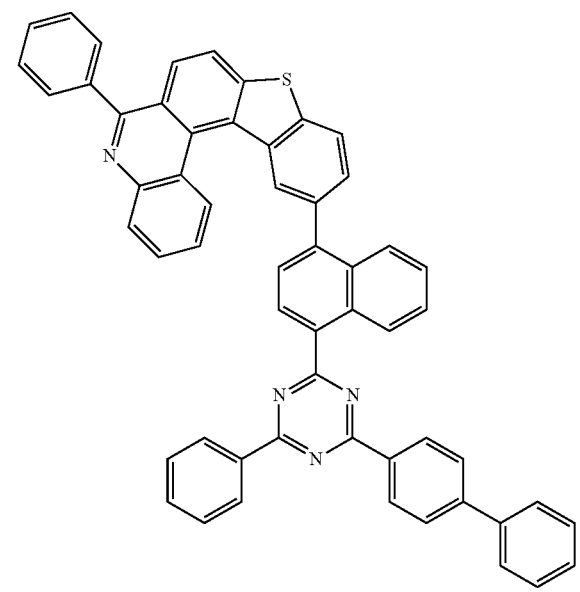

-continued
981
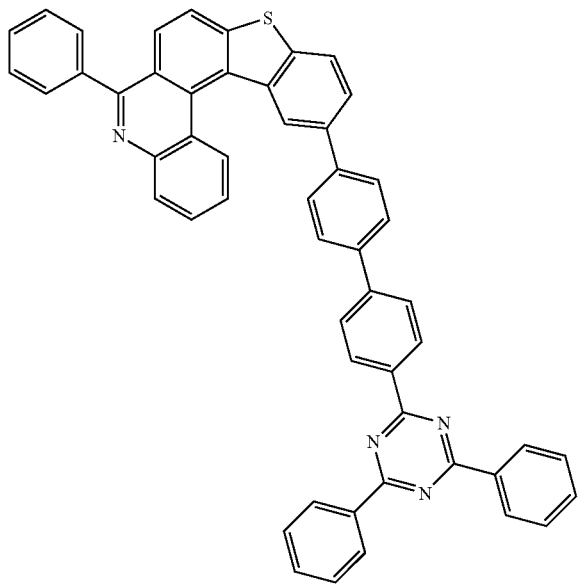
625
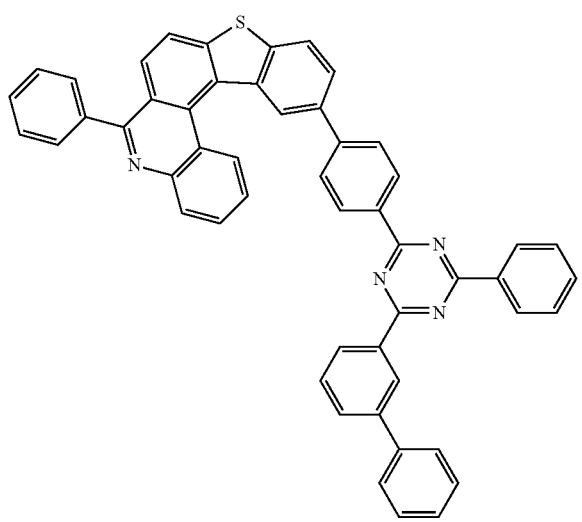
627
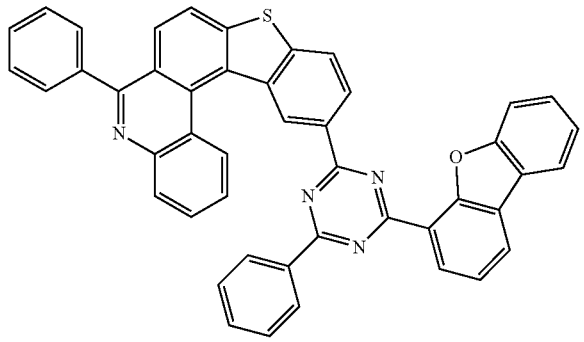
629
982
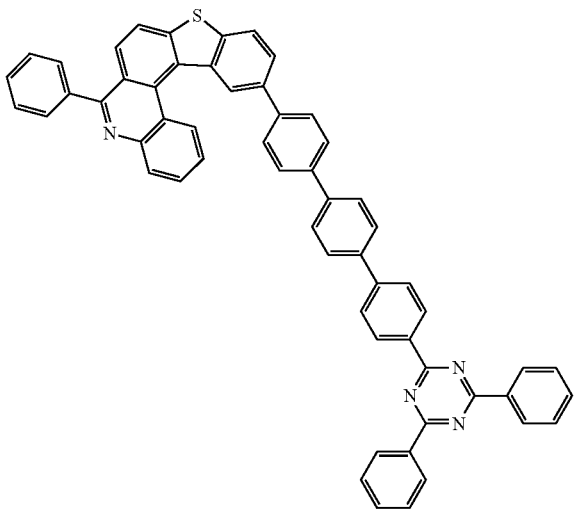
626
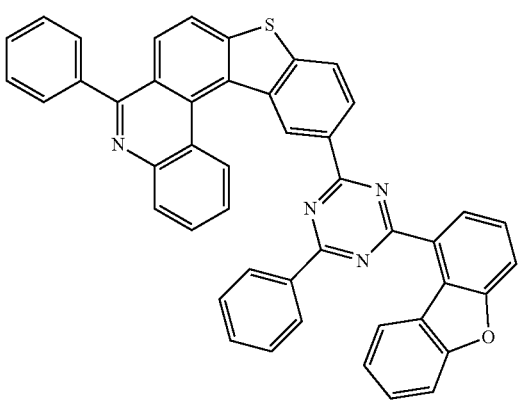
628
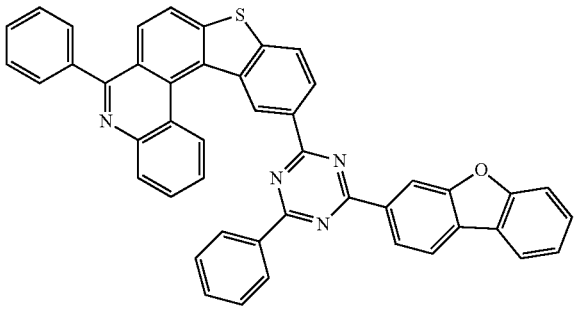
630

-continued
631
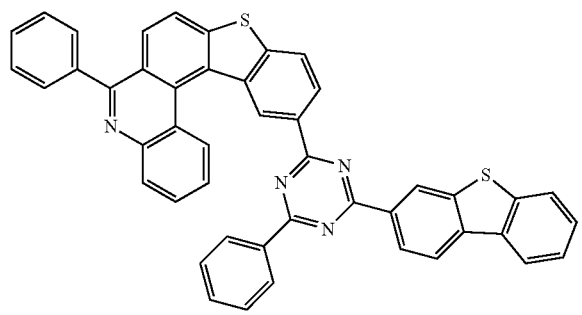
632
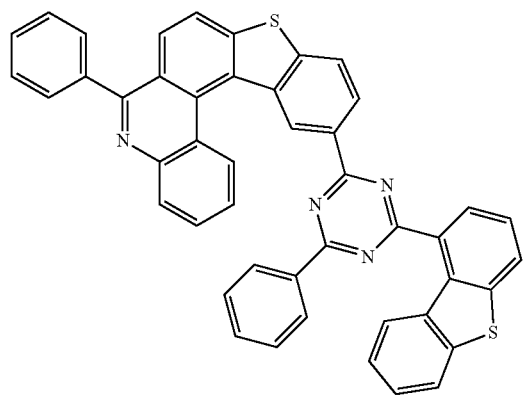
633
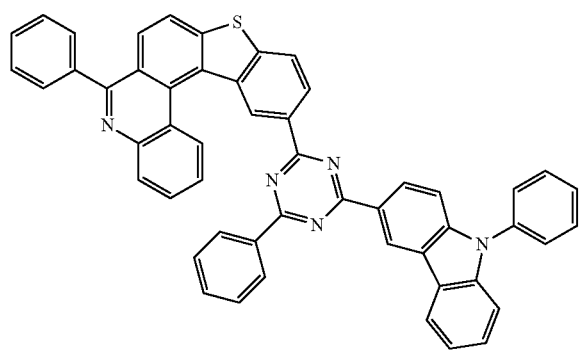
634
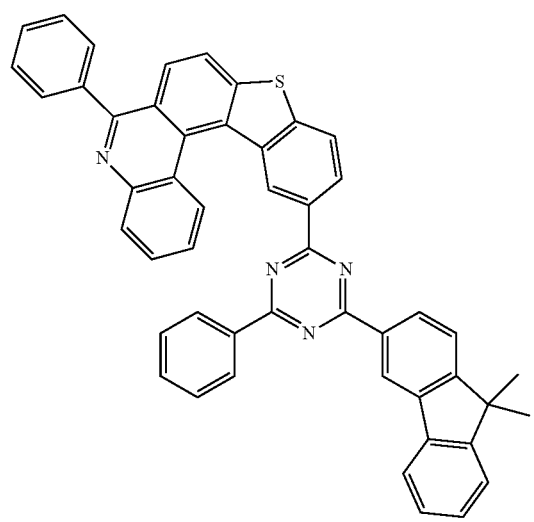
635
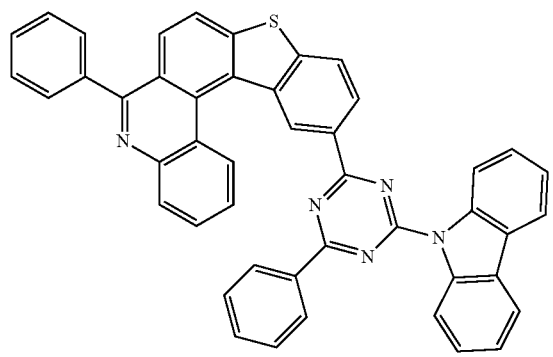
636
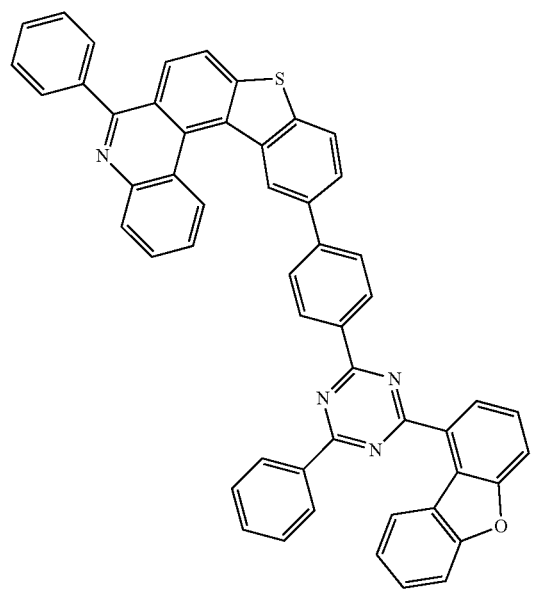 [SMILES: c1ccc(-c2nc(-c3ccc(-c4ccc5sc6ccc7c(-c8ccccc8)nc8ccccc8c7c6c5c4)cc3)nc(-c3cccc4oc5ccccc5c34)n2)cc1]

-continued
637
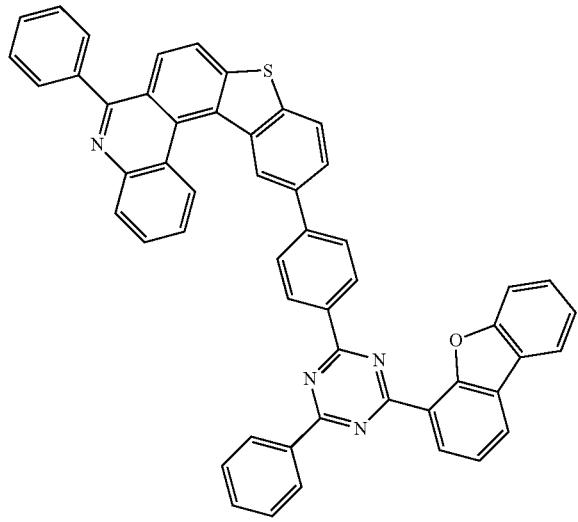
638
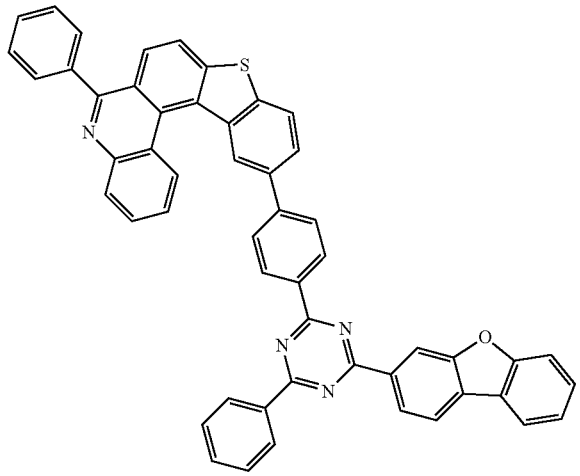
639
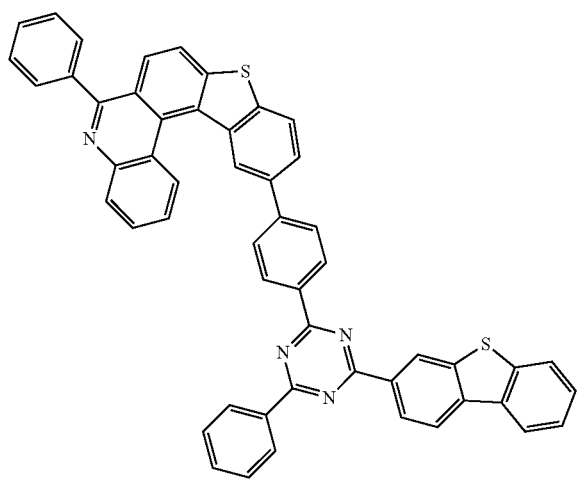
640
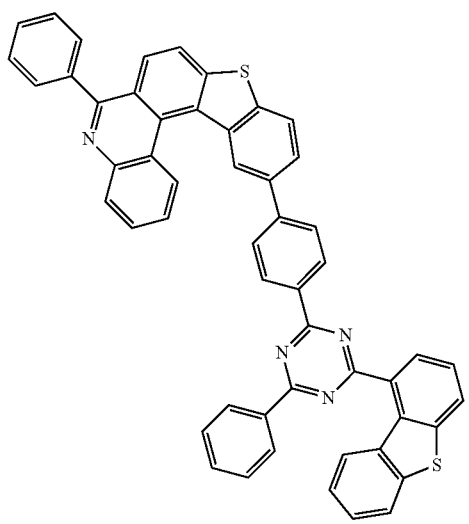
641
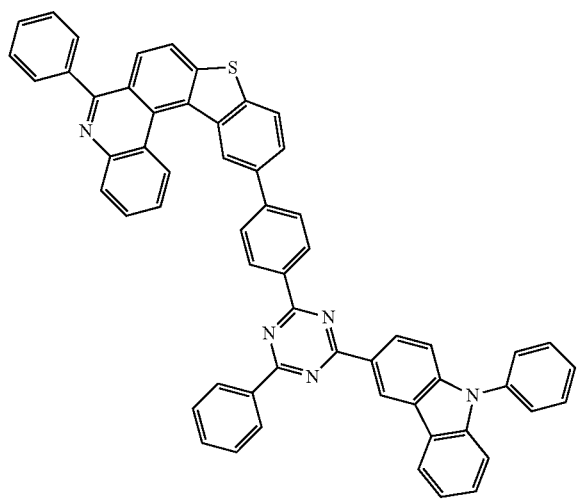
642
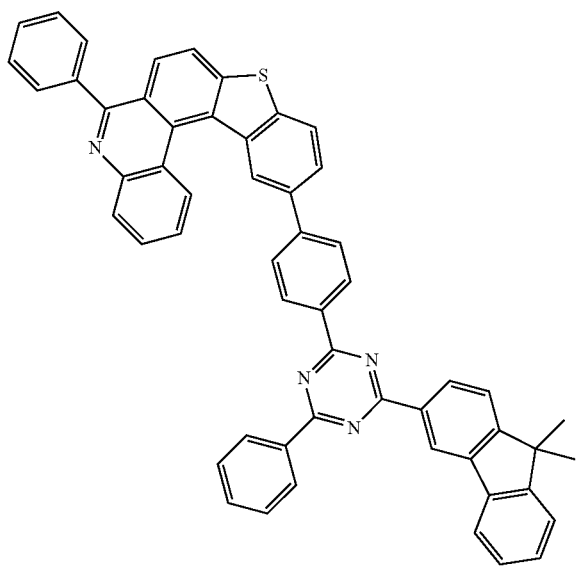

-continued
643
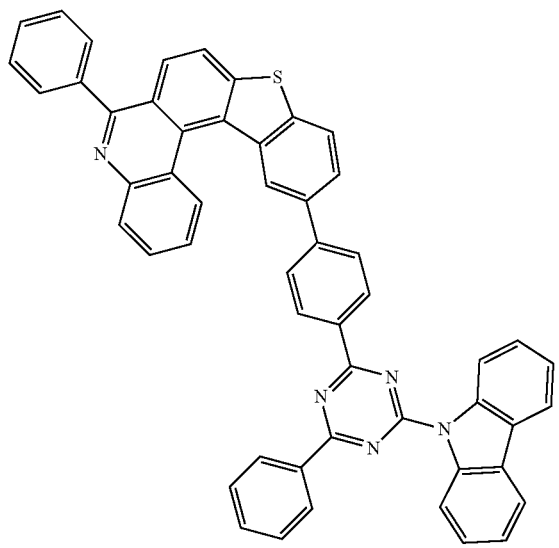
644
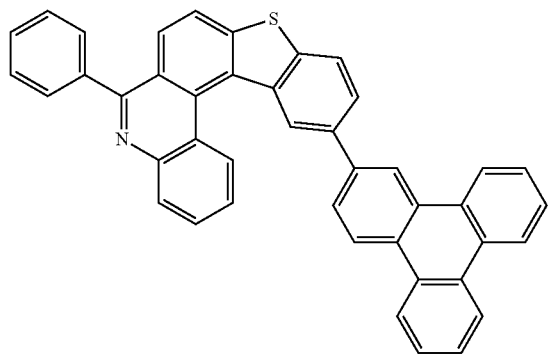
645
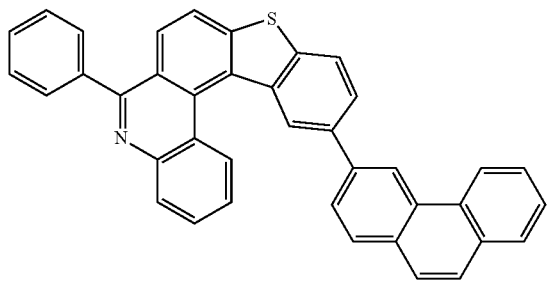
646
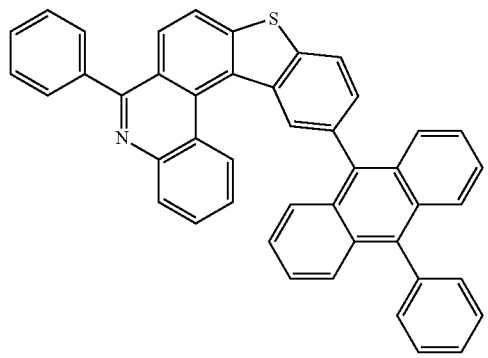
647
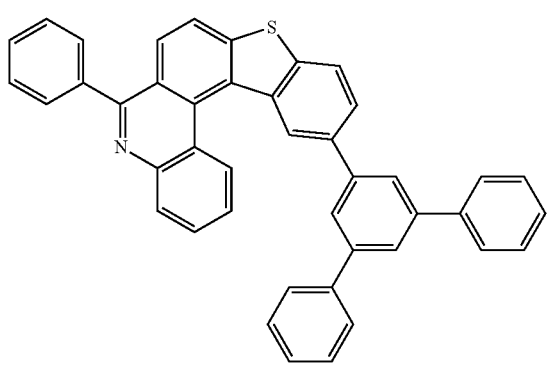
648
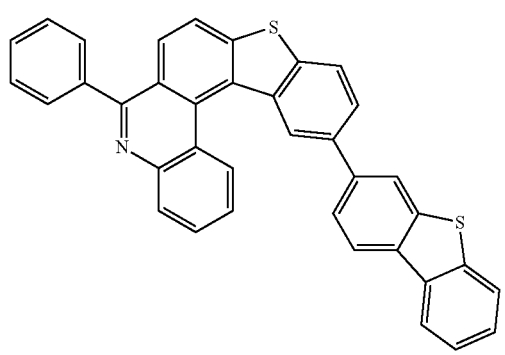

-continued
989
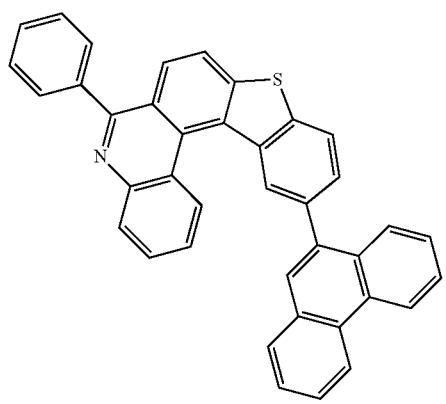 [SMILES: c1ccc(-c2nc3ccccc3c3c2ccc2sc4ccc(-c5cc6ccccc6c6ccccc56)cc4c23)cc1]
649
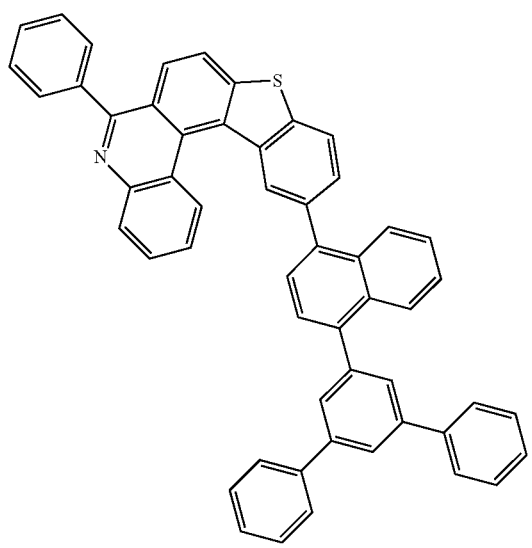 [SMILES: c1ccc(-c2cc(-c3ccccc3)cc(-c3ccc(-c4ccc5sc6ccc7c(-c8ccccc8)nc8ccccc8c7c6c5c4)c4ccccc34)c2)cc1]
651
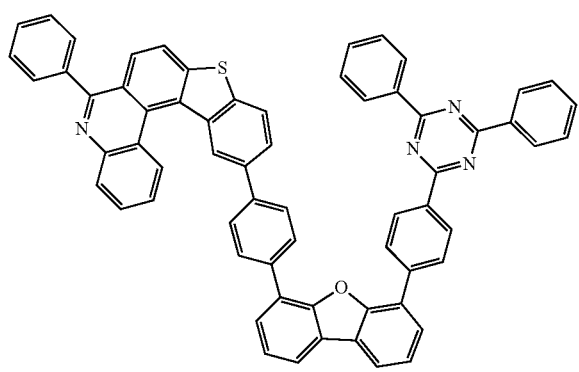 [SMILES: c1ccc(-c2nc(-c3ccccc3)nc(-c3ccc(-c4cccc5c4oc4c(-c6ccc(-c7ccc8sc9ccc%10c(-c%11ccccc%11)nc%11ccccc%11c%10c9c8c7)cc6)cccc45)cc3)n2)cc1]
653
990
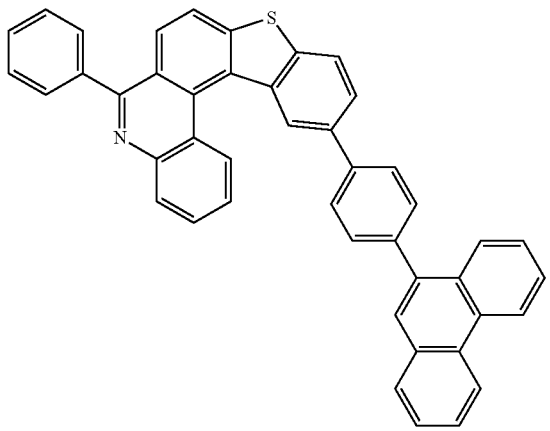
650
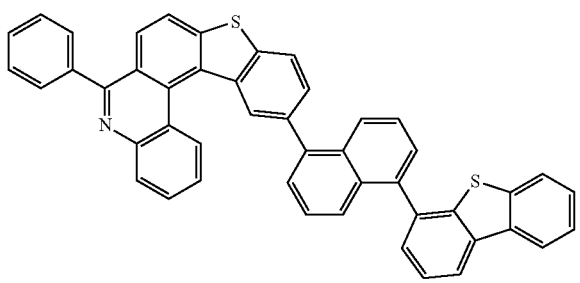
652
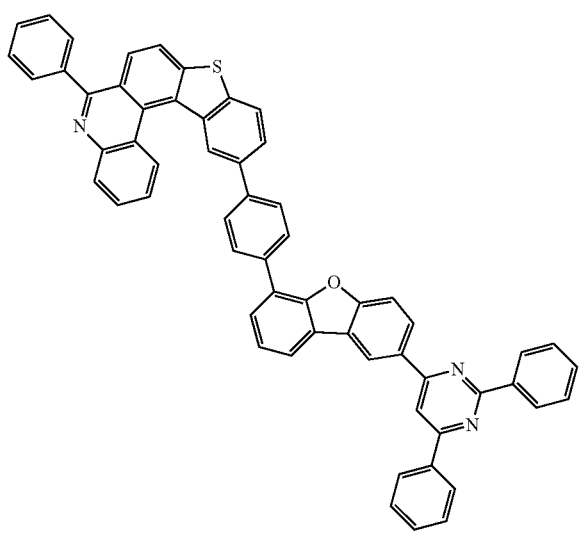 [SMILES: c1ccc(-c2cc(-c3ccc4oc5c(-c6ccc(-c7ccc8sc9ccc%10c(-c%11ccccc%11)nc%11ccccc%11c%10c9c8c7)cc6)cccc5c4c3)nc(-c3ccccc3)n2)cc1]
654

991 992
-continued
655
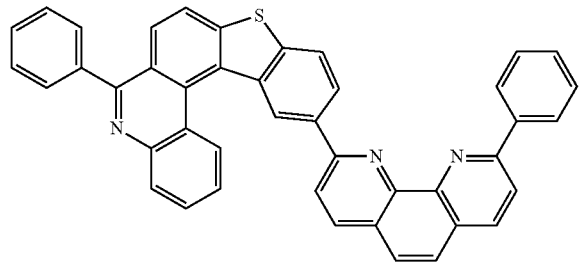
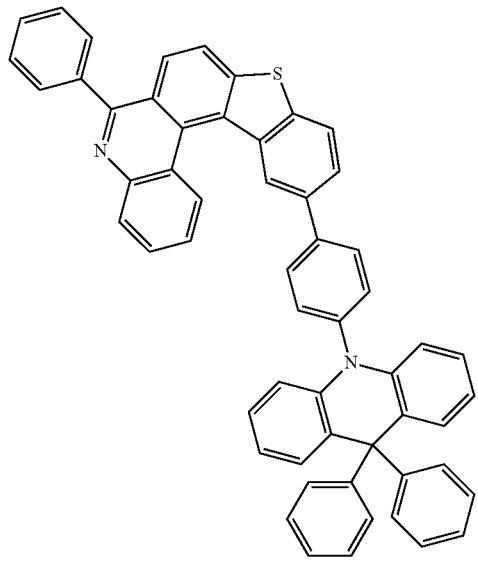 [SMILES: c1ccc(-c2nc3ccccc3c3c2ccc2sc4ccc(-c5ccc(N6c7ccccc7C(c7ccccc7)(c7ccccc7)c7ccccc76)cc5)cc4c23)cc1]
656
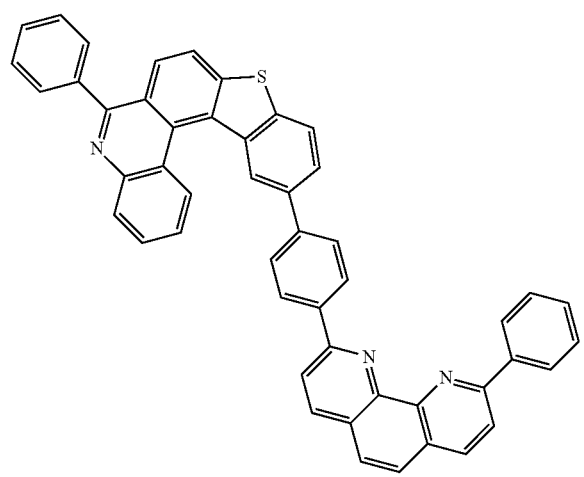
657
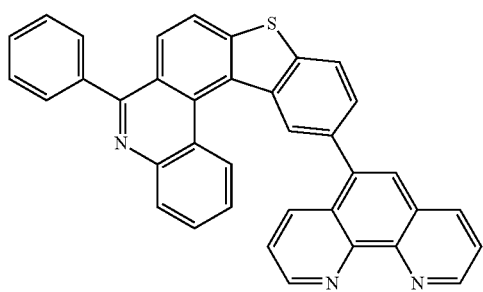
658
659
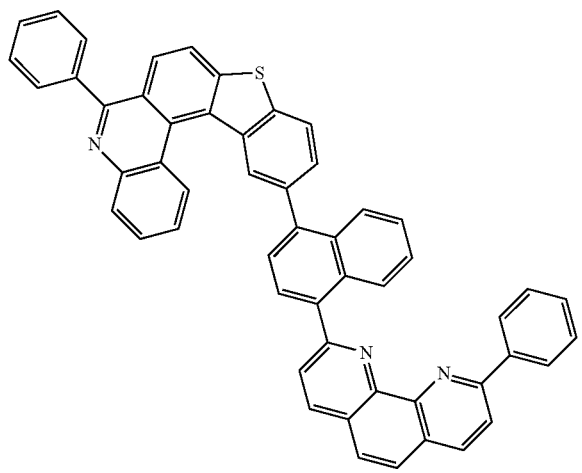 [SMILES: c1ccc(-c2ccc3ccc4ccc(-c5ccc(-c6ccc7sc8ccc9c(-c%10ccccc%10)nc%10ccccc%10c9c8c7c6)c6ccccc56)nc4c3n2)cc1]
660
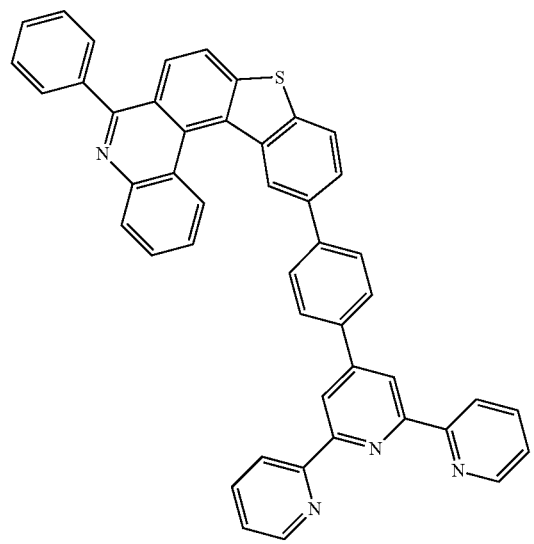 [SMILES: c1ccc(-c2nc3ccccc3c3c2ccc2sc4ccc(-c5ccc(-c6cc(-c7ccccn7)nc(-c7ccccn7)c6)cc5)cc4c23)cc1]

-continued
661
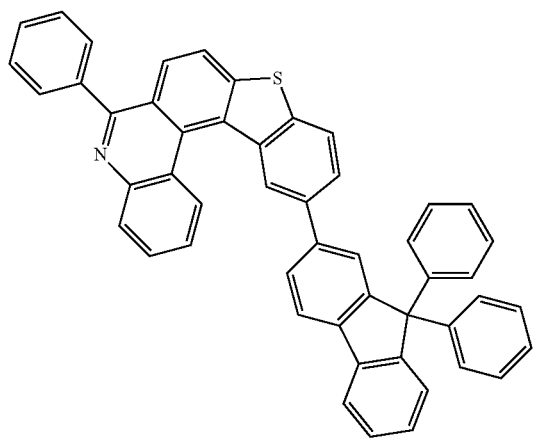 [SMILES: c1ccc(-c2nc3ccccc3c3c2ccc2sc4ccc(-c5ccc6c(c5)C(c5ccccc5)(c5ccccc5)c5ccccc5-6)cc4c23)cc1]
662
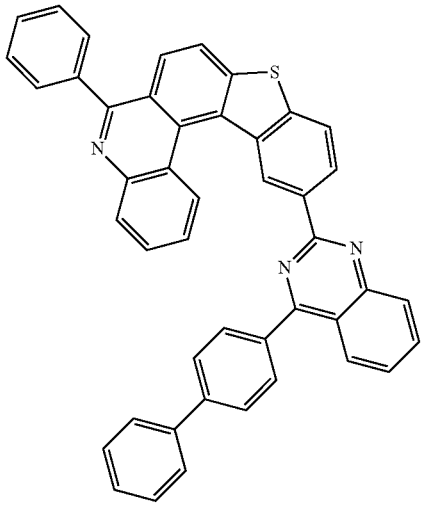
663
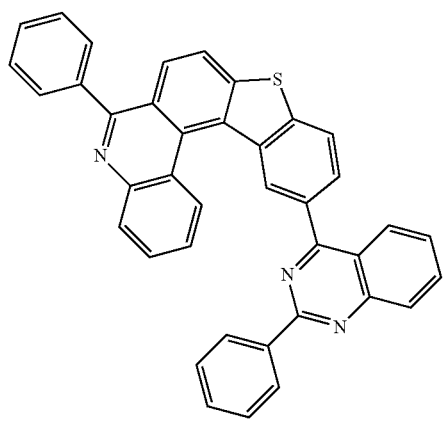
664
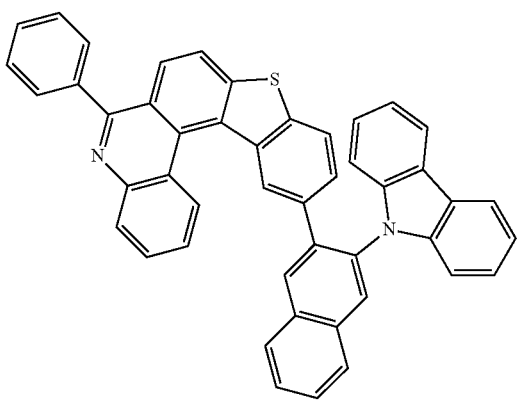 [SMILES: c1ccc(-c2nc3ccccc3c3c2ccc2sc4ccc(-c5cc6ccccc6cc5-n5c6ccccc6c6ccccc65)cc4c23)cc1]
665
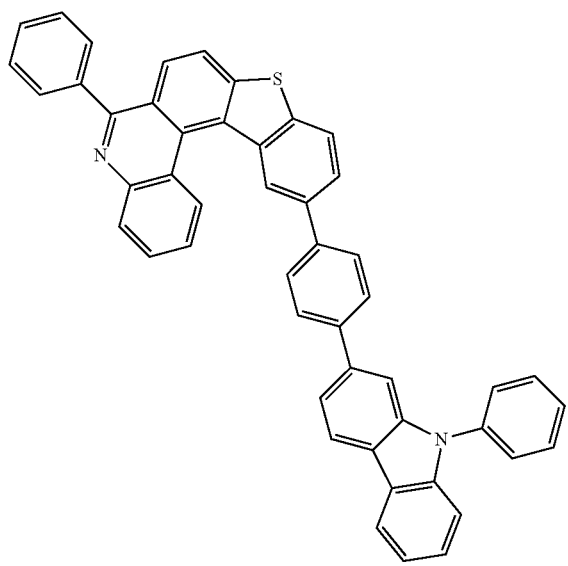
666
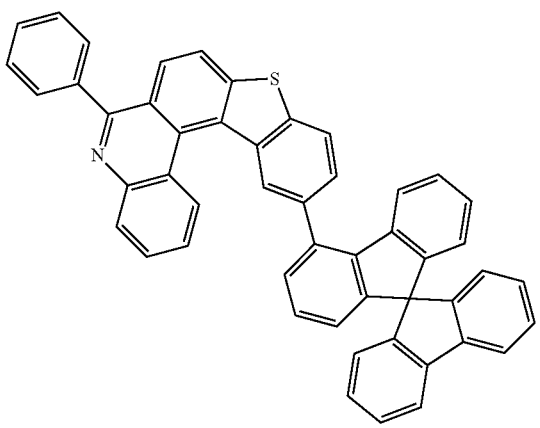 [SMILES: c1ccc(-c2nc3ccccc3c3c2ccc2sc4ccc(-c5cccc6c5-c5ccccc5C65c6ccccc6-c6ccccc65)cc4c23)cc1]

-continued
667
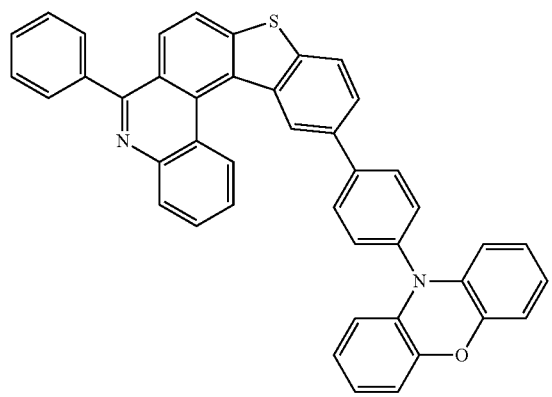
668
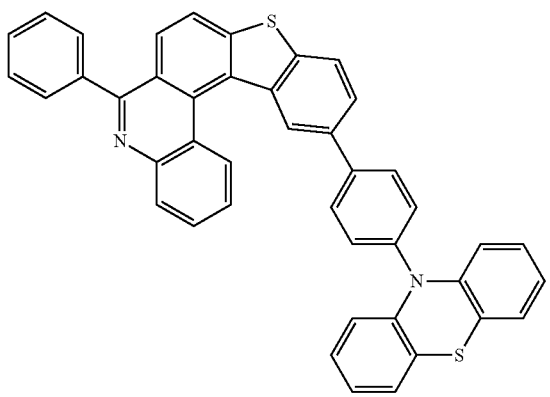
669
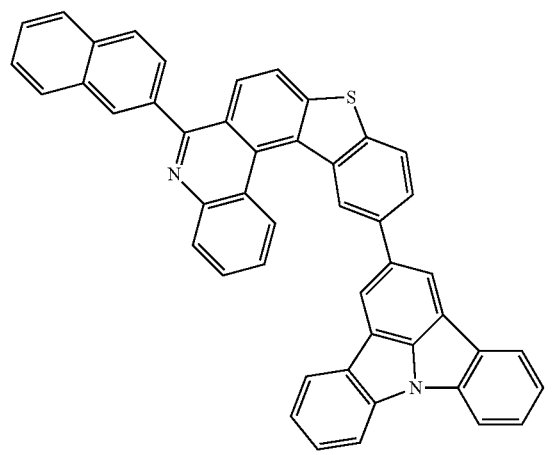
670
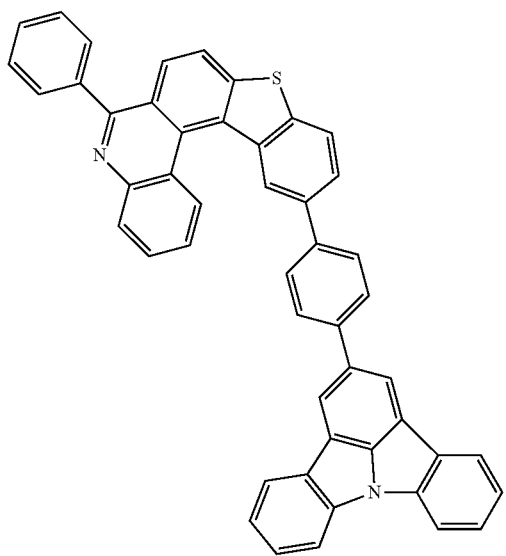 [SMILES: c1ccc(-c2nc3ccccc3c3c2ccc2sc4ccc(-c5ccc(-c6cc7c8ccccc8n8c9ccccc9c(c6)c78)cc5)cc4c23)cc1]
671
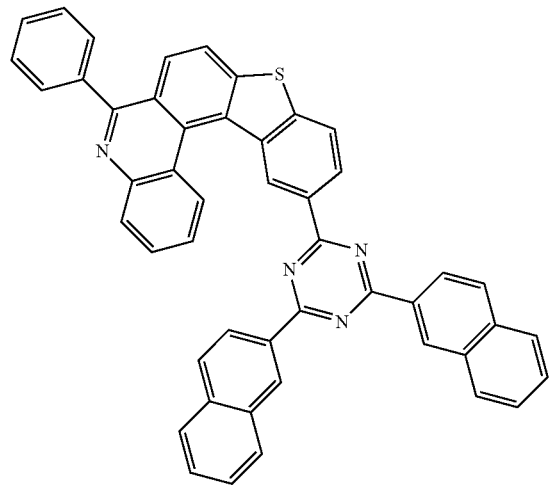
672
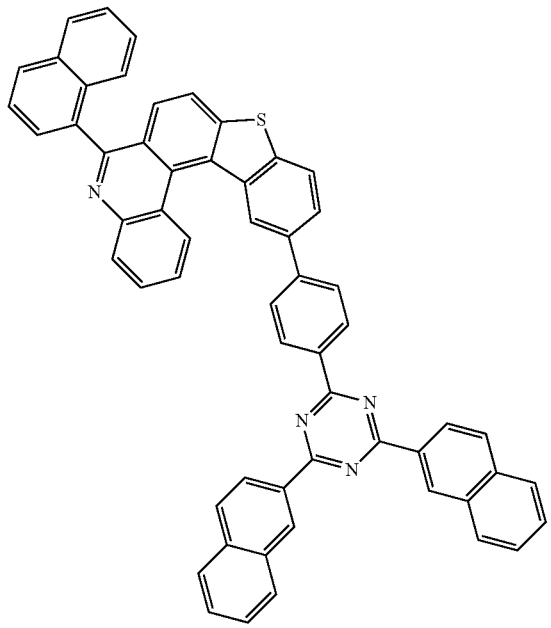

-continued
673
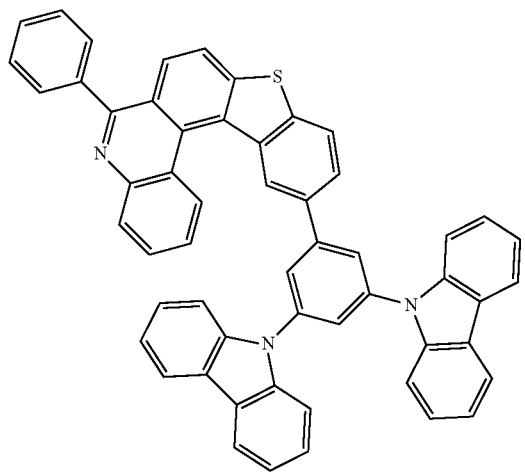
674
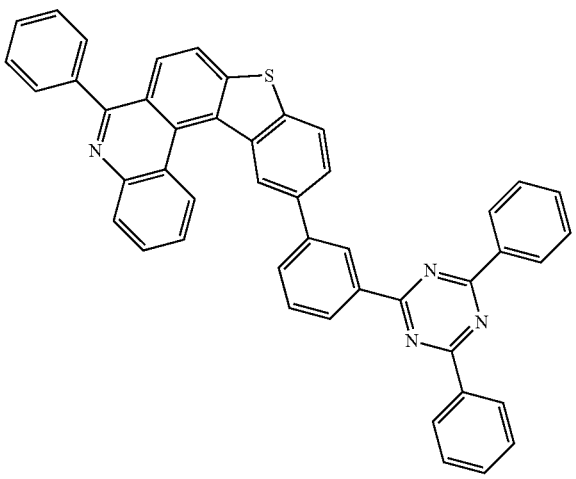 [SMILES: c1ccc(-c2nc(-c3ccccc3)nc(-c3cccc(-c4ccc5sc6ccc7c(-c8ccccc8)nc8ccccc8c7c6c5c4)c3)n2)cc1]
675
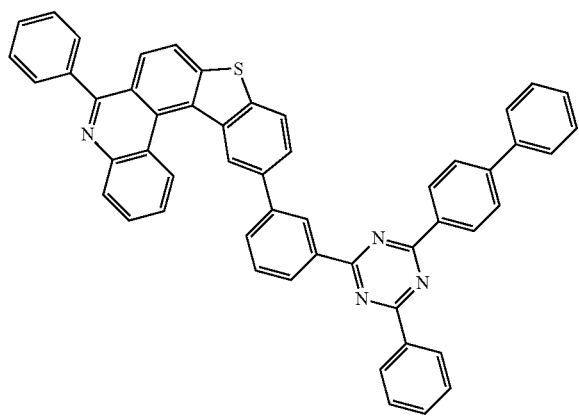 [SMILES: c1ccc(-c2ccc(-c3nc(-c4ccccc4)nc(-c4cccc(-c5ccc6sc7ccc8c(-c9ccccc9)nc9ccccc9c8c7c6c5)c4)n3)cc2)cc1]
676
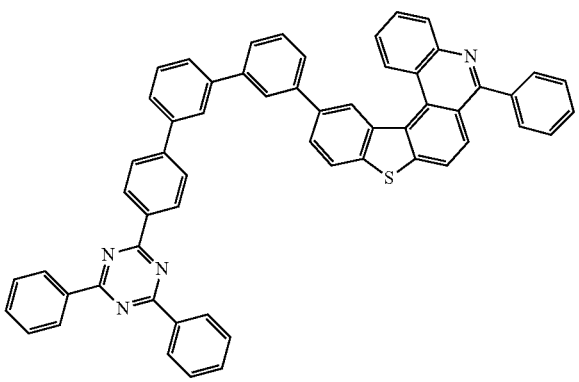
677
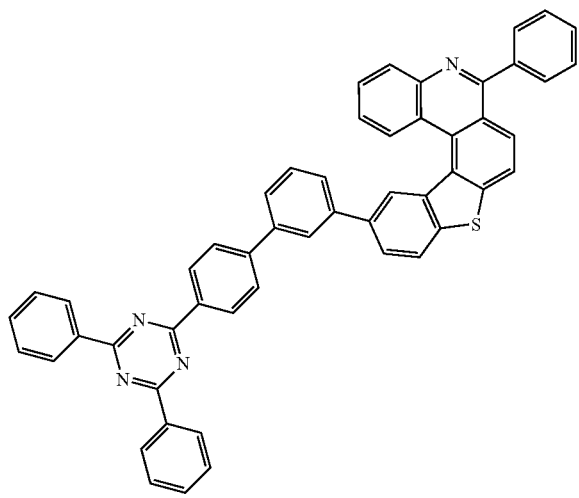 [SMILES: c1ccc(-c2nc(-c3ccccc3)nc(-c3ccc(-c4cccc(-c5ccc6sc7ccc8c(-c9ccccc9)nc9ccccc9c8c7c6c5)c4)cc3)n2)cc1]
678
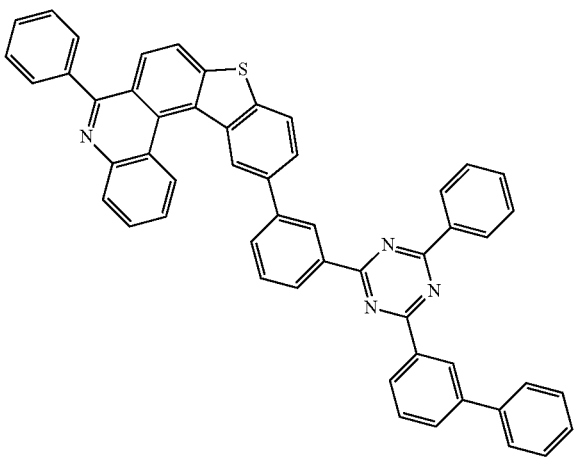

-continued
679
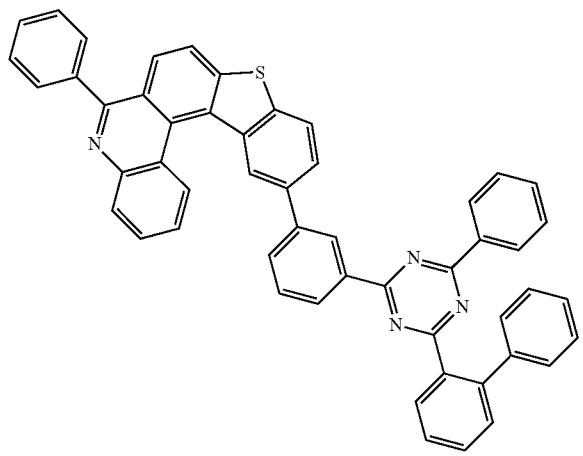
680
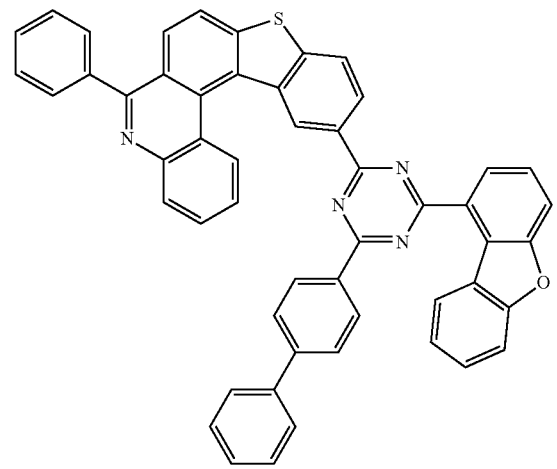 [SMILES: c1ccc(-c2ccc(-c3nc(-c4ccc5sc6ccc7c(-c8ccccc8)nc8ccccc8c7c6c5c4)nc(-c4cccc5oc6ccccc6c45)n3)cc2)cc1]
681
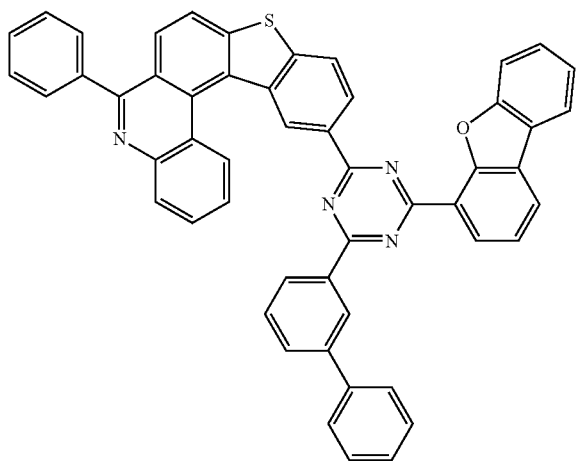
682
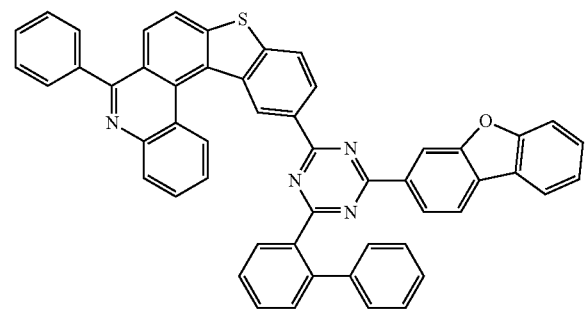 [SMILES: c1ccc(-c2ccccc2-c2nc(-c3ccc4c(c3)oc3ccccc34)nc(-c3ccc4sc5ccc6c(-c7ccccc7)nc7ccccc7c6c5c4c3)n2)cc1]
683
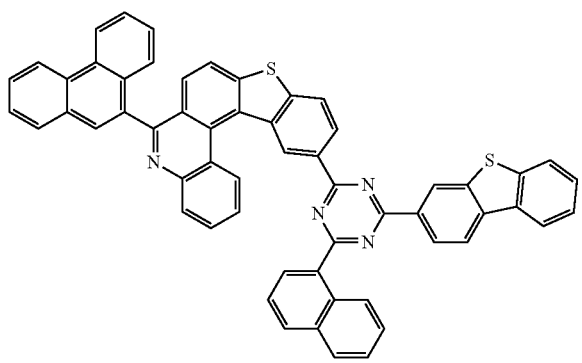
684
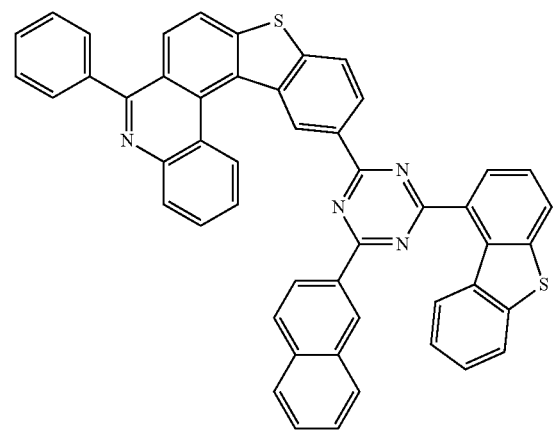

-continued
685
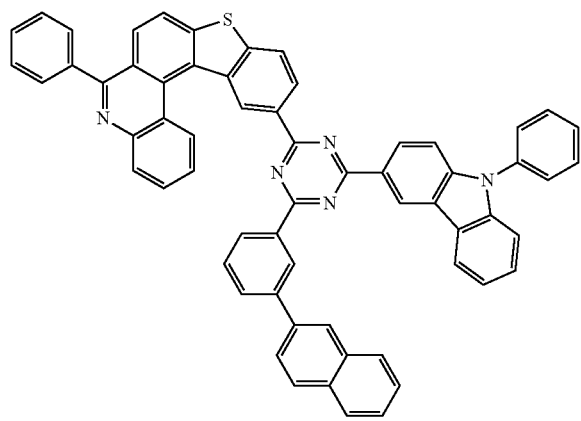
686
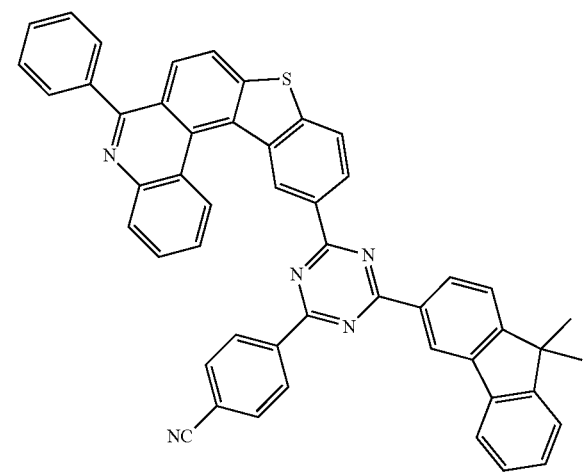
687
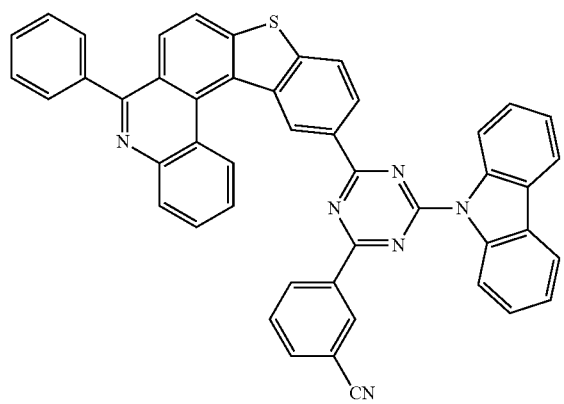 [SMILES: N#Cc1cccc(-c2nc(-c3ccc4sc5ccc6c(-c7ccccc7)nc7ccccc7c6c5c4c3)nc(-n3c4ccccc4c4ccccc43)n2)c1]
688
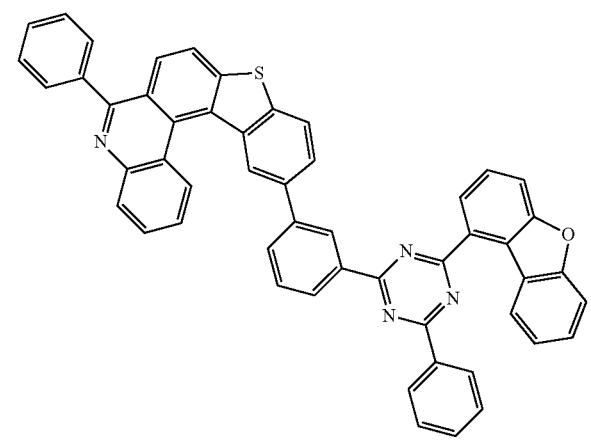 [SMILES: c1ccc(-c2nc(-c3cccc(-c4ccc5sc6ccc7c(-c8ccccc8)nc8ccccc8c7c6c5c4)c3)nc(-c3cccc4oc5ccccc5c34)n2)cc1]
689
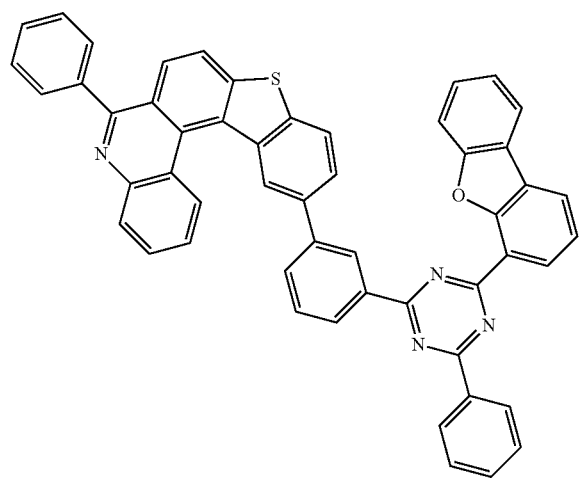
690
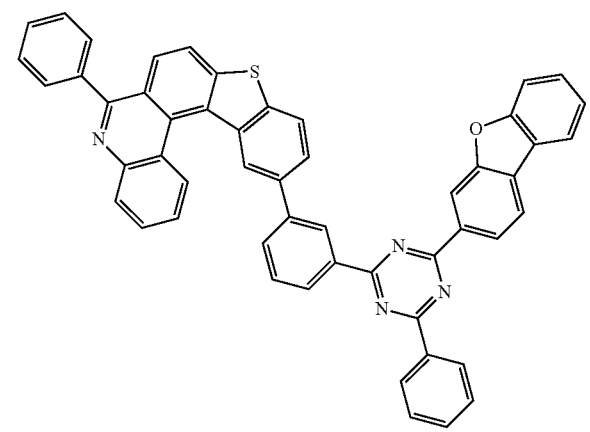 [SMILES: c1ccc(-c2nc(-c3cccc(-c4ccc5sc6ccc7c(-c8ccccc8)nc8ccccc8c7c6c5c4)c3)nc(-c3ccc4c(c3)sc3ccccc34)n2)cc1]

-continued
691
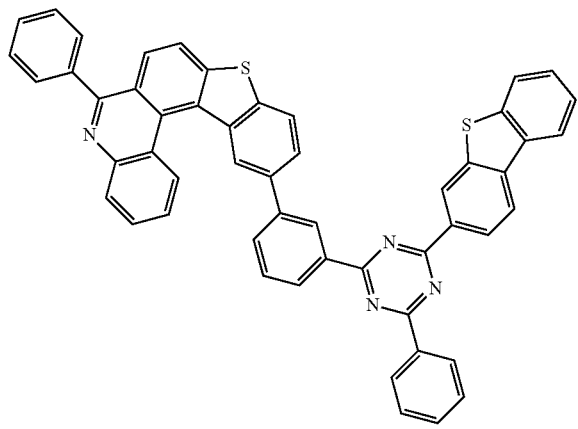
692
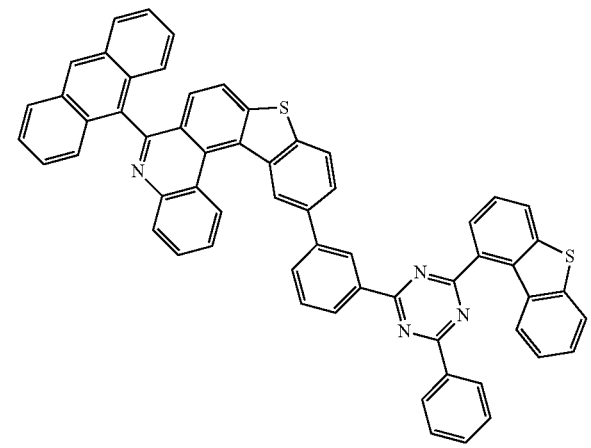
693
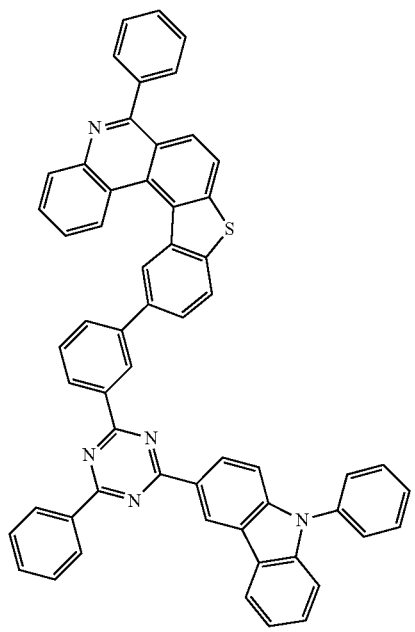
694
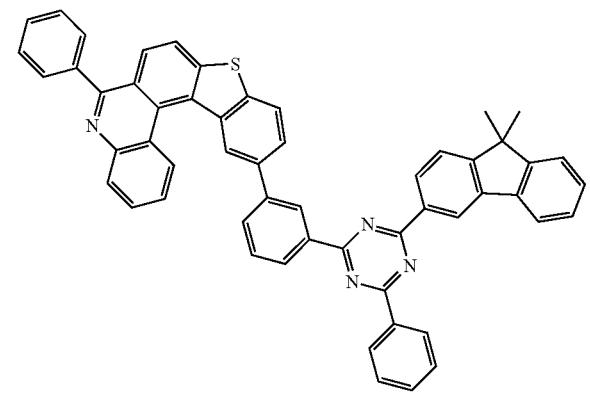
695
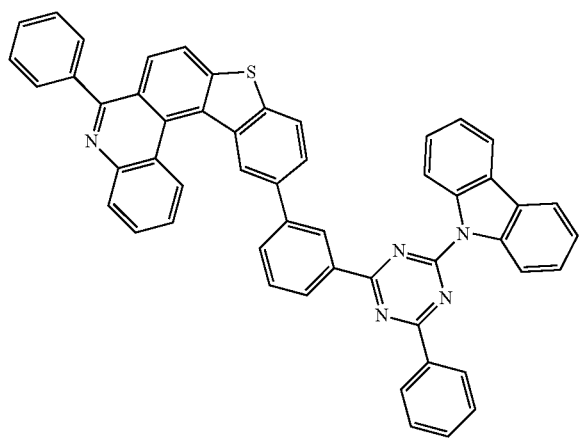 [SMILES: c1ccc(-c2nc(-c3cccc(-c4ccc5sc6ccc7c(-c8ccccc8)nc8ccccc8c7c6c5c4)c3)nc(-n3c4ccccc4c4ccccc43)n2)cc1]
696
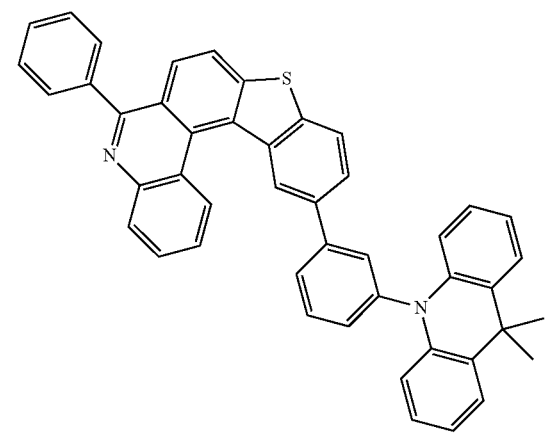 [SMILES: CC1(C)c2ccccc2N(c2cccc(-c3ccc4sc5ccc6c(-c7ccccc7)nc7ccccc7c6c5c4c3)c2)c2ccccc21]

| 1005 | 1006 |
|---|---|
| 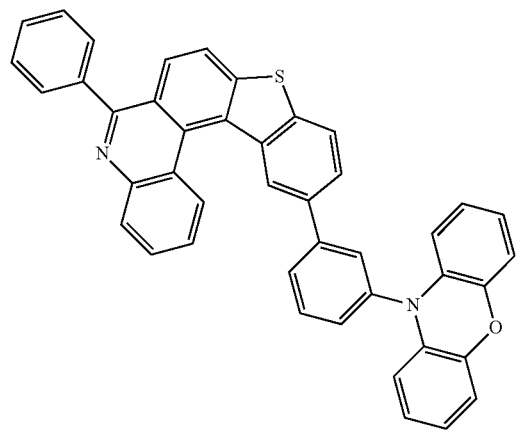 [SMILES: c1ccc(-c2nc3ccccc3c3c2ccc2sc4ccc(-c5cccc(N6c7ccccc7Oc7ccccc76)c5)cc4c23)cc1] | 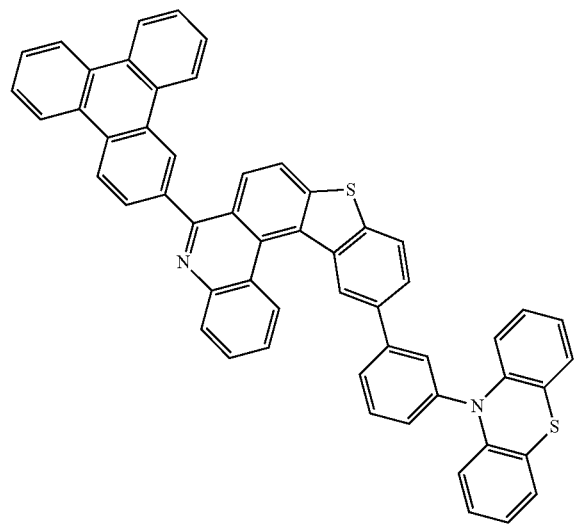 |
| 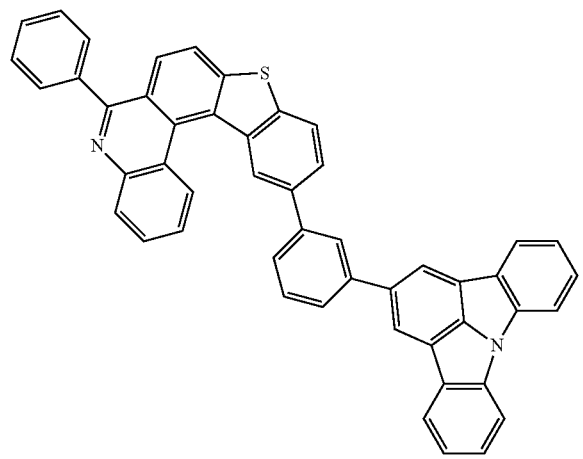 | 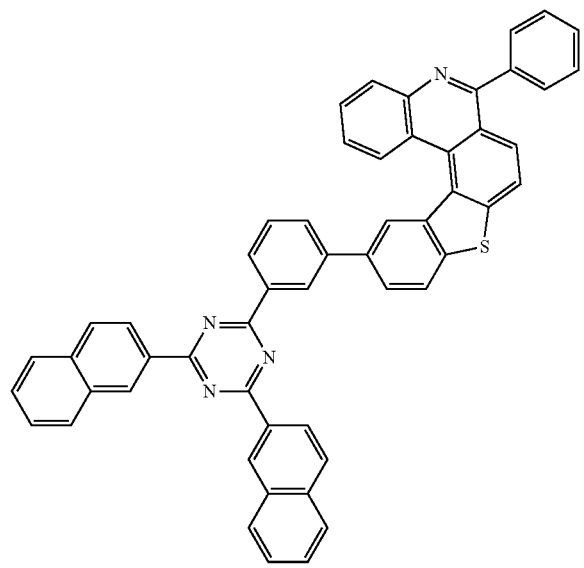 |

-continued
1007
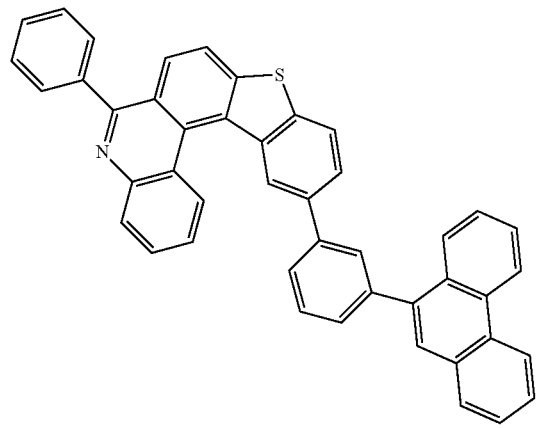
701
1008
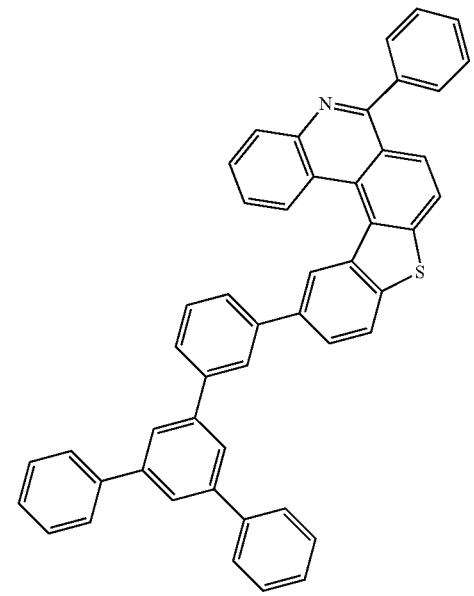
702
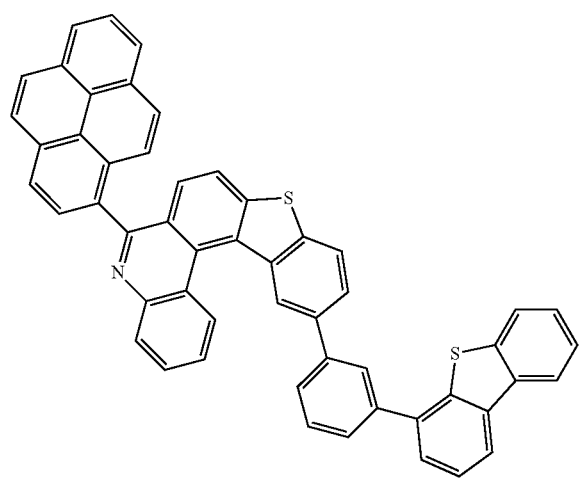
703
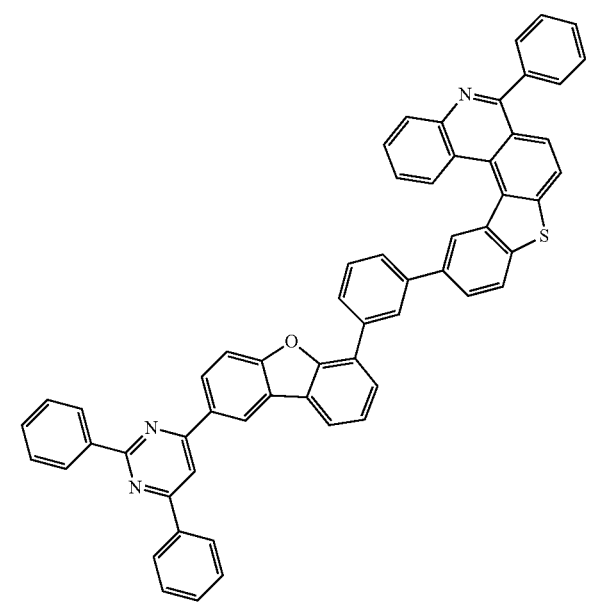
704

-continued
705
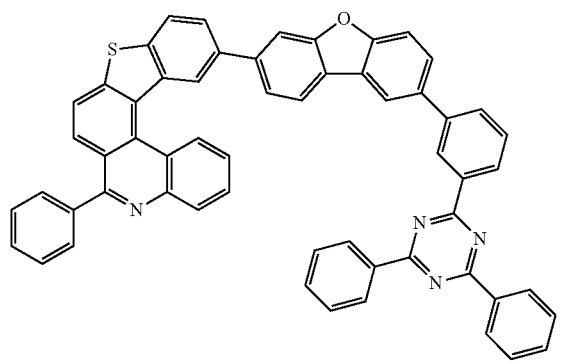
706
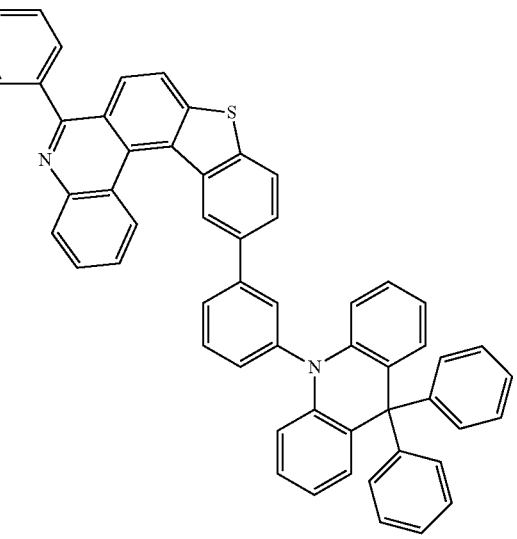
707
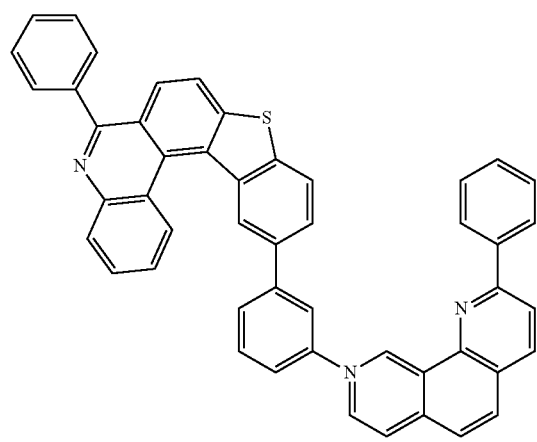 [SMILES: c1ccc(-c2ccc3ccc4ccc(-c5cccc(-c6ccc7sc8ccc9c(-c%10ccccc%10)nc%10ccccc%10c9c8c7c6)c5)nc4c3n2)cc1]
708
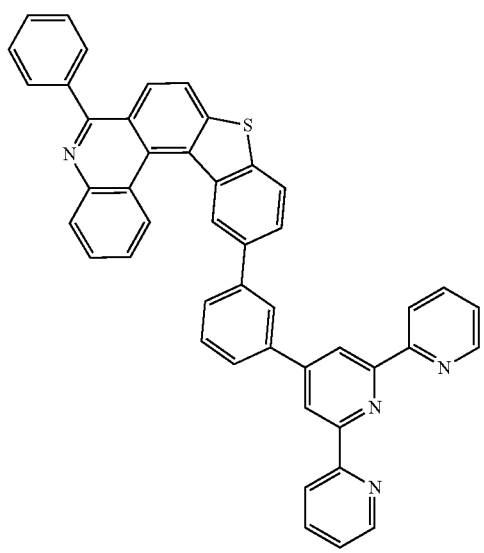
709
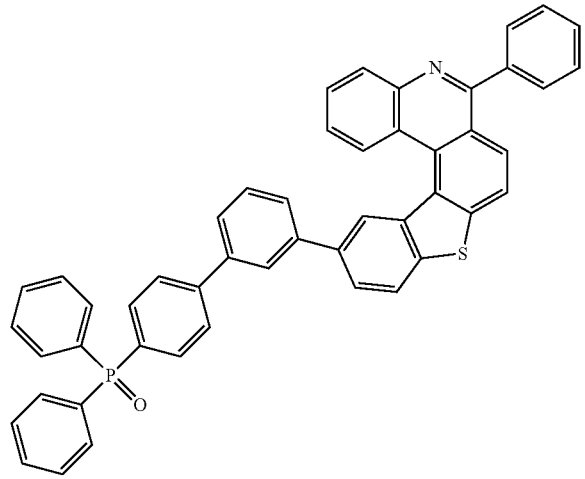
710
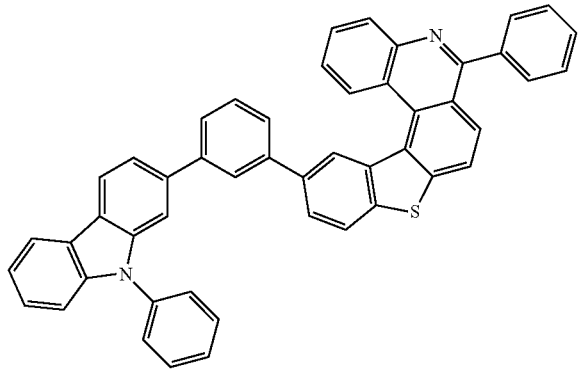

-continued
711
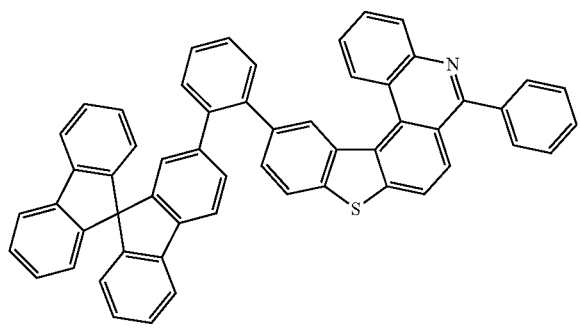
712
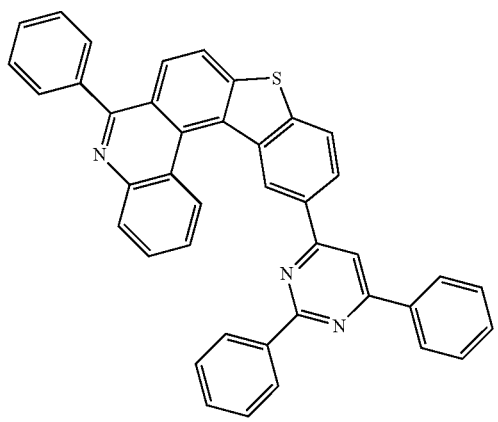
713
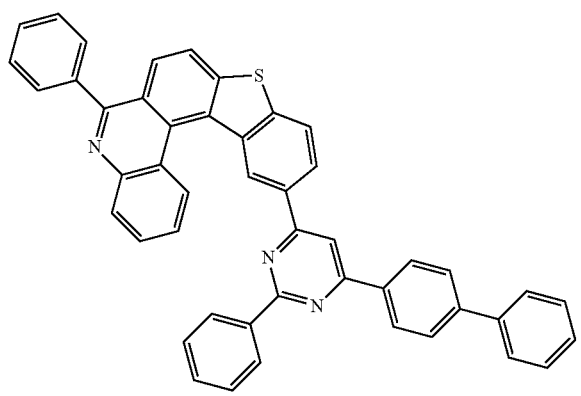 [SMILES: c1ccc(-c2ccc(-c3cc(-c4ccc5sc6ccc7c(-c8ccccc8)nc8ccccc8c7c6c5c4)nc(-c4ccccc4)n3)cc2)cc1]
714
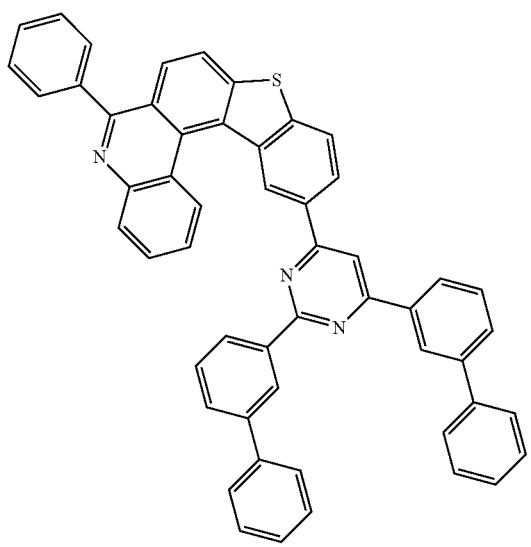 [SMILES: c1ccc(-c2cccc(-c3cc(-c4ccc5sc6ccc7c(-c8ccccc8)nc8ccccc8c7c6c5c4)nc(-c4cccc(-c5ccccc5)c4)n3)c2)cc1]
715
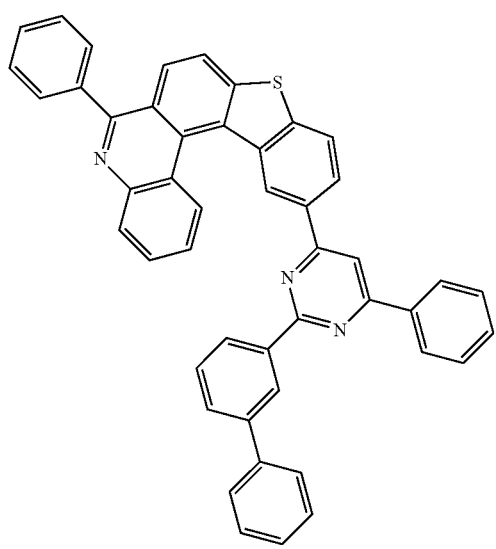
716
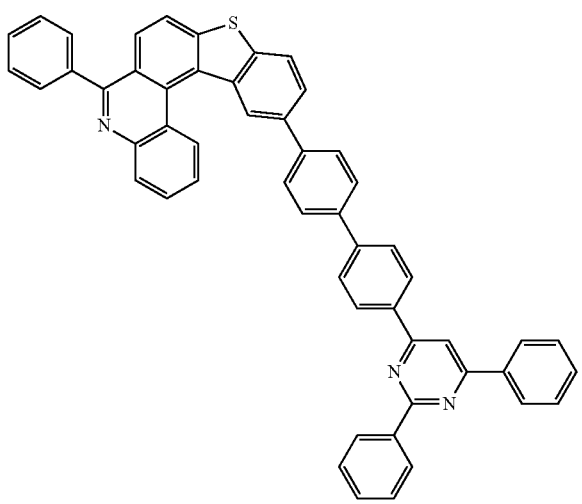 [SMILES: c1ccc(-c2cc(-c3ccc(-c4ccc(-c5ccc6sc7ccc8c(-c9ccccc9)nc9ccccc9c8c7c6c5)cc4)cc3)nc(-c3ccccc3)n2)cc1]

-continued
1013
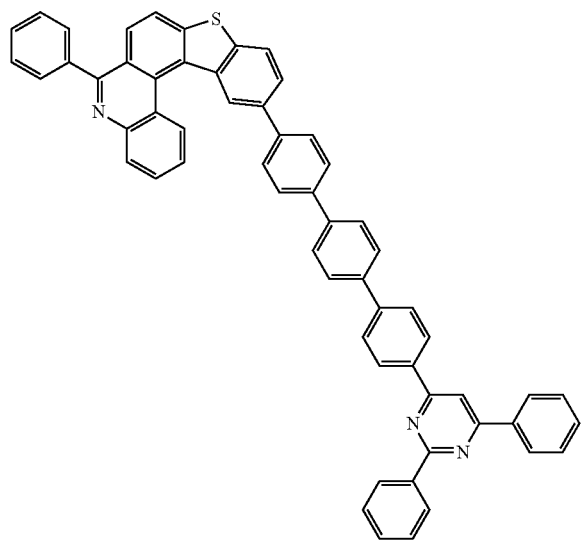 [SMILES: c1ccc(-c2cc(-c3ccc(-c4ccc(-c5ccc(-c6ccc7sc8ccc9c(-c%10ccccc%10)nc%10ccccc%10c9c8c7c6)cc5)cc4)cc3)nc(-c3ccccc3)n2)cc1]
717
1014
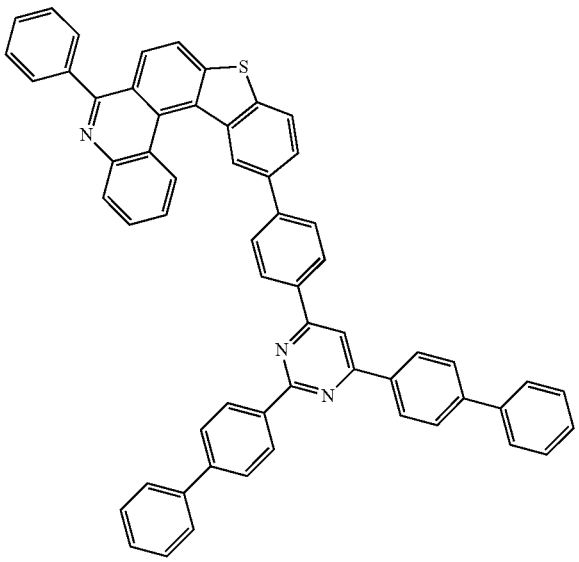
718
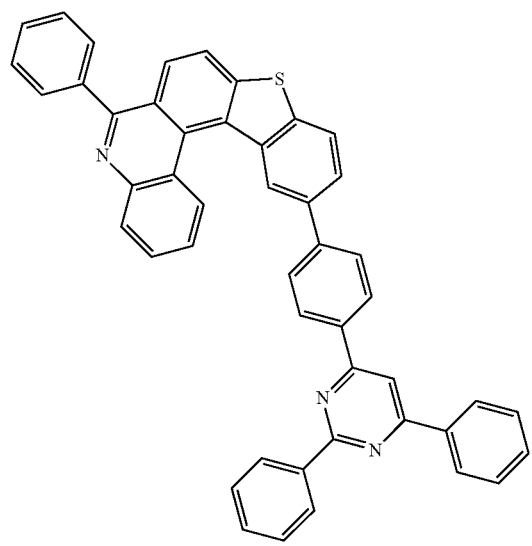
719
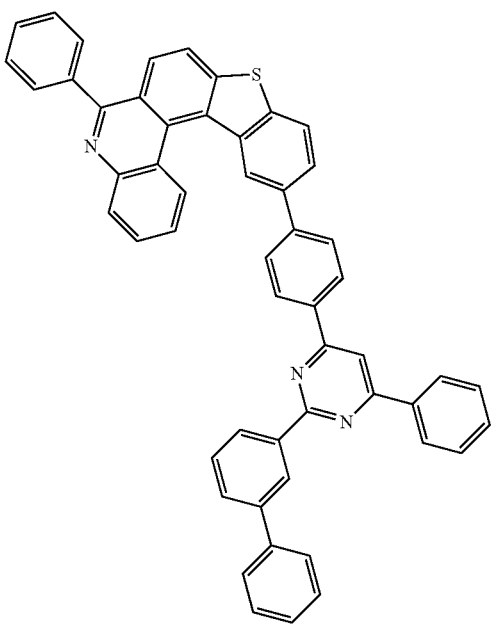
720

1015 1016
-continued
| 721 | 722 |
|---|---|
| 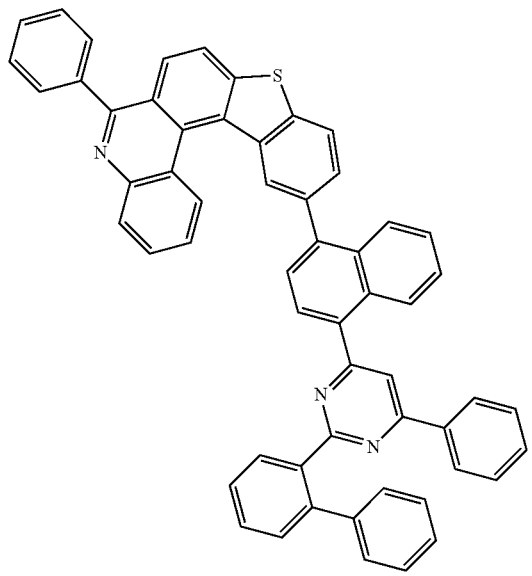 [SMILES: c1ccc(-c2cc(-c3ccc(-c4ccc5sc6ccc7c(-c8ccccc8)nc8ccccc8c7c6c5c4)c4ccccc34)nc(-c3ccccc3-c3ccccc3)n2)cc1] | 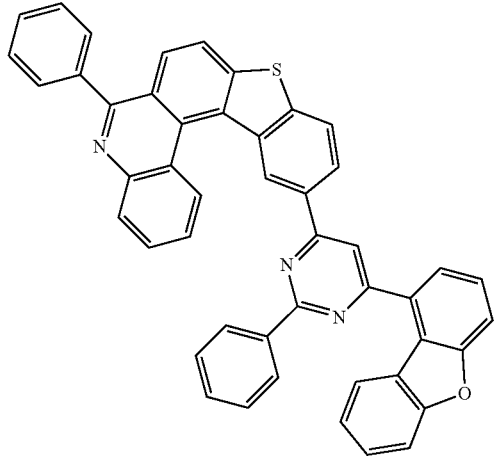 |
| 723 | 724 |
| 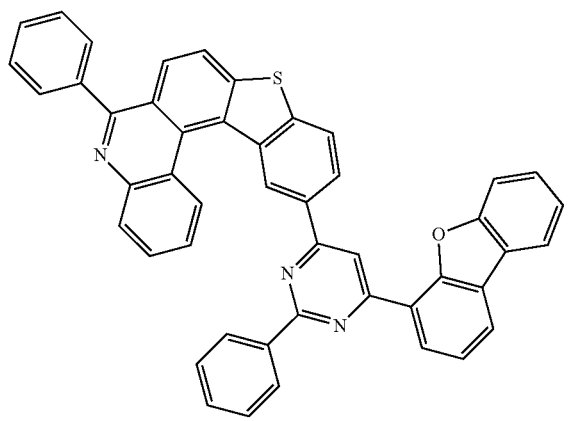 | |
| 725 | 726 |
| | 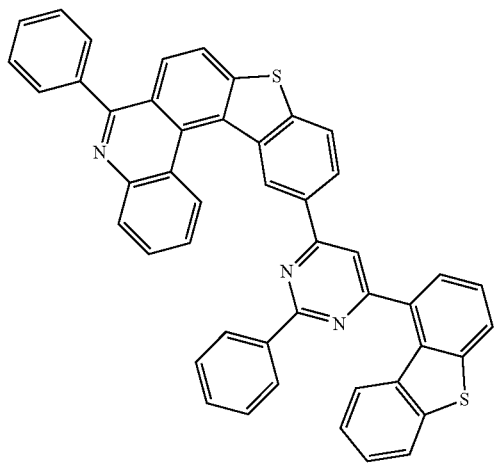 |

-continued
727
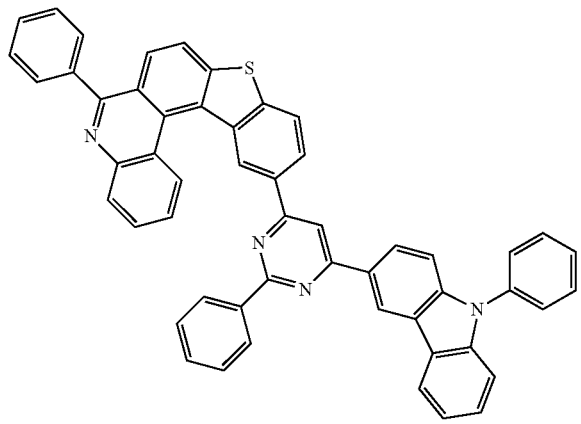
728
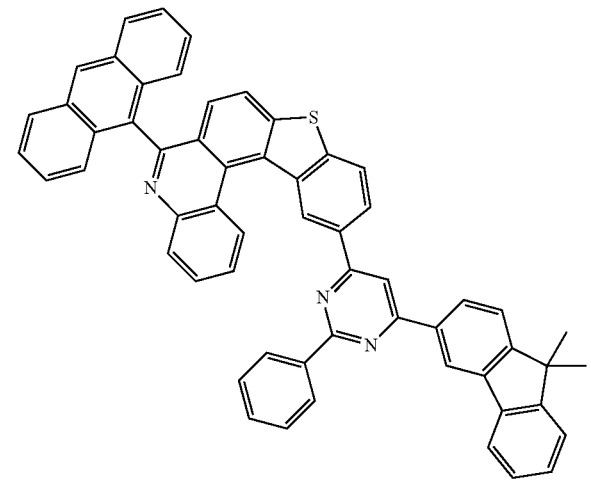 [SMILES: CC1(C)c2ccccc2-c2cc(-c3cc(-c4ccc5sc6ccc7c(-c8c9ccccc9cc9ccccc89)nc8ccccc8c7c6c5c4)nc(-c4ccccc4)n3)ccc21]
729
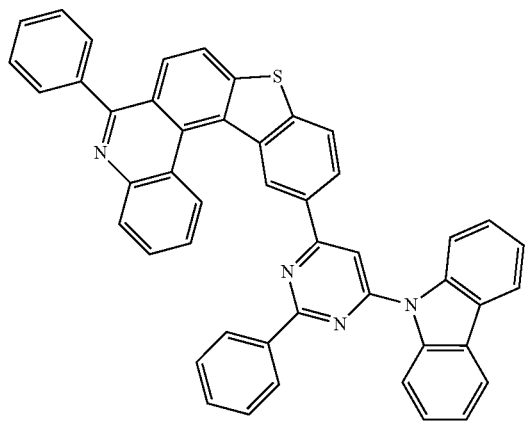 [SMILES: c1ccc(-c2nc(-c3ccc4sc5ccc6c(-c7ccccc7)nc7ccccc7c6c5c4c3)cc(-n3c4ccccc4c4ccccc43)n2)cc1]
730

731
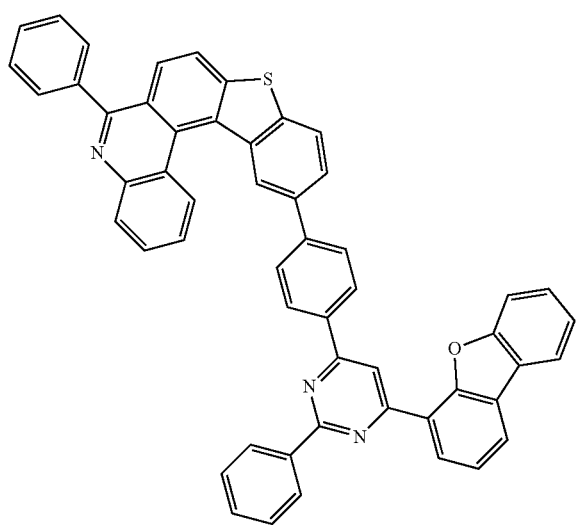
732
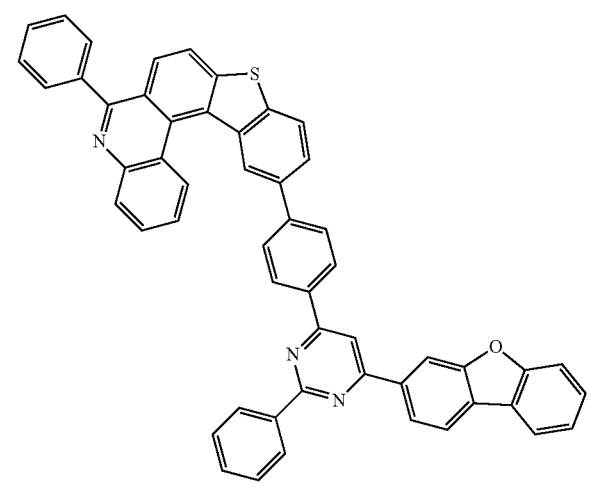 [SMILES: c1ccc(-c2nc(-c3ccc(-c4ccc5sc6ccc7c(-c8ccccc8)nc8ccccc8c7c6c5c4)cc3)cc(-c3ccc4c(c3)oc3ccccc34)n2)cc1]

-continued
733
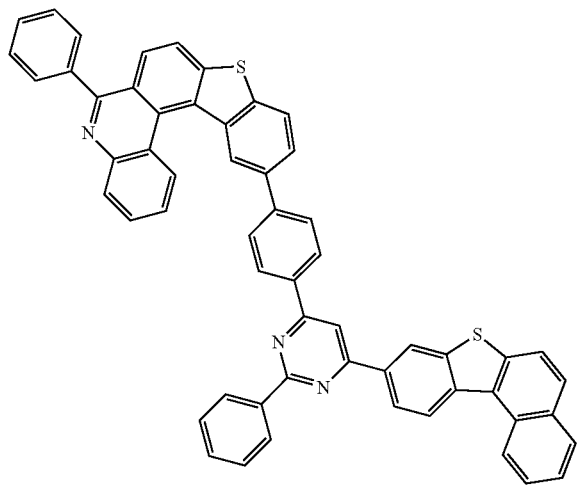
734
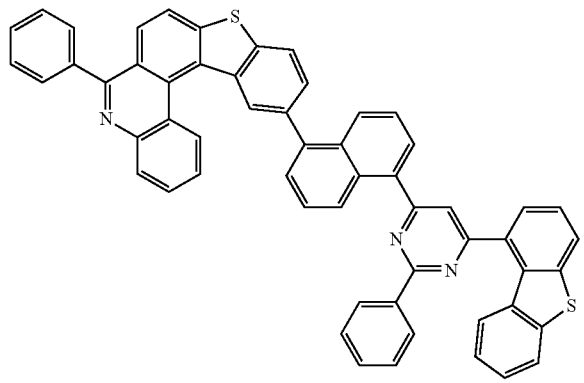 [SMILES: c1ccc(-c2nc(-c3cccc4c(-c5ccc6sc7ccc8c(-c9ccccc9)nc9ccccc9c8c7c6c5)cccc34)cc(-c3cccc4sc5ccccc5c34)n2)cc1]
735
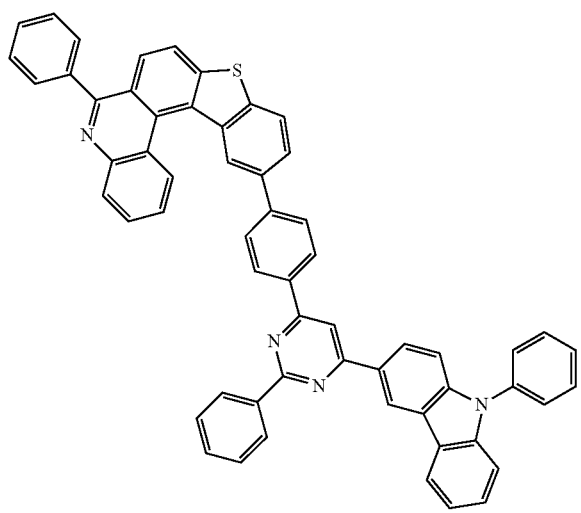
736
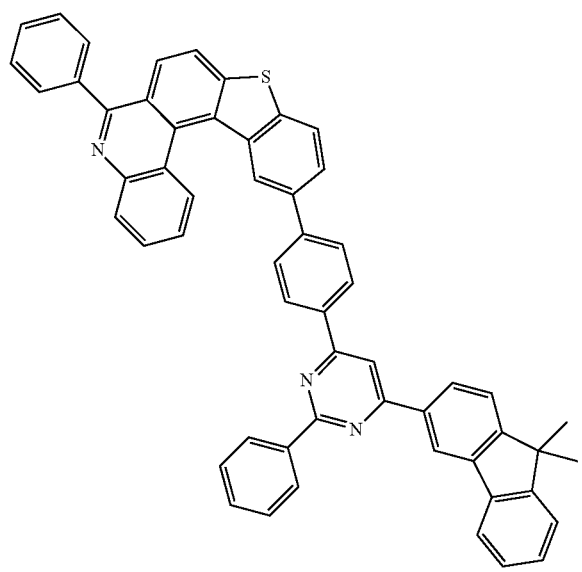 [SMILES: CC1(C)c2ccccc2-c2cc(-c3cc(-c4ccc(-c5ccc6sc7ccc8c(-c9ccccc9)nc9ccccc9c8c7c6c5)cc4)nc(-c4ccccc4)n3)ccc21]
737
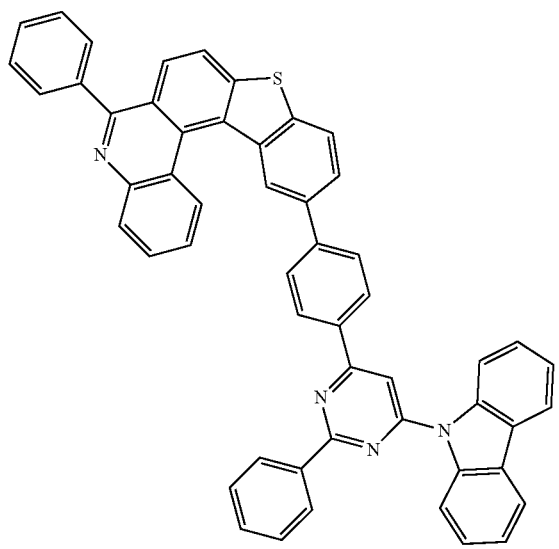
738
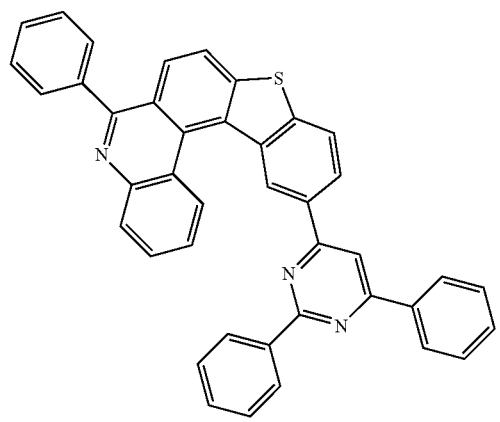

-continued
739
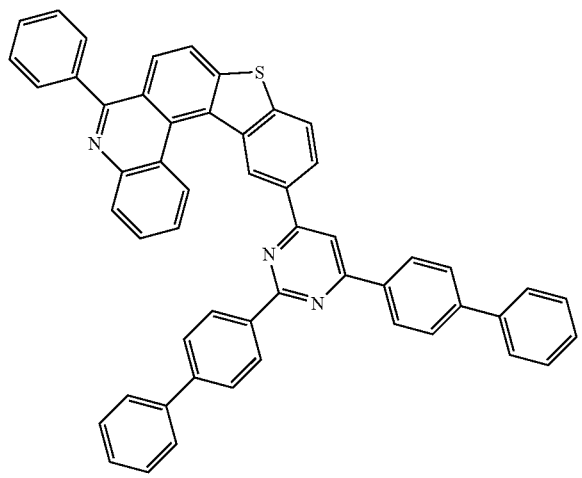
740
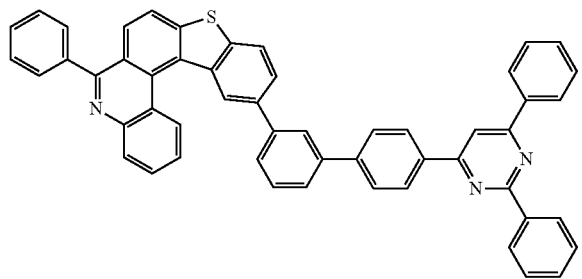
741
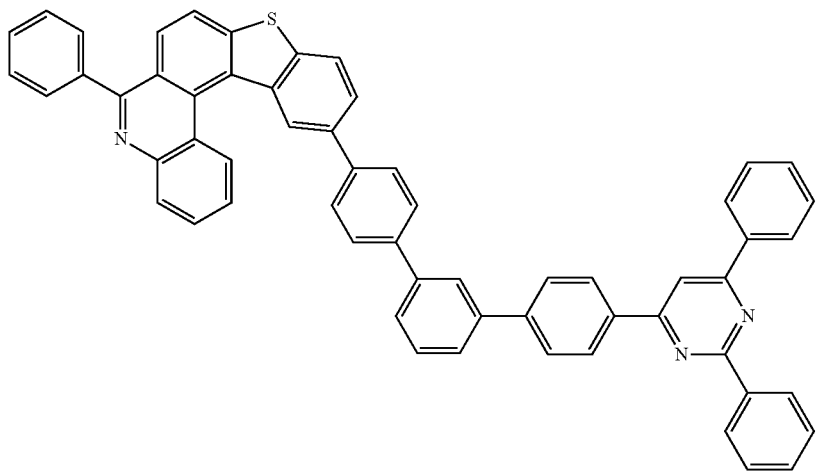
742
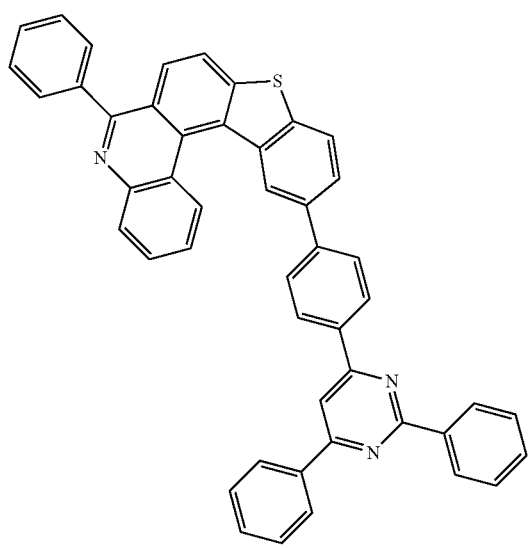
743
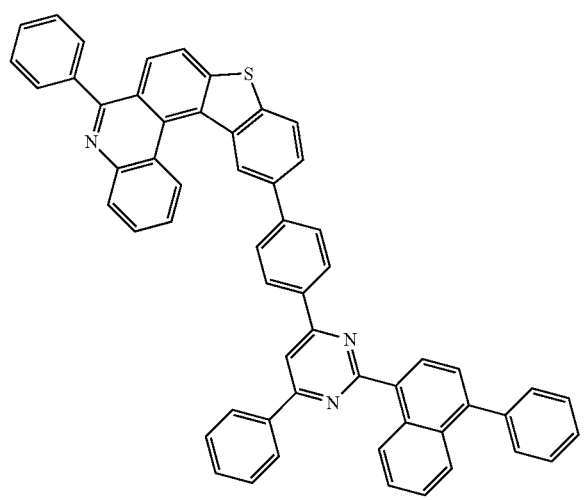 [SMILES: c1ccc(-c2nc(-c3ccc(-c4ccc5sc6ccc7c(-c8ccccc8)nc8ccccc8c7c6c5c4)cc3)cc(-c3ccc(-c4ccccc4)c4ccccc34)n2)cc1]

| 1023 | 1024 |
|---|---|
| 744 | 745 |
| 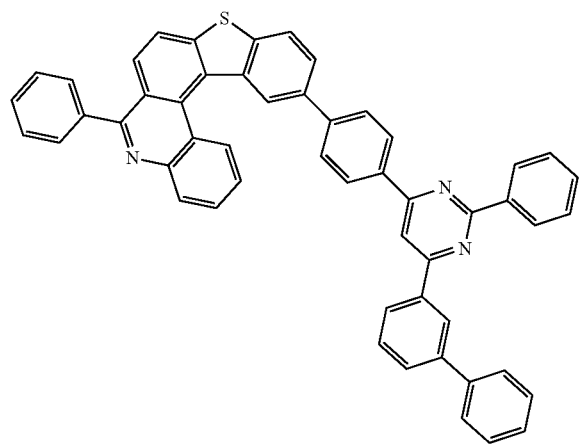 | 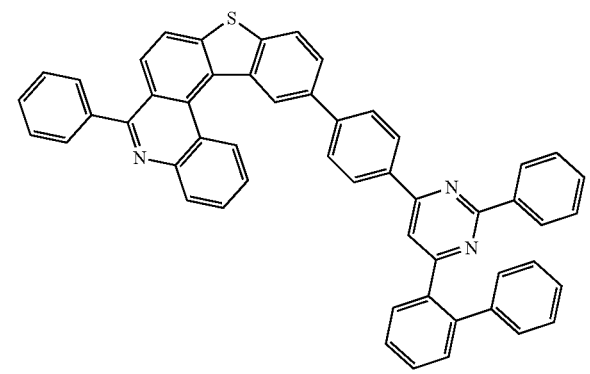 |
| 746 | 747 |
| 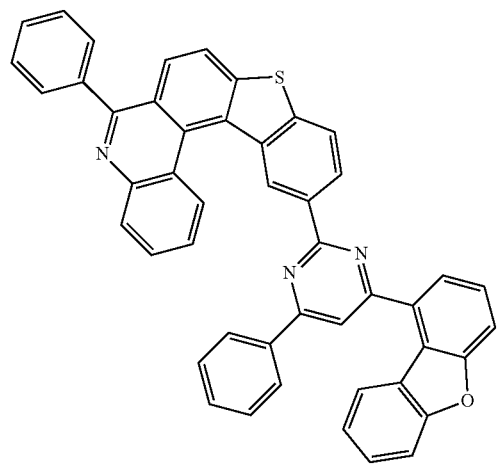 | 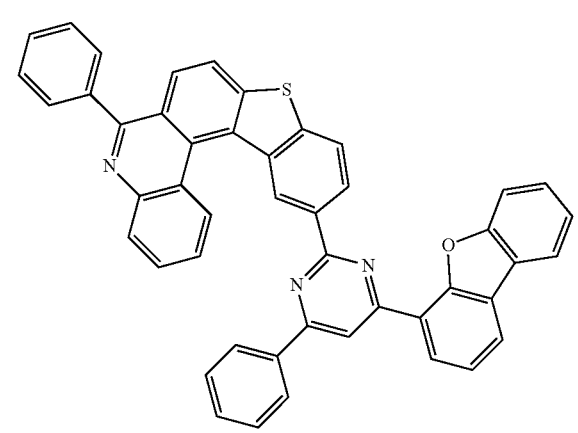 |
| 748 | 749 |
| 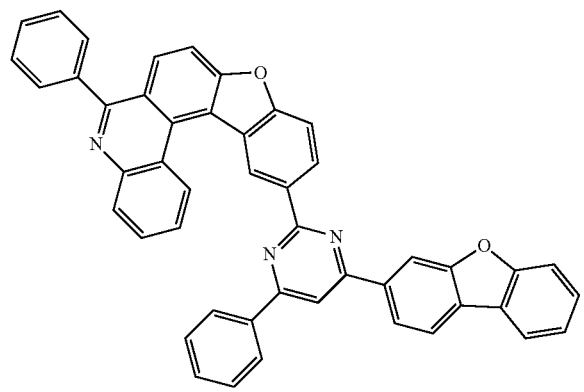 | 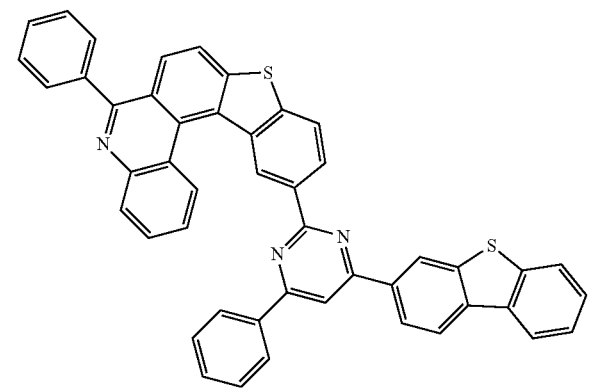 [SMILES: c1ccc(-c2cc(-c3ccc4c(c3)oc3ccccc34)nc(-c3ccc4oc5ccc6c(-c7ccccc7)nc7ccccc7c6c5c4c3)n2)cc1] |

1025  1026
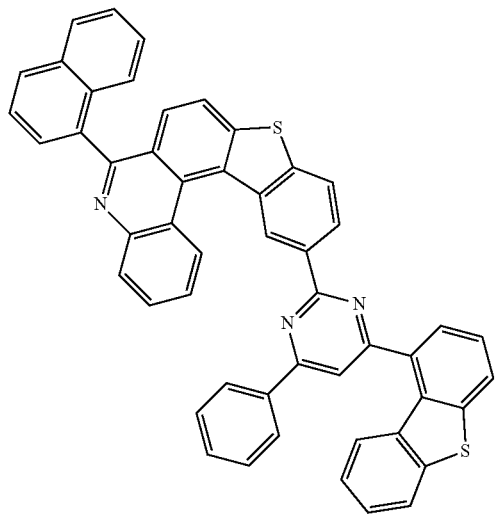
750
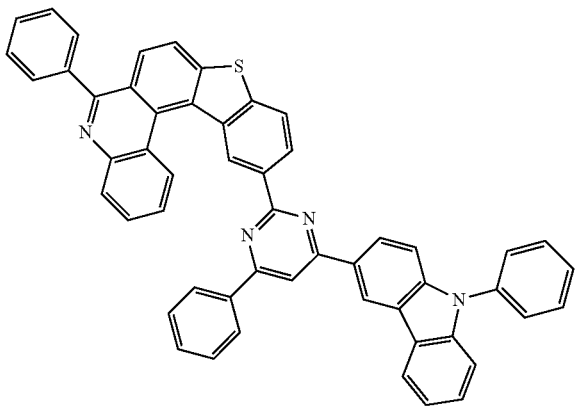
751
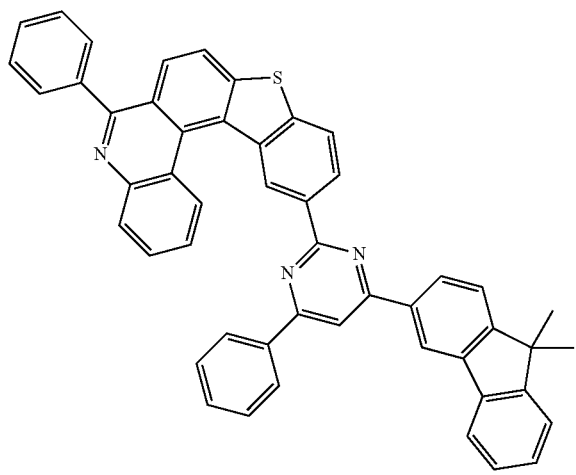 [SMILES: CC1(C)c2ccccc2-c2cc(-c3cc(-c4ccccc4)nc(-c4ccc5sc6ccc7c(-c8ccccc8)nc8ccccc8c7c6c5c4)n3)ccc21]
752
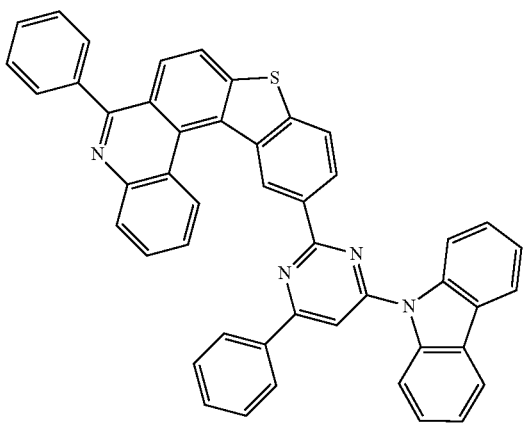
753
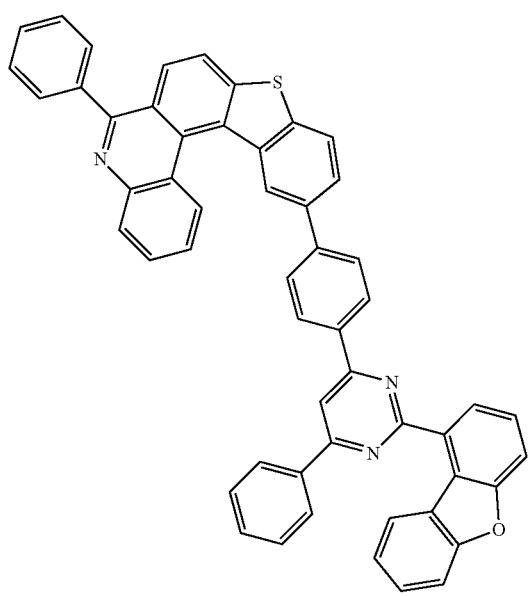
754
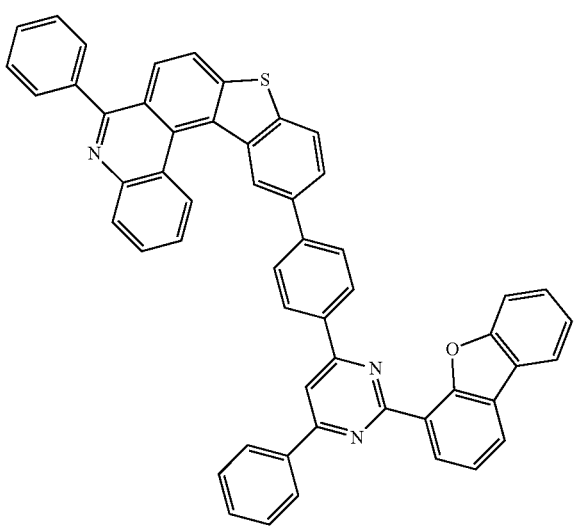
755

-continued
1027
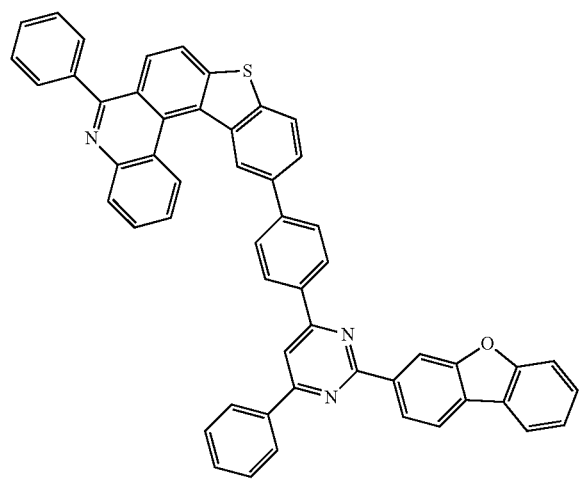 [SMILES: c1ccc(-c2cc(-c3ccc(-c4ccc5sc6ccc7c(-c8ccccc8)nc8ccccc8c7c6c5c4)cc3)nc(-c3ccc4c(c3)oc3ccccc34)n2)cc1]
756
1028
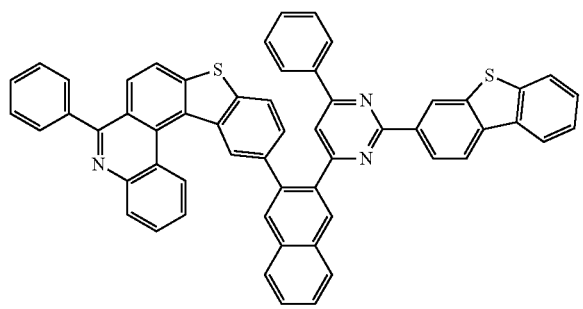 [SMILES: c1ccc(-c2cc(-c3cc4ccccc4cc3-c3ccc4sc5ccc6c(-c7ccccc7)nc7ccccc7c6c5c4c3)nc(-c3ccc4c(c3)sc3ccccc34)n2)cc1]
757
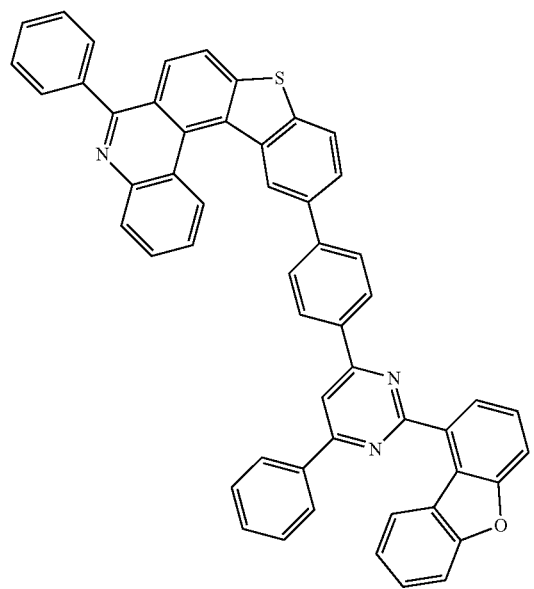
758
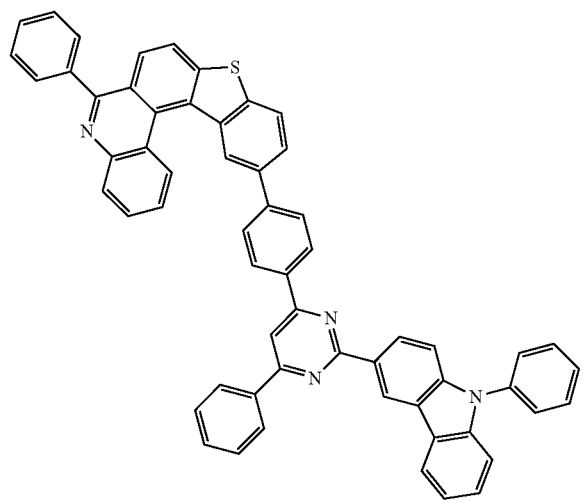
759

-continued
760
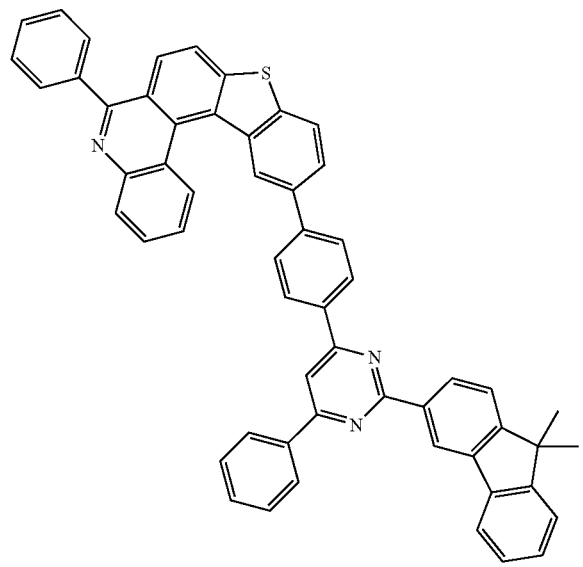
761
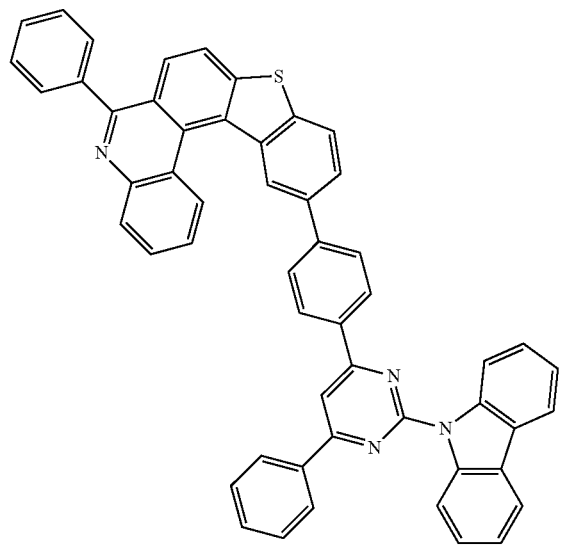 [SMILES: c1ccc(-c2cc(-c3ccc(-c4ccc5sc6ccc7c(-c8ccccc8)nc8ccccc8c7c6c5c4)cc3)nc(-n3c4ccccc4c4ccccc43)n2)cc1]
762
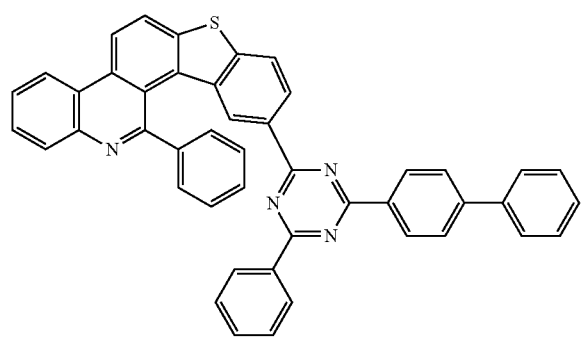
763
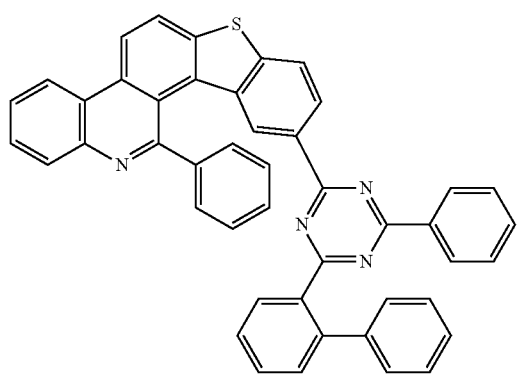
764
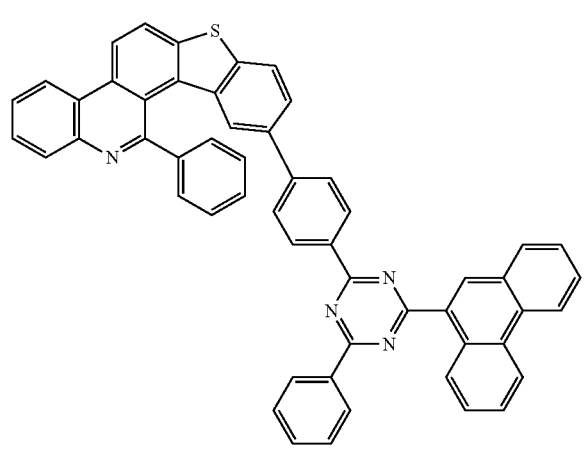
765
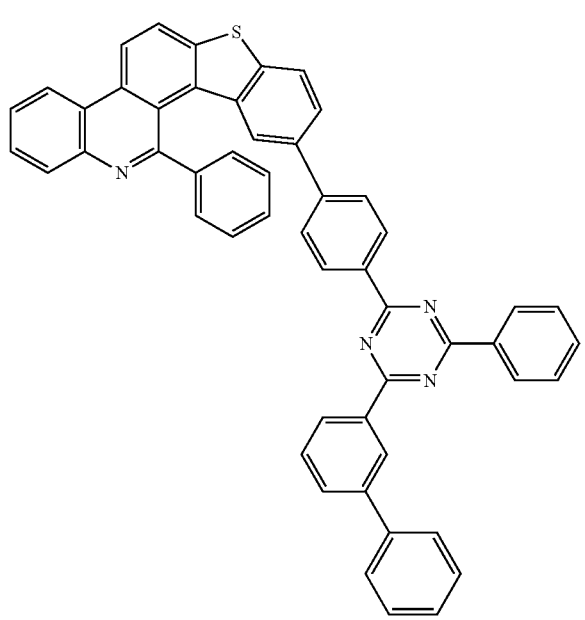

1031 -continued 1032
766
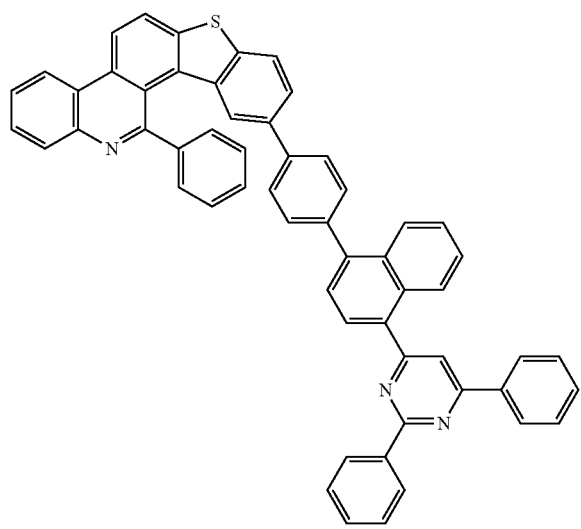
767
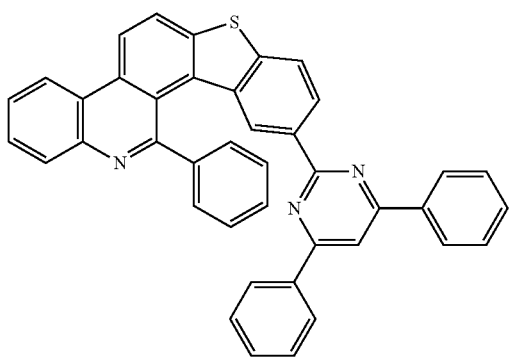
768
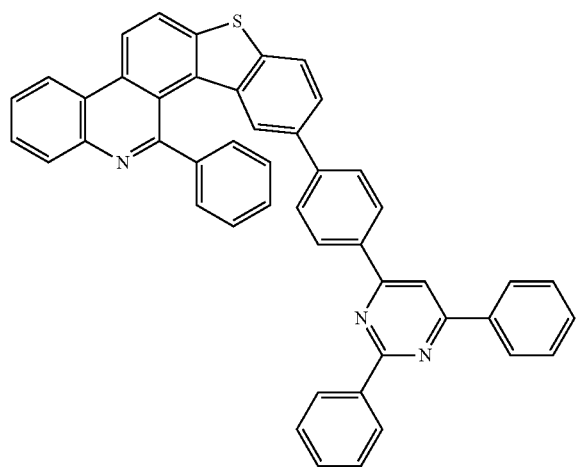
769
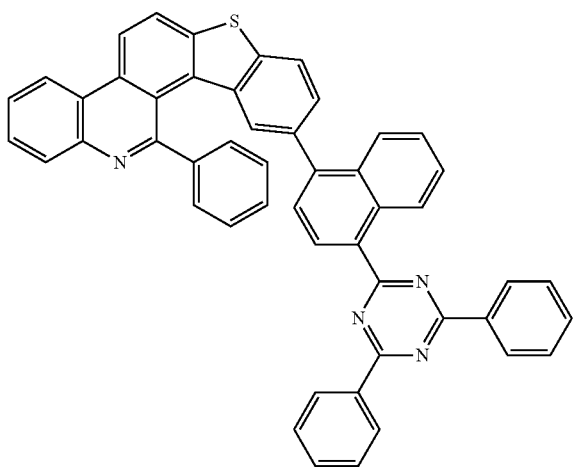
770
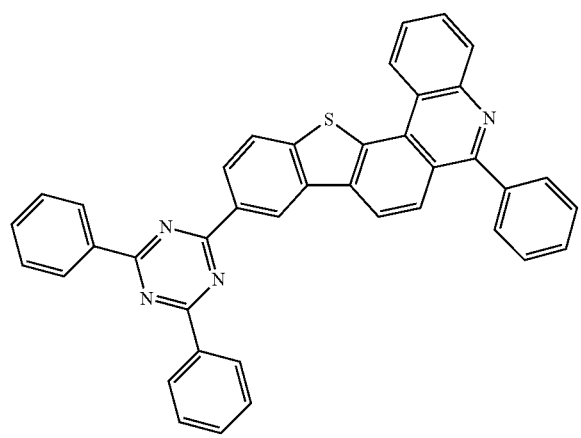
771
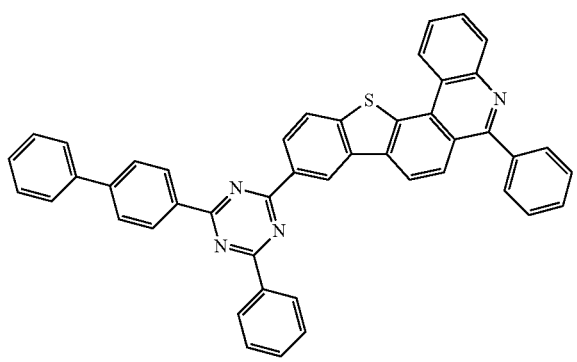

-continued
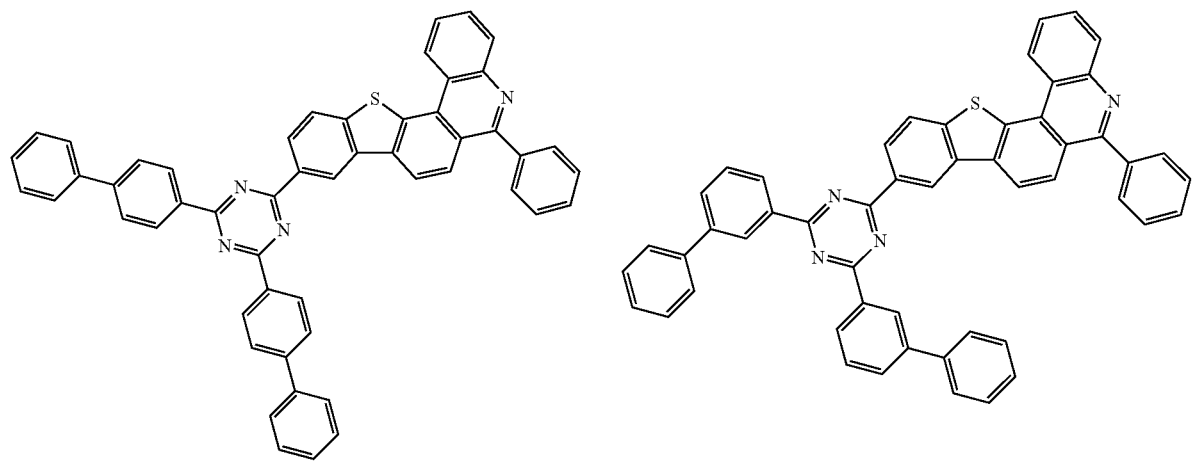
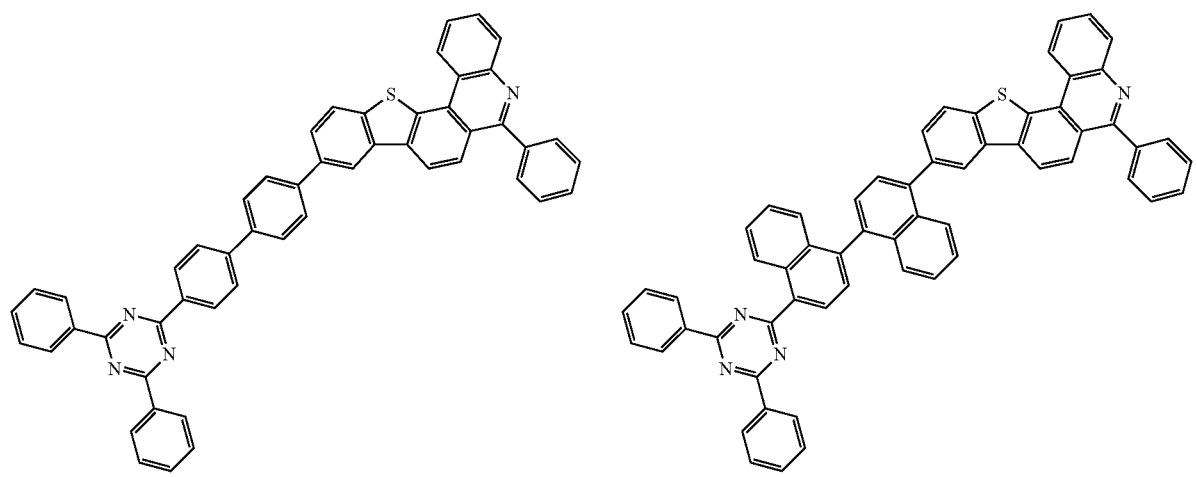
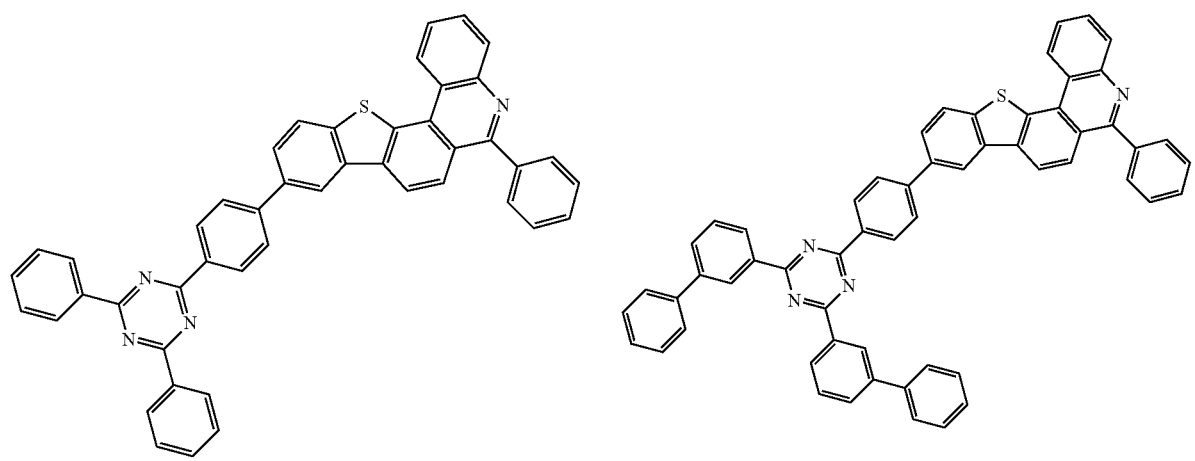

-continued
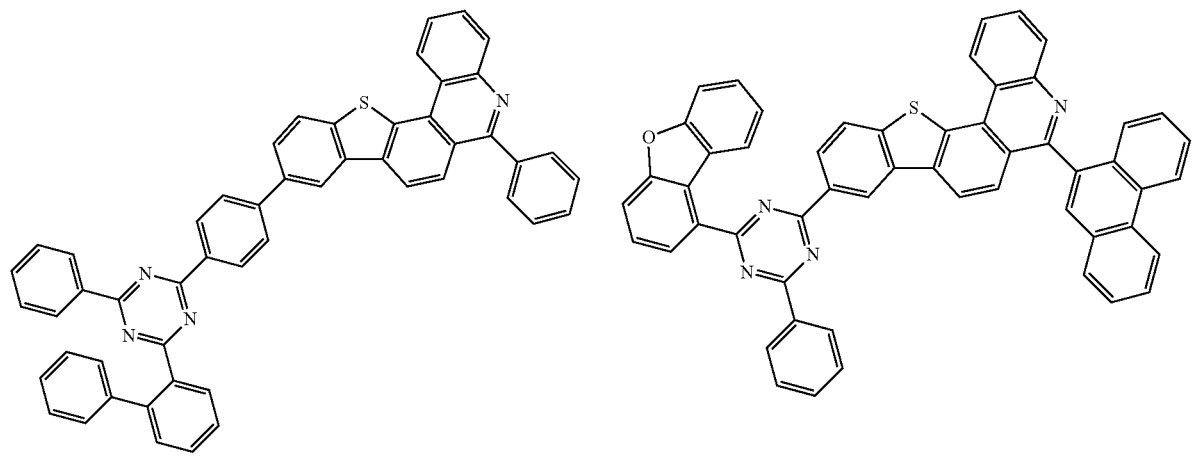
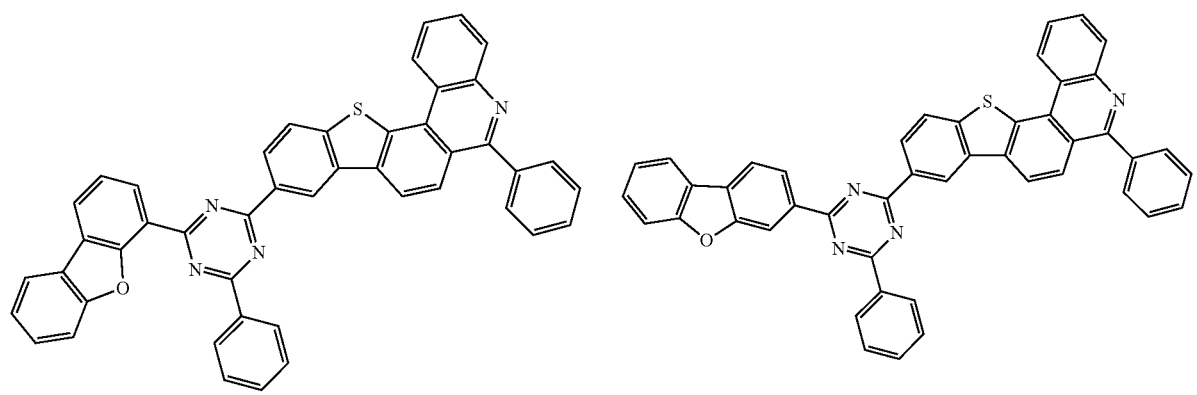
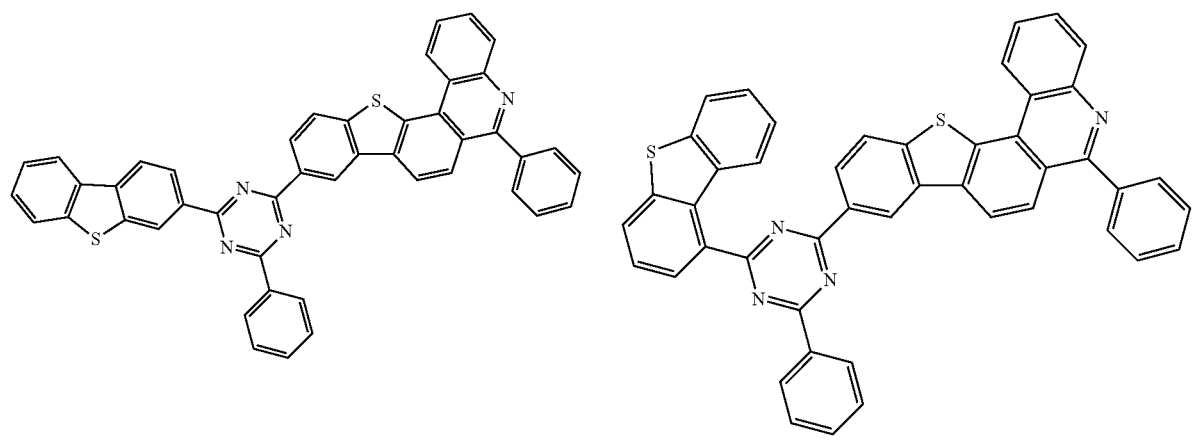

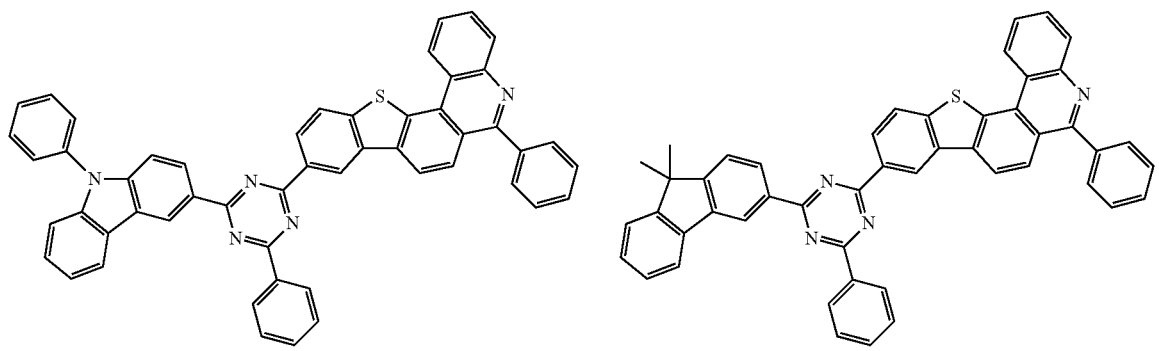
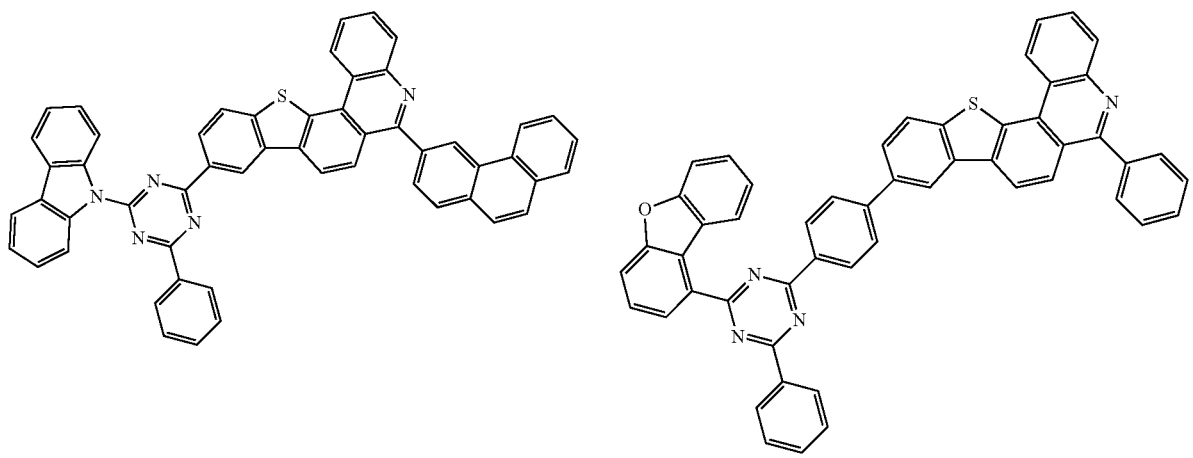
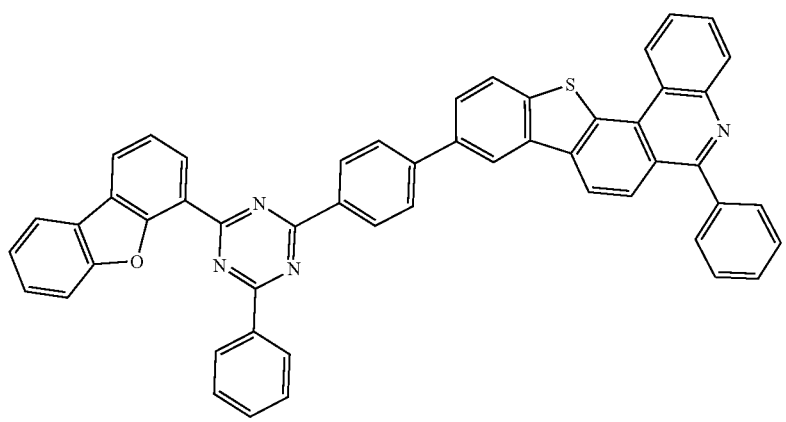

789
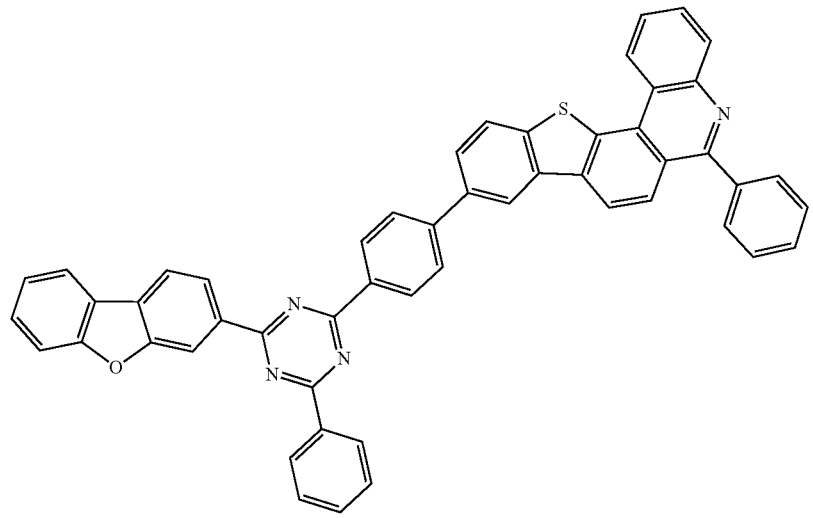
790
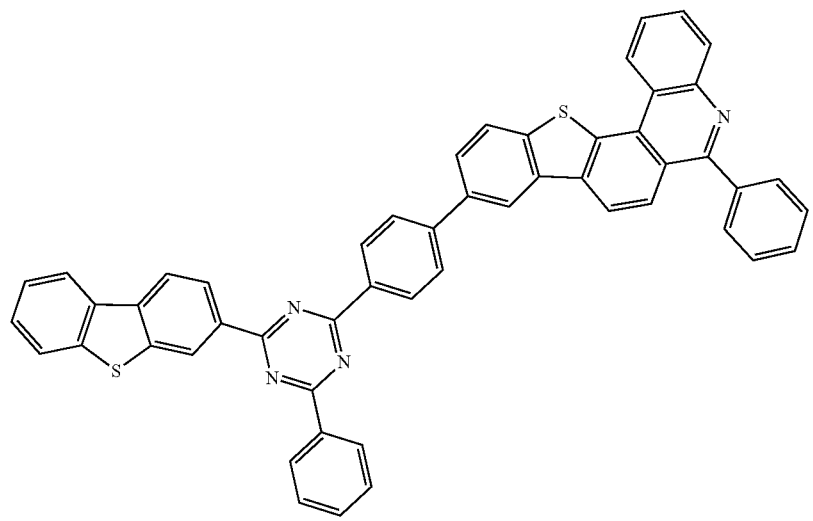
791
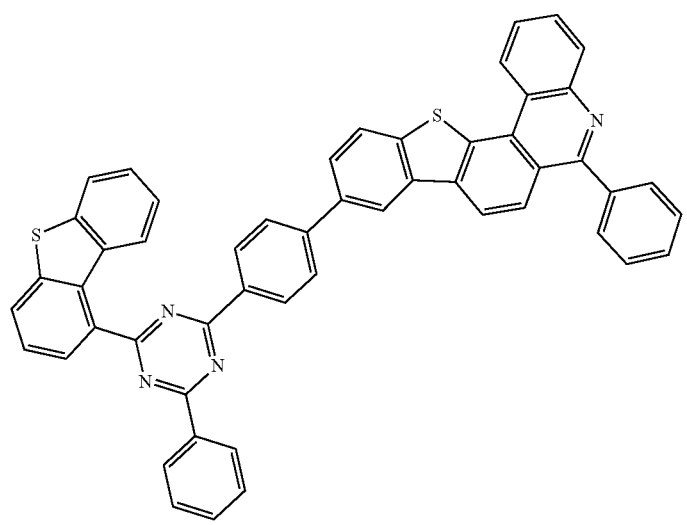

-continued
792
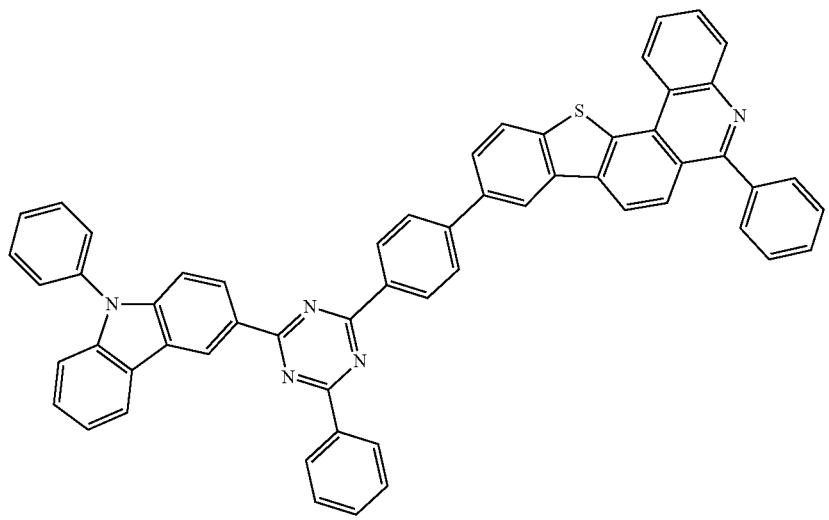
793
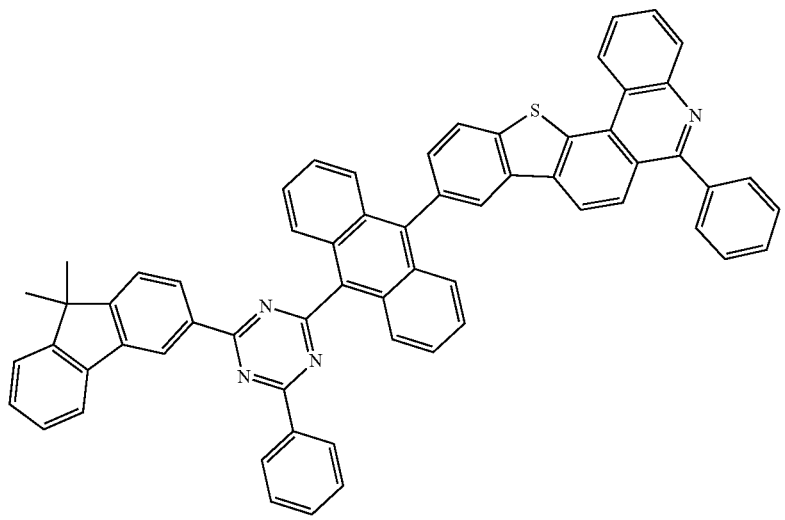
794 795
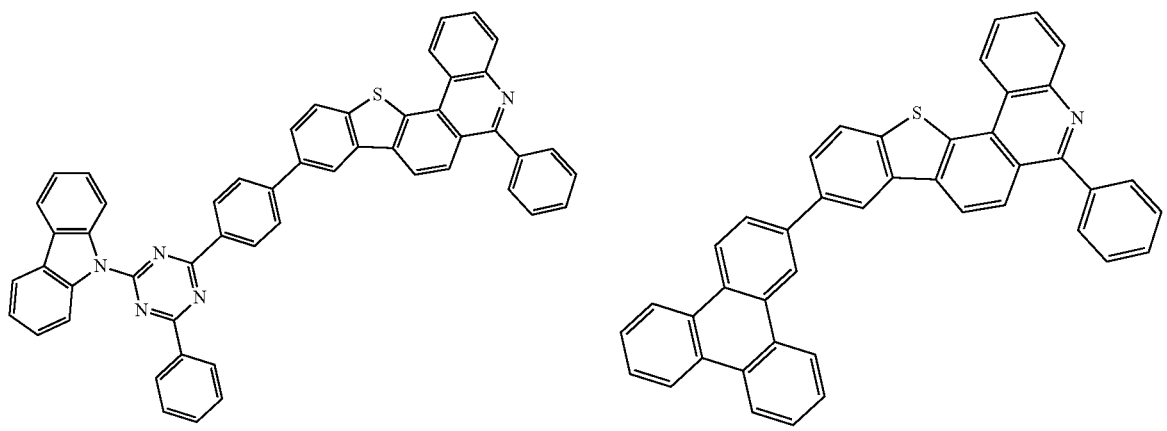

-continued
796
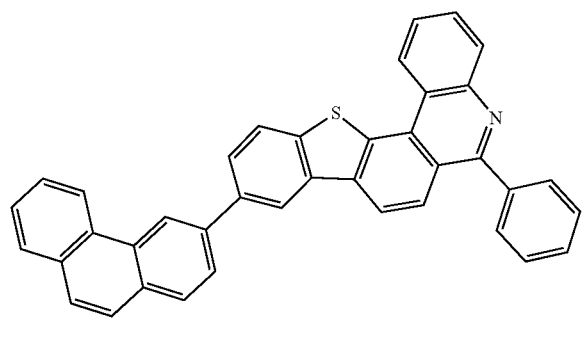
797
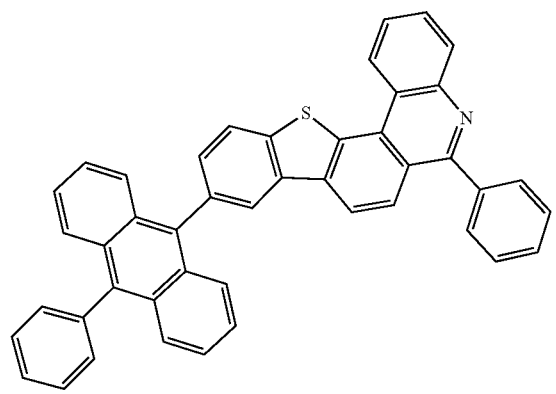
798
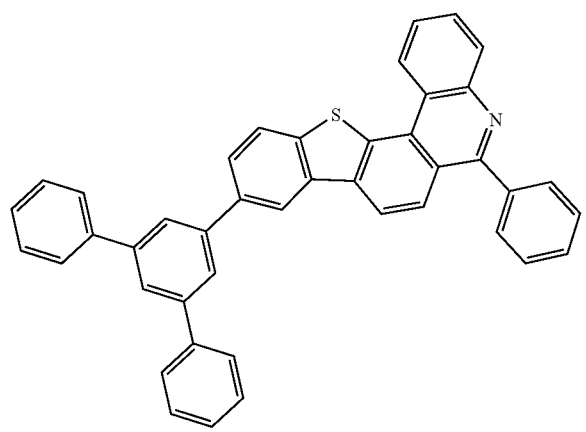
799
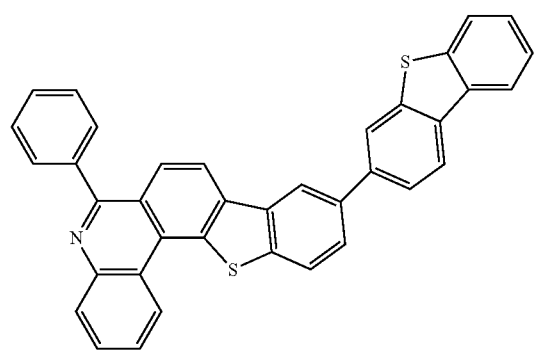
800
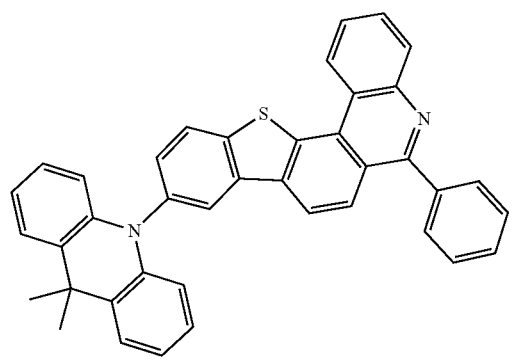
801
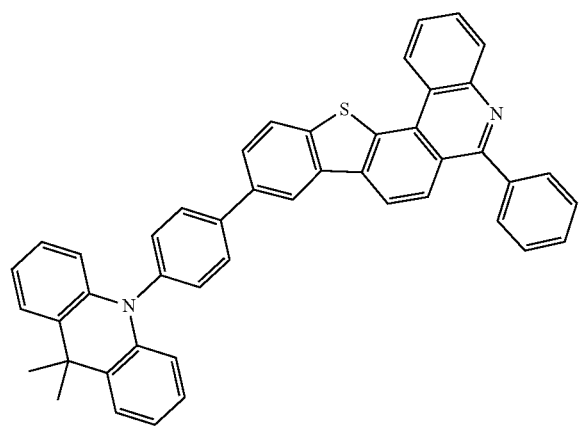

-continued
802
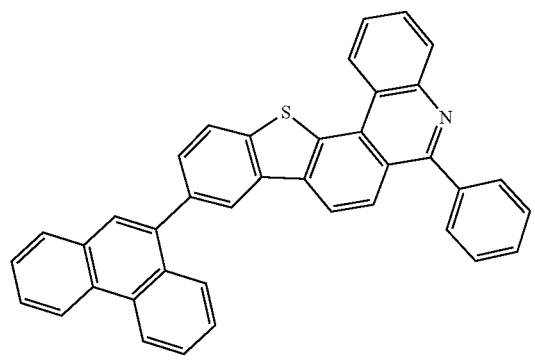
803
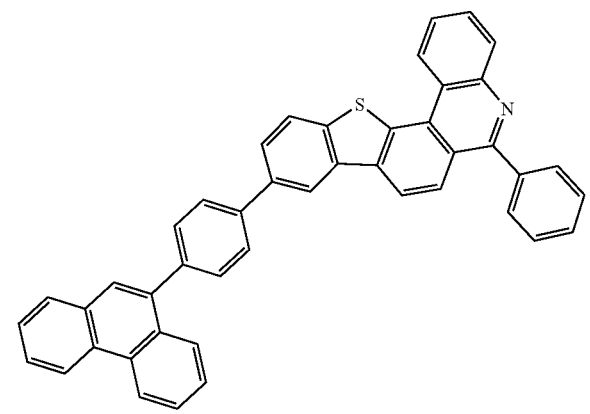
804
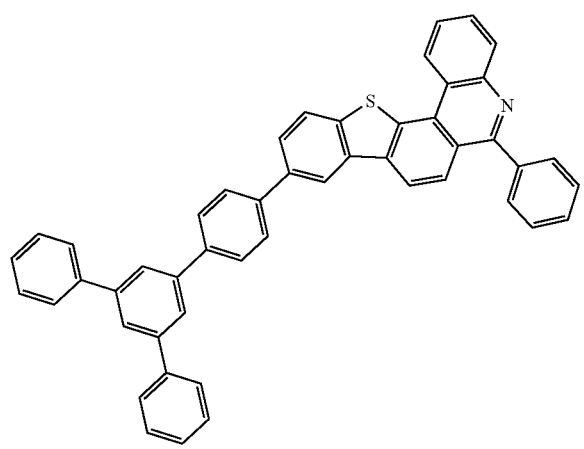
805
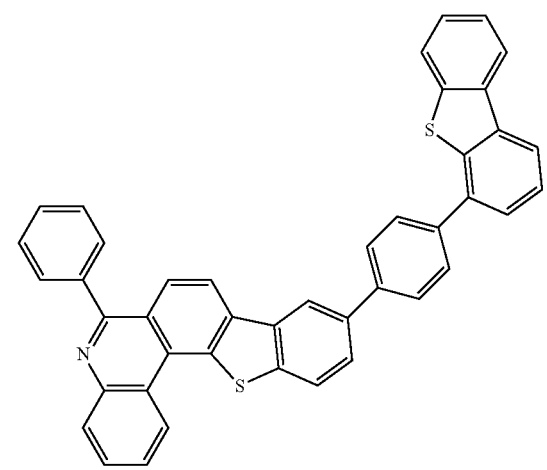
806
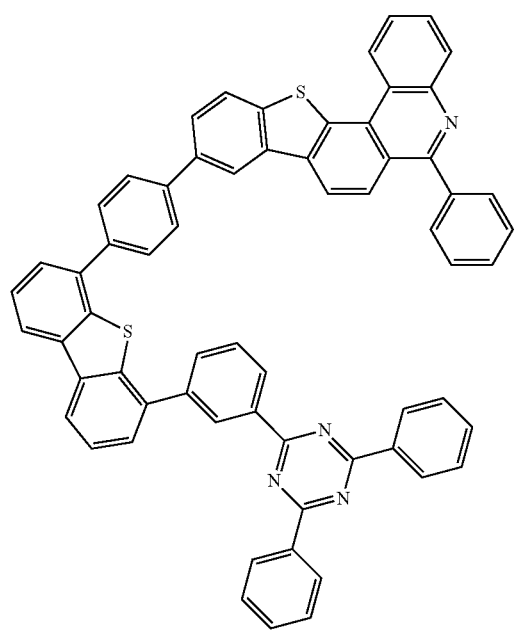
807
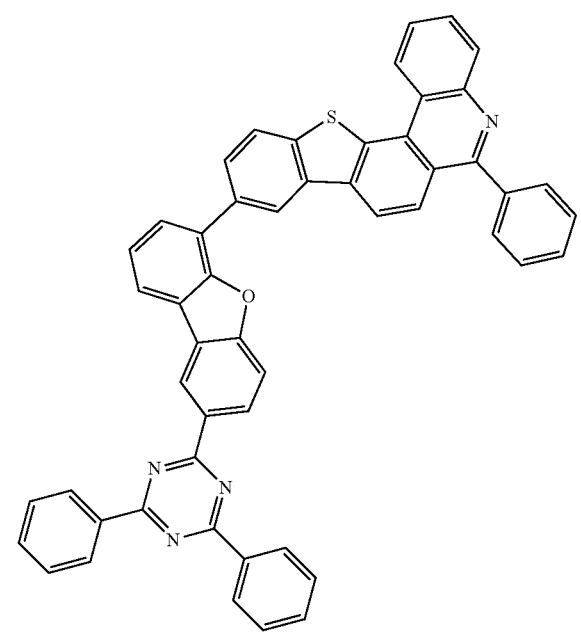

-continued
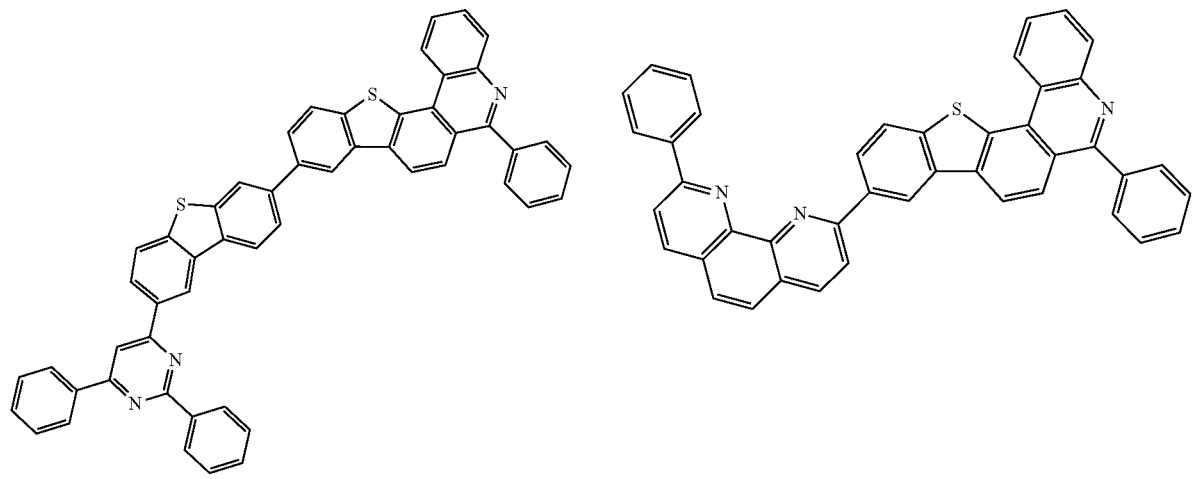
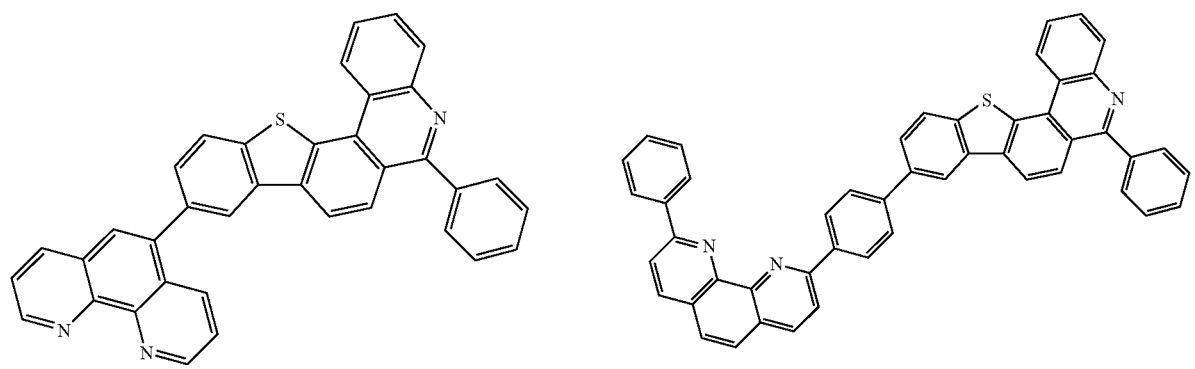
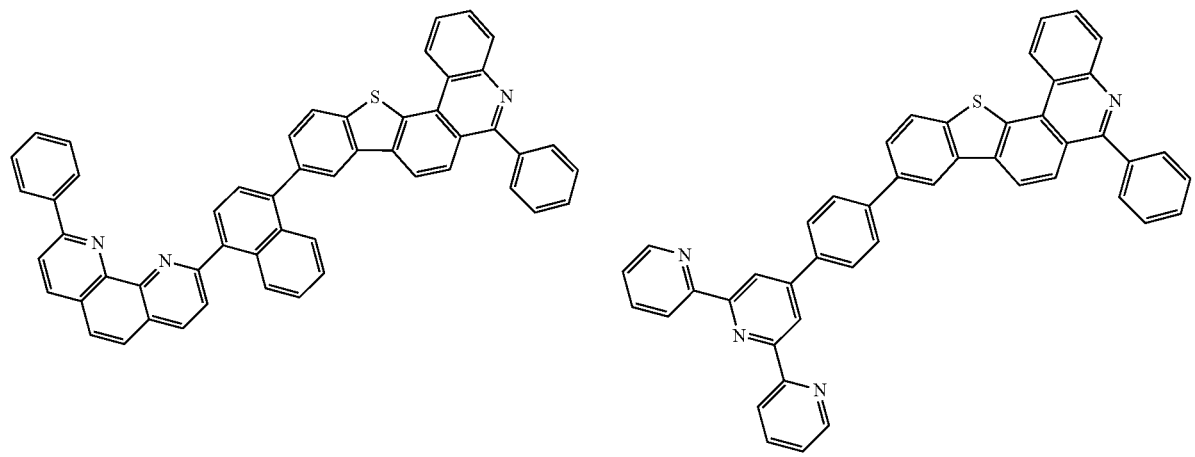

-continued
| 1049 | 1050 |
|---|---|
| 814 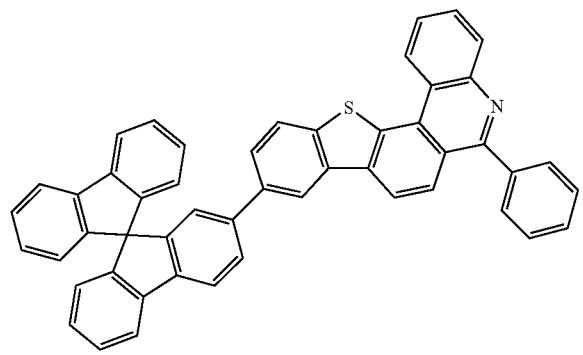 | 815 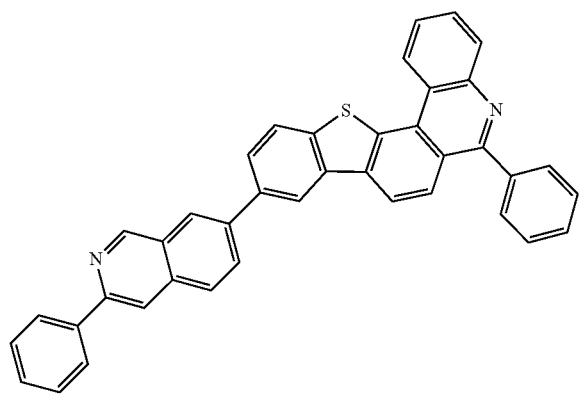 |
| 816 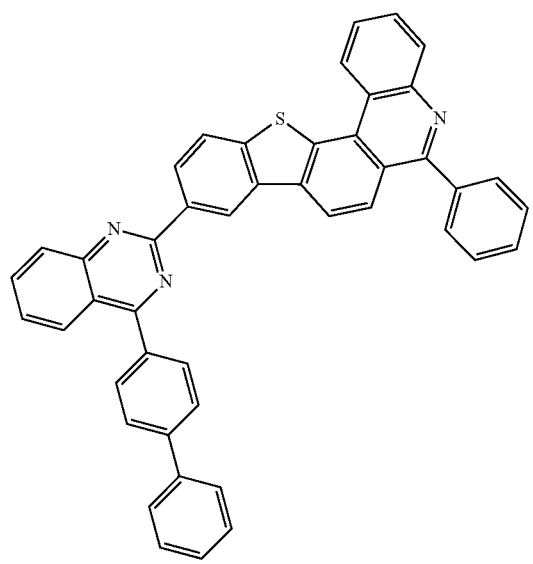 | 817 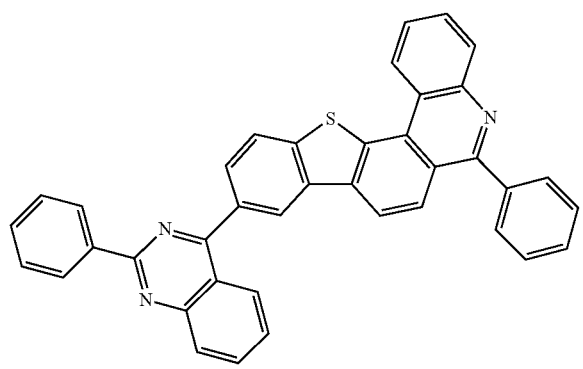 |
| 818 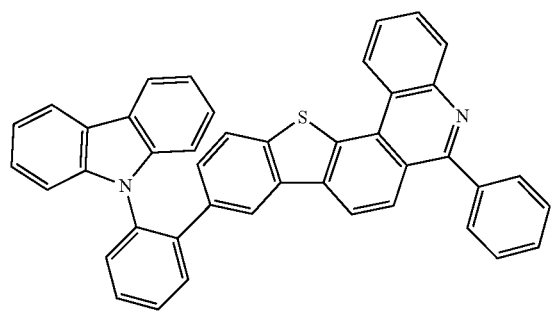 | 819 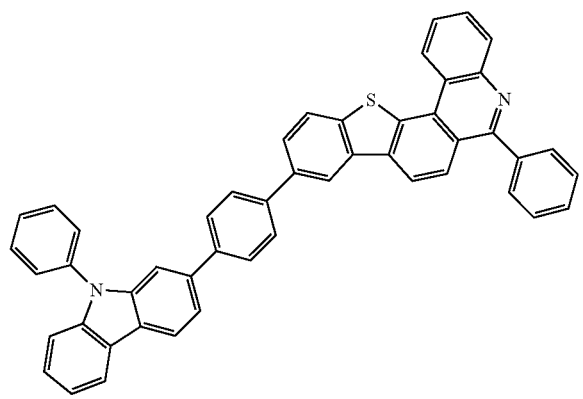 |

-continued
1051
820
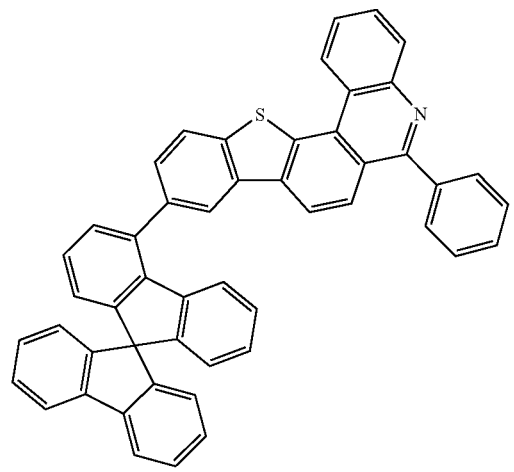
1052
821
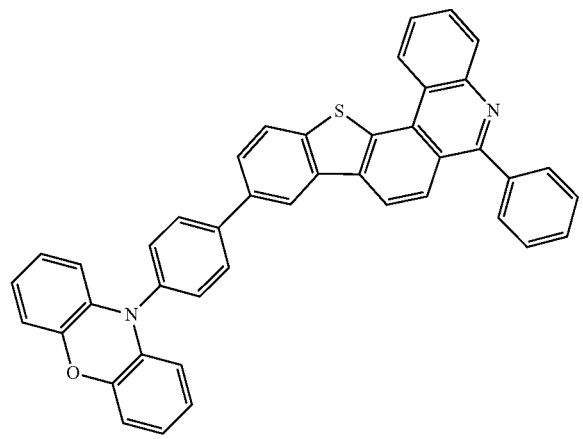
822
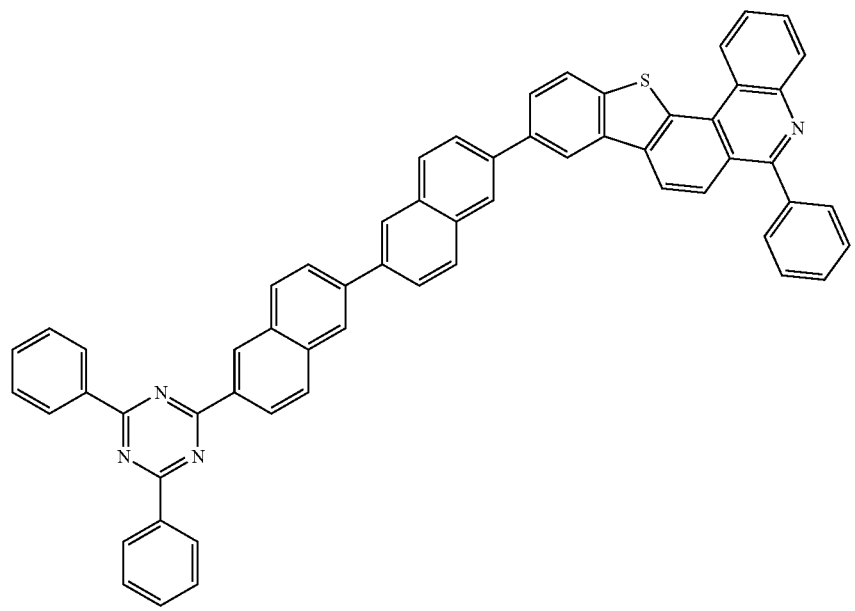 [SMILES: c1ccc(-c2nc(-c3ccccc3)nc(-c3ccc4cc(-c5ccc6cc(-c7ccc8sc9c(ccc%10c(-c%11ccccc%11)nc%11ccccc%11c%109)c8c7)ccc6c5)ccc4c3)n2)cc1]
823
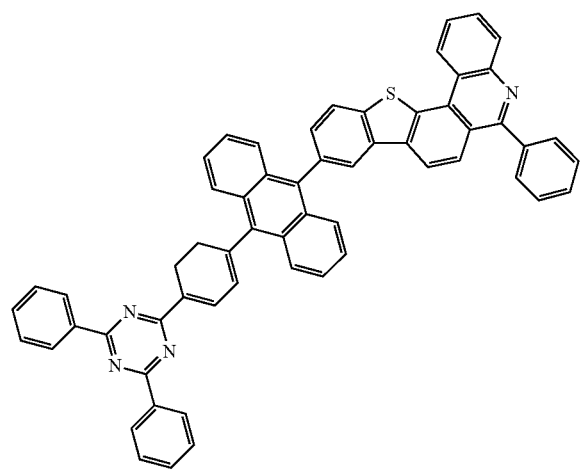
824
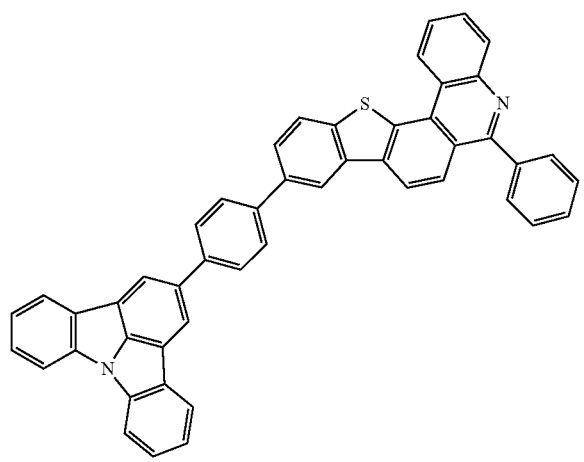

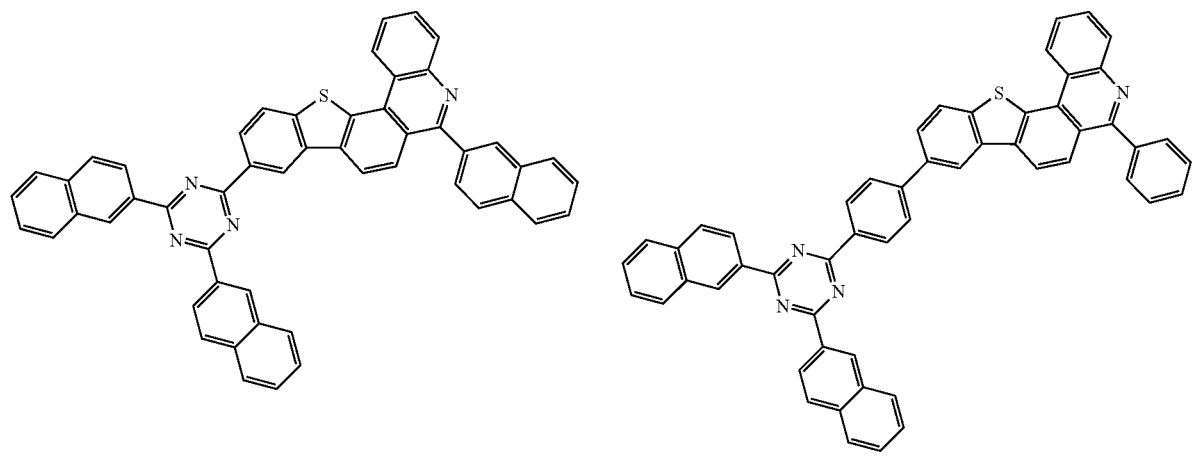
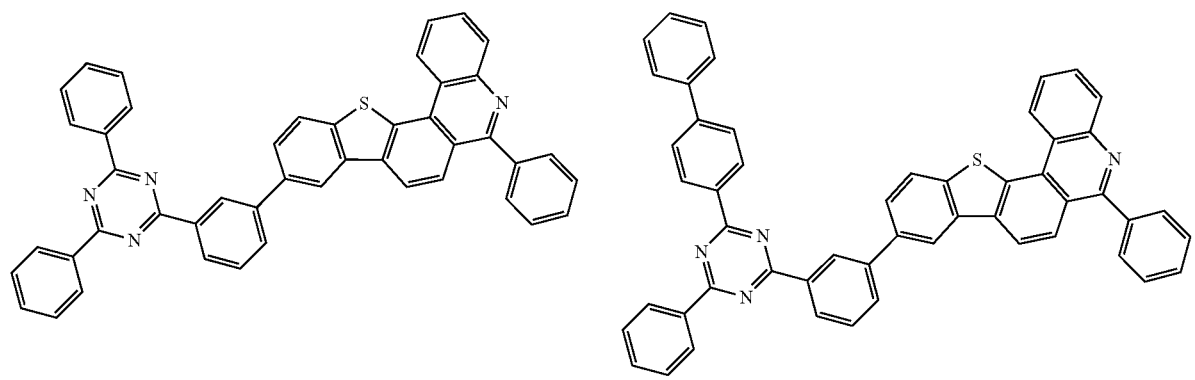
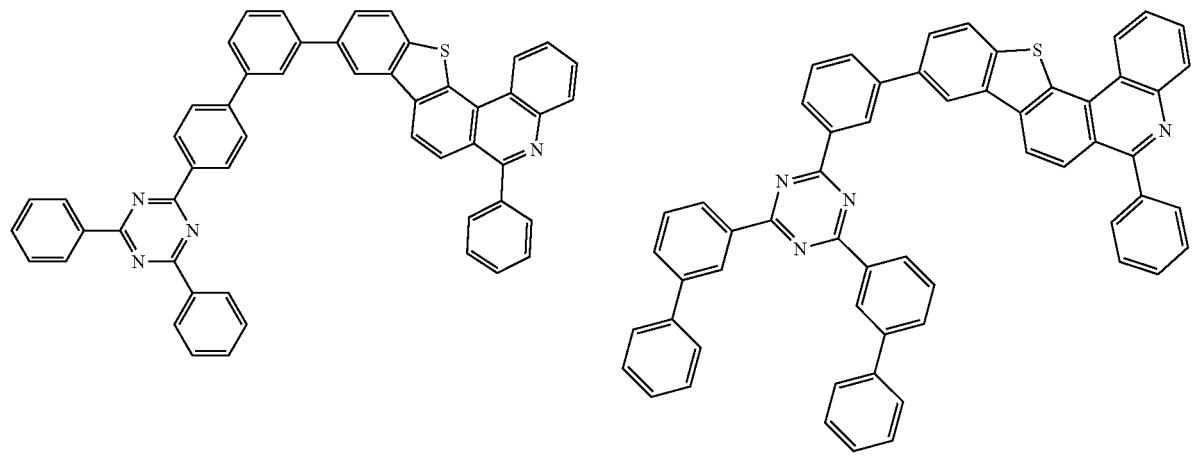

-continued
831
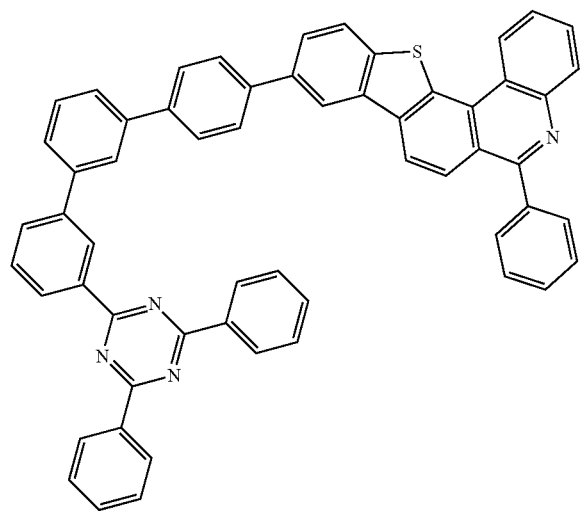
832
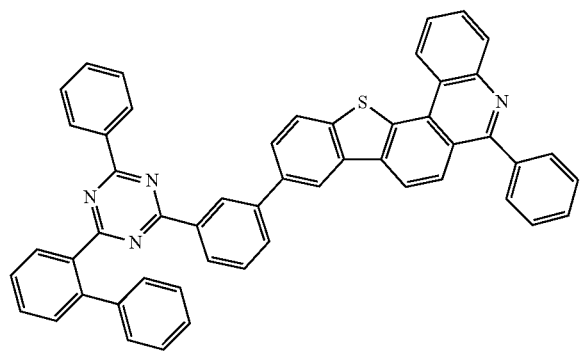
833
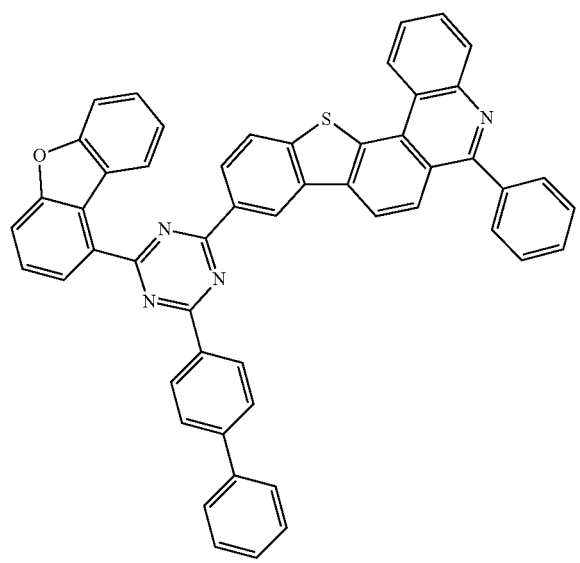
834
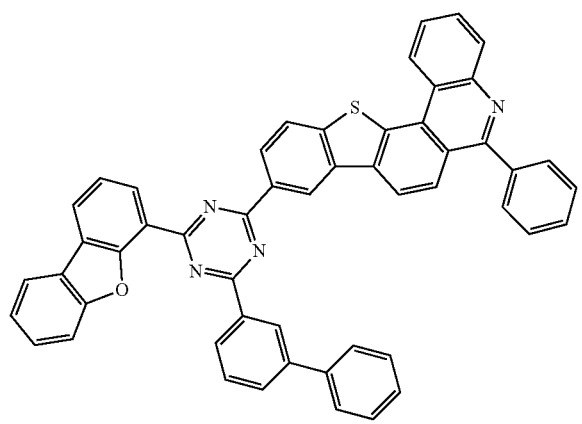
835
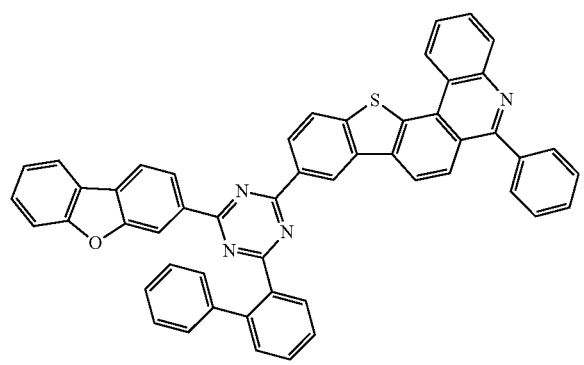
836
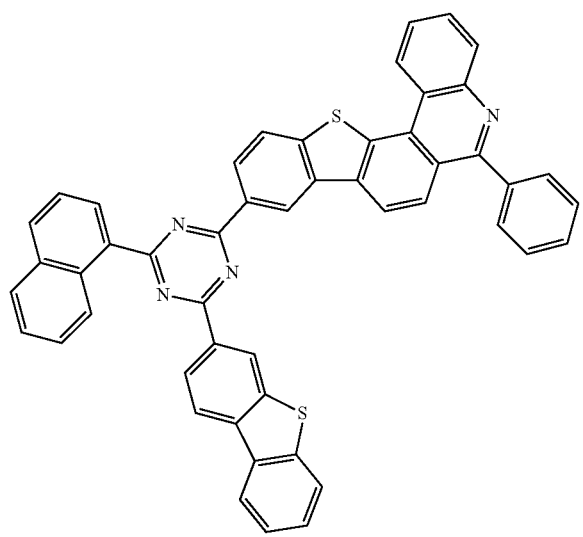

-continued
837
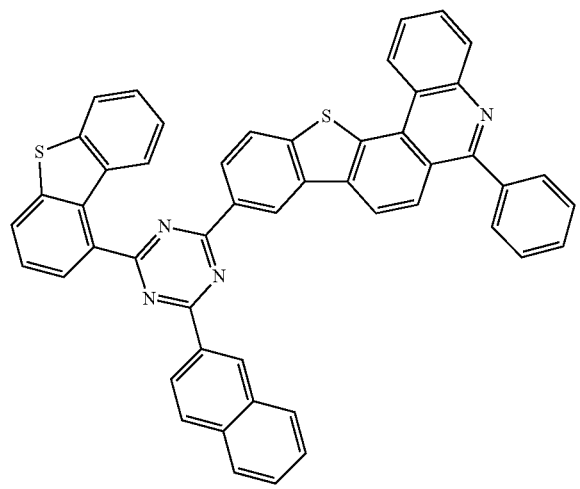
838
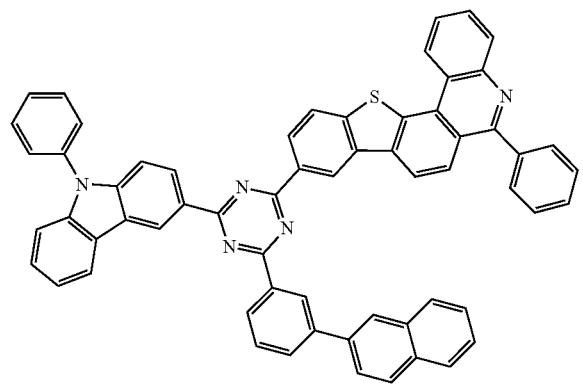
839
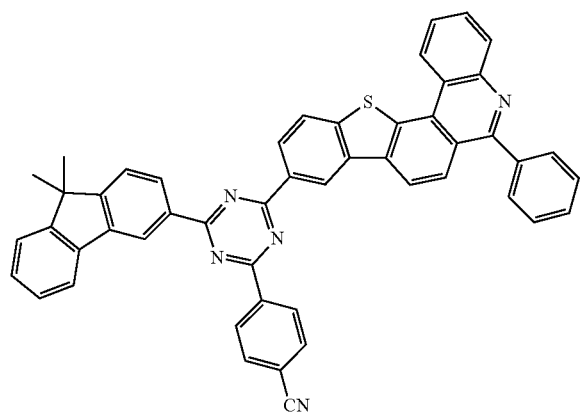
840
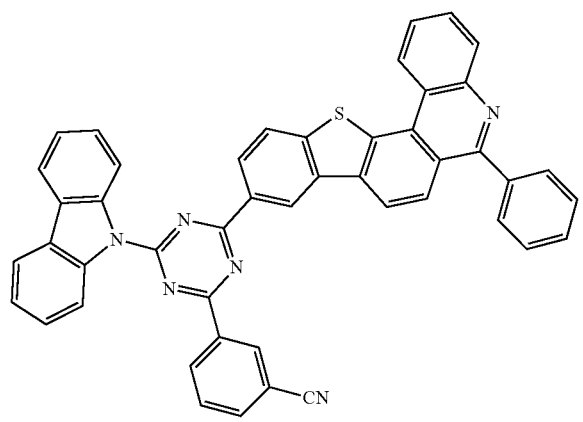
841
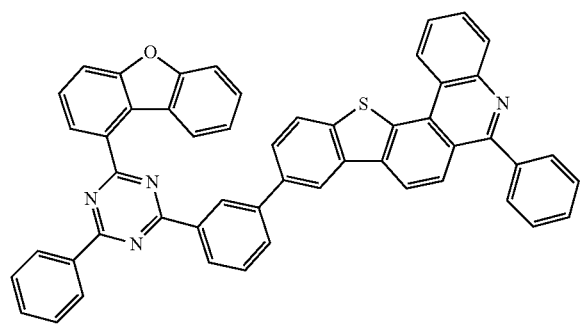
842
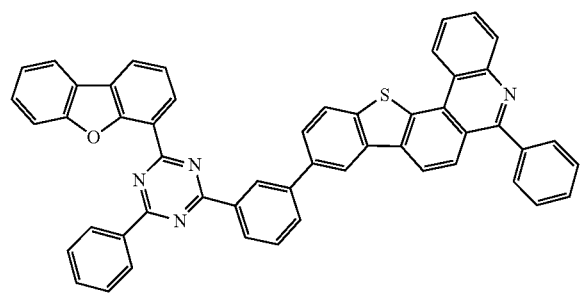

-continued
843
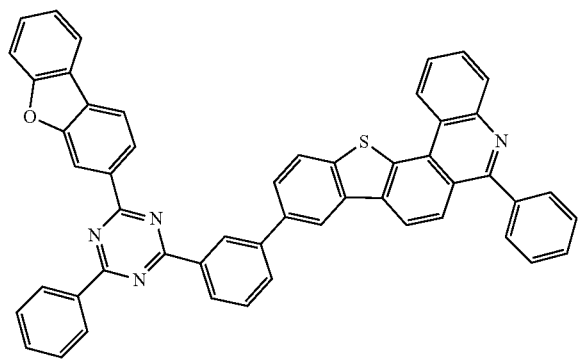
844
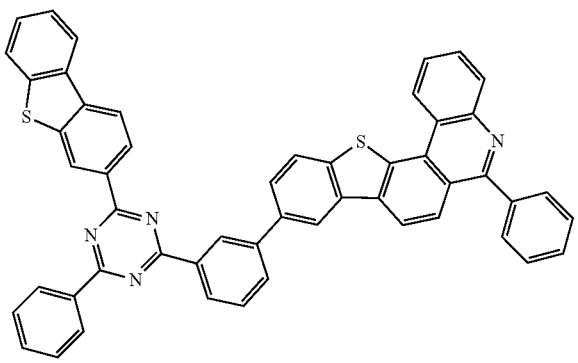
845
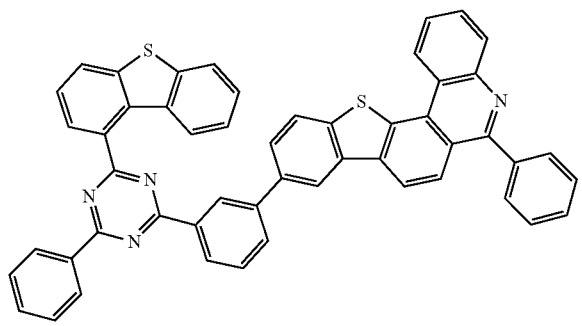
846
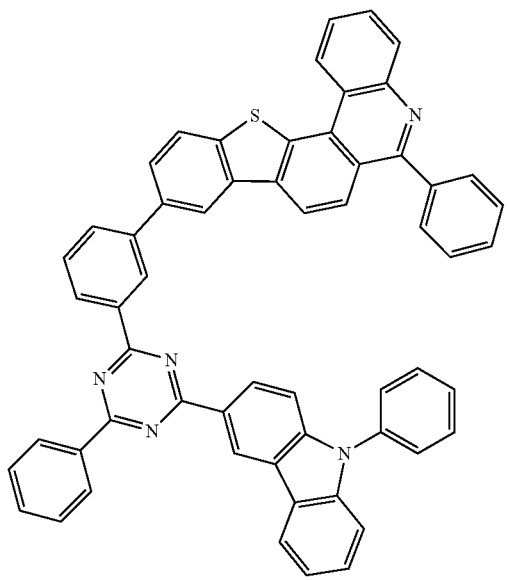
847
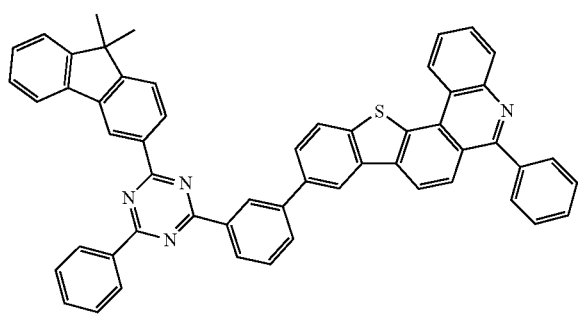
848
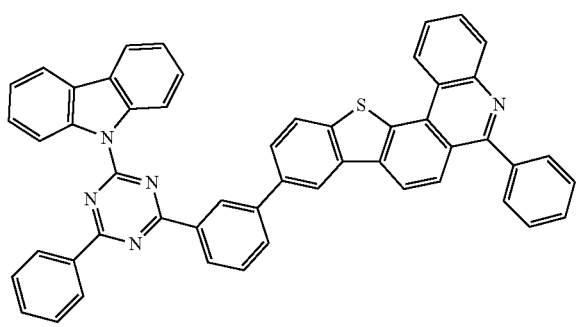

-continued
849
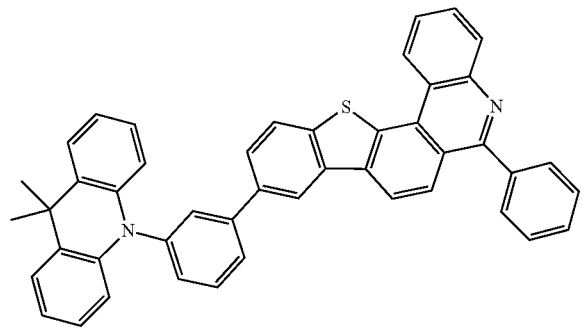
850
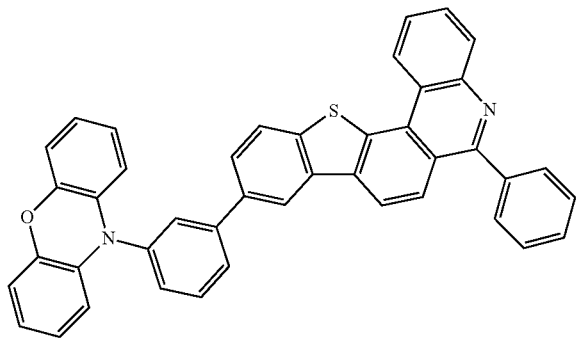
851
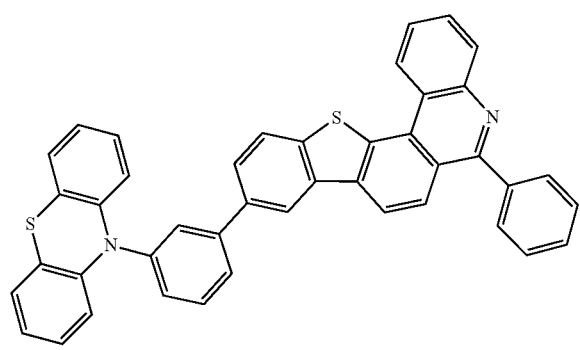
852
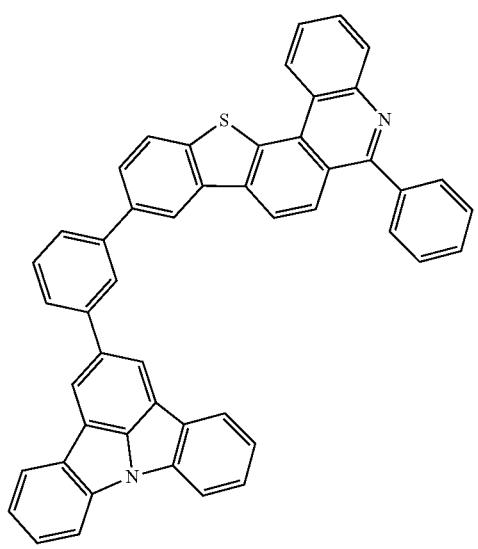
853
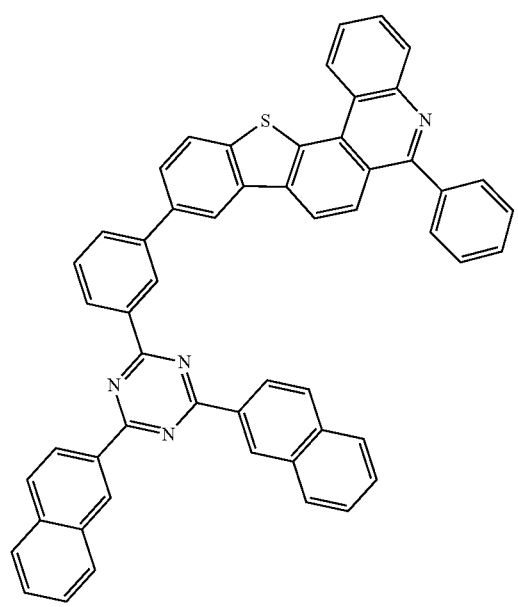
854
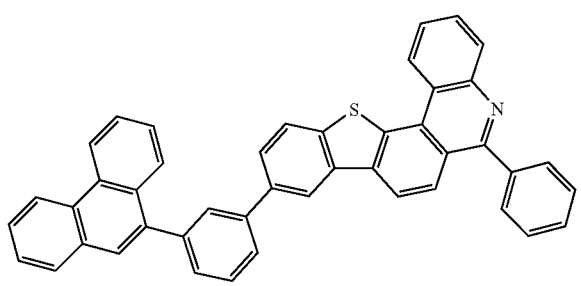

-continued

855

856

857

858

859
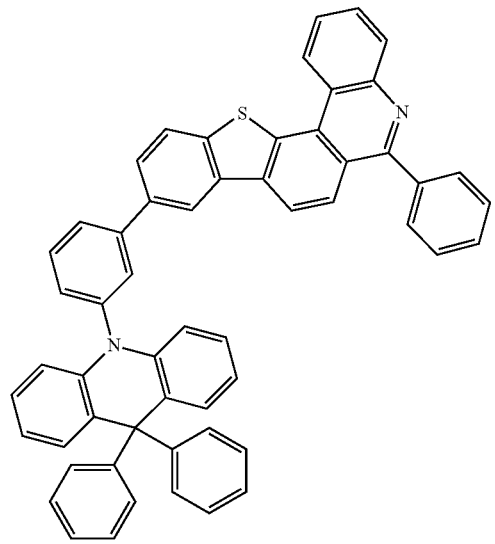
860
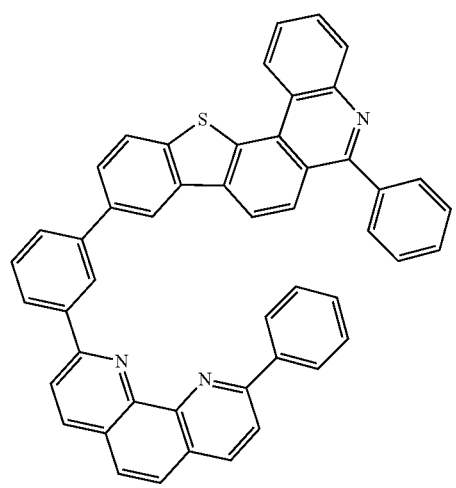
861
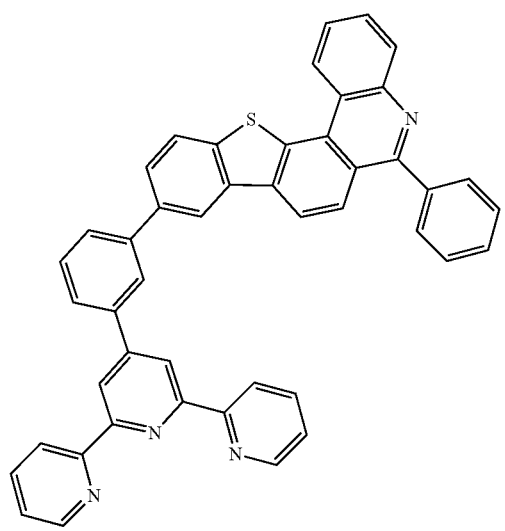
862
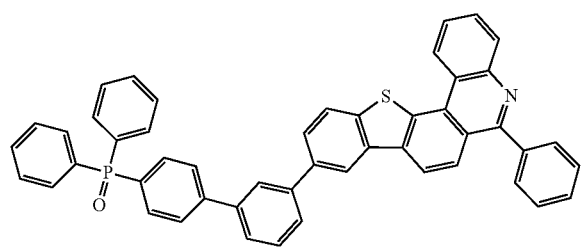
863
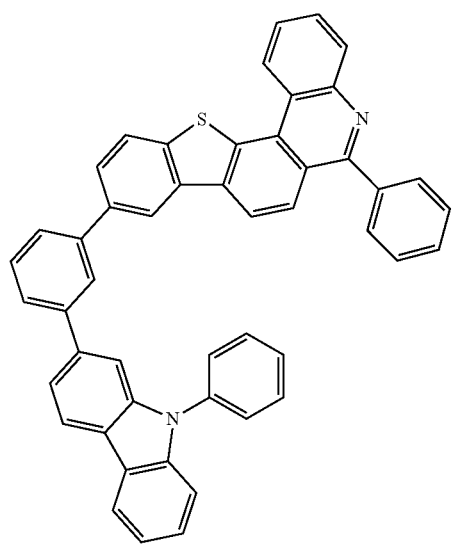

-continued
864
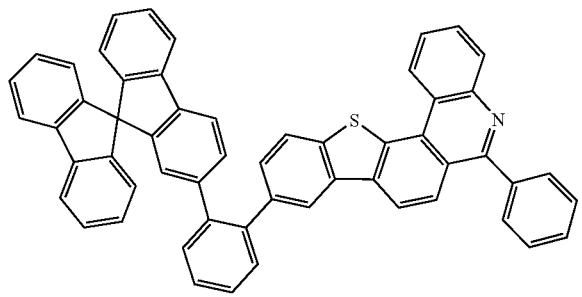
865
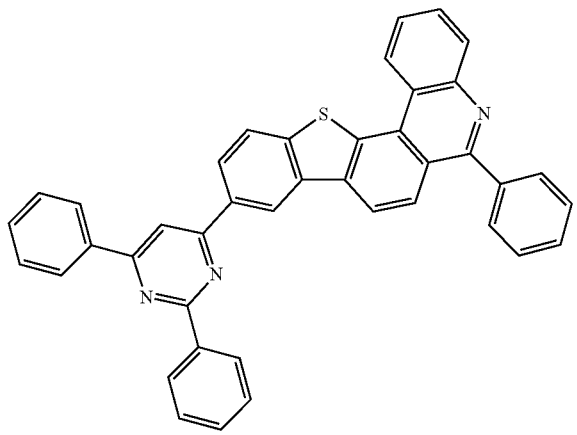
866
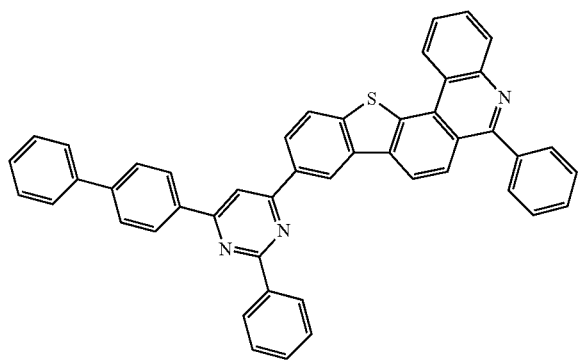
867
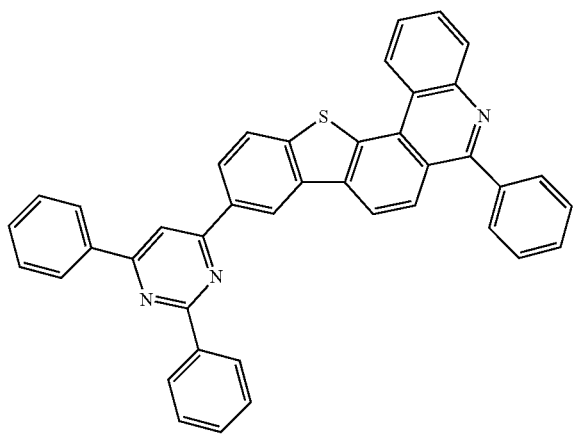
868
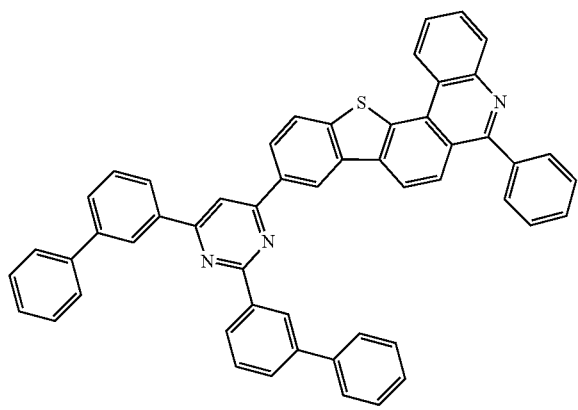
869
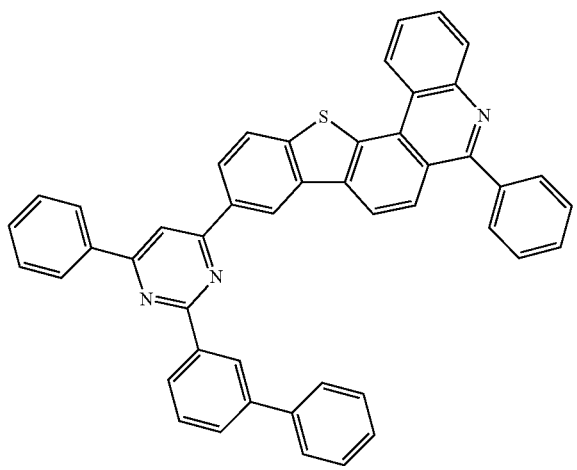

870
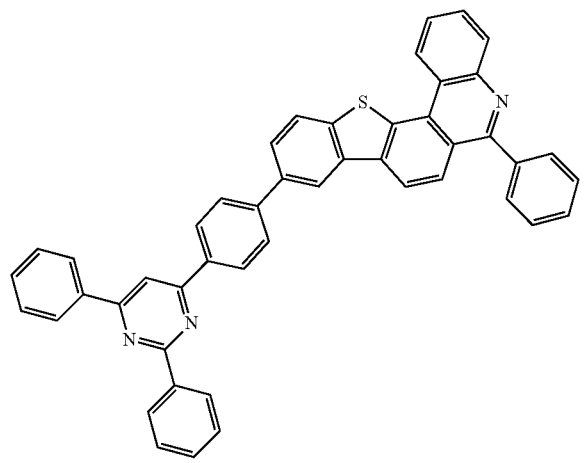
871
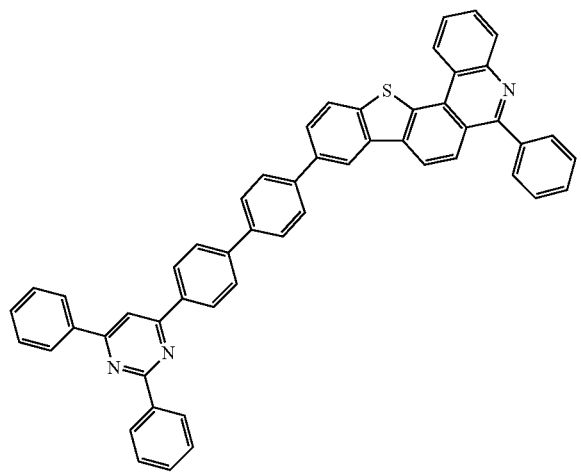
872
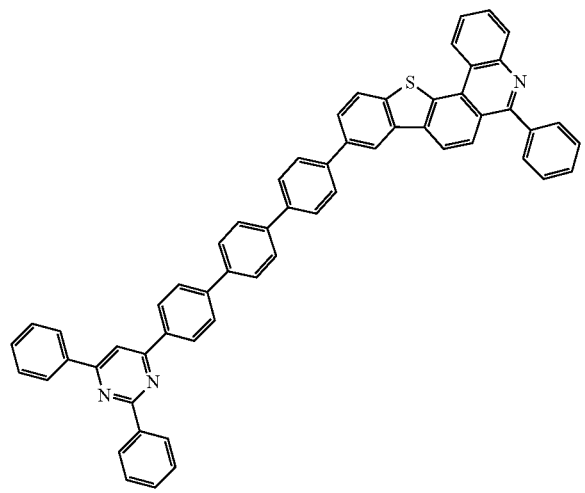
873
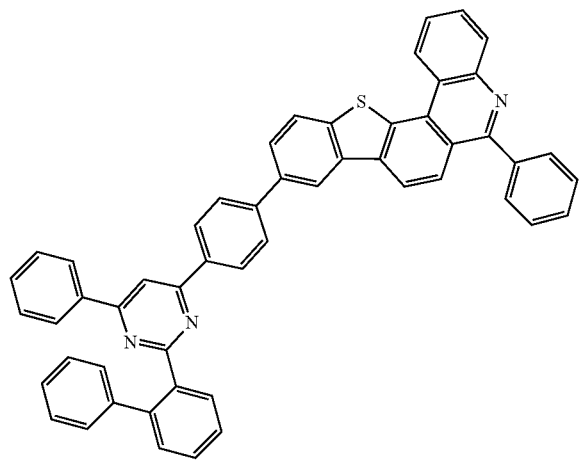
874
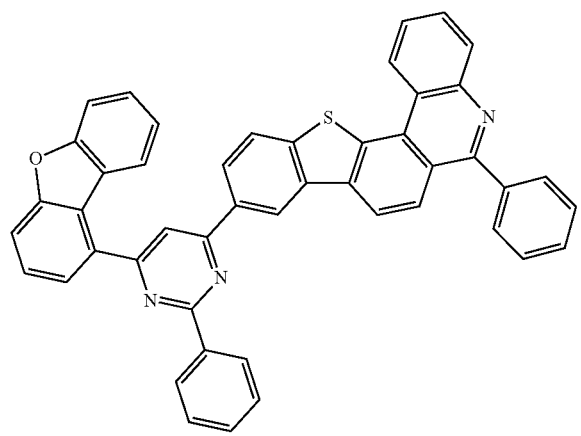
875
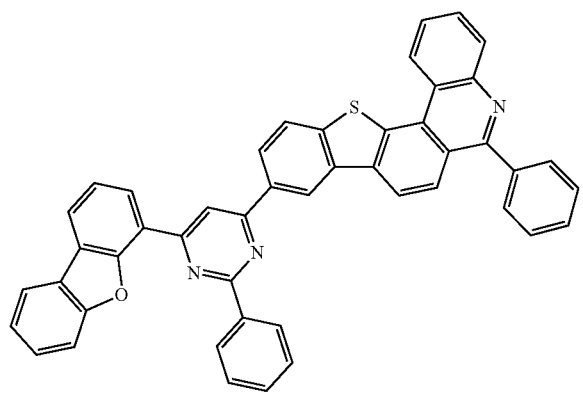

1071                                  1072
-continued
876                                                                  877
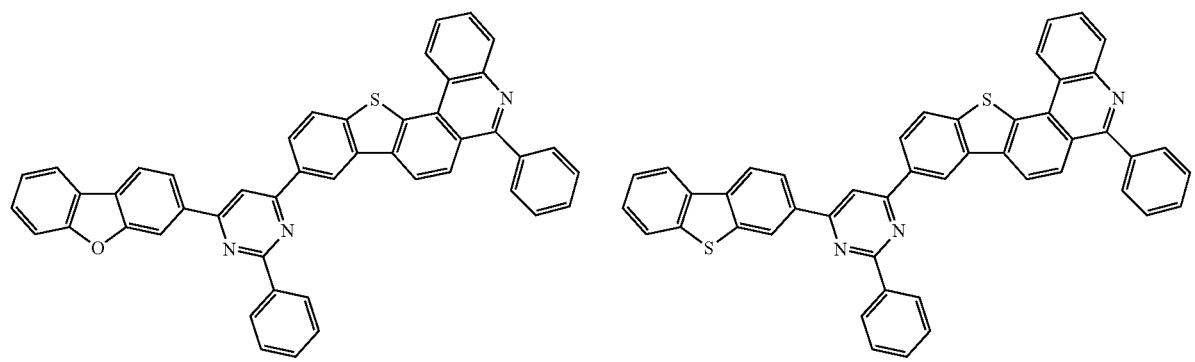
878                                                                  879
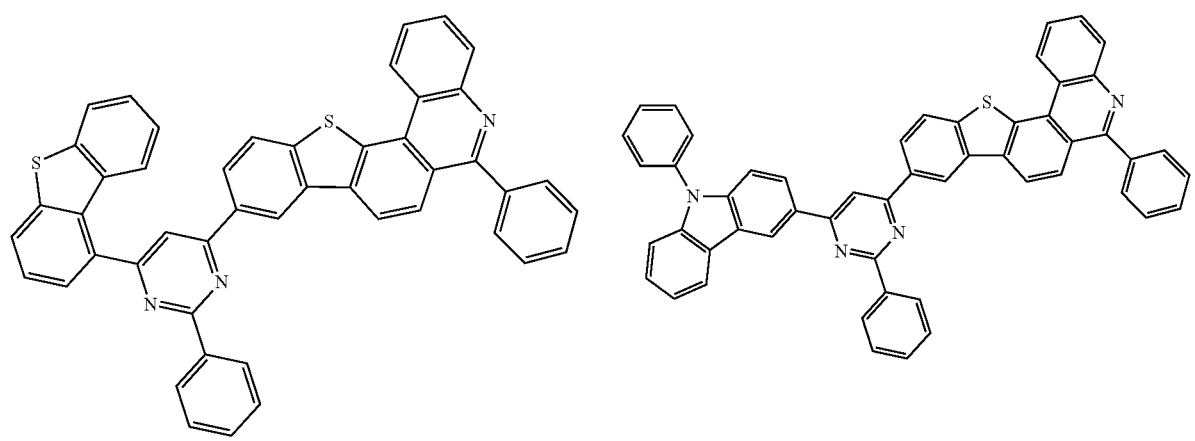
880                                                                  881
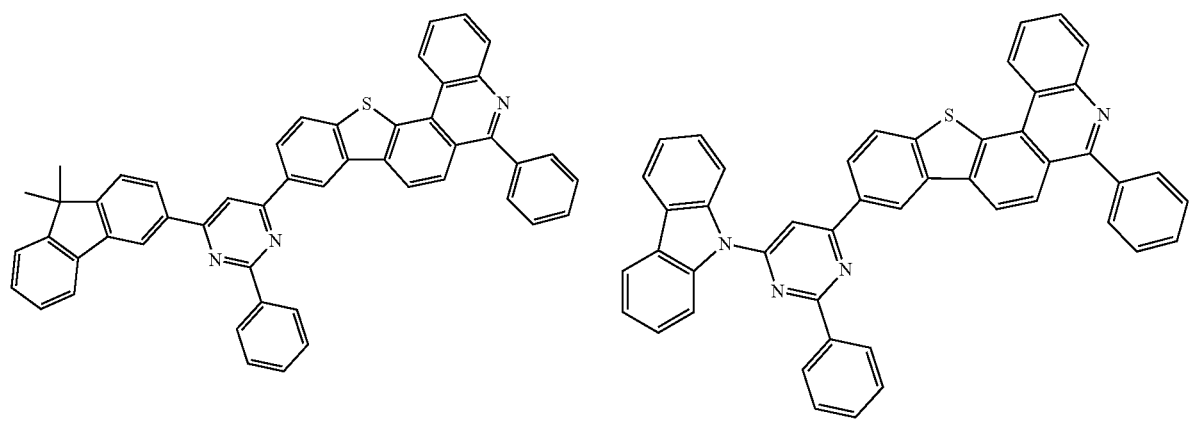

1073 1074
-continued
882 883
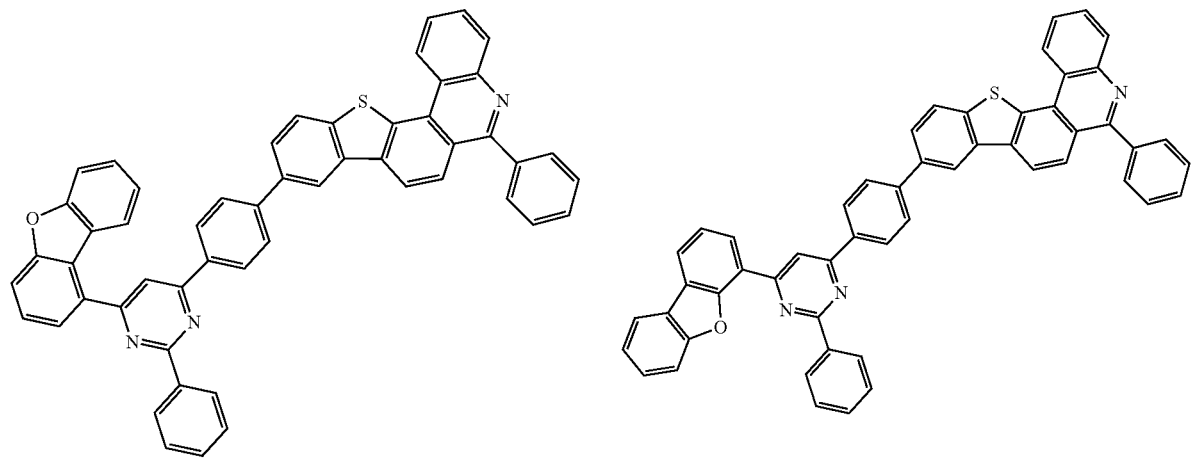
884
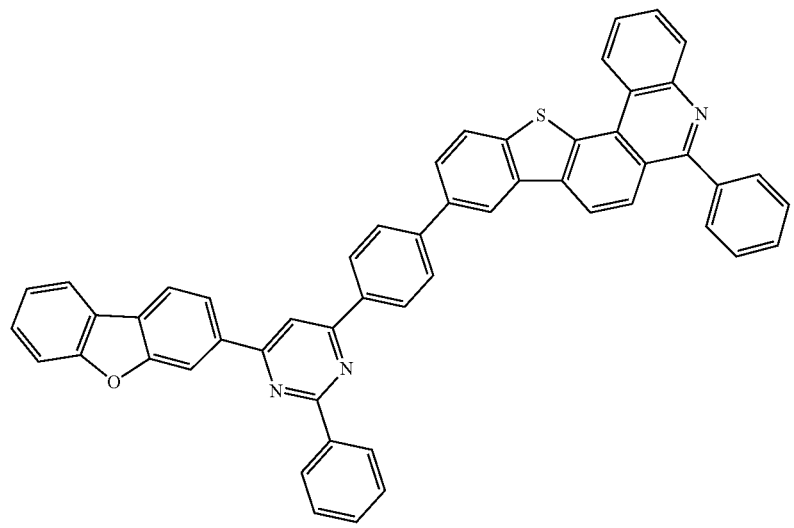
885
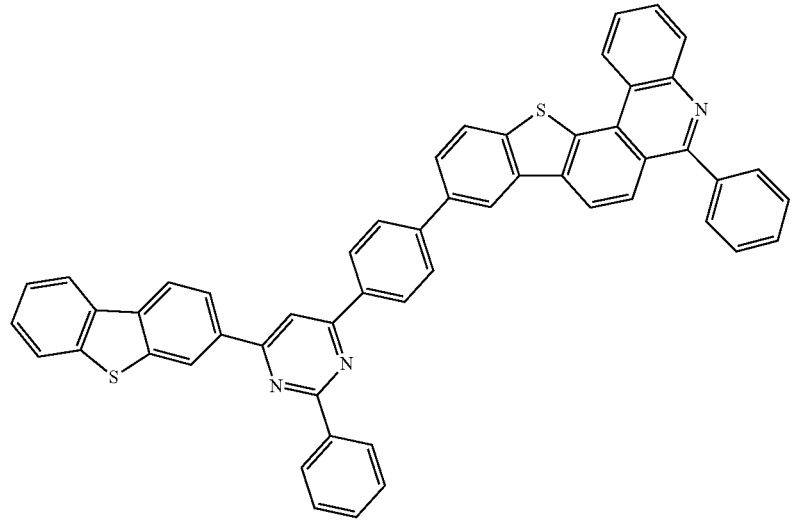

886
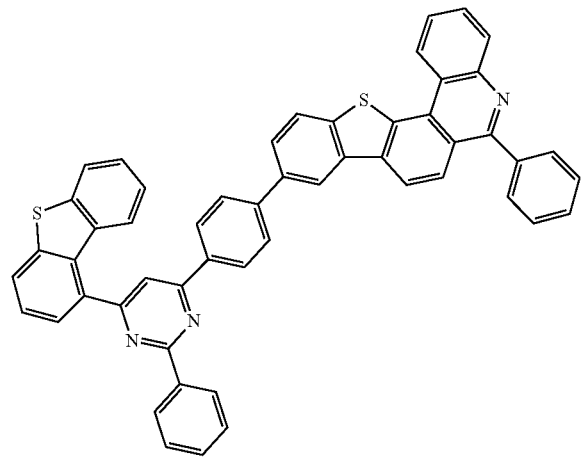
887
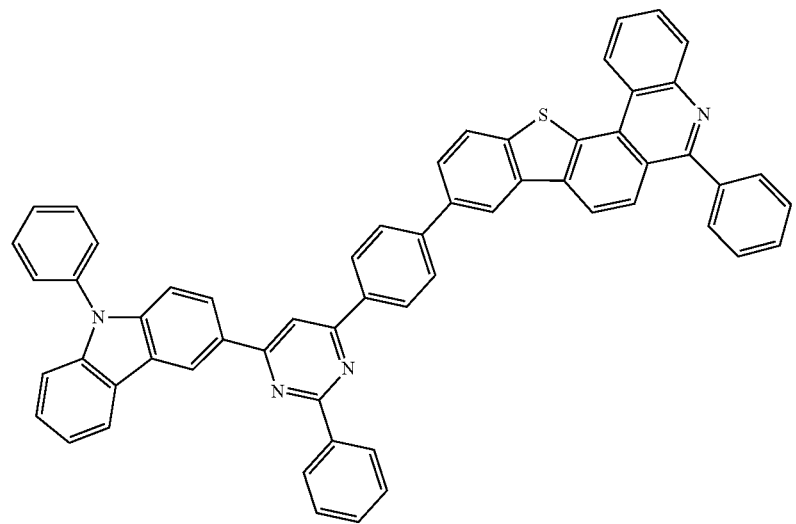
888
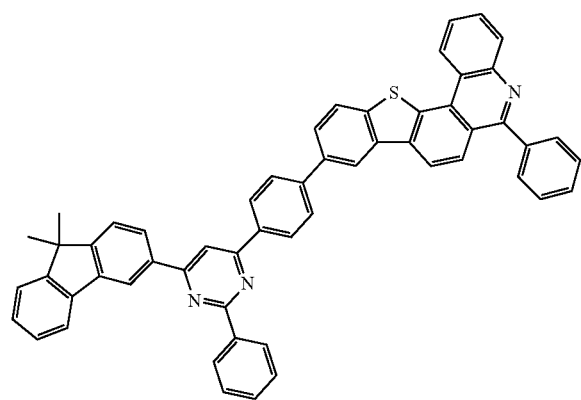
889
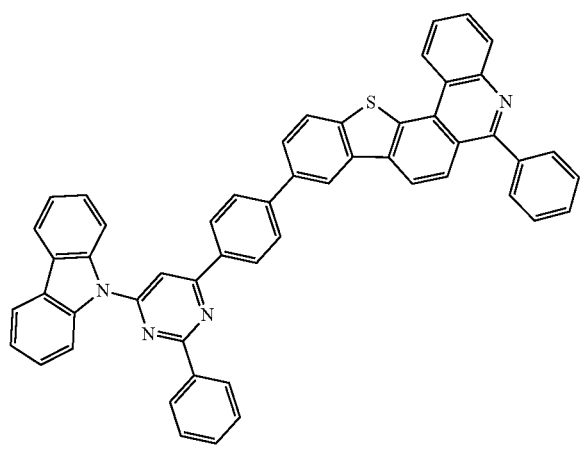

-continued
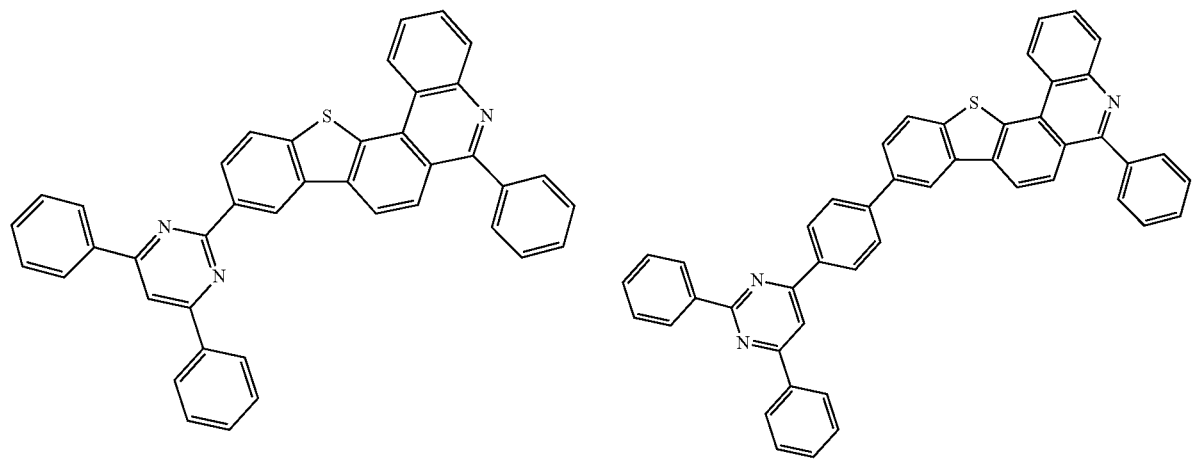
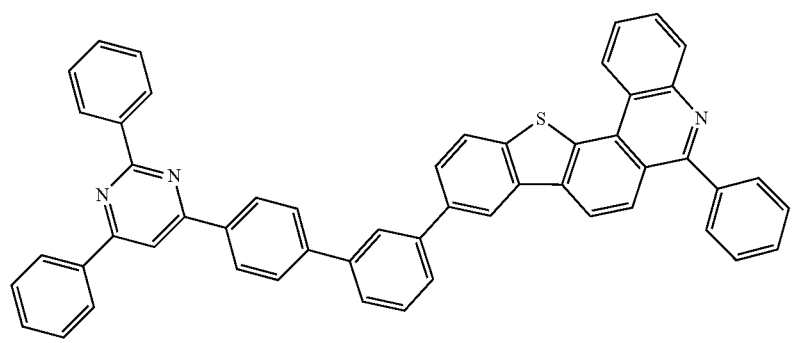
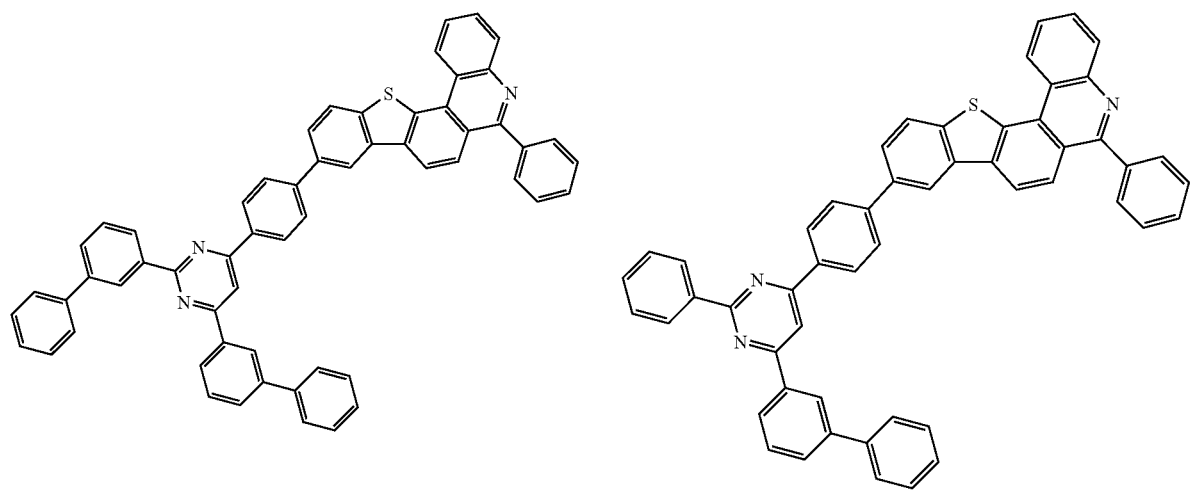

895
896
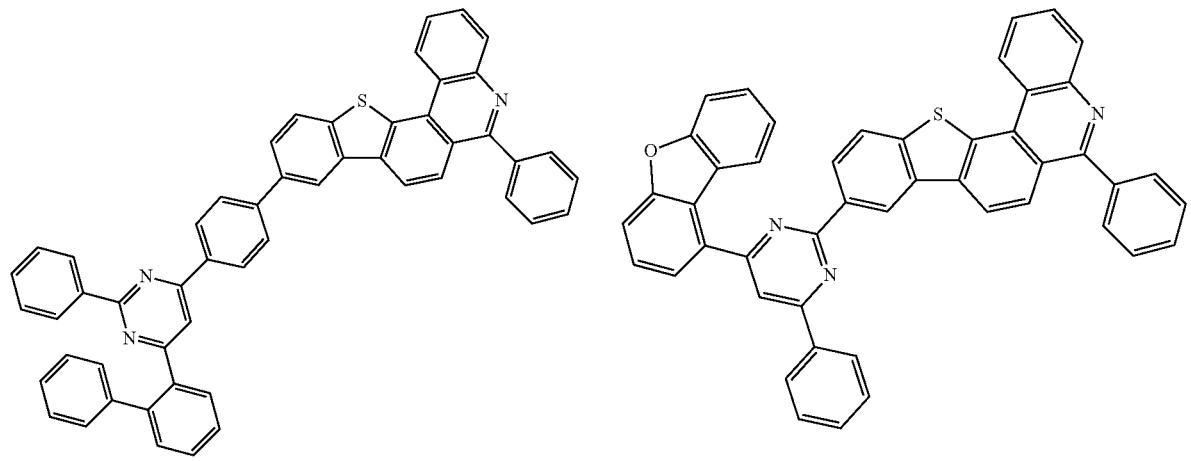
897
898
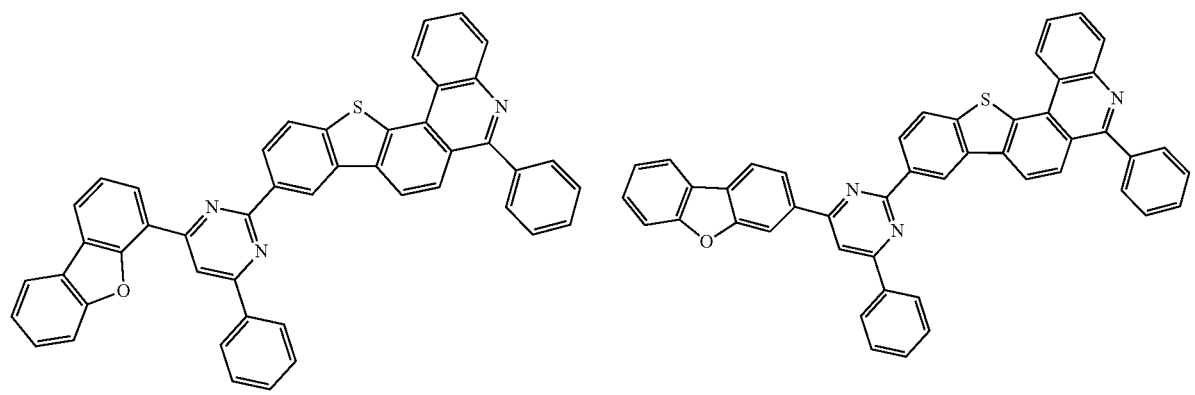
899
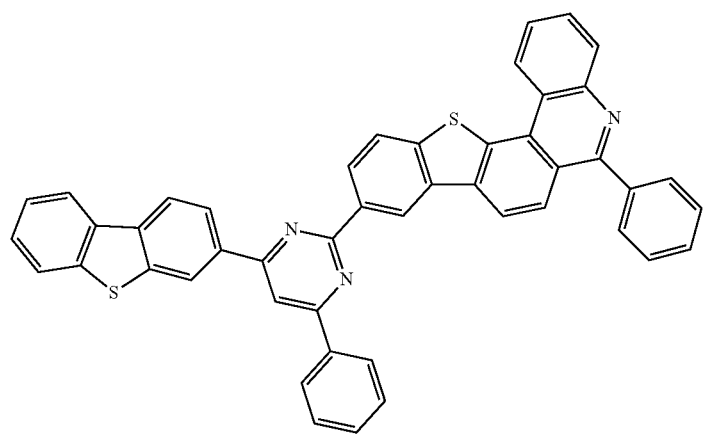

1081 1082
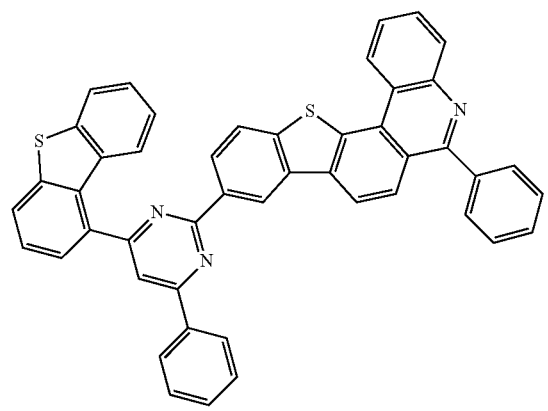
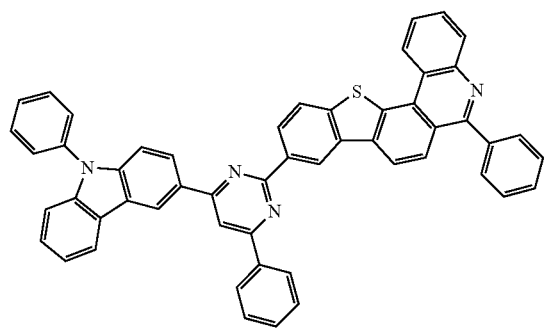
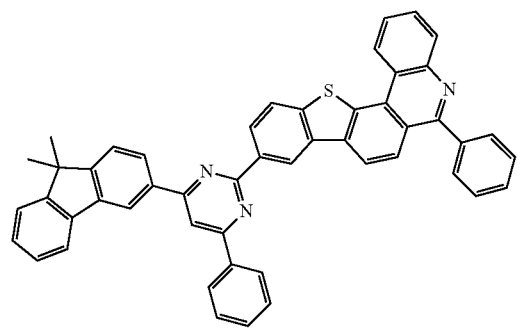
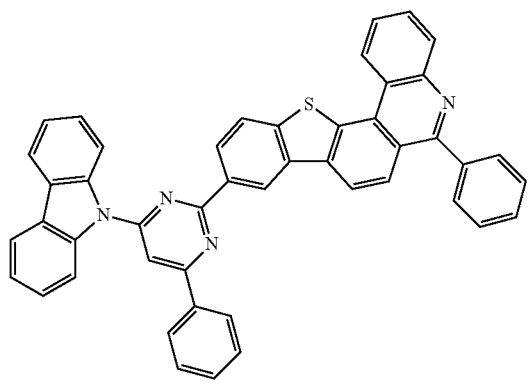
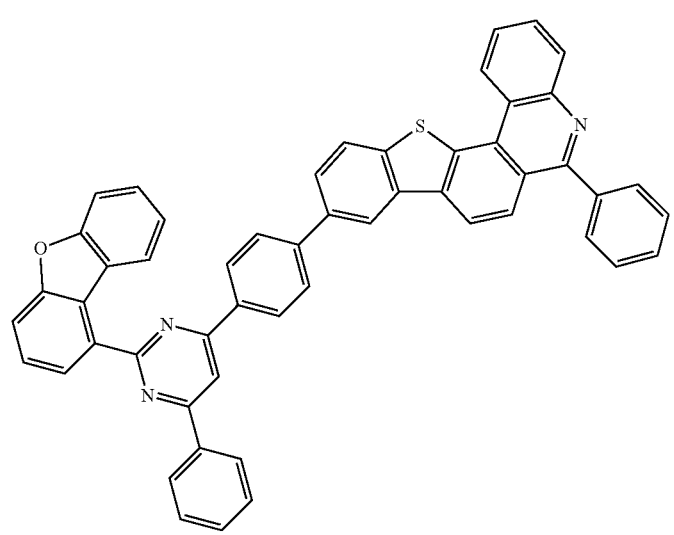

905
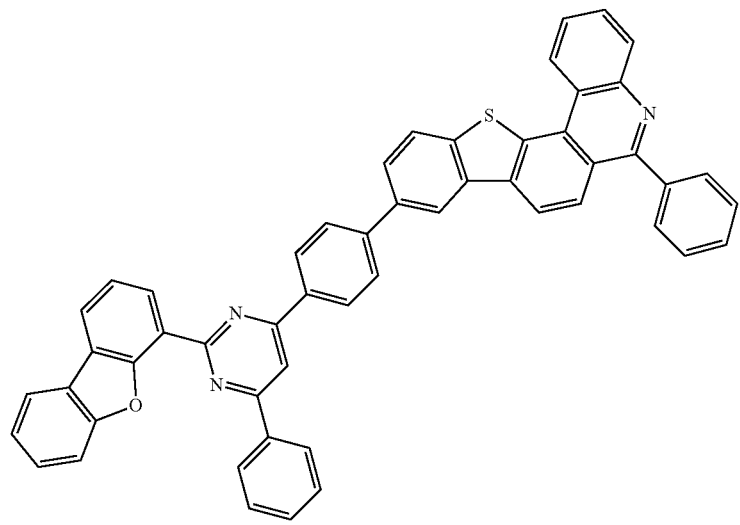
906
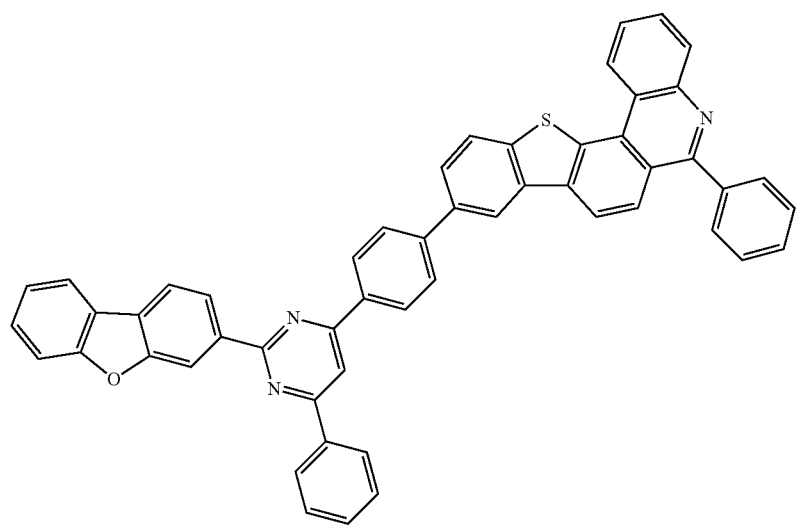
907
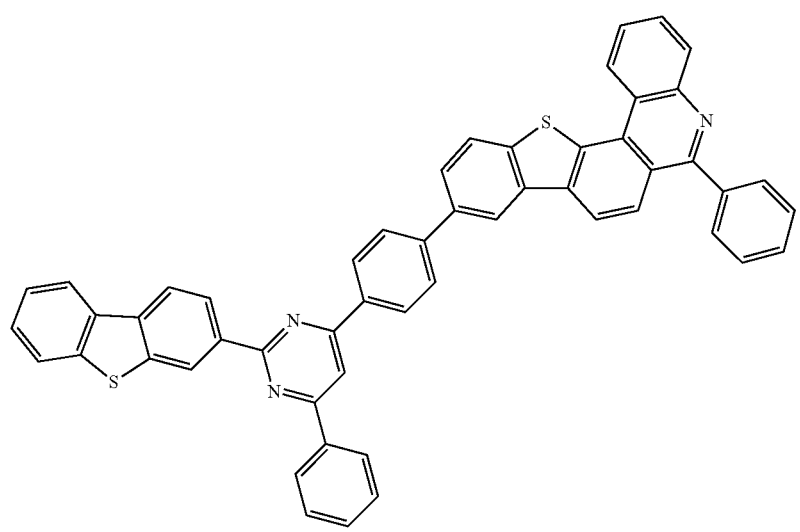

-continued
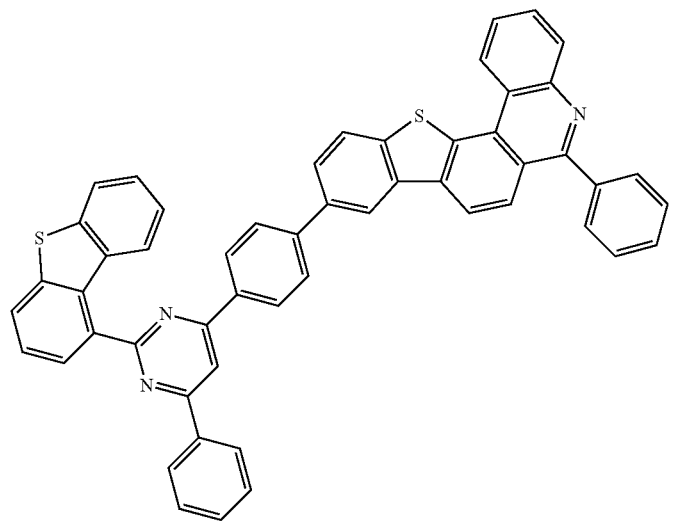
908
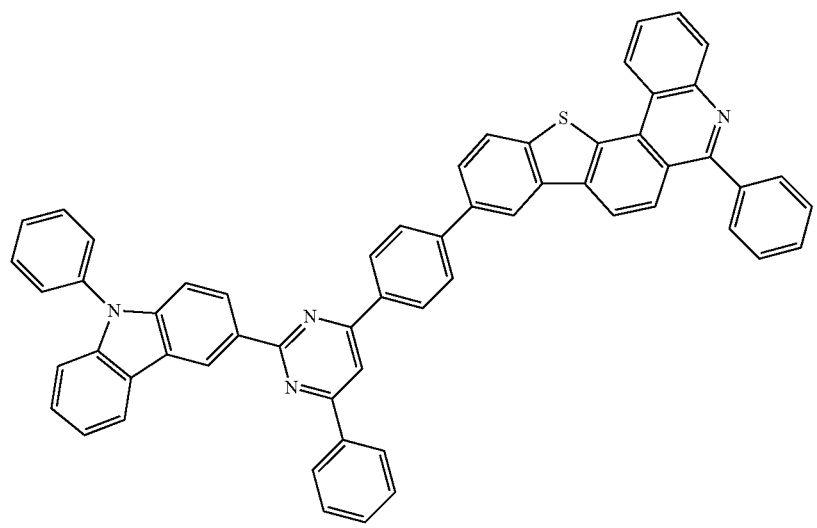
909
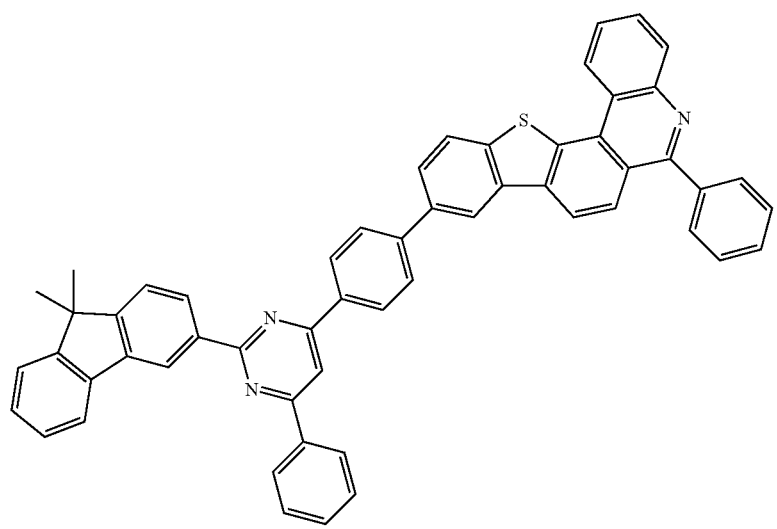
910

-continued
1087
911
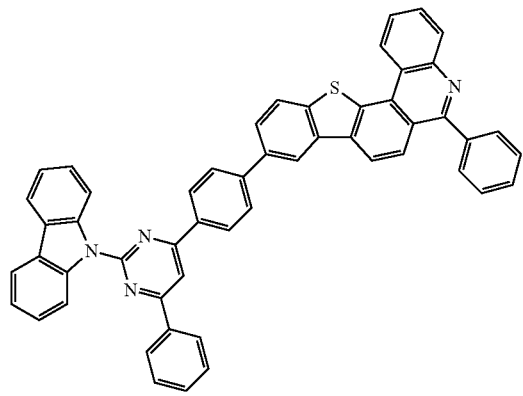
1088
912
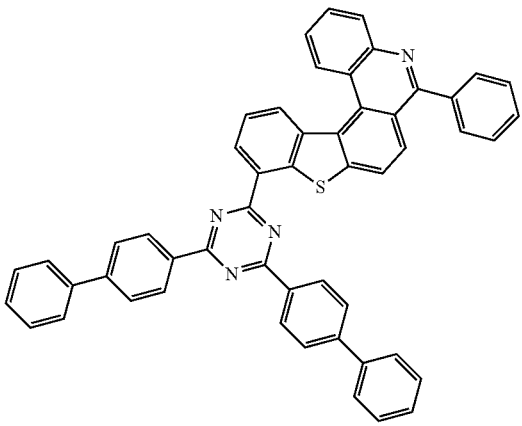
913
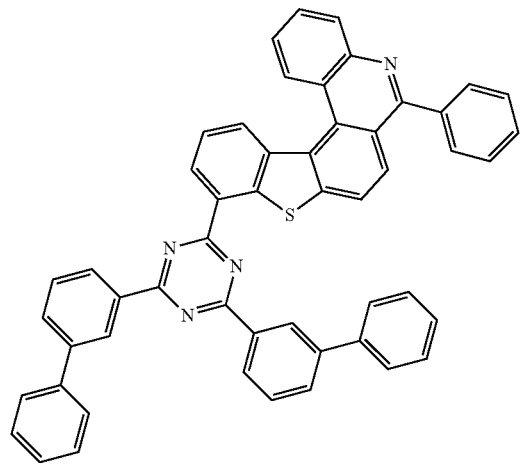
914
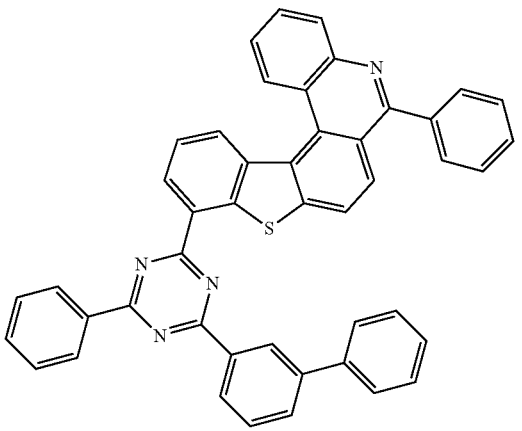
915
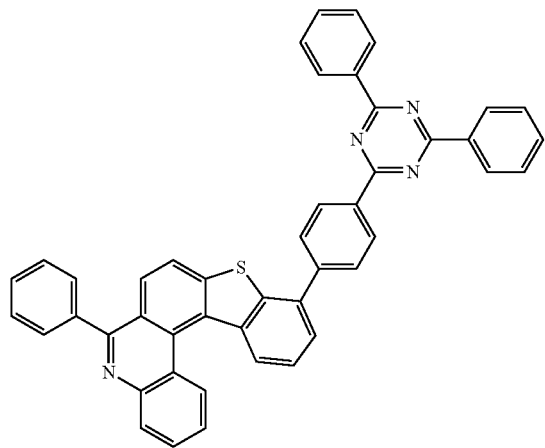
916
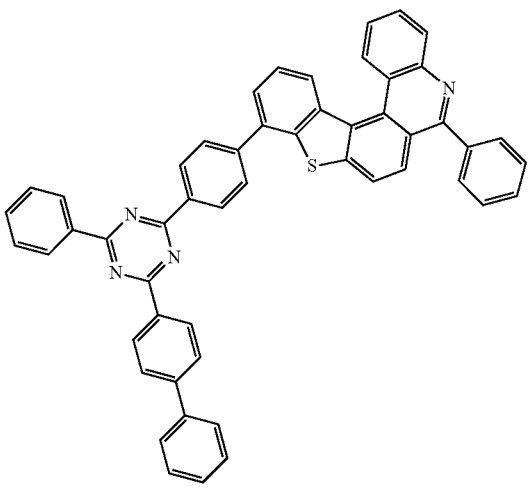

1089 1090
-continued
917
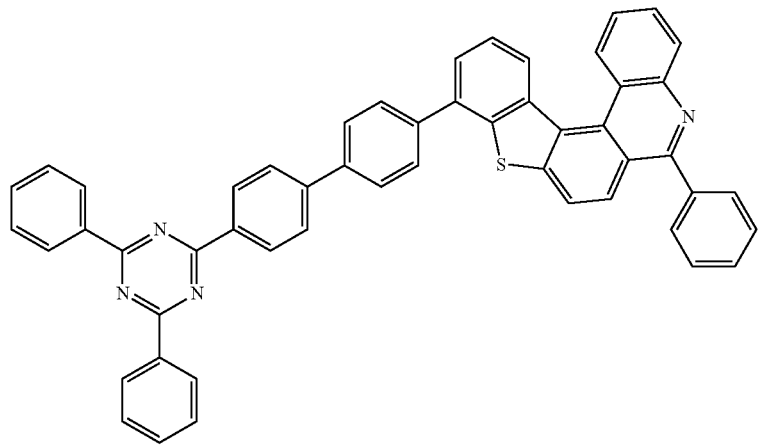
918
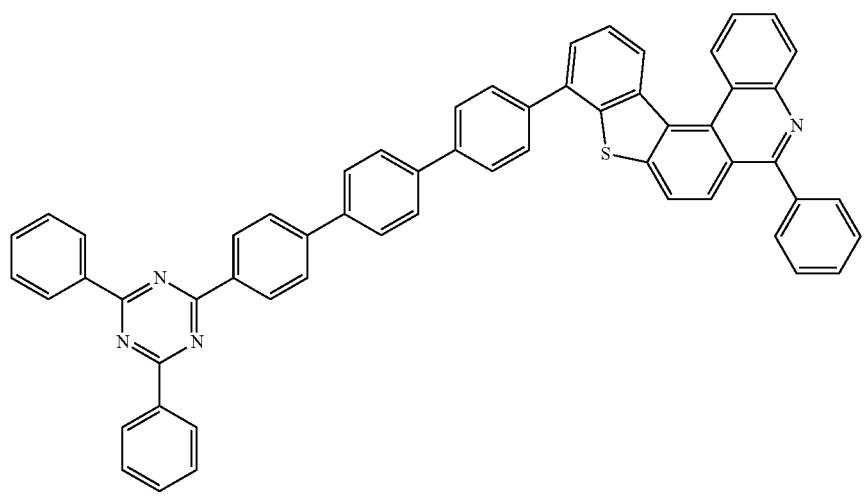
919
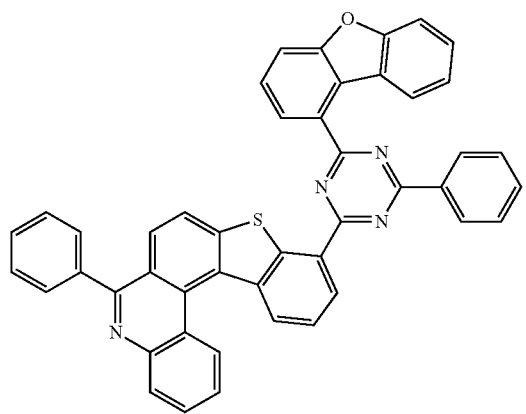
920
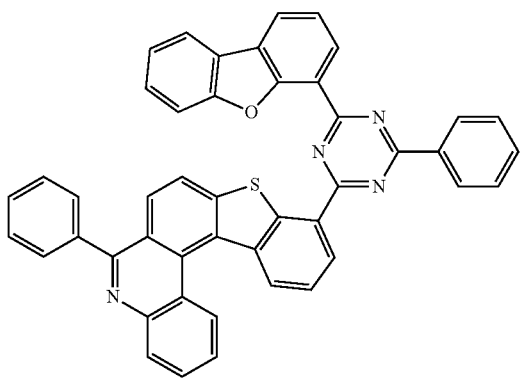

-continued
921
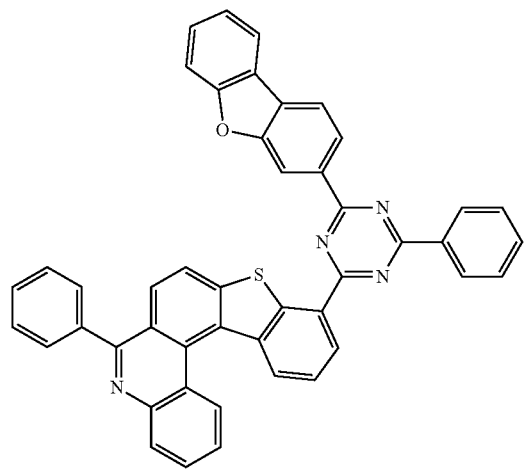
922
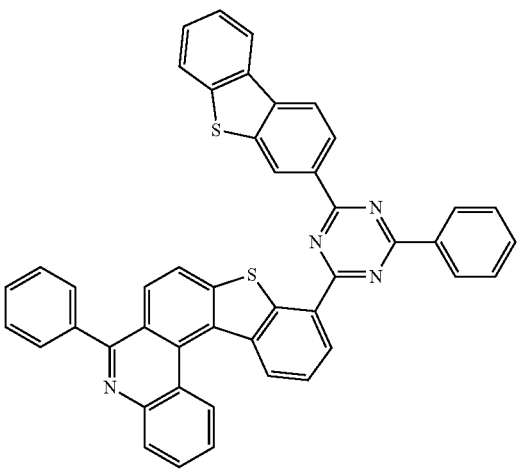
923
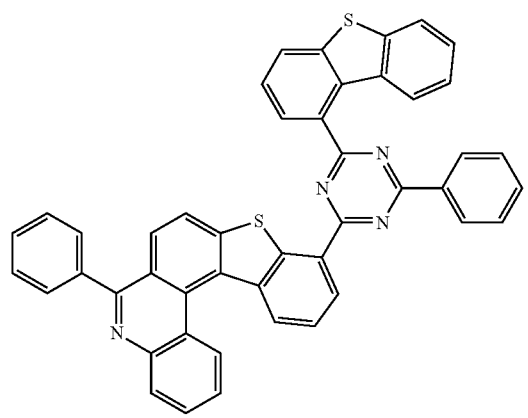
924
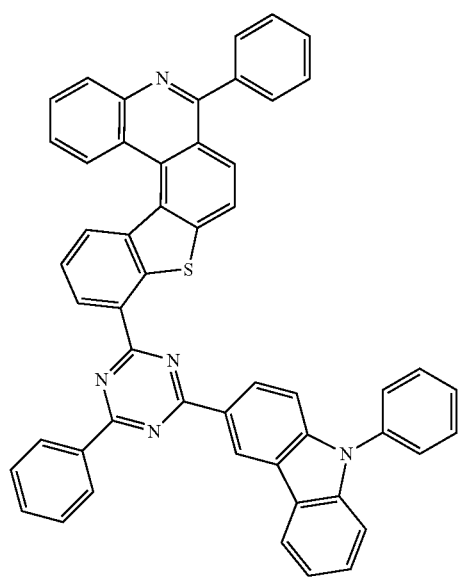
925
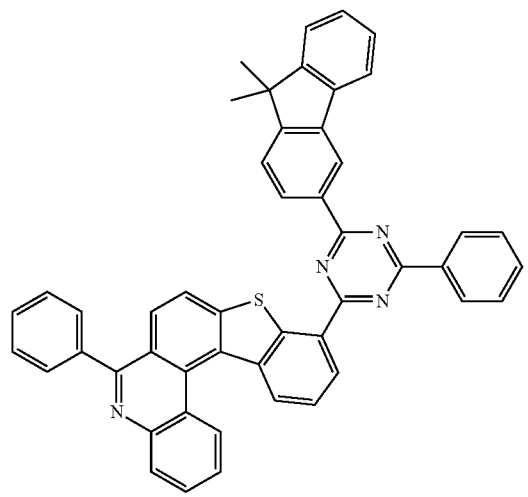
926
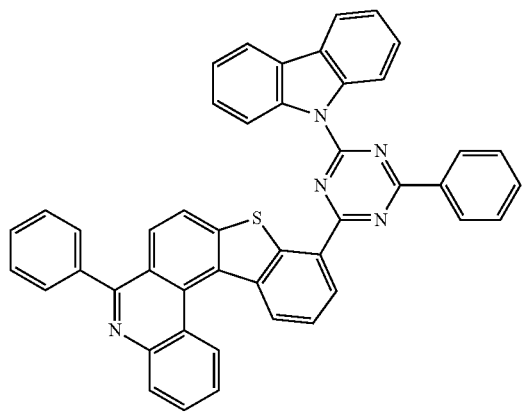

-continued
927
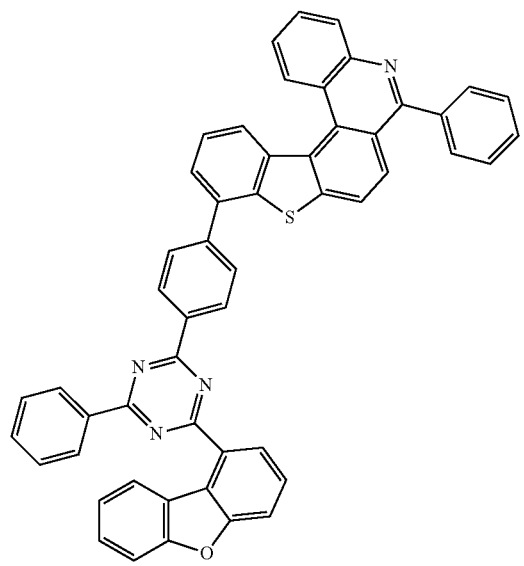
928
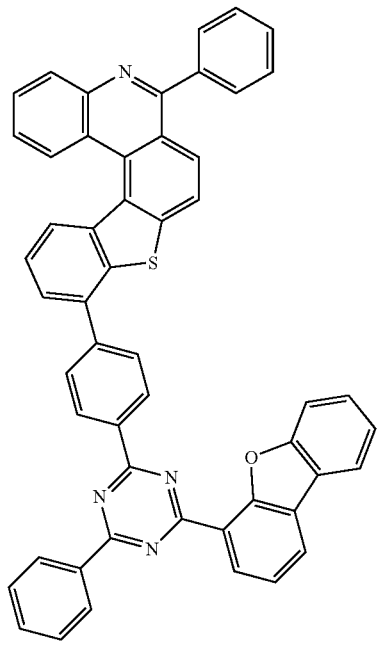
929
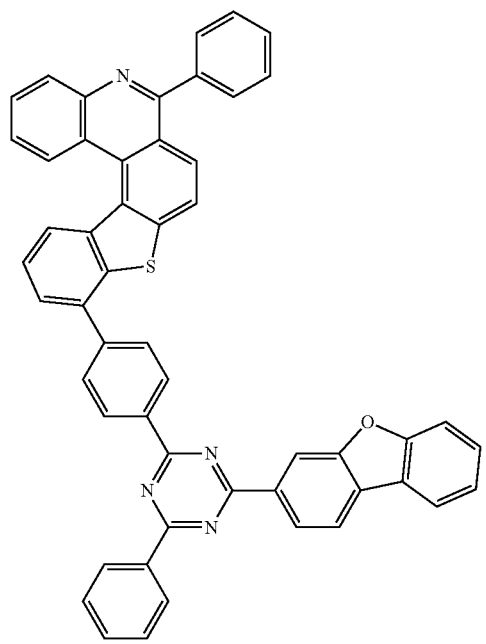
930
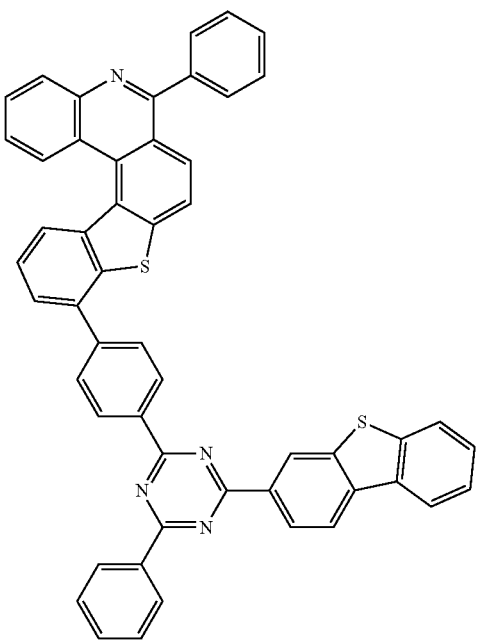

1095 1096
-continued
931 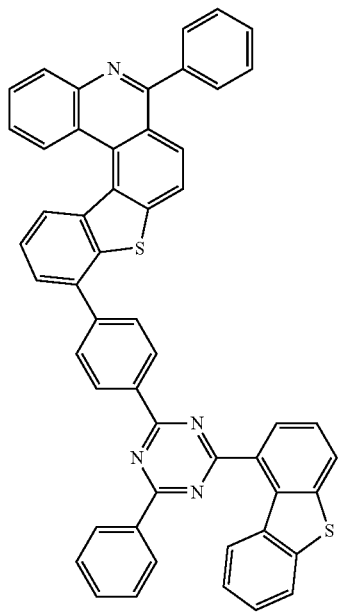 932 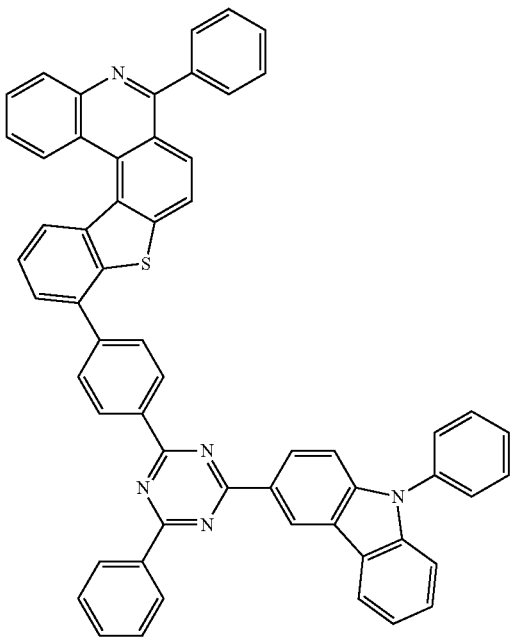
933 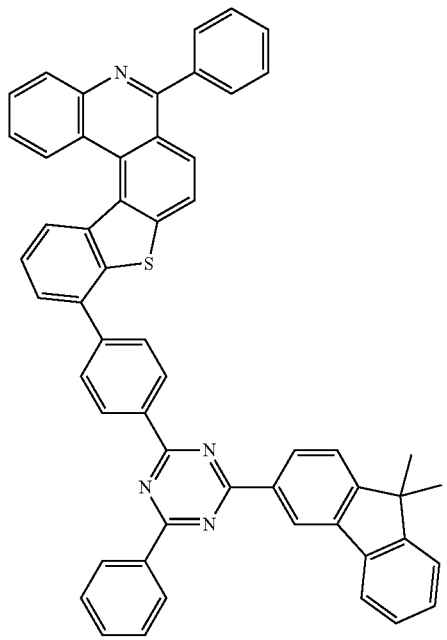 934 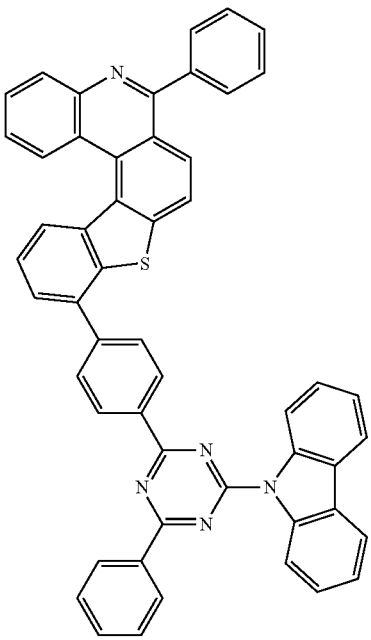

-continued
935
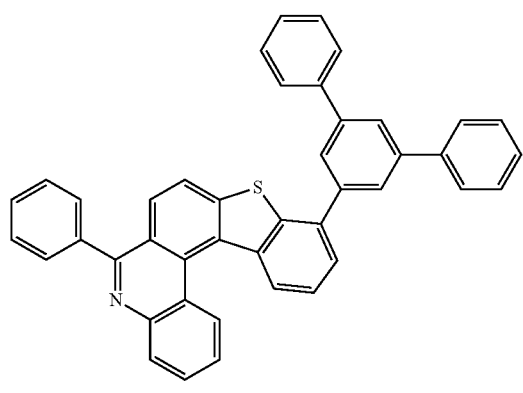
936
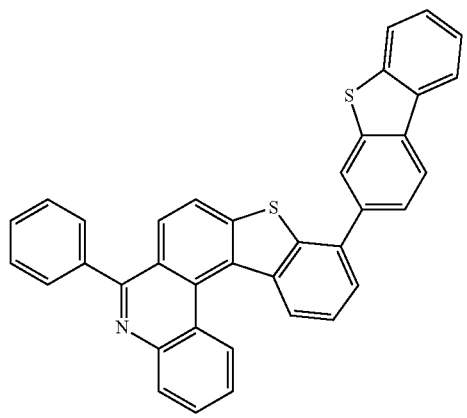
937
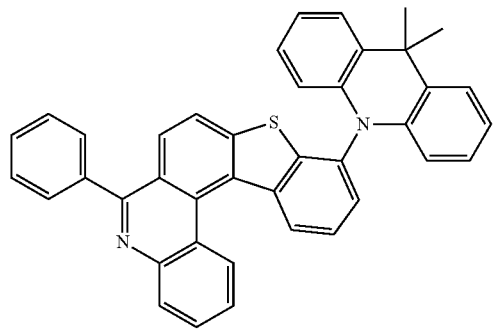
938
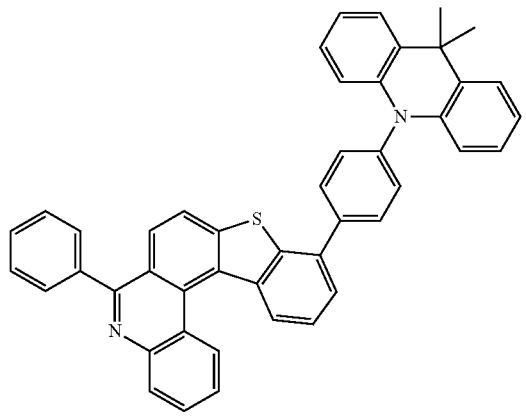
939
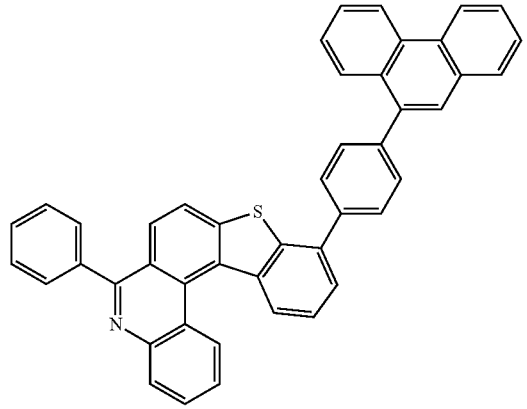
940
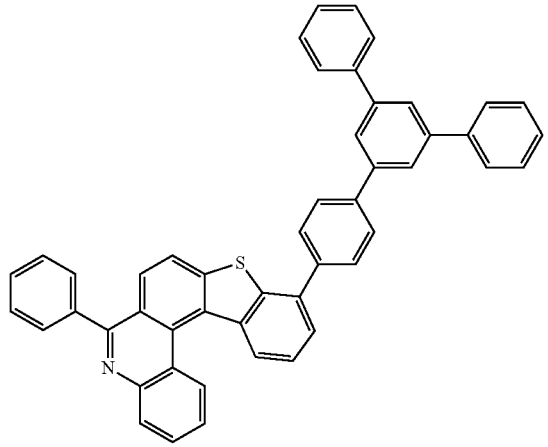

-continued
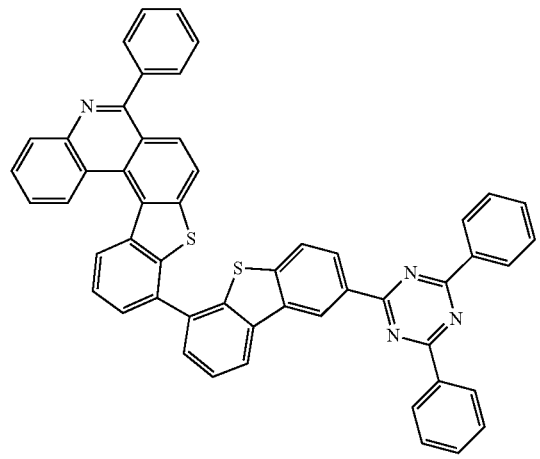
941
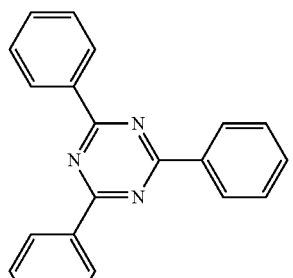
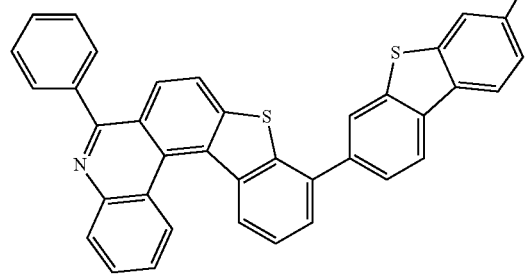
942
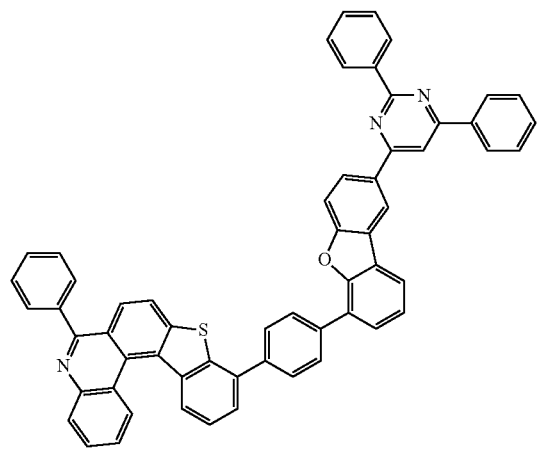 [SMILES: c1ccc(-c2cc(-c3ccc4oc5c(-c6ccc(-c7cccc8c7sc7ccc9c(-c%10ccccc%10)nc%10ccccc%10c9c78)cc6)cccc5c4c3)nc(-c3ccccc3)n2)cc1]
943
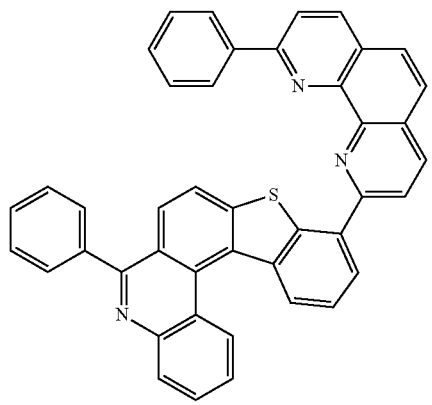
944

-continued
1101
945
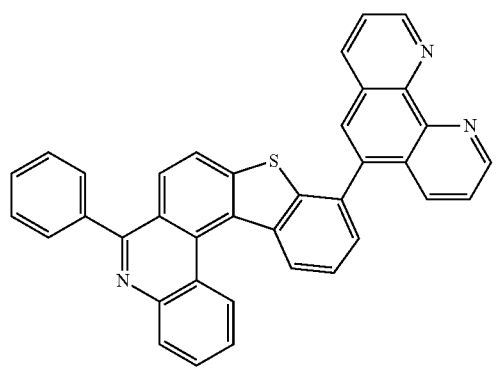
947
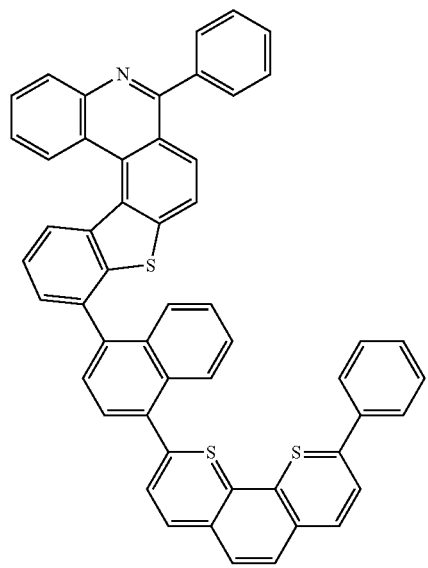
949
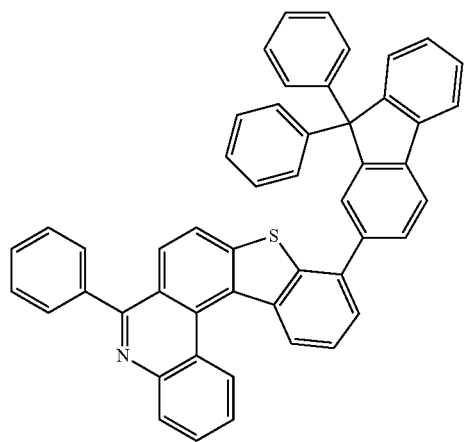
1102
946
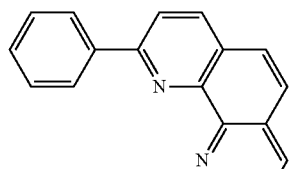
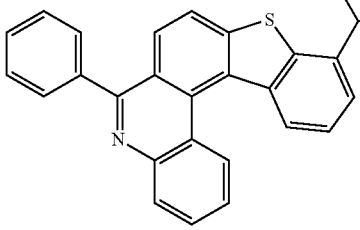
948
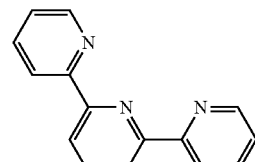
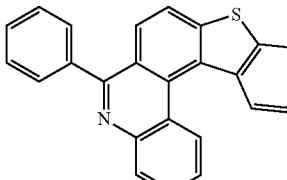
950
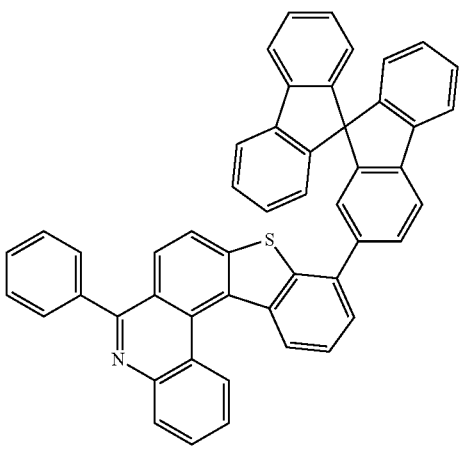

-continued
951
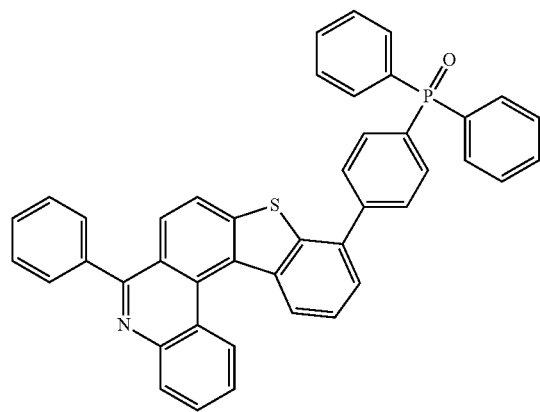
952
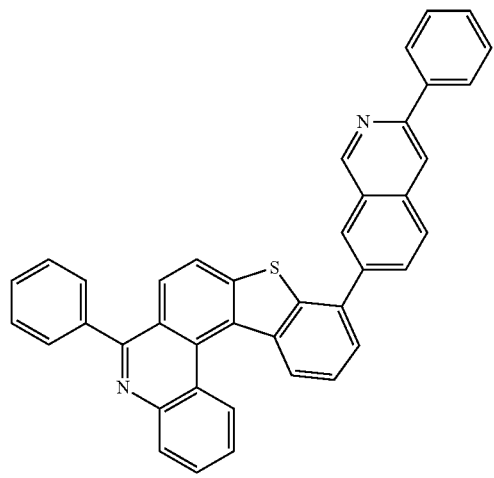
953
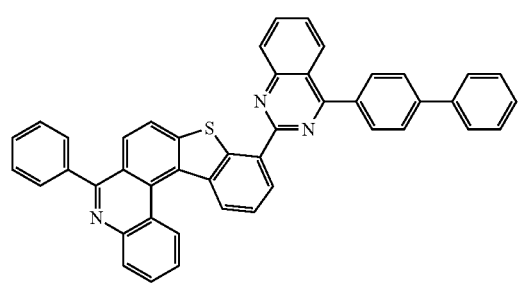
954
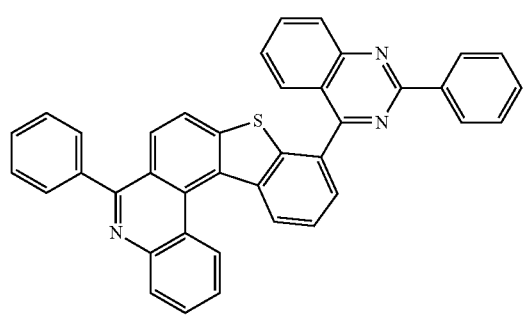
955
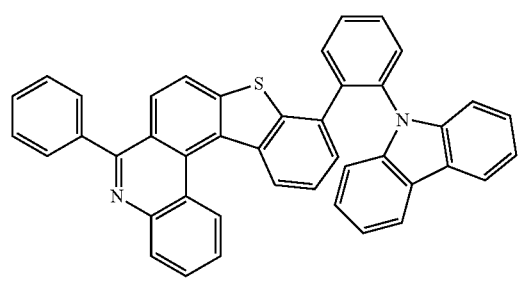
956
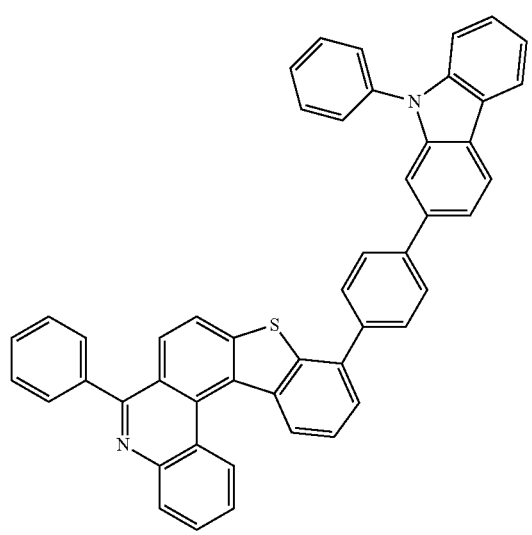

-continued
957
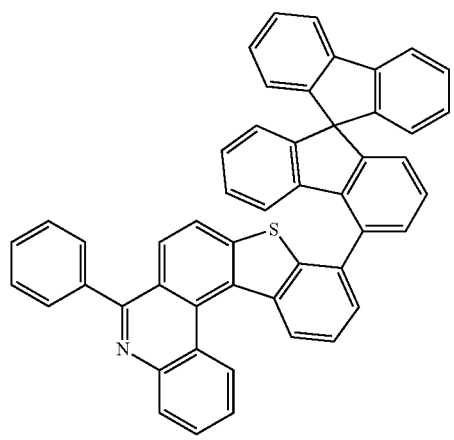
958
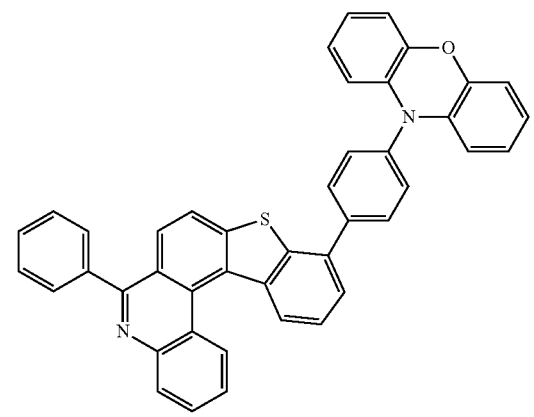
959
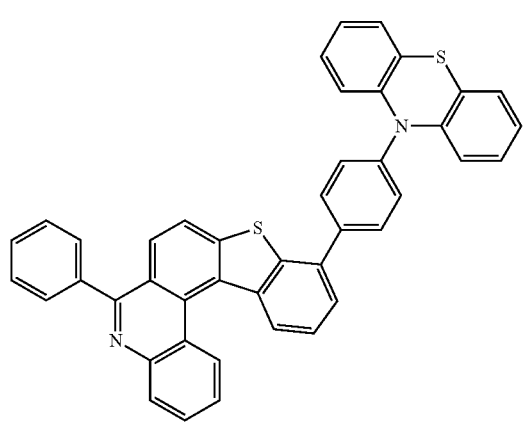
960
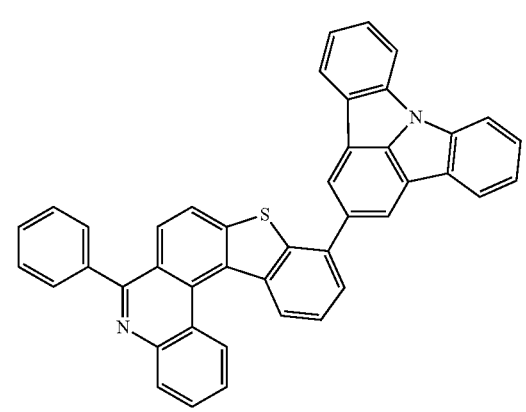
961
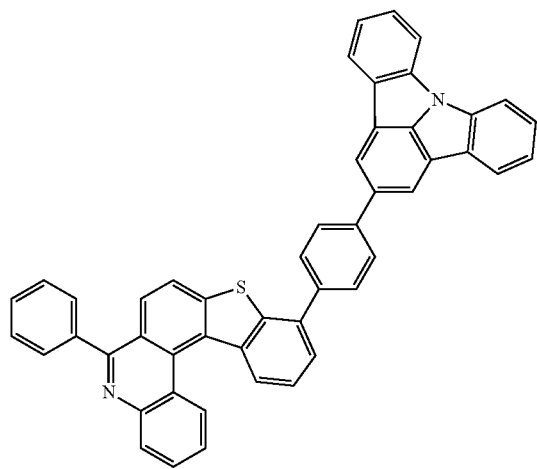
962
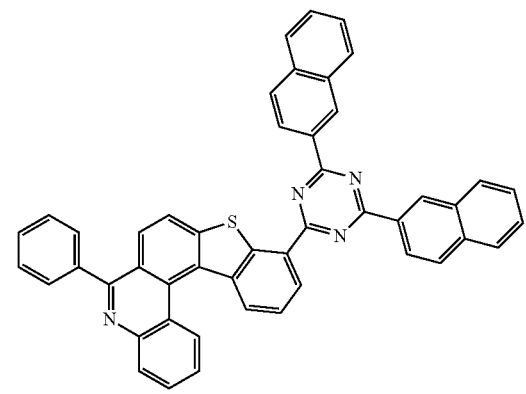

-continued
1107
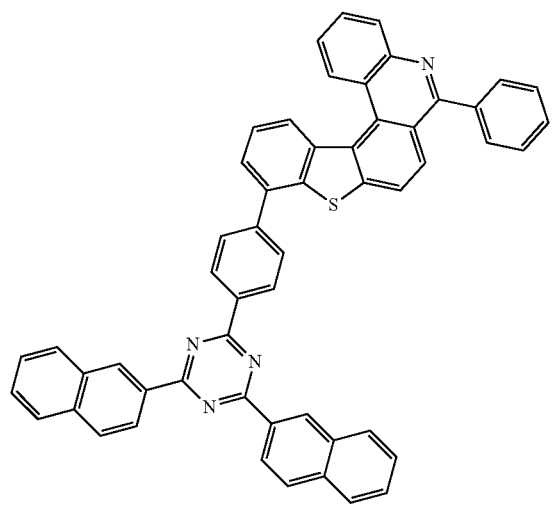
1108
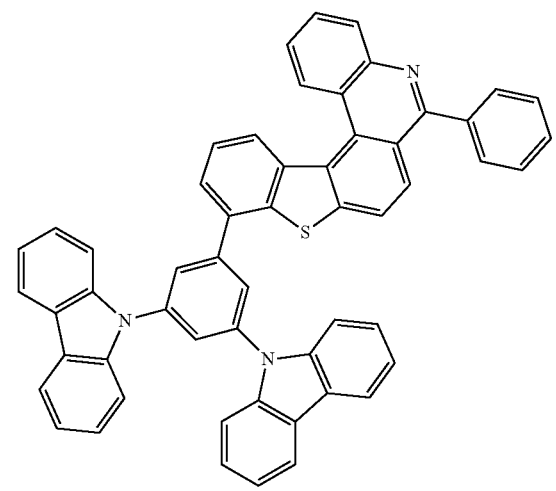
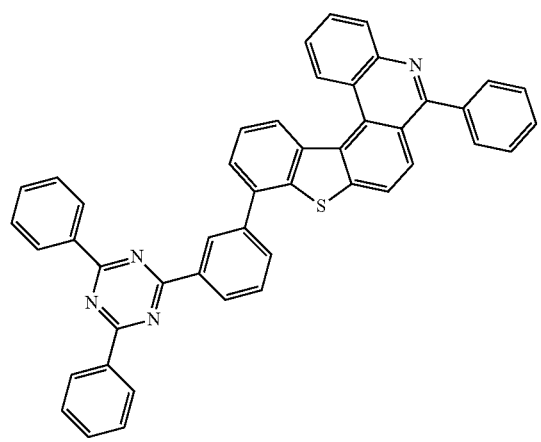
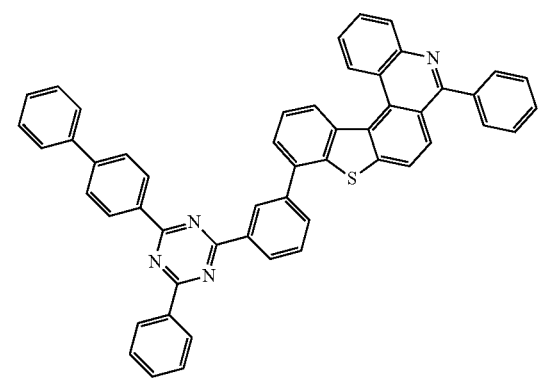
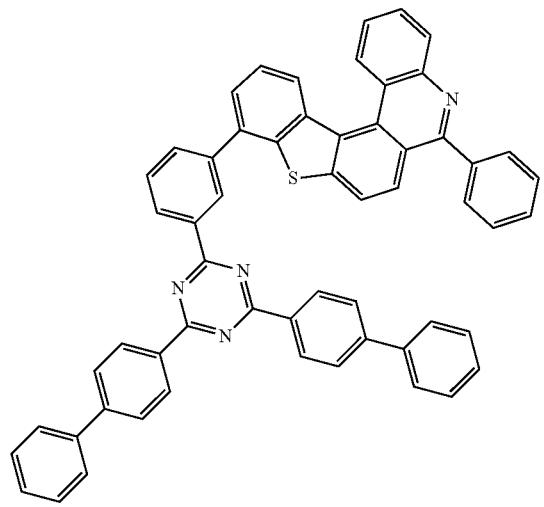
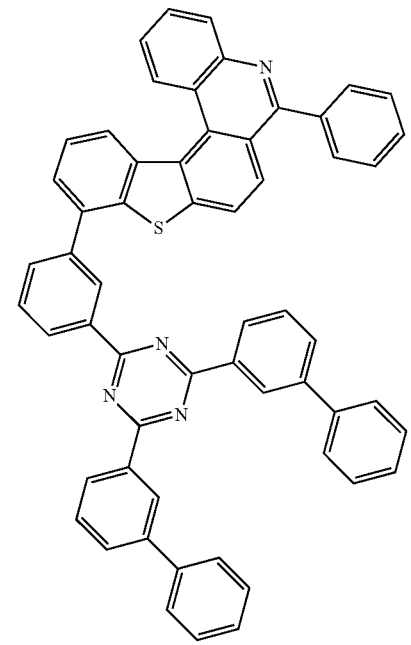

-continued
969
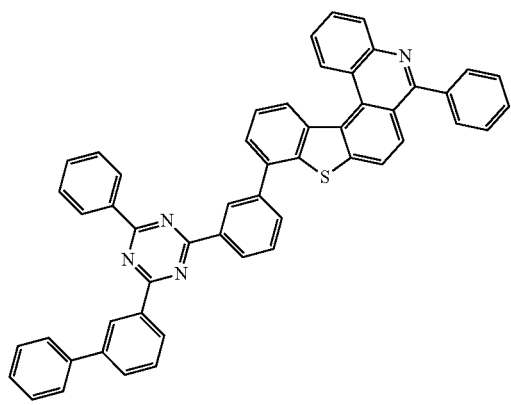
970
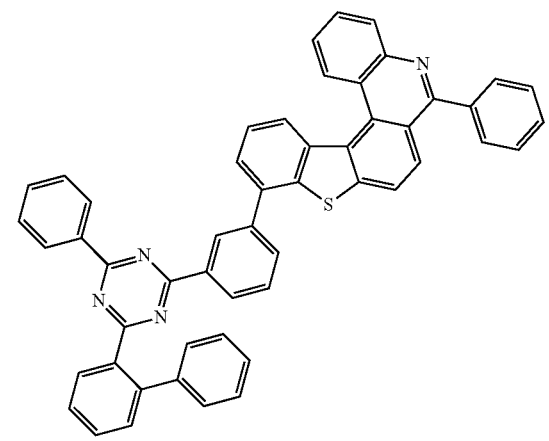
971
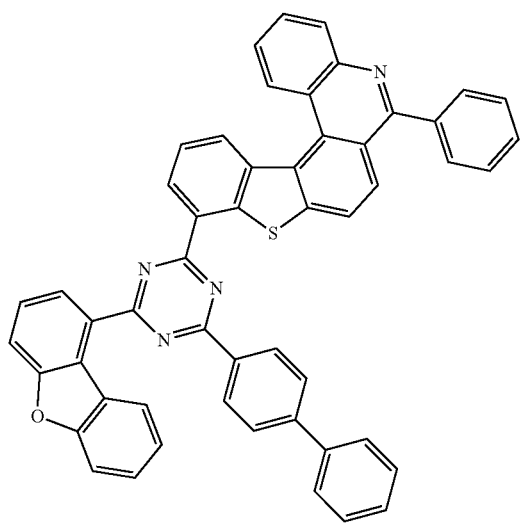
972
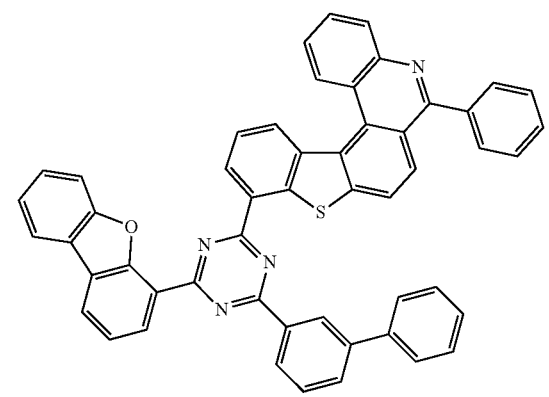
973
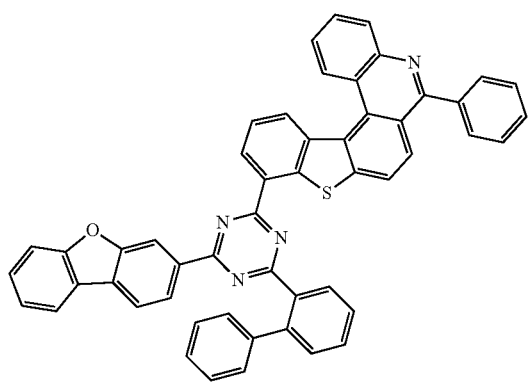
974
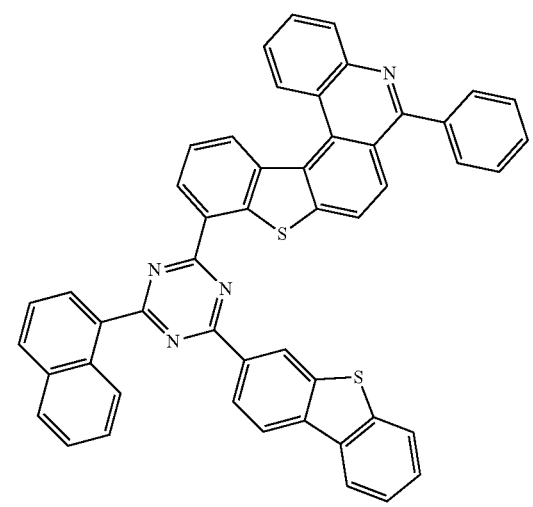

-continued
975
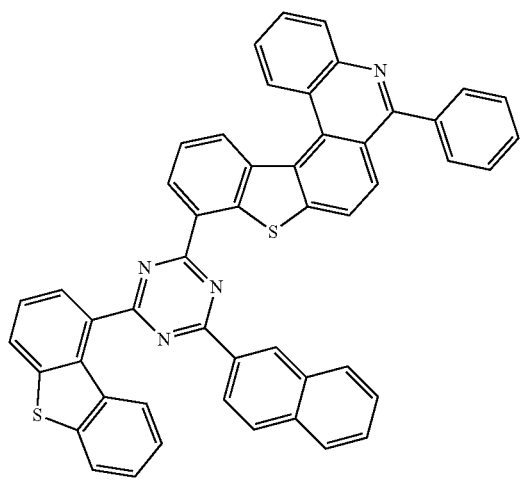
976
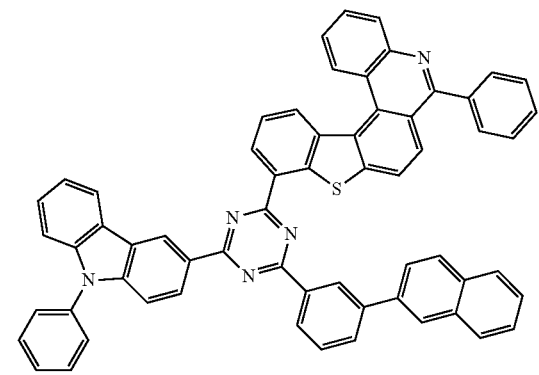
977
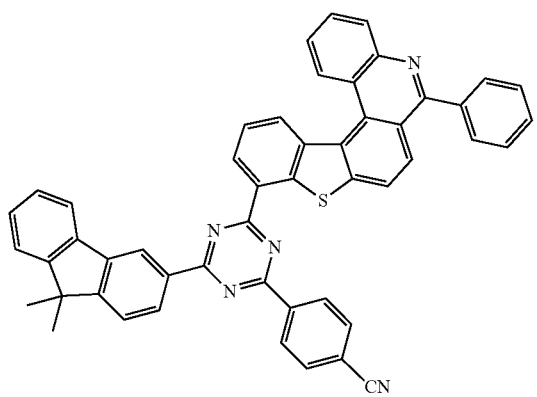
978
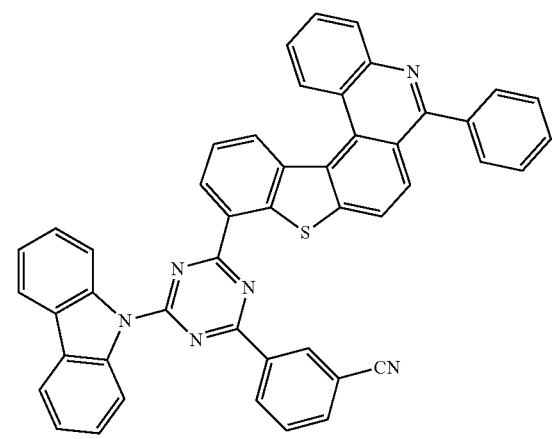
979
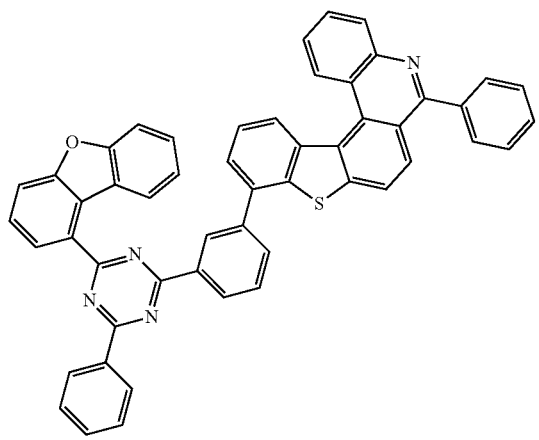
980
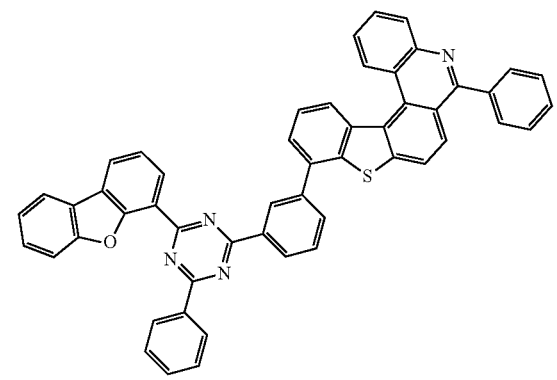

-continued
981
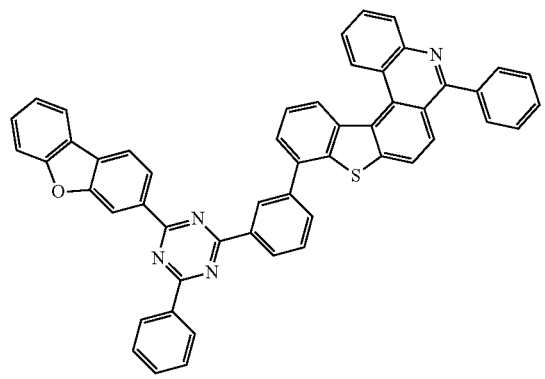
982
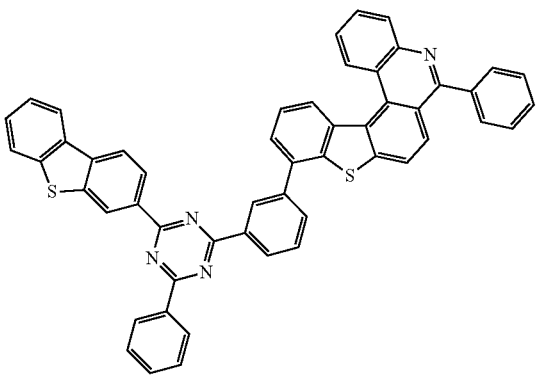
983
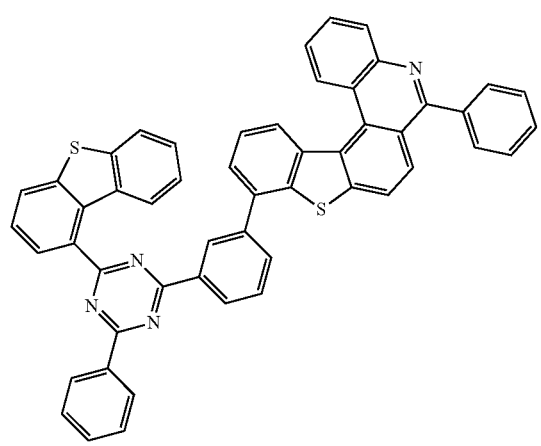
984
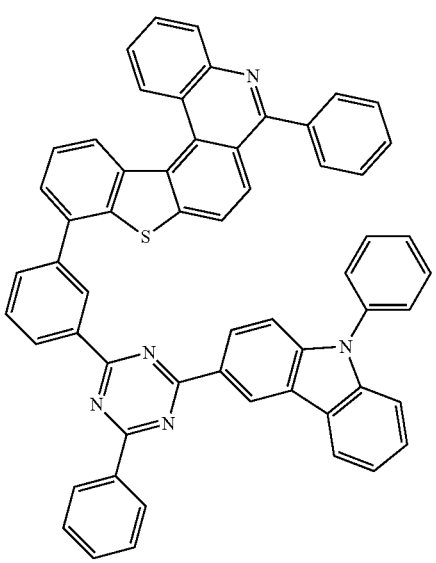
985
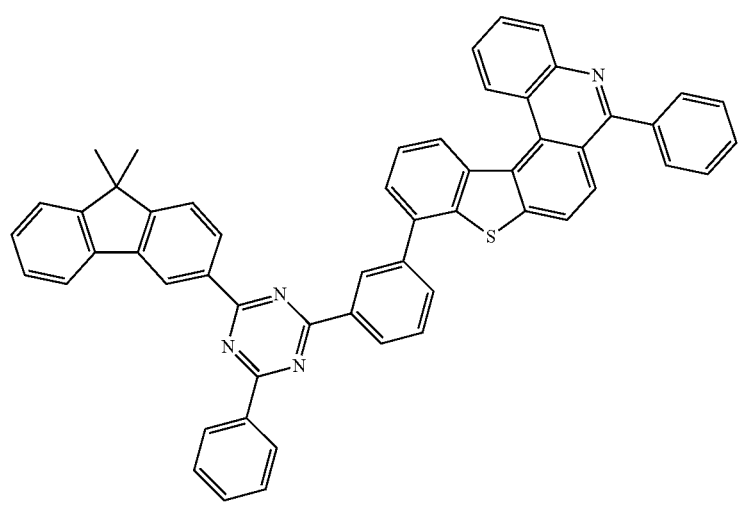

-continued
986
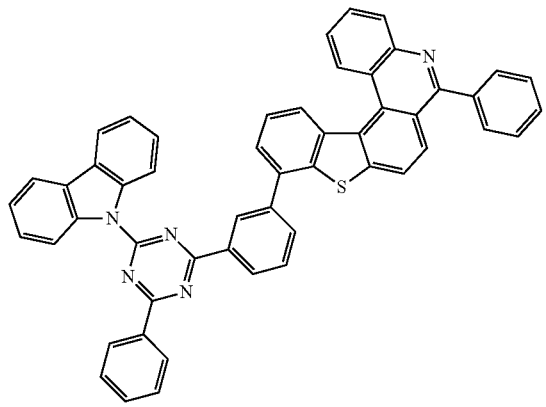
987
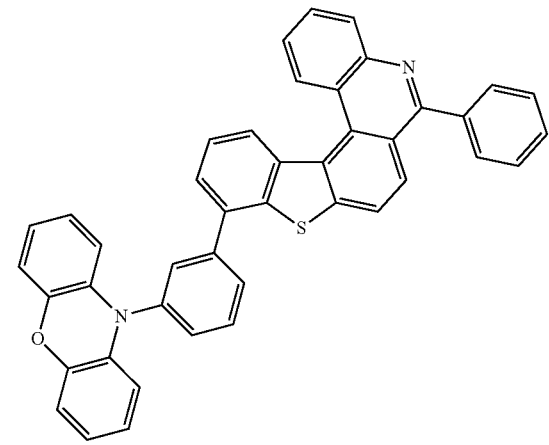
988
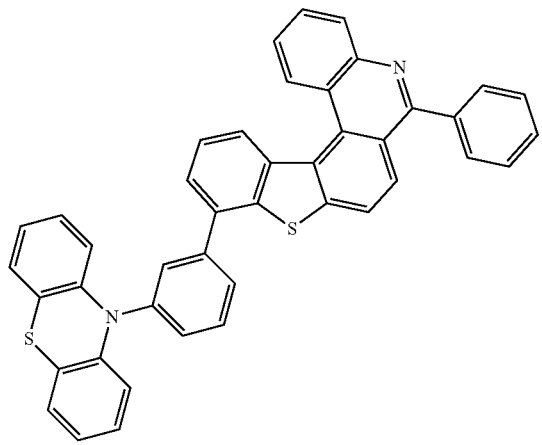
989
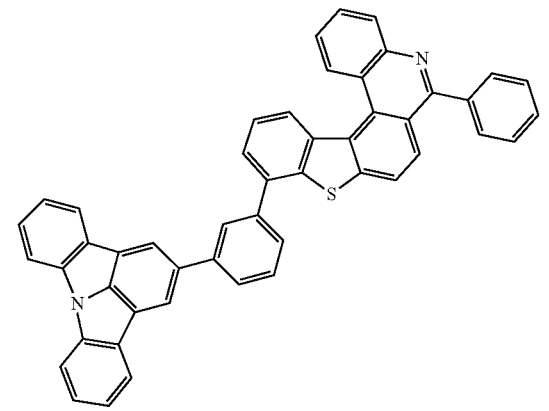
990
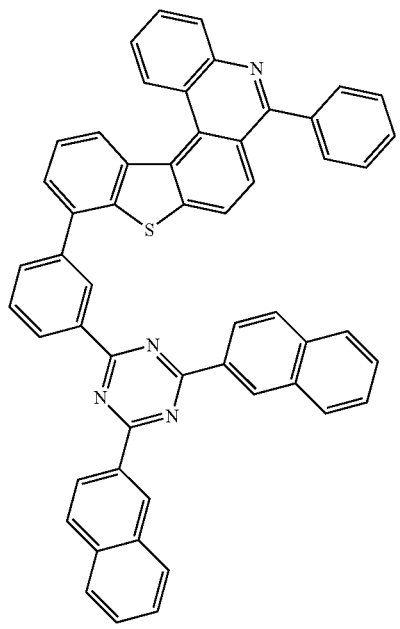
991
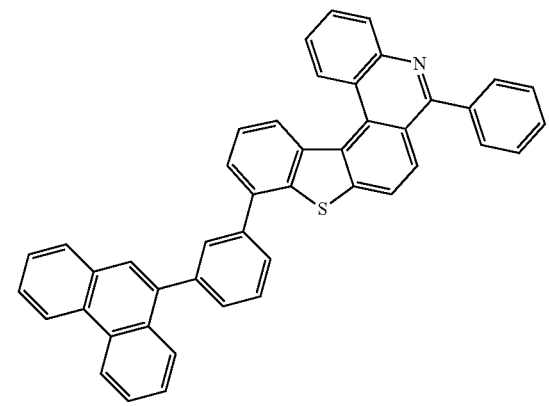

-continued
992
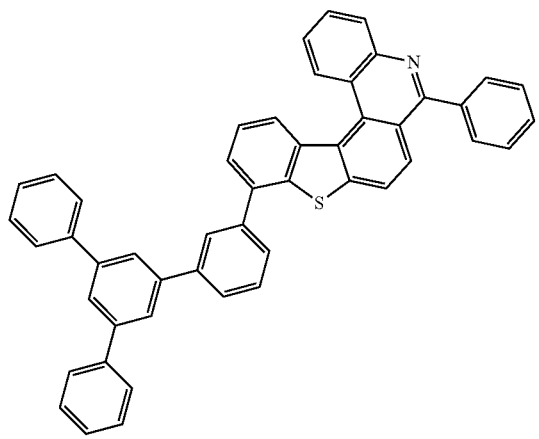
993
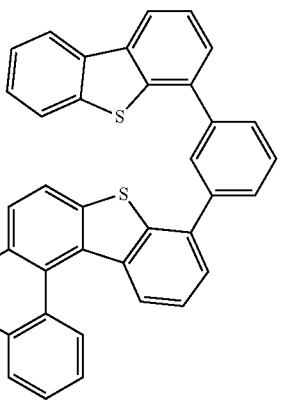
994
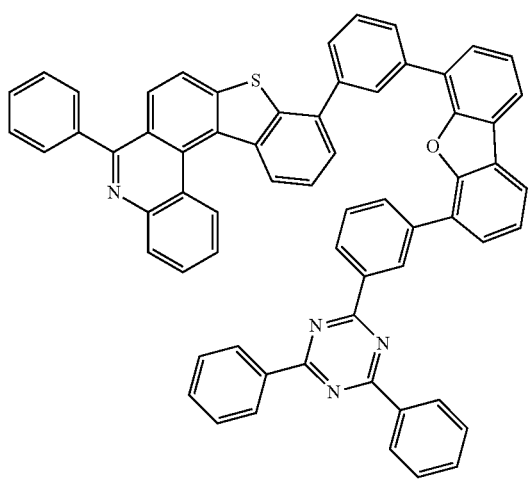
995
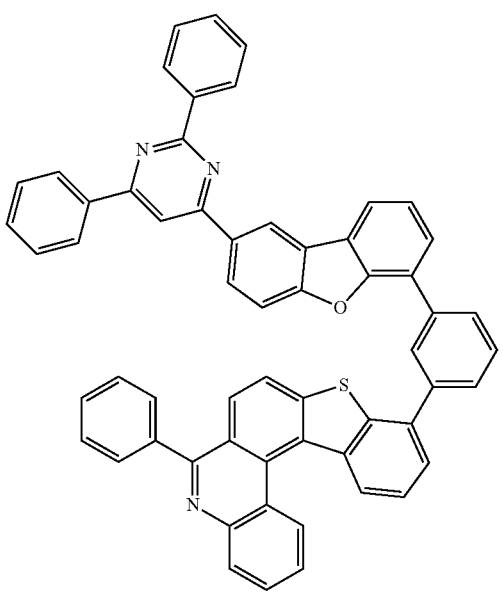
996
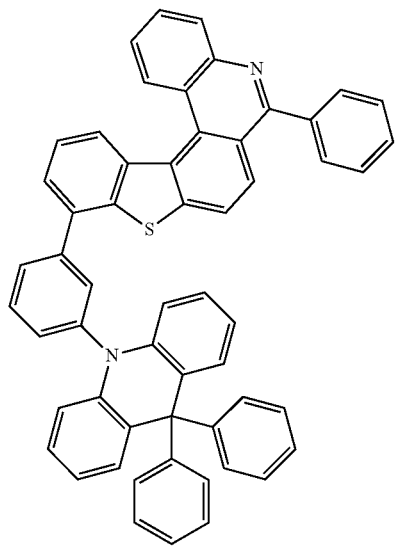
997
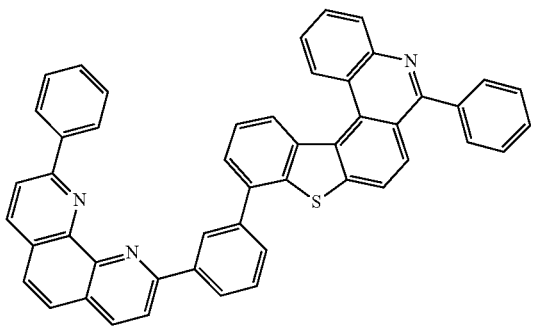

| 1119 | 1120 |
|---|---|
| 998 | 999 |
| 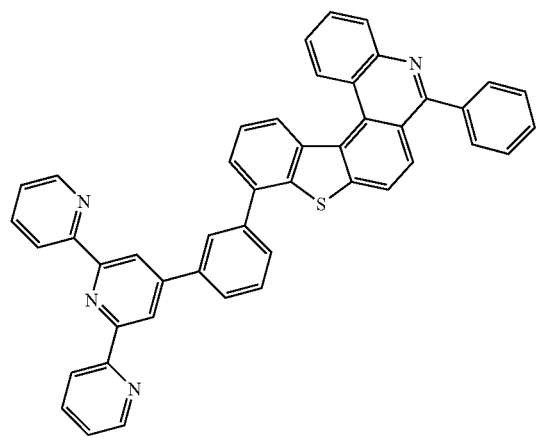 | 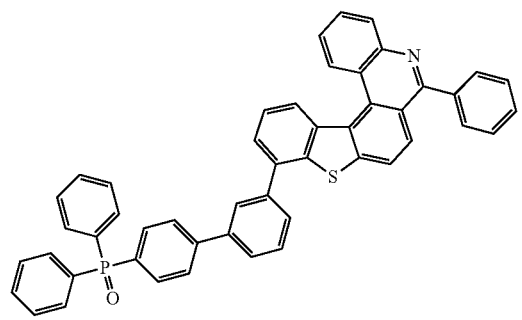 |
| 1000 | 1001 |
| 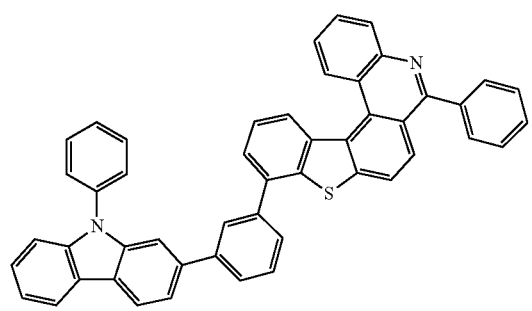 | 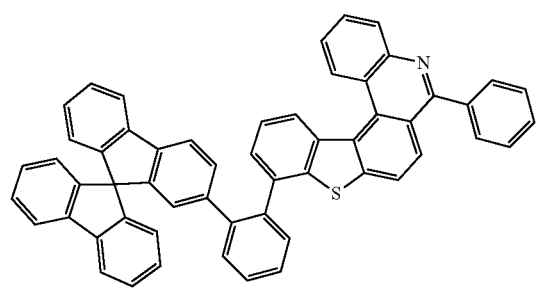 |
| 1002 | 1003 |
| 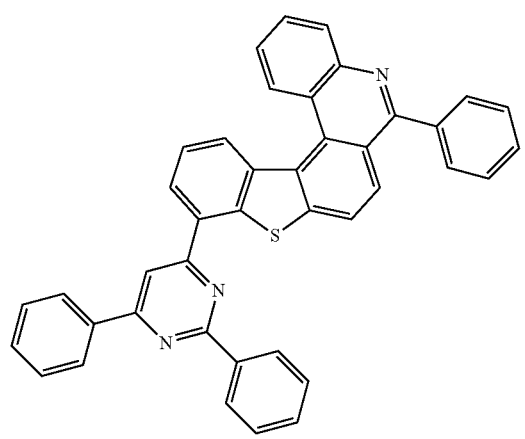 | 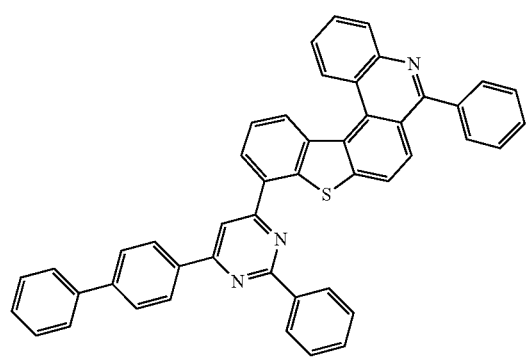 |
-continued 1121 1122
-continued
1004
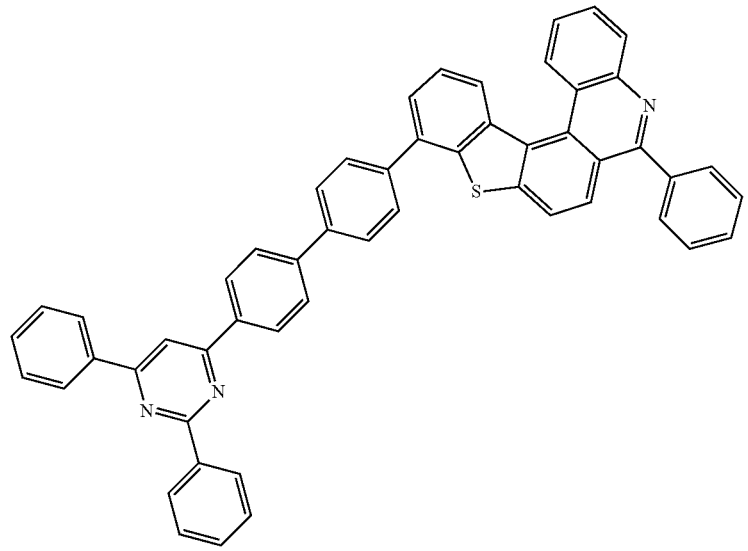
1005
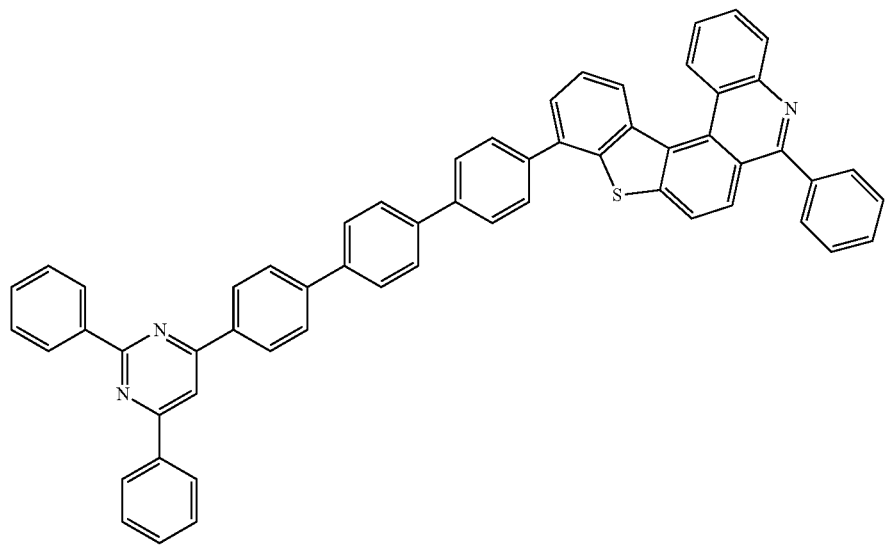
1006
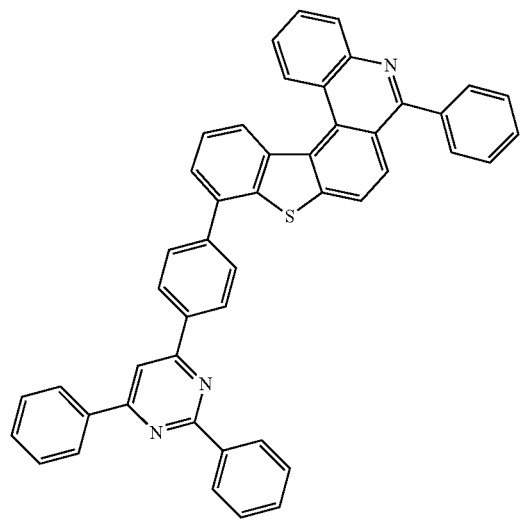
1007
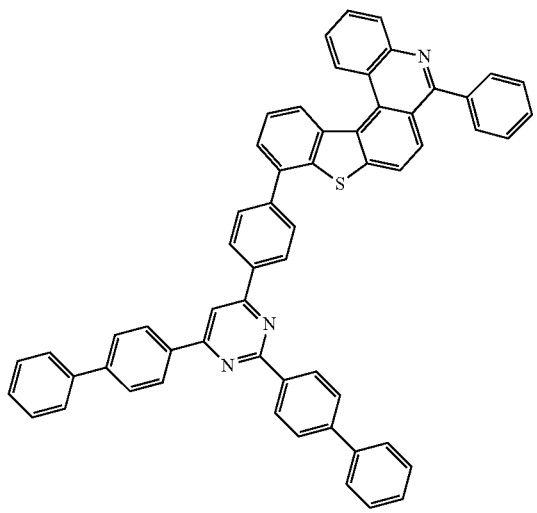

-continued
1123 1008
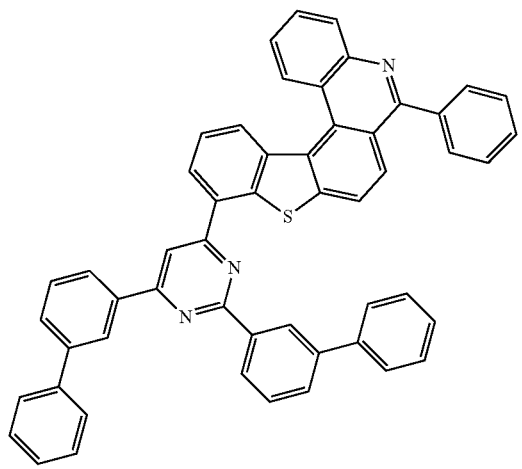
1124 1009
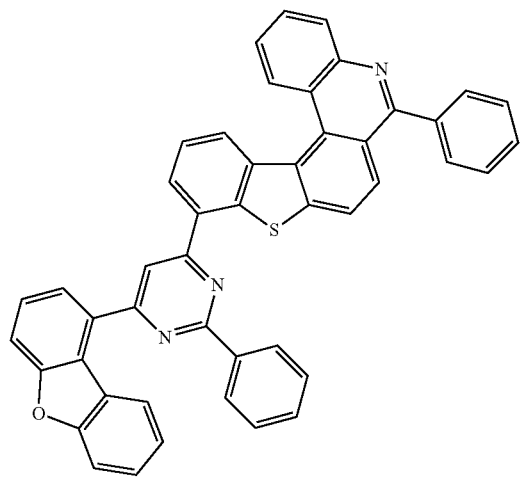
1010
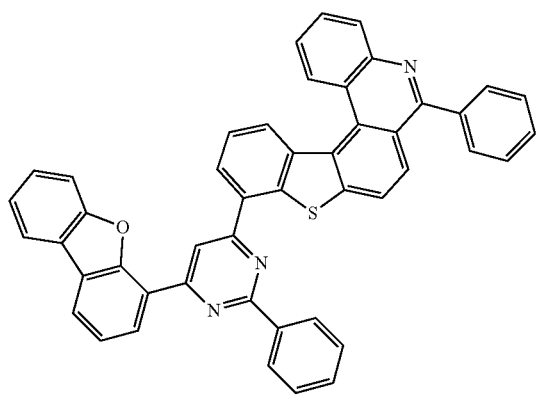
1011
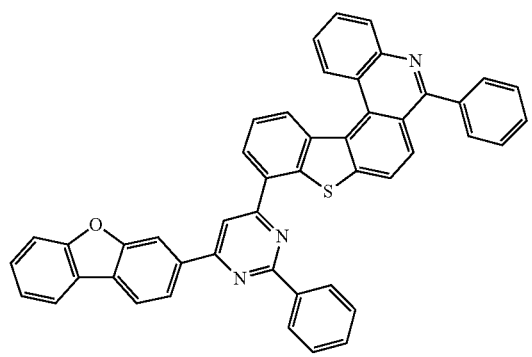
1012
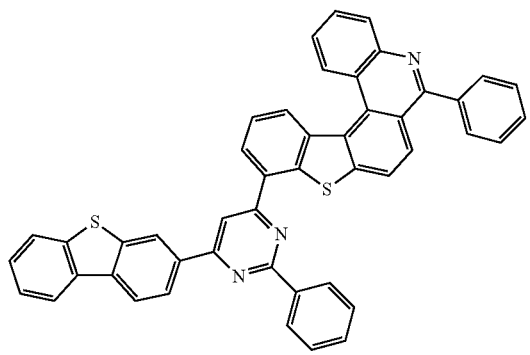
1013
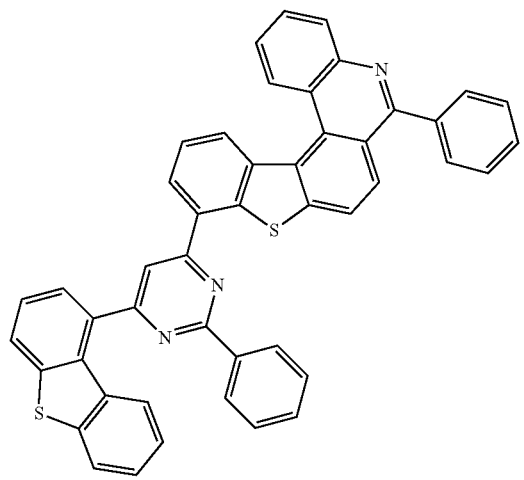

-continued
1014
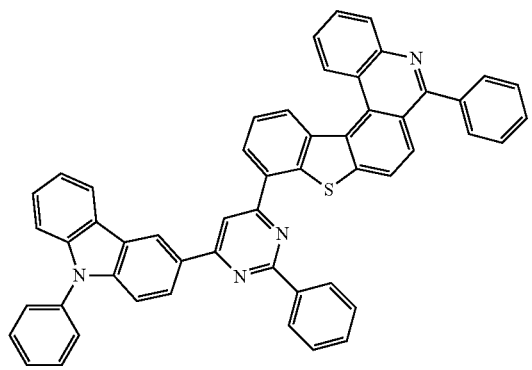
1015
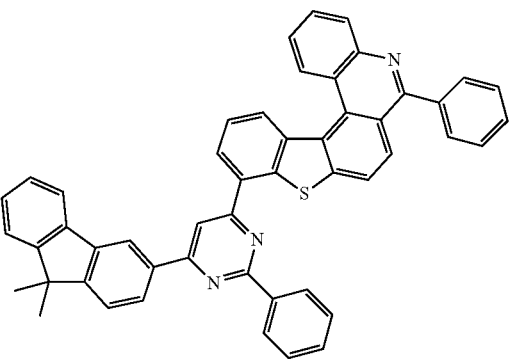
1016
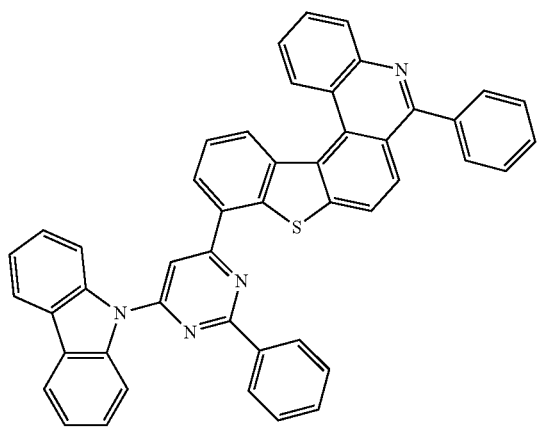
1017
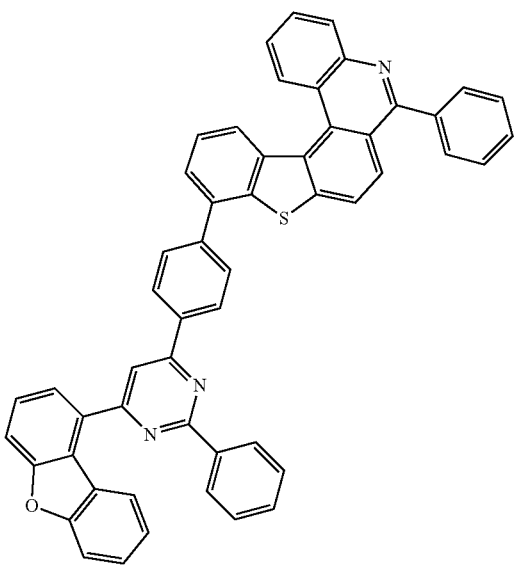
1018
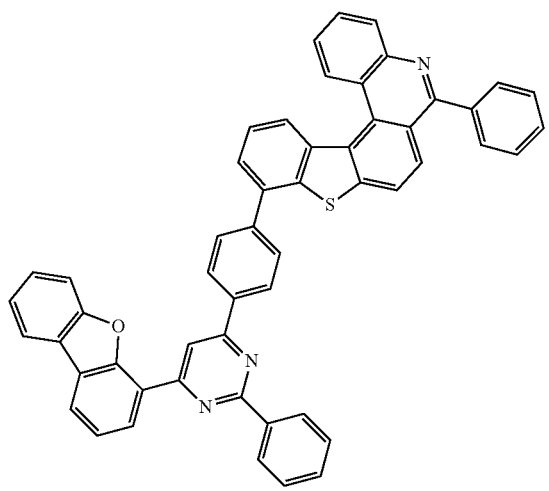
1019
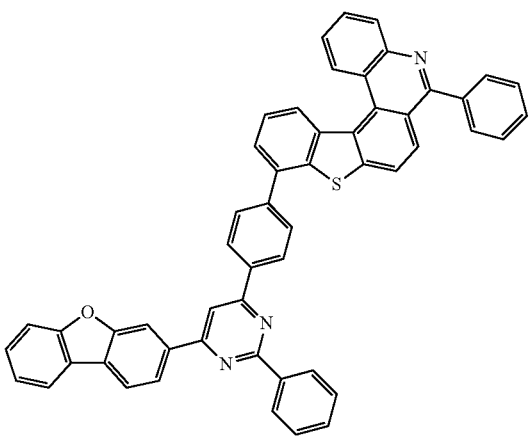

-continued
1020
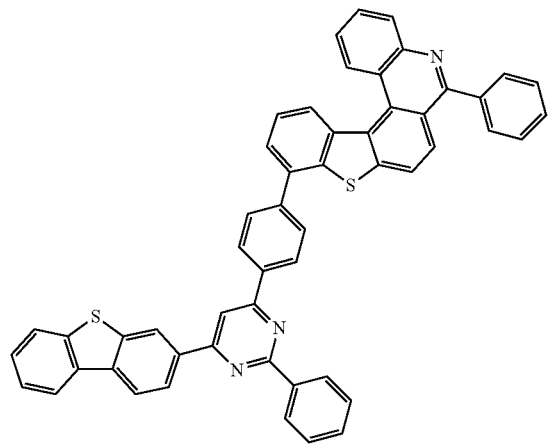
1021
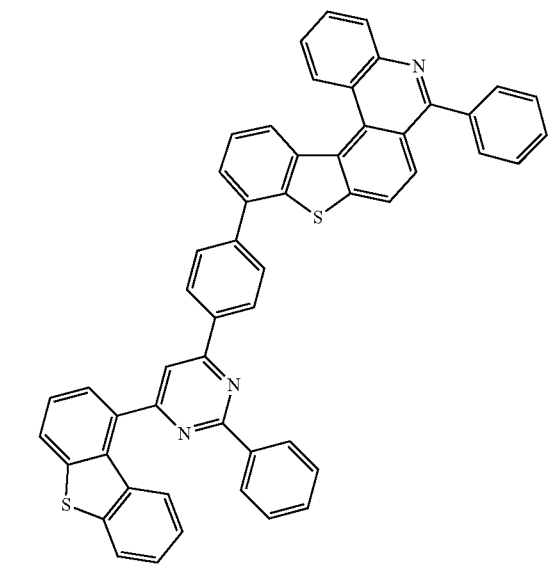
1022
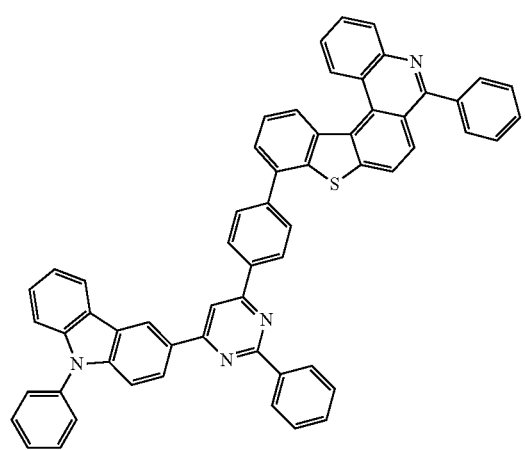
1023
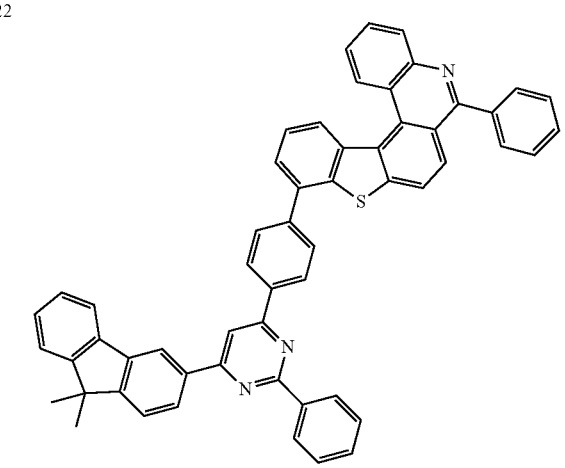
1024
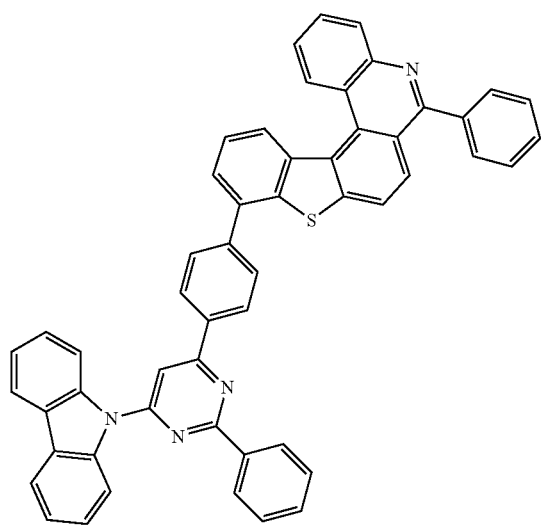
1025
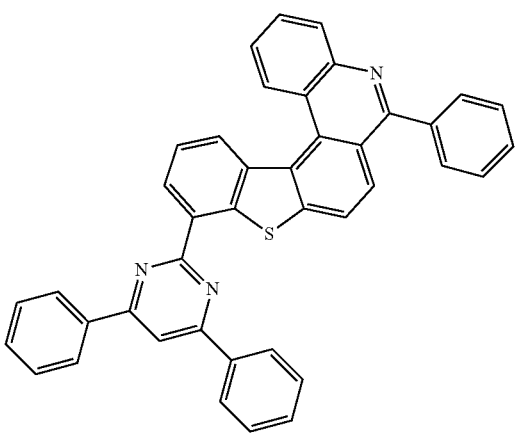

-continued
1026
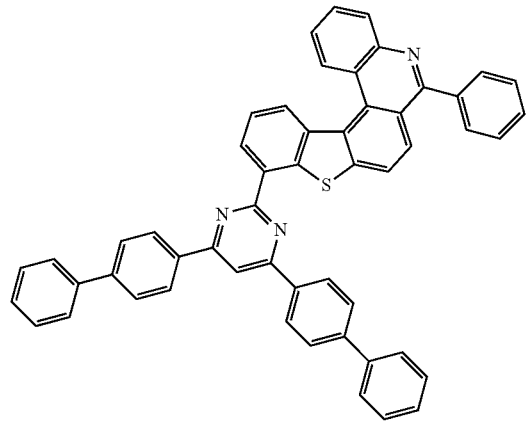
1027
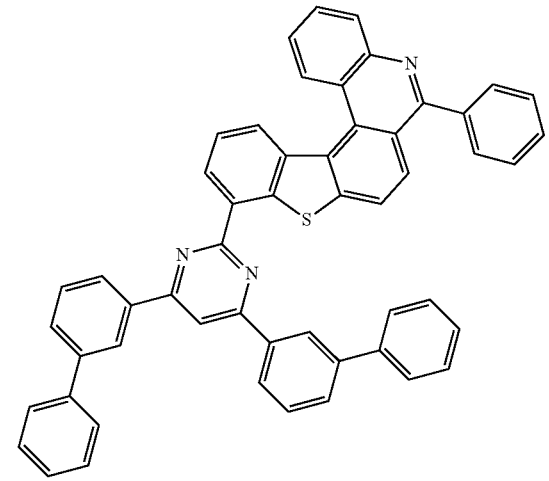
1028
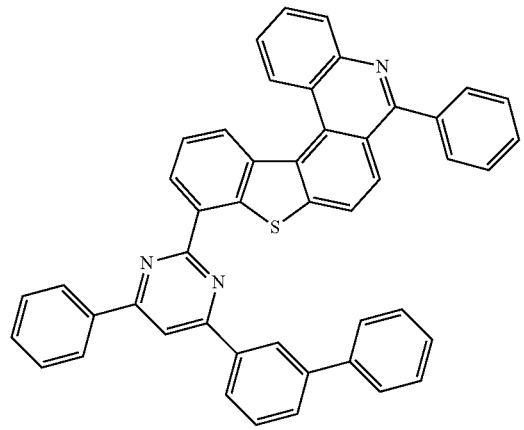
1029
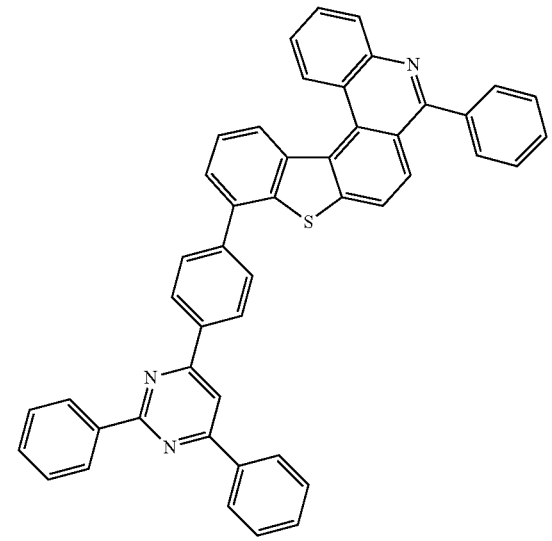
1030
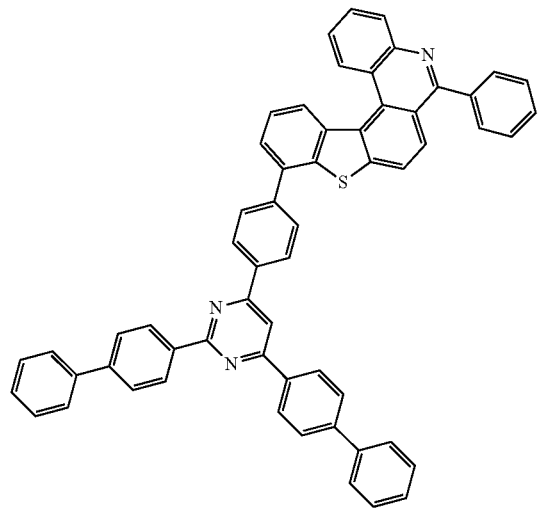
1031
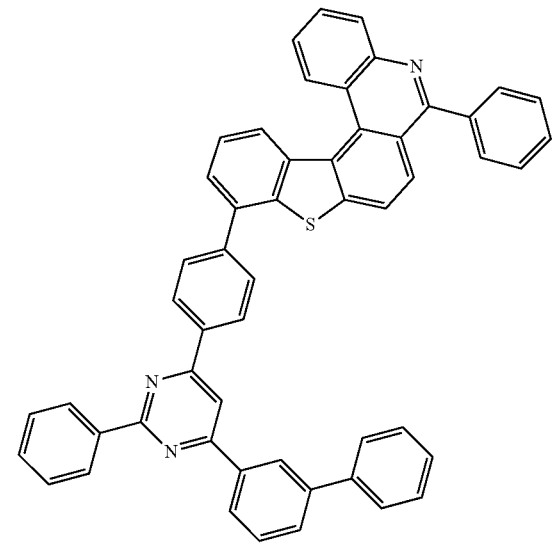

-continued
1131     1132
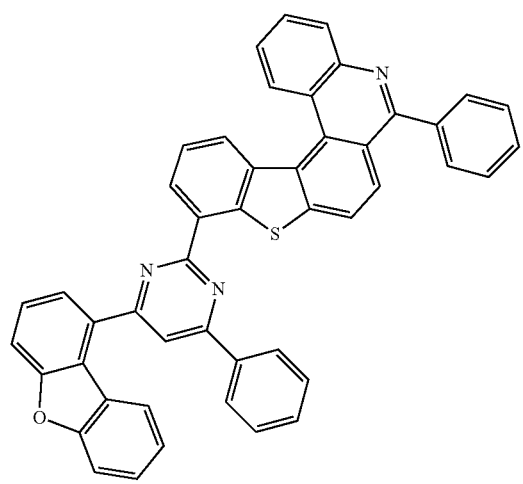
1032
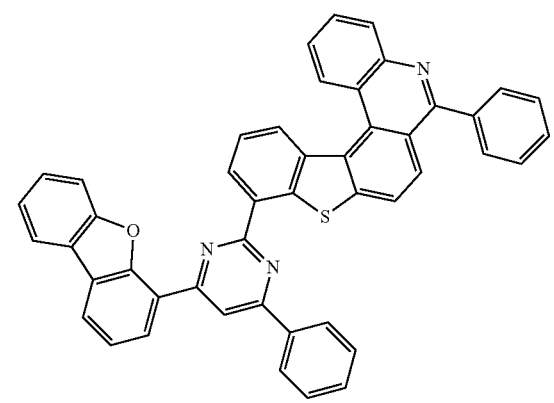
1033
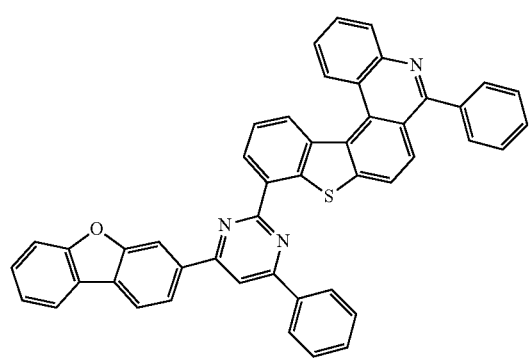
1034
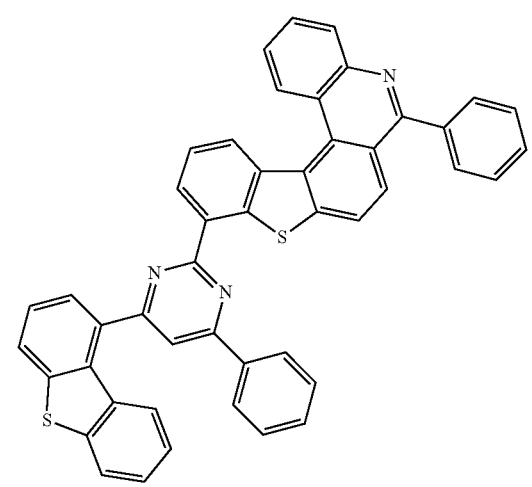
1035
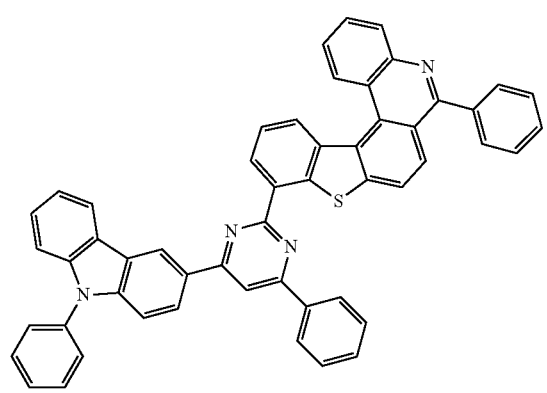
1036
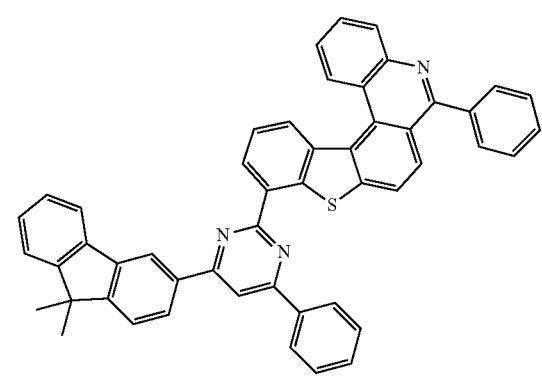
1037

-continued
1038
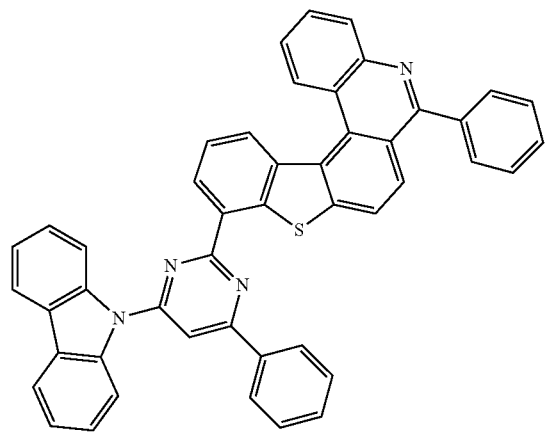
1039
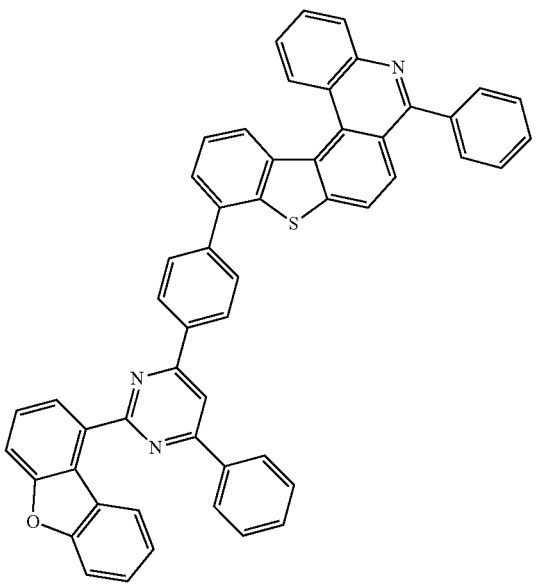
1040
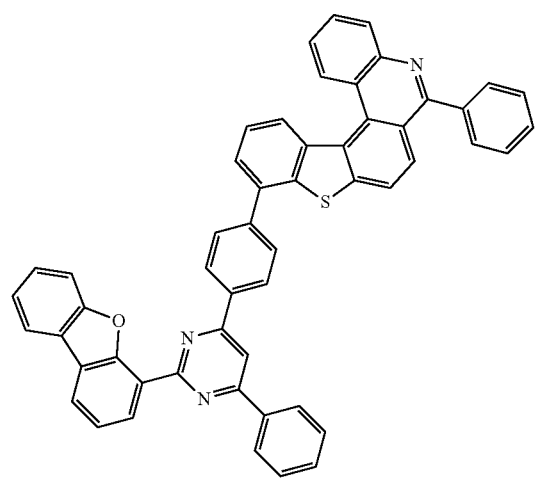
1041
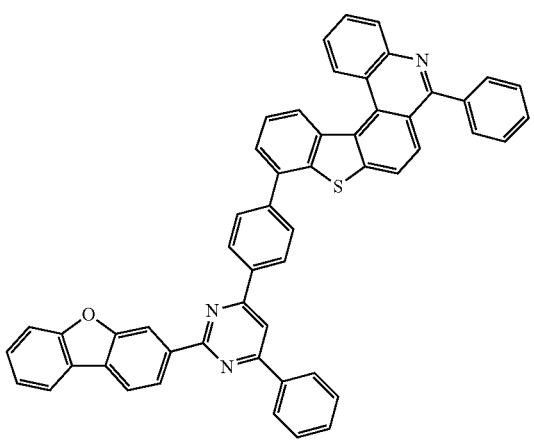
1042
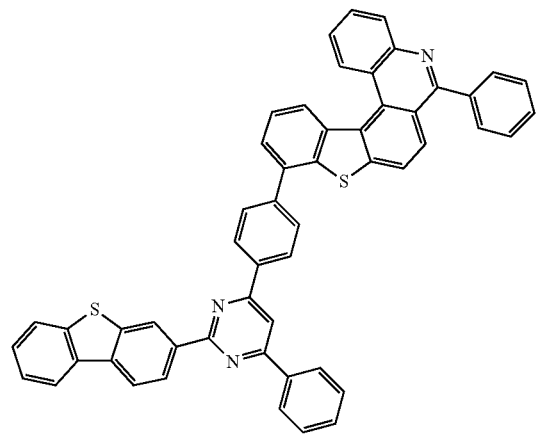
1043
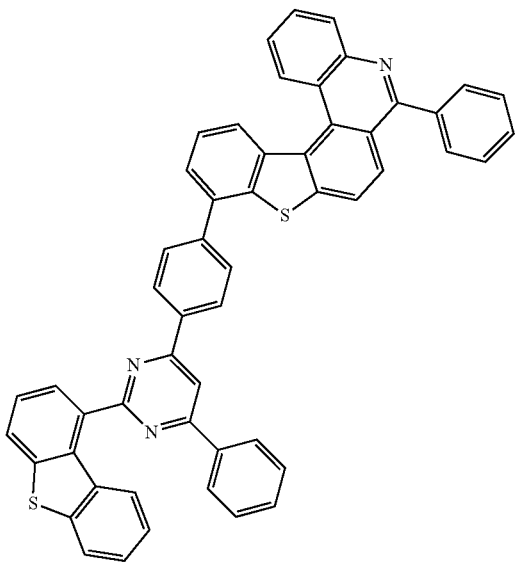

-continued
1044
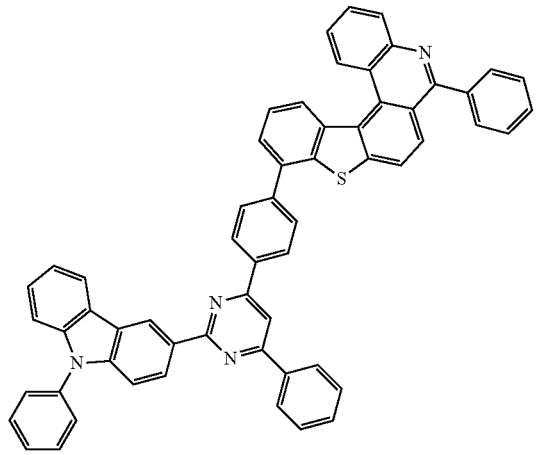
1045
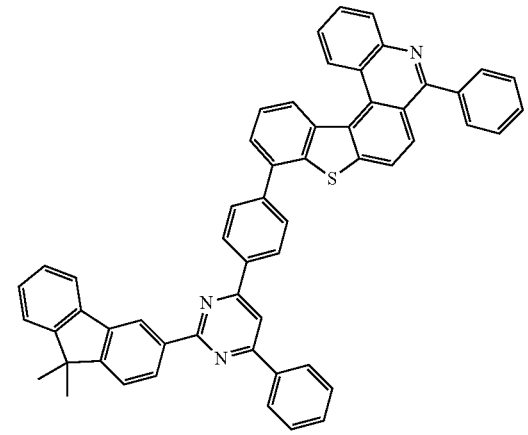
1046
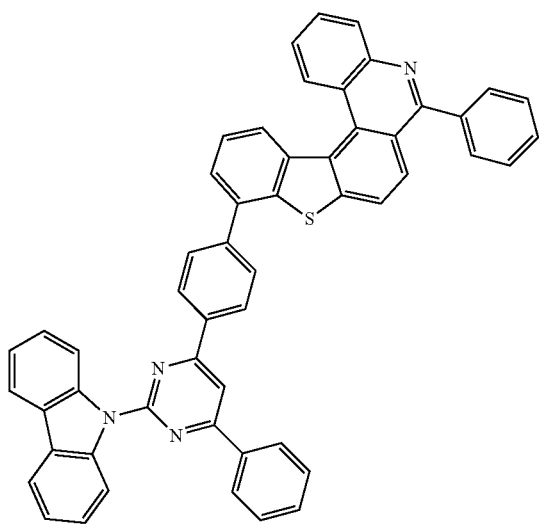
1047
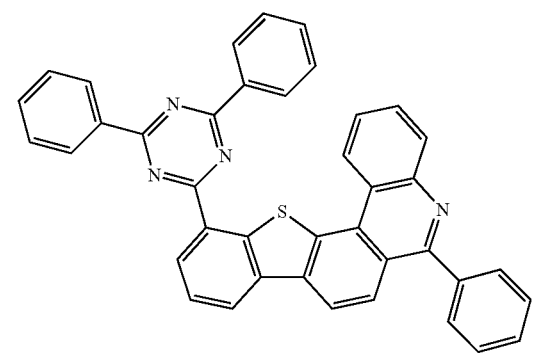
1048
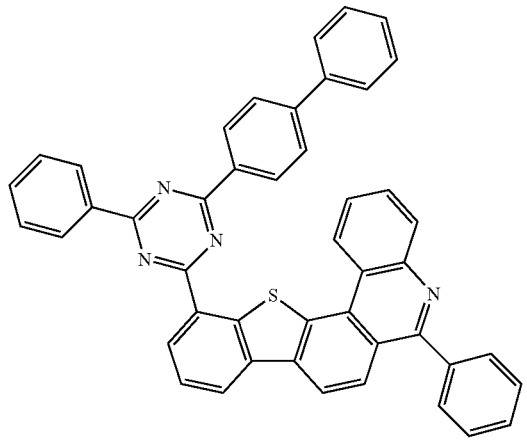
1049
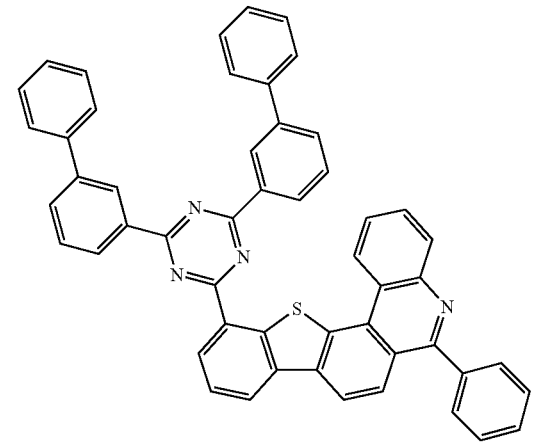

-continued
1050
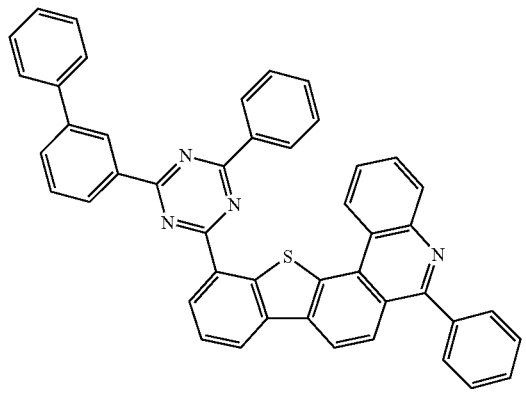
1051
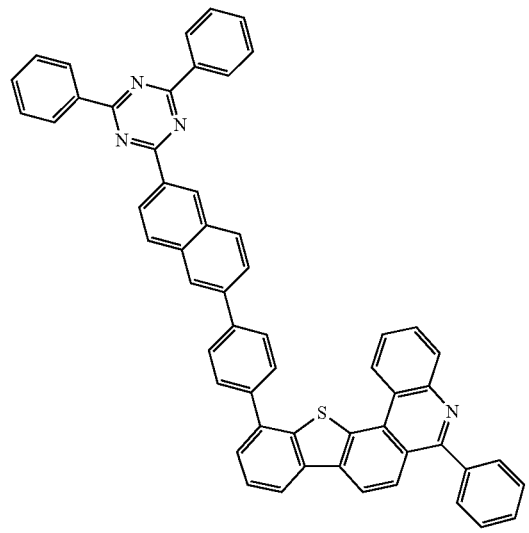
1052
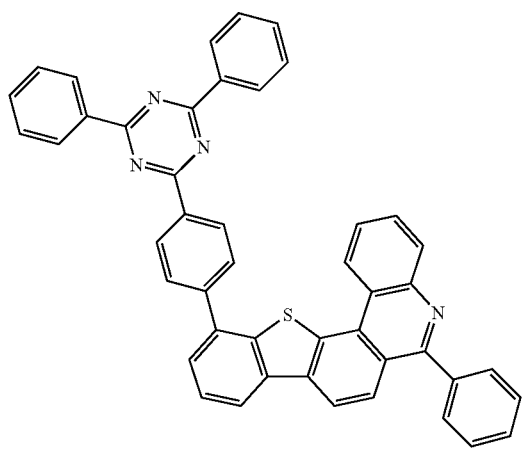
1053
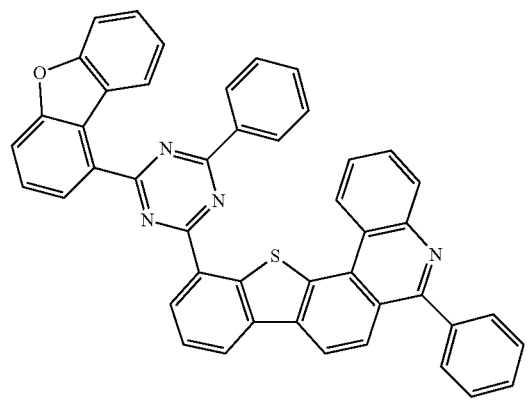
1054
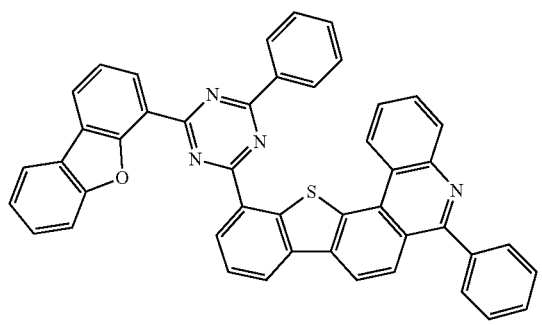
1055
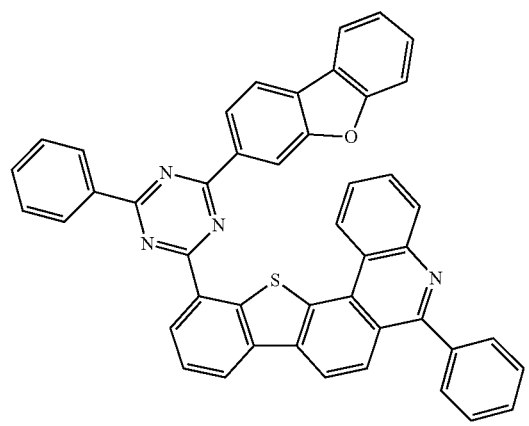

-continued
1056
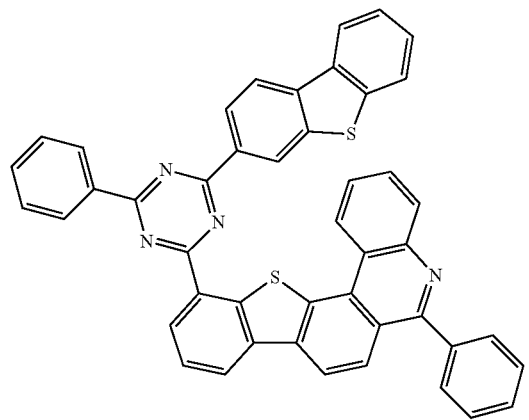
1057
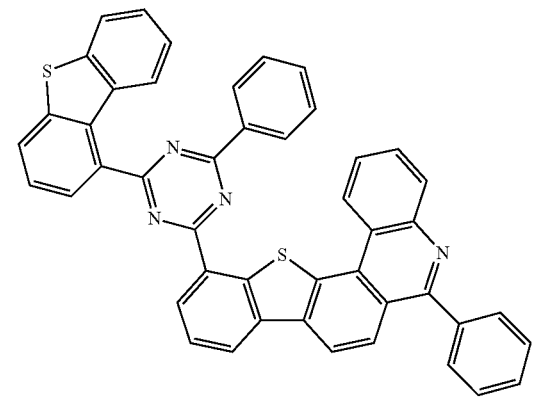
1058
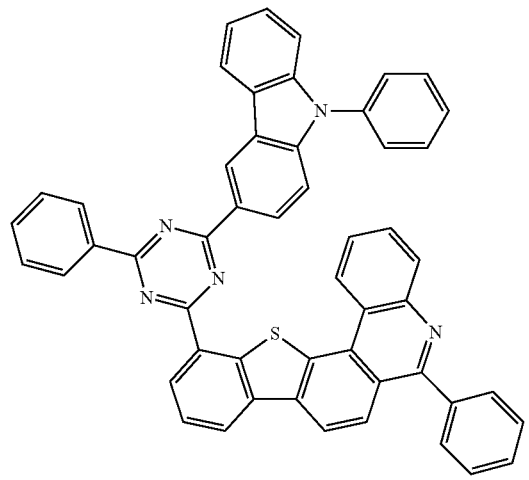
1059
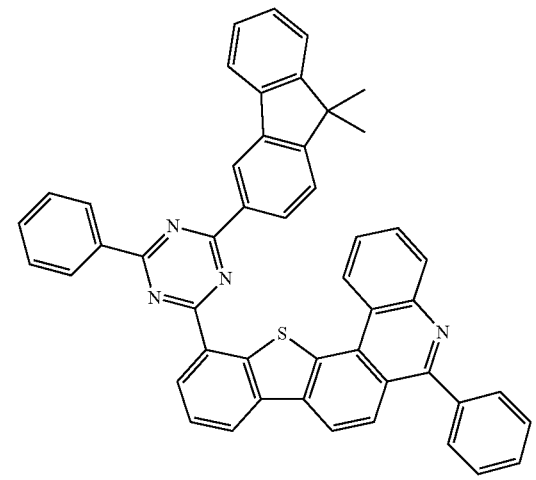
1060
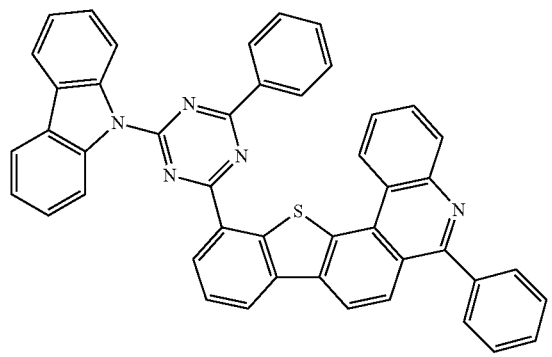
1061
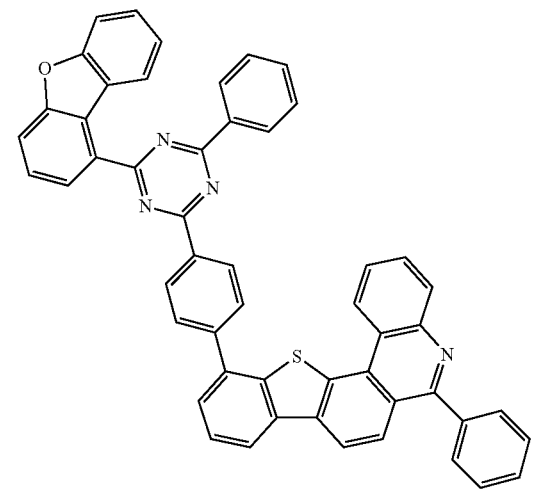

-continued
1062
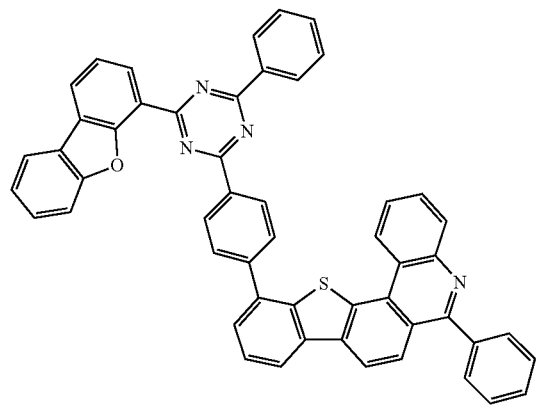
1063
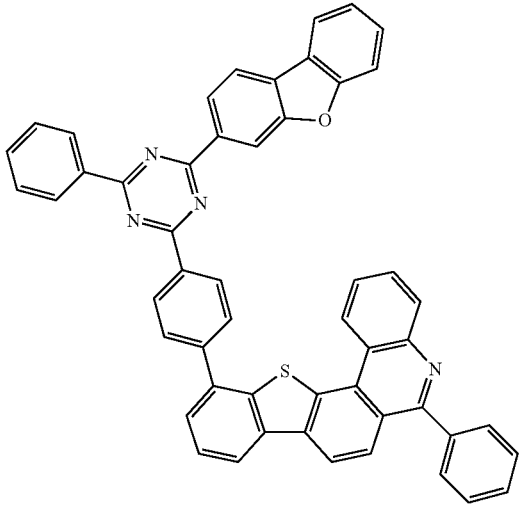
1064
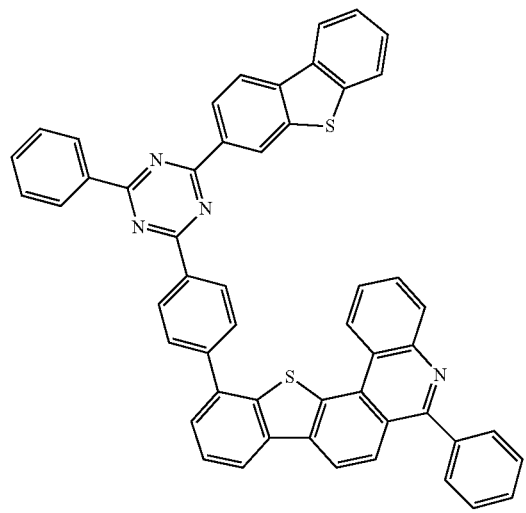
1065
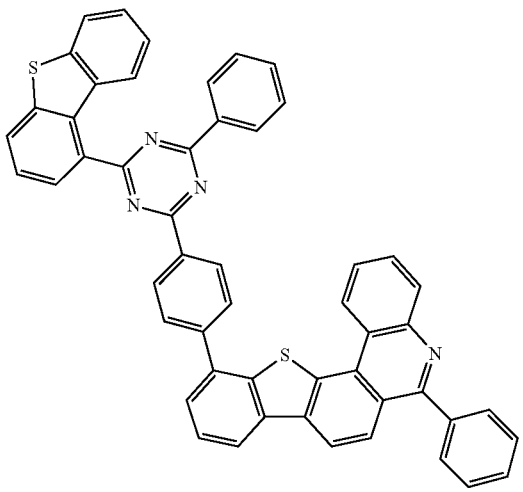
1066
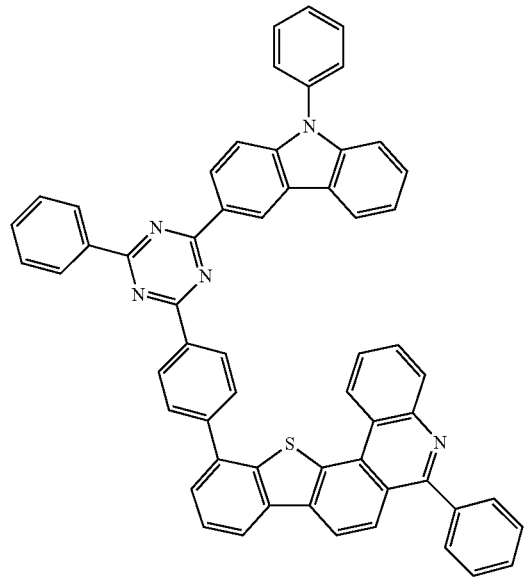
1067
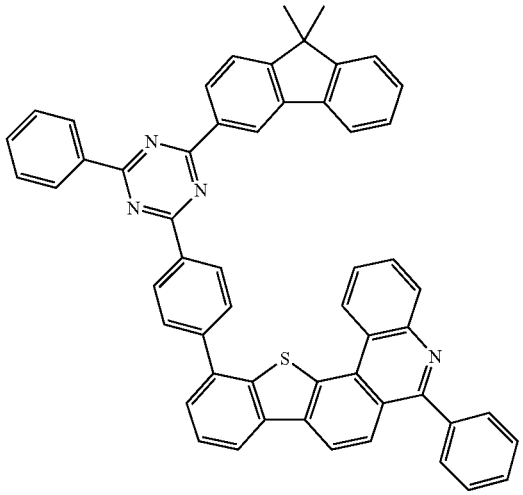

1143 1144
-continued
1068 1069
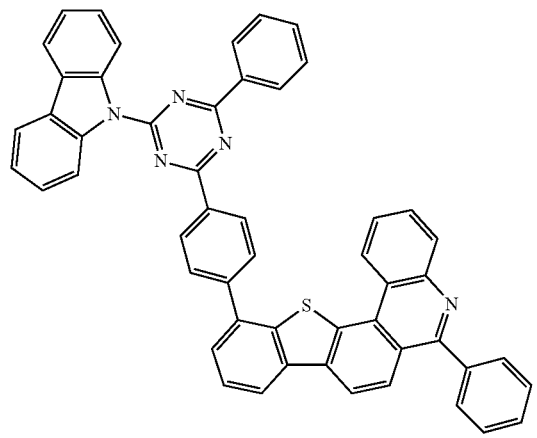
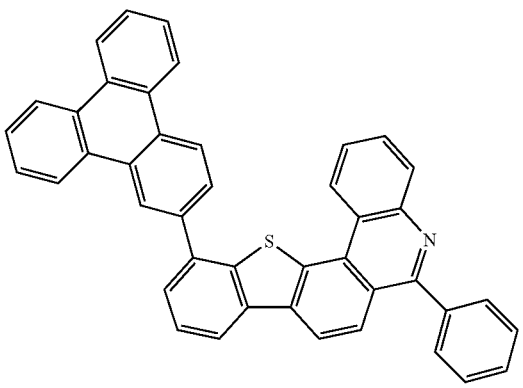
1070 1071
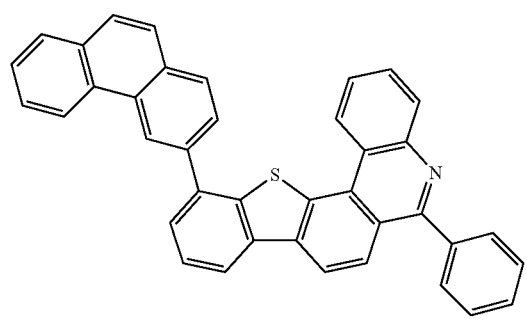
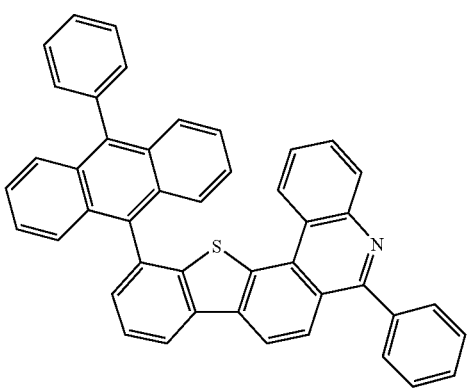
1072 1073
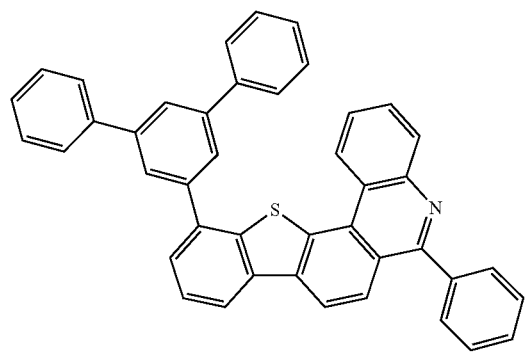
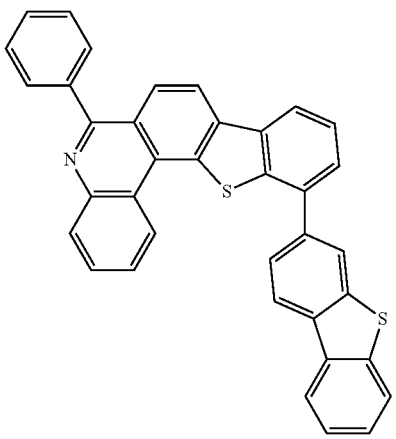

1145 1146
-continued
1074
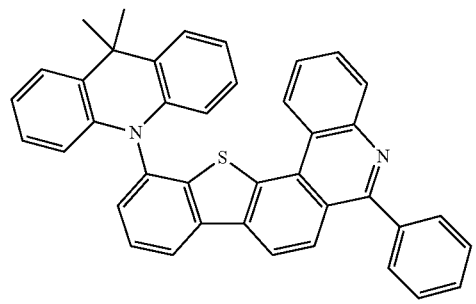
1075
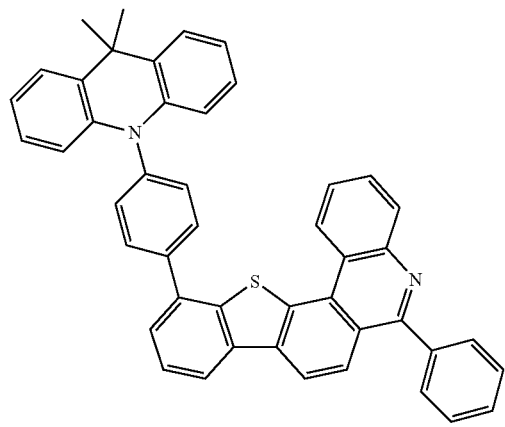
1076
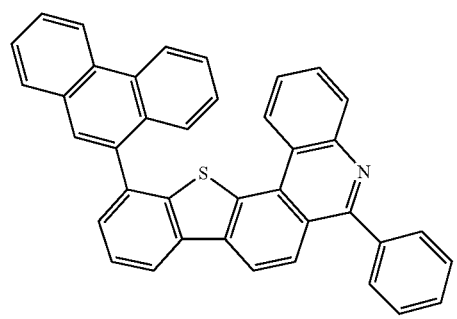
1077
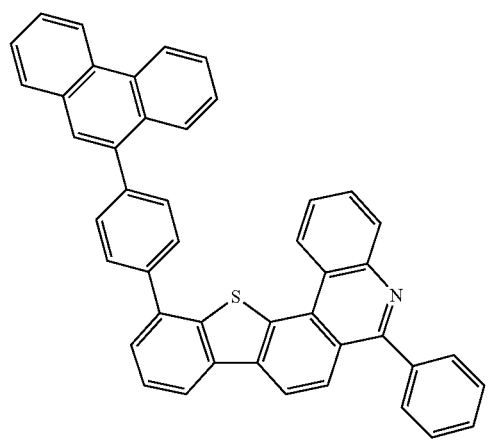
1078
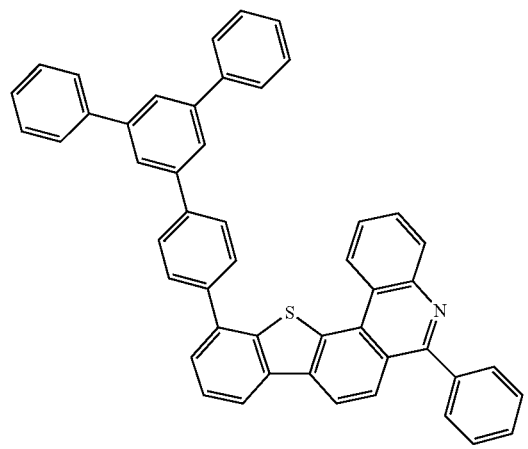
1079
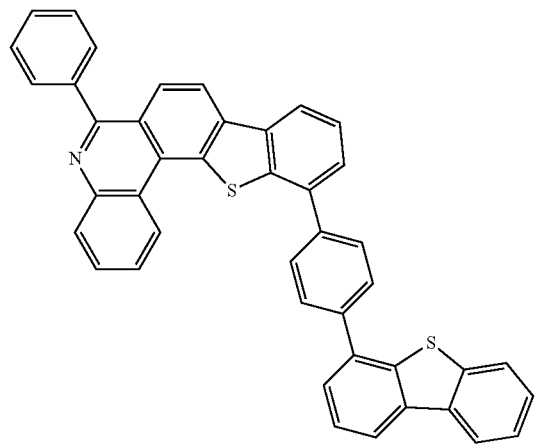

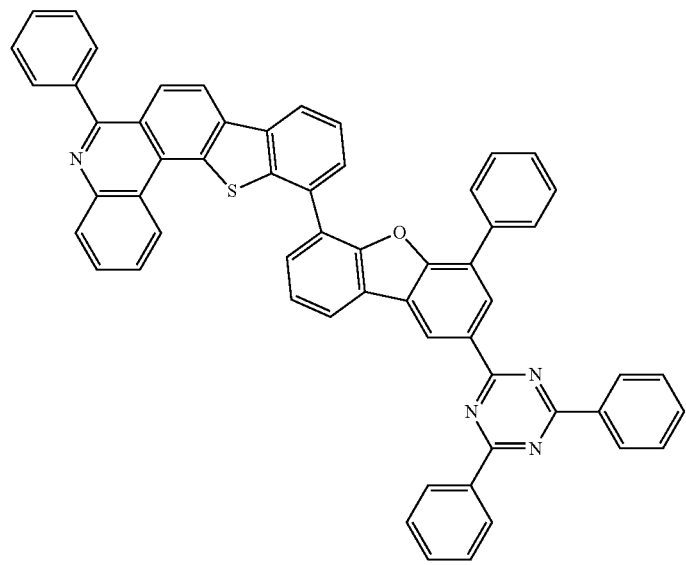
1080
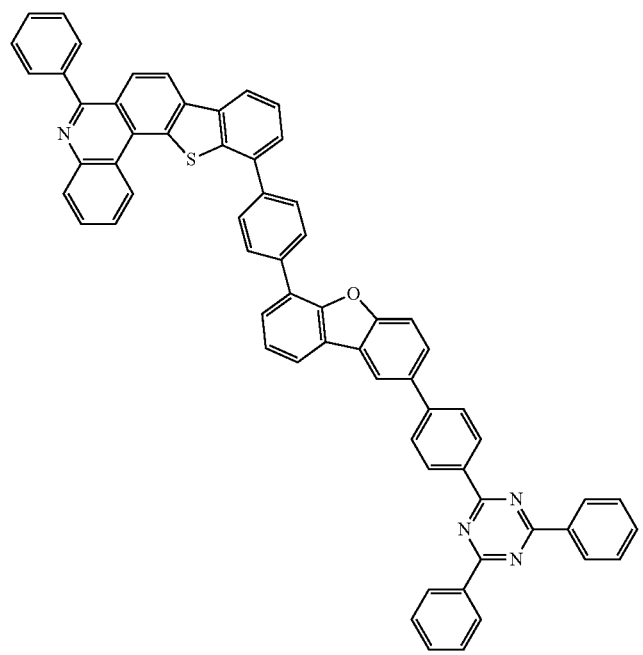
1081

-continued
1082
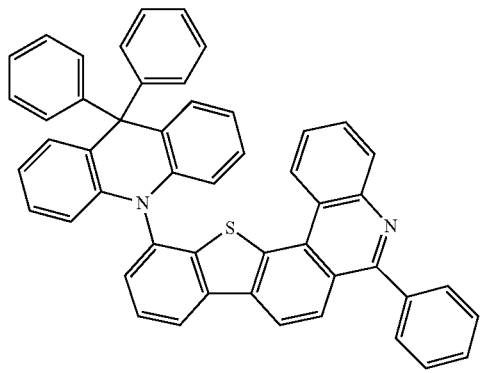
1083
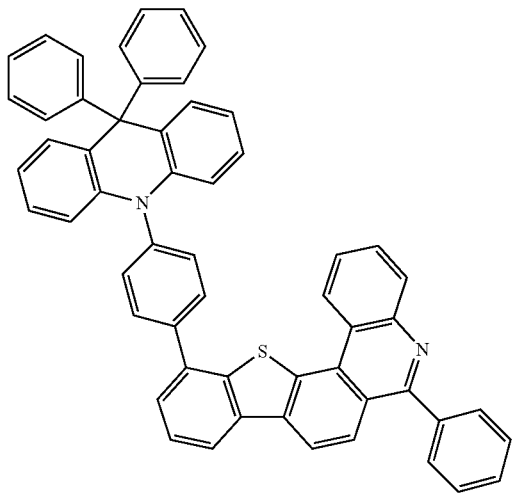
1084
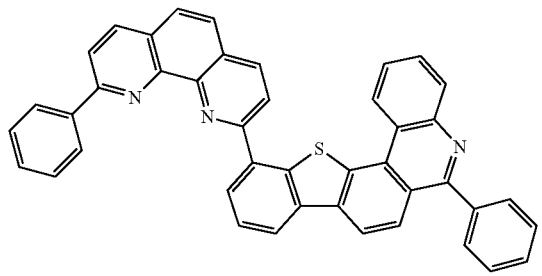
1085
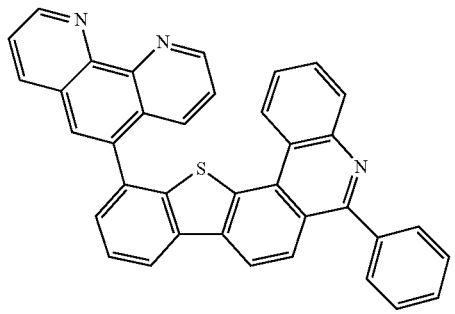
1086
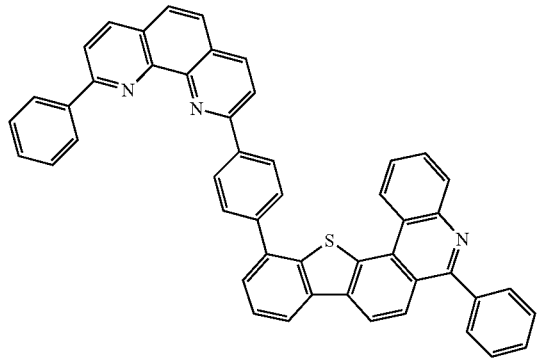
1087
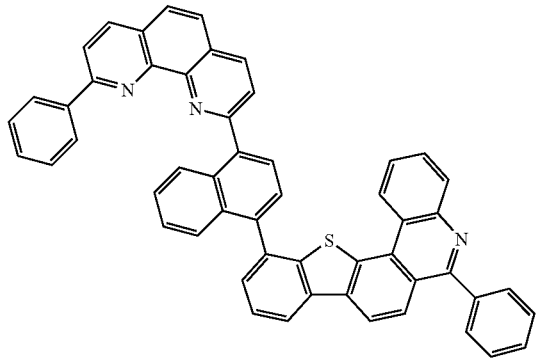
1088
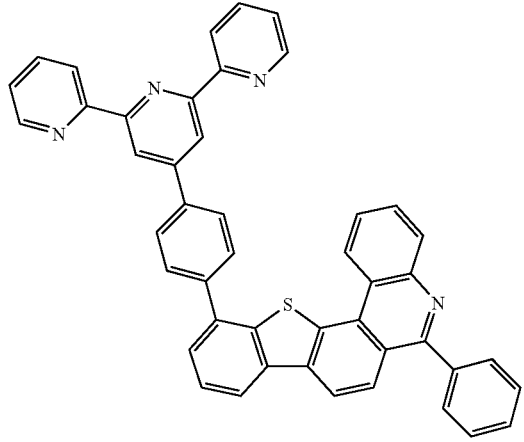
1089
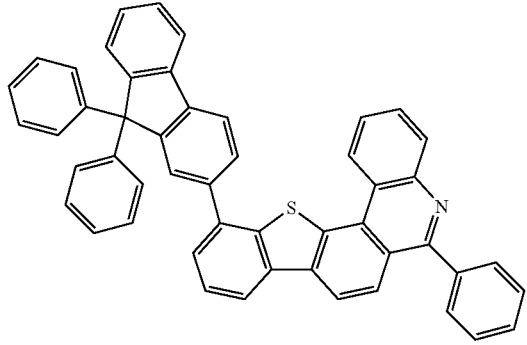

-continued
1090
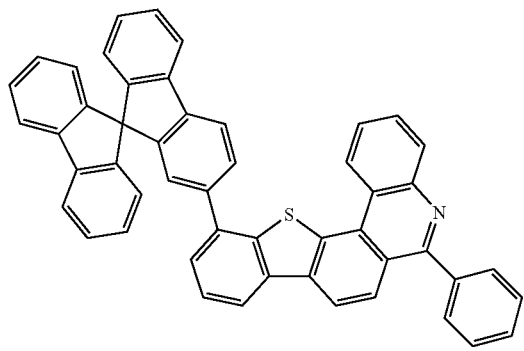
1091
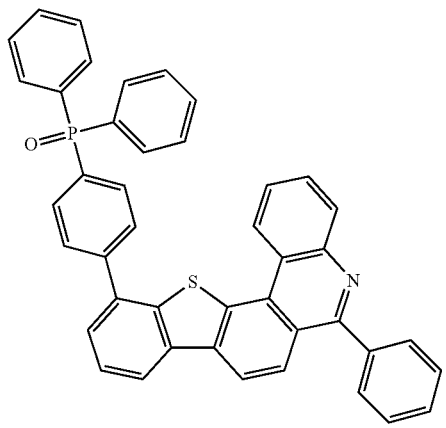
1092
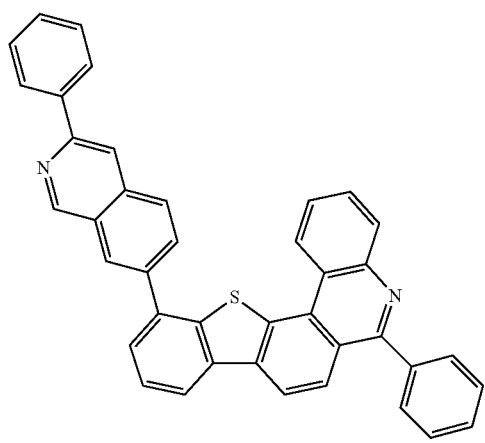
1093
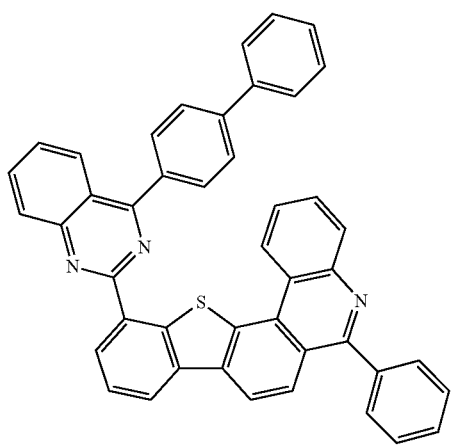
1094
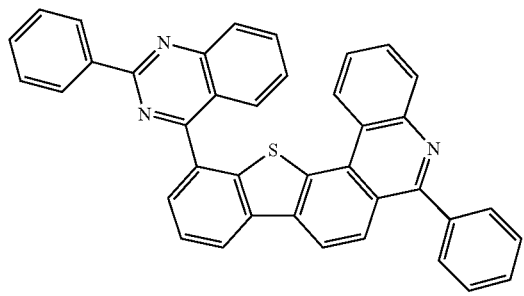
1095
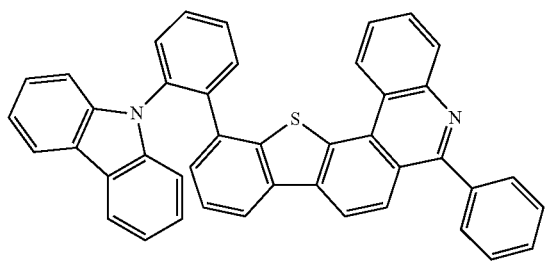
1096
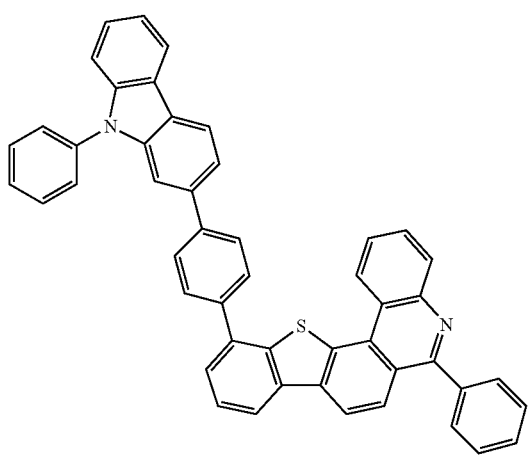
1097
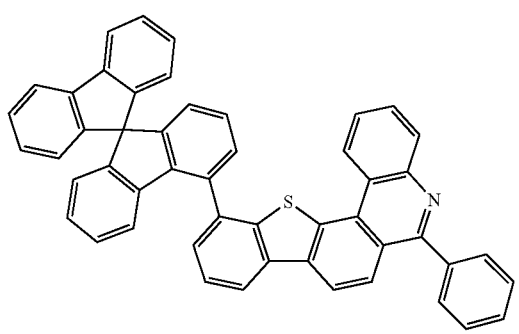

1098
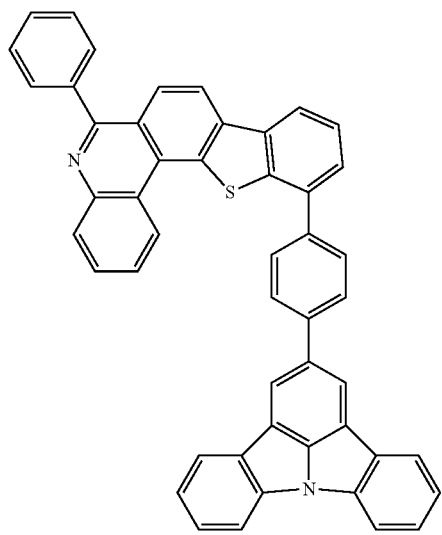
1099
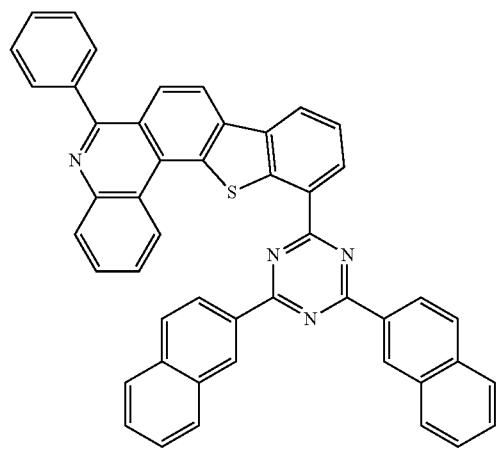
1100
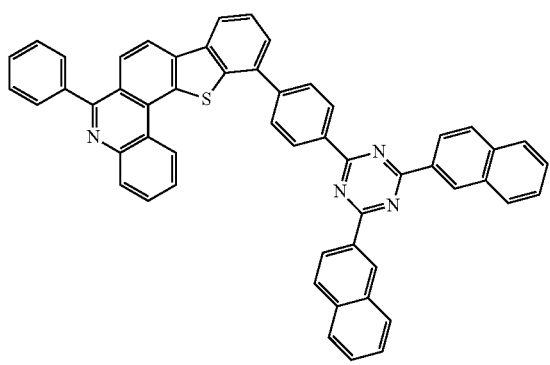
1101
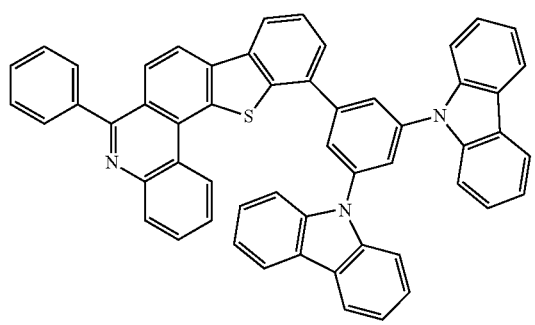
1102
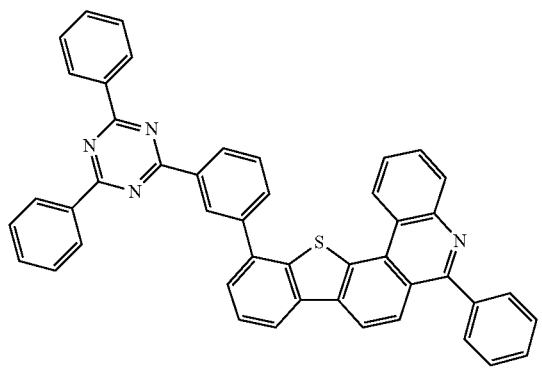
1103
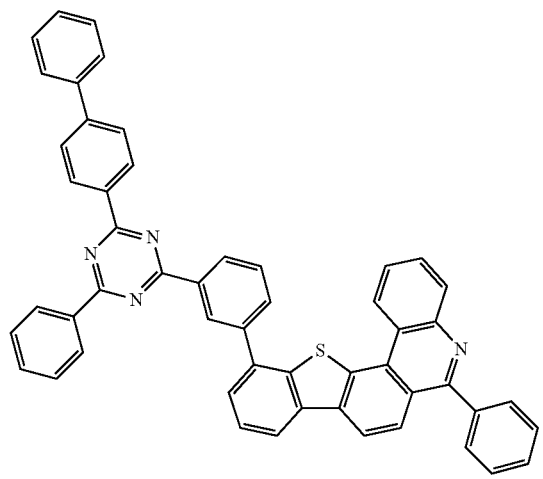

1104
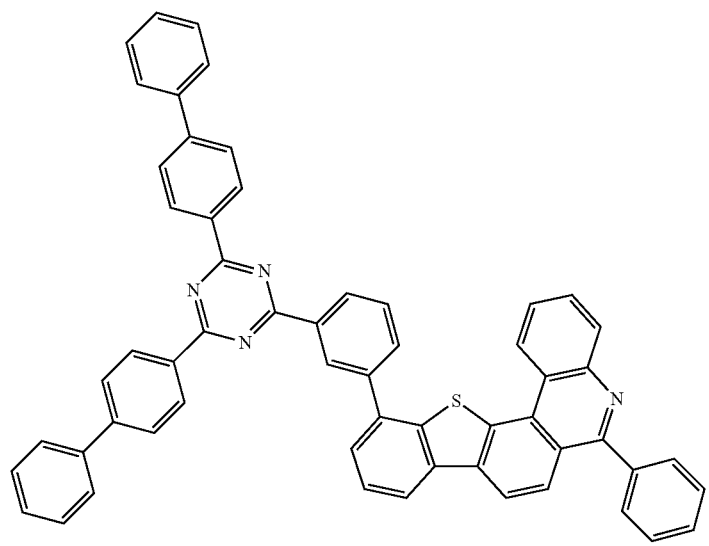
1105
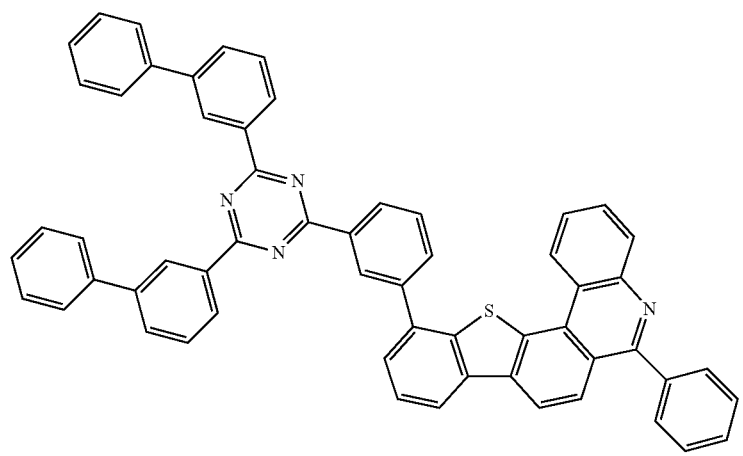
1106
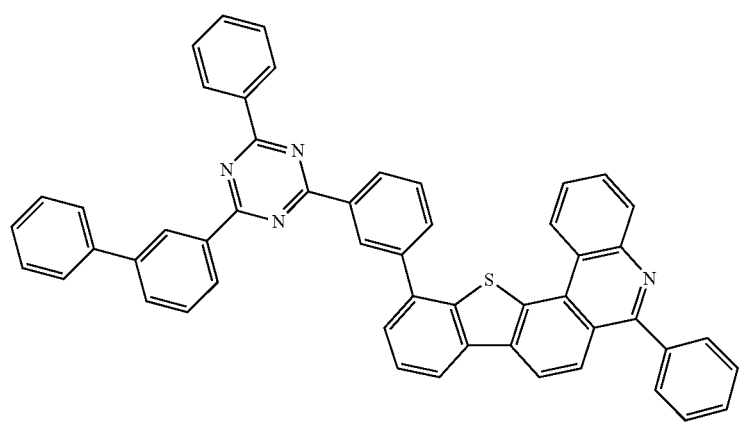

-continued
1107
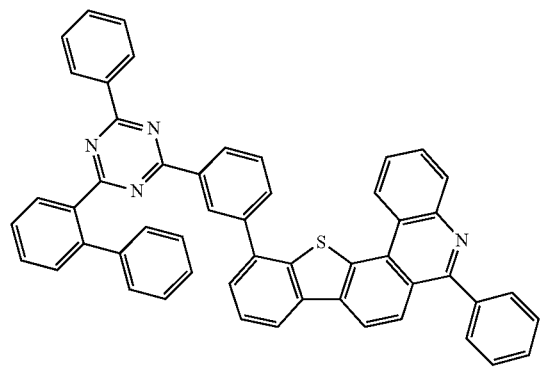
1108
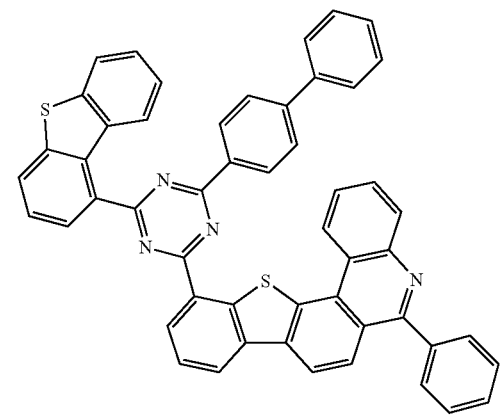
1109
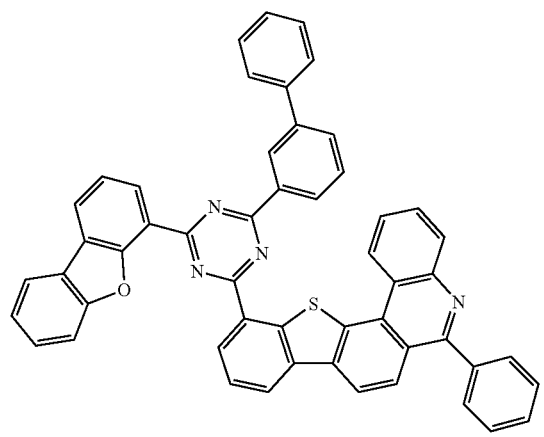
1110
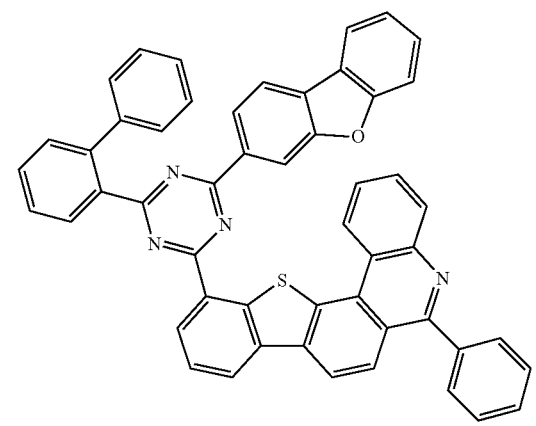
1111
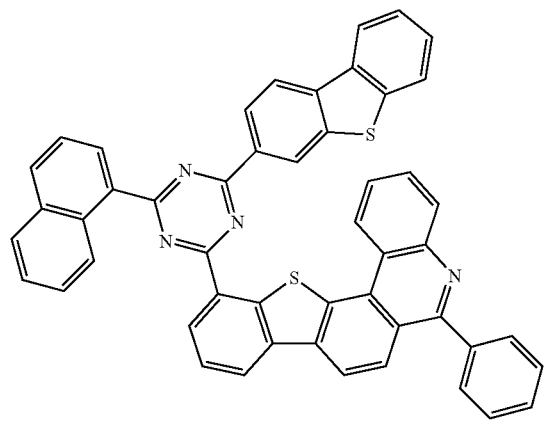
1112
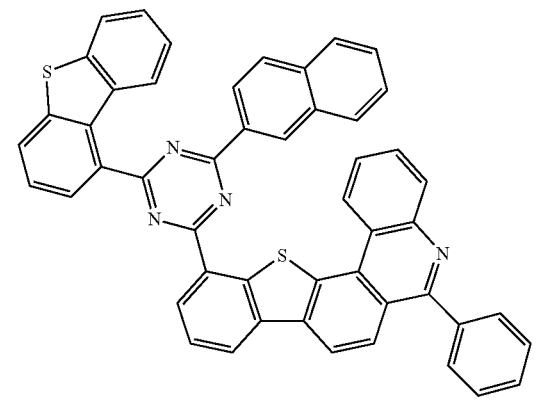

-continued
| 1113 | 1114 |
|---|---|
| 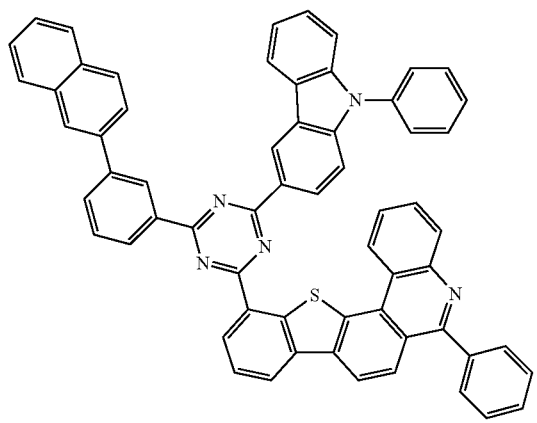 | 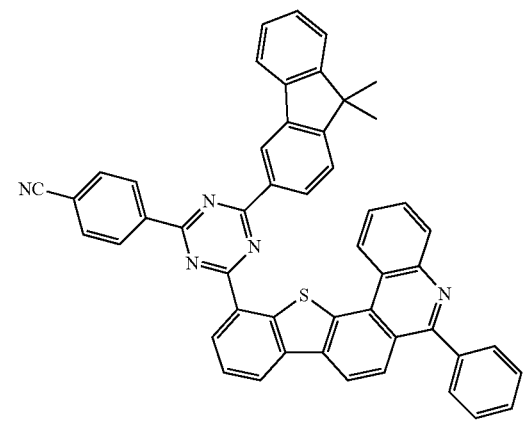 |
| 1115 | 1116 |
|---|---|
| 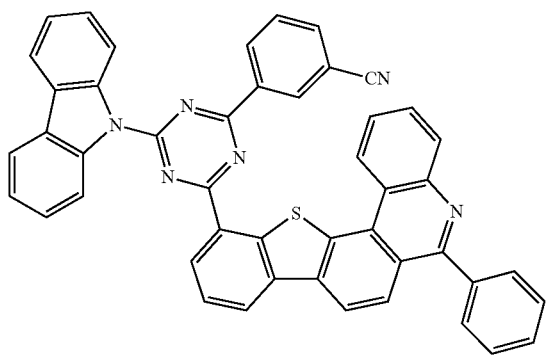 | 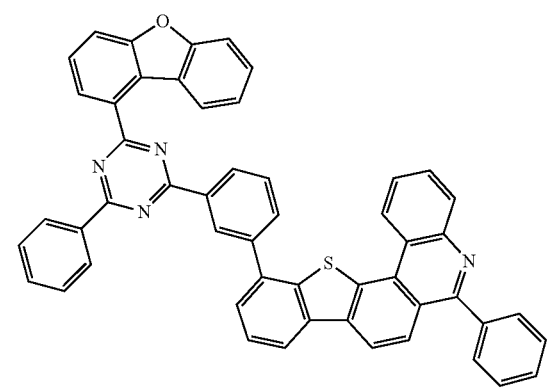 |
| 1117 | 1118 |
|---|---|
| 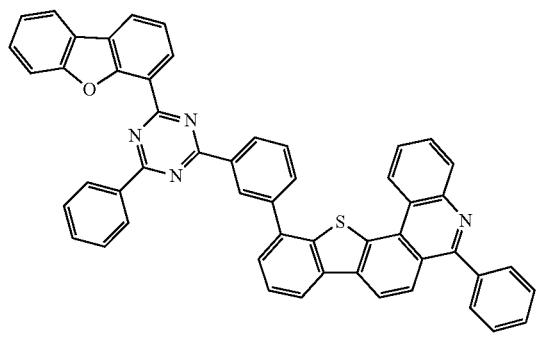 | 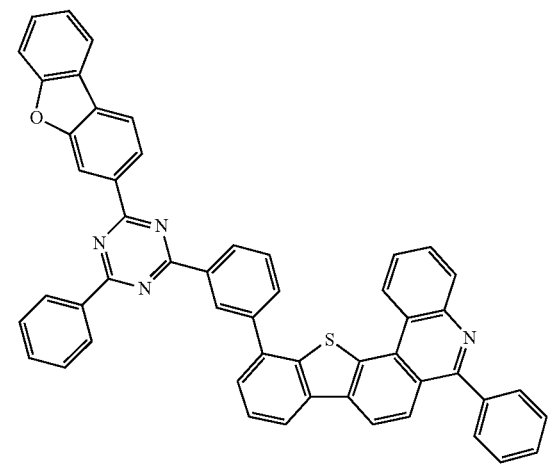 |

-continued
1119
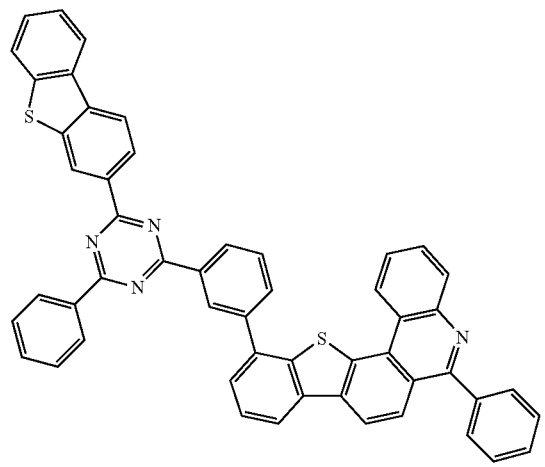
1120
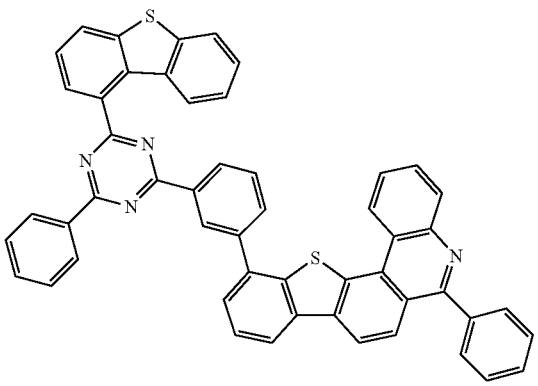
1121
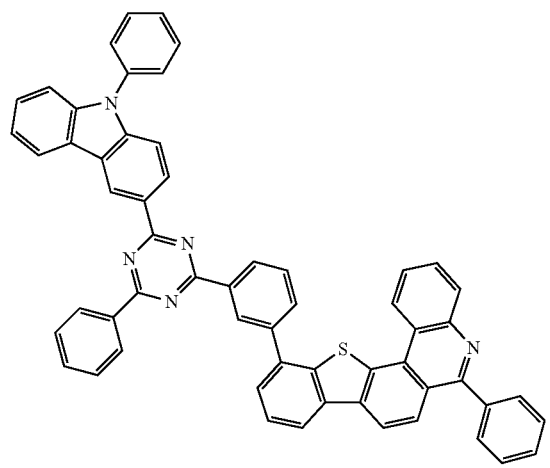
1122
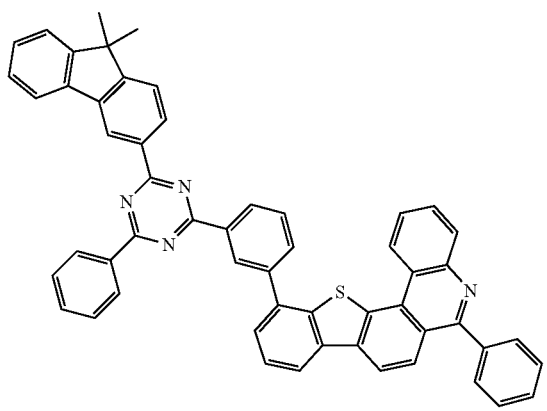
1123
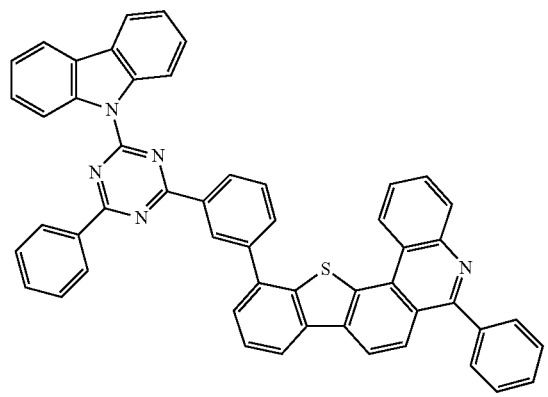
1124
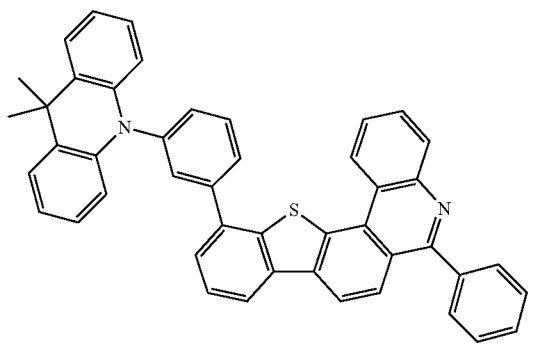

-continued
1125
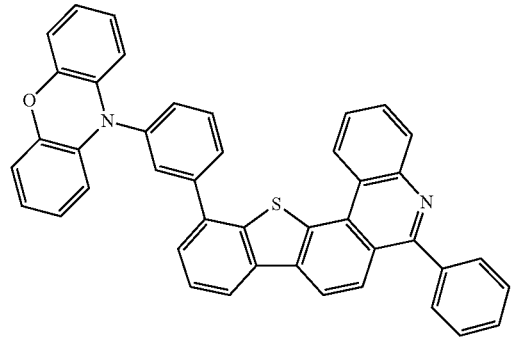
1126
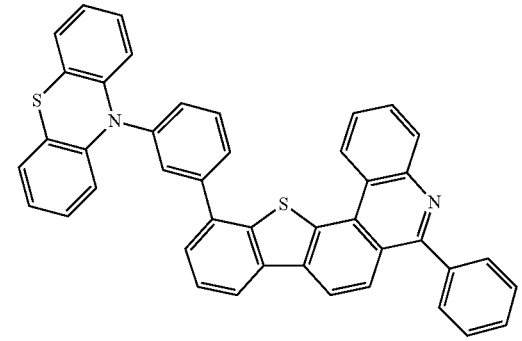
1127
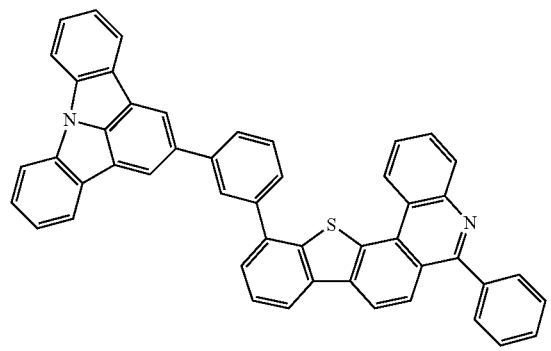
1128
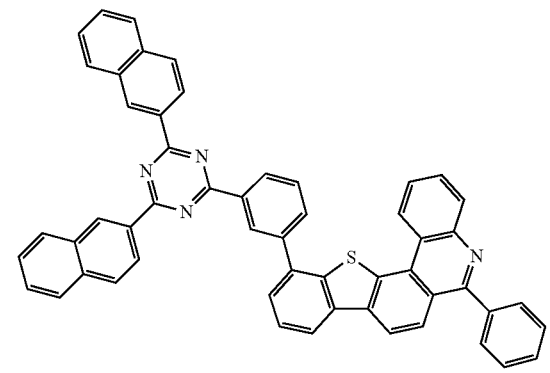
1129
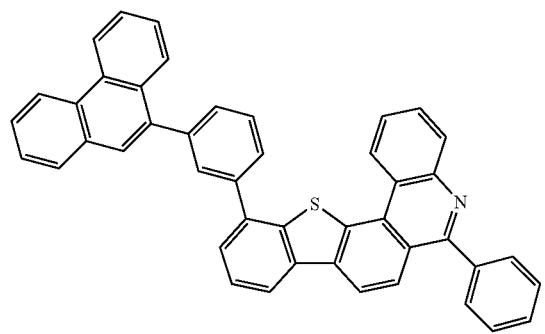
1130
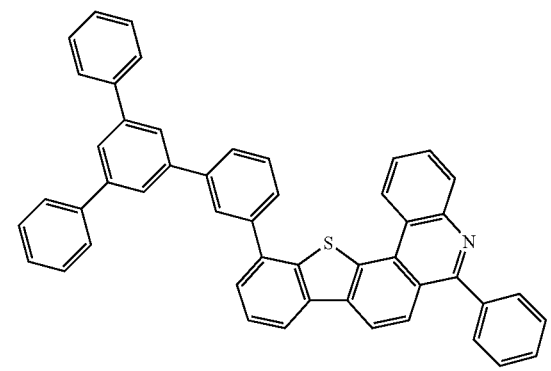
1131
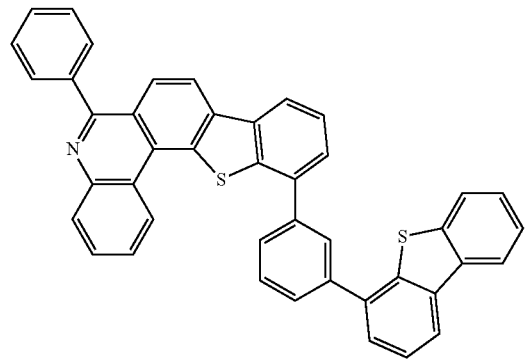
1132
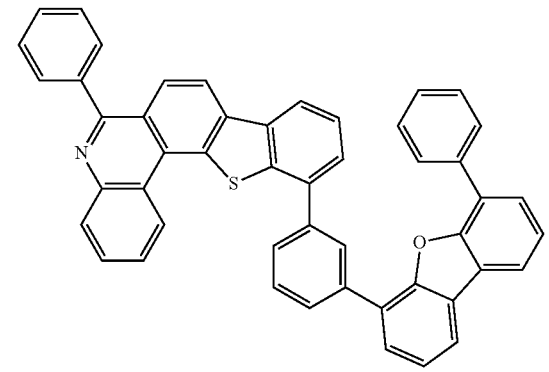

-continued
| 1133 | 1134 |
|---|---|
| 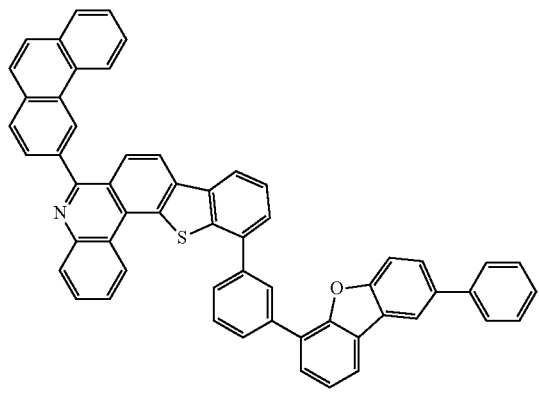 | 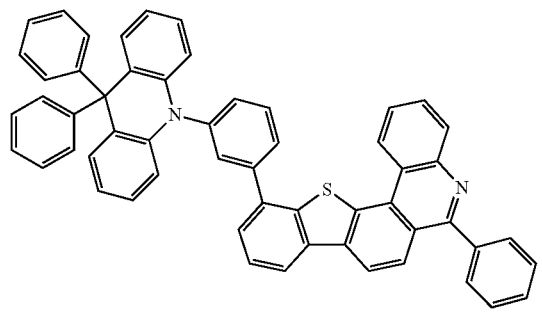 |
| 1135 | 1136 |
| 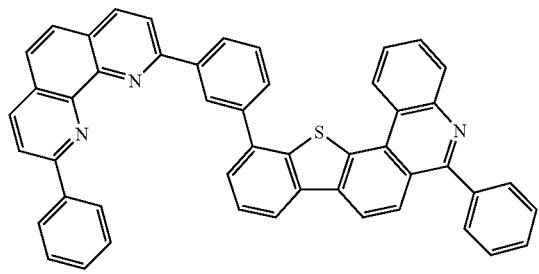 | 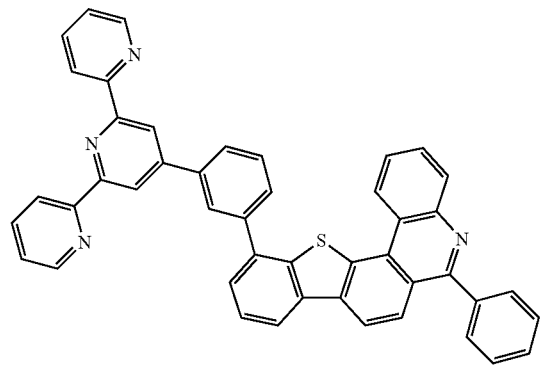 |
| 1137 | 1138 |
| 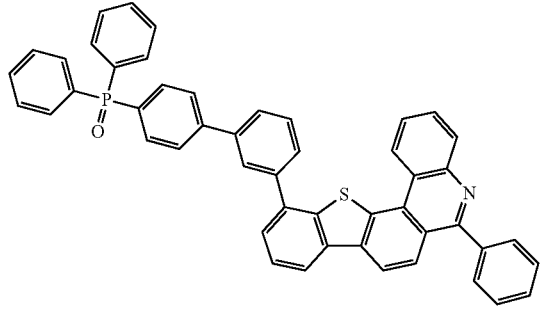 | 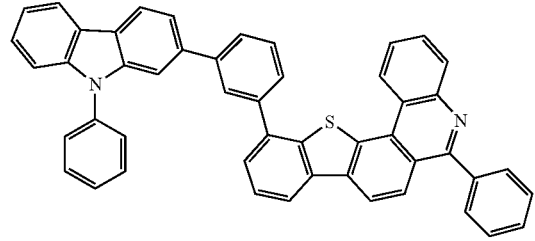 |
| 1139 | 1140 |
| 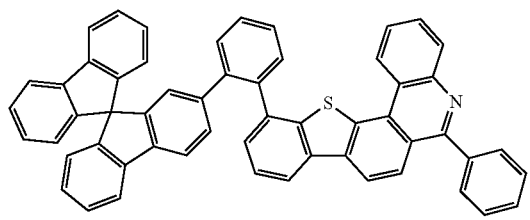 | 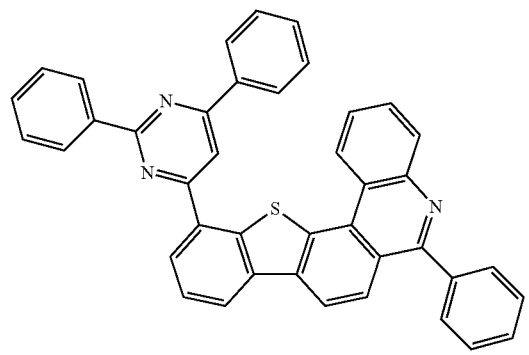 |

-continued
1141
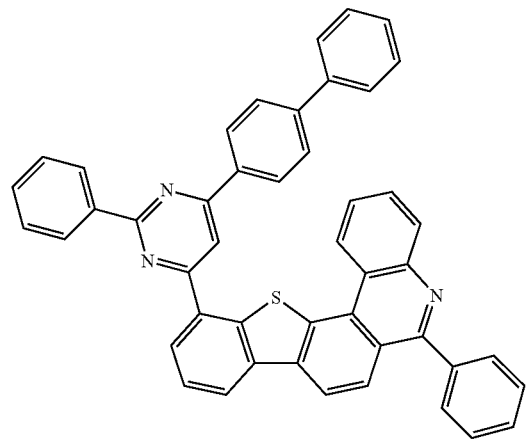
1142
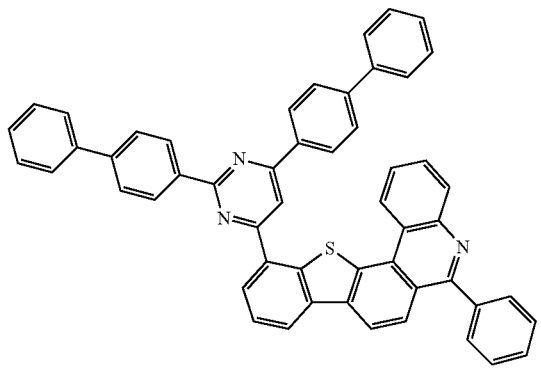
1143
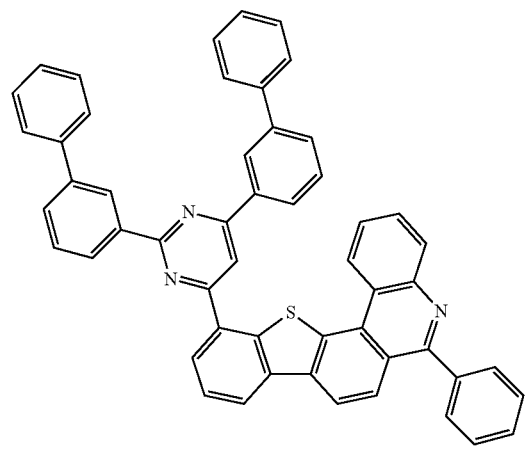
1144
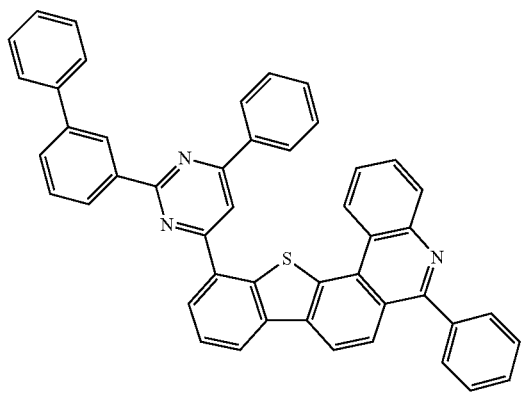
1145
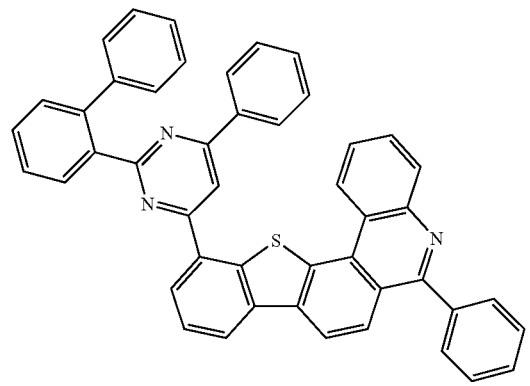
1146
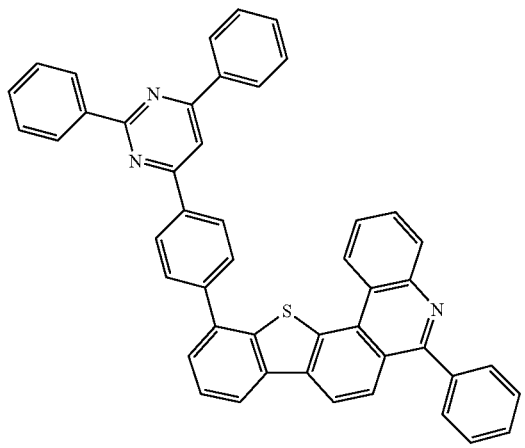

-continued
1147
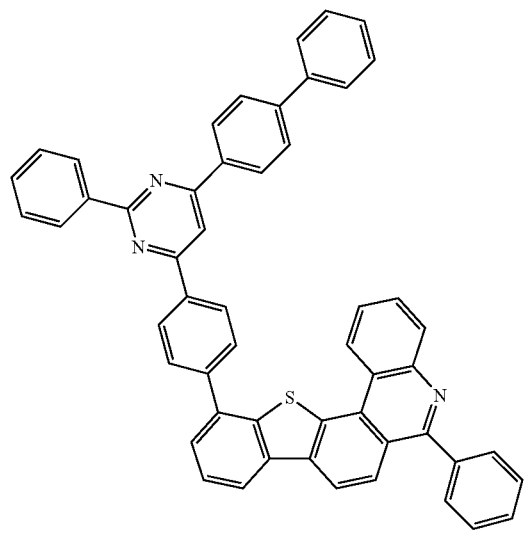
1148
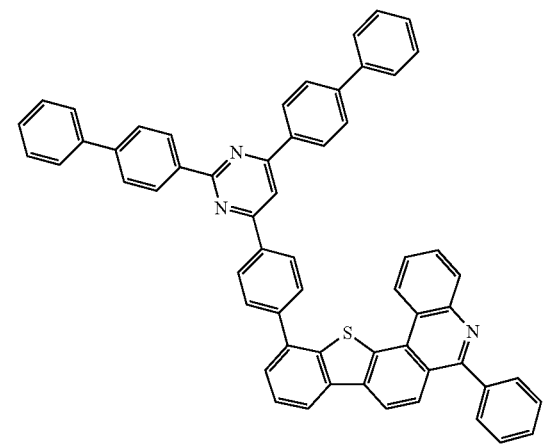
1149
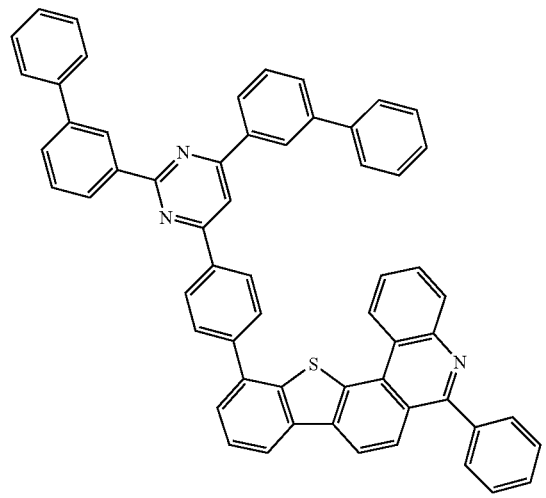
1150
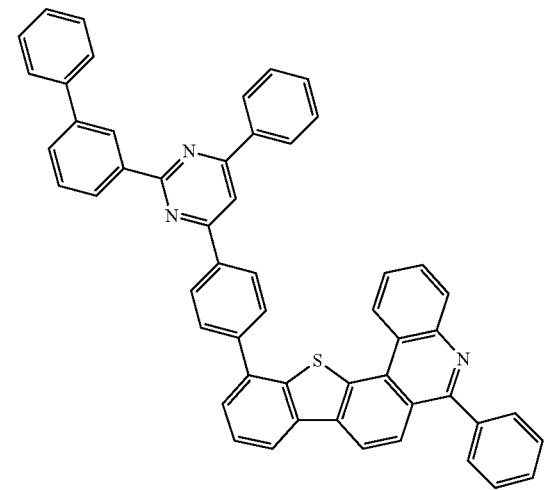
1151
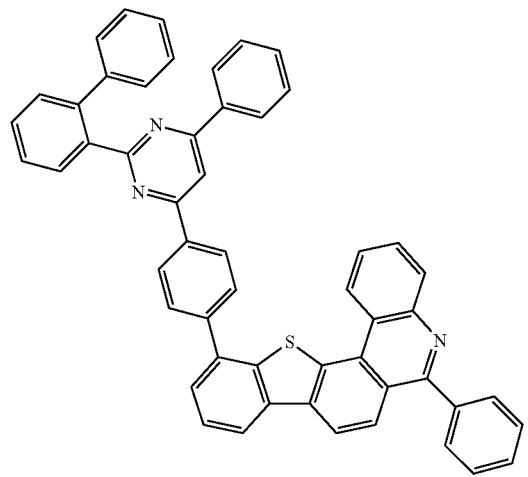
1152
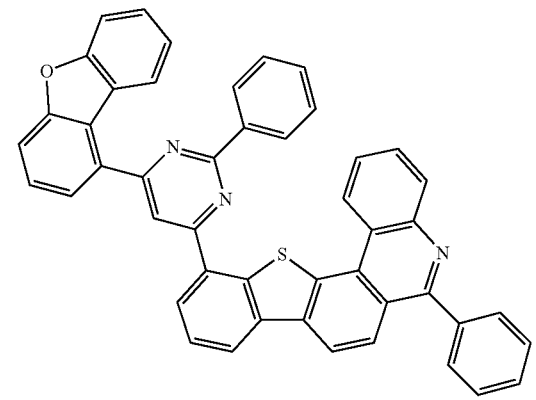

1171  1172
-continued
1153
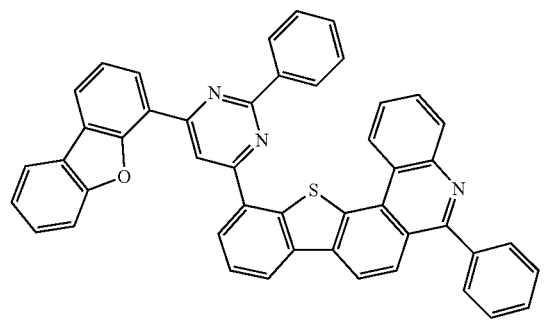
1154
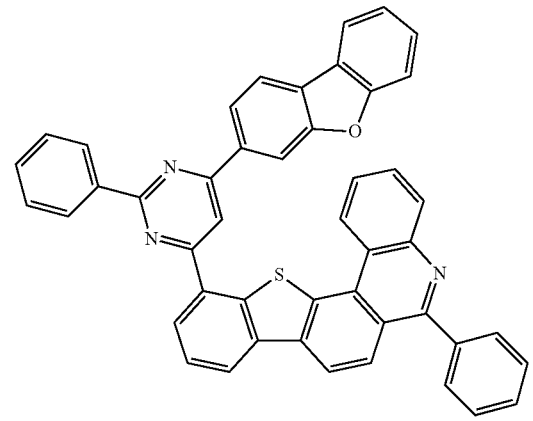
1155
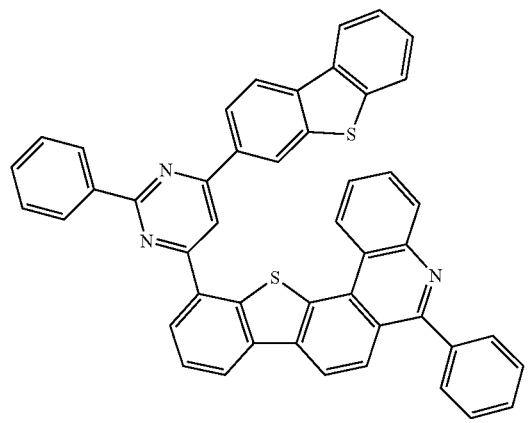
1156
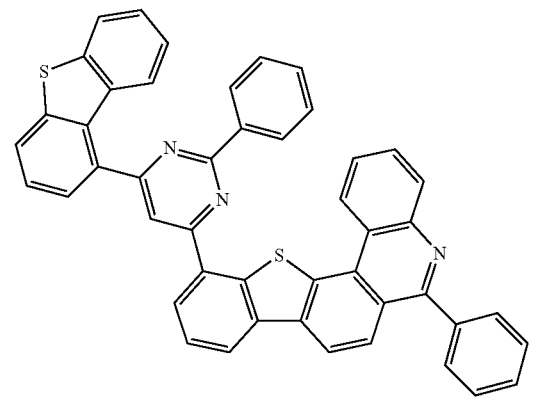
1157
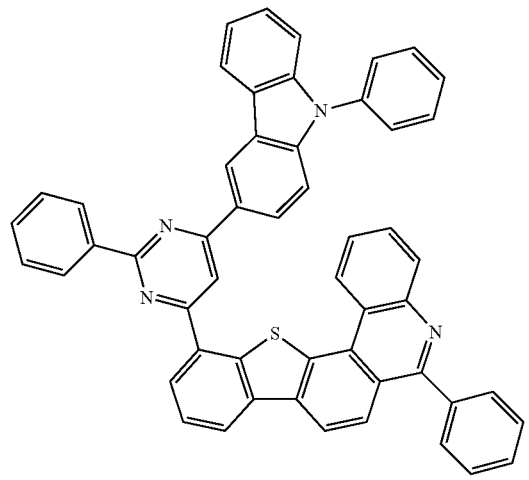
1158
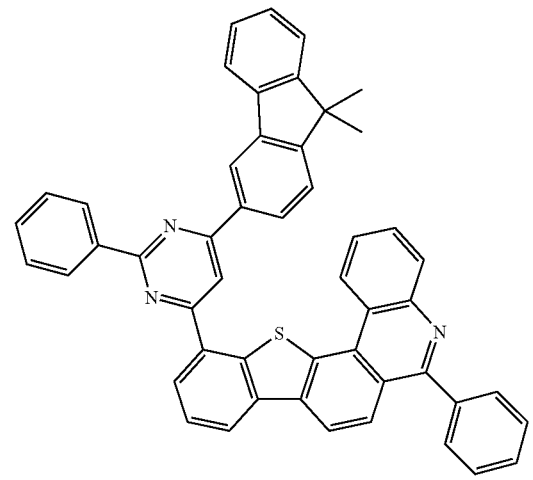

-continued
1159
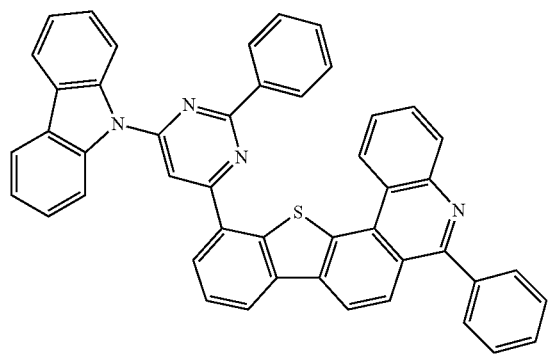
1160
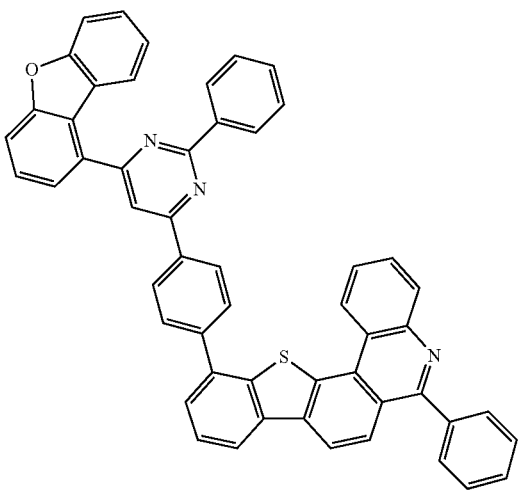
1161
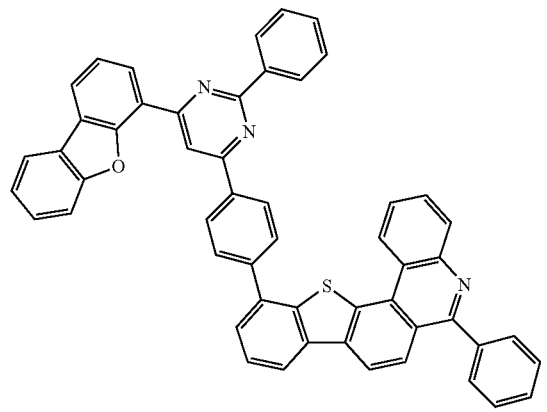
1162
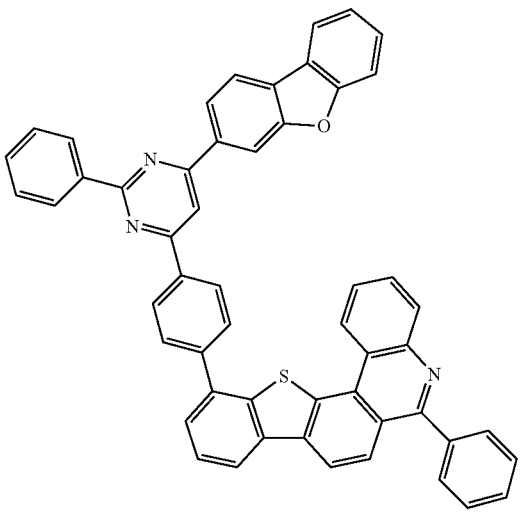
1163
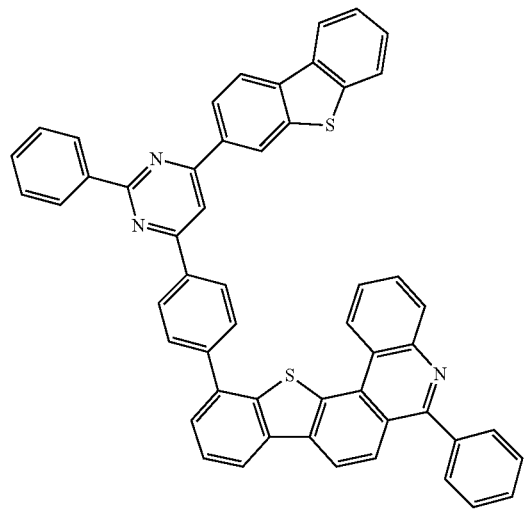
1164
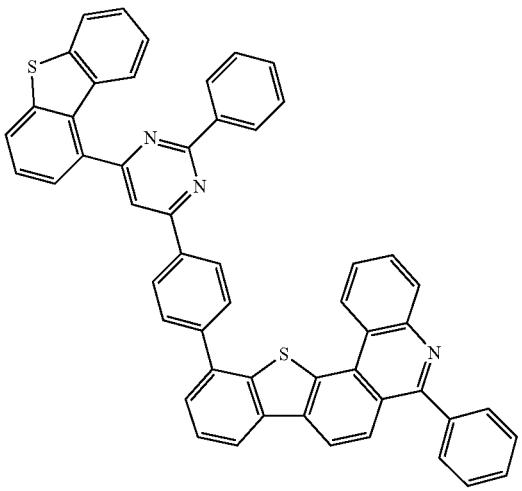

-continued
1165
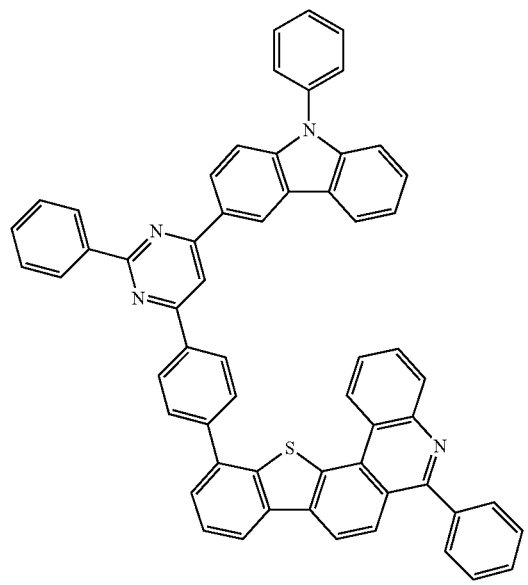
1166
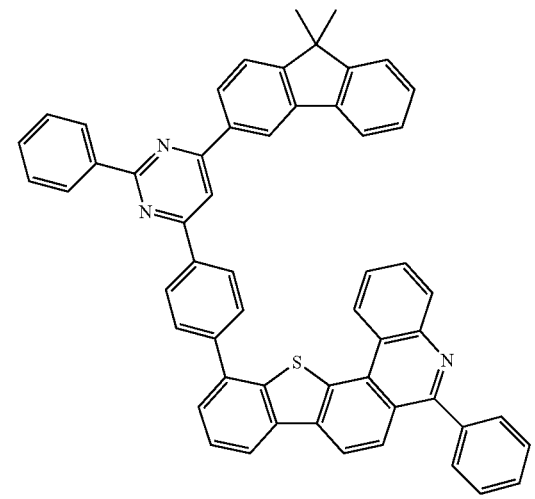
1167
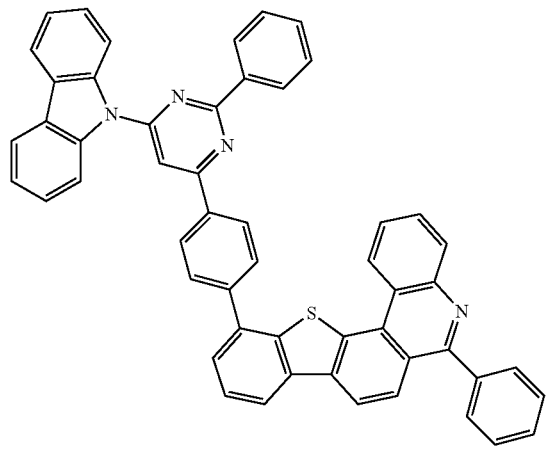
1168
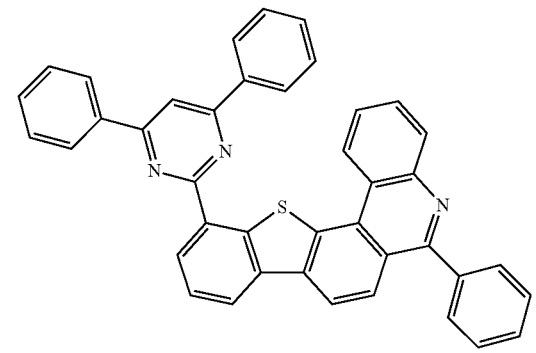
1169
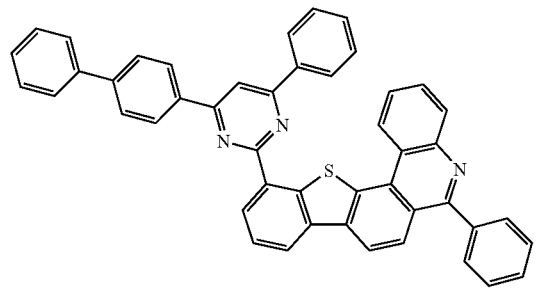
1170
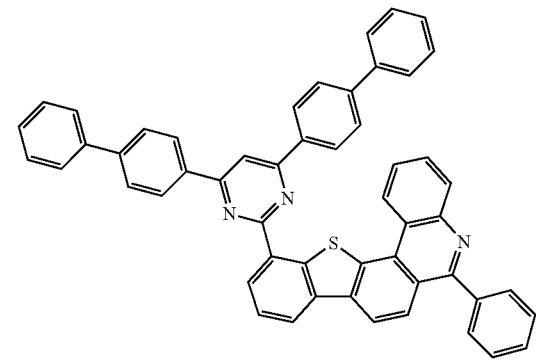

-continued
1177
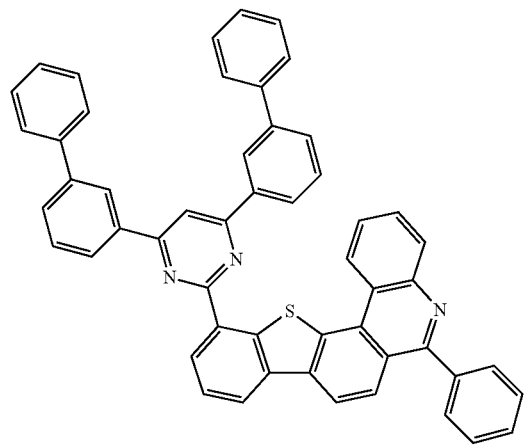
1178
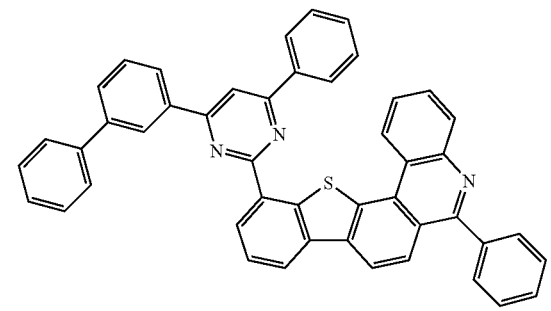
1171
1172
1173
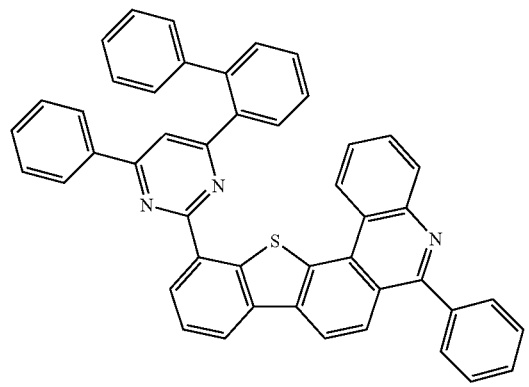
1174
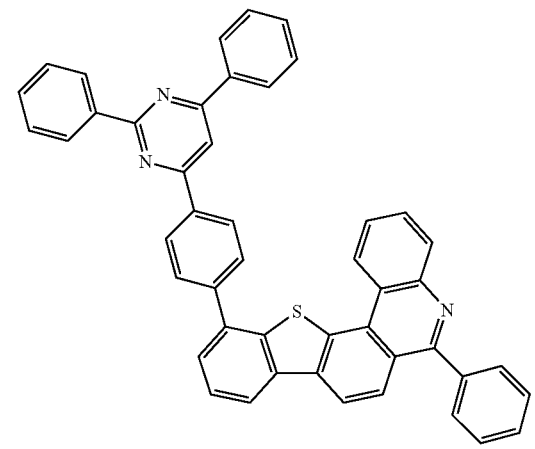
1175
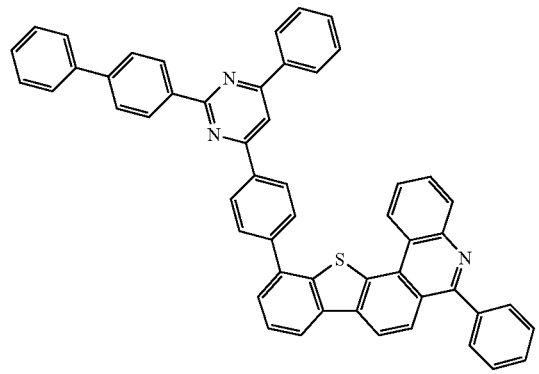
1176
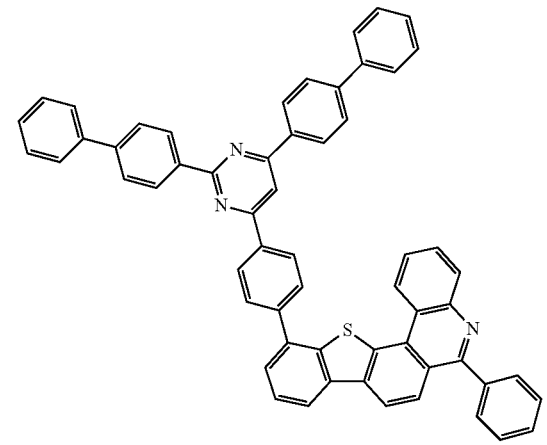

-continued
1177
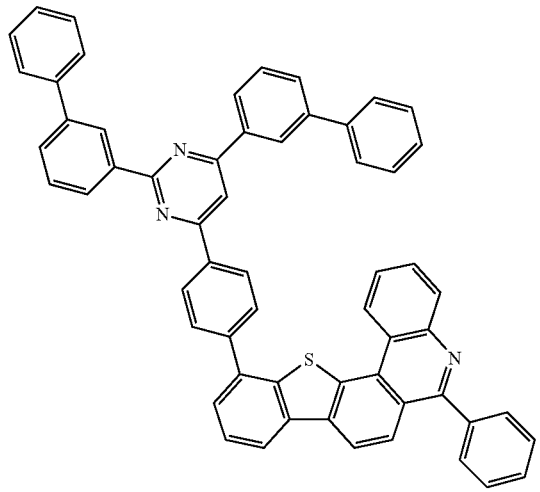
1179
1178
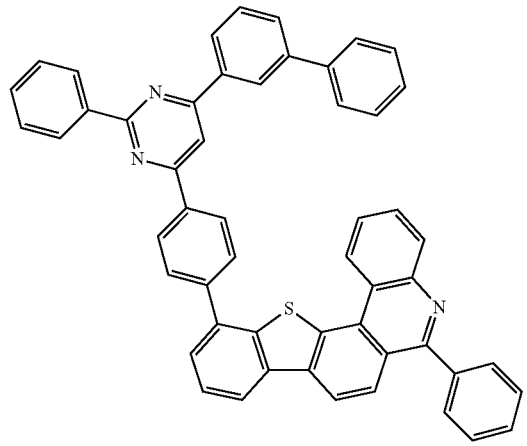
1180
1179
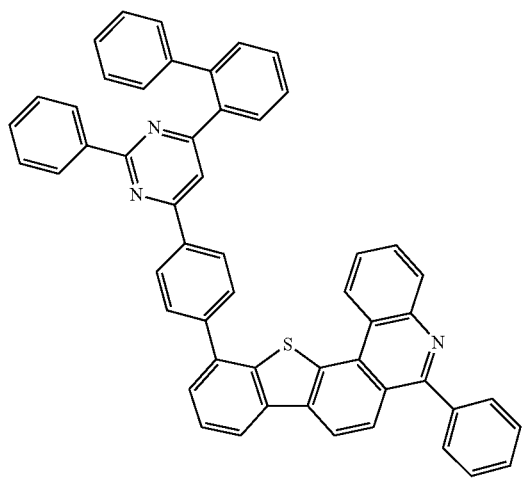
1180
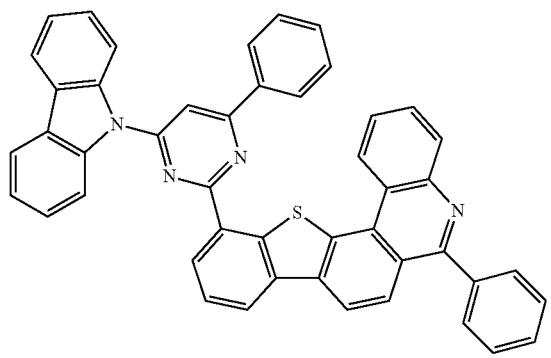
1181
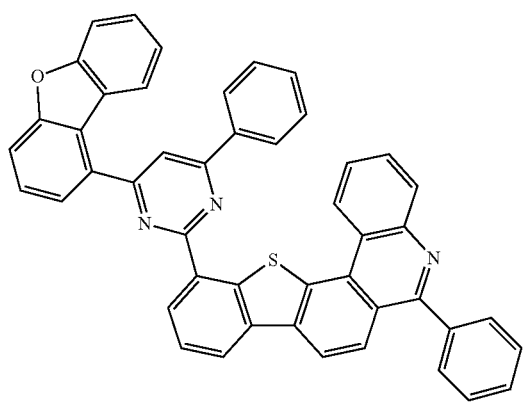
1182
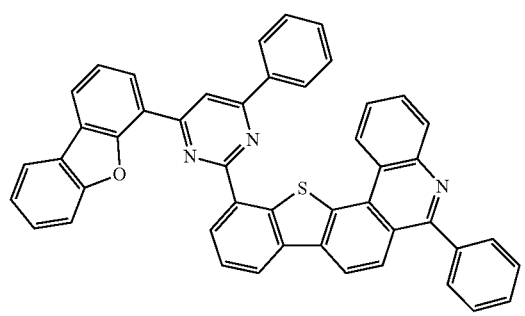

1181 1182
-continued
1183 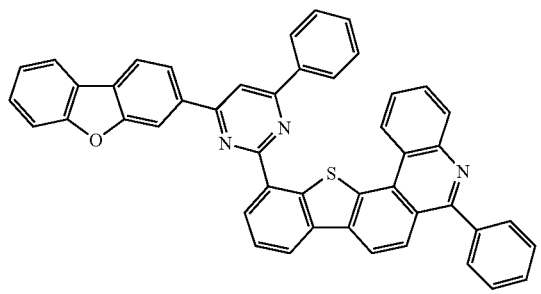 1184 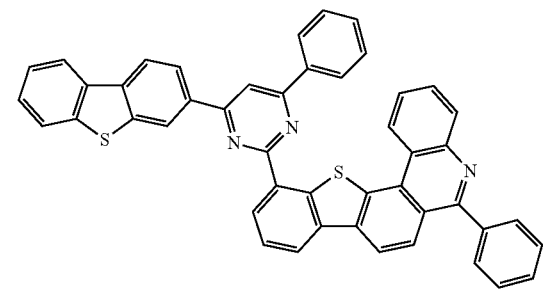
1185 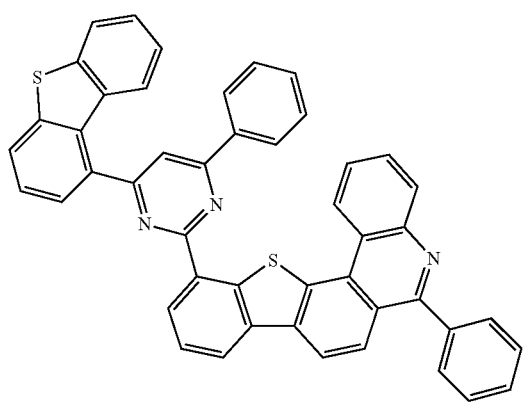 1186 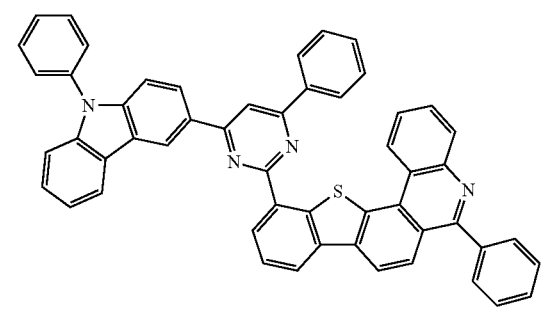
1187 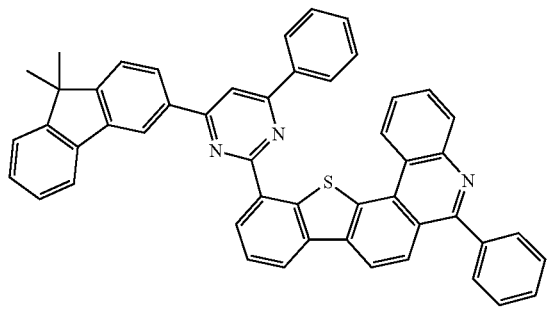 1188 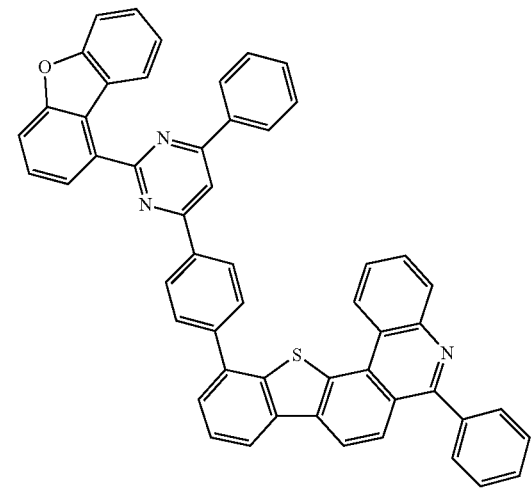
1189 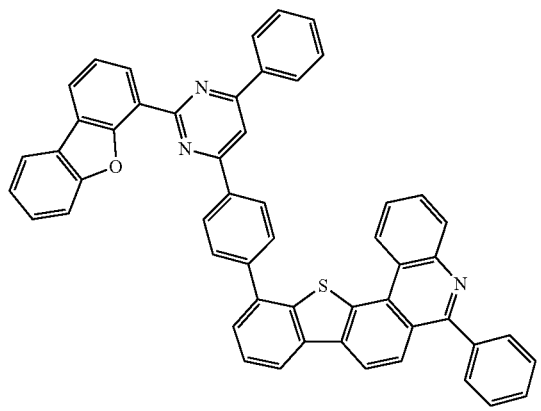 1190 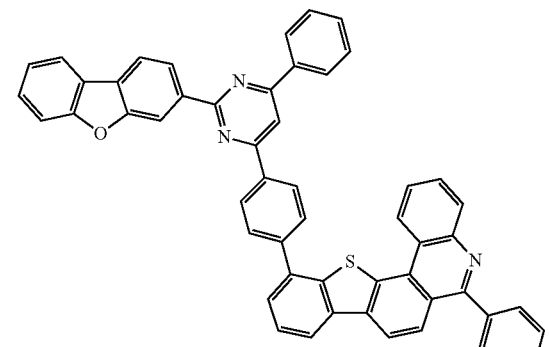

1183 1184
-continued
| 1191 | 1192 |
|---|---|
| 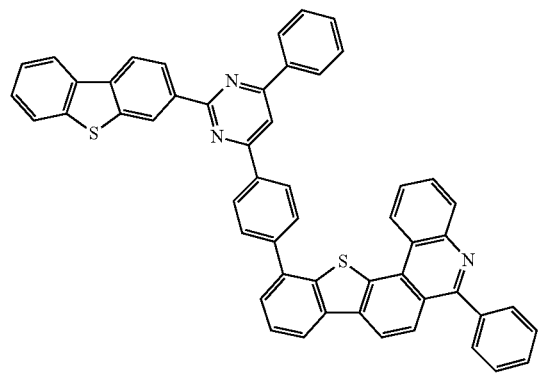 | 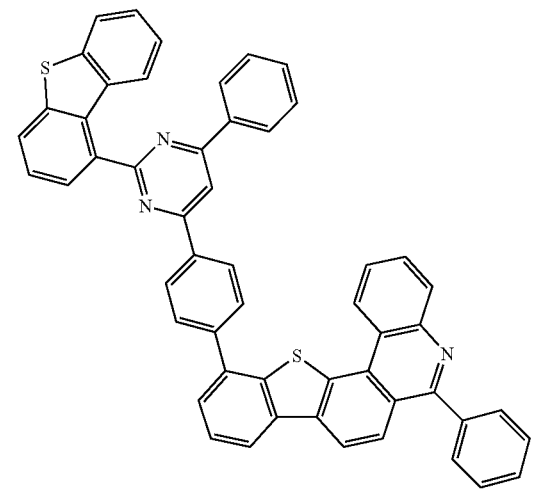 |
| 1193 | 1194 |
| 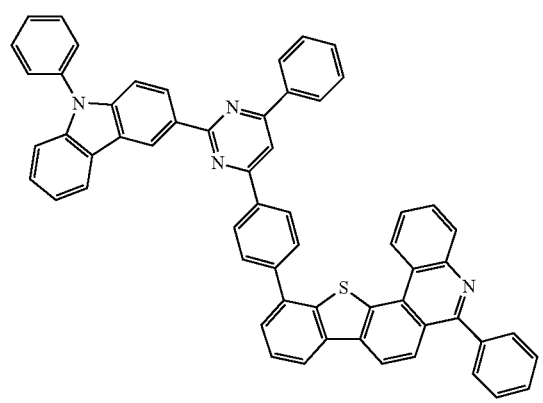 | 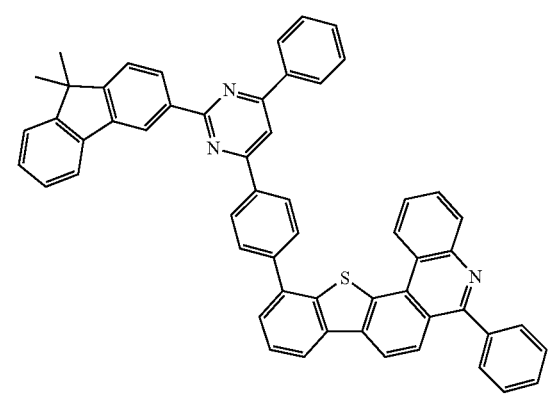 |
| 1195 | 1196 |
| 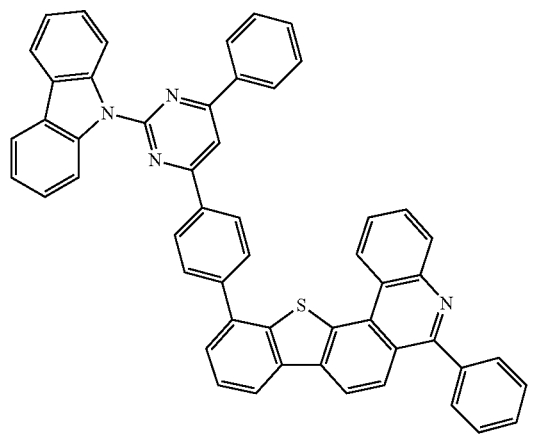 | 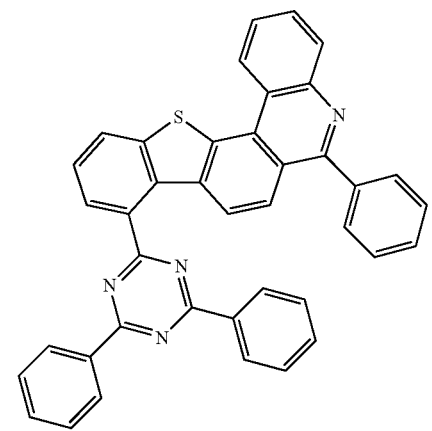 |

1185
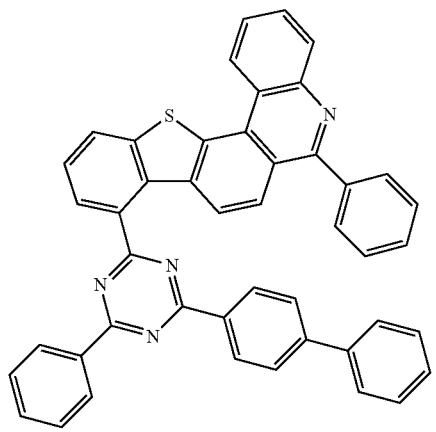
1197
1186
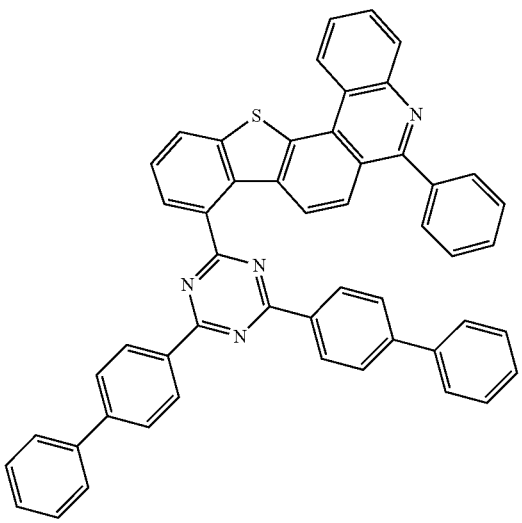
1198
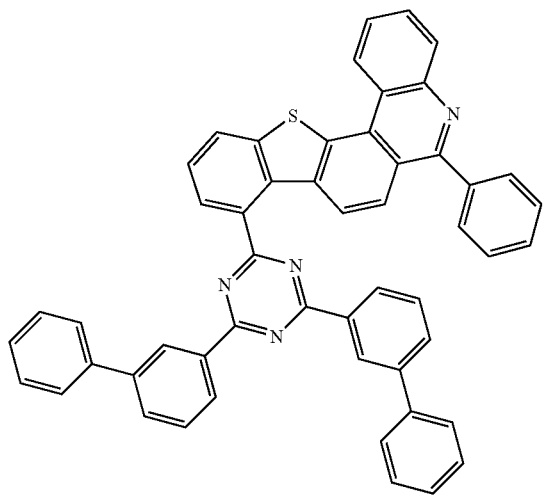
1199
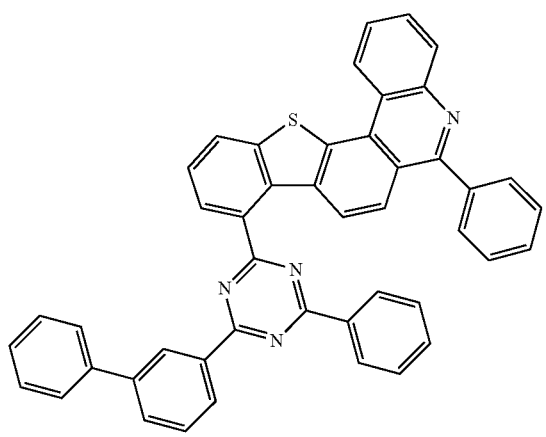
1200
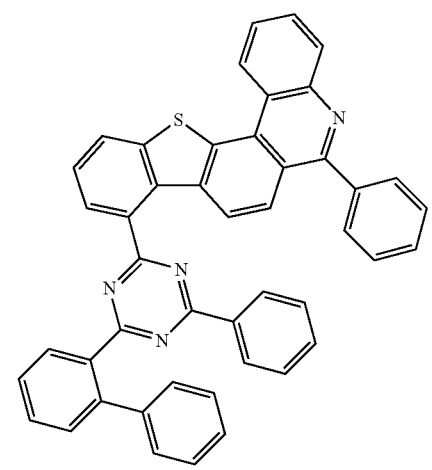
1201

1187 1188
-continued
1202 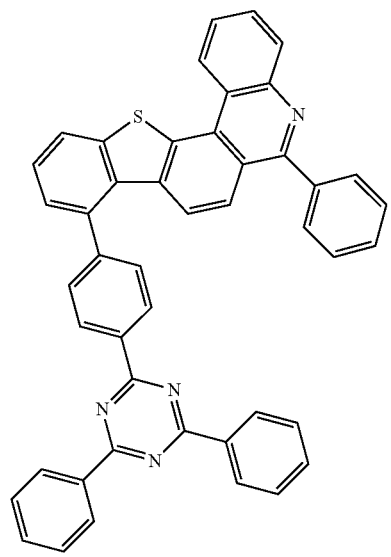 1203 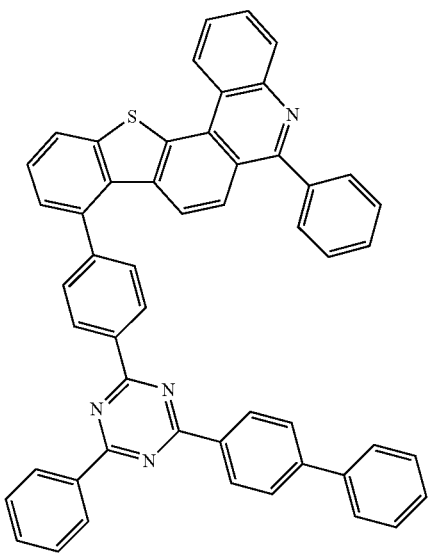
1204 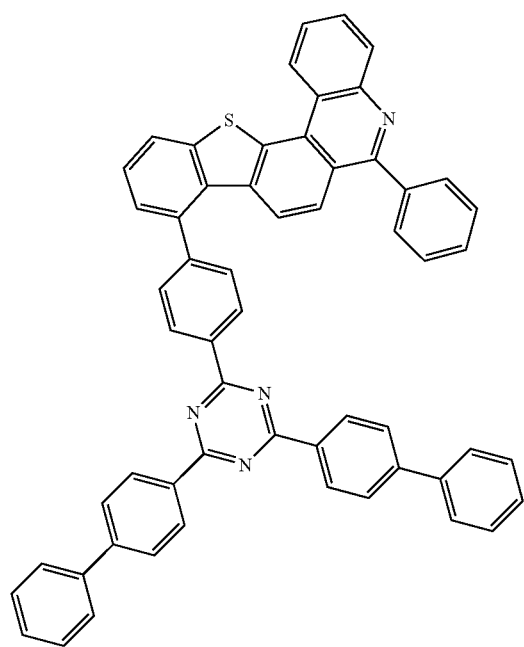 1205 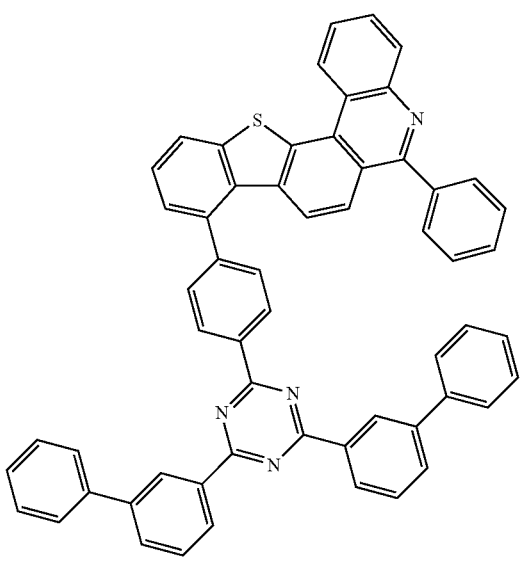

-continued
| 1206 | 1207 |
|---|---|
| 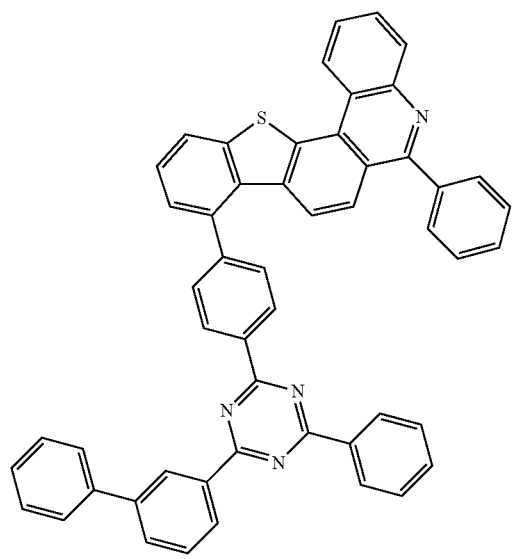 | 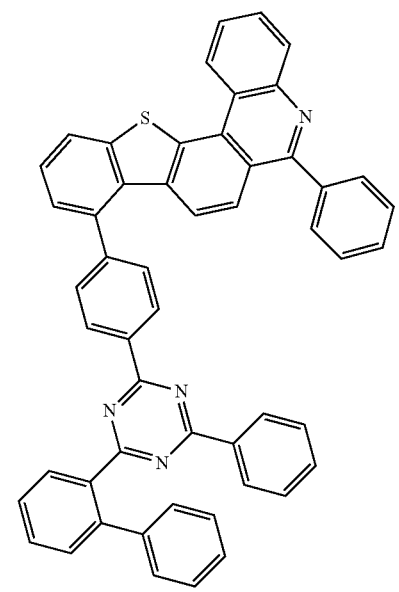 |
| 1208 | 1209 |
| 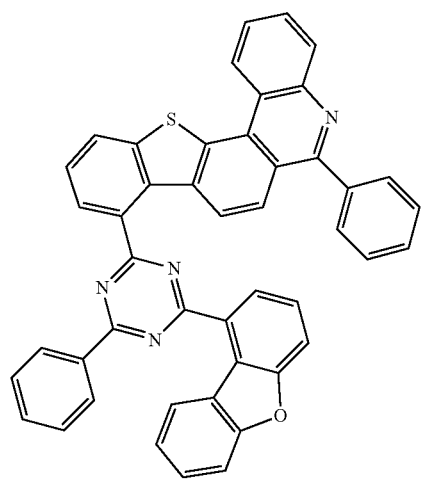 | 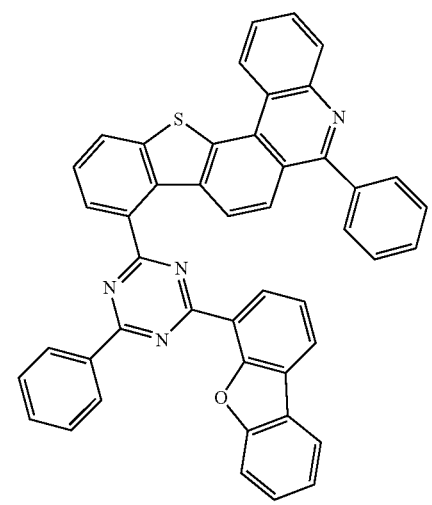 |
| 1210 | 1211 |
| 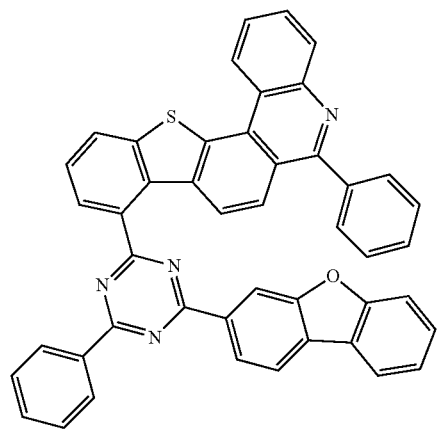 | 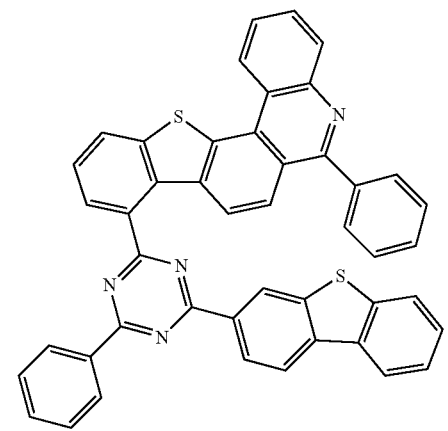 |

-continued
1212
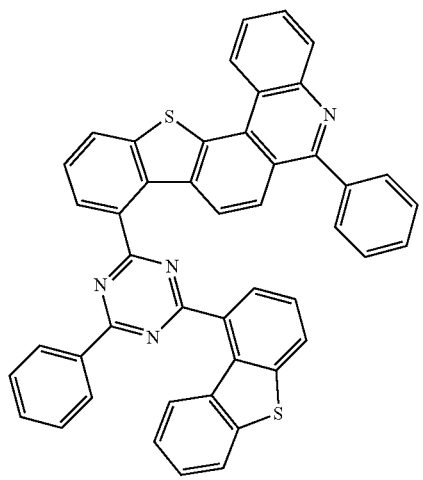
1213
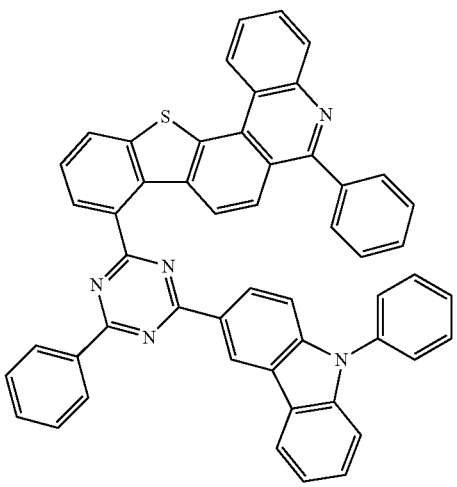
1214
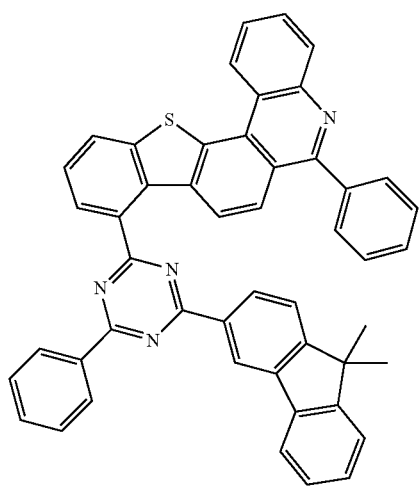
1215
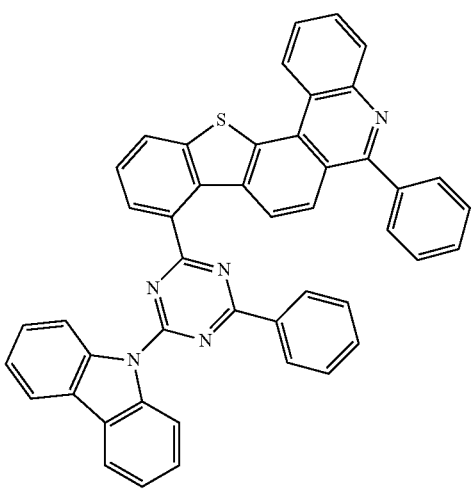
1216
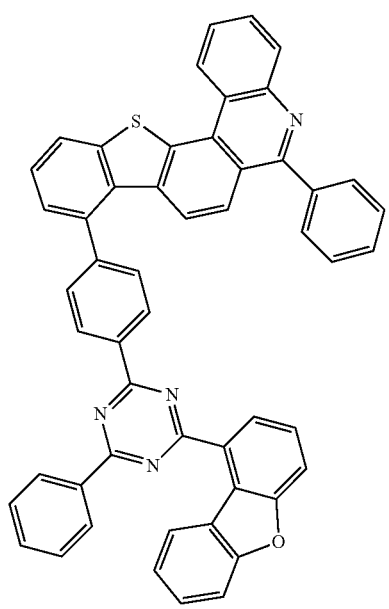
1217
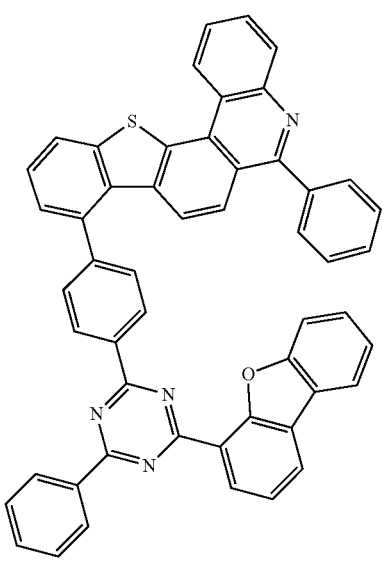

1193 1194
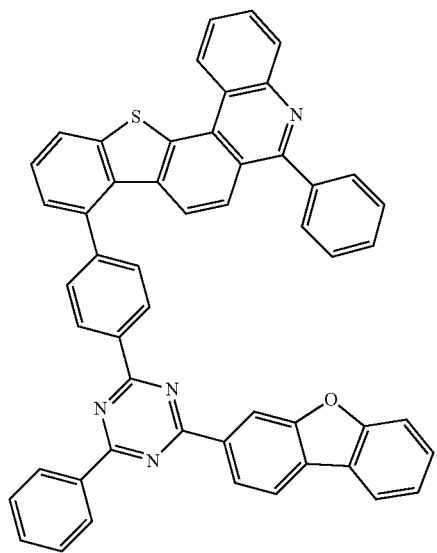
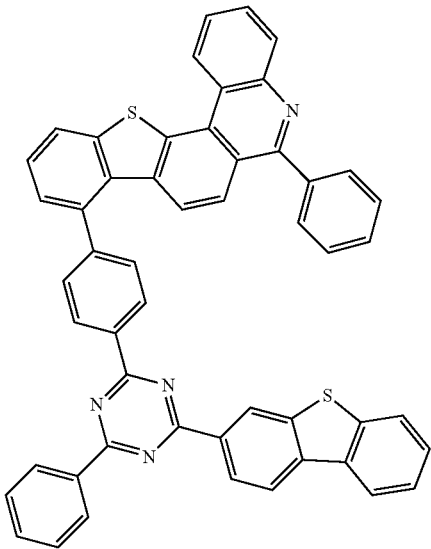
-continued
1218 1219
1220 1221
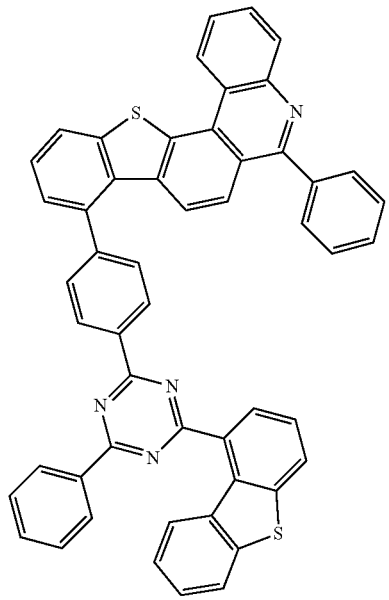

1195
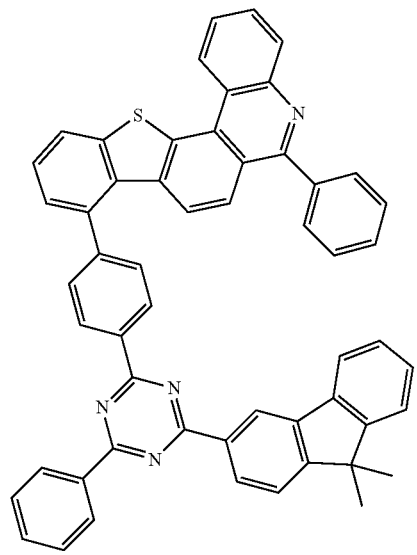
1196
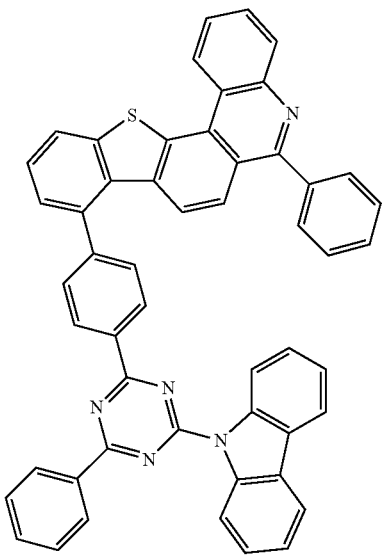
-continued
1222
1223
1224
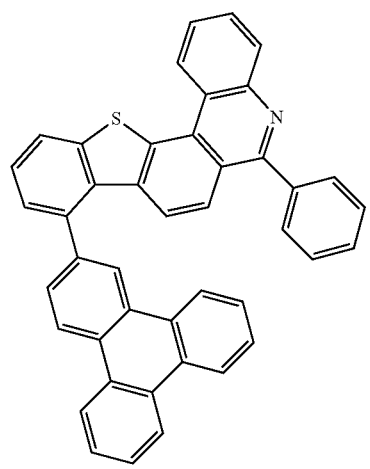
1225
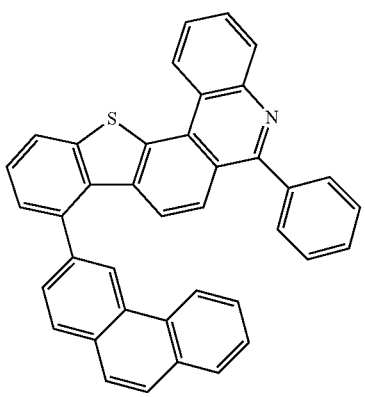
1226
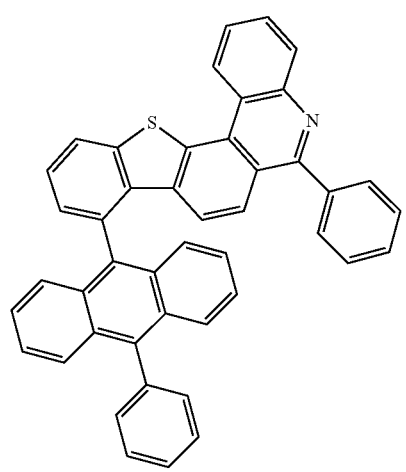
1227
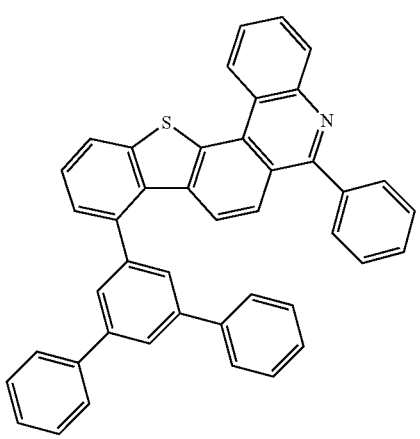

-continued
| 1228 | 1229 |
|---|---|
| 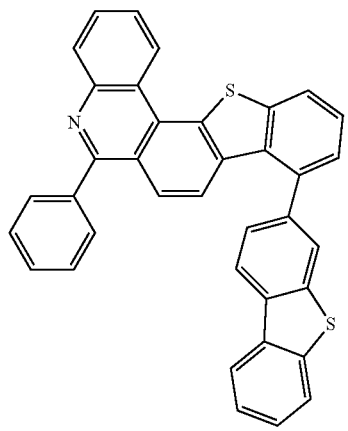 | 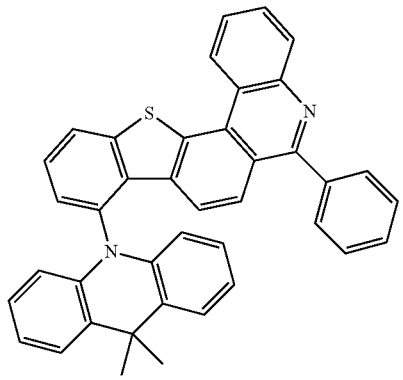 |
| 1230 | 1231 |
|---|---|
| 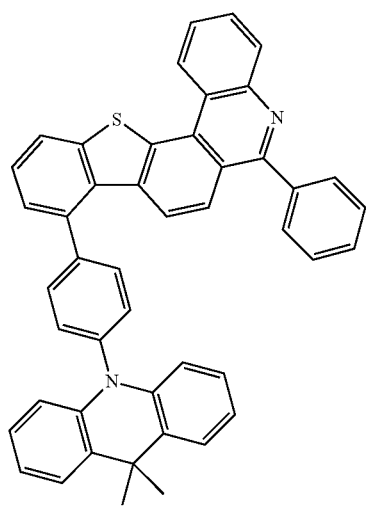 | 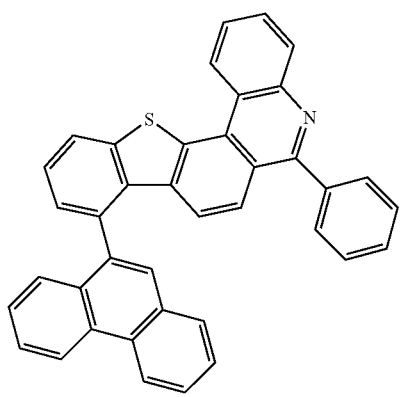 |
| 1232 | 1233 |
|---|---|
| 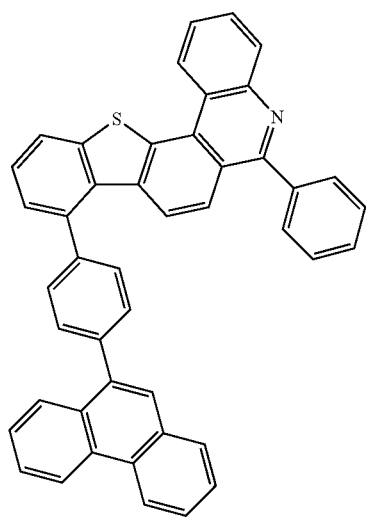 | 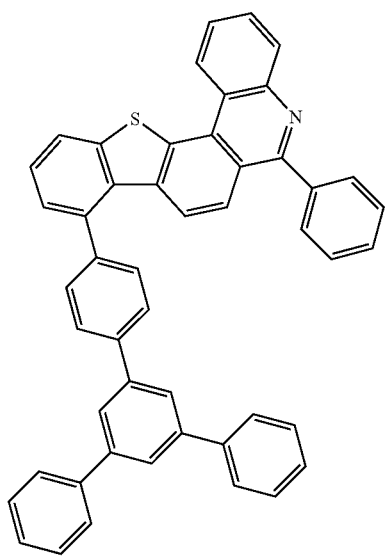 |

-continued
| 1234 | 1235 |
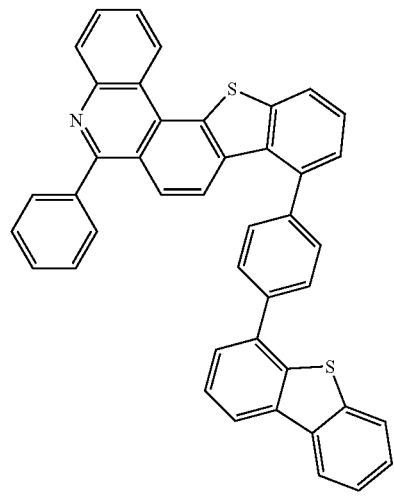
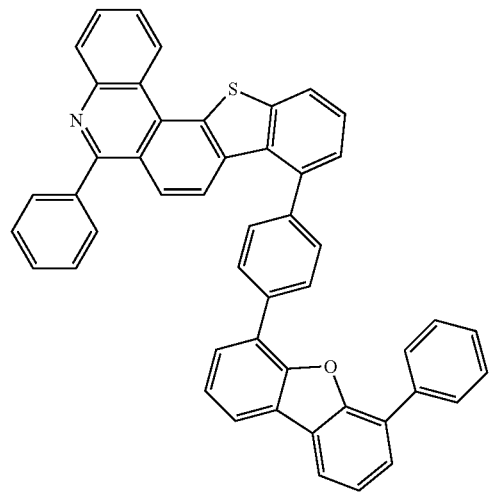
| 1236 | 1237 |
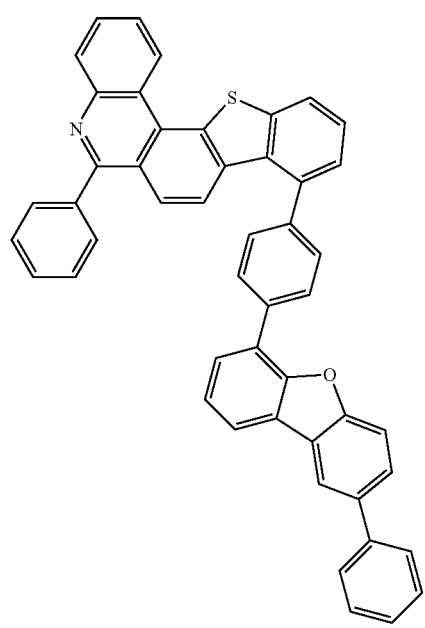
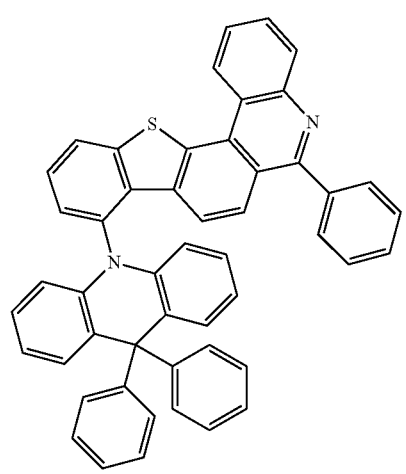

-continued
1238
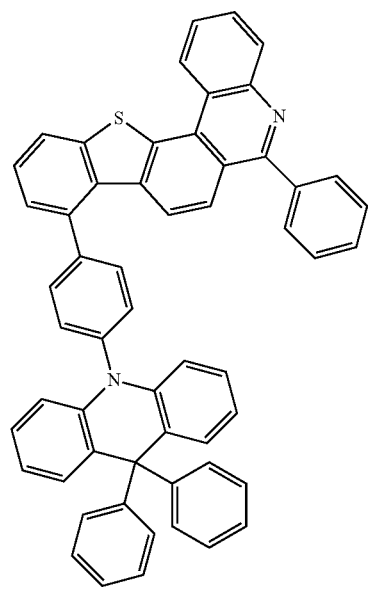
1239
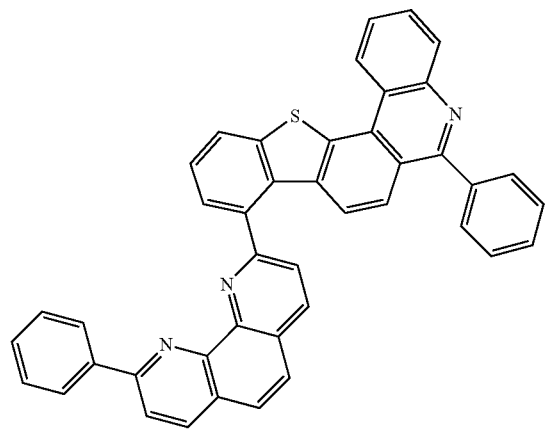
1240
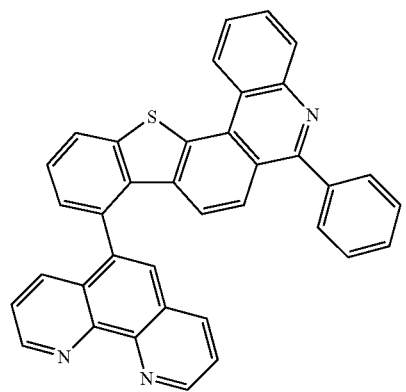
1241
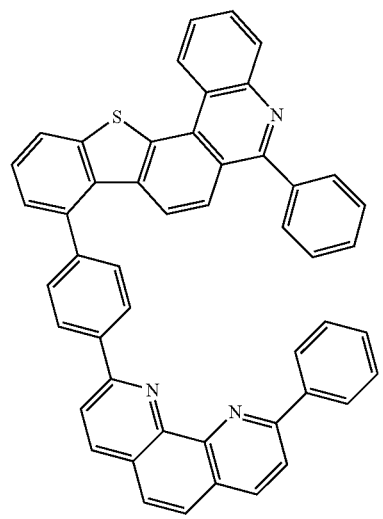

-continued
| 1242 | 1243 |
|---|---|
| 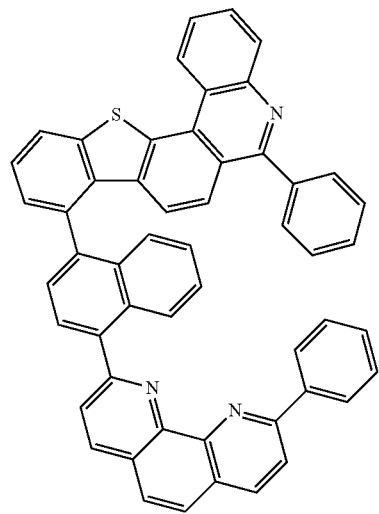 | 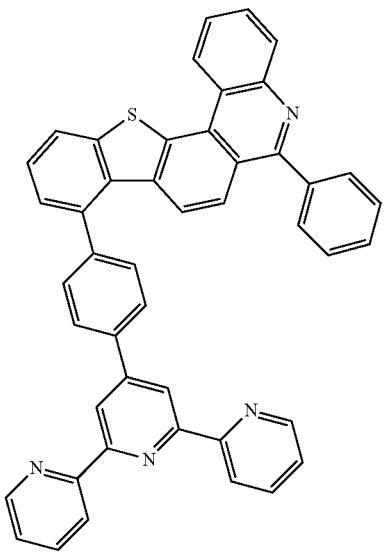 |
| 1244 | 1245 |
| 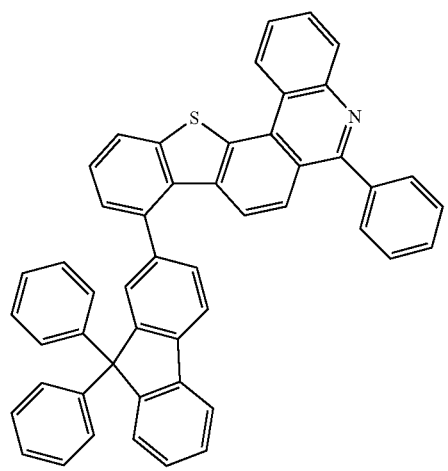 | 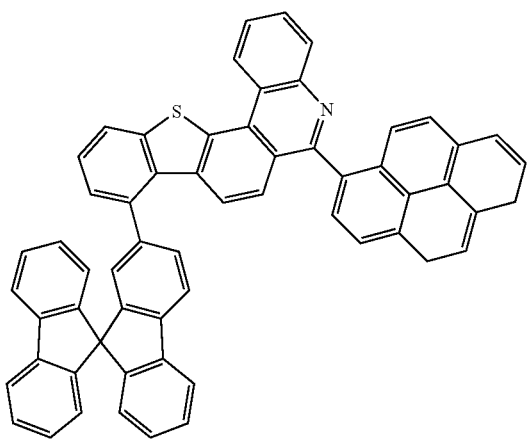 |
| 1246 | 1247 |
| 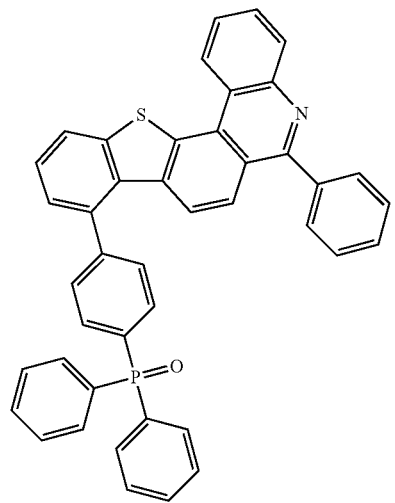 | 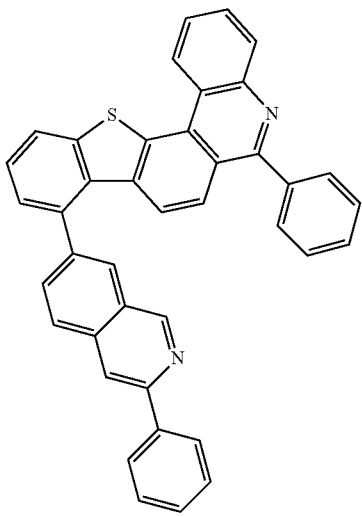 |

-continued
1248
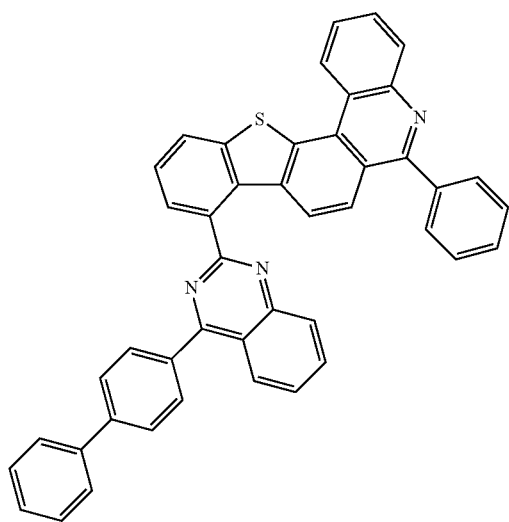
1249
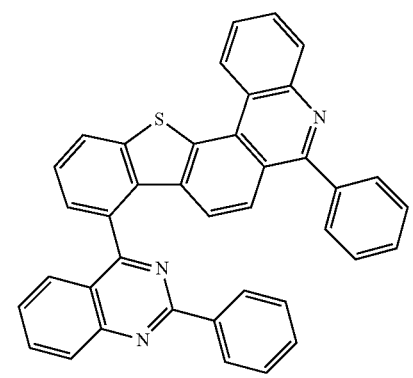
1250
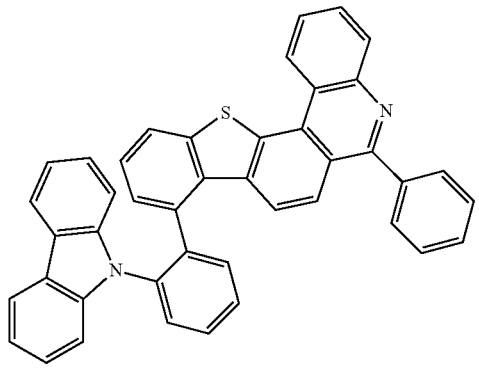
1251
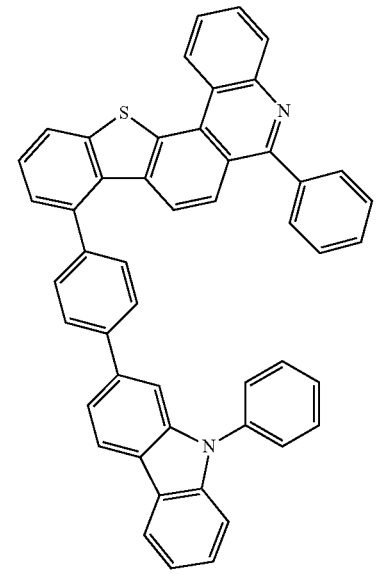
1252
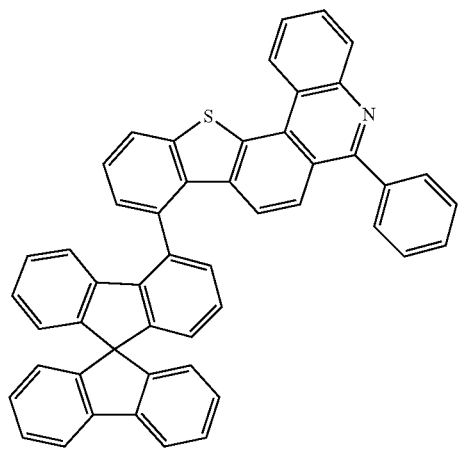
1253
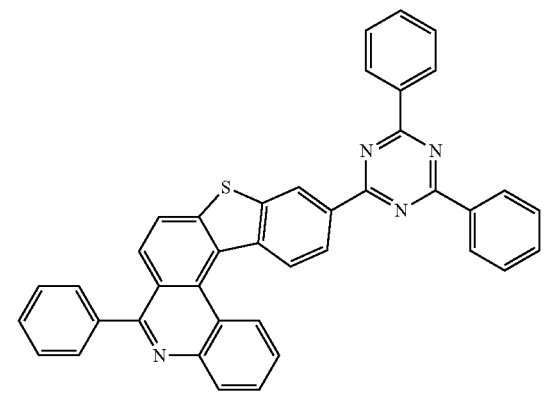

-continued
1254
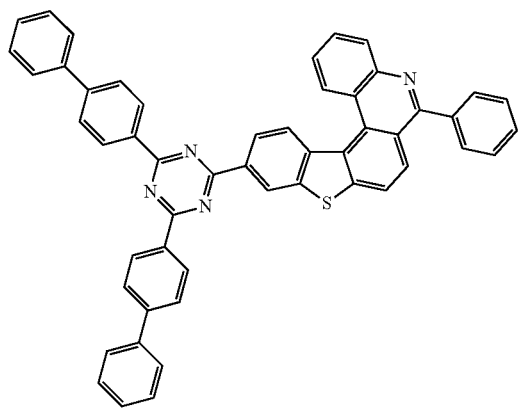
1255
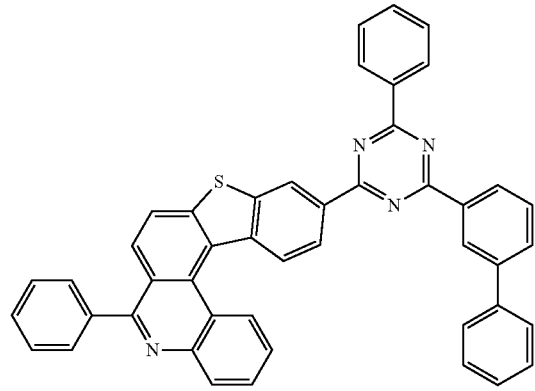
1256
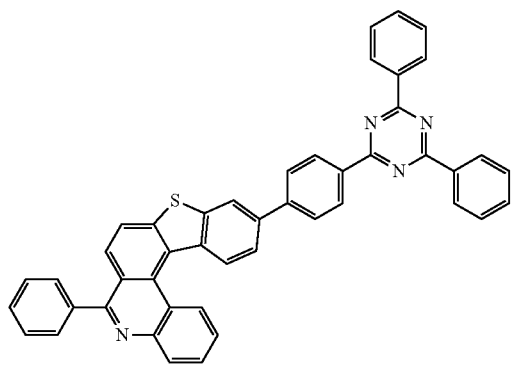
1257
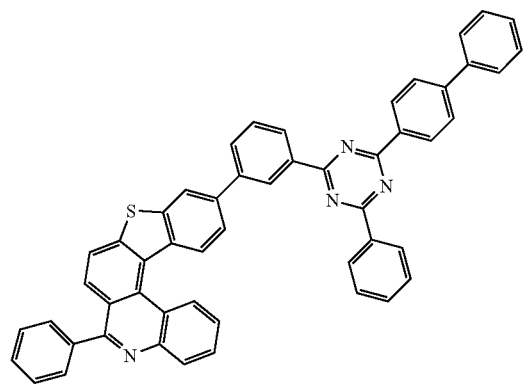
1258
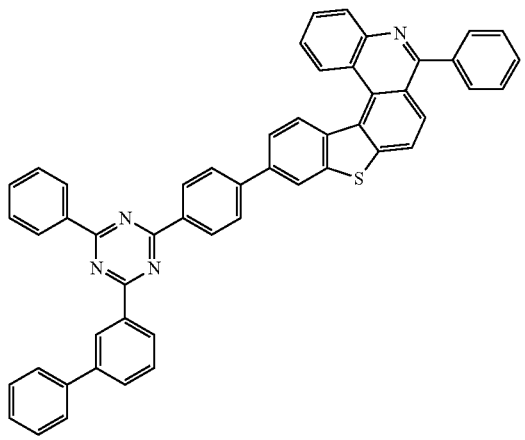
1259
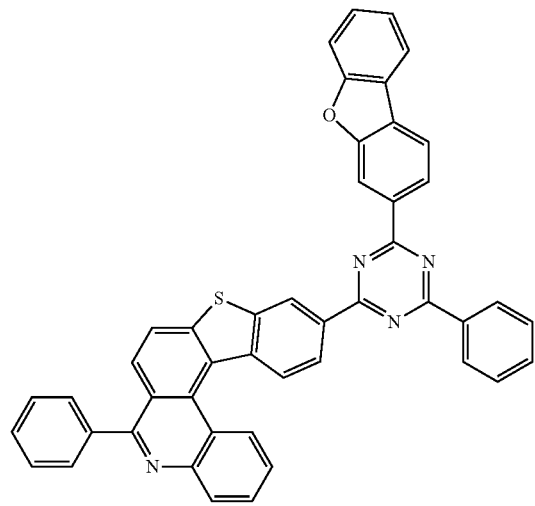

-continued
1260
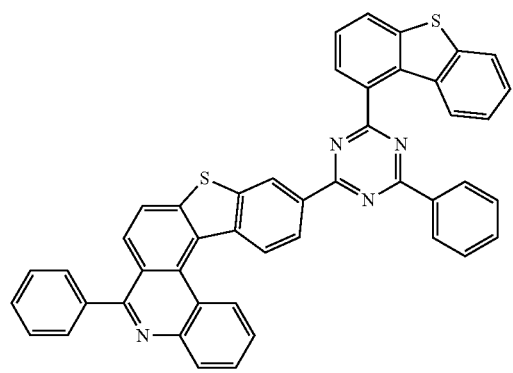
1261
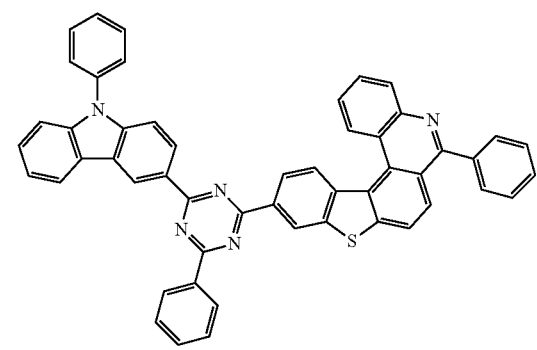
1262
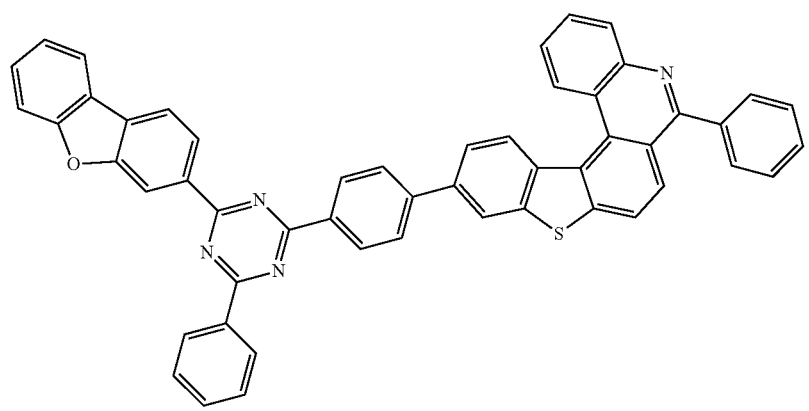
1263
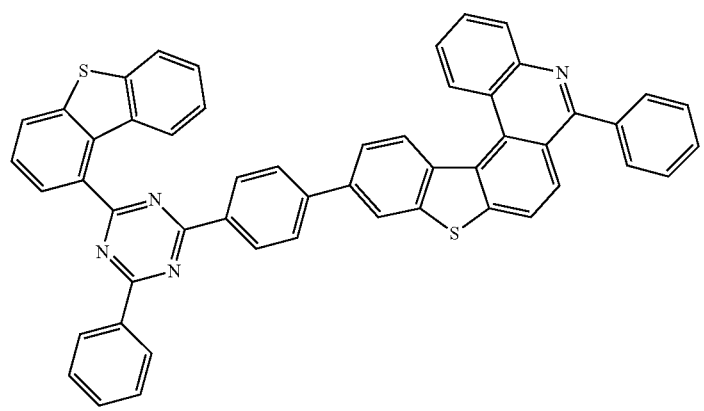
1264
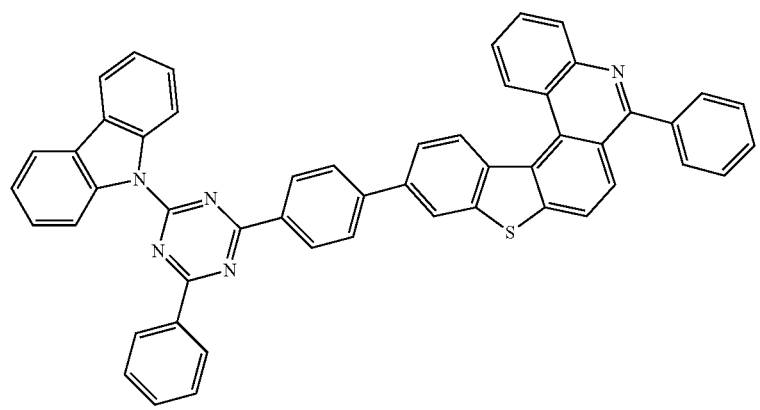

-continued
1265
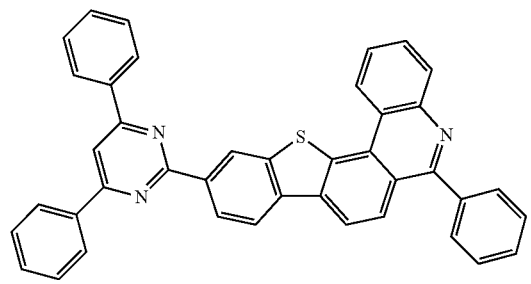
1266
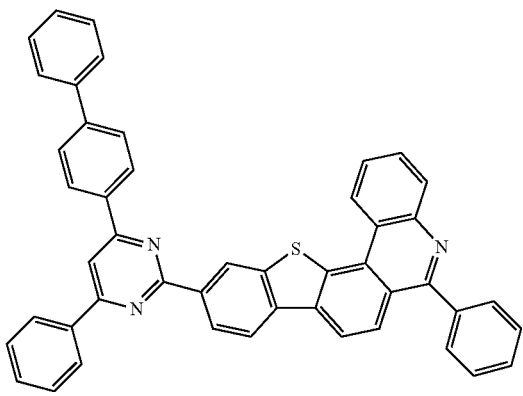
1267
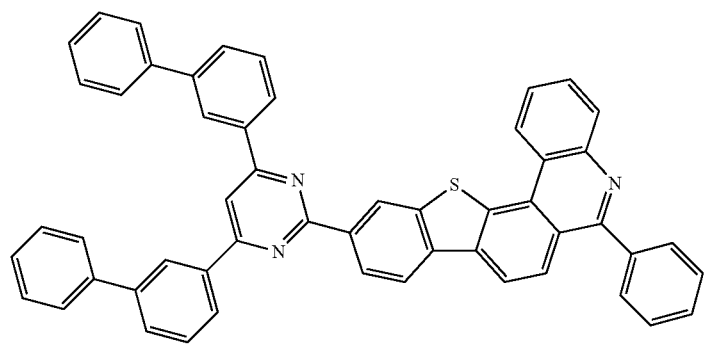
1268
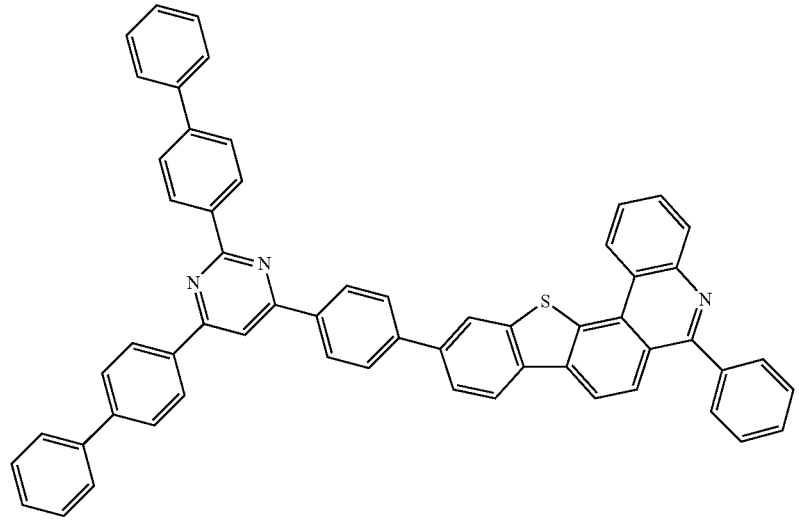
1269
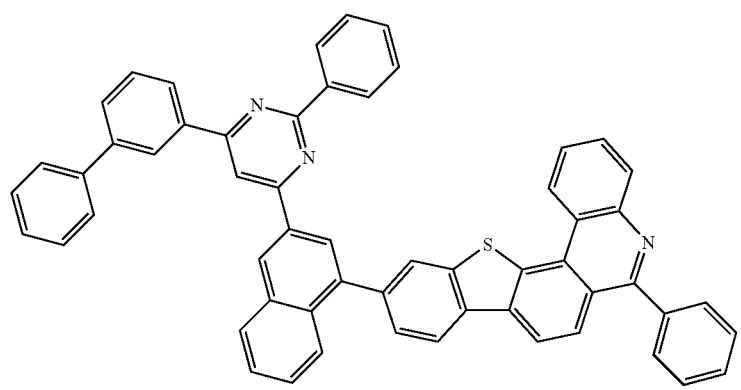

-continued
1270
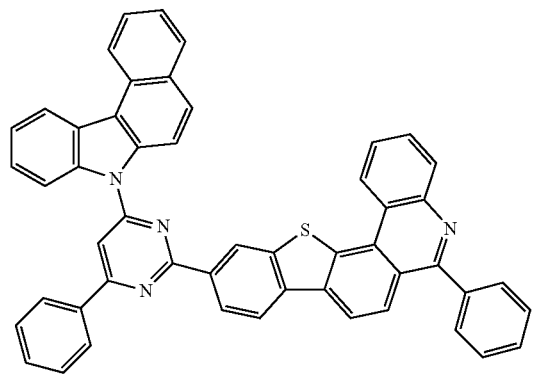
1271
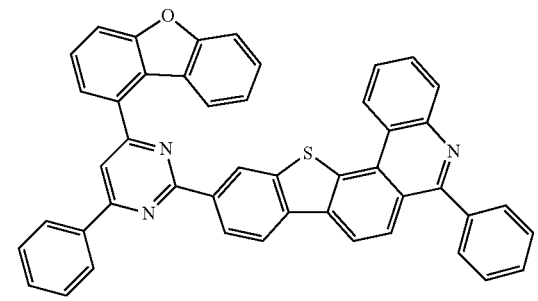
1272
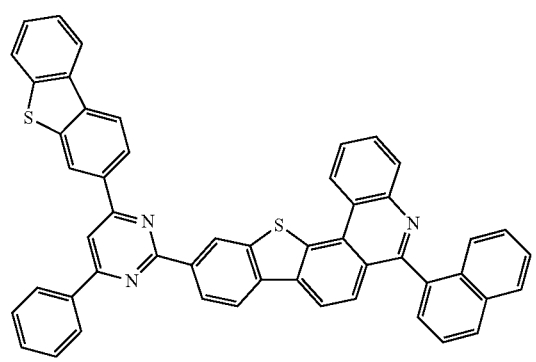
1273
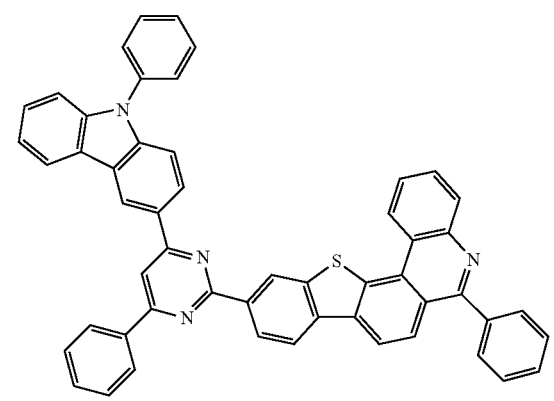
1274
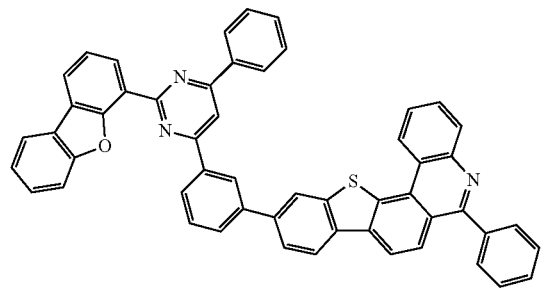
1275
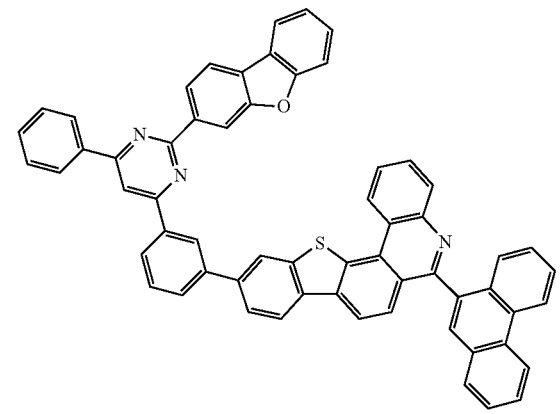
1276
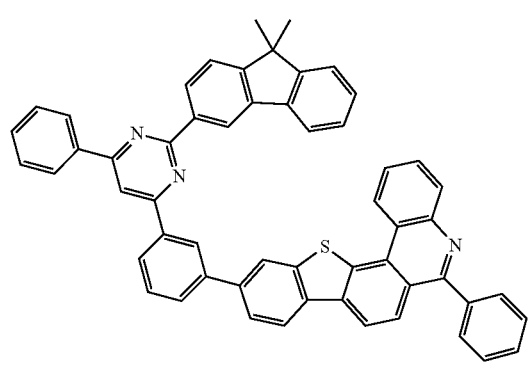
1277
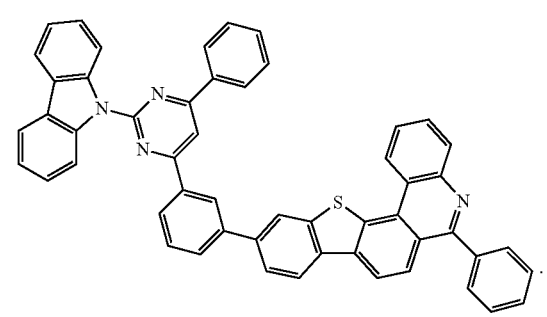

6. An organic light emitting device comprising:
a first electrode;
a second electrode; and
an organic material layer provided between the first electrode and the second electrode,
wherein the organic material layer includes the heterocyclic compound of claim 1.

7. The organic light emitting device of claim 6, wherein the organic material layer includes an electron transfer layer, and the electron transfer layer includes the heterocyclic compound.

8. The organic light emitting device of claim 6, further comprising one, two or more layers selected from the group consisting of a light emitting layer, a hole injection layer, a hole transfer layer, an electron injection layer, an electron transfer layer, an electron blocking layer and a hole blocking layer.

9. The organic light emitting device of claim 6 comprising:
the first electrode;
a first stack provided on the first electrode and including a first light emitting layer;
a charge generation layer provided on the first stack;
a second stack provided on the charge generation layer and including a second light emitting layer; and
the second electrode provided on the second stack.

10. The organic light emitting device of claim 9, wherein the charge generation layer includes the heterocyclic compound.

11. The organic light emitting device of claim 9, wherein the charge generation layer is an N-type charge generation layer, and the charge generation layer includes the heterocyclic compound.

* * * * *